(12) United States Patent
Smith et al.

(10) Patent No.: US 11,236,071 B1
(45) Date of Patent: Feb. 1, 2022

(54) FARNESOID X RECEPTOR AGONISTS AND USES THEREOF

(71) Applicant: Metacrine, Inc., San Diego, CA (US)

(72) Inventors: Nicholas D. Smith, San Diego, CA (US); Steven P. Govek, San Diego, CA (US); Johnny Y. Nagasawa, San Diego, CA (US); Karensa L. Douglas, San Diego, CA (US); Andiliy G. Lai, San Diego, CA (US)

(73) Assignee: METACRINE, INC., San Diego, CA (US)

( * ) Notice: Subject to any disclaimer, the term of this patent is extended or adjusted under 35 U.S.C. 154(b) by 189 days.

(21) Appl. No.: 16/494,272

(22) PCT Filed: Mar. 14, 2018

(86) PCT No.: PCT/US2018/022513
§ 371 (c)(1),
(2) Date: Sep. 13, 2019

(87) PCT Pub. No.: WO2018/170182
PCT Pub. Date: Sep. 20, 2018

Related U.S. Application Data

(60) Provisional application No. 62/563,488, filed on Sep. 26, 2017, provisional application No. 62/563,502, filed on Sep. 26, 2017, provisional application No. 62/471,517, filed on Mar. 15, 2017, provisional application No. 62/471,511, filed on Mar. 15, 2017, provisional application No. 62/471,525, filed on Mar. 15, 2017.

(51) Int. Cl.
| | | |
|---|---|---|
| C07D 403/12 | (2006.01) |
| C07D 277/28 | (2006.01) |
| C07D 417/12 | (2006.01) |
| C07D 231/12 | (2006.01) |
| C07D 401/12 | (2006.01) |
| C07D 417/04 | (2006.01) |
| C07D 275/02 | (2006.01) |
| C07D 413/12 | (2006.01) |
| C07D 417/14 | (2006.01) |
| C07D 401/14 | (2006.01) |
| C07D 413/14 | (2006.01) |
| A61P 1/16 | (2006.01) |
| C07D 263/32 | (2006.01) |
| A61K 45/06 | (2006.01) |

(52) U.S. Cl.
CPC ............. *C07D 403/12* (2013.01); *A61P 1/16* (2018.01); *C07D 231/12* (2013.01); *C07D 263/32* (2013.01); *C07D 275/02* (2013.01); *C07D 277/28* (2013.01); *C07D 401/12* (2013.01); *C07D 401/14* (2013.01); *C07D 413/12* (2013.01); *C07D 413/14* (2013.01); *C07D 417/04* (2013.01); *C07D 417/12* (2013.01); *C07D 417/14* (2013.01); *A61K 45/06* (2013.01)

(58) Field of Classification Search
CPC .. C07D 403/12; C07D 231/12; C07D 263/32; C07D 275/02; C07D 401/12; C07D 401/14; C07D 413/12; C07D 413/14; C07D 417/04; C07D 417/12; C07D 417/14; A61K 45/06; A61P 1/16
See application file for complete search history.

(56) References Cited

U.S. PATENT DOCUMENTS

| | | | |
|---|---|---|---|
| 6,645,980 B1 | 11/2003 | Cuny et al. | |
| 8,212,006 B2 | 7/2012 | Downes et al. | |
| 10,377,717 B2 * | 8/2019 | Smith | C07D 213/75 |
| 10,626,081 B2 * | 4/2020 | Smith | A61K 31/337 |
| 10,703,712 B2 * | 7/2020 | Smith | C07C 237/42 |
| 10,927,082 B2 * | 2/2021 | Smith | A61K 9/0029 |
| 10,961,198 B2 * | 3/2021 | Smith | A61K 9/0029 |
| 2006/0009459 A1 | 1/2006 | Chakka et al. | |
| 2008/0081824 A1 | 4/2008 | Zheng et al. | |
| 2008/0280916 A1 | 11/2008 | Bilich et al. | |
| 2012/0115869 A1 | 5/2012 | Crosignani et al. | |
| 2014/0155247 A1 | 6/2014 | Aoyagi et al. | |
| 2015/0258052 A1 | 9/2015 | Evans et al. | |
| 2017/0066724 A1 | 3/2017 | Evans et al. | |
| 2018/0116993 A1 | 5/2018 | Li et al. | |
| 2018/0282263 A1 | 10/2018 | Smith et al. | |
| 2020/0032195 A1 | 1/2020 | Kuhne | |
| 2020/0092932 A1 | 3/2020 | Youn et al. | |
| 2020/0102308 A1 * | 4/2020 | Smith | C07D 409/14 |
| 2020/0131129 A1 | 4/2020 | Smith et al. | |

(Continued)

FOREIGN PATENT DOCUMENTS

| | | |
|---|---|---|
| FR | 2839974 A1 | 11/2003 |
| JP | 2006199656 A | 8/2006 |

(Continued)

OTHER PUBLICATIONS

U.S. Appl. No. 17/152,548, filed Jan. 2021.*

(Continued)

*Primary Examiner* — D Margaret M Seaman
(74) *Attorney, Agent, or Firm* — Wilson Sonsini Goodrich & Rosati

(57) ABSTRACT

Described herein are compounds that are farnesoid X receptor agonists, methods of making such compounds, pharmaceutical compositions and medicaments comprising such compounds, and methods of using such compounds in the treatment of conditions, diseases, or disorders associated with farnesoid X receptor activity.

18 Claims, No Drawings

(56) References Cited

U.S. PATENT DOCUMENTS

| | | | |
|---|---|---|---|
| 2020/0131134 A1 | 4/2020 | Smith et al. | |
| 2020/0131142 A1 | 4/2020 | Smith et al. | |
| 2020/0290973 A1 | 9/2020 | Smith et al. | |
| 2021/0032195 A1* | 2/2021 | Smith | A61K 31/445 |

FOREIGN PATENT DOCUMENTS

| | | |
|---|---|---|
| JP | 2007530582 A | 11/2007 |
| JP | 2010077109 A | 4/2010 |
| MY | 144229 A | 8/2011 |
| WO | WO-0069810 A1 | 11/2000 |
| WO | WO-0071518 A2 | 11/2000 |
| WO | WO-0185694 A2 | 11/2001 |
| WO | WO-0192226 A1 | 12/2001 |
| WO | WO-0224649 A1 | 3/2002 |
| WO | WO-0230927 A1 | 4/2002 |
| WO | WO-02098852 A2 | 12/2002 |
| WO | WO-2004009549 A2 | 1/2004 |
| WO | WO-2004026823 A1 | 4/2004 |
| WO | WO-2004009549 A3 | 6/2004 |
| WO | WO-2004045511 A2 | 6/2004 |
| WO | WO-2004046162 A2 | 6/2004 |
| WO | WO-2004096771 A1 | 11/2004 |
| WO | WO-2005011655 A2 | 2/2005 |
| WO | WO-2004046162 A8 | 3/2005 |
| WO | WO-2005058822 A1 | 6/2005 |
| WO | WO-2005113522 A1 | 12/2005 |
| WO | WO-2007110237 A2 | 10/2007 |
| WO | WO-2008065500 A2 | 6/2008 |
| WO | WO-2009076747 A1 | 6/2009 |
| WO | WO-2009106991 A2 | 9/2009 |
| WO | WO-2010001869 A1 | 1/2010 |
| WO | WO-2011006935 A2 | 1/2011 |
| WO | WO-2011008915 A1 | 1/2011 |
| WO | WO-2012011081 A1 | 1/2012 |
| WO | WO-2012129495 A1 | 9/2012 |
| WO | WO-2014133414 A2 | 9/2014 |
| WO | WO-2015040425 A1 | 3/2015 |
| WO | WO-2015138969 A1 | 9/2015 |
| WO | WO-2016149111 A1 | 9/2016 |
| WO | WO-2017018751 A1 | 2/2017 |
| WO | WO-2017049172 A1 | 3/2017 |
| WO | WO-2017049173 A1 | 3/2017 |
| WO | WO-2017049176 A1 | 3/2017 |
| WO | WO-2017049177 A1 | 3/2017 |
| WO | WO-2017170182 A1 | 10/2017 |
| WO | WO-2018170165 A1 | 9/2018 |
| WO | WO-2018170166 A1 | 9/2018 |
| WO | WO-2018170167 A1 | 9/2018 |
| WO | WO-2018170173 A1 | 9/2018 |
| WO | WO-2018170182 A1 | 9/2018 |
| WO | WO-2020061112 A1 | 3/2020 |
| WO | WO-2020061113 A1 | 3/2020 |
| WO | WO-2020061114 A1 | 3/2020 |
| WO | WO-2020061116 A1 | 3/2020 |
| WO | WO-2020061117 A1 | 3/2020 |
| WO | WO-2020061118 A1 | 3/2020 |

OTHER PUBLICATIONS

U.S. Appl. No. 17/276,766, filed Mar. 2021.*
U.S. Appl. No. 17/276,785, filed Mar. 2021.*
U.S. Appl. No. 17/276,787, filed Mar. 2021.*
Ali et al. Recent advances in the development of farnesoid X receptor agonists. Ann Transl Med 3(1):5 (2015).
Amidon et al. Colon-Targeted Oral Drug Delivery Systems: Design Trends and Approaches, AAPS PharmSciTech 16(4):731-741 (2015).
Beaulieu et al., Preparation of 2-amido benzoic acid compounds as viral polymerase inhibitors. Chemical Abstracts Service. XP002791354. Database accession No. 2009:771969 (2009).
Berge et al. Pharmaceutical Salts. Journal of Pharmaceutical Sciences 66(1):1-19 (Jan. 1977).
Boss et al., Preparation of N-benzyl N-piperidin-4-yl benzamides as inhibitors of parasitic aspartyl protease. Chemical Abstracts Service. XP002791357. Database accession No. 2005:570873 (2005).
Boss et al., Preparation of piperidines for the treatment of central nervous system disorders. Chemical Abstracts Service. XP002791361. Database accession No. 2004:80651 (2004).
Boss et al., Preparation of substituted amino-aza-cycloalkanes as anti-malarial agents. Chemical Abstracts Service. XP002791363. Database accession No. 2002:240729 (2002).
Boss et al., Achiral, cheap, and potent inhibitors of Plasmepsins I, II, and IV. ChemMedChem. 1(12):1341-1345 (2006).
Brauer et al., Evolutionary chemistry approach toward finding novel inhibitors of the type 2 diabetes target glucose-6-phosphate translocase. Journal of Combinatorial Chemistry. 7(2):218-226 (2005).
Bromidge et al., Preparation of biaryl compounds having activity at the 5-HT5A receptor. Chemical Abstracts Service. XP002791359. Database accession No. 2004:965222 (2004).
Brough et al., Preparation of resorcinol N-Aryl amide compounds, for use as pyruvate dehydrogenase kinase inhibitors. Chemical Abstracts Service. XP002791352 Database accession No. 2015:512259 (2015).
Bundgaard. Design and Application of Prodrugs. Textbook of Drug Design and Development. Krosgaard-Larsen and Bundgaard. Chapter 5, pp. 113-191 (1991).
Bundgaard. Means to Enhance Penetration: Prodrugs as a Means to Improve the Delivery of Peptide Drugs. Advanced Drug Delivery Review 8:1-38 (1992).
Camilleri. Bile Acid diarrhea: prevalence, pathogenesis, and therapy. Gut Liver 9(3):332-339 (2015).
Chemical Abstract compound, STN express RN 1026708-50-8 (Entered STN: Jun. 9, 2008).
Chourasia et al. Pharmaceutical approaches to colon targeted drug delivery systems. J Pharm Pharm Sci. 6(1):33-66 (2003).
Costantino et al. Molecular Dynamics Simulation of the Ligand Binding Domain of Farnesoid X Receptor. Insights into Helix-12 Stability and Coactivator Peptide Stabilization in Response to Agonist Binding. J Med Chem 48:3251-3259 (2005).
Downes et al. A Chemical, Genetic, and Structural Analysis of the Nuclear Bile Acid Receptor FXR. Molecular Cell 11:1079-1092 (2003).
Erb et al. Sequential One-Pot Access to Molecular Diversity through Aniline Aqueous Borylation. J Organ Chem 79:10568-10580 (2014).
Fang et al. Intestinal FXR agonism promotes adipose tissue browning and reduces obesity and insulin resistance. Nat Med 21 (2):159-165 (2015).
Fett et al., Preparation of oxadiazole and pyridazine derivatives as inhibitors of biosynthesis of triglycerides. Chemical Abstracts Service. XP002791353 Database accession No. 2012:125764 (2012).
Fu et al. Fibroblast growth factor 19 increases metabolic rate and reverses dietary and leptin-deficient diabetes. Endocrinology 145:2594-2603 (2004).
Gadaleta et al. Farnesoid X receptor activation inhibits inflammation and preserves the intestinal barrier in inflammatory bowel disease. Gut 60(4):463-472 (2011).
Gangloff et al. Synthesis of 3,5-disubstituted 1,2,4-oxadiazoles using tetrabutylammonium fluoride as a mild and efficient catalyst. Tetrahedron Letters 42(8):1441-1443 (2001).
Gege et al. Knocking on FXR's Door: The "Hammerhead"-Structure Series of FXR Agonists—Amphiphilic Isoxazoles with Potent In Vitro and In Vivo Activi-ties. Current Topics in Medicinal Chemistry 14:2143-2158 (2014).
Genin et al. Discovery of 6-(4-{[5-Cyclopropyl-3-(2,6-dichlorophenyl)isoxazol-4-yl]methoxy}piperidin-1-yl)-1-methyl-1H-indole-3-carboxylic Acid: A Novel FXR Agonist for the Treatment of Dyslipidemia. J Med Chem 58(24):9768-9772 (2015).
Hamada et al. Synthesis and antimicrobial evaluation of some heterocyclic chalcone derivatives. Molecules 16:2304-2312 (2011).
Hambruch et al. On the Pharmacology of Farnesoid X Receptor Agonists: Give me an "A", Like an "Acid". Nuclear Receptor Research 3:Article ID 101207 (2016).
Honorio et al. 3D QSAR Comparative molecular field analysis on nonsteroidal farnesoid X receptor activators. J Mol Graph Model 25:921-927 (2007).

(56) References Cited

OTHER PUBLICATIONS

Honorio et al. Hologram quantitative structure-activity relationships for a series of farnesoid X receptor activators. Bioorg Med Chem Letts 15:3119-3125 (2005).
Hu et al. Predicting biological Functions of Compounds based on Chemical-Chemical Interactions. PLoS One 6(12):e29491 (2011).
Inagaki et al. Regulation of antibacterial defense in the small intestine by the nuclear bile acid receptor. PNA USA 103:3920-3925 (2006).
Johnson et al., Preparation of arylheterocyclylamides as motilin antagonists. Chemical Abstracts Service. XP002791364. Database accession No. 2001:833284 (2001).
Jursic et al. Preparation of 5-substituted 2-methyl-1,3,4-oxadiazoles from 5-substituted tetrazoles and acetic anhydride. Synthetic Communications 24(11):1575-82 (1994).
Kim et al. Inhibitory Effects of Bile Acides and Synthetic Farnesoid X Receptor Agonists on Rotavirus Replication. J Virol 85(23):12570-12577 (2011).
Kumar et al. Colon targeted drug delivery systems—an overview. Curr Drug Deliv 5(3):186-198 (2008).
Lam et al. Bile acids inhibit duodenal secretin expression via orphan nuclear receptor small heterodimer partner (SHP). Am J Physiol Gastrointest Liver Physiol 287:G90-G97 (2009).
Li et al. Microbiome remodelling leads to inhibition of intestinal farnesoid X receptor signalling and decreased obesity. Nat Commun 4:2384 (2013).
Li et al. Progress in the ligands and their complex structures of farnesoid X receptor. ACTA Pharmaceutica Sinica 47(6):704-715 (2012) (English Abstract).
Ling et al., Preparation of 3-(benzoylamino)propionic acid derivatives as glucagon antagonists/inverse agonists. Chemical Abstracts Service. XP002791365. Database accession No. 2000:824211 (2000).
Merk et al. Medicinal chemistry of farnesoid X receptor ligands: from agonists and antagonists to modulators. Future Med Chem 4(8):1015-1036 (2012).
Misawa et al. Discovery and structural development of small molecules that enhance transport activity of bile salt export pump mutant associated with progressive familial intrahepatic cholestasis type 2. Bioorg Med Chem 20:2940-2949 (2012).
Mokale et al. Synthesis and in-vivo hypolipidemic activity of some novel substituted phenyl isoxazol phenoxy acetic acid derivatives. Bioorg Med Chem Lett 24(9):2155-2158 (2014).
Mueller et al. Synthesis of plasmepsin II inhibitors—potential antimalarial agents. Molecules 8(7):556-564 (2003).
Mueller et al., Synthesis of plasmepsin II inhibitors as potential antimalarial agents. Chemical Abstracts Service. XP002791362. Database accession No. 2003:524478 (2003).
Nicolaou et al. Discovery and optimization of non-steroidal FXR agonists from natural product-like libraries. Org Biomol Chem 1:908-920 (2003).
O'Keefe et al., Preparation of amide and sulfonamidel igands for the estrogen receptor. Chemical Abstracts Service. XP002791360. Database accession No. 2004:267292 (2004).
Patel et al.Therapeutic opportunities in colon-specific drug-delivery systems. Crit Rev Ther Drug Carrier Syst. 24(2):147-202 (2007).
PCT/US2016/052270 International Preliminary Report on Patentability dated Mar. 29, 2018.
PCT/US2016/052270 International Search Report and Written Opinion dated Mar. 3, 2017.
PCT/US2018/022488 International Search Report and Written Opinion dated Jul. 30, 2018.
PCT/US2018/022488 Third Party Observation dated Jul. 15, 2019.
PCT/US2018/022489 International Search Report and Written Opinion dated Jul. 30, 2018.
PCT/US2018/022489 Third Party Observation dated Jul. 15, 2019.
PCT/US2018/022497 International Search Report and Written Opinion dated Jul. 30, 2018.
PCT/US2018/022497 Third Party Observation dated Jul. 15, 2019.
PCT/US2018/022513 International Search Report and Written Opinion dated Jul. 24, 2018.
PCT/US2019/051602 International Search Report and Written Opinion dated Dec. 4, 2019.
PCT/US2019/051603 International Search Report and Written Opinion dated Dec. 4, 2019.
PCT/US2019/051606 International Search Report and Written Opinion dated Dec. 4, 2019.
PCT/US2019/051607 International Search Report and Written Opinion dated Dec. 4, 2019.
PCT/US2019/051608 International Search Report and Written Opinion dated Dec. 4, 2019.
Poondra et al., Discovery of Indoline-Based, Natural-Product-like Compounds as Probes of Focal Adhesion Kinase Signaling Pathways. Chemical Abstracts Service. XP002791355 Database accession No. 2009:61531 (2009).
Ramanathan et al. One-Pot Reactions for Synthesis of 2,5-Substituted Tetrazoles from Aryldiazonium Salts and Amidines. Organic Letters 17(23):5886-5889 (2015).
Reschly et al. Ligand specificity and evolution of liver X receptors. J Steroid Biochem Mol Biol 110(1-2):83-94 (2008).
Sanyal et al. Involvement of corepressor complex subunit GPS2 in transcriptional pathways governing human bile acid biosynthesis. PNAS USA 104(40):15665-15670 (2007).
Schuster et al. Pharmacophore-based discovery of FXR agonists. Part I: Model development and experimental validation. Bioorg Med Chem 19:7168-7180 (2011).
Science IP—The CAS Search Service. Jul. 17, 2015 (316 pgs).
Shen et al. Synthesis and structure-activity relationships of thiadiazole-derivatives as potent and orally active peroxisome proliferator-activated receptors alpha/delta dual agonists. Bioorg Med Chem 16(6):3321-3341 (2008).
Steri et al. Antidiabetic sulfonylureas modulate farnesoid X receptor activation and target gene transcription. Future Med Chem 2(4):575-589 (2010).
U.S. Appl. No. 15/758,707 Office Action dated Sep. 5, 2019.
Vallin et al. Efficient Chemoenzymatic Dynamic Kinetic Resolution of 1-Heteroaryl Ethanols. J Org Chem 74(24):9328-9336 (2009).
Van Den Mooter. Colon drug delivery. Expert Opin Drug Deliv. 3(1):111-125 (2006).
Widder et al. Section III: Prodrugs Kinetics. Method in Enzymology. 112:309-396 (1985).
Yang et al. Syntheses of nicotinamide riboside and derivatives: effective agents for increasing nicotinamide adenine dinucleotide concentrations in mammalian cells. J. Med. Chem. 50:6458-61 (2007).
Zheng et al., Preparation of substituted piperidines as modulators of chemokine receptor activity. Chemical Abstracts Service. XP002791356. Database accession No. 2008:419604 (2008).
Braeuer et al. Evolutionary chemistry approach toward finding novel inhibitors of the type 2 diabetes target glucose-6-phosphate translocase. CA, Chemical Abstracts Service, Columbus, Ohio, US, (2005), Database accession No. 2005:154377, URL: STN, XP002791358.
CAS Registry No. 1349456-93-4. CA Index Name: [1,1?-biphenyl]-2-carboxylic acid, 4?-[[[[2-[[acetyl[4-(1-piperidinylmethyl)phenyl]amino]methyl]cyclopropyl]carbonyl]amino]methyl]-3,3?-difluoro-, methyl ester. Entered STN: Dec. 6, 2011.
CAS Registry No. 485347-98-6; CA Index Name: acetamide,N-[2-(aminomethyl)-1H-benzimidazol-6-yl]-N-[[2-(phenylmethoxy)phenyl]methyl]- Entered STN: Feb. 4, 2003.
PCT/US2018/022513 Third Party Observation dated Jul. 15, 2019.
Poondra et al. Discovery of Indoline-Based, Natural-Product-like Compounds as Probes of Focal Adhesion Kinase Signaling Pathways. J Comb Chem 11(2):303-309 (2009).

\* cited by examiner

FARNESOID X RECEPTOR AGONISTS AND USES THEREOF

CROSS-REFERENCE

This application claims benefit of U.S. Provisional Patent Application No. 62/471,511 filed on Mar. 15, 2017; U.S. Provisional Patent Application No. 62/471,517 filed on Mar. 15, 2017; U.S. Provisional Patent Application No. 62/471,525 filed on Mar. 15, 2017; U.S. Provisional Patent Application No. 62/563,488 filed on Sep. 26, 2017; and U.S. Provisional Patent Application No. 62/563,502 filed on Sep. 26, 2017; each of which are incorporated herein by reference in its entirety.

FIELD OF THE INVENTION

Described herein are compounds that are farnesoid X receptor agonists, methods of making such compounds, pharmaceutical compositions and medicaments comprising such compounds, and methods of using such compounds in the treatment of conditions, diseases, or disorders associated with farnesoid X receptor activity.

BACKGROUND OF THE INVENTION

Farnesoid X receptor (FXR) is a nuclear receptor highly expressed in the liver, intestine, kidney, adrenal glands, and adipose tissue. FXR regulates a wide variety of target genes involved in the control of bile acid synthesis and transport, lipid metabolism, and glucose homeostasis. FXR agonism is a treatment modality for many metabolic disorders, liver diseases or conditions, inflammatory conditions, gastrointestinal diseases, or cell proliferation diseases.

SUMMARY OF THE INVENTION

In one aspect, described herein are farnesoid X receptor agonists and uses thereof. In one aspect, described herein is a compound of Formula (I), or a pharmaceutically acceptable salt, or solvate thereof:

Formula (I)

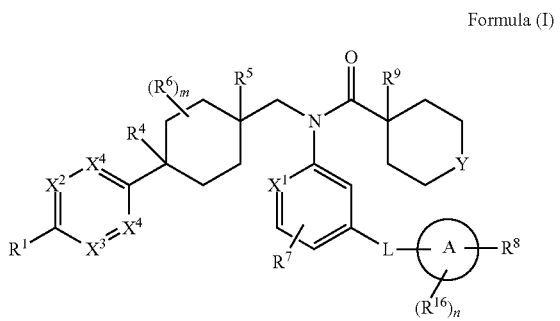

wherein,
ring A is a 5-membered heteroaryl that is thiazolyl, pyrazolyl, furanyl, thienyl, pyrrolyl, oxazolyl, imidazolyl, triazolyl, tetrazolyl, isoxazolyl, isothiazolyl, oxadiazolyl, or thiadiazolyl;
or ring A is a 6-membered heteroaryl that is pyridinyl, pyrimidinyl, pyrazinyl, pyridazinyl, or triazinyl;
or ring A is phenyl;
$X^1$ is CH or N;
$R^1$ is H, D, halogen, —CN, —OH, —N($R^{15}$)$_2$, —N$R^{15}$S(=O)$_2$($C_1$-$C_4$alkyl), —S(=O)$_2$N($R^{15}$)$_2$, —OC(=O)($C_1$-$C_4$alkyl), —CO$_2$H, —CO$_2$($C_1$-$C_4$alkyl), —C(=O)N($R^{15}$)$_2$, —N$R^{15}$C(=O)($C_1$-$C_4$alkyl), —N$R^{15}$C(=O)O($C_1$-$C_4$alkyl), —OC(=O)N($R^{15}$)$_2$, —N$R^{15}$C(=O)N($R^{15}$)$_2$, —SH, —S($C_1$-$C_4$alkyl), —S(=O)($C_1$-$C_4$alkyl), —S(=O)$_2$($C_1$-$C_4$alkyl), $C_1$-$C_4$alkyl, $C_2$-$C_4$alkenyl, $C_2$-$C_4$alkynyl, $C_1$-$C_4$alkoxy, $C_1$-$C_4$deuteroalkyl, $C_1$-$C_4$deuteroalkoxy, $C_1$-$C_4$fluoroalkyl, $C_1$-$C_4$fluoroalkoxy, $C_1$-$C_4$heteroalkyl, or substituted or unsubstituted monocyclic $C_2$-$C_5$heterocycloalkyl;
$X^2$ is $CR_2$ or N;
$R^2$ is H, D, halogen, —CN, —OH, —N($R^{15}$)$_2$, —N$R^{15}$S(=O)$_2$($C_1$-$C_4$alkyl), —S(=O)$_2$N($R^{15}$)$_2$, —OC(=O)($C_1$-$C_4$alkyl), —CO$_2$H, —CO$_2$($C_1$-$C_4$alkyl), —C(=O)N($R^{15}$)$_2$, —N$R^{15}$C(=O)($C_1$-$C_4$alkyl), —N$R^{15}$C(=O)O($C_1$-$C_4$alkyl), —OC(=O)N($R^{15}$)$_2$, —N$R^{15}$C(=O)N($R^{15}$)$_2$, —SH, —S($C_1$-$C_4$alkyl), —S(=O)($C_1$-$C_4$alkyl), —S(=O)$_2$($C_1$-$C_4$alkyl), $C_1$-$C_4$alkyl, $C_2$-$C_4$alkenyl, $C_2$-$C_4$alkynyl, $C_1$-$C_4$alkoxy, $C_1$-$C_4$deuteroalkyl, $C_1$-$C_4$deuteroalkoxy, $C_1$-$C_4$fluoroalkyl, $C_1$-$C_4$fluoroalkoxy, $C_1$-$C_4$heteroalkyl, or substituted or unsubstituted monocyclic $C_2$-$C_5$heterocycloalkyl;
or $R^1$ and $R^2$ are taken together with the intervening atoms to form a substituted or unsubstituted fused 5- or 6-membered ring with 0-3 N atoms and 0-2 O or S atoms in the ring;
$X^3$ is $CR^3$ or N;
$R^3$ is H, D, halogen, —CN, —OH, —N($R^{15}$)$_2$, —N$R^{15}$S(=O)$_2$($C_1$-$C_4$alkyl), —OC(=O)($C_1$-$C_4$alkyl), —CO$_2$H, —CO$_2$($C_1$-$C_4$alkyl), —C(=O)N($R^{15}$)$_2$, —N$R^{15}$C(=O)($C_1$-$C_4$alkyl), $C_1$-$C_4$alkyl, $C_2$-$C_4$alkenyl, $C_2$-$C_4$alkynyl, $C_1$-$C_4$alkoxy, $C_1$-$C_4$deuteroalkyl, $C_1$-$C_4$deuteroalkoxy, $C_1$-$C_4$fluoroalkyl, $C_1$-$C_4$fluoroalkoxy, or $C_1$-$C_4$heteroalkyl;
each $X^4$ is independently CH or N;
$R^4$ is H, D, F, or —CH$_3$;
$R^5$ is H, D, F, or —CH$_3$;
or $R^4$ and $R^5$ are taken together to form a bridge that is —CH$_2$— or —CH$_2$CH$_2$—;
each $R^6$ is independently H, D, F, —OH, or —CH$_3$;
m is 0, 1, or 2;
$R^7$ is H, D, halogen, —CN, —OH, $C_1$-$C_4$alkyl, $C_2$-$C_4$alkenyl, $C_2$-$C_4$alkynyl, $C_1$-$C_4$alkoxy, $C_1$-$C_4$deuteroalkyl, $C_1$-$C_4$deuteroalkoxy, $C_1$-$C_4$fluoroalkyl, $C_1$-$C_4$fluoroalkoxy, or $C_1$-$C_4$heteroalkyl;
L is absent, —$Y^2$-$L^1$-, -$L^1$-$Y^2$—, cyclopropylene, cyclobutylene or bicyclo[1.1.1]pentylene;
$Y^2$ is absent, —O—, —S—, —S(=O)—, —S(=O)$_2$—, —S(=O)$_2$N$R^{15}$—, —CH$_2$—, —CH=CH—, —C≡C—, —C(=O)—, —C(=O)O—, —OC(=O)—, —OC(=O)O—, —C(=O)N$R^{15}$—, —N$R^{15}$C(=O)—, —OC(=O)N$R^{15}$—, —N$R^{15}$C(=O)O—, —N$R^{15}$C(=O)N$R^{15}$—, —N$R^{15}$S(=O)$_2$—, or —N$R^{15}$—;
$L^1$ is absent or substituted or unsubstituted $C_1$-$C_4$alkylene;
$R^8$ is H, D, $C_1$-$C_6$alkyl, $C_1$-$C_6$deuteroalkyl, $C_1$-$C_6$fluoroalkyl, $C_1$-$C_6$heteroalkyl, —C(=O)($C_1$-$C_4$alkyl), —CO$_2$($C_1$-$C_4$alkyl), —C(=O)N($R^{15}$)$_2$, —S(=O)$_2$($C_1$-$C_4$alkyl), —S(=O)$_2$N($R^{15}$)$_2$, substituted or unsubstituted $C_3$-$C_6$cycloalkyl, or substituted or unsubstituted monocyclic $C_2$-$C_6$heterocycloalkyl, substituted or unsubstituted phenyl, or substituted or unsubstituted monocyclic heteroaryl;

$R^9$ is H, D, F or —$CH_3$;

$R^{10}$ is —$CH_2OH$, —$CH_2CH_2OH$, $C_1$-$C_6$heteroalkyl, —$CO_2H$, —$C(=O)R^{14}$, —$C(=O)OR^{14}$, —$OC(=O)R^{14}$, —$OC(=O)OR^{14}$, tetrazolyl, imidazole, 5-oxo-4,5-dihydro-1,2,4-oxadiazol-3-yl, —$S(=O)_2N(R^{12})_2$, —$NR^{15}S(=O)_2R^{14}$, —$C(=O)NR^{15}S(=O)_2R^{14}$, —$S(=O)_2NR^{15}C(=O)R_{14}$, —$CH_2N(R^{12})_2$, —$NR^{15}C(=O)R^{14}$, —$C(=O)N(R^{12})_2$, —$NR^{15}C(=O)OR^{14}$, —$OC(=O)N(R^{12})_2$, —$NR^{15}C(=O)N(R^2)_2$, —$C(=NH)NH_2$, —$NHC(=NH)NH_2$, —$C(=O)NHC(=NH)NH_2$, —$S(=O)_2OH$ or —$OP(=O)(OR^{15})_2$;

or $R^{10}$ is -$L^2$-$L^3$-$L^4$-$R^{13}$ $L^2$ is absent, substituted or unsubstituted $C_1$-$C_6$alkylene, or substituted or unsubstituted $C_1$-$C_6$heteroalkylene;

$L^3$ is absent, —O—, —S—, —S(=O)—, —$S(=O)_2$—, —$NR^{15}$—, —C(=O)—, —$C(=O)NR^{15}$—, —$NR^{15}C(=O)$—, —C(=O)O—, —OC(=O)—, —$OC(=O)NR^{15}$—, —$NR^{15}C(=O)NR^{15}$—, —$NR^{15}C(=O)O$—, —$OP(=O)(OR^{15})O$—, or —$(OCH_2CH_2)_r$—, r is 1 or 2;

$L^4$ is substituted or unsubstituted $C_1$-$C_6$alkylene, or substituted or unsubstituted $C_1$-$C_6$heteroalkylene;

$R^{13}$ is H, —CN, —OH, —$N(R^{12})_2$, —$NR^{15}S(=O)_2R^{14}$, —$S(=O)_2N(R^{12})_2$, —$SR^{12}$, —$S(=O)R^{14}$, —$S(=O)_2R^{14}$, —$SO_3H$, —$OP(=O)(OR^{15})_2$, —$C(=O)R^{14}$, —$OC(=O)R^{14}$, —$CO_2H$, —$CO_2R^{14}$, —$OC(=O)OR^{14}$, —$NR^{15}C(=O)R^{14}$, —$C(=O)N(R^{12})_2$, —$NR^{15}C(=O)OR^{14}$, —$OC(=O)N(R^{12})_2$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_3$-$C_6$cycloalkyl, substituted or unsubstituted $C_2$-$C_6$heterocycloalkyl, substituted or unsubstituted phenyl, or substituted or unsubstituted monocyclic heteroaryl;

$R^{11}$ is H, D, F, or —$CH_3$;

or $R^9$ and $R^{11}$ are taken together to form a bridge that is —$CH_2$— or —$CH_2CH_2$—;

each $R^{12}$ is independently H, $C_1$-$C_4$alkyl, $C_1$-$C_4$deuteroalkyl, $C_1$-$C_4$fluoroalkyl, $C_1$-$C_4$heteroalkyl, substituted or unsubstituted $C_3$-$C_6$cycloalkyl, substituted or unsubstituted $C_2$-$C_6$heterocycloalkyl, substituted or unsubstituted phenyl, substituted or unsubstituted benzyl, or substituted or unsubstituted monocyclic heteroaryl;

$R^{14}$ is $C_1$-$C_4$alkyl, $C_1$-$C_4$deuteroalkyl, $C_1$-$C_4$fluoroalkyl, $C_1$-$C_4$heteroalkyl, substituted or unsubstituted $C_3$-$C_6$cycloalkyl, substituted or unsubstituted $C_2$-$C_6$heterocycloalkyl, substituted or unsubstituted phenyl, substituted or unsubstituted benzyl, or substituted or unsubstituted monocyclic heteroaryl;

$R^{15}$ is H or substituted or unsubstituted $C_1$-$C_6$alkyl;

each $R^{16}$ is independently H, D, halogen, —CN, —OH, —$N(R^{15})_2$, —$NR^{15}S(=O)_2(C_1$-$C_4$alkyl), —$S(C_1$-$C_4$alkyl), —$S(=O)(C_1$-$C_4$alkyl), —$S(=O)_2(C_1$-$C_4$alkyl), —$S(=O)_2N(R^{15})_2$, —$C(=O)(C_1$-$C_4$alkyl), —$OC(=O)(C_1$-$C_4$alkyl), —$CO_2H$, —$CO_2(C_1$-$C_4$alkyl), —$NR^{15}C(=O)(C_1$-$C_4$alkyl), —$C(=O)N(R^{15})_2$, —$NR^{15}C(=O)O(C_1$-$C_4$alkyl), —$OC(=O)N(R^{15})_2$, $C_1$-$C_4$alkyl, $C_2$-$C_4$alkenyl, $C_2$-$C_4$alkynyl, $C_1$-$C_4$alkoxy, $C_1$-$C_4$deuteroalkyl, $C_1$-$C_4$deuteroalkoxy, $C_1$-$C_4$fluoroalkyl, $C_1$-$C_4$fluoroalkoxy, $C_1$-$C_4$heteroalkyl, substituted or unsubstituted $C_3$-$C_6$cycloalkyl, substituted or unsubstituted monocyclic $C_2$-$C_6$heterocycloalkyl, substituted or unsubstituted phenyl, or substituted or unsubstituted monocyclic heteroaryl;

n is 0, 1, or 2.

Any combination of the groups described above for the various variables is contemplated herein. Throughout the specification, groups and substituents thereof are chosen by one skilled in the field to provide stable moieties and compounds.

In one aspect, described herein is a pharmaceutical composition comprising a compound described herein, or a pharmaceutically acceptable salt, or solvate thereof, and at least one pharmaceutically acceptable excipient. In some embodiments, the pharmaceutical composition is formulated for administration to a mammal by intravenous administration, subcutaneous administration, oral administration, inhalation, nasal administration, dermal administration, or ophthalmic administration. In some embodiments, the pharmaceutical composition is formulated for administration to a mammal by intravenous administration, subcutaneous administration, or oral administration. In some embodiments, the pharmaceutical composition is formulated for administration to a mammal by oral administration. In some embodiments, the pharmaceutical composition is in the form of a tablet, a pill, a capsule, a liquid, a suspension, a gel, a dispersion, a solution, an emulsion, an ointment, or a lotion. In some embodiments, the pharmaceutical composition is in the form of a tablet, a pill, or a capsule.

In another aspect, described herein is a method of treating a disease or condition in a mammal that would benefit from FXR agonism comprising administering a compound as described herein, or pharmaceutically acceptable salt, or solvate thereof, to the mammal in need thereof. In some embodiments, the disease or condition is a metabolic condition. In some embodiments, the disease or condition is a liver condition.

In some embodiments, the compound is administered to the mammal by intravenous administration, subcutaneous administration, oral administration, inhalation, nasal administration, dermal administration, or ophthalmic administration.

In one aspect, described herein is a method of treating or preventing any one of the diseases or conditions described herein comprising administering a therapeutically effective amount of a compound described herein, or a pharmaceutically acceptable salt, or solvate thereof, to a mammal in need thereof.

In one aspect, described herein is a method for the treatment or prevention of a metabolic or liver condition in a mammal comprising administering a therapeutically effective amount of a compound described herein, or a pharmaceutically acceptable salt, or solvate thereof, to the mammal in need thereof. In other embodiments, the metabolic or liver condition is amenable to treatment with a FXR agonist. In some embodiments, the method further comprises administering a second therapeutic agent to the mammal in addition to the compound described herein, or a pharmaceutically acceptable salt, or solvate thereof.

In one aspect, described herein is a method of treating or preventing a liver disease or condition in a mammal, comprising administering to the mammal a compound of Formula (I), or a pharmaceutically acceptable salt or solvate thereof. In some embodiments, the liver disease or condition is an alcoholic or non-alcoholic liver disease. In some embodiments, the liver disease or condition is primary biliary cirrhosis, primary sclerosing cholangitis, cholestasis, nonalcoholic steatohepatitis (NASH), or nonalcoholic fatty liver disease (NAFLD). In some embodiments, the alcoholic liver disease or condition is fatty liver (steatosis), cirrhosis, or alcoholic hepatitis. In some embodiments, the non-alcoholic liver disease or condition is nonalcoholic steatohepatitis (NASH), or nonalcoholic fatty liver disease (NAFLD). In some embodiments, the non-alcoholic liver disease or condition is nonalcoholic steatohepatitis (NASH). In some embodiments, the non-alcoholic liver disease or condition is nonalcoholic steatohepatitis (NASH) and is accompanied by liver fibrosis. In some embodiments, the non-alcoholic liver disease or condition is nonalcoholic steatohepatitis (NASH) without liver fibrosis. In some embodiments, the non-alcoholic liver disease or condition is intrahepatic cholestasis or extrahepatic cholestasis.

In one aspect, described herein is a method of treating or preventing a liver fibrosis in a mammal, comprising administering to the mammal a compound of Formula (I), or a pharmaceutically acceptable salt or solvate thereof. In some embodiments, the mammal is diagnosed with hepatitis C virus (HCV), nonalcoholic steatohepatitis (NASH), primary sclerosing cholangitis (PSC), cirrhosis, Wilson's disease, hepatitis B virus (HBV), HIV associated steatohepatitis and cirrhosis, chronic viral hepatitis, non-alcoholic fatty liver disease (NAFLD), alcoholic steatohepatitis (ASH), nonalcoholic steatohepatitis (NASH), primary biliary cirrhosis (PBC), or biliary cirrhosis. In some embodiments, the mammal is diagnosed with nonalcoholic steatohepatitis (NASH).

In one aspect, described herein is a method of treating or preventing a liver inflammation in a mammal, comprising administering to the mammal a compound of Formula (I), or a pharmaceutically acceptable salt or solvate thereof. In some embodiments, the mammal is diagnosed with hepatitis C virus (HCV), nonalcoholic steatohepatitis (NASH), primary sclerosing cholangitis (PSC), cirrhosis, Wilson's disease, hepatitis B virus (HBV), HIV associated steatohepatitis and cirrhosis, chronic viral hepatitis, non-alcoholic fatty liver disease (NAFLD), alcoholic steatohepatitis (ASH), nonalcoholic steatohepatitis (NASH), primary biliary cirrhosis (PBC), or biliary cirrhosis. In some embodiments, the mammal is diagnosed with nonalcoholic steatohepatitis (NASH). In some embodiments, the liver inflammation is associated with inflammation in the gastrointestinal tract. In some embodiments, the mammal is diagnosed with inflammatory bowel disease.

In one aspect, described herein is a method of treating or preventing a gastrointestinal disease or condition in a mammal, comprising administering to the mammal a compound of Formula (I), or a pharmaceutically acceptable salt or solvate thereof. In some embodiments, the gastrointestinal disease or condition is necrotizing enterocolitis, gastritis, ulcerative colitis, Crohn's disease, inflammatory bowel disease, irritable bowel syndrome, gastroenteritis, radiation induced enteritis, pseudomembranous colitis, chemotherapy induced enteritis, gastro-esophageal reflux disease (GERD), peptic ulcer, non-ulcer dyspepsia (NUD), celiac disease, intestinal celiac disease, post-surgical inflammation, gastric carcinogenesis, graft versus host disease or any combination thereof. In some embodiments, the gastrointestinal disease is irritable bowel syndrome (IBS), irritable bowel syndrome with diarrhea (IBS-D), irritable bowel syndrome with constipation (IBS-C), mixed IBS (IBS-M), unsubtyped IBS (IBS-U), or bile acid diarrhea (BAD)

In one aspect, described herein is a method of treating or preventing a disease or condition in a mammal that would benefit from treatment with a FXR agonist, comprising administering to the mammal a compound of Formula (I), or a pharmaceutically acceptable salt or solvate thereof. In some embodiments, the methods described herein further comprise administering at least one additional therapeutic agent in addition to the compound of Formula (I), or a pharmaceutically acceptable salt or solvate thereof.

In any of the aforementioned aspects are further embodiments in which the effective amount of the compound described herein, or a pharmaceutically acceptable salt thereof, is: (a) systemically administered to the mammal; and/or (b) administered orally to the mammal; and/or (c) intravenously administered to the mammal; and/or (d) administered by inhalation; and/or (e) administered by nasal administration; or and/or (f) administered by injection to the mammal; and/or (g) administered topically to the mammal; and/or (h) administered by ophthalmic administration; and/or (i) administered rectally to the mammal; and/or (j) administered non-systemically or locally to the mammal.

In any of the aforementioned aspects are further embodiments comprising single administrations of the effective amount of the compound, including further embodiments in which the compound is administered once a day to the mammal or the compound is administered to the mammal multiple times over the span of one day. In some embodiments, the compound is administered on a continuous dosing schedule. In some embodiments, the compound is administered on a continuous daily dosing schedule.

In any of the aforementioned aspects involving the treatment of a disease or condition are further embodiments comprising administering at least one additional agent in addition to the administration of a compound of Formula (I) described herein, or a pharmaceutically acceptable salt thereof. In various embodiments, each agent is administered in any order, including simultaneously.

In any of the embodiments disclosed herein, the mammal or subject is a human.

In some embodiments, compounds provided herein are administered to a human.

In some embodiments, compounds provided herein are orally administered.

In some embodiments, described herein is method of treating or preventing a metabolic disorder in a subject, comprising: administering to a gastrointestinal tract of the subject a therapeutically effective amount of one or more of the compounds described herein, or a pharmaceutically acceptable salt or solvate thereof, thereby activating farnesoid X receptors (FXR) in the intestines, and treating or preventing a metabolic disorder in the subject. In some embodiments, the compound's absorption is preferentially restricted to within the intestines. In some embodiments, the method substantially enhances FXR target gene expression in the intestines while not substantially enhancing FXR target gene expression in the liver or kidney. In some embodiments, the method substantially enhances FXR target gene expression in the intestines while minimizing systemic plasma levels of the delivered compound. In some embodiments, the method substantially enhances FXR target gene expression in the intestines and the liver while minimizing systemic plasma levels of the delivered compound. In some embodiments, the method substantially enhances FXR target gene expression in the intestines while not substantially enhancing FXR target gene expression in the liver or kidney, and while minimizing systemic plasma levels. In some embodiments, the method substantially enhances FXR target gene expression in the intestines and the liver and provides sustained systemic plasma levels of the delivered compound. In some embodiments, the method reduces or prevents diet-induced weight gain. In some embodiments, the method increases a metabolic rate in the subject. In some embodiments, the increasing the metabolic rate comprises enhancing oxidative phosphorylation in the subject.

In some embodiments, the method further comprises improving glucose and/or lipid homeostasis in the subject. In some embodiments, the method results in no substantial change in food intake and/or fat consumption in the subject. In some embodiments, the method results in no substantial change in appetite in the subject. In some embodiments, the metabolic disorder is selected from obesity, diabetes, insulin resistance, dyslipidemia or any combination thereof. In some embodiments, the metabolic disorder is non-insulin dependent diabetes mellitus. In some embodiments, the method protects against diet-induced weight gain, reduces inflammation, enhances thermogenesis, enhances insulin sensitivity in the liver, reduces hepatic steatosis, promotes activation of BAT, decreases blood glucose, increases weight loss, or any combination thereof. In some embodiments, the method enhances insulin sensitivity in the liver and promotes brown adipose tissue (BAT) activation. In some embodiments, the method further comprises administering to the subject an insulin sensitizing drug, an insulin secretagogue, an alpha-glucosidase inhibitor, a glucagon-like peptide (GLP) agonist, a dipeptidyl peptidase-4 (DPP-4) inhibitor, nicotinamide ribonucleoside, an analog of nicotinamide ribonucleoside, or combinations thereof.

In some embodiments, described herein is a method of treating or preventing inflammation in an intestinal region of a subject, comprising: administering to a gastrointestinal tract of the subject a therapeutically effective amount of one or more of the compounds described herein, or a pharmaceutically acceptable salt or solvate thereof, thereby activating FXR receptors in the intestines, and thereby treating or preventing inflammation in the intestinal region of the subject. In some embodiments, the compound's absorption is preferentially restricted to within the intestines. In some embodiments, the method substantially enhances FXR target gene expression in the intestines while not substantially enhancing FXR target gene expression in the liver or kidney. In some embodiments, the inflammation is associated with a clinical condition selected from necrotizing enterocolitis, gastritis, ulcerative colitis, Crohn's disease, inflammatory bowel disease, irritable bowel syndrome, gastroenteritis, radiation induced enteritis, pseudomembranous colitis, chemotherapy induced enteritis, gastro-esophageal reflux disease (GERD), peptic ulcer, non-ulcer dyspepsia (NUD), celiac disease, intestinal celiac disease, post-surgical inflammation, gastric carcinogenesis or any combination thereof. In some embodiments, the one or more FXR target genes comprises IBABP, OSTα, Perl, FGF15, FGF19, SHP or combinations thereof. In some embodiments, the method further comprises administering a therapeutically effective amount of an antibiotic therapy to the subject, wherein the method treats or prevents inflammation associated with pseudomembranous colitis in the subject. In some embodiments, the method further comprises administering to the subject a therapeutically effective amount of an oral corticosteroid, other anti-inflammatory or immunomodulatory therapy, nicotinamide ribonucleoside, an analog of nicotinamide ribonucleoside, or combinations thereof. In some embodiments, the method increases HSL phosphorylation and β3-adrenergic receptor expression. In some embodiments, a serum concentration of the compound in the subject remains below its $EC_{50}$ following administration of the compound.

In some embodiments, described herein is a method of treating or preventing a cell proliferation disease in a subject, comprising administering to a gastrointestinal tract of the subject a therapeutically effective amount of one or more of the compounds described herein or a pharmaceutically acceptable salt or solvate thereof. In some embodiments, the cell proliferation disease is an adenocarcinoma. In some embodiments, the adenocarcinoma is a colon cancer. In some embodiments, the treating the adenocarcinoma reduces the size of the adenocarcinoma, the volume of the adenocarcinoma, the number of adenocarcinomas, cachexia due to the adenocarcinoma, delays progression of the adenocarcinoma, increases survival of the subject, or combinations thereof. In some embodiments, the method further comprises administering to the subject an additional therapeutic compound selected from the group consisting of a chemotherapeutic, a biologic, a radiotherapeutic, or combinations thereof.

In some embodiments, described herein is a method of treating or preventing a liver disease or condition in a subject, comprising administering to the subject a therapeutically effective amount of one or more of the compounds described herein, or a pharmaceutically acceptable salt or solvate thereof. In some embodiments, the liver disease or condition is an alcoholic or non-alcoholic liver disease. In some embodiments, the liver disease or condition is primary biliary cirrhosis, primary sclerosing cholangitis, cholestasis, nonalcoholic steatohepatitis (NASH), or nonalcoholic fatty liver disease (NAFLD). In some embodiments, the alcoholic liver disease or condition is fatty liver (steatosis), cirrhosis, or alcoholic hepatitis. In some embodiments, the non-alcoholic liver disease or condition is nonalcoholic steatohepatitis (NASH), or nonalcoholic fatty liver disease (NAFLD). In some embodiments, the non-alcoholic liver disease or condition is intrahepatic cholestasis or extrahepatic cholestasis.

Articles of manufacture, which include packaging material, a compound described herein, or a pharmaceutically acceptable salt thereof, within the packaging material, and a label that indicates that the compound or composition, or pharmaceutically acceptable salt, pharmaceutically active metabolite, pharmaceutically acceptable prodrug, or pharmaceutically acceptable solvate thereof, is used for the treatment, prevention or amelioration of one or more symptoms of a disease or condition that would benefit from FXR agonism, are provided.

Other objects, features and advantages of the compounds, methods and compositions described herein will become apparent from the following detailed description.

It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION OF THE INVENTION

The nuclear hormone receptor farnesoid X receptor (also known as FXR or nuclear receptor subfamily 1, group H, member 4 (NR1H4)) (OMIM: 603826) functions as a regulator for bile acid metabolism. FXR is a ligand-activated transcriptional receptor expressed in diverse tissues including the adrenal gland, kidney, stomach, duodenum, jejunum, ileum, colon, gall bladder, liver, macrophages, and white and brown adipose tissue. FXRs are highly expressed in tissues that participate in bile acid metabolism such as the liver, intestines, and kidneys. Bile acids function as endogenous ligands for FXR such that enteric and systemic release of bile acids induces FXR-directed changes in gene expression networks. Bile acids are the primary oxidation product of cholesterol, and in some cases, upon secretion into the intestines, are regulators of cholesterol absorption. The rate-limiting step for conversion of cholesterol into bile acids is catalyzed by cytochrome p450 enzyme cholesterol 7-α-hydroxylase (CYP7A1) and occurs in the liver. The cytochrome p450 enzyme sterol 12-α-hydroxylase (CYP8B1) mediates production of cholic acid and determines the relative amounts of the two primary bile acids, cholic acid and chenodeoxycholic acid. Activation of FXR can represses the transcription of CYP7A1 and CYP8B1 by increasing the expression level of the hepatic small heterodimer partner (SHP) (also known as nuclear receptor subfamily 0, group B, member 2; or NR0B2) and intestinal expression of fibroblast growth factor 15 (FGF15) in mice and fibroblast growth factor 19 (FGF19) in human. SHP represses the liver receptor homolog (LRH-1) and hepatocyte nuclear factor 4alpha (HNFa4), transcription factors that regulate CYP7A1 and CYP8B1 gene expression. CYP8B1 repression by FXR can be species-specific and FXR activation may in some cases increase CYP8B1 expression in humans (Sanyal et al PNAS, 2007, 104, 15665). In some cases, FGF15/19 released from the intestine then activates the fibroblast growth factor receptor 4 in the liver, leading to activation of the mitogen-activated protein kinase (MAPK) signaling pathway which suppress CYP7A1 and CYP8B1.

In some embodiments, elevated levels of bile acids have been associated with insulin resistance. For example, insulin resistance sometimes leads to a decreased uptake of glucose from the blood and increased de novo glucose production in the liver. In some instances, intestinal sequestration of bile acids has been shown to improve insulin resistance by promoting the secretion of glucagon-like peptide-1 (GLP1) from intestinal L-cells. GLP-1 is an incretin derived from the transcription product of the proglucagon gene. It is released in response to the intake of food and exerts control in appetite and gastrointestinal function and promotes insulin secretion from the pancreas. The biologically active forms of GLP-1 include GLP-1-(7-37) and GLP-1-(7-36)NH$_2$, which result from selective cleavage of the proglucagon molecule. In such cases, activation of FXR leading to decreased production of bile acids correlates to a decrease in insulin resistance.

In some embodiments, the activation of FXR also correlates to the secretion of pancreatic polypeptide-fold such as peptide YY (PYY or PYY3-36). In some instances, peptide YY is a gut hormone peptide that modulates neuronal activity within the hypothalamic and brainstem, regions of the brain involved in reward processing. In some instances, reduced level of PYY correlates to increased appetite and weight gain.

In some instances, the activation of FXR indirectly leads to a reduction of plasma triglycerides. The clearance of triglycerides from the bloodstream is due to lipoprotein lipase (LPL). LPL activity is enhanced by the induction of its activator apolipoprotein CII, and the repression of its inhibitor apolipoprotein CIII in the liver occurs upon FXR activation.

In some cases, the activation of FXR further modulates energy expenditure such as adipocyte differentiation and function. Adipose tissue comprises adipocytes or fat cells. In some instances, adipocytes are further differentiated into brown adipose tissue (BAT) or white adipose tissue (WAT). The function of BAT is to generate body heat, while WAT functions as fat storing tissues.

In some instances, FXR is widely expressed in the intestine. In some cases, the activation of FXR has been shown to induce the expression and secretion of FGF19 (or FGF15 in mouse) in the intestine. FGF19 is a hormone that regulates bile acid synthesis as well as exerts an effect on glucose metabolism, lipid metabolism, and on energy expenditure.

In some instances, FGF19 has also been observed to modulate adipocyte function and differentiation. Indeed, a study has shown that the administration of FGF19 to high-fat diet-fed mice increased energy expenditure, modulated adipocytes differentiation and function, reversed weight gain, and improved insulin resistance (see, Fu et al., "Fibroblast growth factor 19 increases metabolic rate and reverses dietary and leptin-deficient diabetes." *Endocrinology* 145: 2594-2603 (2004)).

In some cases, intestinal FXR activity has also been shown to be involved in reducing overgrowth of the microbiome, such as during feeding (Li et al., *Nat Commun* 4:2384, 2013). For example, a study had shown that activation of FXR correlated with increased expression of several genes in the ileum such as Ang2, iNos, and Il18, which have established antimicrobial actions (Inagaki et al., *Proc Natl Acad Sci USA* 103:3920-3925, 2006).

In some cases, FXR has been implicated in barrier function and immune modulation in the intestine. FXR modulates transcription of genes involved in bile salt synthesis, transport and metabolism in the liver and intestine, and in some cases has been shown to lead to improvements in intestinal inflammation and prevention of bacterial translocation into the intestinal tract (Gadaleta et al., *Gut.* 2011 April; 60(4):463-72).

In some cases, over production of bile acids or improper transport and re-cycling of bile acids can lead to diarrhea. FXR modulates transcription of genes involved in bile salt synthesis, transport and metabolism in the liver and intestine, and in some cases may lead to improvements in diarrhea Camilleri, *Gut Liver.* 2015 May; 9(3): 332-339.

G protein-coupled bile acid receptor 1 (also known as GPBAR2, GPCR19, membrane-type receptor for bile acids or M-BAR, or TGR5) is a cell surface receptor for bile acids. Upon activation with bile acid, TGR5 induces the production of intracellular cAMP, which then triggers an increase in triiodothyronine due to the activation of deiodinase (DIO2) in BAT, resulting in increased energy expenditure.

Hence in some embodiments, regulation of metabolic processes such as bile acid synthesis, bile-acid circulation, glucose metabolism, lipid metabolism, or insulin sensitivity is modulated by the activation of FXR. Furthermore, in some embodiments, dis-regulation of metabolic processes such as bile acid synthesis, bile-acid circulation, glucose metabolism, lipid metabolism, or insulin sensitivity results in metabolic diseases such as diabetes or diabetes-related conditions or disorders, alcoholic or non-alcoholic liver disease or condition, intestinal inflammation, or cell proliferative disorders.

Disclosed herein, in certain embodiments, are compounds that have activity as FXR agonists. In some embodiments, the FXR agonists described herein are structurally distinct from bile acids, other synthetic FXR ligands, and other natural FXR ligands.

In some embodiments, also disclosed herein are methods of treating or preventing a metabolic disorder, such as diabetes, obesity, impaired glucose tolerance, dyslipidemia, or insulin resistance by administering a therapeutically effective amount of an FXR agonist. In some instances, the compounds are administered to the GI tract of a subject.

In additional embodiments, disclosed herein are methods for treating or preventing alcoholic or non-alcoholic liver disease or conditions (e.g., cholestasis, primary biliary cirrhosis, steatosis, cirrhosis, alcoholic hepatitis, non-alcoholic steatohepatitis (NASH), non-alcoholic fatty liver disease (NAFLD), primary sclerosing cholangitis (PSC) or elevated liver enzymes) by administering a therapeutically effective amount of an FXR agonist to a subject in need thereof (e.g., via the GI tract). In additional embodiments, disclosed herein include methods for treating or preventing cholestasis, cirrhosis, primary biliary cirrhosis, non-alcoholic steatohepatitis (NASH), non-alcoholic fatty liver disease (NAFLD), or primary sclerosing cholangitis (PSC) by administering a therapeutically effective amount of an FXR agonist to a subject in need thereof. In some embodiments, disclosed herein include methods for treating or preventing cholestasis by administering a therapeutically effective amount of an FXR agonist to a subject in need thereof. In some embodiments, disclosed herein include methods for treating or preventing primary biliary cirrhosis by administering a therapeutically effective amount of an FXR agonist to a subject in need thereof. In some embodiments, disclosed herein include methods for treating or preventing NASH by administering a therapeutically effective amount of an FXR agonist to a subject in need thereof. In some embodiments, disclosed herein include methods for treating or preventing NAFLD by administering a therapeutically effective amount of an FXR agonist to a subject in need thereof.

In further embodiments, disclosed herein include methods for treating or preventing inflammation in the intestines and/or a cell proliferative disorder, such as cancer, by administering a therapeutically effective amount of an FXR agonist to a subject in need thereof (e.g., via the GI tract).

In still further embodiments, disclosed herein include FXR agonists that modulate one or more of the proteins or genes associated with a metabolic process such as bile acid synthesis, glucose metabolism, lipid metabolism, or insulin sensitivity, such as for example, increase in the activity of FGF19 (FGF15 in mouse), increase in the secretion of GLP-1, or increase in the secretion of PYY.

Metabolic Disorders

Disclosed herein, in certain embodiments, are methods of treating a metabolic disorder in a subject in need thereof. Also described herein include methods of preventing a metabolic disorder in a subject in need thereof. In some instances, these methods include administering to the subject in need thereof a therapeutically effective amount of one or more of the compounds disclosed herein. In some instances, the one or more compounds disclosed herein are absorbed in the gastrointestinal (GI) tract. In additional instances, the one or more disclosed compounds absorbed in the GI tract activates FXR receptors thereby treating or preventing a metabolic disorder in the subject.

In some embodiments, the disclosed compounds demonstrate systemic exposure. In some instances, the disclosed compounds have local exposure in the intestines, but limited exposure in the liver or systemically. In some embodiments, local exposure of the disclosed compounds in the intestines maybe demonstrated by regulation of FXR target genes in the intestines. In some embodiments, the target genes may include: SHP, FGF19 (FGF15), IBABP, C3, OST α/β. In some embodiments, exposure of the disclosed compounds is about 40%, 50%, 55%, 60%, 65%, 70%, 75%, 80%, 85%, 90%, 95%, 99%, 99.5%, or more in the intestines. In some instances, exposure of the disclosed compounds is about 0.5%, 1%, 5%, 10%, 15%, 20%, 25%, 30%, 40%, 50%, or less in the systemic circulation. In some embodiments, the exposure of the FXR agonists in the intestinal lumen reduces the chance of side effects which results from systemic action, thereby improving the safety profile of the therapy. In additional embodiments, the disclosed compounds enhance FXR target gene expression in the intestines. In additional embodiments, the disclosed compounds further modulate gene expressions in the FXR-mediated pathway, such as for example, FGF19 (FGF15) which inhibits CYP7A1 and CYP8B1 gene expression in the liver. In some instances, the disclosed compounds enhance gene expression in the FXR-mediated pathway.

In other instances, the disclosed compounds reduce or inhibit gene expression in the FXR-mediated pathway. In some instances, enhancing is about 1%, 5%, 10%, 15%, 20%, 25%, 30%, 40%, 50%, 60%, 70%, 80%, 90%, 100%, 200%, 300%, 500%, 1,000%, 5,000%, 10,000%, 50,000%, 100,000%, 500,000%, or higher in gene expression in the intestines, liver, kidney, or other tissues relative to the gene expression in the absence of the disclosed compound. In some cases, reducing is about 100%, 90%, 80%, 70%, 60%, 50%, 40%, 30%, 25%, 20%, 15%, 10%, 5%, 1%, or less in gene expression in the intestines, liver, kidney, or other tissues relative to the gene expression in the absence of the disclosed compound.

In some embodiments, the method substantially enhances FXR target gene expression in the intestines while minimizing systemic plasma levels of the delivered compound. In some embodiments, the method substantially enhances FXR target gene expression in the intestines and the liver while minimizing systemic plasma levels of the delivered compound. In some embodiments, the method substantially enhances FXR target gene expression in the intestines while not substantially enhancing FXR target gene expression in the liver or kidney, and while minimizing systemic plasma levels. In some embodiments, the method substantially enhances FXR target gene expression in the intestines and the liver and provides sustained systemic plasma levels of the delivered compound.

In some embodiments, metabolic disorder refers to any disorder that involves an alteration in the normal metabolism of carbohydrates, lipids, proteins, nucleic acids or a combination thereof. In some instances, a metabolic disorder is associated with either a deficiency or excess in a metabolic pathway resulting in an imbalance in metabolism of nucleic acids, proteins, lipids, and/or carbohydrates. Factors affecting metabolism include, but are not limited to, the endocrine (hormonal) control system (e.g., the insulin pathway, the enteroendocrine hormones including GLP-1, oxyntomodulin, PYY or the like), or the neural control system (e.g., GLP-1 in the brain). Exemplary metabolic disorders include, but are not limited to, diabetes, insulin resistance, dyslipidemia, liver disease, inflammation related intestinal conditions, cell proliferative disorders, or the like.

Diabetes Mellitus and Diabetes-Related Conditions or Disorders

In some embodiments, disclosed herein are methods of treating a subject having diabetes mellitus or diabetes-related condition or disorder with administration of a FXR agonist described herein. In some instances, diabetes is type II diabetes or non-insulin-dependent diabetes mellitus (NIDDM). In some instances, diabetes-related conditions or disorders include obesity, impaired glucose tolerance, dyslipidemia, and insulin resistance. In some instances, diabetes-related conditions or disorders further include secondary complications such as atherosclerosis, stroke, fatty liver disease, blindness, gallbladder disease, or polycystic ovary disease. In some cases, a FXR agonist is administered for the treatment of type II diabetes, obesity, impaired glucose tolerance, dyslipidemia, insulin resistance, or secondary complications such as atherosclerosis, stroke, fatty liver disease, blindness, gallbladder disease, or polycystic ovary disease.

In some embodiments, a diabetic subject (e.g., a type II diabetic subject) is further characterized with a body mass index (BMI) of 25 or greater, 30 or greater, 35 or greater, 40 or greater, such as a BMI of 25 to 29, 30 to 34, or 35 to 40.

In some examples, a FXR agonist described herein reduces or prevents weight gain in a subject. In some instances, the weight gain is diet-induced weight gain. In other instances, the weight gain is non-diet-related, such as familial/genetic obesity or obesity resulting from medication. In some examples, such methods reduce or prevent weight gain in the subject by at least 5%, at least 10%, at least 15%, at least 20%, at least 30%, at least 40%, at least 50%, or more. In some instances, weight gain is reduced or prevented by about 5% to about 50%, by about 5% to about 25%, by about 10% to about 20%, or by about 10% to about 30%. In some cases, the reduction or prevention of weight gain is relative to the reduction or prevention of weight gain observed in a subject not treated with the FXR agonist.

Similarly, in some cases, the FXR agonist reduces the BMI of a subject. In some examples, such methods reduce the BMI of a subject by at least 5%, at least 10%, at least 15%, at least 20%, at least 25%, at least 30%, or more, relative to a subject not treated with the FXR agonist. In some instances, the subject is overweight but not obese. In other instances, the subject is neither overweight nor obese.

In some instances, administration of a FXR agonist results in a decrease in the amount of serum lipids. In some examples, the decrease in the amount of serum lipids is by at least 5%, at least 10%, at least 15%, at least 20%, at least 30%, at least 50%, at least 60%, at least 70%, at least 75%, or more. In some cases, the decrease in the amount of serum lipids is by about 5% to about 50%, by about 5% to about 25%, by about 10% to about 20%, by about 10% to about 70%, or by about 10% to about 30%. In some cases, the decrease in the amount of serum lipids is relative to the amount of serum lipids observed in a subject not treated with the FXR agonist.

In some examples, administration of a FXR agonist results in a decrease in triglyceride (e.g., hepatic triglyceride) level. In some instances, the decrease in triglyceride (e.g., hepatic triglyceride) level is by at least 5%, at least 10%, at least 15%, at least 20%, at least 30%, at least 50%, at least 60%, at least 70%, at least 75%, or more. In some instances, the decrease in triglyceride (e.g., hepatic triglyceride) level is by about 5% to about 50%, by about 5% to about 25%, by about 10% to about 20%, by about 10% to about 70%, or by about 10% to about 30%. In some cases, the decrease in triglyceride (e.g., hepatic triglyceride) level is relative to the triglyceride (e.g., hepatic triglyceride) level observed in a subject not treated with the FXR agonist.

In some examples, administration of a FXR agonist results in an increased insulin sensitivity to insulin in the liver. In some instances, the increase in insulin sensitivity is by at least 5%, at least 10%, at least 15%, at least 20%, at least 30%, at least 40%, at least 50%, or more. In some cases, the increase in insulin sensitivity is by about 5% to about 50%, by about 5% to about 25%, by about 10% to about 20%, or by about 10% to about 30%. In some cases, the increase in insulin sensitivity is relative to sensitivity observed in a subject not treated with the FXR agonist.

In some embodiments, administration of a FXR agonist results in a decrease in the amount of serum insulin in the subject. In some examples, the decrease in serum insulin is by at least 5%, at least 10%, at least 15%, at least 20%, at least 30%, at least 50%, at least 60%, at least 70%, at least 75%, or more. In some instances, serum insulin is decreased by about 5% to about 50%, by about 5% to about 25%, by about 10% to about 20%, by about 10% to about 70%, or by about 10% to about 30%. In some cases, the decrease in serum insulin level is relative to levels observed in a subject not treated with the FXR agonist.

In some embodiments, administration of a FXR agonist results in a decrease in the amount of serum glucose in the subject. In some examples, the decrease in serum glucose is by at least 5%, at least 10%, at least 15%, at least 20%, at least 30%, at least 50%, at least 60%, at least 70%, at least 75%, or more. In some instances, serum glucose is decreased by about 5% to about 50%, by about 5% to about 25%, by about 10% to about 20%, by about 10% to about 70%, or by about 10% to about 30%. In some cases, the decrease in serum glucose level is relative to levels observed in a subject not treated with the FXR agonist.

In some examples, a FXR agonist described herein increases browning of white adipose tissue in a subject. In some examples, the rate of increase of browning of white adipose tissue in the subject is by at least 5%, at least 10%, at least 15%, at least 20%, at least 30%, at least 40%, at least 50%, or more, relative to a subject not treated with the FXR agonist.

In some embodiments, administration of a FXR agonist does not result in substantial change in food intake and/or fat consumption in the subject. In some instances, food intake and/or fat consumption is reduced, such as by less than 15%, less than 10%, or less than 5%. In some embodiments, no substantial change in appetite in the subject results. In other embodiments, reduction in appetite is minimal as reported by the subject.

In some embodiments, administration of a FXR agonist results in an increase in the metabolic rate in the subject. In some instances, the FXR agonist increases the metabolic rate in a subject. In some cases, the metabolic rate in the subject is increased by at least 5%, at least 10%, at least 15%, at least 20%, at least 30%, at least 40%, at least 50%, at least 60%, at least 70%, at least 75%, or more. In some instances, the metabolic rate is increased by about 5% to about 50%, by about 5% to about 25%, by about 10% to about 20%, by about 10% to about 70%, or by about 10% to about 30%). In some cases, the increase in metabolic rate is relative to the rate observed in a subject not treated with the FXR agonist.

In some embodiments, the increase in metabolism results from enhanced oxidative phosphorylation in the subject, which in turn leads to increased energy expenditure in tissues (such as BAT). In such instances, the FXR agonist helps to increase the activity of BAT. In some examples, the activity of BAT is increased by at least 5%, at least 10%, at least 15%, at least 20%, at least 30%, at least 50%, at least 60%, at least 70%, at least 75%, or more. In some instances, the activity of BAT is increased by about 5% to about 50%, by about 5% to about 25%, by about 10% to about 20%, by about 10% to about 70%, or by about 10% to about 30%. In some cases, the increase in BAT activity is relative to the activity of BAT observed in a subject not treated with the FXR agonist.

Alcoholic and Non-Alcoholic Liver Disease or Condition

Disclosed herein include methods of preventing and/or treating alcoholic or non-alcoholic liver diseases or conditions. Exemplary alcoholic or non-alcoholic liver diseases or conditions include, but are not limited to cholestasis, cirrhosis, steatosis, alcoholic hepatitis, non-alcoholic steatohepatitis (NASH), non-alcoholic fatty liver disease (NAFLD), primary sclerosing cholangitis (PSC), elevated liver enzymes, and elevated triglyceride levels. In some embodiments, a FXR agonist is used in the prevention or treatment of alcoholic or non-alcoholic liver diseases. In some embodiments, a FXR agonist is used in the prevention or treatment of cholestasis, cirrhosis, steatosis, alcoholic hepatitis, non-alcoholic steatohepatitis (NASH), non-alcoholic fatty liver disease (NAFLD), or primary sclerosing cholangitis (PSC).

Cholestasis

In some embodiments, a FXR agonist disclosed herein is used in the treatment of cholestasis in a subject. Cholestasis, an impairment or cessation in the flow of bile, which in some cases, causes hepatotoxicity due to the buildup of bile acids and other toxins in the liver. In some instances, cholestasis is a component of many liver diseases, including cholelithiasis, cholestasis of pregnancy, primary biliary cirrhosis (PBC), and primary sclerosing cholangitis (PSC). In some instances, the obstruction is due to gallstone, biliary trauma, drugs, one or more additional liver diseases, or to cancer. In some cases, the enterohepatic circulation of bile acids enables the absorption of fats and fat-soluble vitamins from the intestine and allows the elimination of cholesterol, toxins, and metabolic by-products such as bilirubin from the liver. In some cases, activation of FXR induces expression of the canalicular bile transporters BSEP (ABCB11) and multidrug resistance-related protein 2 (MRP2; ABCC2, cMOAT), and represses genes involved in bile acid biosynthesis, such as for example sterol 12α-hydroxylase (CYP8B1) and CYP7A1.

In some examples, the FXR agonist reduces cholestasis in the subject by at least 5%, at least 10%, at least 15%, at least 20%, at least 30%, at least 40%, at least 50%, or more. In some cases, cholestasis is reduced by about 5% to about 50%, by about 5% to about 25%, by about 10% to about 20%, or by about 10% to about 30%. In some instances, the level of cholestasis is relative to the level of cholestasis in a subject not treated with the FXR agonist.

Primary Biliary Cirrhosis and Cirrhosis

In some embodiments, a FXR agonist disclosed herein is used in the treatment of primary biliary cirrhosis (PBC) in a subject. PBC is a liver disease that primarily results from autoimmune destruction of the bile ducts that transport bile acids (BAs) out of the liver, resulting in cholestasis. As PBC progresses, persistent toxic buildup of BAs causes progressive liver damage. Chronic inflammation and fibrosis can advance to cirrhosis. In some examples, the FXR agonist reduces PBC in the subject by at least 5%, at least 10%, at least 15%, at least 20%, at least 30%, at least 40%, at least 50%, or more. In some cases, PBC is reduced by about 5% to about 50%, by about 5% to about 25%, by about 10% to about 20%, or by about 10% to about 30%. In some instances, the level of PBC is relative to the level of PBC in a subject not treated with the FXR agonist.

In some embodiments, a FXR agonist disclosed herein reduces cirrhosis in a subject. In some examples, the FXR agonist reduces cirrhosis in the subject by at least 5%, at least 10%, at least 15%, at least 20%, at least 30%, at least 40%, at least 50%, or more. In some cases, cirrhosis is reduced by about 5% to about 50%, by about 5% to about 25%, by about 10% to about 20%, or by about 10% to about 30%. In some instances, the level of cirrhosis is relative to the level of cirrhosis in a subject not treated with the FXR agonist.

Non-Alcoholic Fatty Liver Disease and Non-Alcoholic Steatohepatitis

Non-alcoholic fatty liver disease (NAFLD) is associated with excessive fat in the liver (steatosis) and in some cases progresses to NASH, which is defined by the histologic hallmarks of inflammation, cell death, and fibrosis. In some instances, primary NASH is associated with insulin resistance, while secondary NASH is caused by medical or surgical conditions, or drugs such as, but not limited to, tamoxifen. In some cases, NASH progresses to advanced fibrosis, hepatocellular carcinoma, or end-stage liver disease requiring liver transplantation.

In some instances, NASH develops as a result of triglyceride (TGs) imbalance. For example, dysfunctional adipocytes secrete pro-inflammatory molecules such as cytokines and chemokines leading to insulin resistance and a failure of lipolysis suppression in the adipocytes. In some instances, this failure of lipolysis suppression leads to a release of free fatty acids (FFAs) into the circulation and uptake within the liver. In some cases, over accumulation of FFAs in the form of triglycerides (TGs) in lipid droplets leads to oxidative stress, mitochondrial dysfunction, and upregulation of pro-inflammatory molecules.

In some instances, activation of FXR inhibits triglyceride (TG)/fatty acid (FA) synthesis facilitated by suppressing sterol regulatory element-binding protein 1c (SREBP1c) via activation of SHP. In some cases, FXR additionally increases the clearance of TG by stimulating lipoprotein lipase (LPL) activity as well as the hepatic uptake of remnants and low-density lipoprotein by inducing syndecan 1 (SDC1) and the VLDL receptor (VLDLR).

In some embodiments, a FXR agonist disclosed herein is used in the treatment of non-alcoholic steatohepatitis (NASH). In some examples, the FXR agonist reduces NASH the subject by at least 5%, at least 10%, at least 15%, at least 20%, at least 30%, at least 40%, at least 50%, or more. In some cases, NASH is reduced by about 5% to about 50%, by about 5% to about 25%, by about 10% to about 20%, or by about 10% to about 30%. In some instances, the level of NASH is relative to the level of NASH in a subject not treated with the FXR agonist.

In some embodiments, a FXR agonist disclosed herein is used in the treatment of NAFLD. In some examples, the FXR agonist reduces NAFLD in the subject by at least 5%, at least 10%, at least 15%, at least 20%, at least 30%, at least 40%, at least 50%, or more. In some cases, NAFLD is reduced by about 5% to about 50%, by about 5% to about 25%, by about 10% to about 20%, or by about 10% to about 30%. In some instances, the level of NAFLD is relative to the level of NAFLD in a subject not treated with the FXR agonist.

Steatosis

In some embodiments, a FXR agonist disclosed herein reduces fatty liver (steatosis) in a subject. In some examples, the FXR agonist reduces steatosis in the subject by at least 5%, at least 10%, at least 15%, at least 20%, at least 30%, at least 40%, at least 50%, or more. In some instances, steatosis is reduced by about 5% to about 50%, by about 5% to about 25%, by about 10% to about 20%, or by about 10% to about 30%. In some instances, the level of steatosis is relative to the level of steatosis in a subject not treated with the FXR agonist.

Ballooning

Hepatocyte ballooning, a feature denoting cellular injury, is a feature of NASH. Ballooning is a feature that denotes progressive NAFL (types 3 and 4). The term applies to enlarged, swollen-appearing hepatocytes; the affected cells are often intermixed in areas of steatosis and, in classic steatohepatitis, in the perivenular regions. Hepatocellular ballooning is most commonly noted in regions of H & E-detectable perisinusoidal fibrosis. Ballooned hepatocytes are most easily noted when they contain MH (either typical or poorly formed). Hepatocyte ballooning is a structural manifestation of microtubular disruption and severe cell injury.

In some embodiments, a FXR agonist disclosed herein reduces liver ballooning in a subject. In some examples, the FXR agonist reduces liver ballooning in the subject by at least 5%, at least 10%, at least 15%, at least 20%, at least 30%, at least 40%, at least 50%, or more. In some instances, liver ballooning is reduced by about 5% to about 50%, by about 5% to about 25%, by about 10% to about 20%, or by about 10% to about 30%. In some instances, the liver ballooning is relative to the level of liver ballooning in a subject not treated with the FXR agonist.

Alcoholic Hepatitis

In some embodiments, a FXR agonist disclosed herein reduces alcoholic hepatitis in a subject. In some examples, the FXR agonist reduces alcoholic hepatitis in the subject by at least 5%, at least 10%, at least 15%, at least 20%, at least 30%, at least 40%, at least 50%, or more. In some instances, the level of alcoholic hepatitis is reduced by about 5% to about 50%, by about 5% to about 25%, by about 10% to about 20%, or by about 10% to about 30%. In some instances, the level of alcoholic hepatitis is relative to the level of alcoholic hepatitis in a subject not treated with the FXR agonist.

Primary Sclerosing Cholangitis

In some embodiments, a FXR agonist disclosed herein is used in the treatment of primary sclerosing cholangitis (PSC). PSC is a chronic and progressive cholestatic liver disease. PSC is characterized by progressive inflammation, fibrosis, and stricture formation in liver ducts. Common symptoms include pruritus and jaundice. The disease is strongly associated with inflammatory bowel disease (IBD)—about 5% of patients with ulcerative colitis will have PSC. Up to 70% of patients with PSC also have IBD, most commonly ulcerative colitis.

Additional Alcoholic and Non-Alcoholic Liver Diseases or Conditions

In some embodiments, a FXR agonist disclosed herein reduces liver enzymes in a subject. In some examples, the FXR agonist reduce liver enzymes (e.g., serum ALT and/or AST levels) in the subject by at least 5%, at least 10%, at least 15%, at least 20%, at least 30%, at least 40%, at least 50%, or more. In some instances, the level of liver enzymes is reduced by about 5% to about 50%, by about 5% to about 25%, by about 10% to about 20%, or by about 10% to about 30%. In some instances, the level of liver enzymes is relative to the level of liver enzymes in a subject not treated with the FXR agonist.

In some embodiments, a FXR agonist disclosed herein reduces liver triglycerides in a subject. In some examples, the FXR agonist reduces liver triglycerides in the subject by at least 5%, at least 10%, at least 15%, at least 20%, at least 30%, at least 40%, at least 50%, or more. In some instances, the level of liver triglycerides is reduced by about 5% to about 50%, by about 5% to about 25%, by about 10% to about 20%, or by about 10% to about 30%. In some instances, the level of liver triglycerides is relative to the level of liver triglycerides in a subject not treated with the FXR agonist.

Inflammatory Intestinal Condition

Disclosed herein are methods of treating or preventing an inflammatory intestinal condition. Exemplary inflammatory conditions include necrotizing enterocolitis (NEC), gastritis, ulcerative colitis, inflammatory bowel disease, irritable bowel syndrome, pseudomembranous colitis, gastroenteritis, radiation induced enteritis, chemotherapy induced enteritis, gastro-esophageal reflux disease (GERD), peptic ulcer, non-ulcer dyspepsia (NUD), celiac disease, intestinal celiac disease, gastrointestinal complications following bariatric surgery, gastric carcinogenesis, or gastric carcinogenesis following gastric or bowel resection. In some embodiments, the inflammatory condition is NEC and the subject is a newborn or prematurely born infant. In some embodiments, the subject is enterally-fed infant or formula-fed infant.

In some embodiments, a FXR agonist disclosed herein is administered to a subject having an inflammatory intestinal condition. In some embodiments, a FXR agonist disclosed herein is administered to a subject having necrotizing enterocolitis (NEC), gastritis, ulcerative colitis, inflammatory bowel disease, irritable bowel syndrome, pseudomembranous colitis, gastroenteritis, radiation induced enteritis, chemotherapy induced enteritis, gastro-esophageal reflux disease (GERD), peptic ulcer, non-ulcer dyspepsia (NUD), celiac disease, intestinal celiac disease, gastrointestinal complications following bariatric surgery, gastric carcinogenesis, or gastric carcinogenesis following gastric or bowel resection.

In some embodiments, a FXR agonist disclosed herein reduces inflammation of the intestines in a subject (such as a human). In some examples, the FXR agonist reduces intestinal inflammation in the subject by at least 5%, at least 10%, at least 15%, at least 20%, at least 30%, at least 40%, at least 50%, or more. In some instances, intestinal inflammation is reduced by about 5% to about 50%, by about 5% to about 25%, by about 10% to about 20%, or by about 10% to about 30%. In some instances, the level of intestinal inflammation is relative to the level of intestinal inflammation in a subject not treated with the FXR agonist.

Gastrointestinal Diseases

Disclosed herein, in certain embodiments, are methods of treating or preventing a gastrointestinal disease in a subject in need thereof, comprising administering to the subject a farnesoid X receptor (FXR) agonist as described herein. In some embodiments, the gastrointestinal disease is irritable bowel syndrome (IBS), irritable bowel syndrome with diarrhea (IBS-D), irritable bowel syndrome with constipation (IBS-C), mixed IBS (IBS-M), unsubtyped IBS (IBS-U), or bile acid diarrhea (BAD).

Irritable Bowel Syndrome

Irritable bowel syndrome (IBS) is a combination of symptoms including abdominal pain and changes in bowel movement patterns that persists over an extended period of time, often years. The causes of IBS remain unclear; however, gut motility problems, food sensitivity, genetic factors, small intestinal bacterial overgrowth, and gut-brain axis problems are thought to have a potential role. In some instances, IBS is accompanied with diarrhea and is categorized as IBS with diarrhea (IBS-D). In some instances, IBS is accompanied with constipation and is categorized as IBS with constipation (IBS-C). In some instances, IBS is accompanied with an alternating pattern of diarrhea and constipation and is categorized as mixed IBS (IBS-M). In some instances, IBS is not accompanied with either diarrhea or constipation and is categorized as unsubtyped IBS (IBS-U). In some instances, IBS has four different variations: IBS-D, IBS-C, IBS-M, and IBS-U.

In some embodiments, the symptoms of IBS are mimicked by a different condition. In some embodiments, sugar maldigestion, celiac disease, gluten intolerance without celiac disease, pancreatic exocrine insufficiency, small bowel bacterial overgrowth, microscopic colitis, or bile acid malabsorption (BAM) mimic IBS-D. In some embodiments, anismus, pelvic floor dyssynergia or puborectalis spasm, or descending perineum syndrome mimic IBS-C.

In some embodiments, an FXR agonist disclosed herein is used in the treatment of IBS or any of its variations in a mammal. In some examples, an FXR agonist therapeutic agent reduce IBS symptoms in the mammal by at least 5%, at least 10%, at least 15%, at least 20%, at least 30%, at least 40%, at least 50%, or more.

Bile Acid Malabsorption

Bile acid malabsorption (BAM), also known as bile acid diarrhea (BAD), bile acid-induced diarrhea, cholerheic or choleretic enteropathy, or bile salt malabsorption, is a condition in which the presence of bile acids in the colon causes diarrhea. BAM is caused by a number of conditions such as Crohn's disease, cholecystectomy, coeliac disease, radiotherapy, and pancreatic diseases. In some instances, BAM is caused by medications such as metformin. In some embodiments, BAM is caused by an overproduction of bile acids. Bile acid synthesis is negatively regulated by the ileal hormone fibroblast growth factor 19 (FGF-19); low levels of FGF-19 lead to an increase in bile acids. FXR activation promotes the synthesis of FGF-19, consequently lowering the levels of bile acids.

In some embodiments, an FXR agonist disclosed herein is used in the treatment of BAM in a mammal. In some embodiments, an FXR agonist disclosed herein decreases bile acid synthesis. In some embodiments, an FXR agonist disclosed herein decreases bile acid levels. In some embodiments, an FXR agonist and an additional therapeutic agent disclosed herein prevent BAD. In some examples, an FXR agonist reduces BAM symptoms in the mammal by at least 5%, at least 10%, at least 15%, at least 20%, at least 30%, at least 40%, at least 50%, or more.

Graft vs. Host Disease (GvHD)

Graft vs. host disease (GvHD) is a medical complication that arises after a transplant of tissue or cells from a histo-incompatible donor (i.e. a genetically or immunologically different donor). Immune cells in the donated tissue or cells (graft) recognize the recipient (the host) as foreign and initiate and attack. Non-limiting examples of transplanted tissue or cells that give rise to GvHD are blood products, stem cells such as bone marrow cells, and organs. There are different types of GvHD depending on where the symptoms manifest or develop: skin GvHD, liver GvHD, eye GvHD, neuromuscular GvHD, genitourinary tract GvHD, and gastrointestinal (GI) tract GvHD. Symptoms of GI tract GvHD include difficulty swallowing, pain with swallowing, weight loss, nausea, vomiting, diarrhea, and/or abdominal cramping. GI tract GvHD results in sloughing of the mucosal membrane and severe intestinal inflammation. Inflammation of the biliary epithelium is amenable to be controlled by nuclear receptors such as the glucocorticoid receptor (GR), FXR, or the peroxisome proliferator-activated receptors (PPARs).

In some embodiments, an FXR agonist disclosed herein is used in the treatment of GvHD or a complication of GvHD in a mammal. In some embodiments, an FXR agonist disclosed herein is used in the treatment of GI tract GvHD or a complication of GI tract GvHD in a mammal. In some examples, an FXR agonist reduces GI tract GvHD or a complication of GI tract GvHD in the mammal by at least 5%, at least 10%, at least 15%, at least 20%, at least 30%, at least 40%, at least 50%, or more. In some cases, GI tract GvHD or a complication of GI tract GvHD is reduced by about 5% to about 50%, by about 5% to about 25%, by about 10% to about 20%, or by about 10% to about 30%. In some embodiments, an FXR agonist disclosed herein decreases intestinal inflammation caused by GI tract GvHD. In some embodiments, an FXR agonist disclosed herein reduces intestinal inflammation caused by GI tract GvHD reduced by about 5% to about 50%, by about 5% to about 25%, by about 10% to about 20%, or by about 10% to about 30%.

Kidney Diseases

Disclosed herein, in certain embodiments, are methods of treating or preventing a kidney disease in a subject in need thereof, comprising administering to the subject a farnesoid X receptor (FXR) agonist described herein. In some embodiments, the kidney disease is associated with a liver disease. In some embodiments, the kidney disease is associated with a fibrotic liver disease. In some embodiments, the kidney disease is associated with a metabolic liver disease. In some embodiments, the kidney disease is associated with a metabolic condition such as but not limited to diabetes, metabolic syndrome, NAFLD, insulin resistance, fatty acid metabolism disorder, and cholestasis. In some embodiments, the kidney disease is diabetic nephropathy, kidney disease associated with fibrosis, kidney disease not associated with fibrosis, renal fibrosis, or any combination thereof.

Diabetic Nephropathy

Diabetic nephropathy is a kidney disease characterized by damage to the kidney's glomeruli. Diabetes contributes to an excessive production of reactive oxygen species, which leads to nephrotic syndrome and scarring of the glomeruli. As diabetic nephropathy progresses, the glomerular filtration barrier (GFB) is increasingly damaged and consequently, proteins in the blood leak through the barrier and accumulate in the Bowman's space.

In some embodiments, an FXR agonist disclosed herein is used in the treatment of diabetic nephropathy in a mammal.

Renal Fibrosis

Renal fibrosis is characterized by activation of fibroblasts and excessive deposition of extracellular matrix or connective tissue in the kidney, which is a hallmark of chronic kidney disease. FXR plays an important role in protecting against renal fibrosis. Activation of FXR suppresses renal fibrosis and decreases accumulation of extracellular matrix proteins in the kidney.

In some embodiments, an FXR agonist disclosed herein is used in the treatment of renal fibrosis in a mammal.

In one aspect, described herein is a method of treating or preventing a kidney disease or condition in a mammal, comprising administering to the mammal an FXR agonist disclosed herein, or a pharmaceutically acceptable salt or solvate thereof. In some embodiments, the kidney disease or condition is diabetic nephropathy, kidney disease associated with fibrosis, kidney disease not associated with fibrosis, renal fibrosis, kidney disease associated with a metabolic disease, chronic kidney disease, polycystic kidney disease, acute kidney disease, or any combination thereof.

Cell Proliferation Disease

Further disclosed herein are methods of preventing or treating cell proliferation diseases, for example, in certain types of cancer. In some embodiments, the FXR agonists disclosed herein are used in the prevention or treatment of adenocarcinomas, or a carcinoma derived from glandular tissue or in which the tumor cells form recognizable glandular structures. In some embodiments, adenocarcinomas are classified according to the predominant pattern of cell arrangement, as papillary, alveolar, or according to a particular product of the cells, as mucinous adenocarcinoma. In some instances, adenocarcinomas are observed for example, in colon, kidney, breast, cervix, esophagus, gastric, pancreas, prostate, or lung.

In some embodiments, the compounds disclosed herein are used in the prevention or treatment of a cancer of the intestine, such as colon cancer, e.g. cancer that forms in the tissues of the colon (the longest part of the large intestine), or a cancer of another part of the intestine, such as the jejunum, and/or ileum. In some instances, colon cancer is also referred to as "colorectal cancer." In some instances, the most common type of colon cancer is colon adenocarcinoma.

In some cases, cancer progression is characterized by stages, or the extent of cancer in the body. Staging is usually based on the size of the tumor, the presence of cancer in the lymph nodes, and the presence of the cancer in a site other than the primary cancer site. Stages of colon cancer include stage I, stage II, stage III and stage IV. In some embodiments, colon adenocarcinoma is from any stage. In other embodiments, colon adenocarcinoma is a stage I cancer, a stage II cancer or a stage III cancer.

In some embodiments, a FXR agonist described herein is administered to a subject having a stage I, stage II, stage III, or stage IV cancer. In some instances, a FXR agonist described herein is administered to a subject having a stage I, stage II, or stage III colon adenocarcinoma.

In some embodiments, a FXR agonist disclosed herein further reduces the tumor burden in a subject. In some examples, the FXR agonist reduces tumor burden (such as colon tumor burden) in the subject by at least 5%, at least 10%, at least 15%, at least 20%, at least 30%, at least 40%, at least 50%, or more. In some instances, tumor burden is reduced by about 5% to about 50%, by about 5% to about 25%, by about 10% to about 20%, or by about 10% to about 30%. In some instances, the level of tumor burden is relative to the level of tumor burden in a subject not treated with the FXR agonist.

In some instances, a FXR agonist disclosed herein further reduces tumor size and/or volume in a subject. In some cases, the FXR agonist reduces tumor size and/or volume (such as a colon tumor) in the subject by at least 5%, at least 10%, at least 15%, at least 20%, at least 30%, at least 40%, at least 50%, or more. In some instances, tumor size is reduced by about 5% to about 50%, by about 5% to about 25%, by about 10% to about 20%, or by about 10% to about 30%. In some instances, the tumor size is relative to the tumor size in a subject not treated with the FXR agonist.

In additional embodiments, a FXR agonist disclosed herein reduces effects of cachexia due to a tumor in a subject. In some examples, the FXR agonist reduce the effect of cachexia (such as due to a colon tumor) in the subject by at least 5%, at least 10%, at least 15%, at least 20%, at least 30%, at least 40%, at least 50%, or more. In some instances, the effect of cachexia is reduced by about 5% to about 50%, by about 5% to about 25%, by about 10% to about 20%, or by about 10% to about 30%. In some instances, the effect of cachexia is relative to the effect of cachexia in a subject not treated with the FXR agonist.

In other embodiments, a FXR agonist disclosed herein increases survival rates of a subject with a tumor. In some cases, the FXR agonist increases the survival rate of a subject with a tumor (such as a colon cancer) in the subject by at least 5%, at least 10%, at least 15%, at least 20%, at least 30%, at least 40%, at least 50%, or more. In some instances, survival rate is increased by about 5% to about 50%, by about 5% to about 25%, by about 10% to about 20%, or by about 10% to about 30%. In some instances, the survival rate is relative to the survival rate in a subject not treated with the FXR agonist.

Compounds

Compounds described herein, including pharmaceutically acceptable salts, prodrugs, active metabolites and pharmaceutically acceptable solvates thereof, are farnesoid X receptor agonists.

In one aspect, described herein is a compound of Formula (I), or a pharmaceutically acceptable salt, or solvate thereof:

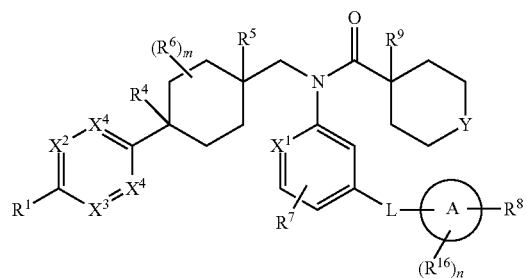

Formula (I)

wherein, ring A is a 5-membered heteroaryl that is thiazolyl, pyrazolyl, furanyl, thienyl, pyrrolyl, oxazolyl, imidazolyl, triazolyl, tetrazolyl, isoxazolyl, isothiazolyl, oxadiazolyl, or thiadiazolyl;

or ring A is a 6-membered heteroaryl that is pyridinyl, pyrimidinyl, pyrazinyl, pyridazinyl, or triazinyl;

or ring A is phenyl;

$X^1$ is CH or N;

$R^1$ is H, D, halogen, —CN, —OH, —N($R^{15}$)$_2$, —NR$^{15}$S (=O)$_2$(C$_1$-C$_4$alkyl), —S(=O)$_2$N(R$^{15}$)$_2$, —OC(=O) (C$_1$-C$_4$alkyl), —CO$_2$H, —CO$_2$(C$_1$-C$_4$alkyl), —C(=O) N(R$^{15}$)$_2$, —NR$^{15}$C(=O)(C$_1$-C$_4$alkyl), —NR$^{15}$C(=O) O(C$_1$-C$_4$alkyl), —OC(=O)N(R$^{15}$)$_2$, —NR$^{15}$C(=O)N (R$^{15}$)$_2$, —SH, —S(C$_1$-C$_4$alkyl), —S(=O)(C$_1$-C$_4$alkyl), —S(=O)$_2$(C$_1$-C$_4$alkyl), C$_1$-C$_4$alkyl, C$_2$-C$_4$alkenyl, C$_2$-C$_4$alkynyl, C$_1$-C$_4$alkoxy, C$_1$-C$_4$deuteroalkyl, C$_1$-C$_4$deuteroalkoxy, C$_1$-C$_4$fluoroalkyl, C$_1$-C$_4$fluoroalkoxy, C$_1$-C$_4$heteroalkyl, or substituted or unsubstituted monocyclic C$_2$-C$_5$heterocycloalkyl;

$X^2$ is CR$_2$ or N;

$R^2$ is H, D, halogen, —CN, —OH, —N($R^{15}$)$_2$, —NR$^{15}$S (=O)$_2$(C$_1$-C$_4$alkyl), —S(=O)$_2$N(R$^{15}$)$_2$, —OC(=O) (C$_1$-C$_4$alkyl), —CO$_2$H, —CO$_2$(C$_1$-C$_4$alkyl), —C(=O) N(R$^{15}$)$_2$, —NR$^{15}$C(=O)(C$_1$-C$_4$alkyl), —NR$^{15}$C(=O) O(C$_1$-C$_4$alkyl), —OC(=O)N(R$^{15}$)$_2$, —NR$^{15}$C(=O)N (R$^{15}$)$_2$, —SH, —S(C$_1$-C$_4$alkyl), —S(=O)(C$_1$-C$_4$alkyl), —S(=O)$_2$(C$_1$-C$_4$alkyl), C$_1$-C$_4$alkyl, C$_2$-C$_4$alkenyl, C$_2$-C$_4$alkynyl, C$_1$-C$_4$alkoxy, C$_1$-C$_4$deuteroalkyl, C$_1$-C$_4$deuteroalkoxy, C$_1$-C$_4$fluoroalkyl, C$_1$-C$_4$fluoroalkoxy, C$_1$-C$_4$heteroalkyl, or substituted or unsubstituted monocyclic C$_2$-C$_5$heterocycloalkyl;

or R$^1$ and R$^2$ are taken together with the intervening atoms to form a substituted or unsubstituted fused 5- or 6-membered ring with 0-3 N atoms and 0-2 O or S atoms in the ring;

$X^3$ is $CR^3$ or N;

$R^3$ is H, D, halogen, —CN, —OH, —N($R^{15}$)$_2$, —$NR^{15}$S(=O)$_2$($C_1$-$C_4$alkyl), —OC(=O)($C_1$-$C_4$alkyl), —CO$_2$H, —CO$_2$($C_1$-$C_4$alkyl), —C(=O)N($R^{15}$)$_2$, —$NR^{15}$C(=O)($C_1$-$C_4$alkyl), $C_1$-$C_4$alkyl, $C_2$-$C_4$alkenyl, $C_2$-$C_4$alkynyl, $C_1$-$C_4$alkoxy, $C_1$-$C_4$deuteroalkyl, $C_1$-$C_4$deuteroalkoxy, $C_1$-$C_4$fluoroalkyl, $C_1$-$C_4$fluoroalkoxy, or $C_1$-$C_4$heteroalkyl;

each $X^4$ is independently CH or N;

$R^4$ is H, D, F, or —CH$_3$;

$R^5$ is H, D, F, or —CH$_3$;

or $R^4$ and $R^5$ are taken together to form a bridge that is —CH$_2$— or —CH$_2$CH$_2$—;

each $R^6$ is independently H, D, F, —OH, or —CH$_3$; m is 0, 1, or 2;

$R^7$ is H, D, halogen, —CN, —OH, $C_1$-$C_4$alkyl, $C_2$-$C_4$alkenyl, $C_2$-$C_4$alkynyl, $C_1$-$C_4$alkoxy, $C_1$-$C_4$deuteroalkyl, $C_1$-$C_4$deuteroalkoxy, $C_1$-$C_4$fluoroalkyl, $C_1$-$C_4$fluoroalkoxy, or $C_1$-$C_4$heteroalkyl;

L is absent, —$Y^2$-$L^1$-, -$L^1$-$Y^2$—, cyclopropylene, cyclobutylene or bicyclo[1.1.1]pentylene;

$Y^2$ is absent, —O—, —S—, —S(=O)—, —S(=O)$_2$—, —S(=O)$_2$$NR^{15}$—, —CH$_2$—, —CH=CH—, —C≡C—, —C(=O)—, —C(=O)O—, —OC(=O)—, —OC(=O)O—, —C(=O)$NR^{15}$—, —$NR^{15}$C(=O)—, —OC(=O)$NR^{15}$—, —$NR^{15}$C(=O)O—, —$NR^{15}$C(=O)$NR^{15}$—, —$NR^{15}$S(=O)$_2$—, or —$NR^{15}$—;

$L^1$ is absent or substituted or unsubstituted $C_1$-$C_4$alkylene;

$R^8$ is H, D, $C_1$-$C_6$alkyl, $C_1$-$C_6$deuteroalkyl, $C_1$-$C_6$fluoroalkyl, $C_1$-$C_6$heteroalkyl, —C(=O)($C_1$-$C_4$alkyl), —CO$_2$($C_1$-$C_4$alkyl), —C(=O)N($R^{15}$)$_2$, —S(=O)$_2$($C_1$-$C_4$alkyl), —S(=O)$_2$N($R^{15}$)$_2$, substituted or unsubstituted $C_3$-$C_6$cycloalkyl, or substituted or unsubstituted monocyclic $C_2$-$C_6$heterocycloalkyl, substituted or unsubstituted phenyl, or substituted or unsubstituted monocyclic heteroaryl;

$R^9$ is H, D, F or —CH$_3$;

$R^{10}$ is —CH$_2$OH, —CH$_2$CH$_2$OH, $C_1$-$C_6$heteroalkyl, —CO$_2$H, —C(=O)$R^{14}$, —C(=O)O$R^{14}$, —OC(=O)$R^{14}$, —OC(=O)O$R^{14}$, tetrazolyl, imidazole, 5-oxo-4,5-dihydro-1,2,4-oxadiazol-3-yl, —S(=O)$_2$N($R^{12}$)$_2$, —$NR^{15}$S(=O)$_2$$R^{14}$, —C(=O)$NR^{15}$S(=O)$_2$$R^{14}$, —S(=O)$_2$$NR^{15}$C(=O)$R_{14}$, —CH$_2$N($R^{12}$)$_2$, —$NR^{15}$C(=O)$R^{14}$, —C(=O)N($R^{12}$)$_2$, —$NR^{15}$C(=O)O$R^{14}$, —OC(=O)N($R^{12}$)$_2$, —$NR^{15}$C(=O)N($R^2$)$_2$, —C(=NH)NH$_2$, —NHC(=NH)NH$_2$, —C(=O)NHC(=NH)NH$_2$, —S(=O)$_2$OH or —OP(=O)(O$R^{15}$)$_2$;

or $R^{10}$ is -$L^2$-$L^3$-$L^4$-$R^{13}$ $L^2$ is absent, substituted or unsubstituted $C_1$-$C_6$alkylene, or substituted or unsubstituted $C_1$-$C_6$heteroalkylene;

$L^3$ is absent, —O—, —S—, —S(=O)—, —S(=O)$_2$—, —$NR^{15}$—, —C(=O)—, —C(=O)$NR^{15}$—, —$NR^{15}$C(=O)—, —C(=O)O—, —OC(=O)—, —OC(=O)$NR^{15}$—, —$NR^{15}$C(=O)$NR^{15}$—, —$NR^{15}$C(=O)O—, —OP(=O)(O$R^{15}$)O—, or —(OCH$_2$CH$_2$)$_r$—, r is 1 or 2;

$L^4$ is substituted or unsubstituted $C_1$-$C_6$alkylene, or substituted or unsubstituted $C_1$-$C_6$heteroalkylene;

$R^{13}$ is H, —CN, —OH, —N($R^{12}$)$_2$, —$NR^{15}$S(=O)$_2$$R^{14}$, —S(=O)$_2$N($R^{12}$)$_2$, —S$R^{12}$, —S(=O)$R^{14}$, —S(=O)$_2$$R^{14}$, —SO$_3$H, —OP(=O)(O$R^{15}$)$_2$, —C(=O)$R^{14}$, —OC(=O)$R^{14}$, —CO$_2$H, —CO$_2$$R^{14}$, —OC(=O)O$R^{14}$, —$NR^{15}$C(=O)$R^{14}$, —C(=O)N($R^{12}$)$_2$, —$NR^{15}$C(=O)O$R^{14}$, —OC(=O)N($R^{12}$)$_2$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_3$-$C_6$cycloalkyl, substituted or unsubstituted $C_2$-$C_6$heterocycloalkyl, substituted or unsubstituted phenyl, or substituted or unsubstituted monocyclic heteroaryl;

$R^{11}$ is H, D, F, or —CH$_3$;

or $R^9$ and $R^{11}$ are taken together to form a bridge that is —CH$_2$— or —CH$_2$CH$_2$—;

each $R^{12}$ is independently H, $C_1$-$C_4$alkyl, $C_1$-$C_4$deuteroalkyl, $C_1$-$C_4$fluoroalkyl, $C_1$-$C_4$heteroalkyl, substituted or unsubstituted $C_3$-$C_6$cycloalkyl, substituted or unsubstituted $C_2$-$C_6$heterocycloalkyl, substituted or unsubstituted phenyl, substituted or unsubstituted benzyl, or substituted or unsubstituted monocyclic heteroaryl;

$R^{14}$ is $C_1$-$C_4$alkyl, $C_1$-$C_4$deuteroalkyl, $C_1$-$C_4$fluoroalkyl, $C_1$-$C_4$heteroalkyl, substituted or unsubstituted $C_3$-$C_6$cycloalkyl, substituted or unsubstituted $C_2$-$C_6$heterocycloalkyl, substituted or unsubstituted phenyl, substituted or unsubstituted benzyl, or substituted or unsubstituted monocyclic heteroaryl;

$R^{15}$ is H or substituted or unsubstituted $C_1$-$C_6$alkyl;

each $R^{16}$ is independently H, D, halogen, —CN, —OH, —N($R^{15}$)$_2$, —$NR^{15}$S(=O)$_2$($C_1$-$C_4$alkyl), —S($C_1$-$C_4$alkyl), —S(=O)($C_1$-$C_4$alkyl), —S(=O)$_2$($C_1$-$C_4$alkyl), —S(=O)$_2$N($R^{15}$)$_2$, —C(=O)($C_1$-$C_4$alkyl), —OC(=O)($C_1$-$C_4$alkyl), —CO$_2$H, —CO$_2$($C_1$-$C_4$alkyl), —$NR^{15}$C(=O)($C_1$-$C_4$alkyl), —C(=O)N($R^{15}$)$_2$, —$NR^{15}$C(=O)O($C_1$-$C_4$alkyl), —OC(=O)N($R^{15}$)$_2$, $C_1$-$C_4$alkyl, $C_2$-$C_4$alkenyl, $C_2$-$C_4$alkynyl, $C_1$-$C_4$alkoxy, $C_1$-$C_4$deuteroalkyl, $C_1$-$C_4$deuteroalkoxy, $C_1$-$C_4$fluoroalkyl, $C_1$-$C_4$fluoroalkoxy, $C_1$-$C_4$heteroalkyl, substituted or unsubstituted $C_3$-$C_6$cycloalkyl, substituted or unsubstituted monocyclic $C_2$-$C_6$heterocycloalkyl, substituted or unsubstituted phenyl, or substituted or unsubstituted monocyclic heteroaryl;

n is 0, 1, or 2.

In another aspect, described herein is a compound of Formula (I), or a pharmaceutically acceptable salt, or solvate thereof:

Formula (I)

wherein, ring A is a 5-membered heteroaryl that is furanyl, thienyl, pyrrolyl, oxazolyl, imidazolyl, triazolyl, tetrazolyl, isoxazolyl, isothiazolyl, oxadiazolyl, or thiadiazolyl;

or ring A is a 6-membered heteroaryl that is pyridinyl, pyrimidinyl, pyrazinyl, pyridazinyl, or triazinyl;

or ring A is phenyl;

$X^1$ is CH or N;

$R^1$ is H, D, halogen, —CN, —OH, —N($R^{15}$)$_2$, —NR$^{15}$S(=O)$_2$($C_1$-$C_4$alkyl), —OC(=O)($C_1$-$C_4$alkyl), —CO$_2$H, —CO$_2$($C_1$-$C_4$alkyl), —C(=O)N($R^{15}$)$_2$, —NR$^{15}$C(=O)($C_1$-$C_4$alkyl), —NR$^{15}$C(=O)O($C_1$-$C_4$alkyl), —OC(=O)N($R^{15}$)$_2$, —NR$^{15}$C(=O)N($R^{15}$)$_2$, $C_1$-$C_4$alkyl, $C_2$-$C_4$alkenyl, $C_2$-$C_4$alkynyl, $C_1$-$C_4$alkoxy, $C_1$-$C_4$deuteroalkyl, $C_1$-$C_4$deuteroalkoxy, $C_1$-$C_4$fluoroalkyl, $C_1$-$C_4$fluoroalkoxy, $C_1$-$C_4$heteroalkyl, or substituted or unsubstituted monocyclic $C_2$-$C_5$heterocycloalkyl;

$X^2$ is $CR_2$ or N;

$R^2$ is H, D, halogen, —CN, —OH, —N($R^{15}$)$_2$, —NR$^{15}$S(=O)$_2$($C_1$-$C_4$alkyl), —OC(=O)($C_1$-$C_4$alkyl), —CO$_2$H, —CO$_2$($C_1$-$C_4$alkyl), —C(=O)N($R^{15}$)$_2$, —NR$^{15}$C(=O)($C_1$-$C_4$alkyl), —NR$^{15}$C(=O)O($C_1$-$C_4$alkyl), —OC(=O)N($R^{15}$)$_2$, —NR$^{15}$C(=O)N($R^{15}$)$_2$, $C_1$-$C_4$alkyl, $C_2$-$C_4$alkenyl, $C_2$-$C_4$alkynyl, $C_1$-$C_4$alkoxy, $C_1$-$C_4$deuteroalkyl, $C_1$-$C_4$deuteroalkoxy, $C_1$-$C_4$fluoroalkyl, $C_1$-$C_4$fluoroalkoxy, or $C_1$-$C_4$heteroalkyl;

or $R^1$ and $R^2$ are taken together with the intervening atoms to form a substituted or unsubstituted fused 5-membered ring with 0-3 N atoms and 0-2 O or S atoms in the ring;

$X^3$ is $CR^3$ or N;

$R^3$ is H, D, halogen, —CN, —OH, —N($R^{15}$)$_2$, —NR$^{15}$S(=O)$_2$($C_1$-$C_4$alkyl), —OC(=O)($C_1$-$C_4$alkyl), —CO$_2$H, —CO$_2$($C_1$-$C_4$alkyl), —C(=O)N($R^{15}$)$_2$, —NR$^{15}$C(=O)($C_1$-$C_4$alkyl), $C_1$-$C_4$alkyl, $C_2$-$C_4$alkenyl, $C_2$-$C_4$alkynyl, $C_1$-$C_4$alkoxy, $C_1$-$C_4$deuteroalkyl, $C_1$-$C_4$deuteroalkoxy, $C_1$-$C_4$fluoroalkyl, $C_1$-$C_4$fluoroalkoxy, or $C_1$-$C_4$heteroalkyl;

each $X^4$ is independently CH or N;

$R^4$ is H, D, F, or —CH$_3$;

$R^5$ is H, D, F, or —CH$_3$;

or $R^4$ and $R^5$ are taken together to form a bridge that is —CH$_2$— or —CH$_2$CH$_2$—;

each $R^6$ is independently H, D, F, —OH, or —CH$_3$;

m is 0, 1, or 2;

$R^7$ is H, D, halogen, —CN, —OH, $C_1$-$C_4$alkyl, $C_1$-$C_4$alkoxy, $C_1$-$C_4$deuteroalkyl, $C_1$-$C_4$deuteroalkoxy, $C_1$-$C_4$fluoroalkyl, $C_1$-$C_4$fluoroalkoxy, or $C_1$-$C_4$heteroalkyl;

L is absent, —$Y^2$-$L^1$-, -$L^1$-$Y^2$—, cyclopropylene, cyclobutylene or bicyclo[1.1.1]pentylene;

$Y^2$ is absent, —O—, —S—, —S(=O)—, —S(=O)$_2$—, —S(=O)$_2$NR$^{15}$—, —CH$_2$—, —CH=CH—, —C≡C—, —C(=O)—, —C(=O)O—, —OC(=O)—, —OC(=O)O—, —C(=O)NR$^{15}$—, —NR$^{15}$C(=O)—, —OC(=O)NR$^{15}$—, —NR$^{15}$C(=O)O—, —NR$^{15}$C(=O)NR$^{15}$—, —NR$^{15}$S(=O)$_2$—, or —NR$^{15}$—;

$L^1$ is absent or substituted or unsubstituted $C_1$-$C_4$alkylene;

$R^8$ is H, D, $C_1$-$C_6$alkyl, $C_1$-$C_6$deuteroalkyl, $C_1$-$C_6$fluoroalkyl, $C_1$-$C_6$heteroalkyl, —C(=O)($C_1$-$C_4$alkyl), —CO$_2$($C_1$-$C_4$alkyl), —C(=O)N($R^{15}$)$_2$, —S(=O)$_2$($C_1$-$C_4$alkyl), —S(=O)$_2$N($R^{15}$)$_2$, substituted or unsubstituted $C_3$-$C_6$cycloalkyl, or substituted or unsubstituted monocyclic $C_2$-$C_6$heterocycloalkyl, substituted or unsubstituted phenyl, or substituted or unsubstituted monocyclic heteroaryl;

$R^9$ is H, D, F or —CH$_3$;

Y is —CR$^{10}$R$^{11}$—;

$R^{10}$ is —CH$_2$OH, —CH$_2$CH$_2$OH, $C_1$-$C_6$heteroalkyl, —CO$_2$H, —C(=O)R$^{14}$, —C(=O)OR$^{14}$, —OC(=O)R$^{14}$, —OC(=O)OR$^{14}$, tetrazolyl, imidazole, —S(=O)$_2$ N(R$^2$)$_2$, —NR S(=O)$_2$R$^4$, —C(=O)NR$^{15}$S(=O)$_2$R$^{14}$, —S(=O)$_2$NR$^{15}$C(=O)R$_{14}$, —CH$_2$N(R$^{12}$)$_2$, —NR$^{15}$C(=O)R$^{14}$, —C(=O)N(R$^{12}$)$_2$, —NR$^{15}$C(=O)OR$^{14}$, —OC(=O)N(R$^{12}$)$_2$, —NR$^{15}$C(=O)N(R$^{12}$)$_2$, —C(=NH)NH$_2$, —NHC(=NH)NH$_2$, —C(=O)NHC(=NH)NH$_2$, —S(=O)$_2$OH or —OP(=O)(OR$^{15}$)$_2$;

or $R^{10}$ is -$L^2$-$L^3$-$L^4$-$R^{13}$ $L^2$ is absent, substituted or unsubstituted $C_1$-$C_6$alkylene, or substituted or unsubstituted $C_1$-$C_6$heteroalkylene;

$L^3$ is absent, —O—, —S—, —S(=O)—, —S(=O)$_2$—, —NR$^{15}$—, —C(=O)—, —C(=O)NR$^{15}$—, —NR$^{15}$C(=O)—, —C(=O)O—, —OC(=O)—, —OC(=O)NR$^{15}$—, —NR$^{15}$C(=O)NR$^{15}$—, —NR$^{15}$C(=O)O—, —OP(=O)(OR$^{15}$)O—, or —(OCH$_2$CH$_2$)$_r$—, r is 1 or 2;

$L^4$ is substituted or unsubstituted $C_1$-$C_6$alkylene, or substituted or unsubstituted $C_1$-$C_6$heteroalkylene;

$R^{13}$ is H, —CN, —OH, —N(R$^{12}$)$_2$, —NR$^{15}$S(=O)$_2$R$^{14}$, —S(=O)$_2$N(R$^{12}$)$_2$, —SR$^{12}$, —S(=O)R$^{14}$, —S(=O)$_2$R$^{14}$, —SO$_3$H, —OP(=O)(OR$^{15}$)$_2$, —C(=O)R$^{14}$, —OC(=O)R$^{14}$, —CO$_2$H, —CO$_2$R$^{14}$, —OC(=O)OR$^{14}$, —NR$^{15}$C(=O)R$^{14}$, —C(=O)N(R$^{12}$)$_2$, —NR$^{15}$C(=O)OR$^{14}$, —OC(=O)N(R$^{12}$)$_2$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_3$-$C_6$cycloalkyl, substituted or unsubstituted $C_2$-$C_6$heterocycloalkyl, substituted or unsubstituted phenyl, or substituted or unsubstituted monocyclic heteroaryl;

$R^{11}$ is H, D, or —CH$_3$;

or $R^9$ and $R^{11}$ are taken together to form a bridge that is —CH$_2$— or —CH$_2$CH$_2$—;

each $R^{12}$ is independently H, $C_1$-$C_4$alkyl, $C_1$-$C_4$deuteroalkyl, $C_1$-$C_4$fluoroalkyl, $C_1$-$C_4$heteroalkyl, substituted or unsubstituted $C_3$-$C_6$cycloalkyl, substituted or unsubstituted $C_2$-$C_6$heterocycloalkyl, substituted or unsubstituted phenyl, substituted or unsubstituted benzyl, or substituted or unsubstituted monocyclic heteroaryl;

$R^{14}$ is $C_1$-$C_4$alkyl, $C_1$-$C_4$deuteroalkyl, $C_1$-$C_4$fluoroalkyl, $C_1$-$C_4$heteroalkyl, substituted or unsubstituted $C_3$-$C_6$cycloalkyl, substituted or unsubstituted $C_2$-$C_6$heterocycloalkyl, substituted or unsubstituted phenyl, substituted or unsubstituted benzyl, or substituted or unsubstituted monocyclic heteroaryl;

$R^{15}$ is H or substituted or unsubstituted $C_1$-$C_6$alkyl;

each $R^{16}$ is independently H, D, halogen, —CN, —OH, —N(R$^{15}$)$_2$, —NR$^{15}$S(=O)$_2$($C_1$-$C_4$alkyl), —S($C_1$-$C_4$alkyl), —S(=O)$_2$($C_1$-$C_4$alkyl), —C(=O)($C_1$-$C_4$alkyl), —OC(=O)($C_1$-$C_4$alkyl), —CO$_2$H, —CO$_2$($C_1$-$C_4$alkyl), —NR$^{15}$C(=O)($C_1$-$C_4$alkyl), —C(=O)N(R$^{15}$)$_2$, —NR$^{15}$C(=O)O($C_1$-$C_4$alkyl), —OC(=O)N(R$^{15}$)$_2$, $C_1$-$C_4$alkyl, $C_2$-$C_4$alkenyl, $C_2$-$C_4$alkynyl, $C_1$-$C_4$alkoxy, $C_1$-$C_4$deuteroalkyl, $C_1$-$C_4$deuteroalkoxy, $C_1$-$C_4$fluoroalkyl, $C_1$-$C_4$fluoroalkoxy, $C_1$-$C_4$heteroalkyl, substituted or unsubstituted $C_3$-$C_6$cycloalkyl, substituted or unsubstituted monocyclic $C_2$-$C_6$heterocycloalkyl, substituted or unsubstituted phenyl, or substituted or unsubstituted monocyclic heteroaryl;

n is 0, 1, or 2.

For any and all of the embodiments, substituents are selected from among a subset of the listed alternatives. For example, in some embodiments m is 0, 1, or 2. In some embodiments, m is 0 or 1. In some embodiments, m is 0. In some embodiments, n is 0, 1, or 2. In some embodiments, n is 0 or 1. In some embodiments, n is 0.

In some embodiments, ring A is a 5-membered heteroaryl that is thiazolyl, isothiazolyl, oxazolyl, or isoxazolyl. In some embodiments, ring A is thiazolyl. In some embodiments, ring A is oxazolyl. In some embodiments, ring A is a 5-membered heteroaryl that is pyrazolyl, pyrrolyl, or oxadiazolyl. In some embodiments, ring A is pyrazolyl. In some embodiments, ring A is a 5-membered heteroaryl that is imidazolyl, triazolyl, tetrazolyl, or thiadiazolyl.

In some embodiments,

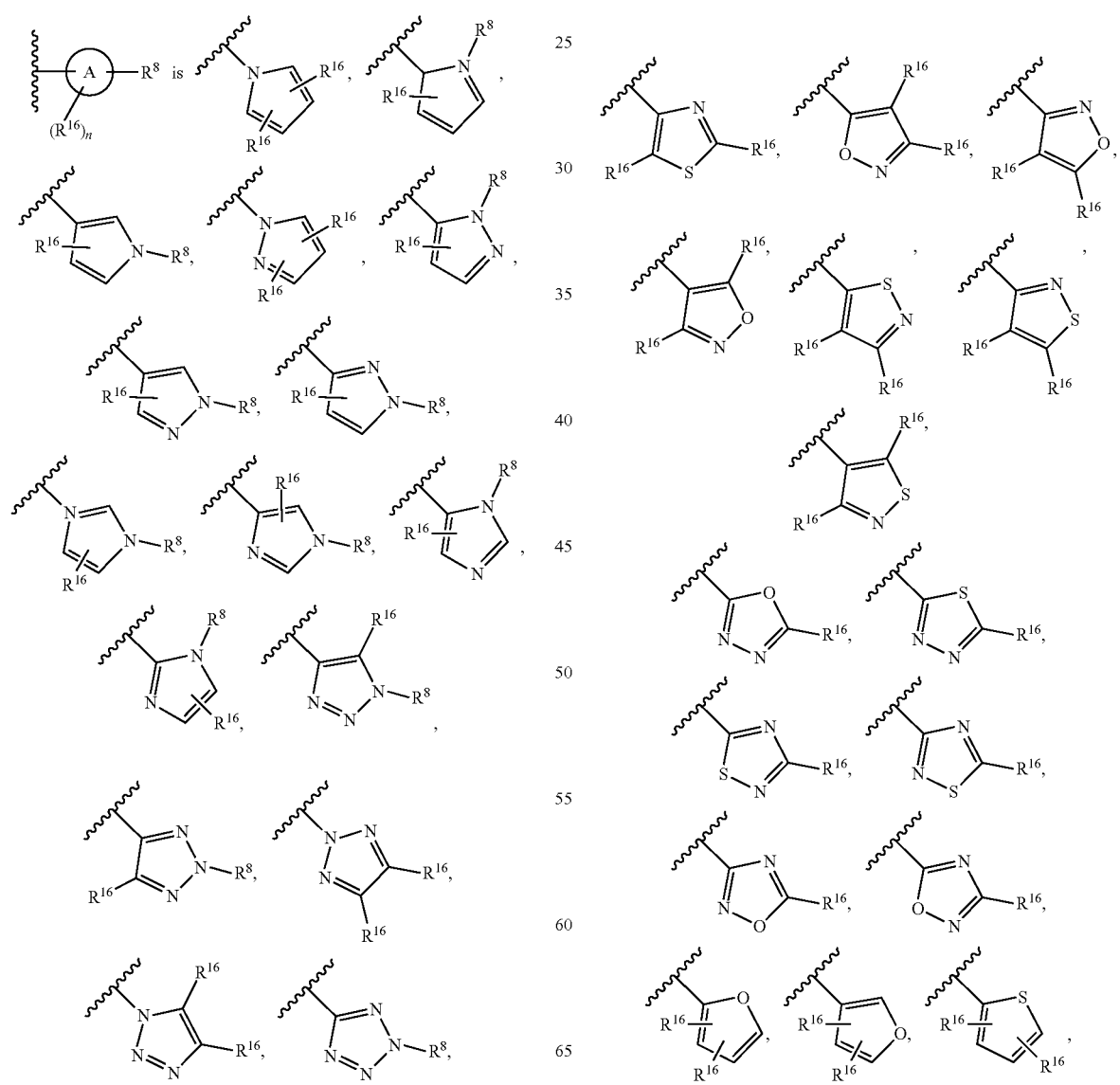

-continued
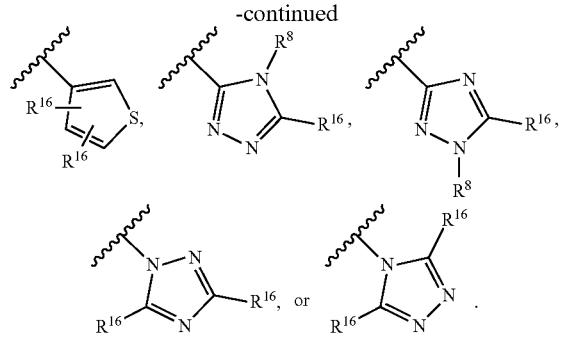
In some embodiments,
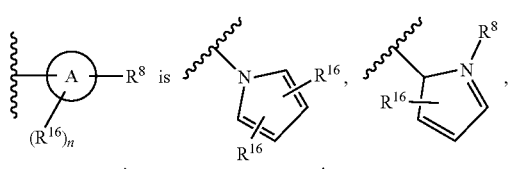 is
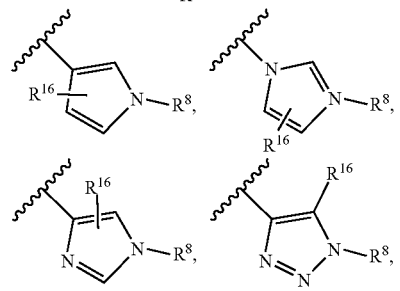
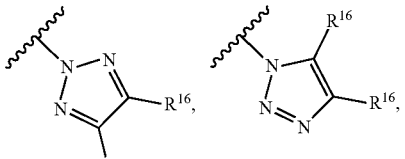
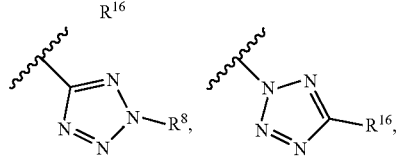
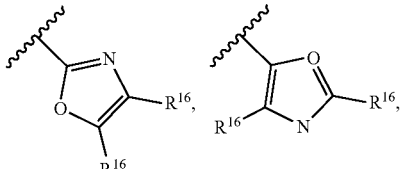
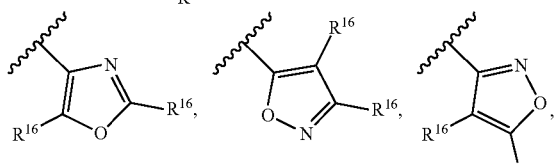
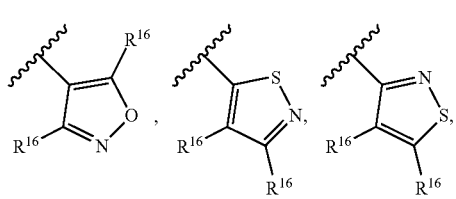
-continued
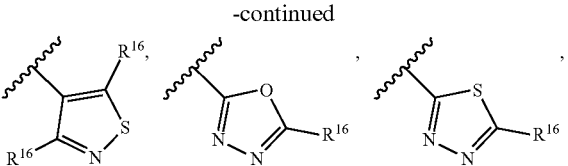
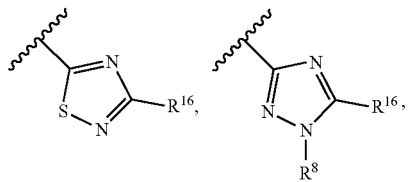
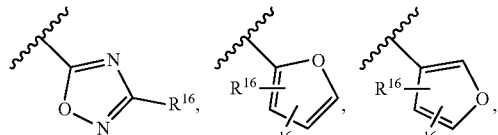
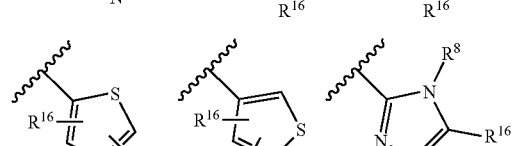
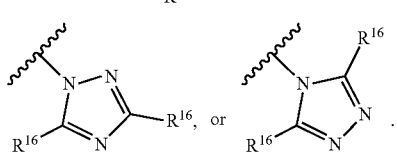
In some embodiments,
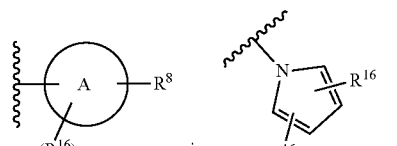
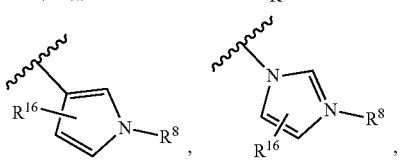
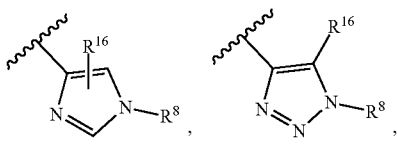
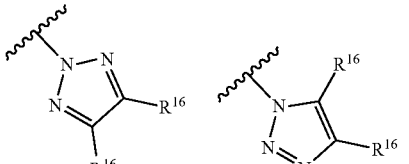
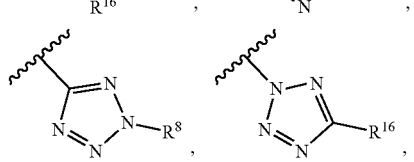

-continued
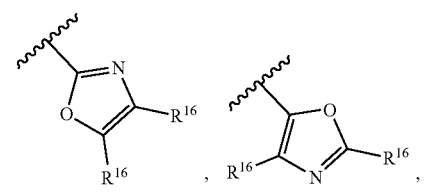
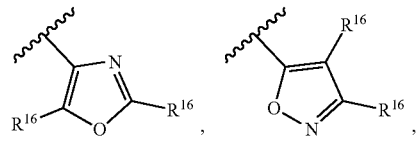
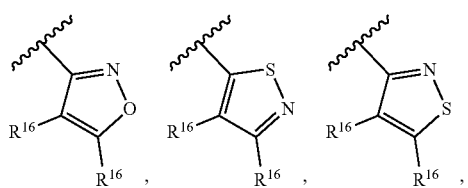
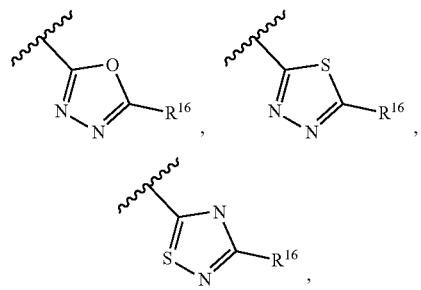
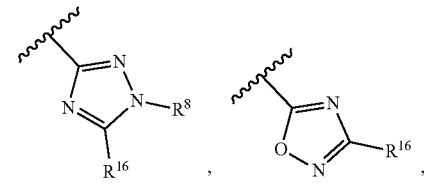
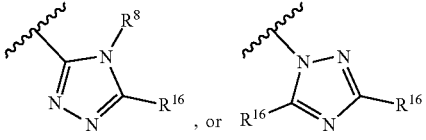
In some embodiments,
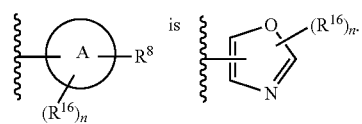
In some embodiments,
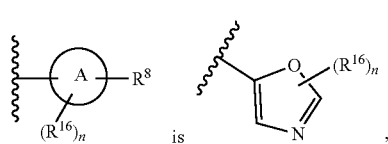
-continued
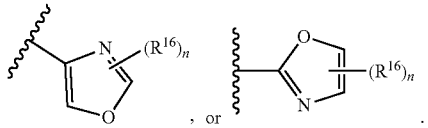, or
In some embodiments,
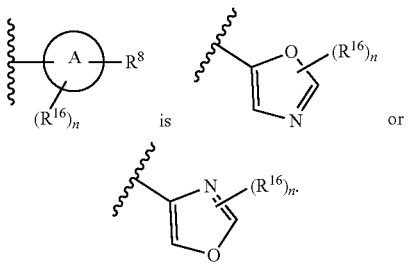
In some embodiments,
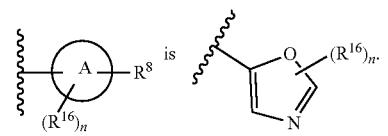
In some embodiments,
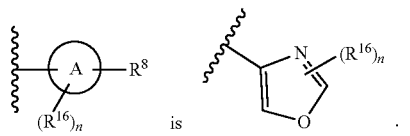
In some embodiments,
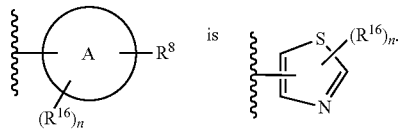
In some embodiments,
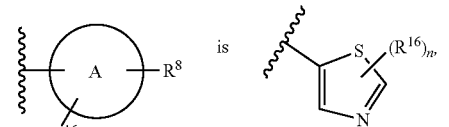
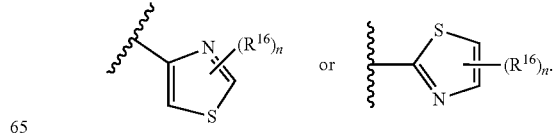

In some embodiments,
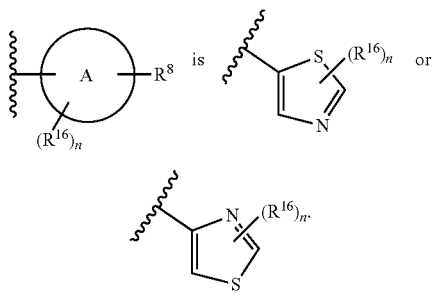
In some embodiments,
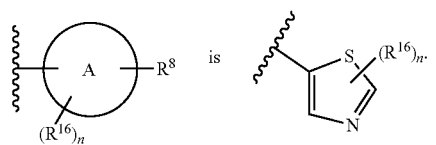
In some embodiments,
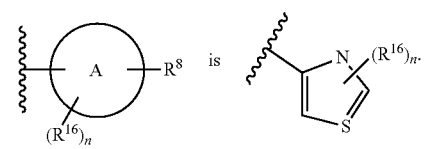
In some embodiments,
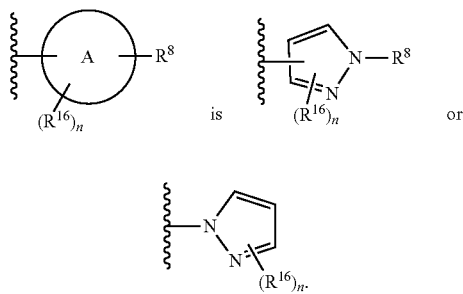
In some embodiments,
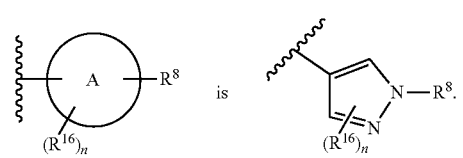
In some embodiments,
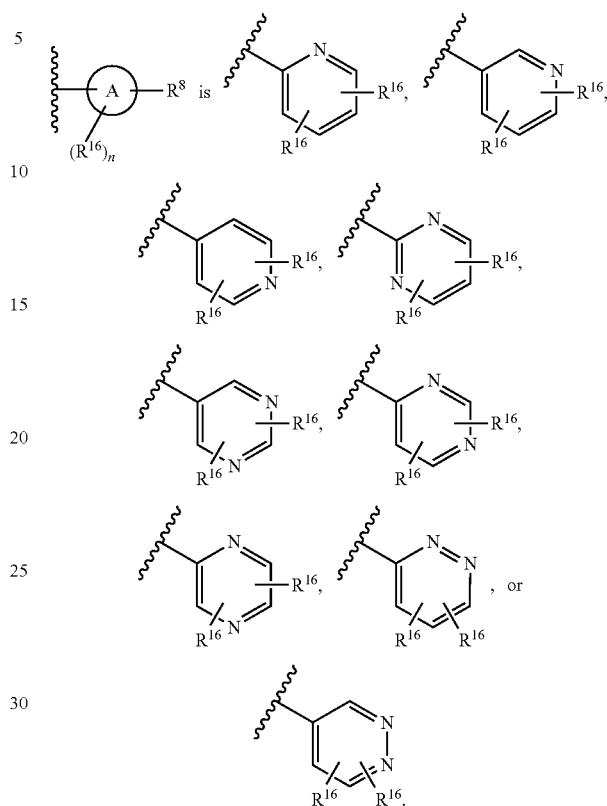
In some embodiments, In some embodiments,

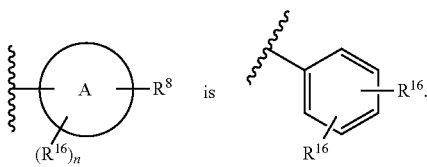

In some embodiments,

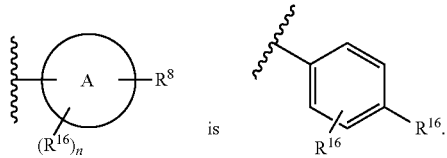

In some embodiments, Y is —CR$^{10}$R$^{11}$—.

In some embodiments, L is absent, —O—, —S—, —CH$_2$—, —CH$_2$CH$_2$—, —CH$_2$O—, —OCH$_2$—, —CH$_2$NR$^{15}$—, —NR$^{15}$CH$_2$—, —CH=CH—, —C≡C—, —C(=O)—, —C(=O)O—, —OC(=O)—, —OC(=O)O—, —C(=O)NR$^{15}$—, —NR$^{15}$C(=O)—, —OC(=O)NR$^{15}$—, —NR$^{15}$C(=O)O—, —NR$^{15}$C(=O)NR$^{15}$—, —NR$^{15}$S(=O)$_2$—, —NR$^{15}$—, cyclopropylene, cyclobutylene or bicyclo[1.1.1]pentylene.

In some embodiments, L is absent, —O—, —S—, —CH$_2$—, —CH$_2$CH$_2$—, —CH$_2$O—, —OCH$_2$—, —CH$_2$NR$^{15}$—, —NR$^{15}$CH$_2$—, —CH=CH—, —C≡C—, —C(=O)NR$^{15}$—, —NR$^{15}$C(=O)—, —OC(=O)NR$^{15}$—, —NR$^{15}$C(=O)O—, —NR$^{15}$C(=O)NR$^{15}$—, —NR$^{15}$S(=O)$_2$—, —NR$^{15}$—, cyclopropylene, cyclobutylene or bicyclo[1.1.1]pentylene. In some embodiments, L is absent or —C≡C—. In some embodiments, L is absent. In some embodiments, L is —C≡C—.

In some embodiments, R$^9$ is H; R$^{11}$ is H; or R$^9$ and R$^{11}$ are taken together to form a bridge that is —CH$_2$CH$_2$—.

In some embodiments, the compound of Formula (I) has the structure of Formula (II), or a pharmaceutically acceptable salt or solvate thereof:

Formula (II)

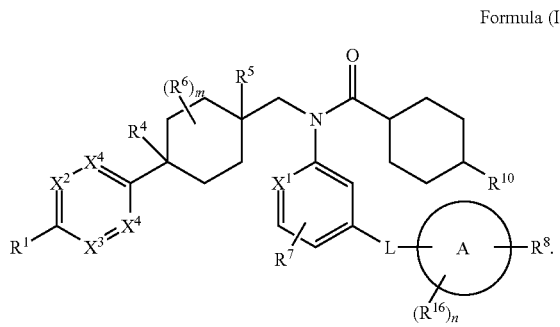

In some embodiments, R$^4$ is H; R$^5$ is H; or R$^4$ and R$^5$ are taken together to form a bridge that is —CH$_2$CH$_2$—.

In some embodiments, L is absent.

In some embodiments, the compound of Formula (I) has the structure of Formula (III), or a pharmaceutically acceptable salt or solvate thereof:

Formula (III)

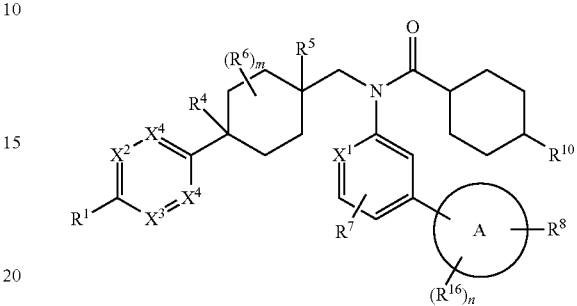

In some embodiments, the compound of Formula (I) has the structure of Formula (IV), or a pharmaceutically acceptable salt or solvate thereof:

Formula (IV)

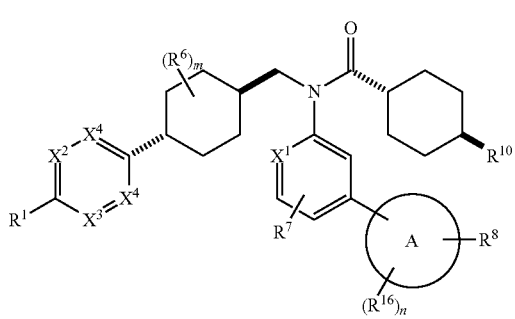

In some embodiments, the compound of Formula (I) has the structure of Formula (V), or a pharmaceutically acceptable salt or solvate thereof:

Formula (V)

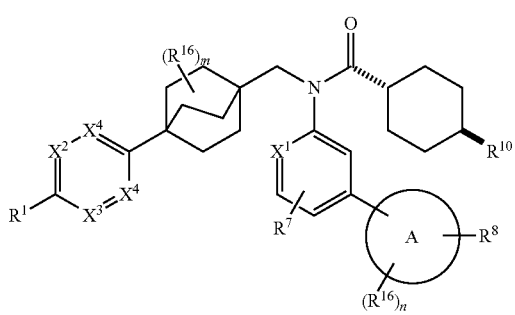

In some embodiments, the compound of Formula (I) has the structure of Formula (VII), or a pharmaceutically acceptable salt or solvate thereof:

Formula (VII)

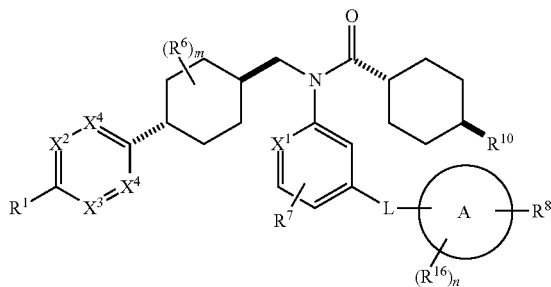

In some embodiments, the compound of Formula (I) has the structure of Formula (VIII), or a pharmaceutically acceptable salt or solvate thereof:

Formula (VIII)

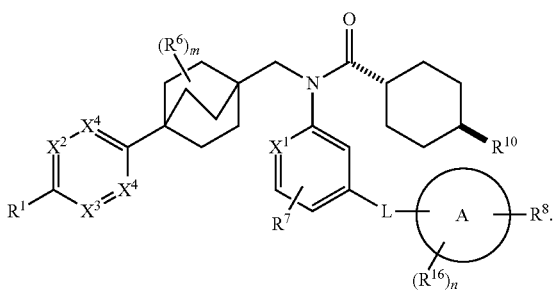

In some embodiments, $R^{10}$ is —$CH_2OH$, —$CH_2CH_2OH$, $C_1$-$C_6$heteroalkyl, —$CO_2H$, —C(=O)$R^{14}$, —C(=O)O$R^{14}$, —OC(=O)$R_{14}$, —OC(=O)O$R^{14}$, —$NR^{15}S(=O)_2R^{14}$, —$CH_2N(R^{12})_2$, —$NR^{15}C(=O)R^{14}$, —C(=O)N$(R^{12})_2$, —$NR^{15}C(=O)OR^{14}$, —OC(=O)N$(R^{12})_2$, —$NR^{15}C(=O)$N$(R^{12})_2$, —S$(=O)_2OH$ or —OP(=O)(O$R^{15})_2$; or $R^{10}$ is -$L^2$-$L^3$-$L^4$-$R^3$; $L^2$ is absent, —$CH_2$—, —$CH_2CH_2$—, —$CH_2OCH_2$—, —$CH_2SCH_2$—, or —$CH_2NHCH_2$—; $L^3$ is absent, —O—, —S—, —S(=O)—, —S$(=O)_2$—, —NH—, —C(=O)—, —C(=O)NH—, —NHC(=O)—, —C(=O)O—, —OC(=O)—, —OC(=O)O—, —OC(=O)NH—, —NHC(=O)NH—, —NHC(=O)O—, —OP(=O)(O$R^{15}$)O—, or —(OCH$_2$CH$_2$)$_r$—, r is 1 or 2; $L^4$ is —$CH_2$—, —$CH_2CH_2$—, —CH(CH$_3$)—, —$CH_2$CH (OH)—, —CH(CH$_2$OH)—, —CH(CH$_2$OH)CH$_2$—, —$CH_2CH_2CH_2$—, —$CH_2$CH(OH)CH$_2$—, —$CH_2$CH (CH$_3$)—, —$CH_2OCH_2$—, —$CH_2OCH_2CH_2$—, —$CH_2CH_2OCH_2$—, —$CH_2CH_2OCH_2CH_2$—, —$CH_2SCH_2$—, —$CH_2SCH_2CH_2$—, —$CH_2NHCH_2$— or —$CH_2NHCH_2CH_2$—.

In some embodiments, $R^{10}$ is —$CH_2OH$, $C_1$-$C_6$heteroalkyl, —$CO_2H$, —C(=O)$R^{14}$, —C(=O)O$R^{14}$, —OC(=O)$R^{14}$, —OC(=O)O$R^{14}$, —$NR^{15}C(=O)R^{14}$, —C(=O)N$(R^{12})_2$, —$NR^{15}C(=O)OR^{14}$, —OC(=O)N $(R^2)_2$, or —$NR^{15}C(=O)$N$(R^{12})_2$; or $R^{10}$ is -$L^2$-$L^3$-$L^4$-$R^3$; $L^2$ is absent, or —$CH_2$—; $L^3$ is absent, —O—, —NH—, —C(=O)NH—, —NHC(=O)—, —OC(=O)NH—, or —NHC(=O)O—; $L^4$ is —$CH_2$—, —$CH_2CH_2$—, —CH (CH$_2$OH)CH$_2$—, —$CH_2CH_2CH_2$— or —$CH_2$CH(OH) CH$_2$—. In some embodiments, $R^{14}$ is $C_1$-$C_4$alkyl, $C_1$-$C_4$heteroalkyl, monosubstituted or unsubstituted $C_3$-$C_6$cycloalkyl, monosubstituted or unsubstituted $C_2$-$C_6$heterocycloalkyl, monosubstituted or unsubstituted phenyl, monosubstituted or unsubstituted benzyl, or monosubstituted or unsubstituted monocyclic heteroaryl.

In some embodiments, $R^{14}$ is $C_1$-$C_4$alkyl, $C_1$-$C_4$deuteroalkyl, $C_1$-$C_4$fluoroalkyl, $C_1$-$C_4$heteroalkyl, substituted or unsubstituted cyclopropyl, substituted or unsubstituted cyclobutyl, substituted or unsubstituted cyclopentyl, substituted or unsubstituted cyclohexyl, substituted or unsubstituted aziridinyl, substituted or unsubstituted azetidinyl, substituted or unsubstituted pyrrolidinyl, substituted or unsubstituted piperidinyl, substituted or unsubstituted oxetanyl, substituted or unsubstituted tetrahydrofuranyl, substituted or unsubstituted tetrahydropyranyl, substituted or unsubstituted tetrahydrothiopyranyl, substituted or unsubstituted morpholinyl, substituted or unsubstituted thiomorpholinyl, or substituted or unsubstituted piperazinyl, substituted or unsubstituted phenyl, substituted or unsubstituted benzyl, or substituted or unsubstituted monocyclic heteroaryl.

In some embodiments, $R^{10}$ is —$CH_2OH$, $C_1$-$C_6$heteroalkyl, —$CO_2H$, —C(=O)$R^{14}$, —C(=O)O$R^{14}$, —OC(=O)$R^{14}$, —OC(=O)O$R^{14}$, —$NR^{15}C(=O)R^{14}$, —C(=O)N$(R^{12})_2$, —$NR^{15}C(=O)OR^{14}$, —OC(=O)N $(R^2)_2$, or —$NR^{15}C(=O)$N$(R^{12})_2$; or $R^{10}$ is -$L^2$-$L^3$-$L^4$-$R^3$; $L^2$ is absent, or —$CH_2$—; $L^3$ is absent, —O—, —NH—, —C(=O)NH—, —NHC(=O)—, —OC(=O)NH—, or —NHC(=O)O—; $L^4$ is —$CH_2$—, —$CH_2CH_2$—, —CH (CH$_2$OH)CH$_2$—, —$CH_2CH_2CH_2$— or —$CH_2$CH(OH) CH$_2$—; $R^{14}$ is $C_1$-$C_4$alkyl, $C_1$-$C_4$deuteroalkyl, $C_1$-$C_4$fluoroalkyl, $C_1$-$C_4$heteroalkyl, substituted or unsubstituted cyclobutyl, substituted or unsubstituted cyclopentyl, substituted or unsubstituted cyclohexyl, substituted or unsubstituted azetidinyl, substituted or unsubstituted pyrrolidinyl, substituted or unsubstituted piperidinyl, substituted or unsubstituted oxetanyl, substituted or unsubstituted tetrahydropyranyl, substituted or unsubstituted tetrahydrothiopyranyl, substituted or unsubstituted morpholinyl, or substituted or unsubstituted piperazinyl.

In some embodiments, $R^{14}$ is $C_1$-$C_4$alkyl, $C_1$-$C_4$deuteroalkyl, $C_1$-$C_4$fluoroalkyl, $C_1$-$C_4$heteroalkyl, substituted or unsubstituted cyclobutyl, substituted or unsubstituted cyclopentyl, substituted or unsubstituted cyclohexyl, substituted or unsubstituted azetidinyl, substituted or unsubstituted pyrrolidinyl, or substituted or unsubstituted piperidinyl.

In some embodiments, $R^{13}$ is H, —CN, —OH, —N$(R^{12})_2$, —CH$_3$, —$CH_2CH_3$, —$CH_2CH_2CH_3$, —CH(CH$_3$)$_2$, —$CH_2CH_2CH_2CH_3$, —$CH_2$CH(CH$_3$)$_2$, —C(CH$_3$)$_3$, —$CH_2OH$, —$CH_2OCH_3$, —$CH_2OCH_2CH_3$, —$CH_2CH_2OH$, —$CH_2CH_2OCH_3$, —$CH_2CH_2OCH_2CH_3$, —$CH_2NH_2$, —$CH_2NHCH_3$, —$CH_2N(CH_3)_2$, —$CO_2H$, —C(=O)NHCH$_3$, —OC(=O)NHCH$_3$, NHC(=O)CH$_3$, NHC(=O)OCH$_3$, NHS$(=O)_2$CH$_3$, SO$_2$CH$_3$, substituted or unsubstituted cyclopropyl, substituted or unsubstituted cyclobutyl, substituted or unsubstituted cyclopentyl, substituted or unsubstituted cyclohexyl, substituted or unsubstituted phenyl, or substituted or unsubstituted monocyclic heteroaryl.

In some embodiments, $R^{10}$ is —$CH_2OH$, $C_1$-$C_6$heteroalkyl, —$CO_2H$, —$NR^{15}C(=O)R^{14}$, —C(=O) N$(R^1)_2$, —$NR^{15}C(=O)OR^{14}$, or —OC(=O)N$(R^1)_2$.

In some embodiments, $R^{10}$ is —$CH_2OH$, —$CH_2CH_2OH$, $C_1$-$C_6$heteroalkyl, —$CO_2H$, —C(=O)$R^{14}$, —C(=O)O$R^{14}$, —OC(=O)$R_{14}$, —$NR^{15}S(=O)_2R^{14}$, —$CH_2N(R^{12})_2$, —$NR^{15}C(=O)R^{14}$, —C(=O)N$(R^1)_2$, —$NR^{15}C(=O)$OR$^{14}$, —OC(=O)N$(R^1)_2$, —$NR^{15}C(=O)$N$(R^{12})_2$, —S$(=O)_2OH$ or —OP(=O)(O$R^{15})_2$; or $R^{10}$ is -$L^2$-$L^3$-$L^4$-

$R^3$; $L^2$ is absent, —$CH_2$—, —$CH_2CH_2$—, —$CH_2OCH_2$—, —$CH_2SCH_2$—, or —$CH_2NHCH_2$—; $L^3$ is absent, —O—, —S—, —S(=O)—, —S(=O)$_2$—, —NH—, —C(=O)—, —C(=O)NH—, —NHC(=O)—, —C(=O)O—, —OC(=O)—, —OC(=O)NH—, —NHC(=O)NH—, —NHC(=O)O—, —OP(=O)(OR$^{15}$)O—, or —(OCH$_2$CH$_2$)$_r$—, r is 1 or 2; $L^4$ is —$CH_2$—, —$CH_2CH_2$—, —$CH_2CH_2CH_2$—, —$CH_2OCH_2$—, —$CH_2OCH_2CH_2$—, —$CH_2CH_2OCH_2$—, —$CH_2SCH_2$—, —$CH_2SCH_2CH_2$—, —$CH_2NHCH_2$— or —$CH_2NHCH_2CH_2$—.

In some embodiments, $R^{10}$ is —$CH_2OH$, $C_1$-$C_6$heteroalkyl, —$CO_2H$, —$NR^{15}C(=O)R^{14}$, —$C(=O)N(R^1)_2$, —$NR^{15}C(=O)OR^{14}$, or —$OC(=O)N(R^{12})_2$; or $R^{10}$ is -$L^2$-$L^3$-$L^4$-$R^3$; $L^2$ is absent, or —$CH_2$—; $L^3$ is absent, —O—, —NH—, —C(=O)NH—, —NHC(=O)—, —OC(=O)NH—, or —NHC(=O)O—; $L^4$ is —$CH_2$—, —$CH_2CH_2$—, or —$CH_2CH_2CH_2$—.

In some embodiments, $R^{13}$ is H, —CN, —OH, —N(R$^{12}$)$_2$, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$C(CH_3)_3$, —$CH_2OH$, —$CH_2OCH_3$, —$CH_2OCH_2CH_3$, —$CH_2CH_2OH$, —$CH_2CH_2OCH_3$, —$CH_2CH_2OCH_2CH_3$, —$CH_2NH_2$, —$CH_2NHCH_3$, —$CH_2N(CH_3)_2$, substituted or unsubstituted cyclopropyl, substituted or unsubstituted cyclobutyl, substituted or unsubstituted cyclopentyl, substituted or unsubstituted cyclohexyl, substituted or unsubstituted phenyl, or substituted or unsubstituted monocyclic heteroaryl.

In some embodiments, $R^0$ is —$CH_2OH$, $C_1$-$C_6$heteroalkyl, —$CO_2H$, —$NR^{15}C(=O)R^1$, —$C(=O)N(R^{12})_2$, —$NR^{15}C(=O)OR^4$, or —$OC(=O)N(R^1)_2$.

In some embodiments, no more than two $X^2$, $X^3$, $X^4$, $X^4$ are N.

In some embodiments, if both $X^4$ are N then $X^2$ is $CR_2$ and $X^3$ is $CR^3$; or if one $X^4$ is N and the other $X^4$ is CH then only one of $X^2$ and $X^3$ is N.

In some embodiments, the 6-membered ring containing $X^2$, $X^3$, $X^4$, $X^4$ has no more than two N atoms in the ring.

In some embodiments, $X^2$ is $CR^2$; $X^3$ is $CR^3$ or N; each $X^4$ is CH; or each $X^4$ is N; or one $X^4$ is N and the other $X^4$ is CH.

In some embodiments, $X^2$ is $CR^2$; $X^3$ is $CR^3$; each $X^4$ is CH; or each $X^4$ is N; or one $X^4$ is N and the other $X^4$ is CH.

In some embodiments, $X^2$ is $CR_2$; $X^3$ is $CR_3$; each $X^4$ is CH.

In some embodiments, $X^2$ is $CR^2$; $X^3$ is $CR^3$; each $X^4$ is N; or one $X^4$ is N and the other $X^4$ is CH.

In some embodiments, $X^2$ is $CR^2$; $X^3$ is N; each $X^4$ is CH; or each $X^4$ is N; or one $X^4$ is N and the other $X^4$ is CH.

In some embodiments, $R^1$ is H, D, F, Cl, —CN, —OH, —$NH_2$, —$NH(CH_3)$, —$N(CH_3)_2$, —$NHS(=O)_2CH_3$, —$OC(=O)CH_3$, —$CO_2H$, —$CO_2CH_3$, —$NHC(=O)CH_3$, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$C(CH_3)_3$, —$OCH_3$, —$OCH_2CH_3$, —$OCH(CH_3)_2$, —$SCH_3$, —$SCH_2CH_3$, —$SCH(CH_3)_2$, —$S(=O)CH_3$, —$S(=O)CH_2CH_3$, —$S(=O)CH(CH_3)_2$, —$S(=O)_2CH_3$, —$S(=O)_2CH_2CH_3$, —$S(=O)_2CH(CH_3)_2$, —$CD_3$, —$OCD_3$, —$CH_2F$, —$CHF_2$, —$CF_3$, —$CH_2CF_3$, —$OCH_2F$, —$OCHF_2$, —$OCF_3$, —$OCH_2CF_3$, —$CH_2OH$, —$CH_2OCH_3$, —$CH_2OCH_2CH_3$, —$CH_2NH_2$, —$CH_2NHCH_3$, or —$CH_2N(CH_3)_2$; $R^2$ is H, D, F, Cl, —CN, —OH, —$NH_2$, —$NH(CH_3)$, —$N(CH_3)_2$, —$NHS(=O)_2CH_3$, —$OC(=O)CH_3$, —$CO_2H$, —$CO_2CH_3$, —$NHC(=O)CH_3$, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$C(CH_3)_3$, —$OCH_3$, —$OCH_2CH_3$, —$OCH(CH_3)_2$, —$CD_3$, —$OCD_3$, —$CH_2F$, —$CHF_2$, —$CF_3$, —$CH_2CF_3$, —$OCH_2F$, —$OCHF_2$, —$OCF_3$, —$OCH_2CF_3$, —$CH_2OH$, —$CH_2OCH_3$, —$CH_2OCH_2CH_3$, —$CH_2NH_2$, —$CH_2NHCH_3$, or —$CH_2N(CH_3)_2$; or $R^1$ and $R^2$ are taken together with the intervening atoms to form a substituted or unsubstituted fused 5- or 6-membered ring with 0-3 N atoms and 0-2 O or S atom in the ring that is a substituted or unsubstituted dihydrofuranyl, substituted or unsubstituted dioxolyl, substituted or unsubstituted furanyl, substituted or unsubstituted thienyl, substituted or unsubstituted pyrrolyl, substituted or unsubstituted oxazolyl, substituted or unsubstituted thiazolyl, substituted or unsubstituted imidazolyl, substituted or unsubstituted pyrazolyl, substituted or unsubstituted triazolyl, substituted or unsubstituted isoxazolyl, substituted or unsubstituted isothiazolyl, substituted or unsubstituted dihydropyrrolyl, substituted or unsubstituted pyridinyl, substituted or unsubstituted pyrimidinyl, substituted or unsubstituted pyrazinyl, substituted or unsubstituted pyridazinyl, or substituted or unsubstituted dioxinyl; $R^3$ is H, D, F, Cl, —CN, —OH, —$NH_2$, —$NH(CH_3)$, —$N(CH_3)_2$, —$NHS(=O)_2CH_3$, —$OC(=O)CH_3$, —$CO_2H$, —$CO_2CH_3$, —$NHC(=O)CH_3$, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$C(CH_3)_3$, —$OCH_3$, —$OCH_2CH_3$, —$OCH(CH_3)_2$, —$CD_3$, —$OCD_3$, —$CH_2F$, —$CHF_2$, —$CF_3$, —$CH_2CF_3$, —$OCH_2F$, —$OCHF_2$, —$OCF_3$, —$OCH_2CF_3$, —$CH_2OH$, —$CH_2OCH_3$, —$CH_2OCH_2CH_3$, —$CH_2NH_2$, —$CH_2NHCH_3$, or —$CH_2N(CH_3)_2$.

In some embodiments, $R^1$ is H, D, F, Cl, —CN, —OH, —$NH_2$, —$NH(CH_3)$, —$N(CH_3)_2$, —$NHS(=O)_2CH_3$, —$OC(=O)CH_3$, —$CO_2H$, —$CO_2CH_3$, —$NHC(=O)CH_3$, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$C(CH_3)_3$, —$OCH_3$, —$OCH_2CH_3$, —$OCH(CH_3)_2$, —$CD_3$, —$OCD_3$, —$CH_2F$, —$CHF_2$, —$CF_3$, —$CH_2CF_3$, —$OCH_2F$, —$OCHF_2$, —$OCF_3$, —$OCH_2CF_3$, —$CH_2OH$, —$CH_2OCH_3$, —$CH_2OCH_2CH_3$, —$CH_2NH_2$, —$CH_2NHCH_3$, or —$CH_2N(CH_3)_2$; or $R^1$ and $R^2$ are taken together with the intervening atoms to form a substituted or unsubstituted fused 5-membered ring with 0-3 N atoms and 0-2 O or S atom in the ring that is a substituted or unsubstituted dihydrofuranyl, substituted or unsubstituted dioxolyl, substituted or unsubstituted furanyl, substituted or unsubstituted thienyl, substituted or unsubstituted pyrrolyl, substituted or unsubstituted oxazolyl, substituted or unsubstituted thiazolyl, substituted or unsubstituted imidazolyl, substituted or unsubstituted pyrazolyl, substituted or unsubstituted triazolyl, substituted or unsubstituted isoxazolyl or substituted or unsubstituted isothiazolyl; $R^3$ is H, D, F, Cl, —CN, —OH, —$NH_2$, —$NH(CH_3)$, —$N(CH_3)_2$, —$NHS(=O)_2CH_3$, —$OC(=O)CH_3$, —$CO_2H$, —$CO_2CH_3$, —$NHC(=O)CH_3$, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$C(CH_3)_3$, —$OCH_3$, —$OCH_2CH_3$, —$OCH(CH_3)_2$, —$CD_3$, —$OCD_3$, —$CH_2F$, —$CHF_2$, —$CF_3$, —$CH_2CF_3$, —OCH$_2$F, —OCHF$_2$, —OCF$_3$, —OCH$_2$CF$_3$, —CH$_2$OH, —CH$_2$OCH$_3$, —CH$_2$OCH$_2$CH$_3$, —CH$_2$NH$_2$, —CH$_2$NHCH$_3$, or —CH$_2$N(CH$_3$)$_2$.

In some embodiments, R$^1$ is H, D, F, Cl, —CN, —OH, —NH$_2$, —NH(CH$_3$), —N(CH$_3$)$_2$, —CH$_3$, —CH$_2$CH$_3$, —OCH$_3$, —OCH$_2$CH$_3$, —SCH$_3$, —CD$_3$, —OCD$_3$, —CH$_2$F, —CHF$_2$, —CF$_3$, —CH$_2$CF$_3$, —OCH$_2$F, —OCHF$_2$, —OCF$_3$, or —OCH$_2$CF$_3$; R$^2$ is H, D, F, Cl, —CH$_3$, —CH$_2$CH$_3$, —OCH$_3$, —OCH$_2$CH$_3$, —SCH$_3$, —CD$_3$, —OCD$_3$, —CH$_2$F, —CHF$_2$, —CF$_3$, —OCH$_2$F, —OCHF$_2$, —OCF$_3$, or —OCH$_2$CF$_3$; R$^3$ is H, D, F, Cl, —CH$_3$, —OCH$_3$, —CD$_3$, —OCD$_3$, —CH$_2$F, —CHF$_2$, —CF$_3$, —CH$_2$CF$_3$, —OCH$_2$F, —OCHF$_2$, or —OCF$_3$.

In some embodiments, R$^1$ is H, D, F, Cl, —CN, —OH, —NH$_2$, —NH(CH$_3$), —N(CH$_3$)$_2$, —CH$_3$, —CH$_2$CH$_3$, —OCH$_3$, —OCH$_2$CH$_3$, —CD$_3$, —OCD$_3$, —CH$_2$F, —CHF$_2$, —CF$_3$, —CH$_2$CF$_3$, —OCH$_2$F, —OCHF$_2$, —OCF$_3$, or —OCH$_2$CF$_3$; R$^2$ is H, D, F, Cl, —CH$_3$, —CH$_2$CH$_3$, —OCH$_3$, —OCH$_2$CH$_3$, —CD$_3$, —OCD$_3$, —CH$_2$F, —CHF$_2$, —CF$_3$, —OCH$_2$F, —OCHF$_2$, —OCF$_3$, or —OCH$_2$CF$_3$; R$^3$ is H, D, F, Cl, —CH$_3$, —OCH$_3$, —CD$_3$, —OCD$_3$, —CH$_2$F, —CHF$_2$, —CF$_3$, —CH$_2$CF$_3$, —OCH$_2$F, —OCHF$_2$, or —OCF$_3$.

In some embodiments, R$^1$ is —OH, —NH$_2$, —NH(CH$_3$), —N(CH$_3$)$_2$, —CH$_3$, —OCH$_3$, —SCH$_3$, —CD$_3$, —OCD$_3$, —CH$_2$F, —CHF$_2$, —CF$_3$, —OCH$_2$F, —OCHF$_2$, —OCF$_3$, or —OCH$_2$CF$_3$; R$^2$ is H, D, F, Cl, —CH$_3$, —CD$_3$, —CH$_2$F, —CHF$_2$, or —CF$_3$; R$^3$ is H.

In some embodiments, R$^1$ is —OH, —NH$_2$, —NH(CH$_3$), —N(CH$_3$)$_2$, —CH$_3$, —OCH$_3$, —CD$_3$, —OCD$_3$, —CH$_2$F, —CHF$_2$, —CF$_3$, —OCH$_2$F, —OCHF$_2$, —OCF$_3$, or —OCH$_2$CF$_3$; R$^2$ is H, D, F, Cl, —CH$_3$, —CD$_3$, —CH$_2$F, —CHF$_2$, or —CF$_3$; R$^3$ is H.

In some embodiments,

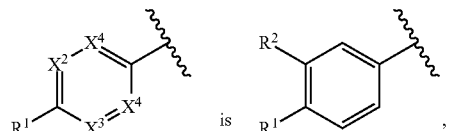

is

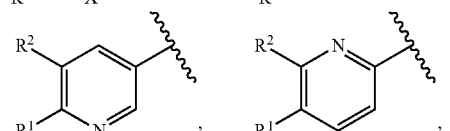

,

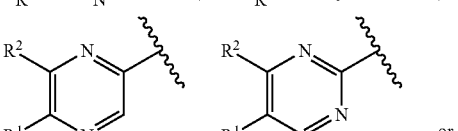

,

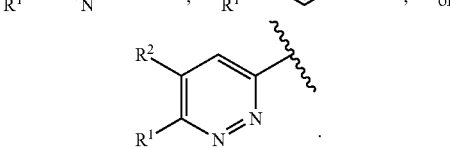

, or

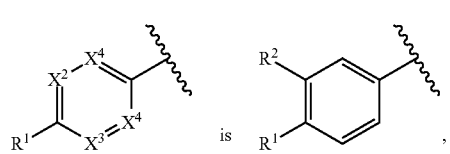

.

In some embodiments,

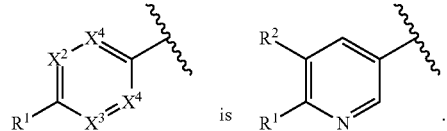 is 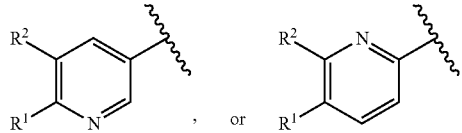

, or

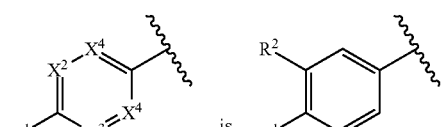

.

In some embodiments,

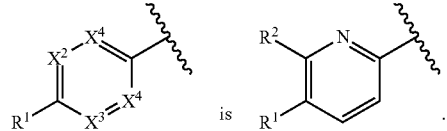 is 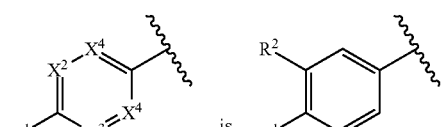

.

In some embodiments,

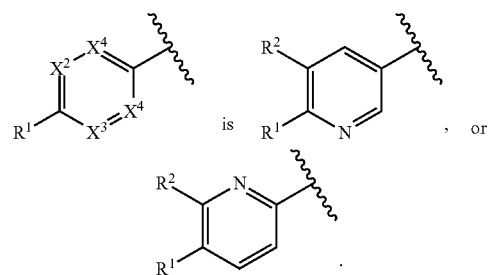

In some embodiments,

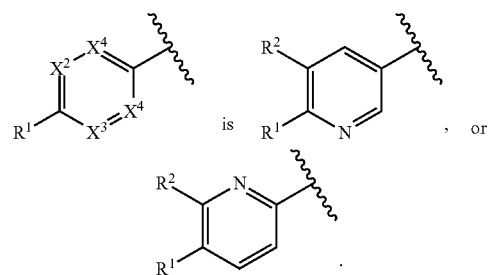

In some embodiments, X$^2$ is N; X$^3$ is N; each X$^4$ is CH.

In some embodiments,

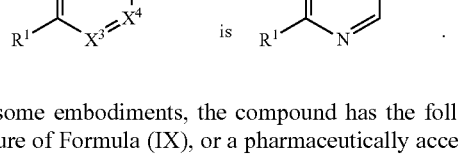

In some embodiments, the compound has the following structure of Formula (IX), or a pharmaceutically acceptable salt or solvate thereof:

Formula (IX)

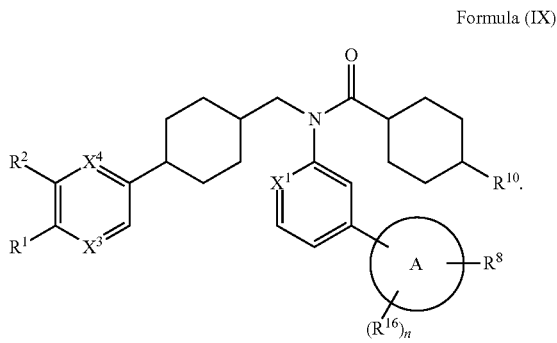

In some embodiments, R¹ is H, D, F, Cl, —CN, —OH, —NH₂, —NH(CH₃), —N(CH₃)₂, —NHS(=O)₂CH₃, —OC(=O)CH₃, —CO₂H, —CO₂CH₃, —NHC(=O)CH₃, —CH₃, —CH₂CH₃, —CH₂CH₂CH₃, —CH(CH₃)₂, —CH₂CH₂CH₂CH₃, —CH₂CH(CH₃)₂, —C(CH₃)₃, —OCH₃, —OCH₂CH₃, —OCH(CH₃)₂, —CD₃, —OCD₃, —CH₂F, —CHF₂, —CF₃, —CH₂CF₃, —OCH₂F, —OCHF₂, —OCF₃, —OCH₂CF₃, —CH₂OH, —CH₂OCH₃, —CH₂OCH₂CH₃, —CH₂NH₂, —CH₂NHCH₃, or —CH₂N(CH₃)₂.

In some embodiments, R¹ is H, D, F, Cl, —CN, —OH, —NH₂, —NH(CH₃), —N(CH₃)₂, —CH₃, —CH₂CH₃, —OCH₃, —OCH₂CH₃, —CD₃, —OCD₃, —CH₂F, —CHF₂, —CF₃, —CH₂CF₃, —OCH₂F, —OCHF₂, —OCF₃, or —OCH₂CF₃.

In some embodiments, R¹ is —OH, —NH₂, —NH(CH₃), —N(CH₃)₂, —CH₃, —OCH₃, —CD₃, —OCD₃, —CH₂F, —CHF₂, —CF₃, —OCH₂F, —OCHF₂, —OCF₃, or —OCH₂CF₃.

In some embodiments, R¹ is H, D, —CH₃, —CH₂CH₃, —CH₂CH₂CH₃, —CH(CH₃)₂, —CH₂CH₂CH₂CH₃, —CH(CH₃)CH₂CH₃, —CH₂CH(CH₃)₂, —C(CH₃)₃, —CD₃, —CH₂F, —CHF₂, —CF₃, —CH₂CF₃, —CHFCH₃, —CH₂CH₂F, —CH₂CH₂OH, —CH₂CH₂OCH₃, —CH₂CH₂NH₂, —CH₂CH₂NHCH₃, —CH₂CH₂N(CH₃)₂, —C(=O)CH₃, —C(=O)CH₂CH₃, —C(=O)CH(CH₃)₂, —CO₂CH₃, —CO₂CH₂CH₃, —CO₂CH(CH₃)₂, —C(=O)NHCH₃, —S(=O)₂CH₃, —S(=O)₂NHCH₃, substituted or unsubstituted cyclopropyl, substituted or unsubstituted cyclobutyl, substituted or unsubstituted cyclopentyl, substituted or unsubstituted cyclohexyl, substituted or unsubstituted oxetanyl, substituted or unsubstituted tetrahydrofuranyl, substituted or unsubstituted tetrahydropyranyl, or substituted or unsubstituted tetrahydrothiopyranyl.

In some embodiments, R⁸ is H, —CH₃, —CH₂CH₃, —CH₂CH₂CH₃, —CH(CH₃)₂, —CH₂CH₂CH₂CH₃, —CH(CH₃)CH₂CH₃, —CH₂CH(CH₃)₂, —C(CH₃)₃, —CD₃, —CH₂F, —CHF₂, —CF₃, —CH₂CF₃, —CHFCH₃, —CH₂CH₂F, —CH₂CH₂OH, —CH₂CH₂OCH₃, —CH₂CH₂NH₂, —CH₂CH₂NHCH₃, —CH₂CH₂N(CH₃)₂, substituted or unsubstituted cyclopropyl, substituted or unsubstituted cyclobutyl, substituted or unsubstituted cyclopentyl, substituted or unsubstituted cyclohexyl, substituted or unsubstituted oxetanyl, substituted or unsubstituted tetrahydrofuranyl, or substituted or unsubstituted tetrahydropyranyl.

In some embodiments, R⁸ is H, —CH₃, —CH₂CH₃, —CH₂CH₂CH₃, —CH(CH₃)₂, —C(CH₃)₃, cyclopropyl, cyclobutyl, cyclopentyl, cyclohexyl, oxetanyl, tetrahydrofuranyl, or tetrahydropyranyl.

In some embodiments, each R¹² is independently H, C₁-C₄alkyl, C₁-C₄deuteroalkyl, C₁-C₄fluoroalkyl, C₁-C₄heteroalkyl, substituted or unsubstituted C₃-C₆cycloalkyl, substituted or unsubstituted C₂-C₆heterocycloalkyl, substituted or unsubstituted phenyl, substituted or unsubstituted benzyl, or substituted or unsubstituted monocyclic heteroaryl. In some embodiments, each R¹² is independently H, C₁-C₄alkyl, C₁-C₄heteroalkyl, substituted or unsubstituted C₃-C₆cycloalkyl, substituted or unsubstituted C₂-C₆heterocycloalkyl, substituted or unsubstituted phenyl, substituted or unsubstituted benzyl, substituted or unsubstituted monocyclic heteroaryl. In some embodiments, each R¹² is independently H, C₁-C₄alkyl, C₁-C₄heteroalkyl, substituted or unsubstituted C₂-C₆heterocycloalkyl, substituted or unsubstituted phenyl, substituted or unsubstituted benzyl, or substituted or unsubstituted monocyclic heteroaryl. In some embodiments, each R¹² is independently H, C₁-C₄alkyl, or substituted or unsubstituted C₂-C₆heterocycloalkyl. In some embodiments, each R¹² is independently H or C₁-C₄alkyl.

In some embodiments, when two R² are attached to an N atom, one R² is independently H or C₁-C₄alkyl, and the other R¹² is H, C₁-C₄alkyl, C₁-C₄deuteroalkyl, C₁-C₄fluoroalkyl, C₁-C₄heteroalkyl, substituted or unsubstituted C₃-C₆cycloalkyl, substituted or unsubstituted C₂-C₆heterocycloalkyl, substituted or unsubstituted phenyl, substituted or unsubstituted benzyl, substituted or unsubstituted monocyclic heteroaryl.

In some embodiments, when two R² are attached to an N atom, one R² is independently H or C₁-C₄alkyl, and the other R¹² is H, C₁-C₄alkyl, C₁-C₄heteroalkyl, substituted or unsubstituted C₃-C₆cycloalkyl, substituted or unsubstituted C₂-C₆heterocycloalkyl, substituted or unsubstituted phenyl, substituted or unsubstituted benzyl, substituted or unsubstituted monocyclic heteroaryl. In some embodiments, when two R² are attached to an N atom, one R² is H or C₁-C₄alkyl, and the other R¹² is H, C₁-C₄alkyl, C₁-C₄heteroalkyl, substituted or unsubstituted C₂-C₆heterocycloalkyl, substituted or unsubstituted phenyl, substituted or unsubstituted benzyl, substituted or unsubstituted monocyclic heteroaryl. In some embodiments, when two R² are attached to an N atom, one R² is independently H or C₁-C₄alkyl, and the other R¹² is H, C₁-C₄alkyl, C₁-C₄heteroalkyl, substituted or unsubstituted C₂-C₆heterocycloalkyl, or substituted or unsubstituted monocyclic heteroaryl. In some embodiments, when two R² are attached to an N atom, one R² is independently H or C₁-C₄alkyl, and the other R¹² is H, C₁-C₄alkyl, C₁-C₄heteroalkyl, or substituted or unsubstituted C₂-C₆heterocycloalkyl.

In some embodiments, R¹⁴ is C₁-C₄alkyl, C₁-C₄deuteroalkyl, C₁-C₄fluoroalkyl, C₁-C₄heteroalkyl, substituted or unsubstituted C₃-C₆cycloalkyl, substituted or unsubstituted C₂-C₆heterocycloalkyl, substituted or unsubstituted phenyl, substituted or unsubstituted benzyl, or substituted or unsubstituted monocyclic heteroaryl.

In some embodiments, R¹⁴ is C₁-C₄alkyl, C₁-C₄heteroalkyl, substituted or unsubstituted C₃-C₆cycloalkyl, substituted or unsubstituted C₂-C₆heterocycloalkyl, substituted or unsubstituted phenyl, substituted or unsubstituted benzyl, or substituted or unsubstituted monocyclic heteroaryl. In some embodiments, R¹⁴ is C₁-C₄alkyl, C₁-C₄heteroalkyl, substituted or unsubstituted C₃-C₆cycloalkyl, substituted or unsubstituted C₂-C₆heterocycloalkyl, substituted or unsubstituted phenyl, or substituted or unsubstituted monocyclic heteroaryl. In some embodiments, R¹⁴ is C₁-C₄alkyl.

In some embodiments, each $R^{16}$ is independently is H, D, F, Cl, —CN, —OH, —NH$_2$, —NH(CH$_3$), —N(CH$_3$)$_2$, —NHS(=O)$_2$CH$_3$, —S(=O)$_2$CH$_3$, —C(=O)CH$_3$, —OC(=O)CH$_3$, —CO$_2$H, —CO$_2$CH$_3$, —NHC(=O)CH$_3$, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —C(CH$_3$)$_3$, —CH=CH$_2$, —CH=CHCH$_3$, —C≡CH, —C≡CCH$_3$, —C≡CCH$_2$CH$_3$, —OCH$_3$, —OCH$_2$CH$_3$, —OCH(CH$_3$)$_2$, —CD$_3$, —OCD$_3$, —CH$_2$F, —CHF$_2$, —CF$_3$, —CH$_2$CF$_3$, —OCH$_2$F, —OCHF$_2$, —OCF$_3$, —OCH$_2$CF$_3$, —CH$_2$OH, —CH$_2$CH$_2$OH, —CH$_2$OCH$_3$, —CH$_2$OCH$_2$CH$_3$, —CH$_2$NH$_2$, —CH$_2$NHCH$_3$, or —CH$_2$N(CH$_3$)$_2$, substituted or unsubstituted cyclopropyl, substituted or unsubstituted cyclobutyl, substituted or unsubstituted cyclopentyl, substituted or unsubstituted cyclohexyl, substituted or unsubstituted aziridinyl, substituted or unsubstituted azetidinyl, substituted or unsubstituted pyrrolidinyl, substituted or unsubstituted piperidinyl, substituted or unsubstituted tetrahydrofuranyl, substituted or unsubstituted tetrahydropyranyl, substituted or unsubstituted tetrahydrothiopyranyl, substituted or unsubstituted morpholinyl, substituted or unsubstituted thiomorpholinyl, or substituted or unsubstituted piperazinyl.

In some embodiments, each $R^{16}$ is independently is H, D, F, Cl, —CN, —OH, —NH$_2$, —NH(CH$_3$), —N(CH$_3$)$_2$, —NHS(=O)$_2$CH$_3$, —S(=O)$_2$CH$_3$, —C(=O)CH$_3$, —OC(=O)CH$_3$, —CO$_2$H, —CO$_2$CH$_3$, —NHC(=O)CH$_3$, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —C(CH$_3$)$_3$, —CH=CH$_2$, —CH=CHCH$_3$, —C≡CH, —C≡CCH$_3$, —C≡CCH$_2$CH$_3$, —OCH$_3$, —OCH$_2$CH$_3$, —OCH(CH$_3$)$_2$, —CD$_3$, —OCD$_3$, —CH$_2$F, —CHF$_2$, —CF$_3$, —CH$_2$CF$_3$, —OCH$_2$F, —OCHF$_2$, —OCF$_3$, —OCH$_2$CF$_3$, —CH$_2$OH, —CH$_2$CH$_2$OH, —CH$_2$OCH$_3$, —CH$_2$OCH$_2$CH$_3$, —CH$_2$NH$_2$, —CH$_2$NHCH$_3$, or —CH$_2$N(CH$_3$)$_2$, cyclopropyl, cyclobutyl, cyclopentyl, cyclohexyl, aziridinyl, azetidinyl, pyrrolidinyl, piperidinyl, tetrahydrofuranyl, tetrahydropyranyl, tetrahydrothiopyranyl, morpholinyl, thiomorpholinyl, or piperazinyl.

In some embodiments, each $R^{16}$ is independently is H, D, F, Cl, —CH$_3$, —CH$_2$CH$_3$, —CH(CH$_3$)$_2$, —C(CH$_3$)$_3$, —OCH$_3$, —OCH$_2$CH$_3$, —OCH(CH$_3$)$_2$, —SCH$_3$, —SCH$_2$CH$_3$, —SCH(CH$_3$)$_2$, —CD$_3$, —CH$_2$F, —CHF$_2$, —CF$_3$, —CH$_2$CF$_3$, substituted or unsubstituted cyclopropyl, or substituted or unsubstituted cyclobutyl. In some embodiments, each $R^{16}$ is independently is H, D, F, Cl, —CH$_3$, —CH$_2$CH$_3$, —CH(CH$_3$)$_2$, —C(CH$_3$)$_3$, —OCH$_3$, —OCH$_2$CH$_3$, —OCH(CH$_3$)$_2$, —CD$_3$, —CH$_2$F, —CHF$_2$, —CF$_3$, —CH$_2$CF$_3$, substituted or unsubstituted cyclopropyl, or substituted or unsubstituted cyclobutyl. In some embodiments, each $R^{16}$ is independently is H, D, F, Cl, —CH$_3$, —CH$_2$CH$_3$, —CD$_3$, —CH$_2$F, —CHF$_2$, —CF$_3$, or —CH$_2$CF$_3$.

In some embodiments, the compound has the following structure of Formula (X), or a pharmaceutically acceptable salt or solvate thereof:

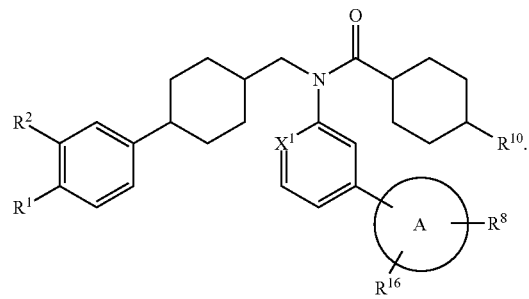

Formula (X)

In some embodiments, the compound has the following structure of Formula (XI) or Formula (XII), or a pharmaceutically acceptable salt or solvate thereof:

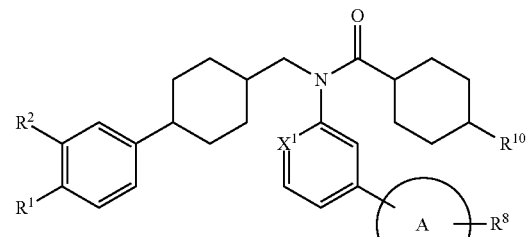

Formula (XI)

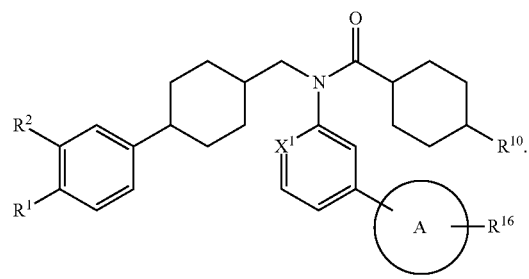

Formula (XII)

Any combination of the groups described above for the various variables is contemplated herein. Throughout the specification, groups and substituents thereof are chosen by one skilled in the field to provide stable moieties and compounds.

In some embodiments, compounds described herein include, but are not limited to, those described in Table 1 and Table 2.

TABLE 1

| Compound No | Structure | Chemical Name |
|---|---|---|
| 1 | 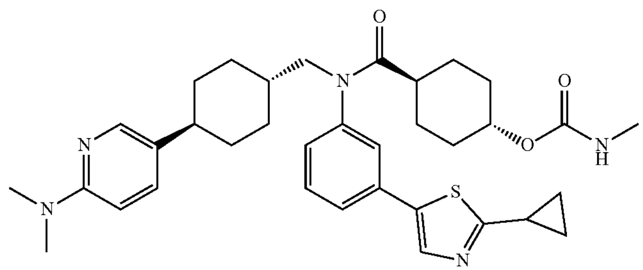 | trans-4-((3-(2-cyclopropylthiazol-5-yl)phenyl)(trans-4-(6-(dimethylamino)pyridin-3-yl)cyclohexyl)methyl)carbamoyl)cyclohexyl methylcarbamate |
| 1.01 | 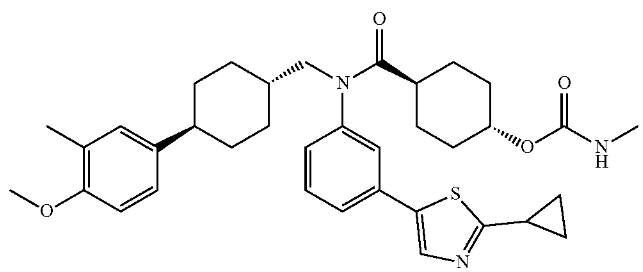 | trans-4-(3-(2-Cyclopropylthiazol-5-yl)phenyl)(trans-4-(4-methoxy-3-methylphenyl)cyclohexyl)methyl)carbamoyl)-cyclohexyl methylcarbamate |
| 1.02 | 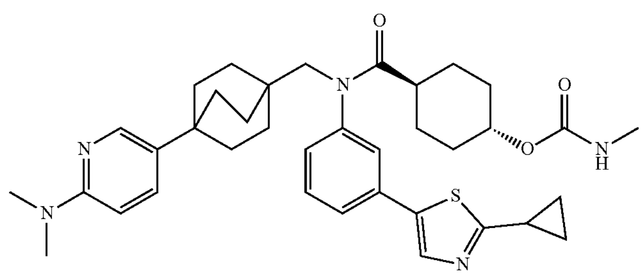 | 4-((3-(2-Cyclopropylthiazol-5-yl)phenyl)(4-(6-(dimethylamino)pyridin-3-yl)bicyclo[2.2.2]octan-1-yl)methyl)carbamoyl)cyclohexyl trans-methylcarbamate |

TABLE 1-continued

| Compound No | Structure | Chemical Name |
|---|---|---|
| 1.03 | 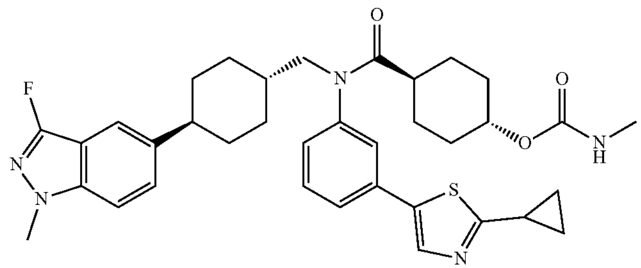 [SMILES: CNC(=O)O[C@H]1CC[C@H](C(=O)N(C[C@H]2CC[C@H](c3ccc4c(c3)c(F)nn4C)CC2)c2cccc(-c3cnc(C4CC4)s3)c2)CC1] | trans-4-((3-(2-Cyclopropylthiazol-5-yl)phenyl)((trans-4-(3-fluoro-1-methyl-1H-indazol-5-yl)cyclohexyl)methyl)carbamoyl)cyclohexyl methylcarbamate |
| 1.04 | 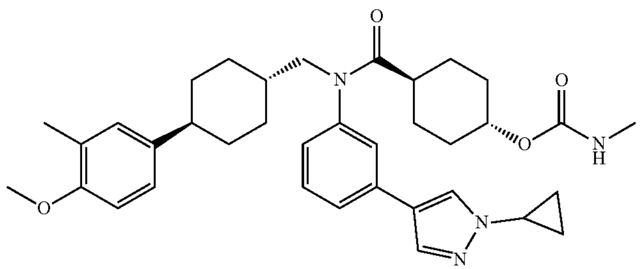 | trans-4-((3-(1-Cyclopropyl-1H-pyrazol-4-yl)phenyl)((trans-4-(4-methoxy-3-methylphenyl)cyclohexyl)methyl)carbamoyl)cyclohexyl methylcarbamate |
| 1.05 | 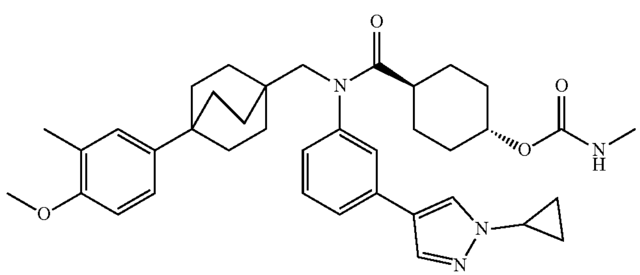 | 4-((3-(1-Cyclopropyl-1H-pyrazol-4-yl)phenyl)((4-(4-methoxy-3-methylphenyl)bicyclo[2.2.2]octan-1-yl)methyl)carbamoyl)cyclohexyl trans-methylcarbamate |

TABLE 1-continued

| Compound No | Structure | Chemical Name |
|---|---|---|
| 1.06 | 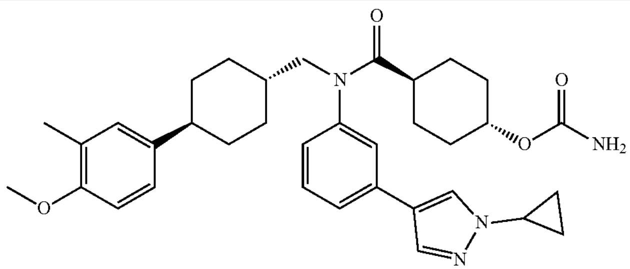 [SMILES: COc1ccc([C@H]2CC[C@H](CN(c3cccc(-c4cnn(C5CC5)c4)c3)C(=O)[C@H]3CC[C@H](OC(N)=O)CC3)CC2)cc1C] | trans-4-((3-(1-Cyclopropyl-1H-pyrazol-4-yl)phenyl)(trans-4-(4-methoxy-3-methylphenyl)cyclohexyl)methyl)carbamoyl)-cyclohexyl carbamate |
| 1.07 | 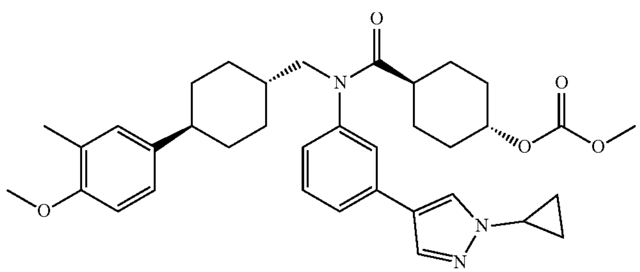 | trans-4-((3-(1-Cyclopropyl-1H-pyrazol-4-yl)phenyl)(trans-4-(4-methoxy-3-methylphenyl)cyclohexyl)methyl)carbamoyl)-cyclohexyl methyl carbonate |
| 1.08 | 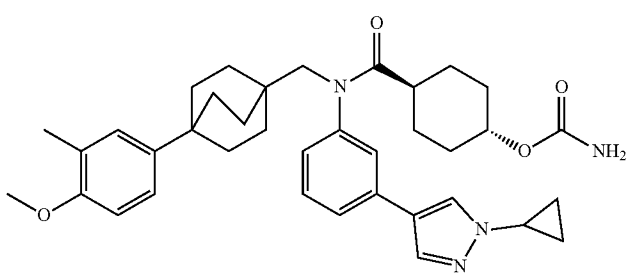 [SMILES: COc1ccc(C23CCC(CN(c4cccc(-c5cnn(C6CC6)c5)c4)C(=O)[C@H]4CC[C@H](OC(N)=O)CC4)(CC2)CC3)cc1C] | 4-((3-(1-Cyclopropyl-1H-pyrazol-4-yl)phenyl)(4-(4-methoxy-3-methylphenyl)bicyclo[2.2.2]octan-1-yl)methyl)carbamoyl)cyclohexyl trans-carbamate |

TABLE 1-continued

| Compound No | Structure | Chemical Name |
|---|---|---|
| 1.09 | 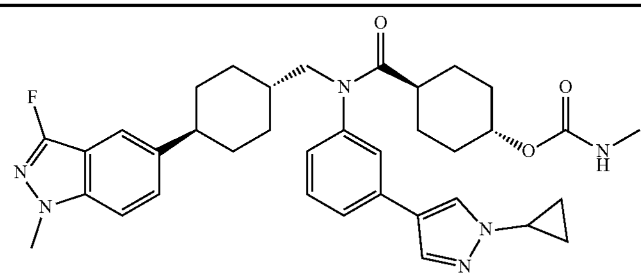 | trans-4-((3-(1-Cyclopropyl-1H-pyrazol-4-yl)phenyl)((trans-4-(3-fluoro-1-methyl-1H-indazol-5-yl)cyclohexyl)methyl)carbamoyl)hexyl methylcarbamate |
| 1.10 | 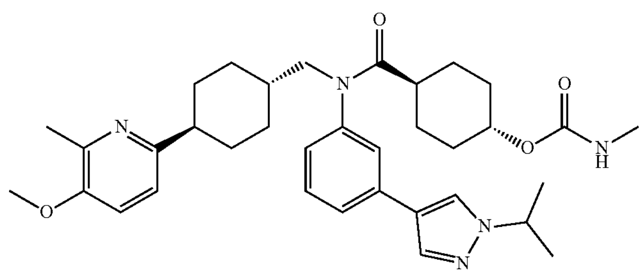 | trans-4-(3-(1-Isopropyl-1H-pyrazol-4-yl)phenyl)((trans-4-(5-methoxy-6-methylpyridin-2-yl)cyclohexyl)methyl)carbamoyl)cyclohexyl methylcarbamate |
| 2 | 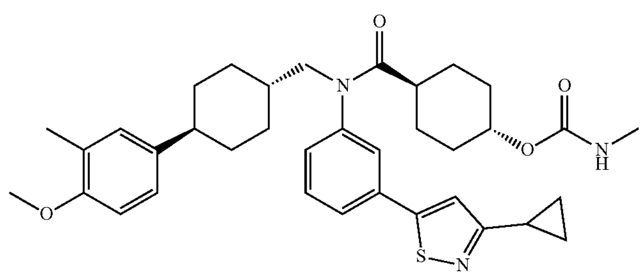 | trans-4-((3-(3-cyclopropylisothiazol-5-yl)phenyl)((trans-4-(4-methoxy-3-methylphenyl)cyclohexyl)methyl)carbamoyl)cyclohexyl methylcarbamate |

TABLE 1-continued

| Compound No | Structure | Chemical Name |
|---|---|---|
| 2.01 | 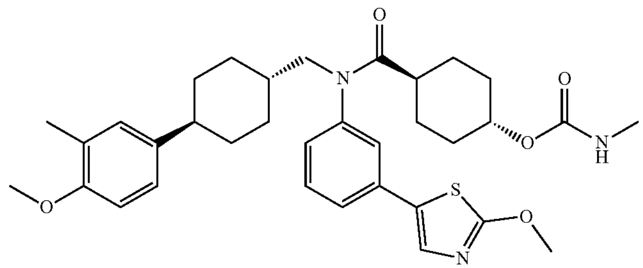 | trans-4-(((trans-4-(4-Methoxy-3-methylphenyl)cyclohexyl)methyl)(3-(2-methoxythiazol-5-yl)phenyl)carbamoyl)cyclohexyl methylcarbamate |
| 2.02 | 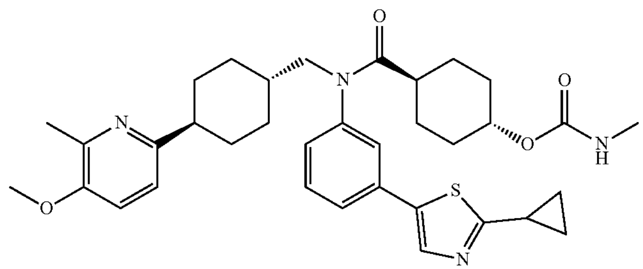 | trans-4-((3-(2-Cyclopropylthiazol-5-yl)phenyl)((trans-4-(5-methoxy-6-methylpyridin-2-yl)cyclohexyl)methyl)carbamoyl)cyclohexyl methylcarbamate |
| 2.03 | 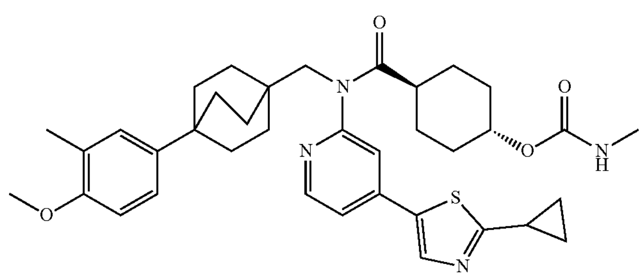 | 4-((4-(2-Cyclopropylthiazol-5-yl)pyridin-2-yl)((4-(4-methoxy-3-methylphenyl)bicyclo[2.2.2]octan-1-yl)methyl)carbamoyl)cyclohexyl trans-methylcarbamate |

TABLE 1-continued

| Compound No | Structure | Chemical Name |
|---|---|---|
| 2.04 | 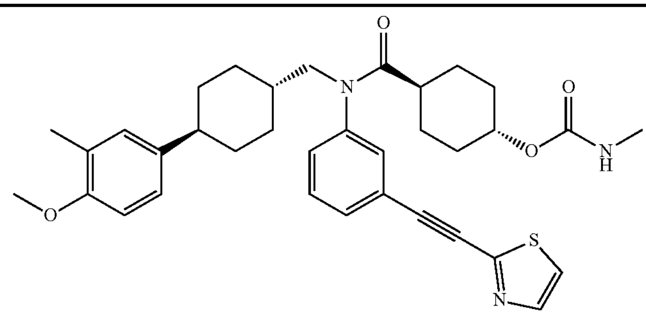 | trans-4-(((trans-4-(4-Methoxy-3-methylphenyl)cyclohexyl)methyl)(3-(thiazol-2-yiethynyl)phenyl)carbamoyl)cyclohexyl methylcarbamate |
| 2.05 | 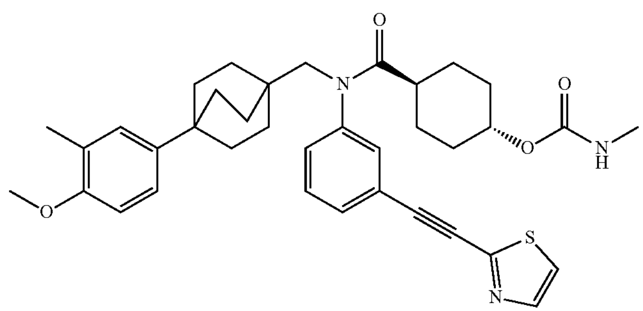 | 4-(((4-(4-Methoxy-3-methylphenyl)bicyclo[2.2.2]octan-1-yl)methyl)(3-(thiazol-2-ylethynyl)phenyl)carbamoyl)cyclohexyl trans-methylcarbamate |
| 2.06 | 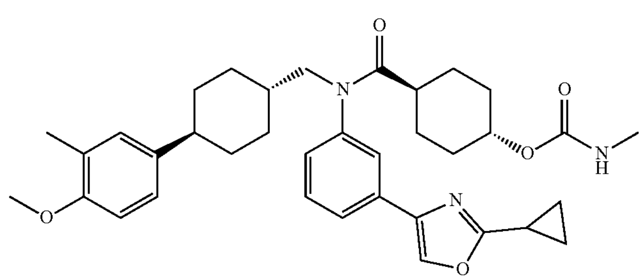 | trans-4-((3-(2-Cyclopropyloxazol-4-yl)phenyl)(trans-4-(4-methoxy-3-methylphenyl)cyclohexyl)methyl)carbamoyl)-cyclohexyl methylcarbamate |

TABLE 1-continued

| Compound No | Structure | Chemical Name |
|---|---|---|
| 2.07 | 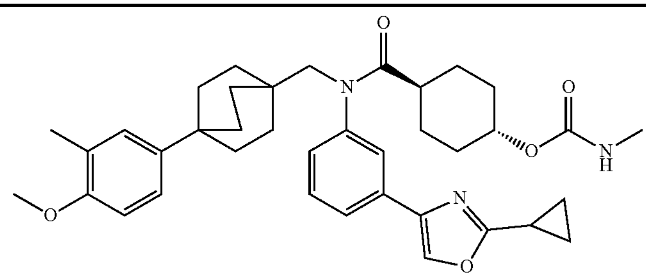 | 4-((3-(2-Cyclopropyloxazol-4-yl)phenyl)(4-(4-methoxy-3-methylphenyl)bicyclo[2.2.2]octan-1-yl)methyl)carbamoyl)cyclohexyl trans-methylcarbamate |
| 2.08 | 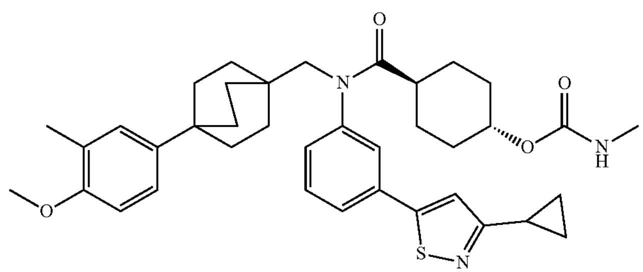 | 4-((3-(3-Cyclopropylisothiazol-5-yl)phenyl)(4-(4-methoxy-3-methylphenyl)bicyclo[2.2.2]octan-1-yl)methyl)carbamoyl)cyclohexyl trans-methylcarbamate |
| 3 | 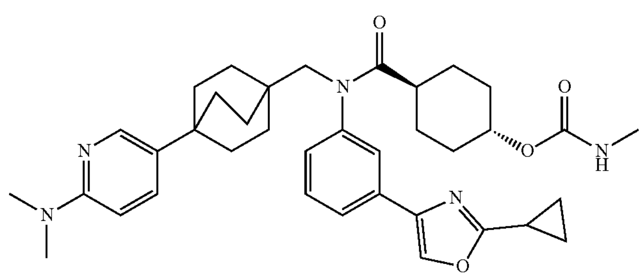 | 4-((3-(2-Cyclopropyloxazol-4-yl)phenyl)(4-(6-(dimethylamino)pyridin-3-yl)bicyclo[2.2.2]octan-1-yl)methyl)carbamoyl)cyclohexyl trans-methylcarbamate |

TABLE 1-continued

| Compound No | Structure | Chemical Name |
|---|---|---|
| 3.01 | 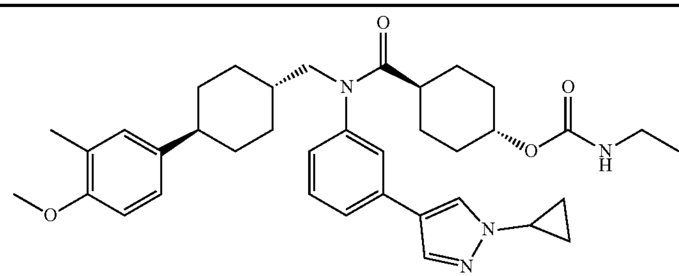 | trans-4-((3-(1-Cyclopropyl-1H-pyrazol-4-yl)phenyl)((trans-4-(4-methoxy-3-methylphenyl)cyclohexyl)methyl)carbamoyl)-cyclohexyl ethylcarbamate |
| 3.02 | 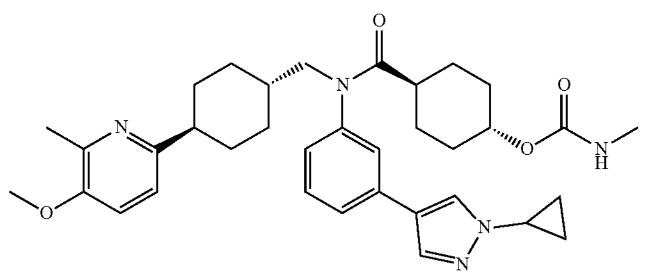 | trans-4-((3-(1-Cyclopropyl-1H-pyrazol-4-yl)phenyl)((trans-4-(5-methoxy-6-methylpyridin-2-yl)cyclohexyl)methyl)carbamoyl)cyclohexyl methylcarbamate |
| 3.03 | 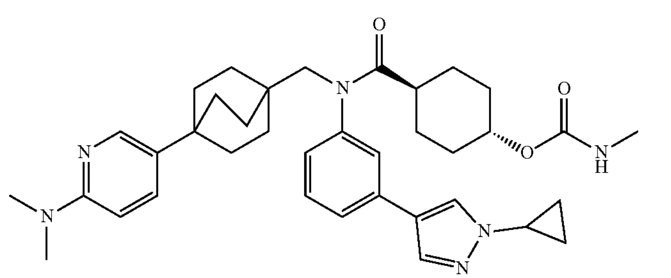 | 4-((3-(1-Cyclopropyl-1H-pyrazol-4-yl)phenyl)(4-(6-(dimethylamino)pyridin-yl)bicyclo[2.2.2]octan-1-yl)methyl)carbamoyl)cyclohexyl trans-methylcarbamate |

TABLE 1-continued

| Compound No | Structure | Chemical Name |
|---|---|---|
| 3.04 | 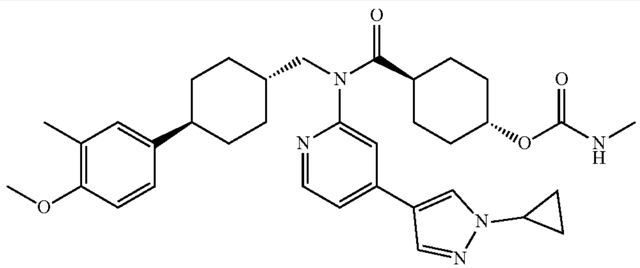 | trans-4-((4-(1-Cyclopropyl-1H-pyrazol-4-yl)pyridin-2-yl)(trans-4-(4-methoxy-3-methylphenyl)cyclohexyl)methyl)carbamoyl)-cyclohexyl methylcarbamate |
| 3.05 | 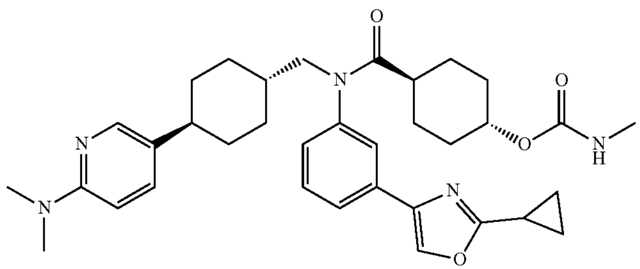 | trans-4-((3-(2-Cyclopropyloxazol-4-yl)phenyl)(trans-4-(6-(dimethylamino)pyridine-3-yl)cyclohexyl)methyl)carbamoyl)cyclohexyl methylcarbamate |
| 4 | 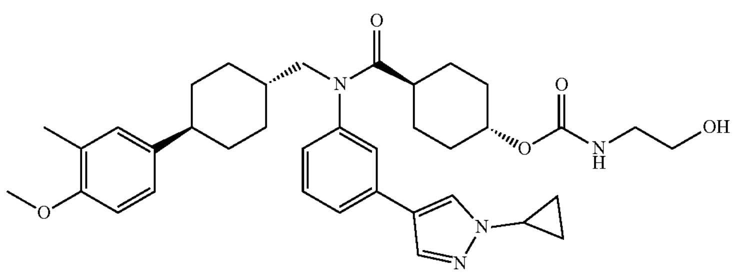 | trans-4-((3-(1-Cyclopropyl-1H-pyrazol-4-yl)phenyl)(trans-4-(4-methoxy-3-methylphenyl)cyclohexyl)methyl)carbamoyl)-cyclohexyl (2-hydroxyethyl)carbamate |

TABLE 1-continued

| Compound No | Structure | Chemical Name |
|---|---|---|
| 4.01 | 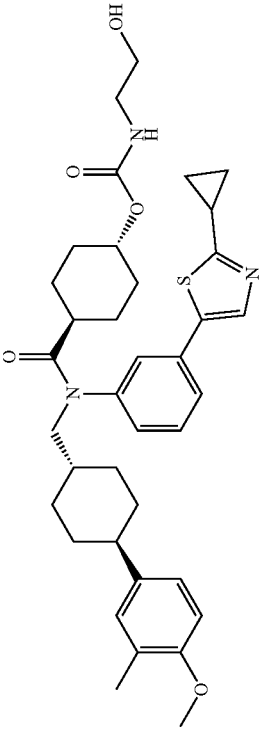 | trans-4-((3-(2-Cyclopropylthiazol-5-yl)phenyl)(trans-4-(4-methoxy-3-methylphenyl)cyclohexyl)methyl)carbamoyl)-cyclohexyl (2-hydroxyethyl)carbamate |
| 4.02 | 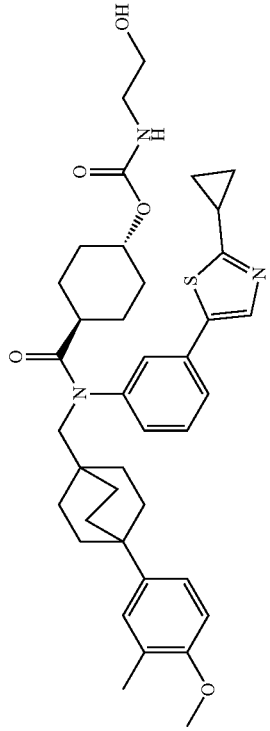 | 4-((3-(2-Cyclopropylthiazol-5-yl)phenyl)(4-(4-methoxy-3-methylphenyl)bicyclo[2.2.2]octan-1-yl)methyl)carbamoyl)cyclohexyl (2-hydroxyethyl)trans-carbamate |
| 4.03 | 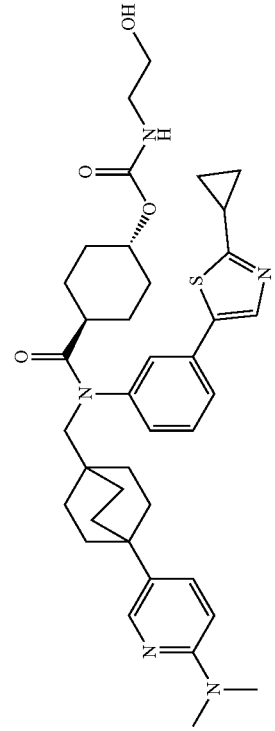 | 4-((3-(2-Cyclopropylthiazol-5-yl)phenyl)(4-(6-(dimethylamino)pyridin-3-yl)bicyclo[2.2.2]octan-1-yl)methyl)carbamoyl)cyclohexyl (2-hydroxyethyl)trans-carbamate |

TABLE 1-continued

| Compound No | Structure | Chemical Name |
|---|---|---|
| 4.04 | 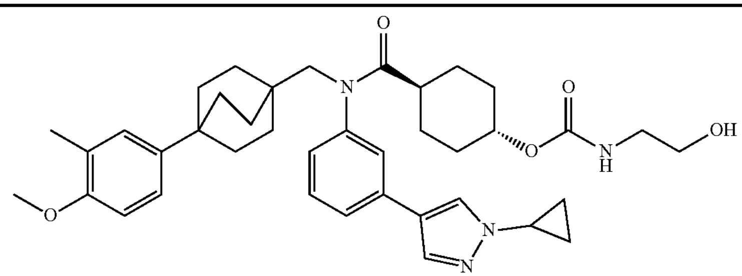 | 4-((3-(1-Cyclopropyl-1H-pyrazol-4-yl)phenyl)(4-(4-methoxy-3-methylphenyl)bicyclo[2.2.2]octan-1-yl)methyl)carbamoyl)cyclohexyl (2-hydroxyethyl)trans-carbamate |
| 4.05 | 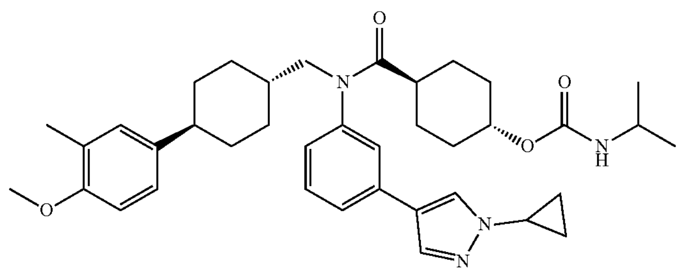 [SMILES: CCNC(=O)O[C@H]1CC[C@H](C(=O)N(C[C@H]2CC[C@H](c3ccc(OC)c(C)c3)CC2)c2cccc(-c3cnn(C4CC4)c3)c2)CC1] | trans-4-((3-(1-Cyclopropyl-1H-pyrazol-4-yl)phenyl)(trans-4-(4-methoxy-3-methylphenyl)cyclohexyl)methyl)carbamoyl)cyclohexyl isopropylcarbamate |
| 4.06 | 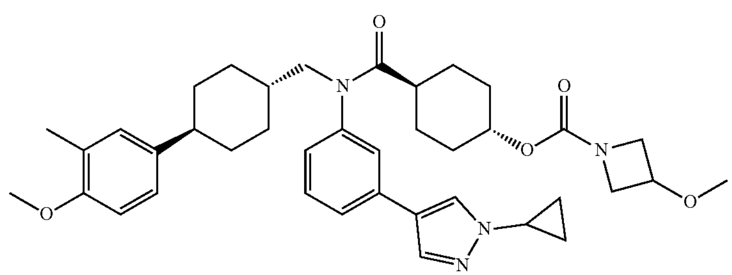 | trans-4-((3-(1-Cyclopropyl-1H-pyrazol-4-yl)phenyl)(trans-4-(4-methoxy-3-methylphenyl)cyclohexyl)methyl)carbamoyl)cyclohexyl 3-methoxyazetidine-1-carboxylate |

TABLE 1-continued

| Compound No | Structure | Chemical Name |
|---|---|---|
| 4.07 | 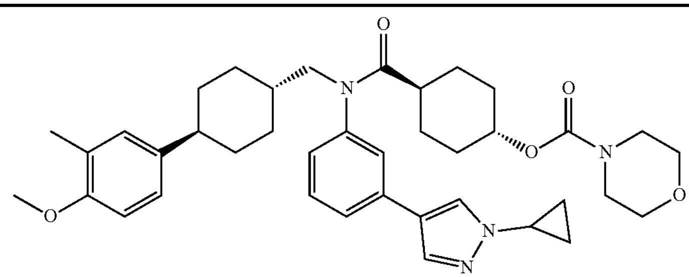 | trans-4-((3-(1-Cyclopropyl-1H-pyrazol-4-yl)phenyl)((trans-4-(4-methoxy-3-methylphenyl)cyclohexyl)methyl)carbamoyl)-cyclohexyl morpholine-4-carboxylate |
| 4.08 | 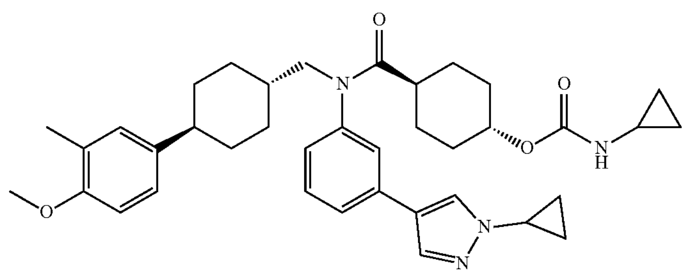 [SMILES: COc1ccc([C@H]2CC[C@H](CN(c3cccc(-c4cnn(C5CC5)c4)c3)C(=O)[C@H]3CC[C@H](OC(=O)NC4CC4)CC3)CC2)cc1C] | trans-4-((3-(1-Cyclopropyl-1H-pyrazol-4-yl)phenyl)((trans-4-(4-methoxy-3-methylphenyl)cyclohexyl)methyl)carbamoyl)-cyclohexyl cyclopropylcarbamate |
| 4.09 | 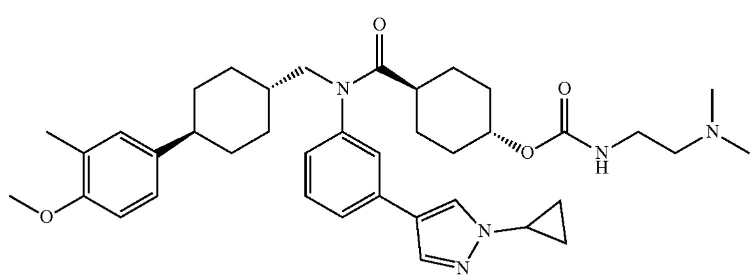 | trans-4-((3-(1-Cyclopropyl-1H-pyrazol-4-yl)phenyl)((trans-4-(4-methoxy-3-methylphenyl)cyclohexyl)methyl)carbamoyl)-cyclohexyl (2-(dimethylamino)ethyl)carbamate |

TABLE 1-continued

| Compound No | Structure | Chemical Name |
|---|---|---|
| 4.10 | 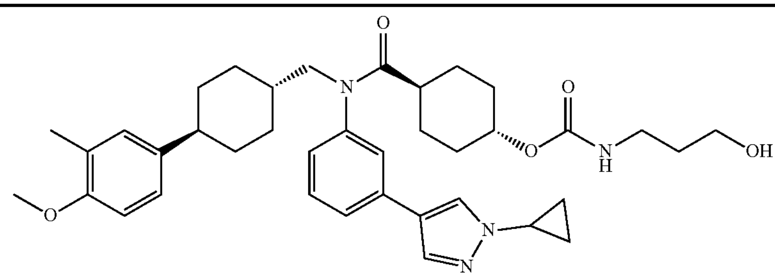 | trans-4-((3-(1-Cyclopropyl-1H-pyrazol-4-yl)phenyl)((trans-4-(4-methoxy-3-methylphenyl)cyclohexyl)methyl)carbamoyl)-cyclohexyl (3-hydroxypropyl)carbamate |
| 4.11 | 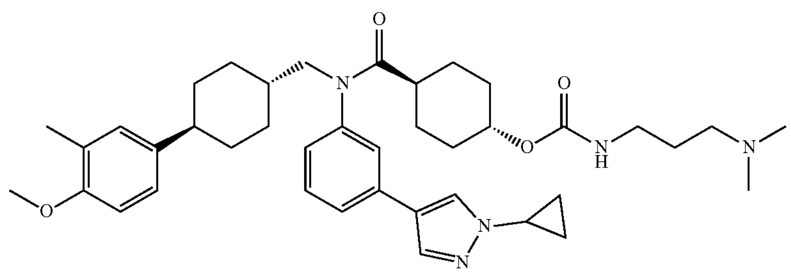 | trans-4-((3-(1-Cyclopropyl-1H-pyrazol-4-yl)phenyl)((trans-4-(4-methoxy-3-methylphenyl)cyclohexyl)methyl)carbamoyl)-cyclohexyl (3-(dimethylamino)propyl)carbamate |
| 4.12 | 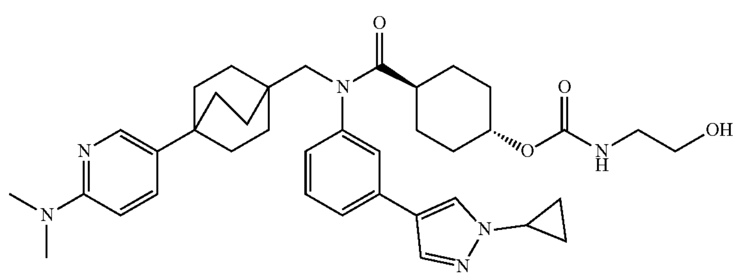 [SMILES: CN(C)c1ccc(C23CCC(CN(c4cccc(-c5cnn(C6CC6)c5)c4)C(=O)[C@H]4CC[C@H](OC(=O)NCCO)CC4)(CC2)CC3)cn1] | 4-((3-(1-Cyclopropyl-1H-pyrazol-4-yl)phenyl)(4-(6-(dimethylamino)pyridin-3-yl)bicyclo[2.2.2]octan-1-yl)methyl)carbamoyl)cyclohexyl (2-hydroxyethyl)trans-carbamate |

TABLE 1-continued

| Compound No | Structure | Chemical Name |
|---|---|---|
| 4.13 | 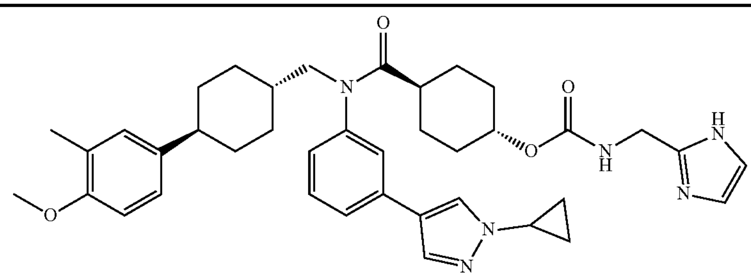 | trans-4-((3-(1-Cyclopropyl-1H-pyrazol-4-yl)phenyl)((trans-4-(4-methoxy-3-methylphenyl)cyclohexyl)methyl)carbamoyl)-cyclohexyl ((1H-imidazol-2-yl)methyl)carbamate |
| 4.14 | 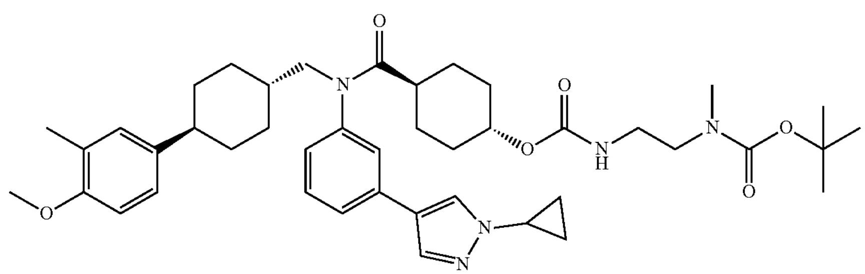 [SMILES: COc1ccc([C@H]2CC[C@H](CN(c3cccc(-c4cnn(C5CC5)c4)c3)C(=O)[C@H]3CC[C@H](OC(=O)NCCN(C)C(=O)OC(C)(C)C)CC3)CC2)cc1C] | tert-Butyl (2-((((trans-4-((3-(1-cyclopropyl-1H-pyrazol-4-yl)phenyl)((trans-4-(4-methoxy-3-methylphenyl)cyclohexyl)methyl)carbamoyl)-cyclohexyl)oxy)carbonyl)amino)ethyl)(methyl)-carbamate |
| 4.15 | 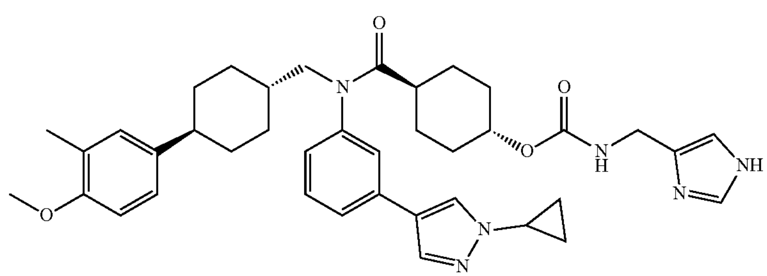 [SMILES: COc1ccc([C@H]2CC[C@H](CN(c3cccc(-c4cnn(C5CC5)c4)c3)C(=O)[C@H]3CC[C@H](OC(=O)NCc4c[nH]cn4)CC3)CC2)cc1C] | trans-4-((3-(1-Cyclopropyl-1H-pyrazol-4-yl)phenyl)((trans-4-(4-methoxy-3-methylphenyl)cyclohexyl)methyl)carbamoyl)-cyclohexyl ((1H-imidazol-4-yl)methyl)carbamate |

TABLE 1-continued

| Compound No | Structure | Chemical Name |
|---|---|---|
| 4.16 | 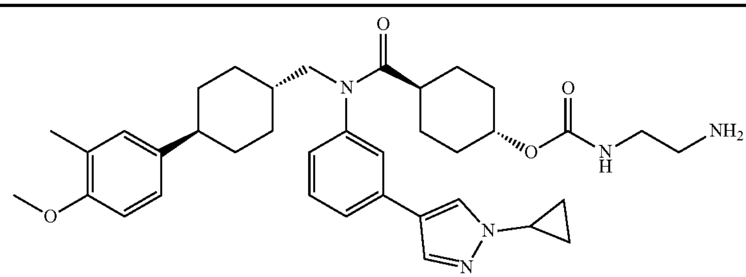 | trans-4-((3-(1-Cyclopropyl-1H-pyrazol-4-yl)phenyl)((trans-4-(4-methoxy-3-methylphenyl)cyclohexyl)methyl)carbamoyl)-cyclohexyl (2-aminoethyl)carbamate |
| 4.17 | 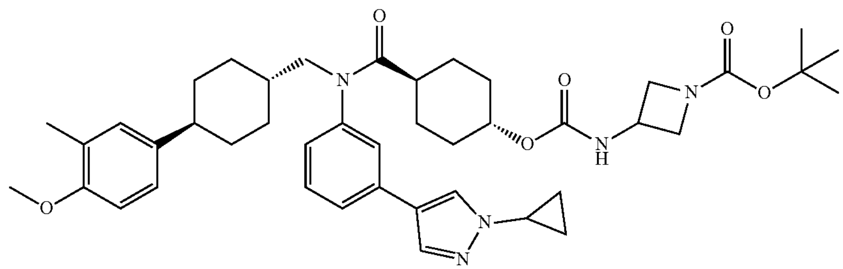 [SMILES: COc1ccc([C@H]2CC[C@H](CN(c3cccc(-c4cnn(C5CC5)c4)c3)C(=O)[C@H]3CC[C@H](OC(=O)NC4CN(C(=O)OC(C)(C)C)C4)CC3)CC2)cc1C] | tert-Butyl 3-((((trans-4-((3-(1-cyclopropyl-1H-pyrazol-4-yl)phenyl)((trans-4-(4-methoxy-3-methylphenyl)cyclohexyl)methyl)carbamoyl)cyclohexyl)oxy)carbonyl)amino)azetidine-1-carboxylate |
| 4.18 | 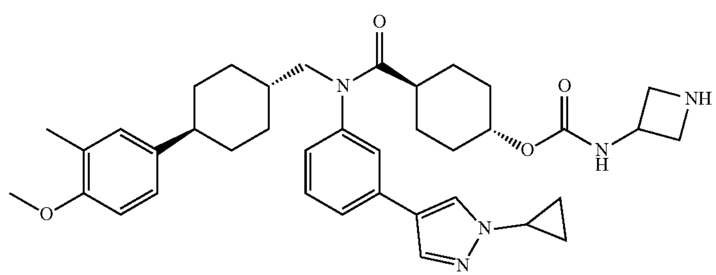 [SMILES: COc1ccc([C@H]2CC[C@H](CN(c3cccc(-c4cnn(C5CC5)c4)c3)C(=O)[C@H]3CC[C@H](OC(=O)NC4CNC4)CC3)CC2)cc1C] | trans-4-((3-(1-Cyclopropyl-1H-pyrazol-4-yl)phenyl)((trans-4-(4-methoxy-3-methylphenyl)cyclohexyl)methyl)carbamoyl)-cyclohexyl azetidin-3-ylcarbamate |

TABLE 1-continued

| Compound No | Structure | Chemical Name |
|---|---|---|
| 4.19 | 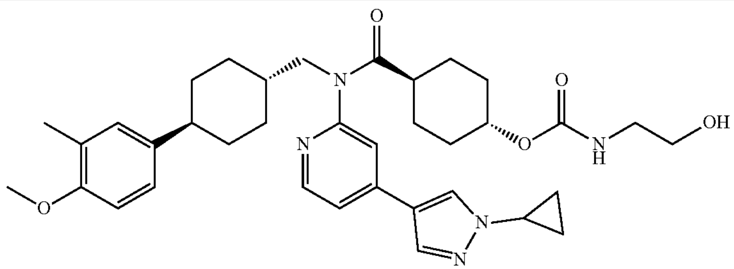 | trans-4-((4-(1-Cyclopropyl-1H-pyrazol-4-yl)pyridin-2-yl)(trans-4-(4-methoxy-3-methylphenyl)cyclohexyl)methyl)carbamoyl)-cyclohexyl (2-hydroxyethyl)carbamate |
| 4.20 | 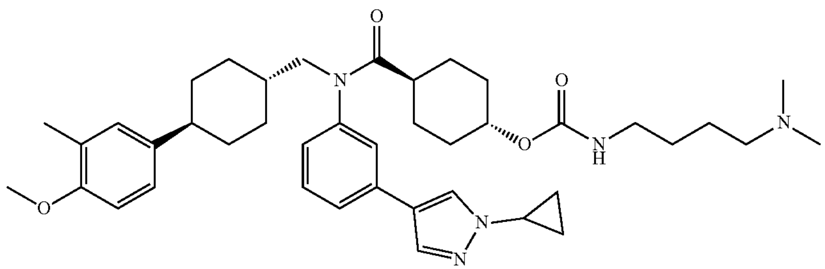 | trans-4-((3-(1-Cyclopropyl-1H-pyrazol-4-yl)phenyl)(trans-4-(4-methoxy-3-methylphenyl)cyclohexyl)methyl)carbamoyl)-cyclohexyl (4-(dimethylamino)butyl)carbamate |
| 4.21 | 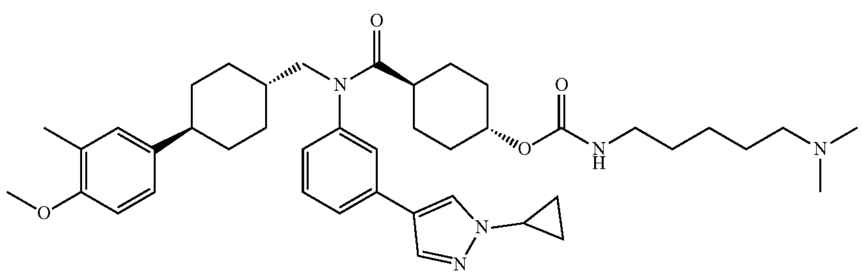 | trans-4-((3-(1-Cyclopropyl-1H-pyrazol-4-yl)phenyl)(trans-4-(4-methoxy-3-methylphenyl)cyclohexyl)methyl)carbamoyl)-cyclohexyl (5-(dimethylamino)pentyl)carbamate |

TABLE 1-continued

| Compound No | Structure | Chemical Name |
|---|---|---|
| 4.22 | 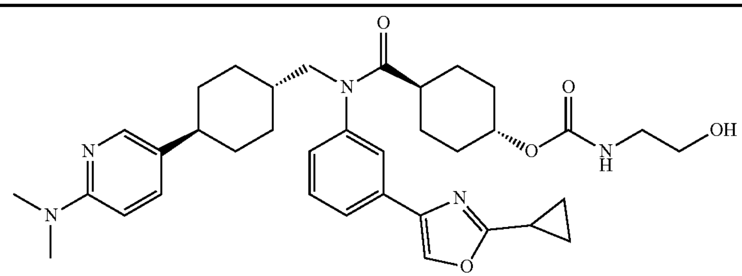 | trans-4-((3-(2-Cyclopropyloxazol-4-yl)phenyl)((trans-4-(6-(dimethylamino)pyridine-3-yl)cyclohexyl)methyl)carbamoyl)cyclohexyl (2-hydroxyethyl)carbamate |
| 4.23 | 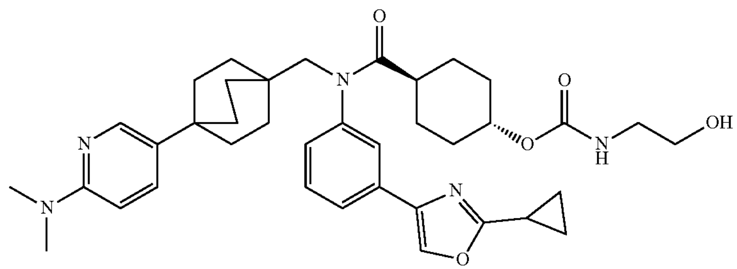 [SMILES: CN(C)c1ccc(C23CCC(CN(c4cccc(-c5coc(C6CC6)n5)c4)C(=O)[C@H]4CC[C@H](OC(=O)NCCO)CC4)(CC2)CC3)cn1] | 4-((3-(2-Cyclopropyloxazol-4-yl)phenyl)((4-(6-(dimethylamino)pyridin-3-yl)bicyclo[2.2.2]octan-1-yl)methyl)carbamoyl)cyclohexyl trans-(2-hydroxyethyl)carbamate |
| 4.24 | 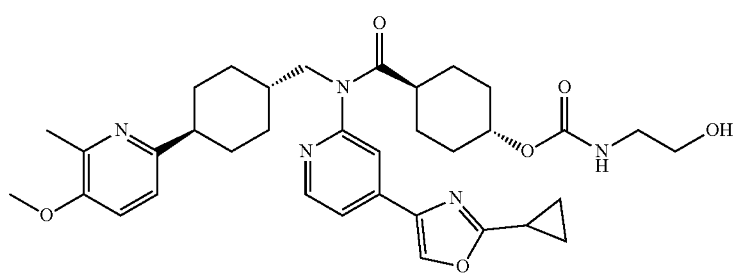 | trans-4-((4-(2-Cyclopropyloxazol-4-yl)pyridine-2-yl)(trans-4-(5-methoxy-6-methylpyridin-2-yl)cyclohexyl)methyl)carbamoyl)cyclohexyl (2-hydroxyethyl)carbamate |

TABLE 1-continued

| Compound No | Structure | Chemical Name |
|---|---|---|
| 4.25 | 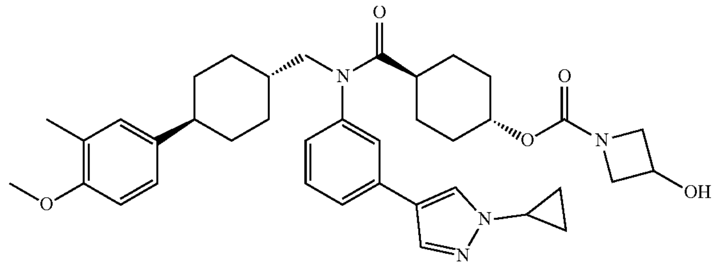 | trans-4-((3-(1-Cyclopropyl-1H-pyrazol-4-yl)phenyl)(trans-4-(4-methoxy-3-methylphenyl)cyclohexyl)methyl)carbamoyl)cyclohexyl 3-hydroxyazetidine-1-carboxylate |
| 4.26 | 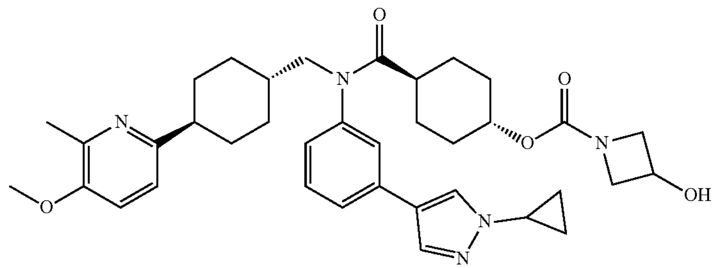 | trans-4-((3-(1-Cyclopropyl-1H-pyrazol-4-yl)phenyl)(trans-4-(5-methoxy-6-methylpyridin-2-yl)cyclohexyl)methyl)carbamoyl)cyclohexyl 3-hydroxyazetidine-1-carboxylate |
| 4.27 | 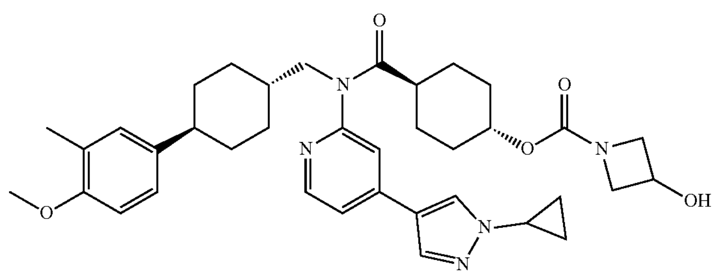 | trans-4-((4-(1-Cyclopropyl-1H-pyrazol-4-yl)pyridin-2-yl)(trans-4-(4-methoxy-3-methylphenyl)cyclohexyl)methyl)carbamoyl)cyclohexyl 3-hydroxyazetidine-1-carboxylate |

TABLE 1-continued

| Compound No | Structure | Chemical Name |
|---|---|---|
| 4.28 | 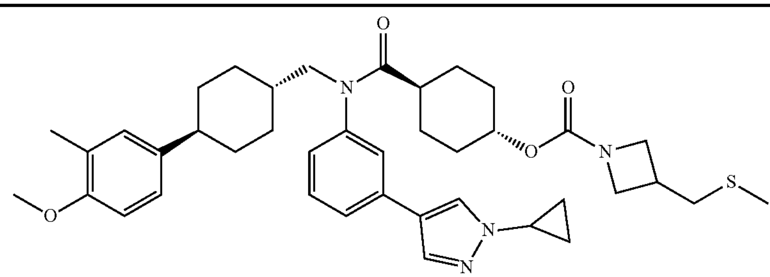 | trans-4-((3-(1-Cyclopropyl-1H-pyrazol-4-yl)phenyl)((trans-4-(4-methoxy-3-methylphenyl)cyclohexyl)methyl)carbamoyl)-cyclohexyl 3-((methylthio)methyl)azetidine-1-carboxylate |
| 5 | 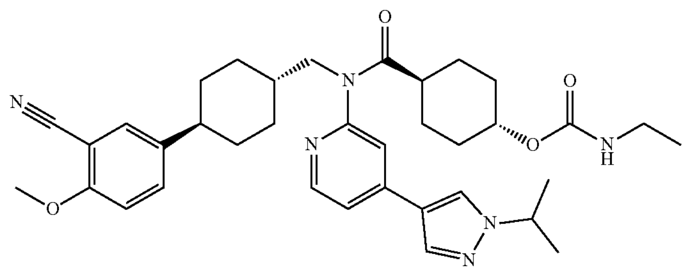 | trans-4-(((trans-4-methoxyphenyl)cyclohexyl)methyl)(4-(1-isopropyl-1H-pyrazol-4-yl)pyridin-2-yl)carbamoyl)cyclohexyl ethylcarbamate |
| 5.01 | 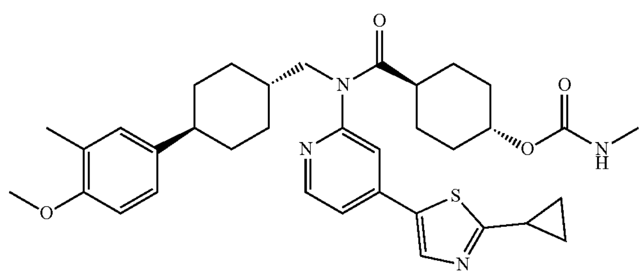 | trans-4-((4-(2-Cyclopropylthiazol-5-yl)pyridin-2-yl)((trans-4-(4-methoxy-3-methylphenyl)cyclohexyl)methyl)carbamoyl)-cyclohexyl methylcarbamate |

TABLE 1-continued

| Compound No | Structure | Chemical Name |
|---|---|---|
| 5.02 | 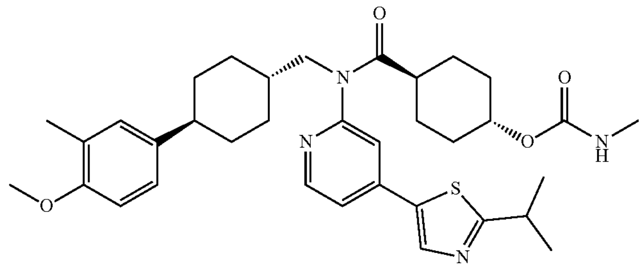 | trans-4-((4-(2-Isopropylthiazol-5-yl)pyridin-2-yl)(trans-4-(4-methoxy-3-methylphenyl)cyclohexyl)methyl)carbamoyl)-cyclohexyl methylcarbamate |
| 5.03 | 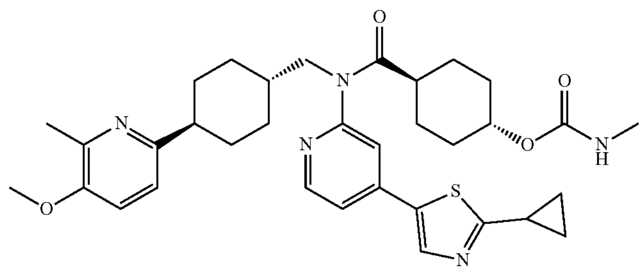 | trans-4-((4-(2-Cyclopropylthiazol-5-yl)pyridin-2-yl)(trans-4-(5-methoxy-6-methylpyridin-2-yl)cyclohexyl)methyl)carbamoyl)cyclohexyl methylcarbamate |
| 5.04 | 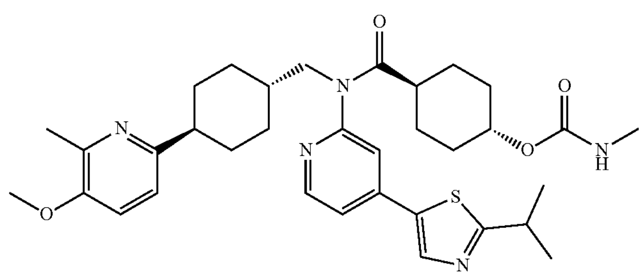 | trans-4-((4-(2-Isopropylthiazol-5-yl)pyridin-2-yl)(trans-4-(5-methoxy-6-methylpyridin-2-yl)cyclohexyl)methyl)carbamoyl)cyclohexyl methylcarbamate |

TABLE 1-continued

| Compound No | Structure | Chemical Name |
|---|---|---|
| 5.05 | 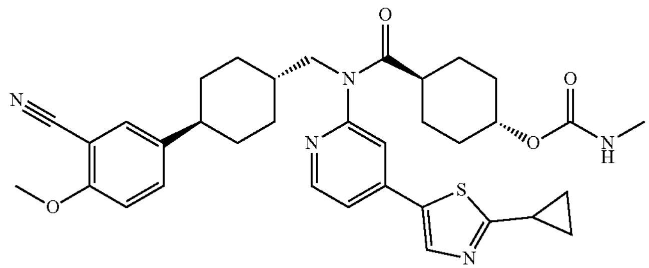 | trans-4-(((trans-4-(3-Cyano-4-methoxyphenyl)cyclohexyl)methyl)(4-(2-cyclopropylthiazol-5-yl)pyridin-2-yl)carbamoyl)cyclohexyl methylcarbamate |
| 5.06 | 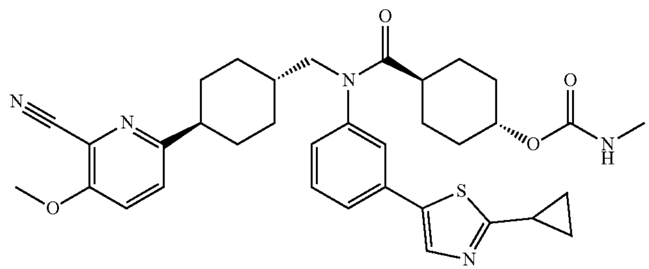 | trans-4-(((trans-4-(6-Cyano-5-methoxypyridin-2-yl)cyclohexyl)methyl)(3-(2-cyclopropylthiazol-5-yl)phenyl)carbamoyl)cyclohexyl methyl carbamate |
| 5.07 | 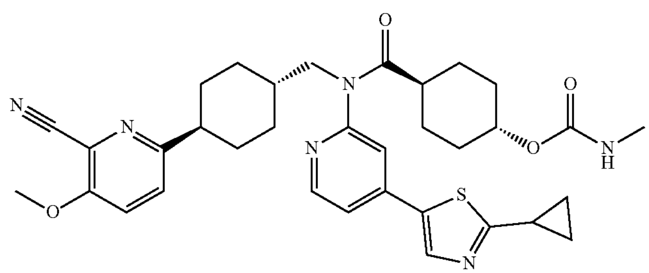 | trans-4-(((trans-4-(6-Cyano-5-methoxypyridin-2-yl)cyclohexyl)methyl)(4-(2-cyclopropylthiazol-5-yl)pyridin-2-yl)carbamoyl)cyclohexyl methylcarbamate |

TABLE 1-continued

| Compound No | Structure | Chemical Name |
|---|---|---|
| 5.08 | 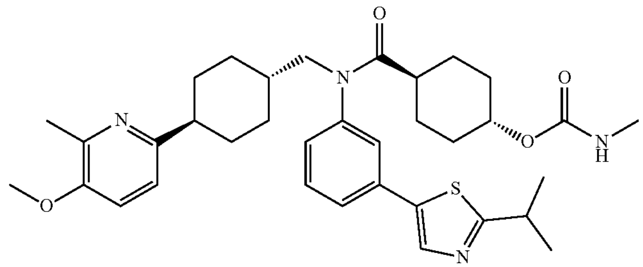 | trans-4-((3-(2-Isopropylthiazol-5-yl)phenyl)(trans-4-(5-methoxy-6-methylpyridin-2-yl)cyclohexyl)methyl)carbamoyl)cyclohexyl methylcarbamate |
| 5.09 | 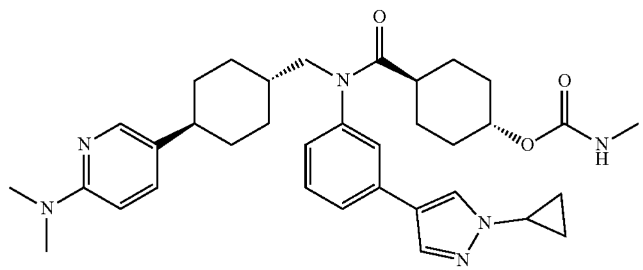 | trans-4-((3-(1-Cyclopropyl-1H-pyrazol-4-yl)phenyl)((trans-4-(6-(dimethylamino)pyridin-3-yl)cyclohexyl)methyl)carbamoyl)cyclohexyl methylcarbamate |
| 5.10 | 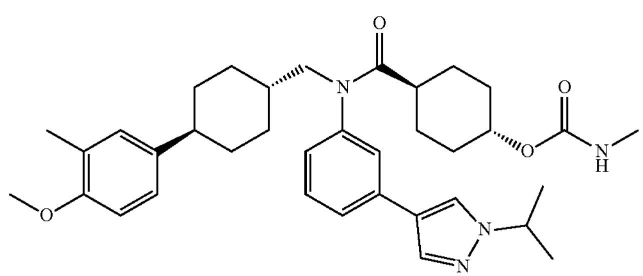 | trans-4-((3-(1-Isopropyl-1H-pyrazol-4-yl)phenyl)(trans-4-(4-methoxy-3-methylphenyl)cyclohexyl)methyl)carbamoyl)cyclohexyl methylcarbamate |

TABLE 1-continued

| Compound No | Structure | Chemical Name |
|---|---|---|
| 5.11 | 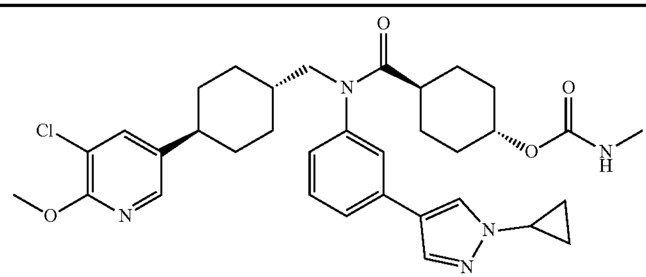 | trans-4-(((trans-4-(5-Chloro-6-methoxypyridin-3-yl)cyclohexyl)methyl)(3-(1-cyclopropyl-1H-pyrazol-4-yl)phenyl)carbamoyl)cyclohexyl methylcarbamate |
| 5.12 | 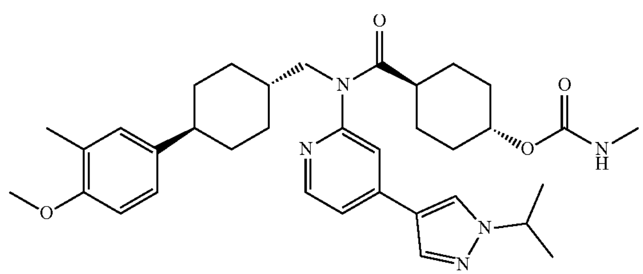 | trans-4-((4-(1-Isopropyl-1H-pyrazol-4-yl)pyridin-2-yl)((trans-4-(4-methoxy-3-methylphenyl)cyclohexyl)methyl)carbamoyl)cyclohexyl methylcarbamate |
| 5.13 | 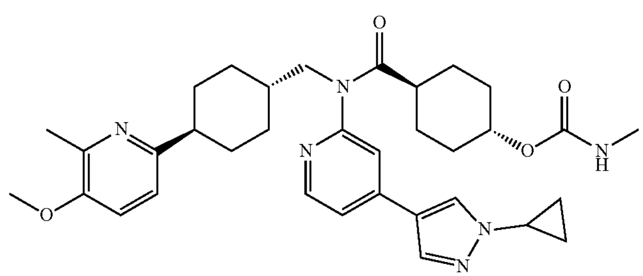 | trans-4-((4-(1-Cyclopropyl-1H-pyrazol-4-yl)pyridin-2-yl)((trans-4-(5-methoxy-6-methylpyridin-2-yl)cyclohexyl)methyl)carbamoyl)cyclohexyl methylcarbamate |

TABLE 1-continued

| Compound No | Structure | Chemical Name |
|---|---|---|
| 5.14 | 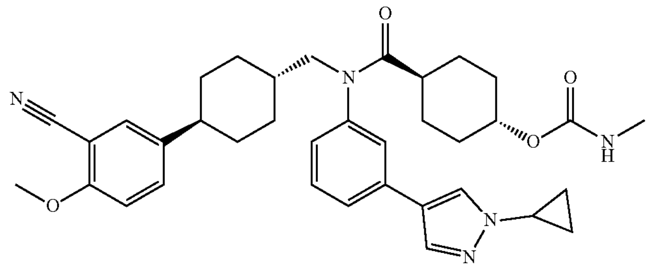 | trans-4-((trans-4-(3-Cyano-4-methoxyphenyl)cyclohexyl)methyl)(3-(1-cyclopropyl-1H-pyrazol-4-yl)phenyl)carbamoyl)cyclohexyl methylcarbamate |
| 5.15 | 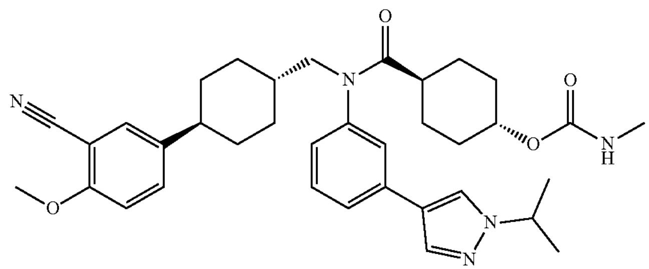 | trans-4-((trans-4-(3-Cyano-4-methoxyphenyl)cyclohexyl)methyl)(3-(1-Isopropyl-1H-pyrazol-4-yl)phenyl)carbamoyl)cyclohexyl methylcarbamate |
| 5.16 | 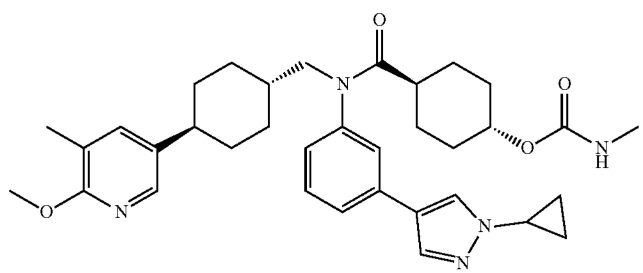 | trans-4-((3-(1-Cyclopropyl-1H-pyrazol-4-yl)phenyl)(trans-4-(6-methoxy-5-methylpyridin-3-yl)cyclohexyl)methyl)carbamoyl)cyclohexyl methylcarbamate |

TABLE 1-continued

| Compound No | Structure | Chemical Name |
|---|---|---|
| 5.17 | 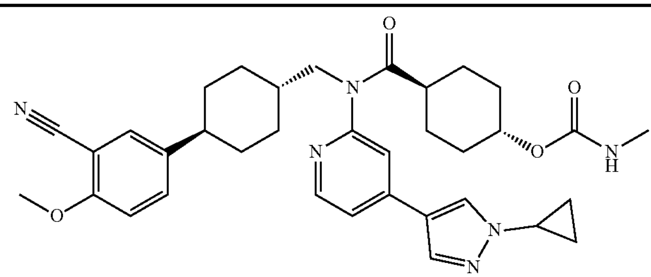 | trans-4-(((trans-4-(3-Cyano-4-methoxyphenyl)cyclohexyl)methyl)(4-(1-cyclopropyl-1H-pyrazol-4-yl)pyridin-2-yl)carbamoyl)cyclohexyl methylcarbamate |
| 5.18 | 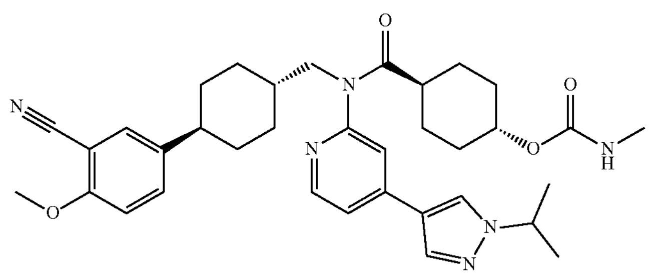 | trans-4-(((trans-4-(3-Cyano-4-methoxyphenyl)cyclohexyl)methyl)(4-(1-isopropyl-1H-pyrazol-4-yl)pyridin-2-yl)carbamoyl)cyclohexyl methylcarbamate |
| 5.19 | 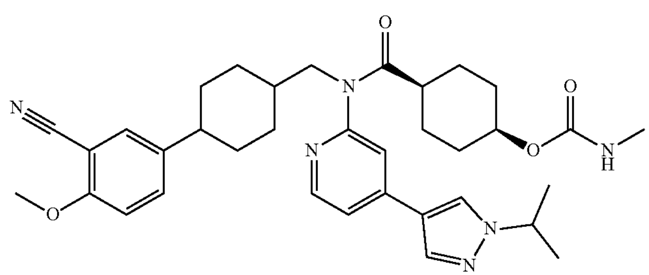 | cis-4-(((4-(3-Cyano-4-methoxyphenyl)cyclohexyl)methyl)(4-(1-isopropyl-1H-pyrazol-4-yl)pyridin-2-yl)carbamoyl)cyclohexyl methylcarbamate |

TABLE 1-continued

| Compound No | Structure | Chemical Name |
|---|---|---|
| 5.20 | 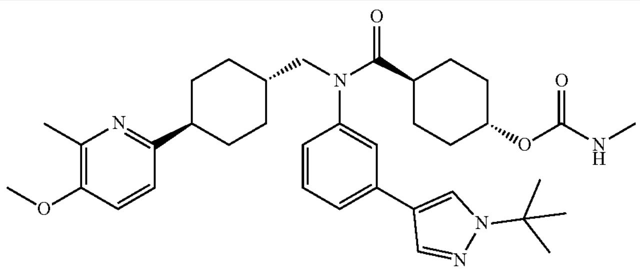 | trans-4-((3-(1-(tert-Butyl)-1H-pyrazol-4-yl)phenyl)((trans-4-(5-methoxy-6-methylpyridin-2-yl)cyclohexyl)methyl)carbamoyl)cyclohexyl methylcarbamate |
| 5.21 | 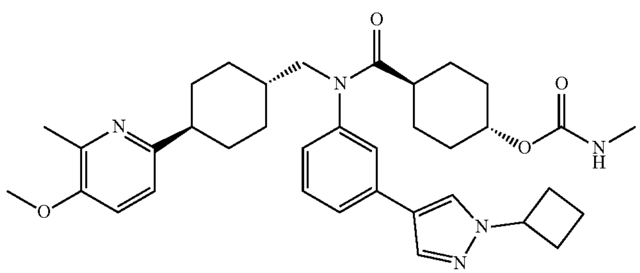 | trans-4-((3-(1-Cyclobutyl-1H-pyrazol-4-yl)phenyl)((trans-4-(5-methoxy-6-methylpyridin-2-yl)cyclohexyl)methyl)carbamoyl)cyclohexyl methylcarbamate |
| 5.22 | 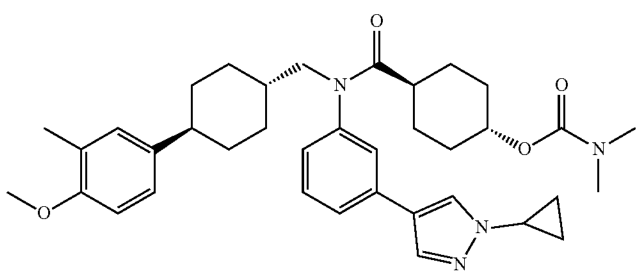 | trans-4-((3-(1-Cyclopropyl-1H-pyrazol-4-yl)phenyl)((trans-4-(4-methoxy-3-methylphenyl)cyclohexyl)methyl)carbamoyl)cyclohexyl dimethylcarbamate |

TABLE 1-continued

| Compound No | Structure | Chemical Name |
|---|---|---|
| 5.23 | 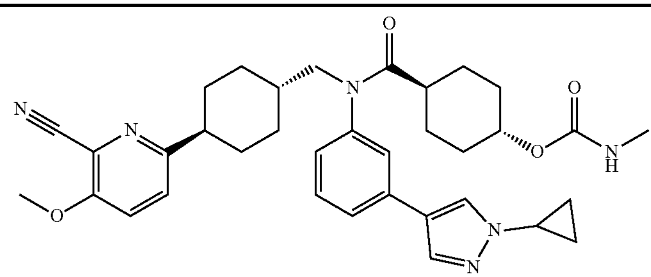 | trans-4-(6-Cyano-5-methoxypyridin-2-yl)cyclohexyl)methyl)(3-(1-cyclopropyl-1H-pyrazol-4-yl)phenyl)carbamoyl)cyclohexyl methylcarbamate |
| 5.24 | 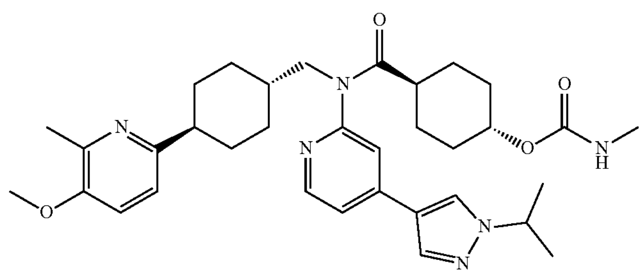 | trans-4-((4-(1-Isopropyl-1H-pyrazol-4-yl)pyridin-2-yl)((trans-4-(5-methoxy-6-methylpyridin-2-yl)cyclohexyl)methyl)carbamoyl)cyclohexyl methylcarbamate |
| 5.25 | 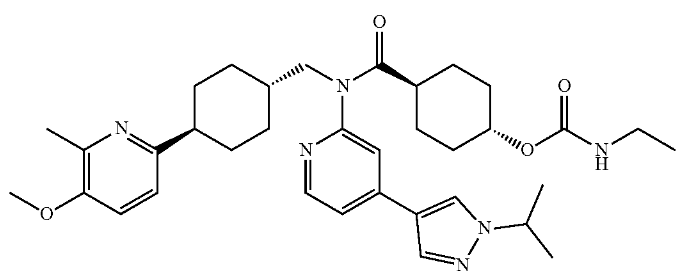 [SMILES: CCNC(=O)O[C@H]1CC[C@H](C(=O)N(C[C@H]2CC[C@H](c3ccc(OC)c(C)n3)CC2)c2cc(-c3cnn(C(C)C)c3)ccn2)CC1] | trans-4-((4-(1-Isopropyl-1H-pyrazol-4-yl)pyridin-2-yl)((trans-4-(5-methoxy-6-methylpyridin-2-yl)cyclohexyl)methyl)carbamoyl)cyclohexyl ethylcarbamate |

TABLE 1-continued

| Compound No | Structure | Chemical Name |
|---|---|---|
| 5.26 | 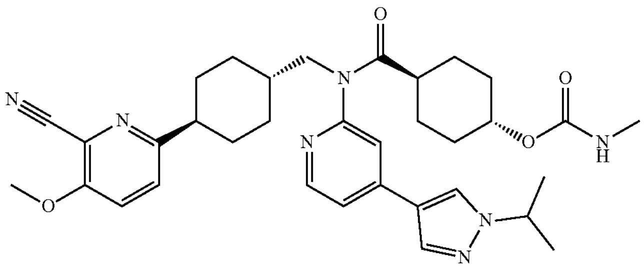 | trans-4-(((trans-4-(6-Cyano-5-methoxypyridin-2-yl)cyclohexyl)methyl)(4-(1-isopropyl-1H-pyrazol-4-yl)pyridin-2-yl)carbamoyl)cyclohexyl methylcarbamate |
| 5.27 | 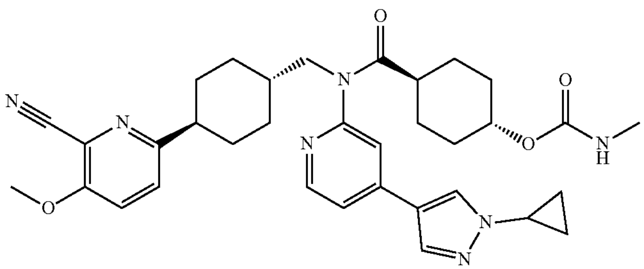 | trans-4-(((trans-4-(6-Cyano-5-methoxypyridin-2-yl)cyclohexyl)methyl)(4-(1-cyclopropyl-1H-pyrazol-4-yl)pyridin-2-yl (carbamoyl)cyclohexyl methylcarbamate |
| 5.28 | 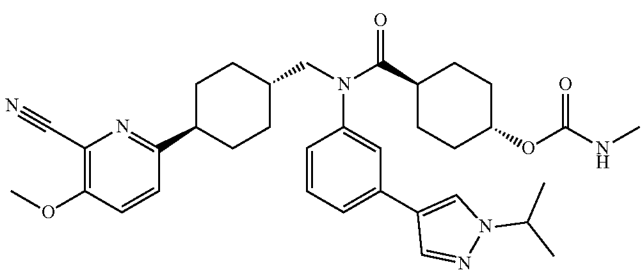 | trans-4-(((trans-4-(6-Cyano-5-methoxypyridin-2-yl)cyclohexyl)methyl)(3-(1-isopropyl-1H-pyrazol-4-yl)phenyl)carbamoyl)cyclohexyl methylcarbamate |

TABLE 1-continued

| Compound No | Structure | Chemical Name |
|---|---|---|
| 5.29 | 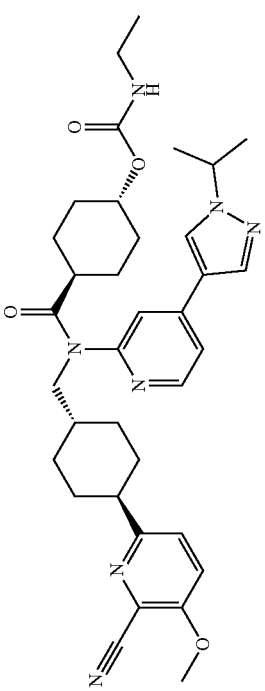 | trans-4-(((trans-4-(6-Cyano-5-methoxypyridin-2-yl)cyclohexyl)methyl)(4-(1-isopropyl-1H-pyrazol-4-yl)pyridin-2-yl)carbamoyl)cyclohexyl ethylcarbamate |
| 5.30 | 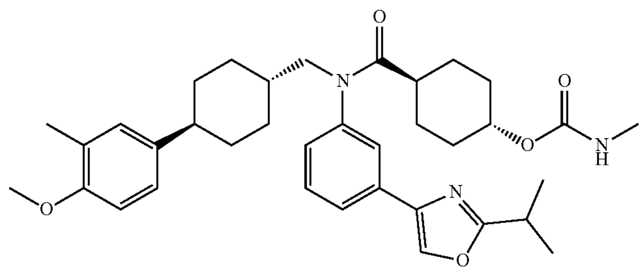 | trans-4-((3-(2-Isopropyloxazol-4-yl)phenyl)((trans-4-(4-methoxy-3-methylphenyl)cyclohexyl)methyl)carbamoyl)-cyclohexyl methylcarbamate |
| 5.31 | 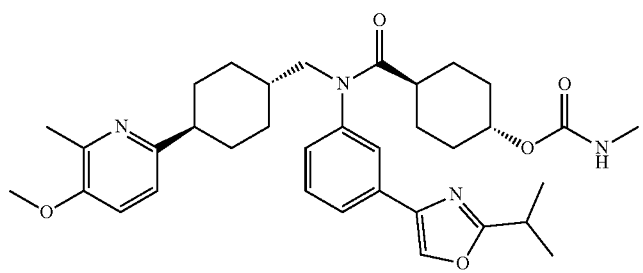 | trans-((3-(2-Isopropyloxazol-4-yl)phenyl)((trans-4-(5-methoxy-6-methylpyridin-2-yl)cyclohexyl)methyl)carbamoyl)cyclohexyl methylcarbamate |

TABLE 1-continued

| Compound No | Structure | Chemical Name |
|---|---|---|
| 5.32 | 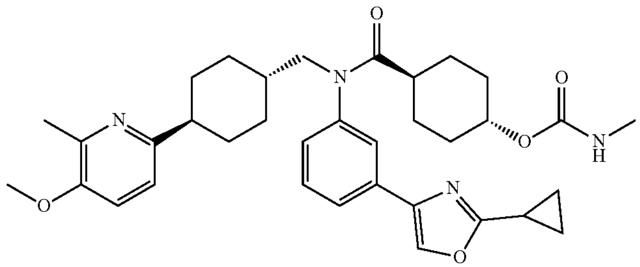 | trans-4-((3-(2-Cyclopropyloxazol-4-yl)phenyl)((trans-4-(5-methoxy-6-methylpyridin-2-yl)cyclohexyl)methyl)carbamoyl)cyclohexyl methylcarbamate |
| 5.33 | 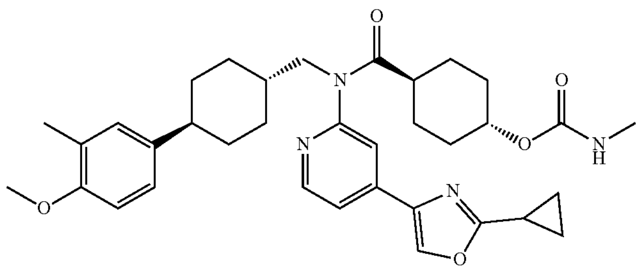 | trans-4-((4-(2-Cyclopropyloxazol-4-yl)pyridine-2-yl)((trans-4-(4-methoxy-3-methylphenyl)cyclohexyl)methyl)carbamoyl)cyclohexyl methylcarbamate |
| 5.34 | 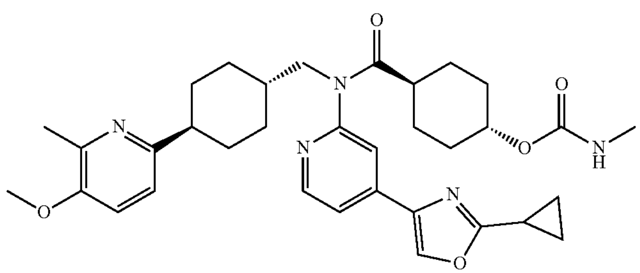 | trans-((4-(2-Cyclopropyloxazol-4-yl)pyridine-2-yl)((trans-4-(5-methoxy-6-methylpyridin-2-yl)cyclohexyl)methyl)carbamoyl)cyclohexyl methylcarbamate |

TABLE 1-continued

| Compound No | Structure | Chemical Name |
|---|---|---|
| 5.35 | 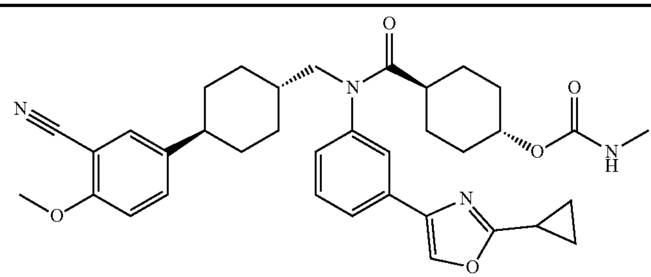 | trans-4-(((trans-4-(3-Cyano-4-methoxyphenyl)cyclohexyl)methyl)(3-(2-cyclopropyloxazol-4-yl)phenyl)carbamoyl)cyclohexyl methylcarbamate |
| 5.36 | 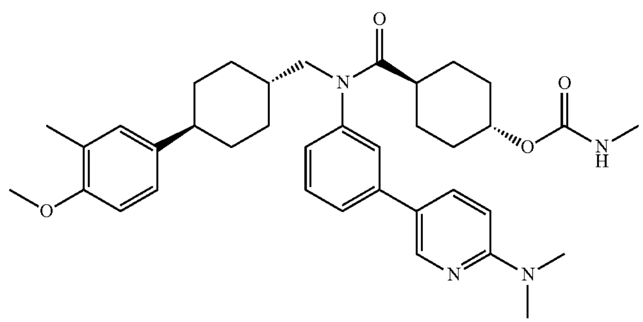 | trans-4-((3-(6-(Dimethylamino)pyridine-3-yl)phenyl)(trans-4-methoxy-3-methylphenyl)cyclohexyl)methyl)carbamoyl)-cyclohexyl methylcarbamate |
| 5.37 | 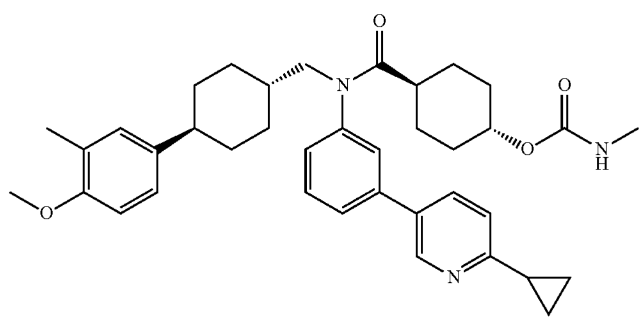 | trans-4-((3-(6-Cyclopropylpyridin-3-yl)phenyl)(trans-4-methoxy-3-methylphenyl)cyclohexyl)methyl)carbamoyl)-cyclohexyl methylcarbamate |

TABLE 1-continued

| Compound No | Structure | Chemical Name |
|---|---|---|
| 5.38 | 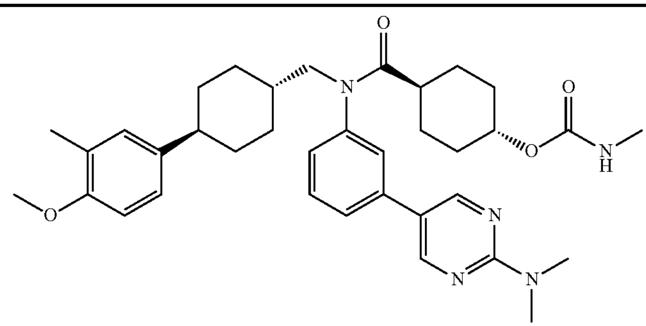 | trans-4-((3-(2-(Dimethylamino)pyrimidin-5-yl)phenyl)(trans-4-(4-methoxy-3-methylphenyl)cyclohexyl)methyl)carbamoyl)-cyclohexyl methylcarbamate |
| 5.39 | 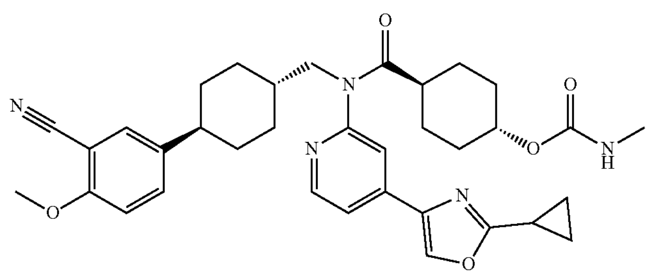 | trans-4-(((trans-4-(3-Cyano-4-methoxyphenyl)cyclohexyl)methyl)(4-(2-cyclopropyloxazol-4-yl)pyridine-2-yl)carbamoyl)cyclohexyl methylcarbamate |
| 5.40 | 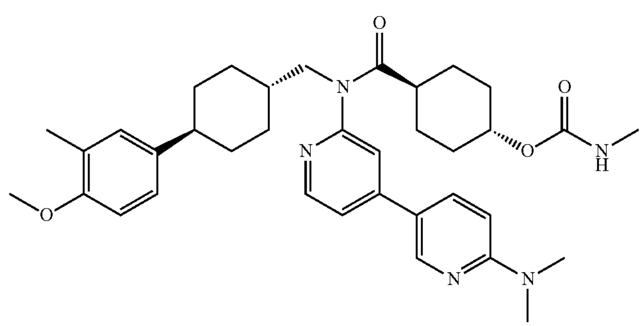 | trans-4-((6-(Dimethylamino)-[3,4'-bipyridin]-2'-yl)(trans-4-(4-methoxy-3-methylphenyl)cyclohexyl)methyl)carbamoyl)-cyclohexyl methylcarbamate |

TABLE 1-continued

| Compound No | Structure | Chemical Name |
|---|---|---|
| 5.41 | 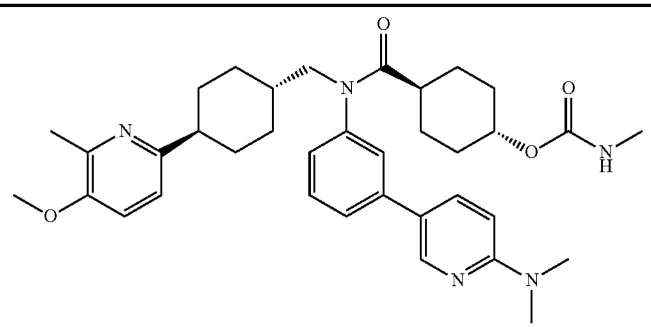 | trans-4-((3-(6-(Dimethylamino)pyridine-3-yl)phenyl)(trans-4-(5-methoxy-6-methylpyridin-2-yl)cyclohexyl)methyl)carbamoyl)cyclohexyl methylcarbamate |
| 5.42 | 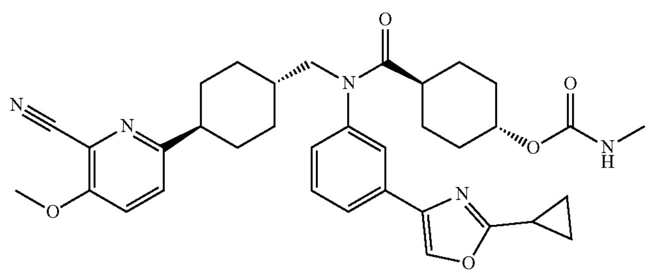 | trans-4-(((trans-4-(6-Cyano-5-methoxypyridin-2-yl)cyclohexyl)methyl)(3-(2-cyclopropyloxazol-4-yl)phenyl)carbamoyl)cyclohexyl methylcarbamate |
| 5.43 | 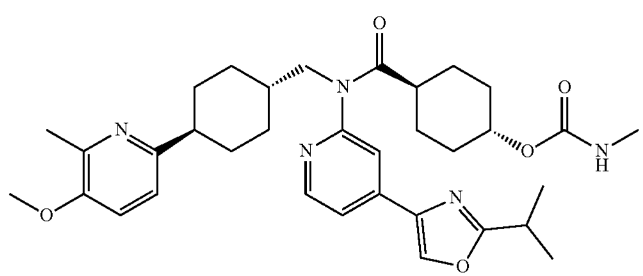 | trans-4-((4-(2-Isopropyloxazol-4-yl)pyridine-2-yl)(trans-4-(5-methoxy-6-methylpyridin-2-yl)cyclohexyl)methyl)carbamoyl)cyclohexyl methylcarbamate |

TABLE 1-continued

| Compound No | Structure | Chemical Name |
|---|---|---|
| 5.44 | 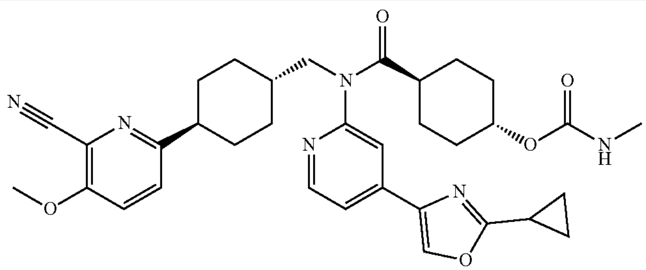 | trans-4-(((trans-4-(6-Cyano-5-methoxypyridin-2-yl)cyclohexyl)methyl)(4-(2-cyclopropyloxazol-4-yl)pyridine-2-yl)carbamoyl)cyclohexyl methylcarbamate |
| 5.45 | 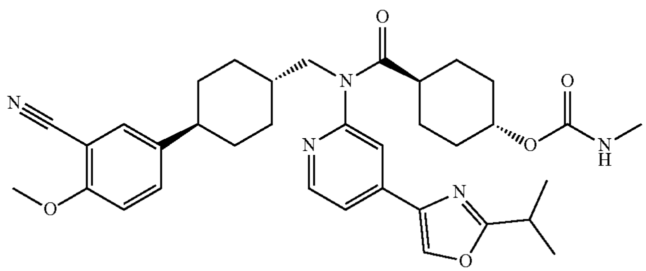 | trans-4-(((trans-4-(3-Cyano-4-methoxyphenyl)cyclohexyl)methyl)(4-(2-isopropyloxazol-4-yl)pyridine-2-yl)carbamoyl)cyclohexyl methylcarbamate |
| 5.46 | 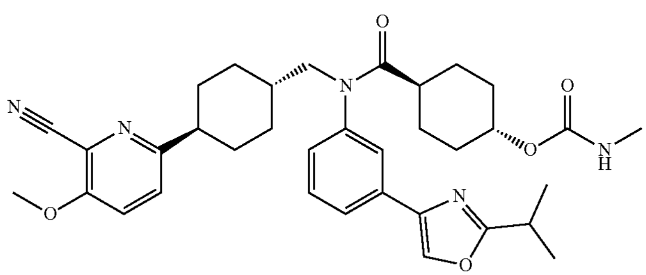 | trans-(((trans-4-(6-Cyano-5-methoxypyridin-2-yl)cyclohexyl)methyl)(3-(2-isopropyloxazol-4-yl)phenyl)carbamoyl)cyclohexyl methylcarbamate |

TABLE 1-continued

| Compound No | Structure | Chemical Name |
|---|---|---|
| 5.47 | 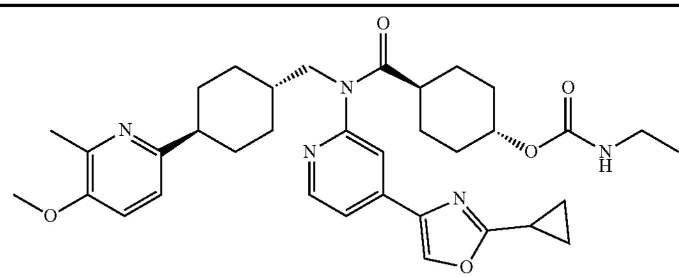 | trans-4-((4-(2-Cyclopropyloxazol-4-yl)pyridine-2-yl)(trans-4-(5-methoxy-6-methyl)pyridin-2-yl)cyclohexyl)methyl)carbamoyl)cyclohexyl ethylcarbamate |
| 5.48 | 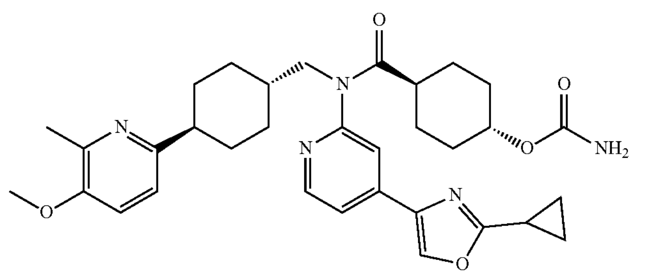 [SMILES: COc1ccc([C@H]2CC[C@H](CN(c3cc(-c4coc(C5CC5)n4)ccn3)C(=O)[C@H]3CC[C@H](OC(N)=O)CC3)CC2)nc1C] | trans-4-((4-(2-Cyclopropyloxazol-4-yl)pyridine-2-yl)(trans-4-(5-methoxy-6-methyl)pyridin-2-yl)cyclohexyl)methyl)carbamoyl)cyclohexyl carbamate |
| 5.49 | 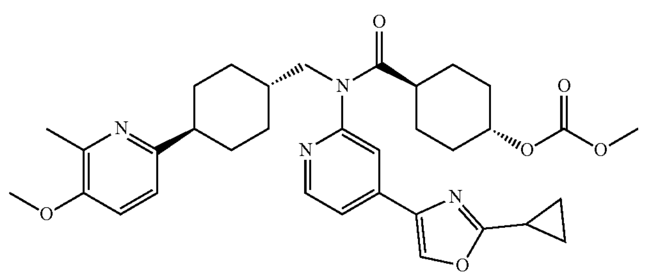 | trans-4-((4-(2-Cyclopropyloxazol-4-yl)pyridine-2-yl)(trans-4-(5-methoxy-6-methyl)pyridin-2-yl)cyclohexyl)methyl)carbamoyl)cyclohexyl methyl carbonate |

TABLE 1-continued

| Compound No | Structure | Chemical Name |
|---|---|---|
| 5.50 | 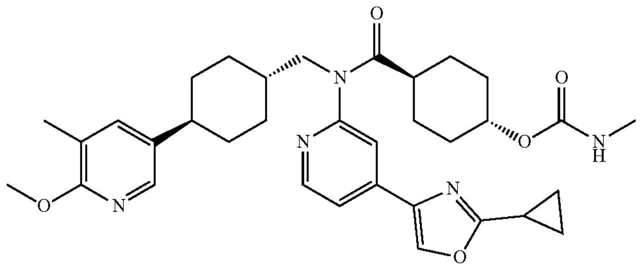 | trans-4-((4-(2-Cyclopropyloxazol-4-yl)pyridine-2-yl)(trans-4-(6-methoxy-5-methylpyridin-3-yl)cyclohexyl)methyl)carbamoyl)cyclohexyl methylcarbamate |
| 5.51 | 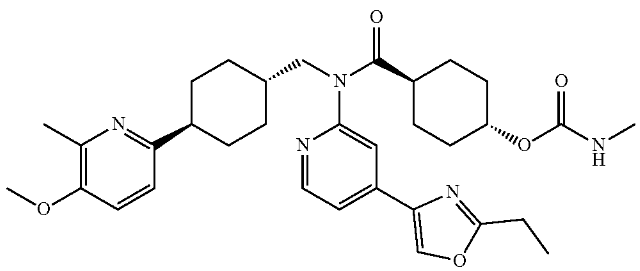 | trans-(4-(2-Ethyloxazol-4-yl)pyridin-2-yl)(trans-4-(5-methoxy-6-methylpyridin-2-yl)cyclohexyl)methyl)carbamoyl)cyclohexyl methylcarbamate |
| 5.52 | 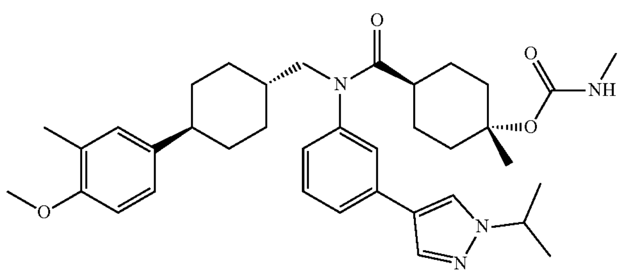 | trans-4-((3-(1-Isopropyl-1H-pyrazol-4-yl)phenyl)(trans-4-(4-methoxy-3-methylphenyl)cyclohexyl)methyl)carbamoyl)-1-methylcyclohexyl methylcarbamate |

TABLE 1-continued

| Compound No | Structure | Chemical Name |
|---|---|---|
| 5.53 | 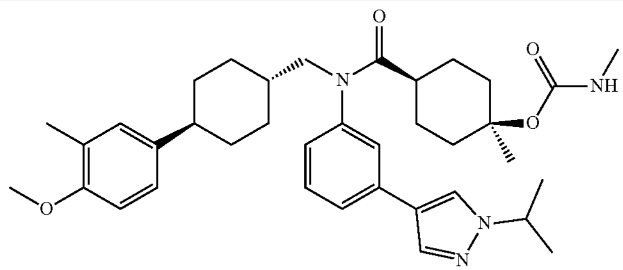 | trans-((3-(1-Isopropyl-1H-pyrazol-4-yl)phenyl)((trans-4-(4-methoxy-3-methylphenyl)cyclohexyl)methyl)carbamoyl)-1-methylcyclohexyl methylcarbamate |
| 6 | 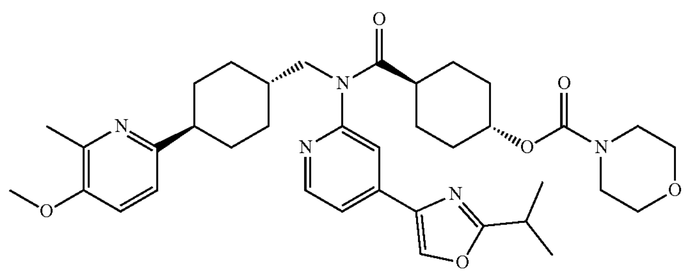 [SMILES: COc1ccc([C@H]2CC[C@H](CN(c3cc(-c4coc(C(C)C)n4)ccn3)C(=O)[C@H]3CC[C@H](OC(=O)N4CCOCC4)CC3)CC2)nc1C] | trans-4-((4-(2-Isopropyloxazol-4-yl)pyridine-2-yl)((trans-4-(5-methoxy-6-methylpyridin-2-yl)cyclohexyl)methyl)carbamoyl)cyclohexyl morpholine-4-carboxylate |
| 6.01 | 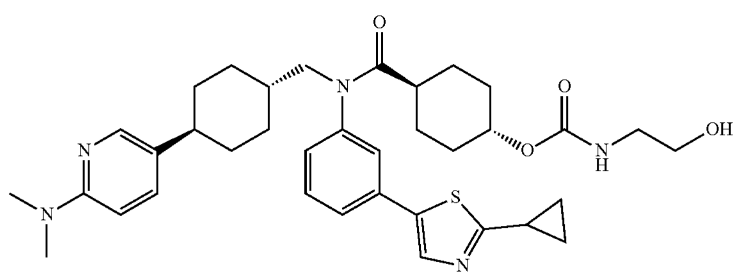 [SMILES: CN(C)c1ccc([C@H]2CC[C@H](CN(c3cccc(-c4cnc(C5CC5)s4)c3)C(=O)[C@H]3CC[C@H](OC(=O)NCCO)CC3)CC2)cn1] | 4-((3-(2-Cyclopropylthiazol-5-yl)phenyl)((trans-4-(6-(dimethylamino)pyridin-3-yl)cyclohexyl)methyl)carbamoyl)cyclohexyl (2-hydroxyethyl)trans-carbamate |

TABLE 1-continued

| Compound No | Structure | Chemical Name |
|---|---|---|
| 6.02 | 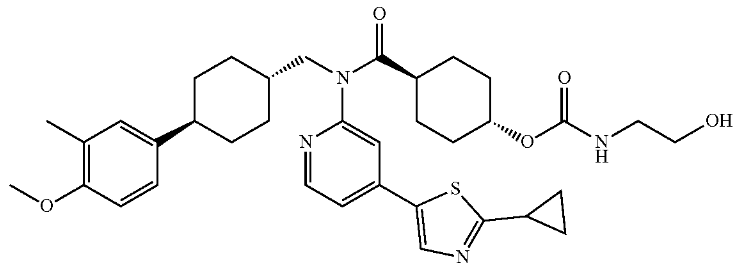 | trans-4-((4-(2-Cyclopropylthiazol-5-yl)pyridin-2-yl)((trans-4-(4-methoxy-3-methylphenyl)cyclohexyl)methyl)carbamoyl)cyclohexyl (2-hydroxyethyl)carbamate |
| 6.03 | 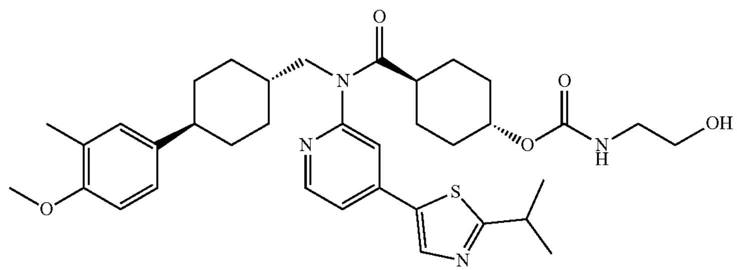 | trans-4-((4-(2-Isopropylthiazol-5-yl)pyridin-2-yl)((trans-4-(4-methoxy-3-methylphenyl)cyclohexyl)methyl)carbamoyl)cyclohexyl (2-hydroxyethyl)carbamate |
| 6.04 | 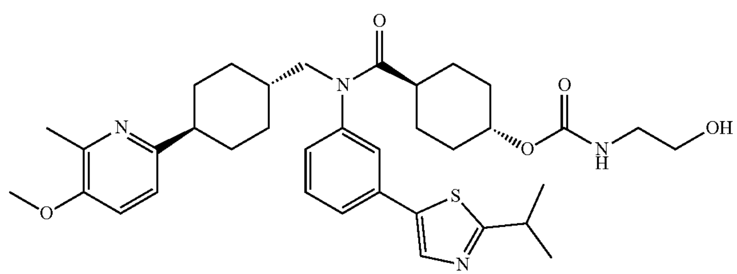 [SMILES: COc1ccc([C@H]2CC[C@H](CN(c3cccc(-c4cnc(C(C)C)s4)c3)C(=O)[C@H]3CC[C@H](OC(=O)NCCO)CC3)CC2)nc1C] | trans-4-((3-(2-Isopropylthiazol-5-yl)phenyl)((trans-4-(5-methoxy-6-methylpyridin-2-yl)cyclohexyl)methyl)carbamoyl)cyclohexyl (2-hydroxyethyl)carbamate |

TABLE 1-continued

| Compound No | Structure | Chemical Name |
|---|---|---|
| 6.05 | 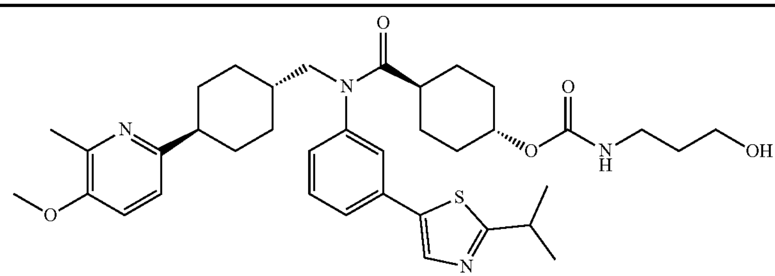 | trans-4-((3-(2-Isopropylthiazol-5-yl)phenyl)((trans-4-(5-methoxy-6-methylpyridin-2-yl)cyclohexyl)methyl)carbamoyl)cyclohexyl (3-hydroxypropyl)carbamate |
| 6.06 | 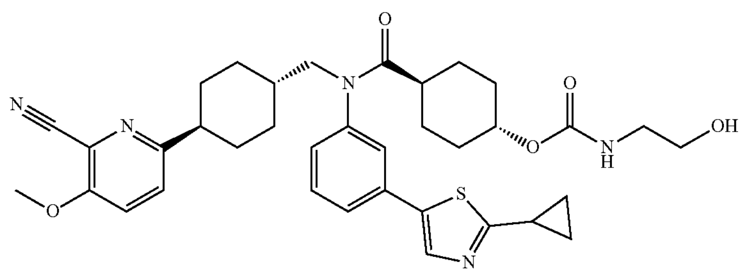 [SMILES: COc1ccc([C@H]2CC[C@H](CN(c3cccc(-c4cnc(C5CC5)s4)c3)C(=O)[C@H]3CC[C@H](OC(=O)NCCO)CC3)CC2)nc1C#N] | trans-4-((trans-4-(6-Cyano-5-methoxypyridin-2-yl)cyclohexyl)methyl)(3-(2-cyclopropylthiazol-5-yl)phenyl)carbamoyl)cyclohexyl (2-hydroxyethyl)carbamate |
| 6.07 | 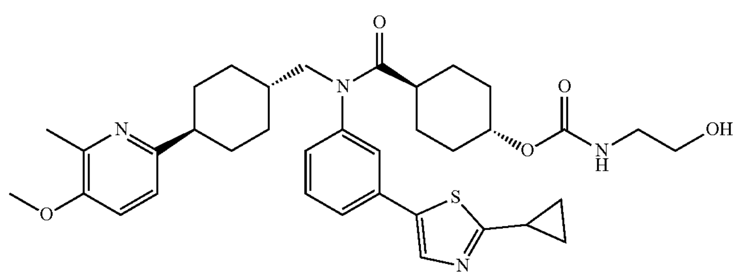 | trans-4-((3-(2-Cyclopropylthiazol-5-yl)phenyl)((trans-4-(5-methoxy-6-methylpyridin-2-yl)cyclohexyl)methyl)carbamoyl)cyclohexyl (2-hydroxyethyl)carbamate |

TABLE 1-continued

| Compound No | Structure | Chemical Name |
|---|---|---|
| 6.08 | 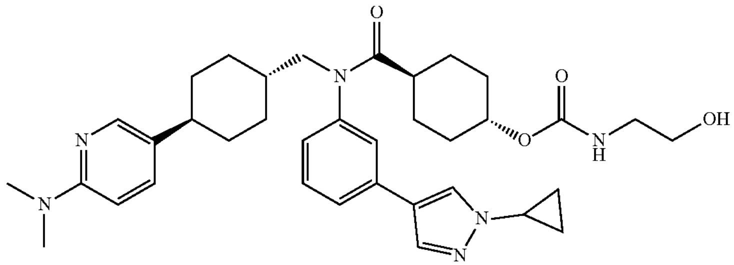 | trans-4-((3-(1-Cyclopropyl-1H-pyrazol-4-yl)phenyl)(trans-4-(6-(dimethylamino)pyridin-3-yl)cyclohexyl)methyl)carbamoyl)cyclohexyl (2-hydroxyethyl)carbamate |
| 6.09 | 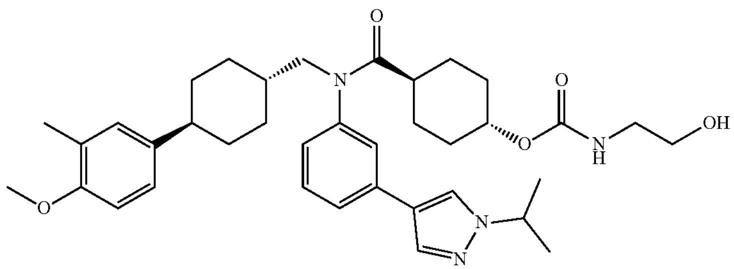 | trans-4-((3-(1-Isopropyl-1H-pyrazol-4-yl)phenyl)(trans-4-(4-methoxy-3-methylphenyl)cyclohexyl)methyl)carbamoyl)-cyclohexyl (2-hydroxyethyl)carbamate |
| 6.10 | 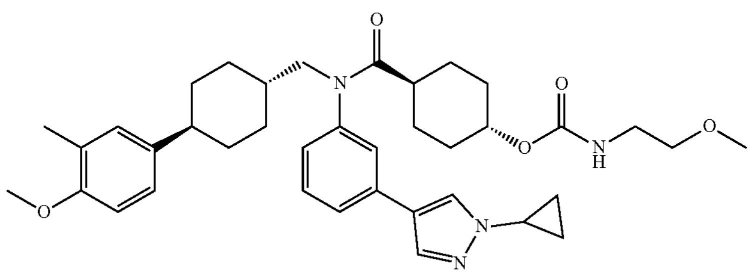 | trans-((3-(1-Cyclopropyl-1H-pyrazol-4-yl)phenyl)(trans-4-(4-methoxy-3-methylphenyl)cyclohexyl)methyl)carbamoyl)-cyclohexyl (2-methoxyethyl)carbamate |

TABLE 1-continued

| Compound No | Structure | Chemical Name |
|---|---|---|
| 6.11 | 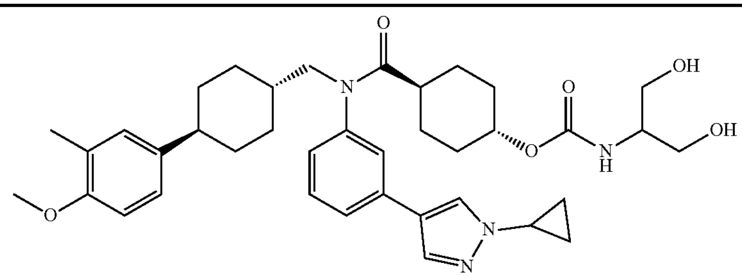 | trans-4-((3-(1-Cyclopropyl-1H-pyrazol-4-yl)phenyl)(trans-4-(4-methoxy-3-methylphenyl)cyclohexyl)methyl)carbamoyl)-cyclohexyl (1,3-dihydroxypropan-2-yl)carbamate |
| 6.12 | 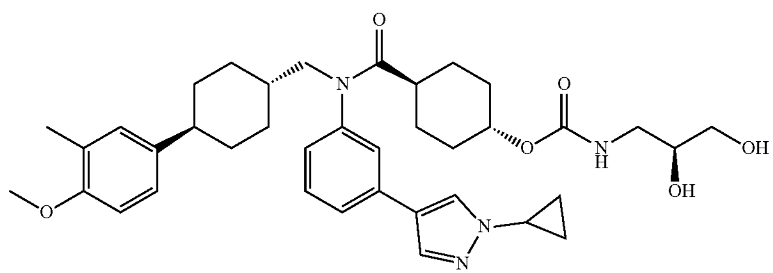 [SMILES: COc1ccc([C@H]2CC[C@H](CN(c3cccc(-c4cnn(C5CC5)c4)c3)C(=O)[C@H]3CC[C@H](OC(=O)NC[C@H](O)CO)CC3)CC2)cc1C] | trans-4-((3-(1-Cyclopropyl-1H-pyrazol-4-yl)phenyl)(trans-4-(4-methoxy-3-methylphenyl)cyclohexyl)methyl)carbamoyl)-cyclohexyl ((S)-2,3-dihydroxypropyl)carbamate |
| 6.13 | 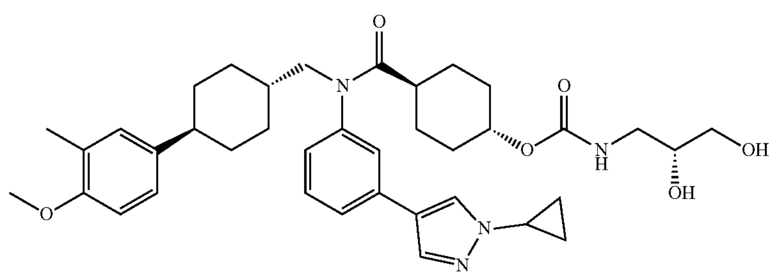 [SMILES: COc1ccc([C@H]2CC[C@H](CN(c3cccc(-c4cnn(C5CC5)c4)c3)C(=O)[C@H]3CC[C@H](OC(=O)NC[C@@H](O)CO)CC3)CC2)cc1C] | trans-4-((3-(1-Cyclopropl-1H-pyrazol-4-yl)phenyl)(trans-4-(4-methoxy-3-methylphenyl)cyclohexyl)methyl)carbamoyl)-cyclohexyl ((R)-2,3-dihydroxypropyl)carbamate |

TABLE 1-continued

| Compound No | Structure | Chemical Name |
|---|---|---|
| 6.14 | 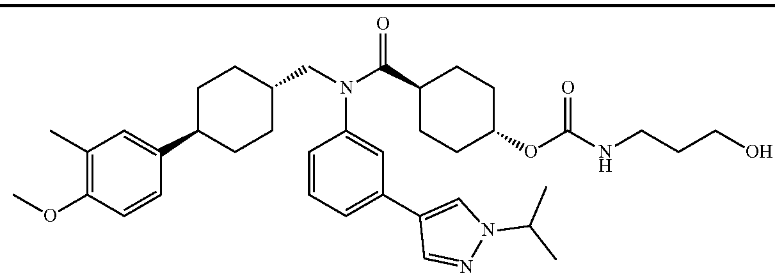 | trans-4-((3-(1-Isopropyl-1H-pyrazol-4-yl)phenyl)(trans-4-(4-methoxy-3-methylphenyl)cyclohexyl)methyl)carbamoyl)-cyclohexyl (3-hydroxypropyl)carbamate |
| 6.15 | 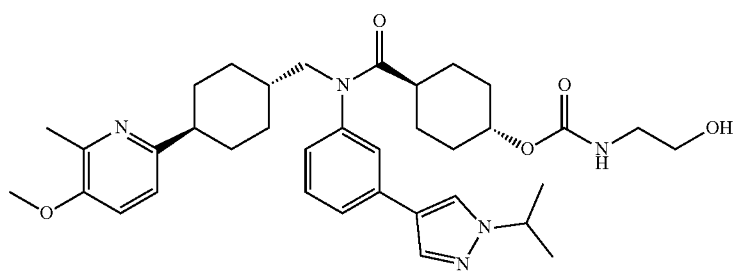 | trans-4-((3-(1-Isopropyl-1H-pyrazol-4-yl)phenyl)(trans-4-(5-methoxy-6-methylpyridin-2-yl)cyclohexyl)methyl)carbamoyl)cyclohexyl (2-hydroxyethyl)carbamate |
| 6.16 | 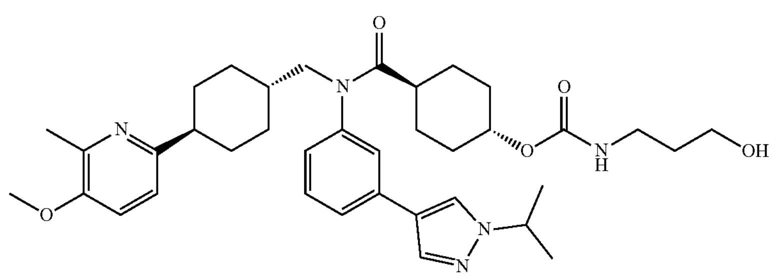 | trans-4-((3-(1-Isopropyl-1H-pyrazol-4-yl)phenyl)(trans-4-(5-methoxy-6-methylpyridin-2-yl)cyclohexyl)methyl)carbamoyl)cyclohexyl (3-hydroxypropyl)carbamate |

TABLE 1-continued

| Compound No | Structure | Chemical Name |
|---|---|---|
| 6.17 | 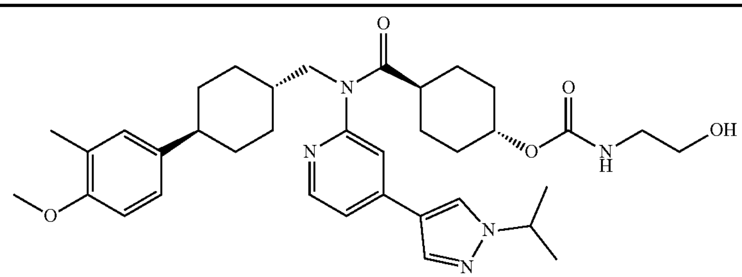 | trans-4-((4-((1-Isopropyl-1H-pyrazol-4-yl)pyridin-2-yl)(trans-4-(4-methoxy-3-methylphenyl)cyclohexyl)methyl)carbamoyl)-cyclohexyl (2-hydroxyethyl)carbamate |
| 6.18 | 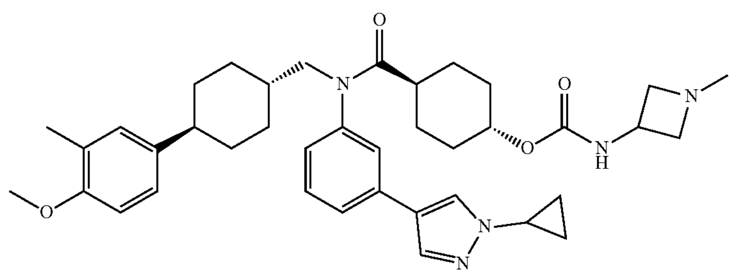 | trans-4-(3-(1-Cyclopropyl-1H-pyrazol-4-yl)phenyl)(trans-4-(4-methoxy-3-methylphenyl)cyclohexyl)methyl)carbamoyl)-cyclohexyl (1-methylazetidin-3-yl)carbamate |
| 6.19 | 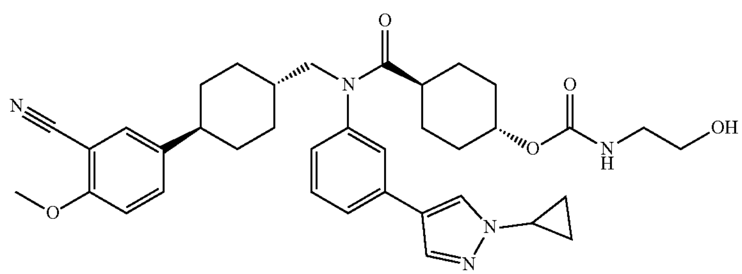 | trans-4-((trans-4-(3-Cyano-4-methoxyphenyl)cyclohexyl)methyl)(3-(1-cyclopropyl-1H-pyrazol-4-yl)phenyl)carbamoyl)cyclohexyl (2-hydroxyethyl)carbamate |

TABLE 1-continued

| Compound No | Structure | Chemical Name |
|---|---|---|
| 6.20 | 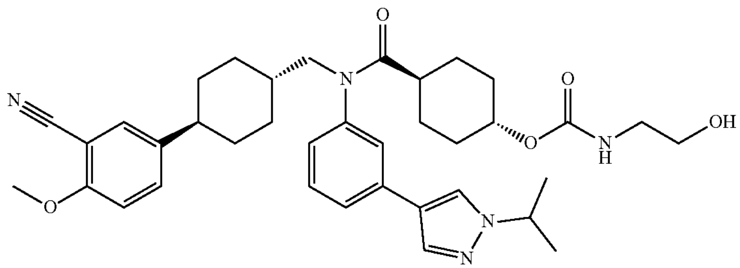 | trans-4-(((trans-4-(3-Cyano-4-methoxyphenyl)cyclohexyl)methyl)(3-(1-isopropyl-1H-pyrazol-4-yl)phenyl)carbamoyl)cyclohexyl (2-hydroxyethyl)carbamate |
| 6.21 | 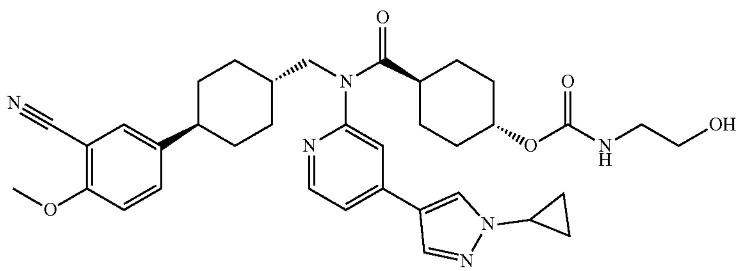 | trans-4-(((trans-4-(3-Cyano-4-methoxyphenyl)cyclohexyl)methyl)(4-(1-cyclopropyl-1H-pyrazol-4-yl)pyridin-2-yl)carbamoyl)cyclohexyl (2-hydroxyethyl)carbamate |
| 6.22 | 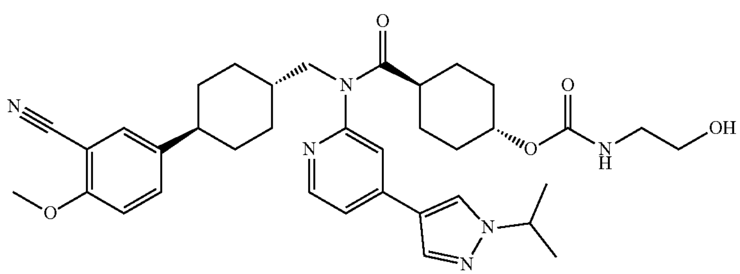 | trans-4-(((trans-4-(3-Cyano-4-methoxyphenyl)cyclohexyl)methyl)(4-(1-isopropyl-1H-pyrazol-4-yl)pyridin-2-yl)carbamoyl)cyclohexyl (2-hydroxyethyl)carbamate |

TABLE 1-continued

| Compound No | Structure | Chemical Name |
|---|---|---|
| 6.23 | 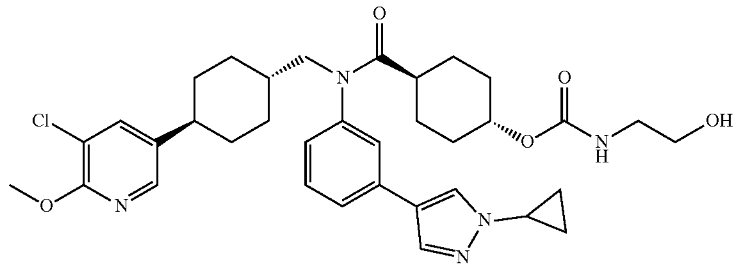 [SMILES: COc1ncc([C@H]2CC[C@H](CN(c3cccc(-c4cnn(C5CC5)c4)c3)C(=O)[C@H]3CC[C@H](OC(=O)NCCO)CC3)CC2)cc1Cl] | trans-4-(((trans-4-(5-Chloro-6-methoxypyridin-3-yl)cyclohexyl)methyl)(3-(1-cyclopropyl-1H-pyrazol-4-yl)phenyl)carbamoyl)cyclohexyl(2-hydroxyethyl)carbamate |
| 6.24 | 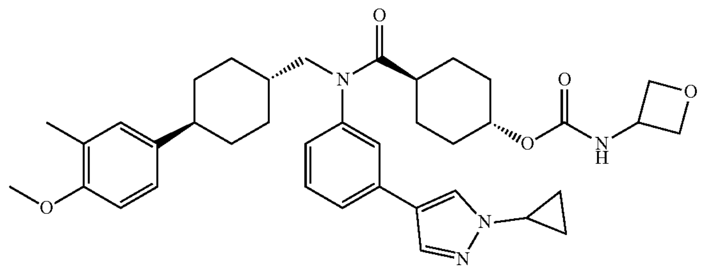 | trans-((3-(1-Cyclopropyl-1H-pyrazol-4-yl)phenyl)(trans-4-(4-methoxy-3-methylphenyl)cyclohexyl)methyl)carbamoyl)-cyclohexyl oxetan-3-ylcarbamate |
| 6.25 | 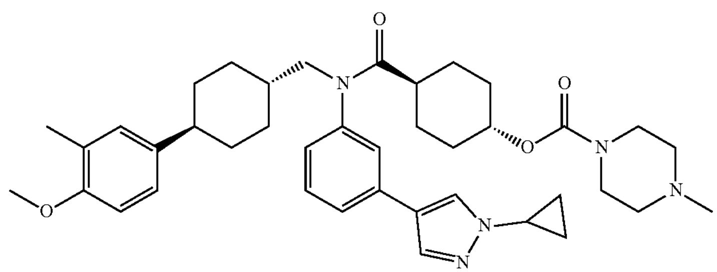 | trans-4-(3-(1-Cyclopropyl-1H-pyrazol-4-yl)phenyl)(trans-4-(4-methoxy-3-methylphenyl)cyclohexyl)methyl)carbamoyl)-cyclohexyl 4-methylpiperazine-1-carboxylate |

TABLE 1-continued

| Compound No | Structure | Chemical Name |
|---|---|---|
| 6.26 | 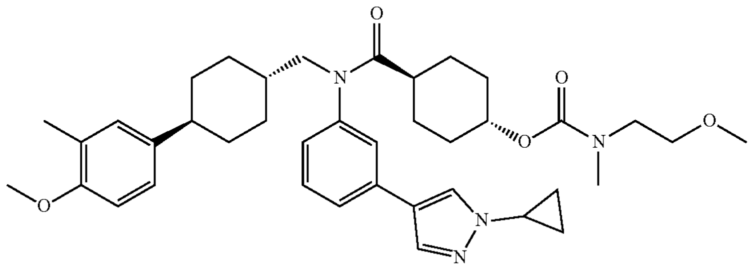 | trans-4-((3-(1-Cyclopropyl-1H-pyrazol-4-yl)phenyl)(trans-4-(4-methoxy-3-methylphenyl)cyclohexyl)methyl)carbamoyl)-cyclohexyl (2-methoxyethyl)(methyl)carbamate |
| 6.27 | 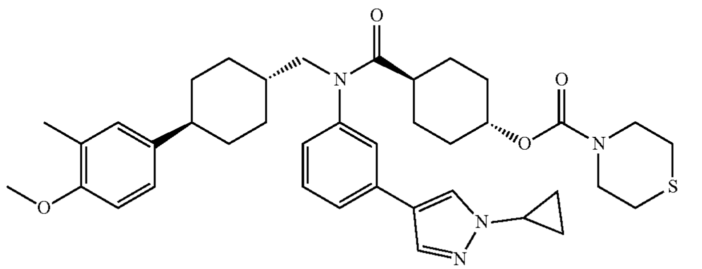 | trans-4-((3-(1-Cyclopropyl-1H-pyrazol-4-yl)phenyl)(trans-4-(4-methoxy-3-methylphenyl)cyclohexyl)methyl)carbamoyl)-cyclohexyl thiomorpholine-4-carboxylate |
| 6.28 | 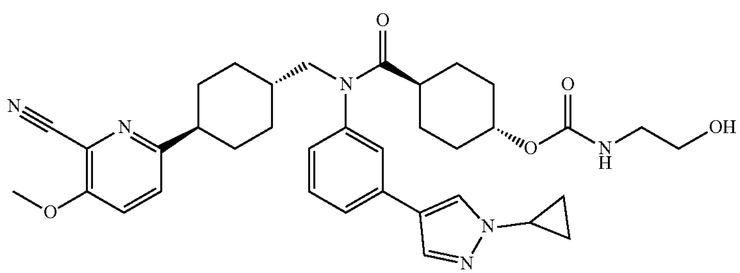 | trans-4-(((trans-4-(6-Cyano-5-methoxypyridin-yl)cyclohexyl)methyl)(3-(1-cyclopropyl-1H-pyrazol-4-yl)phenyl)carbamoyl)cyclohexyl (2-hydroxyethyl)carbamate |

TABLE 1-continued

| Compound No | Structure | Chemical Name |
|---|---|---|
| 6.29 | 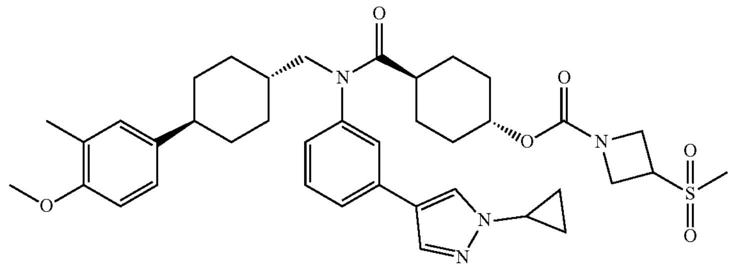 | trans-4-((3-(1-Cyclopropyl-1H-pyrazol-4-yl)phenyl)(trans-4-(4-methoxy-3-methylphenyl)cyclohexyl)methyl)carbamoyl)-cyclohexyl 3-(methylsulfonyl)azetidine-1-carboxylate |
| 6.30 | 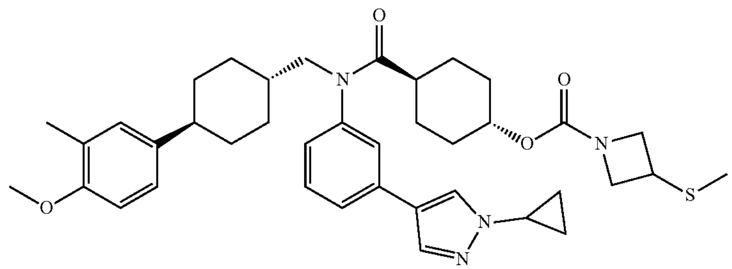 | trans-4-((3-(1-Cyclopropyl-1H-pyrazol-4-yl)phenyl)(trans-4-(4-methoxy-3-methylphenyl)cyclohexyl)methyl)carbamoyl)-cyclohexyl 3-(methylthio)azetidine-1-carboxylate |
| 6.31 | 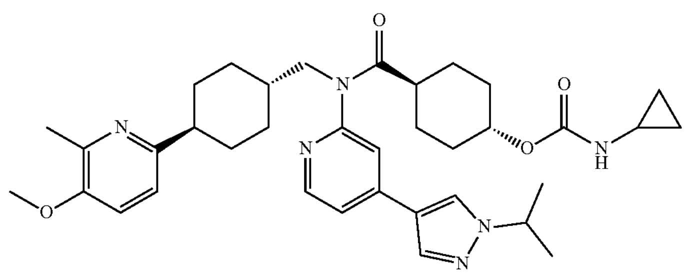 [SMILES: COc1ccc([C@H]2CC[C@H](CN(c3cc(-c4cnn(C(C)C)c4)ccn3)C(=O)[C@H]3CC[C@H](OC(=O)NC4CC4)CC3)CC2)nc1C] | trans-4-((4-(1-Isopropyl-1H-pyrazol-4-yl)pyridin-2-yl)(trans-4-(5-methoxy-6-methylpyridin-2-yl)cyclohexyl)methyl)carbamoyl)cyclohexyl cyclopropylcarbamate |

TABLE 1-continued

| Compound No | Structure | Chemical Name |
|---|---|---|
| 6.32 | 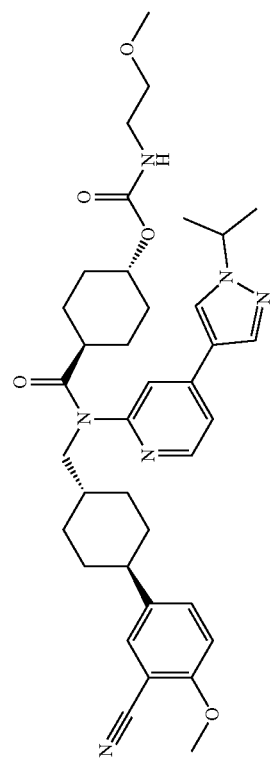 | trans-4-(((trans-4-(6-Cyano-5-methoxypyridin-2-yl)cyclohexyl)methyl)(4-(1-isopropyl-1H-pyrazol-4-yl)pyridin-2-yl)carbamoyl)cyclohexyl isopropyl carbamate |
| 6.33 | 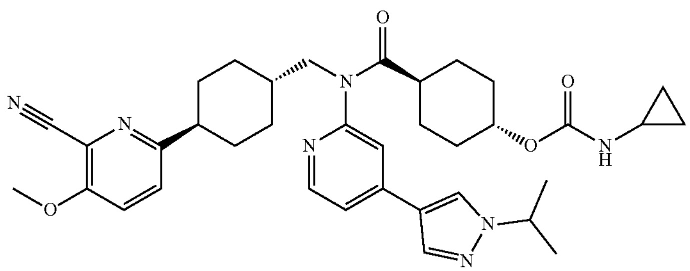 [SMILES: COc1ccc([C@H]2CC[C@H](CN(c3cc(-c4cnn(C(C)C)c4)ccn3)C(=O)[C@H]3CC[C@H](OC(=O)NC4CC4)CC3)CC2)nc1C#N] | trans-4-(((trans-4-(6-Cyano-5-methoxypyridin-2-yl)cyclohexyl)methyl)(4-(1-isopropyl-1H-pyrazol-4-yl)pyridin-2-yl)carbamoyl)cyclohexyl cyclopropyl carbamate |
| 6.34 | 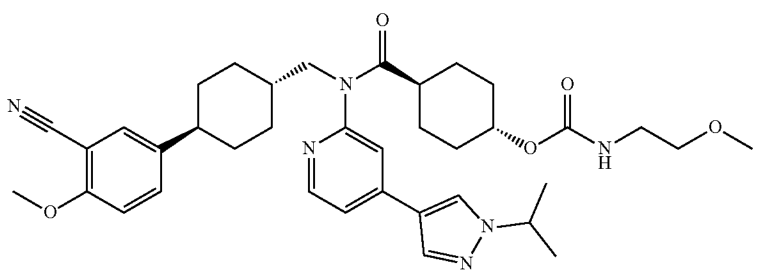 | trans-4-(((trans-4-(3-Cyano-4-methoxyphenyl)cyclohexyl)methyl)(4-(1-isopropyl-1H-pyrazol-4-yl)pyridin-2-yl)carbamoyl)cyclohexyl (2-methoxyethyl)carbamate |

TABLE 1-continued

| Compound No | Structure | Chemical Name |
|---|---|---|
| 6.35 | 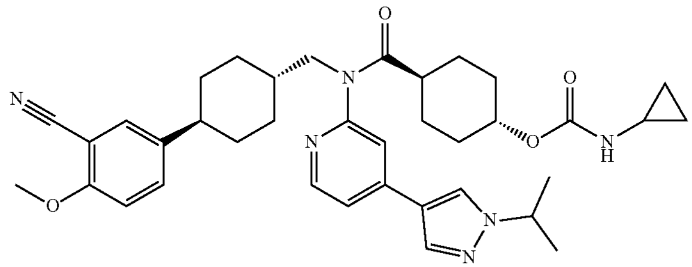 | trans-4-(((trans-4-(3-Cyano-4-methoxyphenyl)cyclohexyl)methyl)(4-(1-isopropyl-1H-pyrazol-4-yl)pyridin-2-yl)carbamoyl)cyclohexyl cyclopropylcarbamate |
| 6.36 | 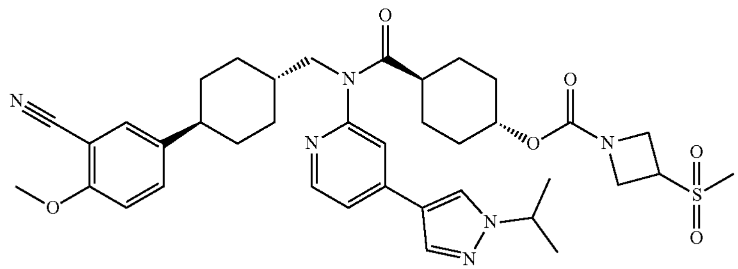 | trans-4-(((trans-4-(3-Cyano-4-methoxyphenyl)cyclohexyl)methyl)(4-(1-isopropyl-1H-pyrazol-4-yl)pyridin-2-yl)carbamoyl)cyclohexyl 3-(methylsulfonyl)azetidine-1-carboxylate |
| 6.37 | 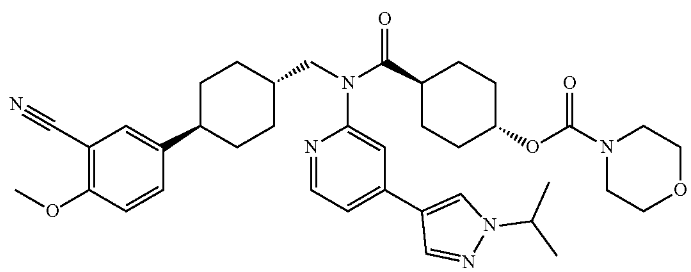 [SMILES: COc1ccc([C@H]2CC[C@H](CN(c3cc(-c4cnn(C(C)C)c4)ccn3)C(=O)[C@H]3CC[C@H](OC(=O)N4CCOCC4)CC3)CC2)cc1C#N] | trans-4-(((trans-4-(3-Cyano-4-methoxyphenyl)cyclohexyl)methyl)(4-(1-isopropyl-1H-pyrazol-4-yl)pyridin-2-yl)carbamoyl)cyclohexyl morpholine-4-carboxylate |

TABLE 1-continued

| Compound No | Structure | Chemical Name |
|---|---|---|
| 6.38 | 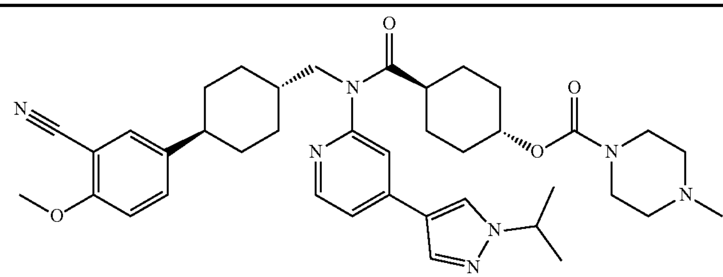 | trans-4-(((trans-4-(3-Cyano-4-methoxyphenyl)cyclohexyl)methyl)(4-(1-isopropyl-1H-pyrazol-4-yl)pyridin-2-yl)carbamoyl)cyclohexyl 4-methylpiperazine-1-carboxylate |
| 6.39 | 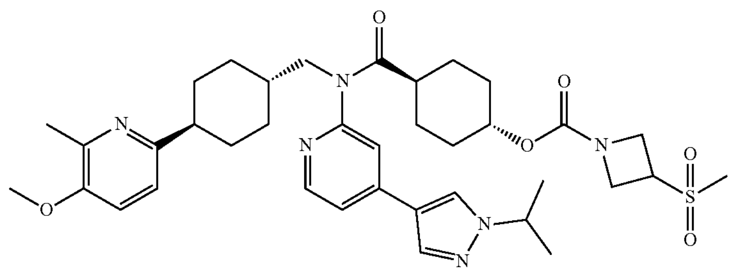 | trans-4-((4-(1-Isopropyl-1H-pyrazol-4-yl)pyridin-2-yl)((trans-4-(5-methoxy-6-methylpyridin-2-yl)cyclohexyl)methyl)carbamoyl)cyclohexyl 3-(methylsulfonyl)azetidine-1-carboxylate |
| 6.40 | 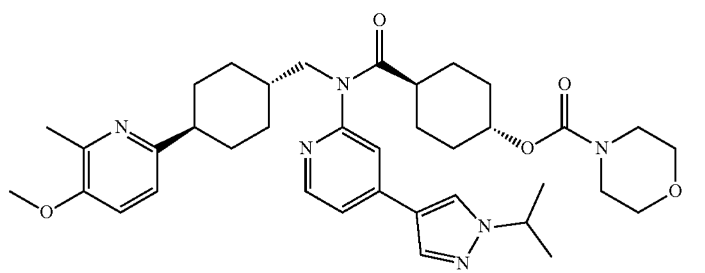 | trans-4-((4-(1-Isopropyl-1H-pyrazol-4-yl)pyridin-2-yl)((trans-4-(5-methoxy-6-methylpyridin-2-yl)cyclohexyl)methyl)carbamoyl)cyclohexyl morpholine-4-carboxylate |

TABLE 1-continued

| Compound No | Structure | Chemical Name |
|---|---|---|
| 6.41 | 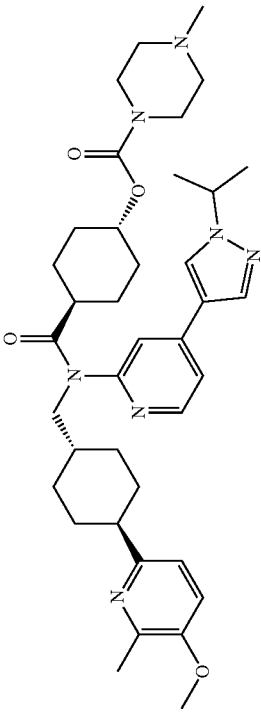 | trans-4-((4-(1-Isopropyl-1H-pyrazol-4-yl)pyridin-2-yl)(trans-4-(5-methoxy-6-methylpyridin-2-yl)cyclohexyl)methyl)carbamoyl)cyclohexyl 4-methylpiperazine-1-carboxylate |
| 6.42 | 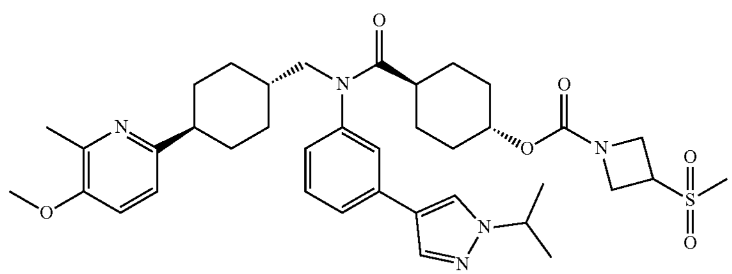 | trans-4-(3-(1-Isopropyl-1H-pyrazol-4-yl)phenyl)(trans-4-(5-methoxy-6-methylpyridin-2-yl)cyclohexyl)methyl(carbamoyl (cyclohexyl 3-(methylsulfonyl)azetidine-1-carboxylate |
| 6.43 | 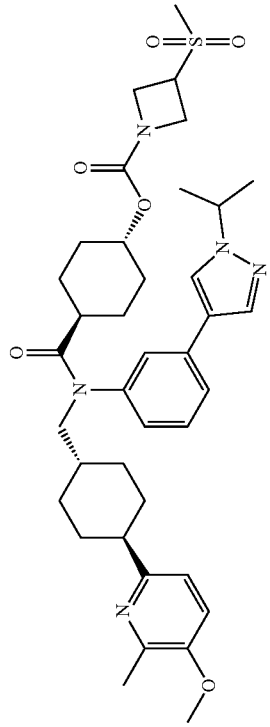 | trans-4-(3-(1-Isopropyl-1H-pyrazol-4-yl)phenyl)(trans-4-(5-methoxy-6-methylpyridin-2-yl)cyclohexyl)methyl)carbamoyl)cyclohexyl morpholine-4-carboxylate |

TABLE 1-continued

| Compound No | Structure | Chemical Name |
|---|---|---|
| 6.44 | 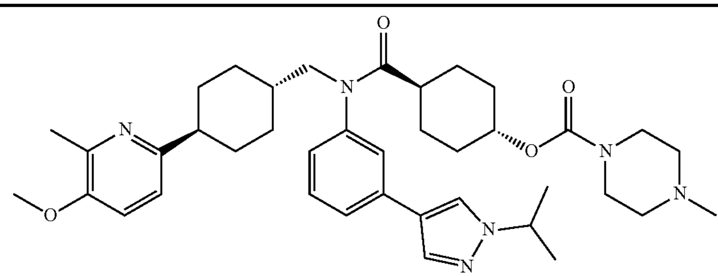 | trans-4-((3-(1-Isopropyl-1H-pyrazol-4-yl)phenyl)(trans-4-(5-methoxy-6-methylpyridin-2-yl)cyclohexyl)methyl)carbamoyl)cyclohexyl 4-methylpiperazine-1-carboxylate |
| 6.45 | 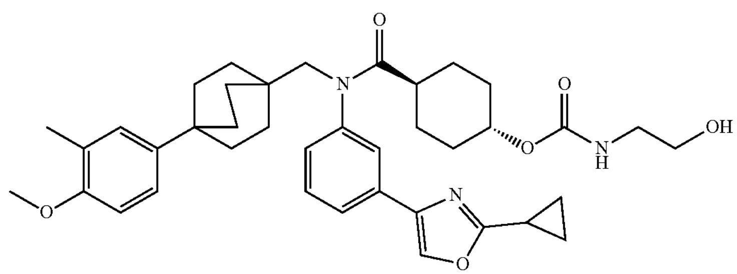 [SMILES: COc1ccc(C23CCC(CN(c4cccc(-c5coc(C6CC6)n5)c4)C(=O)[C@H]4CC[C@H](OC(=O)NCCO)CC4)(CC2)CC3)cc1C] | 4-((3-(2-Cyclopropyloxazol-4-yl)phenyl)((4-(4-methoxy-3-methylphenyl)bicyclo[2.2.2]octan-1-yl)methyl)carbamoyl)cyclohexyl trans-(2-hydroxyethyl)carbamate |
| 6.46 | 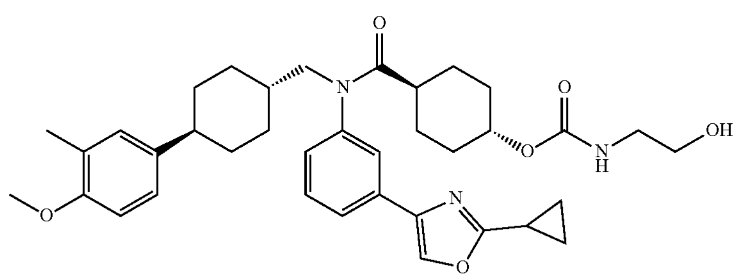 | trans-4-((3-(2-Cyclopropyloxazol-4-yl)phenyl)(trans-4-(4-methoxy-3-methylphenyl)cyclohexyl)methyl)carbamoyl)cyclohexyl (2-hydroxyethyl)carbamate |

TABLE 1-continued

| Compound No | Structure | Chemical Name |
|---|---|---|
| 6.47 | 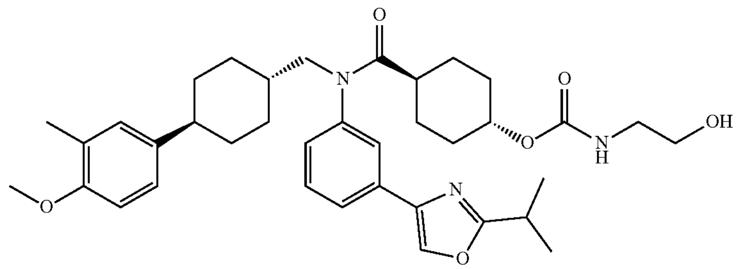 | trans-4-((3-(2-Isopropyloxazol-4-yl)phenyl)(trans-4-(4-methoxy-3-methylphenyl)cyclohexyl)methyl)carbamoyl)-cyclohexyl (2-hydroxyethyl)carbamate |
| 6.48 | 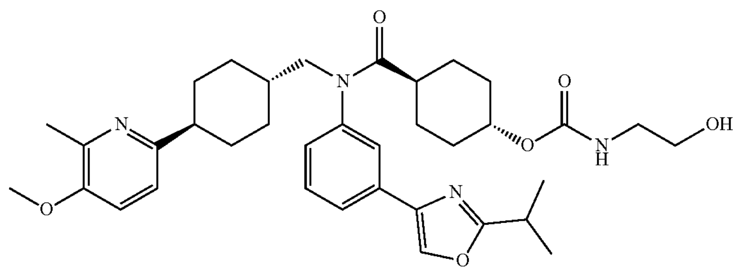 | trans-((3-(2-Isopropyloxazol-4-yl)phenyl)(trans-4-(5-methoxy-6-methylpyridin-2-yl)cyclohexyl)methyl)carbamoyl)cyclohexyl (2-hydroxyethyl)carbamate |
| 6.49 | 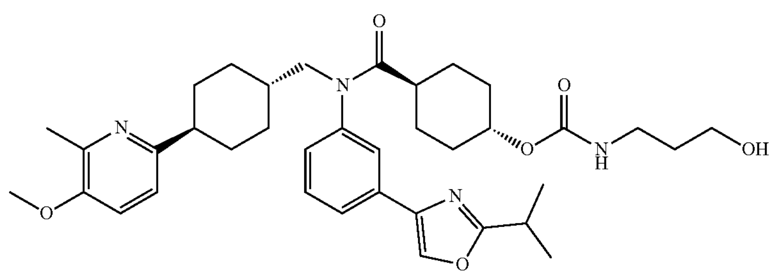 [SMILES: COc1ccc([C@H]2CC[C@H](CN(c3cccc(-c4coc(C(C)C)n4)c3)C(=O)[C@H]3CC[C@H](OC(=O)NCCCO)CC3)CC2)nc1C] | trans-4-((3-(2-Isopropyloxazol-4-yl)phenyl)(trans-4-(5-methoxy-6-methylpyridin-2-yl)cyclohexyl)methyl)carbamoyl)cyclohexyl (3-hydroxypropyl)carbamate |

TABLE 1-continued

| Compound No | Structure | Chemical Name |
|---|---|---|
| 6.50 | 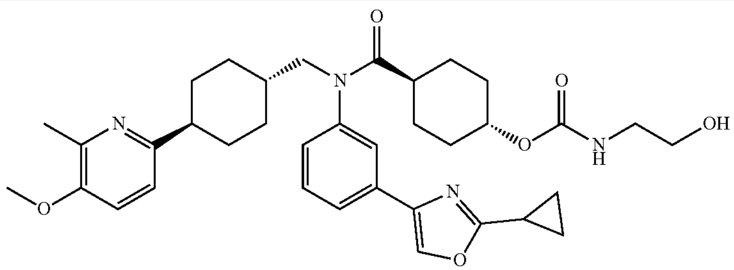 | trans-4-((3-(2-Cyclopropyloxazol-4-yl)phenyl)(trans-4-(5-methoxy-6-methylpyridin-2-yl)cyclohexyl)methyl)carbamoyl)cyclohexyl (2-hydroxyethyl)carbamate |
| 6.51 | 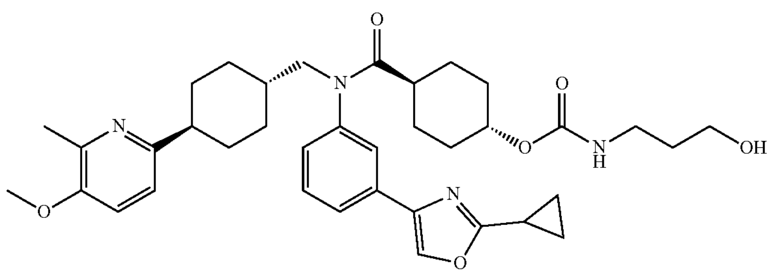 [SMILES: COc1ccc([C@H]2CC[C@H](CN(c3cccc(-c4coc(C5CC5)n4)c3)C(=O)[C@H]3CC[C@H](OC(=O)NCCCO)CC3)CC2)nc1C] | trans-4-((3-(2-Cyclopropyloxazol-4-yl)phenyl)(trans-4-(5-methoxy-6-methylpyridin-2-yl)cyclohexyl)methyl)carbamoyl)cyclohexyl (3-hydroxypropyl)carbamate |
| 6.52 | 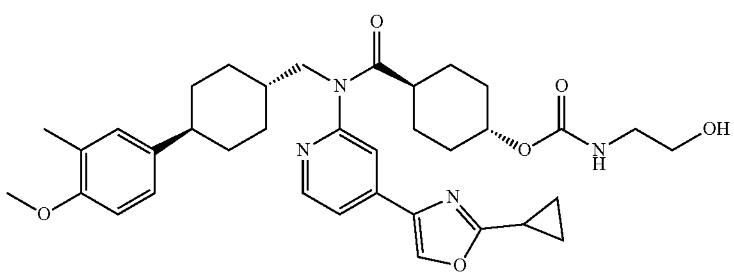 [SMILES: COc1ccc([C@H]2CC[C@H](CN(c3cc(-c4coc(C5CC5)n4)ccn3)C(=O)[C@H]3CC[C@H](OC(=O)NCCO)CC3)CC2)cc1C] | trans-4-((4-(2-Cyclopropyloxazol-4-yl)pyridine-2-yl)(trans-4-(4-methoxy-3-methylphenyl)cyclohexyl)methyl)carbamoyl)cyclohexyl (2-hydroxyethyl)carbamate |

TABLE 1-continued

| Compound No | Structure | Chemical Name |
|---|---|---|
| 6.53 | 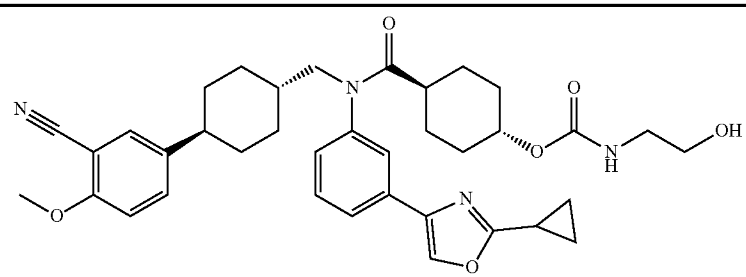 | trans-4-(((trans-4-(3-Cyano-4-methoxyphenyl)cyclohexyl)methyl)(3-(2-cyclopropyloxazol-4-yl)phenyl)carbamoyl)cyclohexyl (2-hydroxyethyl)carbamate |
| 6.54 | 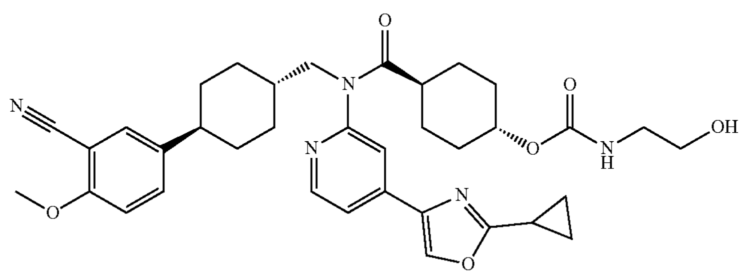 | trans-4-(((trans-4-(3-Cyano-4-methoxyphenyl)cyclohexyl)methyl)(4-(2-cyclopropyloxazol-4-yl)pyridine-2-yl)carbamoyl)cyclohexyl (2-hydroxyethyl)carbamate |
| 6.55 | 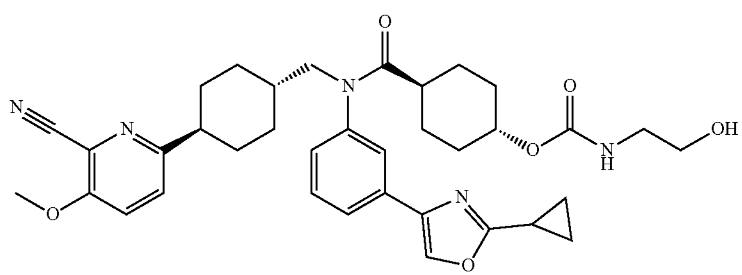 [SMILES: COc1ccc([C@H]2CC[C@H](CN(c3cccc(-c4coc(C5CC5)n4)c3)C(=O)[C@H]3CC[C@H](OC(=O)NCCO)CC3)CC2)nc1C#N] | trans-4-(((trans-4-(6-Cyano-5-methoxypyridin-2-yl)cyclohexyl)methyl)(3-(2-cyclopropyloxazol-4-yl)phenyl)carbamoyl)cyclohexyl (2-hydroxyethyl)carbamate |

TABLE 1-continued

| Compound No | Structure | Chemical Name |
|---|---|---|
| 6.56 | 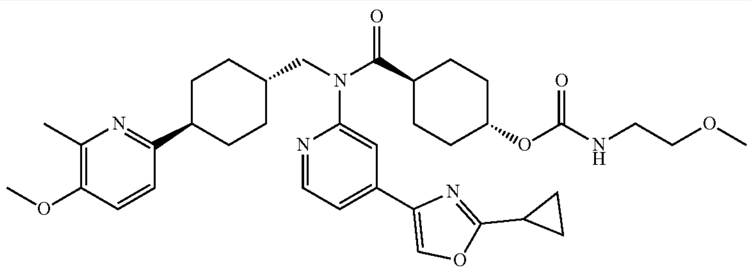 | trans-4-((4-(2-Cyclopropyloxazol-4-yl)pyridine-2-yl)(trans-4-(5-methoxy-6-methylpyridin-2-yl)cyclohexyl)methyl)carbamoyl)cyclohexyl (2-methoxyethyl)carbamate |
| 6.57 | 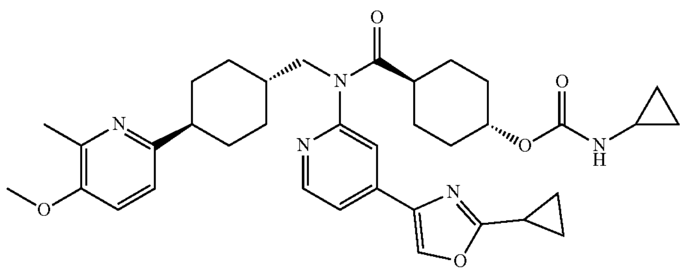 [SMILES: COc1ccc([C@H]2CC[C@H](CN(c3cc(-c4coc(C5CC5)n4)ccn3)C(=O)[C@H]3CC[C@H](OC(=O)NC4CC4)CC3)CC2)nc1C] | trans-4-((4-(2-Cyclopropyloxazol-4-yl)pyridine-2-yl)(trans-4-(5-methoxy-6-methylpyridin-2-yl)cyclohexyl)methyl)carbamoyl)cyclohexyl cyclopropyl carbamate |
| 6.58 | 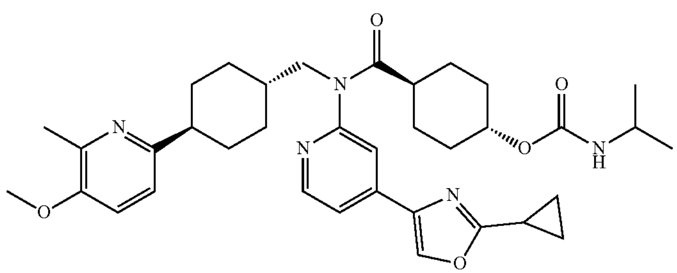 [SMILES: COc1ccc([C@H]2CC[C@H](CN(c3cc(-c4coc(C5CC5)n4)ccn3)C(=O)[C@H]3CC[C@H](OC(=O)NC(C)C)CC3)CC2)nc1C] | trans-4-((4-(2-Cyclopropyloxazol-4-yl)pyridine-2-yl)(trans-4-(5-methoxy-6-methylpyridin-2-yl)cyclohexyl)methyl)carbamoyl)cyclohexyl isopropylcarbamate |

TABLE 1-continued

| Compound No | Structure | Chemical Name |
|---|---|---|
| 6.59 | 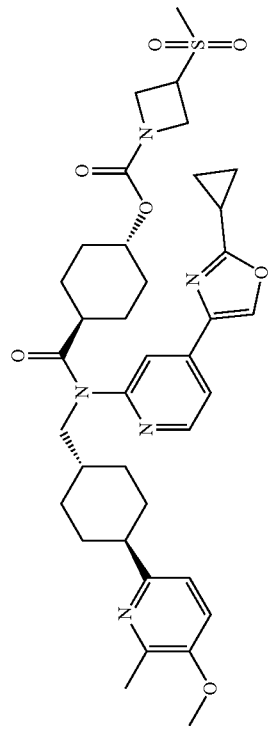 | trans-4-((4-(2-Cyclopropyloxazol-4-yl)pyridine-2-yl)(trans-4-(5-methoxy-6-methylpyridin-2-yl)cyclohexyl)methyl)carbamoyl)cyclohexyl morpholine-4-carboxylate |
| 6.60 | 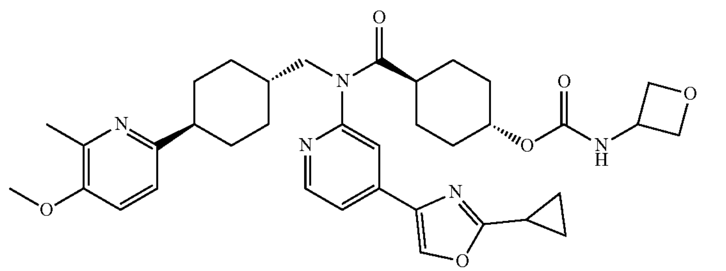 [SMILES: COc1ccc([C@H]2CC[C@H](CN(c3cc(-c4coc(C5CC5)n4)ccn3)C(=O)[C@H]3CC[C@H](OC(=O)NC4COC4)CC3)CC2)nc1C] | trans-4-((4-(2-Cyclopropyloxazol-4-yl)pyridine-2-yl)(trans-4-(5-methoxy-6-methylpyridin-2-yl)cyclohexyl)methyl)carbamoyl)cyclohexyl oxetan-3-ylcarbamate |
| 6.61 | 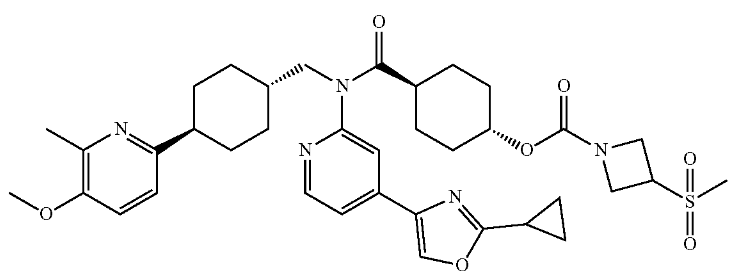 | trans-N-(4-(2-Cyclopropyloxazol-4-yl)pyridine-2-yl)-N-((trans-4-(5-methoxy-6-methylpyridin-2-yl)cyclohexyl)methyl)-4-(2-(3-(methylsulfonyl)azetidin-1-yl)-2-oxoethyl)cyclohexanecarboxamide |

| Compound No | Structure | Chemical Name |
|---|---|---|
| 6.62 | 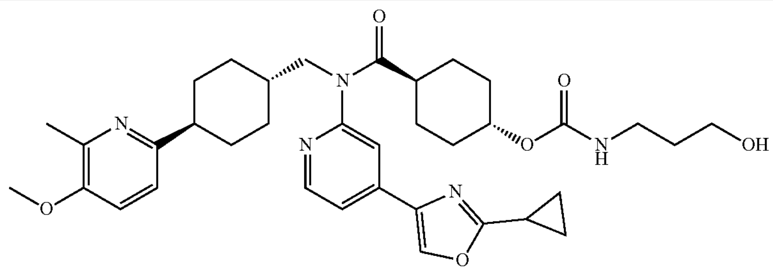 | trans-N-(4-(2-Cyclopropyloxazol-4-yl)pyridine-2-yl)-4-(2-((3-hydroxypropyl)amino)-2-oxoethyl)-N-((trans-4-(5-methoxy-6-methylpyridin-2-yl)cyclohexyl)methyl)cyclohexanecarboxamide |
| 6.63 | 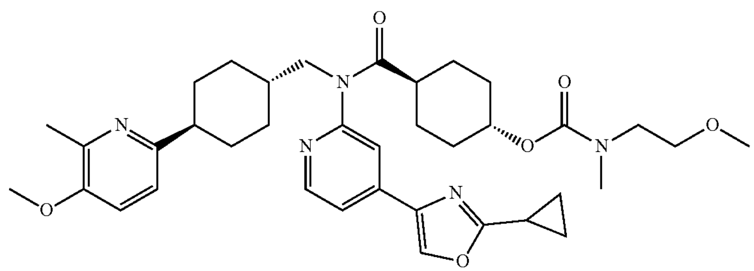 | trans-N-(4-(2-Cyclopropyloxazol-4-yl)pyridine-2-yl)-N-((trans-4-(5-methoxy-6-methylpyridin-2-yl)cyclohexyl)methyl)-4-(2-((2-methoxyethyl)(methyl)amino)-2-oxoethyl)cyclohexanecarboxamide |
| 6.64 | 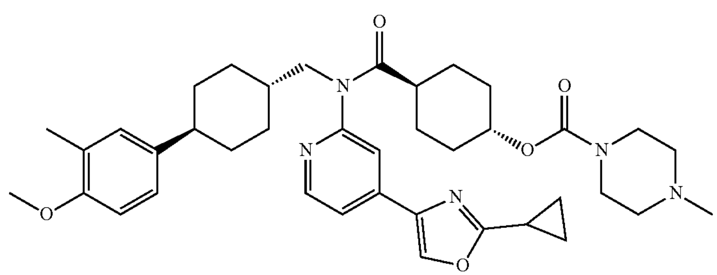 | trans-4-((4-(2-Cyclopropyloxazol-4-yl)pyridine-2-yl)(trans-4-(4-methoxy-3-methylphenyl)cyclohexyl)methyl)carbamoyl)cyclohexyl 4-methylpiperazine-1-carboxylate |

TABLE 1-continued

| Compound No | Structure | Chemical Name |
|---|---|---|
| 6.65 | 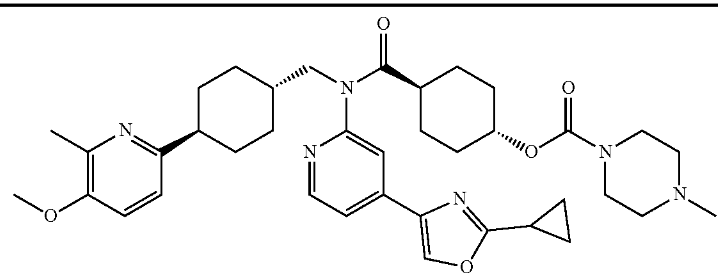 | trans-4-((4-(2-Cyclopropyloxazol-4-yl)pyridin-2-yl)(trans-4-(5-methoxy-6-methylpyridin-2-yl)cyclohexyl)methyl)carbamoyl)cyclohexyl 4-methylpiperazine-1-carboxylate |
| 6.66 | 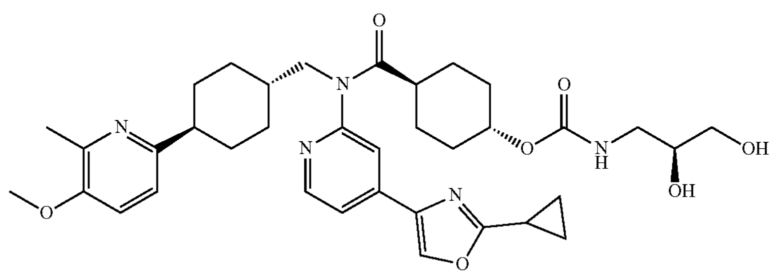 [SMILES: COc1ccc([C@H]2CC[C@H](CN(c3cc(-c4coc(C5CC5)n4)ccn3)C(=O)[C@H]3CC[C@H](OC(=O)NC[C@H](O)CO)CC3)CC2)nc1C] | trans-4-((4-(2-Cyclopropyloxazol-4-yl)pyridin-2-yl)(trans-4-(5-methoxy-6-methylpyridin-2-yl)cyclohexyl)methyl)carbamoyl)cyclohexyl ((S)-2,3-dihydroxypropyl)carbamate |
| 6.67 | 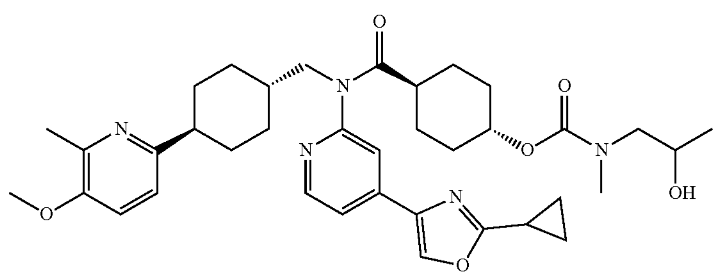 | trans-4-((4-(2-Cyclopropyloxazol-4-yl)pyridin-2-yl)(trans-4-(5-methoxy-6-methylpyridin-2-yl)cyclohexyl)methyl)carbamoyl)cyclohexyl (2-hydroxypropyl)(methyl)carbamate |

TABLE 1-continued

| Compound No | Structure | Chemical Name |
|---|---|---|
| 6.68 | 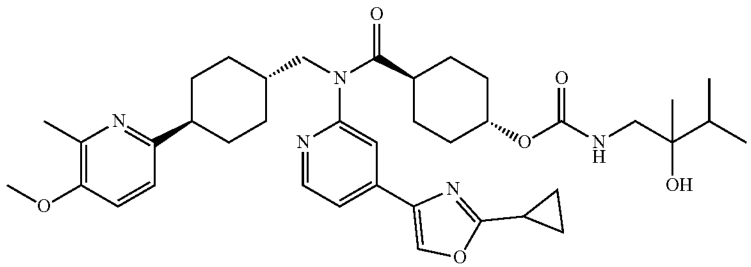 | trans-4-((4-(2-Cyclopropyloxazol-4-yl)pyridin-2-yl)(trans-4-(5-methoxy-6-methylpyridin-2-yl)cyclohexyl)methyl)carbamoyl)cyclohexyl (2-hydroxy-2,3-dimethylbutyl)carbamate |
| 6.69 | 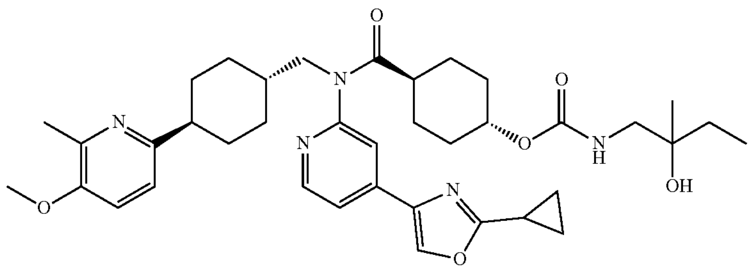 [SMILES: CCC(C)(O)CNC(=O)O[C@H]1CC[C@H](C(=O)N(C[C@H]2CC[C@H](c3ccc(OC)c(C)n3)CC2)c2cc(-c3coc(C4CC4)n3)ccn2)CC1] | trans-4-((4-(2-Cyclopropyloxazol-4-yl)pyridin-2-yl)(trans-4-(5-methoxy-6-methylpyridin-2-yl)cyclohexyl)methyl)carbamoyl)cyclohexyl (2-hydroxy-2-methylbutyl)carbamate |
| 6.70 | 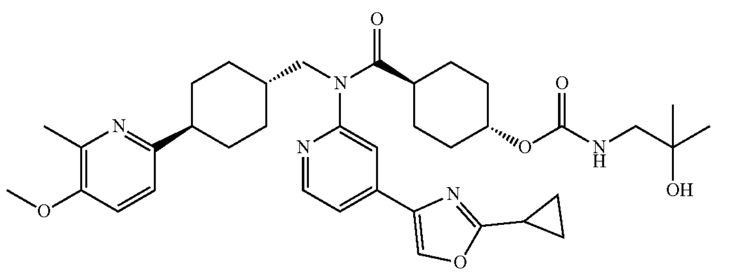 [SMILES: COc1ccc([C@H]2CC[C@H](CN(c3cc(-c4coc(C5CC5)n4)ccn3)C(=O)[C@H]3CC[C@H](OC(=O)NCC(C)(C)O)CC3)CC2)nc1C] | trans-4-((4-(2-Cyclopropyloxazol-4-yl)pyridin-2-yl)(trans-4-(5-methoxy-6-methylpyridin-2-yl)cyclohexyl)methyl)carbamoyl)cyclohexyl (2-hydroxy-2-methylpropyl)carbamate |

TABLE 1-continued

| Compound No | Structure | Chemical Name |
|---|---|---|
| 6.71 | 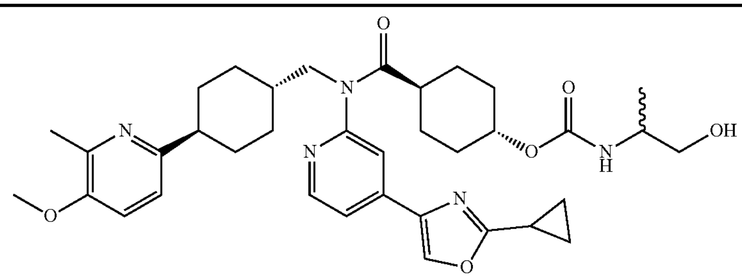 | trans-4-((4-(2-Cyclopropyloxazol-4-yl)pyridin-2-yl)(trans-4-(5-methoxy-6-methylpyridin-2-yl)cyclohexyl)methyl)carbamoyl)cyclohexyl (1-hydroxy propan-2-yl)carbamate |
| 6.72 | 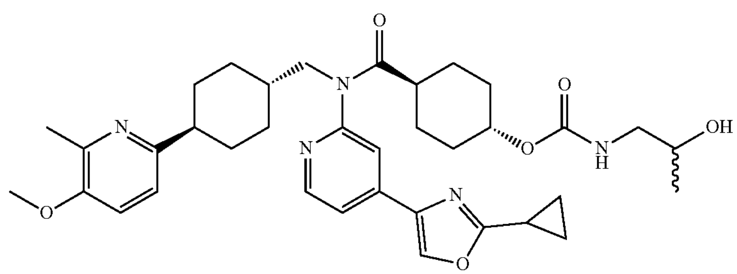 [SMILES: COc1ccc([C@H]2CC[C@H](CN(c3cc(-c4coc(C5CC5)n4)ccn3)C(=O)[C@H]3CC[C@H](OC(=O)NCC(C)O)CC3)CC2)nc1C] | trans-4-((4-(2-Cyclopropyloxazol-4-yl)pyridin-2-yl)(trans-4-(5-methoxy-6-methylpyridin-2-yl)cyclohexyl)methyl)carbamoyl)cyclohexyl (2-hydroxypropyl)carbamate |
| 6.73 | 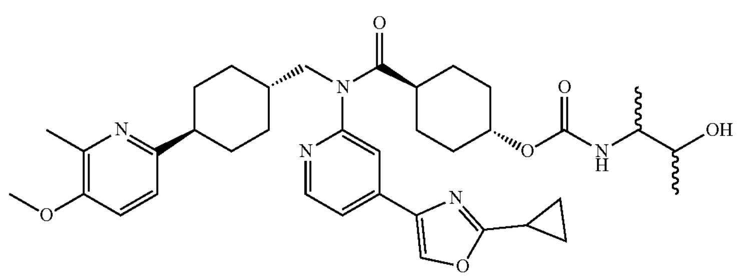 | trans-4-((4-(2-Cyclopropyloxazol-4-yl)pyridin-2-yl)(trans-4-(5-methoxy-6-methylpyridin-2-yl)cyclohexyl)methyl)carbamoyl)cyclohexyl (3-hydroxybutan-2-yl)carbamate |

TABLE 1-continued

| Compound No | Structure | Chemical Name |
|---|---|---|
| 6.74 | 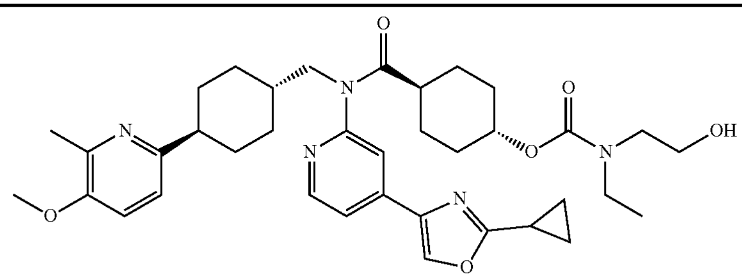 | trans-((4-(2-Cyclopropyloxazol-4-yl)pyridin-2-yl)(trans-4-(5-methoxy-6-methylpyridin-2-yl)cyclohexyl)methyl)carbamoyl)cyclohexyl ethyl(2-hydroxyethyl)carbamate |
| 6.75 | 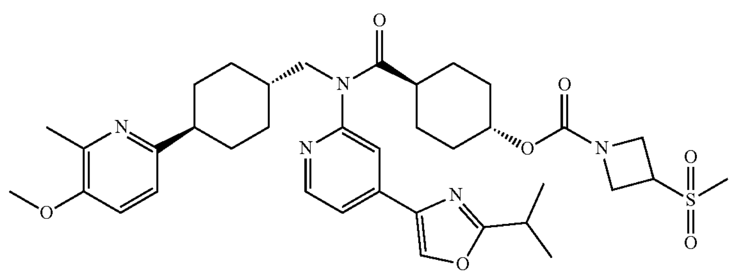 | trans-4-((4-(2-Isopropyloxazol-4-yl)pyridine-2-yl)(trans-4-(5-methoxy-6-methylpyridin-2-yl)cyclohexyl)methyl)carbamoyl)cyclohexyl 3-(methylsulfonyl)azetidine-1-carboxylate |
| 6.76 | 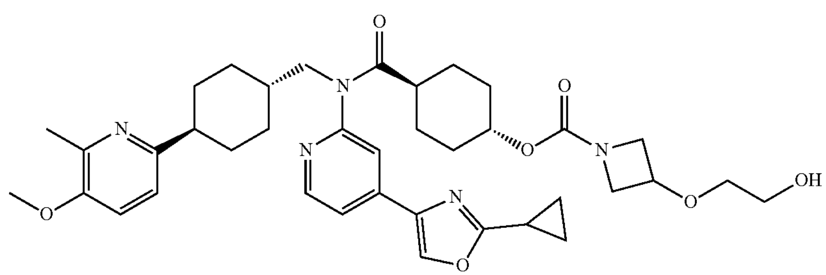 [SMILES: COc1ccc([C@H]2CC[C@H](CN(c3cc(-c4coc(C5CC5)n4)ccn3)C(=O)[C@H]3CC[C@H](OC(=O)N4CC(OCCO)C4)CC3)CC2)nc1C] | trans-((4-(2-Cyclopropyloxazol-4-yl)pyridine-2-yl)(trans-4-(5-methoxy-6-methylpyridin-2-yl)cyclohexyl)methyl)carbamoyl)cyclohexyl 3-(2-hydroxyethoxy)azetidine-1-carboxylate |

TABLE 1-continued

| Compound No | Structure | Chemical Name |
|---|---|---|
| 6.77 | 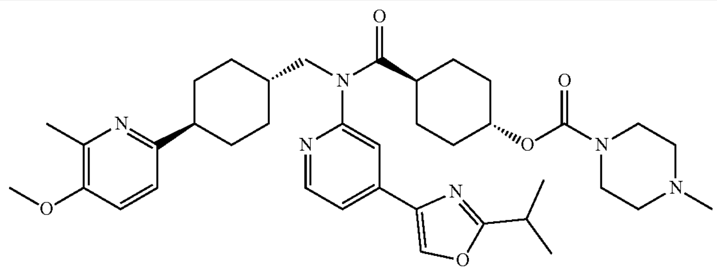 | trans-4-((4-(2-Isopropyloxazol-4-yl)pyridine-2-yl)(trans-4-(5-methoxy-6-methylpyridin-2-yl)cyclohexyl)methyl)carbamoyl)cyclohexyl 4-methylpiperazine-1-carboxylate |
| 6.78 | 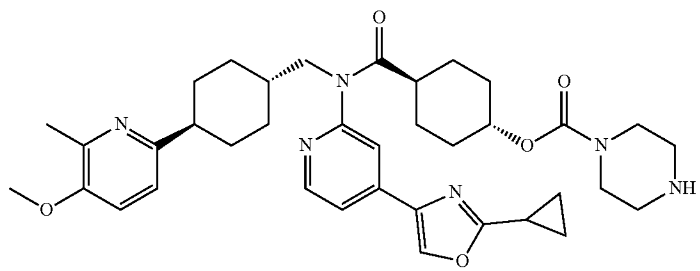 [SMILES: COc1ccc([C@H]2CC[C@H](CN(c3cc(-c4coc(C5CC5)n4)ccn3)C(=O)[C@H]3CC[C@H](OC(=O)N4CCNCC4)CC3)CC2)nc1C] | trans-4-((4-(2-Cyclopropyloxazol-4-yl)pyridine-2-yl)(trans-4-(5-methoxy-6-methylpyridin-2-yl)cyclohexyl)methyl)carbamoyl)cyclohexyl piperazine-1-carboxylate |
| 6.79 | 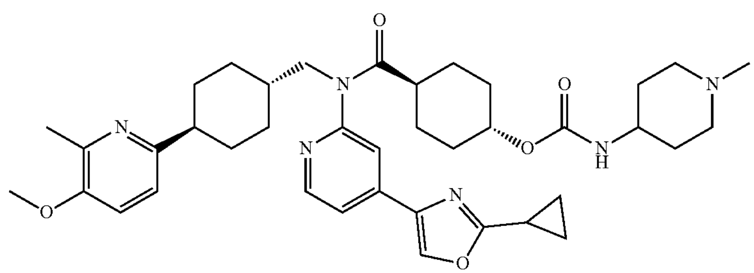 | trans-4-((4-(2-Cyclopropyloxazol-4-yl)pyridine-2-yl)(trans-4-(5-methoxy-6-methylpyridin-2-yl)cyclohexyl)methyl)carbamoyl)cyclohexyl (1-methylpiperidin-4-yl)carbamate |

TABLE 1-continued

| Compound No | Structure | Chemical Name |
|---|---|---|
| 6.80 | 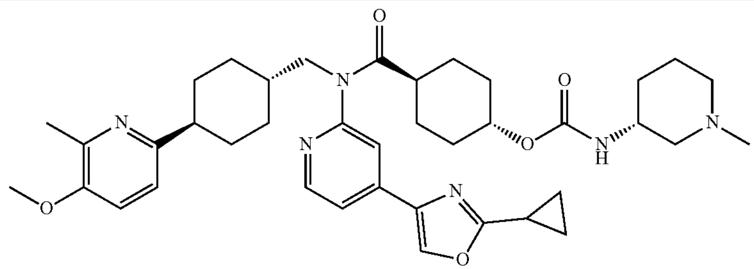 | trans-4-((4-(2-Cyclopropyloxazol-4-yl)pyridin-2-yl)(trans-4-(5-methoxy-6-methylpyridin-2-yl)cyclohexyl)methyl)carbamoyl)cyclohexyl ((R)-1-methylpiperidin-3-yl)carbamate |
| 6.81 | 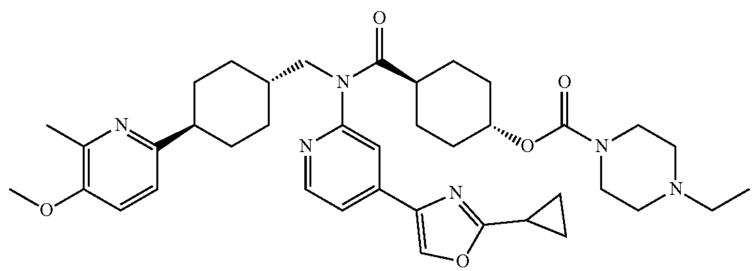 [SMILES: CCN1CCN(C(=O)O[C@H]2CC[C@H](C(=O)N(C[C@H]3CC[C@H](c4ccc(OC)c(C)n4)CC3)c3cc(-c4coc(C5CC5)n4)ccn3)CC2)CC1] | trans-4-((4-(2-Cyclopropyloxazol-4-yl)pyridine-2-yl)(trans-4-(5-methoxy-6-methylpyridin-2-yl)cyclohexyl)methyl)carbamoyl)cyclohexyl 4-ethylpiperazine-1-carboxylate |
| 6.82 | 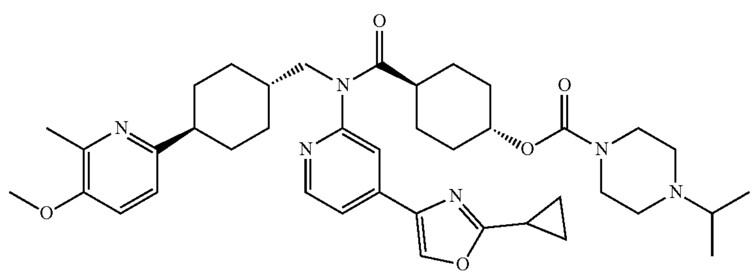 | trans-4-((4-(2-Cyclopropyloxazol-4-yl)pyridine-2-yl)(trans-4-(5-methoxy-6-methylpyridin-2-yl)cyclohexyl)methyl)carbamoyl)cyclohexyl 4-isopropylpiperazine-1-carboxylate |

TABLE 1-continued

| Compound No | Structure | Chemical Name |
|---|---|---|
| 6.83 | 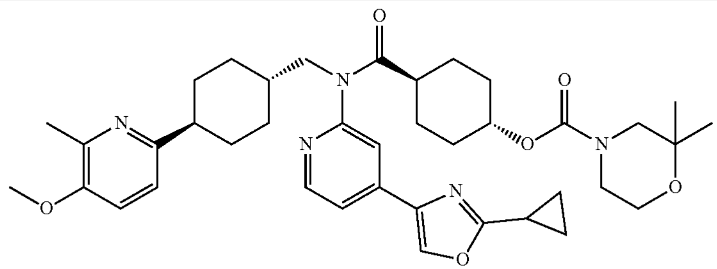 | trans-4-((4-(2-Cyclopropyloxazol-4-yl)pyridin-2-yl)(trans-4-(5-methoxy-6-methylpyridin-2-yl)cyclohexyl)methyl)carbamoyl)cyclohexyl 2,2-dimethylmorpholine-4-carboxylate |
| 6.84 | 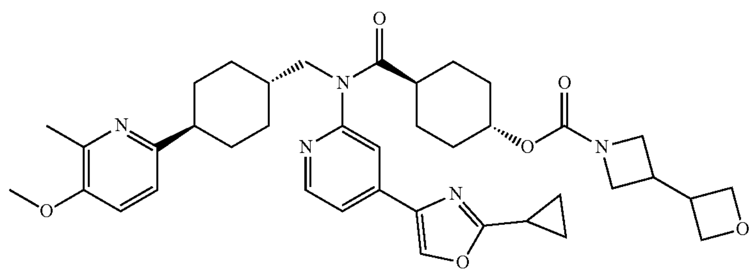 [SMILES: COc1ccc([C@H]2CC[C@H](CN(c3cc(-c4coc(C5CC5)n4)ccn3)C(=O)[C@H]3CC[C@H](OC(=O)N4CC(C5COC5)C4)CC3)CC2)nc1C] | trans-((4-(2-Cyclopropyloxazol-4-yl)pyridin-2-yl)(trans-4-(5-methoxy-6-methylpyridin-2-yl)cyclohexyl)methyl)carbamoyl)cyclohexyl 3-(oxetan-3-yl)azetidine-1-carboxylate |
| 6.85 | 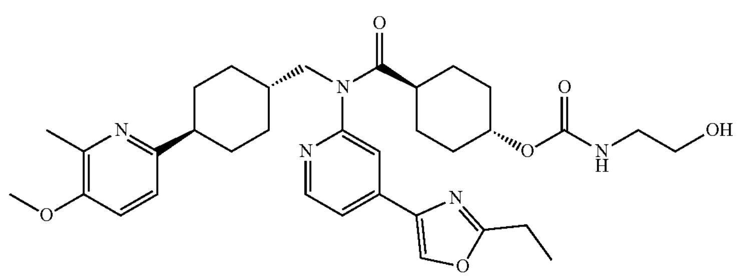 | trans-4-((4-(2-Ethyloxazol-4-yl)pyridin-2-yl)(trans-4-(5-methoxy-6-methylpyridin-2-yl)cyclohexyl)methyl)carbamoyl)cyclohexyl (2-hydroxyethyl)carbamate |

TABLE 1-continued

| Compound No | Structure | Chemical Name |
|---|---|---|
| 6.86 | 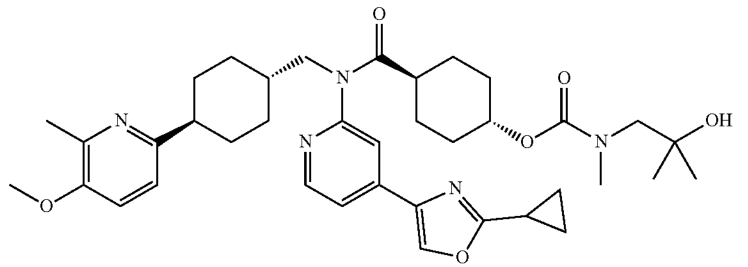 [SMILES: COc1ccc([C@H]2CC[C@H](CN(c3cc(-c4coc(C5CC5)n4)ccn3)C(=O)[C@H]3CC[C@H](OC(=O)N(C)CC(C)(C)O)CC3)CC2)nc1C] | trans-4-((4-(2-Cyclopropyloxazol-4-yl)pyridin-2-yl)(trans-4-(5-methoxy-6-methylpyridin-2-yl)cyclohexyl)methyl)carbamoyl)cyclohexyl (2-hydroxy-2-methylpropyl)(methyl)carbamate |
| 6.87 | 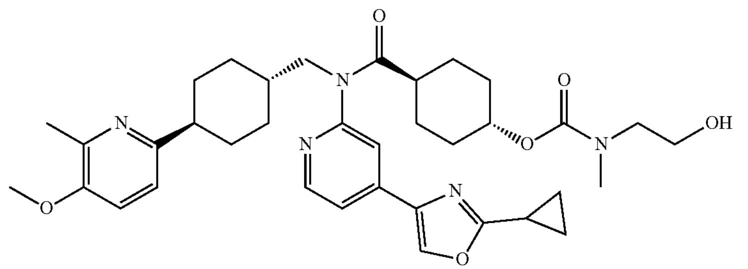 | trans-4-((4-(2-Cyclopropyloxazol-4-yl)pyridin-2-yl)(trans-4-(5-methoxy-6-methylpyridin-2-yl)cyclohexyl)methyl)carbamoyl)cyclohexyl (2-hydroxyethyl)(methyl)carbamate |
| 6.88 | 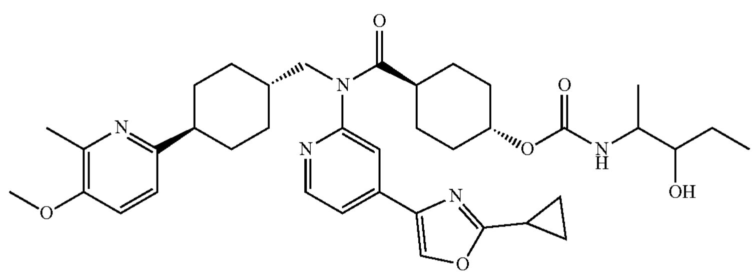 [SMILES: CCC(O)C(C)NC(=O)O[C@H]1CC[C@H](C(=O)N(C[C@H]2CC[C@H](c3ccc(OC)c(C)n3)CC2)c2cc(-c3coc(C4CC4)n3)ccn2)CC1] | trans-4-((4-(2-Cyclopropyloxazol-4-yl)pyridin-2-yl)(trans-4-(5-methoxy-6-methylpyridin-2-yl)cyclohexyl)methyl)carbamoyl)cyclohexyl (3-hydroxypentan-2-yl)carbamate |

TABLE 1-continued

| Compound No | Structure | Chemical Name |
|---|---|---|
| 6.89 | 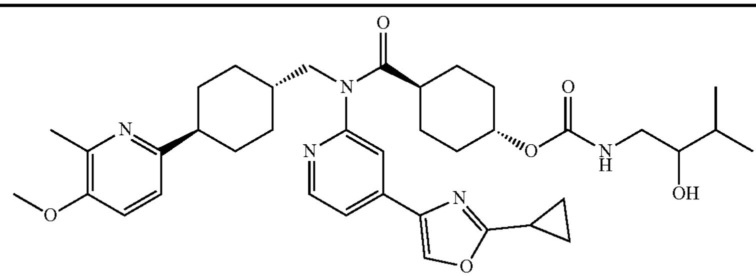 | trans-4-((4-(2-Cyclopropyloxazol-4-yl)pyridin-2-yl)(trans-4-(5-methoxy-6-methylpyridin-2-yl)cyclohexyl)methyl)carbamoyl)cyclohexyl (2-hydroxy-3-methylbutyl)carbamate |
| 6.90 | 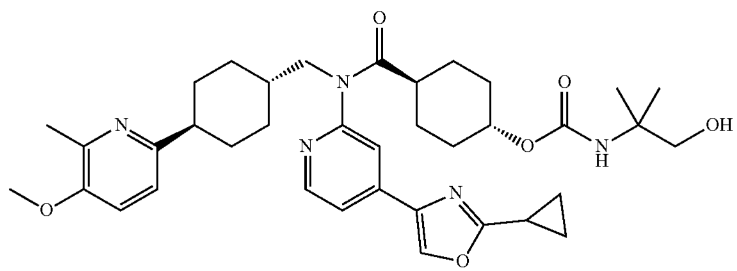 [SMILES: COc1ccc([C@H]2CC[C@H](CN(c3cc(-c4coc(C5CC5)n4)ccn3)C(=O)[C@H]3CC[C@H](OC(=O)NC(C)(C)CO)CC3)CC2)nc1C] | trans-4-((4-(2-Cyclopropyloxazol-4-yl)pyridin-2-yl)(trans-4-(5-methoxy-6-methylpyridin-2-yl)cyclohexyl)methyl)carbamoyl)cyclohexyl (1-hydroxy-2-methylpropan-2-yl)carbamate |
| 6.91 | 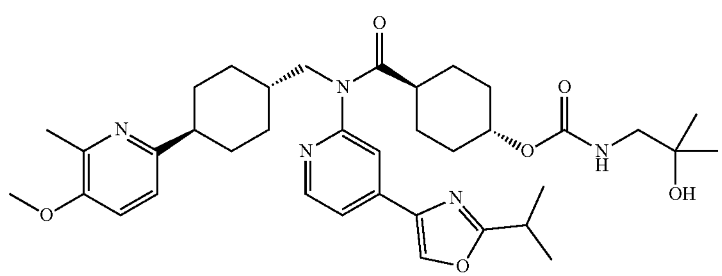 [SMILES: COc1ccc([C@H]2CC[C@H](CN(c3cc(-c4coc(C(C)C)n4)ccn3)C(=O)[C@H]3CC[C@H](OC(=O)NCC(C)(C)O)CC3)CC2)nc1C] | trans-4-((4-(2-Isopropyloxazol-4-yl)pyridin-2-yl)(trans-4-(5-methoxy-6-methylpyridin-2-yl)cyclohexyl)methyl)carbamoyl)cyclohexyl (2-hydroxy-2-methylpropyl)carbamate |

TABLE 1-continued

| Compound No | Structure | Chemical Name |
|---|---|---|
| 6.92 | 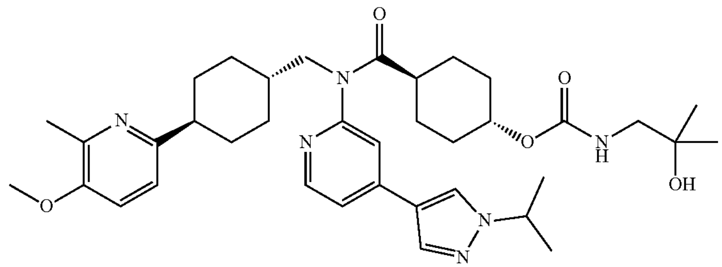 [SMILES: COc1ccc([C@H]2CC[C@H](CN(c3cc(-c4cnn(C(C)C)c4)ccn3)C(=O)[C@H]3CC[C@H](OC(=O)NCC(C)(C)O)CC3)CC2)nc1C] | trans-4-((4-(1-Isopropyl-1H-pyrazol-4-yl)pyridin-2-yl)(trans-4-(5-methoxy-6-methylpyridin-2-yl)cyclohexyl)methyl)carbamoyl)cyclohexyl (2-hydroxy-2-methylpropyl)carbamate |
| 6.93 | 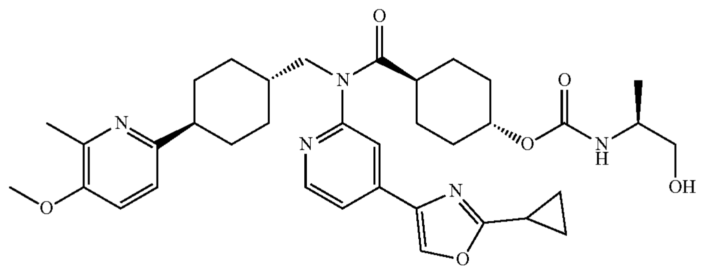 [SMILES: COc1ccc([C@H]2CC[C@H](CN(c3cc(-c4coc(C5CC5)n4)ccn3)C(=O)[C@H]3CC[C@H](OC(=O)N[C@@H](C)CO)CC3)CC2)nc1C] | trans-4-((4-(2-Cyclopropyloxazol-4-yl)pyridin-2-yl)(trans-4-(5-methoxy-6-methylpyridin-2-yl)cyclohexyl)methyl)carbamoyl)cyclohexyl ((S)-1-hydroxypropan-2-yl)carbamate |
| 6.94 | 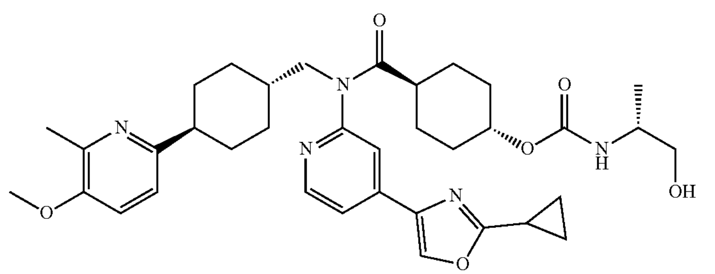 [SMILES: COc1ccc([C@H]2CC[C@H](CN(c3cc(-c4coc(C5CC5)n4)ccn3)C(=O)[C@H]3CC[C@H](OC(=O)N[C@H](C)CO)CC3)CC2)nc1C] | trans-4-((4-(2-Cyclopropyloxazol-4-yl)pyridin-2-yl)(trans-4-(5-methoxy-6-methylpyridin-2-yl)cyclohexyl)methyl)carbamoyl)cyclohexyl ((R)-1-hydroxypropan-2-yl)carbamate |

TABLE 1-continued

| Compound No | Structure | Chemical Name |
|---|---|---|
| 6.95 | 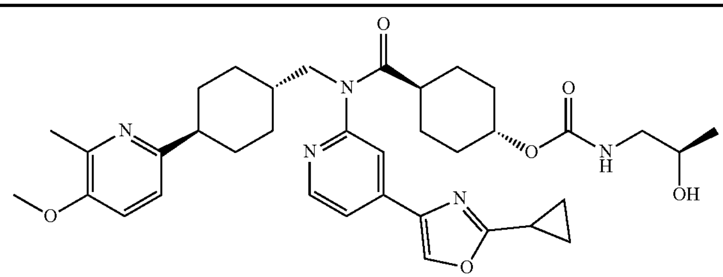 | trans-4-((4-(2-Cyclopropyloxazol-4-yl)pyridin-2-yl)(trans-4-(5-methoxy-6-methylpyridin-2-yl)cyclohexyl)methyl)carbamoyl)cyclohexyl ((R)-2-hydroxypropyl)carbamate |
| 6.96 | 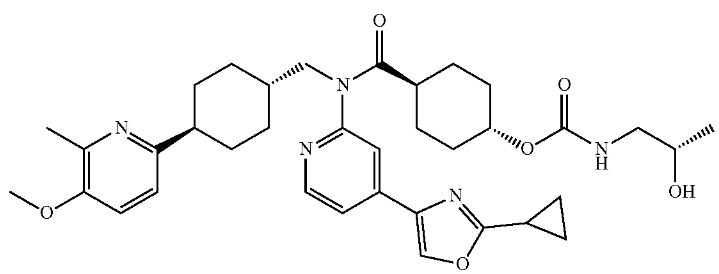 [SMILES: COc1ccc([C@H]2CC[C@H](CN(c3cc(-c4coc(C5CC5)n4)ccn3)C(=O)[C@H]3CC[C@H](OC(=O)NC[C@H](C)O)CC3)CC2)nc1C] | trans-4-((4-(2-Cyclopropyloxazol-4-yl)pyridin-2-yl)(trans-4-(5-methoxy-6-methylpyridin-2-yl)cyclohexyl)methyl)carbamoyl)cyclohexyl ((S)-2-hydroxypropyl)carbamate |
| 7 | 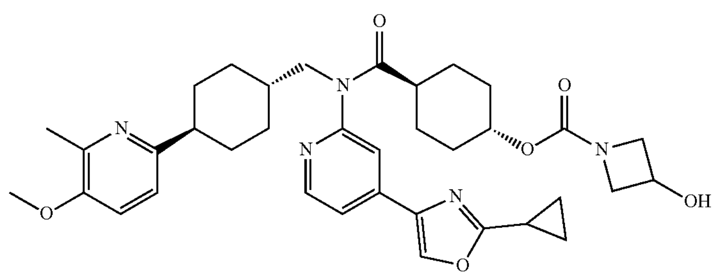 | trans-4-((4-(2-Cyclopropyloxazol-4-yl)pyridine-2-yl)(trans-4-(5-methoxy-6-methylpyridin-2-yl)cyclohexyl)methyl)carbamoyl)cyclohexyl 3-hydroxyazetidine-1-carboxylate |

TABLE 1-continued

| Compound No | Structure | Chemical Name |
|---|---|---|
| 7.01 | 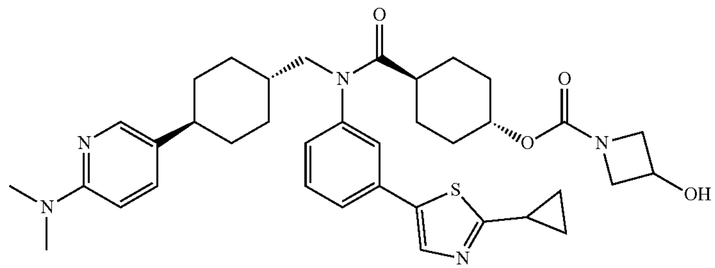 [SMILES: CN(C)c1ccc([C@H]2CC[C@H](CN(c3cccc(-c4cnc(C5CC5)s4)c3)C(=O)[C@H]3CC[C@H](OC(=O)N4CC(O)C4)CC3)CC2)cn1] | trans-4-((3-(2-Cyclopropylthiazol-5-yl)phenyl)(trans-4-(6-(dimethylamino)pyridin-3-yl)cyclohexyl)methyl)carbamoyl)cyclohexyl 3-hydroxyazetidine-1-carboxylate |
| 7.02 | 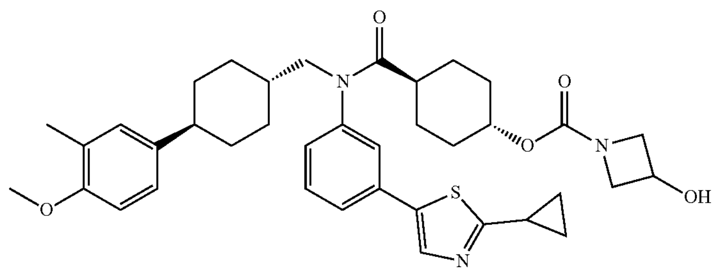 | trans-4-((3-(2-Cyclopropylthiazol-5-yl)phenyl)(trans-4-(4-methoxy-3-methylphenyl)cyclohexyl)methyl)carbamoyl)cyclohexyl 3-hydroxyazetidine-1-carboxylate |
| 7.03 | 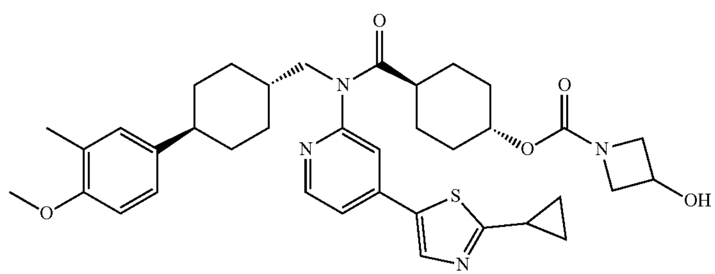 | trans-4-((4-(2-Cyclopropylthiazol-5-yl)pyridin-2-yl)(trans-4-(4-methoxy-3-methylphenyl)cyclohexyl)methyl)carbamoyl)cyclohexyl 3-hydroxyazetidine-1-carboxylate |

TABLE 1-continued

| Compound No | Structure | Chemical Name |
|---|---|---|
| 7.04 | 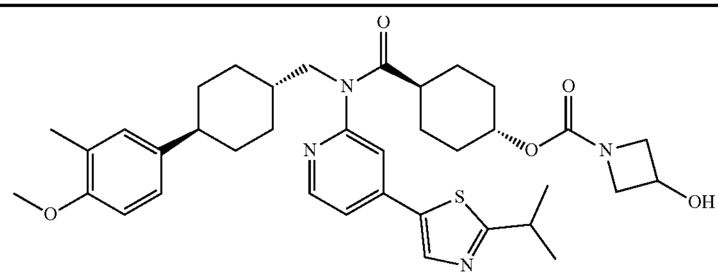 | trans-4-((4-(2-Isopropylthiazol-5-yl)pyridin-2-yl)(trans-4-(4-methoxy-3-methylphenyl)cyclohexyl)methyl)carbamoyl)cyclohexyl 3-hydroxyazetidine-1-carboxylate |
| 7.05 | 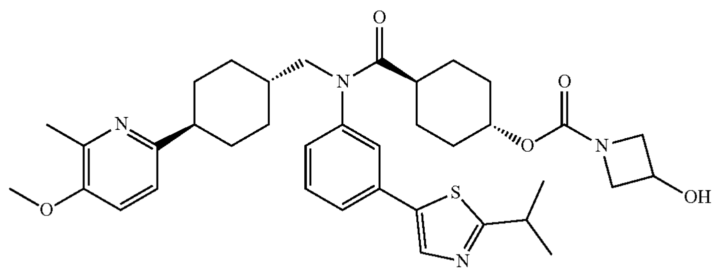 | trans-4-(3-(2-Isopropylthiazol-5-yl)phenyl)(trans-4-(5-methoxy-6-methylpyridin-2-yl)cyclohexyl)methyl)carbamoyl)cyclohexyl 3-hydroxyazetidine-1-carboxylate |
| 7.06 | 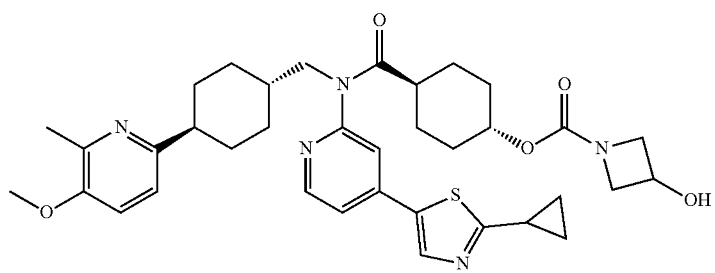 | trans-4-((4-(2-Cyclopropylthiazol-5-yl)pyridin-2-yl)(trans-4-(5-methoxy-6-methylpyridin-2-yl)cyclohexyl)methyl)carbamoyl)cyclohexyl 3-hydroxyazetidine-1-carboxylate |

| Compound No | Structure | Chemical Name |
|---|---|---|
| 7.07 | 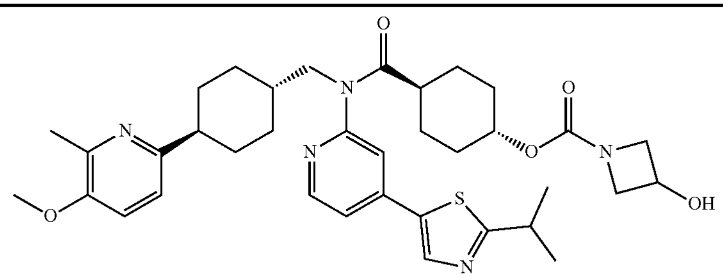 | trans-4-((4-(2-Isopropylthiazol-5-yl)pyridin-2-yl)(trans-4-(5-methoxy-6-methylpyridin-2-yl)cyclohexyl)methyl)carbamoyl)cyclohexyl 3-hydroxyazetidine-1-carboxylate |
| 7.08 | 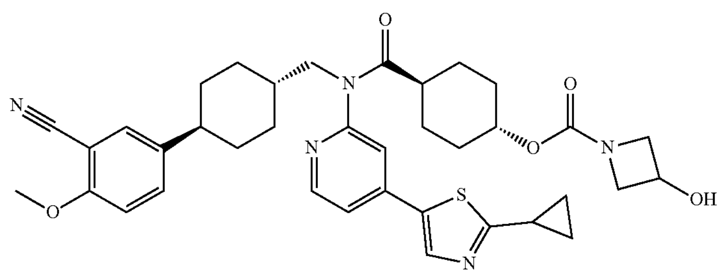 [SMILES: COc1ccc([C@H]2CC[C@H](CN(c3cc(-c4cnc(C5CC5)s4)ccn3)C(=O)[C@H]3CC[C@H](OC(=O)N4CC(O)C4)CC3)CC2)cc1C#N] | trans-4-((trans-4-(3-Cyano-4-methoxyphenyl)cyclohexyl)methyl)(4-(2-cyclopropylthiazol-5-yl)pyridin-2-yl)carbamoyl)cyclohexyl 3-hydroxyazetidine-1-carboxylate |
| 7.09 | 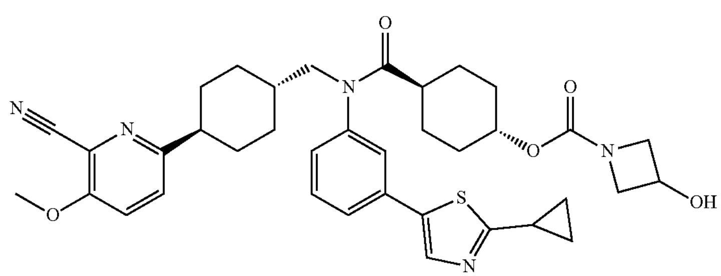 [SMILES: COc1ccc([C@H]2CC[C@H](CN(c3cccc(-c4cnc(C5CC5)s4)c3)C(=O)[C@H]3CC[C@H](OC(=O)N4CC(O)C4)CC3)CC2)nc1C#N] | trans-4-((trans-4-(6-Cyano-5-methoxypyridin-2-yl)cyclohexyl)methyl)(3-(2-cyclopropylthiazol-5-yl)phenyl)carbamoyl)cyclohexyl 3-hydroxyazetidine-1-carboxylate |

TABLE 1-continued

| Compound No | Structure | Chemical Name |
|---|---|---|
| 7.10 | 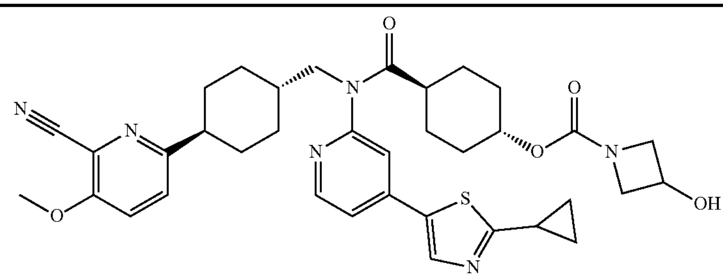 | trans-4-(((trans-4-(6-Cyano-5-methoxypyridin-2-yl)cyclohexyl)methyl)(4-(2-cyclopropylthiazol-5-yl)pyridin-2-yl)carbamoyl)cyclohexyl 3-hydroxyazetidine-1-carboxylate |
| 7.11 | 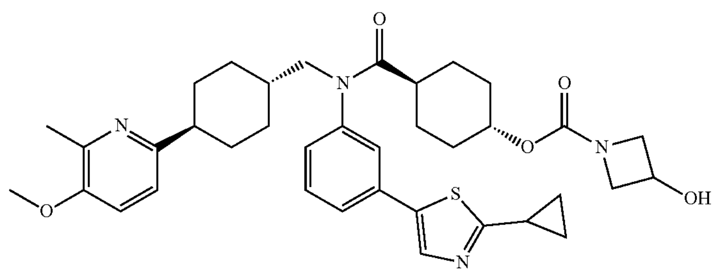 | trans-4-((3-(2-Cyclopropylthiazol-5-yl)phenyl)((trans-4-(5-methoxy-6-methylpyridin-2-yl)cyclohexyl)methyl)carbamoyl)cyclohexyl 3-hydroxyazetidine-1-carboxylate |
| 7.12 | 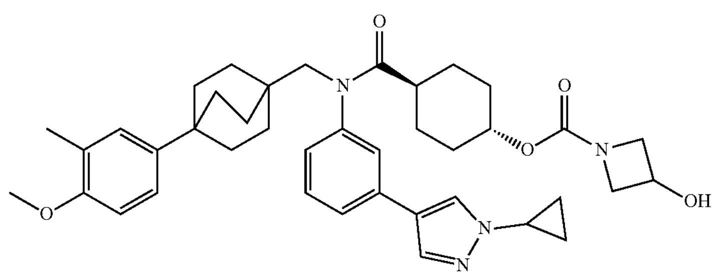 [SMILES: COc1ccc(C23CCC(CN(c4cccc(-c5cnn(C6CC6)c5)c4)C(=O)[C@H]4CC[C@H](OC(=O)N5CC(O)C5)CC4)(CC2)CC3)cc1C] | 4-((3-(1-Cyclopropyl-1H-pyrazol-4-yl)phenyl)((4-(4-methoxy-3-methylphenyl)bicyclo[2.2.2]octan-1-yl)methyl)carbamoyl)cyclohexyl trans-3-hydroxyazelidine-1-carboxylate |

TABLE 1-continued

| Compound No | Structure | Chemical Name |
|---|---|---|
| 7.13 | 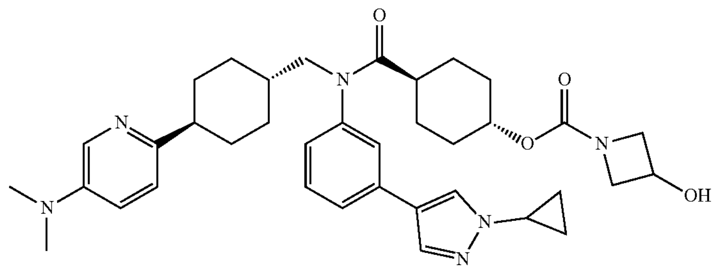 [SMILES: CN(C)c1ccc([C@H]2CC[C@H](CN(c3cccc(-c4cnn(C5CC5)c4)c3)C(=O)[C@H]3CC[C@H](OC(=O)N4CC(O)C4)CC3)CC2)nc1] | trans-4-((3-(1-Cyclopropyl-1H-pyrazol-4-yl)phenyl)(trans-4-(6-(dimethylamino)pyridin-3-yl)cyclohexyl)methyl)carbamoyl)cyclohexyl 3-hydroxyazetidine-1-carboxylate |
| 7.14 | 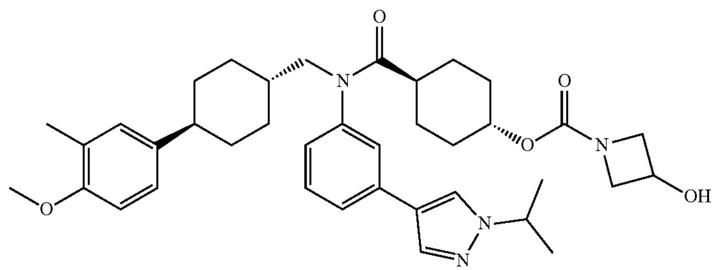 | trans-4-((3-(1-Isopropyl-1H-pyrazol-4-yl)phenyl)(trans-4-(4-methoxy-3-methylphenyl)cyclohexyl)methyl)carbamoyl)cyclohexyl 3-hydroxyazetidine-1-carboxylate |
| 7.15 | 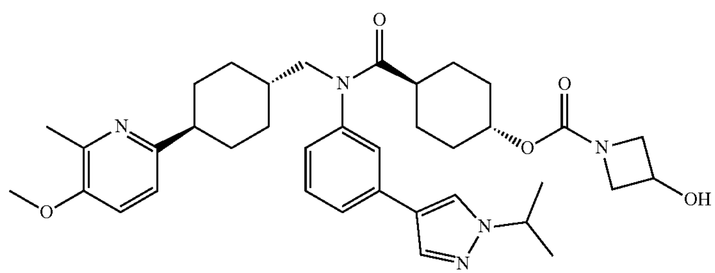 | trans-4-((3-(1-Isopropyl-1H-pyrazol-4-yl)phenyl)(trans-4-(5-methoxy-6-methylpyridin-2-yl)cyclohexyl)methyl)carbamoyl)cyclohexyl 3-hydroxyazetidine-1-carboxylate |

TABLE 1-continued

| Compound No | Structure | Chemical Name |
|---|---|---|
| 7.16 | 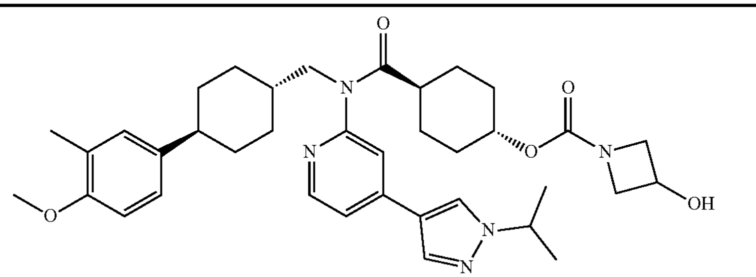 | trans-4-((4-(1-Isopropyl-1H-pyrazol-4-yl)pyridin-2-yl)((trans-4-(4-methoxy-3-methylphenyl)cyclohexyl)methyl)carbamoyl)cyclohexyl 3-hydroxyazetidine-1-carboxylate |
| 7.17 | 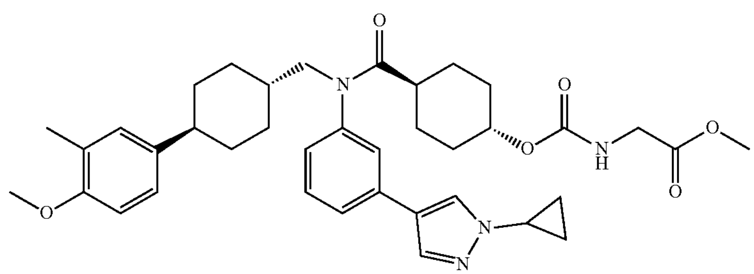 | Methyl 2-((((trans-4-((3-(1-cyclopropyl-1H-pyrazol-4-yl)phenyl)((trans-4-(4-methoxy-3-methylphenyl)cyclohexyl)methyl)carbamoyl)cyclohexyl)oxy)carbonyl)amino)acetate |
| 7.18 | 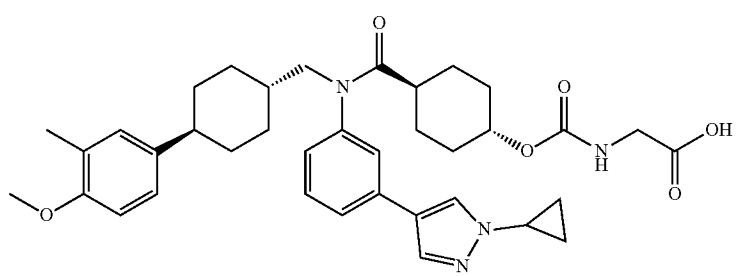 [SMILES: COc1ccc([C@H]2CC[C@H](CN(c3cccc(-c4cnn(C5CC5)c4)c3)C(=O)[C@H]3CC[C@H](OC(=O)NCC(=O)O)CC3)CC2)cc1C] | 2-((((trans-4-((3-(1-Cyclopropyl-1H-pyrazol-4-yl)phenyl)((trans-4-(4-methoxy-3-methylphenyl)cyclohexyl)methyl)carbamoyl)cyclohexyl)oxy)carbonyl)amino)acetic acid |

TABLE 1-continued

| Compound No | Structure | Chemical Name |
|---|---|---|
| 7.19 | 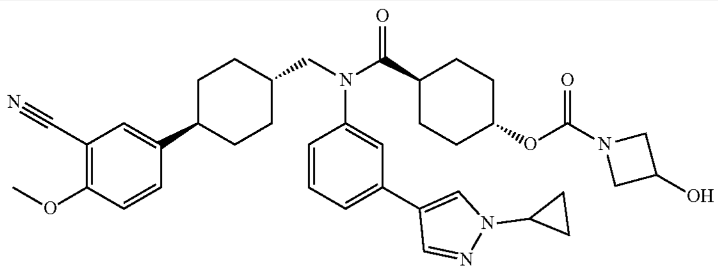 | trans-4-(((trans-4-(3-Cyano-4-methoxyphenyl)cyclohexyl)methyl)(3-(1-cyclopropyl-1H-pyrazol-4-yl)phenyl)carbamoyl)cyclohexyl 3-hydroxyazetidine-1-carboxylate |
| 7.20 | 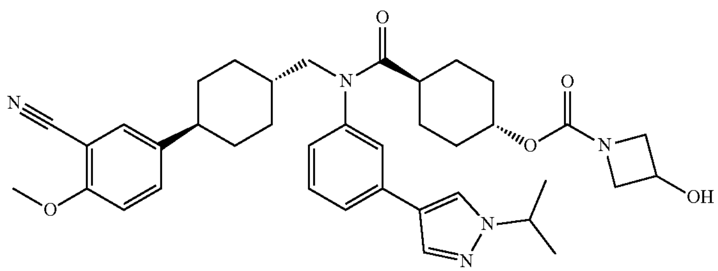 | trans-4-(((trans-4-(3-Cyano-4-methoxyphenyl)cyclohexyl)methyl)(3-(1-isopropyl-1H-pyrazol-4-yl)phenyl)carbamoyl)cyclohexyl 3-hydroxyazetidine-1-carboxylate |
| 7.21 | 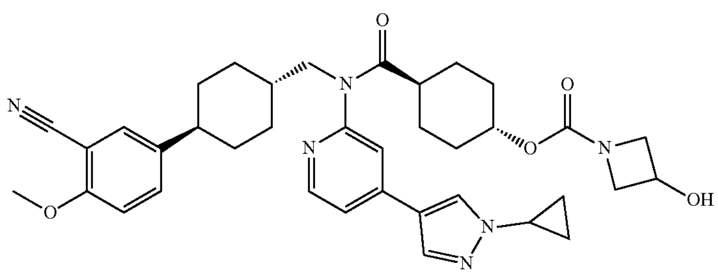 | trans-4-(((trans-4-(3-Cyano-4-methoxyphenyl)cyclohexyl)methyl)(4-(1-cyclopropyl-1H-pyrazol-4-yl)pyridin-2-yl)carbamoyl)cyclohexyl 3-hydroxyazetidine-1-carboxylate |

TABLE 1-continued

| Compound No | Structure | Chemical Name |
|---|---|---|
| 7.22 | 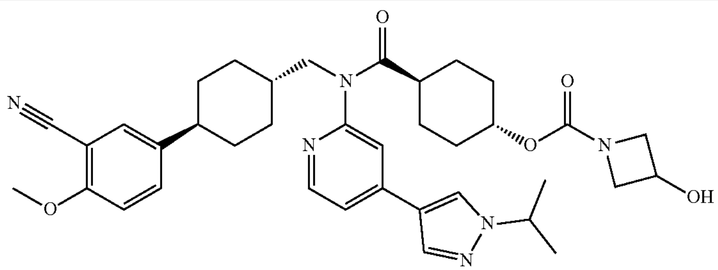 | trans-4-(((trans-4-(3-Cyano-4-methoxyphenyl)cyclohexyl)methyl)(4-(1-isopropyl-1H-pyrazol-4-yl)pyridin-2-yl)carbamoyl)cyclohexyl 3-hydroxyazetidine-1-carboxylate |
| 7.23 | 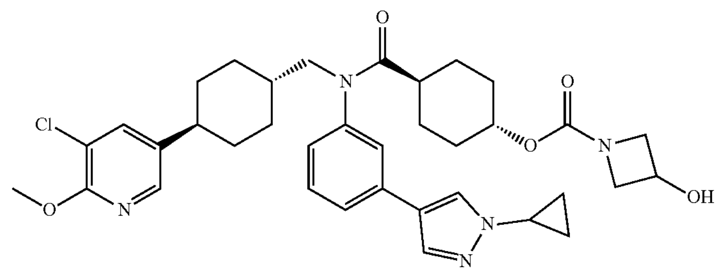 | trans-4-(((trans-4-(5-Chloro-6-methoxypyridin-3-yl)cyclohexyl)methyl)(3-(1-cyclopropyl-1H-pyrazol-4-yl)phenyl)carbamoyl)cyclohexyl 3-hydroxyazetidine-1-carboxylate |
| 7.24 | 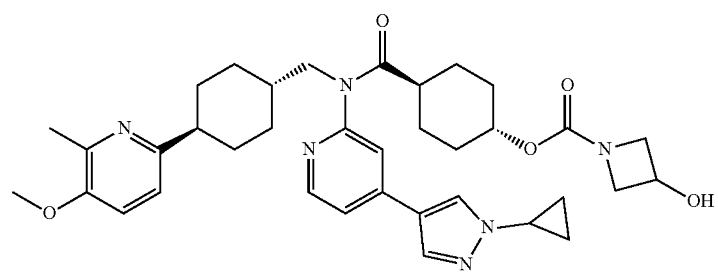 | trans-4-((4-(1-Cyclopropyl-1H-pyrazol-4-yl)pyridin-2-yl)((trans-4-(5-methoxy-6-methylpyridin-2-yl)cyclohexyl)methyl)carbamoyl)cyclohexyl 3-hydroxyazetidine-1-carboxylate |

TABLE 1-continued

| Compound No | Structure | Chemical Name |
|---|---|---|
| 7.25 | 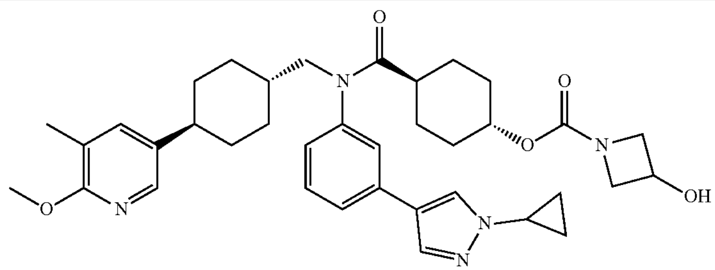 [SMILES: COc1ncc([C@H]2CC[C@H](CN(c3cccc(-c4cnn(C5CC5)c4)c3)C(=O)[C@H]3CC[C@H](OC(=O)N4CC(O)C4)CC3)CC2)cc1C] | trans-4-((3-(1-Cyclopropyl-1H-pyrazol-4-yl)phenyl)(trans-4-(6-methoxy-5-methylpyridin-3-yl)cyclohexyl)methyl)carbamoyl)cyclohexyl 3-hydroxyazetidine-1-carboxylate |
| 7.26 | 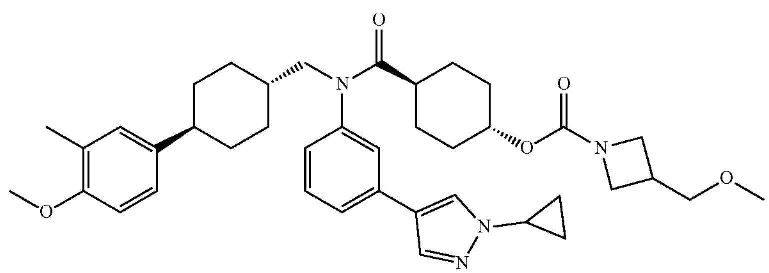 | trans-4-((3-(1-Cyclopropyl-1H-pyrazol-4-yl)phenyl)(trans-4-(4-methoxy-3-methylphenyl)cyclohexyl)methyl)carbamoyl)cyclohexyl 3-(methoxymethyl)azetidine-1-carboxylate |
| 7.27 | 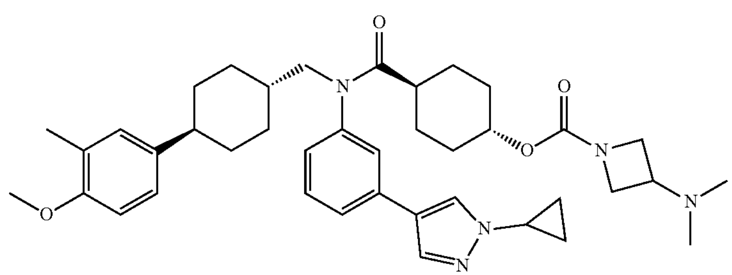 | trans-4-((3-(1-Cyclopropyl-1H-pyrazol-4-yl)phenyl)(trans-4-(4-methoxy-3-methylphenyl)cyclohexyl)methyl)carbamoyl)cyclohexyl 3-(dimethylamino)azetidine-1-carboxylate |

TABLE 1-continued

| Compound No | Structure | Chemical Name |
|---|---|---|
| 7.28 | 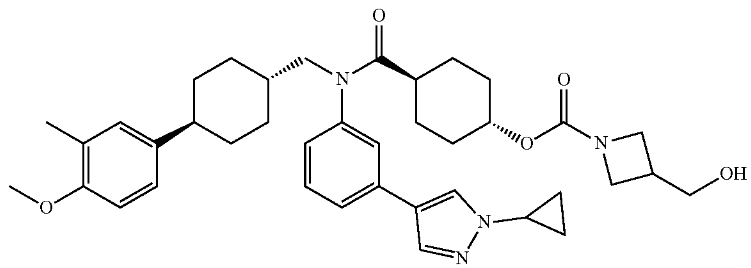 [SMILES: COc1ccc([C@H]2CC[C@H](CN(c3cccc(-c4cnn(C5CC5)c4)c3)C(=O)[C@H]3CC[C@H](OC(=O)N4CC(CO)C4)CC3)CC2)cc1C] | trans-4-((3-(1-Cyclopropyl-1H-pyrazol-4-yl)phenyl)(trans-4-(4-methoxy-3-methylphenyl)cyclohexyl)methyl)carbamoyl)-cyclohexyl 3-(hydroxymethyl)azetidine-1-carboxylate |
| 7.29 | 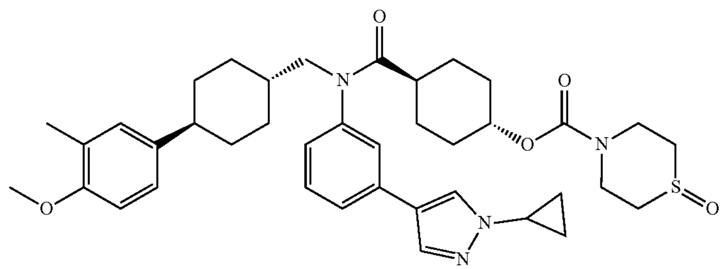 [SMILES: COc1ccc([C@H]2CC[C@H](CN(c3cccc(-c4cnn(C5CC5)c4)c3)C(=O)[C@H]3CC[C@H](OC(=O)N4CCS(=O)CC4)CC3)CC2)cc1C] | trans-4-((3-(1-Cyclopropyl-1H-pyrazol-4-yl)phenyl)(trans-4-(4-methoxy-3-methylphenyl)cyclohexyl)methyl)carbamoyl)-cyclohexyl thiomorpholine-4-carboxylate 1-oxide |
| 7.30 | 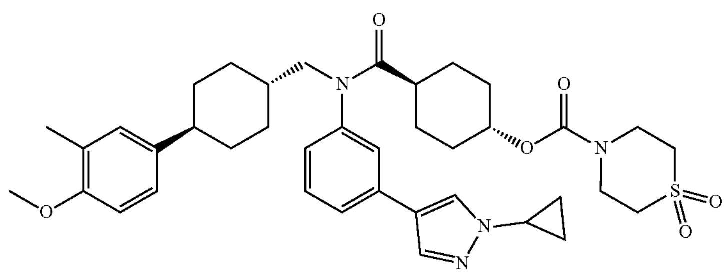 [SMILES: COc1ccc([C@H]2CC[C@H](CN(c3cccc(-c4cnn(C5CC5)c4)c3)C(=O)[C@H]3CC[C@H](OC(=O)N4CCS(=O)(=O)CC4)CC3)CC2)cc1C] | trans-4-((3-(1-Cyclopropyl-1H-pyrazol-4-yl)phenyl)(trans-4-(4-methoxy-3-methylphenyl)cyclohexyl)methyl)carbamoyl)-cyclohexyl thiomorpholine-4-carboxylate 1,1-dioxide |

TABLE 1-continued

| Compound No | Structure | Chemical Name |
|---|---|---|
| 7.31 | 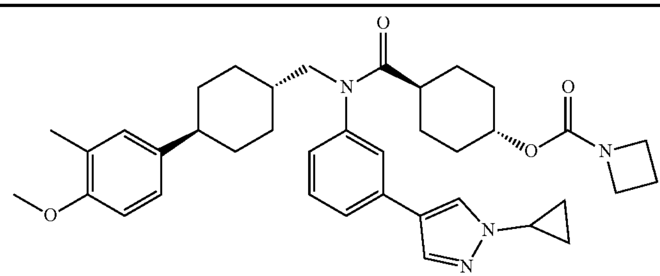 | trans-4-((3-(1-Cyclopropyl-1H-pyrazol-4-yl)phenyl)((trans-4-(4-methoxy-3-methylphenyl)cyclohexyl)methyl)(carbamoyl)-cyclohexyl azetidine-1-carboxylate |
| 7.32 | 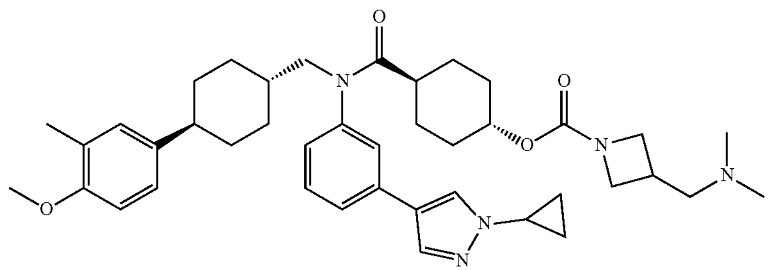 | trans-4-((3-(1-Cyclopropyl-1H-pyrazol-4-yl)phenyl)((trans-4-(4-methoxy-3-methylphenyl)cyclohexyl)methyl)carbamoyl)cyclohexyl 3-((dimethylamino)methyl)azetidine-1-carboxylate |
| 7.33 | 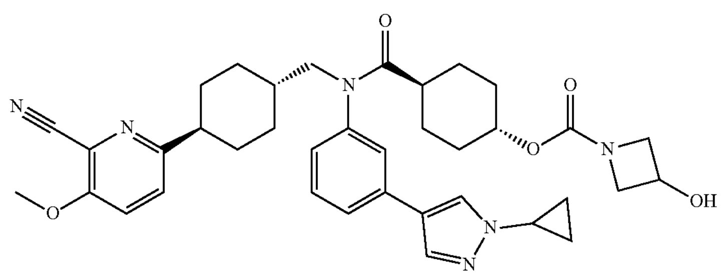 | trans-4-(((trans-4-(6-Cyano-5-methoxypyridin-2-yl)cyclohexyl)methyl)(3-(1-cyclopropyl-1H-pyrazol-4-yl)phenyl)carbamoyl)cyclohexyl 3-hydroxyazetidine-1-carboxylate |

TABLE 1-continued

| Compound No | Structure | Chemical Name |
|---|---|---|
| 7.34 | 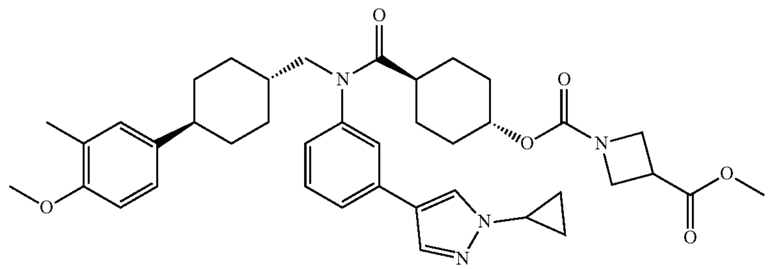 | 1-(trans-4-((3-(1-Cyclopropyl-1H-pyrazol-4-yl)phenyl)(trans-4-(4-methoxy-3-methylphenyl)cyclohexyl)methyl)carbamoyl)-cyclohexyl) 3-methyl azetidine-1,3-dicarboxylate |
| 7.35 | 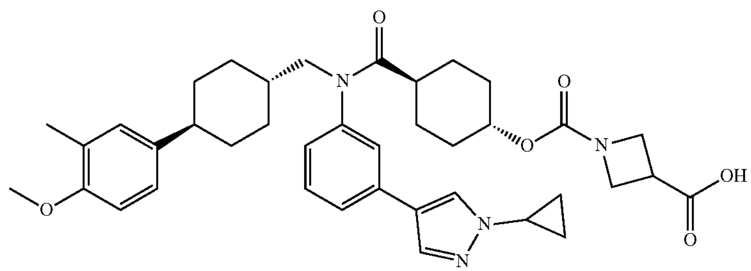 [SMILES: COc1ccc([C@H]2CC[C@H](CN(c3cccc(-c4cnn(C5CC5)c4)c3)C(=O)[C@H]3CC[C@H](OC(=O)N4CC(C(=O)O)C4)CC3)CC2)cc1C] | 1-(((trans-4-((3-(1-Cyclopropyl-1H-pyrazol-4-yl)phenyl)(trans-4-(4-methoxy-3-methylphenyl)cyclohexyl)methyl)carbamoyl)-cyclohexyl)oxy)carbonyl)azetidine-3-carboxylic acid |
| 7.36 | 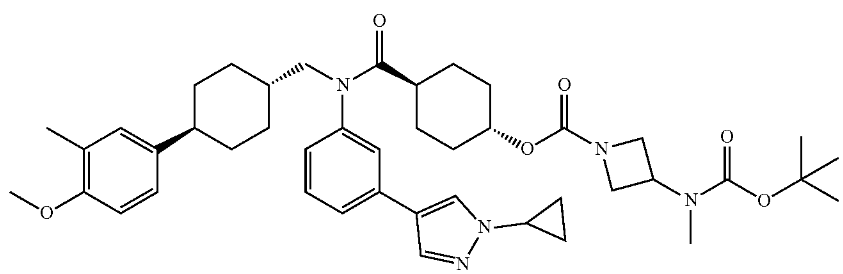 [SMILES: COc1ccc([C@H]2CC[C@H](CN(c3cccc(-c4cnn(C5CC5)c4)c3)C(=O)[C@H]3CC[C@H](OC(=O)N4CC(N(C)C(=O)OC(C)(C)C)C4)CC3)CC2)cc1C] | trans-4-(3-(1-Cyclopropyl-1H-pyrazol-4-yl)phenyl)(trans-4-(4-methoxy-3-methylphenyl)cyclohexyl)methyl)carbamoyl)-cyclohexyl 3-((tert-butoxycarbonyl)(methyl)amino)azetidine-1-carboxylate |

TABLE 1-continued

| Compound No | Structure | Chemical Name |
|---|---|---|
| 7.37 | 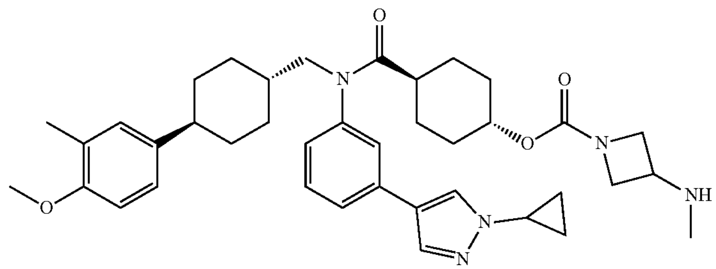 | trans-4-((3-(1-Cyclopropyl-1H-pyrazol-4-yl)phenyl)(trans-4-(4-methoxy-3-methylphenyl)cyclohexyl)methyl)carbamoyl)-cyclohexyl 3-(methylamino)azetidine-1-carboxylate |
| 7.38 | 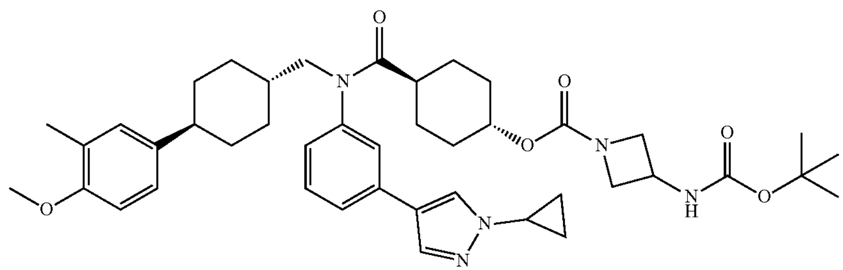 | trans-4-((3-(1-Cyclopropyl-1H-pyrazol-4-yl)phenyl)(trans-4-(4-methoxy-3-methylphenyl)cyclohexyl)methyl)carbamoyl)-cyclohexyl 3-((tert-butoxycarbonyl)amino)azetidine-1-carboxylate |
| 7.39 | 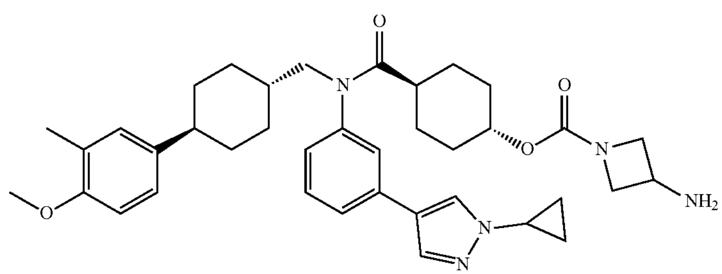 [SMILES: COc1ccc([C@H]2CC[C@H](CN(c3cccc(-c4cnn(C5CC5)c4)c3)C(=O)[C@H]3CC[C@H](OC(=O)N4CC(N)C4)CC3)CC2)cc1C] | trans-4-((3-(1-Cyclopropyl-1H-pyrazol-4-yl)phenyl)(trans-4-(4-methoxy-3-methylphenyl)cyclohexyl)methyl)carbamoyl)-cyclohexyl 3-aminoazetidine-1-carboxylate |

TABLE 1-continued

| Compound No | Structure | Chemical Name |
|---|---|---|
| 7.40 | 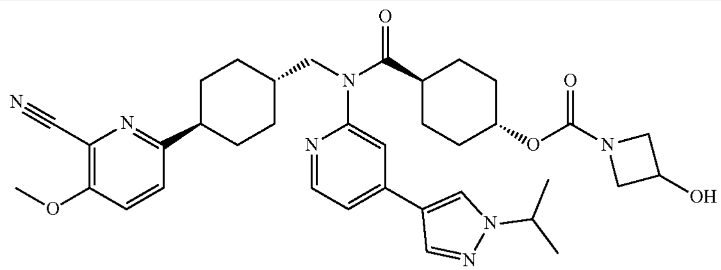 | trans-4-(((trans-4-(6-Cyano-5-methoxypyridin-2-yl)cyclohexyl)methyl)(4-(1-isopropyl-1H-pyrazol-4-yl)pyridin-2-yl)carbamoyl)cyclohexyl 3-hydroxyazetidine-1-carboxylate |
| 7.41 | 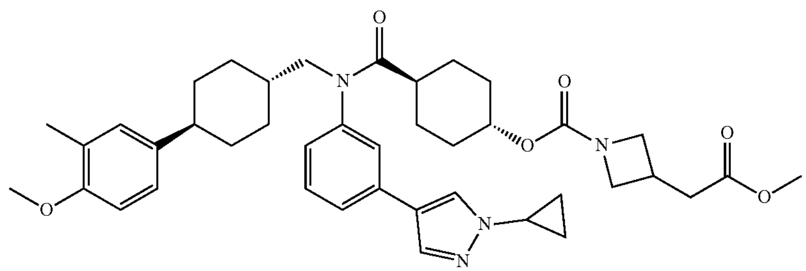 | trans-4-((3-(1-Cyclopropyl-1H-pyrazol-4-yl)phenyl)((trans-4-(4-methoxy-3-methylphenyl)cyclohexyl)methyl)carbamoyl)cyclohexyl 3-(2-methoxy-2-oxoethyl)azetidine-1-carboxylate |
| 7.42 | 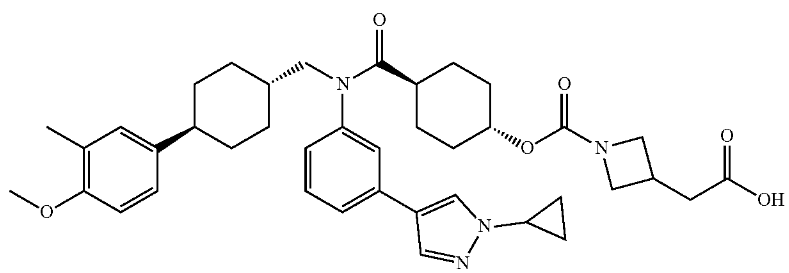 [SMILES: COc1ccc([C@H]2CC[C@H](CN(c3cccc(-c4cnn(C5CC5)c4)c3)C(=O)[C@H]3CC[C@H](OC(=O)N4CC(CC(=O)O)C4)CC3)CC2)cc1C] | 2-(1-(((trans-4-((3-(1-Cyclopropyl-1H-pyrazol-4-yl)phenyl)((trans-4-(4-methoxy-3-methylphenyl)cyclohexyl)methyl)carbamoyl)cyclohexyl)oxy)carbonyl)azetidin-3-yl)acetic acid |

TABLE 1-continued

| Compound No | Structure | Chemical Name |
|---|---|---|
| 7.43 | 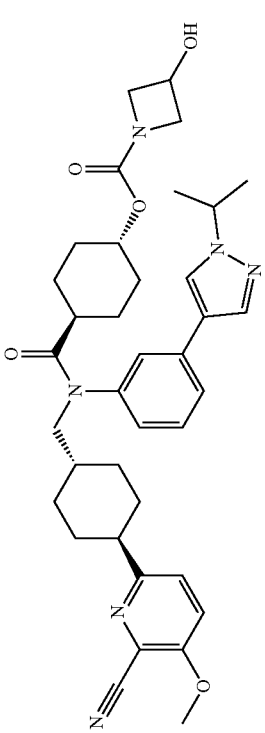 | trans-((trans-(6-Cyano-5-methoxypyridin-2-yl)cyclohexyl)methyl)(3-(1-isopropyl-1H-pyrazol-4-yl)phenyl)carbamoyl)cyclohexyl 3-hydroxyazetidine-1-carboxylate |
| 7.44 | 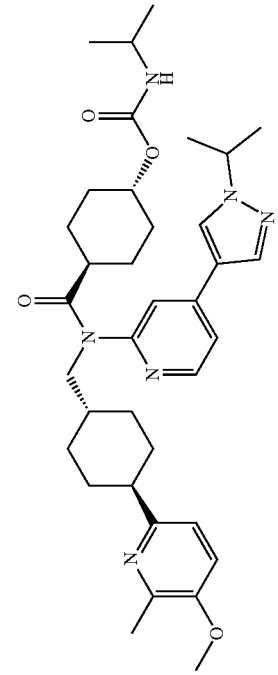 | trans-4-((4-(1-Isopropyl-1H-pyrazol-4-yl)pyridin-2-yl)((trans-4-(5-methoxy-6-methylpyridin-2-yl)cyclohexyl)methyl)carbamoyl)cyclohexyl isopropylcarbamate |
| 7.45 | 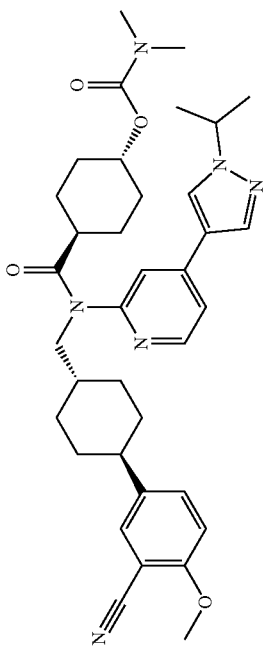 | trans-4-((trans-4-(3-Cyano-4-methoxyphenyl)cyclohexyl)methyl)(4-(1-isopropyl-1H-pyrazol-4-yl)pyridin-2-yl)carbamoyl)cyclohexyl dimethylcarbamate |

TABLE 1-continued

| Compound No | Structure | Chemical Name |
|---|---|---|
| 7.46 | 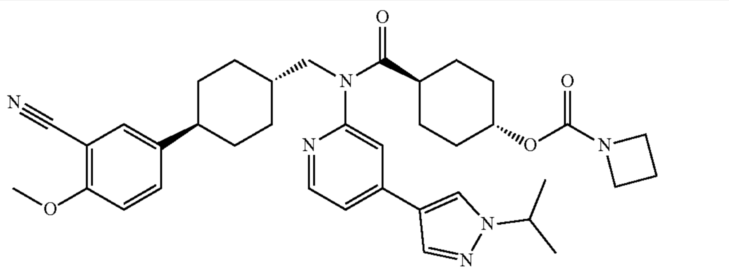 [SMILES: COc1ccc([C@H]2CC[C@H](CN(c3cc(-c4cnn(C(C)C)c4)ccn3)C(=O)[C@H]3CC[C@H](OC(=O)N4CCC4)CC3)CC2)cc1C#N] | trans-4-(((trans-4-(3-Cyano-4-methoxyphenyl)cyclohexyl)methyl)(4-(1-isopropyl-1H-pyrazol-2-yl)pyridin-4-yl)carbamoyl)cyclohexyl azetidine-1-carboxylate |
| 7.47 | 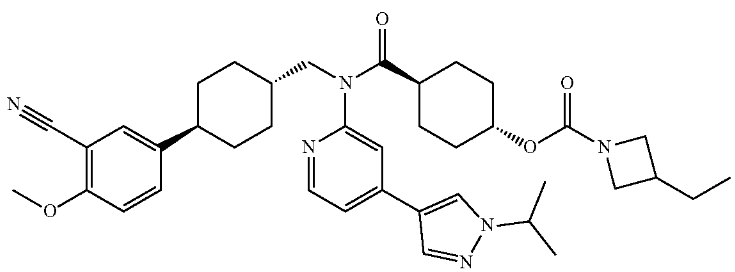 | trans-4-(((trans-4-(3-Cyano-4-methoxyphenyl)cyclohexyl)methyl)(4-(1-isopropyl-1H-pyrazol-2-yl)pyridin-4-yl)carbamoyl)cyclohexyl 3-ethylazetidine-1-carboxylate |
| 7.48 | 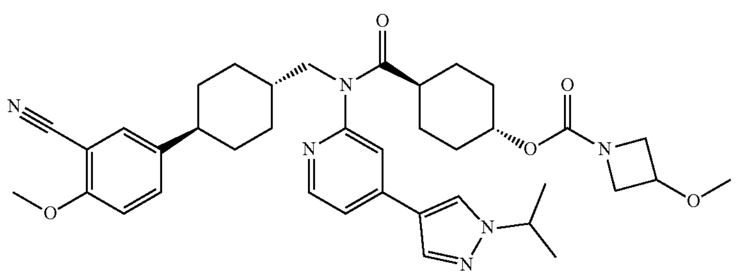 | trans-4-(((trans-4-(3-Cyano-4-methoxyphenyl)cyclohexyl)methyl)(4-(1-isopropyl-1H-pyrazol-2-yl)pyridin-4-yl)carbamoyl)cyclohexyl 3-methoxyazetidine-1-carboxylate |

TABLE 1-continued

| Compound No | Structure | Chemical Name |
|---|---|---|
| 7.49 | 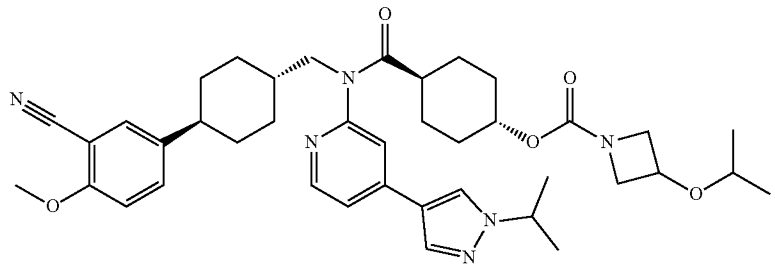 [SMILES: COc1ccc([C@H]2CC[C@H](CN(c3cc(-c4cnn(C(C)C)c4)ccn3)C(=O)[C@H]3CC[C@H](OC(=O)N4CC(OC(C)C)C4)CC3)CC2)cc1C#N] | trans-4-(((trans-4-(3-Cyano-4-methoxyphenyl)cyclohexyl)methyl)(4-(1-isopropyl-1H-pyrazol-4-yl)pyridin-2-yl)carbamoyl)cyclohexyl 3-isopropoxyazetidine-1-carboxylate |
| 7.50 | 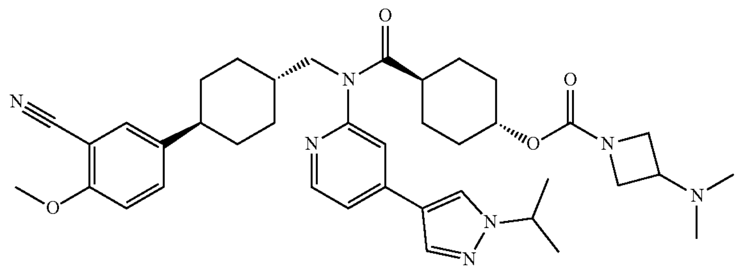 | trans-4-(((trans-4-(3-Cyano-4-methoxyphenyl)cyclohexyl)methyl)(4-(1-isopropyl-1H-pyrazol-4-yl)pyridin-2-yl)carbamoyl)cyclohexyl 3-(dimethylamino)azetidine-1-carboxylate |
| 7.51 | 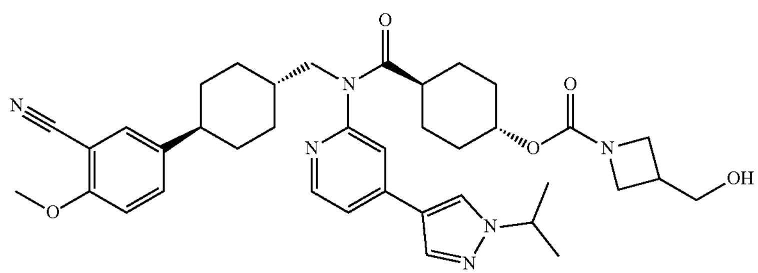 [SMILES: COc1ccc([C@H]2CC[C@H](CN(c3cc(-c4cnn(C(C)C)c4)ccn3)C(=O)[C@H]3CC[C@H](OC(=O)N4CC(CO)C4)CC3)CC2)cc1C#N] | trans-4-(((trans-4-(3-Cyano-4-methoxyphenyl)cyclohexyl)methyl)(4-(1-isopropyl-1H-pyrazol-4-yl)pyridin-2-yl)carbamoyl)cyclohexyl 3-(hydroxymethyl)azetidine-1-carboxylate |

TABLE 1-continued

| Compound No | Structure | Chemical Name |
|---|---|---|
| 7.52 | 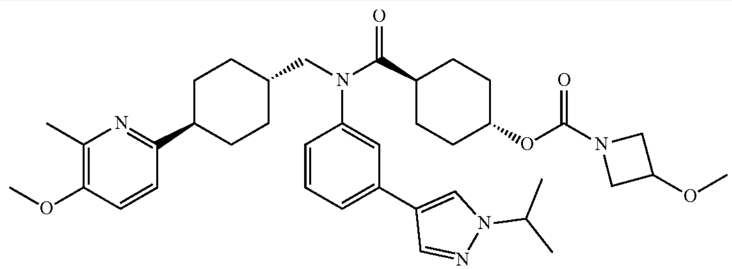 | trans-4-((3-(1-Isopropyl-1H-pyrazol-4-yl)phenyl)(trans-4-(5-methoxy-6-methylpyridin-2-yl)cyclohexyl)methyl)(carbamoyl)cyclohexyl 3-methoxyazetidine-1-carboxylate |
| 7.53 | 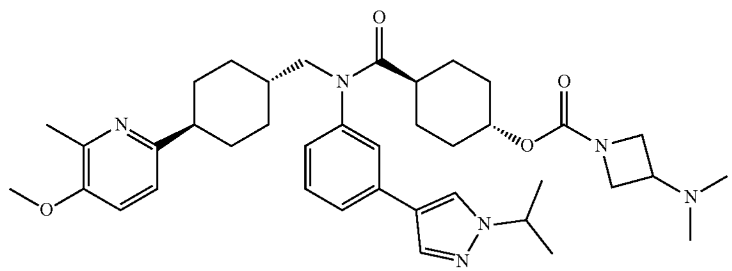 | trans-4-((3-(1-Isopropyl-1H-pyrazol-4-yl)phenyl)(trans-4-(5-methoxy-6-methylpyridin-2-yl)cyclohexyl)methyl)carbamoyl)cyclohexyl 3-(dimethylamino)azetidine-1-carboxylate |
| 7.54 | 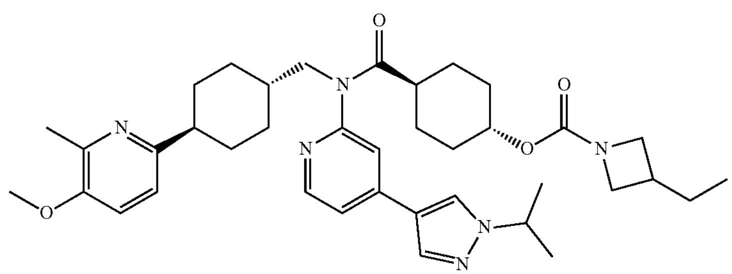 | trans-4-((4-(1-Isopropyl-1H-pyrazol-4-yl)pyridin-2-yl)(trans-4-(5-methoxy-6-methylpyridin-2-yl)cyclohexyl)methyl)carbamoyl)cyclohexyl 3-ethylazetidine-1-carboxylate |

TABLE 1-continued

| Compound No | Structure | Chemical Name |
|---|---|---|
| 7.55 | 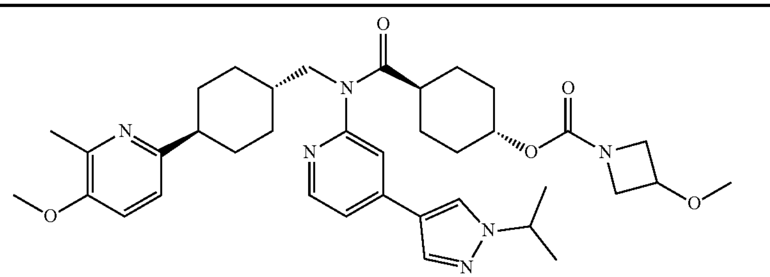 | trans-4-((4-(1-Isopropyl-1H-pyrazol-4-yl)pyridin-2-yl)(trans-4-(5-methoxy-6-methylpyridin-2-yl)cyclohexyl)methyl)carbamoyl)cyclohexyl 3-methoxyazetidine-1-carboxylate |
| 7.56 | 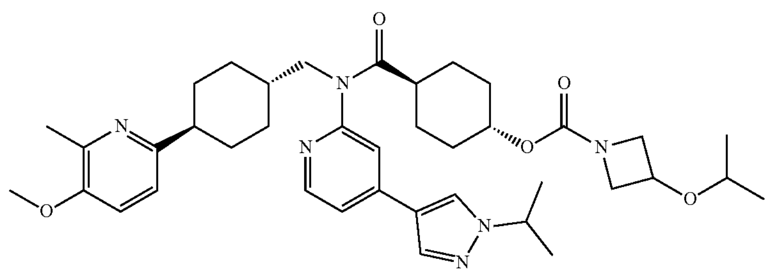 [SMILES: COc1ccc([C@H]2CC[C@H](CN(c3cc(-c4cnn(C(C)C)c4)ccn3)C(=O)[C@H]3CC[C@H](OC(=O)N4CC(OC(C)C)C4)CC3)CC2)nc1C] | trans-4-((4-(1-Isopropyl-1H-pyrazol-4-yl)pyridin-2-yl)(trans-4-(5-methoxy-6-methylpyridin-2-yl)cyclohexyl)methyl)carbamoyl)cyclohexyl 3-isopropoxyazetidine-1-carboxylate |
| 7.57 | 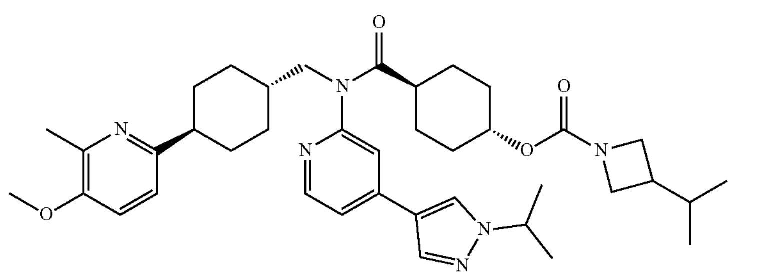 | trans-4-((4-(1-Isopropyl-1H-pyrazol-4-yl)pyridin-2-yl)(trans-4-(5-methoxy-6-methylpyridin-2-yl)cyclohexyl)methyl)carbamoyl)cyclohexyl 3-isopropylazetidine-1-carboxylate |

TABLE 1-continued

| Compound No | Structure | Chemical Name |
|---|---|---|
| 7.58 | 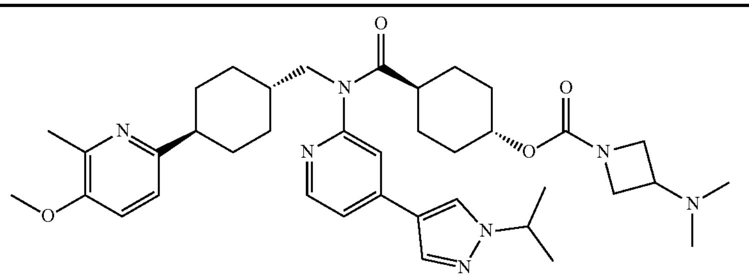 | trans-4-((4-(1-Isopropyl-1H-pyrazol-4-yl)pyridin-2-yl)(trans-4-(5-methoxy-6-methylpyridin-2-yl)cyclohexyl)methyl)carbamoyl)cyclohexyl 3-(dimethylamino)azetidine-1-carboxylate |
| 7.59 | 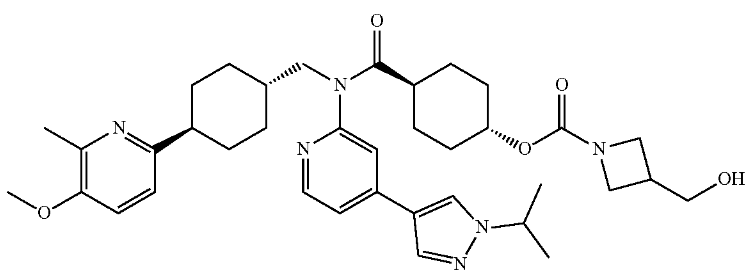 [SMILES: COc1ccc([C@H]2CC[C@H](CN(c3cc(-c4cnn(C(C)C)c4)ccn3)C(=O)[C@H]3CC[C@H](OC(=O)N4CC(CO)C4)CC3)CC2)nc1C] | trans-4-((4-(1-Isopropyl-2H-pyrazol-4-yl)pyridin-2-yl)(trans-4-(5-methoxy-6-methylpyridin-2-yl)cyclohexyl)methyl)carbamoyl)cyclohexyl 3-(hydroxymethyl)azetidine-1-carboxylate |
| 7.60 | 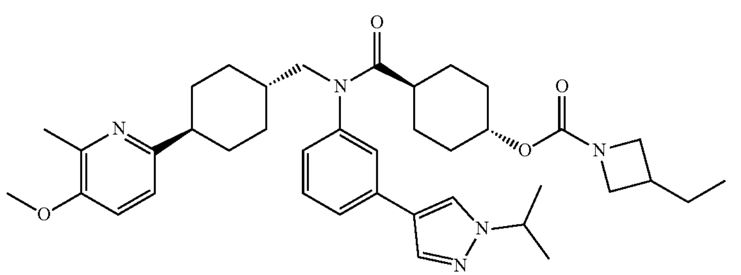 [SMILES: CCC1CN(C(=O)O[C@H]2CC[C@H](C(=O)N(C[C@H]3CC[C@H](c4ccc(OC)c(C)n4)CC3)c3cccc(-c4cnn(C(C)C)c4)c3)CC2)C1] | trans-4-((3-(1-Isopropyl-1H-pyrazol-4-yl)phenyl)(trans-4-(5-methoxy-6-methylpyridin-2-yl)cyclohexyl)methyl)carbamoyl)cyclohexyl 3-ethylazetidine-1-carboxylate |

TABLE 1-continued

| Compound No | Structure | Chemical Name |
|---|---|---|
| 7.61 | 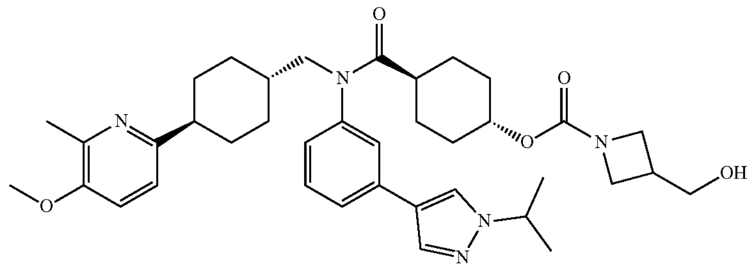 [SMILES: COc1ccc([C@H]2CC[C@H](CN(c3cccc(-c4cnn(C(C)C)c4)c3)C(=O)[C@H]3CC[C@H](OC(=O)N4CC(CO)C4)CC3)CC2)nc1C] | trans-4-((3-(1-Isopropyl-1H-pyrazol-4-yl)phenyl)(trans-4-(5-methoxy-6-methylpyridin-2-yl)cyclohexyl)methyl)carbamoyl)cyclohexyl 3-(hydroxymethyl)azetidine-1-carboxylate |
| 7.62 | 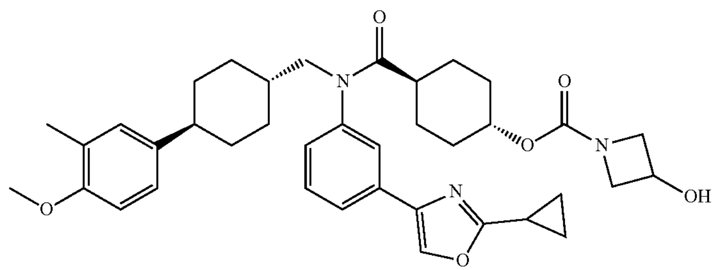 [SMILES: COc1ccc([C@H]2CC[C@H](CN(c3cccc(-c4coc(C5CC5)n4)c3)C(=O)[C@H]3CC[C@H](OC(=O)N4CC(O)C4)CC3)CC2)cc1C] | trans-4-((3-(2-Cyclopropyloxazol-4-yl)phenyl)(trans-4-(4-methoxy-3-methylphenyl)cyclohexyl)methyl)carbamoyl)-cyclohexyl 3-hydroxyazetidine-1-carboxylate |
| 7.63 | 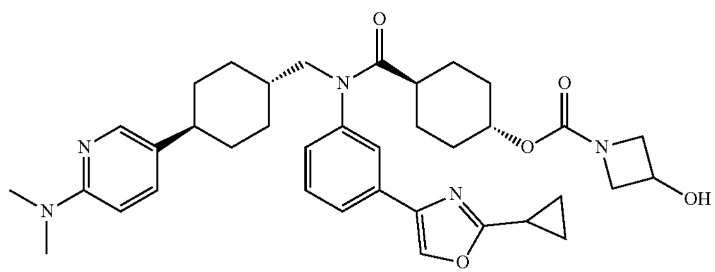 [SMILES: CN(C)c1ccc([C@H]2CC[C@H](CN(c3cccc(-c4coc(C5CC5)n4)c3)C(=O)[C@H]3CC[C@H](OC(=O)N4CC(O)C4)CC3)CC2)cn1] | trans-4-((3-(2-Cyclopropyloxazol-4-yl)phenyl)(trans-4-(6-(dimethylamino)pyridine-3-yl)cyclohexyl)methyl)carbamoyl)cyclohexyl 3-hydroxyazetidine-1-carboxylate |

TABLE 1-continued

| Compound No | Structure | Chemical Name |
|---|---|---|
| 7.64 | 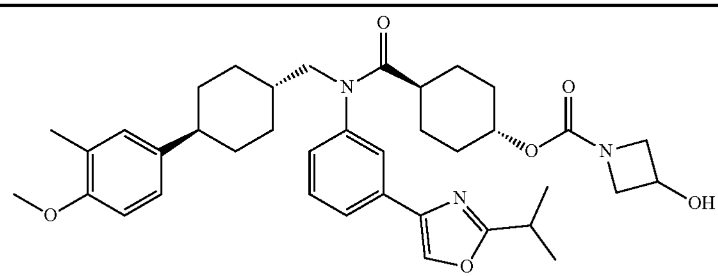 | trans-4-((3-(2-Isopropyloxazol-4-yl)phenyl)((trans-4-(4-methoxy-3-methylphenyl)cyclohexyl)methyl)carbamoyl)-cyclohexyl 3-hydroxyazetidine-1-carboxylate |
| 7.65 | 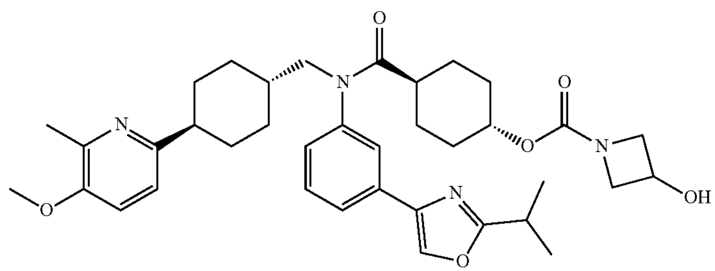 | trans-4-((3-(2-Isopropyloxazol-4-yl)phenyl)((trans-4-(5-methoxy-6-methylpyridin-2-yl)cyclohexyl)methyl)carbamoyl)cyclohexyl 3-hydroxyazetidine-1-carboxylate |
| 7.66 | 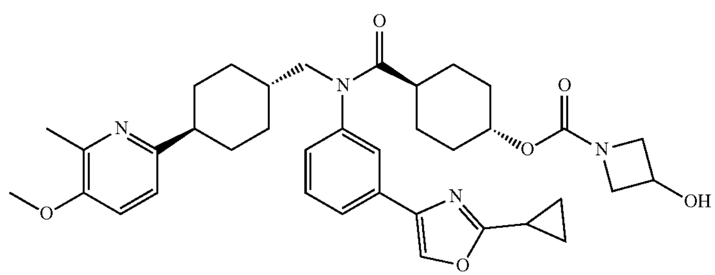 [SMILES: COc1ccc([C@H]2CC[C@H](CN(c3cccc(-c4coc(C5CC5)n4)c3)C(=O)[C@H]3CC[C@H](OC(=O)N4CC(O)C4)CC3)CC2)nc1C] | trans-4-((3-(2-Cyclopropyloxazol-4-yl)phenyl)((trans-4-(5-methoxy-6-methylpyridin-2-yl)cyclohexyl)methyl)carbamoyl)cyclohexyl 3-hydroxyazetidine-1-carboxylate |

TABLE 1-continued

| Compound No | Structure | Chemical Name |
|---|---|---|
| 7.67 | 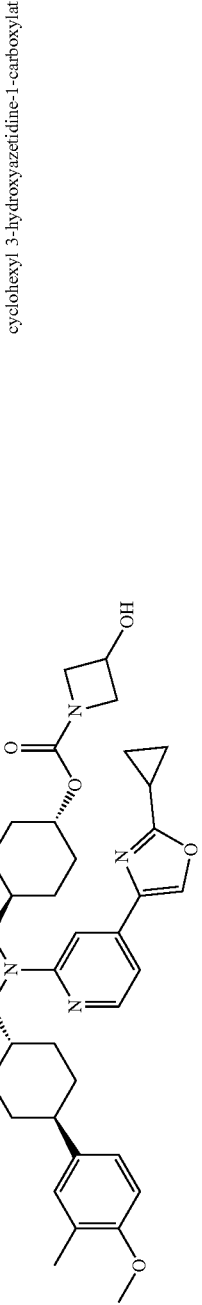 | trans-4-((4-(2-Cyclopropyloxazol-4-yl)pyridine-2-yl)(trans-4-(4-methoxy-3-methylphenyl)cyclohexyl)methyl)carbamoyl)cyclohexyl 3-hydroxyazetidine-1-carboxylate |
| 7.68 | 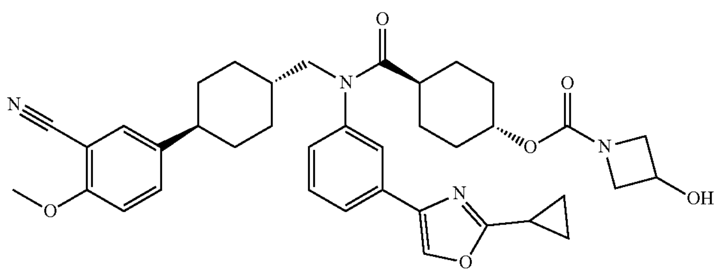 [SMILES: COc1ccc([C@H]2CC[C@H](CN(c3cccc(-c4coc(C5CC5)n4)c3)C(=O)[C@H]3CC[C@H](OC(=O)N4CC(O)C4)CC3)CC2)cc1C#N] | trans-4-((trans-4-(3-Cyano-4-methoxyphenyl)cyclohexyl)methyl)(3-(2-cyclopropyloxazol-4-yl)phenyl)carbamoyl)cyclohexyl 3-hydroxyazetidine-1-carboxylate |
| 7.69 | 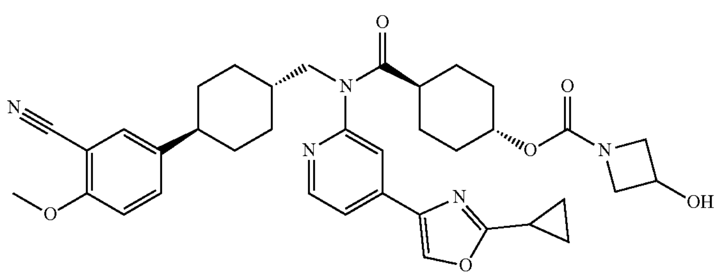 | trans-4-((trans-4-(3-Cyano-4-methoxyphenyl)cyclohexyl)methyl)(4-(2-cyclopropyloxazol-4-yl)pyridine-2-yl)carbamoyl)cyclohexyl 3-hydroxyazetidine-1-carboxylate |

TABLE 1-continued

| Compound No | Structure | Chemical Name |
|---|---|---|
| 7.70 | 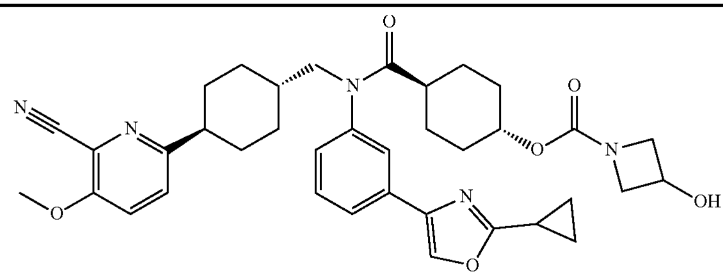 | trans-4-(((trans-4-(6-Cyano-5-methoxypyridin-2-yl)cyclohexyl)methyl)(3-(2-cyclopropyloxazol-4-yl)phenyl)carbamoyl)cyclohexyl 3-hydroxyazetidine-1-carboxylate |
| 7.71 | 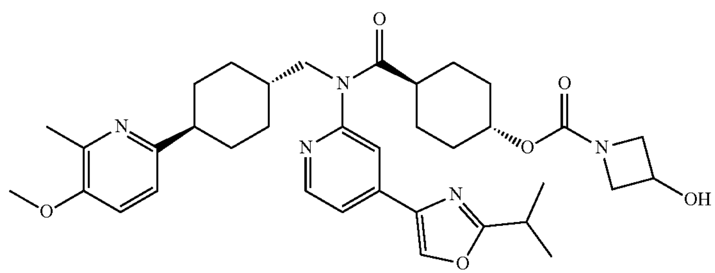 [SMILES: COc1ccc([C@H]2CC[C@H](CN(c3cc(-c4coc(C(C)C)n4)ccn3)C(=O)[C@H]3CC[C@H](OC(=O)N4CC(O)C4)CC3)CC2)nc1C] | trans-4-((4-(2-Isopropyloxazol-4-yl)pyridine-2-yl)((trans-4-(5-methoxy-6-methylpyridin-2-yl)cyclohexyl)methyl)carbamoyl)cyclohexyl 3-hydroxyazetidine-1-carboxylate |
| 7.72 | 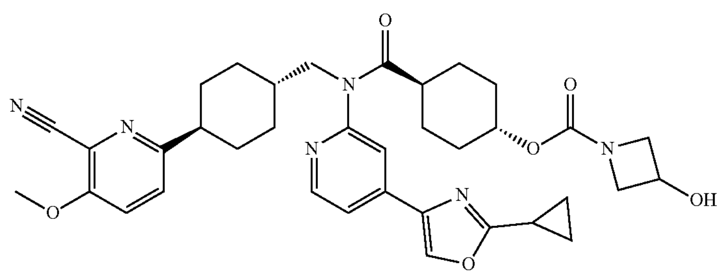 | trans-4-(((trans-4-(6-Cyano-5-methoxypyridin-2-yl)cyclohexyl)methyl)(4-(2-cyclopropyloxazol-4-yl)pyridine-2-yl)carbamoyl)cyclohexyl 3-hydroxyazetidine-1-carboxylate |

TABLE 1-continued

| Compound No | Structure | Chemical Name |
|---|---|---|
| 7.73 | 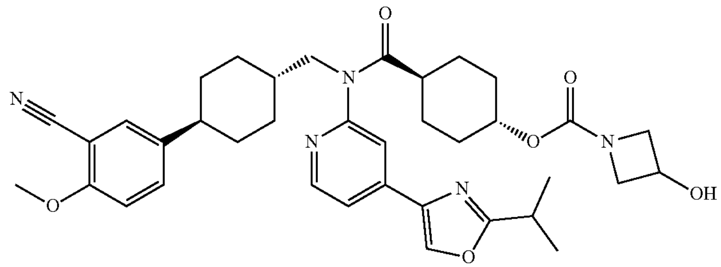 [SMILES: COc1ccc([C@H]2CC[C@H](CN(c3cc(-c4coc(C(C)C)n4)ccn3)C(=O)[C@H]3CC[C@H](OC(=O)N4CC(O)C4)CC3)CC2)cc1C#N] | trans-4-(((trans-4-(3-Cyano-4-methoxyphenyl)cyclohexyl)methyl)(4-(2-isopropyloxazol-4-yl)pyridine-2-yl)carbamoyl)cyclohexyl 3-hydroxyazetidine-1-carboxylate |
| 7.74 | 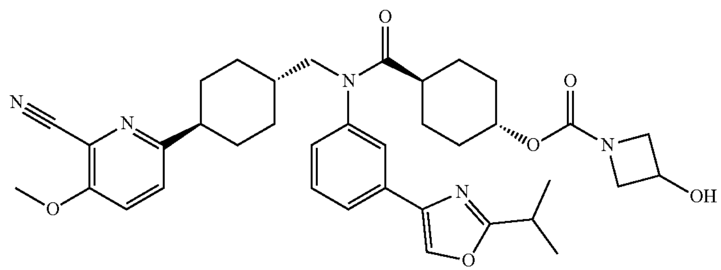 [SMILES: COc1ccc([C@H]2CC[C@H](CN(c3cccc(-c4coc(C(C)C)n4)c3)C(=O)[C@H]3CC[C@H](OC(=O)N4CC(O)C4)CC3)CC2)nc1C#N] | trans-4-(((trans-4-(6-Cyano-5-methoxypyridin-2-yl)cyclohexyl)methyl)(3-(2-isopropyloxazol-4-yl)phenyl)carbamoyl)cyclohexyl 3-hydroxyazetidine-1-carboxylate |
| 7.75 | 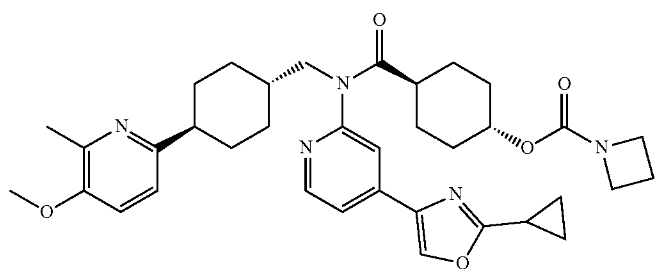 [SMILES: COc1ccc([C@H]2CC[C@H](CN(c3cc(-c4coc(C5CC5)n4)ccn3)C(=O)[C@H]3CC[C@H](OC(=O)N4CCC4)CC3)CC2)nc1C] | trans-4-((4-(2-Cyclopropyloxazol-4-yl)pyridine-2-yl)((trans-4-(5-methoxy-6-methylpyridin-2-yl)cyclohexyl)methyl)carbamoyl)cyclohexyl azetidine-1-carboxylate |

TABLE 1-continued

| Compound No | Structure | Chemical Name |
|---|---|---|
| 7.76 | 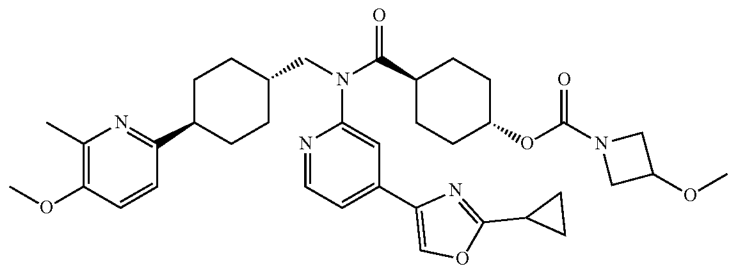 | trans-4-((4-(2-Cyclopropyloxazol-4-yl)pyridine-2-yl)(trans-4-(5-methoxy-6-methylpyridin-2-yl)cyclohexyl)methyl)carbamoyl)cyclohexyl 3-methoxyazetidine-1-carboxylate |
| 7.77 | 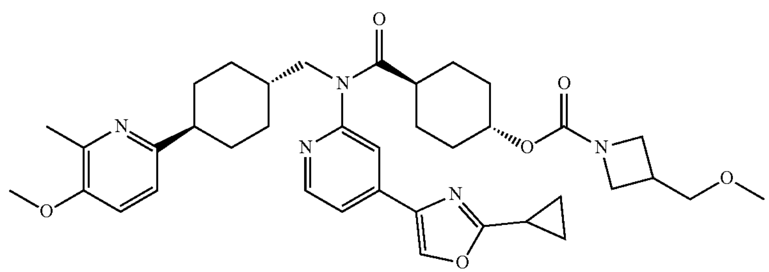 | trans-4-((4-(2-Cyclopropyloxazol-4-yl)pyridin-2-yl)(trans-4-(5-methoxy-6-methylpyridin-2-yl)cyclohexyl)methyl)carbamoyl)cyclohexyl 3-(methoxymethyl)azetidine-1-carboxylate |
| 7.78 | 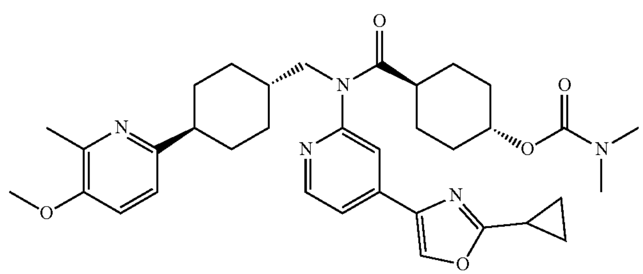 | trans-4-((4-(2-Cyclopropyloxazol-4-yl)pyridine-2-yl)(trans-4-(5-methoxy-6-methylpyridin-2-yl)cyclohexyl)methyl)carbamoyl)cyclohexyl dimethylcarbamate |

TABLE 1-continued

| Compound No | Structure | Chemical Name |
|---|---|---|
| 7.79 | 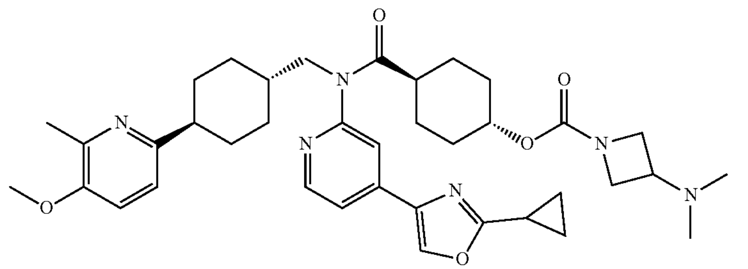 | trans-4-((4-(2-Cyclopropyloxazol-4-yl)pyridine-2-yl)((trans-4-(5-methoxy-6-methylpyridin-2-yl)cyclohexyl)methyl)carbamoyl)cyclohexyl 3-(dimethylamino)azetidine-1-carboxylate |
| 7.80 | 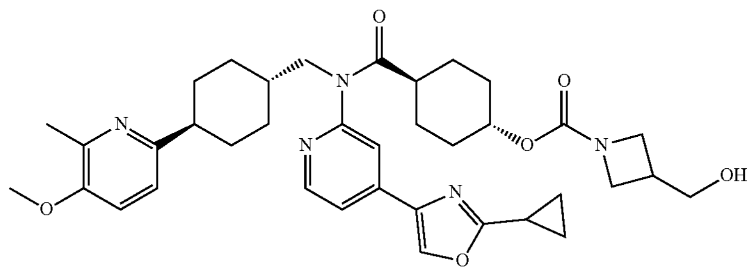 [SMILES: COc1ccc([C@H]2CC[C@H](CN(c3cc(-c4coc(C5CC5)n4)ccn3)C(=O)[C@H]3CC[C@H](OC(=O)N4CC(CO)C4)CC3)CC2)nc1C] | trans-4-((4-(2-Cyclopropyloxazol-4-yl)pyridine-2-yl)((trans-4-(5-methoxy-6-methylpyridin-2-yl)cyclohexyl)methyl)carbamoyl)cyclohexyl 3-(hydroxymethyl)azetidine-1-carboxylate |
| 7.81 | 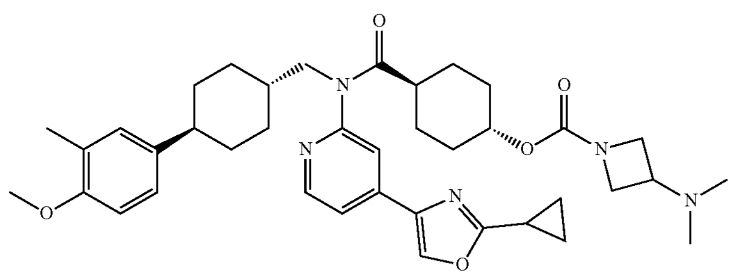 | trans-4-((4-(2-Cyclopropyloxazol-4-yl)pyridine-2-yl)((trans-4-(4-methoxy-3-methylphenyl)cyclohexyl)methyl)carbamoyl)cyclohexyl 3-(dimethylamino)azetidine-1-carboxylate |

TABLE 1-continued

| Compound No | Structure | Chemical Name |
|---|---|---|
| 7.82 | 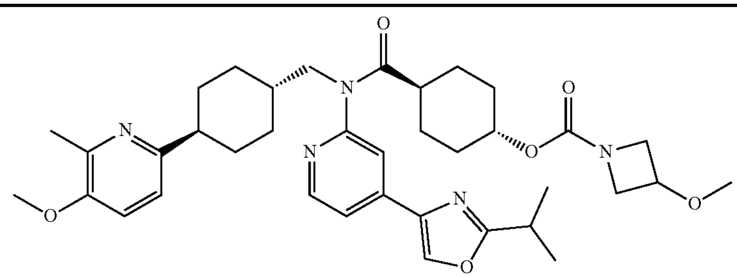 | trans-4-((4-(2-Isopropyloxazol-4-yl)pyridine-2-yl)(trans-4-(5-methoxy-6-methylpyridin-2-yl)cyclohexyl)methyl)carbamoyl)cyclohexyl 3-methoxyazetidine-1-carboxylate |
| 7.83 | 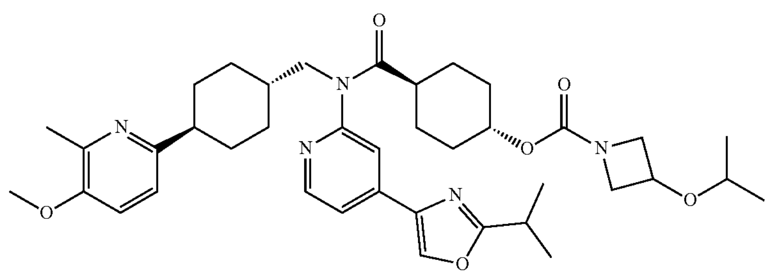 [SMILES: COc1ccc([C@H]2CC[C@H](CN(c3cc(-c4coc(C(C)C)n4)ccn3)C(=O)[C@H]3CC[C@H](OC(=O)N4CC(OC(C)C)C4)CC3)CC2)nc1C] | trans-4-((4-(2-Isopropyloxazol-4-yl)pyridin-2-yl)(trans-4-(5-methoxy-6-methylpyridin-2-yl)cyclohexyl)methyl)carbamoyl)cyclohexyl 3-isopropoxyazetidine-1-carboxylate |
| 7.84 | 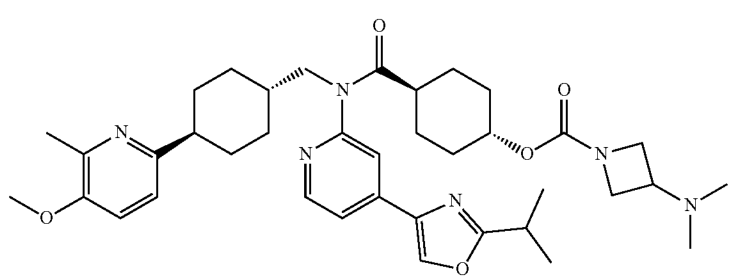 | trans-4-((4-(2-Isopropyloxazol-4-yl)pyridine-2-yl)(trans-4-(5-methoxy-6-methylpyridin-2-yl)cyclohexyl)methyl)carbamoyl)cyclohexyl 3-(dimethylamino)azetidine-1-carboxylate |

TABLE 1-continued

| Compound No | Structure | Chemical Name |
|---|---|---|
| 7.85 | 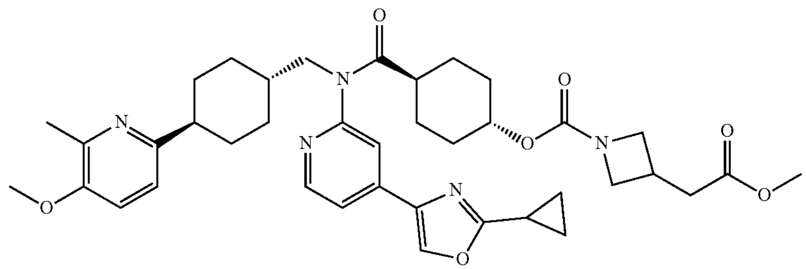 | trans-4-((4-(2-Cyclopropyloxazol-4-yl)pyridine-2-yl)(trans-4-(5-methoxy-6-methylpyridin-2-yl)cyclohexyl)methyl)carbamoyl)cyclohexyl 3-(2-methoxy-2-oxoethyl)azetidine-1-carboxylate |
| 7.86 | 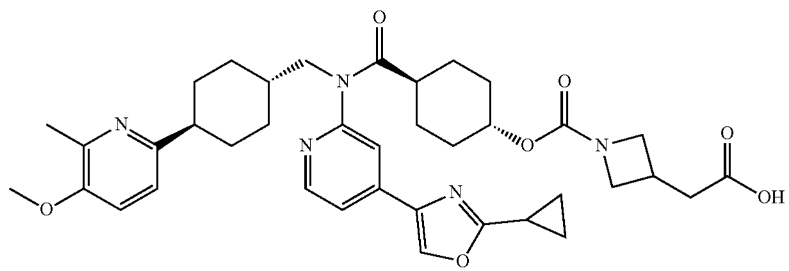 [SMILES: COc1ccc([C@H]2CC[C@H](CN(c3cc(-c4coc(C5CC5)n4)ccn3)C(=O)[C@H]3CC[C@H](OC(=O)N4CC(CC(=O)O)C4)CC3)CC2)nc1C] | 2-(1-(((trans-4-((4-(2-Cyclopropyloxazol-4-yl)pyridine-2-yl)((trans-4-(5-methoxy-6-methylpyridin-2-yl)cyclohexyl)methyl)carbamoyl)cyclohexyl)oxy)carbonyl)azetidin-3-yl)acetic acid |
| 7.87 | 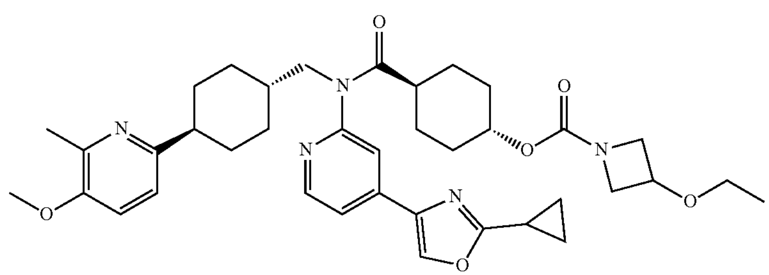 | trans-4-((4-(2-Cyclopropyloxazol-4-yl)pyridine-2-yl)(trans-4-(5-methoxy-6-methylpyridin-2-yl)cyclohexyl)methyl)carbamoyl)cyclohexyl 3-ethoxyazetidine-1-carboxylate |

TABLE 1-continued

| Compound No | Structure | Chemical Name |
|---|---|---|
| 7.88 | 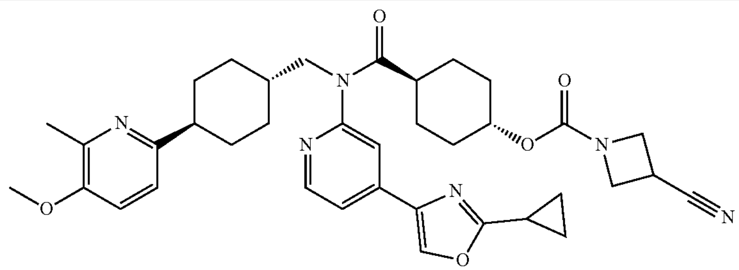 [SMILES: COc1ccc([C@H]2CC[C@H](CN(c3cc(-c4coc(C5CC5)n4)ccn3)C(=O)[C@H]3CC[C@H](OC(=O)N4CC(C#N)C4)CC3)CC2)nc1C] | trans-4-((4-(2-Cyclopropyloxazol-4-yl)pyridine-2-yl)((trans-4-(5-methoxy-6-methylpyridin-2-yl)cyclohexyl)methyl)carbamoyl)cyclohexyl 3-cyanoazetidine-1-carboxylate |
| 7.89 | 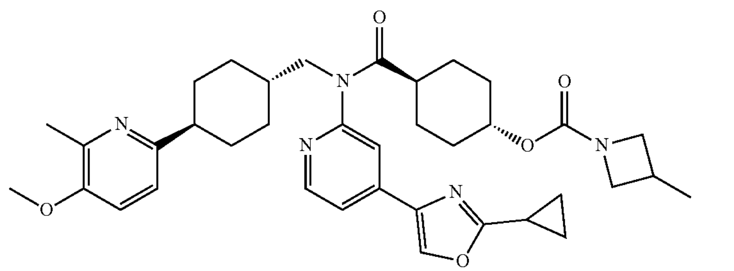 | trans-4-((4-(2-Cyclopropyloxazol-4-yl)pyridine-2-yl)((trans-4-(5-methoxy-6-methylpyridin-2-yl)cyclohexyl)methyl)carbamoyl)cyclohexyl 3-methylazetidine-1-carboxylate |
| 7.90 | 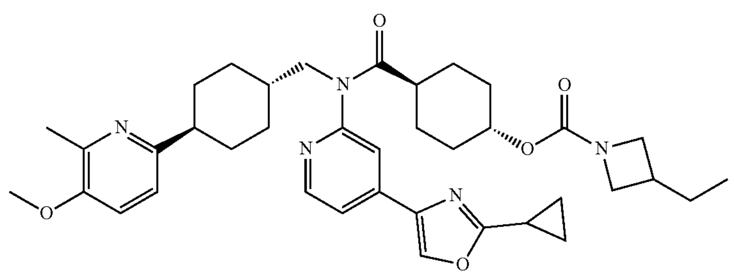 | trans-4-((4-(2-Cyclopropyloxazol-4-yl)pyridine-2-yl)((trans-4-(5-methoxy-6-methylpyridin-2-yl)cyclohexyl)methyl)carbamoyl)cyclohexyl 3-ethylazetidine-1-carboxylate |

TABLE 1-continued

| Compound No | Structure | Chemical Name |
|---|---|---|
| 7.91 | 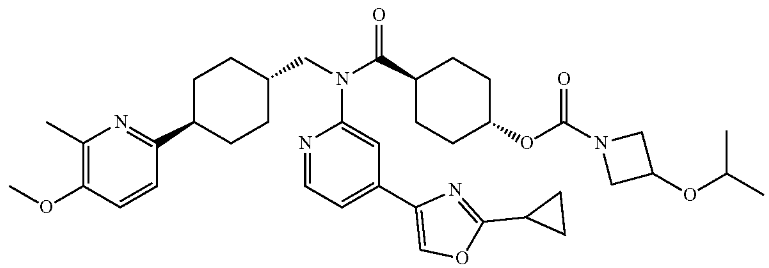 | trans-4-((4-(2-Cyclopropyloxazol-4-yl)pyridine-2-yl)(trans-4-(5-methoxy-6-methylpyridin-2-yl)cyclohexyl)methyl)carbamoyl)cyclohexyl 3-isopropoxyazetidine-1-carboxylate |
| 7.92 | 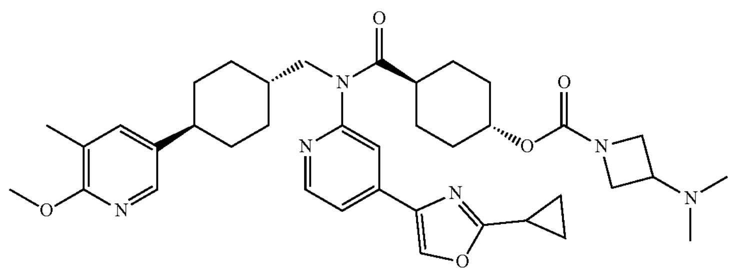 | trans-4-((4-(2-Cyclopropyloxazol-4-yl)pyridine-2-yl)(trans-4-(6-methoxy-5-methylpyridin-3-yl)cyclohexyl)methyl)carbamoyl)cyclohexyl 3-(dimethylamino)azetidine-1-carboxylate |
| 7.93 | 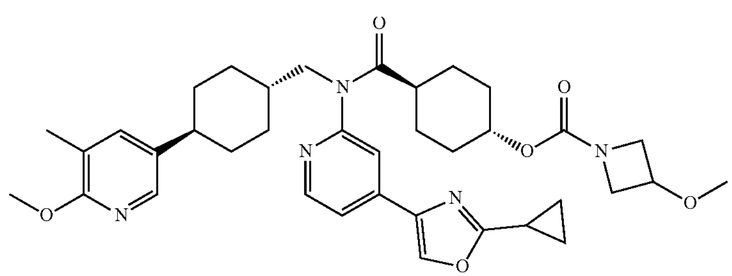 | trans-4-((4-(2-Cyclopropyloxazol-4-yl)pyridine-2-yl)(trans-4-(6-methoxy-5-methylpyridin-3-yl)cyclohexyl)methyl)carbamoyl)cyclohexyl 3-methoxyazetidine-1-carboxylate |

TABLE 1-continued

| Compound No | Structure | Chemical Name |
|---|---|---|
| 7.94 | 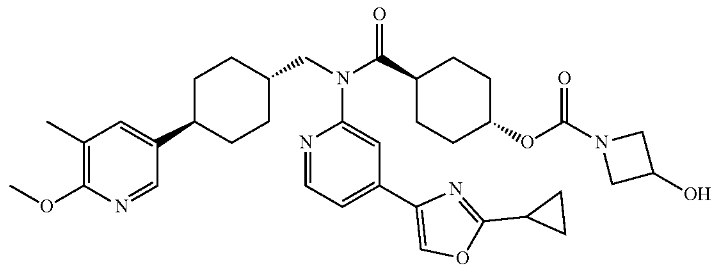 [SMILES: COc1ncc([C@H]2CC[C@H](CN(c3cc(-c4coc(C5CC5)n4)ccn3)C(=O)[C@H]3CC[C@H](OC(=O)N4CC(O)C4)CC3)CC2)cc1C] | trans-4-((4-(2-Cyclopropyloxazol-4-yl)pyridine-2-yl)(trans-4-(6-methoxy-5-methylpyridin-3-yl)cyclohexyl)methyl)carbamoyl)cyclohexyl 3-hydroxyazetidine-1-carboxylate |
| 7.95 | 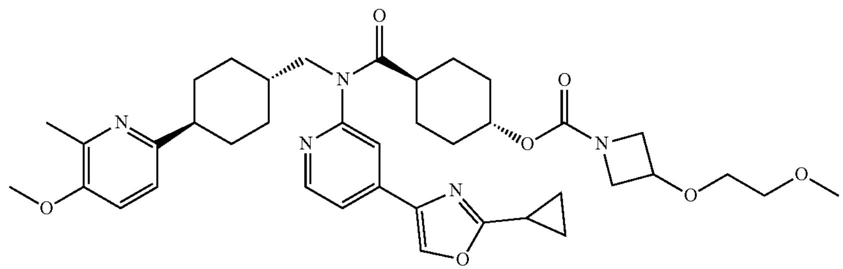 | trans-4-((4-(2-Cyclopropyloxazol-4-yl)pyridine-2-yl)(trans-4-(5-methoxy-6-methylpyridin-2-yl)cyclohexyl)methyl)carbamoyl)cyclohexyl 3-(2-methoxyethoxy)azetidine-1-carboxylate |
| 7.96 | 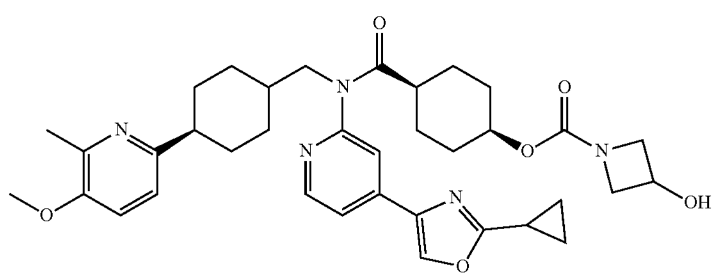 | 4-((4-(2-Cyclopropyloxazol-4-yl)pyridine-2-yl)(4-(5-methoxy-6-methylpyridin-2-yl)cyclohexyl)methyl)carbamoyl)cyclohexyl-cis-3-hydroxyazetidine-1-carboxylate |

| Compound No | Structure | Chemical Name |
|---|---|---|
| 7.97 | 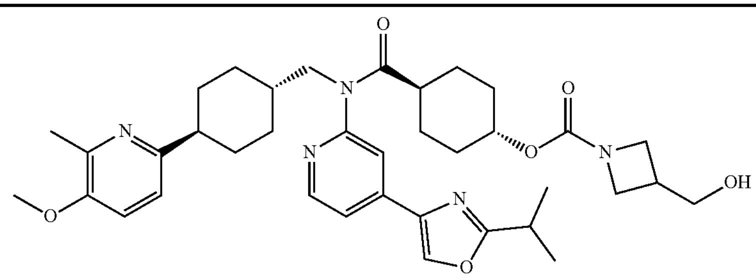 | trans-4-((4-(2-Isopropyloxazol-4-yl)pyridine-2-yl)(trans-4-(5-methoxy-6-methylpyridin-2-yl)cyclohexyl)methyl)carbamoyl)cyclohexyl 3-(hydroxymethyl)azetidine-1-carboxylate |
| 7.98 | 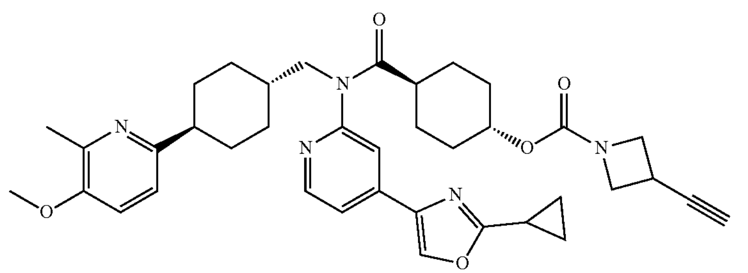 [SMILES: C#CC1CN(C(=O)O[C@H]2CC[C@H](C(=O)N(C[C@H]3CC[C@H](c4ccc(OC)c(C)n4)CC3)c3cc(-c4coc(C5CC5)n4)ccn3)CC2)C1] | trans-4-((4-(2-Cyclopropyloxazol-4-yl)pyridine-2-yl)(trans-4-(5-methoxy-6-methylpyridin-2-yl)cyclohexyl)methyl)carbamoyl)cyclohexyl 3-ethynylazetidine-1-carboxylate |
| 7.99 | 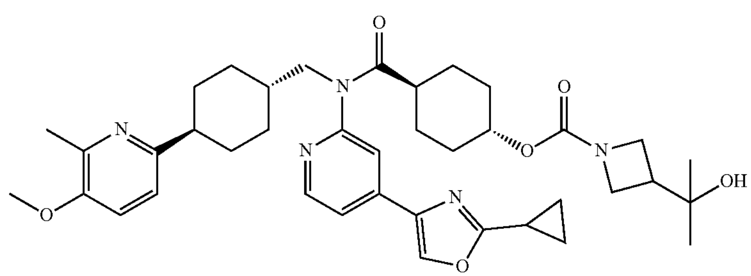 [SMILES: COc1ccc([C@H]2CC[C@H](CN(c3cc(-c4coc(C5CC5)n4)ccn3)C(=O)[C@H]3CC[C@H](OC(=O)N4CC(C(C)(C)O)C4)CC3)CC2)nc1C] | trans-4-((4-(2-Cyclopropyloxazol-4-yl)pyridine-2-yl)(trans-4-(5-methoxy-6-methylpyridin-2-yl)cyclohexyl)methyl)carbamoyl)cyclohexyl 3-(2-hydroxypropan-2-yl)azetidine-1-carboxylate |

TABLE 1-continued

| Compound No | Structure | Chemical Name |
|---|---|---|
| 7.100 | 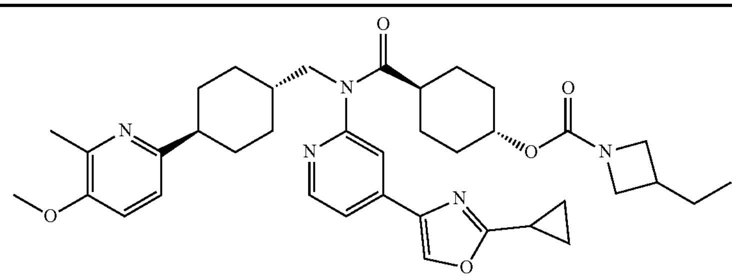 | trans-4-((4-(2-Isopropyloxazol-4-yl)pyridine-2-yl)(trans-4-(5-methoxy-6-methylpyridin-2-yl)cyclohexyl)methyl)carbamoyl)cyclohexyl 3-ethylazetidine-1-carboxylate |
| 7.101 | 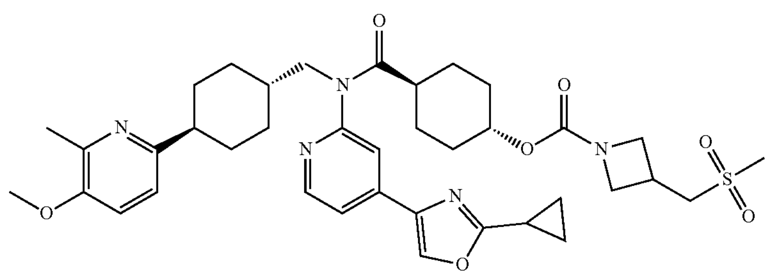 | trans-4-((4-(2-Cyclopropyloxazol-4-yl)pyridine-2-yl)(trans-4-(5-methoxy-6-methylpyridin-2-yl)cyclohexyl)methyl)carbamoyl)cyclohexyl 3-((methylsulfonyl)methyl)azetidine-1-carboxylate |
| 7.102 | 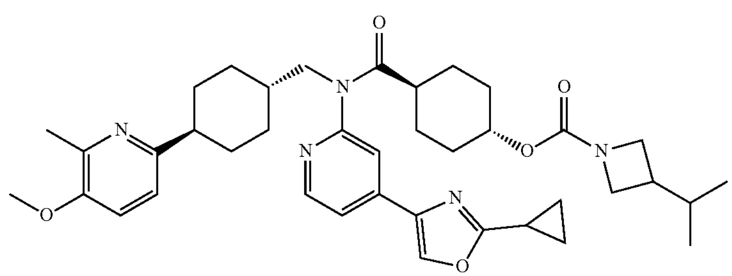 | trans-4-((4-(2-Cyclopropyloxazol-4-yl)pyridine-2-yl)(trans-4-(5-methoxy-6-methylpyridin-2-yl)cyclohexyl)methyl)carbamoyl)cyclohexyl 3-isopropylazetidine-1-carboxylate |

TABLE 1-continued

| Compound No | Structure | Chemical Name |
|---|---|---|
| 7.103 | 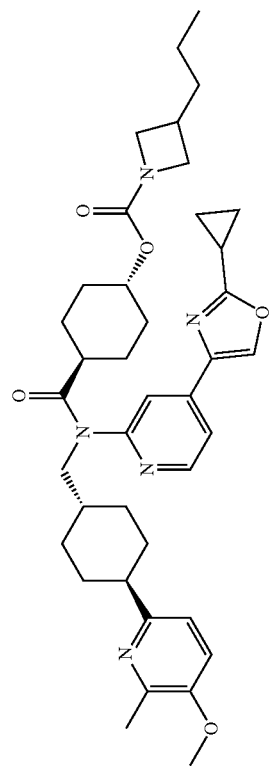 | trans-4-((4-(2-Cyclopropyloxazol-4-yl)pyridine-2-yl)(trans-4-(5-methoxy-6-methylpyridin-2-yl)cyclohexyl)methyl)carbamoyl)cyclohexyl 3-(tert-butyl)azetidine-1-carboxylate |
| 7.104 | 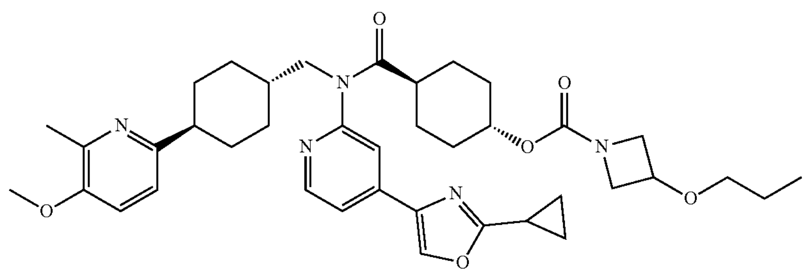 [SMILES: CCCOC1CN(C(=O)O[C@H]2CC[C@H](C(=O)N(C[C@H]3CC[C@H](c4ccc(OC)c(C)n4)CC3)c3cc(-c4coc(C5CC5)n4)ccn3)CC2)C1] | trans-4-((4-(2-Cyclopropyloxazol-4-yl)pyridine-2-yl)(trans-4-(5-methoxy-6-methylpyridin-2-yl)cyclohexyl)methyl)carbamoyl(cyclohexyl 3-propoxyazetidine-1-carboxylate |
| 7.105 | 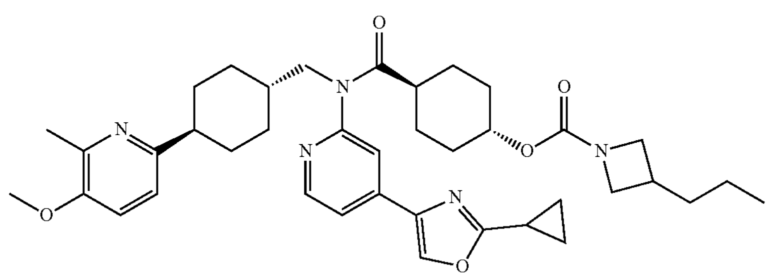 [SMILES: CCCC1CN(C(=O)O[C@H]2CC[C@H](C(=O)N(C[C@H]3CC[C@H](c4ccc(OC)c(C)n4)CC3)c3cc(-c4coc(C5CC5)n4)ccn3)CC2)C1] | trans-4-((4-(2-Cyclopropyloxazol-4-yl)pyridin-2-yl)(trans-4-(5-methoxy-6-methylpyridin-2-yl)cyclohexyl)methyl)carbamoyl)cyclohexyl 3-propylazetidine-1-carboxylate |

TABLE 1-continued

| Compound No | Structure | Chemical Name |
|---|---|---|
| 7.106 | 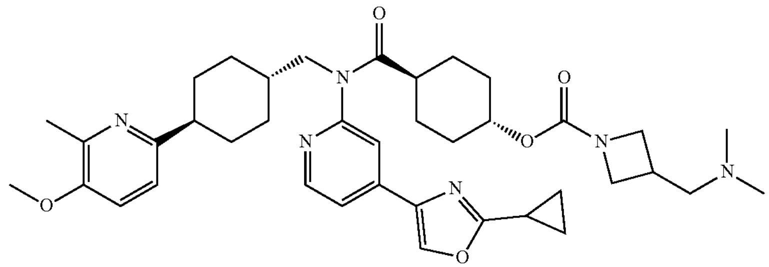 | trans-4-((4-(2-Cyclopropyloxazol-4-yl)pyridin-2-yl)((trans-4-(5-methoxy-6-methylpyridin-2-yl)cyclohexyl)methyl)carbamoyl)cyclohexyl 3-((dimethylamino)methyl)azetidine-1-carboxylate |
| 7.107 | 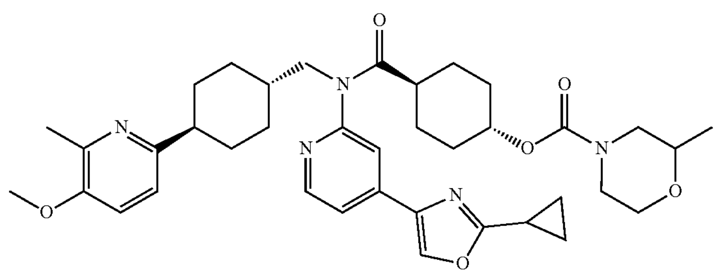 | trans-4-((4-(2-Cyclopropyloxazol-4-yl)pyridin-2-yl)((trans-4-(5-methoxy-6-methylpyridin-2-yl)cyclohexyl)methyl)carbamoyl)cyclohexyl 2-methylmorpholine-4-carboxylate |
| 7.108 | 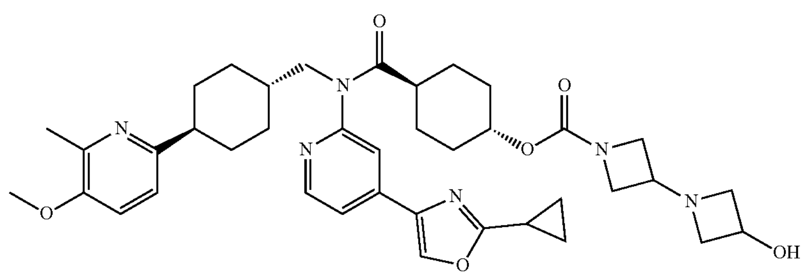 [SMILES: COc1ccc([C@H]2CC[C@H](CN(c3cc(-c4coc(C5CC5)n4)ccn3)C(=O)[C@H]3CC[C@H](OC(=O)N4CC(N5CC(O)C5)C4)CC3)CC2)nc1C] | trans-4-((4-(2-Cyclopropyloxazol-4-yl)pyridin-2-yl)((trans-4-(5-methoxy-6-methylpyridin-2-yl)cyclohexyl)methyl)carbamoyl)cyclohexyl 3-hydroxy-[1,3'-biazetidine]-1'-carboxylate |

TABLE 1-continued

| Compound No | Structure | Chemical Name |
|---|---|---|
| 7.109 | 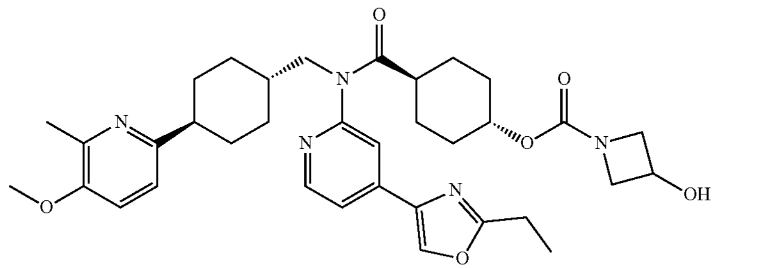 [SMILES: CCc1nc(-c2ccnc(N(C[C@H]3CC[C@H](c4ccc(OC)c(C)n4)CC3)C(=O)[C@H]3CC[C@H](OC(=O)N4CC(O)C4)CC3)c2)co1] | trans-4-((4-(2-Ethyloxazol-4-yl)pyridin-2-yl)(trans-4-(5-methoxy-6-methylpyridin-2-yl)cyclohexyl)methyl)carbamoyl)cyclohexyl 3-hydroxyazetidine-1-carboxylate |
| 8 | 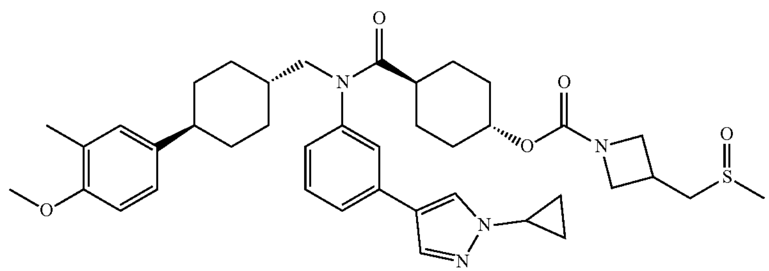 | trans-4-((3-(1-Cyclopropyl-1H-pyrazol-4-yl)phenyl)(trans-4-(4-methoxy-3-methylphenyl)cyclohexyl)methyl)carbamoyl)-cyclohexyl 3-((methylsulfinyl)methyl)azetidine-1-carboxylate |
| 8.01 | 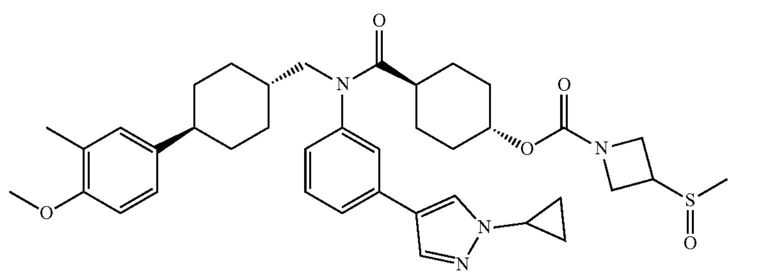 | trans-4-((3-(1-Cyclopropyl-1H-pyrazol-4-yl)phenyl)(trans-4-(4-methoxy-3-methylphenyl)cyclohexyl)methyl)carbamoyl)-cyclohexyl 3-(methylsulfinyl)azetidine-1-carboxylate |

TABLE 1-continued

| Compound No | Structure | Chemical Name |
|---|---|---|
| 9 | 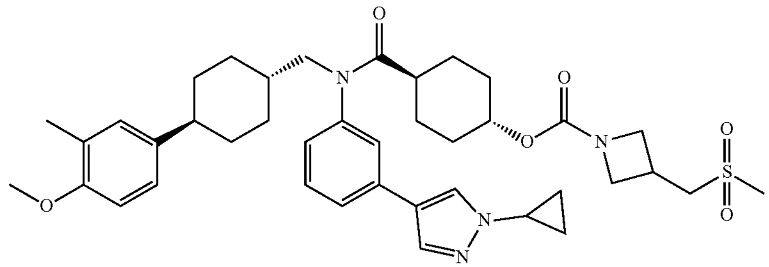 | trans-4-((3-(1-cyclopropyl-1H-pyrazol-4-yl)phenyl)((trans-4-(4-methoxy-3-methylphenyl)cyclohexyl)methyl)carbamoyl)cyclohexyl 3-((methylsulfonyl)methyl)azetidine-1-carboxylate |
| 10 | 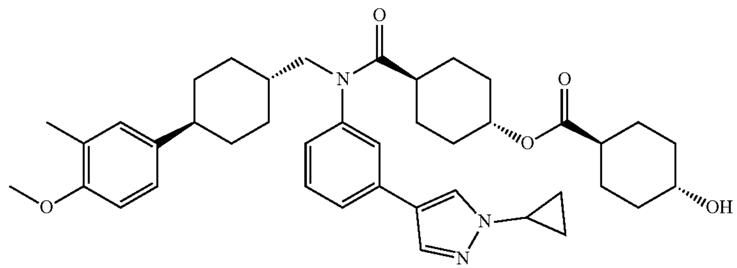 [SMILES: COc1ccc([C@H]2CC[C@H](CN(c3cccc(-c4cnn(C5CC5)c4)c3)C(=O)[C@H]3CC[C@H](OC(=O)[C@H]4CC[C@H](O)CC4)CC3)CC2)cc1C] | trans-4-(3-(1-Cyclopropyl-1H-pyrazol-4-yl)phenyl)((trans-4-(4-methoxy-3-methylphenyl)cyclohexyl)methyl)carbamoyl)cyclohexyl trans-4-hydroxycyclohexanecarboxylate |
| 11 | 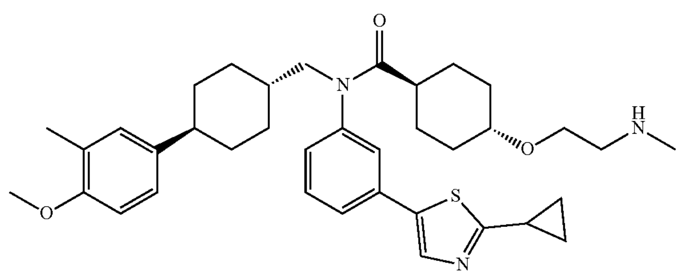 | trans-N-(3-(2-Cyclopropylthiazol-5-yl)phenyl)-N-((trans-4-(4-methoxy-3-methylphenyl)cyclohexyl)methyl)-4-(2-(methylamino)ethoxy)cyclohexanecarboxamide hydrochloride |

TABLE 1-continued

| Compound No | Structure | Chemical Name |
|---|---|---|
| 12 | 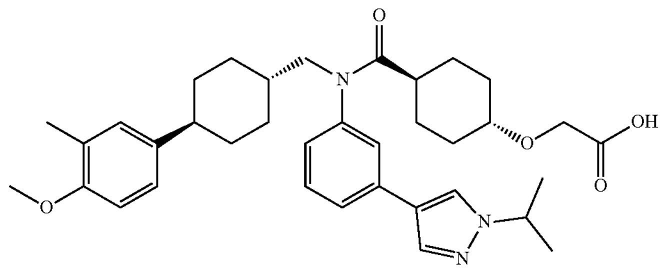 [SMILES: COc1ccc([C@H]2CC[C@H](CN(c3cccc(-c4cnn(C(C)C)c4)c3)C(=O)[C@H]3CC[C@H](OCC(=O)O)CC3)CC2)cc1C] | 2-((trans-4-((3-(1-Isopropyl-2H-pyrazol-4-yl)phenyl)((trans-4-(4-methoxy-3-methylphenyl)cyclohexyl)methyl)carbamoyl)-cyclohexyl)oxy)acetic acid |
| 13 | 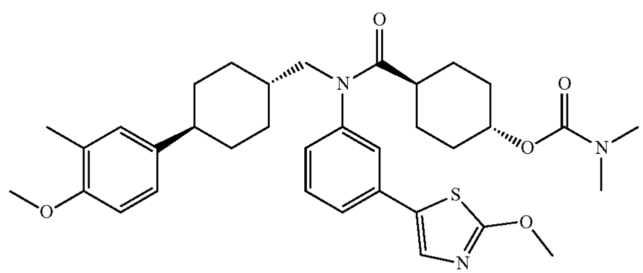 | trans-4-((trans-4-(4-Methoxy-3-methylphenyl)cyclohexyl)methyl)(3-(2-methoxythiazol-5-yl)phenyl)carbamoyl)cyclohexyl dimethylcarbamate |
| 13.01 | 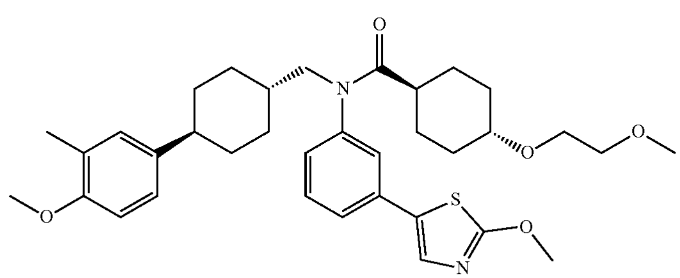 | trans-N-((trans-4-(4-Methoxy-3-methylphenyl)cyclohexyl)methyl)-4-(2-methoxyethoxy)-N-(3-(2-methoxythiazol-5-yl)phenyl)cyclohexanecarboxamide |

TABLE 1-continued

| Compound No | Structure | Chemical Name |
|---|---|---|
| 13.02 | 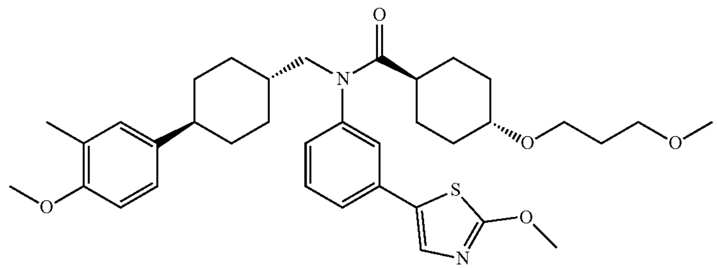 | trans-N-((trans-(4-Methoxy-3-methylphenyl)cyclohexyl)methyl)-4-(3-methoxypropoxy)-N-(3-(2-methoxythiazol-5-yl)phenyl)cyclohexanecarboxamide |
| 13.03 | 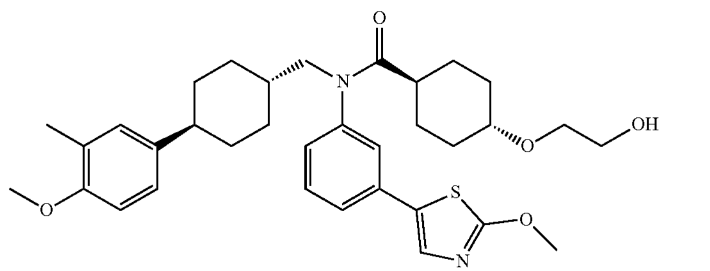 [SMILES: COc1ncc(-c2cccc(N(C[C@H]3CC[C@H](c4ccc(OC)c(C)c4)CC3)C(=O)[C@H]3CC[C@H](OCCO)CC3)c2)s1] | trans-4-(2-Hydroxyethoxy)-N-((trans-4-(4-methoxy-3-methylphenyl)cyclohexyl)methyl)-N-(3-(2-methoxythiazol-5-yl)phenyl)cyclohexanecarboxamide |
| 13.04 | 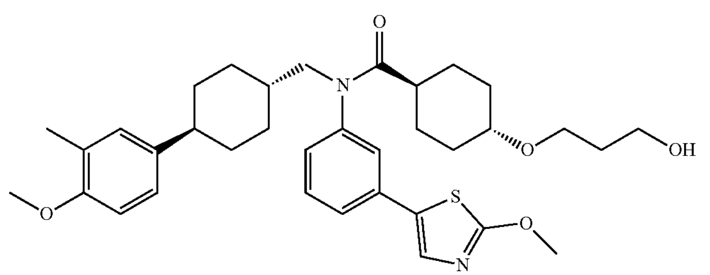 [SMILES: COc1ncc(-c2cccc(N(C[C@H]3CC[C@H](c4ccc(OC)c(C)c4)CC3)C(=O)[C@H]3CC[C@H](OCCCO)CC3)c2)s1] | trans-4-(3-Hydroxypropoxy)-N-((trans-4-(4-methoxy-3-methylphenyl)cyclohexyl)methyl)-N-(3-(2-methoxythiazol-5-yl)phenyl)cyclohexanecarboxamide |

TABLE 1-continued

| Compound No | Structure | Chemical Name |
|---|---|---|
| 13.05 | 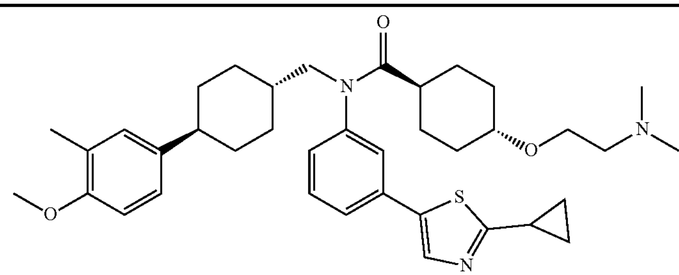 | trans-N-(3-(2-Cyclopropylthiazol-5-yl)phenyl)-4-(2-(dimethylamino)ethoxy)-N-((trans-4-(4-methoxy-3-methylphenyl)cyclohexyl)methyl)cyclohexanecarboxamide |
| 14 | 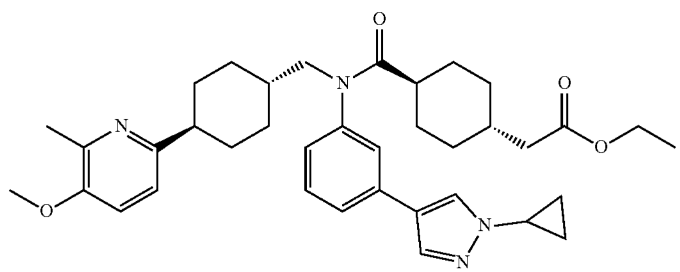 [SMILES: CCOC(=O)C[C@H]1CC[C@H](C(=O)N(C[C@H]2CC[C@H](c3ccc(OC)c(C)n3)CC2)c2cccc(-c3cnn(C4CC4)c3)c2)CC1] | Ethyl 2-(trans-4-((3-(1-cyclopropyl-1H-pyrazol-4-yl)phenyl)((trans-4-(5-methoxy-6-methylpyridin-2-yl)cyclohexyl)methyl)carbamoyl)cyclohexyl)acetate |
| 15 | 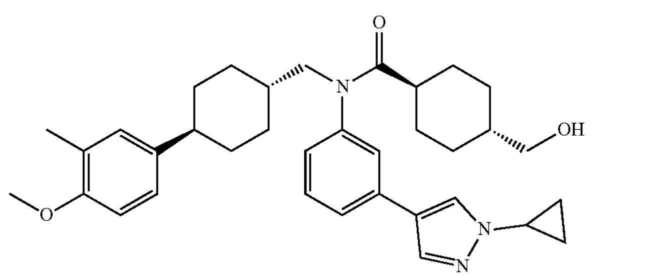 [SMILES: COc1ccc([C@H]2CC[C@H](CN(c3cccc(-c4cnn(C5CC5)c4)c3)C(=O)[C@H]3CC[C@H](CO)CC3)CC2)cc1C] | trans-N-(3-(1-Cyclopropyl-1H-pyrazol-4-yl)phenyl)-4-(hydroxymethyl)-N-((trans-4-(4-methoxy-3-methylphenyl)cyclohexyl)methyl)cyclohexanecarboxamide |

TABLE 1-continued

| Compound No | Structure | Chemical Name |
|---|---|---|
| 15.01 | 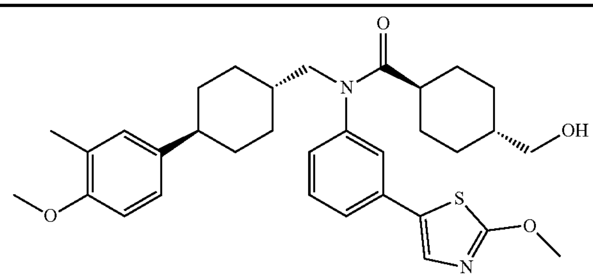 | trans-4-(Hydroxymethyl)-N-((trans-4-(4-methoxy-3-methylphenyl)cyclohexyl)methyl)-N-(3-(2-methoxythiazol-5-yl)phenyl)cyclohexanecarboxamide |
| 15.02 | 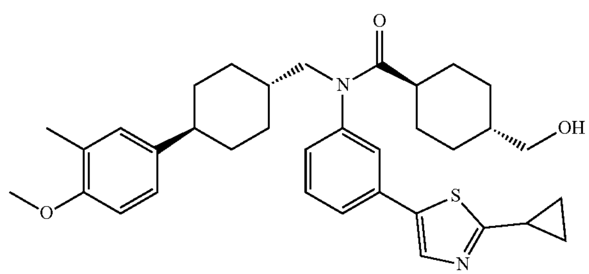 [SMILES: COc1ccc([C@H]2CC[C@H](CN(c3cccc(-c4cnc(C5CC5)s4)c3)C(=O)[C@H]3CC[C@H](CO)CC3)CC2)cc1C] | trans-N-(3-(2-Cyclopropylthiazol-5-yl)phenyl)-4-(hydroxymethyl)-N-((trans-4-(4-methoxy-3-methylphenyl)cyclohexyl)methyl)cyclohexanecarboxamide |
| 15.03 | 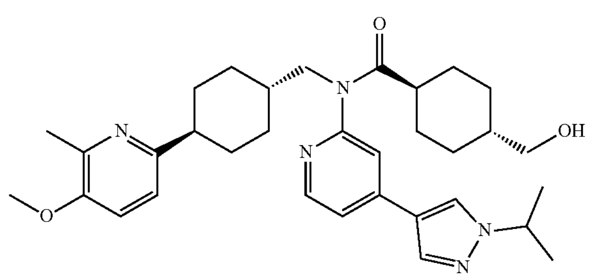 [SMILES: COc1ccc([C@H]2CC[C@H](CN(c3cc(-c4cnn(C(C)C)c4)ccn3)C(=O)[C@H]3CC[C@H](CO)CC3)CC2)nc1C] | trans-4-(Hydroxymethyl)-N-(4-(1-isopropyl-1H-pyrazol-4-yl)pyridin-2-yl)-N-((trans-4-(5-methoxy-6-methylpyridin-2-yl)cyclohexyl)methyl)cyclohexanecarboxamide |

TABLE 1-continued

| Compound No | Structure | Chemical Name |
|---|---|---|
| 15.04 | 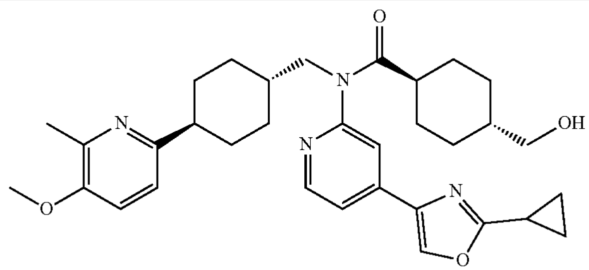 [SMILES: COc1ccc([C@H]2CC[C@H](CN(c3cc(-c4coc(C5CC5)n4)ccn3)C(=O)[C@H]3CC[C@H](CO)CC3)CC2)nc1C] | trans-N-(4-(2-Cyclopropyloxazol-4-yl)pyridin-2-yl)-4-(hydroxymethyl)-N-((trans-4-(5-methoxy-6-methylpyridin-2-yl)cyclohexyl)methyl)cyclohexanecarboxamide |
| 16 | 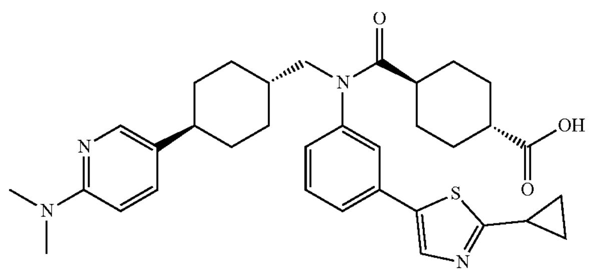 [SMILES: CN(C)c1ccc([C@H]2CC[C@H](CN(c3cccc(-c4cnc(C5CC5)s4)c3)C(=O)[C@H]3CC[C@H](C(=O)O)CC3)CC2)cn1] | trans-4-((3-(2-Cyclopropylthiazol-5-yl)phenyl)(trans-4-(6-(dimethylamino)pyridin-3-yl)cyclohexyl)methyl)carbamoyl)-cyclohexanecarboxylic acid |
| 17 | 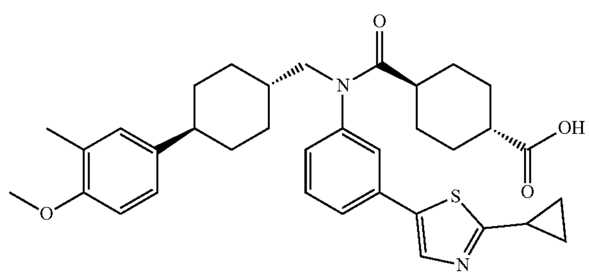 | trans-4-((3-(2-Cyclopropylthiazol-5-yl)phenyl)(trans-4-(4-methoxy-3-methylphenyl)cyclohexyl)methyl)carbamoyl)-cyclohexanecarboxylic acid |

TABLE 1-continued

| Compound No | Structure | Chemical Name |
|---|---|---|
| 17.01 | 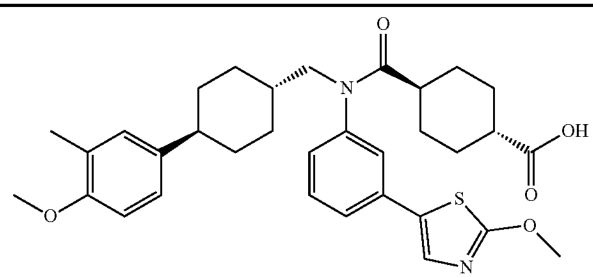 | trans-4-(((trans-4-(4-Methoxy-3-methylphenyl)cyclohexyl)methyl)(3-(2-methoxythiazol-5-yl)phenyl)carbamoyl)cyclohexanecarboxylic acid |
| 17.02 | 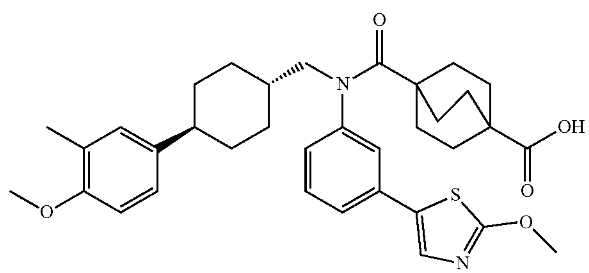 [SMILES: COc1ncc(-c2cccc(N(C[C@H]3CC[C@H](c4ccc(OC)c(C)c4)CC3)C(=O)C34CCC(C(=O)O)(CC3)CC4)c2)s1] | 4-(((trans-4-(4-Methoxy-3-methylphenyl)cyclohexyl)methyl)(3-(2-methoxythiazol-5-yl)phenyl)carbamoyl)bicyclo[2.2.2]octane-1-carboxylic acid |
| 17.03 | 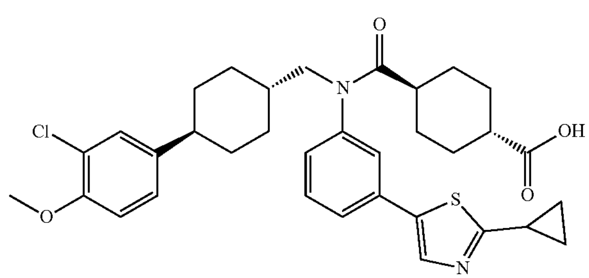 | trans-4-(((trans-4-(3-Chloro-4-methoxyphenyl)cyclohexyl)methyl)(3-(2-cyclopropylthiazol-5-yl)phenyl)carbamoyl)cyclohexanecarboxylic acid |

TABLE 1-continued

| Compound No | Structure | Chemical Name |
|---|---|---|
| 17.04 | 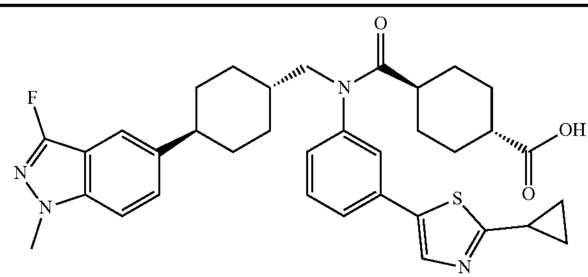 | trans-4-((3-(2-Cyclopropylthiazol-5-yl)phenyl)((trans-4-(3-fluoro-1-methyl-1H-indazol-5-yl)cyclohexyl)methyl)carbamoyl)cyclohexanecarboxylic acid |
| 17.05 | 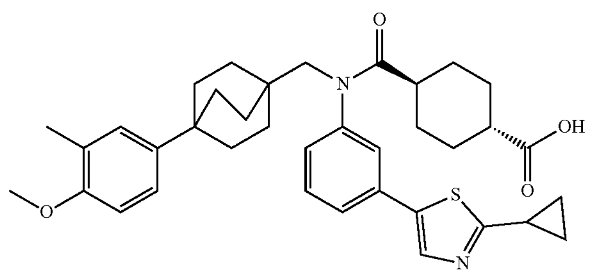 | trans-4-((3-(2-Cyclopropylthiazol-5-yl)phenyl)((4-(4-methoxy-3-methylphenyl)bicyclo[2.2.2]octan-1-yl)methyl)carbamoyl)cyclohexanecarboxylic acid |
| 17.06 | 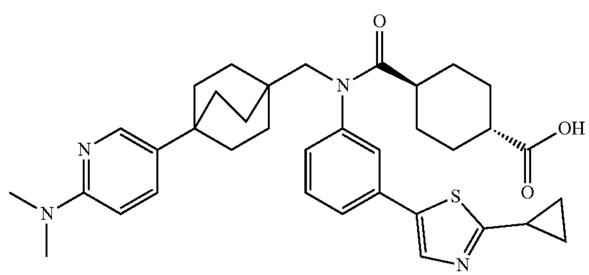 [SMILES: CN(C)c1ccc(C23CCC(CN(c4cccc(-c5cnc(C6CC6)s5)c4)C(=O)[C@H]4CC[C@H](C(=O)O)CC4)(CC2)CC3)cn1] | trans-4-((3-(2-Cyclopropylthiazol-5-yl)phenyl)((4-(6-(dimethylamino)pyridin-3-yl)bicyclo[2.2.2]octan-1-yl)methyl)carbamoyl)cyclohexanecarboxylic acid |

TABLE 1-continued

| Compound No | Structure | Chemical Name |
|---|---|---|
| 17.07 | 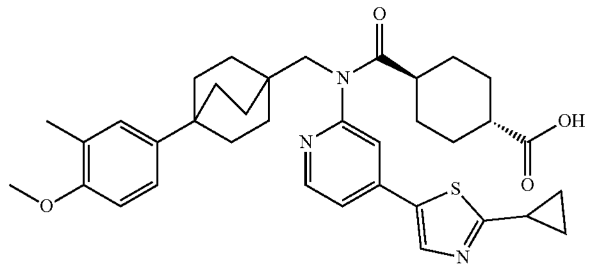 | trans-4-((4-(2-Cyclopropylthiazol-5-yl)pyridin-2-yl)(4-(4-methoxy-3-methylphenyl)bicyclo[2.2.2]octan-1-yl)methyl)carbamoyl)cyclohexanecarboxylic acid |
| 17.08 | 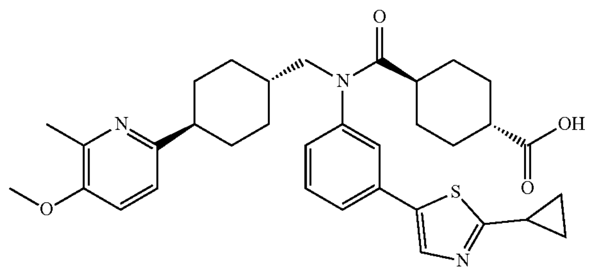 [SMILES: COc1ccc([C@H]2CC[C@H](CN(c3cccc(-c4cnc(C5CC5)s4)c3)C(=O)[C@H]3CC[C@H](C(=O)O)CC3)CC2)nc1C] | trans-4-(3-(2-Cyclopropylthiazol-5-yl)phenyl)((trans-4-(5-methoxy-6-methylpyridin-2-yl)cyclohexyl)methyl)carbamoyl)-cyclohexanecarboxylic acid |
| 17.09 | 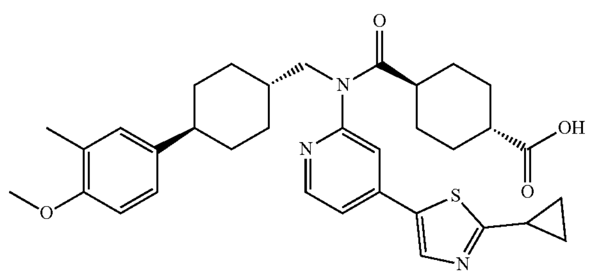 | trans-4-((4-(2-Cyclopropylthiazol-5-yl)pyridin-2-yl)((trans-4-(4-methoxy-3-methylphenyl)cyclohexyl)methyl)carbamoyl)-cyclohexanecarboxylic acid |

TABLE 1-continued

| Compound No | Structure | Chemical Name |
|---|---|---|
| 17.10 | 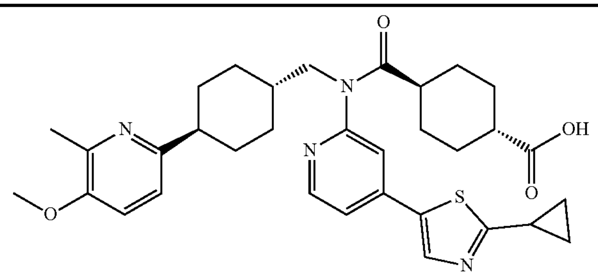 | trans-4-(((4-(2-Cyclopropylthiazol-5-yl)pyridin-2-yl)(trans-4-(5-methoxy-6-methylpyridin-2-yl)cyclohexyl)methyl)carbamoyl)-cyclohexanecarboxylic acid |
| 17.11 | 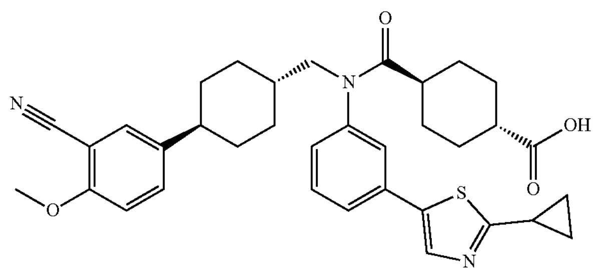 | trans-4-(((trans-4-(3-Cyano-4-methoxyphenyl)cyclohexyl)methyl)(3-(2-cyclopropylthiazol-5-yl)phenyl)carbamoyl)cyclohexanecarboxylic acid |
| 17.12 | 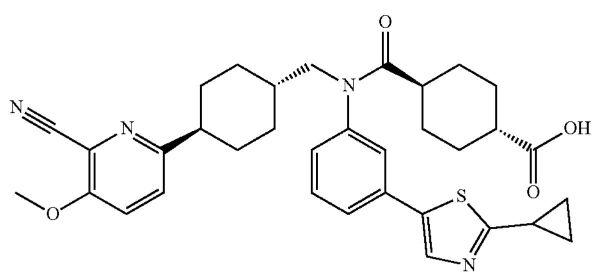 [SMILES: COc1ccc([C@H]2CC[C@H](CN(c3cccc(-c4cnc(C5CC5)s4)c3)C(=O)[C@H]3CC[C@H](C(=O)O)CC3)CC2)nc1C#N] | trans-4-(((trans-4-(6-Cyano-5-methoxypyridin-2-yl)cyclohexyl)methyl)(3-(2-cyclopropylthiazol-5-yl)phenyl)carbamoyl)cyclohexanecarboxylic acid |

TABLE 1-continued

| Compound No | Structure | Chemical Name |
|---|---|---|
| 17.13 | 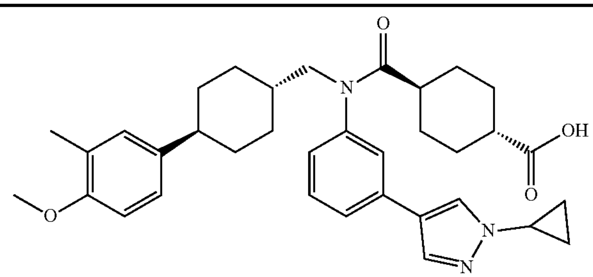 | trans-4-((3-(1-Cyclopropyl-1H-pyrazol-4-yl)phenyl)((trans-4-(4-methoxy-3-methylphenyl)cyclohexyl)methyl)carbamoyl)-cyclohexanecarboxylic acid |
| 17.14 | 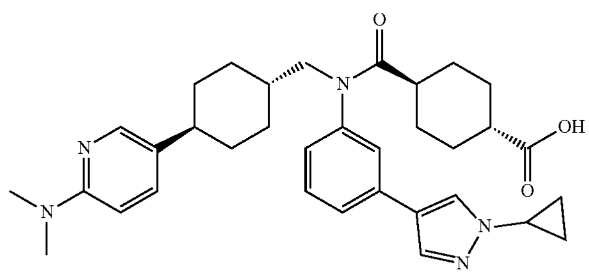 [SMILES: CN(C)c1ccc([C@H]2CC[C@H](CN(c3cccc(-c4cnn(C5CC5)c4)c3)C(=O)[C@H]3CC[C@H](C(=O)O)CC3)CC2)cn1] | trans-4-((3-(1-Cyclopropyl-1H-pyrazol-4-yl)phenyl)((trans-4-(6-(dimethylamino)pyridin-3-yl)cyclohexyl)methyl)carbamoyl)-cyclohexanecarboxylic acid |
| 17.15 | 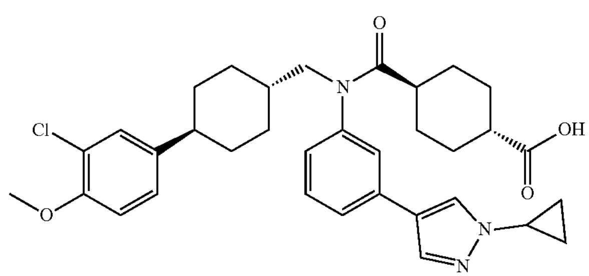 | trans-4-(((trans-4-(3-Chloro-4-methoxyphenyl)cyclohexyl)methyl)(3-(1-cyclopropyl-1H-pyrazol-4-yl)phenyl)carbamoyl)cyclohexanecarboxylic acid |

TABLE 1-continued

| Compound No | Structure | Chemical Name |
|---|---|---|
| 17.16 | 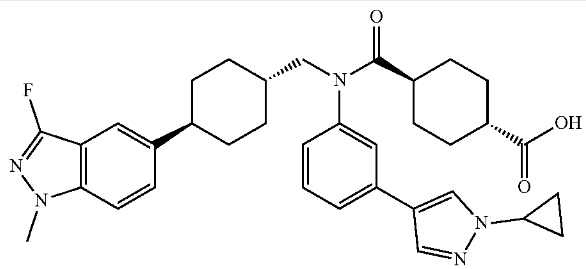 [SMILES: Cn1nc(F)c2cc([C@H]3CC[C@H](CN(c4cccc(-c5cnn(C6CC6)c5)c4)C(=O)[C@H]4CC[C@H](C(=O)O)CC4)CC3)ccc21] | trans-4-((3-(1-Cyclopropyl-1H-pyrazol-4-yl)phenyl)(trans-4-(3-fluoro-1-methyl-1H-indazol-5-yl)cyclohexyl)methyl)carbamoyl)-cyclohexanecarboxylic acid |
| 17.17 | 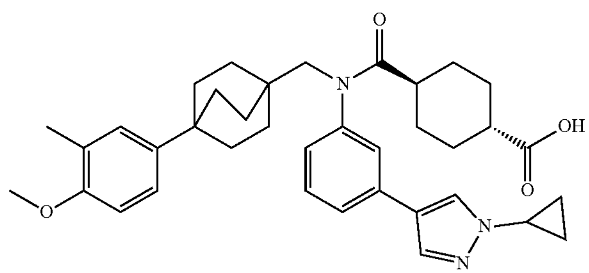 [SMILES: COc1ccc(C23CCC(CN(c4cccc(-c5cnn(C6CC6)c5)c4)C(=O)[C@H]4CC[C@H](C(=O)O)CC4)(CC2)CC3)cc1C] | trans-4-((3-(1-Cyclopropyl-1H-pyrazol-4-yl)phenyl)((4-(4-methoxy-3-methylphenyl)bicyclo[2.2.2]octan-1-yl)methyl)carbamoyl)cyclohexanecarboxylic acid |
| 17.18 | 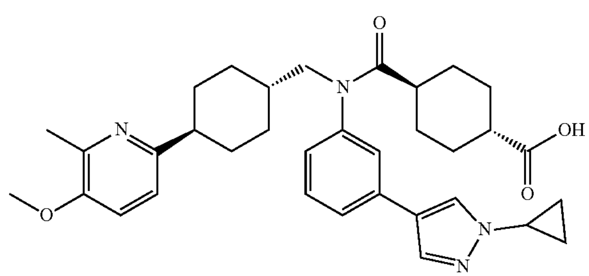 | trans-4-((3-(1-Cyclopropyl-1H-pyrazol-4-yl)phenyl)(trans-4-(5-methoxy-6-methylpyridin-2-yl)cyclohexyl)methyl)carbamoyl)-cyclohexanecarboxylic acid |

TABLE 1-continued

| Compound No | Structure | Chemical Name |
|---|---|---|
| 17.19 | 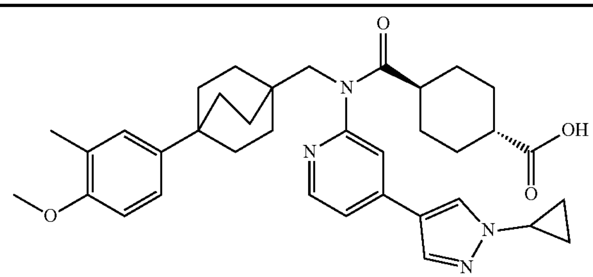 | trans-4-((4-(1-Cyclopropyl-1H-pyrazol-4-yl)pyridin-2-yl)(4-(4-methoxy-3-methylphenyl)bicyclo[2.2.2]octan-1-yl)methyl)carbamoyl)cyclohexanecarboxylic acid |
| 17.20 | 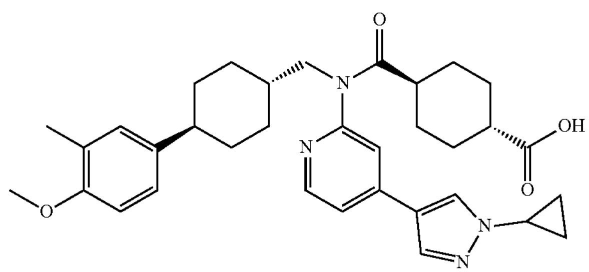 | trans-4-((4-(1-Cyclopropyl-1H-pyrazol-4-yl)pyridin-2-yl)((trans-4-(4-methoxy-3-methylphenyl)cyclohexyl)methyl)carbamoyl)-cyclohexanecarboxylic acid |
| 17.21 | 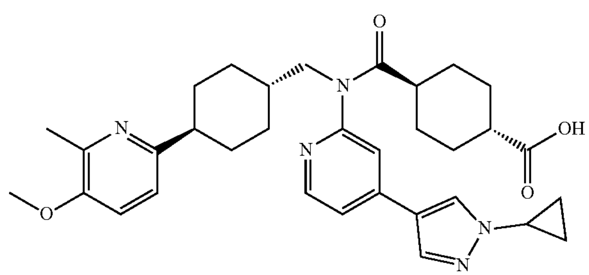 [SMILES: COc1ccc([C@H]2CC[C@H](CN(c3cc(-c4cnn(C5CC5)c4)ccn3)C(=O)[C@H]3CC[C@H](C(=O)O)CC3)CC2)cc1C] | tran-4-((4-(1-Cyclopropyl-1H-pyrazol-4-yl)pyridin-2-yl)((trans-4-(5-methoxy-6-methylpyridin-2-yl)cyclohexyl)methyl)-carbamoyl)cyclohexanecarboxylic acid |

TABLE 1-continued

| Compound No | Structure | Chemical Name |
|---|---|---|
| 17.22 | 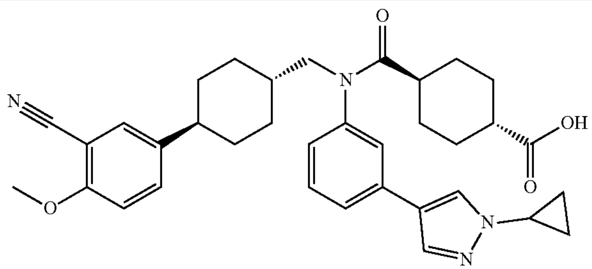 [SMILES: COc1ccc([C@H]2CC[C@H](CN(c3cccc(-c4cnn(C5CC5)c4)c3)C(=O)[C@H]3CC[C@H](C(=O)O)CC3)CC2)cc1C#N] | trans-4-(((trans-4-(3-Cyano-4-methoxyphenyl)cyclohexyl)methyl)(3-(1-cyclopropyl-1H-pyrazol-4-yl)phenyl)carbamoyl)cyclohexanecarboxylic acid |
| 17.23 | 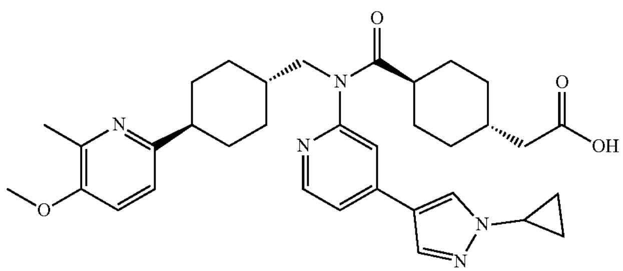 [SMILES: COc1ccc([C@H]2CC[C@H](CN(c3cc(-c4cnn(C5CC5)c4)ccn3)C(=O)[C@H]3CC[C@H](CC(=O)O)CC3)CC2)nc1C] | 2-(trans-4-((4-(1-Cyclopropyl-1H-pyrazol-4-yl)pyridin-2-yl)((trans-4-(5-methoxy-6-methylpyridin-2-yl)cyclohexyl)methyl)carbamoyl)cyclohexyl)acetic acid |
| 17.24 | 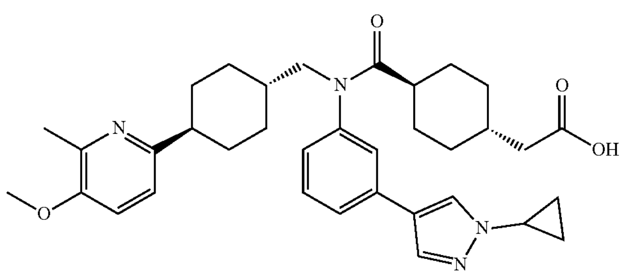 | 2-(trans-4-((3-(1-Cyclopropyl-1H-pyrazol-4-yl)phenyl)((trans-4-(5-methoxy-6-methylpyridin-2-yl)cyclohexyl)methyl)carbamoyl)cyclohexyl)-acetic acid |

TABLE 1-continued

| Compound No | Structure | Chemical Name |
|---|---|---|
| 17.25 | 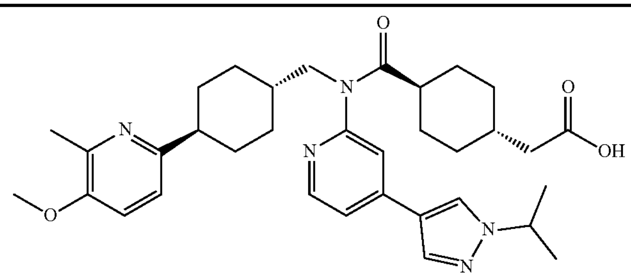 | 2-(trans-4-((4-(1-Isopropyl-1H-pyrazol-4-yl)pyridin-2-yl)((trans-4-(5-methoxy-6-methylpyridin-2-yl)cyclohexyl)methyl)carbamoyl)cyclohexyl)acetic acid |
| 17.26 | 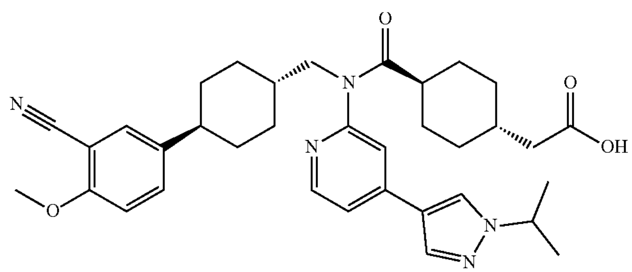 | 2-(trans-4-(((trans-4-(3-Cyano-4-methoxyphenyl)cyclohexyl)methyl)(4-(1-isopropyl-1H-pyrazol-4-yl)pyridin-2-yl)carbamoyl)cyclohexyl)acetic acid |
| 17.27 | 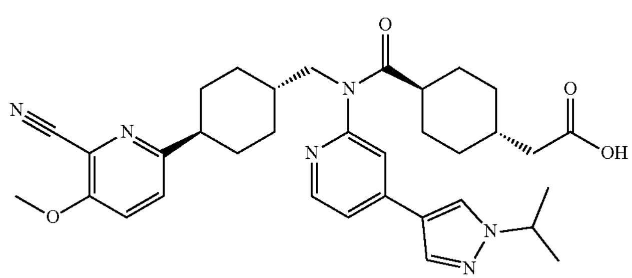 | 2-(trans-4-(((trans-4-(6-Cyano-5-methoxypyridin-2-yl)cyclohexyl)methyl)(4-(1-isopropyl-1H-pyrazol-4-yl)pyridin-2-yl)carbamoyl)cyclohexyl)acetic acid |

TABLE 1-continued

| Compound No | Structure | Chemical Name |
|---|---|---|
| 18 | 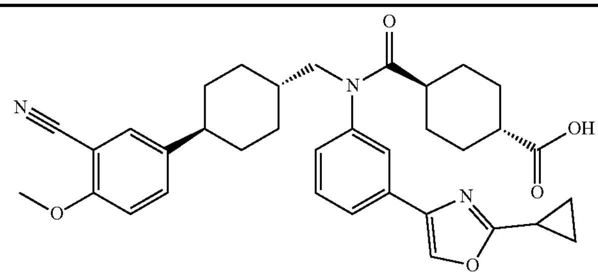 | trans-4-(((trans-4-(3-Cyano-4-methoxyphenyl)cyclohexyl)methyl)(3-(2-cyclopropyloxazol-4-yl)phenyl)carbamoyl)cyclohexanecarboxylic acid |
| 18.01 | 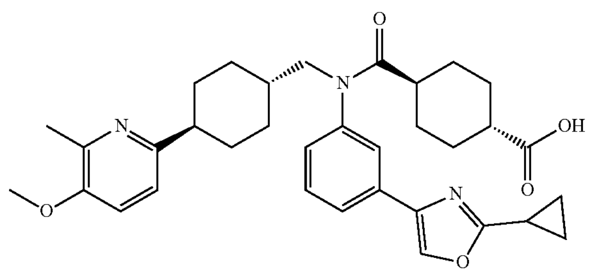 | trans-4-((3-(2-Cyclopropyloxazol-4-yl)phenyl)(trans-4-(5-methoxy-6-methylpyridin-2-yl)cyclohexyl)methyl)carbamoyl)-cyclohexanecarboxylic acid |
| 18.02 | 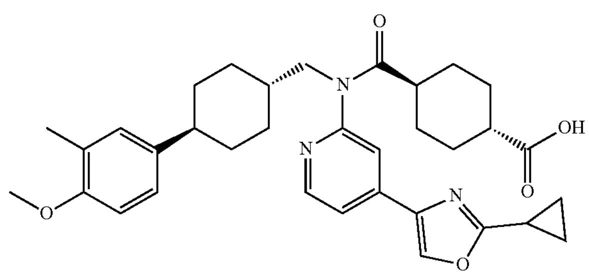 [SMILES: COc1ccc([C@H]2CC[C@H](CN(c3cc(-c4coc(C5CC5)n4)ccn3)C(=O)[C@H]3CC[C@H](C(=O)O)CC3)CC2)cc1C] | trans-4-((4-(2-Cyclopropyloxazol-4-yl)pyridine-2-yl)(trans-4-(4-methoxy-3-methylphenyl)cyclohexyl)methyl)carbamoyl)-cyclohexanecarboxylic acid |

TABLE 1-continued

| Compound No | Structure | Chemical Name |
|---|---|---|
| 18.03 | 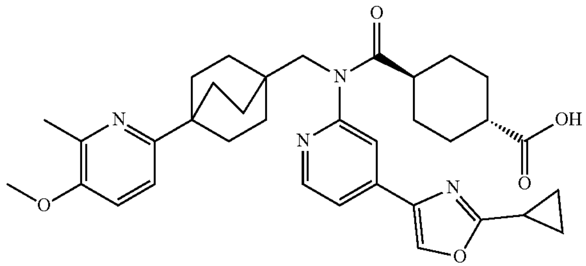 | trans-4-((4-(2-Cyclopropyloxazol-4-yl)pyridin-2-yl)(4-(4-methoxy-3-methylphenyl)bicyclo[2.2.2]octan-1-yl)methyl)carbamoyl)cyclohexanecarboxylic acid |
| 18.04 | 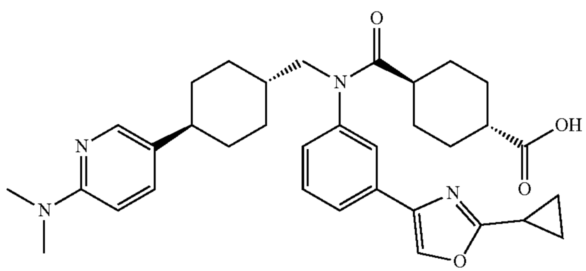 | trans-4-((3-(2-Cyclopropyloxazol-4-yl)phenyl)((trans-4-(6-(diethylamino)pyridine-3-yl)cyclohexyl)methyl)carbamoyl)-cyclohexanecarboxylic acid |
| 18.05 | 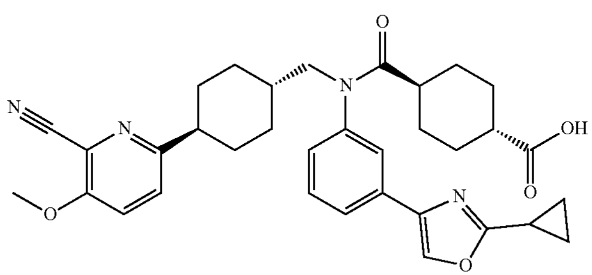 | trans-4-(((trans-4-(6-Cyano-5-methoxypyridin-2-yl)cyclohexyl)methyl)(3-(2-cyclopropyloxazol-4-yl)phenyl)carbamoyl)cyclohexanecarboxylic acid |

TABLE 1-continued

| Compound No | Structure | Chemical Name |
|---|---|---|
| 18.06 | 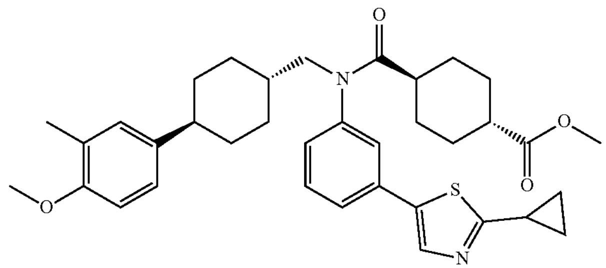 | trans-Methyl 4-((3-(2-cyclopropylthiazol-5-yl)phenyl)(trans-4-(4-methoxy-3-methylphenyl)cyclohexyl)methyl)carbamoyl)-cyclohexanecarboxylate |
| 18.07 | 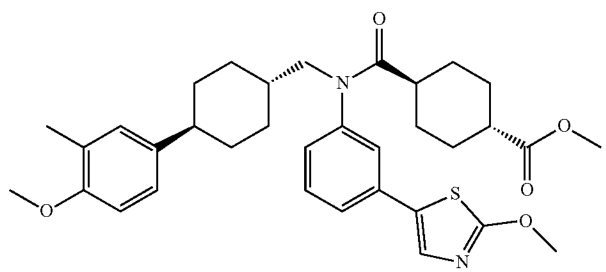 | trans-Methyl 4-(((trans-4-(4-methoxy-3-methylphenyl)cyclohexyl)methyl)(3-(2-methoxythiazol-5-yl)phenyl)carbamoyl)cyclohexanecarboxylate |
| 18.08 | 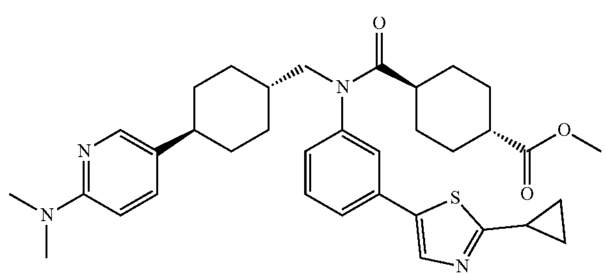 | trans-Methyl 4-((3-(2-cyclopropylthiazol-5-yl)phenyl)(trans-4-(6-(dimethylamino)pyridin-3-yl)cyclohexyl)methyl)carbamoyl)-cyclohexanecarboxylate |

TABLE 1-continued

| Compound No | Chemical Name |
|---|---|
| 18.09 | trans-Methyl 4-(((trans-4-(6-cyano-5-methoxypyridin-2-yl)cyclohexyl)methyl)(3-(2-cyclopropylthiazol-5-yl)phenyl)carbamoyl)cyclohexanecarboxylate |
| 18.10 | Methyl 4-(((trans-4-(4-methoxy-3-methylphenyl)cyclohexyl)methyl)(3-(2-methoxythiazol-5-yl)phenyl)carbamoyl)bicyclo[2.2.2]octane-1-carboxylate |
| 18.11 | trans-4-(Benzyloxy)-N-((trans-4-(4-methoxy-3-methylphenyl)cyclohexyl)methyl)-N-(3-(2-methoxythiazol-5-yl)phenyl)cyclohexanecarboxamide |

TABLE 1-continued

| Compound No | Structure | Chemical Name |
|---|---|---|
| 18.12 | 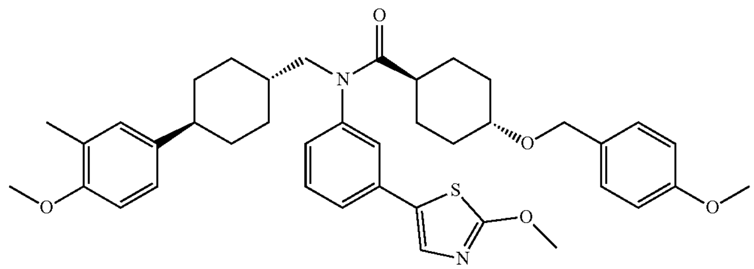 | trans-N-((trans-4-(4-Methoxy-3-methylphenyl)cyclohexyl)methyl)-4-((4-methoxybenzyl)oxy)-N-(3-(2-methoxythiazol-5-yl)phenyl)cyclohexanecarboxamide |
| 18.13 | 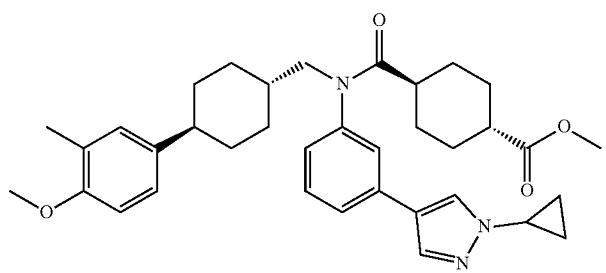 | trans-Methyl 4-((3-(1-cyclopropyl-1H-pyrazol-4-yl)phenyl)(trans-4-(4-methoxy-3-methylphenyl)cyclohexyl)methyl)carbamoyl)-cyclohexanecarboxylate |
| 18.14 | 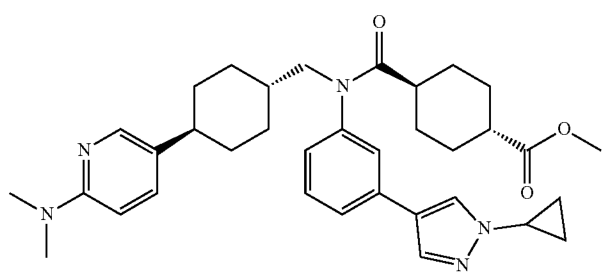 | trans-Methyl 4-((3-(1-cyclopropyl-1H-pyrazol-4-yl)phenyl)(trans-4-(6-(dimethylamino)pyridin-3-yl)cyclohexyl)methyl)carbamoyl)-cyclohexanecarboxylate |

TABLE 1-continued

| Compound No | Structure | Chemical Name |
|---|---|---|
| 18.15 | 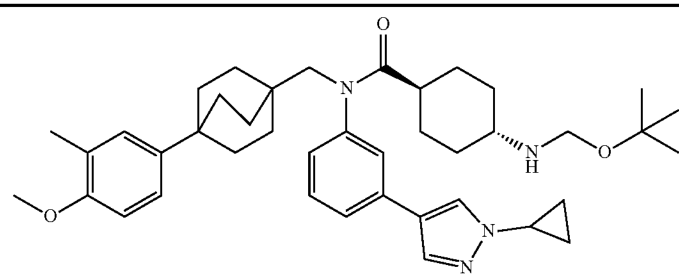 | tert-Butyl (4-((3-(1-cyclopropyl-1H-pyrazol-4-yl)phenyl)(4-(4-methoxy-3-methylphenyl)bicyclo[2.2.2]octan-1-yl)methyl)carbamoyl)cyclohexyl)trans-carbamate |
| 18.16 | 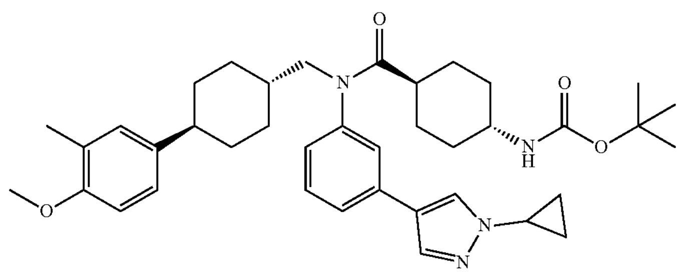 | tert-Butyl (trans-4-(3-(1-isopropyl-1H-pyrazol-4-yl)phenyl)((trans-4-(4-methoxy-3-methylphenyl)cyclohexyl)methyl)carbamoyl)cyclohexyl)carbamate |
| 18.17 | 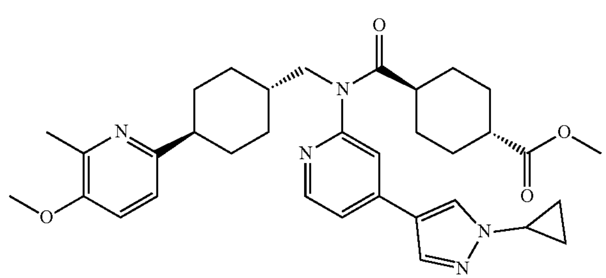 | trans-Methyl 4-((4-((1-cyclopropyl-1H-pyrazol-4-yl)pyridin-2-yl)((trans-4-(5-methoxy-6-methylpyridin-2-yl)cyclohexyl)methyl)carbamoyl)-cyclohexanecarboxylate |

TABLE 1-continued

| Compound No | Structure | Chemical Name |
|---|---|---|
| 18.18 | 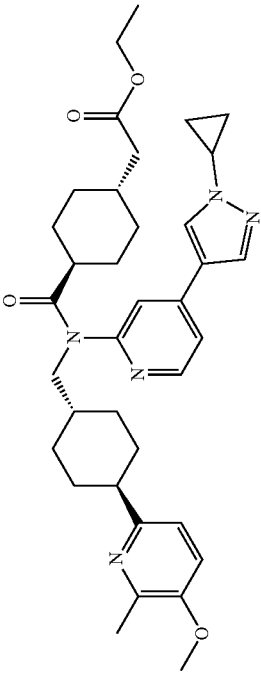 | Ethyl 2-(trans-4-((4-(1-cyclopropyl-1H-pyrazol-4-yl)pyridin-2-yl)((trans-4-(5-methoxy-6-methylpyridin-2-yl)cyclohexyl)methyl)carbamoyl)cyclohexyl)acetate |
| 18.19 | 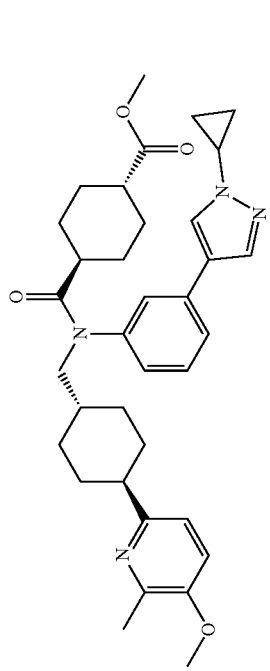 | trans-Methyl 4-((3-(1-cyclopropyl-1H-pyrazol-4-yl)phenyl)((trans-4-(5-methoxy-6-methylpyridin-2-yl)cyclohexyl)methyl)carbamoyl)-cyclohexanecarboxylate |
| 18.20 | 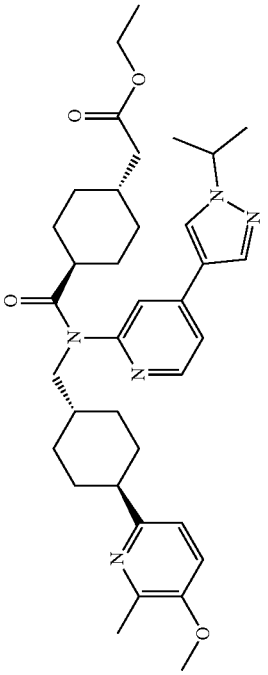 | Ethyl 2-(trans-4-((4-(1-isopropyl-2H-pyrazol-4-yl)pyridin-2-yl)((trans-4-(5-methoxy-6-methylpyridin-2-yl)cyclohexyl)methyl)carbamoyl)cyclohexyl)acetate |

TABLE 1-continued

| Compound No | Structure | Chemical Name |
|---|---|---|
| 18.21 | 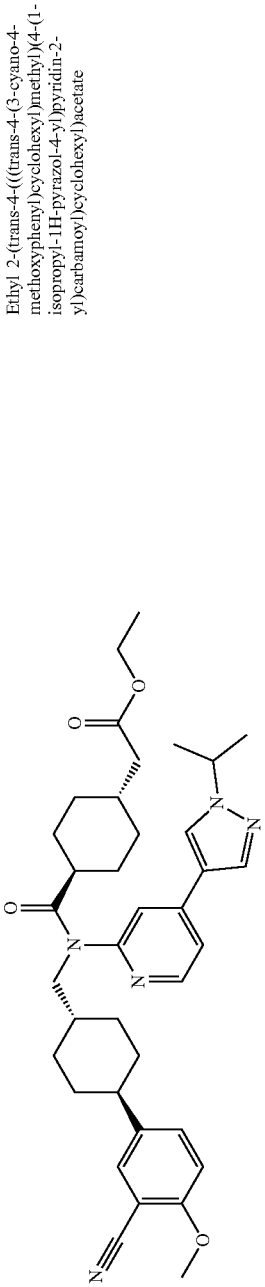 | Ethyl 2-(trans-4-((trans-4-(3-cyano-4-methoxyphenyl)cyclohexyl)methyl)(4-(1-isopropyl-1H-pyrazol-4-yl)pyridin-2-yl)carbamoyl)cyclohexyl)acetate |
| 18.22 | 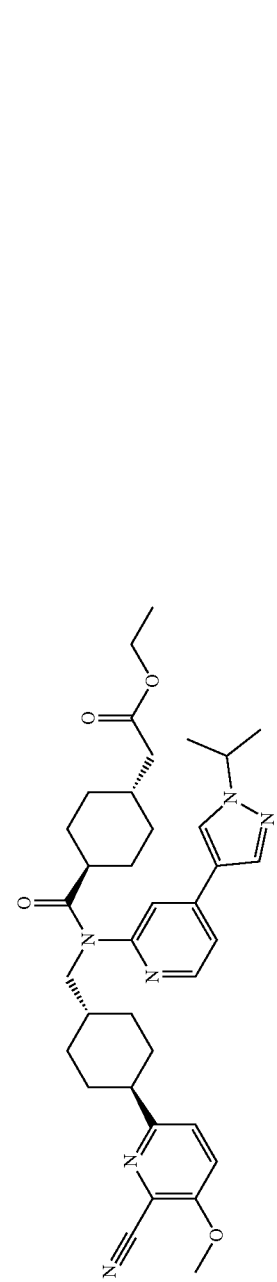 | Ethyl 2-(trans-4-((trans-4-(6-cyano-5-methoxypyridin-2-yl)cyclohexyl)methyl)(4-(1-isopropyl-1H-pyrazol-4-yl)pyridin-2-yl)carbamoyl)cyclohexyl)acetate |
| 18.23 | 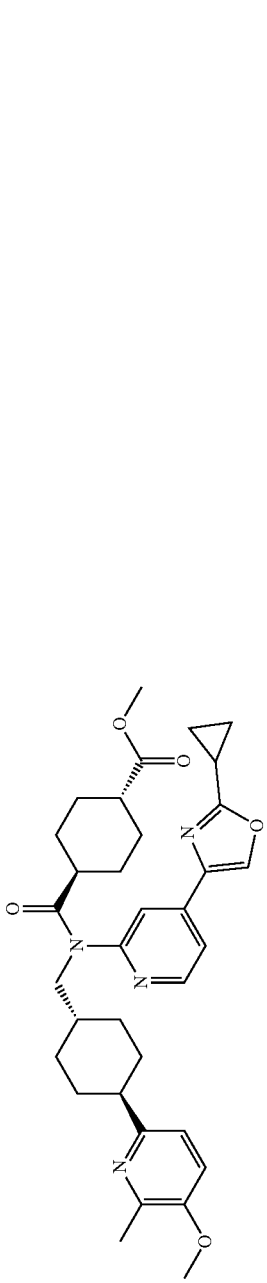 | trans-Methyl 4-((4-(2-cyclopropyloxazol-4-yl)pyridin-2-yl)((trans-4-(5-methoxy-6-methylpyridin-2-yl)cyclohexyl)methyl)carbamoyl)-cyclohexanecarboxylate |

TABLE 1-continued

| Compound No | Structure | Chemical Name |
|---|---|---|
| 18.24 | 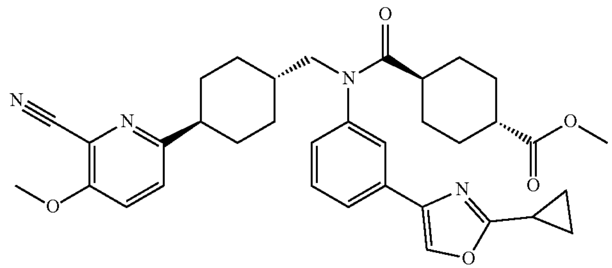 | trans-Methyl 4-(((trans-4-(6-cyano-5-methoxypyridin-2-yl)cyclohexyl)methyl)(3-(2-cyclopropyloxazol-4-yl)phenyl)carbamoyl)cyclohexanecarboxylate |
| 19 | 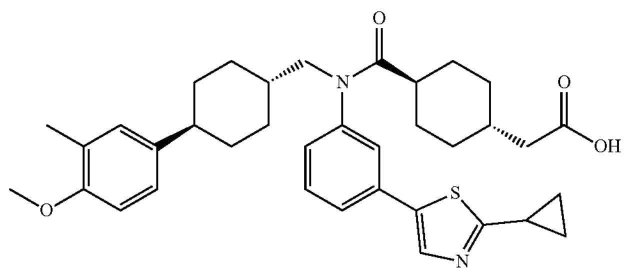 [SMILES: COc1ccc([C@H]2CC[C@H](CN(c3cccc(-c4cnc(C5CC5)s4)c3)C(=O)[C@H]3CC[C@H](CC(=O)O)CC3)CC2)cc1C] | 2-(trans-4-((3-(2-Cyclopropylthiazol-5-yl)phenyl)((trans-4-(4-methoxy-3-methylphenyl)cyclohexyl)methyl)carbamoyl)cyclohexyl)acetic acid |
| 20 | 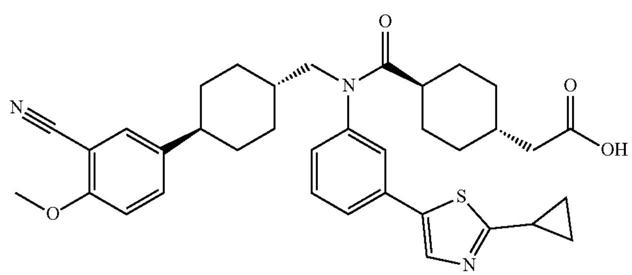 | 2-(trans-4-(((trans-4-(3-Cyano-4-methoxyphenyl)cyclohexyl)methyl)(3-(2-cyclopropylthiazol-5-yl)phenyl)carbamoyl)cyclohexyl)acetic acid |

TABLE 1-continued

| Compound No | Structure | Chemical Name |
|---|---|---|
| 20.01 | 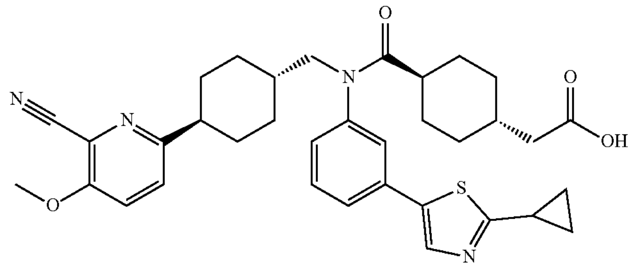 [SMILES: COc1ccc([C@H]2CC[C@H](CN(c3cccc(-c4cnc(C5CC5)s4)c3)C(=O)[C@H]3CC[C@H](CC(=O)O)CC3)CC2)nc1C#N] | 2-(trans-4-(((trans-4-(6-Cyano-5-methoxypyridin-2-yl)cyclohexyl)methyl)(3-(2-cyclopropylthiazol-5-yl)phenyl)carbamoyl)cyclohexyl)acetic acid |
| 20.02 | 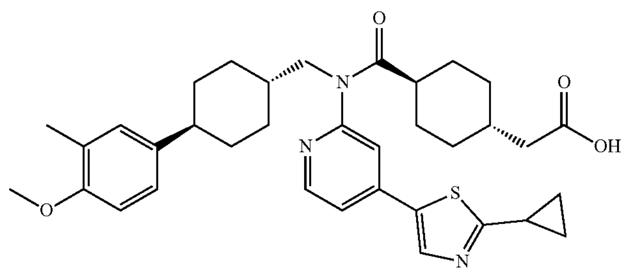 [SMILES: COc1ccc([C@H]2CC[C@H](CN(c3cc(-c4cnc(C5CC5)s4)ccn3)C(=O)[C@H]3CC[C@H](CC(=O)O)CC3)CC2)cc1C] | 2-(trans-4-((4-(2-Cyclopropylthiazol-5-yl)pyridin-2-yl)((trans-4-(4-methoxy-3-methyl phenyl)cyclohexyl)methyl)carbamoyl)-cyclohexyl)acetic acid |
| 20.03 | 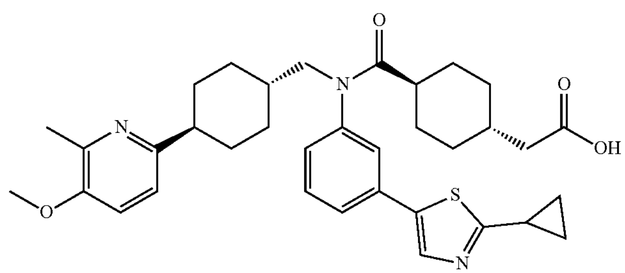 [SMILES: COc1ccc([C@H]2CC[C@H](CN(c3cccc(-c4cnc(C5CC5)s4)c3)C(=O)[C@H]3CC[C@H](CC(=O)O)CC3)CC2)nc1C] | 2-(trans-4-((3-(2-Cyclopropylthiazol-5-yl)phenyl)((trans-4-(5-methoxy-6-methylpyridin-2-yl)cyclohexyl)methyl)carbamoyl)-cyclohexyl)acetic acid |

TABLE 1-continued

| Compound No | Structure | Chemical Name |
|---|---|---|
| 20.04 | 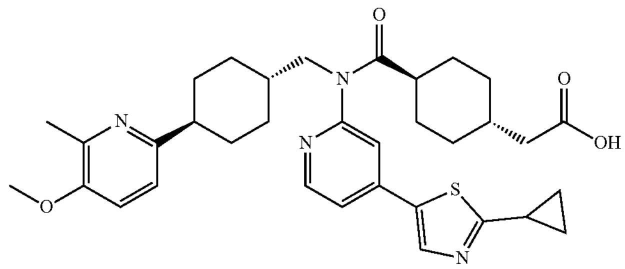 [SMILES: COc1ccc([C@H]2CC[C@H](CN(c3cc(-c4cnc(C5CC5)s4)ccn3)C(=O)[C@H]3CC[C@H](CC(=O)O)CC3)CC2)nc1C] | 2-(trans-4-((4-(2-Cyclopropylthiazol-5-yl)pyridin-2-yl)((trans-4-(5-methoxy-6-methylpyridin-2-yl)cyclohexyl)methyl)carbamoyl)cyclohexyl)acetic acid |
| 20.05 | 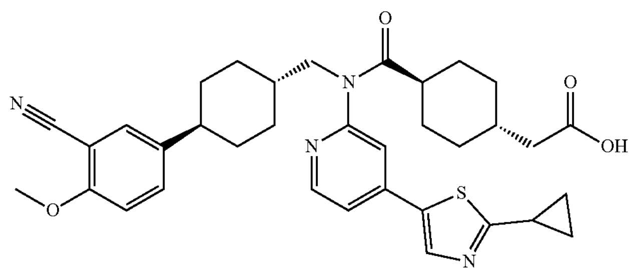 [SMILES: COc1ccc([C@H]2CC[C@H](CN(c3cc(-c4cnc(C5CC5)s4)ccn3)C(=O)[C@H]3CC[C@H](CC(=O)O)CC3)CC2)cc1C#N] | 2-(trans-4-(((trans-4-(3-Cyano-4-methoxyphenyl)cyclohexyl)methyl)(4-(2-cyclopropylthiazol-5-yl)pyridin-2-yl)carbamoyl)cyclohexyl)acetic acid |
| 20.06 | 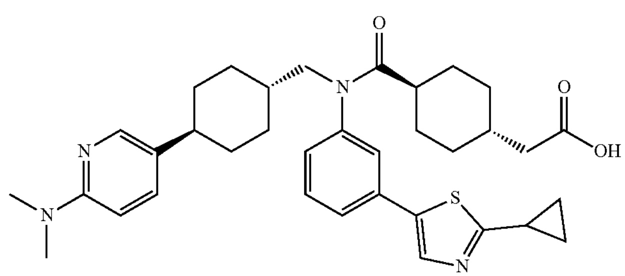 [SMILES: CN(C)c1ccc([C@H]2CC[C@H](CN(c3cccc(-c4cnc(C5CC5)s4)c3)C(=O)[C@H]3CC[C@H](CC(=O)O)CC3)CC2)cn1] | 2-(trans-4-((3-(2-Cyclopropylthiazol-5-yl)phenyl)((trans-4-(6-(dimethylamino)pyridin-3-yl)cyclohexyl)methyl)carbamoyl)cyclohexyl)acetic acid |

TABLE 1-continued

| Compound No | Structure | Chemical Name |
|---|---|---|
| 20.07 | 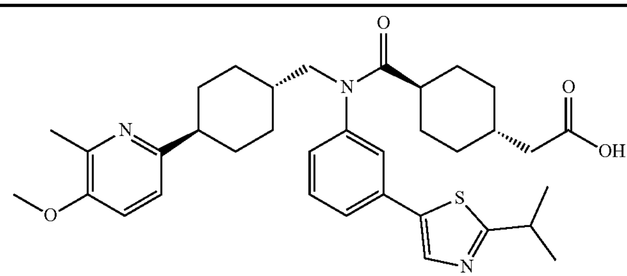 | 2-(trans-4-((3-(2-Isopropylthiazol-5-yl)phenyl)((trans-4-(5-methoxy-6-methylpyridin-2-yl)cyclohexyl)methyl)carbamoyl)cyclohexyl)acetic acid |
| 20.08 | 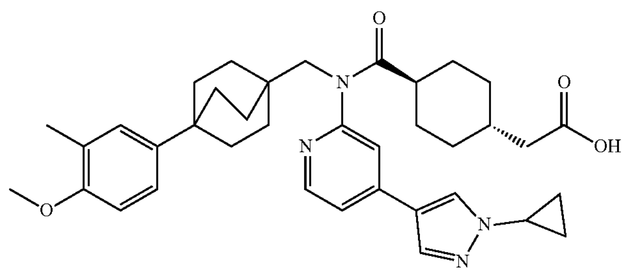 [SMILES: COc1ccc(C23CCC(CN(c4cc(-c5cnn(C6CC6)c5)ccn4)C(=O)[C@H]4CC[C@H](CC(=O)O)CC4)(CC2)CC3)cc1C] | trans-2-(4-(4-((4-(1-Cyclopropyl-1H-pyrazol-4-yl)pyridin-2-yl)((4-(4-methoxy-3-methylphenyl)bicyclo[2.2.2]octan-1-yl)methyl)carbamoyl)cyclohexyl)acetic acid |
| 20.09 | 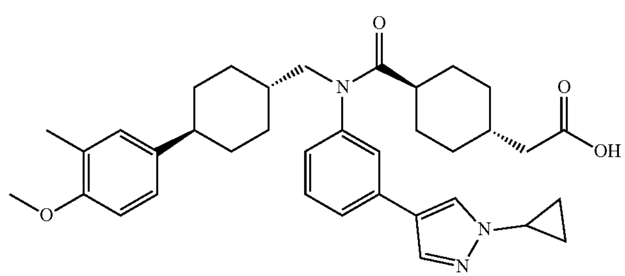 [SMILES: COc1ccc([C@H]2CC[C@H](CN(c3cccc(-c4cnn(C5CC5)c4)c3)C(=O)[C@H]3CC[C@H](CC(=O)O)CC3)CC2)cc1C] | 2-(trans-4-((3-(1-Cyclopropyl-1H-pyrazol-4-yl)phenyl)((trans-4-(4-methoxy-3-methylphenyl)cyclohexyl)methyl)carbamoyl)cyclohexyl)acetic acid |

TABLE 1-continued

| Compound No | Structure | Chemical Name |
|---|---|---|
| 20.10 | 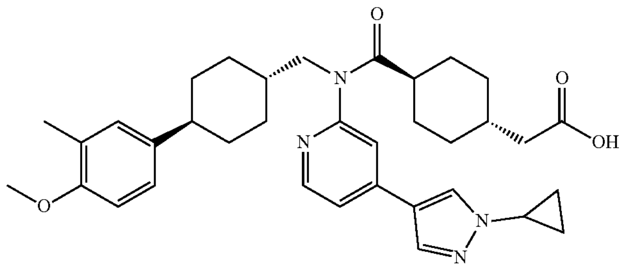 | 2-(trans-4-((4-(1-Cyclopropyl-1H-pyrazol-4-yl)pyridin-2-yl)((trans-4-(4-methoxy-3-methylphenyl)cyclohexyl)methyl)carbamoyl)-cyclohexyl)acetic acid |
| 20.11 | 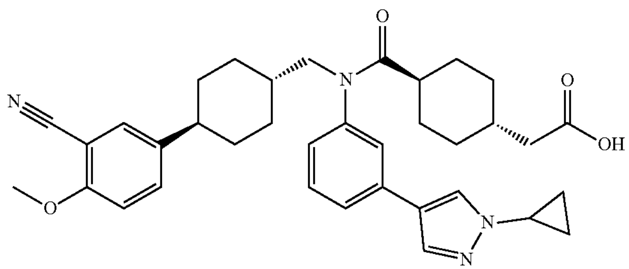 [SMILES: COc1ccc([C@H]2CC[C@H](CN(c3cccc(-c4cnn(C5CC5)c4)c3)C(=O)[C@H]3CC[C@H](CC(=O)O)CC3)CC2)cc1C#N] | 2-(trans-4-(((trans-4-(3-Cyano-4-methoxyphenyl)cyclohexyl)methyl)(3-(1-cyclopropyl-1H-pyrazol-4-yl)phenyl)carbamoyl)cyclohexyl)acetic acid |
| 20.12 | 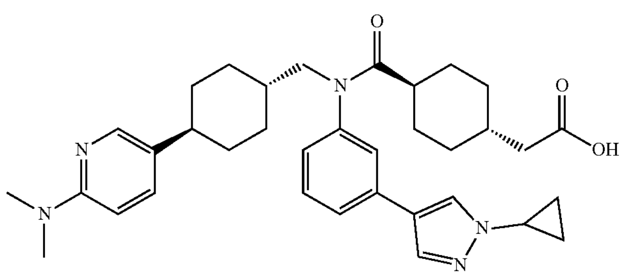 | 2-(trans-4-((3-(1-Cyclopropyl-1H-pyrazol-4-yl)phenyl)((trans-4-(6-(dimethylamino)pyridin-3-yl)cyclohexyl)methyl)carbamoyl)cyclohexyl)acetc acid |

TABLE 1-continued

| Compound No | Structure | Chemical Name |
|---|---|---|
| 20.13 | 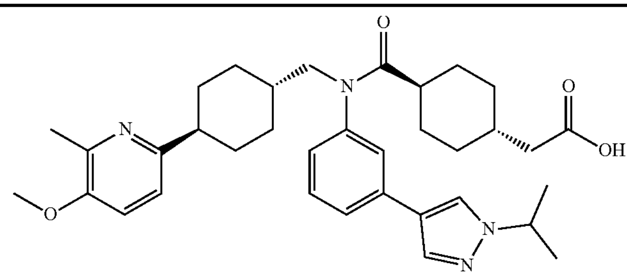 | 2-(trans-4-((3-(1-Isopropyl-1H-pyrazol-4-yl)phenyl)((trans-4-(5-methoxy-6-methylpyridin-2-yl)cyclohexyl)methyl)carbamoyl)cyclohexyl)acetic acid |
| 20.14 | 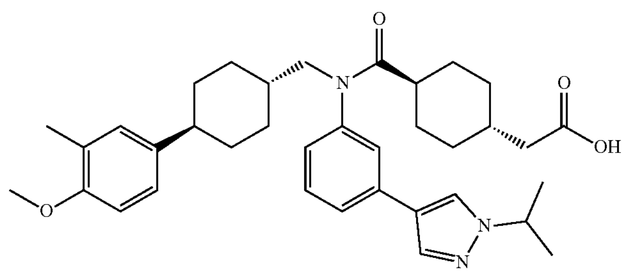 | 2-(trans-4-((3-(1-Isopropyl-1H-pyrazol-4-yl)phenyl)((trans-4-(4-methoxy-3-methylphenyl)cyclohexyl)methyl)carbamoyl)cyclohexyl)acetic acid |
| 20.15 | 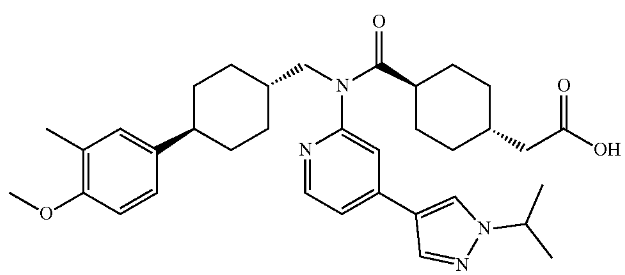 | 2-(trans-4-((4-(1-Isopropyl-1H-pyrazol-4-yl)pyridin-2-yl)((trans-4-(4-methoxy-3-methylphenyl)cyclohexyl)methyl)carbamoyl)cyclohexyl)acetic acid |

TABLE 1-continued

| Compound No | Structure | Chemical Name |
|---|---|---|
| 20.16 | 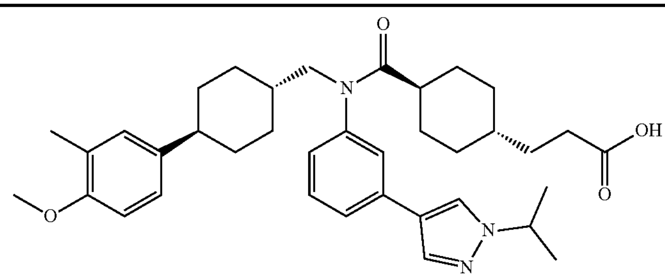 | 3-(trans-4-((3-(1-Isopropyl-1H-pyrazol-4-yl)phenyl)((trans-4-(4-methoxy-3-methylphenyl)cyclohexyl)methyl)carbamoyl)cyclohexyl)propanoic acid |
| 21 | 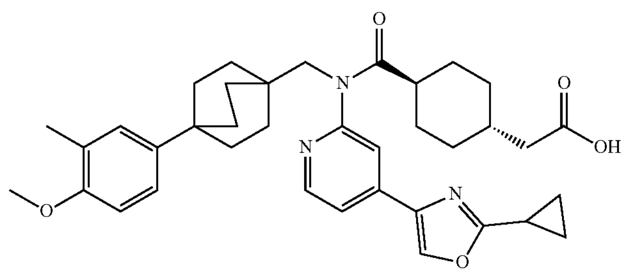 [SMILES: COc1ccc(C23CCC(CN(c4cc(-c5coc(C6CC6)n5)ccn4)C(=O)[C@H]4CC[C@H](CC(=O)O)CC4)(CC2)CC3)cc1C] | trans-2-(4-(4-(2-Cyclopropyloxazol-4-yl)pyridin-2-yl)((4-(4-methoxy-3-methylphenyl)bicyclo[2.2.2]octan-1-yl)methyl)carbamoyl)cyclohexyl)acetic acid |
| 21.01 | 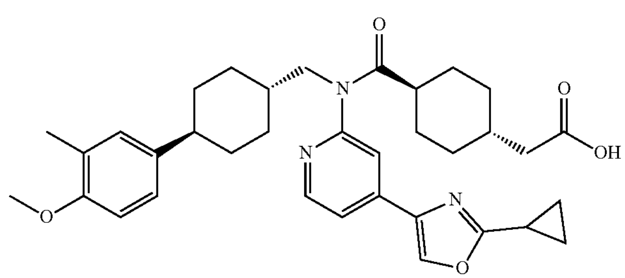 [SMILES: COc1ccc([C@H]2CC[C@H](CN(c3cc(-c4coc(C5CC5)n4)ccn3)C(=O)[C@H]3CC[C@H](CC(=O)O)CC3)CC2)cc1C] | 2-(trans-4-(4-(2-Cyclopropyloxazol-4-yl)pyridin-2-yl)((trans-4-(4-methoxy-3-methylphenyl)cyclohexyl)methyl)carbamoyl)cyclohexyl)acetic acid |

TABLE 1-continued

| Compound No | Structure | Chemical Name |
|---|---|---|
| 21.02 | 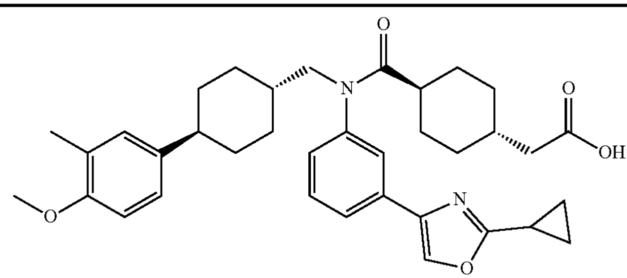 | 2-(trans-4-((3-(2-Cyclopropyloxazol-4-yl)phenyl)((trans-4-(4-methoxy-3-methylphenyl)cyclohexyl)methyl)carbamoyl)cyclohexyl)acetic acid |
| 21.03 | 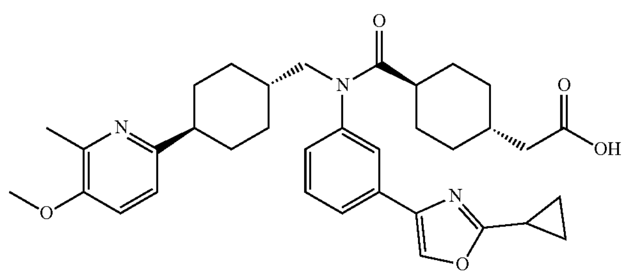 [SMILES: COc1ccc([C@H]2CC[C@H](CN(c3cccc(-c4coc(C5CC5)n4)c3)C(=O)[C@H]3CC[C@H](CC(=O)O)CC3)CC2)cc1C] | 2-(trans-4-((3-(2-Cyclopropyloxazol-4-yl)phenyl)((trans-4-(5-methoxy-6-methylpyridin-2-yl)cyclohexyl)methyl)carbamoyl)cyclohexyl)acetic acid |
| 21.04 | 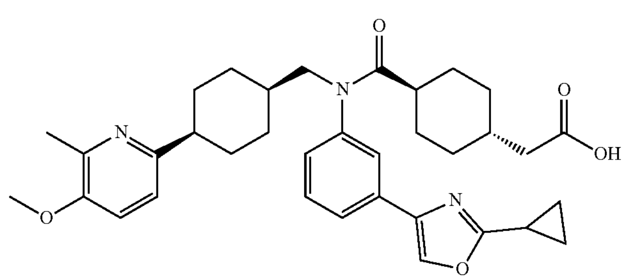 [SMILES: COc1ccc([C@H]2CC[C@@H](CN(c3cccc(-c4coc(C5CC5)n4)c3)C(=O)[C@H]3CC[C@H](CC(=O)O)CC3)CC2)nc1C] | 2-(trans-4-((3-(2-Cyclopropyloxazol-4-yl)phenyl)((cis-4-(5-methoxy-6-methylpyridin-2-yl)cyclohexyl)methyl)carbamoyl)cyclohexyl)acetic acid |

TABLE 1-continued

| Compound No | Structure | Chemical Name |
|---|---|---|
| 21.05 | 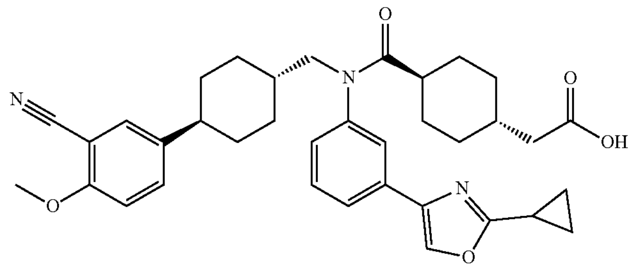 | 2-(trans-4-(((trans-4-(3-Cyano-4-methoxyphenyl)cyclohexyl)methyl)(3-(2-cyclopropyloxazol-4-yl)phenyl)carbamoyl)cyclohexyl)acetic acid |
| 21.06 | 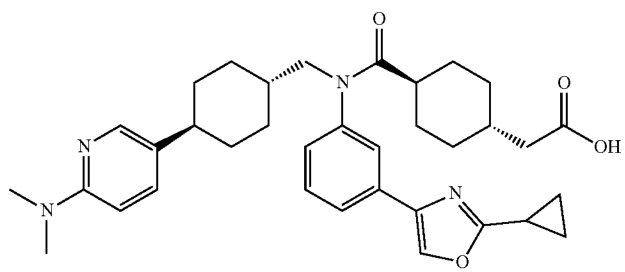 [SMILES: CN(C)c1ccc([C@H]2CC[C@H](CN(c3cccc(-c4coc(C5CC5)n4)c3)C(=O)[C@H]3CC[C@H](CC(=O)O)CC3)CC2)cn1] | 2-(trans-4-((3-(2-Cyclopropyloxazol-4-yl)phenyl)((trans-4-(6-(dimethylamino)pyridin-3-yl)cyclohexyl)methyl)carbamoyl)cyclohexyl)acetic acid |
| 21.07 | 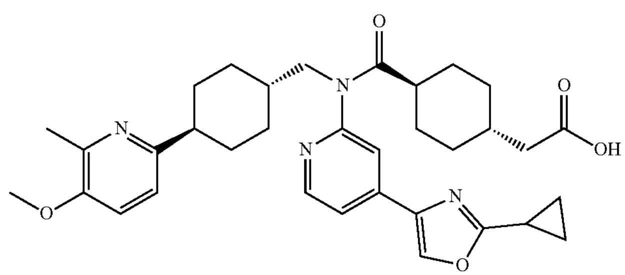 | 2-(trans-4-((4-(2-Cyclopropyloxazol-4-yl)pyridin-2-yl)((trans-4-(5-methoxy-6-methylpyridin-2-yl)cyclohexyl)methyl)carbamoyl)cyclohexyl)acetic acid |

TABLE 1-continued

| Compound No | Structure | Chemical Name |
|---|---|---|
| 21.08 | 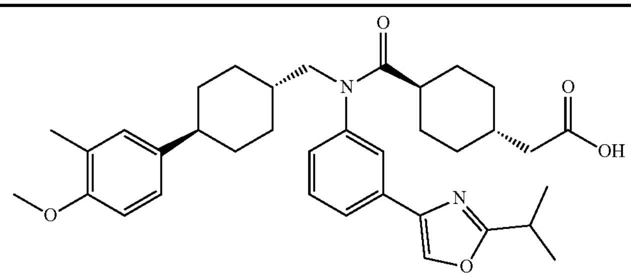 | 2-(trans-4-(((3-(2-Isopropyloxazol-4-yl)phenyl)(trans-4-(4-methoxy-3-methylphenyl)cyclohexyl)methyl)carbamoyl)-cyclohexyl)acetic acid |
| 21.09 | 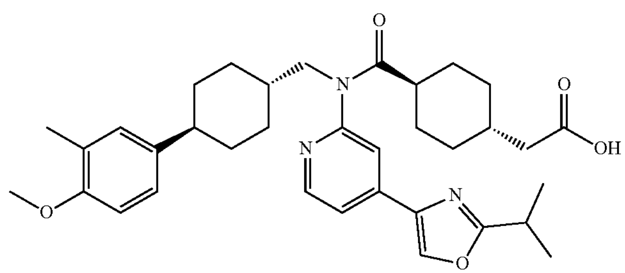 | 2-(trans-4-((4-(2-Isopropyloxazol-4-yl)pyridin-2-yl)(trans-4-(4-methoxy-3-methylphenyl)cyclohexyl)methyl)carbamoyl)-cyclohexyl)acetic acid |
| 21.10 | 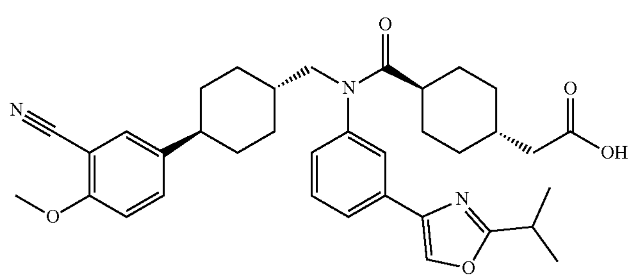 [SMILES: COc1ccc([C@H]2CC[C@H](CN(c3cccc(-c4coc(C(C)C)n4)c3)C(=O)[C@H]3CC[C@H](CC(=O)O)CC3)CC2)cc1C#N] | 2-(trans-4-(((trans-4-(3-Cyano-4-methoxyphenyl)cyclohexyl)methyl)(3-(2-isopropyloxazol-4-yl)phenyl)carbamoyl)cyclohexyl)acetic acid |

TABLE 1-continued

| Compound No | Structure | Chemical Name |
|---|---|---|
| 21.11 | 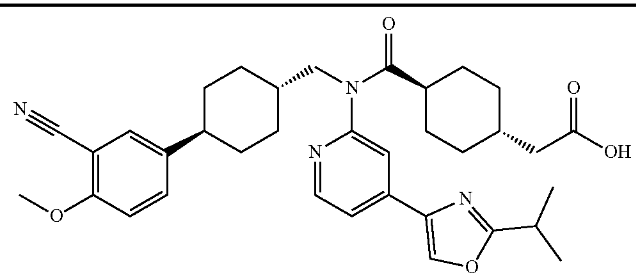 | 2-(trans-4-(((trans-4-(3-Cyano-4-methoxyphenyl)cyclohexyl)methyl)(4-(2-isopropyloxazol-4-yl)pyridin-2-yl)carbamoyl)cyclohexyl)acetic acid |
| 21.12 | 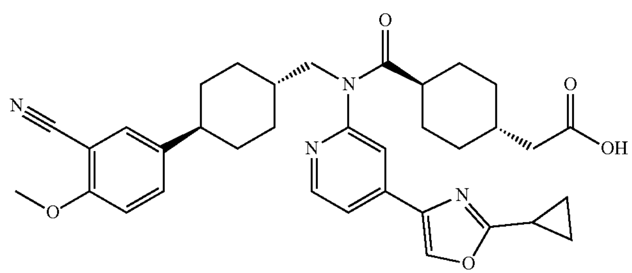 | 2-(trans-4-(((trans-4-(3-Cyano-4-methoxyphenyl)cyclohexyl)methyl)(4-(2-cyclopropyloxazol-4-yl)pyridin-2-yl)carbamoyl)cyclohexyl)acetic acid |
| 21.13 | 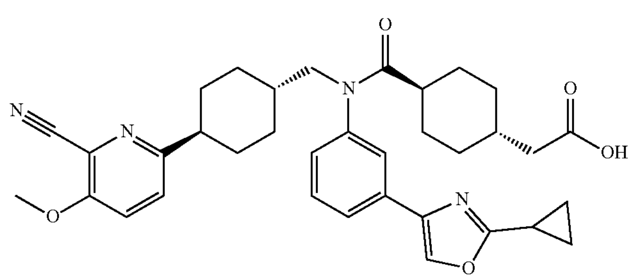 | 2-(trans-4-(((trans-4-(6-Cyano-5-methoxypyridin-2-yl)cyclohexyl)methyl)(3-(2-cyclopropyloxazol-4-yl)phenyl)carbamoyl)cyclohexyl)acetic acid |

TABLE 1-continued

| Compound No | Structure | Chemical Name |
|---|---|---|
| 22 | 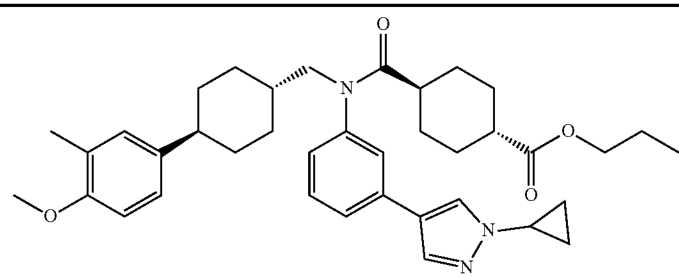 | trans-Propyl 4-((3-(1-cyclopropyl-1H-pyrazol-4-yl)phenyl)(trans-4-(4-methoxy-3-methylphenyl)cyclohexyl)methyl)carbamoyl)-cyclohexanecarboxylate |
| 22.01 | 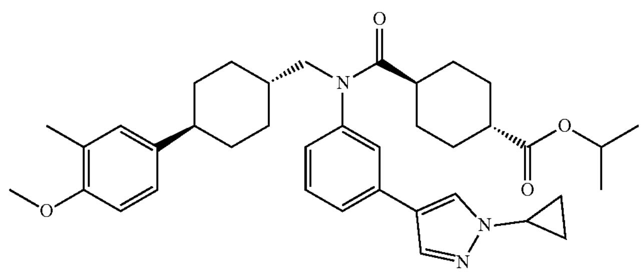 [SMILES: COc1ccc([C@H]2CC[C@H](CN(c3cccc(-c4cnn(C5CC5)c4)c3)C(=O)[C@H]3CC[C@H](C(=O)OC(C)C)CC3)CC2)cc1C] | trans-Isopropyl 4-((3-(1-cyclopropyl-1H-pyrazol-4-yl)phenyl)(trans-4-(4-methoxy-3-methylphenyl)cyclohexyl)methyl)carbamoyl)-cyclohexanecarboxylate |
| 22.02 | 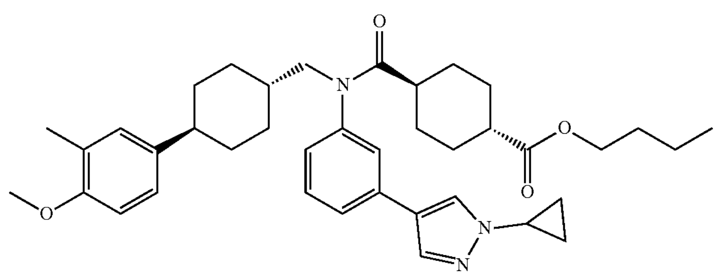 [SMILES: CCCCOC(=O)[C@H]1CC[C@H](C(=O)N(C[C@H]2CC[C@H](c3ccc(OC)c(C)c3)CC2)c2cccc(-c3cnn(C4CC4)c3)c2)CC1] | trans-Butyl 4-((3-(1-cyclopropyl-1H-pyrazol-4-yl)phenyl)(trans-4-(4-methoxy-3-methylphenyl)cyclohexyl)methyl)carbamoyl)-cyclohexanecarboxylate |

TABLE 1-continued

| Compound No | Structure | Chemical Name |
|---|---|---|
| 22.03 | 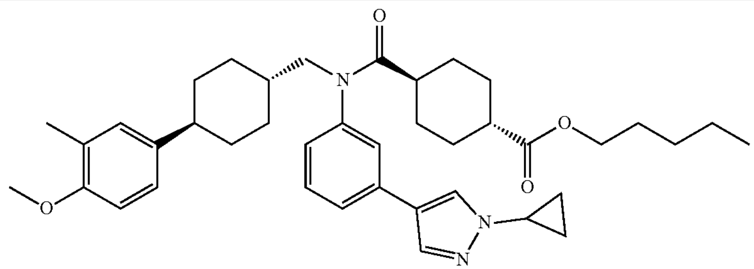 [SMILES: CCCCCOC(=O)[C@H]1CC[C@H](C(=O)N(C[C@H]2CC[C@H](c3ccc(OC)c(C)c3)CC2)c2cccc(-c3cnn(C4CC4)c3)c2)CC1] | trans-Pentyl 4-((3-(1-cyclopropyl-1H-pyrazol-4-yl)phenyl)(trans-4-(4-methoxy-3-methylphenyl)cyclohexyl)methyl)carbamoyl)-cyclohexanecarboxylate |
| 22.04 | 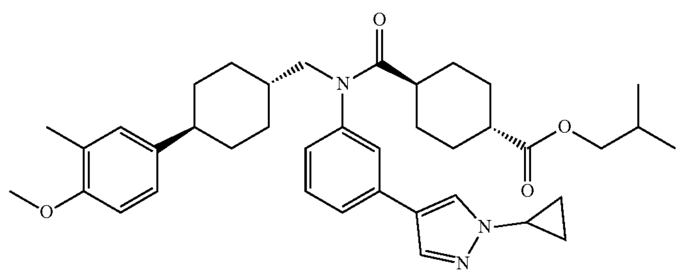 | trans-Isobutyl 4-((3-(1-cyclopropyl-1H-pyrazol-4-yl)phenyl)(trans-4-(4-methoxy-3-methylphenyl)cyclohexyl)methyl)carbamoyl)-cyclohexanecarboxylate |
| 22.05 | 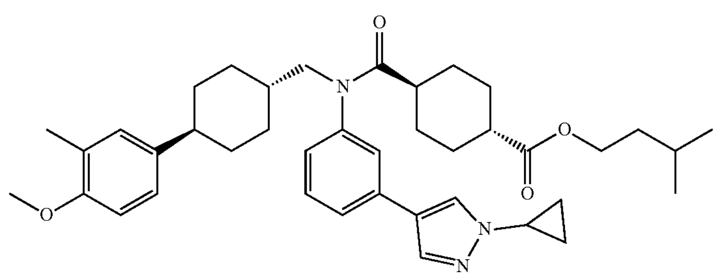 [SMILES: COc1ccc([C@H]2CC[C@H](CN(c3cccc(-c4cnn(C5CC5)c4)c3)C(=O)[C@H]3CC[C@H](C(=O)OCCC(C)C)CC3)CC2)cc1C] | trans-Isopentyl 4-((3-(1-cyclopropyl-1H-pyrazol-4-yl)phenyl)(trans-4-(4-methoxy-3-methylphenyl)cyclohexyl)methyl)carbamoyl)-cyclohexanecarboxylate |

TABLE 1-continued

| Compound No | Structure | Chemical Name |
|---|---|---|
| 22.06 | 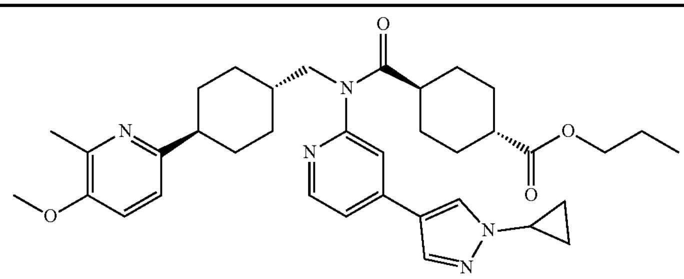 | trans-Propyl 4-((4-(1-cyclopropyl-1H-pyrazol-4-yl)pyridin-2-yl)((trans-4-(5-methoxy-6-methylpyridin-2-yl)cyclohexyl)methyl)carbamoyl)-cyclohexanecarboxylate |
| 23 | 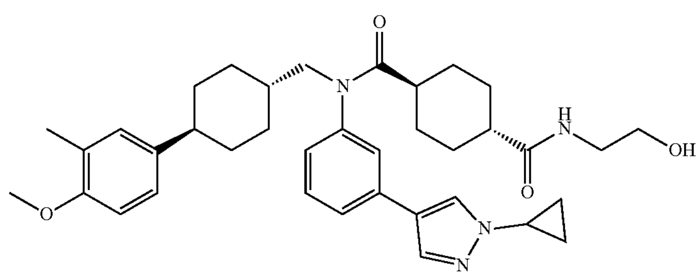 [SMILES: COc1ccc([C@H]2CC[C@H](CN(c3cccc(-c4cnn(C5CC5)c4)c3)C(=O)[C@H]3CC[C@H](C(=O)NCCO)CC3)CC2)cc1C] | trans-$N^1$-(3-(1-cyclopropyl-1H-pyrazol-4-yl)phenyl)-$N^4$-(2-hydroxyethyl)-$N^1$-((trans-4-(4-methoxy-3-methylphenyl)cyclohexyl)methyl)cyclohexane-1,4-dicarboxamide |
| 24 | 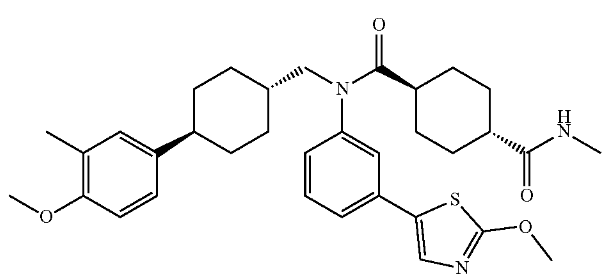 | trans-N-((trans-4-(4-Methoxy-3-methylphenyl)cyclohexyl)methyl)-$N^1$-(3-(2-methoxythiazol-5-yl)phenyl)-$N^4$-methylcyclohexane-1,4-dicarboxamide |

TABLE 1-continued

| Compound No | Structure | Chemical Name |
|---|---|---|
| 24.01 | 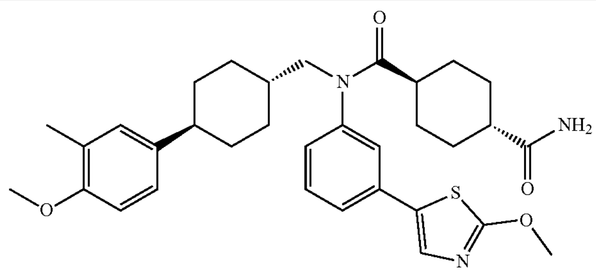 [SMILES: COc1ncc(-c2cccc(N(C[C@H]3CC[C@H](c4ccc(OC)c(C)c4)CC3)C(=O)[C@H]3CC[C@H](C(N)=O)CC3)c2)s1] | trans-N-((trans-4-(4-Methoxy-3-methylphenyl)cyclohexyl)methyl)-N¹-(3-(2-methoxythiazol-5-yl)phenyl)cyclohexane-1,4-dicarboxamide |
| 24.02 | 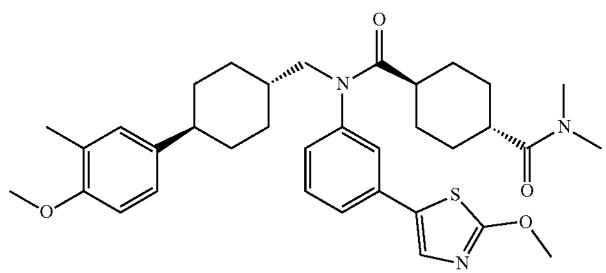 | trans-N¹-((trans-4-(4-Methoxy-3-methylphenyl)cyclohexyl)methyl)-N¹-(3-(2-methoxythiazol-5-yl)phenyl)-N⁴,N⁴-dimethylcyclohexane-1,4-dicarboxamide |
| 24.03 | 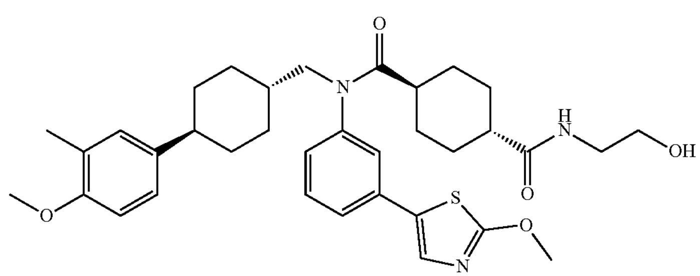 [SMILES: COc1ncc(-c2cccc(N(C[C@H]3CC[C@H](c4ccc(OC)c(C)c4)CC3)C(=O)[C@H]3CC[C@H](C(=O)NCCO)CC3)c2)s1] | trans-N¹-(2-Hydroxyethyl)-N⁴-((trans-4-(4-methoxy-3-methylphenyl)cyclohexyl)methyl)-N⁴-(3-(2-methoxythiazol-5-yl)phenyl)cyclohexane-1,4-dicarboxamide |

TABLE 1-continued

| Compound No | Structure | Chemical Name |
|---|---|---|
| 24.04 | 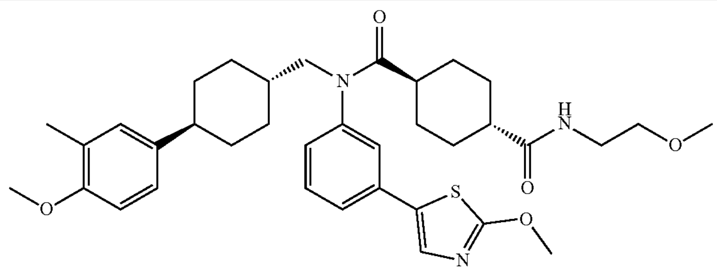 | trans-N$^1$-((trans-4-(4-Methoxy-3-methylphenyl)cyclohexyl)methyl)-N$^1$-(2-methoxyethyl)-N$^4$-(3-(2-methoxythiazol-5-yl)phenyl)cyclohexane-1,4-dicarboxamide |
| 24.05 | 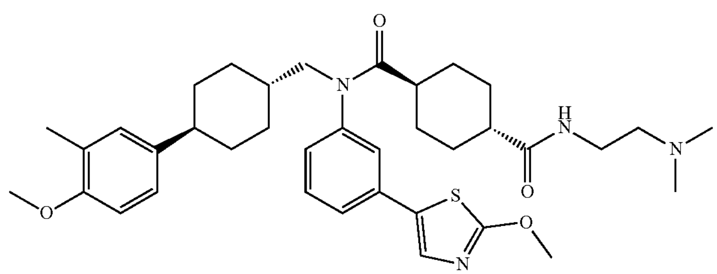 | trans-N$^1$-(2-(Dimethylamino)ethyl)-N$^1$-((trans-4-(4-methoxy-3-methylphenyl)cyclohexyl)methyl)-N$^4$-(3-(2-methoxythiazol-5-yl)phenyl)cyclohexane-1,4-dicarboxamide |
| 24.06 | 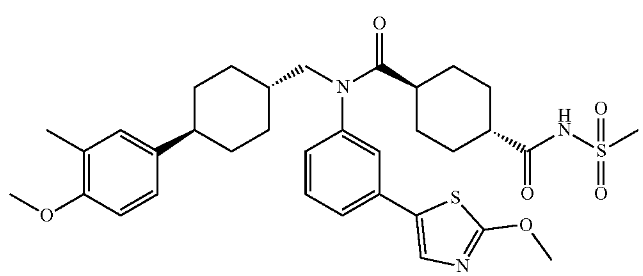 | trans-N$^1$-((trans-4-(4-Methoxy-3-methylphenyl)cyclohexyl)methyl)-N$^1$-(3-(2-methoxythiazol-5-yl)phenyl)-N$^4$-(methylsulfonyl)cyclohexane-1,4-dicarboxamide |

TABLE 1-continued

| Compound No | Structure | Chemical Name |
|---|---|---|
| 25 | 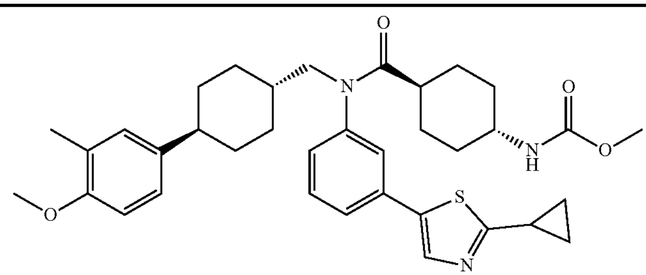 | Methyl (trans-4-((3-(2-cyclopropylthiazol-5-yl)phenyl)(trans-4-(4-methoxy-3-methylphenyl)cyclohexyl)methyl)carbamoyl)cyclohexyl)carbamate |
| 25.01 | 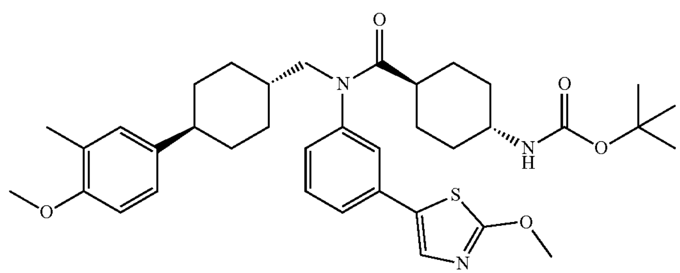 [SMILES: COc1ncc(-c2cccc(N(C[C@H]3CC[C@H](c4ccc(OC)c(C)c4)CC3)C(=O)[C@H]3CC[C@H](NC(=O)OC(C)(C)C)CC3)c2)s1] | tert-Butyl (trans-4-(((trans-4-(4-methoxy-3-methylphenyl)cyclohexyl)methyl)(3-(2-methoxythiazol-5-yl)phenyl)carbamoyl)cyclohexyl)carbamate |
| 25.02 | 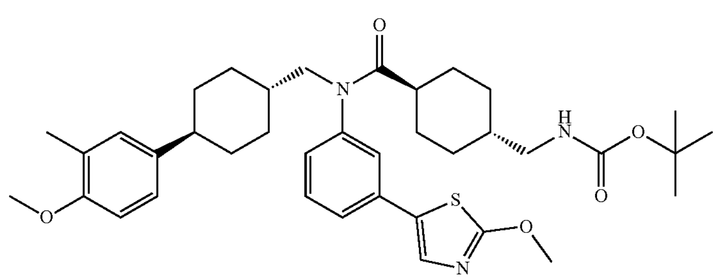 [SMILES: COc1ncc(-c2cccc(N(C[C@H]3CC[C@H](c4ccc(OC)c(C)c4)CC3)C(=O)[C@H]3CC[C@H](CNC(=O)OC(C)(C)C)CC3)c2)s1] | tert-Butyl ((trans-4-(((trans-4-(4-methoxy-3-methylphenyl)cyclohexyl)methyl)(3-(2-methoxythiazol-5-yl)phenyl)carbamoyl)cyclohexyl)methyl)carbamate |

TABLE 1-continued

| Compound No | Structure | Chemical Name |
|---|---|---|
| 25.03 | 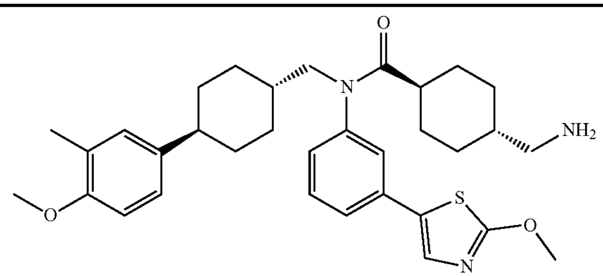 | trans-4-(Aminomethyl)-N-((trans-4-(4-methoxy-3-methylphenyl)cyclohexyl)methyl)-N-(3-(2-methoxythiazol-5-yl)phenyl)cyclohexanecarboxamide |
| 25.04 | 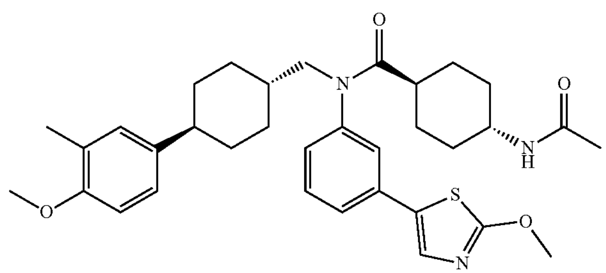 [SMILES: COc1ncc(-c2cccc(N(C[C@H]3CC[C@H](c4ccc(OC)c(C)c4)CC3)C(=O)[C@H]3CC[C@H](NC(C)=O)CC3)c2)s1] | trans-4-Acetamido-N-((trans-4-(4-methoxy-3-methylphenyl)cyclohexyl)methyl)-N-(3-(2-methoxythiazol-5-yl)phenyl)cyclohexanecarboxamide |
| 25.05 | 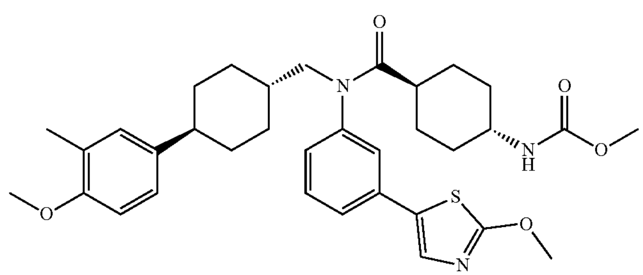 | Methyl (trans-4-(((trans-4-(4-methoxy-3-methylphenyl)cyclohexyl)methyl)(3-(2-methoxythiazol-5-yl)phenyl)carbamoyl)cyclohexyl)carbamate |

TABLE 1-continued

| Compound No | Structure | Chemical Name |
|---|---|---|
| 25.06 | 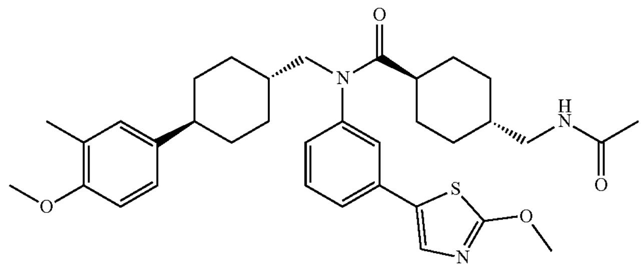 [SMILES: COc1ncc(-c2cccc(N(C[C@H]3CC[C@H](c4ccc(OC)c(C)c4)CC3)C(=O)[C@H]3CC[C@H](CNC(C)=O)CC3)c2)s1] | trans-4-(Acetamidomethyl)-N-((trans-4-(4-methoxy-3-methylphenyl)cyclohexyl)methyl)-N-(3-(2-methoxythiazol-5-yl)phenyl)cyclohexanecarboxamide |
| 25.07 | 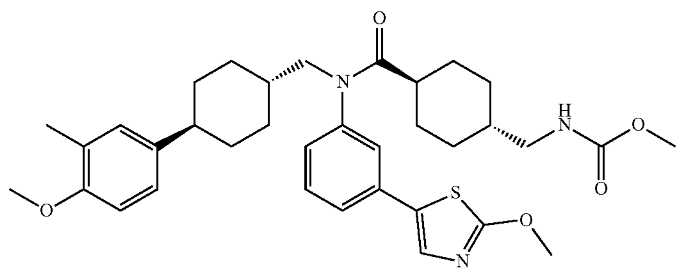 | Methyl ((trans-4-((trans-4-(4-methoxy-3-methylphenyl)cyclohexyl)methyl)(3-(2-methoxythiazol-5-yl)phenyl)carbamoyl)cyclohexyl)methyl)carbamate |
| 25.08 | 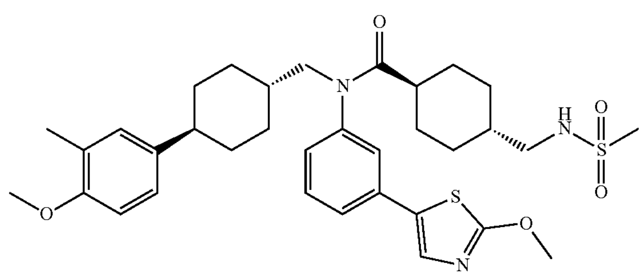 | trans-N-((trans-4-(4-Methoxy-3-methylphenyl)cyclohexyl)methyl)-N-(3-(2-methoxythiazol-5-yl)phenyl)-4-(methylsulfonamidomethyl)cyclohexanecarboxamide |

TABLE 1-continued

| Compound No | Structure | Chemical Name |
|---|---|---|
| 25.09 | 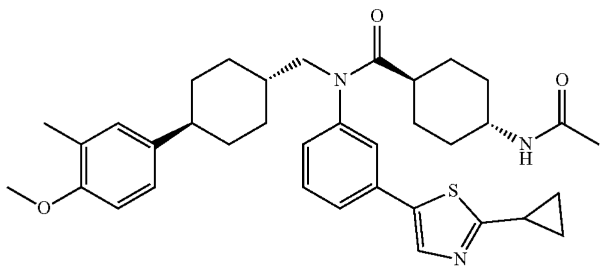 | trans-4-Acetamido-N-(3-(2-cyclopropylthiazol-5-yl)phenyl)-N-((trans-4-(4-methoxy-3-methylphenyl)cyclohexyl)methyl)-cyclohexanecarboxamide |
| 25.10 | 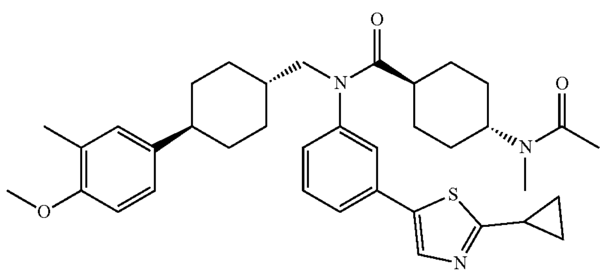 | trans-N-(3-(2-Cyclopropylthiazol-5-yl)phenyl)-N-((trans-4-(4-methoxy-3-methylphenyl)cyclohexyl)methyl)-4-(N-methylacetamido)cyclohexanecarboxamide |
| 25.11 | 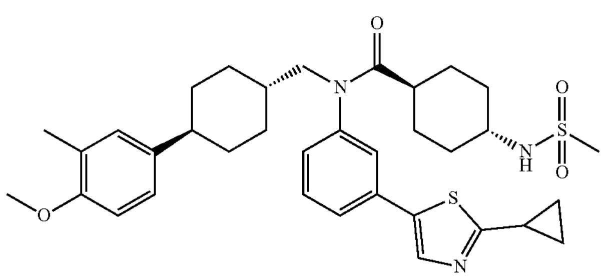 | trans-N-(3-(2-Cyclopropylthiazol-5-yl)phenyl)-N-((trans-4-(4-methoxy-3-methylphenyl)cyclohexyl)methyl)-4-(methylsulfonamido)cyclohexanecarboxamide |

TABLE 1-continued

| Compound No | Structure | Chemical Name |
|---|---|---|
| 25.12 | 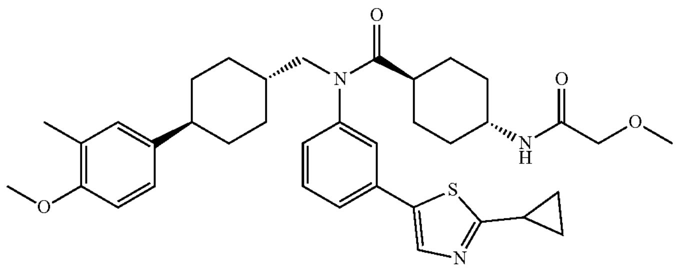 | trans-N-(3-(2-Cyclopropylthiazol-5-yl)phenyl)-N-((trans-4-(4-methoxy-3-methylphenyl)cyclohexyl)methyl)-4-(2-methoxyacetamido)cyclohexanecarboxamide |
| 25.13 | 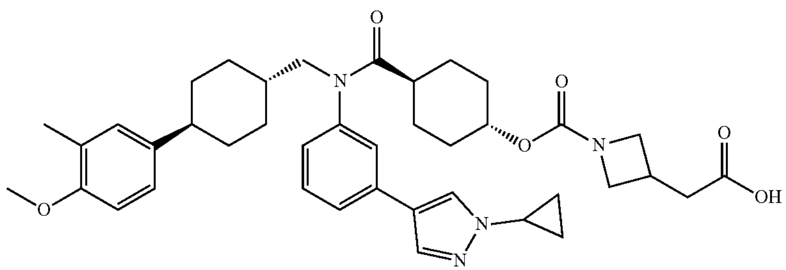 [SMILES: COc1ccc([C@H]2CC[C@H](CN(c3cccc(-c4cnn(C5CC5)c4)c3)C(=O)[C@H]3CC[C@H](OC(=O)N4CC(CC(=O)O)C4)CC3)CC2)cc1C] | 2-((trans-4-(3-(2-Cyclopropylthiazol-5-yl)phenyl)((trans-4-(4-methoxy-3-methylphenyl)cyclohexyl)methyl)carbamoyl)cyclohexyl)amino)-2-oxoethyl acetate |
| 25.14 | 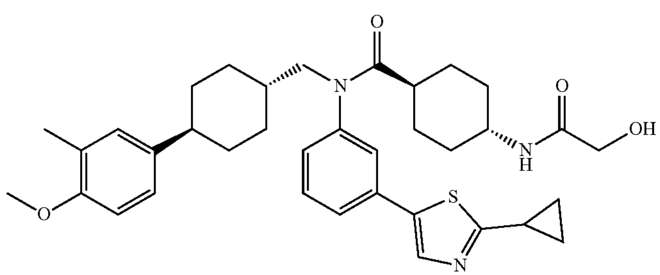 | trans-N-(3-(2-Cyclopropylthiazol-5-yl)phenyl)-4-(2-hydroxyacetamido)-N-((trans-4-(4-methoxy-3-methylphenyl)cyclohexyl)methyl)-cyclohexanecarboxamide |

TABLE 1-continued

| Compound No | Structure | Chemical Name |
|---|---|---|
| 25.15 | 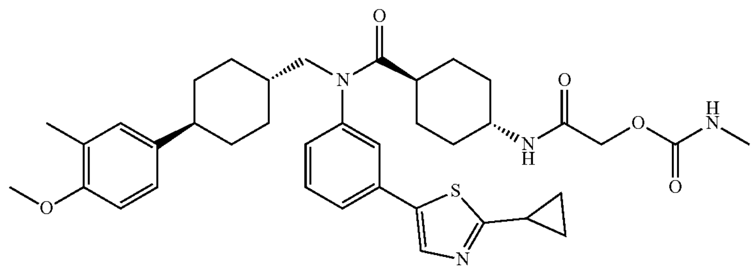 | 2-((trans-4-(3-(2-Cyclopropylthiazol-5-yl)phenyl)(trans-4-(4-methoxy-3-methylphenyl)cyclohexyl)methyl)carbamoyl)cyclohexyl)amino)-2-oxoethyl methylcarbamate |
| 25.16 | 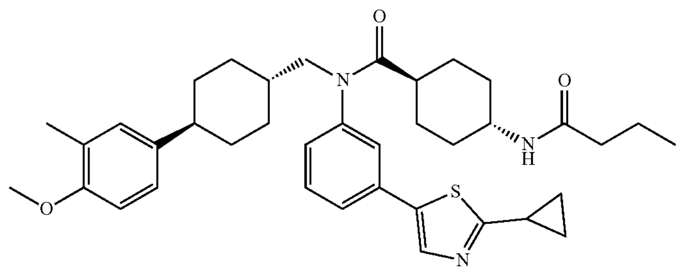 | trans-4-Butyramido-N-(3-(2-cyclopropylthiazol-5-yl)phenyl)-N-((trans-4-(4-methoxy-3-methylphenyl)cyclohexyl)methyl)cyclohexanecarboxamide |
| 25.17 | 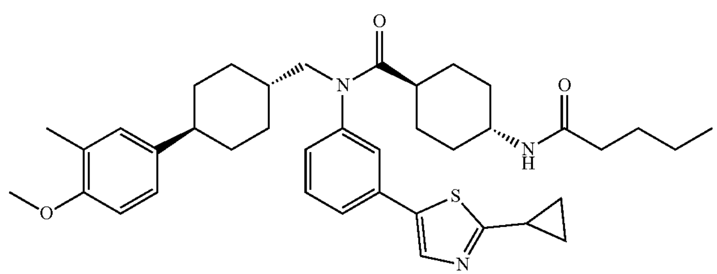 [SMILES: CCCCC(=O)N[C@H]1CC[C@H](C(=O)N(C[C@H]2CC[C@H](c3ccc(OC)c(C)c3)CC2)c2cccc(-c3cnc(C4CC4)s3)c2)CC1] | trans-N-(3-(2-Cyclopropylthiazol-5-yl)phenyl)-N-((trans-4-(4-methoxy-3-methylphenyl)cyclohexyl)methyl)-4-pentanamidocyclohexanecarboxamide |

TABLE 1-continued

| Compound No | Structure | Chemical Name |
|---|---|---|
| 25.18 | 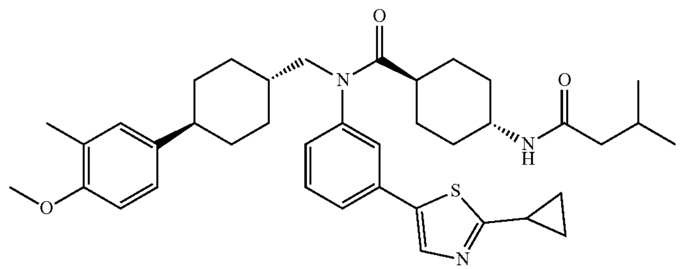 | trans-N-(3-(2-Cyclopropylthiazol-5-yl)phenyl)-N-((trans-4-(4-methoxy-3-methylphenyl)cyclohexyl)methyl)-4-(3-methylbutanamido)cyclohexanecarboxamide |
| 26 | 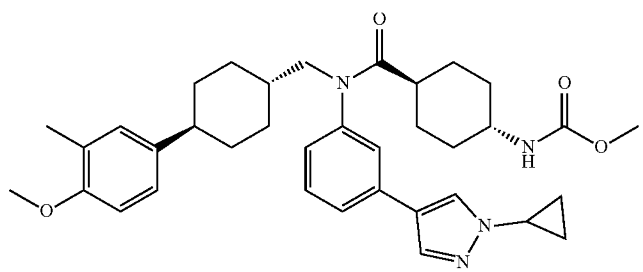 | Methyl (trans-4-((3-(1-cyclopropyl-1H-pyrazol-4-yl)phenyl)((trans-4-(4-methoxy-3-methylphenyl)cyclohexyl)methyl)carbamoyl)cyclohexyl)carbamate |
| 26.01 | 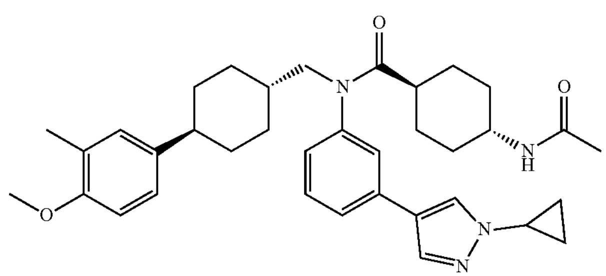 | trans-4-Acetamido-N-(3-(1-cyclopropyl-1H-pyrazol-4-yl)phenyl)-N-(trans-4-(4-methoxy-3-methylphenyl)cyclohexyl)methyl)-cyclohexanecarboxamide |

TABLE 1-continued

| Compound No | Structure | Chemical Name |
|---|---|---|
| 26.02 | 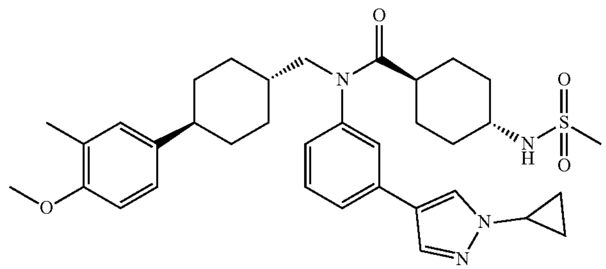 | trans-N-(3-(1-Cyclopropyl-1H-pyrazol-4-yl)phenyl)-N-((trans-4-(4-methoxy-3-methylphenyl)cyclohexyl)methyl)-4-(methylsulfonamido)cyclohexanecarboxamide |
| 26.03 | 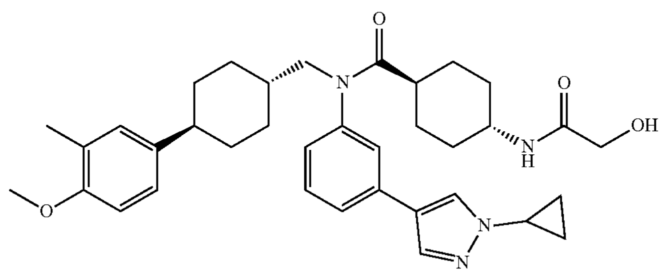 | trans-N-(3-(1-Cyclopropyl-1H-pyrazol-4-yl)phenyl)-4-(2-hydroxyacetamido)-N-((trans-4-(4-methoxy-3-methylphenyl)cyclohexyl)methyl)-cyclohexanecarboxamide |
| 26.04 | 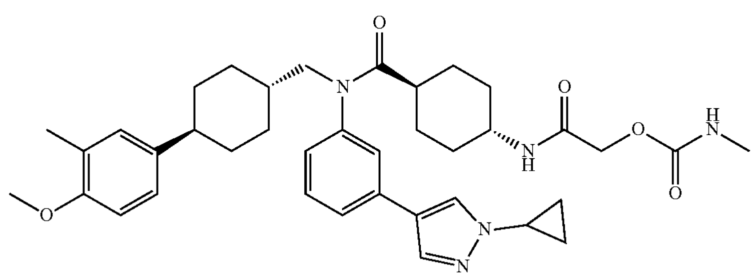 | 2-((trans-4-(3-(1-Cyclopropyl-1H-pyrazol-4-yl)phenyl)(trans-4-(4-methoxy-3-methylphenyl)cyclohexyl)methyl)carbamoyl)-cyclohexyl)amino)-2-oxoethyl methylcarbamate |

TABLE 1-continued

| Compound No | Structure | Chemical Name |
|---|---|---|
| 26.05 | 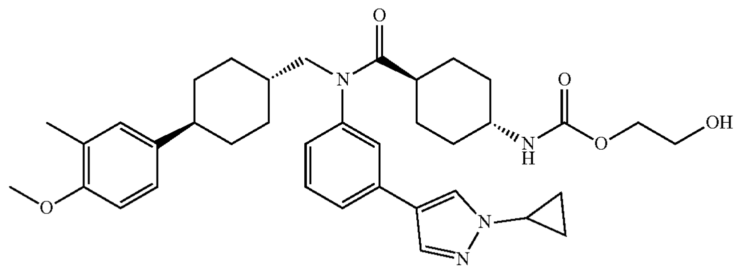 [SMILES: COc1ccc([C@H]2CC[C@H](CN(c3cccc(-c4cnn(C5CC5)c4)c3)C(=O)[C@H]3CC[C@H](NC(=O)OCCO)CC3)CC2)cc1C] | 2-Hydroxyethyl (trans-4-((3-(1-cyclopropyl-1H-pyrazol-4-yl)phenyl)((trans-4-(4-methoxy-3-methylphenyl)cyclohexyl)methyl)carbamoyl)-cyclohexyl)carbamate |
| 26.06 | 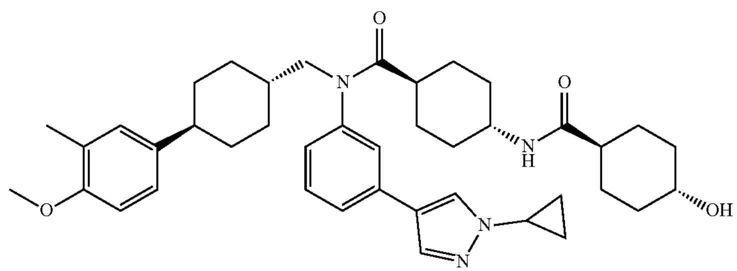 | trans-N-(3-(1-Cyclopropyl-1H-pyrazol-4-yl)phenyl)-4-(trans-4-hydroxycyclohexanecarboxamido)-N-((trans-4-(4-methoxy-3-methylphenyl)cyclohexyl)methyl)-cyclohexanecarboxamide |
| 26.07 | 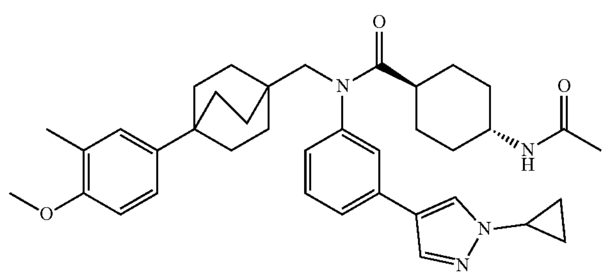 [SMILES: COc1ccc(C23CCC(CN(c4cccc(-c5cnn(C6CC6)c5)c4)C(=O)[C@H]4CC[C@H](NC(C)=O)CC4)(CC2)CC3)cc1C] | trans-4-Acetamido-N-(3-(1-cyclopropyl-1H-pyrazol-4-yl)phenyl)-N-((4-(4-methoxy-3-methylphenyl)bicyclo[2.2.2]octan-1-yl)methyl)cyclohexanecarboxamide |

TABLE 1-continued

| Compound No | Structure | Chemical Name |
|---|---|---|
| 26.08 | 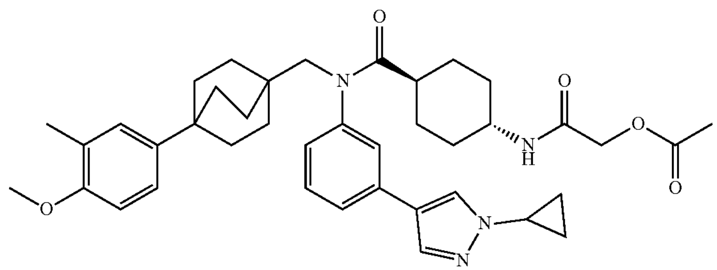 [SMILES: COc1ccc(C23CCC(CN(c4cccc(-c5cnn(C6CC6)c5)c4)C(=O)[C@H]4CC[C@H](NC(=O)COC(C)=O)CC4)(CC2)CC3)cc1C] | 2-((4-((3-(1-Cyclopropyl-1H-pyrazol-4-yl)phenyl)(4-(4-methoxy-3-methylphenyl)bicyclo[2.2.2]octan-1-yl)methyl)carbamoyl)cyclohexyl)amino)-2-oxoethyl trans-acetate |
| 26.09 | 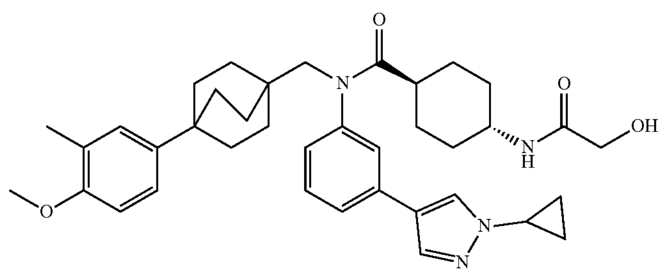 [SMILES: COc1ccc(C23CCC(CN(c4cccc(-c5cnn(C6CC6)c5)c4)C(=O)[C@H]4CC[C@H](NC(=O)CO)CC4)(CC2)CC3)cc1C] | trans-N-(3-(1-Cyclopropyl-1H-pyrazol-4-yl)phenyl)-4-(2-hydroxyacetamido)-N-((4-(4-methoxy-3-methylphenyl)bicyclo[2.2.2]octan-1-yl)methyl)cyclohexanecarboxamide |
| 26.10 | 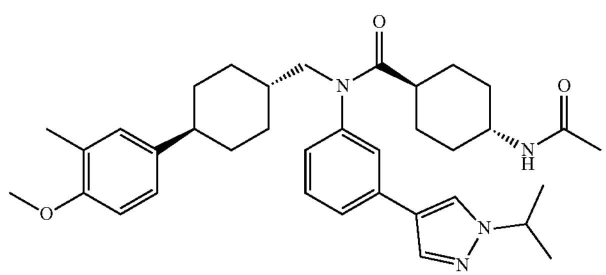 | trans-4-Acetamido-N-(3-(1-isopropyl-1H-pyrazol-4-yl)phenyl)-N-((trans-4-(4-methoxy-3-methylphenyl)cyclohexyl)methyl)-cyclohexanecarboxamide |

TABLE 1-continued

| Compound No | Structure | Chemical Name |
|---|---|---|
| 26.11 | 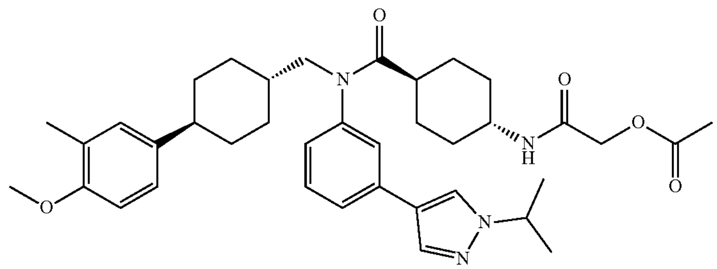 | 2-((trans-4-((3-(1-Isopropyl-1H-pyrazol-4-yl)phenyl)(trans-4-(4-methoxy-3-methylphenyl)cyclohexyl)methyl)carbamoyl)cyclohexyl)amino)-2-oxoethyl acetate |
| 26.12 | 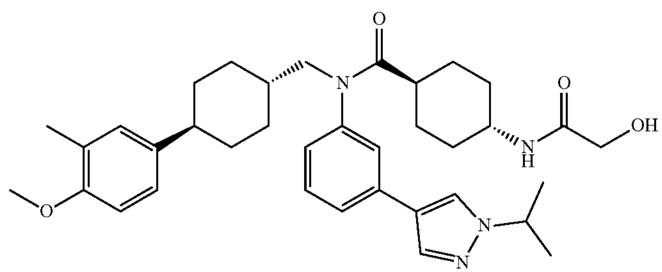 | trans-4-(2-Hydroxyacetamido)-N-(3-(1-isopropyl-1H-pyrazol-4-yl)phenyl)-N-((trans-4-(4-methoxy-3-methylphenyl)cyclohexyl)methyl)cyclohexanecarboxamide |
| 26.13 | 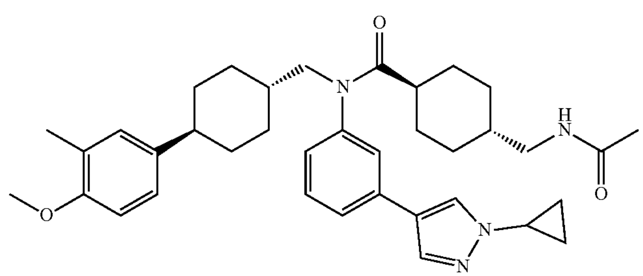 [SMILES: COc1ccc([C@H]2CC[C@H](CN(c3cccc(-c4cnn(C5CC5)c4)c3)C(=O)[C@H]3CC[C@H](CNC(C)=O)CC3)CC2)cc1C] | trans-4-(Acetamidomethyl)-N-(3-(1-cyclopropyl-1H-pyrazol-4-yl)phenyl)-N-((trans-4-(4-methoxy-3-methylphenyl)cyclohexyl)methyl)cyclohexanecarboxamide |

TABLE 1-continued

| Compound No | Structure | Chemical Name |
|---|---|---|
| 26.14 | 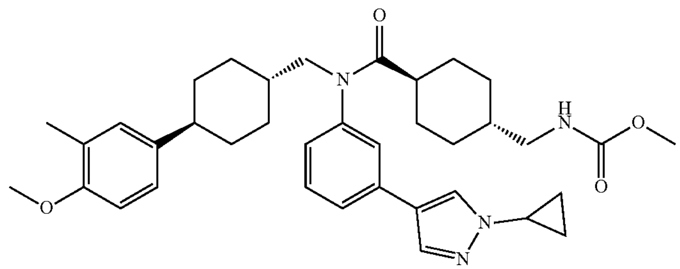 | Methyl ((trans-4-((3-(1-cyclopropyl-1H-pyrazol-4-yl)phenyl)(trans-4-(4-methoxy-3-methylphenyl)cyclohexyl)methyl)carbamoyl)cyclohexyl)methyl)carbamate |
| 26.15 | 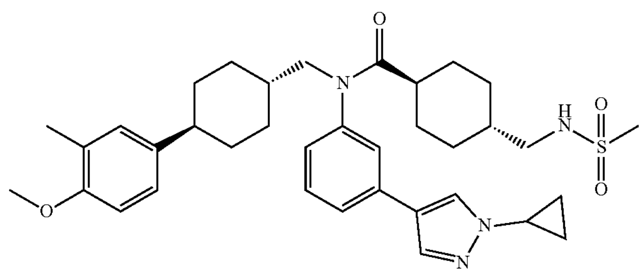 | trans-N-(3-(1-Cyclopropyl-1H-pyrazol-4-yl)phenyl)-N-((trans-4-(4-methoxy-3-methylphenyl)cyclohexyl)methyl)-4-(methylsulfonamidomethyl)cyclohexanecarboxamide |
| 26.16 | 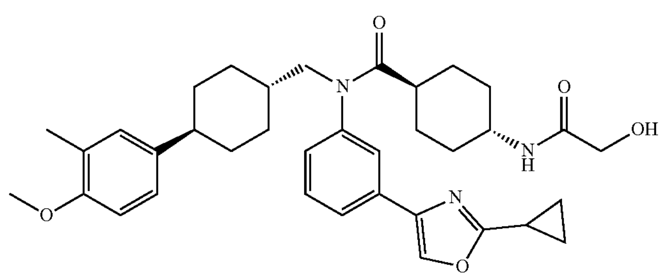 [SMILES: COc1ccc([C@H]2CC[C@H](CN(c3cccc(-c4coc(C5CC5)n4)c3)C(=O)[C@H]3CC[C@H](NC(=O)CO)CC3)CC2)cc1C] | trans-N-(3-(2-Cyclopropyloxazol-4-yl)phenyl)-4-(2-hydroxyacetamido)-N-((trans-4-(4-methoxy-3-methylphenyl)cyclohexyl)methyl)cyclohexanecarboxamide |

TABLE 1-continued

| Compound No | Structure | Chemical Name |
|---|---|---|
| 26.17 | 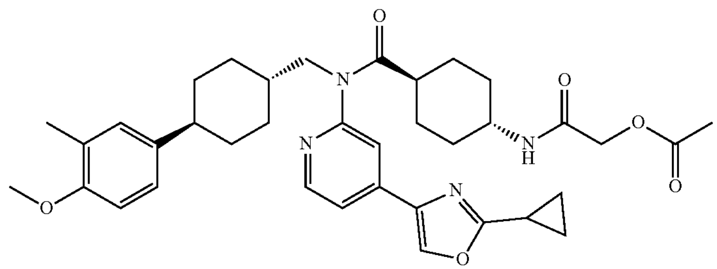 [SMILES: COc1ccc([C@H]2CC[C@H](CN(c3cc(-c4coc(C5CC5)n4)ccn3)C(=O)[C@H]3CC[C@H](NC(=O)COC(C)=O)CC3)CC2)cc1C] | 2-((trans-4-((4-(2-cyclopropyloxazol-4-yl)pyridine-2-yl)(trans-4-(4-methoxy-3-methylphenyl)cyclohexyl)methyl)carbamoyl)-cyclohexyl)amino)-2-oxoethyl acetate |
| 26.18 | 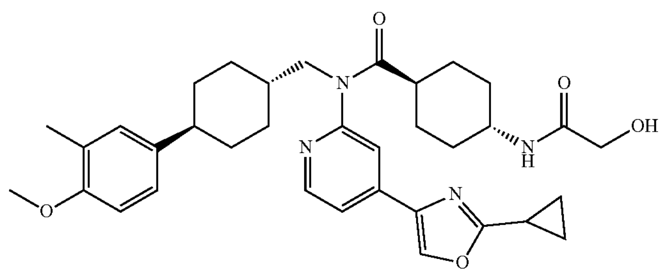 [SMILES: COc1ccc([C@H]2CC[C@H](CN(c3cc(-c4coc(C5CC5)n4)ccn3)C(=O)[C@H]3CC[C@H](NC(=O)CO)CC3)CC2)cc1C] | trans-N-(4-(2-Cyclopropyloxazol-4-yl)pyridin-2-yl)-4-(2-hydroxyacetamido)-N-((trans-4-(4-methoxy-3-methylphenyl)cyclohexyl)methyl)-cyclohexanecarboxamide |
| 26.19 | 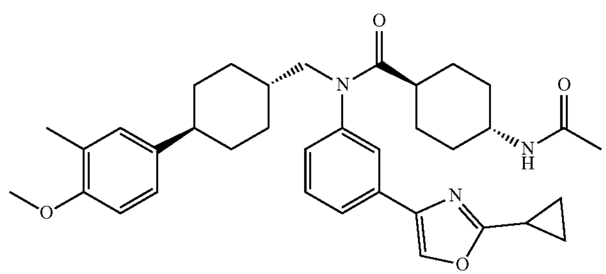 [SMILES: COc1ccc([C@H]2CC[C@H](CN(c3cccc(-c4coc(C5CC5)n4)c3)C(=O)[C@H]3CC[C@H](NC(C)=O)CC3)CC2)cc1C] | trans-4-Acetamido-N-(3-(2-cyclopropyloxazol-4-yl)phenyl)-N-((trans-4-(4-methoxy-3-methylphenyl)cyclohexyl)methyl)-cyclohexanecarboxamide |

TABLE 1-continued

| Compound No | Structure | Chemical Name |
|---|---|---|
| 26.20 | 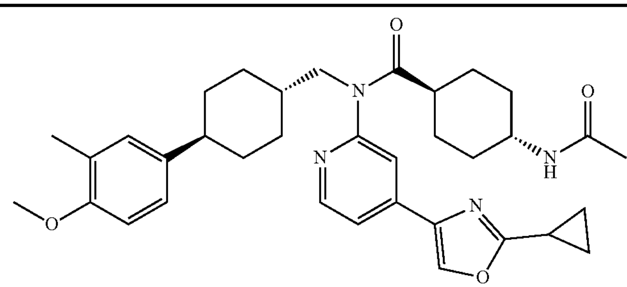 | trans-4-Acetamido-N-(4-(2-cyclopropyloxazol-4-yl)pyridine-2-yl)-N-((trans-4-(4-methoxy-3-methylphenyl)cyclohexyl)methyl)-cyclohexanecarboxamide |
| 26.21 | 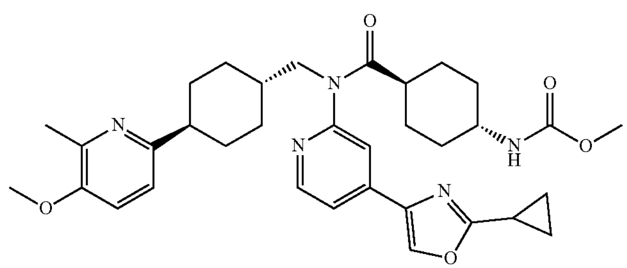 | Methyl (trans-4-((4-(2-cyclopropyloxazol-4-yl)pyridine-2-yl)((trans-4-(5-methoxy-6-methylpyridin-2-yl)cyclohexyl)methyl)carbamoyl)cyclohexyl)-carbamate |
| 26.22 | 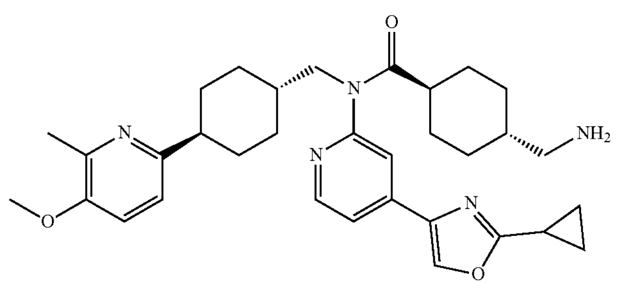 [SMILES: COc1ccc([C@H]2CC[C@H](CN(c3cc(-c4coc(C5CC5)n4)ccn3)C(=O)[C@H]3CC[C@H](CN)CC3)CC2)nc1C] | trans-4-(Aminomethyl)-N-(4-(2-cyclopropyloxazol-4-yl)pyridin-2-yl)-N-((trans-4-(5-methoxy-6-methylpyridin-2-yl)cyclohexyl)methyl)cyclohexanecarboxamide |

TABLE 1-continued

| Compound No | Structure | Chemical Name |
|---|---|---|
| 26.23 | 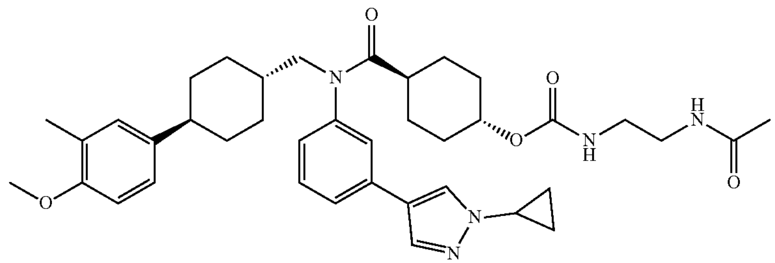 [SMILES: COc1ccc([C@H]2CC[C@H](CN(c3cccc(-c4cnn(C5CC5)c4)c3)C(=O)[C@H]3CC[C@H](OC(=O)NCCNC(C)=O)CC3)CC2)cc1C] | trans-N-((3-(1-Cyclopropyl-1H-pyrazol-4-yl)phenyl)(trans-4-(4-methoxy-3-methylphenyl)cyclohexyl)methyl)carbamoyl)-cyclohexyl (2-acetamidoethyl)carbamate |
| 26.24 | 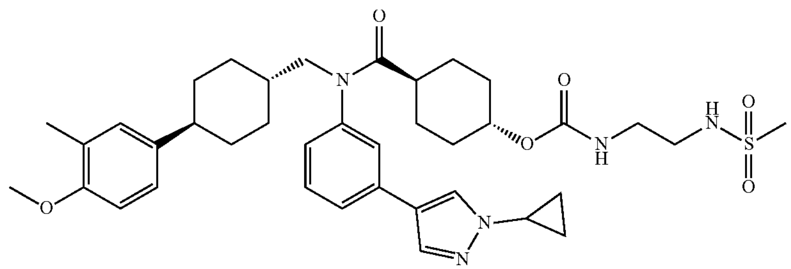 | trans-4-((3-(1-Cyclopropyl-1H-pyrazol-4-yl)phenyl)(trans-4-(4-methoxy-3-methylphenyl)cyclohexyl)methyl)carbamoyl)-cyclohexyl (2-(methylsulfonamido)ethyl)carbamate |
| 26.25 | 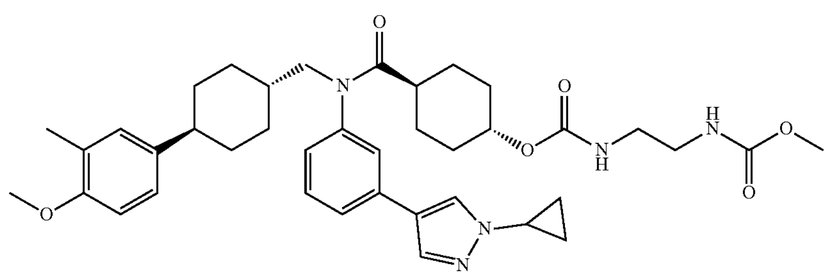 | trans-4-(3-(1-Cyclopropyl-1H-pyrazol-4-yl)phenyl)(trans-4-(4-methoxy-3-methylphenyl)cyclohexyl)methyl)carbamoyl)-cyclohexyl methyl ethane-1,2-diyldicarbamate |

TABLE 1-continued

| Compound No | Structure | Chemical Name |
|---|---|---|
| 26.26 | 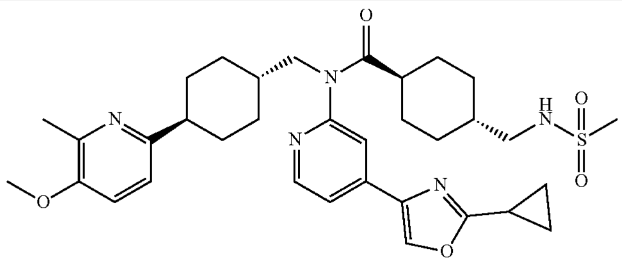 | trans-N-(4-(2-Cyclopropyloxazol-4-yl)pyridin-2-yl)-N-((trans-4-(5-methoxy-6-methylpyridin-2-yl)cyclohexyl)methyl)-4-(methylsulfonamidomethyl)cyclohexanecarboxamide |
| 26.27 | 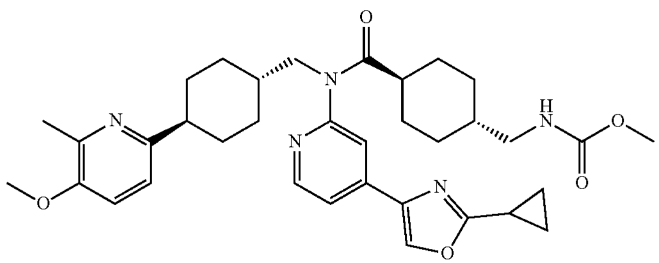 | Methyl ((trans-4-((4-(2-cyclopropyloxazol-4-yl)pyridin-2-yl)((trans-4-(5-methoxy-6-methylpyridin-2-yl)cyclohexyl)methyl)carbamoyl)cyclohexyl)methyl)carbamate |
| 26.28 | 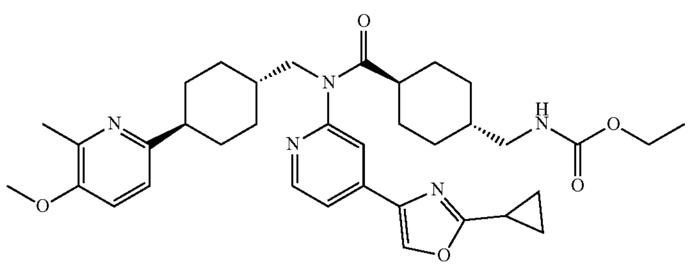 [SMILES: CCOC(=O)NC[C@H]1CC[C@H](C(=O)N(C[C@H]2CC[C@H](c3ccc(OC)c(C)n3)CC2)c2cc(-c3coc(C4CC4)n3)ccn2)CC1] | Ethyl ((trans-4-((4-(2-cyclopropyloxazol-4-yl)pyridin-2-yl)((trans-4-(5-methoxy-6-methylpyridin-2-yl)cyclohexyl)methyl)carbamoyl)cyclohexyl)methyl)carbamate |
| 26.29 | 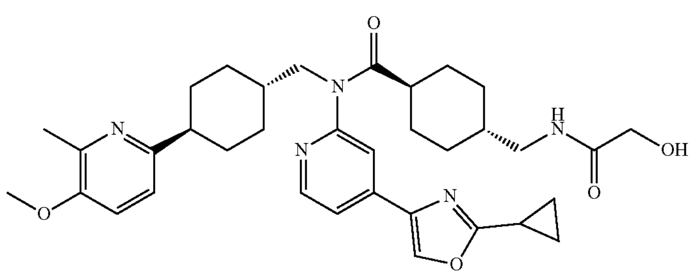 [SMILES: COc1ccc([C@H]2CC[C@H](CN(c3cc(-c4coc(C5CC5)n4)ccn3)C(=O)[C@H]3CC[C@H](CNC(=O)CO)CC3)CC2)nc1C] | trans-N-(4-(2-Cyclopropyloxazol-4-yl)pyridin-2-yl)-4-((2-hydroxyacetamido)methyl)-N-((trans-4-(5-methoxy-6-methylpyridin-2-yl)cyclohexyl)methyl)cyclohexanecarboxamide |

TABLE 1-continued

| Compound No | Structure | Chemical Name |
|---|---|---|
| 26.30 | 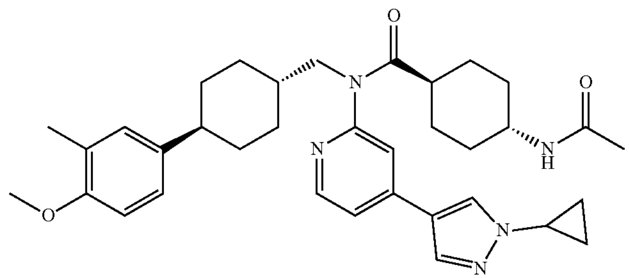 [SMILES: COc1ccc([C@H]2CC[C@H](CN(c3cc(-c4cnn(C5CC5)c4)ccn3)C(=O)[C@H]3CC[C@H](NC(C)=O)CC3)CC2)cc1C] | trans-4-Acetimido-N-(4-(1-cyclopropyl-1H-pyrazol-4-yl)pyridin-2-yl)-N-((trans-4-(4-methoxy-3-methylphenyl)cyclohexyl)methyl)-cyclohexanecarboxamide |
| 26.31 | 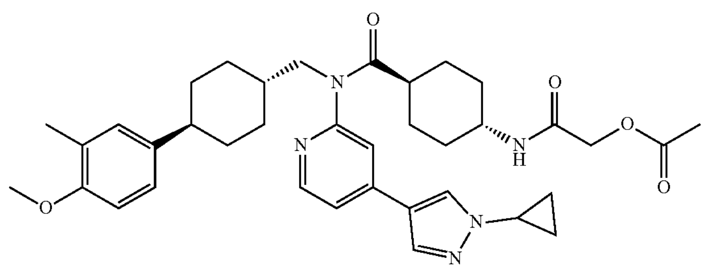 [SMILES: COc1ccc([C@H]2CC[C@H](CN(c3cc(-c4cnn(C5CC5)c4)ccn3)C(=O)[C@H]3CC[C@H](NC(=O)COC(C)=O)CC3)CC2)cc1C] | 2-((trans-4-((4-(1-Cyclopropyl-1H-pyrazol-4-yl)pyridin-2-yl)((trans-4-(4-methoxy-3-methylphenyl)cyclohexyl)methyl)carbamoyl)-cyclohexyl)amino)-2-oxoethyl acetate |
| 26.32 | 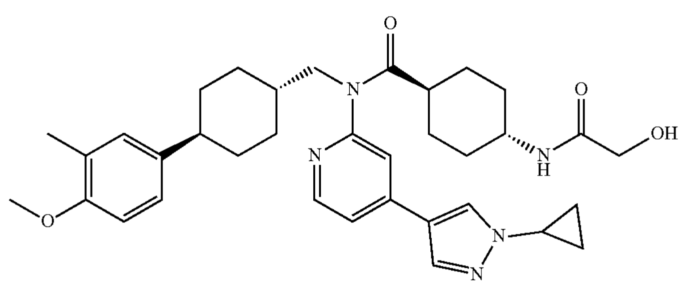 [SMILES: COc1ccc([C@H]2CC[C@H](CN(c3cc(-c4cnn(C5CC5)c4)ccn3)C(=O)[C@H]3CC[C@H](NC(=O)CO)CC3)CC2)cc1C] | trans-N-(4-(1-Cyclopropyl-1H-pyrazol-4-yl)pyridin-2-yl)-4-(2-hydroxyacetamido)-N-((trans-4-(4-methoxy-3-methylphenyl)cyclohexyl)methyl)-cyclohexanecarboxamide |

| Compound No | Structure | Chemical Name |
|---|---|---|
| 26.33 | 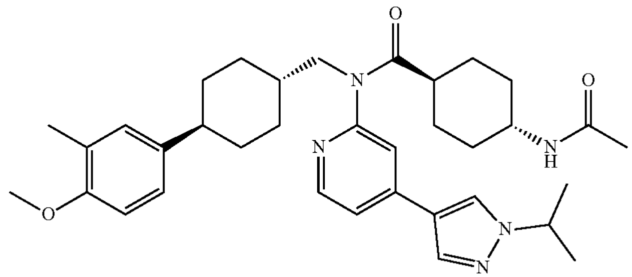 [SMILES: COc1ccc([C@H]2CC[C@H](CN(c3cc(-c4cnn(C(C)C)c4)ccn3)C(=O)[C@H]3CC[C@H](NC(C)=O)CC3)CC2)cc1C] | trans-4-Acetamido-N-(4-(1-isopropyl-1H-pyrazol-yl)pyridin-2-yl)-N-((trans-4-(4-methoxy-3-methylphenyl)cyclohexyl)methyl)-cyclohexanecarboxamide |
| 26.34 | 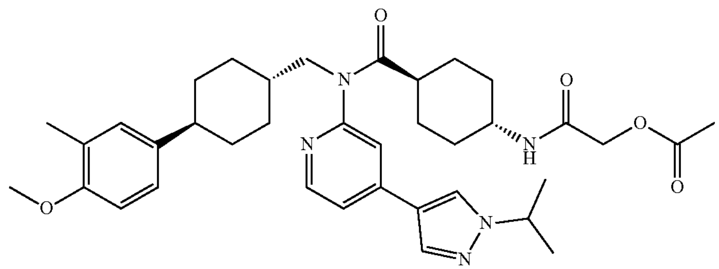 [SMILES: COc1ccc([C@H]2CC[C@H](CN(c3cc(-c4cnn(C(C)C)c4)ccn3)C(=O)[C@H]3CC[C@H](NC(=O)COC(C)=O)CC3)CC2)cc1C] | 2-((trans-4-((4-(1-Isopropyl-1H-pyrazol-4-yl)pyridin-2-yl)((trans-4-(4-methoxy-3-methylphenyl)cyclohexyl)methyl)carbamoyl)-cyclohexyl)amino)-2-oxoethyl acetate |
| 26.35 | 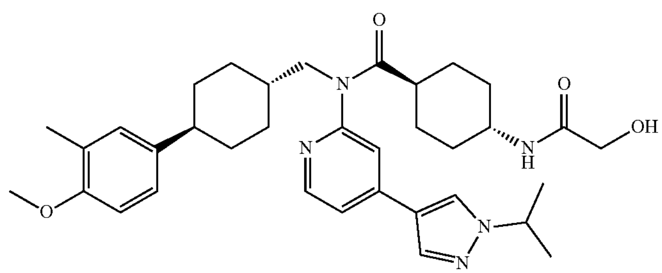 [SMILES: COc1ccc([C@H]2CC[C@H](CN(c3cc(-c4cnn(C(C)C)c4)ccn3)C(=O)[C@H]3CC[C@H](NC(=O)CO)CC3)CC2)cc1C] | trans-4-(2-Hydroxyacetamido)-N-(4-(1-isopropyl-1H-pyrazol-4-yl)pyridin-2-yl)-N-((trans-4-(4-methoxy-3-methylphenyl)cyclohexyl)methyl)-cyclohexanecarboxamide |

TABLE 1-continued

| Compound No | Structure | Chemical Name |
|---|---|---|
| 26.36 | 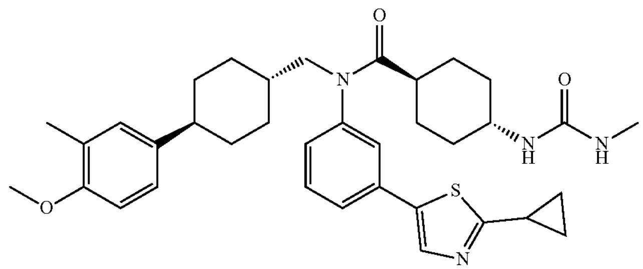 | trans-N-(3-(2-Cyclopropylthiazol-5-yl)phenyl)-N-((trans-4-(4-methoxy-3-methylphenyl)cyclohexyl)methyl)-4-(3-methylureido)cyclohexanecarboxamide |
| 26.37 | 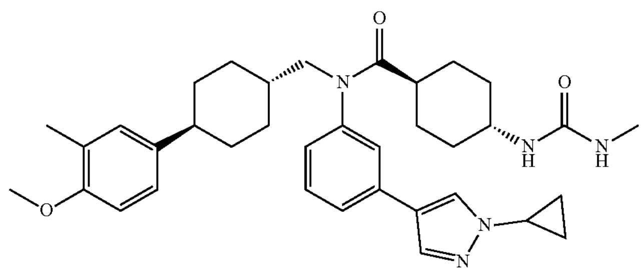 | trans-N-(3-(1-Cyclopropyl-1H-pyrazol-4-yl)phenyl)-N-((trans-4-(4-methoxy-3-methylphenyl)cyclohexyl)methyl)-4-(3-methylureido)cyclohexanecarboxamide |
| 27 | 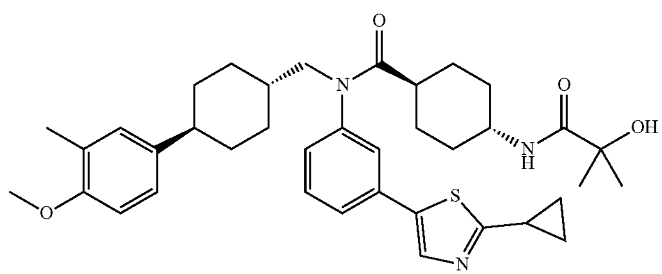 [SMILES: COc1ccc([C@H]2CC[C@H](CN(c3cccc(-c4cnc(C5CC5)s4)c3)C(=O)[C@H]3CC[C@H](NC(=O)C(C)(C)O)CC3)CC2)cc1C] | trans-N-(3-(2-Cyclopropylthiazol-5-yl)phenyl)-4-(2-hydroxy-2-methylpropanamido)-N-((trans-4-(4-methoxy-3-methylphenyl)cyclohexyl)methyl)-cyclohexanecarboxamide |

TABLE 1-continued

| Compound No | Structure | Chemical Name |
|---|---|---|
| 27.01 | 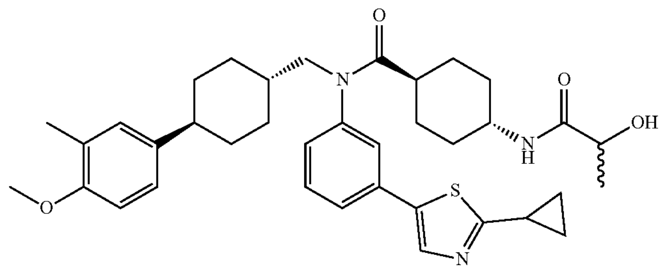 [SMILES: COc1ccc([C@H]2CC[C@H](CN(c3cccc(-c4cnc(C5CC5)s4)c3)C(=O)[C@H]3CC[C@H](NC(=O)C(C)O)CC3)CC2)cc1C] | trans-N-(3-(2-Cyclopropylthiazol-5-yl)phenyl)-4-(2-hydroxypropanamido)-N-((trans-4-(4-methoxy-3-methylphenyl)cyclohexyl)methyl)-cyclohexanecarboxamide |
| 27.02 | 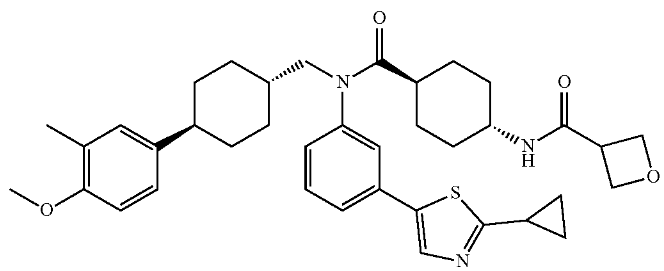 [SMILES: COc1ccc([C@H]2CC[C@H](CN(c3cccc(-c4cnc(C5CC5)s4)c3)C(=O)[C@H]3CC[C@H](NC(=O)C4COC4)CC3)CC2)cc1C] | N-(trans-4-((3-(2-Cyclopropylthiazol-5-yl)phenyl)(trans-4-(4-methoxy-3-methylphenyl)cyclohexyl)methylcarbamoyl)-cyclohexyl)methyl)oxetane-3-carboxamide |
| 27.03 | 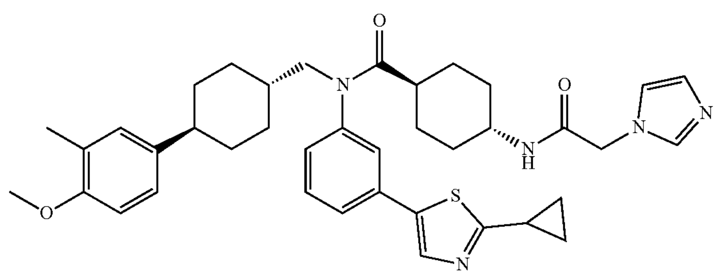 [SMILES: COc1ccc([C@H]2CC[C@H](CN(c3cccc(-c4cnc(C5CC5)s4)c3)C(=O)[C@H]3CC[C@H](NC(=O)Cn4ccnc4)CC3)CC2)cc1C] | trans-4-(2-(1H-Imidazol-1-yl)acetamido)-N-(3-(2-cyclopropylthiazol-5-yl)phenyl)-N-((trans-4-(4-methoxy-3-methylphenyl)cyclohexyl)methyl)-cyclohexanecarboxamide |

TABLE 1-continued

| Compound No | Structure | Chemical Name |
|---|---|---|
| 27.04 | 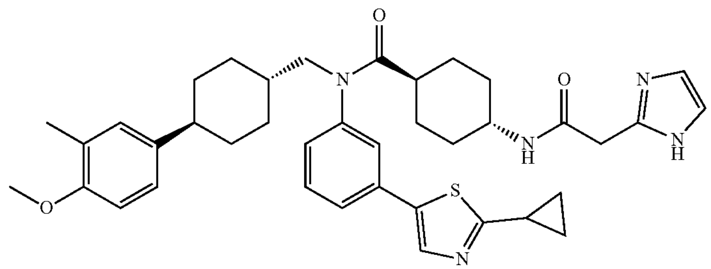 [SMILES: COc1ccc([C@H]2CC[C@H](CN(c3cccc(-c4cnc(C5CC5)s4)c3)C(=O)[C@H]3CC[C@H](NC(=O)Cc4ncc[nH]4)CC3)CC2)cc1C] | trans-4-(2-(1H-Imidazol-2-yl)acetamido)-N-(3-(2-cyclopropylthiazol-5-yl)phenyl)-N-((trans-4-(4-methoxy-3-methylphenyl)cyclohexyl)methyl)cyclohexanecarboxamide |
| 27.05 | 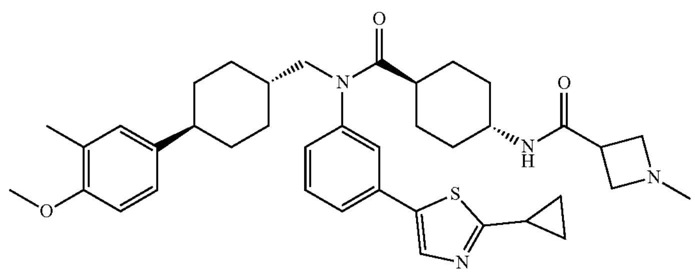 | N-(trans-4-((3-(2-Cyclopropylthiazol-5-yl)phenyl)(trans-4-(4-methoxy-3-methylphenyl)cyclohexyl)methylcarbamoyl)cyclohexyl)-1-methylazetidine-3-carboxamide |
| 27.06 | 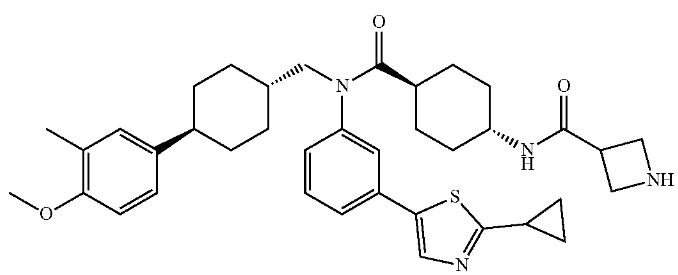 [SMILES: COc1ccc([C@H]2CC[C@H](CN(c3cccc(-c4cnc(C5CC5)s4)c3)C(=O)[C@H]3CC[C@H](NC(=O)C4CNC4)CC3)CC2)cc1C] | N-(trans-4-((3-(2-Cyclopropylthiazol-5-yl)phenyl)(trans-4-(4-methoxy-3-methylphenyl)cyclohexyl)methylcarbamoyl)cyclohexyl)azetidine-3-carboxamide |

TABLE 1-continued

| Compound No | Structure | Chemical Name |
|---|---|---|
| 28 | 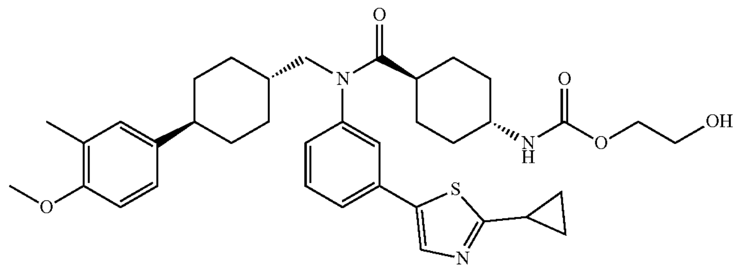 [SMILES: COc1ccc([C@H]2CC[C@H](CN(c3cccc(-c4cnc(C5CC5)s4)c3)C(=O)[C@H]3CC[C@H](NC(=O)OCCO)CC3)CC2)cc1C] | 2-Hydroxyethyl (trans-4-((3-(2-cyclopropylthiazol-5-yl)phenyl)((trans-4-(4-methoxy-3-methylphenyl)cyclohexyl)methyl)carbamoyl)cyclohexyl)carbamate |
| 29 | 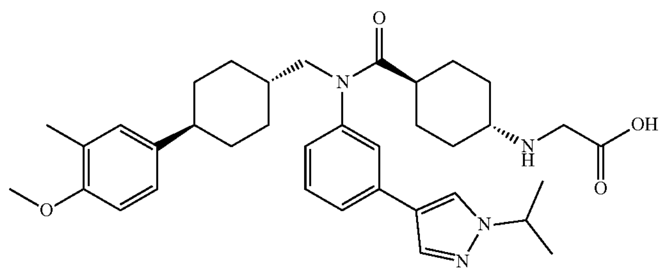 [SMILES: COc1ccc([C@H]2CC[C@H](CN(c3cccc(-c4cnn(C(C)C)c4)c3)C(=O)[C@H]3CC[C@H](NCC(=O)O)CC3)CC2)cc1C] | 2-((trans-4-((3-(1-Isopropyl-1H-pyrazol-4-yl)phenyl)((trans-4-(4-methoxy-3-methylphenyl)cyclohexyl)methyl)carbamoyl)cyclohexyl)amino)acetic acid |
| 30 | 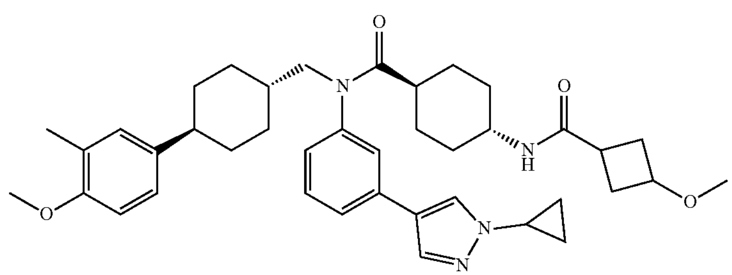 | trans-N-(3-(1-Cyclopropyl-1H-pyrazol-4-yl)phenyl)-N-((trans-4-(4-methoxy-3-methylphenyl)cyclohexyl)methyl)-4-(3-methoxycyclobutanecarboxamido)-cyclohexanecarboxamide |

TABLE 1-continued

| Compound No | Structure | Chemical Name |
|---|---|---|
| 30.01 | 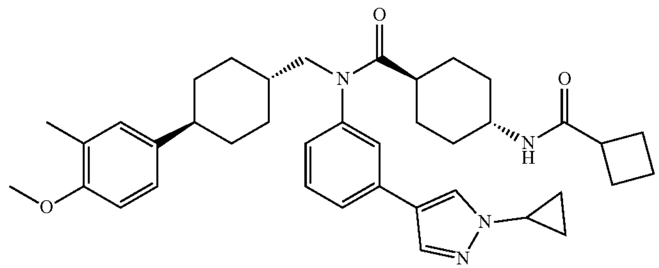 | trans-4-(Cyclobutanecarboxamido)-N-(3-(1-cyclopropyl-2H-pyrazol-4-yl)phenyl)-N-((trans-4-(4-methoxy-3-methylphenyl)cyclohexyl)methyl)-cyclohexanecarboxamide |
| 30.02 | 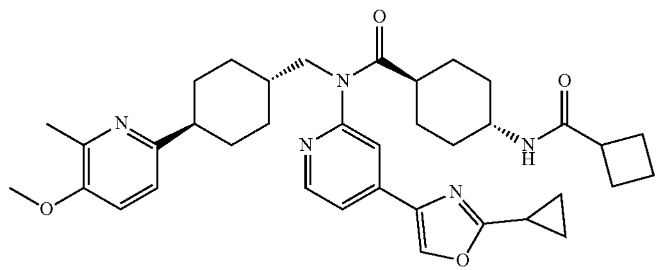 [SMILES: COc1ccc([C@H]2CC[C@H](CN(c3cc(-c4coc(C5CC5)n4)ccn3)C(=O)[C@H]3CC[C@H](NC(=O)C4CCC4)CC3)CC2)nc1C] | trans-4-(cyclobutanecarboxamido)-trans-(4-(2-cyclopropyloxazol-4-yl)pyridine-2-yl)-N-((trans-4-(5-methoxy-6-methylpyridin-2-yl)cyclohexyl)methyl)cyclohexanecarboxamide |
| 30.03 | 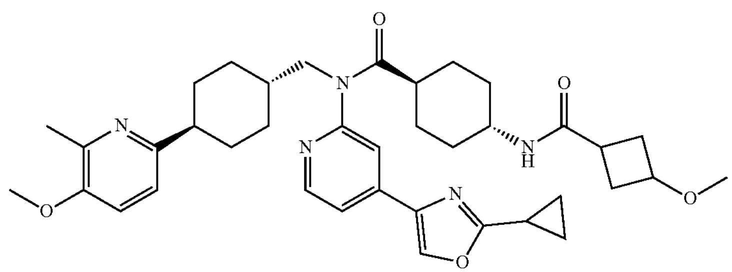 | trans-N-(4-(2-Cyclopropyloxazol-4-yl)pyridin-2-yl)-N-((trans-4-(5-methoxy-6-methylpyridin-2-yl)cyclohexyl)methyl)-4-(3-methoxycyclobutanecarboxamido)-cyclohexanecarboxamide |

TABLE 1-continued

| Compound No | Structure | Chemical Name |
|---|---|---|
| 30.04 | 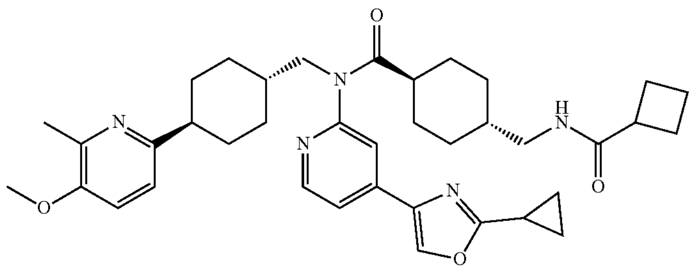 [SMILES: COc1ccc([C@H]2CC[C@H](CN(c3cc(-c4coc(C5CC5)n4)ccn3)C(=O)[C@H]3CC[C@H](CNC(=O)C4CCC4)CC3)CC2)nc1C] | trans-4-(Cyclobutanecarboxamidomethyl)-N-(4-(2-cyclopropyloxazol-4-yl)pyridin-2-yl)-N-((trans-4-(5-methoxy-6-methylpyridin-2-yl)cyclohexyl)methyl)cyclohexanecarboxamide |
| 30.05 | 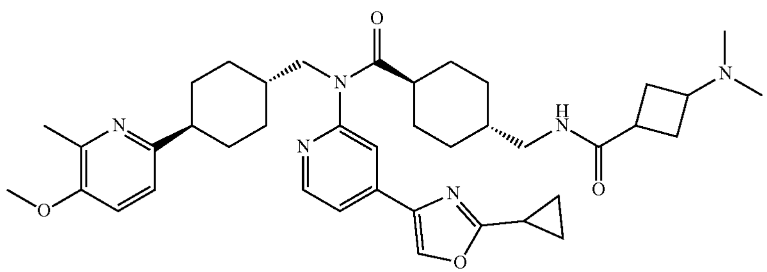 | trans-N-(4-(2-Cyclopropyloxazol-4-yl)pyridin-2-yl)-4-((3-(dimethylamino)cyclobutanecarboxamido)methyl)-N-((trans-4-(5-methoxy-6-methylpyridin-2-yl)cyclohexyl)methyl)cyclohexanecarboxamide |
| 30.06 | 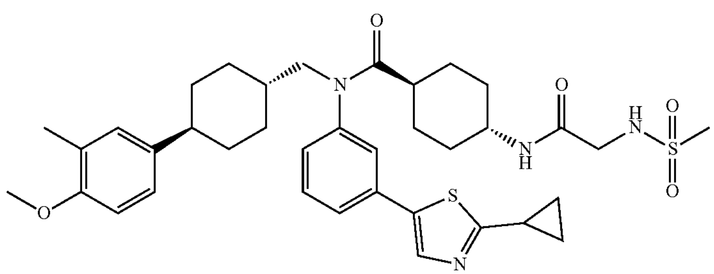 | trans-N-(3-(2-Cyclopropylthiazol-5-yl)phenyl)-N-((trans-4-(4-methoxy-3-methylphenyl)cyclohexyl)methyl)-4-(2-(methylsulfonamido)acetamido)cyclohexanecarboxamide |

TABLE 1-continued

| Compound No | Structure | Chemical Name |
|---|---|---|
| 31 | 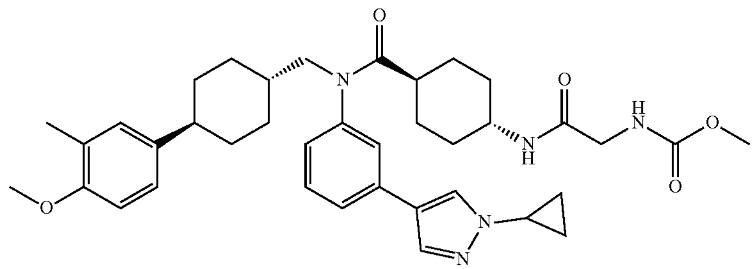 | Methyl (2-((trans-4-((3-(1-cyclopropyl-1H-pyrazol-4-yl)phenyl)((trans-4-(4-methoxy-3-methylphenyl)cyclohexyl)methyl)carbamoyl)-cyclohexyl)amino)-2-oxoethyl)carbamate |
| 31.01 | 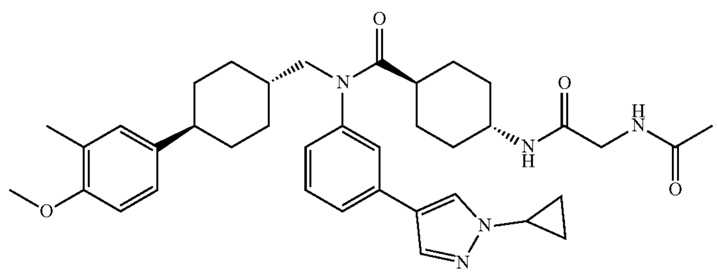 [SMILES: COc1ccc([C@H]2CC[C@H](CN(c3cccc(-c4cnn(C5CC5)c4)c3)C(=O)[C@H]3CC[C@H](NC(=O)CNC(C)=O)CC3)CC2)cc1C] | trans-4-(2-Acetamidoacetamido)-N-(3-(1-cyclopropyl-1H-pyrazol-4-yl)phenyl)-N-((trans-4-(4-methoxy-3-methylphenyl)cyclohexyl)methyl)-cyclohexanecarboxamide |
| 31.02 | 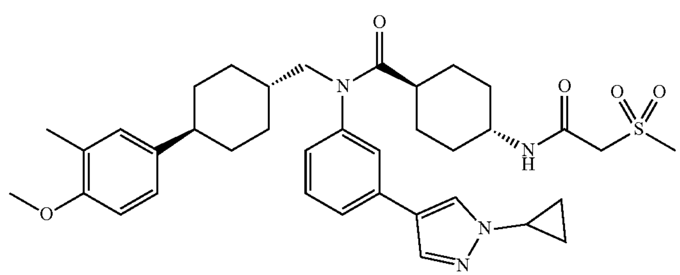 | trans-N-(3-(1-Cyclopropyl-1H-pyrazol-4-yl)phenyl)-N-((trans-4-(4-methoxy-3-methylphenyl)cyclohexyl)methyl)-4-(2-(methylsulfonyl)acetamido)-cyclohexanecarboxamide |

TABLE 1-continued

| Compound No | Structure | Chemical Name |
|---|---|---|
| 31.03 | 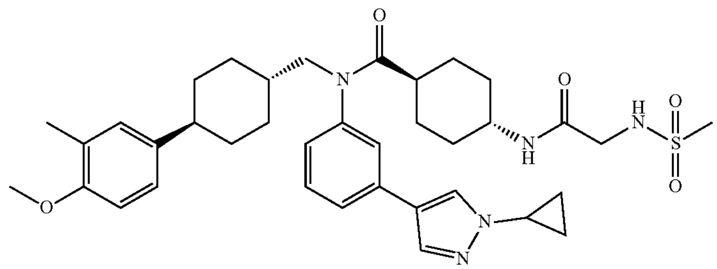 | trans-N-(3-(1-Cyclopropyl-1H-pyrazol-4-yl)phenyl)-N-((trans-4-(4-methoxy-3-methylphenyl)cyclohexyl)methyl)-4-(2-(methylsulfonamido)acetamido)cyclohexanecarboxamide |
| 31.04 | 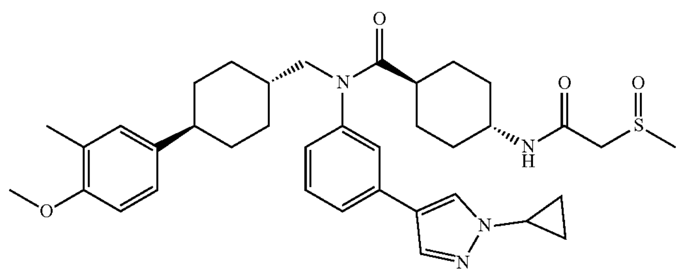 | trans-N-(3-(1-Cyclopropyl-1H-pyrazol-4-yl)phenyl)-N-((trans-4-(4-methoxy-3-methylphenyl)cyclohexyl)methyl)-4-(2-(methylsulfinyl)acetamido)cyclohexanecarboxamide |
| 31.05 | 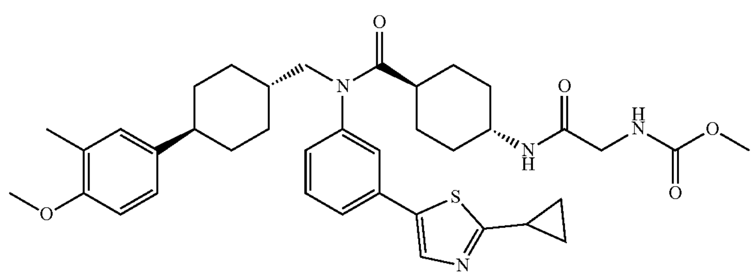 | Methyl (2-((trans-4-((3-(2-cyclopropylthiazol-5-yl)phenyl)((trans-4-(4-methoxy-3-methylphenyl)cyclohexyl)methyl)carbamoyl)cyclohexyl)amino)-2-oxoethyl)carbamate |

TABLE 1-continued

| Compound No | Structure | Chemical Name |
|---|---|---|
| 31.06 | 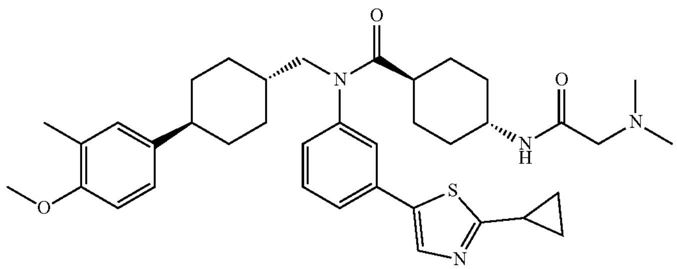 | trans-N-(3-(2-Cyclopropylthiazol-5-yl)phenyl)-4-(2-(dimethylamino)acetamido)-N-((trans-4-(4-methoxy-3-methylphenyl)cyclohexyl)methyl)-cyclohexanecarboxamide |
| 31.07 | 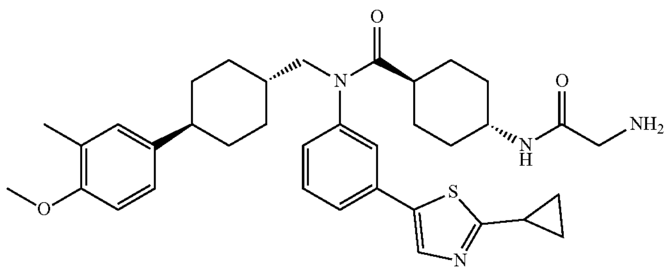 [SMILES: COc1ccc([C@H]2CC[C@H](CN(c3cccc(-c4cnc(C5CC5)s4)c3)C(=O)[C@H]3CC[C@H](NC(=O)CN)CC3)CC2)cc1C] | trans-4-(2-Aminoacetamido)-N-(3-(2-cyclopropylthiazol-5-yl)phenyl)-N-((trans-4-(4-methoxy-3-methylphenyl)cyclohexyl)methyl)-cyclohexanecarboxamide |
| 31.08 | 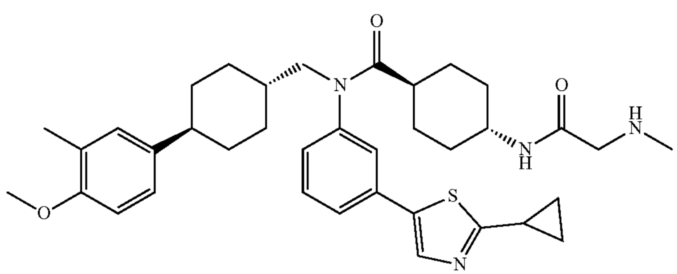 | trans-N-(3-(2-Cyclopropylthiazol-5-yl)phenyl)-N-((trans-4-(4-methoxy-3-methylphenyl)cyclohexyl)methyl)-4-(2-(methylamino)acetamido)cyclohexanecarboxamide |

TABLE 1-continued

| Compound No | Structure | Chemical Name |
|---|---|---|
| 31.09 | 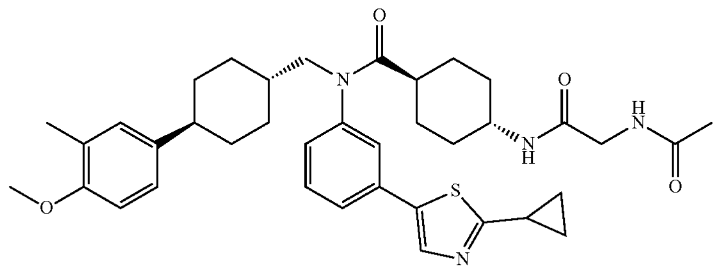 | trans-4-(2-Acetamidoacetamido)-N-(3-(2-cyclopropylthiazol-5-yl)phenyl)-N-((trans-4-(4-methoxy-3-methylphenyl)cyclohexyl)methyl)-cyclohexanecarboxamide |
| 31.10 | 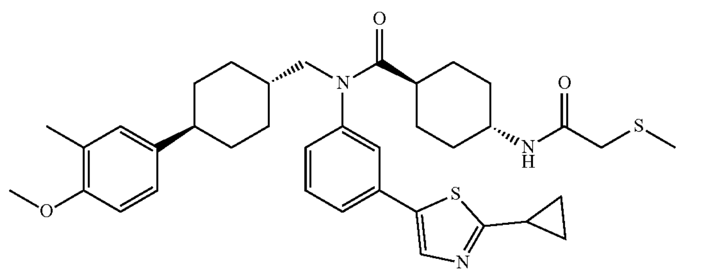 | trans-N-(3-(2-Cyclopropylthiazol-5-yl)phenyl)-N-((trans-4-(4-methoxy-3-methylphenyl)cyclohexyl)methyl)-4-(2-(methylthio)acetamido)cyclohexanecarboxamide |
| 31.11 | 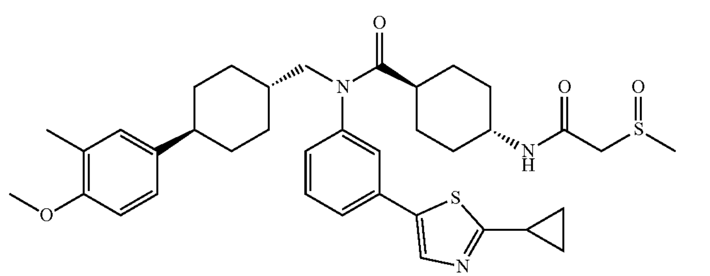 | trans-N-(3-(2-Cyclopropylthiazol-5-yl)phenyl)-N-((trans-4-(4-methoxy-3-methylphenyl)cyclohexyl)methyl)-4-(2-(methylsulfinyl)acetamido)cyclohexanecarboxamide |

TABLE 1-continued

| Compound No | Structure | Chemical Name |
|---|---|---|
| 31.12 | 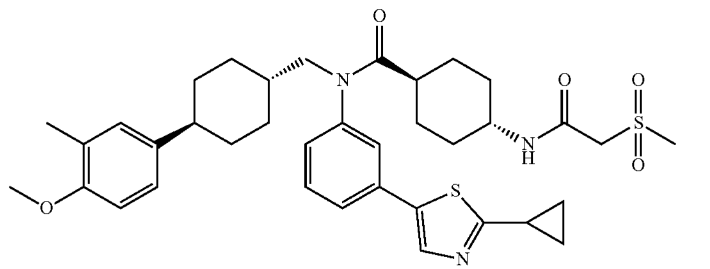 | trans-N-(3-(2-Cyclopropylthiazol-5-yl)phenyl)-N-((trans-4-(4-methoxy-3-methylphenyl)cyclohexyl)methyl)-4-(2-(methylsulfonyl)acetamido)cyclohexanecarboxamide |
| 31.13 | 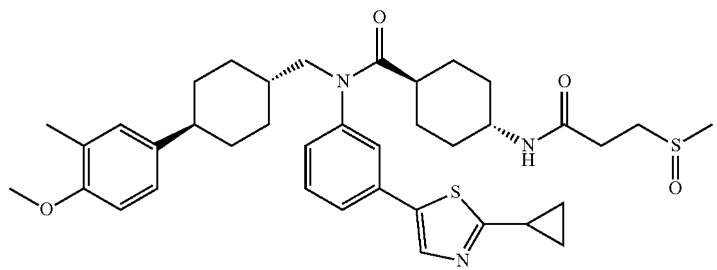 | trans-N-(3-(2-Cyclopropylthiazol-5-yl)phenyl)-N-((trans-4-(4-methoxy-3-methylphenyl)cyclohexyl)methyl)-4-(3-(methylsulfinyl)propanamido)cyclohexanecarboxamide |
| 31.14 | 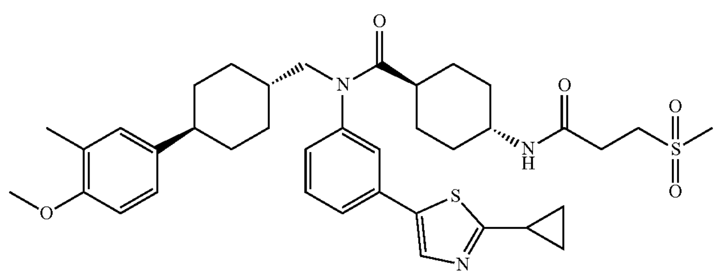 | trans-N-(3-(2-Cyclopropylthiazol-5-yl)phenyl)-N-((trans-4-(4-methoxy-3-methylphenyl)cyclohexyl)methyl)-4-(3-(methylsulfonyl)propanamido)cyclohexanecarboxamide |

TABLE 1-continued

| Compound No | Structure | Chemical Name |
|---|---|---|
| 31.15 | 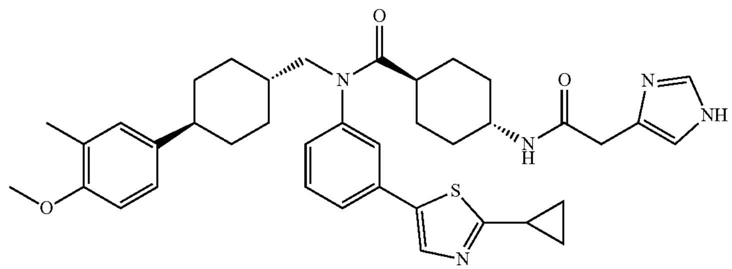 [SMILES: COc1ccc([C@H]2CC[C@H](CN(c3cccc(-c4cnc(C5CC5)s4)c3)C(=O)[C@H]3CC[C@H](NC(=O)Cc4c[nH]cn4)CC3)CC2)cc1C] | trans-4-(2-(1H-Imidazol-4-yl)acetamido)-N-(3-(2-cyclopropylthiazol-5-yl)phenyl)-N-((trans-4-(4-methoxy-3-methylphenyl)cyclohexyl)methyl)-cyclohexanecarboxamide |
| 32 | 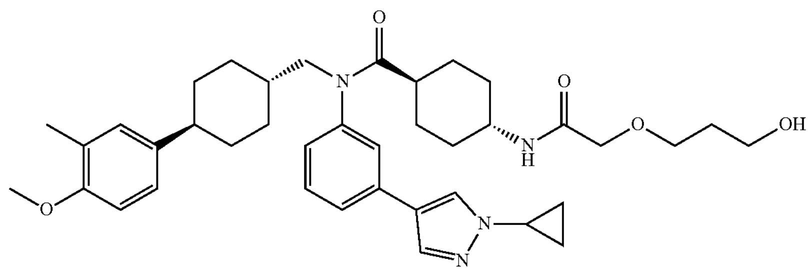 [SMILES: COc1ccc([C@H]2CC[C@H](CN(c3cccc(-c4cnn(C5CC5)c4)c3)C(=O)[C@H]3CC[C@H](NC(=O)COCCCO)CC3)CC2)cc1C] | trans-N-(3-(1-Cyclopropyl-1H-pyrazol-4-yl)phenyl)-4-(2-(3-hydroxypropoxy)acetamido)-N-((trans-4-(4-methoxy-3-methylphenyl)cyclohexyl)methyl)-cyclohexanecarboxamide |
| 32.01 | 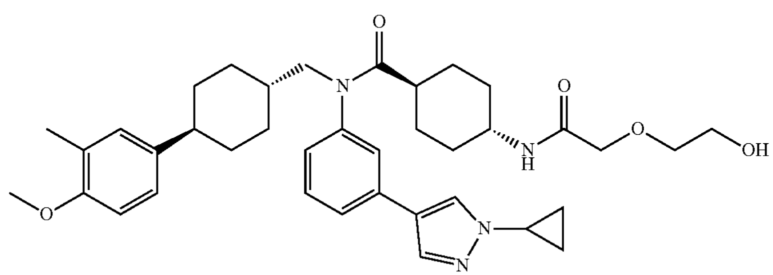 [SMILES: COc1ccc([C@H]2CC[C@H](CN(c3cccc(-c4cnn(C5CC5)c4)c3)C(=O)[C@H]3CC[C@H](NC(=O)COCCO)CC3)CC2)cc1C] | trans-N-(3-(1-Cyclopropyl-1H-pyrazol-4-yl)phenyl)-4-(2-(2-hydroxyethoxy)acetamido)-N-((trans-4-(4-methoxy-3-methylphenyl)cyclohexyl)methyl)-cyclohexanecarboxamide |

TABLE 1-continued

| Compound No | Structure | Chemical Name |
|---|---|---|
| 32.02 | 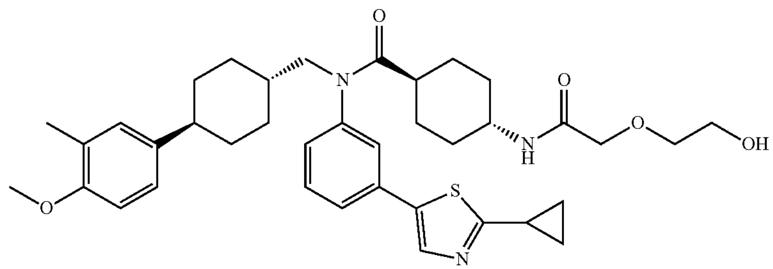 [SMILES: COc1ccc([C@H]2CC[C@H](CN(c3cccc(-c4cnc(C5CC5)s4)c3)C(=O)[C@H]3CC[C@H](NC(=O)COCCO)CC3)CC2)cc1C] | trans-N-(3-(2-Cyclopropylthiazol-5-yl)phenyl)-4-(2-(2-hydroxyethoxy)acetamido)-N-((trans-4-(4-methoxy-3-methylphenyl)cyclohexyl)methyl)-cyclohexanecarboxamide |
| 32.03 | 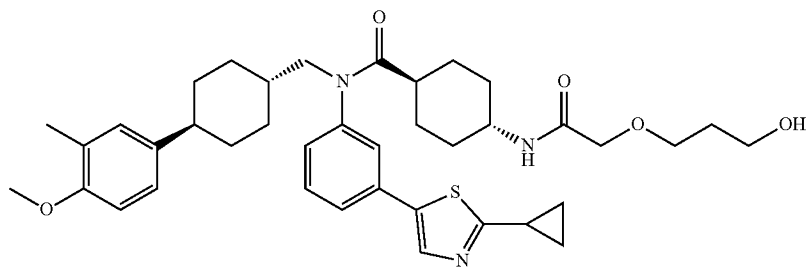 [SMILES: COc1ccc([C@H]2CC[C@H](CN(c3cccc(-c4cnc(C5CC5)s4)c3)C(=O)[C@H]3CC[C@H](NC(=O)COCCCO)CC3)CC2)cc1C] | trans-N-(3-(2-Cyclopropylthiazol-5-yl)phenyl)-4-(2-(3-hydroxypropoxy)acetamido)-N-((trans-4-(4-methoxy-3-methylphenyl)cyclohexyl)methyl)-cyclohexanecarboxamide |
| 32.04 | 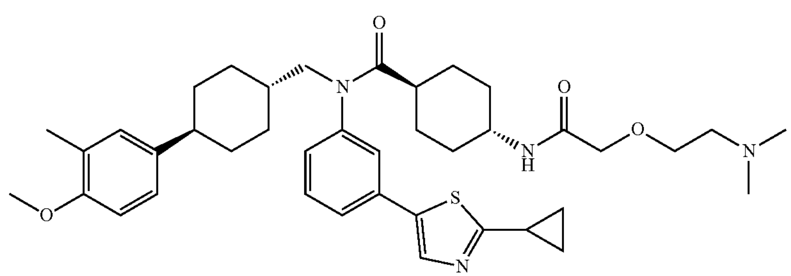 | trans-N-(3-(2-Cyclopropylthiazol-5-yl)phenyl)-4-(2-(2-(dimethylamino)ethoxy)acetamido)-N-((trans-4-(4-methoxy-3-methylphenyl)cyclohexyl)methyl)-cyclohexanecarboxamide |

TABLE 1-continued

| Compound No | Structure | Chemical Name |
|---|---|---|
| 32.05 | 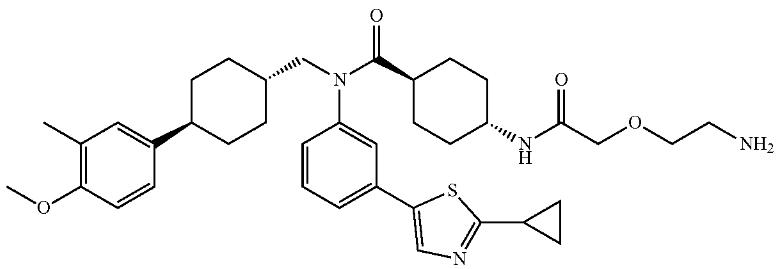 [SMILES: COc1ccc([C@H]2CC[C@H](CN(c3cccc(-c4cnc(C5CC5)s4)c3)C(=O)[C@H]3CC[C@H](NC(=O)COCCN)CC3)CC2)cc1C] | trans-4-(2-(2-Aminoethoxy)acetamido)-N-(3-(2-cyclopropylthiazol-5-yl)phenyl)-Af-((trans-4-(4-methoxy-3-methylphenyl)cyclohexyl)methyl)-cyclohexanecarboxamide |
| 32.06 | 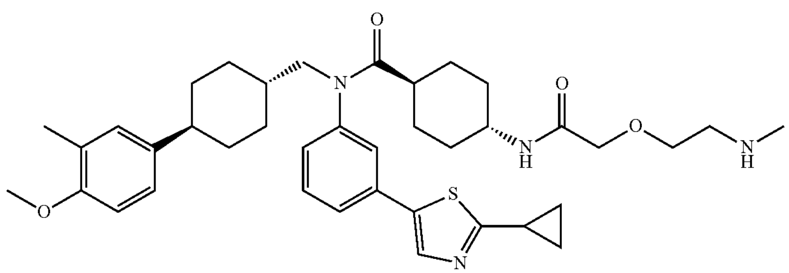 | trans-N-(3-(2-Cyclopropylthiazol-5-yl)phenyl)-N-((trans-4-(4-methoxy-3-methylphenyl)cyclohexyl)methyl)-4-(2-(2-(methylamino)ethoxy)acetamido)-cyclohexanecarboxamide |
| 33 | 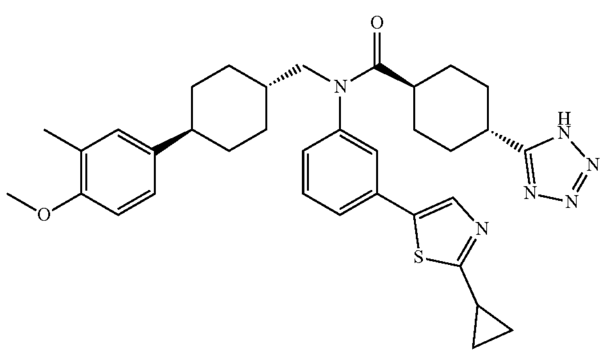 [SMILES: COc1ccc([C@H]2CC[C@H](CN(c3cccc(-c4cnc(C5CC5)s4)c3)C(=O)[C@H]3CC[C@H](c4nnn[nH]4)CC3)CC2)cc1C] | trans-N-(3-(2-Cyclopropylthiazol-5-yl)phenyl)-N-((trans-4-(4-methoxy-3-methylphenyl)cyclohexyl)methyl)-4-(2H-tetrazol-5-yl)cyclohexanecarboxamide |

TABLE 1-continued
| Compound No | Structure | Chemical Name |
|---|---|---|
| 33.01 | 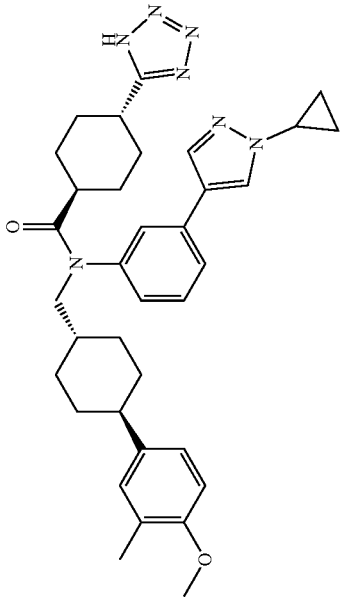 | trans-N-(3-(1-Cyclopropyl-1H-pyrazol-4-yl)phenyl)-N-((trans-4-(4-methoxy-3-methylphenyl)cyclohexyl)methyl)-4-(2H-tetrazol-5-yl)cyclohexanecarboxamide |
| 34 | 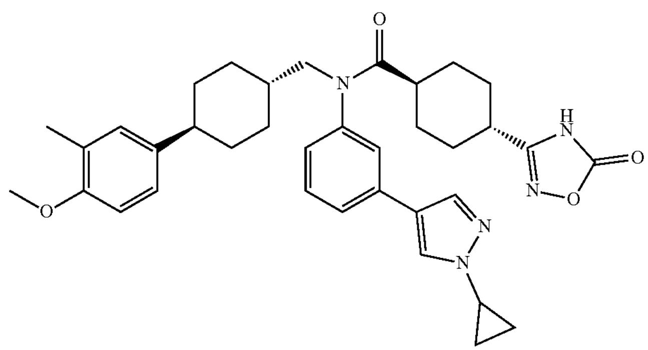 [SMILES: COc1ccc([C@H]2CC[C@H](CN(c3cccc(-c4cnn(C5CC5)c4)c3)C(=O)[C@H]3CC[C@H](c4noc(=O)[nH]4)CC3)CC2)cc1C] | trans-N-(3-(1-Cyclopropyl-1H-pyrazol-4-yl)phenyl)-N-((trans-4-(4-methoxy-3-methylphenyl)cyclohexyl)methyl)-4-(5-oxo-4,5-dihydro-1,2,4-oxadiazol-3-yl)cyclohexanecarboxamide |

In some embodiments, provided herein is a pharmaceutically acceptable salt or solvate of a compound that is described in Table 1.

TABLE 2

| Structure | Chemical Name |
|---|---|
| 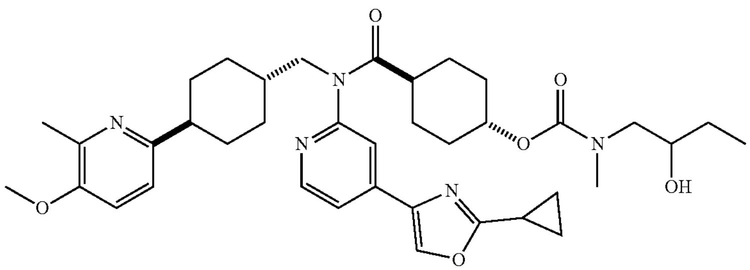 [SMILES: CCC(O)CN(C)C(=O)O[C@H]1CC[C@H](C(=O)N(C[C@H]2CC[C@H](c3ccc(OC)c(C)n3)CC2)c2cc(-c3coc(C4CC4)n3)ccn2)CC1] | trans-4-((4-(2-Cyclopropyloxazol-4-yl)pyridin-2-yl)((trans-4-(5-methoxy-6-methylpyridin-2-yl)cyclohexyl)methyl)carbamoyl)cyclohexyl (2-hydroxybutyl)(methyl)carbamate |
| 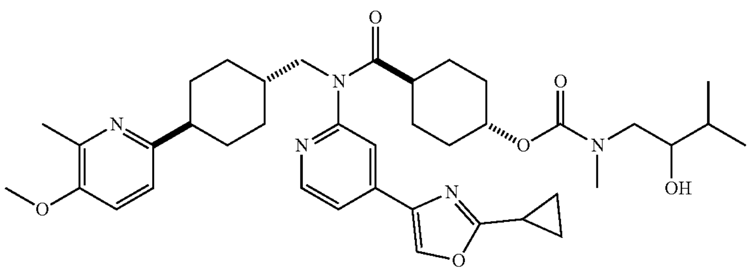 [SMILES: COc1ccc([C@H]2CC[C@H](CN(c3cc(-c4coc(C5CC5)n4)ccn3)C(=O)[C@H]3CC[C@H](OC(=O)N(C)CC(O)C(C)C)CC3)CC2)nc1C] | trans-4-((4-(2-Cyclopropyloxazol-4-yl)pyridin-2-yl)((trans-4-(5-methoxy-6-methylpyridin-2-yl)cyclohexyl)methyl)carbamoyl)cyclohexyl (2-hydroxy-3-methylbutyl)(methyl)carbamate |

In some embodiments, provided herein is a pharmaceutically acceptable salt or solvate of a compound that is described in Table 2.

In one aspect, compounds described herein are in the form of pharmaceutically acceptable salts. As well, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

"Pharmaceutically acceptable," as used herein, refers a material, such as a carrier or diluent, which does not abrogate the biological activity or properties of the compound, and is relatively nontoxic, i.e., the material is administered to an individual without causing undesirable biological effects or interacting in a deleterious manner with any of the components of the composition in which it is contained.

The term "pharmaceutically acceptable salt" refers to a form of a therapeutically active agent that consists of a cationic form of the therapeutically active agent in combination with a suitable anion, or in alternative embodiments, an anionic form of the therapeutically active agent in combination with a suitable cation. Handbook of Pharmaceutical Salts: Properties, Selection and Use. International Union of Pure and Applied Chemistry, Wiley-VCH 2002. S. M. Berge, L. D. Bighley, D. C. Monkhouse, J. Pharm. Sci. 1977, 66, 1-19. P. H. Stahl and C. G. Wermuth, editors, *Handbook of Pharmaceutical Salts: Properties, Selection and Use*, Weinheim/Zürich: Wiley-VCH/VHCA, 2002. Pharmaceutical salts typically are more soluble and more rapidly soluble in stomach and intestinal juices than non-ionic species and so are useful in solid dosage forms. Furthermore, because their solubility often is a function of pH, selective dissolution in one or another part of the digestive tract is possible, and this capability can be manipulated as one aspect of delayed and sustained release behaviors. Also, because the salt-forming molecule can be in equilibrium with a neutral form, passage through biological membranes can be adjusted.

In some embodiments, pharmaceutically acceptable salts are obtained by reacting a compound described herein with an acid to provide a "pharmaceutically acceptable acid addition salt." In some embodiments, the compound described herein (i.e. free base form) is basic and is reacted with an organic acid or an inorganic acid. Inorganic acids include, but are not limited to, hydrochloric acid, hydrobromic acid, sulfuric acid, phosphoric acid, nitric acid, and metaphosphoric acid. Organic acids include, but are not limited to, 1-hydroxy-2-naphthoic acid; 2,2-dichloroacetic acid; 2-hydroxyethanesulfonic acid; 2-oxoglutaric acid; 4-acetamidobenzoic acid; 4-aminosalicylic acid; acetic acid; adipic acid; ascorbic acid (L); aspartic acid (L); benzenesulfonic acid; benzoic acid; camphoric acid (+); camphor-10-sulfonic acid (+); capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; glucoheptonic acid (D); gluconic acid (D); glucuronic acid (D); glutamic acid; glutaric acid; glycerophosphoric acid; glycolic acid; hippuric acid; isobutyric acid; lactic acid (DL); lactobionic acid; lauric acid; maleic acid; malic acid (−L); malonic acid; mandelic acid (DL); methanesulfonic acid; monomethyl fumarate, naphthalene-1,5-disulfonic acid; naphthalene-2-sulfonic acid; nicotinic acid; oleic acid; oxalic acid; palmitic acid; pamoic acid; phosphoric acid; proprionic acid; pyroglutamic acid (−L); salicylic acid; sebacic acid; stearic acid; succinic acid; sulfuric acid; tartaric acid (+L); thiocyanic acid; toluenesulfonic acid (p); and undecylenic acid.

In some embodiments, a compound described herein is prepared as a chloride salt, sulfate salt, bromide salt, mesylate salt, maleate salt, citrate salt or phosphate salt.

In some embodiments, pharmaceutically acceptable salts are obtained by reacting a compound described herein with a base to provide a "pharmaceutically acceptable base addition salt."

In some embodiments, the compound described herein is acidic and is reacted with a base. In such situations, an acidic proton of the compound described herein is replaced by a metal ion, e.g., lithium, sodium, potassium, magnesium, calcium, or an aluminum ion. In some cases, compounds described herein coordinate with an organic base, such as, but not limited to, ethanolamine, diethanolamine, triethanolamine, tromethamine, meglumine, N-methylglucamine, dicyclohexylamine, tris(hydroxymethyl)methylamine. In other cases, compounds described herein form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, potassium carbonate, sodium hydroxide, lithium hydroxide, and the like. In some embodiments, the compounds provided herein are prepared as a sodium salt, calcium salt, potassium salt, magnesium salt, meglumine salt, N-methylglucamine salt or ammonium salt.

It should be understood that a reference to a pharmaceutically acceptable salt includes the solvent addition forms. In some embodiments, solvates contain either stoichiometric or non-stoichiometric amounts of a solvent, and are formed during the process of isolating or purifying the compound with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein optionally exist in unsolvated as well as solvated forms.

The methods and formulations described herein include the use of N-oxides (if appropriate), crystalline forms (also known as polymorphs), or pharmaceutically acceptable salts of compounds described herein, as well as active metabolites of these compounds having the same type of activity.

In some embodiments, sites on the organic groups (e.g. alkyl groups, aromatic rings) of compounds described herein are susceptible to various metabolic reactions. Incorporation of appropriate substituents on the organic groups will reduce, minimize or eliminate this metabolic pathway. In specific embodiments, the appropriate substituent to decrease or eliminate the susceptibility of the aromatic ring to metabolic reactions is, by way of example only, a halogen, deuterium, an alkyl group, a haloalkyl group, or a deuteroalkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as, for example, $^2H$, $^3H$, $^{13}C$, $^{14}C$, $^{15}N$, $^{18}O$, $^{17}O$, $^{35}S$, $^{18}F$, $^{36}Cl$. In one aspect, isotopically-labeled compounds described herein, for example those into which radioactive isotopes such as $^3H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements. In some embodiments, one or more hydrogen atoms of the compounds described herein is replaced with deuterium.

In some embodiments, the compounds described herein possess one or more stereocenters and each stereocenter exists independently in either the R or S configuration. The compounds presented herein include all diastereomeric, enantiomeric, atropisomers, and epimeric forms as well as the appropriate mixtures thereof. The compounds and methods provided herein include all cis, trans, syn, anti, entgegen (E), and zusammen (Z) isomers as well as the appropriate mixtures thereof.

Individual stereoisomers are obtained, if desired, by methods such as, stereoselective synthesis and/or the separation of stereoisomers by chiral chromatographic columns. In certain embodiments, compounds described herein are prepared as their individual stereoisomers by reacting a racemic mixture of the compound with an optically active resolving agent to form a pair of diastereoisomeric compounds/salts, separating the diastereomers and recovering the optically pure enantiomers. In some embodiments, resolution of enantiomers is carried out using covalent diastereomeric derivatives of the compounds described herein. In another embodiment, diastereomers are separated by separation/resolution techniques based upon differences in solubility. In other embodiments, separation of steroisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley and Sons, Inc., 1981. In some embodiments, stereoisomers are obtained by stereoselective synthesis.

In some embodiments, compounds described herein are prepared as prodrugs. A "prodrug" refers to an agent that is converted into the parent drug in vivo. Prodrugs are often useful because, in some situations, they are easier to administer than the parent drug. They are, for instance, bioavailable by oral administration whereas the parent is not. The prodrug may be a substrate for a transporter. Further or alternatively, the prodrug also has improved solubility in pharmaceutical compositions over the parent drug. In some embodiments, the design of a prodrug increases the effective water solubility. An example, without limitation, of a prodrug is a compound described herein, which is administered as an ester (the "prodrug") but then is metabolically hydrolyzed to provide the active entity. A further example of a prodrug is a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

Prodrugs of the compounds described herein include, but are not limited to, esters, ethers, carbonates, thiocarbonates, N-acyl derivatives, N-acyloxyalkyl derivatives, quaternary derivatives of tertiary amines, N-Mannich bases, Schiff bases, amino acid conjugates, phosphate esters, and sulfonate esters. See for example Design of Prodrugs, Bundgaard, A. Ed., Elseview, 1985 and Method in Enzymology, Widder, K. et al., Ed.; Academic, 1985, vol. 42, p. 309-396; Bundgaard, H. "Design and Application of Prodrugs" in A Textbook of Drug Design and Development, Krosgaard-Larsen and H. Bundgaard, Ed., 1991, Chapter 5, p. 113-191; and Bundgaard, H., Advanced Drug Delivery Review, 1992, 8, 1-38, each of which is incorporated herein by reference. In some embodiments, a hydroxyl group in the compounds disclosed herein is used to form a prodrug, wherein the hydroxyl group is incorporated into an acyloxyalkyl ester, alkoxycarbonyloxyalkyl ester, alkyl ester, aryl ester, phosphate ester, sugar ester, ether, and the like. In some embodiments, a hydroxyl group in the compounds disclosed herein is a prodrug wherein the hydroxyl is then metabolized in vivo to provide a carboxylic acid group. In some embodiments, a carboxyl group is used to provide an ester or amide (i.e. the prodrug), which is then metabolized in vivo to provide a carboxylic acid group. In some embodiments, compounds described herein are prepared as alkyl ester prodrugs.

Prodrug forms of the herein described compounds, wherein the prodrug is metabolized in vivo to produce a compound described herein as set forth herein are included within the scope of the claims. In some cases, some of the herein-described compounds is a prodrug for another derivative or active compound. In some embodiments, a prodrug of the compound disclosed herein permits targeted delivery of the compound to a particular region of the gastrointestinal tract. Formation of a pharmacologically active metabolite by the colonic metabolism of drugs is a commonly used "prodrug" approach for the colon-specific drug delivery systems.

In some embodiments, a prodrug is formed by the formation of a covalent linkage between drug and a carrier in such a manner that upon oral administration the moiety remains intact in the stomach and small intestine. This approach involves the formation of prodrug, which is a pharmacologically inactive derivative of a parent drug molecule that requires spontaneous or enzymatic transformation in the biological environment to release the active drug. Formation of prodrugs has improved delivery properties over the parent drug molecule.

The problem of stability of certain drugs from the adverse environment of the upper gastrointestinal tract can be eliminated by prodrug formation, which is converted into parent drug molecule once it reaches into the colon. Site specific drug delivery through site specific prodrug activation may be accomplished by the utilization of some specific property at the target site, such as altered pH or high activity of certain enzymes relative to the non-target tissues for the prodrug-drug conversion.

In some embodiments, covalent linkage of the drug with a carrier forms a conjugate conjugate. Such conjugates include, but are not limited to, azo bond conjugates, glycoside conjugates, glucuronide conjugates, cyclodextrin conjugates, dextran conjugates or amino-acid conjugates.

In additional or further embodiments, the compounds described herein are metabolized upon administration to an organism in need to produce a metabolite that is then used to produce a desired effect, including a desired therapeutic effect.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Metabolites of the compounds disclosed herein are optionally identified either by administration of compounds to a host and analysis of tissue samples from the host, or by incubation of compounds with hepatic cells in vitro and analysis of the resulting compounds.

In some embodiments, the compounds described herein are rapidly metabolized following absorption from the gastro-intestinal tract to metabolites that have greatly reduced FXR agonist activity.

In additional or further embodiments, the compounds are rapidly metabolized in plasma.

In additional or further embodiments, the compounds are rapidly metabolized by the intestines.

In additional or further embodiments, the compounds are rapidly metabolized by the liver.

Synthesis of Compounds

Compounds described herein are synthesized using standard synthetic techniques or using methods known in the art in combination with methods described herein.

Unless otherwise indicated, conventional methods of mass spectroscopy, NMR, HPLC, protein chemistry, biochemistry, recombinant DNA techniques and pharmacology are employed.

Compounds are prepared using standard organic chemistry techniques such as those described in, for example, March's Advanced Organic Chemistry, $6^{th}$ Edition, John Wiley and Sons, Inc. Alternative reaction conditions for the synthetic transformations described herein may be employed such as variation of solvent, reaction temperature, reaction time, as well as different chemical reagents and other reaction conditions. The starting materials are available from commercial sources or are readily prepared.

Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modem Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

The compounds described herein are prepared by the general synthetic routes described below in Schemes 1 to 16.

In some embodiments, intermediates used in the preparation of compounds described herein are prepared as outlined in Scheme 1.

Scheme 1

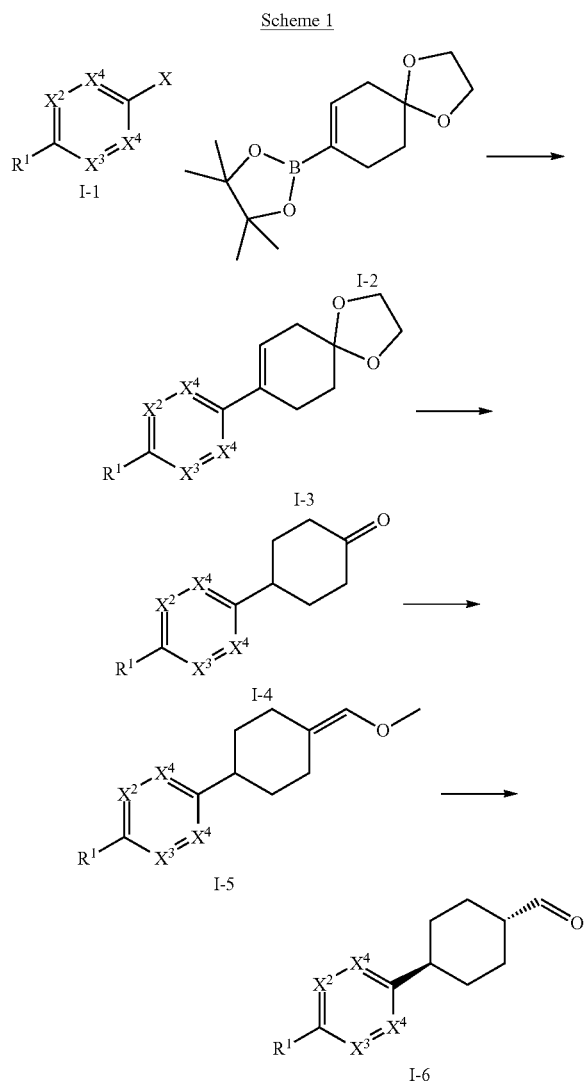

In Scheme 1, substituents $X^2$, $X^3$, $X^4$, $R^1$, and $R^2$ are as described herein. In some embodiments, $X^2$ is C—$R^2$, $X^3$ is C—H, and each $X^4$ is C—H. In some embodiments, X is a halide. In some embodiments, X is chloro, bromo, or iodo.

In some embodiments, boronic ester I-2 is reacted with halide I-1 under suitable metal-catalyzed cross-coupling reaction conditions to provide I-3. In some embodiments, suitable metal-catalyzed cross-coupling conditions include the use of palladium. In some embodiments, suitable palladium-catalyzed cross-coupling reaction conditions include Pd(dppf)Cl$_2$ or Pd(PPh$_3$)$_4$ with an appropriate base, with an appropriate solvent or solvent mixture for an appropriate time and at an appropriate temperature. In some embodiments, the base is an inorganic base. In some embodiments, the inorganic base is a carbonate base such as Na$_2$CO$_3$ or Cs$_2$CO$_3$. In some embodiments, the appropriate solvent or solvent mixture is dioxane, acetonitrile, DME/EtOH, or ethanol. In some embodiments, the appropriate time and appropriate temperature is about 2 to about 18 hours (overnight) hours at about 50° C. or about 100° C.

In some embodiments, I-3 is subjected to suitable hydrogenation conditions followed by treatment under appropriate acidic conditions to provide cyclohexanone I-4. In some embodiments, suitable hydrogenation conditions include the use of palladium. Palladium-catalyzed hydrogenation conditions include the use of 10% Pd/C with hydrogen (1 atm) in a suitable solvent, such as EtOAc, ethanol, methanol or a combination of these solvents, for an appropriate amount of time at an appropriate temperature. In some embodiments, the appropriate amount of time is about 4.5 hours to about 18 hours (overnight) at about rt. In some embodiments, appropriate acidic conditions include formic acid in water and toluene for a suitable amount of time at an appropriate temperature. In some embodiments, the suitable amount of time at an appropriate temperature is about 4 hours at about 120° C. In some embodiments, the suitable amount of time at an appropriate temperature is about 18 hours (overnight) at reflux. In some embodiments, appropriate acidic conditions include PPTS in acetone and water for a suitable amount of time at an appropriate temperature. In some embodiments, the suitable amount of time at an appropriate temperature is about 10 hours at about 60° C. In some embodiments, appropriate acidic conditions include 3 M HCl and THF for a suitable amount of time at an appropriate temperature. In some embodiments, the suitable amount of time at an appropriate temperature is about 3 hours to about overnight at about 60° C.

In some embodiments, I-4 is reacted under suitable one carbon-homologation conditions to provide I-5. In some embodiments, suitable one carbon-homologation conditions include the use of phosphonium reagents. In some embodiments, suitable one-carbon-homologation conditions, includes pre-treating (methoxymethyl)triphenyl phosphonium chloride [Ph$_3$P$^+$CH$_2$OCH$_3$ Cl$^-$] with an appropriate base, with an appropriate solvent for an appropriate amount of time at an appropriate temperature before the addition of cyclohexanone I-4. In some embodiments, the appropriate base is NaHMDS. In some embodiments, the appropriate base is KHMDS or LiHMDS. In some embodiments, the appropriate solvent is THF. In some embodiments, the appropriate amount of time before addition of cyclohexanone I-4 at an appropriate temperature is about 30 mins to about 2 hours at about 0° C. In some embodiments, after I-4 is added the reaction is continued for an additional about 30 mins to about 3 hours at about 0° C. In some embodiments, the reaction is allowed to warm to about room temperature overnight.

In some embodiments, I-5 is then subjected under suitable acidic conditions to provide a mixture of cis and trans aldehydes I-6. In some embodiments, suitable acidic conditions include formic acid in water/toluene at about 120° C.

to about 130° C. for about 2 hours to about overnight. In some embodiments, suitable acidic conditions include HCl in THF at about 60° C. for about 1 hour or about 6 hours. In some embodiments, further subjection of aldehyde I-6 under appropriate basic conditions provides a mostly trans aldehyde I-6. In some embodiments, appropriate basic conditions include NaOH in a suitable solvent mixture, such as H₂O, EtOH and PhMe, for an appropriate amount of time at an appropriate temperature. In some embodiments, THF is used instead of PhMe. In some embodiments, the appropriate amount of time at an appropriate temperature is about 5.5 hours to about overnight at about rt. In some embodiments, appropriate basic conditions include NaOMe in a suitable solvent, such as MeOH, for an appropriate amount of time at an appropriate temperature. In some embodiments, the appropriate amount of time at an appropriate temperature is at about 4 hours to about 18 hours at about room temperature. In some embodiments, further purification via crystallization or chromatography provides pure trans aldehyde I-6.

In some embodiments, intermediates used in the preparation of compounds described herein are prepared as outlined in Scheme 2.

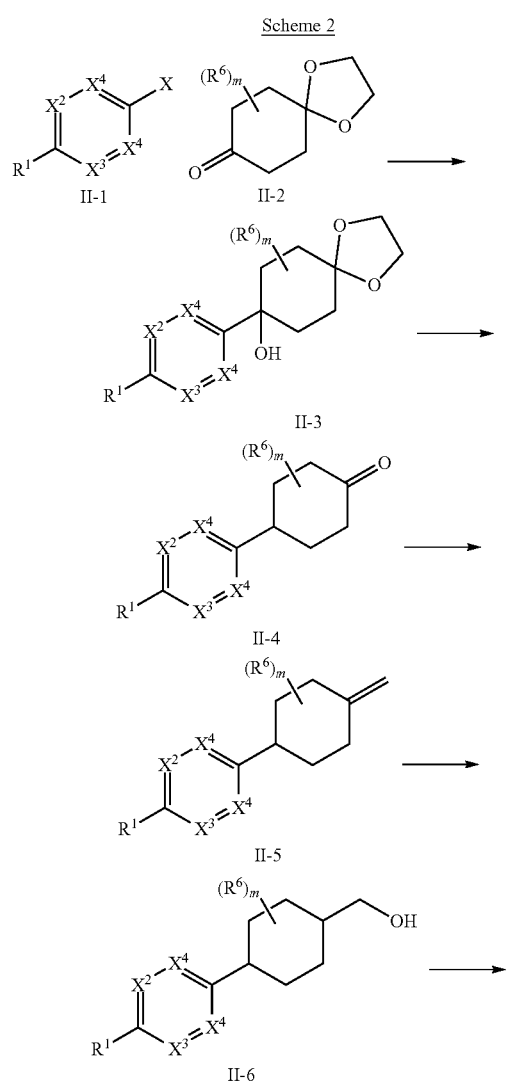

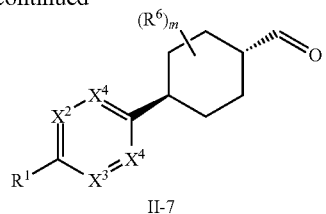

In Scheme 2, substituents X², X³, X⁴, R¹, R², and m are as described herein. In some embodiments, X² is C—R², X³ is C—H, and each X⁴ is C—H. In some embodiments, R⁶ is alkyl. In some embodiments, R⁶ is methyl. In some embodiments, X is a halogen. In some embodiments, X is chloro, bromo, or iodo.

In some embodiments, II-1 is cooled to a suitable temperature, reacted under suitable metal-halogen exchange conditions with an appropriate solvent for an appropriate time and at an appropriate temperature, and then later reacted with an appropriate ketone II-2 for an appropriate time and at an appropriate temperature to provide II-3. In some embodiments, suitable metal-halogen exchange conditions include an organometallic reagent. In some embodiments, an appropriate solvent is THF. In some embodiments, the organometallic reagent is an alkyl lithium. In some embodiments, the alkyllithium is n-butyl lithium. In some embodiments, II-1 is cooled to about −78° C. before addition of an organometallic reagent. In some embodiments, II-1 is reacted for about two hours at about −78° C. before addition of the appropriate ketone II-2. In some embodiments, the intermediate organometallic reagent is reacted for about 3 hours after addition of ketone II-2. In some embodiments, the intermediate organometallic reagent is reacted at about −78° C. after addition of ketone II-2.

In some embodiments, alcohol II-3 is reacted under appropriate reduction conditions with an appropriate solvent for an appropriate time and at an appropriate temperature to form a mixture of dehydrated and reduced products. In some embodiments, conditions include the use of trifluoracetic acid and a silyl hydride. In some embodiments, the silyl hydride is triethylsilane. In some embodiments, the appropriate solvent is dichloromethane. In some embodiments, the temperature is about 0° C. to about rt or about 0° C. In some embodiments, the appropriate time is about overnight or about 1 hour. In some embodiments, the mixture of reduced and dehydrated products is reacted under the appropriate conditions with an appropriate solvent for an appropriate time and at an appropriate temperature to form a ketone. In some embodiments, the appropriate solvent is a formic acid, toluene, and water mixture. In some embodiments, the appropriate temperature is about 130° C. In some embodiments, the appropriate time is about overnight. In some embodiments, the appropriate solvent is a formic acid, THF, and water mixture. In some embodiments, the appropriate temperature is about 80° C. In some embodiments, the appropriate time is about 18 hours. In some embodiments, this ketone, containing the dehydrated side product, is fully reduced under suitable reduction conditions with an appropriate solvent for an appropriate time and at an appropriate temperature to form II-4. In some embodiments, the appropriate reduction conditions include the use of hydrogen as a reducing agent. In some embodiments, the hydrogen is at a pressure of about 15 psi or about 30 psi. In some embodiments, the alkene reduction includes use of a palladium catalyst. In some embodiments, the palladium catalyst is 10% palladium on carbon. In some embodiments, the solvent is ethyl acetate and concentrated HCl. In some embodiments, the solvent is ethyl acetate. In some embodiments, the temperature is about rt. In some embodiments, the appropriate time is about 30 min to about 18 hours.

In some embodiments, II-4 is pre-treated with an electrophile $R^6X$ in an appropriate solvent and at an appropriate temperature. In some embodiments, the electrophile is an alkyl halide. In some embodiments, X is chloro, bromo, or iodo. In some embodiments, the electrophile is methyl iodide. In some embodiments, the temperature is about −78° C. In some embodiments, the mixture is further reacted with a base for an appropriate time and at an appropriate temperature to form an alkylated product. In some embodiments, the base is lithium diisopropyldiamide. In some embodiments, the appropriate time is about 2 hours. In some embodiments, the temperature is about −78° C. In some embodiments, the mixture is further allowed to warm to about rt over a suitable amount of time. In some embodiments, a suitable amount of time is about overnight.

In some embodiments, ketone II-4 is transformed into aldehyde II-7 as described in Scheme 1.

Alternatively in some embodiments, II-4 is reacted under suitable one carbon-homologation conditions to provide alkene II-5. In some embodiments, suitable one carbon-homologation conditions include the use of phosphonium reagents. In some embodiments, suitable one-carbon-homologation conditions, includes pre-treating methyltriphenyl phosphonium bromide [$Ph_3P^+CH_3$ $Br^-$] with an appropriate base, in an appropriate solvent for an appropriate amount of time at an appropriate temperature before the addition of cyclohexanone II-4. In some embodiments, the appropriate base is an organic base. In some embodiments, the appropriate base is an alkoxide base. In some embodiments, the appropriate base is potassium tert-butoxide. In some embodiments, the appropriate solvent is toluene. In some embodiments, the appropriate time before adding the ketone is about 30 min. In some embodiments, the temperature of the reaction before adding the ketone is about 100° C. In some embodiments, ketone II-4 is added in the appropriate solvent, at the appropriate temperature, and for the appropriate amount of time. In some embodiments, the reaction temperature is about 50° C. after the addition of the ketone. In some embodiments, the ketone is added in toluene. In some embodiments, the ketone is further reacted at a suitable temperature for a suitable amount of time. In some embodiments, the ketone is further reacted at about 100° C. In some embodiments, the ketone is further reacted for about 2 hours.

In some embodiments, alkene II-5 is subjected to hydration conditions to form II-6. In some embodiments, the hydration conditions include treatment with a reducing agent followed by an oxidizing agent. The reducing agent is reacted with II-5 in the appropriate solvent, at the appropriate temperature, and for the appropriate amount of time. In some embodiments, the reducing agent is a borane. In some embodiments, the reducing agent is $BH_3$—$SMe_2$. In some embodiments, the reducing agent is reacted with II-5 in THF. In some embodiments, the reaction temperature is about 0° C. In some embodiments, the reaction proceeds for about one hour after addition of the reducing agent. In some embodiments, the reaction further continues at about rt. In some embodiments, the reaction further continues for about 3 hours. In some embodiments, the intermediate borane product is further oxidized with an oxiding agent to form alcohol II-6 in the appropriate solvent, at the appropriate temperature, and for the appropriate amount of time. In some embodiments, the oxidizing agent is 30% $H_2O_2$. In some embodiments, the oxidation reaction is carried out in the prescence of a base. In some embodiments, the base is NaOH. In some embodiments, the solvent is $H_2O$. In some embodiments, the appropriate amount of time is about overnight. In some embodiments, the appropriate temperature is about rt.

In some embodiments, alcohol II-6 is subjected to an oxidizing agent to form aldehyde II-7. In some embodiments, the oxidizing agent is a Swern oxidant in the appropriate solvent, at the appropriate temperature, and for the appropriate amount of time. In some embodiments, the Swern oxidant is formed with DMSO and oxalyl chloride. In some embodiments, the appropriate solvent is dichloromethane. In some embodiments, the appropriate temperature for Swern oxidant formation is about −78° C. In some embodiments, the appropriate time for Swern oxidant formation is 30 min. In some embodiments, II-6 is reacted with the Swern oxidant at about −78° C. In some embodiments, 6 is reacted with the Swern oxidant for about one hour. In some embodiments, a base is then added at the appropriate temperature for the appropriate amount of time. In some embodiments, the base is an amine base. In some embodiments, the amine base is triethylamine. In some embodiments, the appropriate temperature is about −78° C. In some embodiments, the appropriate reaction time after addition of the base is about one hour. In some embodiments, oxidation produces II-7 as a mixture of cis and trans isomers.

In some embodiments, the cis/trans mixture of II-7 is equilibrated to mostly trans II-7 with an appropriate reagent, in the appropriate solvent, at the appropriate temperature, and for the appropriate time. In some embodiments, the appropriate reagent is a base. In some embodiments, the base is an inorganic base. In some embodiments, the base is sodium hydroxide. In some embodiments, the appropriate solvent is a mixture, such as $H_2O$, EtOH and PhMe. In some embodiments, the appropriate time is about 3 hours. In some embodiments, the appropriate temperature is about rt. In some embodiments, further purification via crystallization or chromatography provides pure trans aldehyde II-7.

In some embodiments, intermediates used in the preparation of compounds described herein are prepared as outlined in Scheme 3

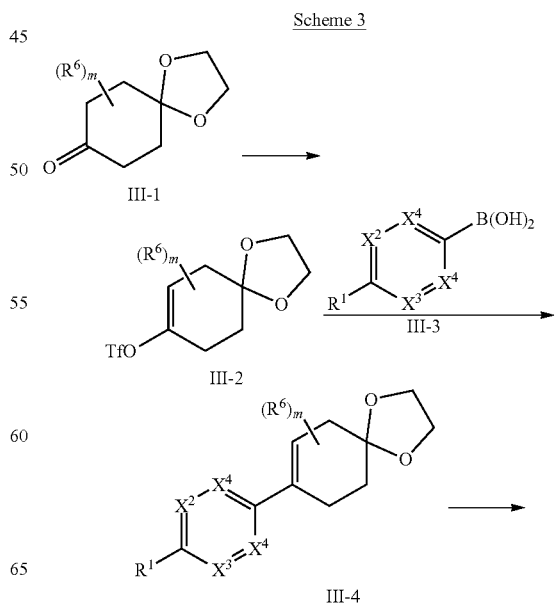

Scheme 3

-continued

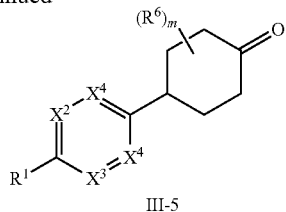

III-5

In Scheme 3, substituents $X^2$, $X^3$, $X^4$, $R^1$, $R^2$, and m are as described herein. In some embodiments, $X^2$ is C—$R^2$, $X^3$ is C—H, and each $X^4$ is C—H. In some embodiments, $R^6$ is alkyl. In some embodiments, $R^6$ is methyl.

In some embodiments, ketone III-1 is treated with a base to form an enolate with an appropriate base, in an appropriate solvent, for an appropriate amount of time, at an appropriate temperature. In some embodiments, the base is an organic base. In some embodiments, the organic base is LiHMDS. In some embodiments, enolate formation takes place at about −78° C. In some embodiments, the appropriate solvent is THF. In some embodiments, the appropriate time is about one hour. In some embodiments, the enolate of ketone III-1 is reacted with a suitable electrophile in an appropriate solvent to form enol ether III-2 at the appropriate temperature, for an appropriate amount of time. In some embodiments, the electrophile forms a sulfate ester. In some embodiments, the electrophile is PhNTf$_2$. In some embodiments, the appropriate temperature is about −78° C. and the appropriate time is about 2 hours. In some embodiments, the reaction is further warmed to a suitable temperature over a suitable period of time. In some embodiments, the suitable temperature is about rt for about overnight.

In some embodiments, boronic acid III-3 is reacted with enol triflate III-2 under suitable metal-catalyzed cross-coupling reaction conditions to provide III-4. In some embodiments, suitable metal-catalyzed cross-coupling conditions include palladium. In some embodiments, suitable palladium-catalyzed cross-coupling reaction conditions include Pd(dppf)Cl$_2$ with an appropriate base, with an appropriate solvent for an appropriate time and at an appropriate temperature. In some embodiments, the base is an inorganic base. In some embodiments, the inorganic base is a carbonate base such as Na$_2$CO$_3$. In some embodiments, the appropriate solvent is a dioxane/water mixture. In some embodiments, the appropriate time and appropriate temperature is about 6 hours at about 30° C.

In some embodiments, III-4 is subjected under suitable olefin reduction conditions followed by treatment under appropriate acidic conditions to provide cyclohexanone III-5. In some embodiments, suitable reduction conditions include palladium-catalyzed hydrogenation conditions. In some embodiments, palladium-catalyzed hydrogenation conditions include use of 10% Pd/C with hydrogen (1 atm) in a suitable solvent, such as EtOAc, for an appropriate amount of time at an appropriate temperature. In some embodiments, the appropriate amount of time is about overnight at about rt. In some embodiments, appropriate acidic conditions include the use of formic acid in water and toluene for a suitable amount of time at an appropriate temperature. In some embodiments, the suitable amount of time at an appropriate temperature is about overnight at about 120° C.

In some embodiments, ketone III-5 is transformed into aldehyde I-6 or II-7, as shown in Scheme 1 and Scheme 2, respectively.

In some embodiments, compounds described herein are prepared as outlined in Scheme 4.

Scheme 4

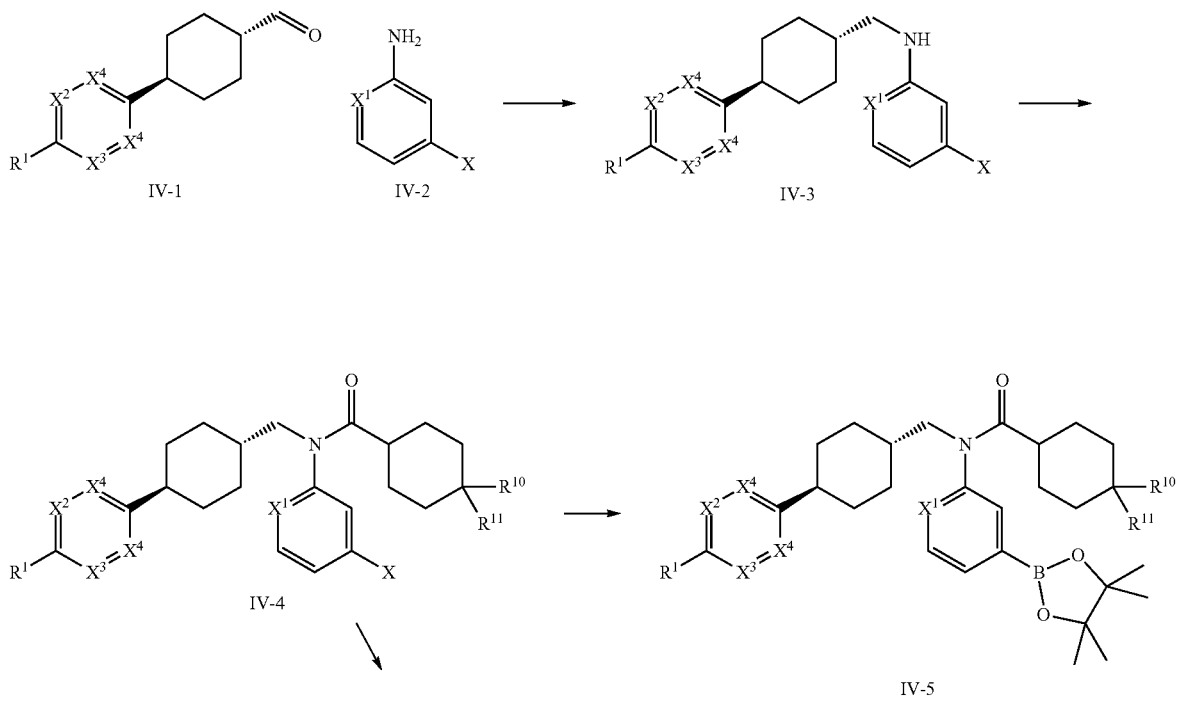

-continued

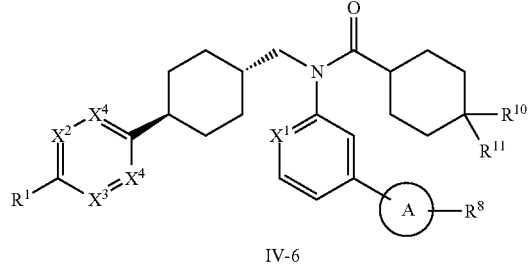

IV-6

In Scheme 4, ring A and substituents $X^1$, $X^2$, $X^3$, $X^4$, $R^1$, $R^2$, $R^8$, $R^{10}$ and $R^{11}$ are as described herein. In some embodiments, $X^2$ is C—$R^2$, $X^3$ is C—H, and each $X^4$ is C—H. In some embodiments, X is a halide. In some embodiments, X is iodo or bromo.

In some embodiments, trans aldehyde IV-1 is reacted with an appropriate aniline IV-2 under suitable reductive amination conditions. In some embodiments, suitable reductive amination conditions include use of a suitable reducing agent and acetic acid in an appropriate solvent, such as DCE or DCM, at an appropriate temperature for a suitable amount of time. In some embodiments, NaBH(OAc)$_3$ is used as a reducing agent. In some embodiments, the appropriate temperature is about rt. In some embodiments, the suitable amount of time is about one hour to about 2.5 hours. In some embodiments, suitable reaction conditions include acetic acid in an appropriate solvent, such as methanol, at an appropriate temperature for a suitable amount of time before the addition of the reducing agent. In some embodiments, the appropriate temperature and time is about rt for about 5 minutes to about 4 hours. In some embodiments, the reaction is then further subjected to a suitable reducing agent, such as NaBH$_3$CN, for the appropriate time and at the appropriate temperature. In some embodiments, the appropriate amount of time is about overnight at about rt.

In some embodiments, the acylation of amine IV-3 with an acyl chloride affords compound IV-4. Suitable acylation conditions include but are not limited to the use of a suitable base, such as TEA or pyridine in a suitable solvent, such as DCM or toluene, for an appropriate amount of time and at a suitable temperature, such as about rt to about 80° C. for about 1 hour to about overnight. In some embodiments, pyridine is used as both the base and the solvent. Other suitable conditions include the addition of DMAP.

Boronic ester IV-5 may be prepared from IV-4 using boron-halogen exchange conditions in some embodiments. Suitable boron-halogen exchange conditions include but are not limited to use of a suitable organometallic reagent and a suitable boron reagent. In some embodiments, suitable organometallic reagents include palladium. In some embodiments, suitable boron reagents include bis(pinacolato)diboron. In some embodiments, suitable palladium-catalyzed boron-halogen exchange conditions include Pd(dppf)Cl$_2$ with an appropriate base, in an appropriate solvent for an appropriate time and at an appropriate temperature. In some embodiments, the base is an inorganic base. In some embodiments, the inorganic base is an acetate base such as KOAc. In some embodiments, the appropriate solvent is toluene. In some embodiments, the appropriate time and appropriate temperature is about 4 hours to about overnight and about 100° C. to about 115° C.

In some embodiments, boronic ester IV-5 is reacted with an aromatic halide under suitable metal-catalyzed cross-coupling reaction conditions to provide IV-6. In some embodiments, the aromatic halide is an aromatic bromide or iodide. In some embodiments, suitable metal-catalyzed cross-coupling conditions include use of palladium. In some embodiments, suitable palladium-catalyzed cross-coupling reaction conditions include Pd(dppf)Cl$_2$, Pd(PPh$_3$)$_4$, or chloro[(di(1-adamantyl)-N-butylphosphine)-2-(2-aminobiphenyl)]palladium(II) with an appropriate base, in an appropriate solvent for an appropriate time and at an appropriate temperature. In some embodiments, the base is an inorganic base. In some embodiments, the inorganic base is a carbonate base such as K$_2$CO$_3$, Na$_2$CO$_3$ or Cs$_2$CO$_3$. In some embodiments, the inorganic base is K$_3$PO$_4$. In some embodiments, the appropriate solvent is a dioxane/water, or DMF/water mixture. In some embodiments, the appropriate solvent is EtOH or dioxane. In some embodiments, the appropriate time and appropriate temperature is about 10 min to about 4 hours at about 50° C. to about 80° C. In some embodiments, the appropriate time and appropriate temperature is about 0.5 hours to about 6 hours at about 80° C. In some embodiments, the appropriate time and appropriate temperature is about 15 mins to about 3.5 hours at about 80° C. In some embodiments, the appropriate time and appropriate temperature is about 15 hours at about 90° C. In some embodiments, the appropriate time and appropriate temperature is about one hour at about 50° C. In some embodiments, the appropriate time and appropriate temperature is about 3 hours at about 80° C. to about 100° C.

In some embodiments, boronic ester IV-5 is reacted with a nitrogen-containing heterocycle under suitable metal-catalyzed cross-coupling reaction conditions to provide IV-6. In some embodiments, suitable metal-catalyzed cross-coupling conditions include use of copper. In some embodiments, suitable copper-catalyzed cross-coupling reaction conditions include Cu(OAc)$_2$ with an appropriate ligand, an appropriate oxidant, in an appropriate solvent for an appropriate time and at an appropriate temperature. In some embodiments, an appropriate ligand is N,N,N',N'-tetramethylethylenediamine. In some embodiments, an appropriate oxidant is O$_2$. An appropriate solvent is a water and methanol mixture. In some embodiments, the appropriate time and appropriate temperature is about overnight at about rt.

In some embodiments, aryl halide IV-4 is reacted with a boron reagent under suitable metal-catalyzed cross-coupling reaction conditions to provide IV-6. In some embodiments, the boron reagent is an aromatic boronic acid. In some embodiments, the boron reagent is an aromatic boronic ester. In some embodiments, the boron reagent is an aromatic pinacolyl boronic ester. In some embodiments, suitable metal-catalyzed cross-coupling conditions include palladium. In some embodiments, suitable palladium-catalyzed cross-coupling reaction conditions include Pd(dppf)Cl$_2$ or Pd(PPh$_3$)$_4$ with an appropriate base, with an appropriate solvent for an appropriate time and at an appropriate temperature. In some embodiments, the base is an inorganic base. In some embodiments, the inorganic base is a carbonate base such as $Cs_2CO_3$, $Na_2CO_3$, or $K_2CO_3$. In some embodiments, the appropriate solvent is a DMF/water mixture. In some embodiments, the appropriate solvent is a dioxane/water mixture. In some embodiments, the appropriate time and appropriate temperature is about 10 min to about 2 hours at about 50° C. to about 100° C. In some embodiments, the appropriate time and appropriate temperature is about 15 min to about 30 min at about 80° C.

In some embodiments, compound IV-6 is prepared from appropriate metal-catalyzed cross coupling conditions of halide IV-4 with a nitrogen-containing heterocycle. In some embodiments, halide IV-4 is an iodide. In some embodiments, metal-catalyzed cross couplings include Buchwald-Hartwig palladium-catalyzed amination conditions. Suitable palladium catalysts for cross-coupling include but are not limited to $Pd_2(dba)_3$ with a suitable ligand in a suitable solvent, such as dioxane, with an appropriate base at a suitable temperature for an appropriate amount of time. In some embodiments, the suitable ligand is a phosphine ligand. In some embodiments, a suitable phosphine is 2-(di-tert-butylphosphino)biphenyl. In some embodiments, the appropriate base is an organic base. In some embodiments, a suitable organic base is sodium tert-butoxide. In some embodiments, the suitable temperature is 80° C. In some embodiments, the appropriate amount of time is about overnight.

In some embodiments, compound IV-6 is prepared from appropriate metal-catalyzed cross coupling conditions of halide IV-4 with a tin reagent. In some embodiments, halide IV-4 is a bromide. In some embodiments, the tin reagent is an aromatic tin reagent. In some embodiments, metal-catalyzed cross couplings include Stille palladium-catalyzed cross-coupling conditions. Suitable palladium catalysts for cross-coupling include but are not limited to $Pd(PPh_3)_4$ in a suitable solvent, such as DMF or dioxane, at a suitable temperature for an appropriate amount of time. In some embodiments, the suitable temperature is 90° C. In some embodiments, the appropriate amount of time is about 2 hours. In some embodiments, the suitable temperature is 100° C. In some embodiments, the appropriate amount of time is about 4 hours.

In some embodiments, compound IV-6 is prepared from appropriate metal-catalyzed cross coupling conditions of halide IV-4 with an aromatic compound. In some embodiments, halide IV-4 is a bromide. In some embodiments, metal-catalyzed cross couplings include C—H activation cross-coupling conditions. In some embodiments, C—H activation cross-coupling conditions include use of palladium catalysts. Suitable palladium catalysts for cross-coupling include but are not limited to $Pd(OAc)_2$ with a suitable ligand in a suitable solvent, such as dioxane, with an appropriate base at a suitable temperature for an appropriate amount of time. In some embodiments, the suitable ligand is a phosphine ligand. In some embodiments, a suitable phosphine is (2-biphenyl)dicyclohexylphosphine. In some embodiments, the appropriate base is an inorganic base. In some embodiments, a suitable inorganic base is $K_2CO_3$. In some embodiments, the suitable temperature is 110° C. In some embodiments, the appropriate amount of time is about overnight.

In some embodiments, $R^{10}$ or $R^{11}$ is a protected alcohol. In some embodiments, $R^{10}$ or $R^{11}$ is an alcohol protected with a silyl ether. In some embodiments, protecting groups are removed to produce a free alcohol using suitable deprotection conditions including appropriate solvent, temperature and time to produce IV-6. In some embodiments, suitable deprotection conditions include the use of aqueous HCl. In some embodiments, the appropriate solvent is water, THF, methanol, or a combination of solvents. In some embodiments, the appropriate time at the appropriate temperature is about 1 hour at about 0° C. to about rt.

In some embodiments, compounds described herein are prepared as outlined in Scheme 5.

Scheme 5

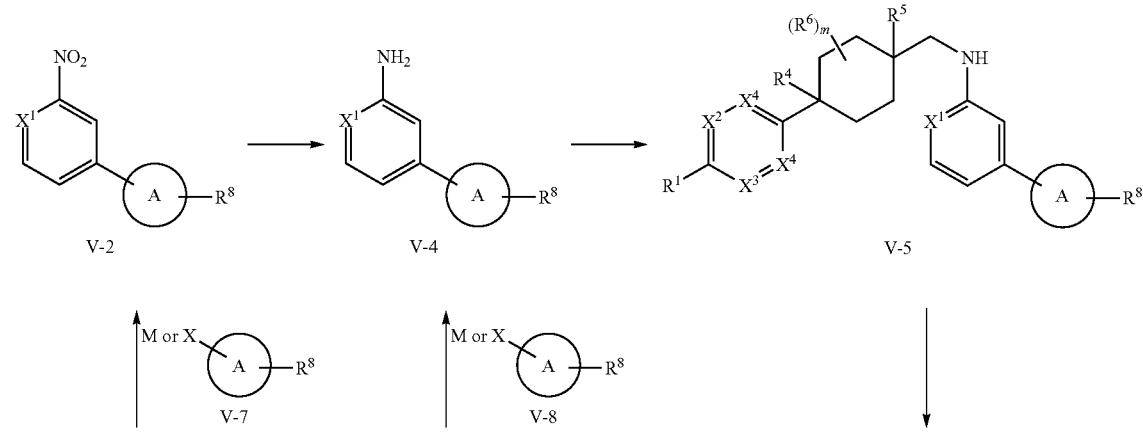

421

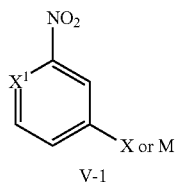

V-1

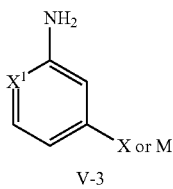

V-3

422

-continued

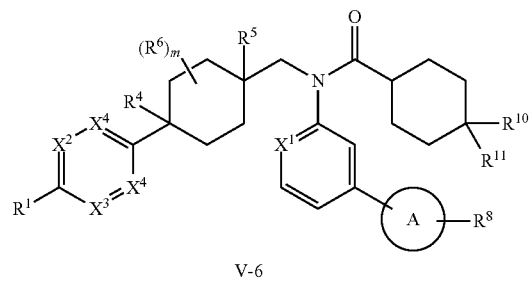

V-6

In Scheme 5, ring A and substituents $X^1$, $X^2$, $X^3$, $X^4$, $R^1$, $R^2$, $R^4$, $R^5$, $R^6$, $R^8$, $R^{10}$, $R^{11}$, and m are as described herein. In some embodiments, $X^2$ is C—$R^2$, $X^3$ is C—H, and each $X^4$ is C—H. In some embodiments, X is a halide. In some embodiments, X is iodo or bromo. In some embodiments, X is hydrogen. In some embodiments, M is a metal or metalloid-containing substituent. In some embodiments, metal or metalloids include boron, tin, or zinc.

In some embodiments, boron reagent V-1 is reacted with an aromatic halide V-7 under suitable metal-catalyzed cross-coupling reaction conditions to provide V-2. In some embodiments, the aromatic halide is an aromatic bromide or aromatic iodide. In some embodiments, suitable metal-catalyzed cross-coupling conditions include palladium. In some embodiments, suitable palladium-catalyzed cross-coupling reaction conditions include $Pd(dppf)Cl_2$ with an appropriate base, with an appropriate solvent for an appropriate time and at an appropriate temperature. In some embodiments, the base is an inorganic base. In some embodiments, the inorganic base is a carbonate base such as $Na_2CO_3$. In some embodiments, the appropriate solvent is a mixture of dioxane, ethanol and water. In some embodiments, the appropriate time and appropriate temperature is about overnight at about 80° C.

In some embodiments, compound V-2 is prepared from appropriate metal-catalyzed cross coupling conditions of an aromatic halide V-1 with a boron reagent V-7. In some embodiments, appropriate metal-catalyzed cross coupling conditions, such as Suzuki cross-coupling conditions, are described in Schemes 4 and 5.

In some embodiments, compound V-2 is prepared from appropriate metal-catalyzed cross coupling conditions of halide V-1 with a nitrogen-containing heterocycle V-7. In some embodiments, appropriate metal-catalyzed cross coupling conditions, such as Buchwald-Hartwig amination conditions, are described in Scheme 4.

In some embodiments, compound V-2 is prepared from appropriate metal-catalyzed cross coupling conditions of halide V-1 with a tin reagent V-7. In some embodiments, appropriate metal-catalyzed cross coupling conditions, such as Stille cross-coupling conditions, are described in Scheme 4.

In some embodiments, compound V-2 is prepared from appropriate metal-catalyzed cross coupling conditions of tin reagent V-1 with an aromatic halide V-7. In some embodiments, appropriate metal-catalyzed cross coupling conditions, such as Stille cross-coupling conditions, are described in Scheme 4.

In some embodiments, compound V-2 is prepared from appropriate metal-catalyzed cross coupling conditions of halide V-1 with an aromatic compound V-7. In some embodiments, appropriate metal-catalyzed cross coupling conditions, such as C—H activation conditions, are described in Scheme 4.

In some embodiments, boron reagent V-3 is reacted with an aromatic halide V-8 under suitable metal-catalyzed cross-coupling reaction conditions to provide V-4. In some embodiments, boron reagent V-3 is a boronic acid or boronic ester. In some embodiments, the aromatic halide is aromatic bromide or aromatic iodide. In some embodiments, suitable metal-catalyzed cross-coupling conditions include palladium. In some embodiments, suitable palladium-catalyzed cross-coupling reaction conditions include $Pd(dppf)Cl_2$ with an appropriate base, with an appropriate solvent for an appropriate time and at an appropriate temperature. In some embodiments, the base is an inorganic base. In some embodiments, the inorganic base is a carbonate base such as $K_2CO_3$. In some embodiments, the appropriate solvent is a dioxane. In some embodiments, the appropriate time and appropriate temperature is about 4 hours at about 80° C.

In some embodiments, aryl halide V-3 is reacted with boron reagent V-8 under suitable metal-catalyzed cross-coupling reaction conditions to provide V-4. In some embodiments, the boron reagent is an aromatic boronic acid. In some embodiments, the boron reagent is an aromatic boronic ester. In some embodiments, the aryl halide is an aryl iodide or aryl bromide. In some embodiments, suitable metal-catalyzed cross-coupling conditions include palladium. In some embodiments, suitable palladium-catalyzed cross-coupling reaction conditions include $Pd(dppf)Cl_2$ with an appropriate base, with an appropriate solvent for an appropriate time and at an appropriate temperature. In some embodiments, the base is an inorganic base. In some embodiments, the inorganic base is a carbonate base such as $K_2CO_3$. In some embodiments, the appropriate solvent is dioxane. In some embodiments, the appropriate time and appropriate temperature is about 20 min at about 90° C.

In some embodiments, compound V-4 is prepared from appropriate metal-catalyzed cross coupling conditions of halide V-3 with nitrogen-containing heterocycle V-8. In some embodiments, appropriate metal-catalyzed cross coupling conditions, such as Buchwald-Hartwig amination conditions, are described in Scheme 4.

In some embodiments, compound V-4 is prepared from appropriate metal-catalyzed cross coupling conditions of halide V-3 with a tin reagent V-8. In some embodiments, appropriate metal-catalyzed cross coupling conditions, such as Stille cross-coupling conditions, are described in Scheme 4.

In some embodiments, compound V-4 is prepared from appropriate metal-catalyzed cross coupling conditions of tin reagent V with an aromatic halide V-8. In some embodiments, appropriate metal-catalyzed cross coupling conditions, such as Stille cross-coupling conditions, are described in Scheme 4.

In some embodiments, compound V-4 is prepared from appropriate metal-catalyzed cross coupling conditions of halide V-3 with an aromatic compound V-8. In some embodiments, appropriate metal-catalyzed cross coupling conditions, such as C—H activation conditions, are described in Scheme 4.

In some embodiments, V-2 is subjected to suitable nitro reduction conditions to provide aniline V-4. Suitable nitro reduction conditions include the use of metal catalysts. Suitable metal-catalyzed reductions include palladium-catalyzed hydrogenation conditions. In some embodiments, suitable palladium-catalyzed hydrogenation conditions include use of 10% Pd/C with hydrogen (1 atm) in a suitable solvent, such as methanol, for an appropriate amount of time at an appropriate temperature. In some embodiments, appropriate conditions include addition of HCl in water. In some embodiments, the appropriate amount of time at the appropriate temperature is about one hour at about rt.

Alternatively in some embodiments, suitable nitro reduction conditions include use of a tin reducing agent in the appropriate solvent, for the appropriate amount of time at the appropriate temperature. In some embodiments, suitable tin reducing agents include $SnCl_2$—$H_2O$. In some embodiments, the appropriate solvent is a water and ethanol mixture. In some embodiments, the appropriate amount of time at the appropriate temperature is about two hours to about 16 hours at about 80° C. In some embodiments, the appropriate amount of time at the appropriate temperature is about two hours to about 2 hours at about rt.

Alternatively in some embodiments, suitable nitro reduction conditions include use of a zinc reducing agent and an acid in the appropriate solvent, for the appropriate amount of time at the appropriate temperature. In some embodiments, the appropriate acid includes acetic acid. In some embodiments, suitable zinc reducing agents include metallic Zn. In some embodiments, the appropriate solvent is ACN. In some embodiments, the appropriate amount of time at the appropriate temperature is about one hour at about 0° C. to about rt.

In some embodiments, an appropriate aldehyde is reacted with aniline V-4 under suitable reductive amination conditions to obtain V-5. In some embodiments, suitable reductive amination conditions include use of a suitable reducing agent in an appropriate solvent, at an appropriate temperature for a suitable amount of time. In some embodiments, an appropriate solvent is DCE or DCM. In some embodiments, an appropriate solvent is DCE/acetic acid or DCM/acetic acid mixtures. In some embodiments, $NaBH(OAc)_3$ is used as a reducing agent. In some embodiments, the appropriate temperature is about 0° C. to about rt. In some embodiments, the suitable amount of time is about one hour to about overnight. In some embodiments, suitable reaction conditions include acetic acid in an appropriate solvent, such as methanol, at an appropriate temperature for a suitable amount of time before addition of a reducing agent. In some embodiments, the appropriate temperature and time is about rt for about 5 minutes to about 4 hours. In some embodiments, the reaction is subjected to a suitable reducing agent, such as $NaBH_3CN$, for the appropriate time and at the appropriate temperature. In some embodiments, the appropriate amount of time at the appropriate temperature after addition of $NaBH_3CN$ is about overnight at about rt.

In some embodiments, the acylation of amine V-5 with an acyl chloride affords compound V-6. Suitable acylation conditions include but are not limited to the use of a suitable base, such as TEA or pyridine in a suitable solvent, such as DCM, toluene or pyridine, for an appropriate amount of time and at a suitable temperature after addition of the acyl chloride. In some embodiments, a suitable temperature and appropriate amount of time are about rt to about 80° C. for about one hour to about overnight. Other suitable conditions include the addition of DMAP. In some embodiments, the acyl chloride is added in an appropriate solvent, such as toluene. In some embodiments, a suitable temperature and appropriate amount of time after addition of the acid chloride are about 0° C. to about 50° C. or about 0° C. to about 80° C. for about 10 min to about overnight.

In some embodiments, $R^{10}$ or $R^{11}$ is a protected alcohol. In some embodiments, $R^{10}$ or $R^{11}$ is an alcohol protected with a silyl ether. In some embodiments, protecting groups are removed to produce a free alcohol using suitable deprotection conditions as described in Scheme 4.

In some embodiments, compounds described herein are prepared as outlined in Scheme 6.

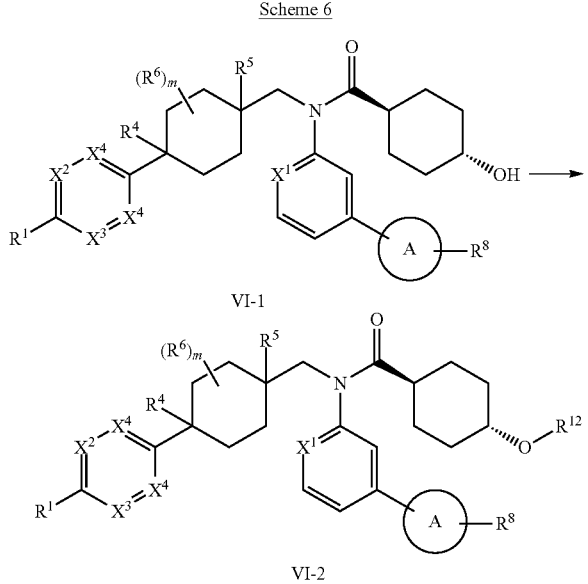

Scheme 6

In Scheme 6, ring A and substituents $X^1$, $X^2$, $X^3$, $X^4$, $R^1$, $R^2$, $R^4$, $R^5$, $R^6$, $R^8$, $R^{12}$, and m are as described herein. In some embodiments, $X^2$ is C—$R^2$, $X^3$ is C—H, and each $X^4$ is C—H.

In some embodiments, compound VI-2 is prepared from the O-alkylation of VI-1 with $R^{12}X$, a suitable base, and suitable solvent, such as THF, at a suitable temperature for a suitable amount of time. In some embodiments, X is a halide. In some embodiments, a suitable base is NaH. In some embodiments, the compound VI-1 is pretreated with the suitable base for an appropriate amount of time at an appropriate temperature, such as about 0.5 h at about 0° C., before the addition of the halide $R^{12}X$. In some embodiments, the appropriate time and temperature is about overnight at about 60° C.

In some embodiments, compounds described herein are prepared as outlined in Scheme 7.

Scheme 7

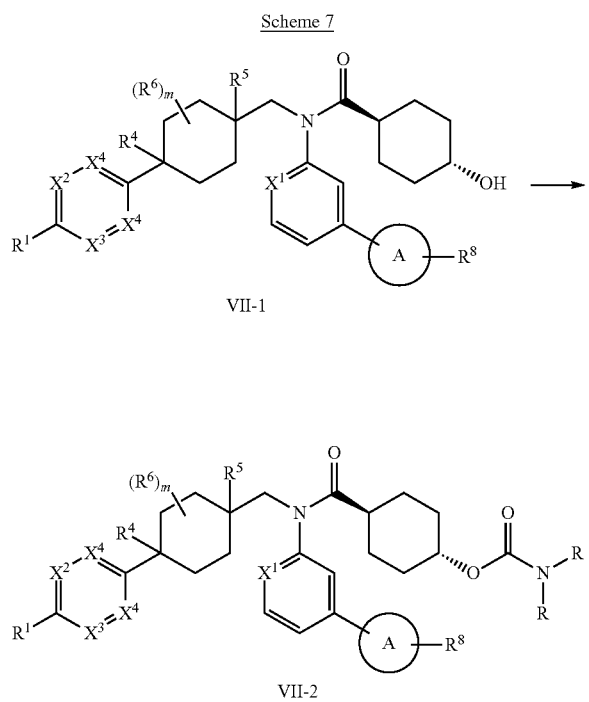

Scheme 8

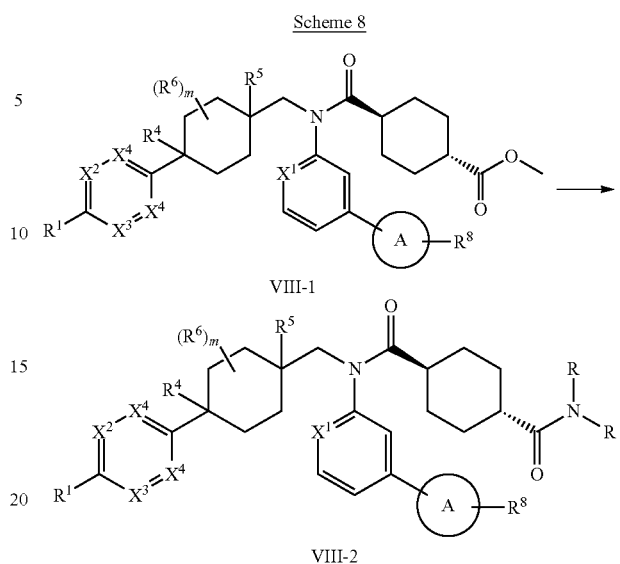

In Scheme 7, ring A and substituents $X^1$, $X^2$, $X^3$, $X^4$, $R^1$, $R^2$, $R^4$, $R^5$, $R^6$, $R^8$, and m are as described herein. In some embodiments, $X^2$ is C—$R^2$, $X^3$ is C—H, and each $X^4$ is C—H. In some embodiments, each R is independently alkyl, heteroalkyl, or hydroxyalkyl or hydrogen, or both R are taken together to form a substituted or unsubstituted fused 4-, 5-, or 6-membered ring with 0-3 N atoms and 0-2 O or S atoms in the ring.

In some embodiments, VII-2 is prepared from VII-1 and an amine $NHR_2$. In some embodiments, VII-1 is subjected to carbonyldiimidazole in an appropriate solvent, such as ACN, at a suitable temperature, such as at about 80° C., for an appropriate amount of time to provide the intermediate carbamoyl imidazole. In some embodiments, the appropriate amount of time is about 2 hours to about 6 hours or about overnight. In some embodiments, the intermediate carbamoyl imidazole is treated with $NHR_2$ in a suitable solvent, and the reaction is allowed to proceed for an appropriate amount of time at an appropriate temperature. In some embodiments, the suitable solvent is acetonitrile. In some embodiments, the suitable solvent is MeOH, THF, or DCM. In some embodiments, the $NHR_2$ is added as a solution in MeOH, THF, or DCM. In some embodiments, the $NHR_2$ is added neat. In some embodiments, the appropriate amount of time at the appropriate temperature is about 15 minutes to about overnight at about rt. In some embodiments, the appropriate amount of time is about 1 day to about 7 days. In some embodiments, the appropriate temperature is about rt to about 50° C. or about rt to about 100° C. In some embodiments, when an $NHR_2$ hydrochloride is used instead of $NHR_2$, then a suitable base, such as $iPr_2NEt$, is added prior to addition of the $NHR_2$ hydrochloride.

In some embodiments, compounds described herein are prepared as outlined in Scheme 8.

In Scheme 8, ring A and substituents $X^1$, $X^2$, $X^3$, $X^4$, $R^1$, $R^2$, $R^4$, $R^5$, $R^6$, $R^8$, and m are as described herein. In some embodiments, $X^2$ is C—$R^2$, $X^3$ is C—H, and each $X^4$ is C—H. In some embodiments, each R is independently alkyl, heteroalky, hydroxyalkyl or hydrogen, or both R are taken together to form a substituted or unsubstituted fused 4-, 5-, or 6-membered ring with 0-3 N atoms and 0-2 O or S atoms in the ring.

In some embodiments, VIII-2 is prepared from VIII-1 and an amine $NHR_2$ via an acid. In some embodiments, VIII-1 is subjected to hydrolysis conditions to form an intermediate acid, in an appropriate solvent, at a suitable temperature, for a suitable period of time. In some embodiments, the hydrolysis conditions are basic. In some embodiments, the hydrolysis conditions include the use of NaOH or LiOH. In some embodiments, the solvent is a THF/methanol/water mixture or a THF/water mixture. In some embodiments, a suitable temperature is about rt, and a suitable time is about 2 hours to about overnight. In some embodiments, the intermediate hydrolysis product is the desired compound. In some embodiments, the intermediate hydrolysis product and an amine $NHR_2$ are reacted under amidation conditions to form VIII-2. In some embodiments, a coupling agent, such as HATU is added to the acid in the presence of a base for a suitable period of time, at a suitable temperature, and in a suitable solvent. In some embodiments, the base is an amine base, such as N,N-diisopropylethylamine. In some embodiments, the solvent is DMF. In some embodiments, after an appropriate amount of time at a suitable temperature, such as about 10 minutes at about 0° C., $NHR_2$ is added and the reaction is allowed to proceed for an appropriate amount of time at an appropriate temperature to form VIII-2. In some embodiments, DBU is also added. In some embodiments, the appropriate amount of time at the appropriate temperature is about 10 minutes to about 30 minutes at about 0° C. to about rt.

In some embodiments, the intermediate hydrolysis product is treated with N-(3-dimethylaminopropyl)-N'-ethylcarbodiimide hydrochloride (EDC), $Et_3N$, DMAP, and HOBt at a suitable temperature in a suitable solvent. In some embodiments, the suitable solvent is DCM. In some embodiments, the suitable temperature is 0° C. In some embodiments, after a suitable period of time, such as about 10 minutes, $NHR_2$ is added, and the reaction is allowed to proceed for an appropriate amount of time at an appropriate temperature to form VIII-2. In some embodiments, the appropriate amount of time at the appropriate temperature is about overnight at about 0° C. to about rt.

In some embodiments, compounds described herein are prepared as outlined in Scheme 9.

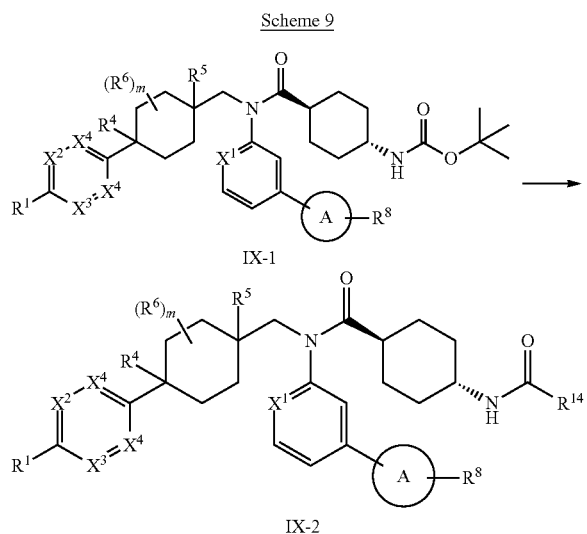

In Scheme 9, ring A and substituents $X^1$, $X^2$, $X^3$, $X^4$, $R^1$, $R^2$, $R^4$, $R^5$, $R^6$, $R^8$, $R^{14}$, and m are as described herein. In some embodiments, $X^2$ is C—$R^2$, $X^3$ is C—H, and each $X^4$ is C—H.

In some embodiments, IX-1 is subjected under appropriate acidic conditions to provide an amine. In some embodiments, the appropriate acidic conditions include the use of TFA in a suitable solvent, such as DCM, at an appropriate temperature for an appropriate amount of time. In some embodiments, the appropriate acidic conditions include the use of HCl in a suitable solvent, such as dioxane, at an appropriate temperature for an appropriate amount of time. In some embodiments, the appropriate temperature for an appropriate amount of time is about 0° C. to about rt for about 0.5 hours to about 2 hours. In some embodiments, the amine is reacted with an anhydride $(R^{14}CO)_2O$ to provide IX-2 in the presence of a suitable base and solvent at an appropriate temperature for an appropriate amount of time. In some embodiments, the suitable base is TEA or pyridine. In some embodiments, the suitable solvent is ethyl acetate or DCM. In some embodiments, the appropriate temperature for an appropriate amount of time is about 0° C. to about rt for about 10 minutes to about 2 hours. Alternatively, the amine is reacted with acyl chloride $R^{14}COCl$ or chloroformate $ClCO_2R^{14}$ to provide IX-2 in the presence of a suitable base and solvent at an appropriate temperature for an appropriate amount of time. In some embodiments, the suitable base is pyridine or TEA. In some embodiments, the suitable solvent is DCM or ethyl acetate. In some embodiments, the appropriate temperature for an appropriate amount of time is about 0° C. to about rt for about 10 minutes to about 2 hours. Alternatively, the amine is reacted with sulfonyl chloride $R^{14}SO_2Cl$ to provide IX-2 in the presence of a suitable base and solvent at an appropriate temperature for an appropriate amount of time. In some embodiments, the suitable base is TEA or pyridine. In some embodiments, the suitable solvent is DCM or ethyl acetate. In some embodiments, the appropriate temperature for an appropriate amount of time is about 0° C. for about 10 min to about 2 hours. Alternatively, the amine is reacted with carboxylic acid $R^{14}CO_2H$ to provide IX-2 in the presence of a suitable base and solvent for an appropriate amount of time. In some embodiments, the suitable base is TEA. In some embodiments, the suitable solvent is DMF. In some embodiments, the appropriate temperature is about 0° C. In some embodiments, propylphosphonic anhydride is added after an appropriate amount of time, and the reaction is allowed to proceed at an appropriate temperature for an appropriate amount of time. In some embodiments, the appropriate temperature for an appropriate amount of time is about 0° C. to about rt for about overnight.

In some embodiments, intermediates used in the preparation of compounds described herein are prepared as outlined in Scheme 10.

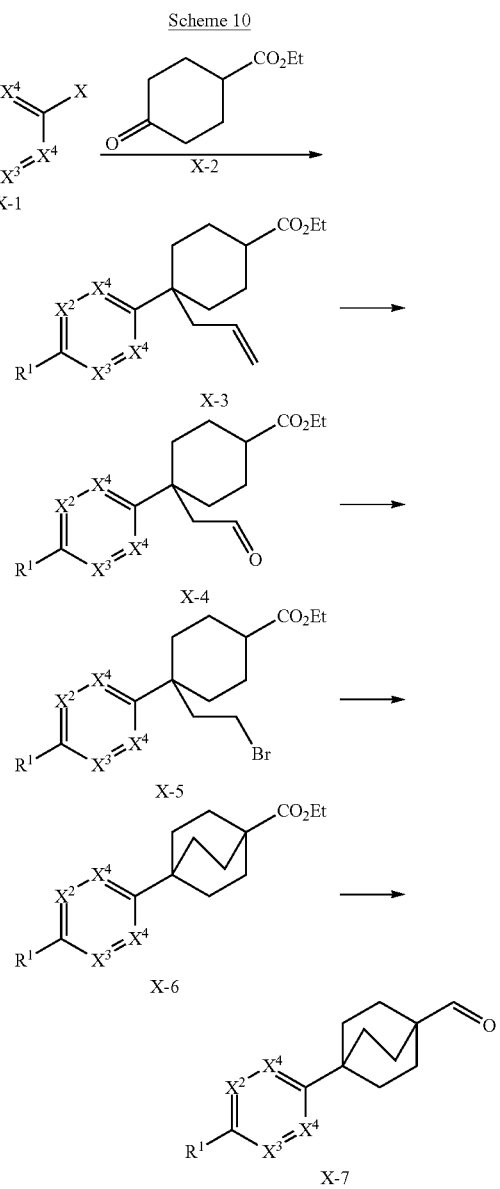

In Scheme 10, substituents $X^2$, $X^3$, $X^4$, $R^1$, and $R^2$ are as described herein. In some embodiments, $X^2$ is C—$R^2$, $X^3$ is C—H, and each $X^4$ is C—H. In some embodiments, X is a halide. In some embodiments, X is chloro, bromo or iodo.

In some embodiments, halide X-1 is cooled to a suitable temperature, reacted under suitable metal-halogen exchange conditions with an appropriate solvent for an appropriate time and at an appropriate temperature, and then later reacted with an appropriate ketone X-2 for an appropriate time and at an appropriate temperature to provide a tertiary alcohol. In some embodiments, suitable metal-halogen exchange conditions include an organometallic reagent. In some embodiments, an appropriate solvent is THF. In some embodiments, the organometallic reagent is an alkyl lithium. In some embodiments, the alkyllithium is n-butyl lithium. In some embodiments, X-1 is cooled to about −78° C. before addition of an organometallic reagent. In some embodiments, X-1 is reacted for about one hour at about −78° C. before addition of the appropriate ketone X-2. In some embodiments, X is reacted for about 2 hours after the addition of ketone X-2. In some embodiments, the appropriate temperature for reacting X-1 and ketone X-2 is about −78° C. In some embodiments, the tertiary alcohol is reacted under appropriate allylation conditions which include use of an allylating reagent and a Lewis acid, in an appropriate solvent for an appropriate time and at an appropriate temperature to form X-3. In some embodiments, the appropriate allylating reagent is allyltrimethylsilane. In some embodiments, the appropriate Lewis acid is $BF_3$-$OEt_2$. In some embodiments, the appropriate solvent is DCM. In some embodiments, the appropriate temperature for the appropriate time is about −78° C. for about 1 hour. In some embodiments, the reaction is further warmed to about rt for about overnight. In some embodiments, the appropriate temperature for the appropriate time is about 0° C. for about overnight.

In some embodiments, X-3 is reacted under suitable oxidative cleavage conditions for the appropriate time period, in the appropriate solvent, and at the appropriate temperature to produce X-4. In some embodiments, oxidative cleavage conditions include the use of an osmium reagent and N-methylmorpholine N-oxide to form an intermediate diol. In some embodiments, the osmium reagent is $OsO_4$ or $K_2OsO_4 \cdot 2H_2O$. In some embodiments, an appropriate solvent is an ACN/water mixture. In some embodiments, an appropriate temperature for the appropriate time is about 0° C. to about rt for about overnight. In some embodiments, the diol is cleaved to form X-4 under the appropriate oxidative cleavage conditions for the appropriate time period, in the appropriate solvent, and at the appropriate temperature. In some embodiments, appropriate oxidative cleavage conditions include the use of $NaIO_4$. In some embodiments, an appropriate solvent is a THF/water mixture. In some embodiments, the appropriate temperature for the appropriate time is about 0° C. to about rt for about overnight.

In some embodiments, X is reduced to a primary alcohol under suitable reducing conditions, and then halogenated under suitable halogenation conditions to produce X-5. In some embodiments, suitable reducing conditions include the use of a borohydride reagent. In some embodiments, reducing conditions include the use of $NaBH_4$ in the appropriate solvent, at an appropriate temperature for the appropriate amount of time. In some embodiments, an appropriate solvent is THF. In some embodiments, an appropriate temperature for the appropriate time is about 0° C. for about one hour. In some embodiments, the reaction is warmed to about rt for about overnight. The alcohol is reacted under suitable halogenation conditions to produce an alkyl halide in some embodiments. In some embodiments, suitable halogenation conditions are bromination conditions that include use of $CBr_4$ in an appropriate solvent at an appropriate initial temperature followed by $PPh_3$ in the appropriate solvent, at an appropriate temperature for an appropriate time. In some embodiments, the appropriate solvent is a halogenated solvent, such as DCM. In some embodiments, an appropriate initial temperature is about 0° C. In some embodiments, an appropriate temperature and time after addition of $PPh_3$ is about 0° C. for about 1 hour. In some embodiments, an appropriate solvent for addition of $PPh_3$ is THF. In some embodiments, the reaction is further warmed to about rt for about overnight.

In some embodiments, X is subjected to intramolecular alkylation conditions to form X-6. In some embodiments, intramolecular alkylation conditions include a suitable base. In some embodiments, the suitable base is lithium diisopropylamide in the appropriate solvent, at an appropriate temperature for an appropriate amount of time. In some embodiments, the appropriate solvent is a HMPA and THF mixture. In some embodiments, the appropriate temperature for the appropriate amount of time is about −78° C. for about 3 hours or about −78° C. to rt for about overnight.

Ester X-6 is reduced to an alcohol by suitable reduction conditions followed by oxidation to aldehyde X-7 by suitable oxidation conditions in some embodiments. In some embodiments, suitable reduction conditions include the use of DIBALH in an appropriate solvent at an appropriate temperature for an appropriate time. In some embodiments, the appropriate solvent is DCM. In some embodiments, the appropriate temperature for the appropriate time is about −78° C. for about one hour. In some embodiments, the reaction is further warmed to about rt for about two hours to produce an alcohol. In some embodiments, suitable oxidation conditions are chromium-based oxidations. In some embodiments, suitable oxidation conditions include the use of PCC in an appropriate solvent at an appropriate temperature for an appropriate time. In some embodiments, silica gel is added. In some embodiments, the appropriate solvent is DCM. In some embodiments, the appropriate temperature is about rt for about 2 hours. Alternatively in some embodiments, the oxidations conditions include the use of oxalyl chloride and DMSO with an amine base in an appropriate solvent at an appropriate temperature for an appropriate time. In some embodiments, the appropriate amine base is TEA. In some embodiments, the appropriate solvent is DCM. In some embodiments, the appropriate temperature for the appropriate amount of time is about −78° C. for about 1 hour.

In some embodiments, intermediates used in the preparation of compounds described herein are prepared as outlined in Scheme 11.

Scheme 11

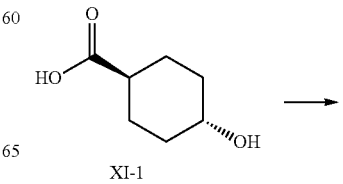

XI-1

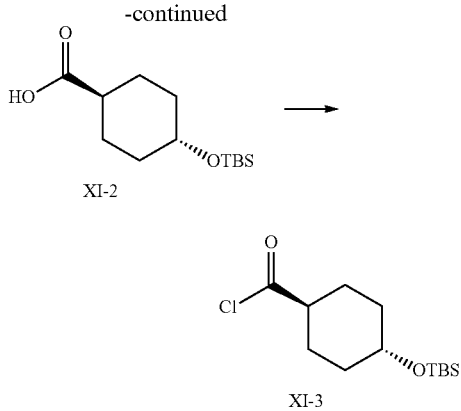

XI-2

XI-3

In some embodiments, XI-1 is subjected to alcohol protection conditions to form a bis-silyl intermediate, followed by hydrolysis conditions to form XI-2. In some embodiments, the alcohol protection conditions include the use of TBSCl and an appropriate base at the appropriate temperature, in the appropriate solvent, and for an appropriate period of time. In some embodiments, the appropriate solvent is DMF. In some embodiments, the appropriate base is imidazole. In some embodiments, the appropriate temperature for the appropriate time is about rt for about 2 hours. In some embodiments, the intermediate silyl ester is subjected to hydrolysis conditions to form XI-2. In some embodiments, hydrolysis conditions include treatment with a base, at an appropriate temperature, in an appropriate solvent, and for an appropriate period of time. In some embodiments, the appropriate solvent is an EtOH, $H_2O$, THF mixture. In some embodiments, the appropriate base is $K_2CO_3$. In some embodiments, the appropriate temperature for the appropriate time is about rt for about 3 hours.

Compound XI-2 is converted to acid chloride XI-3, in some embodiments, under chlorinating conditions. In some embodiments, chlorinating conditions include the use of (chloromethylene)dimethyliminium chloride and a base at a suitable temperature, in a suitable solvent. In some embodiments, the suitable base is anhydrous $K_2CO_3$. In some embodiments, the suitable temperature is about 0° C. In some embodiments, a suitable solvent is toluene. In some embodiments, XI-2 is added and the mixture stirred at a suitable temperature for a suitable time to produce XI-3. In some embodiments, the suitable temperature for the suitable time is about rt for about 0.5 to about one hour.

In some embodiments, compounds described herein are prepared as outlined in Scheme 12.

Scheme 12

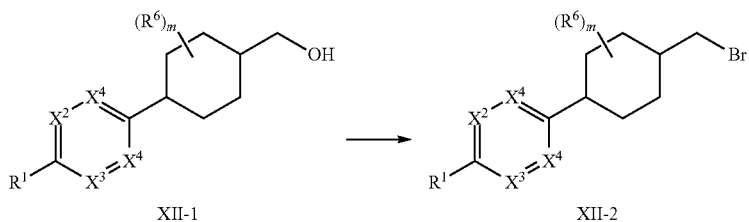

XII-1

XII-2

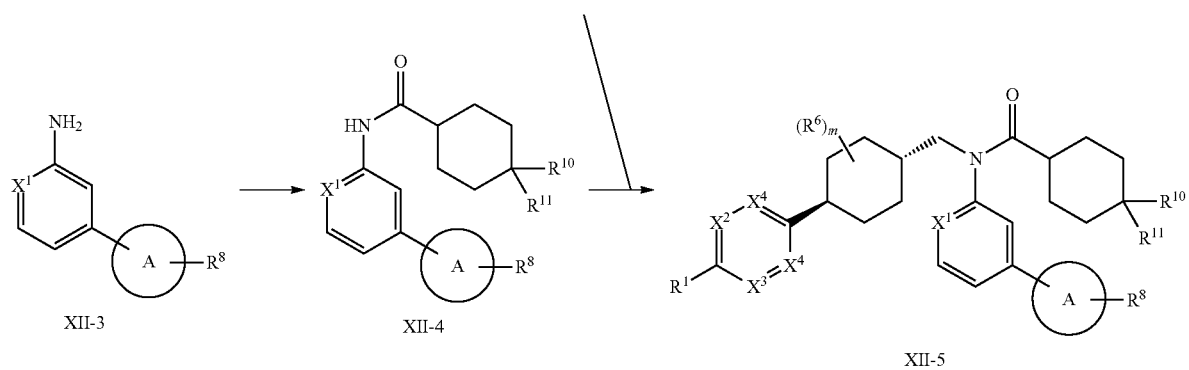

XII-3

XII-4

XII-5

433

In Scheme 12, ring A and substituents $X^1$, $X^2$, $X^3$, $X^4$, $R^1$, $R^2$, $R^6$, $R^8$, $R^{10}$, $R^{11}$, and m are as described herein. In some embodiments, $X^2$ is C—$R^2$, $X^3$ is C—H, and each $X^4$ is C—H.

Alcohol XII-1 is reacted under suitable halogenation conditions to produce an alkyl halide XII-2 in some embodiments. In some embodiments, suitable halogenation conditions are bromination conditions including the use of $CBr_4$ in an appropriate solvent at an appropriate initial temperature followed by $PPh_3$ in the appropriate solvent, at an appropriate temperature for an appropriate time. In some embodiments, the appropriate solvent is a halogenated solvent, such as DCM. In some embodiments, an appropriate initial temperature is about 0° C. In some embodiments, an appropriate temperature and time after addition of $PPh_3$ is about 0° C. for about one hour. In some embodiments, the reaction is further warmed to about rt for about overnight.

In some embodiments, the acylation of amine XII-3 with an acyl chloride affords compound XII-4. Suitable acylation conditions include but are not limited to the use of a suitable base, such as pyridine in a suitable solvent, such as DCM or toluene at a suitable temperature, such as about 0° C. In some embodiments, an acyl chloride is added in an appropriate solvent at an appropriate temperature for an appropriate amount of time. In some embodiments, the appropriate solvent is toluene. In some embodiments, the appropriate temperature is about 0° C. then warming to rt for about overnight.

In some embodiments, compound XII-5 is prepared from the N-alkylation of XII-4 with bromide XII-2 and a suitable base in suitable solvent, such as DMF, at a suitable temperature for a suitable amount of time. Suitable bases include NaH. In some embodiments, the compound XII-4 is pretreated with the suitable base for an appropriate amount of time at an appropriate temperature, such as about two hours at about 0° C. to about rt, before the addition of bromide XII-2. In some embodiments, the appropriate time and temperature after addition of bromide XII-2 is about rt for about overnight. In some embodiments, $R^{10}$ or $R^{11}$ is a protected alcohol. In some embodiments, $R^{10}$ or $R^{11}$ is an alcohol protected with a silyl ether. In some embodiments, protecting groups are removed to produce a free alcohol using suitable deprotection conditions including an appropriate solvent, temperature and time to produce XII-5. In some embodiments, suitable deprotection conditions include the use of fluoride reagents. In some embodiments, the fluoride reagent is $NH_4F$. In some embodiments, the appropriate solvent is methanol. In some embodiments, the appropriate time at the appropriate temperature is about overnight at about 60° C.

In some embodiments, compounds described herein are prepared as outlined in Scheme 13.

Scheme 13

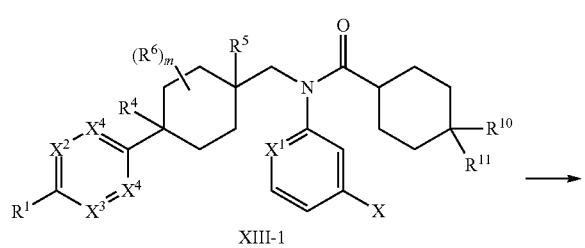

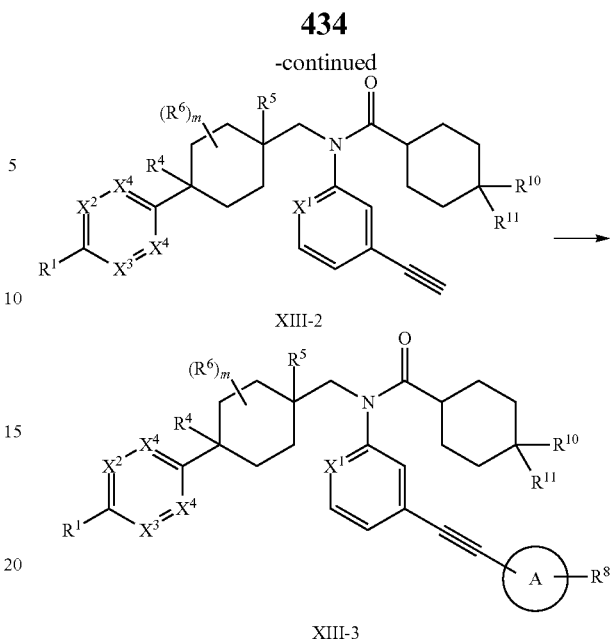

In Scheme 13, ring A and substituents $X^1$, $X^2$, $X^3$, $X^4$, $R^1$, $R^2$, $R^4$, $R^5$, $R^6$, $R^8$, $R^{10}$, $R^{11}$, and m are as described herein. In some embodiments, $X^2$ is C—$R^2$, $X^3$ is C—H, and each $X^4$ is C—H. In some embodiments, X is a suitable cross-coupling substituent. In some embodiments, X is a halide. In some embodiments, X is chloro, bromo, or iodo.

In some embodiments, compound XIII-1 is reacted with a suitable acetylene source under suitable metal-catalyzed cross-coupling reaction conditions to provide XIII-2. In some embodiments, suitable metal-catalyzed cross-coupling conditions include palladium. In some embodiments, a suitable acetylene source is trimethylsilylacetylene. In some embodiments, suitable palladium-catalyzed cross-coupling reaction conditions include $Pd(PPh_3)_2Cl_2$, a copper catalyst, with an appropriate base, for an appropriate time and at an appropriate temperature. In some embodiments, the copper catalyst is CuI. In some embodiments, the base is an amine base, such as TEA. In some embodiments, the appropriate time and appropriate temperature is about 6 hours at about 90° C. In some embodiments, the TMS-group is removed after the cross-coupling, under suitable deprotection conditions including an appropriate solvent, temperature and time to produce to form XIII-2. In some embodiments, suitable deprotection conditions include the use of fluoride reagents. In some embodiments, the fluoride reagent is $NH_4F$. In some embodiments, the appropriate solvent is methanol. In some embodiments, the appropriate time is about one hour at about 60° C.

In some embodiments, acetylene XIII-2 is reacted with a suitable aromatic halide under suitable metal-catalyzed cross-coupling reaction conditions to provide XIII-3. In some embodiments, suitable metal-catalyzed cross-coupling conditions include palladium. In some embodiments, the aromatic halide is an aromatic iodide. In some embodiments, suitable palladium-catalyzed cross-coupling reaction conditions include $Pd(PPh_3)_2Cl_2$, a copper catalyst, with an appropriate base, for an appropriate time and at an appropriate temperature. In some embodiments, the copper catalyst is CuI. In some embodiments, the base is an amine base, such as TEA. In some embodiments, the appropriate time and appropriate temperature is about one hour at about 80° C. to about 90° C. or about 70° C. to about 90° C.

In some embodiments, $R^{10}$ or $R^{11}$ is a protected alcohol. In some embodiments, $R^{10}$ or $R^{11}$ is an alcohol protected with a silyl ether. In some embodiments, protecting groups are removed to produce a free alcohol using suitable deprotection conditions including appropriate solvent, temperature and time to produce XIII-3. In some embodiments, suitable deprotection conditions include the use of aqueous HCl. In some embodiments, the appropriate solvent is water, THF, methanol, or a combination of solvents. In some embodiments, the appropriate time at the appropriate temperature is about 30 min to about 1 hour at about 0° C. to about rt.

In some embodiments, intermediates used in the preparation of compounds described herein are prepared as outlined in Scheme 14.

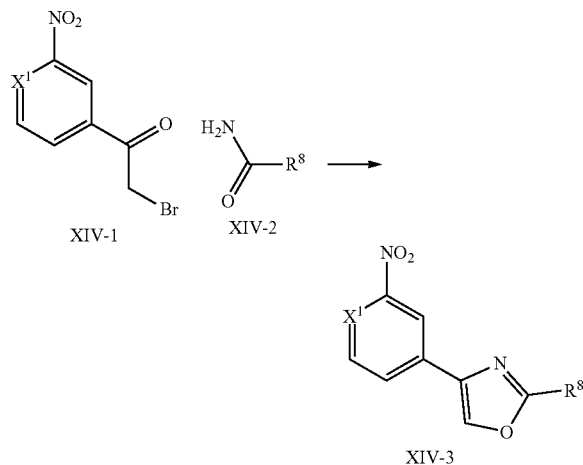

In Scheme 14, substituent $X^1$ and $R^8$ are as described herein.

In some embodiments, XIV-3 is prepared from reacting amide XIV-2 and bromide XIV-1 under appropriate addition/cyclization conditions. In some embodiments, addition/cyclization conditions include a suitable solvent, at a suitable temperature for an appropriate amount of time. In some embodiments, the suitable solvent is toluene. In some embodiments, the suitable temperature for a suitable time is about 110° C. for about overnight.

In some embodiments, intermediates used in the preparation of compounds described herein are prepared as outlined in Scheme 15.

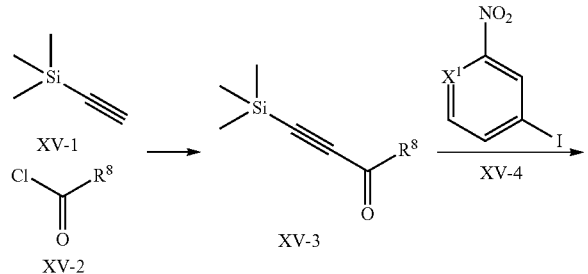

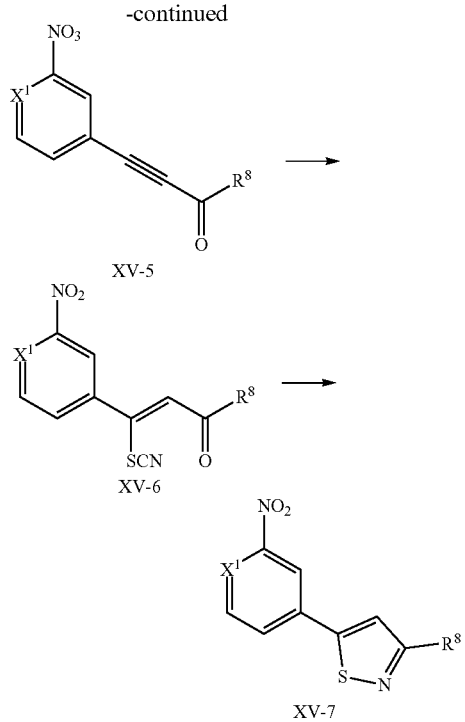

In Scheme 15, substituent $X^1$ and $R^8$ are as described herein.

In some embodiments, chloride XV-2 is reacted with acetylene XV-1 under suitable metal-catalyzed cross-coupling reaction conditions to provide XV-3. In some embodiments, suitable metal-catalyzed cross-coupling conditions include palladium. In some embodiments, suitable palladium-catalyzed cross-coupling reaction conditions include $Pd(PPh_3)_2Cl_2$, a copper catalyst, with an appropriate base, in an appropriate solvent, for an appropriate time and at an appropriate temperature. In some embodiments, the copper catalyst is CuI. In some embodiments, the base is an amine base, such as TEA. In some embodiments, a suitable solvent is THF. In some embodiments, the appropriate time and appropriate temperature is about one hour at about rt.

In some embodiments, acetylene XV-3 is reacted with a suitable aromatic halide XV-4 under suitable metal-catalyzed cross-coupling reaction conditions in the presence of TBAF to provide XV-5. In some embodiments, suitable metal-catalyzed cross-coupling conditions include palladium. In some embodiments, the aromatic halide is an aromatic iodide. In some embodiments, suitable palladium-catalyzed cross-coupling reaction conditions include $Pd(PPh_3)_2Cl_2$, a ligand, a copper catalyst, in an appropriate solvent, with an appropriate base, for an appropriate time and at an appropriate temperature. In some embodiments, the copper catalyst is CuI. In some embodiments, an appropriate ligand is a phosphine ligand. In some embodiments, an appropriate ligand is $PPh_3$. In some embodiments, the base is an amine base, such as TEA. In some embodiments, the appropriate solvent is DMF. In some embodiments, the appropriate temperature is 60° C. In some embodiments, TBAF is added and the reaction is maintained at 60° C. for the appropriate amount of time. In some embodiments, the appropriate time is about 3 hours.

In some embodiments, compound XV-6 is prepared from reaction of XV-5 and a thiocyanate under conjugate addition conditions. In some embodiments, conjugate addition conditions include use of a suitable thiocyanate salt in a suitable solvent for a suitable time at a suitable temperature. In some embodiments, a suitable thiocyanate salt is NH₄SCN. In some embodiments, a suitable solvent is methyl tert-butyl ether. In some embodiments, a suitable time is about overnight. In some embodiments, a suitable temperature is 60° C.

In some embodiments, compound XV-7 is prepared from reaction of XV-6 and an ammonia source for a suitable time at a suitable temperature. In some embodiments, a suitable ammonia source is NH₃. In some embodiments, a suitable temperature is −78° C. In some embodiments, a suitable time is about 2 hours. In some embodiments, the reaction is further warmed to a suitable temperature, such as about rt.

In some embodiments, intermediates used in the preparation of compounds described herein are prepared as outlined in Scheme 16.

In some embodiments, when X is bromo, α-diazocarbonyl XVI-6 is treated with HBr/H₂O in a suitable solvent for a suitable time at a suitable temperature to provide α-bromoketone XVI-2. In some embodiments, the suitable solvent is THF/ACN. In some embodiments, the suitable time is about 30 minutes. In some embodiments, a suitable temperature is about 0° C. to about room temperature.

In some embodiments, when X is chloro, α-diazocarbonyl XVI-6 is treated with concentrated HCl in a suitable solvent for a suitable time at a suitable temperature to provide α-chloroketone XVI-2. In some embodiments, the suitable solvent is THF/ACN. In some embodiments, the suitable time is about 30 minutes. In some embodiments, a suitable temperature is about 0° C. to about room temperature.

In some embodiments, α-haloketone XVI-2 is treated with amide XVI-3 and AgOTf in a suitable solvent for a Scheme 16

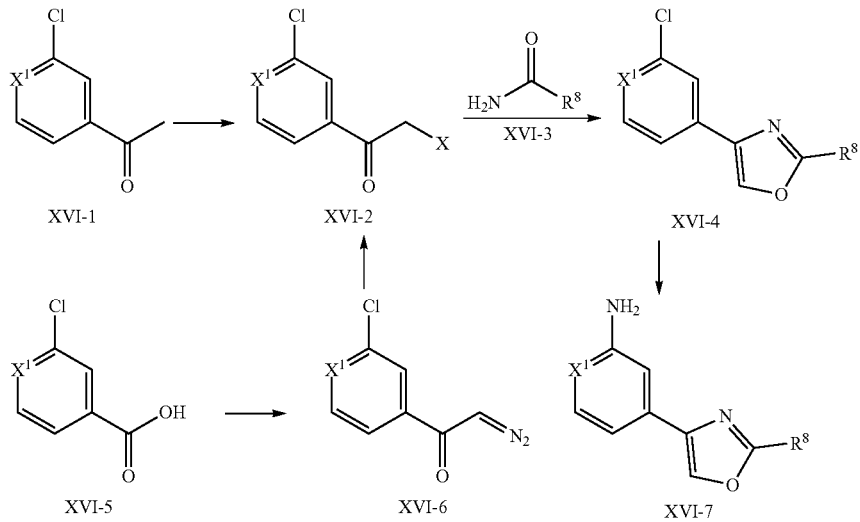

In Scheme 16, substituent X¹ and R⁸ are as described herein. In some embodiments, X is halo, such as bromo or chloro.

In some embodiments, when X is bromo, α-bromoketone XVI-2 is obtained from subjecting ketone XVI-1 under suitable bromination conditions. In some embodiments, suitable bromination conditions include bromine, HBr, and acetic acid for a suitable time at a suitable temperature. In some embodiments, the suitable time is about overnight. In some embodiments, a suitable temperature is about room temperature.

Alternatively, in some embodiments, α-haloketone XVI-2 is prepared from acid XVI-5. In some embodiments, XVI-5 is treated with (COCl)₂ in a suitable solvent for a suitable time at a suitable temperature to provide an intermediate acid chloride. In some embodiments, the suitable solvent is DMF and DCM. In some embodiments, the suitable time is about 2.5 hours. In some embodiments, a suitable temperature is about 0° C. to about room temperature. In some embodiments, the intermediate acid chloride is treated with TMSCHN₂ in a suitable solvent for a suitable time at a suitable temperature to provide α-diazocarbonyl XVI-6. In some embodiments, the suitable solvent is THF/ACN. In some embodiments, the suitable time is about 1 hour. In some embodiments, a suitable temperature is about 0° C. to about room temperature.

suitable time at a suitable temperature to provide XVI-4. In some embodiments, the suitable solvent is EtOAc or dioxane. In some embodiments, the suitable time is about overnight. In some embodiments, a suitable temperature is about 70° C. or about 100° C.

In some embodiments, XVI-4 is subjected under palladium-catalyzed cross coupling reaction conditions in the presence of a suitable ammonia source to provide XVI-7. In some embodiments, the suitable ammonia source is LiHMDS. In some embodiments, suitable palladium-catalyzed cross-coupling reaction conditions include Pd₂(dba)₃ with an appropriate ligand in an appropriate solvent for an appropriate time at an appropriate temperature. In some embodiments, the appropriate ligand is X-Phos. In some embodiments, the appropriate solvent is dioxane or THF. In some embodiments, the appropriate time and appropriate temperature is about 2 hours to about overnight at about 100° C. In some embodiments, the appropriate time and appropriate temperature is about overnight at about 60° C.

Additional procedures for the preparation of alternative ring A groups not shown in the preceding schemes are known, and are described in: Gangloff, A. R., et al. Synthesis of 3,5-disubstituted 1,2,4-oxadiazoles using tetrabutylammonium fluoride as a mild and efficient catalyst, Tetrahedron Letters (2001), 42(8), 1441-1443; Ramanathan, Mani, et al. One-Pot Reactions for Synthesis of 2,5-Substituted Tetrazoles from Aryldiazonium Salts and Amidines, Organic Letters (2015), 17(23), 5886-5889; Vallin, Karl S. A. et al., Efficient Chemoenzymatic Dynamic Kinetic Resolution of 1-Heteroaryl Ethanols, Journal of Organic Chemistry (2009), 74(24), 9328-9336; Shen, Lan et al, Synthesis and structure-activity relationships of thiadiazole-derivatives as potent and orally active peroxisome proliferator-activated receptors ?/? dual agonists, Bioorganic & Medicinal Chemistry, 16(6), 3321-3341; 2008; Genin, Michael J. et al, Discovery of 6-(4-{[5-Cyclopropyl-3-(2,6-dichlorophenyl) isoxazol-4-yl]methoxy}piperidin-1-yl)-1-methyl-1H-indole-3-carboxylic Acid: A Novel FXR Agonist for the Treatment of Dyslipidemia, Journal of Medicinal Chemistry (2015) 58(24), 9768-9772; Li, Xiaobing et al, PCT Int. Appl., 2005113522, 1 Dec. 2005 (Preparation of azole carboxamides as inhibitors of bacterial type III protein secretion systems); Hamada, Nagwa Mohamed Mahrous et al, Synthesis and antimicrobial evaluation of some heterocyclic chalcone derivatives, Molecules, 16, 2304-2312; 2011; Mokale, Santosh N. et al Synthesis and in-vivo hypolipidemic activity of some novel substituted phenyl isoxazol phenoxy acetic acid derivatives, Bioorganic & Medicinal Chemistry Letters, 24(9), 2155-2158; 2014; Jursic, Branko S. et. al. Preparation of 5-substituted 2-methyl-1,3,4-oxadiazoles from 5-substituted tetrazoles and acetic anhydride, Synthetic Communications (1994), 24(11), 1575-82.

In some embodiments, compounds are prepared as described in the Examples.

Certain Terminology

Unless otherwise stated, the following terms used in this application have the definitions given below. The use of the term "including" as well as other forms, such as "include", "includes," and "included," is not limiting. The section headings used herein are for organizational purposes only and are not to be construed as limiting the subject matter described.

As used herein, $C_1$-$C_x$ includes $C_1$-$C_2$, $C_1$-$C_3$ ... $C_1$-$C_x$. By way of example only, a group designated as "$C_1$-$C_4$" indicates that there are one to four carbon atoms in the moiety, i.e. groups containing 1 carbon atom, 2 carbon atoms, 3 carbon atoms or 4 carbon atoms. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl.

An "alkyl" group refers to an aliphatic hydrocarbon group. The alkyl group is branched or straight chain. In some embodiments, the "alkyl" group has 1 to 10 carbon atoms, i.e. a $C_1$-$C_{10}$alkyl. Whenever it appears herein, a numerical range such as "1 to 10" refers to each integer in the given range; e.g., "1 to 10 carbon atoms" means that the alkyl group consist of 1 carbon atom, 2 carbon atoms, 3 carbon atoms, 4 carbon atoms, 5 carbon atoms, 6 carbon atoms, etc., up to and including 10 carbon atoms, although the present definition also covers the occurrence of the term "alkyl" where no numerical range is designated. In some embodiments, an alkyl is a $C_1$-$C_6$alkyl. In one aspect the alkyl is methyl, ethyl, propyl, iso-propyl, n-butyl, iso-butyl, sec-butyl, or t-butyl. Typical alkyl groups include, but are in no way limited to, methyl, ethyl, propyl, isopropyl, butyl, isobutyl, sec-butyl, tertiary butyl, pentyl, neopentyl, or hexyl.

An "alkylene" group refers to a divalent alkyl group. Any of the above mentioned monovalent alkyl groups may be an alkylene by abstraction of a second hydrogen atom from the alkyl. In some embodiments, an alkylene is a $C_1$-$C_6$alkylene. In other embodiments, an alkylene is a $C_1$-$C_4$alkylene. In certain embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises two carbon atoms (e.g., $C_2$ alkylene). In other embodiments, an alkylene comprises two to four carbon atoms (e.g., $C_2$-$C_4$ alkylene). Typical alkylene groups include, but are not limited to, —CH$_2$—, —CH(CH$_3$)—, —C(CH$_3$)$_2$—, —CH$_2$CH$_2$—, —CH$_2$CH(CH$_3$)—, —CH$_2$C(CH$_3$)$_2$—, —CH$_2$CH$_2$CH$_2$—, —CH$_2$CH$_2$CH$_2$CH$_2$—, and the like.

"Deuteroalkyl" refers to an alkyl group where 1 or more hydrogen atoms of an alkyl are replaced with deuterium.

The term "alkenyl" refers to a type of alkyl group in which at least one carbon-carbon double bond is present. In one embodiment, an alkenyl group has the formula —C(R)═CR$_2$, wherein R refers to the remaining portions of the alkenyl group, which may be the same or different. In some embodiments, R is H or an alkyl. In some embodiments, an alkenyl is selected from ethenyl (i.e., vinyl), propenyl (i.e., allyl), butenyl, pentenyl, pentadienyl, and the like. Non-limiting examples of an alkenyl group include —CH═CH$_2$, —C(CH$_3$)═CH$_2$, —CH═CHCH$_3$, —C(CH$_3$)═CHCH$_3$, and —CH$_2$CH═CH$_2$.

The term "alkynyl" refers to a type of alkyl group in which at least one carbon-carbon triple bond is present. In one embodiment, an alkenyl group has the formula —C≡C—R, wherein R refers to the remaining portions of the alkynyl group. In some embodiments, R is H or an alkyl. In some embodiments, an alkynyl is selected from ethynyl, propynyl, butynyl, pentynyl, hexynyl, and the like. Non-limiting examples of an alkynyl group include —C≡CH, —C≡CCH$_3$—C≡CCH$_2$CH$_3$, —CH$_2$C≡CH.

An "alkoxy" group refers to a (alkyl)O— group, where alkyl is as defined herein.

The term "alkylamine" refers to the —N(alkyl)$_x$H$_y$ group, where x is 0 and y is 2, or where x is 1 and y is 1, or where x is 2 and y is 0.

The term "aromatic" refers to a planar ring having a delocalized π-electron system containing 4n+2 π electrons, where n is an integer. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon or nitrogen atoms) groups.

The term "carbocyclic" or "carbocycle" refers to a ring or ring system where the atoms forming the backbone of the ring are all carbon atoms. The term thus distinguishes carbocyclic from "heterocyclic" rings or "heterocycles" in which the ring backbone contains at least one atom which is different from carbon. In some embodiments, at least one of the two rings of a bicyclic carbocycle is aromatic. In some embodiments, both rings of a bicyclic carbocycle are aromatic. Carbocycle includes cycloalkyl and aryl.

As used herein, the term "aryl" refers to an aromatic ring wherein each of the atoms forming the ring is a carbon atom. In one aspect, aryl is phenyl or a naphthyl. In some embodiments, an aryl is a phenyl. In some embodiments, an aryl is a $C_6$-$C_{10}$aryl. Depending on the structure, an aryl group is a monoradical or a diradical (i.e., an arylene group).

The term "cycloalkyl" refers to a monocyclic or polycyclic aliphatic, non-aromatic group, wherein each of the atoms forming the ring (i.e. skeletal atoms) is a carbon atom. In some embodiments, cycloalkyls are spirocyclic or bridged compounds. In some embodiments, cycloalkyls are optionally fused with an aromatic ring, and the point of attachment is at a carbon that is not an aromatic ring carbon atom. Cycloalkyl groups include groups having from 3 to 10 ring atoms. In some embodiments, cycloalkyl groups are selected from among cyclopropyl, cyclobutyl, cyclopentyl, cyclopentenyl, cyclohexyl, cyclohexenyl, cycloheptyl, cyclooctyl, spiro[2.2]pentyl, norbornyl and bicyclo[1.1.1]pentyl. In some embodiments, a cycloalkyl is a $C_3$-$C_6$cycloalkyl. In some embodiments, a cycloalkyl is a monocyclic cycloalkyl. Monocyclic cycloalkyls include, but are not limited to, cyclopropyl, cyclobutyl, cyclopentyl, cyclohexyl, cycloheptyl, and cyclooctyl. Polycyclic cycloalkyls include, for example, adamantyl, norbornyl (i.e., bicyclo[2.2.1]heptanyl), norbornenyl, decalinyl, 7,7-dimethyl-bicyclo[2.2.1]heptanyl, and the like The term "halo" or, alternatively, "halogen" or "halide" means fluoro, chloro, bromo or iodo. In some embodiments, halo is fluoro, chloro, or bromo.

The term "haloalkyl" refers to an alkyl in which one or more hydrogen atoms are replaced by a halogen atom. In one aspect, a fluoroalkyl is a $C_1$-$C_6$fluoroalkyl.

The term "fluoroalkyl" refers to an alkyl in which one or more hydrogen atoms are replaced by a fluorine atom. In one aspect, a fluoroalkyl is a $C_1$-$C_6$fluoroalkyl. In some embodiments, a fluoroalkyl is selected from trifluoromethyl, difluoromethyl, fluoromethyl, 2,2,2-trifluoroethyl, 1-fluoromethyl-2-fluoroethyl, and the like.

The term "heteroalkyl" refers to an alkyl group in which one or more skeletal atoms of the alkyl are selected from an atom other than carbon, e.g., oxygen, nitrogen (e.g. —NH—, —N(alkyl)-, sulfur, or combinations thereof. A heteroalkyl is attached to the rest of the molecule at a carbon atom of the heteroalkyl. In one aspect, a heteroalkyl is a $C_1$-$C_6$heteroalkyl.

The term "heteroalkylene" refers to a divalent heteroalkyl group.

The term "heterocycle" or "heterocyclic" refers to heteroaromatic rings (also known as heteroaryls) and heterocycloalkyl rings (also known as heteroalicyclic groups) containing one to four heteroatoms in the ring(s), where each heteroatom in the ring(s) is selected from O, S and N, wherein each heterocyclic group has from 3 to 10 atoms in its ring system, and with the proviso that any ring does not contain two adjacent O or S atoms. In some embodiments, heterocycles are monocyclic, bicyclic, polycyclic, spirocyclic or bridged compounds. Non-aromatic heterocyclic groups (also known as heterocycloalkyls) include rings having 3 to 10 atoms in its ring system and aromatic heterocyclic groups include rings having 5 to 10 atoms in its ring system. The heterocyclic groups include benzo-fused ring systems. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, indolin-2-onyl, isoindolin-1-onyl, isoindoline-1,3-dionyl, 3,4-dihydroisoquinolin-1(2H)-onyl, 3,4-dihydroquinolin-2(1H)-onyl, isoindoline-1,3-dithionyl, benzo[d]oxazol-2(3H)-onyl, 1H-benzo[d]imidazol-2(3H)-onyl, benzo[d]thiazol-2(3H)-onyl, and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups are either C-attached (or C-linked) or N-attached where such is possible. For instance, a group derived from pyrrole includes both pyrrol-1-yl (N-attached) or pyrrol-3-yl (C-attached). Further, a group derived from imidazole includes imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles are optionally substituted with one or two oxo (=O) moieties, such as pyrrolidin-2-one. In some embodiments, at least one of the two rings of a bicyclic heterocycle is aromatic. In some embodiments, both rings of a bicyclic heterocycle are aromatic.

The terms "heteroaryl" or, alternatively, "heteroaromatic" refers to an aryl group that includes one or more ring heteroatoms selected from nitrogen, oxygen and sulfur. Illustrative examples of heteroaryl groups include monocyclic heteroaryls and bicyclic heteroaryls. Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Bicyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring. In some embodiments, heteroaryl is a $C_1$-$C_9$heteroaryl. In some embodiments, monocyclic heteroaryl is a $C_1$-$C_5$heteroaryl. In some embodiments, monocyclic heteroaryl is a 5-membered or 6-membered heteroaryl. In some embodiments, bicyclic heteroaryl is a $C_6$-$C_9$heteroaryl.

A "heterocycloalkyl" or "heteroalicyclic" group refers to a cycloalkyl group that includes at least one heteroatom selected from nitrogen, oxygen and sulfur. In some embodiments, a heterocycloalkyl is fused with an aryl or heteroaryl. In some embodiments, the heterocycloalkyl is oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, piperidin-2-onyl, pyrrolidine-2,5-dithionyl, pyrrolidine-2,5-dionyl, pyrrolidinonyl, imidazolidinyl, imidazolidin-2-onyl, or thiazolidin-2-onyl. The term heteroalicyclic also includes all ring forms of the carbohydrates, including but not limited to the monosaccharides, the disaccharides and the oligosaccharides. In one aspect, a heterocycloalkyl is a $C_2$-$C_{10}$heterocycloalkyl. In another aspect, a heterocycloalkyl is a $C_4$-$C_{10}$heterocycloalkyl. In some embodiments, a heterocycloalkyl contains 0-2 N atoms in the ring. In some embodiments, a heterocycloalkyl contains 0-2 N atoms, 0-2 O atoms and 0-1 S atoms in the ring.

The term "bond" or "single bond" refers to a chemical bond between two atoms, or two moieties when the atoms joined by the bond are considered to be part of larger substructure. In one aspect, when a group described herein is a bond, the referenced group is absent thereby allowing a bond to be formed between the remaining identified groups.

The term "moiety" refers to a specific segment or functional group of a molecule. Chemical moieties are often recognized chemical entities embedded in or appended to a molecule.

The term "optionally substituted" or "substituted" means that the referenced group is optionally substituted with one or more additional group(s). In some other embodiments, optional substituents are individually and independently selected from D, halogen, —CN, —NH$_2$, —NH(alkyl), —N(alkyl)$_2$, —OH, —CO$_2$H, —CO$_2$alkyl, —C(=O)NH$_2$, —C(=O)NH(alkyl), —C(=O)N(alkyl)$_2$, —S(=O)$_2$NH$_2$, —S(=O)$_2$NH(alkyl), —S(=O)$_2$N(alkyl)$_2$, —CH$_2$CO$_2$H, —CH$_2$CO$_2$alkyl, —CH$_2$C(=O)NH$_2$, —CH$_2$C(=O)NH(alkyl), —CH$_2$C(=O)N(alkyl)$_2$, —CH$_2$S(=O)$_2$NH$_2$, —CH$_2$S(=O)$_2$NH(alkyl), —CH$_2$S(=O)$_2$N(alkyl)$_2$, alkyl, alkenyl, alkynyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. The term "optionally substituted" or "substituted" means that the referenced group is optionally substituted with one or more additional group(s) individually and independently selected from D, halogen, —CN, —NH$_2$, —NH(alkyl), —N(alkyl)$_2$, —OH, —CO$_2$H, —CO$_2$alkyl, —C(=O)NH$_2$, —C(=O)NH(alkyl), —C(=O)N(alkyl)$_2$, —S(=O)$_2$NH$_2$, —S(=O)$_2$NH(alkyl), —S(=O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some other embodiments, optional substituents are independently selected from D, halogen, —CN, —NH$_2$, —NH(CH$_3$), —N(CH$_3$)$_2$, —OH, —CO$_2$H, —CO$_2$(C$_1$-C$_4$alkyl), —C(=O)NH$_2$, —C(=O)NH(C$_1$-C$_4$alkyl), —C(=O)N(C$_1$-C$_4$alkyl)$_2$, —S(=O)$_2$NH$_2$, —S(=O)$_2$NH(C$_1$-C$_4$alkyl), —S(=O)$_2$N(C$_1$-C$_4$alkyl)$_2$, C$_1$-C$_4$alkyl, C$_3$-C$_6$cycloalkyl, C$_1$-C$_4$fluoroalkyl, C$_1$-C$_4$heteroalkyl, C$_1$-C$_4$alkoxy, C$_1$-C$_4$fluoroalkoxy, —SC$_1$-C$_4$alkyl, —S(=O)C$_1$-C$_4$alkyl, and —S(=O)$_2$C$_1$-C$_4$alkyl. In some embodiments, optional substituents are independently selected from D, halogen, —CN, —NH$_2$, —OH, —NH(CH$_3$), —N(CH$_3$)$_2$, —CH$_3$, —CH$_2$CH$_3$, —CF$_3$, —OCH$_3$, and —OCF$_3$. In some embodiments, substituted groups are substituted with one or two of the preceding groups. In some embodiments, substituted groups are substituted with one of the preceding groups. In some embodiments, an optional substituent on an aliphatic carbon atom (acyclic or cyclic) includes oxo (=O).

The term "acceptable" with respect to a formulation, composition or ingredient, as used herein, means having no persistent detrimental effect on the general health of the subject being treated.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an agonist.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein. In some embodiments, the compounds and compositions described herein are administered orally.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound described herein, or a pharmaceutically acceptable salt thereof, and a co-agent, are both administered to a patient simultaneously in the form of a single entity or dosage. The term "non-fixed combination" means that the active ingredients, e.g. a compound described herein, or a pharmaceutically acceptable salt thereof, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The terms "kit" and "article of manufacture" are used as synonyms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Pharmaceutical Compositions

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that are used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins1999), herein incorporated by reference for such disclosure.

In some embodiments, the compounds described herein are administered either alone or in combination with pharmaceutically acceptable carriers, excipients or diluents, in a pharmaceutical composition. Administration of the compounds and compositions described herein can be affected by any method that enables delivery of the compounds to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route may depend upon for example the condition and disorder of the recipient. By way of example only, compounds described herein can be administered locally to the area in need of treatment, by for example, local infusion during surgery, topical application such as creams or ointments, injection, catheter, or implant. The administration can also be by direct injection at the site of a diseased tissue or organ.

In some embodiments, pharmaceutical compositions suitable for oral administration are presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary or paste.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

In some embodiments, pharmaceutical compositions are formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The compositions may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Pharmaceutical compositions for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical compositions may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

Pharmaceutical compositions may also be formulated in rectal compositions such as suppositories or retention enemas, e.g., containing conventional suppository bases such as cocoa butter, polyethylene glycol, or other glycerides.

Pharmaceutical compositions may be administered topically, that is by non-systemic administration. This includes the application of a compound of the present invention externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Pharmaceutical compositions suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient may comprise, for topical administration, from 0.001% to 10% w/w, for instance from 1% to 2% by weight of the formulation.

Pharmaceutical compositions for administration by inhalation are conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, pharmaceutical preparations may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

In some embodiments, a compound disclosed herein is formulated in such a manner that delivery of the compound to a particular region of the gastrointestinal tract is achieved. For example, a compound disclosed herein is formulated for oral delivery with bioadhesive polymers, pH-sensitive coatings, time dependent, biodegradable polymers, microflora activated systems, and the like, in order to effect delivering of the compound to a particular region of the gastrointestinal tract.

In some embodiments, a compound disclosed herein is formulated to provide a controlled release of the compound. Controlled release refers to the release of the compound described herein from a dosage form in which it is incorporated according to a desired profile over an extended period of time. Controlled release profiles include, for example, sustained release, prolonged release, pulsatile release, and delayed release profiles. In contrast to immediate release compositions, controlled release compositions allow delivery of an agent to a subject over an extended period of time according to a predetermined profile. Such release rates can provide therapeutically effective levels of agent for an extended period of time and thereby provide a longer period of pharmacologic response while minimizing side effects as compared to conventional rapid release dosage forms. Such longer periods of response provide for many inherent benefits that are not achieved with the corresponding short acting, immediate release preparations.

Approaches to deliver the intact therapeutic compound to the particular regions of the gastrointestinal tract (e.g. such as the colon), include:

(i) Coating with polymers: The intact molecule can be delivered to the colon without absorbing at the upper part of the intestine by coating of the drug molecule with the suitable polymers, which degrade only in the colon.

(ii) Coating with pH-sensitive polymers: The majority of enteric and colon targeted delivery systems are based on the coating of tablets or pellets, which are filled into conventional hard gelatin capsules. Most commonly used pH-dependent coating polymers are methacrylic acid copolymers, commonly known as Eudragit® S, more specifically Eudragit® L and Eudragit® S. Eudragit® $L^{100}$ and S 100 are copolymers of methacrylic acid and methyl methacrylate.

(iii) Coating with biodegradable polymers;
(iv) Embedding in matrices;
(v) Embedding in biodegradable matrices and hydrogels;
(vi) Embedding in pH-sensitive matrices;
(vii) Timed release systems;
(viii) Redox-sensitive polymers;
(ix) Bioadhesive systems;
(x) Coating with microparticles;
(xi) Osmotic controlled drug delivery;

Another approach towards colon-targeted drug delivery or controlled-release systems includes embedding the drug in polymer matrices to trap it and release it in the colon. These matrices can be pH-sensitive or biodegradable. Matrix-Based Systems, such as multi-matrix (MMX)-based delayed-release tablets, ensure the drug release in the colon.

Additional pharmaceutical approaches to targeted delivery of therapeutics to particular regions of the gastrointestinal tract are known. Chourasia M K, Jain S K, Pharmaceutical approaches to colon targeted drug delivery systems. J Pharm Pharm Sci. 2003 January-April; 6(1):33-66. Patel M, Shah T, Amin A. Therapeutic opportunities in colon-specific drug-delivery systems Crit Rev Ther Drug Carrier Syst. 2007; 24(2):147-202. Kumar P, Mishra B. Colon targeted drug delivery systems—an overview. Curr Drug Deliv. 2008 July; 5(3):186-98. Van den Mooter G. Colon drug delivery. Expert Opin Drug Deliv. 2006 January; 3(1): 111-25. Seth Amidon, Jack E. Brown, and Vivek S. Dave, Colon-Targeted Oral Drug Delivery Systems: Design Trends and Approaches, AAPS PharmSciTech. 2015 August; 16(4): 731-741.

It should be understood that in addition to the ingredients particularly mentioned above, the compounds and compositions described herein may include other agents conventional in the art having regard to the type of formulation in question, for example those suitable for oral administration may include flavoring agents.

Methods of Dosing and Treatment Regimens

In one embodiment, the compounds described herein, or a pharmaceutically acceptable salt thereof, are used in the preparation of medicaments for the treatment of diseases or conditions in a mammal that would benefit from administration of a FXR agonist. Methods for treating any of the diseases or conditions described herein in a mammal in need of such treatment, involves administration of pharmaceutical compositions that include at least one compound described herein or a pharmaceutically acceptable salt, active metabolite, prodrug, or pharmaceutically acceptable solvate thereof, in therapeutically effective amounts to said mammal.

Disclosed herein, are methods of administering a FXR agonist in combination with an additional therapeutic agent. In some embodiments, the additional therapeutic agent comprises a therapeutic agent for treatment of diabetes or diabetes related disorder or conditions, alcoholic or non-alcoholic liver disease, inflammation related intestinal conditions, or cell proliferative disorders.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of the disease being treated and is currently in remission, a pharmaceutical composition comprising a compound described herein, or a pharmaceutically acceptable salt thereof, in order to prevent a return of the symptoms of the disease or condition.

In certain embodiments wherein the patient's condition does not improve, upon the doctor's discretion, the compounds are administered chronically, that is, for an extended period of time, including throughout the duration of the patient's life in order to ameliorate or otherwise control or limit the symptoms of the patient's disease or condition.

In certain embodiments wherein a patient's status does improve, the dose of drug being administered is temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg-5000 mg per day. In one aspect, doses employed for adult human treatment are from about 1 mg to about 1000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the compound described herein, or a pharmaceutically acceptable salt thereof, are from about 0.01 to about 50 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{50}$ and the $ED_{50}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

In any of the aforementioned aspects are further embodiments in which the effective amount of the compound described herein, or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal.

In any of the aforementioned aspects are further embodiments comprising single administrations of the effective amount of the compound, including further embodiments in which (i) the compound is administered once a day; or (ii) the compound is administered to the mammal multiple times over the span of one day.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

In certain instances, it is appropriate to administer at least one compound described herein, or a pharmaceutically acceptable salt thereof, in combination with one or more other therapeutic agents.

In one embodiment, the therapeutic effectiveness of one of the compounds described herein is enhanced by administration of an adjuvant (i.e., by itself the adjuvant has minimal therapeutic benefit, but in combination with another therapeutic agent, the overall therapeutic benefit to the patient is enhanced). Or, in some embodiments, the benefit experienced by a patient is increased by administering one of the compounds described herein with another agent (which also includes a therapeutic regimen) that also has therapeutic benefit.

In one specific embodiment, a compound described herein, or a pharmaceutically acceptable salt thereof, is co-administered with a second therapeutic agent, wherein the compound described herein, or a pharmaceutically acceptable salt thereof, and the second therapeutic agent modulate different aspects of the disease, disorder or condition being treated, thereby providing a greater overall benefit than administration of either therapeutic agent alone.

In any case, regardless of the disease, disorder or condition being treated, the overall benefit experienced by the patient may be additive of the two therapeutic agents or the patient may experience a synergistic benefit.

In certain embodiments, different therapeutically-effective dosages of the compounds disclosed herein will be utilized in formulating pharmaceutical composition and/or in treatment regimens when the compounds disclosed herein are administered in combination with one or more additional agent, such as an additional therapeutically effective drug, an adjuvant or the like. Therapeutically-effective dosages of drugs and other agents for use in combination treatment regimens is optionally determined by means similar to those set forth hereinabove for the actives themselves. Furthermore, the methods of prevention/treatment described herein encompasses the use of metronomic dosing, i.e., providing more frequent, lower doses in order to minimize toxic side effects. In some embodiments, a combination treatment regimen encompasses treatment regimens in which administration of a compound described herein, or a pharmaceutically acceptable salt thereof, is initiated prior to, during, or after treatment with a second agent described herein, and continues until any time during treatment with the second agent or after termination of treatment with the second agent. It also includes treatments in which a compound described herein, or a pharmaceutically acceptable salt thereof, and the second agent being used in combination are administered simultaneously or at different times and/or at decreasing or increasing intervals during the treatment period. Combination treatment further includes periodic treatments that start and stop at various times to assist with the clinical management of the patient.

It is understood that the dosage regimen to treat, prevent, or ameliorate the condition(s) for which relief is sought, is modified in accordance with a variety of factors (e.g. the disease, disorder or condition from which the subject suffers; the age, weight, sex, diet, and medical condition of the subject). Thus, in some instances, the dosage regimen actually employed varies and, in some embodiments, deviates from the dosage regimens set forth herein.

For combination therapies described herein, dosages of the co-administered compounds vary depending on the type of co-drug employed, on the specific drug employed, on the disease or condition being treated and so forth. In additional embodiments, when co-administered with one or more other therapeutic agents, the compound provided herein is administered either simultaneously with the one or more other therapeutic agents, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

The compounds described herein, or a pharmaceutically acceptable salt thereof, as well as combination therapies, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject. For example, in specific embodiments, a compound described herein or a formulation containing the compound is administered for at least 2 weeks, about 1 month to about 5 years.

In some embodiments, a FXR agonist is administered in combination with an additional therapeutic agent for the treatment of diabetes or diabetes related disorder or conditions.

In some instances, the additional therapeutic agent comprises a statin, an insulin sensitizing drug, an insulin secretagogue, an alpha-glucosidase inhibitor, a GLP agonist, a DPP-4 inhibitor (such as sitagliptin, vildagliptin, saxagliptin, linagliptin, anaglptin, teneligliptin, alogliptin, gemigliptin, or dutoglpitin), a catecholamine (such as epinephrine, norepinephrine, or dopamine), peroxisome proliferator-activated receptor (PPAR)-gamma agonist (e.g., a thiazolidinedione (TZD) [such as pioglitazone, rosiglitazone, rivoglitazone, or troglitazone], aleglitazar, farglitazar, muraglitazar, or tesaglitazar), or a combination thereof.

In some cases, the statin is a HMG-CoA reductase inhibitor. In other instances, additional therapeutic agents include fish oil, fibrate, vitamins such as niacin, retinoic acid (e.g., 9 cis-retinoic acid), nicotinamide ribonucleoside or its analogs thereof, or combinations thereof. In some instances, nicotinamide ribonucleoside or its analogs thereof, which promote $NAD^+$ production, a substrate for many enzymatic reactions including p450s which is a target for FXR (e.g., see Yang et al., *J. Med. Chem.* 50:6458-61, 2007).

In some embodiments, a FXR agonist is administered in combination with an additional therapeutic agent such as a statin, an insulin sensitizing drug, an insulin secretagogue, an alpha-glucosidase inhibitor, a GLP agonist, a DPP-4 inhibitor (such as sitagliptin, vildagliptin, saxagliptin, linagliptin, anaglptin, teneligliptin, alogliptin, gemiglptin, or dutoglpitin), a catecholamine (such as epinephrine, norepinephrine, or dopamine), peroxisome proliferator-activated receptor (PPAR)-gamma agonist (e.g., a thiazolidinedione (TZD) [such as pioglitazone, rosiglitazone, rivoglitazone, or troglitazone], aleglitazar, farglitazar, muraglitazar, or tesaglitazar), or combinations thereof, for the treatment of diabetes or diabetes related disorder or conditions. In some embodiments, a FXR agonist is administered in combination with an additional therapeutic agent such as fish oil, fibrate, vitamins such as niacin, retinoic acid (e.g., 9 cis-retinoic acid), nicotinamide ribonucleoside or its analogs thereof, or combinations thereof, for the treatment of diabetes or diabetes related disorder or conditions.

In some embodiments, a FXR agonist is administered in combination with a statin such as a HMG-CoA reductase inhibitor, fish oil, fibrate, niacin or a combination thereof, for the treatment of dyslipidemia.

In additional embodiments, a FXR agonist is administered in combination with a vitamin such as retinoic acid for the treatment of diabetes and diabetes related disorder or condition such as lowering elevated body weight and/or lowering elevated blood glucose from food intake.

In some embodiments, the farnesoid X receptor agonist is administered with at least one additional therapy. In some embodiments, the at least one additional therapy is a glucose-lowering agent. In some embodiments, the at least one additional therapy is an anti-obesity agent. In some embodiments, the at least one additional therapy is selected from among a peroxisome proliferator activated receptor (PPAR) agonist (gamma, dual, or pan), a dipeptidyl peptidase (IV) inhibitor, a glucagon-like peptide-1 (GLP-I) analog, insulin or an insulin analog, an insulin secretagogue, a sodium glucose co-transporter 2 (SGLT2) inhibitor, a glucophage, a human amylin analog, a biguanide, an alpha-glucosidase inhibitor, a meglitinide, a thiazolidinedione, and sulfonylurea. In some embodiments, the at least one additional therapy is metformin, sitagliptin, saxaglitpin, repaglinide, nateglinide, exenatide, liraglutide, insulin lispro, insulin aspart, insulin glargine, insulin detemir, insulin isophane, and glucagon-like peptide 1, or any combination thereof. In some embodiments, the at least one additional therapy is a lipid-lowering agent. In certain embodiments, the at least one additional therapy is administered at the same time as the farnesoid X receptor agonist. In certain embodiments, the at least one additional therapy is administered less frequently than the farnesoid X receptor agonist. In certain embodiments, the at least one additional therapy is administered more frequently than the farnesoid X receptor agonist. In certain embodiments, the at least one additional therapy is administered prior to administration of the farnesoid X receptor agonist. In certain embodiments, the at least one additional therapy is administered after administration of the farnesoid X receptor agonist.

In some embodiments, a compound described herein, or a pharmaceutically acceptable salt thereof, is administered in combination with chemotherapy, anti-inflammatory agents, radiation therapy, monoclonal antibodies, or combinations thereof.

In some embodiments, a FXR agonist is administered in combination with an additional therapeutic agent for the treatment of alcoholic or non-alcoholic liver disease. In some embodiments, the additional therapeutic agent includes antioxidant, corticosteroid, anti-tumor necrosis factor (TNF) or a combination thereof.

In some embodiments, a FXR agonist is administered in combination with an additional therapeutic agent such as antioxidant, corticosteroid, anti-tumor necrosis factor (TNF), or a combination thereof, for the treatment of alcoholic or non-alcoholic liver disease. In some embodiments, a FXR agonist is administered in combination with an antioxidant, a vitamin precursor, a corticosteroid, an anti-tumor necrosis factor (TNF), or a combination thereof, for the treatment of alcoholic or non-alcoholic liver disease.

In some embodiments, a FXR agonist is administered in combination with an additional therapeutic agent for the treatment of inflammation related intestinal conditions. In some instances, the additional therapeutic agent comprises an antibiotic (such as metronidazole, vancomycin, and/or fidaxomicin), a corticosteroid, or an additional anti-inflammatory or immuno-modulatory therapy.

In some instances, a FXR agonist is administered in combination with an additional therapeutic agent such as an antibiotic, a corticosteroid, or an additional anti-inflammatory or immuno-modulatory therapy, for the treatment of inflammation related intestinal conditions. In some cases, a FXR agonist is administered in combination with metronidazole, vancomycin, fidaxomicin, corticosteroid, or combinations thereof, for the treatment of inflammation related intestinal conditions.

As discussed above, inflammation is sometimes associated with pseudomembranous colitis. In some instances, pseudomembranous colitis is associated with bacterial overgrowth (such as *C. difficile* overgrowth). In some embodiments, a FXR agonist is administered in combination with an antibiotic such as metronidazole, vancomycin, fidaxomicin, or a combination thereof, for the treatment of inflammation associated with bacterial overgrowth (e.g., pseudomembranous colitis).

In some embodiments, the FXR agonist is administered in combination with an additional therapeutic agent for the treatment of cell proliferative disorders. In some embodiments, the additional therapeutic agent includes a chemotherapeutic, a biologic (e.g., antibody, for example bevacizumab, cetuximab, or panitumumab), a radiotherapeutic (e.g., FOLFOX, FOLFIRI, CapeOX, 5-FU, leucovorin, regorafenib, irinotecan, or oxaliplatin), or combinations thereof.

In some embodiments, the FXR agonist is administered in combination with an additional therapeutic agent for the treatment of primary biliary cirrhosis. In some embodiments, the additional therapeutic agent includes ursodeoxycholic acid (UDCA).

In some embodiments, a FXR agonist is administered in combination with an additional therapeutic agent such as a chemotherapeutic, a biologic, a radiotherapeutic, or combinations thereof, for the treatment of a cell proliferative disorder. In some instances, a FXR agonist is administered in combination with an antibody (e.g., bevacizumab, cetuximab, or panitumumab), chemotherapeutic, FOLFOX, FOLFIRI, CapeOX, 5-FU, leucovorin, regorafenib, irinotecan, oxaliplatin, or combinations thereof, for the treatment of a cell proliferative disorder.

EXAMPLES

The following examples are provided for illustrative purposes only and not to limit the scope of the claims provided herein.

As used above, and throughout the description of the invention, the following abbreviations, unless otherwise indicated, shall be understood to have the following meanings:

ACN or MeCN acetonitrile
AcOH acetic acid
Ac acetyl
BINAP 2,2'-bis(diphenylphosphino)-1,1'-binaphthalene
Bn benzyl
BOC or Boc tert-butyl carbamate
t-Bu tert-butyl
Cy cyclohexyl
DBA or dba dibenzylideneacetone
CDI 1,1-carbonyldiimidazole
DCE dichloroethane ($ClCH_2CH_2Cl$)
DCM dichloromethane ($CH_2Cl_2$)
DIPEA or DIEA diisopropylethylamine
DMAP 4-(N,N-dimethylamino)pyridine
DME 1,2-dimethoxyethane
DMF N,N-dimethylformamide
DMA N,N-dimethylacetamide
DMSO dimethylsulfoxide
Dppf or dppf 1,1'-bis(diphenylphosphino)ferrocene
EDC or EDCI N-(3-dimethylaminopropyl)-N'-ethylcarbodiimide hydrochloride
EEDQ 2-Ethoxy-1-ethoxycarbonyl-1,2-dihydroquinoline
eq equivalent(s)
Et ethyl
$Et_2O$ diethyl ether
EtOH ethanol
EtOAc ethyl acetate
HATU 1-[bis(dimethylamino)methylene]-1H-1,2,3-triazolo[4,5-b]pyridinium 3-oxid hexafluorophosphate
HMPA hexamethylphosphoramide
HOBt 1-hydroxybenzotriazole
HPLC high performance liquid chromatography
KHMDS potassium bis(trimethylsilyl)amide
NaHMDS sodium bis(trimethylsilyl)amide
LiHMDS lithium bis(trimethylsilyl)amide
LAH lithium aluminum anhydride
LCMS liquid chromatography mass spectrometry
Me methyl
MeOH methanol
MS mass spectroscopy
Ms mesyl
MTBE methyl tert-butyl ether
NBS N-bromosuccinimide
NMM N-methyl-morpholine
NMP N-methyl-pyrrolidin-2-one
NMR nuclear magnetic resonance
OTf trifluoromethanesulfonate
PCC pyridinium chlorochromate
PE petroleum ether
Ph phenyl
PPTS pyridium p-toluenesulfonate
iPr/i-Pr iso-propyl
TBS tert-butyldimethylsilyl
TBAF tetra-n-butylammonium fluoride
TBAI tetra-n-butylammonium iodide
RP-HPLC reverse phase-high pressure liquid chromatography
TFA trifluoroacetic acid
TEA triethylamine
THF tetrahydrofuran
TLC thin layer chromatography
TMEDA N,N,N',N'-tetramethylethylenediamine Intermediate 1

6-Chloro-3-methoxypicolinonitrile

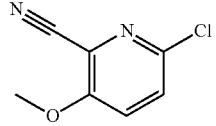

Step 1: 2-Cyano-3-methoxypyridine 1-oxide

3-Chloroperbenzoic acid (90.8 g, 447 mmol, 85% purity) was added to a solution of 3-methoxypicolinonitrile (50 g, 373 mmol) in DCE (500 mL) at rt. The reaction mixture was heated at 65° C. overnight, and then allowed to cool to rt. The mixture was washed with $NaHCO_3$ (5×300 mL), dried over $Na_2SO_4$, filtered, concentrated, and then triturated in petroleum ether/EtOAc=5/1 (300 mL) to give 2-cyano-3-methoxypyridine 1-oxide (50 g, 89%) as a yellow solid. $^1H$ NMR (400 MHz, $CDCl_3$): δ 7.95 (d, 1H), 7.37 (t, 1H), 6.90 (d, 1H), 4.03 (s, 3H); LCMS: 151.0 $[M+H]^+$.

Step 2: 6-Chloro-3-methoxypicolinonitrile

A mixture of 2-cyano-3-methoxypyridine 1-oxide (30 g, 200 mmol) and $POCl_3$ (333 g, 2.17 mol) was heated to 100° C. for 2 h under $N_2$. The mixture was concentrated to dryness, diluted with $NaHCO_3$ (300 mL), extracted with EtOAc (2×100 mL). The organic layers were combined, dried ($Na_2SO_4$), filtered, concentrated, and then purified by silica gel chromatography (petroleum ether/EtOAc=2/1) to give 6-chloro-3-methoxypicolinonitrile (20 g, 59%) as a yellow solid. $^1H$ NMR (400 MHz, $CDCl_3$): δ 7.51 (d, 1H), 7.38 (d, 1H), 3.99 (s, 3H); LCMS: 169.0 $[M+H]^+$.

Intermediate 2

5-Bromo-3-fluoro-1-methyl-1H-indazole

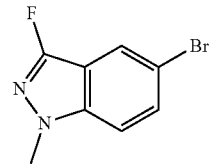

1-(Chloromethyl)-4-fluoro-1,4-diazabicyclo[2.2.2]octane-1,4-diium tetrafluoroborate (16.11 g, 45.48 mmol) was added to a solution of 5-bromo-1-methyl-1H-indazole (8.00 g, 37.90 mmol) in $CH_3CN$ (80 mL) at rt. The mixture was stirred at 80° C. overnight, quenched with $H_2O$ (50 mL) at rt, and then diluted with EtOAc (50 mL). The mixture was extracted with EtOAc (3×50 mL). The combined organic layers were dried over $Na_2SO_4$, filtered and concentrated under reduced pressure to give a residue. The residue was purified by column chromatography (petroleum ether/EtOAc=50 to 5:1) to give 5-bromo-3-fluoro-1-methyl-1H- indazole (3.95 g, 46%) as a white solid. H NMR (400 MHz, DMSO-d$_6$): δ 7.93 (s, 1H), 7.53-7.65 (m, 2H), 3.90 (s, 3H).

Intermediate 3

Trans-4-(4-Methoxy-3-methylphenyl)cyclohexanecarbaldehyde

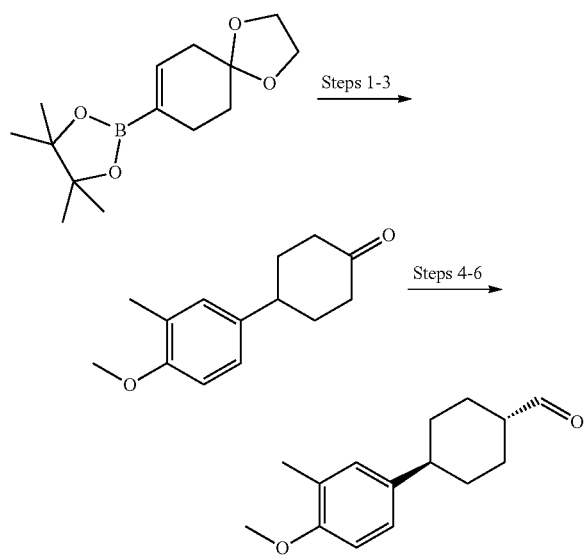

Step 1: 8-(4-Methoxy-3-methylphenyl)-1,4-dioxaspiro[4.5]dec-7-ene

A mixture of 1,4-dioxa-spiro[4.5]dec-7-en-8-boronic acid pinacol ester (25.0 g, 93.9 mmol), 4-iodo-2-methylanisole (28.0 g, 113 mmol), Pd(dppf)Cl$_2$ (1.38 g, 1.89 mmol), dioxane (470 mL) and 1 M Na$_2$CO$_3$ (282 mL, 282 mmol) was degassed with 3 vacuum/N$_2$ cycles, stirred at 50° C. for 2.5 h, and then allowed to cool to rt. The mixture was diluted with EtOAc (500 mL) and washed with saturated NaHCO$_3$ (2×500 mL). The aqueous layers were back extracted with EtOAc (200 mL). The combined EtOAc extracts were dried (Na$_2$SO$_4$), filtered, concentrated and purified by silica gel chromatography (0-5% EtOAc in hexanes) to give 8-(4-methoxy-3-methylphenyl)-1,4-dioxaspiro[4.5]dec-7-ene (19.9 g, 81%). $^1$H NMR (400 MHz, DMSO-d$_6$): δ 7.21-7.16 (m, 2H), 6.85 (d, 1H), 5.89-5.84 (m, 1H), 3.90 (s, 4H), 3.76 (s, 3H), 2.52-2.47 (m, 2H), 2.32 (br s, 2H), 2.13 (s, 3H), 1.77 (t, 2H); LCMS: 261.1 [M+H]$^+$.

Step 2: 8-(4-Methoxy-3-methylphenyl)-1,4-dioxaspiro[4.5]decane

Palladium on carbon (10 wt %, 8.08 g, 7.59 mmol) was added to a solution of 8-(4-methoxy-3-methylphenyl)-1,4-dioxaspiro[4.5]dec-7-ene (19.8 g, 76.1 mmol) in EtOAc (300 mL) at rt under N$_2$. The N$_2$ inlet was replaced with a balloon of H$_2$. The reaction was stirred for 4.5 h, filtered through Celite with EtOAc, and then concentrated to give 8-(4-methoxy-3-methylphenyl)-1,4-dioxaspiro[4.5]decane (18.2 g; contains 13% ketone) as a white solid. $^1$H NMR (400 MHz, DMSO-d$_6$): δ 7.00-6.95 (m, 2H), 6.81 (d, 1H), 3.91-3.84 (m, 4H), 3.73 (s, 3H), 2.49-2.42 (m, 1H), 2.11 (s, 3H), 1.76-1.68 (m, 4H), 1.67-1.55 (m, 4H); LCMS: 263.1 [M+H]$^+$.

Step 3: 4-(4-Methoxy-3-methylphenyl)cyclohexanone

Formic acid (96%, 14 mL, 356 mmol) and then H$_2$O (2.20 mL, 122 mmol) were added to a solution of 8-(4-methoxy-3-methylphenyl)-1,4-dioxaspiro[4.5]decane (18.2 g) in toluene (60 mL) at rt under N$_2$. The reaction was heated at 120° C. for 4 hours, allowed to cool to rt, and then poured into H$_2$O (200 mL) and toluene (200 mL). The toluene layer was washed (200 mL H$_2$O and then 200 mL saturated NaHCO$_3$). The aqueous layers were back extracted with toluene (100 mL). The combined toluene extracts were dried (Na$_2$SO$_4$), filtered and concentrated to give 4-(4-methoxy-3-methylphenyl)cyclohexanone (15.5 g, 88% over 2 steps) as a white solid. $^1$H NMR (400 MHz, DMSO-d$_6$): δ 7.08-7.03 (m, 2H), 6.84 (d, 1H), 3.74 (s, 3H), 3.00-2.91 (m, 1H), 2.61-2.51 (m, 2H), 2.28-2.20 (m, 2H), 2.12 (s, 3H), 2.06-1.98 (m, 2H), 1.88-1.76 (m, 2H); LCMS: 219.0 [M+H]$^+$.

Step 4: 1-Methoxy-4-(4-(methoxymethylene)cyclohexyl)-2-methylbenzene

A mixture of (methoxymethyl)triphenyl phosphonium chloride (35.74 g, 104.3 mmol) and THF (260 mL) under N$_2$ was cooled to −2.2° C. in an ice/brine bath. Sodium bis(trimethylsilyl)amide solution (2 M in THF, 50 mL, 100 mmol) was added dropwise via addition funnel over 12 min (internal temp ≤0.6° C.) with THF rinsing (5 mL). The reaction was stirred for 30 min, and then 4-(4-methoxy-3-methylphenyl)cyclohexanone (14.5 g, 66.6 mmol) was added portionwise over 5 min (exotherm to 7.3° C.). Residual cyclohexanone was rinsed into the reaction with THF (20 mL). The reaction was stirred at 0° C. for 25 min, and then poured into H$_2$O (400 mL) and toluene (400 mL). The toluene layer was washed (400 mL H$_2$O), dried (Na$_2$SO$_4$), filtered, concentrated and purified by silica gel chromatography (0-5% EtOAc in hexanes) to give 1-methoxy-4-(4-(methoxymethylene)cylcohexyl)-2-methylbenzene (15.6 g, 95%) as a pale gold oil. $^1$H NMR (400 MHz, DMSO-d$_6$): δ 6.99-6.94 (m, 2H), 6.80 (d, 1H), 5.87 (s, 1H), 3.73 (s, 3H), 3.48 (s, 3H), 2.78-2.71 (m, 1H), 2.56-2.44 (m, 1H), 2.10 (s, 3H), 2.17-2.09 (m, 1H), 2.01-1.91 (m, 1H), 1.83-1.73 (m, 2H), 1.72-1.63 (m, 1H), 1.38-1.23 (m, 2H); LCMS: 247.1 [M+H]$^+$.

Step 5: 4-(4-Methoxy-3-methylphenyl)cyclohexanecarbaldehyde

Formic acid (96%, 12.5 mL, 331 mmol) and then water (2.5 mL, 139 mmol) were added to a solution of 1-methoxy-4-(4-(methoxymethylene)cylcohexyl)-2-methylbenzene (16.05 g, 65.15 mmol) in toluene (130 mL) under N$_2$. The reaction was heated at 120° C. for 2 h, allowed to cool to rt, and then poured into 350 mL EtOAc and 350 mL H$_2$O. The organic layer was washed with 350 mL H$_2$O, dried (Na$_2$SO$_4$), filtered and concentrated to give 4-(4-methoxy-3-methylphenyl)cyclohexanecarbaldehyde (15.05 g) as a 1:1 mixture of stereoisomers.

Step 6: Trans-4-(4-Methoxy-3-methylphenyl)cyclohexanecarbaldehyde

Aqueous sodium hydroxide (3.2 M, 31 mL, 99 mmol) was added to the crude mixture from Step 5 (14.68 g, 63.19 mmoL), toluene (60 mL) and ethanol (250 mL) at rt. The reaction was stirred for 5.5 hours (equilibration monitored by NMR) and then poured into 350 mL H$_2$O and 350 mL EtOAc. The organic layer was washed with 350 mL H$_2$O, and the aqueous layers were back extracted with 150 mL EtOAc. The combined extracts were dried (Na$_2$SO$_4$), filtered, concentrated and purified by silica gel chromatography (0-5% EtOAc in hexanes) to give trans-4-(4-methoxy-3-methylphenyl)cyclohexanecarbaldehyde (10.17 g, 69%) as a white solid. $^1$H NMR (400 MHz, DMSO-d$_6$): δ 9.60 (s, 1H), 7.01-6.97 (m, 2H), 6.82 (d, 1H), 3.74 (s, 3H), 2.41-2.27 (m, 2H), 2.12 (s, 3H), 2.03-1.96 (m, 2H), 1.87-1.80 (m, 2H), 1.51-1.39 (m, 2H), 1.35-1.23 (m, 2H); LCMS: 233.0 [M+H]$^+$.

The Intermediates below were synthesized from the appropriate aryl halide (SM or Intermediate) following the procedures described for Intermediate 3.

| Int | Structure | Name | [M + H]$^+$ |
|---|---|---|---|
| 3.01 | 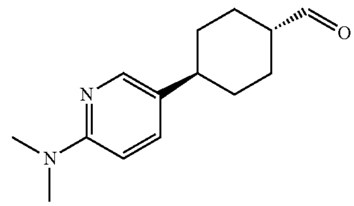 [SMILES: CN(C)c1ccc([C@H]2CC[C@H](C=O)CC2)cn1] | trans-4-(6-(Dimethylamino)pyridin-3-yl)cyclohexanecarbaldehyde | 233.0 |
| 3.02[10,11,12] | 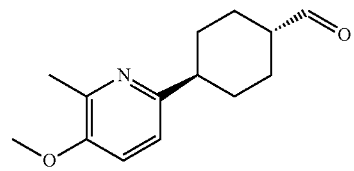 [SMILES: COc1ccc([C@H]2CC[C@H](C=O)CC2)nc1C] | trans-4-(5-Methoxy-6-methylpyridin-2-yl)cyclohexanecarbaldehyde | 234.1 |
| 3.03[9,10,11] | 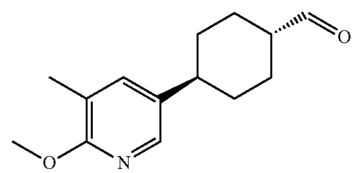 | trans-4-(6-Methoxy-5-methylpyridin-3-yl)cyclohexanecarbaldehyde | 234.1 |
| 3.04[3,7,10] | 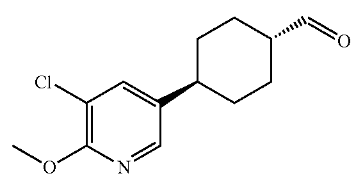 [SMILES: COc1ncc([C@H]2CC[C@H](C=O)CC2)cc1Cl] | trans-4-(5-Chloro-6-methoxypyridin-3-yl)cyclohexanecarbaldehyde | 254.4 |
| 3.05 | 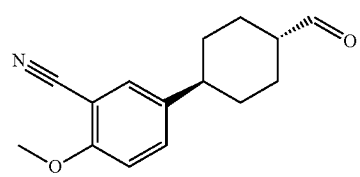 [SMILES: COc1ccc([C@H]2CC[C@H](C=O)CC2)cc1C#N] | 5-(trans-4-Formylcyclohexyl)-2-methoxybenzonitrile | 244.0 |
| 3.06[1,8,10,11,12] | 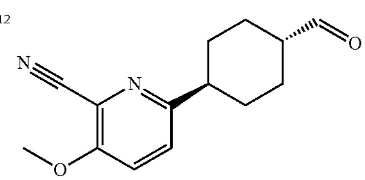 | 6-(trans-4-formylcyclohexyl)-3-methoxypicolinonitrile | 245.1 |
| 3.07[6,10] | 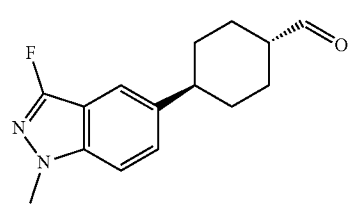 [SMILES: Cn1nc(F)c2cc([C@H]3CC[C@H](C=O)CC3)ccc21] | trans-4-(3-Fluoro-1-methyl-1H-indazol-5-yl)cyclohexanecarbaldehyde | 261.2 |

Alternate conditions: Step 1: [1]EtOH, DME, 100° C., 5 h; [2]EtOH, dioxane, 100° C., overnight; [3]Cs$_2$CO$_3$, dioxane, 100° C., 6 h; [4]Pd(PPh$_3$)$_4$, 100° C., 5h; [5]Pd(PPh$_3$)$_4$, CH$_3$CN/H$_2$O, reflux, overnight; Step 2: [6]CH$_3$OH; [7]HCl, EtOAc; Step 3: [8]PPTS, acetone, H$_2$O, 60° C. 10 h; [9]3 M HCl, THF, 60° C., 3 h to overnight; Step 4: [10]LiHMDS (1 M THF), 0° C. or rt, 0.5-2 h; Step 5: [11]3 M HCl, THF, rt or 60° C., 1-6 h; Step 6: [12]NaOMe, CH3OH, rt, 4 h to overnight.

Intermediate 4

Trans-4-(3-Chloro-4-methoxyphenyl)cyclohexanecarbaldehyde

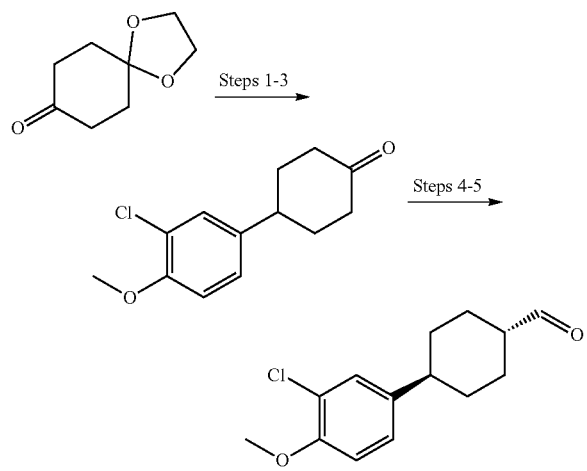

Step 1: 8-(3-Chloro-4-methoxyphenyl)-1,4-dioxaspiro[4.5]decan-8-ol

To a 3-necked round bottom flask was added 4-bromo-2-chloro-1-methoxy-benzene (45.00 g, 203.18 mmol) and THF (450 mL), n-Butyllithium (2.5 M in hexanes, 90.21 mL, 1.11 eq) was added at −78° C. The mixture was stirred for 2 h at −78° C. A solution of 1,4-dioxaspiro[4.5]decan-8-one (34.91 g, 223.50 mmol) in THF (90 mL) was added dropwise to the reaction mixture. The resulting mixture was stirred for 3 h at −78° C. The reaction was quenched with aqueous $NH_4Cl$ (100 mL) and extracted with EtOAc (500 mL). The organic layer was dried ($Na_2SO_4$), filtered and concentrated. The residue was washed with hexanes (350 mL), filtered and dried under high vacuum. The solid was triturated with hexanes (15 mL), filtered and dried under high vacuum to give 8-(3-chloro-4-methoxy-phenyl)-1,4-dioxaspiro[4.5]decan-8-ol (37 g, 61%) as a white solid. $^1$H NMR (400 MHz, $CDCl_3$): δ 7.31 (d, 1H), 7.29 (dd, 1H), 7.10 (d, 1H), 3.90-3.92 (m, 4H), 3.89 (s, 3H), 1.99-2.02 (m, 4H), 1.70-1.73 (m, 4H); LCMS: 281.2 $[M-OH]^+$.

Step 2: 8-(3-Chloro-4-methoxyphenyl)-1,4-dioxaspiro[4.5]decane

A solution of triethylsilane (19.26 g, 165.6 mmol), TFA (25.18 g, 220.8 mmol), and $CH_2Cl_2$ (100 mL) was added dropwise to a solution of 8-(3-chloro-4-methoxyphenyl)-1,4-dioxaspiro[4.5]decan-8-ol (31.0 g, 110.4 mmol) and $CH_2Cl_2$ (200 mL) at 0° C. The reaction mixture was stirred at rt overnight and then cooled to 0° C. The pH was adjusted to ~8 with aqueous $NaHCO_3$ and the mixture was extracted with $CH_2Cl_2$ (2×100 mL). The organic layer was dried ($Na_2SO_4$), filtered, and concentrated to dryness to give 8-(3-chloro-4-methoxyphenyl)-1,4-dioxaspiro[4.5]decane, containing a small amount of 8-(3-chloro-4-methoxyphenyl)-1,4-dioxaspiro[4.5]dec-7-ene, (38 g, crude) as a yellow oil. LCMS: 283.1 $[M+H]^+$.

Step 3: 4-(3-Chloro-4-methoxyphenyl)cyclohexanone 8-(3-chloro-4-methoxyphenyl)-1,4-dioxaspiro[4.5]decane (38.0 g, 134 mmol), formic acid (32.3 g, 672 mmol), $H_2O$ (4.84 g, 269 mmol), and toluene (400 mL) was degassed with 3 vacuum/$N_2$ cycles, stirred at 130° C. overnight and then washed with $H_2O$ (200 mL) and sat'd $NaHCO_3$ (200 mL). The combined aqueous layers were extracted with toluene (300 mL). The organic layer was dried ($Na_2SO_4$), filtered, and concentrated to dryness. The residue was triturated (petroleum ether:EtOAc=10:1, 80 mL) to give 4-(3-chloro-4-methoxyphenyl)cyclohexanone, containing a small amount of 3'-chloro-4'-methoxy-5,6-dihydro-[1,1'-biphenyl]-4(3H)-one, (20 g, 54%) as a light yellow solid. This solid (5.00 g, 21.12 mmol) was added to a mixture of Pd/C (10 wt. %, 820 mg, 0.77 mmol), HCl (12 M, 1.00 mL), and EtOAc (100 mL). The resulting mixture was degassed with 3 vacuum/$H_2$ cycles, stirred at rt for 30 min under $H_2$ (15 psi), filtered and then diluted with EtOAc (50 mL). The mixture was washed water (100 mL) and washed with sat'd $NaHCO_3$ (100 mL). The aqueous phase was extracted with EtOAc (100 mL). The combined organic layers were dried ($Na_2SO_4$), filtered, and concentrated to dryness to give 4-(3-chloro-4-methoxyphenyl)cyclohexanone (4.60 g, 84%) as a yellow solid. $^1$H NMR (400 MHz, $CDCl_3$): δ 7.24 (d, 1H), 7.09 (dd, 1H), 6.88 (d, 1H), 3.90 (s, 3H), 2.88-3.05 (m, 1H), 2.44-2.54 (m, 4H), 2.12-2.25 (m, 2H), 1.79-1.96 (m, 2H); LCMS: 239.1 $[M+H]^+$.

Step 4: 2-Chloro-1-methoxy-4-(4-(methoxymethylene)cyclohexyl)benzene

Lithium bis(trimethylsilyl)amide (1 M, 36 mL) was added dropwise to a mixture of methoxymethyl(triphenyl)phosphonium chloride (12.24 g, 35.71 mmol) and THF (80 mL) at 0° C. The mixture was stirred for 2 h at 0° C. A solution of 4-(3-chloro-4-methoxy-phenyl)cyclohexanone (5.50 g, 23.04 mmol) in THF (20 mL) was added dropwise at 0° C. The resulting mixture was stirred for 3 h at 0° C. The reaction mixture was quenched with $H_2O$ (100 mL) and extracted with EtOAc (3×100 mL). The combined organic layers were washed with brine (200 mL), dried ($Na_2SO_4$), filtered, concentrated, and purified by silica gel chromatography (petroleum ether:EtOAc=20:1) to give 2-chloro-1-methoxy-4-(4-(methoxymethylene)cyclohexyl)benzene (5 g, 77%) as yellow oil. LCMS: 267.1 $[M+H]^+$.

Step 5: 4-(3-Chloro-4-methoxyphenyl)cyclohexanecarbaldehyde

A mixture of 2-chloro-1-methoxy-4-(4-(methoxymethylene)cyclohexyl)benzene (5.00 g, 18.74 mmol), formic acid (4.50 g, 93.7 mmol), $H_2O$ (675.5 mg, 37.48 mmol), and toluene (100 mL) was degassed with 3 vacuum/$N_2$ cycles, stirred at 130° C. overnight, allowed to cool to rt, and then washed with $H_2O$ (200 mL), and washed with sat'd $NaHCO_3$ (200 mL). The combined aqueous layers were extracted with toluene (300 mL). The organic layer was dried ($Na_2SO_4$), filtered, and concentrated to dryness to give 4-(3-chloro-4-methoxy-phenyl)cyclohexanecarbaldehyde (5.60 g, crude), a mixture of cis/trans isomers, as a yellow oil.

Step 6: Trans-4-(3-Chloro-4-methoxyphenyl)cyclohexanecarbaldehyde

A solution of NaOH (992.6 mg, 24.82 mmol) in $H_2O$ (12 mL) was added to the crude mixture from Step 5 (5.60 g, 15.51 mmol), EtOH (90 mL), and toluene (15 mL). The mixture was stirred at rt overnight, quenched with H₂O (100 mL), and then extracted with EtOAc (3×100 mL). The combined organic layers were washed by brine (200 mL), dried (Na$_2$SO$_4$), filtered and concentrated to dryness to give a residue. The residue was purified by silica gel chromatography (petroleum ether:EtOAc=20:1) and then triturated with MTBE (20 mL) to give trans-4-(3-chloro-4-methoxyphenyl)cyclohexanecarbaldehyde (1.96 g, 49%) as a white solid. $^1$H NMR (400 MHz, DMSO-d$_6$): δ 9.60 (s, 1H), 7.27 (d, 1H), 7.16 (dd, 1H), 7.05 (d, 1H), 3.81 (s, 3H), 2.43 (m, 1H), 2.27-2.37 (m, 1H), 1.95-2.05 (m, 2H), 1.84 (m, 2H), 1.45 (m, 2H), 1.21-1.35 (m, 2H); LCMS: 253.1 [M+H]$^+$.

The Intermediate below was synthesized from 4-bromo-1-methoxy-2-methylbenzene following the procedures described for Intermediate 4.

| Int | Structure | Name | [M + H]$^+$ |
|---|---|---|---|
| 3 | 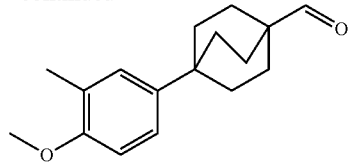 | trans-4-(4-Methoxy-3-methylphenyl)cyclohexanecarbaldehyde | 233.0 |

Alternate conditions: Step 1: −60° C.; Step 2: 0° C., 1 h; Step 3a: THF in place of PhMe, 80° C., 18 h; Step 3b: no HCl, 30 psi H$_2$, 18 h; Step 4: 15 h; Step 5: 3 N HCl, THF, 60° C., 1 h; Step 6: THF in place of PhMe.

Intermediate 5

4-(4-Methoxy-3-methylphenyl)pyridin[2.2.2]octane-1-carbaldehyde

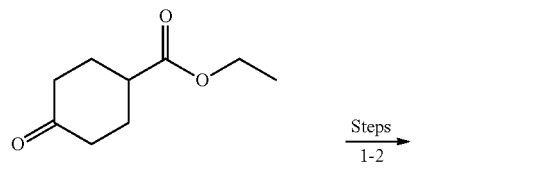

Steps 1-2 →

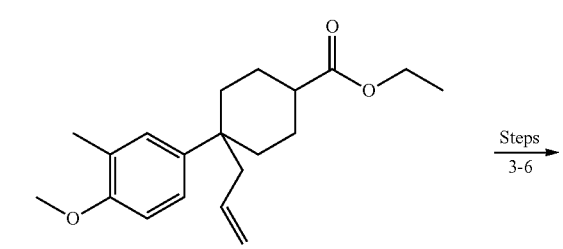

Steps 3-6 →

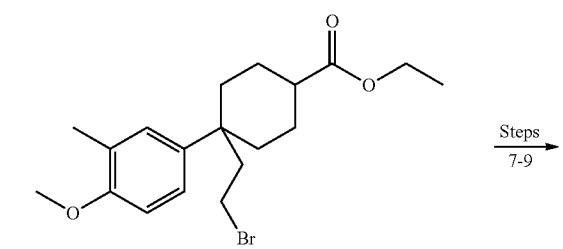

Steps 7-9 →

Step 1: Ethyl 4-hydroxy-4-(4-methoxy-3-methylphenyl)cyclohexanecarboxylate n-Butyllithium (2.5M in hexanes, 60 mL, 150.0 mmol) was added dropwise to a solution of 4-bromo-1-methoxy-2-methylbenzene (27.78 g, 138.2 mmol) in THF (300 mL) at −78° C. The mixture was stirred at −78° C. for 1 h and then added dropwise to a solution of ethyl 4-oxocyclohexanecarboxylate (22.34 g, 131.3 mmol) and THF (300 mL) at −78° C. The reaction mixture was stirred at −78° C. for 2 h, added to saturated NH$_4$Cl (600 mL) and then extracted with EtOAc (2×600 mL). The combined organic extracts were washed (400 mL water and then 400 mL brine), dried (Na$_2$SO$_4$), filtered, and concentrated. The crude was purified by silica gel chromatography (petroleum ether/EtOAc=10/1) to give ethyl 4-hydroxy-4-(4-methoxy-3-methylphenyl)cyclohexanecarboxylate (18.9 g, 45%) as a yellow oil. $^1$H NMR (400 MHz, DMSO-d$_6$): δ 7.11-7.26 (m, 2H), 6.75-6.84 (m, 1H), 4.59-4.64 (m, 1H), 3.98-4.11 (m, 2H), 3.72 (s, 3H), 2.25-2.39 (m, 1H), 2.07-2.13 (s, 3H), 1.77-1.93 (m, 3H), 1.42-1.75 (m, 5H), 1.11-1.23 (m, 3H); LCMS: 275.2 [M-OH]$^+$.

Step 2: Ethyl 4-allyl-4-(4-methoxy-3-methylphenyl)cyclohexanecarboxylate

Boron trifluoride diethyl etherate (24.85 g, 84.03 mmol) was added to a solution of ethyl 4-hydroxy-4-(4-methoxy-3-methylphenyl)cyclohexanecarboxylate (18.90 g, 64.64 mmol), allyltrimethylsilane (11.82 g, 103.42 mmol), and CH$_2$Cl$_2$ (400 mL) at −78° C. The mixture was stirred at −78° C. for 1 h, stirred at rt overnight, and then added to brine (200 mL) and CH$_2$Cl$_2$ (200 mL). The organic layer was separated, washed (2×200 mL saturated NaHCO$_3$ and then 200 mL brine), dried (Na$_2$SO$_4$), filtered, and then concentrated. The crude was purified by silica gel chromatography (petroleum ether/EtOAc=20/1) to give ethyl 4-allyl-4-(4-methoxy-3-methylphenyl)cyclohexanecarboxylate (15 g, 71%) as a yellow oil. $^1$H NMR (400 MHz, CDCl$_3$): δ 7.00-7.10 (m, 2H), 6.76 (d, 1H), 5.26-5.50 (m, 1H), 4.81-4.98 (m, 2H), 4.15 (q, 0.5H), 4.03 (q, 1.5H), 3.81 (s, 3H), 2.26-2.42 (m, 3H), 2.21 (s, 3H), 2.15 (d, 1.5H), 1.98 (d, 0.5H), 1.75-1.88 (m, 2.5H), 1.60-1.72 (m, 0.5H), 1.33-1.55 (m, 3H), 1.27 (t, 0.8H), 1.18 (t, 2.2H); LCMS: 339.3 [M+Na]$^+$.

Step 3: Ethyl 4-(2,3-dihydroxypropyl)-4-(4-methoxy-3-methylphenyl)cyclohexane Carboxylate Osmium tetroxide (0.1 M in tert-butanol, 7.6 mL, 0.76 mmol) was added to a solution of ethyl 4-allyl-4-(4-methoxy-3-methylphenyl)cyclohexanecarboxylate (4.81 g, 15.2 mmol), 4-methylmorpholine N-oxide (2.67 g, 22.8 mmol), CH$_3$CN (100 mL), and H$_2$O (25 mL) at 0° C. The reaction was stirred at rt overnight, and saturated Na$_2$SO$_3$ (50 mL) was added. The mixture was stirred at rt for 30 min, concentrated, dissolved in water (80 mL), and then extracted with EtOAc (2×100 mL). The organic layers were dried (Na$_2$SO$_4$), filtered, and concentrated. The reside was purified by silica gel chromatography (petroleum ether/EtOAc=1/1) to give ethyl 4-(2,3-dihydroxypropyl)-4-(4-methoxy-3-methylphenyl)cyclohexanecarboxylate (5.23 g, 94%) as a yellow oil. $^1$H NMR (400 MHz, CDCl$_3$): δ 7.05-7.16 (m, 2H), 6.78 (d, 1H), 4.06-4.17 (m, 0.5H), 3.95-4.05 (m, 1.5H), 3.80 (s, 3H), 3.48-3.66 (m, 1H), 3.18-3.32 (m, 2H), 2.40-2.53 (m, 2H), 2.27-2.37 (m, 1H), 2.19 (s, 3H), 1.80 (t, 3H), 1.32-1.68 (m, 7H), 1.24 (td, 0.8H), 1.17 (t, 2.2H); LCMS: 373.3 [M+Na]$^+$.

Step 4: Ethyl 4-(4-methoxy-3-methylphenyl)-4-(2-oxoethyl)cyclohexanecarboxylate Sodium periodate (3.83 g, 17.90 mmol) was added to a solution of ethyl 4-(2,3-dihydroxypropyl)-4-(4-methoxy-3-methylphenyl)cyclohexanecarboxylate (5.23 g, 14.9 mmol), THF (70 mL), and H$_2$O (35 mL) at 0° C. The mixture was stirred at rt overnight and added to water (50 mL) and EtOAc (2×100 mL). The organic layer was separated, washed (80 mL water and then 80 mL brine), dried (Na$_2$SO$_4$), filtered, and concentrated. The residue was purified by silica gel chromatography (petroleum ether/EtOAc=5/1) to give ethyl 4-(4-methoxy-3-methylphenyl)-4-(2-oxoethyl)cyclohexanecarboxylate (3.95 g, 82%) as a yellow oil. $^1$H NMR (400 MHz, CDCl$_3$): δ 9.28-9.42 (m, 1H), 7.07-7.19 (m, 2H), 6.79 (d, 1H), 4.15 (q, 0.5H), 4.04 (q, 1.5H), 3.82 (s, 3H), 2.41-2.52 (m, 3H), 2.33 (s, 1H), 2.21 (s, 3H), 1.75-1.92 (m, 3H), 1.46-1.63 (m, 4H), 1.23-1.31 (t, 0.5H), 1.19 (t, 2.5H); LCMS: 341.3 [M+Na]$^+$.

Step 5: Ethyl 4-(2-hydroxyethyl)-4-(4-methoxy-3-methylphenyl)cyclohexanecarboxylate Sodium borohydride (704 mg, 18.6 mmol) was added to a solution of ethyl 4-(4-methoxy-3-methylphenyl)-4-(2-oxoethyl)cyclohexanecarboxylate (3.95 g, 12.41 mmol) and THF (100 mL) at 0° C. The mixture was stirred at 0° C. for 1 h, stirred at rt overnight, and then diluted with water (100 mL). The organic solvent was removed under reduced pressure, and the aqueous layer was extracted with CH$_2$C$_2$ (2×300 mL). The organic extracts were dried (Na$_2$SO$_4$), filtered, and concentrated The residue was purified by silica gel chromatography (petroleum ether/EtOAc=3/1) to give ethyl 4-(2-hydroxyethyl)-4-(4-methoxy-3-methylphenyl)cyclohexanecarboxylate (3.11 g, 67%) as a yellow oil. $^1$H NMR (400 MHz, CDCl$_3$): δ 6.96-7.04 (m, 2H), 6.71 (d, 1H), 4.03-4.12 (q, 0.4H), 3.97 (q, 1.6H), 3.74 (s, 3H), 3.28-3.38 (m, 2H), 2.19-2.39 (m, 3H), 2.14 (s, 3H), 1.71-1.80 (m, 2H), 1.60-1.70 (m, 2H), 1.28-1.50 (m, 4H), 1.17-1.24 (t, 1H), 1.12 (t, 2H); LCMS: 343.2 [M+Na]$^+$.

Step 6: Ethyl 4-(2-bromoethyl)-4-(4-methoxy-3-methylphenyl)cyclohexanecarboxylate A solution of triphenylphosphine (4.60 g, 17.54 mmol) and CH$_2$Cl$_2$ (20 mL) was added dropwise to a solution of ethyl 4-(2-hydroxyethyl)-4-(4-methoxy-3-methylphenyl)cyclohexanecarboxylate (2.81 g, 8.77 mmol), CBr$_4$ (4.36 g, 13.16 mmol), and CH$_2$Cl$_2$ (40 mL) at 0° C. The mixture was stirred at 0° C., stirred at rt overnight, and then concentrated. The residue was purified by silica gel chromatography (petroleum ether/EtOAc=20/1) to give ethyl 4-(2-bromoethyl)-4-(4-methoxy-3-methylphenyl)cyclohexanecarboxylate (2.62 g, 77%) as a yellow oil. $^1$H NMR (400 MHz, CDCl$_3$): δ 6.96-7.08 (m, 2H), 6.77 (d, 1H), 4.15 (q, 0.3H), 4.03 (q, 1.7H), 3.81 (s, 3H), 2.91-3.06 (m, 2H), 2.24-2.41 (m, 3H), 2.15-2.24 (s, 3H), 1.95-2.06 (m, 2H), 1.77-1.87 (m, 2H), 1.34-1.53 (m, 4H), 1.27 (t, 1H), 1.18 (t, 2H); LCMS: 405.1 [M+Na]$^+$.

Step 7: Ethyl 4-(4-methoxy-3-methylphenyl)pyridin[2.2.2]octane-1-carboxylate Lithium diisopropylamide (2 M in THF, 4.8 mL, 9.60 mmol) was added dropwise to a solution of ethyl 4-(2-bromoethyl)-4-(4-methoxy-3-methylphenyl)cyclohexanecarboxylate (1.81 g, 4.72 mmol), HMPA (4.23 g, 23.61 mmol), and THF (90 mL) at −78° C. The mixture was stirred at −78° C. for 3 h, added to saturated NH$_4$Cl (90 mL), and then extracted with EtOAc (2×150 mL). The combined organic layers were washed (100 mL H$_2$O and then 100 mL brine), dried (Na$_2$SO$_4$), filtered, and concentrated. The residue was purified by silica gel chromatography (petroleum ether/EtOAc=30/1) to give ethyl 4-(4-methoxy-3-methylphenyl)177yridin[2.2.2]octane-1-carboxylate (1.17 g, 82%) as a yellow solid. $^1$H NMR (400 MHz, CDCl$_3$): δ 6.98-7.05 (m, 2H), 6.69 (d, 1H), 4.05 (q, 2H), 3.73 (s, 3H), 2.14 (s, 3H), 1.70-1.87 (m, 12H), 1.18 (t, 3H); LCMS: 303.3 [M+H]$^+$.

Step 8: (4-(4-Methoxy-3-methylphenyl)pyridin[2.2.2]octan-1-yl)methanol

Diisobutylaluminum hydride (1 M in toluene, 14 mL, 14.0 mmol) was added to a solution of ethyl 4-(4-methoxy-3-methylphenyl)pyridin[2.2.2]octane-1-carboxylate (1.64 g, 5.42 mmol) and CH$_2$Cl$_2$ (100 mL) at −78° C. The mixture was stirred at −78° C. for 1 h, stirred at rt for 2 h, and then added to ice H$_2$O (80 mL). The pH was adjusted (pH=6) with 1 N HCl, and the mixture was filtered. The layers were separated, and the aqueous layer was extracted with CH$_2$Cl$_2$ (2×200 mL). The combined organic layers were washed (100 mL water and then 100 mL brine), dried (Na$_2$SO$_4$), filtered, and concentrated. The residue was purified by silica gel chromatography (petroleum ether/EtOAc=10/1) to give (4-(4-methoxy-3-methylphenyl)pyridin[2.2.2]octan-1-yl)methanol (1.22 g, 82%) as a yellow solid. $^1$H NMR (400 MHz, CDCl$_3$): δ 6.99-7.07 (m, 2H), 6.64-6.72 (m, 1H), 3.73 (s, 3H), 3.25 (s, 2H), 2.14 (s, 3H), 1.69-1.81 (m, 6H), 1.40-1.50 (m, 6H); LCMS: 261.2 [M+H]$^+$.

Step 9: 4-(4-Methoxy-3-methylphenyl)pyridin[2.2.2]octane-1-carbaldehyde

Pyridinium chlorochromate (1.03 g, 4.78 mmol) was added to a mixture of (4-(4-methoxy-3-methylphenyl)pyridin[2.2.2]octan-1-yl)methanol (621 mg, 2.39 mmol), SiO$_2$ (1.93 g, 32.19 mmol) and CH$_2$Cl$_2$ (120 mL). The mixture was stirred at rt for 2 h, filtered through a neutral alumina plug and then concentrated to give Intermediate 3 (601 mg, 93%) as a white solid. $^1$H NMR (400 MHz, CDCl$_3$): δ 9.48-9.56 (s, 1H), 7.06-7.11 (m, 2H), 6.72-6.78 (m, 1H), 3.81 (s, 3H), 2.22 (s, 3H), 1.83-1.91 (m, 6H), 1.71-1.80 (m, 6H); LCMS: 259.3 [M+H]$^+$.

The Intermediate below was synthesized from 5-bromo-N,N-dimethylpyridin-2-amine following the procedures described for Intermediate 5.

| Int | Structure | Name | [M + H]⁺ |
|---|---|---|---|
| 5.01 | 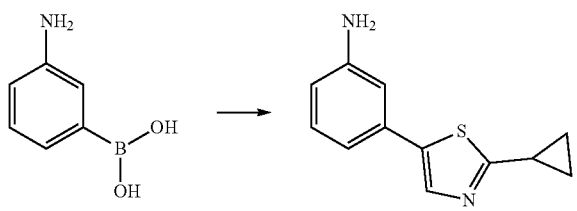 [SMILES: Nc1cccc(B(O)O)c1 ; Nc1cccc(-c2cnc(C3CC3)s2)c1] | trans-4-(6-(Dimethylamino)pyridine-3-yl)cyclohexanecarbaldehyde | 259.2 |

Alternate conditions: Step 2: 0° C., overnight; Step 3: K₂OsO₄•2H₂O; Step 7: −78° C., 1 h then rt, overnight; Step 9: oxalyl chloride, DMSO, Et₃N, −78° C.

Intermediate 6

3-(2-Cyclopropylthiazol-5-yl)aniline

A mixture of 3-aminophenylboronic acid (2.02 g, 14.7 mmol), Pd(dppf)Cl₂ (363 mg, 0.50 mmol), aqueous K₂CO₃ (2.2 M, 13.5 mL, 29.7 mmol), and dioxane (17.5 mL) was degassed with 3 vacuum/N₂ cycles. 5-Bromo-2-cyclopropylthiazole (2.01 g, 9.85 mmol) was added, and the reaction was heated at 80° C. for 4.25 h. The reaction was allowed to cool to rt and then poured into 100 mL water. The mixture was extracted with 100 mL EtOAc, and the organics were washed with 75 mL brine. The combined aqueous washes were back extracted with 50 mL EtOAc. The combined extracts were dried (Na₂SO₄), filtered, concentrated, and purified by silica gel chromatography (10-40% EtOAc in hexanes) to give 3-(2-cyclopropylthiazol-5-yl)aniline (1.84 g, 87%) as a yellow solid. ¹H NMR (400 MHz, DMSO-d₆): δ 7.79 (s, 1H), 7.04 (t, 1H), 6.76-6.71 (m, 2H), 6.55-6.49 (m, 1H), 5.23 (s, 2H), 2.41-2.33 (m, 1H), 1.14-1.08 (m, 2H), 1.00-0.94 (m, 2H); LCMS: 217.4 [M+H]⁺.

The Intermediates below were synthesized from the appropriate boronic acid and the appropriate heteroaryl bromide following the procedure described for Intermediate 6.

| Int | Structure | Name | [M + H]⁺ |
|---|---|---|---|
| 6.01 | 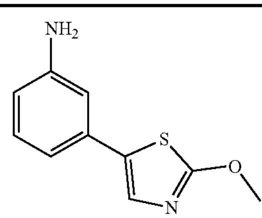 | 3-(2-Methoxythiazol-5-yl)aniline | 207.4 |
| 6.02[1] | 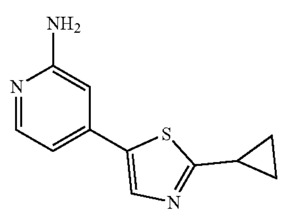 [SMILES: Nc1cc(-c2cnc(C3CC3)s2)ccn1] | 4-(2-Cyclopropylthiazol-5-yl)pyridin-2-amine | 218.0 |
| 6.03[2] | 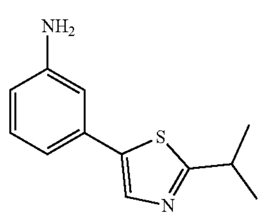 | 3-(2-Isopropylthiazol-5-yl)aniline | 219.3 |

| Int | Structure | Name | [M + H]⁺ |
|---|---|---|---|
| 6.04[2] | 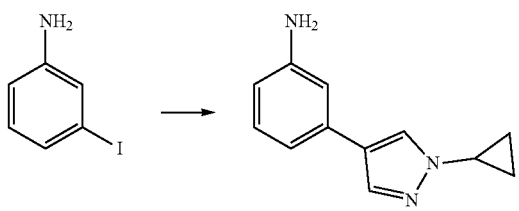 [SMILES: Nc1cccc(I)c1 ; Nc1cccc(-c2cnn(C3CC3)c2)c1] | 4-(2-Isopropylthiazol-5-yl)pyridin-2-amine | 220.3 |

Alternate conditions: [1]Cs$_2$CO$_3$, dioxane/H$_2$O (4:1), 80° C., overnight; [2]Heated at 90° C..

Intermediate 7

3-(1-Cyclopropyl-1H-pyrazol-4-yl)aniline

A mixture of 3-iodoaniline (63.36 g, 289.9 mmol), Pd(dppf)Cl$_2$ (7.05 g, 9.63 mmol), K$_2$CO$_3$ (2.2 M, 265 mL, 583.0 mmol), and dioxane (340 mL) was degassed with vacuum/N$_2$ cycles (3×). 1-cyclopropyl-4-(4,4,5,5-tetramethyl-1,3,2-dioxaborolan-2-yl)-1H-pyrazole (~90%, 50.09 g, 192.6 mmol) was added, and the mixture was heated in a pre-heated oil bath (90° C.) for 20 min (internal temp at 20 min was 72° C.). The reaction was allowed to cool to rt, diluted with EtOAc (800 mL) and H$_2$O (800 mL), and then filtered through Celite with EtOAc washing (~400 mL). The layers were separated, and the organic layer was washed (800 mL H$_2$O), dried (Na$_2$SO$_4$), filtered, and concentrated (73.88 g). The residue was dry loaded onto silica gel and purified by silica gel chromatography (20-60% EtOAc in hexanes) to give 3-(1-cyclopropyl-1H-pyrazol-4-yl)aniline (31.5 g, 82%) as a beige solid. $^1$H NMR (400 MHz, DMSO-d$_6$): δ 8.03 (s, 1H), 7.66 (d, 1H), 6.97 (t, 1H), 6.73-6.72 (m, 1H), 6.71-6.68 (in 1H), 6.42-6.38 (m, 1H), 5.00 (s, 2H), 3.75-3.68 (m, 1H), 1.08-1.00 (m, 2H), 1.00-0.92 (in 2H); LCMS: 200.3 [M+H]⁺.

The Intermediates below were synthesized from the appropriate boronic acid/ester and the appropriate aryl halide following the procedure described for Intermediate 7.

| Int | Structure | Name | [M + H]⁺ |
|---|---|---|---|
| 7.01[1] | 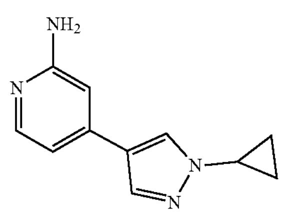 [SMILES: Nc1cc(-c2cnn(C3CC3)c2)ccn1] | 4-(1-Cyclopropyl-1H-pyrazol-4-yl)pyridin-2-amine | 201.3 |
| 7.02[1] | 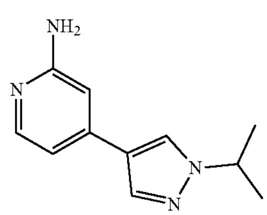 | 4-(1-Isopropyl-1H-pyrazol-4-yl)pyridin-2-amine | 203.0 |
| 7.03 | 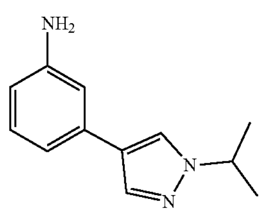 | 3-(1-Isopropyl-1H-pyrazol-4-yl)aniline | 202.0 |

-continued

| Int | Structure | Name | [M + H]+ |
|---|---|---|---|
| 7.04 | 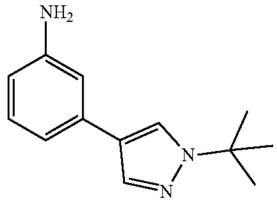 [SMILES: CC(C)(C)n1cc(-c2cccc(N)c2)cn1] | 3-(1-(tert-Butyl)-1H-pyrazol-4-yl)aniline | 216.4 |
| 7.05 | 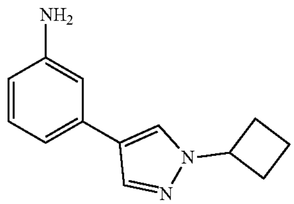 [SMILES: Nc1cccc(-c2cnn(C3CCC3)c2)c1] | 3-(1-Cyclobutyl-1H-pyrazol-4-yl)aniline | 214.4 |
| 7.062 | 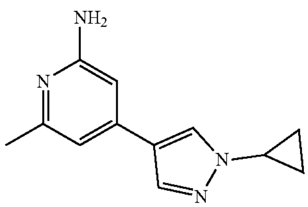 [SMILES: Cc1cc(-c2cnn(C3CC3)c2)cc(N)n1] | 4-(1-Cyclopropyl-1H-pyrazol-4-yl)-6-methylpyridin-2-amine | 215.1 |

[1] 4-bromopyridin-2-amine was used. [2] 4-bromo-6-methylpyridin-2-amine was used Intermediate 8

3-(2-Isopropyloxazol-4-yl)aniline

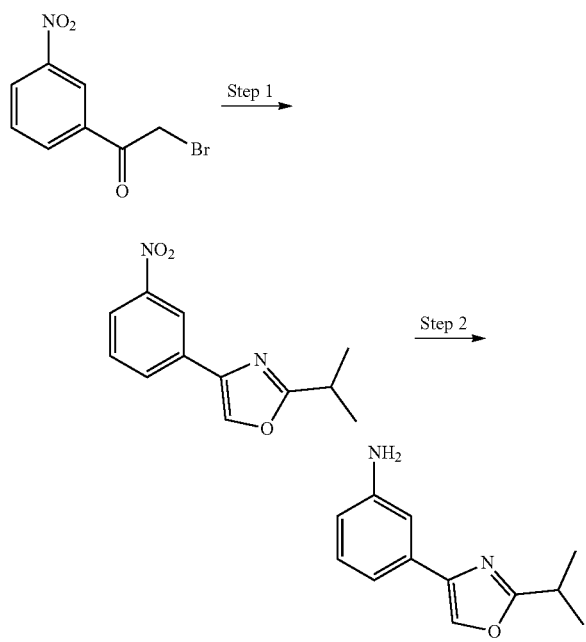

Step 1: 2-Isopropyl-4-(3-nitrophenyl)oxazole

Isobutyramide (44.62 g, 512.2 mmol) was added to a solution of 2-bromo-1-(3-nitrophenyl)ethanone (50 g, 205 mmol) in toluene (100 mL) at rt. The mixture was refluxed for 4 h, allowed to cool to rt, and then filtered through filter paper. The filtrate was diluted with diethyl ether (80 mL). The organics were successively washed with $H_2O$ (50 mL), aq. NaOH (0.5 M, 50 mL), aq. HCl (0.5 M, 50 mL), and brine (100 mL), dried over $Na_2SO_4$, filtered, concentrated, and then purified by silica gel chromatography (petroleum ether/EtOAc=I/O to 10/1) to give 2-isopropyl-4-(3-nitrophenyl)oxazole (28 g, 59%) as a white solid. $^1$H NMR (400 MHz, DMSO-$d_6$): δ 8.76 (s, 1H), 8.54 (s, 1H), 8.19-8.13 (m, 2H), 7.71 (t, 1H), 3.20-3.09 (m, 1H), 1.33 (d, 6H); LCMS: 233.1 [M+H]+.

Step 2: 3-(2-Isopropyloxazol-4-yl)aniline

A mixture of palladium on carbon (10 wt. %, 3 g, 2.8 mmol), 2-isopropyl-4-(3-nitrophenyl)oxazole (27 g, 116 mmol), and $CH_3OH$ (80 mL) was degassed with vacuum/$H_2$ cycles (3×). The mixture was stirred under $H_2$ at rt for 4 h and then filtered through Celite. The filtrate was concentrated and then purified by silica gel chromatography (petroleum ether/EtOAc=30/1 to 10/1) to give 3-(2-isopropyloxazol-4-yl)aniline (15 g, 64%) as a yellow solid. $^1$H NMR (400 MHz, DMSO-$d_6$): δ 7.77 (s, 1H), 7.19-7.09 (m, 3H), 6.64-6.62 (m, 1H), 3.72 (s, 2H), 3.18-3.11 (m, 1H), 1.38 (d, 6H); LCMS: 203.1 [M+H]+.

The following Intermediate was synthesized from cyclopropanecarboxamide following the procedure described for Intermediate 8.

| Int | Structure | Name | [M +H]+ |
|---|---|---|---|
| 8.01 | 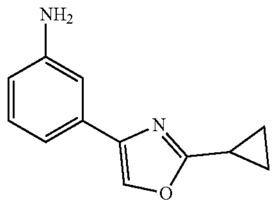 [SMILES: Nc1cccc(-c2coc(C3CC3)n2)c1] | 3-(2-Cyclopropyloxazol-4-yl)aniline | 201.1 |

Intermediate 9

3-Cyclopropyl-5-(3-nitrophenyl)isothiazole

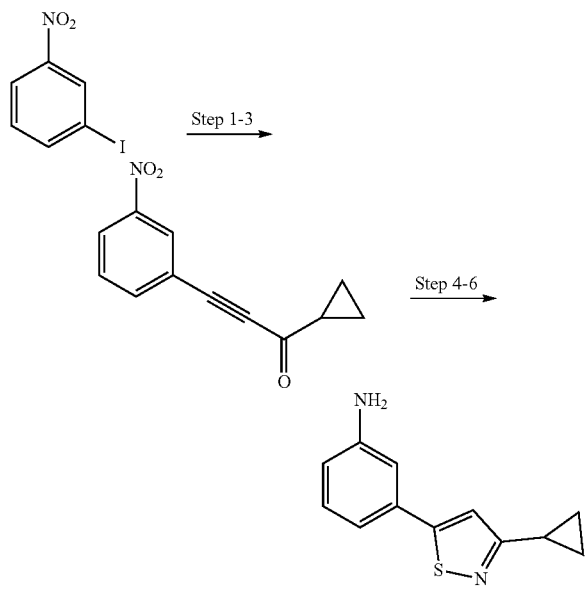

Step 1:
1-Cyclopropyl-3-(trimethylsilyl)prop-2-yn-1-one

A mixture of ethynyltrimethylsilane (1.00 g, 10.18 mmol), cyclopropanecarbonyl chloride (1.06 g, 10.18 mmol), Et$_3$N (1.03 g, 10.18 mmol), CuI (78 mg, 0.407 mmol), Pd(PPh$_3$)$_2$Cl$_2$ (143 mg, 0.204 mmol), and THF (20 mL) was degassed with vacuum/N$_2$ cycles (3×), stirred at rt for 1 h, quenched with NH$_4$Cl (20 mL), and then extracted with EtOAc (3×20 m). The combined organic layers were washed (2×25 mL brine), dried (Na$_2$SO$_4$), filtered, and concentrated. The residue was purified by silica gel chromatography (petroleum ether/EtOAc=50/1) to give 1-cyclopropyl-3-(trimethylsilyl)prop-2-yn-1-one (350 mg, 21%) as a colorless oil. $^1$H NMR (400 MHz, CDCl$_3$): δ 1.76-1.89 (m, 1H), 0.95-1.10 (m, 2H), 0.79-0.82 (m, 2H), 0.00 (s, 9H); LCMS: 167.1 [M+H]+.

Step 2:
1-Cyclopropyl-3-(3-nitrophenyl)prop-2-yn-1-one

A mixture of 1-cyclopropyl-3-(trimethylsilyl)prop-2-yn-1-one (50 mg, 0.301 mmol), 1-iodo-3-nitrobenzene (115 mg, 0.460 mmol), Pd(PPh$_3$)$_2$Cl$_2$ (27 mg, 0.039 mmol), PPh$_3$ (21 mg, 0.081 mmol), Et$_3$N (107.4 mg, 1.06 mmol), CuI (4 mg, 0.021 mmol), and DMF (4 mL) was degassed with vacuum/N$_2$ cycles (3×) and heated to 60° C. TBAF (1 M, 300 uL, 0.3 mmol) was added over 30 minutes to the mixture, and the reaction was stirred at 60° C. for 3 h. The solution was concentrated and purified by silica gel chromatography (petroleum ether/EtOAc=20/1 to 5/1) to give 1-cyclopropyl-3-(3-nitrophenyl)prop-2-yn-1-one (40 mg, 62%) as a white solid. H NMR (400 MHz, CDCl$_3$): δ 8.38-8.47 (m, 1H), 8.26-8.35 (m, 1H), 7.82-7.91 (m, 1H), 7.56-7.66 (m, 1H), 2.18-2.27 (m, 1H), 1.33-1.38 (m, 2H), 1.15-1.19 (m, 2H).

Step 3:
1-Cyclopropyl-3-(3-nitrophenyl)prop-2-yn-1-one

A mixture of 1-cyclopropyl-3-(3-nitrophenyl)prop-2-yn-1-one (800 mg, 3.72 mmol), NH$_4$SCN (314 mg, 4.13 mmol), and 2-methoxy-2-methylpropane (10 mL) was degassed with vacuum/N$_2$ cycles (3×), stirred at 60° C. overnight, and quenched with H$_2$O (10 mL). The layers were separated, and the aqueous phase was extracted with 2-methoxy-2-methyl-propane (10 mL). The combined organic extracts were washed (5 mL H$_2$O), dried (K$_2$CO$_3$), filtered, and concentrated. The crude (Z)-1-cyclopropyl-3-(3-nitrophenyl)-3-thiocyanatoprop-2-en-1-one (800 mg) was used in the next step without further purification. LCMS: 248.0 [M-CN]+.

Step 4: 3-Cyclopropyl-5-(3-nitrophenyl)isothiazole

A mixture of (Z)-1-cyclopropyl-3-(3-nitrophenyl)-3-thiocyanatoprop-2-en-1-one (800 mg, 2.92 mmol) and NH$_3$ (50 mL) at −78° C. was allowed to slowly warm to rt over 2 h. The residue was purified by silica gel chromatography (petroleum ether/EtOAc=5/1) to give 3-cyclopropyl-5-(3-nitrophenyl)isothiazole (200 mg, 28%) as a white solid. $^1$H NMR (400 MHz, CDCl$_3$): δ 8.35 (s, 1H), 8.17 (d, 1H), 7.80 (d, 1H), 7.55 (t, 1H), 7.15 (s, 1H), 2.08-2.22 (m, 1H), 0.95-1.01 (m, 4H); LCMS: 247.1 [M+H]+.

Step 6: 3-(3-Cyclopropylisothiazol-5-yl)aniline

A mixture of 3-cyclopropyl-5-(3-nitrophenyl)isothiazole (300 mg, 1.22 mmol), SnCl$_2$.2H$_2$O (1.10 g, 4.87 mmol), EtOH (5 mL), and H$_2$O (500 uL) was degassed with vacuum/N$_2$ cycles (3×), stirred at 78° C. for 2 h, poured into CH$_2$Cl$_2$ (10 mL), and then filtered. The filtrate was diluted with H$_2$O (10 mL), extracted with CH$_2$Cl$_2$ (3×10 mL), washed (15 mL brine), concentrated, and then purified by silica gel chromatography (petroleum ether/EtOAc=5/1) to give 3-(3-cyclopropylisothiazol-5-yl)aniline (140 mg, 53%) as a white solid. H NMR (400 MHz, CDCl$_3$): δ 7.20 (t, 1H), 7.06 (s, 1H), 6.98 (d, 1H), 6.87 (t, 1H), 6.68-6.73 (m, 1H), 3.78 (s, 2H), 2.11-2.27 (m, 1H), 0.93-1.14 (m, 4H); LCMS: 217.2 [M+H]+.

Intermediate 10

4-(2-Cyclopropyloxazol-4-yl)pyridine-2-amine

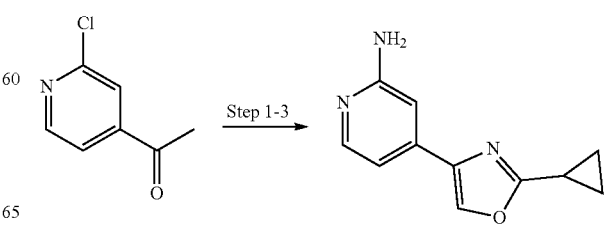

Step 1: 2-Bromo-1-(2-chloropyridin-4-yl)ethanone

Bromine (12.94 g, 80.99 mmol) and HBr (19.5 mL, 108.0 mmol, 30% in AcOH) were added to a mixture of 1-(2-chloropyridin-4-yl)ethanone (14 g, 90 mmol) and AcOH (280 mL) at rt. The mixture was stirred at rt overnight, diluted with MTBE (400 mL), and filtered. The filter cake was washed (400 mL MTBE), added to a mixture of saturated NaHCO$_3$ (300 mL) and EtOAc (500 mL), and then stirred for 1 h. The organic layer was separated and washed (300 mL saturated NaHCO$_3$). The combined aqueous layers were extracted with EtOAc (2×300 mL). The combined organic layers were dried (Na$_2$SO$_4$), filtered, and concentrated to give 2-bromo-1-(2-chloropyridin-4-yl)ethanone (15 g, crude) as a red solid. $^1$H NMR (400 MHz, CDCl$_3$): δ 8.65 (d, 1H), 7.80 (s, 1H), 7.70 (d, 1H), 4.40 (s, 2H); LCMS 234.0 [M+H]$^+$.

Step 2: 4-(2-Chloropyridin-4-yl)-2-cyclopropyloxazole

A mixture of 2-bromo-1-(2-chloropyridin-4-yl)ethanone (20 g, 85 mmol), cyclopropanecarboxamide (9.07 g, 106 mmol), AgOTf (43.83 g, 170.6 mmol), and EtOAc (300 mL) was stirred at 70° C. overnight in darkness under N$_2$ and then allowed to cool to rt. Brine (300 mL) was added to the mixture, and the mixture was stirred for 3 h and filtered. The aqueous layer was separated and extracted with EtOAc (3×300 mL). The combined organic layers were washed (2×300 mL saturated NaHCO$_3$ and then 200 mL brine), dried (Na$_2$SO$_4$), filtered, and concentrated. The residue was purified by silica gel chromatography (petroleum ether/EtOAc=9/1) to give 4-(2-chloropyridin-4-yl)-2-cyclopropyloxazole (13.2 g, 70%) as a yellow solid. $^1$H NMR (400 MHz, CDCl$_3$): δ 8.38 (d, 1H), 7.92 (s, 1H), 7.66 (d, 1H), 7.49 (d, 1H), 2.17-2.09 (m, 1H), 1.18-1.07 (m, 4H); LCMS 220.9 [M+H]$^+$.

Step 3: 4-(2-Cyclopropyloxazol-4-yl)pyridin-2-amine

Lithium bis(trimethylsilyl)amide (126 mL, 126 mmol, 1 M in THF) was added to a mixture of 4-(2-chloro-4-pyridyl)-2-cyclopropyl-oxazole (13.2 g, 59.8 mmol), XPhos (2.28 g, 4.80 mmol), Pd$_2$(dba)$_3$ (2.19 g, 2.394 mmol), and THF (150 mL) at rt under N$_2$. The reaction mixture was heated at 60° C. overnight, allowed to cool to rt, added to ice-cold HCl (200 mL, 1 M), and then stirred for 2 h. Sodium hydroxide (1 M) was added to the mixture (pH=11), and the mixture was extracted with EtOAc (3×300 mL). The combined organic layers were washed (200 mL brine), dried (Na$_2$SO$_4$), filtered, and concentrated. The residue was purified by silica gel chromatography (petroleum ether/EtOAc/EtOH=36/3/1) and then triturated (petroleum ether/EtOAc/EtOH=36/3/1) to give 4-(2-cyclopropyloxazol-4-yl)pyridine-2-amine (3.53 g, 29%) as a yellow solid. $^1$H NMR (400 MHz, DMSO-d$_6$): δ 8.46 (s, 1H), 7.88 (d, 1H), 6.80 (s, 1H), 6.77 (d, 1H), 5.96 (s, 2H), 2.25-2.05 (m, 1H), 1.09-1.03 (m, 2H), 1.02-0.96 (m, 2H); LCMS 202.1 [M+H]$^+$.

The following Intermediate was synthesized from isobutyramide following the procedure described for Intermediate 10.

| Int | Structure | Name | [M + H]$^+$ |
|---|---|---|---|
| 10.01 | 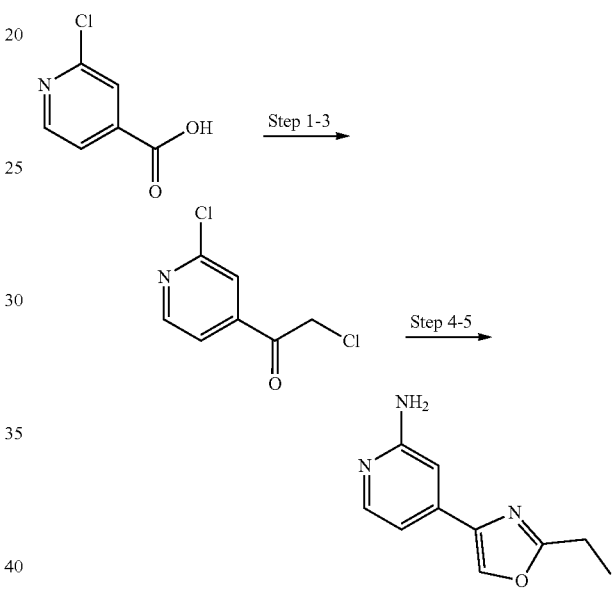 | 4-(2-Isopropyloxazol-4-yl)pyridine-2-amine | 204.2 |

Intermediate 11

4-(2-Ethyloxazol-4-yl)pyridin-2-amine

Step 1: 2-Chloroisonicotinoyl Chloride

Oxalyl chloride (96.67 g, 761.64 mmol) was added to a solution of 2-chloropyridine-4-carboxylic acid (75 g, 476.03 mmol), DMF (3.48 g, 47.60 mmol), and CH$_2$Cl$_2$ (850 mL) at 0° C. under N$_2$. The reaction was stirred at rt for 2.5 h and then concentrated to dryness to give 2-chloroisonicotinoyl chloride (85 g, crude) as a black brown oil.

Step 2: 1-(2-Chloropyridin-4-yl)-2-diazoethanone

A suspension of 2-chloropyridine-4-carbonyl chloride (85 g, crude) in CH$_3$CN (50 mL) and THF (50 mL) was added to a solution of diazomethyl(trimethyl)silane (2 M in n-hexane, 483 mL, 966 mmol), CH$_3$CN (400 mL), and THF (400 mL) at 0° C. under N$_2$. The reaction was stirred at rt for 1 h and then concentrated to dryness to give 1-(2-chloropyridin-4-yl)-2-diazoethanone (90 g, crude) as a black brown oil. LCMS: 182.2 [M+H]$^+$.

Step 3: 2-Chloro-1-(2-chloropyridin-4-yl)ethanone

Hydrochloric acid (12 M, 85.4 mL, 1025 mmols) was added to a solution of 1-(2-chloro-4-pyridyl)-2-diazo-ethanone (60 g, crude), THF (200 mL), and CH$_3$CN (200 mL) at 0° C. under N$_2$. The reaction was stirred at rt for 30 min, quenched with NaHCO$_3$ (100 g), and then filtered. The filtrate was diluted with H$_2$O (1000 mL) and extracted with EtOAc (2×250 mL). The combined organic layers were washed with water (2×150 mL), dried (Na$_2$SO$_4$), filtered, and concentrated. The residue was purified by silica gel chromatography (petroleum ether/EtOAc=20/1) to give 2-chloro-1-(2-chloropyridin-4-yl)ethanone (36 g) as a green solid. $^1$H NMR (400 MHz, CDCl$_3$): δ 8.63 (d, 1H), 7.78 (s, 1H), 7.67 (d, 1H), 4.65 (s, 2H); LCMS: 189.8 [M+H]$^+$.

Step 4: 4-(2-Chloropyridin-4-yl)-2-ethyloxazole

Silver trifluoromethanesulfonate (59.5 g, 231.55 mmol) was added to a solution of 2-chloro-1-(2-chloropyridin-4-yl)ethanone (22 g, 115.77 mmol), propanamide (11.00 g, 150.51 mmol), and dioxane (250 mL) at rt under N$_2$. The mixture was refluxed overnight in the dark, allowed to cool to rt, poured into a mixture of saturated NaHCO$_3$ (800 mL) and EtOAc (1000 mL), and then filtered. The filtrate was extracted with EtOAc (2×1000 mL), and the combined organic phase was washed (800 mL brine), dried over Na$_2$SO$_4$, filtered, and concentrated. The residue was purified by silica gel chromatography (petroleum ether/EtOAc=3/1 to give 4-(2-chloropyridin-4-yl)-2-ethyloxazole (15.1 g, 60%) as a yellow solid. $^1$H NMR (400 MHz, CDCl$_3$): δ 8.31 (d, 1H), 7.92 (s, 1H), 7.60 (s, 1H), 7.53-7.37 (m, 1H), 2.79 (q, 2H), 1.32 (t, 3H); LCMS: 209.1 [M+H]$^+$.

Step 5: 4-(2-Ethyloxazol-4-yl)pyridin-2-amine

Lithium bis(trimethylsilyl)amide (1 M in THF, 76 mL, 76 mmol) was added to a solution of 4-(2-chloropyridin-4-yl)-2-ethyloxazole (16 g, 76.69 mmol), XPhos (3.66 g, 7.67 mmol), Pd$_2$(dba)$_3$ (3.51 g, 3.83 mmol), and dioxane (320 mL) at rt. The mixture was heated to 100° C. under N$_2$ for 2 h, allowed to cool to rt, poured into water (500 mL), and then extracted with EtOAc (2×600 mL). The combined organic layers were washed (300 mL brine), dried (Na$_2$SO$_4$), filtered and concentrated. The residue was purified by silica gel chromatography (petroleum ether/EtOAc=3/1-1/1) and then triturated (100 mL 1:1 petroleum ether:MTBE) to give 4-(2-ethyloxazol-4-yl)pyridin-2-amine (8.02 g, 55%) as a yellow solid. $^1$H NMR (400 MHz, DMSO-d$_6$): δ 8.51 (s, 1H), 7.87 (d, 1H), 6.82 (s, 1H), 6.77 (d, 1H), 5.95 (s, 2H), 2.78 (q, 2H), 1.25 (t, 3H); LCMS: 190.1 [M+H]$^+$.

Intermediate 12

5-(3-Aminophenyl)-N,N-dimethylpyridin-2-amine

A mixture of 3-iodoaniline (3.96 g, 18.08 mmol), (6-(dimethylamino)pyridine-3-yl)boronic acid (2.04 g, 12.26 mmol), 2.2 M K$_2$CO$_3$ (16 mL, 35 mmol), Pd(dppf)Cl$_2$ (443 mg, 0.61 mmol), and dioxane (21 mL) was degassed with vacuum/nitrogen cycles (3×), heated at 90° C. for 60 min, and then cooled to rt. The reaction was diluted with EtOAc (100 mL), washed (2×100 mL H$_2$O and then 100 mL brine), dried (Na$_2$SO$_4$), and concentrated. The residue was purified by silica gel chromatography (20-50% EtOAc in hexanes) to give 5-(3-aminophenyl)-N,N-dimethylpyridin-2-amine as a beige solid (2.18 g, 84%). $^1$H NMR (400 MHz, DMSO-d$_6$): δ 8.30 (d, 1H), 7.68 (dd, 1H), 7.05 (t, 1H), 6.75 (t, 1H), 6.72-6.66 (m, 2H), 6.49 (dd, 1H), 5.08 (s, 2H), 3.04 (s, 6H); LCMS: 214.4 [M+H]$^+$.

Intermediate 13

3-Iodo-N-((trans-4-(4-methoxy-3-methylphenyl)cyclohexyl)methyl)aniline

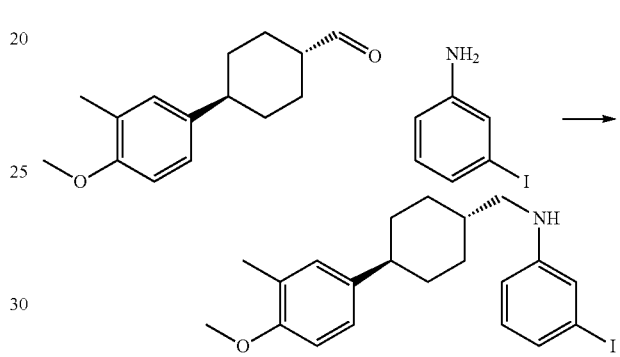

Sodium triacetoxyborohydride (3.74 g, 17.6 mmol) was added to a solution of Intermediate 3 (2.56 g, 11.0 mmol), 3-iodoaniline (2.56 g, 11.7 mmol), acetic acid (1.3 mL, 23 mmol) and dichloroethane (45 mL) at rt under N$_2$. The reaction was stirred for 80 min, poured into 50 mL sat'd NaHCO$_3$ and extracted with 50 mL EtOAc. The EtOAc layer was washed with 50 mL sat'd NaHCO$_3$ and washed with 50 mL brine. The aqueous layers were combined and back extracted with 25 mL EtOAc. The combined organics were dried (Na$_2$SO$_4$), filtered, concentrated and purified by silica gel chromatography (0-5% EtOAc in hexanes) to give 3-iodo-N-((trans-4-(4-methoxy-3-methylphenyl)cyclohexyl)methyl)aniline (4.43 g, 88%) as a yellow oil. $^1$H NMR (400 MHz, DMSO-d$_6$): δ 7.01-6.95 (m, 2H), 6.91 (s, 1H), 6.86-6.77 (m, 3H), 6.57 (d, 1H), 5.92 (t, 1H), 3.73 (s, 3H), 2.85 (t, 2H), 2.42-2.31 (m, 1H), 2.11 (s, 3H), 1.94-1.85 (m, 2H), 1.82-1.73 (m, 2H), 1.63-1.50 (m, 1H), 1.45-1.31 (m, 2H), 1.14-1.00 (m, 2H); LCMS: 436.4 [M+H]$^+$.

Intermediate 14

3-(1-Cyclopropyl-1H-pyrazol-4-yl)-N-((4-(4-methoxy-3-methylphenyl)bicyclo[2.2.2]octan-1-yl)methyl)aniline

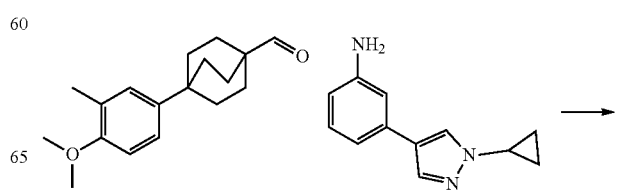

-continued

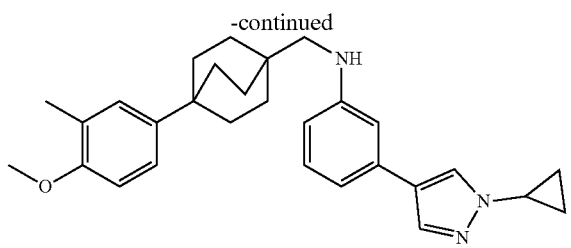

Dichloroethane was cooled in an ice/water bath under N₂. Intermediate 5 (151 mg, 0.58 mmol), Intermediate 7 (118 mg, 0.59 mmol), and then sodium triacetoxyborohydride (198 mg, 0.93 mmol) were added to the reaction at 0° C. The reaction was allowed to warm to rt, stirred at rt for 85 min, poured into 20 mL saturated NaHCO₃, and then extracted with 20 mL EtOAc. The organic layer was washed with 20 mL brine, dried (Na₂SO₄), filtered, concentrated, and purified by silica gel chromatography (10-30% EtOAc in hexanes) to give 3-(1-cyclopropyl-1H-pyrazol-4-yl)-N-((4-(4-methoxy-3-methylphenyl)bicyclo[2.2.2]octan-1-yl)methyl)aniline (233 mg, 90%) as a white foam. $^1$H NMR (400 MHz, DMSO-d₆): δ 8.09 (s, 1H), 7.71 (s, 1H), 7.11-7.05 (m, 2H), 7.00 (t, 1H), 6.84-6.76 (m, 2H), 6.68 (d, 1H), 6.47 (d, 1H), 5.32 (t, 1H), 3.75-3.68 (m, 4H), 2.83 (d, 2H), 2.12 (s, 3H), 1.78-1.69 (m, 6H), 1.62-1.52 (m, 6H), 1.10-1.04 (m, 2H), 1.00-0.93 (m, 2H); LCMS: 442.3 [M+H]⁺.

The Intermediates below were synthesized from the appropriate amine (SM or Intermediate) and the appropriate aldehyde Intermediate following the procedures described for Intermediate 14.

| Int | Structure | Name | [M + H]⁺ |
|---|---|---|---|
| 14.01[1] | 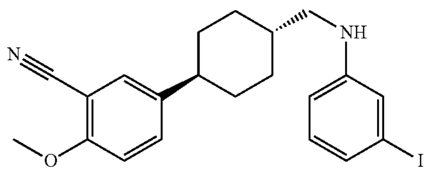 [SMILES: COc1ccc([C@H]2CC[C@H](CNc3cccc(I)c3)CC2)cc1C#N] | 5-(trans-4-(((3-Iodophenyl)amino)methyl)cyclohexyl)-2-methoxybenzonitrile | 447.1 |
| 14.02[1] | 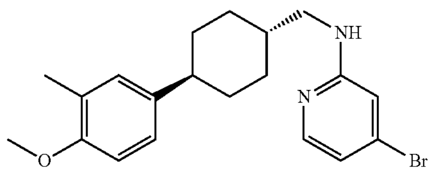 [SMILES: COc1ccc([C@H]2CC[C@H](CNc3cc(Br)ccn3)CC2)cc1C] | 4-Bromo-N-((trans-4-(4-methoxy-3-methylphenyl)cyclohexyl)methyl)pyridin-2-amine | 389.1 |
| 14.03 | 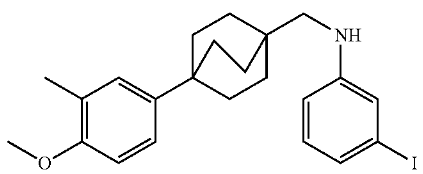 [SMILES: COc1ccc(C23CCC(CNc4cccc(I)c4)(CC2)CC3)cc1C] | 3-Iodo-N-((4-(4-methoxy-3-methylphenyl)bicyclo[2.2.2]octan-1-yl)methyl)aniline | 462.0 |
| 14.04 | 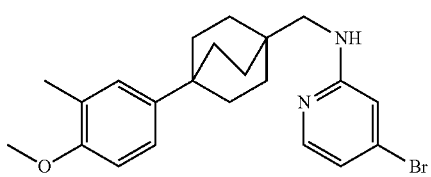 [SMILES: COc1ccc(C23CCC(CNc4cc(Br)ccn4)(CC2)CC3)cc1C] | 4-Bromo-N-((4-(4-methoxy-3-methylphenyl)bicyclo[2.2.2]octan-1-yl)methyl)pyridin-2-amine | 415.2 |
| 14.05 | 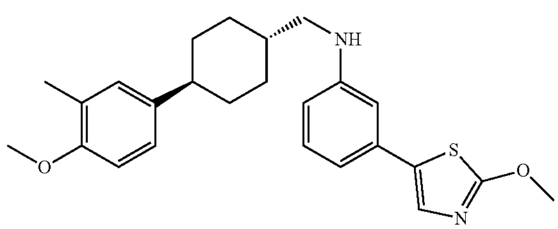 | N-((trans-4-(4-Methoxy-3-methylphenyl)cyclohexyl)methyl)-3-(2-methoxythiazol-5-yl)aniline | 423.2 |
| 14.06 | 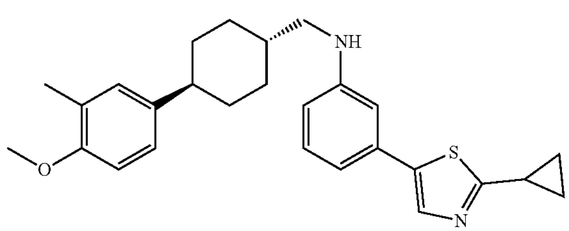 [SMILES: COc1ccc([C@H]2CC[C@H](CNc3cccc(-c4cnc(C5CC5)s4)c3)CC2)cc1C] | 3-(2-Cyclopropylthiazol-5-yl)-N-((trans-4-(4-methoxy-3-methylphenyl)cyclohexyl)methyl)aniline | 433.3 |

| Int | Structure | Name | [M + H]+ |
|---|---|---|---|
| 14.07 | 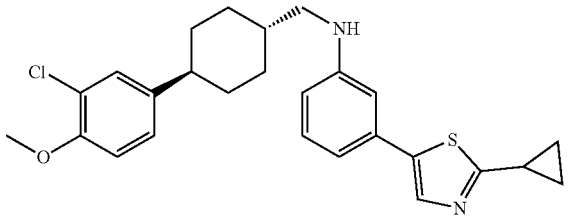 [SMILES: COc1ccc([C@H]2CC[C@H](CNc3cccc(-c4cnc(C5CC5)s4)c3)CC2)cc1Cl] | N-((trans-4-(3-Chloro-4-methoxyphenyl)cyclohexyl)methyl)-3-(2-cyclopropylthiazol-5-yl)aniline | 453.3 |
| 14.08 | 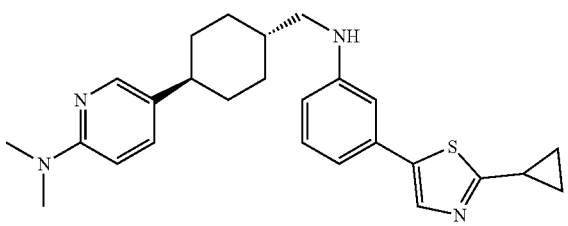 [SMILES: CN(C)c1ccc([C@H]2CC[C@H](CNc3cccc(-c4cnc(C5CC5)s4)c3)CC2)cn1] | 5-(trans-4-(((3-(2-Cyclopropylthiazol-5-yl)phenyl)amino)methyl)cyclohexyl)-N,N-dimethylpyridin-2-amine | 433.4 |
| 14.09 | 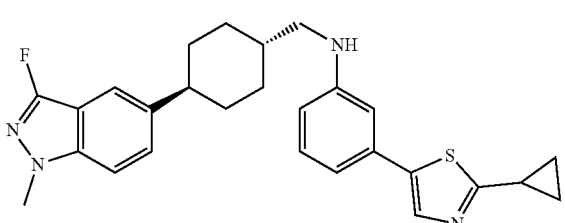 | 3-(2-Cyclopropylthiazol-5-yl)-N-((trans-4-(3-fluoro-1-methyl-1H-indazol-5-yl)cyclohexyl)methyl)aniline | 461.2 |
| 14.10 | 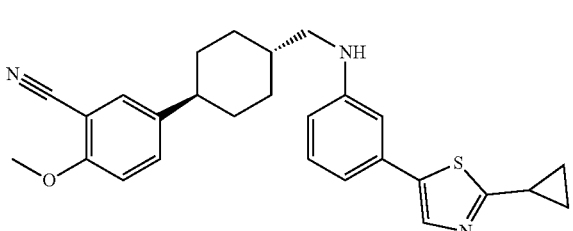 | 5-(trans-4-(((3-(2-Cyclopropylthiazol-5-yl)phenyl)amino)methyl)cyclohexyl)-2-methoxybenzonitrile | 444.3 |
| 14.11[2] | 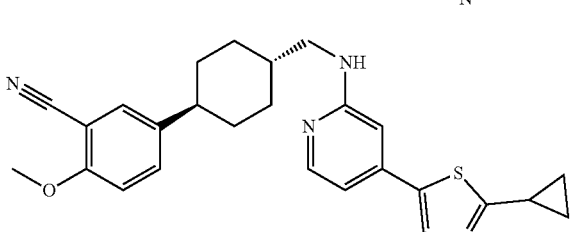 | 5-(trans-4-(((4-(2-Cyclopropylthiazol-5-yl)pyridin-2-yl)amino)methyl)cyclohexyl)-2-methoxybenzonitrile | 445.9 |
| 14.12 | 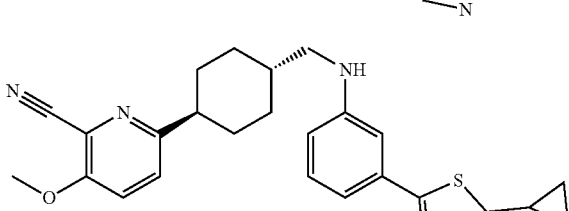 | 6-(trans-4-(((3-(2-Cyclopropylthiazol-5-yl)phenyl)amino)methyl)cyclohexyl)-3-methoxypicolinonitrile | 445.3 |
| 14.13[2] | 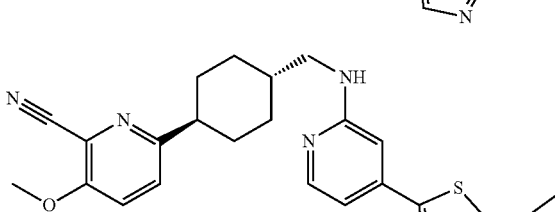 | 6-(trans-4-(((4-(2-Cyclopropylthiazol-5-yl)pyridin-2-yl)amino)methyl)cyclohexyl)-3-methoxypicolinonitrile | 446.6 |

-continued

| Int | Structure | Name | [M + H]⁺ |
|---|---|---|---|
| 14.14 | 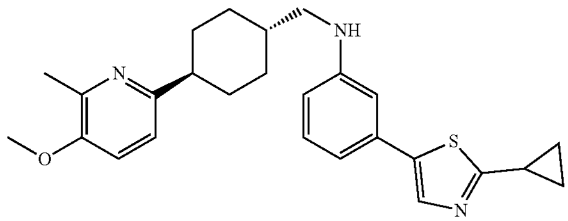 [SMILES: COc1ccc([C@H]2CC[C@H](CNc3cccc(-c4cnc(C5CC5)s4)c3)CC2)nc1C] | 3-(2-Cyclopropylthiazol-5-yl)-N-((trans-4-(5-methoxy-6-methylpyridin-2-yl)cyclohexyl)methyl)aniline | 434.1 |
| 14.15 | 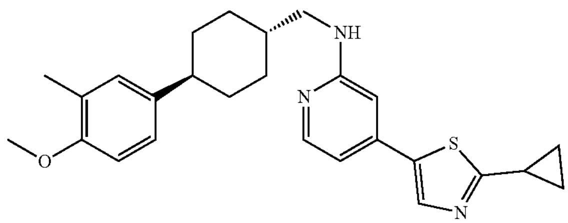 [SMILES: COc1ccc([C@H]2CC[C@H](CNc3cc(-c4cnc(C5CC5)s4)ccn3)CC2)cc1C] | 4-(2-Cyclopropylthiazol-5-yl)-N-((trans-4-(4-methoxy-3-methylphenyl)cyclohexyl)methyl)pyridin-2-amine | 434.3 |
| 14.16 | 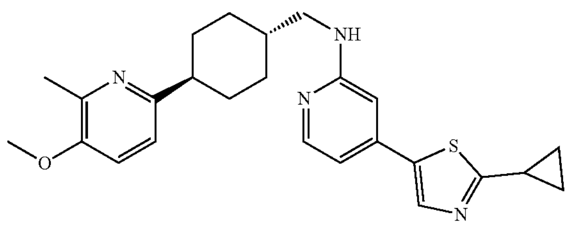 [SMILES: COc1ccc([C@H]2CC[C@H](CNc3cc(-c4cnc(C5CC5)s4)ccn3)CC2)nc1C] | 4-(2-Cyclopropylthiazol-5-yl)-N-((trans-4-(5-methoxy-6-methylpyridin-2-yl)cyclohexyl)methyl)pyridin-2-amine | 435.3 |
| 14.17 | 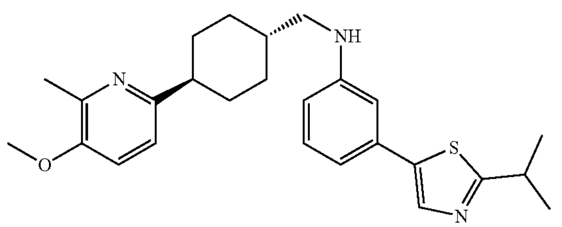 [SMILES: COc1ccc([C@H]2CC[C@H](CNc3cccc(-c4cnc(C(C)C)s4)c3)CC2)nc1C] | 3-(2-Isopropylthiazol-5-yl)-N-((trans-4-(5-methoxy-6-methylpyridin-2-yl)cyclohexyl)methyl)aniline | 436.2 |
| 14.18[2] | 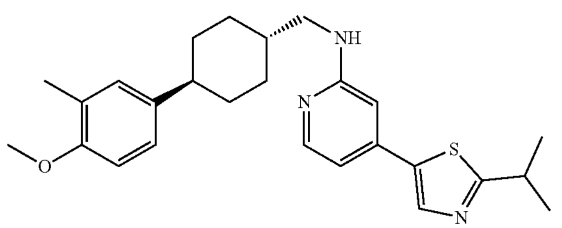 [SMILES: COc1ccc([C@H]2CC[C@H](CNc3cc(-c4cnc(C(C)C)s4)ccn3)CC2)cc1C] | 4-(2-Isopropylthiazol-5-yl)-N-((trans-4-(4-methoxy-3-methylphenyl)cyclohexyl)methyl)pyridin-2-amine | 436.6 |
| 14.19[1] | 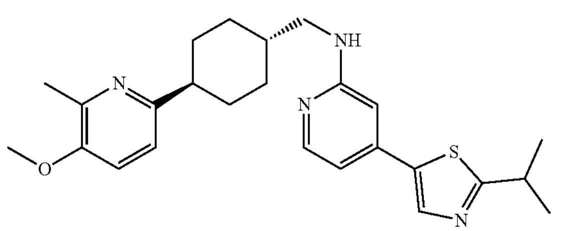 [SMILES: COc1ccc([C@H]2CC[C@H](CNc3cc(-c4cnc(C(C)C)s4)ccn3)CC2)nc1C] | 4-(2-Isopropylthiazol-5-yl)-N-((tarns-4-(5-methoxy-6-methylpyridin-2-yl)cyclohexyl)methyl)pyridin-2-amine | 437.5 |
| 14.20 | 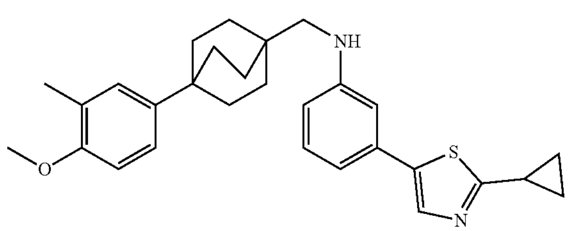 [SMILES: COc1ccc(C23CCC(CNc4cccc(-c5cnc(C6CC6)s5)c4)(CC2)CC3)cc1C] | 3-(2-Cyclopropylthiazol-5-yl)-N-((4-(4-methoxy-3-methylphenyl)bicyclo[2.2.2]octan-1-yl)methyl)aniline | 459.3 |

-continued

| Int | Structure | Name | [M + H]⁺ |
|---|---|---|---|
| 14.21 | 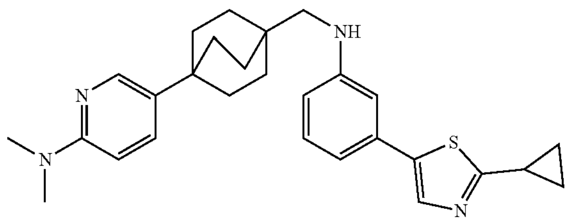 [SMILES: CN(C)c1ccc(C23CCC(CNc4cccc(-c5cnc(C6CC6)s5)c4)(CC2)CC3)cn1] | 5-(4-(((3-(2-Cyclopropylthiazol-5-yl)phenyl)amino)methyl)bicyclo[2.2.2]octan-1-yl)-N,N-dimethylpyridin-2-amine | 459.4 |
| 14.22 | 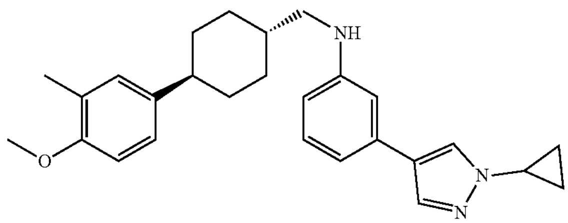 [SMILES: COc1ccc([C@H]2CC[C@H](CNc3cccc(-c4cnn(C5CC5)c4)c3)CC2)cc1C] | 3-(1-Cyclopropyl-1H-pyraz ((trans-4-(4-methoxy-3-methylphenyl)cyclohexyl)methyl)aniline | 416.3 |
| 14.23 | 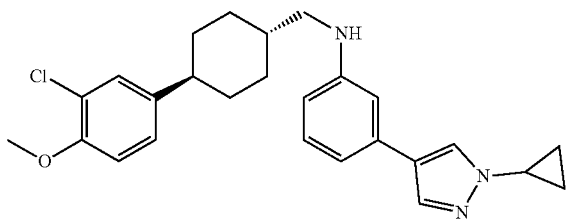 [SMILES: COc1ccc([C@H]2CC[C@H](CNc3cccc(-c4cnn(C5CC5)c4)c3)CC2)cc1Cl] | N-((trans-4-(3-Chloro-4-methoxyphenyl)cyclohexyl)methyl)-3-(1-cyclopropyl-1H-pyrazol-4-yl)aniline | 436.6 |
| 14.24 | 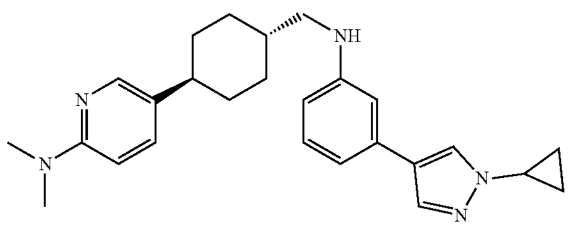 [SMILES: CN(C)c1ccc([C@H]2CC[C@H](CNc3cccc(-c4cnn(C5CC5)c4)c3)CC2)cn1] | 5-(trans-4-(((3-(1-Cyclopropyl-1H-pyrazol-4-yl)phenyl)amino)methyl)cyclohexyl)-N,N-dimethylpyridin-2-amine | 416.3 |
| 14.25 | 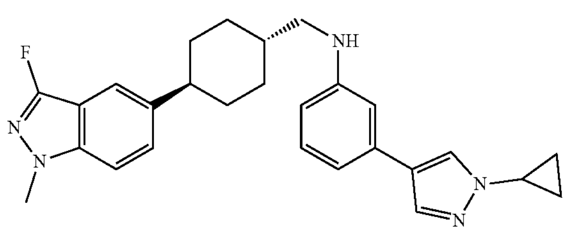 | 3-(1-Cyclopropyl-1H-pyrazol-4-yl)-N-((trans-4-(3-fluoro-1-methyl-1H-indazol-5-yl)cyclohexyl)methyl)aniline | 444.6 |
| 14.26 | 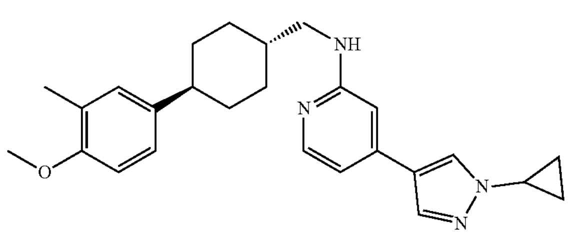 [SMILES: COc1ccc([C@H]2CC[C@H](CNc3cc(-c4cnn(C5CC5)c4)ccn3)CC2)cc1C] | 4-(1-Cyclopropyl-1H-pyrazol-4-yl)-N-((trans-4-(4-methoxy-3-methylphenyl)cyclohexyl)methyl)pyridin-2-amine | 417.1 |

-continued

| Int | Structure | Name | [M + H]⁺ |
|---|---|---|---|
| 14.27[3] | 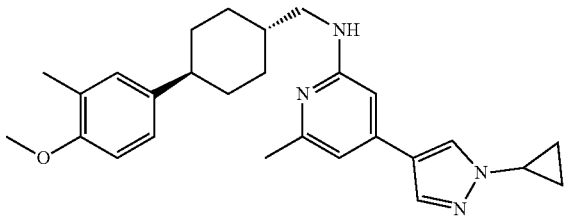 [SMILES: COc1ccc([C@H]2CC[C@H](CNc3cc(-c4cnn(C5CC5)c4)cc(C)n3)CC2)cc1C] | 4-(1-Cyclopropyl-1H-pyrazol-4-yl)-N-((trans-4-(4-methoxy-3-methylphenyl)cyclohexyl)methyl)-6-methylpyridin-2-amine | 431.6 |
| 14.28 | 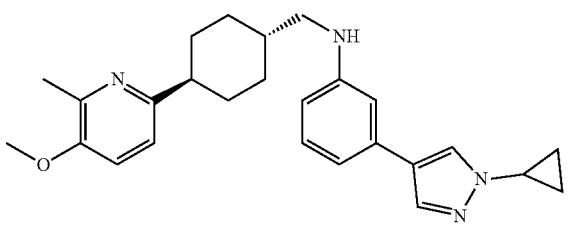 [SMILES: COc1ccc([C@H]2CC[C@H](CNc3cccc(-c4cnn(C5CC5)c4)c3)CC2)nc1C] | 3-(1-Cyclopropyl-1H-pyrazol-4-yl)-N-((trans-4-(5-methoxy-6-methylpyridin-2-yl)cyclohexyl)methyl)aniline | 417.1 |
| 14.29 | 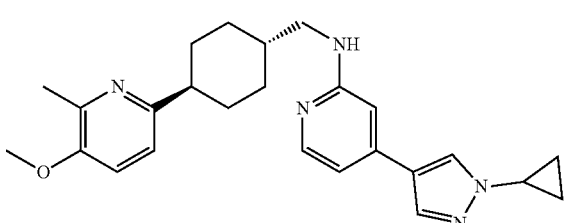 | 4-(1-Cyclopropyl-1H-pyrazol-4-yl)-N-((trans-4-(5-methoxy-6-methylpyridin-2-yl)cyclohexyl)methyl)pyridin-2-amine | 418.3 |
| 14.30 | 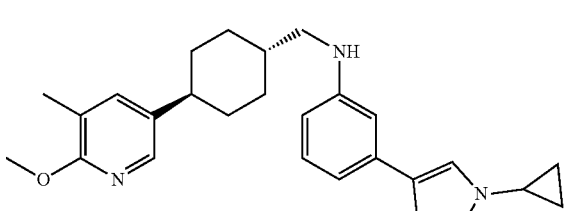 | 3-(1-Cyclopropyl-1H-pyrazol-4-yl)-N-((trans-4-(6-methoxy-5-methylpyridin-3-yl)cyclohexyl)methyl)aniline | 417.3 |
| 14.31 | 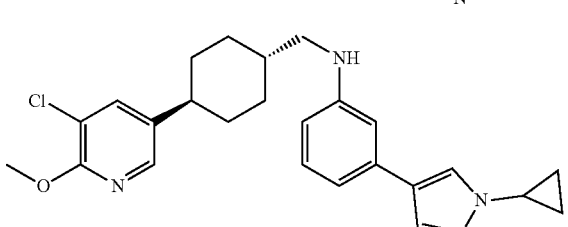 | N-((trans-4-(5-Chloro-6-methoxypyridin-3-yl)cyclohexyl)methyl)-3-(1-cyclopropyl-1H-pyrazol-4-yl)aniline | 437.4 |
| 14.32 | 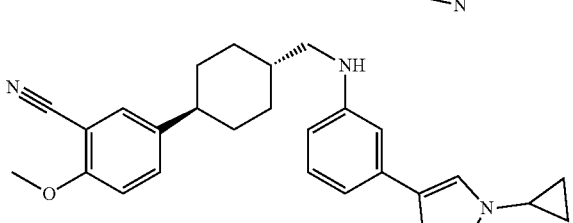 | 5-(trans-4-(((3-(1-Cyclopropyl-1H-pyrazol-4-yl)phenyl)amino)methyl)cyclohexyl)-2-methoxybenzonitrile | 427.3 |
| 14.33 | 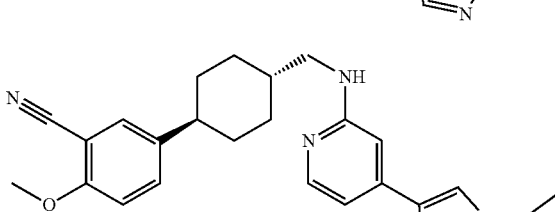 | 5-(trans-4-(((4-(1-Cyclopropyl-1H-pyrazol-4-yl)pyridin-2-yl)amino)methyl)cyclohexyl)-2-methoxybenzonitrile | 428.3 |

-continued

| Int | Structure | Name | [M + H]⁺ |
|---|---|---|---|
| 14.34 | 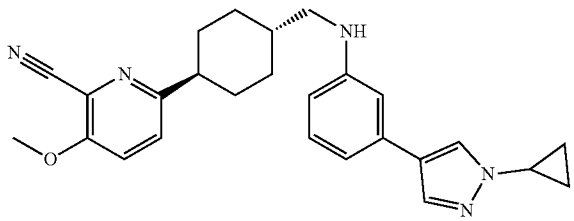 [SMILES: COc1ccc([C@H]2CC[C@H](CNc3cccc(-c4cnn(C5CC5)c4)c3)CC2)nc1C#N] | 6-(trans-4-(((3-(1-Cyclopropyl-1H-pyrazol-4-yl)phenyl)amino)methyl)cyclohexyl)-3-methoxypicolinonitrile | 428.3 |
| 14.35 | 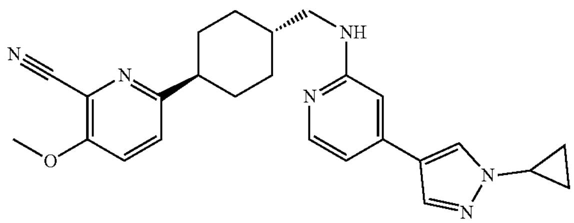 [SMILES: COc1ccc([C@H]2CC[C@H](CNc3cc(-c4cnn(C5CC5)c4)ccn3)CC2)nc1C#N] | 6-(trans-4-(((4-(1-Cyclopropyl-1H-pyrazol-4-yl)pyridin-2-yl)amino)methyl)cyclohexyl)-3-methoxypicolinonitrile | 429.4 |
| 14.36 | 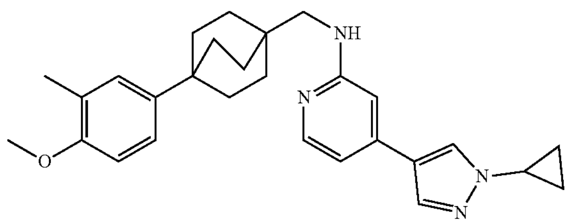 [SMILES: COc1ccc(C23CCC(CNc4cc(-c5cnn(C6CC6)c5)ccn4)(CC2)CC3)cc1C] | 4-(1-Cyclopropyl-1H-pyrazol-4-yl)-N-((4-(4-methoxy-3-methylphenyl)bicyclo[2.2.2]octan-1-yl)methyl)pyridin-2-amine | 443.1 |
| 14.37 | 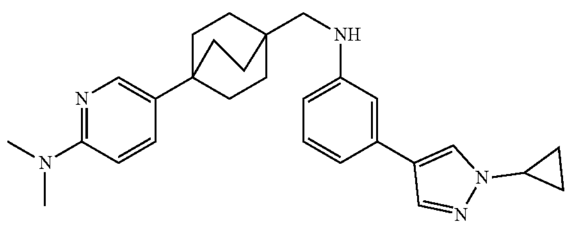 [SMILES: CN(C)c1ccc(C23CCC(CNc4cccc(-c5cnn(C6CC6)c5)c4)(CC2)CC3)cn1] | 5-(4-(((3-(1-Cyclopropyl-1H-pyrazol-4-yl)phenyl)amino)methyl)bicyclo[2.2.2]octan-1-yl)-N,N-dimethylpyridin-2-amine | 442.4 |
| 14.38 | 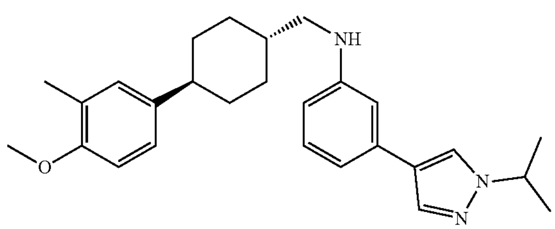 [SMILES: COc1ccc([C@H]2CC[C@H](CNc3cccc(-c4cnn(C(C)C)c4)c3)CC2)cc1C] | 3-(1-Isopropyl-1H-pyrazol-4-yl)-N-((trans-4-(4-methoxy-3-methylphenyl)cyclohexyl)methyl)aniline | 418.3 |
| 14.39 | 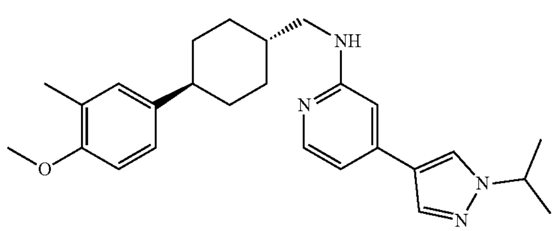 [SMILES: COc1ccc([C@H]2CC[C@H](CNc3cc(-c4cnn(C(C)C)c4)ccn3)CC2)cc1C] | 4-(1-Isopropyl-1H-pyrazol-4-yl)-N-((trans-4-(4-methoxy-3-methylphenyl)cyclohexyl)methyl)pyridin-2-amine | 419.3 |

-continued

| Int | Structure | Name | [M + H]⁺ |
|---|---|---|---|
| 14.40 | 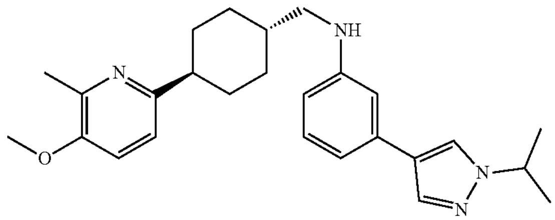 [SMILES: COc1ccc([C@H]2CC[C@H](CNc3cccc(-c4cnn(C(C)C)c4)c3)CC2)nc1C] | 3-(1-Isopropyl-1H-pyrazol-4-yl)-N-((trans-4-(5-methoxy-6-methylpyridin-2-yl)cyclohexyl)methyl)aniline | 419.7 |
| 14.41[3] | 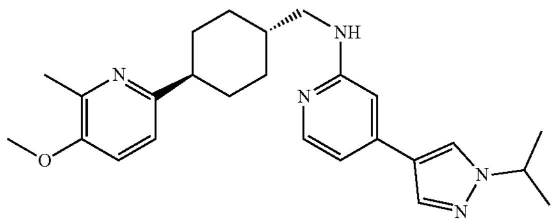 [SMILES: COc1ccc([C@H]2CC[C@H](CNc3cc(-c4cnn(C(C)C)c4)ccn3)CC2)nc1C] | 4-(1-Isopropyl-1H-pyrazol-4-yl)-N-((trans-4-(5-methoxy-6-methylpyridin-2-yl)cyclohexyl)methyl)pyridin-2-amine | 420.3 |
| 14.42 | 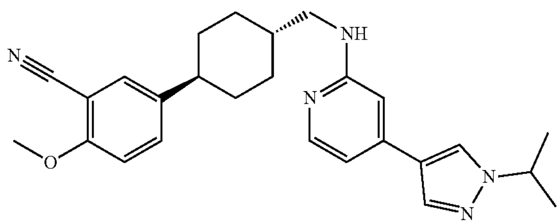 [SMILES: COc1ccc([C@H]2CC[C@H](CNc3cc(-c4cnn(C(C)C)c4)ccn3)CC2)cc1C#N] | 5-(trans-4-(((4-(1-Isopropyl-1H-pyrazol-4-yl)pyridin-2-yl)amino)methyl)cyclohexyl)-2-methoxybenzonitrile | 430.4 |
| 14.43[2,3,4] | 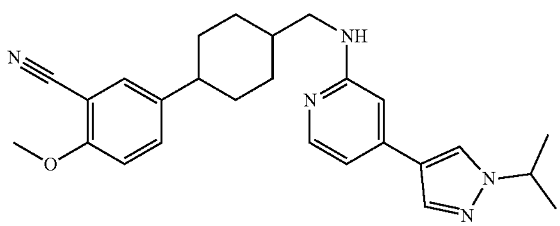 [SMILES: COc1ccc(C2CCC(CNc3cc(-c4cnn(C(C)C)c4)ccn3)CC2)cc1C#N] | 5-(4-(((4-(1-Isopropyl-1H-pyrazol-4-yl)pyridin-2-yl)amino)methyl)cyclohexyl)-2-methoxybenzonitrile | 430.3 |
| 14.44[2] | 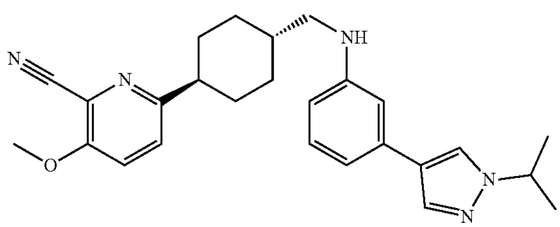 [SMILES: COc1ccc([C@H]2CC[C@H](CNc3cccc(-c4cnn(C(C)C)c4)c3)CC2)nc1C#N] | 6-(trans-4-(((3-(1-Isopropyl-1H-pyrazol-4-yl)phenyl)amino)methyl)cyclohexyl)-3-methoxypicolinonitrile | 430.4 |
| 14.45 | 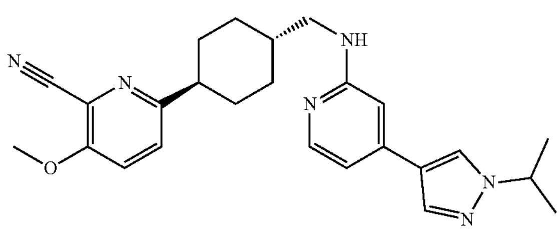 [SMILES: COc1ccc([C@H]2CC[C@H](CNc3cc(-c4cnn(C(C)C)c4)ccn3)CC2)nc1C#N] | 6-(trans-4-(((4-(1-Isopropyl-1H-pyrazol-4-yl)pyridin-2-yl)amino)methyl)cyclohexyl)-3-methoxypicolinonitrile | 431.4 |
| 14.46 | 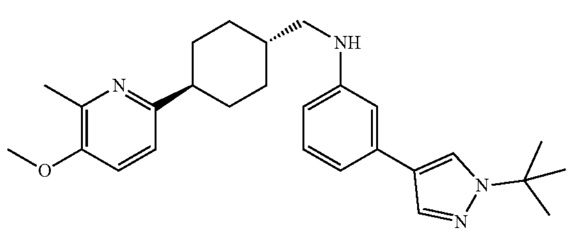 [SMILES: COc1ccc([C@H]2CC[C@H](CNc3cccc(-c4cnn(C(C)(C)C)c4)c3)CC2)nc1C] | 3-(1-(tert-Butyl)-1H-pyrazol-4-yl)-N-((trans-4-(5-methoxy-6-methylpyridin-2-yl)cyclohexyl)methyl)aniline | 433.4 |

-continued

| Int | Structure | Name | [M + H]+ |
|---|---|---|---|
| 14.47 | 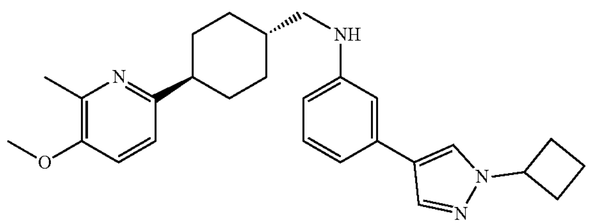 [SMILES: COc1ccc([C@H]2CC[C@H](CNc3cccc(-c4cnn(C5CCC5)c4)c3)CC2)nc1C] | 3-(1-Cyclobutyl-1H-pyrazol-4-yl)-N-((trans-4-(5-methoxy-6-methylpyridin-2-yl)cyclohexyl)methyl)aniline | 431.8 |
| 14.48 | 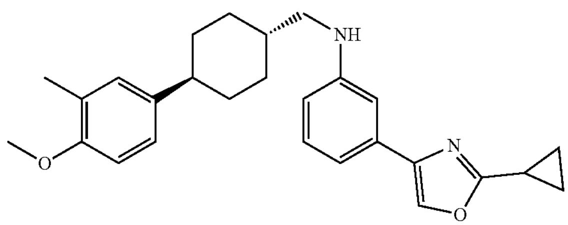 [SMILES: COc1ccc([C@H]2CC[C@H](CNc3cccc(-c4coc(C5CC5)n4)c3)CC2)cc1C] | 3-(2-Cyclopropyloxazol-4-yl)-N-((trans-4-(4-methoxy-3-methylphenyl)cyclohexyl)methyl)aniline | 417.3 |
| 14.49[2] | 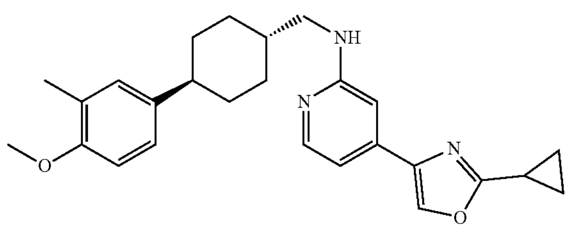 [SMILES: COc1ccc([C@H]2CC[C@H](CNc3cc(-c4coc(C5CC5)n4)ccn3)CC2)cc1C] | 4-(2-Cyclopropyloxazol-4-yl)-N-((trans-4-(4-methoxy-3-methylphenyl)cyclohexyl)methyl)pyridin-2-amine | 418.6 |
| 14.50[3] | 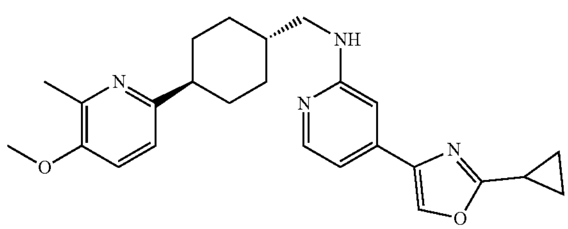 [SMILES: COc1ccc([C@H]2CC[C@H](CNc3cc(-c4coc(C5CC5)n4)ccn3)CC2)nc1C] | 4-(2-Cyclopropyloxazol-4-yl)-N-((trans-4-(5-methoxy-6-methylpyridin-2-yl)cyclohexyl)methyl)pyridin-2-amine | 419.5 |
| 14.51 | 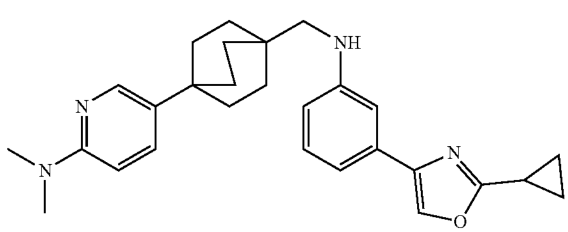 [SMILES: CN(C)c1ccc(C23CCC(CNc4cccc(-c5coc(C6CC6)n5)c4)(CC2)CC3)cn1] | 5-(4-(((3-(2-Cyclopropyloxazol-4-yl)phenyl)amino)methyl)bicyclo[2.2.2]octan-1-yl)-N,N-dimethylpyridin-2-amine | 443.3 |
| 14.52[2] | 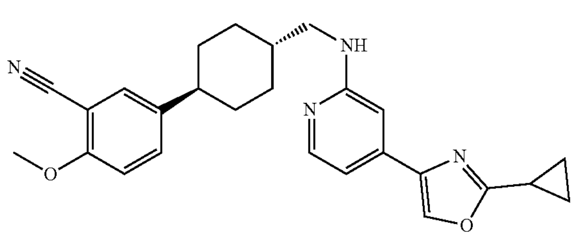 [SMILES: COc1ccc([C@H]2CC[C@H](CNc3cc(-c4coc(C5CC5)n4)ccn3)CC2)cc1C#N] | 5-(trans-4-(((4-(2-Cyclopropyloxazol-4-yl)pyridin-2-yl)amino)methyl)cyclohexyl)-2-methoxybenzonitrile | 429.3 |

| Int | Structure | Name | [M + H]⁺ |
|---|---|---|---|
| 14.53[2] | 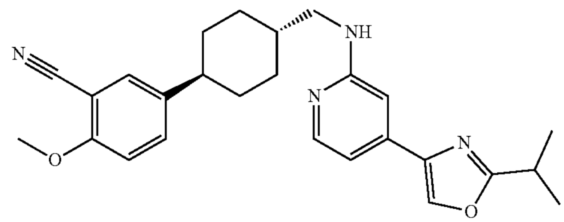 [SMILES: COc1ccc([C@H]2CC[C@H](CNc3cc(-c4coc(C(C)C)n4)ccn3)CC2)cc1C#N] | 5-(trans-4-(((4-(2-Isopropyloxazol-4-yl)pyridin-2-yl)amino)methyl)cyclohexyl)-2-methoxybenzonitrile | 431.4 |
| 14.54[2] | 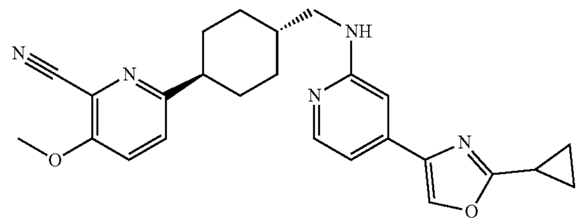 [SMILES: COc1ccc([C@H]2CC[C@H](CNc3cc(-c4coc(C5CC5)n4)ccn3)CC2)nc1C#N] | 6-(trans-4-(((4-(2-Cyclopropyloxazol-4-yl)pyridin-2-yl)amino)methyl)cyclohexyl)-3-methoxypicolinonitrile | 430.4 |
| 14.55[3] | 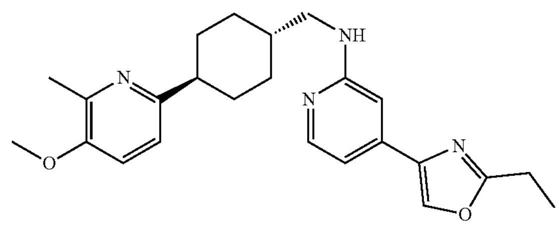 [SMILES: CCc1nc(-c2ccnc(NC[C@H]3CC[C@H](c4ccc(OC)c(C)n4)CC3)c2)co1] | 4-(2-Ethyloxazol-4-yl)-N-((trans-4-(5-methoxy-6-methylpyridin-2-yl)cyclohexyl)methyl)pyridin-2-amine | 407.4 |

Alternate conditions: [1]Utilized procedure for Intermediate 13; [2]Heated at 40° C.. 3Solvent was CH₂Cl₂; [4]Synthesized from an isomeric mixture of Intermediate 3.05.

Intermediate 15

Trans-4-(Cyanomethyl)cyclohexanecarboxylic Acid

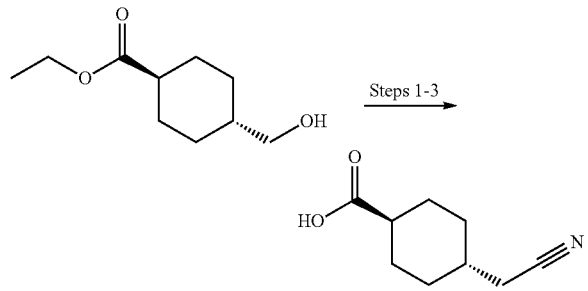

Step 1: Trans-Ethyl 4-((tosyloxy)methyl)cyclohexanecarboxylate p-Toluenesulfonyl chloride (1.54 g, 8.05 mmol) was added to a solution of trans-ethyl 4-(hydroxymethyl)cyclohexanecarboxylate (1 g, 5.37 mmol), Et₃N (1.63 g, 16.11 mmol), DMAP (131.19 mg, 1.07 mmol) and CH₂Cl₂ (60 mL) at 0° C. The mixture was allowed to warm to rt overnight. Water (10 mL) was added, and the layers were separated. The aqueous layer was extracted with CH₂Cl₂ (20 mL). The organic layers were combined, dried (Na₂SO₄), filtered, concentrated, and then purified by chromatography on silica gel (petroleum ether/EtOAc=20/1) to give trans-ethyl 4-((tosyloxy)methyl)cyclohexanecarboxylate (1.49 g, 82%) as a yellow oil. ¹H NMR (400 MHz, CDCl₃): δ 7.80 (d, 2H), 7.37 (d, 2H), 4.19-4.06 (m, 2H), 3.85 (d, 2H), 2.47 (s, 3H), 2.20 (t, 1H), 2.05-1.96 (m, 2H), 1.86-1.77 (m, 2H), 1.73-1.61 (m, 1H), 1.43-1.39 (m, 2H), 1.27 (t, 3H), 1.08-0.91 (m, 2H); LCMS: 341.2 [M+H]⁺.

Step 2: Trans-Ethyl 4-(cyanomethyl)cyclohexanecarboxylate

Potassium cyanide (903.8 mg, 13.88 mmol) was added to a solution of trans-ethyl 4-((tosyloxy)methyl)cyclohexanecarboxylate (1.89 g, 5.55 mmol) in DMSO (30 mL) at rt. The mixture was heated to 50° C. overnight. Water (50 mL) was added, and then the mixture was extracted with EtOAc (2×100 mL). The organic layers were combined, washed with water (50 mL), dried (Na₂SO₄), filtered, concentrated and then purified by chromatography on silica gel (petroleum ether/EtOAc=10/1) to give trans-ethyl 4-(cyanomethyl)cyclohexanecarboxylate (807 mg, 74.45%) as a yellow oil. ¹H NMR (400 MHz, CDCl₃): δ 4.05 (q, 2H), 2.27-2.09 (m, 3H), 2.04-1.93 (m, 2H), 1.91-1.80 (m, 2H), 1.68-1.55 (m, 1H), 1.46-1.32 (m, 2H), 1.18 (t, 3H), 1.14-1.00 (m, 2H).

Step 3: Trans-4-(Cyanomethyl)cyclohexanecarboxylic Acid

Lithium hydroxide monohydrate (2.60 g, 62.00 mmol) was added to a solution of trans-ethyl 4-(cyanomethyl)cyclohexanecarboxylate (807 mg, 4.13 mmol), THF (15 mL) and H₂O (15 mL) at rt. The mixture was stirred at rt overnight, and then the organic layer was removed. The aqueous layer was adjusted to pH=1 with 1N HCl and extracted with CH₂Cl₂ (5×20 mL). The organic layers were combined, dried (Na₂SO₄), filtered and concentrated to give trans-4-(cyanomethyl)cyclohexanecarboxylic acid (500 mg, crude) as a yellow oil. $^1$H NMR (400 MHz, CDCl$_3$): δ 2.37-2.22 (m, 3H), 2.12-2.06 (m, 2H), 2.00-1.91 (m, 2H), 1.75-1.63 (m, 1H), 1.50-1.45 (m, 2H), 1.24-1.09 (m, 2H).

Intermediate 16

Tert-Butyl 2-(trans-4-(chlorocarbonyl)cyclohexyl)acetate

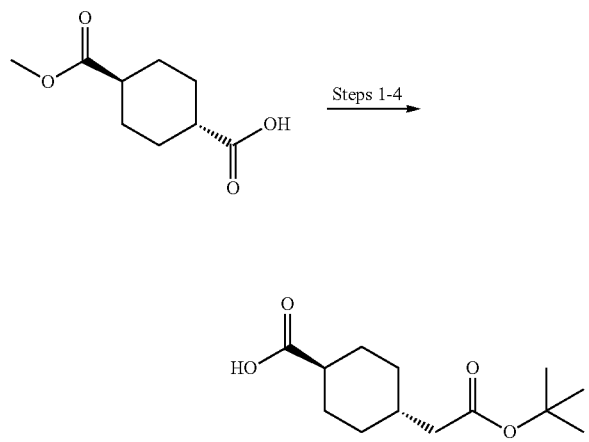

Step 1: Trans-Methyl 4-(chlorocarbonyl)cyclohexanecarboxylate

Oxalyl chloride (47.72 g, 375.9 mmol) was added dropwise to a solution of trans-4-(methoxycarbonyl)cyclohexanecarboxylic acid (35 g, 188 mmol) and DMF (1.37 g, 18.8 mmol), and CH$_2$Cl$_2$ (700 mL) at rt. The mixture was stirred for 2 h and concentrated to dryness to give trans-methyl 4-(chlorocarbonyl)cyclohexanecarboxylate (38.5 g, crude) as a yellow oil.

Step 2: Trans-Methyl 4-(2-diazoacetyl)cyclohexanecarboxylate (Trimethylsilyl)diazomethane (2 M in hexanes, 385 mL, 770 mmol) was added to a solution of trans-methyl 4-(chlorocarbonyl)cyclohexanecarboxylate (38.5 g, 188.1 mmol), CH$_3$CN (700 mL), and THF (700 mL) at 0° C. The reaction was allowed to warm to rt, stirred overnight, concentrated, and then dissolved in EtOAc (1000 mL). The organic phase was washed with water (300 mL), dried (Na$_2$SO$_4$), filtered, and concentrated. The residue was purified by silica gel chromatography (petroleum ether/EtOAc=40/1) to give trans-methyl 4-(2-diazoacetyl)cyclohexanecarboxylate (35 g, 166 mmol, 89%) as a yellow oil. $^1$H NMR (400 MHz, CDCl$_3$): δ 5.27 (s, 1H), 3.66 (s, 3H), 2.33-2.12 (m, 2H), 2.11-2.00 (m, 2H), 1.98-1.85 (m, 2H), 1.53-1.35 (m, 4H).

Step 3: Trans-Methyl 4-(2-(tert-butoxy)-2-oxoethyl)cyclohexanecarboxylate

Silver benzoate (8.17 g, 35.7 mmol) was added to a solution of methyl 4-(2-diazoacetyl)cyclohexanecarboxylate (25 g, 119 mmol), dioxane (300 mL), and tert-BuOH (300 mL) at rt under N$_2$. The mixture was stirred for 15 h, poured into water (500 mL), filtered, and extracted with EtOAc (2×1000 mL). The combined organic layers were washed with water (2×300 mL), dried (Na$_2$SO$_4$), filtered and concentrated. The residue was purified by silica gel chromatography (petroleum ether/EtOAc=40/1) to give trans-methyl 4-(2-(tert-butoxy)-2-oxoethyl)cyclohexanecarboxylate (21.43 g, 67%) as a yellow oil. $^1$H NMR (400 MHz, CDCl$_3$): δ 3.65 (s, 3H), 2.28-2.13 (m, 1H), 2.09 (d, 2H), 1.97 (d, 2H), 1.87-1.78 (m, 2H), 1.75-1.66 (m, 1H), 1.55-1.43 (d, 11H), 1.07-0.90 (m, 2H).

Step 4: Trans-4-(2-(tert-Butoxy)-2-oxoethyl)cyclohexanecarboxylic Acid

Lithium hydroxide monohydrate (65.48 g, 1.56 mol) was added to a solution of methyl 4-(2-tert-butoxy-2-oxo-ethyl)cyclohexanecarboxylate (20 g, 78 mmol), THF (400 mL), and water (400 mL) at rt. The mixture was stirred overnight and concentrated to remove organic solvent. Hydrochloric acid (3 M) was added to the mixture (pH=4), and the resulting precipitate was collected by filtration and dried under vacuum to give trans-4-(2-(tert-butoxy)-2-oxoethyl)cyclohexanecarboxylic acid (7.2 g, crude) as a yellow solid. $^1$H NMR (400 MHz, CDCl$_3$): δ 2.29-2.21 (m, 1H), 2.10 (d, 2H), 2.0-1.97 (m, 2H), 1.87-1.80 (m, 2H), 1.78-1.66 (m, 1H), 1.53-1.39 (m, 11H), 1.05-0.95 (m, 2H).

Intermediate 17

Trans-4-(3-(tert-Butoxy)-3-oxopropyl)cyclohexanecarboxylic Acid

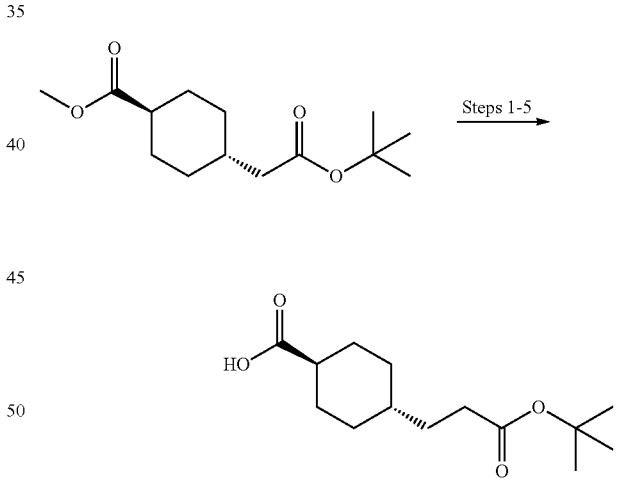

Step 1: 2-(trans-4-(Methoxycarbonyl)cyclohexyl)acetic Acid

A mixture of Intermediate 16, Step 3 (2 g, 7.80 mmol) and hydrochloric acid (4 M in dioxane, 50 mL) was stirred at rt for 1 h. The mixture was concentrated to dryness to give 2-(trans-4-(methoxycarbonyl)cyclohexyl)acetic acid (1.56 g, crude) as a yellow oil. $^1$H NMR (400 MHz, CDCl$_3$): δ 3.67 (s, 3H), 2.32-2.19 (m, 3H), 2.05-1.95 (m, 2H), 1.93-1.84 (m, 2H), 1.84-1.72 (m, 1H), 1.55-1.39 (m, 2H), 1.11-0.97 (m, 2H).

Step 2: Trans-Methyl 4-(2-chloro-2-oxoethyl)cyclohexanecarboxylate

Oxalyl chloride (1.98 g, 15.58 mmol) was added to a solution of 2-(trans-4-(methoxycarbonyl)cyclohexyl)acetic acid (1.56 g, 7.79 mmol), DMF (57.0 mg, 0.779 mmol), and $CH_2Cl_2$ (20 mL) at rt. The mixture was stirred at rt for 2 h and then concentrated to dryness to give trans-methyl 4-(2-chloro-2-oxoethyl)cyclohexanecarboxylate (1.7 g, crude) as a yellow oil.

Step 3: Trans-Methyl 4-(3-diazo-2-oxopropyl)cyclohexanecarboxylate (Trimethylsilyl)diazomethane (2 M in hexanes, 11.6 mL) was added to a solution of trans-methyl 4-(2-chloro-2-oxoethyl)cyclohexanecarboxylate (1.7 g, 7.77 mmol), $CH_3CN$ (10 mL), and THF (10 mL) at 0° C. The mixture was allowed to warm to rt overnight, concentrated to dryness, and then purified by silica gel chromatography (petroleum ether/EtOAc=10/1) to give trans-methyl 4-(3-diazo-2-oxopropyl)cyclohexanecarboxylate (1.2 g, 62%) as a yellow oil. $^1$H NMR (400 MHz, $CDCl_3$): δ 5.06 (s, 1H), 3.50 (s, 3H), 2.14-1.99 (m, 3H), 1.88-1.78 (m, 2H), 1.73-1.58 (m, 3H), 1.32-1.29 (m, 2H), 0.93-0.75 (m, 2H).

Step 4: Trans-Methyl 4-(3-(tert-butoxy)-3-oxopropyl)cyclohexanecarboxylate

Silver benzoate (367.5 mg, 1.61 mmol) was added to a solution of trans-methyl 4-(3-diazo-2-oxopropyl)cyclohexanecarboxylate (1.2 g, 5.35 mmol), dioxane (10 mL), and t-BuOH (10 mL) at rt. The mixture was stirred at rt overnight, poured into water (50 mL), and then filtered. The filtrate was extracted with EtOAc (2×50 mL). The organic layers were combined, washed with water (30 mL), dried ($Na_2SO_4$), filtered, concentrated, and then purified by silica gel chromatography (petroleum ether/EtOAc=40/1) to give trans-methyl 4-(3-(tert-butoxy)-3-oxopropyl)cyclohexanecarboxylate (730 mg, 50%) as a yellow oil. $^1$H NMR (400 MHz, $CDCl_3$): δ 3.59 (s, 3H), 2.22-2.09 (m, 3H), 1.95-1.85 (m, 2H), 1.79-1.69 (m, 2H), 1.48-1.25 (m, 13H), 1.22-1.10 (m, 1H), 0.94-0.78 (m, 2H).

Step 5: Trans-4-(3-(tert-Butoxy)-3-oxopropyl)cyclohexanecarboxylic Acid

Lithium hydroxide monohydrate (113.3 mg, 2.70 mmol) was added to a solution of trans-methyl 4-(3-(tert-butoxy)-3-oxopropyl)cyclohexanecarboxylate (730 mg, 2.70 mmol), THF (10 mL), and $H_2O$ (10 mL). The mixture was stirred at 30° C. overnight, concentrated to remove THF, adjusted to pH=5 with 3 M HCl, and then filtered. The cake was dried under vacuum to give trans-4-(3-(tert-butoxy)-3-oxopropyl) cyclohexanecarboxylic acid (330 mg, crude) as a white solid. $^1$H NMR (400 MHz, $CDCl_3$): δ 2.27-2.08 (m, 3H), 1.95 (d, 2H), 1.76 (d, 2H), 1.49-1.27 (m, 13H), 1.26-1.10 (m, 1H), 0.97-0.76 (m, 2H).

Intermediate 18

Trans-4-(Benzyloxy)cyclohexanecarbonyl Chloride

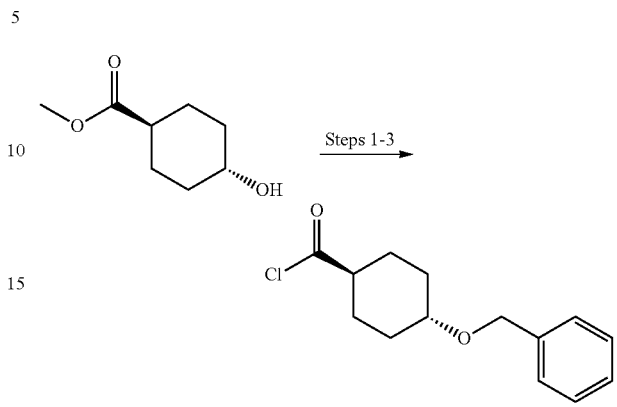

Step 1: Trans-Methyl 4-(benzyloxy)cyclohexanecarboxylate

Benzyl bromide (4.76 g, 27.81 mmol) was added in one portion to a mixture of trans-methyl 4-hydroxycyclohexanecarboxylate (4.00 g, 25.28 mmol) and $iPr_2NEt$ (7.40 g, 57.26 mmol) under $N_2$. The mixture was stirred at 150° C. for 8 h in sealed tube and then allowed to cool to rt. Aqueous hydrochloric acid (1 N, 40 mL) was added to the resulting heterogeneous mixture. The mixture was extracted with EtOAc (3×20 mL). The combined organics were dried ($MgSO_4$) and concentrated to give trans-methyl 4-(benzyloxy)cyclohexanecarboxylate (6.00 g, crude) as a yellow oil.

Step 2: Trans-4-(Benzyloxy)cyclohexanecarboxylic Acid

Aqueous sodium hydroxide (5 M, 10 mL) was added in one portion to a mixture of trans-methyl 4-(benzyloxy)cyclohexanecarboxylate (6.00 g, 24.16 mmol), $CH_3OH$ (20 mL), and THF (20 mL) at rt under $N_2$. The mixture was stirred at rt overnight, neutralized to pH=1 with 5 N HCl and then concentrated. The mixture was partitioned between EtOAc (30 mL) and water (30 mL). The layers were separated. The aqueous layer was extracted with EtOAc (2×15 mL). The combined organics were concentrated to give trans-4-(benzyloxy)cyclohexanecarboxylic acid (4.00 g, 71%) as a yellow solid. $^1$H NMR (400 MHz, $CDCl_3$): δ 7.32-7.36 (m, 4H), 7.23-7.29 (m, 1H), 4.56 (s, 2H) 3.26-3.41 (m, 1H), 2.27-2.37 (m, 1H), 2.13-2.18 (m, 2H), 2.04-2.08 (m, 2H), 1.42-1.55 (m, 2H), 1.26-1.40 (m, 2H); LCMS: 233.1 [M−H]$^+$.

Step 3: Trans-4-(Benzyloxy)cyclohexanecarbonyl Chloride trans-4-(Benzyloxy)cyclohexanecarboxylic acid (600.3 mg, 2.56 mmol) was added in one portion to a mixture of N-(chloromethylene)-N-methylmethanaminium chloride (655.6 mg, 5.12 mmol), $K_2CO_3$ (1.06 g, 7.68 mmol), and toluene (10.0 mL) under $N_2$. The mixture was stirred at rt for 1 h and then filtered to give trans-4-(benzyloxy)cyclohexanecarbonyl chloride as a clear solution. The solution was used immediately without purification.

The Intermediate below was synthesized using 4-methoxybenzyl bromide following the procedures described for Intermediate 18.

| Int | Structure | Name |
|---|---|---|
| 18.01 | 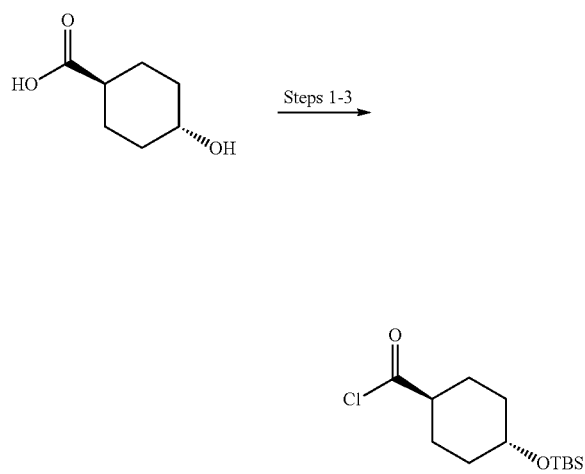 | trans-4-((4-Methoxybenzyl)oxy)cyclohexanecarbonyl chloride |

Intermediate 19

Trans-4-((tert-Butyldimethylsilyl)oxy)cyclohexanecarbonyl Chloride

Steps 1-3

Step 1: Trans-tert-Butyldimethylsilyl 4-((tert-butyldimethylsilyl)oxy)cyclohexanecarboxylate tert-Butyldimethylsilyl chloride (31.47 g, 208.8 mmol) was added to a mixture of trans-4-hydroxy-cyclohexanecarboxylic acid (10.03 g, 69.57 mmol), imidazole (18.96 g, 278.5 mmol), and DMF (140 mL) at rt under $N_2$ (reaction exothermed to 32° C.). The reaction was stirred at rt for 2 h and then diluted with diethyl ether (300 mL). The organic layer was washed (2×300 mL 1 N HCl and then 300 mL brine), dried ($Na_2SO_4$), filtered and concentrated to give trans-tert-butyldimethylsilyl 4-((tert-butyldimethylsilyl)oxy)cyclohexanecarboxylate (31.5 g) as a clear oil. $^1H$ NMR (400 MHz, DMSO-$d_6$): δ 3.61-3.53 (m, 1H), 2.26-2.18 (m, 1H), 2.04-1.96 (m, 2H), 1.92-1.85 (m, 2H), 1.51-1.39 (m, 2H), 1.39-1.27 (m, 2H), 0.94 (s, 9H), 0.89 (s, 9H), 0.26 (s, 6H), 0.06 (s, 6H).

Step 2: Trans-4-((tert-Butyldimethylsilyl)oxy)cyclohexanecarboxylic Acid

Potassium carbonate (58.01 g, 419.7 mmol) in $H_2O$ (300 mL) was added to a mixture of trans-tert-butyldimethylsilyl 4-((tert-butyldimethylsilyl)oxy)cyclohexanecarboxylate (31.5 g crude, 69.6 mmol), ethanol (1000 mL) and THF (300 mL) at rt under $N_2$. The reaction was stirred at rt for 3 h, concentrated until 300 mL remained, diluted with brine (600 mL), and then acidified to pH 2-3 with 20% $NaHSO_4$ (550 mL). The aqueous layer was extracted with diethyl ether (800 mL). The organic layer was washed (800 mL brine), dried ($Na_2SO_4$), filtered and concentrated to give trans-4-((tert-butyldimethylsilyl)oxy)cyclohexanecarboxylic acid (17.3 g, 96% over 2 steps) as a white solid. $^1H$ NMR (400 MHz, DMSO-$d_6$): δ 12.30 (br s, 1H), 3.59-3.51 (m, 1H), 2.15-2.05 (m, 1H), 1.88-1.74 (m, 4H), 1.41-1.29 (m, 2H), 1.28-1.16 (m, 2H), 0.84 (s, 9H), 0.02 (s, 6H).

Step 3: Trans-4-((tert-Butyldimethylsilyl)oxy)cyclohexanecarbonyl Chloride (Chloromethylene)dimethyl iminium chloride (34.02 g, 265.78 mmol) was weighed into a 1000 mL round bottom flask (3 neck) and degassed with vacuum/$N_2$ cycles (3×). Toluene (240 mL) was added to the flask, and the mixture was cooled (1.3° C.) in an ice bath. Anhydrous potassium carbonate* (68.71 g, 497.14 mmol) and trans-4-((tert-butyldimethylsilyl)oxy)cyclohexanecarboxylic acid (34.29 g, 132.69 mmol) were sequentially added to the reaction. The ice bath was removed, and the mixture was stirred for 35 min. Celite (7 g) was added to the reaction, and then the reaction was filtered through Celite (70 g, Chemglass 465 mL fritted funnel) with toluene washes (3×100 mL). This solution (451 g, 8.5% acid chloride, 100% yield, 72 mg/mL) was used immediately in the acylation reaction. $^1H$ NMR (400 MHz, CDCl$_3$): δ 3.77-3.68 (m, 1H), 2.83-2.74 (m, 1H), 2.31-2.22 (m, 2H), 2.09-1.99 (m, 2H), 1.76-1.63 (m, 2H), 1.54-1.42 (m, 2H), 1.02 (s, 9H), 0.20 (s, 6H).

Potassium carbonate was dried under vacuum by heating with a heat gun for ~5 min and then allowing to cool overnight.

The Intermediates below were synthesized from the appropriate starting material or Intermediate following the procedures described for Intermediate 19.

| Int | Structure | Name |
|---|---|---|
| 19.01 | 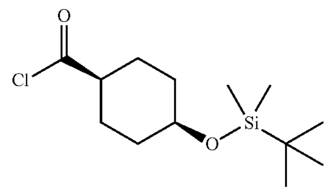 [SMILES: CC(C)(C)[Si](C)(C)O[C@H]1CC[C@@H](C(=O)Cl)CC1] | cis-4-((tert-Butyldimethylsilyl)oxy)cyclohexanecarbonyl chloride |
| 19.02[1] | 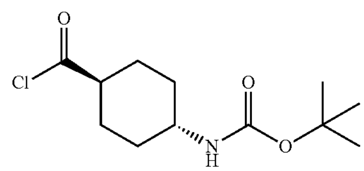 [SMILES: CC(C)(C)OC(=O)N[C@H]1CC[C@H](C(=O)Cl)CC1] | tert-Butyl (trans-4-(chlorocarbonyl)cyclohexyl)carbamate |
| 19.03[1] | 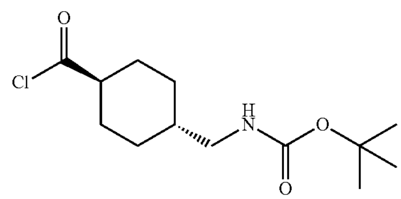 [SMILES: CC(C)(C)OC(=O)NC[C@H]1CC[C@H](C(=O)Cl)CC1] | tert-Butyl ((trans-4-(chlorocarbonyl)cyclohexyl)methyl)-carbamate |
| 19.04[1] | 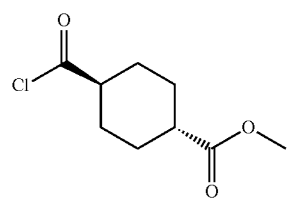 | trans-methyl 4-(Chlorocarbonyl)cyclohexanecarboxylate |
| 19.05[1] | 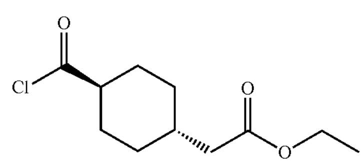 | Ethyl 2-(trans-4-(chlorocarbonyl)cyclohexyl)acetate |
| 19.06[1] | 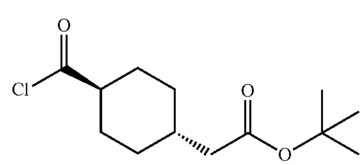 [SMILES: CC(C)(C)OC(=O)C[C@H]1CC[C@H](C(=O)Cl)CC1] | tert-Butyl 2-(trans-4-(chlorocarbonyl)cyclohexyl)acetate |
| 19.07[1] | 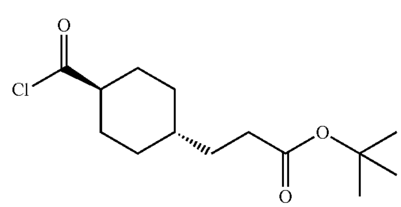 [SMILES: CC(C)(C)OC(=O)CC[C@H]1CC[C@H](C(=O)Cl)CC1] | tert-Butyl 3-(trans-4-(chlorocarbonyl)cyclohexyl)propanoate |
| 19.08[1] | 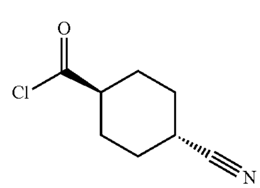 [SMILES: N#C[C@H]1CC[C@H](C(=O)Cl)CC1] | trans-4-Cyanocyclohexanecarbonyl chloride |

-continued

| Int | Structure | Name |
|---|---|---|
| 19.09[1] | 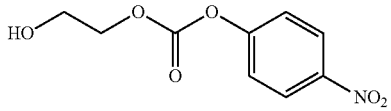 [SMILES: O=C(OCCO)Oc1ccc([N+](=O)[O-])cc1] | trans-4-(Cyanomethyl)cyclohexanecarbonyl chloride |
| 19.10[2] | 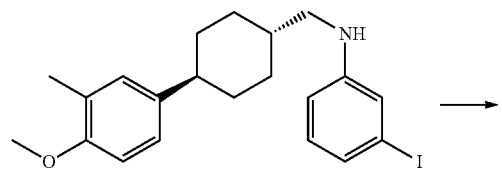 | 4-((tert-Butyldimethylsilyl)oxy)-4-methylcyclohexanecarbonyl chloride |

[1]Step 3 only;
[2]Step 1: Ethyl 4-oxocyclohexanecarboxylate, AlMe₃, toluene, 0° C., 1 h gave ethyl 4-hydroxy-4-methylcyclohexanecarboxylate as a cis/trans mixture; Step 2: TBSOTf, 2,6-lutidine, DCM, 0° C.-rt, overnight; Step 3: LiOH•H₂O, H₂O, THF; Step 4: Step 3 for Intermediate 19.

Intermediate 20

2-Hydroxyethyl (4-nitrophenyl) carbonate

4-Nitrophenyl carbonochloridate was added to a solution of ethane-1,2-diol (230 mg, 3.70 mmol) and pyridine (293 mg, 3.70 mmol) in CH₂Cl₂ (10 mL) at 0° C. under N₂. The mixture was allowed to warm to rt and stirred at rt for 3 h. The reaction mixture was used in the next step without purification.

Intermediate 21

Trans-4-((tert-Butyldimethylsilyl)oxy)-N-(3-iodophenyl)-N-((trans-4-(4-methoxy-3-methylphenyl)cyclohexyl)methyl)cyclohexanecarboxamide Intermediate 19 (74 mg/mL in toluene, 43 mL, 11.49 mmol) was added to a solution of Intermediate 13 (3.32 g, 7.63 mmol), pyridine (2.5 mL, 31 mmol), and toluene (15 mL). The mixture was stirred at rt for 90 min, diluted with EtOAc (50 mL), and washed (50 mL H₂O, 50 mL sat'd NaHCO₃ and then 50 mL brine). The organic layer was dried (Na₂SO₄), filtered, concentrated, and purified by silica gel chromatography (0-10% EtOAc in hexanes) to give trans-4-((tert-butyldimethylsilyl)oxy)-N-(3-iodophenyl)-N-((trans-4-(4-methoxy-3-methylphenyl)cyclohexyl)methyl)cyclohexanecarboxamide (4.05 g, 79%) as a white foam. ¹H NMR (400 MHz, DMSO-d₆): δ 7.76 (d, 1H), 7.72 (s, 1H), 7.31 (d, 1H), 7.27 (t, 1H), 6.97-6.92 (m, 2H), 6.80-6.76 (m, 1H), 3.72 (s, 3H), 3.60-3.40 (m, 3H), 2.37-2.27 (m, 1H), 2.09 (s, 3H), 2.01-1.91 (m, 1H), 1.78-1.67 (m, 6H), 1.65-1.56 (m, 2H), 1.49-1.21 (m, 5H), 1.10-0.94 (m, 2H), 0.92-0.76 (m, 11H), −0.01 (s, 6H); LCMS: 676.6 [M+H]⁺.

The Intermediates below were synthesized from the appropriate Intermediate following the procedure described for Intermediate 21.

| Int | Structure | Name | [M + H]⁺ |
|---|---|---|---|
| 21.01 | 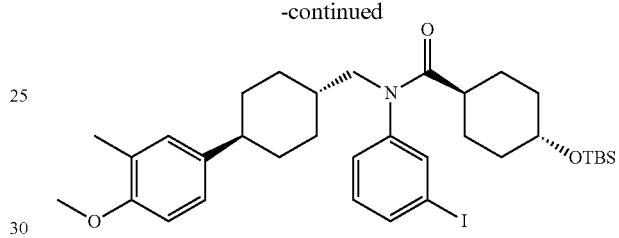 | trans-4-((tert-Butyldimethylsilyl)oxy)-N-((trans-4-(3-cyano-4-methoxyphenyl)cyclohexyl)methyl)-N-(3-iodophenyl)cyclohexanecarboxamide | 687.5 |

-continued

| Int | Structure | Name | [M + H]+ |
|---|---|---|---|
| 21.02[1] | 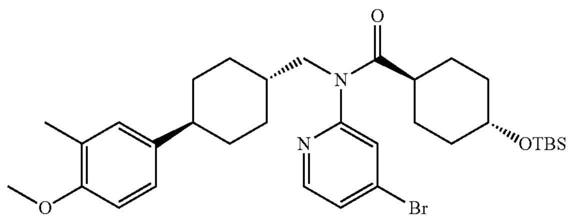 [SMILES: COc1ccc([C@H]2CC[C@H](CN(c3cc(Br)ccn3)C(=O)[C@H]3CC[C@H](O[Si](C)(C)C(C)(C)C)CC3)CC2)cc1C] | trans-N-(4-Bromopyridin-2-yl butyldimethylsilyl)oxy)-N-((trans-4-(4-methoxy-3-methylphenyl)cyclohexyl)methyl)-cyclohexanecarboxamide | 629.2 |
| 21.03[2] | 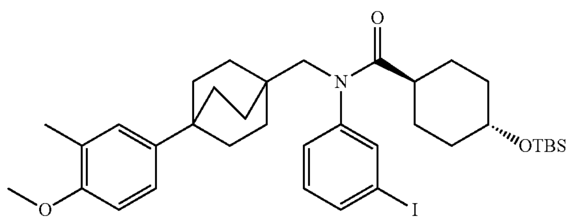 [SMILES: COc1ccc(C23CCC(CN(c4cccc(I)c4)C(=O)[C@H]4CC[C@H](O[Si](C)(C)C(C)(C)C)CC4)(CC2)CC3)cc1C] | trans-4-((tert-Butyldimethylsilyl)oxy)-N-(3-iodophenyl)-N-((4-(4-methoxy-3-methylphenyl)bicyclo[2.2.2]octan-1-yl)methyl)cyclohexanecarboxamide | 702.2 |
| 21.04[1] | 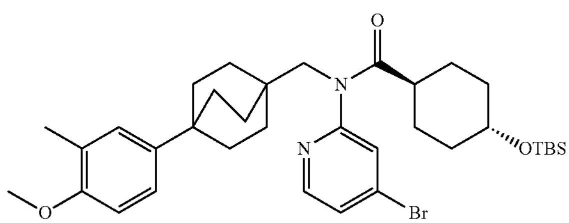 [SMILES: COc1ccc(C23CCC(CN(c4cc(Br)ccn4)C(=O)[C@H]4CC[C@H](O[Si](C)(C)C(C)(C)C)CC4)(CC2)CC3)cc1C] | trans-N-(4-Bromopyridin-2-yl)-4-((tert-butyldimethylsilyl)oxy)-N-((4-(4-methoxy-3-methylphenyl)bicyclo[2.2.2]octan-1-yl)methyl)cyclohexanecarboxamide | 655.2 |
| 21.05[1] | 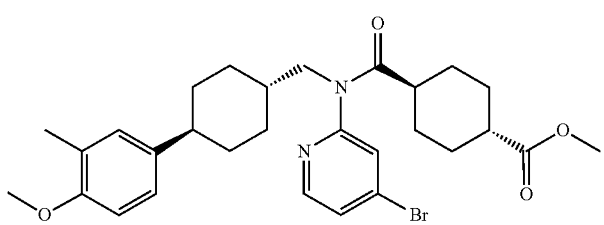 | trans-Methyl 4-((4-bromopyridin-2-yl)((tert-4-(4-methoxy-3-methylphenyl)cyclohexyl)methyl)-carbamoyl)cyclohexanecarboxylate | 557.1 |
| 21.06[1] | 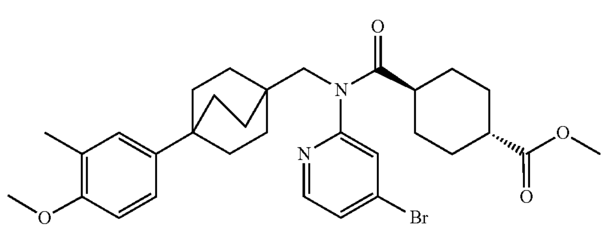 | trans-Methyl 4-((4-bromopyridin-2-yl)((4-(4-methoxy-3-methylphenyl)bicyclo[2.2.2]octan-1-yl)methyl)carbamoyl)cyclohexane-carboxylate | 583.1 |
| 21.07[4] | 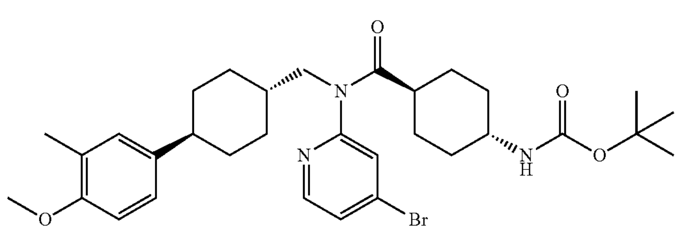 [SMILES: COc1ccc([C@H]2CC[C@H](CN(c3cc(Br)ccn3)C(=O)[C@H]3CC[C@H](NC(=O)OC(C)(C)C)CC3)CC2)cc1C] | tert-butyl ((1R,4r)-4-((4-bromopyridin-2-yl)(((1r,4R)-4-(4-methoxy-3-methylphenyl)cyclohexyl)methyl)-carbamoyl)cyclohexyl)carbamate | 614.0 |

-continued

| Int | Structure | Name | [M + H]+ |
|---|---|---|---|
| 21.08[2] | 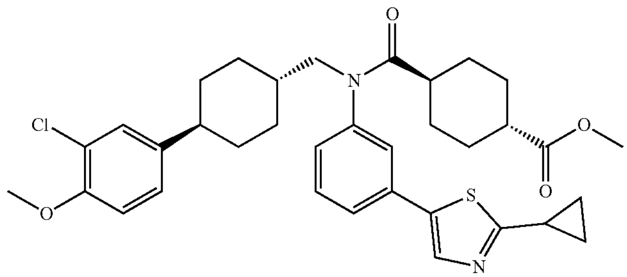 | trans-Methyl 4-(((trans-4-(3-chloro-4-methoxyphenyl)cyclohexyl)methyl)(3-(2-cyclopropylthiazol-5-yl)phenyl)carbamoyl)-cyclohexanecarboxylate | 621.6 |
| 21.09[2] | 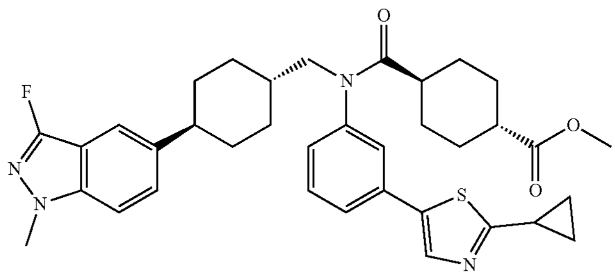 [SMILES: COC(=O)[C@H]1CC[C@H](C(=O)N(C[C@H]2CC[C@H](c3ccc4c(c3)c(F)nn4C)CC2)c2cccc(-c3cnc(C4CC4)s3)c2)CC1] | trans-Methyl 4-((3-(2-cyclopropylthiazol-5-yl)phenyl)((trans-4-(3-fluoro-1-methyl-1H-indazol-5-yl)cyclohexyl)methyl)carbamoyl)-cyclohexanecarboxylate | 629.4 |
| 21.10[2] | 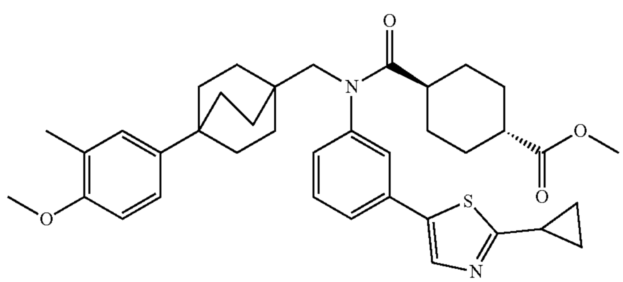 | trans-Methyl 4-((3-(2-cyclopropylthiazol-5-yl)phenyl)((4-(4-methoxy-3-methylphenyl)bicyclo[2.2.2]octan-1-yl)methyl)carbamoyl)-cyclohexanecarboxylate | 627.5 |
| 21.11[2] | 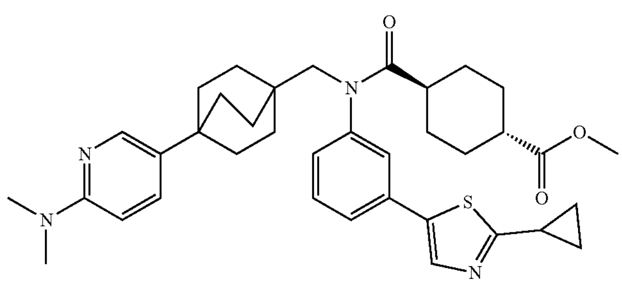 | trans-Methyl 4-((3-(2-cyclopropylthiazol-5-yl)phenyl)((4-(6-(dimethylamino)pyridin-3-yl)bicyclo[2.2.2]octan-1-yl)methyl)carbamoyl)-cyclohexanecarboxylate | 627.8 |
| 21.12[4] | 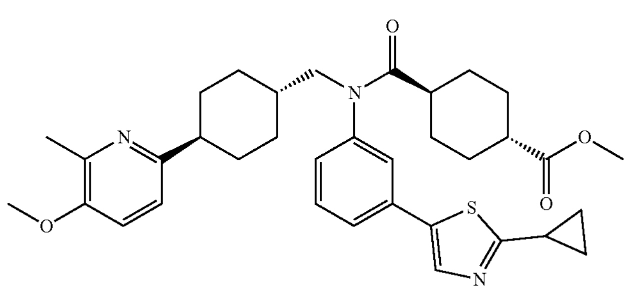 | trans-Methyl 4-((3-(2-cyclopropylthiazol-5-yl)phenyl)((trans-4-(5-methoxy-6-methylpyridin-2-yl)cyclohexyl)methyl)carbamoyl)-cyclohexanecarboxylate | 602.2 |

-continued

| Int | Structure | Name | [M + H]+ |
|---|---|---|---|
| 21.13[3] | 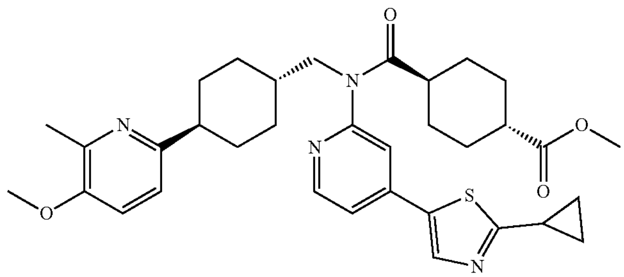 | trans-Methyl 4-((4-(2-cyclopropylthiazol-5-yl)pyridin-2-yl)((trans-4-(5-methoxy-6-methylpyridin-2-yl)cyclohexyl)methyl)carbamoyl)-cyclohexanecarboxylate | 603.4 |
| 21.14[2] | 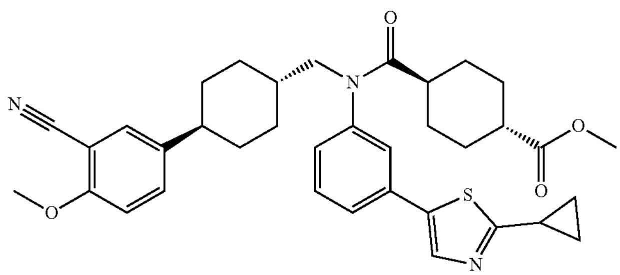 | trans-Methyl 4-(((trans-4-(3-cyano-4-methoxyphenyl)cyclohexyl)methyl)3-(2-cyclopropylthiazol-5-yl)phenyl)carbamoyl)-cyclohexanecarboxylate | 612.4 |
| 21.15[2] | 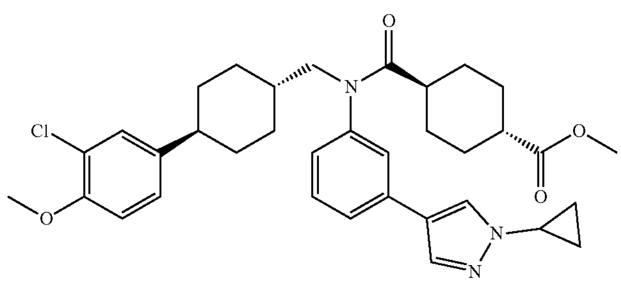 | trans-Methyl 4-(((trans-4-(3-chloro-4-methoxyphenyl)cyclohexyl)methyl)(3-(1-cyclopropyl-1H-pyrazol-4-yl)phenyl)carbamoyl)-cyclohexanecarboxylate | 604.7 |
| 21.16[2] | 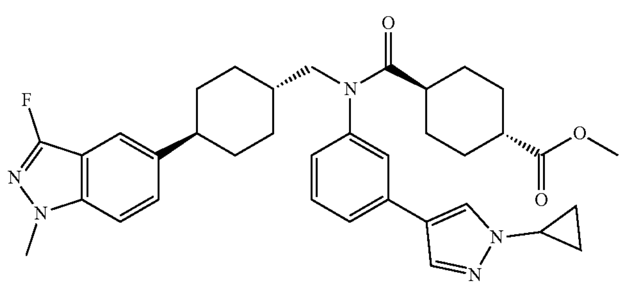 [SMILES: COC(=O)[C@H]1CC[C@H](C(=O)N(C[C@H]2CC[C@H](c3ccc4c(c3)c(F)nn4C)CC2)c2cccc(-c3cnn(C4CC4)c3)c2)CC1] | trans-Methyl 4-((3-(1-cyclopropyl-1H-pyrazol-4-yl)phenyl)((trans-4-(3-fluoro-1-methyl-1H-indazol-5-yl)cyclohexyl)methyl)carbamoyl)-cyclohexanecarboxylate | 612.4 |
| 21.17[2] | 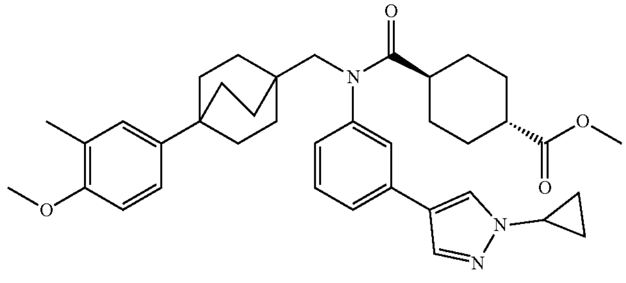 | trans-Methyl 4-((3-(1-cyclopropyl-1H-pyrazol-4-yl)phenyl)((4-(4-methoxy-3-methylphenyl)bicyclo[2.2.2]octan-1-yl)methyl)carbamoyl)-cyclohexanecarboxylate | 610.4 |

-continued

| Int | Structure | Name | [M + H]+ |
|---|---|---|---|
| 21.18[4] | 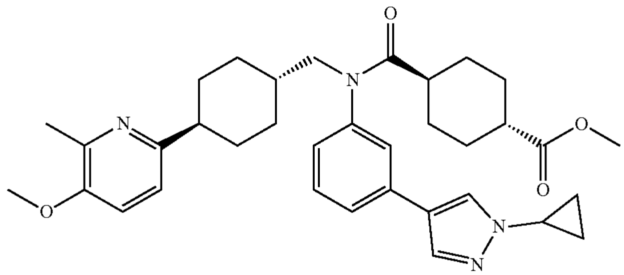 | trans-Methyl 4-((3-(1-cyclopropyl-1H-pyrazol-4-yl)phenyl)((trans-4-(5-methoxy-6-methylpyridin-2-yl)cyclohexyl)methyl)carbamoyl)-cyclohexanecarboxylate | 585.4 |
| 21.19[2] | 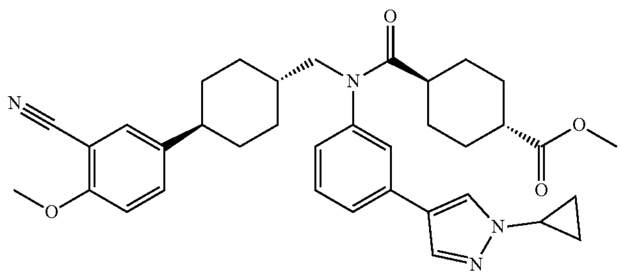 | trans-Methyl 4-(((trans-4-(3-cyano-4-methoxyphenyl)cyclohexyl)methyl)(3-(1-cyclopropyl-1H-pyrazol-4-yl)phenyl)carbamoyl)-cyclohexanecarboxylate | 595.4 |
| 21.20[5] | 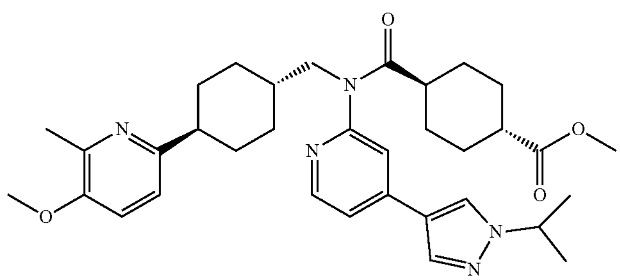 | trans-Methyl 4-((4-(1-isopropyl-1H-pyrazol-4-yl)pyridin-2-yl)((trans-4-(5-methoxy-6-methylpyridin-2-yl)cyclohexyl)methyl)carbamoyl)-cyclohexanecarboxylate | 588.7 |
| 21.21[2] | 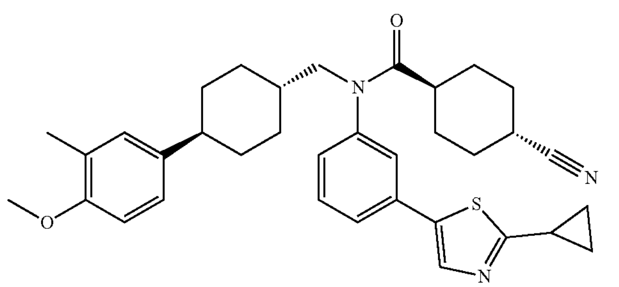 [SMILES: COc1ccc([C@H]2CC[C@H](CN(c3cccc(-c4cnc(C5CC5)s4)c3)C(=O)[C@H]3CC[C@H](C#N)CC3)CC2)cc1C] | trans-4-Cyano-N-(3-(2-cyclopropylthiazol-5-yl)phenyl)-N-((trans-4-(4-methoxy-3-methylphenyl)cyclohexyl)methyl)-cyclohexanecarboxamide | 568.4 |
| 21.22[2] | 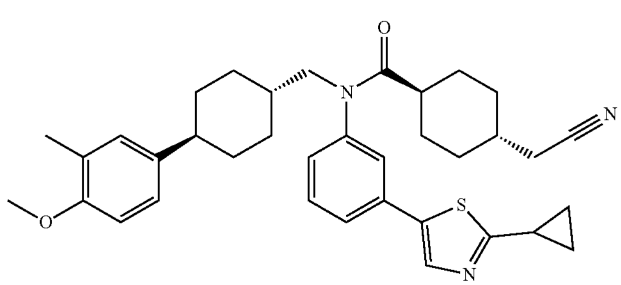 [SMILES: COc1ccc([C@H]2CC[C@H](CN(c3cccc(-c4cnc(C5CC5)s4)c3)C(=O)[C@H]3CC[C@H](CC#N)CC3)CC2)cc1C] | trans-4-(Cyanomethyl)-N-(3-(2-cyclopropylthiazol-5-yl)phenyl)-N-((trans-4-(4-methoxy-3-methylphenyl)cyclohexyl)methyl)-cyclohexanecarboxamide | 582.4 |

| Int | Structure | Name | [M + H]+ |
|---|---|---|---|
| 21.23[2] | 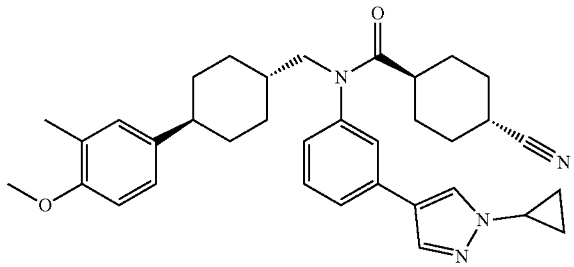 [SMILES: COc1ccc([C@H]2CC[C@H](CN(c3cccc(-c4cnn(C5CC5)c4)c3)C(=O)[C@H]3CC[C@H](C#N)CC3)CC2)cc1C] | trans-4-Cyano-N-(3-(1-cyclopropyl-1H-pyrazol-4-yl)phenyl)-N-((trans-4-(4-methoxy-3-methylphenyl)cyclohexyl)methyl)-cyclohexanecarboxamide | 551.4 |

Alternate conditions:
[1]Et₃N, CH₂Cl₂, rt, overnight;
[2]Solvent was CH₂Cl₂;
[3]Amine in pyridine only (no toluene);
[4]DMAP, pyridine, 80° C., overnight;
[5]DMAP, Et₃N, toluene, 80° C., 90 min.

Intermediate 22

Trans-4-Hydroxy-N-((trans-4-(4-methoxy-3-methylphenyl)cyclohexyl)methyl)-N-(3-(2-methoxythiazol-5-yl)phenyl)cyclohexanecarboxamide

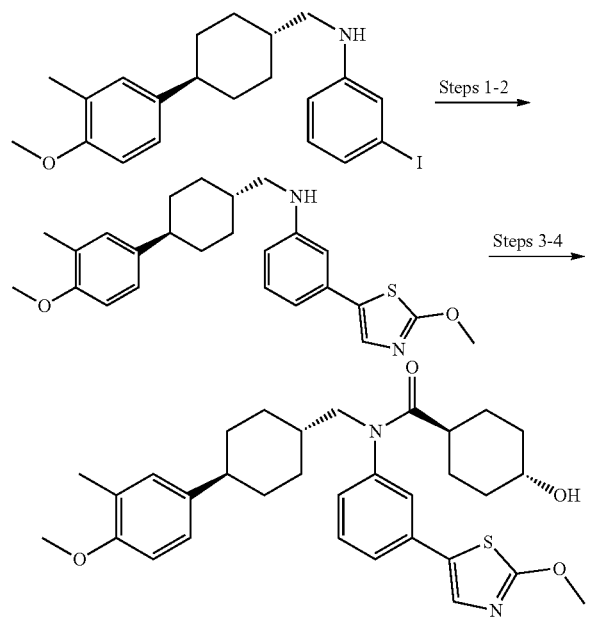

Step 1: N-((trans-4-(4-Methoxy-3-methylphenyl)cyclohexyl)methyl)-3-(4,4,5,5-tetramethyl-1,3,2-dioxaborolan-2-yl)aniline A mixture of Intermediate 13 (824 mg, 1.89 mmol), bis(pinacolato)diboron (727 mg, 2.86 mmol), potassium acetate (373 mg, 3.80 mmol), Pd(dppf)Cl₂ (141 mg, 0.19 mmol), and DMF (12 mL) was degassed with 3 vacuum/N₂ cycles, heated at 80° C. for 24 h, and then allowed to cool to rt. The mixture was filtered through Celite with EtOAc rinsing. The filtrate was washed with 50 mL water, washed with 50 mL brine, dried (Na₂SO₄), filtered, concentrated, and purified by silica gel chromatography (0-10% EtOAc in hexanes) to give N-((trans-4-(4-methoxy-3-methylphenyl)cyclohexyl)methyl)-3-(4,4,5,5-tetramethyl-1,3,2-dioxaborolan-2-yl)aniline (563 mg, ~90% pure, ~60% yield) as a green, sticky foam. H NMR (400 MHz, DMSO-d₆): δ 7.07 (t, 1H), 7.01-6.95 (m, 2H), 6.95-6.91 (m, 1H), 6.84-6.79 (m, 2H), 6.70-6.65 (m, 1H), 5.63 (t, 1H), 3.73 (s, 3H), 2.90-2.85 (m, 2H), 2.43-2.33 (m, 1H), 2.11 (s, 3H), 1.96-1.88 (m, 2H), 1.82-1.75 (m, 2H), 1.63-1.52 (m, 1H), 1.44-1.33 (m, 2H), 1.27 (s, 12H), 1.13-1.03 (m, 2H); LCMS: 436.0 [M+H]+.

Step 2: N-((trans-4-(4-Methoxy-3-methylphenyl)cyclohexyl)methyl)-3-(2-methoxythiazol-5-yl)aniline A mixture of N-((trans-4-(4-methoxy-3-methylphenyl)cyclohexyl)methyl)-3-(4,4,5,5-tetramethyl-1,3,2-dioxaborolan-2-yl)aniline (532 mg, 1.22 mmol), 5-bromo-2-methoxythiazole (363 mg, 1.87 mmol), Cs₂CO₃ (1.23 g, 3.77 mmol), Pd(PPh₃)₄ (284 mg, 0.246 mmol), and DMF (6 mL) was degassed with 3 vacuum/N₂ cycles. Water (60 μL, 1% by vol) was added, and the reaction was heated at 80° C. for 4.5 h then allowed to cool to rt. The mixture was poured into 40 mL sat'd NaHCO₃ and extracted with EtOAc (2×40 mL). Each extract was washed with 40 mL brine. The combined extracts were dried (Na₂SO₄), filtered, concentrated, and purified by silica gel chromatography (5-20% EtOAc in hexanes) to give N-((trans-4-(4-methoxy-3-methylphenyl)cyclohexyl)methyl)-3-(2-methoxythiazol-5-yl)aniline (351 mg, 68%). ¹H NMR (400 MHz, DMSO-d₆): δ 7.50-7.48 (m, 1H), 7.08 (t, 1H), 7.01-6.96 (m, 2H), 6.82-6.79 (m, 1H), 6.69-6.65 (m, 2H), 6.54-6.49 (m, 1H), 5.83 (t, 1H), 4.03 (s, 3H), 3.73 (s, 3H), 2.92 (t, 2H), 2.43-2.34 (m, 1H), 2.11 (s, 3H), 1.98-1.89 (m, 2H), 1.84-1.74 (m, 2H), 1.65-1.52 (m, 1H), 1.46-1.32 (m, 2H), 1.17-1.04 (m, 2H); LCMS: 423.4 [M+H]+.

Step 3: Trans-4-((tert-Butyldimethylsilyl)oxy)-N-((trans-4-(4-methoxy-3-methylphenyl) cyclohexyl)methyl)-N-(3-(2-methoxythiazol-5-yl)phenyl)cyclohexanecarboxamide A solution of Intermediate 19 (0.1 mL, 0.36 mmol) was added to a solution of N-((trans-4-(4-methoxy-3-methylphenyl)cyclohexyl)methyl)-3-(2-methoxythiazol-5-yl)aniline (148 mg, 0.35 mmol), pyridine (0.11 mL, 1.4 mmol), and CH₂Cl₂ (3.5 mL) at rt. The reaction was stirred for 10 min, poured into 20 mL sat'd NaHCO₃ and then extracted with CH₂Cl₂. The organics were washed with 20 mL brine, dried (Na₂SO₄), filtered, concentrated, and purified by silica gel chromatography (10-30% EtOAc in hexanes) to give trans-4-((tert-butyldimethylsilyl)oxy)-N-((trans-4-(4-methoxy-3-methylphenyl)cyclohexyl)methyl)-N-(3-(2-methoxythiazol-5-yl)phenyl)cyclohexanecarboxamide (181 mg, ~86% pure, 67% yield) as a white foam. ¹H NMR (400 MHz, DMSO-d₆): δ 7.75 (s, 1H), 7.56-7.46 (m, 3H), 7.26-7.20 (m, 1H), 6.98-6.92 (m, 2H), 6.81-6.76 (m, 1H), 4.06 (s, 3H), 3.72 (s, 3H), 3.60-3.44 (m, 3H), 2.38-2.28 (m, 1H), 2.09 (s, 3H), 2.07-1.99 (m, 1H), 1.79-1.68 (m, 6H), 1.68-1.60 (m, 2H), 1.50-1.37 (m, 3H), 1.36-1.23 (m, 2H), 1.12-0.98 (m, 2H), 0.91-0.76 (m, 11H), −0.02 (s, 6H); LCMS: 663.5 [M+H]⁺.

Step 4: Trans-4-Hydroxy-N-((trans-4-(4-methoxy-3-methylphenyl)cyclohexyl)methyl)-N-(3-(2-methoxythiazol-5-yl)phenyl)cyclohexanecarboxamide Aqueous hydrochloric acid (6 N, 0.35 mL, 2.1 mmol) was added to a solution of trans-4-((tert-butyldimethylsilyl)oxy)-N-((trans-4-(4-methoxy-3-methylphenyl)cyclohexyl)methyl)-N-(3-(2-methoxythiazol-5-yl)phenyl)cyclohexanecarboxamide (176 mg, 0.265 mmol), CH₃OH (1 mL) and THF (1 mL) at rt. The reaction was stirred for 1 min, poured into 20 mL sat'd NaHCO₃, and then extracted with EtOAc (2×20 mL). The combined extracts were washed with 20 mL sat'd NaHCO₃, washed with 20 mL brine, dried (Na₂SO₄), filtered, concentrated, and purified by silica gel chromatography (40-90% EtOAc in hexanes) to give trans-4-hydroxy-N-((trans-4-(4-methoxy-3-methylphenyl)cyclohexyl)methyl)-N-(3-(2-methoxythiazol-5-yl)phenyl)cyclohexanecarboxamide (68 mg, 93% pure, 50% yield) as an off-white foam. ¹H NMR (400 MHz, DMSO-d₆): δ 7.76 (s, 1H), 7.57-7.47 (m, 3H), 7.27-7.21 (m, 1H), 6.98-6.92 (m, 2H), 6.81-6.75 (m, 1H), 4.41 (br s, 1H), 4.06 (s, 3H), 3.71 (s, 3H), 3.63-3.50 (m, 2H), 3.31-3.21 (m, 1H), 2.38-2.28 (m, 1H), 2.09 (s, 3H), 2.03-2.00 (m, 1H), 1.81-1.68 (m, 6H), 1.68-1.58 (m, 2H), 1.49-1.35 (m, 3H), 1.35-1.22 (m, 2H), 1.13-1.00 (m, 2H), 0.83-0.69 (m, 2H); LCMS: 549.4 [M+H]⁺.

Intermediate 23

Trans-N-(4-(1-Cyclopropyl-1H-pyrazol-4-yl)pyridin-2-yl)-4-hydroxy-N-((trans-4-(4-methoxy-3-methylphenyl)cyclohexyl)methyl)cyclohexanecarboxamide

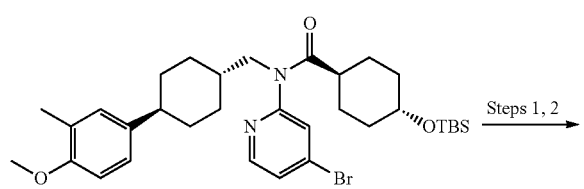

Steps 1, 2

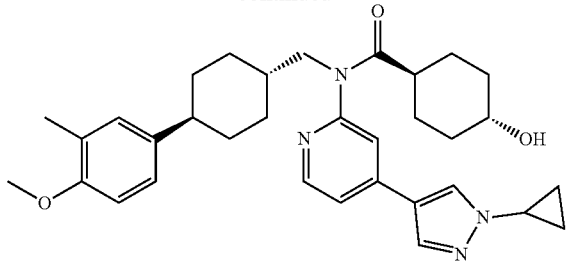

Step 1: Trans-4-((tert-Butyldimethylsilyl)oxy)-N-(4-(1-cyclopropyl-1H-pyrazol-4-yl)pyridin-2-yl)-N-((trans-4-(4-methoxy-3-methylphenyl)cyclohexyl)methyl)cyclohexanecarboxamide A mixture of Intermediate 21.02 (800 mg, 1.27 mmol), 1-cyclopropyl-4-(4,4,5,5-tetramethyl-1,3,2-dioxaborolan-2-yl)pyrazole (297.4 mg, 1.27 mmol), Cs₂CO₃ (827.8 mg, 2.54 mmol), Pd(PPh₃)₄ (146.8 mg, 0.127 mmol), DMF (10 mL) and H₂O (0.2 mL) was degassed with 3 vacuum/N₂ cycles. The mixture was stirred at 50° C. under N₂ for 1 h, allowed to cool to rt, poured into water (50 mL), and then extracted with EtOAc (3×50 mL). The combined organic layers were washed with brine (50 mL), dried over Na₂SO₄, filtered, concentrated and then purified by chromatography on silica gel (petroleum ether/EtOAc=80/20) to give trans-4-((tert-butyldimethylsilyl)oxy)-N-(4-(1-cyclopropyl-1H-pyrazol-4-yl)pyridin-2-yl)-N-((trans-4-(4-methoxy-3-methylphenyl)cyclohexyl)methyl)cyclohexanecarboxamide (720 mg, 86%) as a yellow oil. ¹H NMR (400 MHz, CDCl₃): δ 8.46 (d, 1H), 7.86 (d, 2H), 7.29 (d, 1H), 7.22 (s, 1H), 6.97-6.92 (m, 2H), 6.73 (d, 1H), 3.79 (s, 3H), 3.76 (d, 2H), 3.72-3.65 (m, 1H), 3.60-3.50 (m, 1H), 2.41-2.31 (m, 1H), 2.27-2.16 (m, 4H), 1.90-1.79 (m, 8H), 1.67-1.57 (m, 3H), 1.41-1.30 (m, 2H), 1.23-1.05 (m, 8H), 0.84 (s, 9H), 0.02 (s, 6H); LCMS: 657.5 [M+H]⁺.

Step 2: Trans-N-(4-(1-Cyclopropyl-1H-pyrazol-4-yl)pyridin-2-yl)-4-hydroxy-N-((trans-4-(4-methoxy-3-methylphenyl)cyclohexyl)methyl)cyclohexanecarboxamide Aqueous hydrochloric acid (1 M, 1.7 mL, 1.7 mmol) was added to a solution of trans-4-((tert-butyldimethylsilyl)oxy)-N-(4-(1-cyclopropyl-1H-pyrazol-4-yl)pyridin-2-yl)-N-((trans-4-(4-methoxy-3-methylphenyl)cyclohexyl)methyl)cyclohexanecarboxamide (720 mg, 1.10 mmol), CH₃OH (10 mL) and THF (10 mL) at 0° C. The mixture was allowed to warm to rt and stirred for 1 h. Saturated aq. NaHCO₃ (40 mL) was added, and the mixture was extracted with EtOAc (3×40 mL). The combined organic layers were washed by brine (20 mL), dried over Na₂SO₄ filtered, concentrated, and then purified by chromatography on silica gel (petroleum ether/EtOAc=60/40) to give trans-N-(4-(1-cyclopropyl-1H-pyrazol-4-yl)pyridin-2-yl)-4-hydroxy-N-((trans-4-(4-methoxy-3-methylphenyl)cyclohexyl)methyl)cyclohexanecarboxamide (395.8 mg, 66%) as a white solid. ¹H NMR (400 MHz, DMSO-d₆): δ 8.57 (s, 1H), 8.44 (d, 1H), 8.13 (s, 1H), 7.64 (s, 1H), 7.57 (d, 1H), 6.97-6.89 (m, 2H), 6.80-6.72 (m, 1H), 4.41 (d, 1H), 3.81-3.73 (m, 1H), 3.71 (s, 3H), 3.67 (d, 2H), 3.31-3.21 (m, 1H), 2.33-2.26 (m, 1H), 2.19-2.10 (m, 1H), 2.08 (s, 3H), 1.81-1.67 (m, 8H), 1.47-1.35 (m, 3H), 1.30-1.20 (m, 2H), 1.12-1.06 (m, 2H), 1.06-0.94 (m, 4H), 0.88-0.74 (m, 2H); LCMS: 543.3 [M+H]⁺.

The Intermediates below were synthesized from Intermediate 21.02 or Intermediate 21.04 and the appropriate boronic acid/ester following the procedures described for Intermediate 23.

| Int | Structure | Name | [M + H]⁺ |
|---|---|---|---|
| 23.01 | 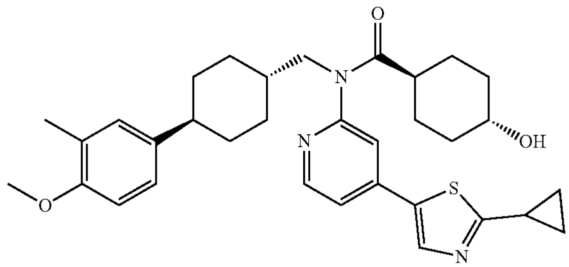 [SMILES: COc1ccc([C@H]2CC[C@H](CN(c3cc(-c4cnc(C5CC5)s4)ccn3)C(=O)[C@H]3CC[C@H](O)CC3)CC2)cc1C] | trans-N-(4-(2-Cyclopropylthiazol-5-yl)pyridin-2-yl)-4-hydroxy-N-((trans-4-(4-methoxy-3-methylphenyl)cyclohexyl)methyl)-cyclohexanecarboxamide | 560.4 |
| 23.02 | 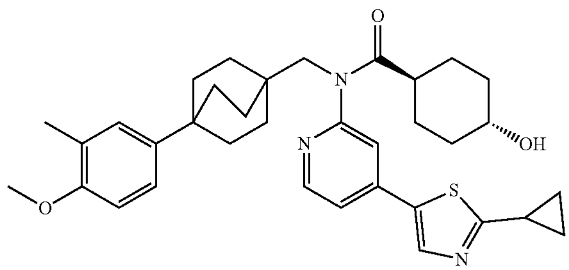 [SMILES: COc1ccc(C23CCC(CN(c4cc(-c5cnc(C6CC6)s5)ccn4)C(=O)[C@H]4CC[C@H](O)CC4)(CC2)CC3)cc1C] | trans-N-(4-(2-Cyclopropylthiazol-5-yl)pyridin-2-yl)-4-hydroxy-N-((4-(4-methoxy-3-methylphenyl)bicyclo[2.2.2]octan-1-yl)methyl)cyclohexanecarboxamide | 586.3 |
| 23.03 | 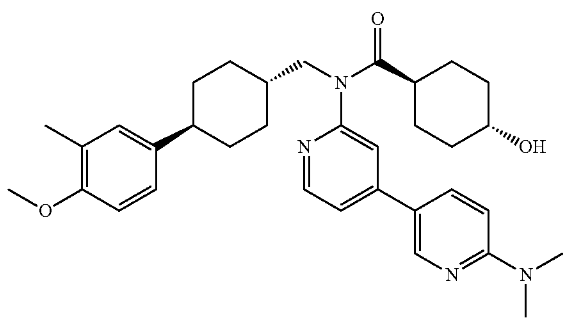 | trans-N-(6-(Dimethylamino)-[3,4'-bipyridin]-2'-yl)-4-hydroxy-N-((trans-4-(4-methoxy-3-methylphenyl)cyclohexyl)methyl)-cyclohexanecarboxamide | 557.5 |

The Intermediates below were synthesized from the appropriate Intermediate and the appropriate boronic acid/ester following the procedure described for Intermediate 23, Step 1.

| Int | Structure | Name | [M + H]⁺ |
|---|---|---|---|
| 23.04 | 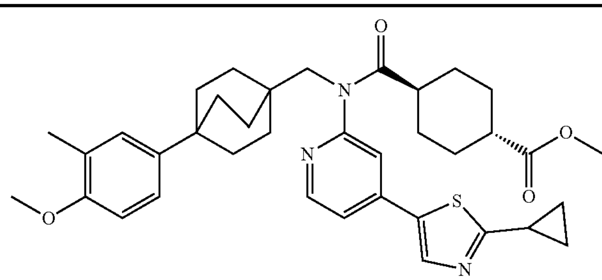 | trans-Methyl 4-((4-(2-cyclopropylthiazol-5-yl)pyridin-2-yl)((4-(4-methoxy-3-methylphenyl)bicyclo[2.2.2]octan-1-yl)methyl)carbamoyl)cyclohexane-carboxylate | 628.4 |
| 23.05 | 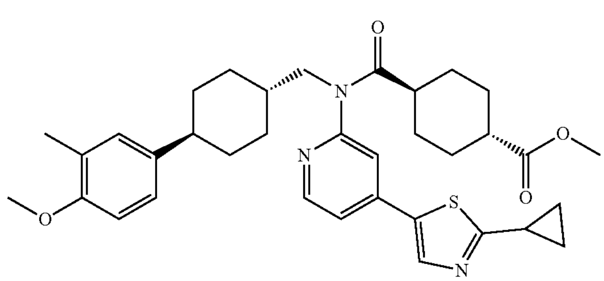 | trans-Methyl 4-((4-(2-cyclopropylthiazol-5-yl)pyridin-2-yl)((trans-4-(4-methoxy-3-methylphenyl)cyclohexyl)methyl)-carbamoyl)cyclohexanecarboxylate | 602.2 |

-continued

| Int | Structure | Name | [M + H]+ |
|---|---|---|---|
| 23.06[1] | 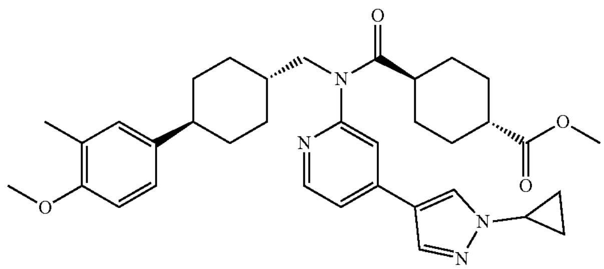 | trans-Methyl 4-((4-(1-cyclopropyl-1H-pyrazol-4-yl)pyridin-2-yl)((trans-4-(4-methoxy-3-methylphenyl)cyclohexyl)methyl)-carbamoyl)cyclohexanecarboxylate | 585.2 |
| 23.07 | 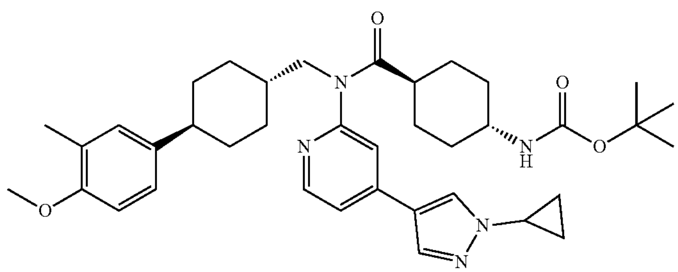 [SMILES: COc1ccc([C@H]2CC[C@H](CN(c3cc(-c4cnn(C5CC5)c4)ccn3)C(=O)[C@H]3CC[C@H](NC(=O)OC(C)(C)C)CC3)CC2)cc1C] | tert-Butyl (trans-4-((4-(1-cyclopropyl-1H-pyrazol-4-yl)pyridin-2-yl)((trans-4-(4-methoxy-3-methylphenyl)cyclohexyl)methyl)-carbamoyl)cyclohexyl)carbamate | 642.9 |
| 23.08 | 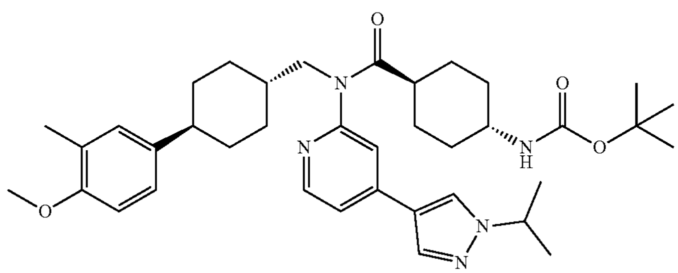 [SMILES: COc1ccc([C@H]2CC[C@H](CN(c3cc(-c4cnn(C(C)C)c4)ccn3)C(=O)[C@H]3CC[C@H](NC(=O)OC(C)(C)C)CC3)CC2)cc1C] | tert-Butyl (trans-4-((4-(1-isopropyl-1H-pyrazol-4-yl)pyridin-2-yl)((trans-4-(4-methoxy-3-methylphenyl)cyclohexyl)methyl)-carbamoyl)cyclohexyl)carbamate | 644.6 |

Alternate conditions:
[1]Pd(PPh3)4, K2CO3, dioxane, water (10%), 100° C., 2 h.

Intermediate 24

Trans-N-(3-(6-(Dimethylamino)pyridine-3-yl)phenyl)-4-hydroxy-N-((trans-4-(4-methoxy-3-methylphenyl)cyclohexyl)methyl)cyclohexanecarboxamide

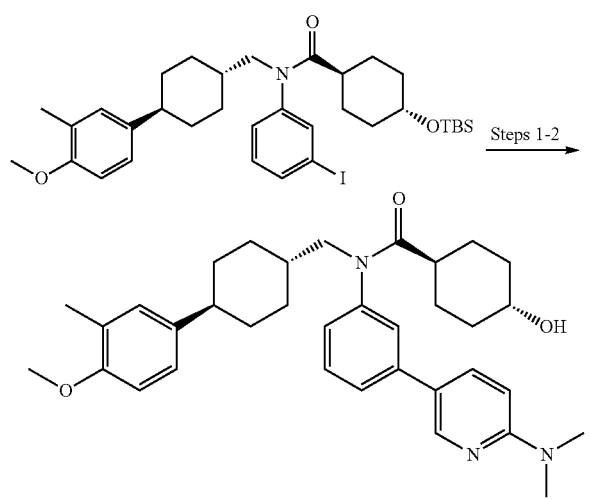

Step 1: Trans-4-((tert-Butyldimethylsilyl)oxy)-N-(3-(6-(dimethylamino)pyridine-3-yl)phenyl)-N-((trans-4-(4-methoxy-3-methylphenyl)cyclohexyl)methyl)cyclohexanecarboxamide A mixture of Intermediate 21 (130 mg, 0.192 mmol), (6-(dimethylamino)pyridine-3-yl)boronic acid (50 mg, 0.301 mmol), K2CO3 (85 mg, 0.615 mmol), Pd(dppf)Cl2 (15 mg, 0.021 mmol), dioxane (1.8 mL), and H2O (1.3 mL) was degassed with vacuum/nitrogen cycles (3×), heated at 80° C. for 25 min, and then cooled to rt. The reaction was diluted with EtOAc (20 mL), washed (2×20 mL H2O), dried (Na2SO4), and concentrated. The residue was purified by silica gel chromatography (0-25% EtOAc in hexanes) to give trans-4-((tert-butyldimethylsilyl)oxy)-N-(3-(6-(dimethylamino)pyridine-3-yl)phenyl)-N-((trans-4-(4-methoxy-3-methylphenyl)cyclohexyl)methyl)cyclohexanecarboxamide as a white foam (93 mg, 72%). $^1$H NMR (400 MHz, DMSO-$d_6$): δ 8.47 (d, 1H), 7.87 (dd, 1H), 7.64 (d, 1H), 7.54-7.48 (m, 2H), 7.19 (d, 1H), 6.96-6.92 (m, 2H), 6.79-6.76 (m, 1H), 6.74 (d, 1H), 3.71 (s, 3H), 3.61-3.54 (m, 2H), 3.53-3.43 (m, 1H), 3.07 (s, 6H), 2.39-2.28 (m, 1H), 2.11-2.00 (m, 4H), 1.81-1.60 (m, 8H), 1.51-1.38 (m, 3H), 1.35-1.21 (m, 2H), 1.12-0.99 (m, 2H), 0.90-0.73 (m, 11H), −0.03 (s, 6H); LCMS: 670.6 [M+H]+.

Step 2: Trans-N-(3-(6-(Dimethylamino)pyridine-3-yl)phenyl)-4-hydroxy-N-((trans-4-(4-methoxy-3-methylphenyl)cyclohexyl)methyl)cyclohexanecarboxamide Aqueous hydrochloric acid (1 N, 0.25 mL, 0.25 mmol) was added to a solution of trans-4-((tert-butyldimethylsilyl)oxy)-N-(3-(6-(dimethylamino) pyridine-3-yl)phenyl)-N-((trans-4-(4-methoxy-3-methylphenyl)cyclohexyl)methyl) cyclohexanecarboxamide (85 mg, 0.127 mmol), $CH_3OH$ (0.5 mL), and THF (0.5 mL) at 0° C. The ice bath was removed, and the mixture was stirred for 1 h. The reaction was diluted with EtOAc (20 mL), washed (20 mL saturated $NaHCO_3$ and then 20 mL brine), dried ($Na_2SO_4$), and concentrated. The residue was purified by silica gel chromatography (0-5% $CH_3OH$ in $CH_2Cl_2$) to give trans-N-(3-(6-(dimethylamino)pyridine-3-yl)phenyl)-4-hydroxy-N-((trans-4-(4-methoxy-3-methylphenyl)cyclohexyl)methyl) cyclohexanecarboxamide as a white foam (61 mg, 86%). $^1$H NMR (400 MHz, DMSO-$d_6$): δ 8.47 (d, 1H), 7.87 (dd, 1H), 7.64 (d, 1H), 7.54-7.48 (m, 2H), 7.19 (d, 1H), 6.96-6.92 (m, 2H), 6.79-6.76 (m, 1H), 6.74 (d, 1H), 4.39 (d, 1H), 3.71 (s, 3H), 3.63-3.51 (m, 2H), 3.31-3.20 (m, 1H), 3.07 (s, 6H), 2.39-2.28 (m, 1H), 2.15-2.00 (m, 4H), 1.84-1.69 (m, 6H), 1.68-1.56 (m, 2H), 1.51-1.36 (m, 3H), 1.35-1.22 (m, 2H), 1.13-0.98 (m, 2H), 0.85-0.69 (in, 2H); LCMS: 556.5 $[M+H]^+$.

The following Intermediates were synthesized from the appropriate iodide Intermediate and the appropriate boronic acid/ester following the procedure described for Intermediate 24.

| Int | Structure | Name | [M + H]$^+$ |
|---|---|---|---|
| 24.01 | 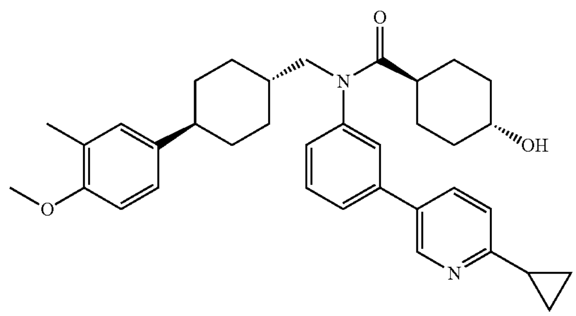 [SMILES: COc1ccc([C@H]2CC[C@H](CN(c3cccc(-c4ccc(C5CC5)nc4)c3)C(=O)[C@H]3CC[C@H](O)CC3)CC2)cc1C] | trans-(3-(6-Cyclopropylpyridin-3-yl)phenyl)-4-hydroxy-N-((trans-4-(4-methoxy-3-methylphenyl)cyclohexyl)methyl)-cyclohexanecarboxamide | 553.5 |
| 24.02 | 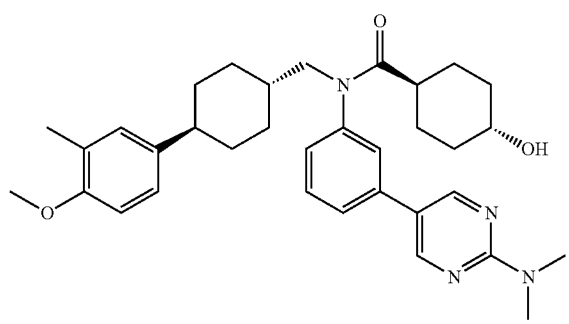 | trans-N-(3-(2-(Dimethylamino)pyrimidin-5-yl)phenyl)-4-hydroxy-N-((trans-4-(4-methoxy-3-methylphenyl)cyclohexyl)methyl)-cyclohexanecarboxamide | 557.3 |
| 24.03 | 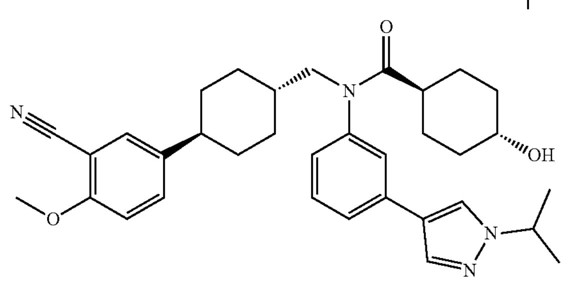 | trans-N-((trans-4-(3-Cyano-4-methoxyphenyl)cyclohexyl)methyl)-4-hydroxy-N-(3-(1-isopropyl-1H-pyrazol-4-yl)phenyl)cyclohexanecarboxamide | 555.5 |
| 24.04 | 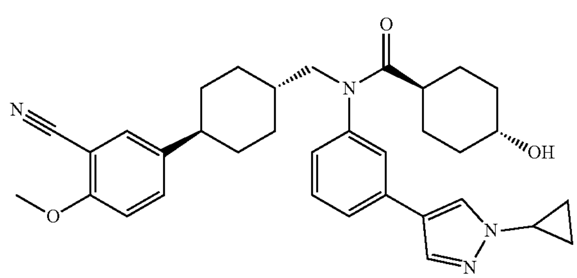 | trans-N-((trans-4-(3-Cyano-4-methoxyphenyl)cyclohexyl)methyl)-N-(3-(1-cyclopropyl-1H-pyrazol-4-yl)phenyl)-4-hydroxycyclohexanecarboxamide | 553.5 |

Intermediate 25

Trans-4-((tert-Butyldimethylsilyl)oxy)-N-((trans-4-(4-methoxy-3-methylphenyl)cyclohexyl)methyl)-N-(3-(4,4,5,5-tetramethyl-1,3,2-dioxaborolan-2-yl)phenyl)cyclohexanecarboxamide

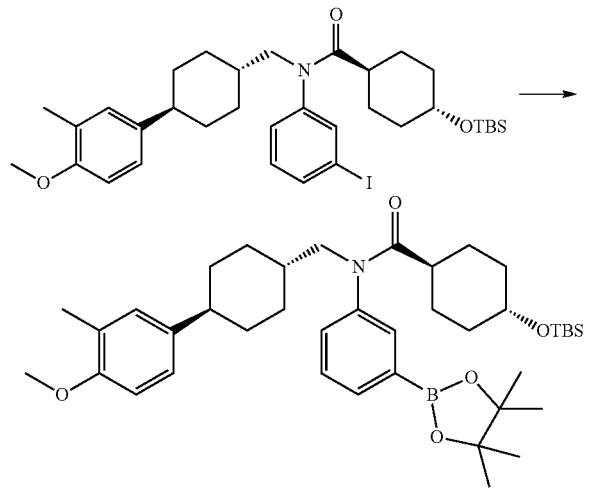

A mixture of bis(pinacolato)diboron (1.42 g, 5.59 mmol), potassium acetate (1.45 g, 14.8 mmol), Pd(dppf)Cl$_2$ (135 mg, 0.18 mmol), and toluene (23 mL) was degassed with 3 vacuum/N$_2$ cycles. Intermediate 21 (2.50 g, 3.70 mmol) was added to the mixture, and the reaction was degassed with 2 vacuum/N$_2$ cycles, heated at 115° C. for 3.5 h, and then allowed to cool to rt. The mixture was diluted with 75 mL EtOAc. The organics were washed with sat'd NaHCO$_3$ (2×75 mL), dried (Na$_2$SO$_4$), filtered, concentrated, and dried on high vacuum overnight to give trans-4-((tert-butyldimethylsilyl)oxy)-N-((trans-4-(4-methoxy-3-methylphenyl)cyclohexyl)methyl)-N-(3-(4,4,5,5-tetramethyl-1,3,2-dioxaborolan-2-yl)phenyl)cyclohexanecarboxamide (2.99 g, 120% crude product) as a brown solid. $^1$H NMR (400 MHz, CDCl$_3$): δ 7.82-7.78 (m, 1H), 7.61-7.57 (m, 1H), 7.43 (t, 1H), 7.27-7.24 (m, 1H), 6.99-6.94 (m, 2H), 6.74 (d, 1H), 3.80 (s, 3H), 3.72-3.45 (m, 3H), 2.44-2.33 (m, 1H), 2.20 (s, 3H), 2.11-2.01 (m, 1H), 1.90-1.76 (m, 6H), 1.75-1.65 (m, 3H), 1.58-1.47 (m, 2H), 1.42-1.32 (m, 14H), 1.24-1.10 (m, 2H), 1.06-0.92 (m, 2H), 0.84 (s, 9H), 0.01 (s, 6H); LCMS: 676.6 [M+H]$^+$. Note: Intermediate 25 was also synthesized from bromo version of Intermediate 21.

Intermediate 26

Trans-N-(3-(2-Cyclopropylthiazol-5-yl)phenyl)-4-hydroxy-N-((trans-4-(4-methoxy-3-methylphenyl)cyclohexyl)methyl)cyclohexanecarboxamide

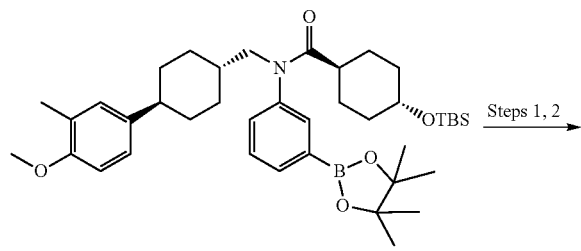
Steps 1, 2

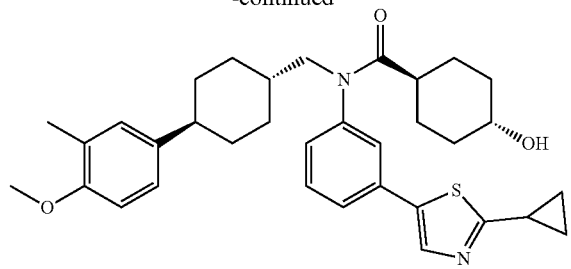

Step 1: Trans-4-((tert-Butyldimethylsilyl)oxy)-N-(3-(2-cyclopropylthiazol-5-yl)phenyl)-N-((trans-4-(4-methoxy-3-methylphenyl)cyclohexyl)methyl)cyclohexanecarboxamide A mixture of 5-bromo-2-cyclopropylthiazole (93 mg, 0.45 mmol), Intermediate 25 (204 mg, 0.302 mmol), Pd(dppf)Cl$_2$ (23 mg, 0.031 mmol), Cs$_2$CO$_3$ (290 mg, 0.89 mmol), DMF (3 mL), and water (30 μL, 1% by vol) was degassed with 3 vacuum/N$_2$ cycles, stirred at 80° C. for 25 min, and then allowed to cool to rt. The reaction was poured into 20 mL sat'd NaHCO$_3$ and then extracted with 20 mL EtOAc. The organic layer was washed with 20 mL brine, dried (Na$_2$SO$_4$), filtered, concentrated, and purified by silica gel chromatography (5-20% EtOAc in hexanes) to give trans-4-((tert-butyldimethylsilyl)oxy)-N-(3-(2-cyclopropylthiazol-5-yl)phenyl)-N-((trans-4-(4-methoxy-3-methylphenyl)cyclohexyl)methyl)cyclohexanecarboxamide (179 mg, 88%) as a white foam. $^1$H NMR (400 MHz, DMSO-d$_6$): δ 8.09 (s, 1H), 7.63-7.55 (m, 2H), 7.52 (t, 1H), 7.29-7.22 (m, 1H), 6.98-6.91 (m, 2H), 6.82-6.75 (m, 1H), 3.71 (s, 3H), 3.62-3.44 (m, 3H), 2.47-2.38 (m, 1H), 1.38-2.28 (m, 1H), 2.09 (s, 3H), 2.07-1.99 (m, 1H), 1.79-1.68 (m, 6H), 1.68-1.60 (m, 2H), 1.51-1.37 (m, 3H), 1.36-1.23 (m, 2H), 1.18-1.11 (m, 2H), 1.11-0.96 (m, 4H), 0.91-0.72 (m, 11H), −0.03 (s, 6H); LCMS: 673.4 [M+H]$^+$.

Step 2: Trans-N-(3-(2-Cyclopropylthiazol-5-yl)phenyl)-4-hydroxy-N-((trans-4-(4-methoxy-3-methylphenyl)cyclohexyl)methyl)cyclohexanecarboxamide Aqueous hydrochloric acid (6 N, 0.35 mL, 2.1 mmol) was added to a solution of trans-4-((tert-butyldimethylsilyl)oxy)-N-(3-(2-cyclopropylthiazol-5-yl)phenyl)-N-((trans-4-(4-methoxy-3-methylphenyl)cyclohexyl)methyl)cyclohexanecarboxamide (174 mg, 0.26 mmol), CH$_3$OH (0.7 mL), and THF (0.7 mL) at 0° C. The reaction was allowed to warm to rt, stirred at rt for 30 min, and then poured into 20 mL of cold sat'd NaHCO$_3$. The mixture was extracted with 20 mL EtOAc. The organic layer was washed with 20 mL sat'd NaHCO$_3$ and washed with 20 mL brine. The first aqueous wash was back extracted with 10 mL EtOAc. The combined EtOAc extracts were dried (Na$_2$SO$_4$), filtered, concentrated, and purified by silica gel chromatography (0-5% CH$_3$OH in CH$_2$CO$_2$) to give trans-N-(3-(2-cyclopropylthiazol-5-yl)phenyl)-4-hydroxy-N-((trans-4-(4-methoxy-3-methylphenyl)cyclohexyl)methyl)cyclohexanecarboxamide (131 mg, 90%) as a white foam. $^1$H NMR (400 MHz, DMSO-d$_6$): δ 8.10 (s, 1H), 7.63-7.55 (m, 2H), 7.53 (t, 1H), 7.30-7.23 (m, 1H), 6.98-6.91 (m, 2H), 6.82-6.75 (m, 1H), 4.40 (d, 1H), 3.71 (s, 3H), 3.62-3.50 (m, 2H), 3.31-3.20 (m, 1H), 2.48-2.39 (m, 1H), 2.38-2.27 (m, 1H), 2.09 (s, 3H), 2.06-1.96 (m, 1H), 1.80-1.68 (m, 6H), 1.68-1.58 (m, 2H), 1.49-1.35 (m, 3H), 1.35-1.22 (m, 2H), 1.18-1.11 (m, 2H), 1.11-0.97 (m, 4H), 0.83-0.69 (m, 2H); LCMS: 559.9 [M+H]$^+$.

Intermediate 27

Trans-4-Hydroxy-N-((trans-4-(4-methoxy-3-methylphenyl)cyclohexyl)methyl)-N-(3-(thiazol-2-ylethynyl)phenyl)cyclohexanecarboxamide

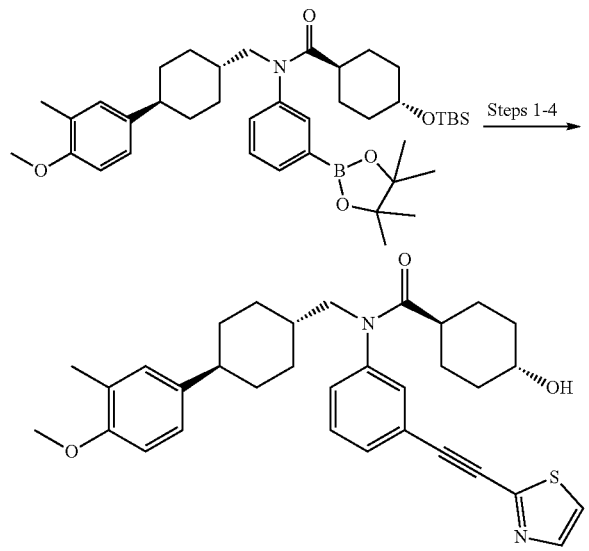

Step 1: 5-Bromo-2-((trimethylsilyl)ethynyl)thiazole n-Butyllithium (2.5 M in hexanes, 4.50 mL) was added to a solution of 2-((trimethylsilyl)ethynyl)thiazole (2.00 g, 11.03 mmol) in THF (50 mL) at −78° C. The mixture was stirred for 1 h at −78° C. Bromine (1.59 g, 9.93 mmol) was added to the mixture. The mixture was stirred for 1 h at −78° C., poured into saturated aq. NH$_4$Cl (100 mL), and then extracted with EtOAc (2×100 mL). The combined organic phases were dried over Na$_2$SO$_4$, filtered, concentrated, and then purified by silica gel chromatography (petroleum ether/EtOAc=600/1 to 300/1) to obtain 5-bromo-2-((trimethylsilyl)ethynyl)thiazole (1.80 g, 62% yield) as a red oil. $^1$H NMR (400 MHz, CDCl$_3$): δ 7.77 (s, 1H), 0.36 (s, 9H); LCMS: 260.0 [M+H]$^+$.

Step 2: Trans-4-((tert-Butyldimethylsilyl)oxy)-N-((trans-4-(4-methoxy-3-methylphenyl)cyclohexyl)methyl)-N-(3-((5-(trimethylsilyl)thiazol-2-yl)ethynyl)phenyl)cyclohexanecarboxamide To a solution of Intermediate 25 (900 mg, 1.33 mmol), 5-bromo-2-((trimethylsilyl)ethynyl)thiazole (693 mg, 2.66 mmol), dioxane (12 mL) and H$_2$O (2 mL) was added Pd(dppf)Cl$_2$ (195 mg, 0.266 mmol) and Na$_2$CO$_3$ (285.9 mg, 2.70 mmol). The mixture was degassed with 3 vacuum/N$_2$ cycles, stirred for 2 h at 80° C., and then allowed to cool to rt. The reaction was diluted with H$_2$O (30 mL) and then extracted with EtOAc (2×50 mL). The combined organics were dried over Na$_2$SO$_4$, filtered, concentrated, and then purified by column chromatography on silica gel (eluted with petroleum ether/EtOAc=30/1 to 10/1) to give trans-4-((tert-butyldimethylsilyl)oxy)-N-((trans-4-(4-methoxy-3-methylphenyl)cyclohexyl)methyl)-N-(3-((5-(trimethylsilyl)thiazol-2-yl)ethynyl)phenyl)cyclohexanecarboxamide (230 mg, 24% yield) as a yellow oil. $^1$H NMR (400 MHz, CDCl$_3$) δ: 7.86 (s, 1H), 7.58 (d, 1H), 7.44 (t, 1H), 7.41 (s, 1H), 7.21 (d, 1H), 6.97-6.95 (m, 2H), 6.73 (d, 1H), 3.78 (s, 3H), 3.60 (d, 2H), 3.55-3.51 (m, 1H), 2.43-2.34 (m, 1H), 2.18 (s, 3H), 2.08-2.03 (m, 1H), 1.88-1.78 (m, 6H), 1.67-1.58 (m, 4H), 1.44-1.37 (m, 3H), 1.21-1.17 (m, 2H), 1.07-1.03 (m, 2H), 0.83 (s, 9H), 0.38 (s, 9H), 0.00 (s, 6H); LCMS: 729.3 [M+H]$^+$.

Step 3: Trans-4-Hydroxy-N-((trans-4-(4-methoxy-3-methylphenyl)cyclohexyl)methyl)-N-(3-((5-(trimethylsilyl)thiazol-2-yl)ethynyl)phenyl)cyclohexanecarboxamide Aqueous hydrochloric acid (1 M, 1 mL) was added to a solution of trans-4-((tert-butyldimethylsilyl)oxy)-N-((trans-4-(4-methoxy-3-methylphenyl)cyclohexyl)methyl)-N-(3-((5-(trimethylsilyl)thiazol-2-yl)ethynyl)phenyl)cyclohexanecarboxamide (230 mg, 0.315 mmol) in CH$_3$OH (6 mL) at 0° C. The mixture was stirred for 1 h at rt and concentrated under reduced pressure. The reaction was diluted with saturated aq. NaHCO$_3$ (10 mL) and then extracted with CH$_2$C$_2$(2×10 mL). The combined organic phases were dried over Na$_2$SO$_4$, filtered and concentrated to give trans-4-hydroxy-N-((trans-4-(4-methoxy-3-methylphenyl)cyclohexyl)methyl)-N-(3-((5-(trimethylsilyl)thiazol-2-yl)ethynyl)phenyl)cyclohexanecarboxamide (180 mg, crude) as a yellow oil. LCMS: 615.5 [M+H]$^+$.

Step 4: Trans-4-Hydroxy-N-((trans-4-(4-methoxy-3-methylphenyl)cyclohexyl)methyl)-N-(3-(thiazol-2-ylethynyl)phenyl)cyclohexanecarboxamide Potassium fluoride (68.7 mg, 1.18 mmol) was added to a solution of trans-4-hydroxy-N-((trans-4-(4-methoxy-3-methylphenyl)cyclohexyl)methyl)-N-(3-((5-(trimethylsilyl)thiazol-2-yl)ethynyl)phenyl)cyclohexanecarboxamide (180 mg, 0.293 mmol) in CH$_3$CN (10 mL). The mixture was stirred overnight at 70° C. The resulting mixture was filtered through filter paper to remove excess potassium fluoride. The filtrate was concentrated and then purified by reverse-phase HPLC (water (10 mM NH$_4$HCO$_3$)-MeCN) to obtain trans-4-hydroxy-N-((trans-4-(4-methoxy-3-methylphenyl)cyclohexyl)methyl)-N-(3-(thiazol-2-ylethynyl)phenyl)cyclohexanecarboxamide (82.4 mg, 51% yield) as a white solid. $^1$H NMR (400 MHz, DMSO-d$_6$) δ: 7.98 (d, 1H), 7.95 (d, 1H), 7.68-7.64 (m, 2H), 7.57 (t, 1H), 7.44 (d, 1H), 6.92 (s, 2H), 6.76 (d, 1H), 4.40 (d, 1H), 3.69 (s, 3H), 3.53 (d, 2H), 3.27-3.25 (m, 1H), 2.33-2.28 (m, 1H), 2.07 (s, 3H), 1.96 (t, 1H), 1.71-1.59 (m, 8H), 1.42-1.26 (m, 5H), 1.03-1.00 (m, 2H), 0.77-0.74 (m, 2H); LCMS: 543.2 [M+H]$^+$.

Intermediate 28

Trans-4-Hydroxy-N-((4-(4-methoxy-3-methylphenyl)bicyclo[2.2.2]octan-1-yl)methyl)-N-(3-(thiazol-2-ylethynyl)phenyl)cyclohexanecarboxamide

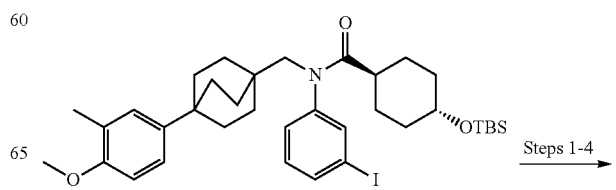

529

-continued

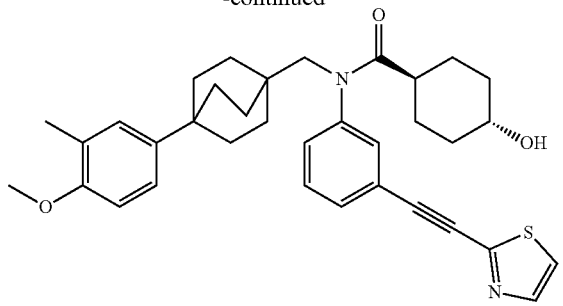

Step 1: Trans-4-((tert-Butyldimethylsilyl)oxy)-N-((4-(4-methoxy-3-methylphenyl)bicyclo[2.2.2]octan-1-yl)methyl)-N-(3-((trimethylsilyl)ethynyl)phenyl)cyclohexanecarboxamide A mixture of Intermediate 21.03 (2.75 g, 3.92 mmol), ethynyl(trimethyl)silane (384.9 mg, 3.92 mmol), CuI (74.6 mg, 0.392 mmol), Pd(dppf)Cl$_2$ (286.7 mg, 0.392 mmol) and dry Et$_3$N (30 mL) was degassed with 3 vacuum/N$_2$ cycles, stirred at 90° C. under N$_2$ for 2 h, and then allowed to cool to rt. The reaction was poured into 100 mL water and extracted with EtOAc (2×100 mL). The combined organic layers were dried over Na$_2$SO$_4$, filtered, concentrated, and then purified by chromatography on silica gel (petroleum ether/EtOAc=95/5) to give trans-4-((tert-butyldimethylsilyl)oxy)-N-((4-(4-methoxy-3-methylphenyl)bicyclo[2.2.2]octan-1-yl)methyl)-N-(3-((trimethylsilyl)ethynyl)phenyl)cyclohexanecarboxamide (2.12 g, 81%) as a white solid. $^1$H NMR (400 MHz, CDCl$_3$): δ 7.43-7.39 (m, 1H), 7.35-7.30 (m, 2H), 7.20 (d, 1H), 7.07-7.02 (m, 2H), 6.73 (d, 1H), 3.79 (s, 3H), 3.73-3.39 (m, 3H), 2.23-2.17 (m, 4H), 1.84-1.79 (m, 2H), 1.76-1.63 (m, 10H), 1.50-1.43 (m, 6H), 1.09-0.99 (m, 2H), 0.93-0.82 (m, 9H), 0.29 (s, 9H), 0.02 (s, 6H); LCMS: 672.3 [M+H]$^+$.

Step 2: Trans-4-((tert-Butyldimethylsilyl)oxy)-N-(3-ethynylphenyl)-N-((4-(4-methoxy-3-methylphenyl)bicyclo[2.2.2]octan-1-yl)methyl)cyclohexanecarboxamide Ammonium fluoride (688.8 mg, 18.60 mmol) was added to a solution of trans-4-((tert-butyldimethylsilyl)oxy)-N-((4-(4-methoxy-3-methylphenyl)bicyclo[2.2.2]octan-1-yl)methyl)-N-(3-((trimethylsilyl)ethynyl)phenyl)cyclohexanecarboxamide (2.5 g, 3.72 mmol) in CH$_3$OH (50 mL) at rt. The reaction was warmed to 60° C., stirred for 3 h, and then allowed to cool to rt. The reaction mixture was concentrated to dryness and purified by chromatography on silica gel (petroleum ether/EtOAc=95/5) to give trans-4-((tert-butyldimethylsilyl)oxy)-N-(3-ethynylphenyl)-N-((4-(4-methoxy-3-methylphenyl)bicyclo[2.2.2]octan-1-yl)methyl)cyclohexanecarboxamide (1.6 g, 72%) as a yellow solid. $^1$H NMR (400 MHz, CDCl$_3$): δ 7.47-7.42 (m, 1H), 7.40-7.34 (m, 2H), 7.24 (d, 1H), 7.08-7.02 (m, 2H), 6.74 (d, 1H), 3.79 (s, 3H), 3.62 (s, 2H), 3.57-3.50 (m, 1H), 3.16 (s, 1H), 2.24-2.12 (m, 4H), 1.86-1.78 (m, 2H), 1.77-1.57 (m, 10H), 1.50-1.43 (m, 6H), 1.10-0.97 (m, 2H), 0.85 (s, 9H), 0.02 (s, 6H); LCMS: 600.5 [M+H]$^+$.

Step 3: Trans-4-((tert-Butyldimethylsilyl)oxy)-N-((4-(4-methoxy-3-methylphenyl)bicyclo[2.2.2]octan-1-yl)methyl)-N-(3-(thiazol-2-ylethynyl)phenyl)cyclohexanecarboxamide A mixture of trans-4-((tert-butyldimethylsilyl)oxy)-N-(3-ethynylphenyl)-N-((4-(4-methoxy-3-methylphenyl)bicyclo[2.2.2]octan-1-yl)methyl)cyclohexanecarboxamide (1.4 g, 2.33 mmol), 2-bromothiazole (765.6 mg, 4.67 mmol), CuI (44.4 mg, 0.233 mmol), Pd(PPh$_3$)$_2$Cl$_2$ (163.8 mg, 0.233 mmol) and dry Et$_3$N (15 mL) was degassed with 3 vacuum/N$_2$ cycles, stirred at 90° C. under N$_2$ for 1 h, and then allowed to cool to rt. The reaction was poured into 90 mL water and then extracted with EtOAc (3×100 mL). The combined organic layers were dried over Na$_2$SO$_4$, filtered, concentrated, and then purified by chromatography on silica gel (petroleum ether/EtOAc=95/5) to give trans-4-((tert-butyldimethylsilyl)oxy)-N-((4-(4-methoxy-3-methylphenyl)bicyclo[2.2.2]octan-1-yl)methyl)-N-(3-(thiazol-2-ylethynyl)phenyl)cyclohexanecarboxamide (1.36 g) as a yellow solid. $^1$H NMR (400 MHz, CDCl$_3$): δ 7.91 (d, 1H), 7.49 (d, 1H), 7.46 (d, 1H), 7.43-7.39 (m, 2H), 7.29 (s, 1H), 7.07-7.03 (m, 2H), 6.76-6.72 (m, 1H), 3.79 (s, 3H), 3.62 (s, 2H), 3.57-3.50 (m, 1H), 2.21-2.13 (m, 4H), 1.87-1.79 (m, 2H), 1.77-1.56 (m, 10H), 1.50-1.43 (m, 6H), 1.10-0.97 (m, 2H), 0.85 (s, 9H), 0.02 (s, 6H).

Step 4: Trans-4-Hydroxy-N-((4-(4-methoxy-3-methylphenyl)bicyclo[2.2.2]octan-1-yl)methyl)-N-(3-(thiazol-2-ylethynyl)phenyl)cyclohexanecarboxamide Aqueous hydrochloric acid (1 M, 3 mL, 3.0 mmol) was added to a solution of trans-4-((tert-butyldimethylsilyl)oxy)-N-((4-(4-methoxy-3-methylphenyl)bicyclo[2.2.2]octan-1-yl)methyl)-N-(3-(thiazol-2-ylethynyl)phenyl)cyclohexanecarboxamide (1.36 g) in CH$_3$OH (10 mL) and THF (10 mL) at 0° C. The reaction was allowed to warm to rt and stirred for 1 h. Saturated aq. NaHCO$_3$ (40 mL) was added, and the mixture was extracted with EtOAc (3×40 mL). The combined organic layers were washed by brine (20 mL), dried over Na$_2$SO$_4$, filtered, concentrated, and then purified by chromatography on silica gel (CH$_2$Cl$_2$/CH$_3$OH=97/3). The impure material was further purified by reverse-phase prep-HPLC (water(10 mmol NH$_4$HCO$_3$)/MeCN) to give trans-4-hydroxy-N-((4-(4-methoxy-3-methylphenyl)bicyclo[2.2.2]octan-1-yl)methyl)-N-(3-(thiazol-2-ylethynyl)phenyl)cyclohexanecarboxamide (47.3 mg, 13%) as a white solid. $^1$H NMR (400 MHz, DMSO-d$_6$): δ 7.98 (d, 2H), 7.73 (s, 1H), 7.62 (s, 1H), 7.58-7.50 (m, 2H), 7.05-6.97 (m, 2H), 6.76 (d, 1H), 4.45-4.41 (m, 1H), 3.70 (s, 3H), 3.65-3.45 (m, 2H), 3.30-3.21 (m, 1H), 2.15-2.05 (m, 4H), 1.75 (d, 2H), 1.70-1.55 (m, 8H), 1.45-1.32 (m, 8H), 0.90-0.70 (m, 2H); LCMS: 569.3 [M+H]$^+$.

Intermediate 29

Trans-N-(3-(1-Cyclopropyl-1H-pyrazol-4-yl)phenyl)-N-((trans-4-(3-fluoro-1-methyl-1H-indazol-5-yl)cyclohexyl)methyl)-4-hydroxycyclohexanecarboxamide

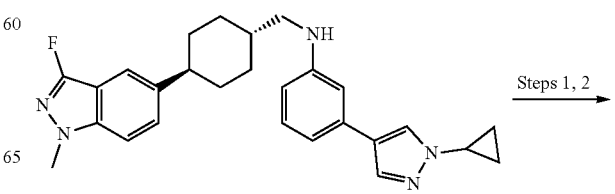

Steps 1, 2 →

531

-continued

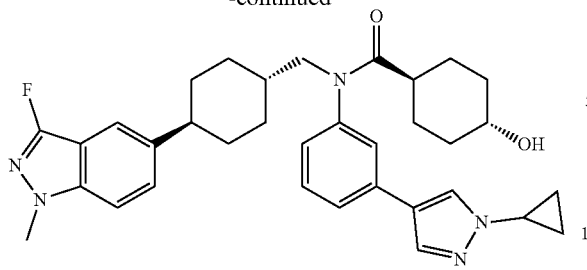

Step 1: Trans-4-((tert-Butyldimethylsilyl)oxy)-N-(3-(1-cyclopropyl-1H-pyrazol-4-yl)phenyl)-N-((trans-4-(3-fluoro-1-methyl-1H-indazol-5-yl)cyclohexyl)methyl)cyclohexanecarboxamide Intermediate 19 (75 mg/mL toluene solution, 1.7 mL, 0.461 mmol) was added to a solution of Intermediate 14.25 (130 mg, 0.293 mmol), pyridine (95 µL, 1.17 mmol), and toluene (2.5 mL) in an rt $H_2O$ bath. The mixture was stirred at rt for 2 h, diluted with EtOAc (20 mL), washed (20 mL saturated $NaHCO_3$ and then 20 mL brine), dried ($Na_2SO_4$), filtered, and concentrated. The residue was purified by silica gel chromatography (0-40% EtOAc in hexanes) to give trans-4-((tert-butyldimethylsilyl)oxy)-N-(3-(1-cyclopropyl-1H-pyrazol-4-yl)phenyl)-N-((trans-4-(3-fluoro-1-methyl-1H-indazol-5-yl)cyclohexyl)methyl)cyclohexanecarboxamide (184 mg, 90%) as a white foam. $^1$H NMR (400 MHz, DMSO-$d_6$): δ 8.34 (s, 1H), 7.93 (s, 1H), 7.60 (d, 1H), 7.54 (s, 1H), 7.50 (dd, 1H), 7.48-7.41 (m, 2H), 7.36 (d, 1H), 7.10 (d, 1H), 3.86 (s, 3H), 3.77-3.70 (m, 1H), 3.68-3.42 (m, 3H), 2.61-2.52 (m, 1H), 2.13-2.02 (m, 1H), 1.84-1.75 (m, 4H), 1.75-1.68 (m, 2H), 1.68-1.59 (m, 2H), 1.54-1.33 (m, 5H), 1.14-1.03 (m, 4H), 1.02-0.92 (m, 2H), 0.90-0.72 (m, 11H), −0.03 (s, 6H); LCMS: 684.2 [M+H]$^+$.

Step 2: Trans-N-(3-(1-Cyclopropyl-1H-pyrazol-4-yl)phenyl)-N-((trans-4-(3-fluoro-1-methyl-1H-indazol-5-yl)cyclohexyl)methyl)-4-hydroxycyclohexanecarboxamide Aqueous hydrochloric acid (1 N, 0.5 mL, 0.5 mmol) was added to a solution of trans-4-((tert-butyldimethylsilyl)oxy)-N-(3-(1-cyclopropyl-1H-pyrazol-4-yl)phenyl)-N-((trans-4-(3-fluoro-1-methyl-1H-indazol-5-yl)cyclohexyl)methyl)cyclohexanecarboxamide (180 mg, 0.263 mmol), THF (1 mL), and $CH_3OH$ (1 mL) at 0° C. The ice bath was removed after 10 min, and the reaction was stirred for 50 min. The mixture was diluted with EtOAc (20 mL), washed (2×20 mL saturated $NaHCO_3$ and then 20 mL brine), dried ($Na_2SO_4$), filtered, and concentrated. The residue was purified by silica gel chromatography (0-5% $CH_3OH$ in $CH_2Cl_2$) to give trans-N-(3-(1-cyclopropyl-1H-pyrazol-4-yl)phenyl)-N-((trans-4-(3-fluoro-1-methyl-NH-indazol-5-yl)cyclohexyl)methyl)-4-hydroxycyclohexanecarboxamide (150 mg, 100% , 95% pure) as a white foam. $^1$H NMR (400 MHz, DMSO-$d_6$): δ 8.34 (s, 1H), 7.94 (s, 1H), 7.60 (d, 1H), 7.54 (s, 1H), 7.50 (dd, 1H), 7.48-7.41 (m, 2H), 7.36 (dd, 1H), 7.10 (d, 1H), 4.38 (d, 1H), 3.86 (s, 3H), 3.77-3.70 (m, 1H), 3.68-3.43 (i, 2H), 3.31-3.20 (i, 1H), 2.61-2.52 (m, 1H), 2.16-2.00 (m, 1H), 1.84-1.68 (m, 6H), 1.68-1.59 (m, 2H), 1.52-1.33 (m, 5H), 1.15-1.04 (m, 4H), 1.02-0.96 (m, 2H), 0.81-0.67 (in, 2H); LCMS: 570.4 [M+H]$^+$.

The Intermediates below were synthesized from the appropriate secondary amine Intermediate and Intermediate 19 following the procedures described for Intermediate 29.

| Int | Structure | Name | [M + H]$^+$ |
|---|---|---|---|
| 29.01 | 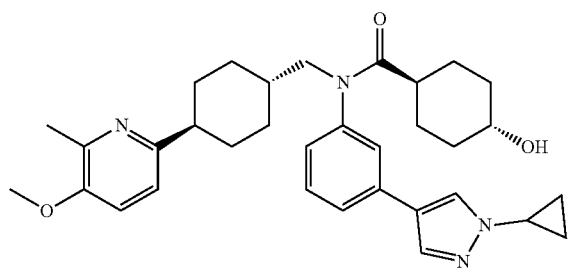 | trans-N-(3-(1-Cyclopropyl-1H-pyrazol-4-yl)phenyl)-N-((trans-N-(6-(dimethylamino)pyridin-3-yl)cyclohexyl)methyl)-4-hydroxycyclohexanecarboxamide | 542.4 |
| 29.02 | 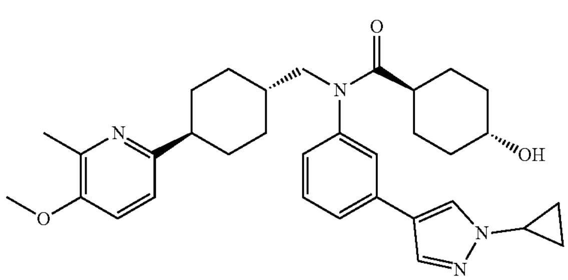 | trans-N-(3-(1-cyclopropyl-1H-pyrazol-4-yl)phenyl)-4-hydroxy-N-((trans-4-(5-methoxy-6-methylpyridin-2-yl)cyclohexyl)methyl)cyclohexanecarboxamide | 543.5 |

| Int | Structure | Name | [M + H]+ |
|---|---|---|---|
| 29.03[1] | 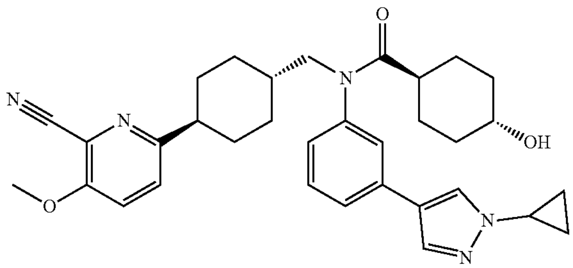 [SMILES: COc1ccc([C@H]2CC[C@H](CN(c3cccc(-c4cnn(C5CC5)c4)c3)C(=O)[C@H]3CC[C@H](O)CC3)CC2)cc1C#N] | trans-N-((trans-4-(6-Cyano-5-methoxypyridin-2-yl)cyclohexyl)methy)-N-(3-(1-cyclopropyl-1H-pyrazol-4-yl)phenyl)-4-hydroxycyclohexanecarboxamide | 554.5 |
| 29.04[1] | 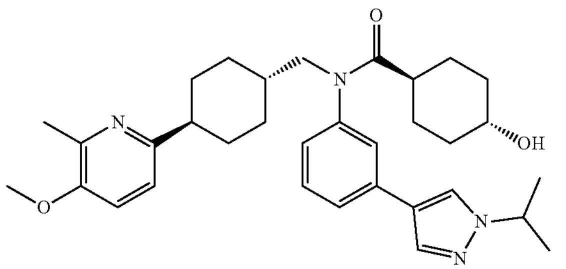 [SMILES: COc1ccc([C@H]2CC[C@H](CN(c3cccc(-c4cnn(C(C)C)c4)c3)C(=O)[C@H]3CC[C@H](O)CC3)CC2)nc1C] | trans-4-Hydroxy-N-(3-(1-isopropyl-1H-pyrazol-4-yl)phenyl)-N-((trans-4-(5-methoxy-6-methylpyridin-2-yl)cyclohexyl)methyl)cyclohexanecarboxamide | 545.5 |
| 29.05[1] | 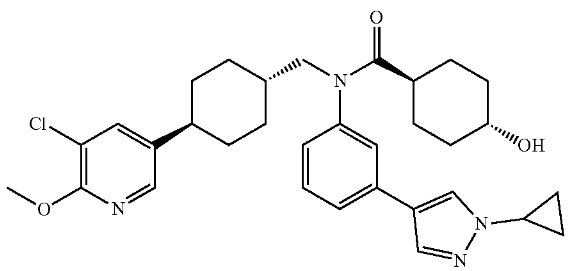 [SMILES: COc1ncc([C@H]2CC[C@H](CN(c3cccc(-c4cnn(C5CC5)c4)c3)C(=O)[C@H]3CC[C@H](O)CC3)CC2)cc1Cl] | trans-N-((trans-4-(5-chloro-6-methoxypyridin-3-yl)cyclohexyl)methy)-N-(3-(1-cyclopropyl-1H-pyrazol-4-yl)phenyl)-4-hydroxycyclohexanecarboxamide | 563.5 |
| 29.06[1] | 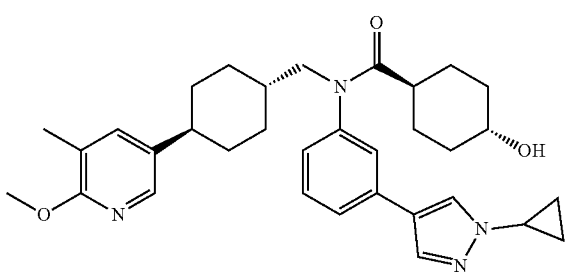 [SMILES: COc1ncc([C@H]2CC[C@H](CN(c3cccc(-c4cnn(C5CC5)c4)c3)C(=O)[C@H]3CC[C@H](O)CC3)CC2)cc1C] | trans-N-(3-(1-Cyclopropyl-1H-pyrazol-4-yl)phenyl)-4-hydroxy-N-((trans-4-(6-methoxy-5-methylpyridin-3-yl)cyclohexyl)methyl)cyclohexane-carboxamide | 543.4 |
| 29.07[1] | 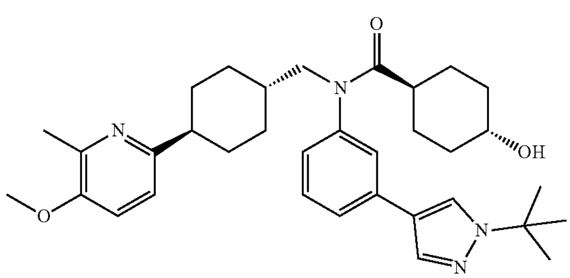 [SMILES: COc1ccc([C@H]2CC[C@H](CN(c3cccc(-c4cnn(C(C)(C)C)c4)c3)C(=O)[C@H]3CC[C@H](O)CC3)CC2)nc1C] | trans-N-(3-(1-(tert-Butyl)-1H-pyrazol-4-yl)phenyl)-4-hydroxy-N-((trans-4-(5-methoxy-6-methylpyridin-2-yl)cyclohexyl)methyl)cyclohexane-carboxamide | 559.5 |

| Int | Structure | Name | [M + H]⁺ |
|---|---|---|---|
| 29.08[1] | 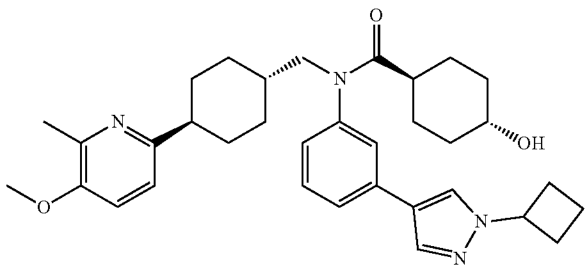 [SMILES: COc1ccc([C@H]2CC[C@H](CN(c3cccc(-c4cnn(C5CCC5)c4)c3)C(=O)[C@H]3CC[C@H](O)CC3)CC2)nc1C] | trans-N-(3-(1-Cyclobutyl-1H-pyrazol-4-yl)phenyl)-4-hydroxy-N-((trans-4-(5-methoxy-6-methylpyridin-2-yl)cyclohexyl)methyl)cyclohexanecarboxamide | 557.5 |
| 29.09[1,2] | 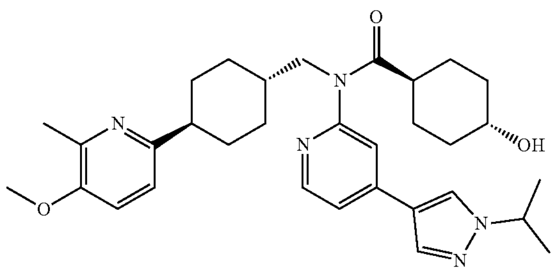 [SMILES: COc1ccc([C@H]2CC[C@H](CN(c3cc(-c4cnn(C(C)C)c4)ccn3)C(=O)[C@H]3CC[C@H](O)CC3)CC2)nc1C] | trans-4-Hydroxy-N-(4-(1-isopropyl-1H-pyrazol-4-yl)pyridin-2-yl)-N-((trans-A-(5-methoxy-6-methylpyridin-2-yl)cyclohexyl)methyl)cyclohexanecarboxamide | 546.5 |
| 29.10[1] | 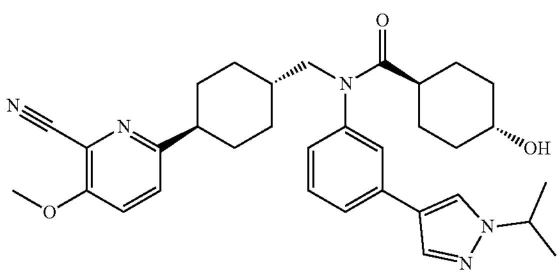 [SMILES: COc1ccc([C@H]2CC[C@H](CN(c3cccc(-c4cnn(C(C)C)c4)c3)C(=O)[C@H]3CC[C@H](O)CC3)CC2)nc1C#N] | trans-N-((trans-4-(6-Cyano-5-methoxypyridin-2-yl)cyclohexyl)methyl)-4-hydroxy-N-(3-(1-isopropyl-1H-pyrazol-4-yl)phenyl)cyclohexanecarboxamide | 556.5 |
| 29.11 | 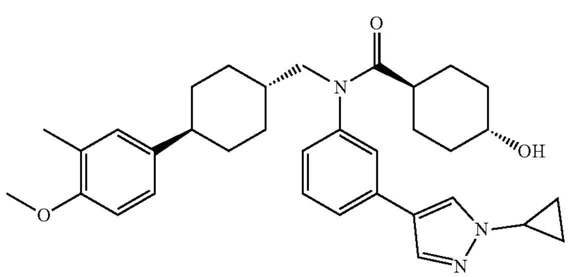 [SMILES: COc1ccc([C@H]2CC[C@H](CN(c3cccc(-c4cnn(C5CC5)c4)c3)C(=O)[C@H]3CC[C@H](O)CC3)CC2)cc1C] | trans-N-(3-(1-Cyclopropyl-1H-pyrazol-4-yl)phenyl)-4-hydroxy-N-((trans-4-(4-methoxy-3-methylphenyl)cyclohexyl)methyl)-cyclohexanecarboxamide | 542.5 |
| 29.12 | 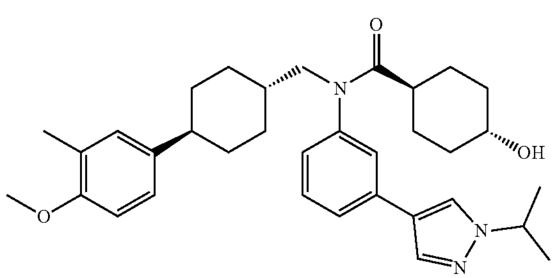 | trans-4-Hydroxy-N-(3-(1-isopropyl-1H-pyrazol-4-yl)phenyl)-N-((trans-4-(4-methoxy-3-methylphenyl)cyclohexyl)methyl)-cyclohexanecarboxamide | 544.4 |

-continued

| Int | Structure | Name | [M + H]+ |
|---|---|---|---|
| 29.13[1] | 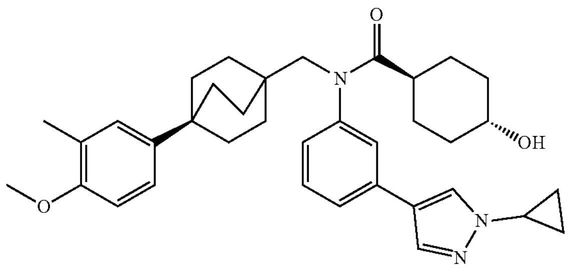 | trans-N-(3-(1-cyclopropyl-1H-pyrazol-4-yl)phenyl)-4-hydroxy-N-((4-(4-methoxy-3-methylphenyl)bicyclo[2.2.2]octan-1-yl)methyl)cyclohexanecarboxamide | 568.4 |
| 29.14 | 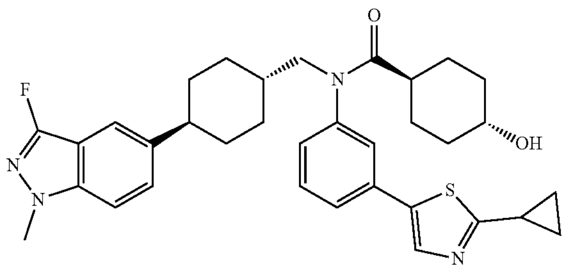 [SMILES: Cn1nc(F)c2cc([C@H]3CC[C@H](CN(c4cccc(-c5cnc(C6CC6)s5)c4)C(=O)[C@H]4CC[C@H](O)CC4)CC3)ccc21] | trans-N-(3-(2-cyclopropylthiazol-5-yl)phenyl)-N-((trans-4-(3-fluoro-1-methyl-1H-indazol-5-yl)cyclohexyl)methyl)-4-hydroxycyclohexanecarboxamide | 587.9 |
| 29.15 | 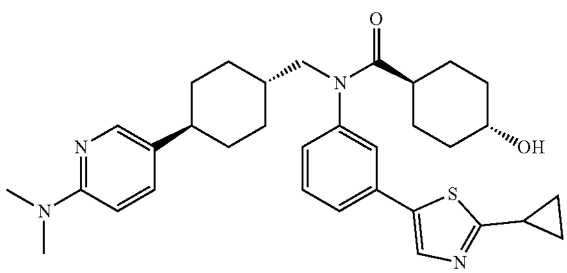 [SMILES: CN(C)c1ccc([C@H]2CC[C@H](CN(c3cccc(-c4cnc(C5CC5)s4)c3)C(=O)[C@H]3CC[C@H](O)CC3)CC2)cn1] | trans-N-(3-(2-Cyclopropylthiazol-5-yl)phenyl)-N-((trans-4-(6-(dimethylamino)pyridin-3-yl)cyclohexyl)methyl)-4-hydroxycyclohexanecarboxamide | 559.4 |
| 29.16[1] | 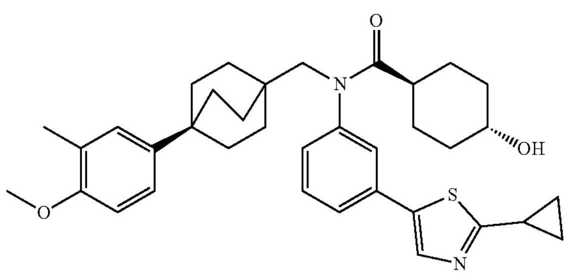 | trans-N-(3-(2-Cyclopropylthiazol-5-yl)phenyl)-4-hydroxy-N-((4-(4-methoxy-3-methylphenyl)bicyclo[2.2.2]octan-1-yl)methyl)cyclohexanecarboxamide | 585.4 |
| 29.17[1,2] | 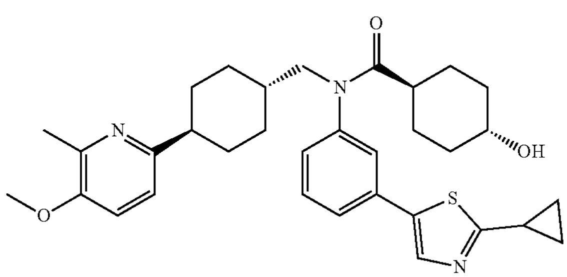 [SMILES: COc1ccc([C@H]2CC[C@H](CN(c3cccc(-c4cnc(C5CC5)s4)c3)C(=O)[C@H]3CC[C@H](O)CC3)CC2)nc1C] | trans-N-(3-(2-Cyclopropylthiazol-5-yl)phenyl)-4-hydroxy-N-((trans-4-(5-methoxy-6-methylpyridin-2-yl)cyclohexyl)methyl)cyclohexane-carboxamide | 560.3 |

| Int | Structure | Name | [M + H]+ |
|---|---|---|---|
| 29.18[1,2] | 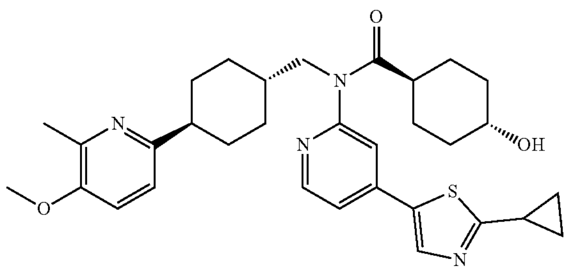 | trans-N-(4-(2-Cyclopropylthiazol-5-yl)pyridin-2-yl)-4-hydroxy-N-((trans-4-(5-methoxy-6-methylpyridin-2-yl)cyclohexyl)methyl)cyclohexanecarboxamide | 561.4 |
| 29.19[1] | 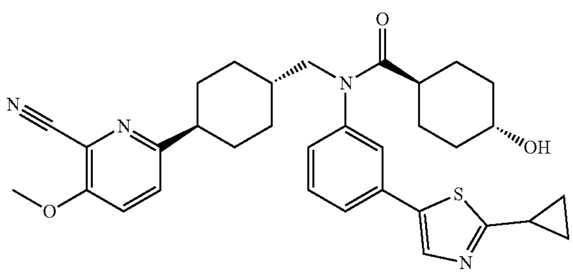 [SMILES: COc1ccc([C@H]2CC[C@H](CN(c3cccc(-c4cnc(C5CC5)s4)c3)C(=O)[C@H]3CC[C@H](O)CC3)CC2)nc1C#N] | trans-N-((trans-4-(6-Cyano-5-methoxypyridin-2-yl)cyclohexyl)methyl)-N-(3-(2-cyclopropylthiazol-5-yl)phenyl)-4-hydroxycyclohexanecarboxamide | 571.3 |
| 29.20[1] | 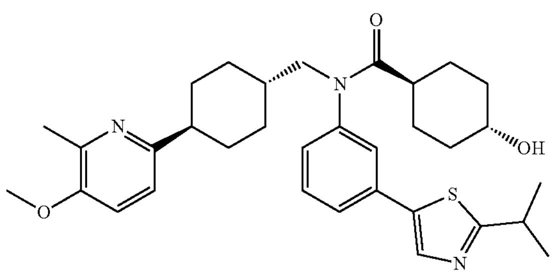 | trans-4-Hydroxy-N-(3-(2-isopropylthiazol-5-yl)phenyl)-N-((trans-4-(5-methoxy-6-methylpyridin-2-yl)cyclohexyl)methyl)cyclohexanecarboxamide | 562.4 |
| 29.21[1,3] | 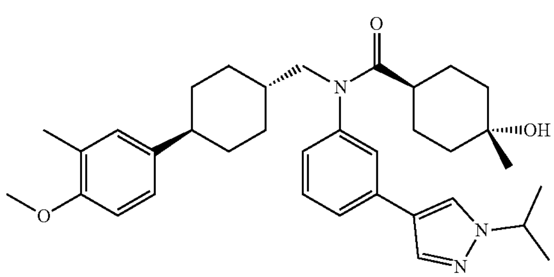 [SMILES: COc1ccc([C@H]2CC[C@H](CN(c3cccc(-c4cnn(C(C)C)c4)c3)C(=O)[C@H]3CC[C@](C)(O)CC3)CC2)cc1C] | (1r,4r)-4-Hydroxy-N-(3-(1-isopropyl-1H-pyrazol-4-yl)phenyl)-N-((trans-4-(4-methoxy-3-methylphenyl)cyclohexyl)methyl)-4-methylcyclohexanecarboxamide | 558.3 |
| 29.22[4] | 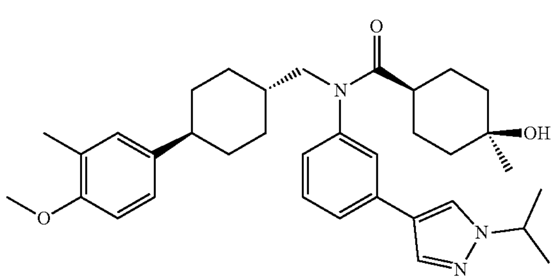 [SMILES: COc1ccc([C@H]2CC[C@H](CN(c3cccc(-c4cnn(C(C)C)c4)c3)C(=O)[C@H]3CC[C@@](C)(O)CC3)CC2)cc1C] | (1s,4s)-4-Hydroxy-N-(3-(1-isopropyl-1H-pyrazol-4-yl)phenyl)-N-((trans-4-(4-methoxy-3-methylphenyl)cyclohexyl)methyl)-4-methylcyclohexanecarboxamide | 558.3 |

Alternate conditions: Step 1:

[1]Solvent was CH$_2$Cl$_2$;

[2]Base was Et$_3$N; Step 2:

[3]3M HCl, THF, MeOH, 45° C., overnight.

[4]Isolated during the purification of Intermediate 29.21.

Intermediate 30 (M1125, 050-102/106)

Trans-N-(4-(1-Cyclopropyl-1H-pyrazol-4-yl)pyridin-2-yl)-4-hydroxy-N-((trans-4-(5-methoxy-6-methylpyridin-2-yl)cyclohexyl)methyl)cyclohexanecarboxamide

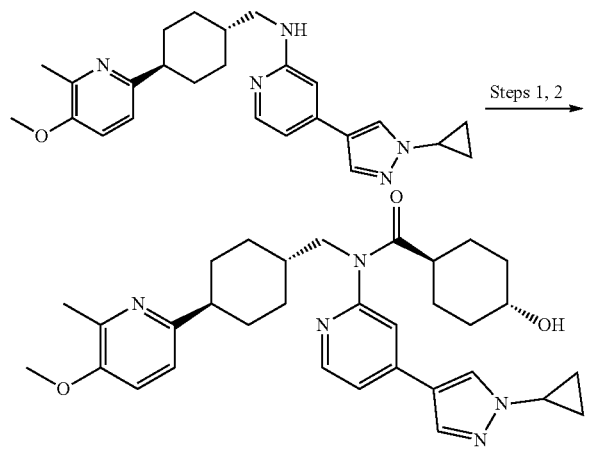

Steps 1, 2

Step 1: Trans-4-((tert-Butyldimethylsilyl)oxy)-N-(4-(1-cyclopropyl-1H-pyrazol-4-yl)pyridin-2-yl)-N-((trans-4-(5-methoxy-6-methylpyridin-2-yl)cyclohexyl)methyl)cyclohexanecarboxamide Intermediate 19 (1.6 mL, 0.42 mmol, 73 mg/mL in toluene) was added to a mixture of Intermediate 14.29 (87 mg, 0.21 mmol), DMAP (26 mg, 0.21 mmol) and pyridine (1.5 mL) at rt. The reaction was heated at 80° C. for 75 min, allowed to cool to rt and then diluted with EtOAc (20 mL). The organic layer was washed with saturated NaHCO$_3$ (20 mL), washed with water (20 mL), washed with brine (20 mL), dried (Na$_2$SO$_4$), filtered, concentrated, and then purified by silica gel chromatography (30-60% EtOAc in hexanes) to give trans-4-((tert-butyldimethylsilyl)oxy)-N-(4-(1-cyclopropyl-1H-pyrazol-4-yl)pyridin-2-yl)-N-((trans-4-(5-methoxy-6-methylpyridin-2-yl)cyclohexyl)methyl)cyclohexanecarboxamide (114 mg, 82% yield) as an off-white foam. $^1$H NMR (400 MHz, DMSO-d$_6$): δ 8.57 (s, 1H), 8.43 (d, 1H), 8.13 (s, 1H), 7.64 (s, 1H), 7.57 (d, 1H), 7.18 (d, 1H), 6.97 (d, 1H), 3.81-3.72 (m, 4H), 3.67 (d, 2H), 3.57-3.47 (m, 1H), 2.51-2.42 (m, 1H), 2.28 (s, 3H), 2.25-2.11 (m, 1H), 1.84-1.69 (m, 8H), 1.50-1.26 (m, 5H), 1.12-0.84 (m, 8H), 0.80 (s, 9H), −0.02 (s, 6H); LCMS: 658.6 [M+H]$^+$.

Step 2: Trans-N-(4-(1-Cyclopropyl-1H-pyrazol-4-yl)pyridin-2-yl)-4-hydroxy-N-((trans-4-(5-methoxy-6-methylpyridin-2-yl)cyclohexyl)methyl)cyclohexanecarboxamide A solution of trans-4-((tert-butyldimethylsilyl)oxy)-N-(4-(1-cyclopropyl-1H-pyrazol-4-yl)pyridin-2-yl)-N-((trans-4-(5-methoxy-6-methylpyridin-2-yl)cyclohexyl)methyl)cyclohexanecarboxamide (107 mg, 0.16 mmol) in THF (1 mL) and CH$_3$OH (1 mL) was cooled in an ice/water bath. Aqueous hydrochloric acid (1 N, 0.22 mL, 0.22 mmol) was added at 0° C. The reaction was allowed to warm to rt, stirred for 20 min and then diluted with chilled saturated NaHCO$_3$ (20 mL) and EtOAc (20 mL). The organic layer was washed with saturated NaHCO$_3$ (20 mL), washed with brine (20 mL), dried (Na$_2$SO$_4$), filtered, concentrated, and then purified by silica gel chromatography (0-7% methanol in dichloromethane) to give trans-N-(4-(1-cyclopropyl-1H-pyrazol-4-yl)pyridin-2-yl)-4-hydroxy-N-((trans-4-(5-methoxy-6-methylpyridin-2-yl)cyclohexyl)methyl)cyclohexanecarboxamide (79 mg, 89% yield) as a white foam. $^1$H NMR (400 MHz, DMSO-d$_6$): δ 8.57 (s, 1H), 8.44 (d, 1H), 8.13 (s, 1H), 7.64 (s, 1H), 7.57 (dd, 1H), 7.19 (d, 1H), 6.98 (d, 1H), 4.41 (d, 1H), 3.81-3.72 (m, 4H), 3.67 (d, 2H), 3.31-3.22 (in 1H), 2.51-2.42 (m, 1H), 2.28 (s, 3H), 2.19-2.09 (m, 1H), 1.83-1.67 (m, 8H), 1.48-1.26 (in 5H), 1.12-0.94 (m, 6H), 0.88-0.75 (in, 2H); LCMS: 544.5 [M+H]$^+$.

The Intermediates below were synthesized from the appropriate secondary amine Intermediate and Intermediate 19 following the procedures described for Intermediate 30.

| Int | Structure | Name | [M + H]$^+$ |
| --- | --- | --- | --- |
| 30.01 | 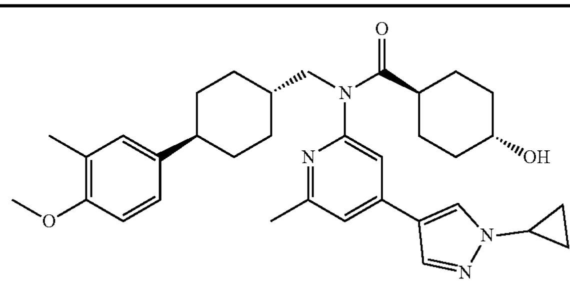 | trans-N-(4-(1-Cyclopropyl-1H-pyrazol-4-yl)-6-methylpyridin-2-yl)-4-hydroxy-N-((trans-4-(4-methoxy-3-methylphenyl)cyclohexyl)methyl)-cyclohexanecarboxamide | 557.7 |
| 30.02 | 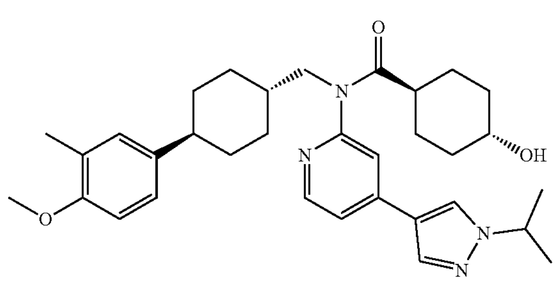 | trans-4-Hydroxy-N-(4-(1-isopropyl-1H-pyrazol-4-yl)pyridin-2-yl)-N-((trans-4-(4-methoxy-3-methylphenyl)cyclohexyl)methyl)-cyclohexanecarboxamide | 545.5 |

-continued

| Int | Structure | Name | [M + H]+ |
|---|---|---|---|
| 30.03[1] | 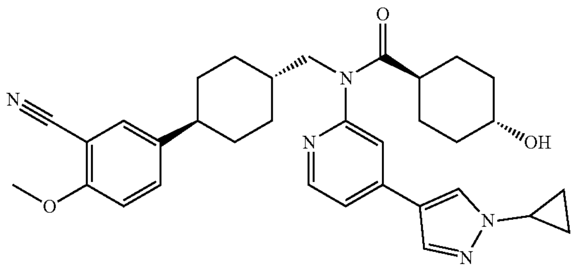 [SMILES: COc1ccc([C@H]2CC[C@H](CN(c3cc(-c4cnn(C5CC5)c4)ccn3)C(=O)[C@H]3CC[C@H](O)CC3)CC2)cc1C#N] | trans-N-((trans-4-(2-Cyano-4-methoxyphenyl)cyclohexyl)methyl)-N-(4-(1-cyclopropyl-1H-pyrazol-4-yl)pyridin-2-yl)-4-hydroxycyclohexanecarboxamide | 554.4 |
| 30.04[1] | 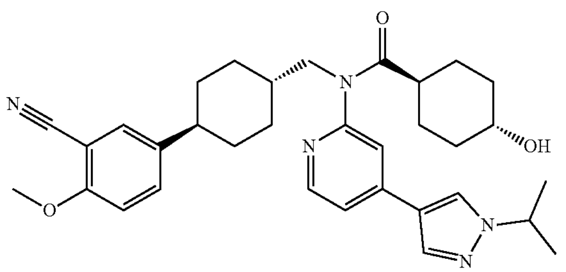 [SMILES: COc1ccc([C@H]2CC[C@H](CN(c3cc(-c4cnn(C(C)C)c4)ccn3)C(=O)[C@H]3CC[C@H](O)CC3)CC2)cc1C#N] | trans-N-((trans-4-(3-Cyano-4-methoxyphenyl)cyclohexyl)methyl)-4-hydroxy-N-(4-(1-isopropyl-1H-pyrazol-4-yl)pyridin-2-yl)cyclohexanecarboxamide | 556.4 |
| 30.05[1] | 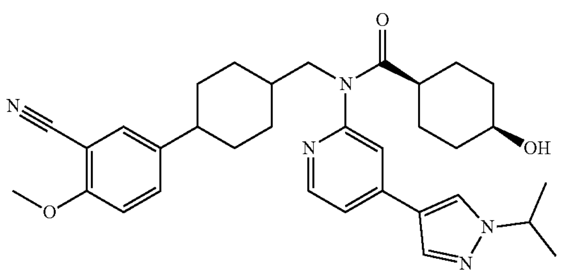 [SMILES: COc1ccc(C2CCC(CN(c3cc(-c4cnn(C(C)C)c4)ccn3)C(=O)[C@H]3CC[C@@H](O)CC3)CC2)cc1C#N] | trans-N-((4-(3-Cyano-4-methoxyphenyl)cyclohexyl)methyl)-4-hydroxy-N-(4-(1-isopropyl-1H-pyrazol-4-yl)pyridin-2-yl)cyclohexanecarboxamide | 556.4 |
| 30.06[1] | 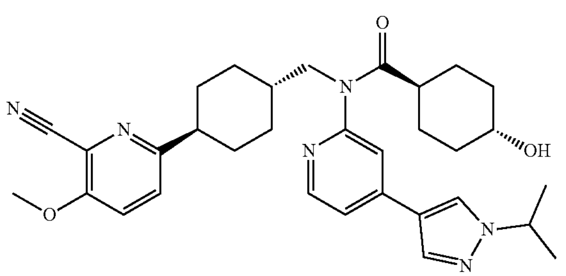 | trans-N-((trans-4-(6-Cyano-5-methoxypyridin-2-yl)cyclohexyl)methyl)-4-hydroxy-N-(4-(1-isopropyl-1H-pyrazol-4-yl)pyridin-2-yl)cyclohexanecarboxamide | 557.4 |
| 30.07[1,2] | 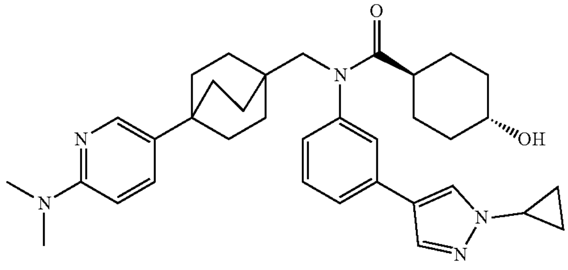 [SMILES: CN(C)c1ccc(C23CCC(CN(c4cccc(-c5cnn(C6CC6)c5)c4)C(=O)[C@H]4CC[C@H](O)CC4)(CC2)CC3)cn1] | trans-N-(3-(1-Cyclopropyl-1H-pyrazol-4-yl)phenyl)-N-((4-(6-(dimethylamino)pyridin-3-yl)bicyclo[2.2.2]octan-1-yl)methyl)-4-hydroxycyclohexanecarboxamide | 568.5 |

-continued

| Int | Structure | Name | [M + H]+ |
|---|---|---|---|
| 30.08[1] | 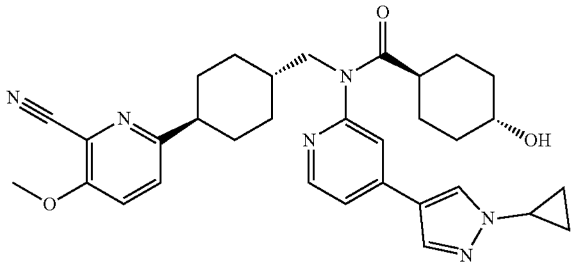 [SMILES: COc1ccc([C@H]2CC[C@H](CN(c3cc(-c4cnn(C5CC5)c4)ccn3)C(=O)[C@H]3CC[C@H](O)CC3)CC2)nc1C#N] | trans-N-((trans-4-(6-Cyano-5-methoxypyridin-2-yl)cyclohexyl)methyl)-N-(4-(1-cyclopropyl-1H-pyrazol-4-yl)pyridin-2-yl)-4-hydroxycyclohexanecarboxamide | 555.5 |
| 30.09 | 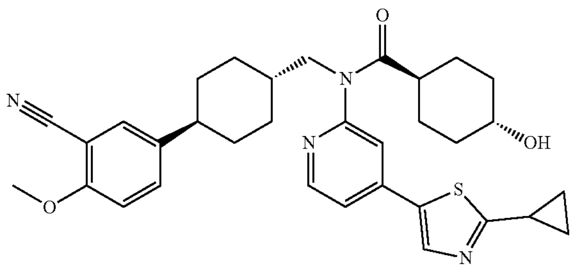 [SMILES: COc1ccc([C@H]2CC[C@H](CN(c3cc(-c4cnc(C5CC5)s4)ccn3)C(=O)[C@H]3CC[C@H](O)CC3)CC2)cc1C#N] | trans-N-((trans-4-(3-Cyano-4-methoxyphenyl)cyclohexyl)methyl)-N-(4-(2-cyclopropylthiazol-5-yl)pyridin-2-yl)-4-hydroxycyclohexanecarboxamide | 571.4 |
| 30.10[1] | 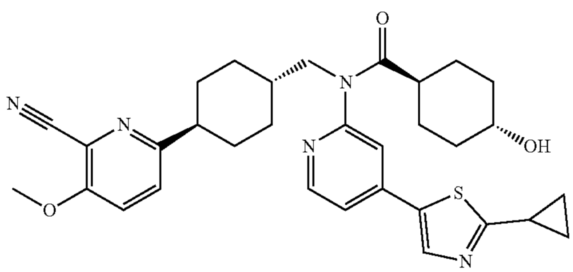 | trans-N-((trans-4-(6-Cyano-5-methoxypyridin-2-yl)cyclohexyl)methyl)-N-(4-(2-cyclopropylthiazol-5-yl)pyridin-2-yl)-4-hydroxycyclohexanecarboxamide | 572.4 |
| 30.11 | 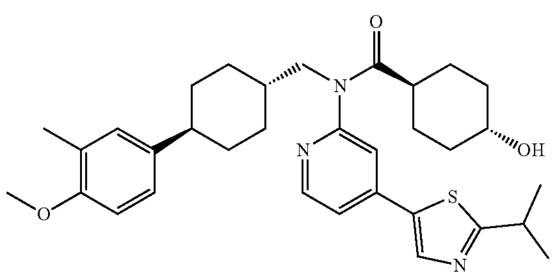 [SMILES: COc1ccc([C@H]2CC[C@H](CN(c3cc(-c4cnc(C(C)C)s4)ccn3)C(=O)[C@H]3CC[C@H](O)CC3)CC2)cc1C] | trans-4-Hydroxy-N-(4-(2-isopropylthiazol-5-yl)pyridin-2-yl)-N-((trans-4-(4-methoxy-3-methylphenyl)cyclohexyl)methyl)-cyclohexanecarboxamide | 562.5 |
| 30.12[1] | 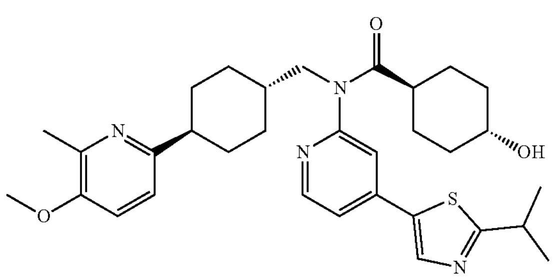 [SMILES: COc1ccc([C@H]2CC[C@H](CN(c3cc(-c4cnc(C(C)C)s4)ccn3)C(=O)[C@H]3CC[C@H](O)CC3)CC2)nc1C] | trans-4-Hydroxy-N-(4-(2-isopropylthiazol-5-yl)pyridin-2-yl)-N-((trans-4-(5-methoxy-6-methylpyridin-2-yl)cyclohexyl)methyl)cyclohexane-carboxamide | 563.4 |

| Int | Structure | Name | [M + H]⁺ |
|---|---|---|---|
| 30.13 | 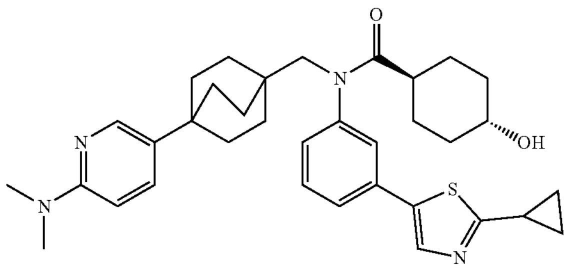 [SMILES: CN(C)c1ccc(C23CCC(CN(c4cccc(-c5cnc(C6CC6)s5)c4)C(=O)[C@H]4CC[C@H](O)CC4)(CC2)CC3)cn1] | trans-N-(3-(2-Cyclopropylthiazol-5-yl)phenyl)-N-((4-(6-(dimethylamino)pyridin-3-yl)bicyclo[2.2.2]octan-1-yl)methyl)-4-hydroxycyclohexanecarboxamide | 585.5 |
| 30.14[2] | 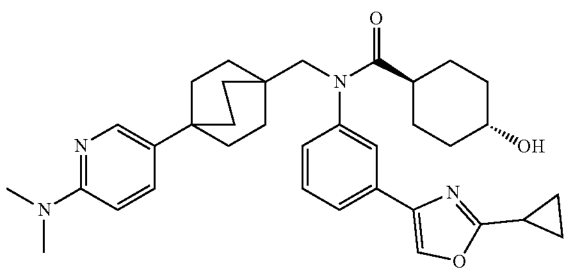 [SMILES: CN(C)c1ccc(C23CCC(CN(c4cccc(-c5coc(C6CC6)n5)c4)C(=O)[C@H]4CC[C@H](O)CC4)(CC2)CC3)cn1] | trans-N-(3-(2-Cyclopropyloxazol-4-yl)phenyl)-N-((4-(6-(dimethylamino)pyridine-3-yl)pyridin[2.2.2]octan-1-yl)methyl)-4-hydroxycyclohexanecarboxamide | 569.5 |
| 30.15[1] | 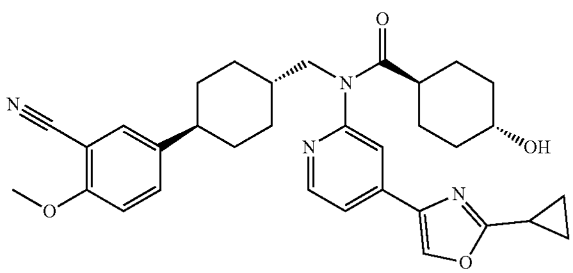 [SMILES: COc1ccc([C@H]2CC[C@H](CN(c3cc(-c4coc(C5CC5)n4)ccn3)C(=O)[C@H]3CC[C@H](O)CC3)CC2)cc1C#N] | trans-N-((trans-4-(3-Cyano-4-methoxyphenyl)cyclohexyl)methyl)-N-(4-(2-cyclopropyloxazol-4-yl)pyridine-2-yl)-4-hydroxycyclohexanecarboxamide | 555.5 |
| 30.16 | 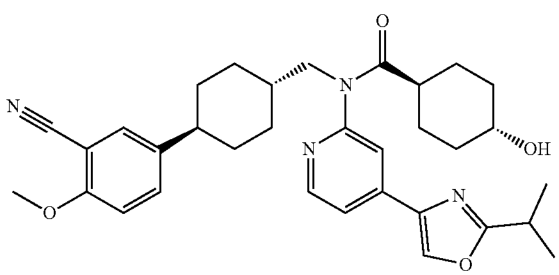 [SMILES: COc1ccc([C@H]2CC[C@H](CN(c3cc(-c4coc(C(C)C)n4)ccn3)C(=O)[C@H]3CC[C@H](O)CC3)CC2)cc1C#N] | trans-N-((trans-4-(3-Cyano-4-methoxyphenyl)cyclohexyl)methyl)-N-(4-(2-cyclopropyloxazol-4-yl)pyridine-2-yl)-4-hydroxycyclohexanecarboxamide | 557.4 |
| 30.17 | 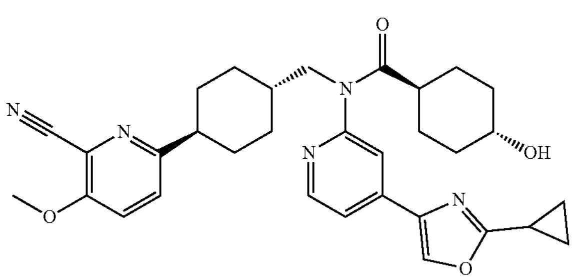 [SMILES: COc1ccc([C@H]2CC[C@H](CN(c3cc(-c4coc(C5CC5)n4)ccn3)C(=O)[C@H]3CC[C@H](O)CC3)CC2)nc1C#N] | trans-N-((trans-4-(6-Cyano-5-methoxypyridin-2-yl)cyclohexyl)methyl)-N-(4-(2-cyclopropyloxazol-4-yl)pyridine-2-yl)-4-hydroxycyclohexanecarboxamide | 556.4 |

| Int | Structure | Name | [M + H]+ |
|---|---|---|---|
| 30.18[3] | 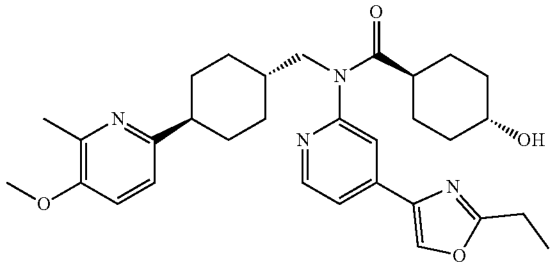 [SMILES: CCc1nc(-c2ccnc(N(C[C@H]3CC[C@H](c4ccc(OC)c(C)n4)CC3)C(=O)[C@H]3CC[C@H](O)CC3)c2)co1] | trans-N-(4-(2-Ethyloxazol-4-yl)pyridin-2-yl)-4-hydroxy-N-((trans-4-(5-methoxy-6-methylpyridin-2-yl)cyclohexyl)methyl)cyclohexane-carboxamide | 533.4 |

Alternate conditions: Step 1:
[1]Additional acid chloride needed, 2.5-3.5 eq total;
[2]Heated at 50° C.;
[3]DMAP, Et3N, toluene, 80° C., 20 min.

Intermediate 31

Trans-N-(3-(3-Cyclopropylisothiazol-5-yl)phenyl)-4-hydroxy-N-((trans-4-(4-methoxy-3-methylphenyl)cyclohexyl)methyl)cyclohexanecarboxamide

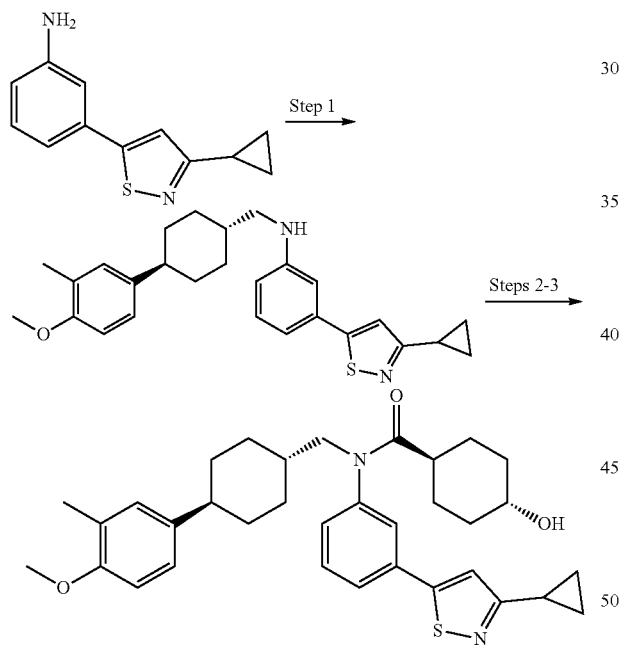

Step 1: 3-(3-Cyclopropylisothiazol-5-yl)-N-((trans-4-(4-methoxy-3-methylphenyl)cyclohexyl)methyl)aniline A mixture of Intermediate 9 (140 mg, 0.647 mmol), Intermediate 3 (165 mg, 0.712 mmol), AcOH (117 mg, 1.94 mmol), and CH₃OH (10 mL) was degassed with vacuum/N₂ cycles (3×) and stirred at rt for 2 h. NaBH₃CN (81 mg, 1.29 mmol) was added to the mixture, and the reaction was stirred at rt overnight. The solution was concentrated and purified by silica gel chromatography (petroleum ether/EtOAc=5/1) to give 3-(3-cyclopropylisothiazol-5-yl)-N-((trans-4-(4-methoxy-3-methylphenyl)cyclohexyl)methyl)aniline (200 mg, 71%) as a yellow solid. H NMR (400 MHz, CDCl₃): δ 7.22 (t, 1H), 7.07 (s, 1H), 7.00-7.05 (m, 2H), 6.86-6.93 (m, 1H), 6.77 (d, 2H), 6.65-6.67 (m, 1H), 3.86-3.93 (m, 1H), 3.82 (s, 3H), 3.06 (d, 2H), 2.35-2.52 (m, 1H), 2.22 (s, 3H), 2.13-2.20 (m, 1H), 1.89-2.03 (m, 4H), 1.61-1.75 (m, 1H), 1.43-1.53 (m, 2H), 1.17-1.25 (m, 2H), 0.98-1.08 (m, 4H); LCMS: 433.2 [M+H]+.

Step 2: Trans-4-((tert-Butyldimethylsilyl)oxy)-N-(3-(3-cyclopropylisothiazol-5-yl)phenyl)-N-((trans-4-(4-methoxy-3-methylphenyl)cyclohexyl)methyl)cyclohexanecarboxamide Pyridine (110 mg, 1.39 mmol) was added to a solution of 3-(3-cyclopropylisothiazol-5-yl)-N-((trans-4-(4-methoxy-3-methylphenyl)cyclohexyl)methyl)aniline (200 mg, 0.462 mmol) and CH₂C₂(10.0 mL) at rt. The solution was stirred at rt for 30 min, and Intermediate 19 (384 mg, 1.39 mmol) was added. The mixture was stirred overnight, concentrated, and purified by silica gel chromatography (petroleum ether/EtOAc=5/1) to give trans-4-((tert-butyldimethylsilyl)oxy)-N-(3-(3-cyclopropylisothiazol-5-yl)phenyl)-N-((trans-4-(4-methoxy-3-methylphenyl)cyclohexyl)methyl)cyclohexanecarboxamide (250 mg, 80%) as a colorless oil. LCMS: 673.5 [M+H]+.

Step 3: Trans-N-(3-(3-Cyclopropylisothiazol-5-yl)phenyl)-4-hydroxy-N-((trans-4-(4-methoxy-3-methylphenyl)cyclohexyl)methyl)cyclohexanecarboxamide Aqueous hydrochloric acid (2 M, 450 uL, 0.9 mmol) was slowly added to a solution of trans-4-((tert-butyldimethylsilyl)oxy)-N-(3-(3-cyclopropylisothiazol-5-yl)phenyl)-N-((trans-4-(4-methoxy-3-methylphenyl)cyclohexyl)methyl)cyclohexanecarboxamide (250 mg, 0.371 mmol) and CH₃OH (10 mL). The solution was stirred at rt for 1 h, concentrated, and then purified by RP-HPLC (H₂O(10 mM NH₄HCO₃)/CH₃CN) to give trans-N-(3-(3-cyclopropylisothiazol-5-yl)phenyl)-4-hydroxy-N-((trans-4-(4-methoxy-3-methylphenyl)cyclohexyl)methyl)cyclohexanecarboxamide (112 mg, 54%) as a white solid. ¹H NMR (400 MHz, DMSO-d₆): δ 7.67-7.71 (m, 2H), 7.65 (s, 1H), 7.58 (t, 1H), 7.38 (d, 1H), 6.91-6.97 (m, 2H), 6.75-6.81 (m, 1H), 3.71 (s, 3H), 3.53-3.64 (m, 2H), 3.20-3.29 (m, 1H), 2.33 (t, 1H), 2.17-2.25 (m, 1H), 2.09 (s, 3H), 2.01-2.07 (m, 1H), 1.62-

1.81 (m, 8H), 1.23-1.48 (m, 5H), 0.92-1.11 (m, 6H), 0.69-0.84 (m, 2H); LCMS: 559.6 [M+H]+.

Intermediate 32

Trans-N-(3-(2-Cyclopropyloxazol-4-yl)phenyl)-4-hydroxy-N-((4-(4-methoxy-3-methylphenyl)pyridin[2.2.2]octan-1-yl)methyl)cyclohexanecarboxamide

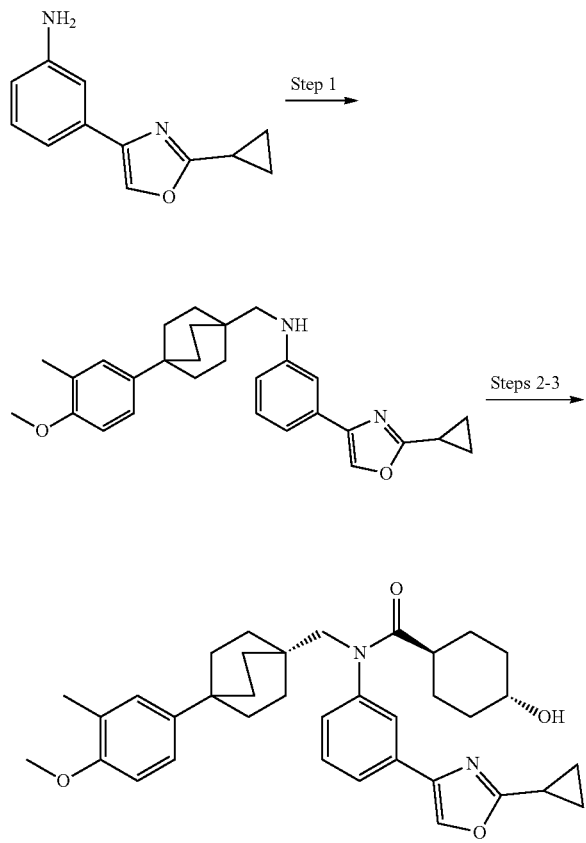

Step 1: 3-(2-Cyclopropyloxazol-4-yl)-N-((4-(4-methoxy-3-methylphenyl) pyridin[2.2.2]octan-1-yl) methyl)aniline Sodium triacetoxyborohydride (496 mg, 2.34 mmol) was added to a solution of Intermediate 5 (302 mg, 1.17 mmol), Intermediate 8.01 (236 mg, 1.18 mmol), and DCE (6 mL) at 0° C. The ice bath was removed, and the reaction was stirred at rt for 1 h. The mixture was diluted with EtOAc (50 mL), washed (2×50 mL saturated NaHCO3 and then 50 mL brine), dried (Na2SO4), filtered, and then concentrated. The residue was purified by silica gel chromatography (petroleum ether/EtOAc=20:1 to 5:1) to give 3-(2-cyclopropyloxazol-4-yl)-N-((4-(4-methoxy-3-methylphenyl)pyridin[2.2.2]octan-1-yl)methyl)aniline (471 mg, 90%) as a colorless oil. $^1$H NMR (400 MHz, CDCl$_3$): δ 7.71 (s, 1H), 7.14-7.21 (m, 1H), 7.08-7.14 (m, 2H), 7.02 (s, 1H), 6.96 (d, 1H), 6.77 (d, 1H), 6.52-6.59 (m, 1H), 3.81 (s, 3H), 3.72 (br s, 1H), 2.95-2.96 (m, 2H), 2.22 (s, 3H), 2.11-2.16 (m, 1H), 1.80-1.91 (m, 6H), 1.58-1.68 (m, 6H), 1.00-1.20 (m, 4H); LCMS: 443.3 [M+H]+.

Step 2: Trans-4-((tert-Butyldimethylsilyl)oxy)-N-(3-(2-cyclopropyloxazol-4-yl)phenyl)-N-((4-(4-methoxy-3-methylphenyl)pyridin[2.2.2]octan-1-yl) methyl)cyclohexanecarboxamide Intermediate 19 (20 mL, 2.79 mmol, 4.3 wt % toluene solution) was added to a solution of 3-(2-cyclopropyloxazol-4-yl)-N-((4-(4-methoxy-3-methylphenyl)pyridin[2.2.2]octan-1-yl)methyl)aniline (471 mg, 1.06 mmol), pyridine (337 mg, 4.26 mmol), and toluene (8 mL) at 0° C. The ice bath was removed, and the reaction was stirred at rt for 1 h. The mixture was diluted with H$_2$O (50 mL) and extracted with EtOAc (3×50 mL). The combined organic extracts were washed (100 mL brine), dried (Na$_2$SO$_4$), filtered, and then concentrated. The residue was purified by silica gel chromatography (petroleum ether/EtOAc=20/1 to 5/1) to give trans-4-((tert-butyldimethylsilyl)oxy)-N-(3-(2-cyclopropyloxazol-4-yl)phenyl)-N-((4-(4-methoxy-3-methylphenyl)pyridin[2.2.2]octan-1-yl)methyl)cyclohexanecarboxamide (533 mg, 74%) as a colorless oil. $^1$H NMR (400 MHz, DMSO-d$_6$): δ 8.50 (s, 1H), 7.63-7.69 (m, 2H), 7.45 (t, 1H), 7.28 (d, 1H), 6.95-7.02 (m, 2H), 6.74 (d, 1H), 3.68 (s, 3H), 3.42-3.61 (m, 3H), 2.10-2.18 (m, 2H) 2.06 (s, 3H), 1.67-1.85 (m, 4H), 1.55-1.63 (m, 7H), 1.29-1.46 (m, 9H), 0.93-1.10 (m, 4H), 0.76 (s, 9H), −0.05 (s, 6H); LCMS: 683.5 [M+H]+.

Step 3: Trans-N-(3-(2-Cyclopropyloxazol-4-yl)phenyl)-4-hydroxy-N-((4-(4-methoxy-3-methylphenyl) pyridin[2.2.2]octan-1-yl)methyl)cyclohexanecarboxamide Aqueous hydrochloric acid (1 N, 1.2 mL, 1.2 mmol) was slowly added to a solution of trans-4-((tert-butyldimethylsilyl)oxy)-N-(3-(2-cyclopropyloxazol-4-yl)phenyl)-N-((4-(4-methoxy-3-methylphenyl)pyridin[2.2.2]octan-1-yl)methyl)cyclohexanecarboxamide (533 mg, 0.780 mmol), THF (4 mL), and CH$_3$OH (4 mL) at 0° C. The ice bath was removed, and the reaction was stirred at rt for 1 h. The mixture was diluted with H$_2$O (50 mL) and extracted with EtOAc (3×50 mL). The combined organic extracts were washed (100 mL brine), dried (Na$_2$SO$_4$), filtered, and then concentrated. The residue was purified by silica gel chromatography (petroleum ether/EtOAc=10/1 to 2/1 and then CH$_2$Cl$_2$/CH$_3$OH=10/1) to give trans-N-(3-(2-cyclopropyloxazol-4-yl)phenyl)-4-hydroxy-N-((4-(4-methoxy-3-methylphenyl)pyridin[2.2.2]octan-1-yl)methyl)cyclohexanecarboxamide (364 mg, 820) as a white solid. $^1$H NMR (400 MHz, DMSO-d$_6$): δ 8.53 (s, 1H), 7.73-7.76 (m, 2H), 7.48 (t, 1H), 7.31 (d, 1H), 6.95-7.07 (m, 2H), 6.77 (d, 1H), 4.41 (d, 1H), 3.52-3.70 (m, 5H), 3.19-3.30 (m, 1H), 2.11-2.22 (m, 2H), 2.08 (s, 3H), 1.71-1.75 (m, 2H), 1.54-1.67 (m, 8H), 1.32-1.47 (m, 8H), 0.96-1.11 (m, 4H), 0.68-0.82 (in, 2H); LCMS: 569.3 [M+H]+.

The following Intermediates were synthesized from the appropriate amine and aldehyde Intermediates following the procedures described for Intermediate 32.

| Int | Structure | Name | [M + H]+ |
|---|---|---|---|
| 32.01[2] | 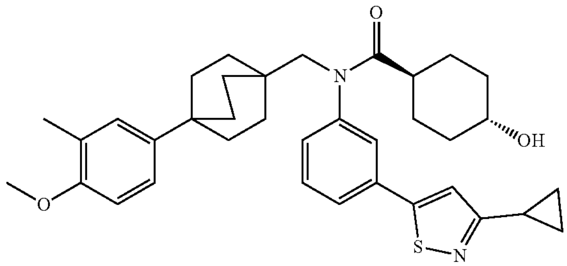 [SMILES: COc1ccc(C23CCC(CN(c4cccc(-c5cc(C6CC6)ns5)c4)C(=O)[C@H]4CC[C@H](O)CC4)(CC2)CC3)cc1C] | trans-N-(3-(3-Cyclopropylisothiazol-5-yl)phenyl)-4-hydroxy-N-((4-(4-methoxy-3-methylphenyl)pyridin[2.2.2]octan-1-yl)methyl)cyclohexanecarboxamide | 585.4 |
| 32.02[2] | 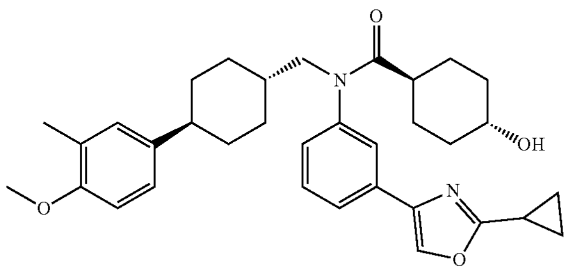 [SMILES: COc1ccc([C@H]2CC[C@H](CN(c3cccc(-c4coc(C5CC5)n4)c3)C(=O)[C@H]3CC[C@H](O)CC3)CC2)cc1C] | trans-N-(3-(2-Cyclopropyloxazol-4-yl)phenyl)-4-hydroxy-N-(trans-4-(4-methoxy-3-methylphenyl)cyclohexyl)methyl)-cyclohexanecarboxamide | 543.3 |
| 32.03[2] | 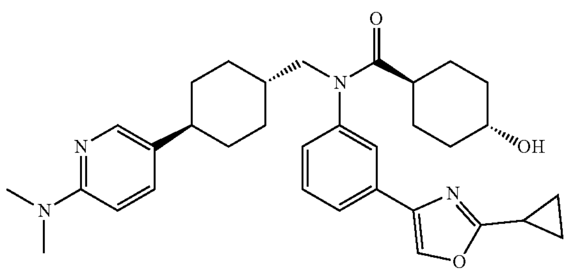 [SMILES: CN(C)c1ccc([C@H]2CC[C@H](CN(c3cccc(-c4coc(C5CC5)n4)c3)C(=O)[C@H]3CC[C@H](O)CC3)CC2)cn1] | trans-N-(3-(2-Cyclopropyloxazol-4-yl)phenyl)-N-((trans-4-(6-(dimethylamino)pyridine-3-yl)cyclohexyl)methyl)-4-hydroxycyclohexanecarboxamide | 543.5 |
| 32.04 | 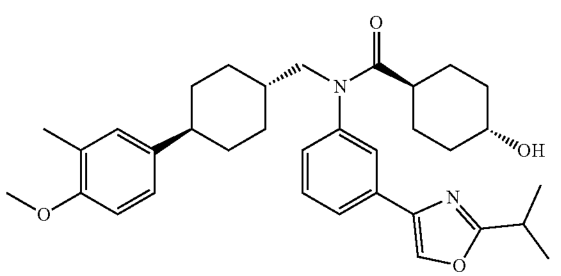 [SMILES: COc1ccc([C@H]2CC[C@H](CN(c3cccc(-c4coc(C(C)C)n4)c3)C(=O)[C@H]3CC[C@H](O)CC3)CC2)cc1C] | trans-4-Hydroxy-N-(3-(2-isopropyloxazol-4-yl)phenyl)-N-((trans-4-(4-methoxy-3-methylphenyl)cyclohexyl)methyl)-cyclohexanecarboxamide | 545.4 |
| 32.05[2] | 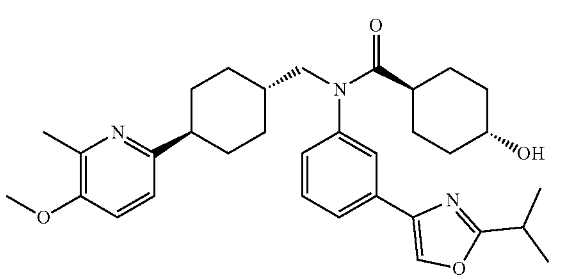 [SMILES: COc1ccc([C@H]2CC[C@H](CN(c3cccc(-c4coc(C(C)C)n4)c3)C(=O)[C@H]3CC[C@H](O)CC3)CC2)nc1C] | trans-4-Hydroxy-N-(3-(2-isopropyloxazol-4-yl)phenyl)-N-((trans-4-(5-methoxy-6-methylpyridin-2-yl)cyclohexyl)methyl)cyclohexane-carboxamide | 546.5 |

-continued

| Int | Structure | Name | [M + H]+ |
|---|---|---|---|
| 32.06[2] | 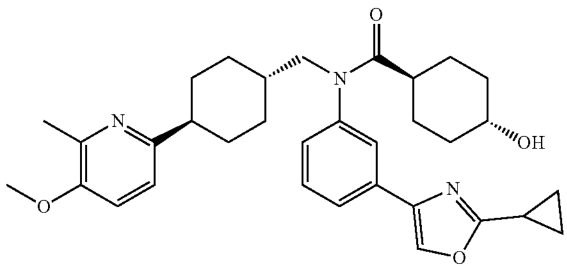 [SMILES: COc1ccc([C@H]2CC[C@H](CN(c3cccc(-c4coc(C5CC5)n4)c3)C(=O)[C@H]3CC[C@H](O)CC3)CC2)nc1C] | trans-N-(3-(2-Cyclopropyloxazol-4-yl)phenyl)-4-hydroxy-N-((trans-4-(5-methoxy-6-methylpyridin-2-yl)cyclohexyl)methyl)cyclohexanecarboxamide | 544.4 |
| 32.07 | 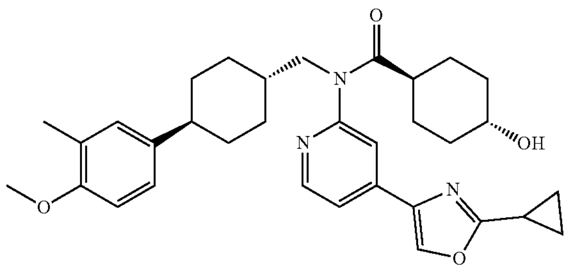 [SMILES: COc1ccc([C@H]2CC[C@H](CN(c3cc(-c4coc(C5CC5)n4)ccn3)C(=O)[C@H]3CC[C@H](O)CC3)CC2)cc1C] | trans-N-(4-(2-Cyclopropyloxazol-4-yl)pyridine-2-yl)-4-hydroxy-N-((trans-4-(4-methoxy-3-methylphenyl)cyclohexyl)methyl)-cyclohexanecarboxamide | 544.4 |
| 32.08[4] | 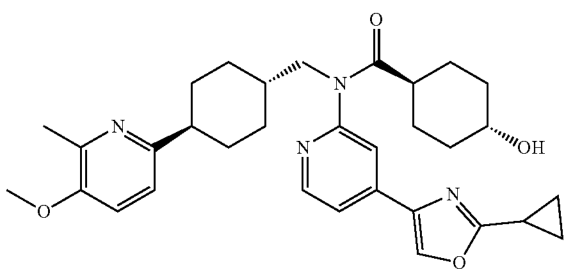 | trans-N-(4-(2-Cyclopropyloxazol-4-yl)pyridine-2-yl)-4-hydroxy-N-((trans-4-(5-methoxy-6-methylpyridin-2-yl)cyclohexyl)methyl)cyclohexanecarboxamide | 545.9 |
| 32.09[1,4,6] | 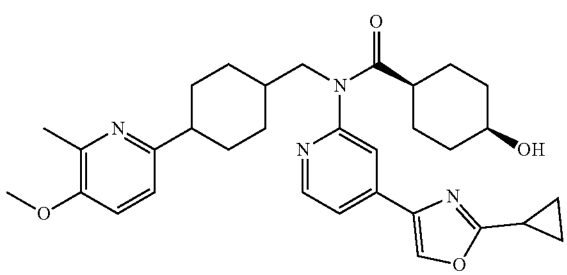 [SMILES: COc1ccc(C2CCC(CN(c3cc(-c4coc(C5CC5)n4)ccn3)C(=O)[C@H]3CC[C@@H](O)CC3)CC2)nc1C] | cis-N-(4-(2-Cyclopropyloxazol-4-yl)pyridin-2-yl)-4-hydroxy-N-((4-(5-methoxy-6-methylpyridin-2-yl)cyclohexyl)methyl)cyclohexanecarboxamide | 545.3 |
| 32.10[2] | 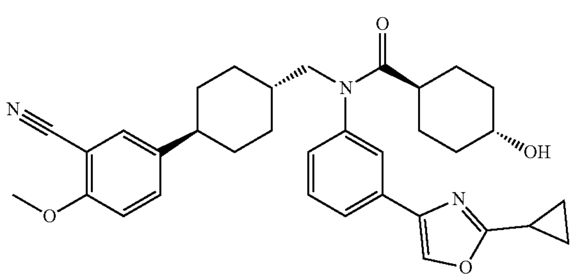 [SMILES: COc1ccc([C@H]2CC[C@H](CN(c3cccc(-c4coc(C5CC5)n4)c3)C(=O)[C@H]3CC[C@H](O)CC3)CC2)cc1C#N] | trans-N-((trans-4-(3-Cyano-4-methoxyphenyl)cyclohexyl)methyl)-N-(3-(2-cyclopropyloxazol-4-yl)phenyl)-4-hydroxycyclohexanecarboxamide | 554.5 |

-continued

| Int | Structure | Name | [M + H]+ |
|---|---|---|---|
| 32.11[2] | 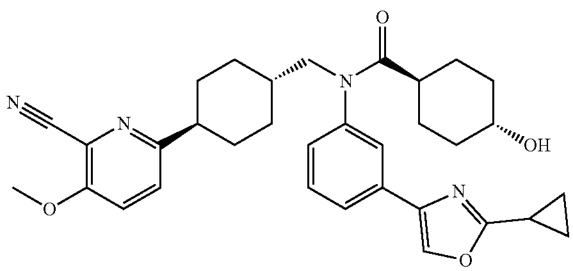 [SMILES: COc1ccc([C@H]2CC[C@H](CN(c3cccc(-c4coc(C5CC5)n4)c3)C(=O)[C@H]3CC[C@H](O)CC3)CC2)nc1C#N] | trans-N-((trans-4-(6-Cyano-5-methoxypyridin-2-yl)cyclohexyl)methyl)-N-(3-(2-cyclopropyloxazol-4-yl)phenyl)-4-hydroxycyclohexanecarboxamide | 555.5 |
| 32.12[5] | 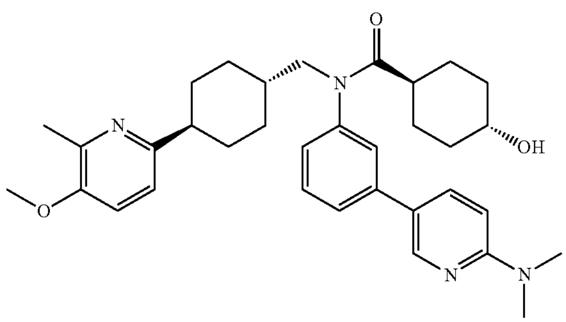 | trans-(3-(6-(Dimethylamino)pyridine-3-yl)phenyl)-4-hydroxy-N-((trans-4-(5-methoxy-6-methylpyridin-2-yl)cyclohexyl)methyl)cyclohexane-carboxamide | 557.5 |
| 32.13[2,3] | 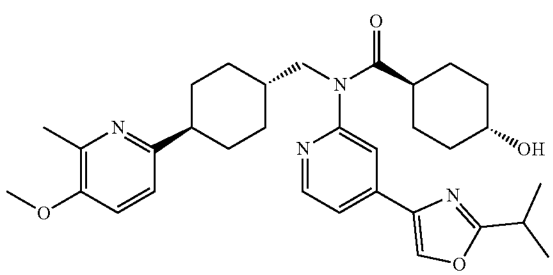 [SMILES: COc1ccc([C@H]2CC[C@H](CN(c3cc(-c4coc(C(C)C)n4)ccn3)C(=O)[C@H]3CC[C@H](O)CC3)CC2)nc1C] | trans-4-Hydroxy-N-(4-(2-isopropyloxazol-4-yl)pyridine-2-yl)-N-((trans-4-(5-methoxy-6-methylpyridin-2-yl)cyclohexyl)methyl)cyclohexane-carboxamide | 547.4 |
| 32.14[2] | 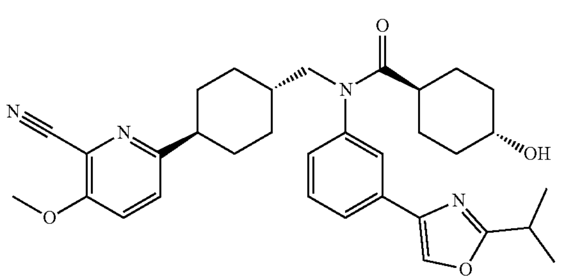 [SMILES: COc1ccc([C@H]2CC[C@H](CN(c3cccc(-c4coc(C(C)C)n4)c3)C(=O)[C@H]3CC[C@H](O)CC3)CC2)nc1C#N] | trans-N-((trans-4-(6-Cyano-5-methoxypyridin-2-yl)cyclohexyl)methyl)-4-hydroxy-N-(3-(2-isopropyloxazol-4-yl)phenyl)cyclohexanecarboxamide | 557.5 |

Alternate conditions: Step 1:

[1]Solvent was $CH_2Cl_2$; Step 2:

[2]Solvent was $CH_2Cl_2$;

[3]Base was $Et_3N$;

[4]DMAP, $Et_3N$, toluene, 80° C.;

[5]trans-4-((tert-butyldimethylsilyl)oxy)cyclohexane-carboxylic acid, 1-propylphosphonic acid, cyclic anhydride (50 wt. % in $CH_2Cl_2$), pyridine, rt, 200 min.

[6]Synthesized from an isomeric mixture of Intermediate 3.02.

Compound 1

Trans-4-((3-(2-Cyclopropylthiazol-5-yl)phenyl)((trans-4-(6-(dimethylamino)pyridin-3-yl)cyclohexyl)methyl)carbamoyl)cyclohexyl methylcarbamate

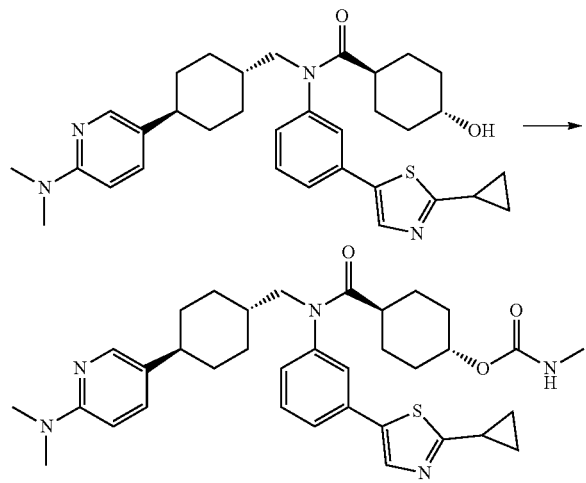

A mixture of Intermediate 29.15 (101 mg, 0.181 mmol), CDI (59 mg, 0.364 mmol), and CH₃CN (2 mL) was heated at 80° C. for 130 min, cooled to rt, and concentrated. Methylamine (40% in CH₃OH, 1.5 mL) was added to the reaction. The mixture was stirred for 15 min, diluted with EtOAc (20 mL), washed (20 mL H₂O and then 20 mL brine), dried (Na₂SO₄), filtered and then concentrated. The residue was purified by silica gel chromatography (60-100% EtOAc in hexanes) to give trans-4-((3-(2-cyclopropylthiazol-5-yl)phenyl)((trans-4-(6-(dimethylamino)pyridin-3-yl)cyclohexyl)methyl)carbamoyl)cyclohexyl methylcarbamate (103 mg, 93%) as a white foam. $^{1}$H NMR (400 MHz, CDCl₃): δ 8.00 (d, 1H), 7.78 (d, 1H), 7.55-7.50 (m, 1H), 7.46 (t, 1H), 7.30-7.27 (m, 3H), 7.15-7.09 (m, 1H), 6.47 (d, 1H), 4.65-4.51 (m, 1H), 4.49-4.37 (m, 1H), 3.61 (d, 2H), 3.03 (s, 6H), 2.75 (d, 3H), 2.41-2.30 (m, 2H), 2.20-2.07 (m, 1H), 2.04-1.94 (m, 2H), 1.91-1.69 (m, 8H), 1.60-1.50 (m, 1H), 1.39-1.28 (m, 2H), 1.23-1.10 (m, 5H), 1.11-0.96 (m, 2H); LCMS: 616.5 [M+H]⁺.

The Compounds below were synthesized from the appropriate Intermediate and the appropriate amine following the procedure described for Compound 1.

| Cmpd | Structure | Name | [M + H]⁺ |
|---|---|---|---|
| 1.01 | 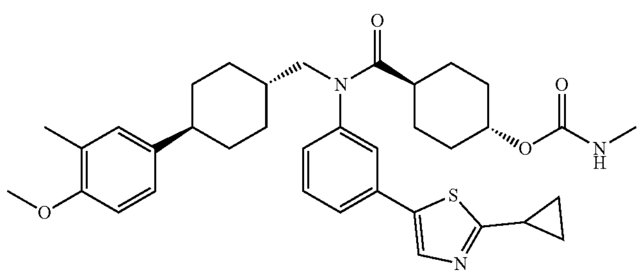 | trans-4-((3-(2-Cyclopropylthiazol-5-yl)phenyl)((trans-4-(4-methoxy-3-methylphenyl)cyclohexyl)methyl)carbamoyl)cyclohexyl methylcarbamate | 616.5 |
| 1.02 | 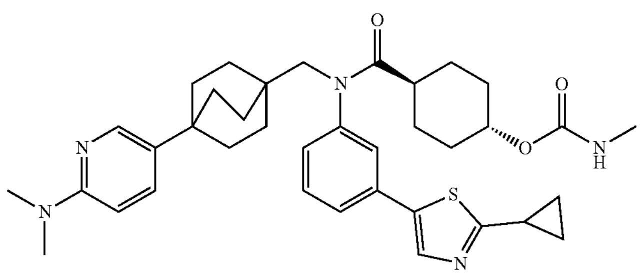 | 4-((3-(2-Cyclopropylthiazol-5-yl)phenyl)((4-(6-(dimethylamino)pyridin-3-yl)bicyclo[2.2.2]octan-1-yl)methyl)carbamoyl)cyclohexyl trans-methylcarbamate | 642.4 |
| 1.03 | 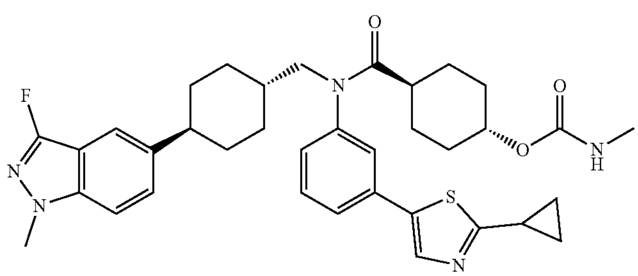 [SMILES: CNC(=O)O[C@H]1CC[C@H](C(=O)N(C[C@H]2CC[C@H](c3ccc4c(c3)c(F)nn4C)CC2)c2cccc(-c3cnc(C4CC4)s3)c2)CC1] | trans-4-((3-(2-Cyclopropylthiazol-5-yl)phenyl((trans-4-(3-fluoro-1-methyl-1H-indazol-5-yl)cyclohexyl)methyl)carbamoyl)cyclohexyl methylcarbamate | 644.3 |

| Cmpd | Structure | Name | [M + H]⁺ |
|---|---|---|---|
| 1.04 | 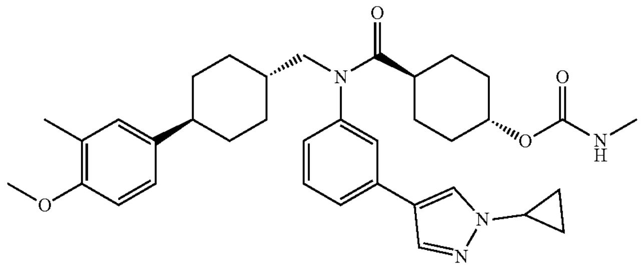 | trans-4-((3-(1-Cyclopropyl-1H-pyrazol-4-yl)phenyl)((trans-4-(4-methoxy-3-methylphenyl)cyclohexyl)methyl)-carbamoyl)cyclohexyl methylcarbamate | 599.5 |
| 1.05 | 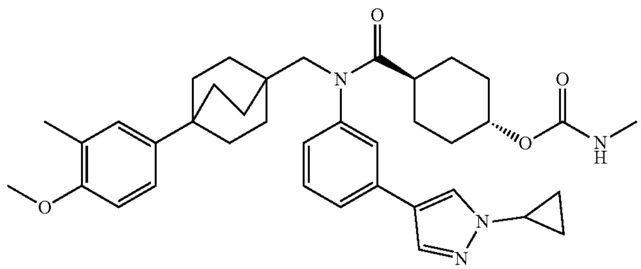 | 4-((3-(1-Cyclopropyl-1H-pyrazol-4-yl)phenyl)((4-(4-methoxy-3-methylphenyl)bicyclo[2.2.2]octan-1-yl)methyl)carbamoyl)cyclohexyl trans-methylcarbamate | 625.6 |
| 1.06[1] | 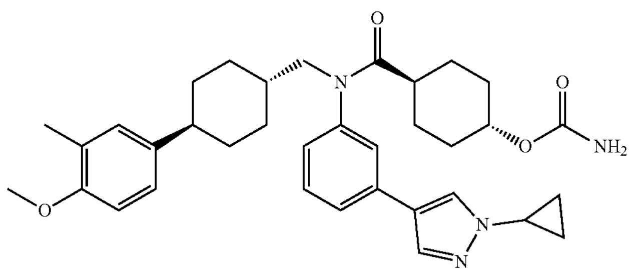 [SMILES: COc1ccc([C@H]2CC[C@H](CN(c3cccc(-c4cnn(C5CC5)c4)c3)C(=O)[C@H]3CC[C@H](OC(N)=O)CC3)CC2)cc1C] | trans-4-((3-(1-Cyclopropyl-1H-pyrazol-4-yl)phenyl)((trans-4-(4-methoxy-3-methylphenyl)cyclohexyl)methyl)-carbamoyl)cyclohexyl carbamate | 585.5 |
| 1.07[3] | 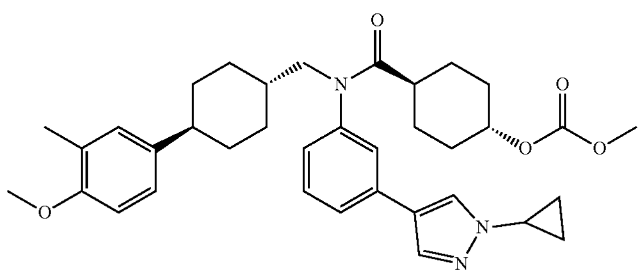 | trans-4-((3-(1-Cyclopropyl-1H-pyrazol-4-yl)phenyl)((trans-4-(4-methoxy-3-methylphenyl)cyclohexyl)methyl)-carbamoyl)cyclohexyl methyl carbonate | 600.1 |
| 1.08[2] | 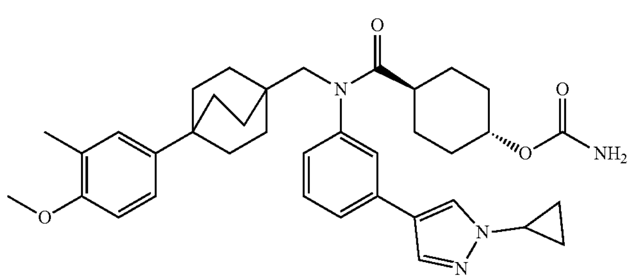 [SMILES: COc1ccc(C23CCC(CN(c4cccc(-c5cnn(C6CC6)c5)c4)C(=O)[C@H]4CC[C@H](OC(N)=O)CC4)(CC2)CC3)cc1C] | 4-((3-(1-Cyclopropyl-1H-pyrazol-4-yl)phenyl)((4-(4-methoxy-3-methylphenyl)bicyclo[2.2.2]octan-1-yl)methyl)carbamoyl)cyclohexyl trans-carbamate | 611.4 |

-continued

| Cmpd | Structure | Name | [M + H]+ |
|---|---|---|---|
| 1.09 | 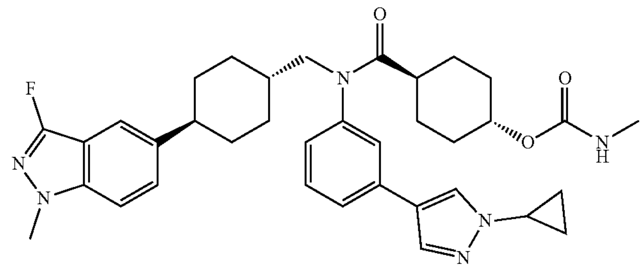 [SMILES: CNC(=O)O[C@H]1CC[C@H](C(=O)N(C[C@H]2CC[C@H](c3ccc4c(c3)c(F)nn4C)CC2)c2cccc(-c3cnn(C4CC4)c3)c2)CC1] | trans-4-((3-(1-Cyclopropyl-1H-pyrazol-4-yl)phenyl)((trans-4-(3-fluoro-1-methyl-1H-indazol-5-yl)cyclohexyl)methyl)carbamoyl)-cyclohexyl methyl carbamate | 627.6 |
| 1.10 | 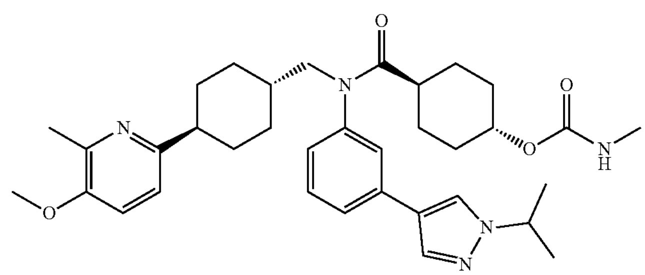 | trans-4-((3-(1-Isopropyl-1H-pyrazol-4-yl)phenyl)((trans-4-(5-methoxy-6-methylpyridin-2-yl)cyclohexyl)methyl)carbamoyl)-cyclohexyl methylcarbamate | 602.4 |

Alternate conditions:
[1] 40% ammonia in CH3OH;
[2] 0.4M ammonia in THF then 40% ammonia in CH3OH;
[3] Isolated during the purification of Compound 1.06.

Compound 2

Trans-4-((3-(3-Cyclopropylisothiazol-5-yl)phenyl)((trans-4-(4-methoxy-3-methylphenyl)cyclohexyl)methyl)carbamoyl)cyclohexyl methylcarbamate

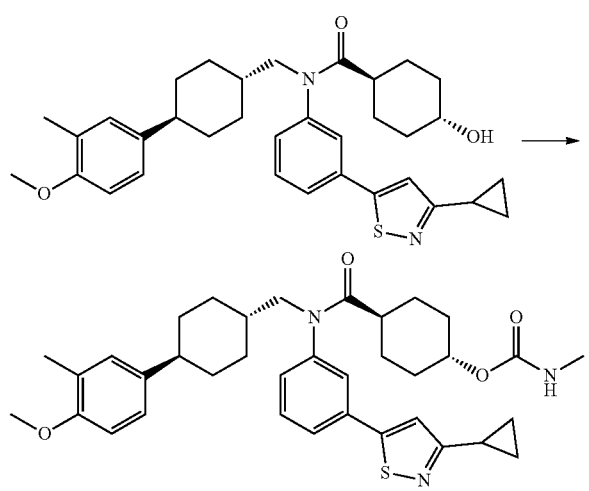

CDI (44.1 mg, 0.272 mmol) was added to a solution of Intermediate 31 (101.3 mg, 0.181 mmol) in CH3CN (5 mL). The reaction mixture was heated at 80° C. overnight, allowed to cool to rt, and then concentrated to give a colorless oil. This oil was dissolved in CH2C2(3 mL). Methylamine (2 M in THF, 1.10 mL) was added to the solution, and the reaction was stirred at rt overnight. The reaction mixture was concentrated and purified by reverse-phase HPLC [water(10 mM NH4HCO3)—CH3CN] to obtain trans-4-((3-(3-cyclopropylisothiazol-5-yl)phenyl)((trans-4-(4-methoxy-3-methylphenyl)cyclohexyl)methyl)carbamoyl)cyclohexyl methylcarbamate (70 mg, 63% yield) as a white solid. H NMR (400 MHz, CDCl3): δ 7.61-7.55 (m, 1H), 7.52 (t, 1H), 7.38 (s, 1H), 7.22 (d, 1H), 7.15 (s, 1H), 6.99-6.93 (m, 2H), 6.74 (d, 1H), 4.57 (br s, 1H), 4.42 (s, 1H), 3.80 (s, 3H), 3.64 (d, 2H), 2.74 (d, 3H), 2.39 (t, 1H), 2.24-2.17 (m, 4H), 2.16-2.09 (m, 1H), 1.97-2.02 (m, 2H), 1.88 (d, 2H), 1.83-1.70 (m, 6H), 1.60-1.58 (m, 1H), 1.42-1.29 (m, 2H), 1.27-1.12 (m, 2H), 1.10-0.95 (m, 6H); LCMS: 616.3 [M+H]+.

The Compounds below were synthesized from the appropriate Intermediate and the appropriate amine following the procedure described for Compound 2.

| Cmpd | Structure | Name | [M +H]+ |
|---|---|---|---|
| 2.01 | 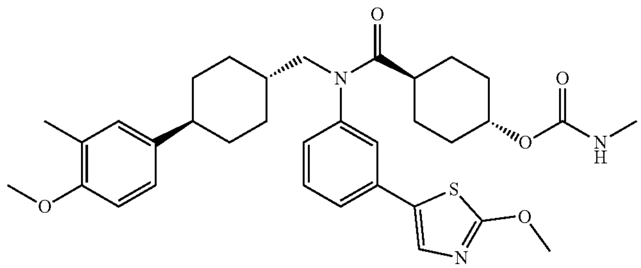 | trans-4-(((trans-4-(4-Methoxy-3-methylphenyl)cyclohexyl)methyl)(3-(2-methoxythiazol-5-yl)phenyl)carbamoyl)cyclohexyl methylcarbamate | 606.3 |
| 2.02 | 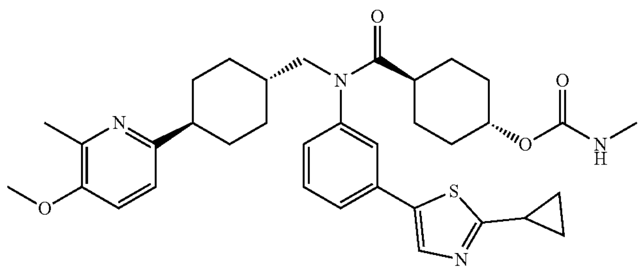 | trans-4-((3-(2-Cyclopropylthiazol-5-yl)phenyl)((trans-4-(5-methoxy-6-methylpyridin-2-yl)cyclohexyl)methyl)carbamoyl)-cyclohexyl methylcarbamate | 617.4 |
| 2.03 | 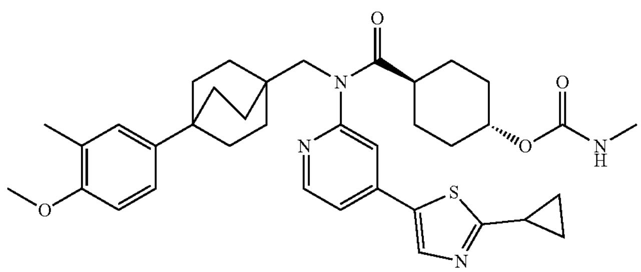 | 4-((4-(2-Cyclopropylthiazol-5-yl)pyridin-2-yl)((4-(4-methoxy-3-methylphenyl)bicyclo[2.2.2]octan-1-yl)methyl)carbamoyl)cyclohexyl trans-methylcarbamate | 643.5 |
| 2.04 | 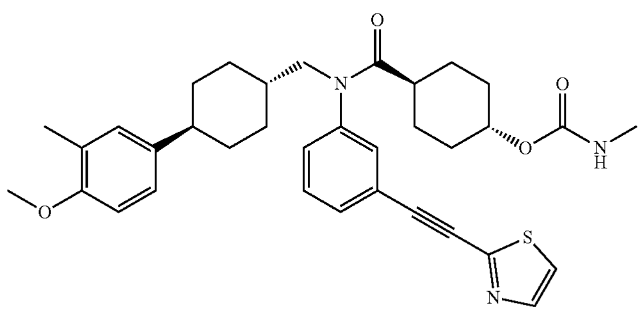 | trans-4-(((trans-4-(4-Methoxy-3-methylphenyl)cyclohexyl)methyl)(3-(thiazol-2-ylethynyl)phenyl)carbamoyl)cyclohexyl methylcarbamate | 600.2 |
| 2.05 | 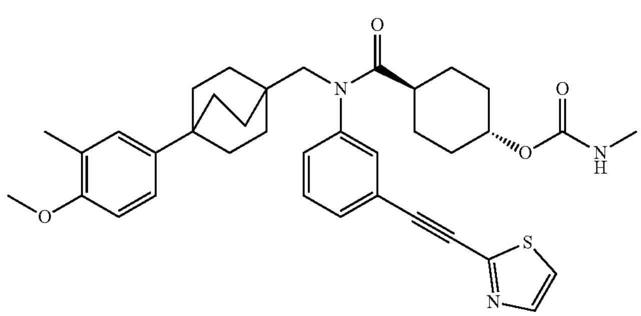 | 4-(((4-(4-Methoxy-3-methylphenyl)bicyclo[2.2.2]octan-1-yl)methyl)(3-(thiazol-2-ylethynyl)phenyl)carbamoyl)cyclohexyl trans-methylcarbamate | 626.3 |

-continued

| Cmpd | Structure | Name | [M +H]+ |
|---|---|---|---|
| 2.06 | 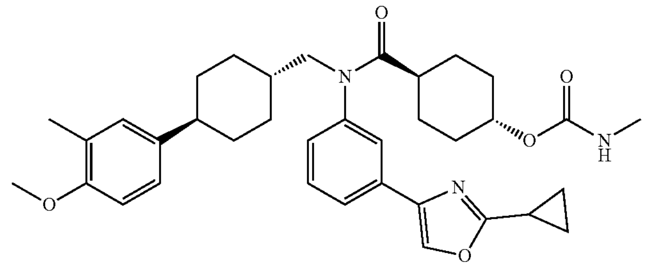 | trans-4-((3-(2-Cyclopropyloxazol-4-yl)phenyl)((trans-4-(4-methoxy-3-methylphenyl)cyclohexyl)methyl)-carbamoyl)cyclohexyl methylcarbamate | 600.3 |
| 2.07 | 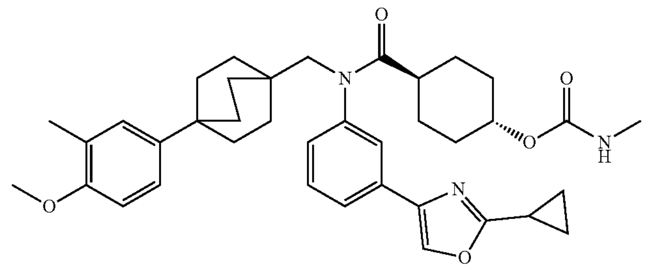 | 4-((3-(2-Cyclopropyloxazol-4-yl)phenyl)((4-(4-methoxy-3-methylphenyl)bicyclo[2.2.2]octan-1-yl)methyl)carbamoyl)cyclohexyl trans-methylcarbamate | 626.5 |
| 2.08 | 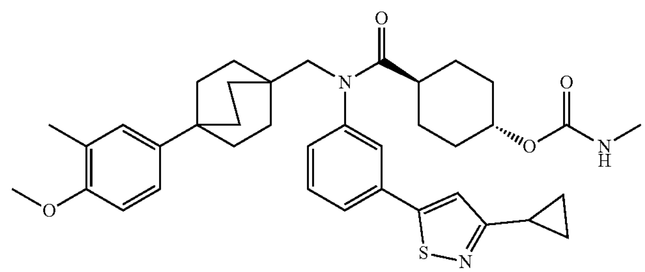 | 4-((3-(3-Cyclopropylisothiazol-5-yl)phenyl)((4-(4-methoxy-3-methylphenyl)bicyclo[2.2.2]octan-1-yl)methyl)carbamoyl)cyclohexyl trans-methylcarbamate | 642.3 |

Compound 3

4-((3-(2-Cyclopropyloxazol-4-yl)phenyl)((4-(6-(dimethylamino)pyridin-3-yl)bicyclo[2.2.2]octan-1-yl)methyl)carbamoyl)cyclohexyl trans-methylcarbamate

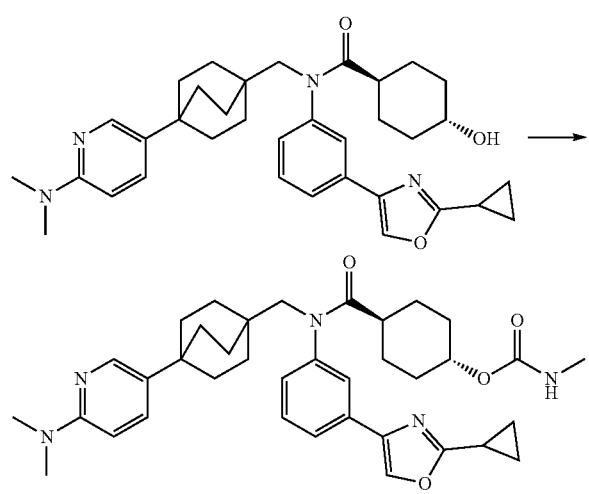

A mixture of Intermediate 30.14 (81 mg, 0.14 mmol), CDI (46 mg, 0.29 mmol), and CH$_3$CN (1.5 mL) was heated at 80° C. for 2 h, allowed to cool to rt, and then concentrated. The residue was dissolved in CH$_2$Cl$_2$ (3 mL). A portion of this solution (1.5 mL, 0.071 mmol) was concentrated and then diluted with methylamine (4000 in CH$_3$OH, 1.5 mL). The mixture was stirred at rt for 2 h, diluted with EtOAc (20 mL), washed (20 mL H$_2$O and then 20 mL brine), dried (Na$_2$SO$_4$), filtered, concentrated, and then purified by silica gel chromatography (0-5%0 CH$_3$OH in CH$_2$Cl$_2$) to give 4-((3-(2-Cyclopropyloxazol-4-yl)phenyl)((4-(6-(dimethylamino) pyridin-3-yl)bicyclo[2.2.2]octan-3-yl)methyl)carbamoyl) cyclohexyl trans-methylcarbamate (39 mg, 89%) as a white foam. NMR (400 MHz, DMSO-d$_6$): δ 8.53 (s, 1H), 7.96-7.94 (m, 1H), 7.74-7.67 (m, 2H), 7.48 (t, 1H), 7.40 (dd, 1H), 7.33 (d, 1H), 6.84-6.77 (m, 1H), 6.52 (d, 1H), 4.39-4.28 (m, 1H), 3.78-3.44 (m, 2H), 2.94 (s, 6H), 2.27-2.12 (m, 2H), 1.89-1.79 (m, 2H), 1.74-1.58 (m, 8H), 1.53-1.32 (m, 8H), 1.11-1.02 (m, 2H), 1.02-0.97 (m, 2H), 0.97-0.82 (in, 2H), NHCH$_3$ under DMSO; LCMS: 626.5 [M+H]+.

The Compounds below were synthesized from the appropriate Intermediate and the appropriate amine following the procedure described for Compound 3.

| Cmpd | Structure | Name | [M + H]+ |
|---|---|---|---|
| 3.01[1] | 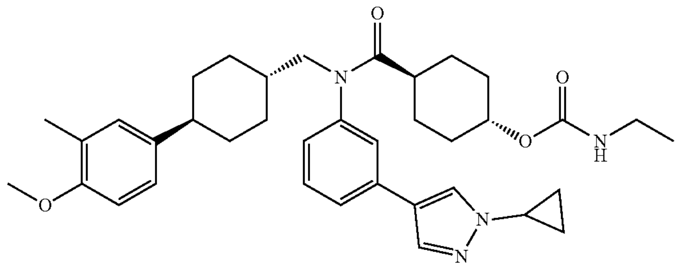 [SMILES: CCNC(=O)O[C@H]1CC[C@H](C(=O)N(C[C@H]2CC[C@H](c3ccc(OC)c(C)c3)CC2)c2cccc(-c3cnn(C4CC4)c3)c2)CC1] | trans-4-((3-(1-Cyclopropyl-1H-pyrazol-4-yl)phenyl)((trans-4-(4-methoxy-3-methylphenyl)cyclohexyl)methyl)-carbamoyl)cyclohexyl ethylcarbamate | 613.5 |
| 3.02 | 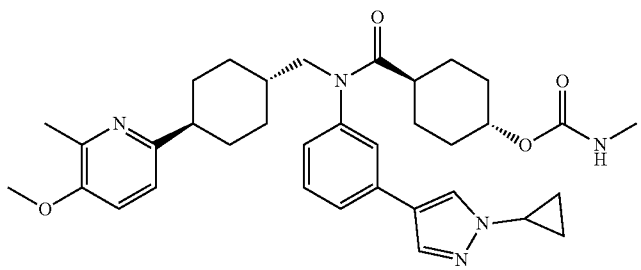 | trans-4-((3-(1-Cyclopropyl-1H-pyrazol-4-yl)phenyl)((trans-4-(5-methoxy-6-methylpyridin-2-yl)cyclohexyl)methyl)carbamoyl)-cyclohexyl methylcarbamate | 600.4 |
| 3.03 | 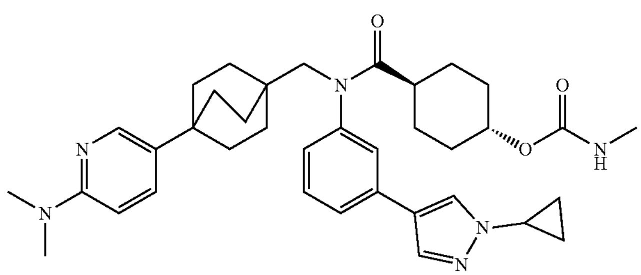 | 4-((3-(1-Cyclopropyl-1H-pyrazol-4-yl)phenyl)((4-(6-(dimethylamino)pyridin-3-yl)bicyclo[2.2.2]octan-1-yl)methyl)carbamoyl)cyclohexyl trans-methylcarbamate | 625.6 |
| 3.04 | 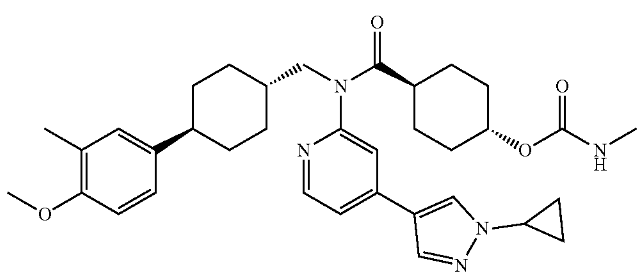 | trans-4-((4-(1-Cyclopropyl-1H-pyrazol-4-yl)pyridin-2-yl)((trans-4-(4-methoxy-3-methylphenyl)cyclohexyl)methyl)-carbamoyl)cyclohexyl methyl carbamate | 600.5 |
| 3.05 | 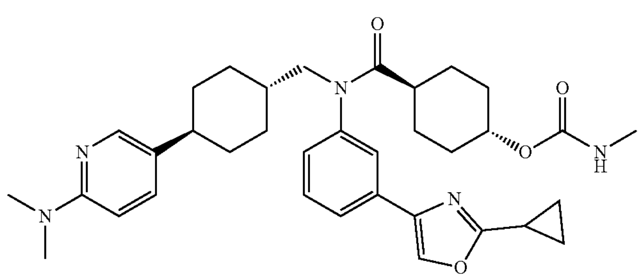 | trans-4-((3-(2-Cyclopropyloxazol-4-yl)phenyl)((trans-4-(6-(dimethylamino)pyridine-3-yl)cyclohexyl)methyl)carbamoyl)-cyclohexyl methylcarbamate | 600.4 |

[1] 2M ethylamine in THF.

Compound 4

Trans-4-((3-(1-Cyclopropyl-1H-pyrazol-4-yl)phenyl)((trans-4-(4-methoxy-3-methylphenyl)cyclohexyl)methyl)carbamoyl)cyclohexyl (2-hydroxyethyl)carbamate

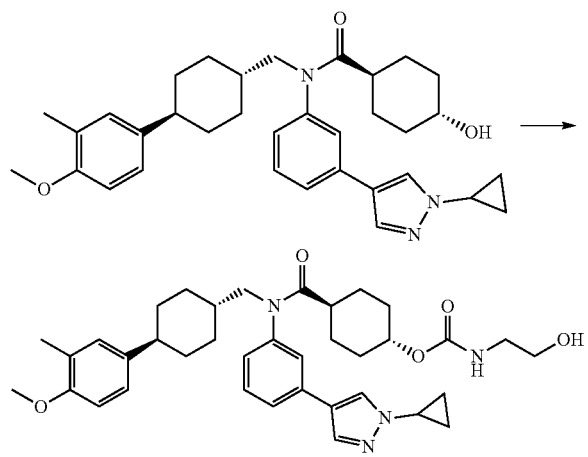

A mixture of Intermediate 29.11 (130 mg, 0.240 mmol), CDI (59 mg, 0.364 mmol), and $CH_3CN$ (2 mL) was heated at 80° C. for 2 h, allowed to cool to rt, and concentrated. The residue was dissolved in $CH_2Cl_2$ (2 mL). Ethanolamine (149 mg, 2.44 mmol) was added to the reaction, and the mixture was stirred for 40 min, diluted with EtOAc (20 mL), washed (20 mL $H_2O$ and then 20 mL brine), dried ($Na_2SO_4$), filtered and concentrated. The residue was purified by silica gel chromatography (0-5% $CH_3OH$ in $CH_2Cl_2$) to give trans-4-((3-(1-cyclopropyl-1H-pyrazol-4-yl)phenyl)((trans-4-(4-methoxy-3-methylphenyl)cyclohexyl)methyl)carbamoyl) cyclohexyl (2-hydroxyethyl)carbamate (131 mg, 87%) as a white foam. $^1$H NMR (400 MHz, DMSO-$d_6$): δ 8.34 (s, 1H), 7.93 (s, 1H), 7.60 (d, 1H), 7.55 (s, 1H), 7.44 (t, 1H), 7.10 (d, 1H), 6.98-6.92 (m, 2H), 6.85 (t, 0.87H), 6.80-6.45 (m, 1H), 6.60-6.45 (m, 0.13H), 4.55 (t, 1H), 4.40-4.26 (m, 1H), 3.80-3.69 (m, 4H), 3.66-3.40 (m, 2H), 3.35-3.25 (m, 2H), 3.03-2.82 (m, 2H), 2.38-2.27 (m, 1H), 2.18-2.03 (m, 4H), 1.90-1.80 (m, 2H), 1.80-1.63 (m, 6H), 1.56-1.38 (m, 3H), 1.35-1.21 (m, 2H), 1.12-0.95 (m, 6H), 0.95-0.82 (m, 2H); LCMS: 629.6 [M+H]$^+$.

The Compounds below were synthesized from the appropriate Intermediate and the appropriate amine following the procedure described for Compound 4.

| Cmpd | Structure | Name | [M + H]$^+$ |
|---|---|---|---|
| 4.01 | 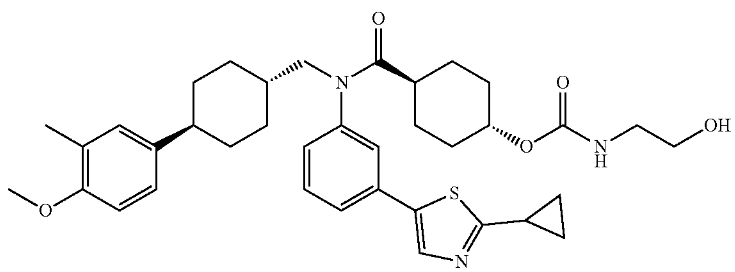 | trans-4-((3-(2-Cyclopropylthiazol-5-yl)phenyl)((trans-4-(4-methoxy-3-methylphenyl)-cyclohexyl)-methyl)carbamoyl)cyclohexyl (2-hydroxyethyl)carbamate | 646.4 |
| 4.02 | 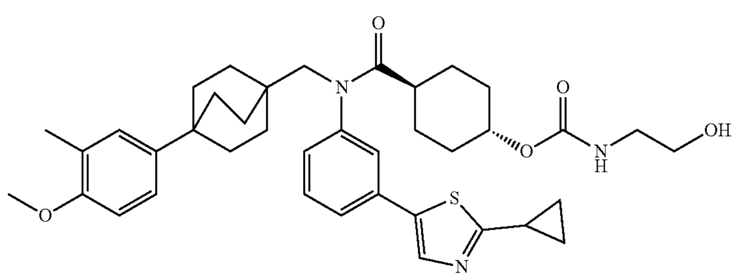 [SMILES: COc1ccc(C23CCC(CN(c4cccc(-c5cnc(C6CC6)s5)c4)C(=O)[C@H]4CC[C@H](OC(=O)NCCO)CC4)(CC2)CC3)cc1C] | 4-((3-(2-Cyclopropylthiazol-5-yl)phenyl)((4-(4-methoxy-3-methylphenyl)bicyclo[2.2.2]octan-1-yl)methyl)carbamoyl)-cyclohexyl (2-hydroxyethyl)trans-carbamate | 672.5 |
| 4.03 | 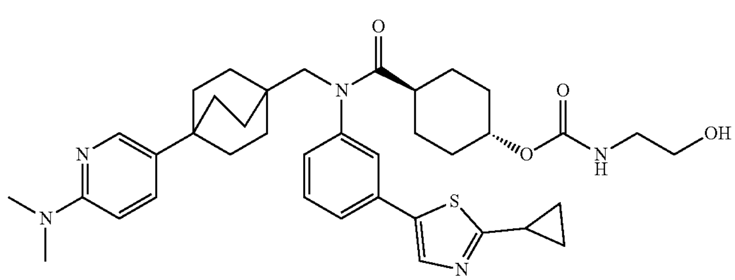 [SMILES: CN(C)c1ccc(C23CCC(CN(c4cccc(-c5cnc(C6CC6)s5)c4)C(=O)[C@H]4CC[C@H](OC(=O)NCCO)CC4)(CC2)CC3)cn1] | 4-((3-(2-Cyclopropylthiazol-5-yl)phenyl)((4-(6-(dimethylamino)-pyridin-3-yl)bicyclo[2.2.2]octan-1-yl)methyl)carbamoyl) cyclohexyl (2-hydroxyethyl)trans-carbamate | 672.6 |

| Cmpd | Structure | Name | [M + H]+ |
|---|---|---|---|
| 4.04 | 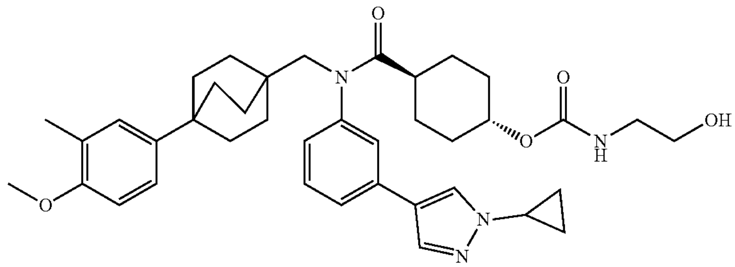 [SMILES: COc1ccc(C23CCC(CN(c4cccc(-c5cnn(C6CC6)c5)c4)C(=O)[C@H]4CC[C@H](OC(=O)NCCO)CC4)(CC2)CC3)cc1C] | 4-((3-(1-Cyclopropyl-1H-pyrazol-4-yl)phenyl)((4-(4-methoxy-3-methylphenyl)bicyclo-[2.2.2]octan-1-yl)methyl)carbamoyl)-cyclohexyl (2-hydroxyethyl)trans-carbamate | 655.7 |
| 4.05 | 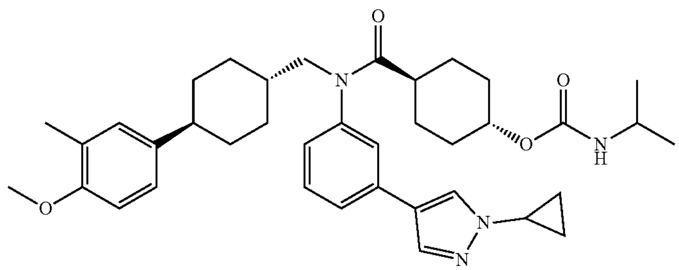 [SMILES: COc1ccc([C@H]2CC[C@H](CN(c3cccc(-c4cnn(C5CC5)c4)c3)C(=O)[C@H]3CC[C@H](OC(=O)NC(C)C)CC3)CC2)cc1C] | trans-4-((3-(1-Cyclopropyl-1H-pyrazol-4-yl)phenyl)((trans-4-(4-methoxy-3-methylphenyl)-cyclohexyl)methyl)carbamoyl)cyclohexyl isopropylcarbamate | 627.6 |
| 4.06 | 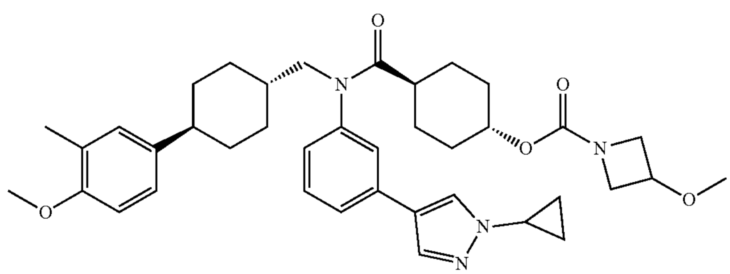 | trans-4-((3-(1-Cyclopropyl-1H-pyrazol-4-yl)phenyl)((trans-4-(4-methoxy-3-methylphenyl)-cyclohexyl)methyl)carbamoyl)cyclohexyl 3-methoxyazetidine-1-carboxylate | 655.4 |
| 4.07 | 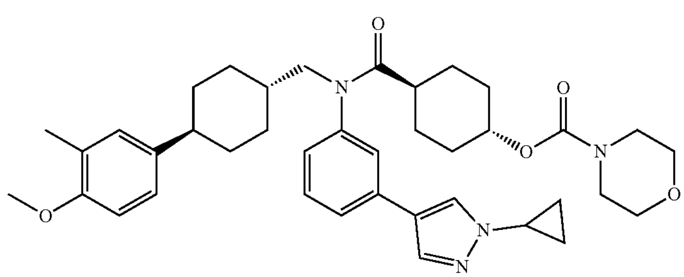 [SMILES: COc1ccc([C@H]2CC[C@H](CN(c3cccc(-c4cnn(C5CC5)c4)c3)C(=O)[C@H]3CC[C@H](OC(=O)N4CCOCC4)CC3)CC2)cc1C] | trans-4-((3-(1-Cyclopropyl-1H-pyrazol-4-yl)phenyl)((trans-4-(4-methoxy-3-methylphenyl)-cyclohexyl)-methyl)carbamoyl)cyclohexyl morpholine-4-carboxylate | 655.5 |
| 4.08 | 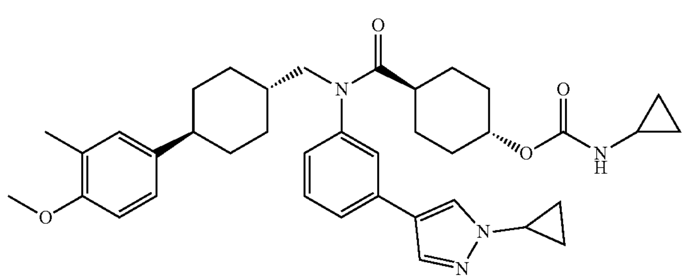 [SMILES: COc1ccc([C@H]2CC[C@H](CN(c3cccc(-c4cnn(C5CC5)c4)c3)C(=O)[C@H]3CC[C@H](OC(=O)NC4CC4)CC3)CC2)cc1C] | trans-4-((3-(1-Cyclopropyl-1H-pyrazol-4-yl)phenyl)((trans-4-(4-methoxy-3-methylphenyl)-cyclohexyl)-methyl)carbamoyl)cyclohexyl cyclopropylcarbamate | 625.6 |

-continued

| Cmpd | Structure | Name | [M + H]+ |
|---|---|---|---|
| 4.09 | 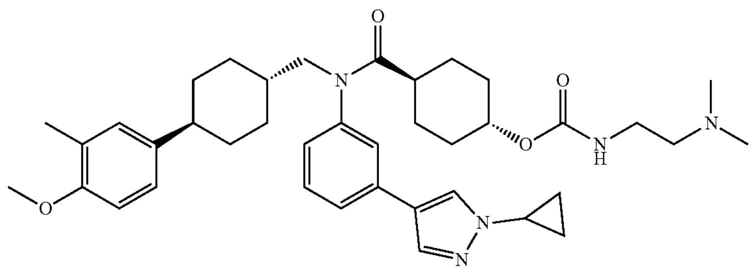 | trans-4-((3-(1-Cyclopropyl-1H-pyrazol-4-yl)phenyl)((trans-4-(4-methoxy-3-methylphenyl)-cyclohexyl)-methyl)carbamoyl)cyclohexyl (2-(dimethylamino)ethyl)-carbamate | 656.5 |
| 4.10 | 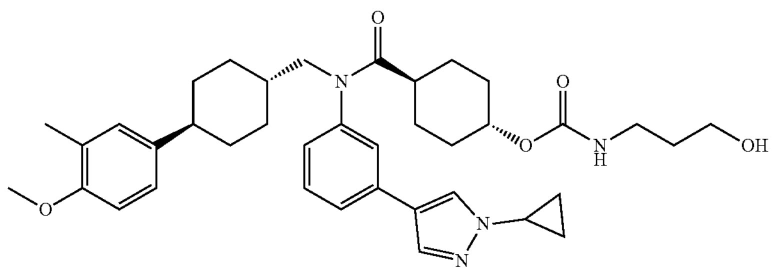 [SMILES: COc1ccc([C@H]2CC[C@H](CN(c3cccc(-c4cnn(C5CC5)c4)c3)C(=O)[C@H]3CC[C@H](OC(=O)NCCCO)CC3)CC2)cc1C] | trans-4-((3-(1-Cyclopropyl-1H-pyrazol-4-yl)phenyl)((trans-4-(4-methoxy-3-methylphenyl)cyclohexyl)methyl)carbamoyl)cyclohexyl (3-hydroxypropyl)-carbamate | 643.7 |
| 4.11 | 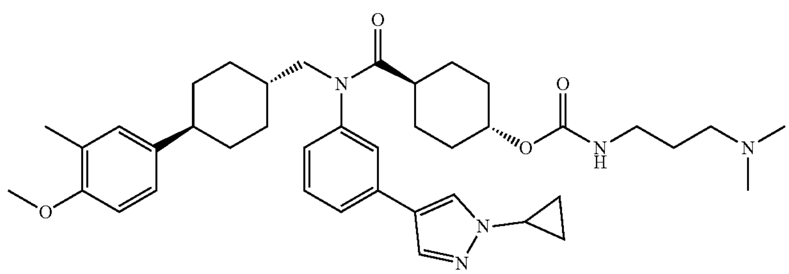 | trans-4-((3-(1-Cyclopropyl-1H-pyrazol-4-yl)phenyl)((trans-4-(4-methoxy-3-methylphenyl)-cyclohexyl)-methyl)carbamoyl)cyclohexyl (3-(dimethylamino)-propyl)carbamate | 670.5 |
| 4.12 | 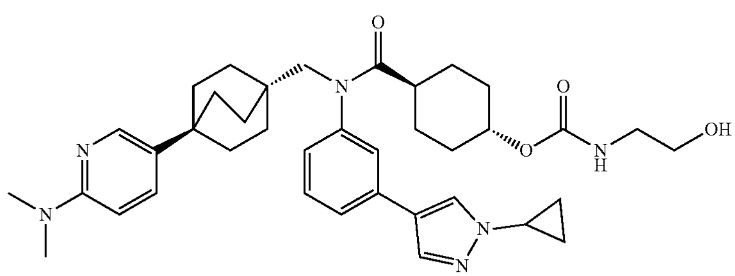 [SMILES: CN(C)c1ccc([C@]23CC[C@@](CN(c4cccc(-c5cnn(C6CC6)c5)c4)C(=O)[C@H]4CC[C@H](OC(=O)NCCO)CC4)(CC2)CC3)cn1] | 4-((3-(1-Cyclopropyl-1H-pyrazol-4-yl)phenyl)((4-(6-(dimethylamino)-pyridin-3-yl)bicyclo[2.2.2]octan-1-yl)methyl)carbamoyl)-cyclohexyl (2-hydroxyethyptrans-carbamate | 655.5 |
| 4.13 | 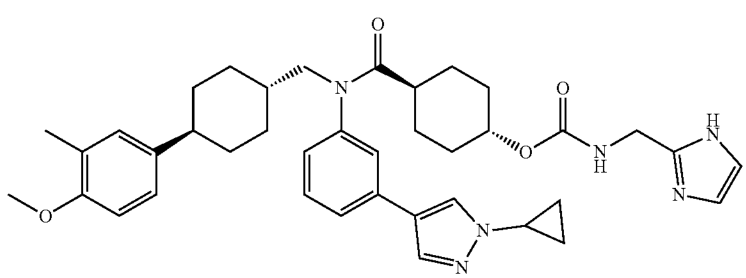 [SMILES: COc1ccc([C@H]2CC[C@H](CN(c3cccc(-c4cnn(C5CC5)c4)c3)C(=O)[C@H]3CC[C@H](OC(=O)NCc4ncc[nH]4)CC3)CC2)cc1C] | trans-4-((3-(1-Cyclopropyl-1H-pyrazol-4-yl)phenyl)((trans-4-(4-methoxy-3-methylphenyl)-cyclohexyl)methyl)carbamoyl)cyclohexyl ((1H-imidazol-2-yl)methyl)carbamate | 665.6 |

-continued

| Cmpd | Structure | Name | [M + H]+ |
|---|---|---|---|
| 4.14 | 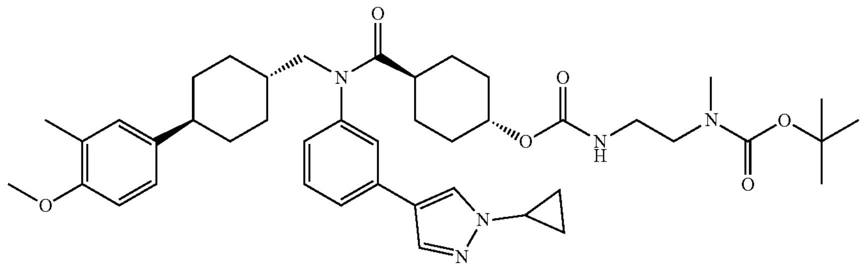 [SMILES: COc1ccc([C@H]2CC[C@H](CN(c3cccc(-c4cnn(C5CC5)c4)c3)C(=O)[C@H]3CC[C@H](OC(=O)NCCN(C)C(=O)OC(C)(C)C)CC3)CC2)cc1C] | tert-Butyl (2-(((((trans-4-((3-(1-cyclopropyl-1H-pyrazol-4-yl)phenyl)((trans-4-(4-methoxy-3-methylphenyl)-cyclohexyl)-methyl)carbamoyl)cyclohexyl)oxy)-carbonyl)amino)ethyl)(methyl)carbamate | 742.9 |
| 4.15[1] | 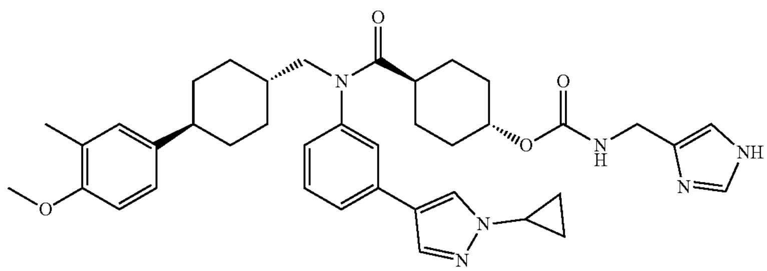 [SMILES: COc1ccc([C@H]2CC[C@H](CN(c3cccc(-c4cnn(C5CC5)c4)c3)C(=O)[C@H]3CC[C@H](OC(=O)NCc4c[nH]cn4)CC3)CC2)cc1C] | trans-4-((3-(1-Cyclopropyl-1H-pyrazol-4-yl)phenyl)((trans-4-(4-methoxy-3-methylphenyl)-cyclohexyl)methyl)carbamoyl)cyclohexyl ((1H-imidazol-4-yl)methyl)carbamate | 665.7 |
| 4.16 | 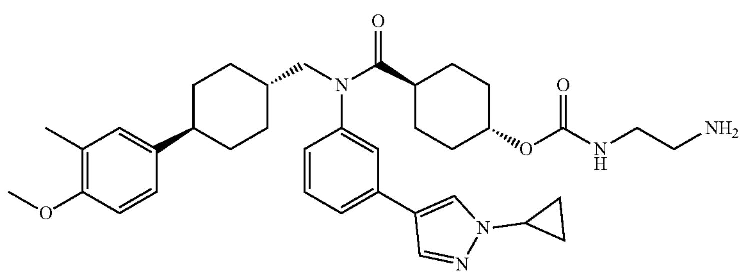 [SMILES: COc1ccc([C@H]2CC[C@H](CN(c3cccc(-c4cnn(C5CC5)c4)c3)C(=O)[C@H]3CC[C@H](OC(=O)NCCN)CC3)CC2)cc1C] | trans-4-((3-(1-Cyclopropyl-1H-pyrazol-4-yl)phenyl)((trans-4-(4-methoxy-3-methylphenyl)-cyclohexyl)methyl)carbamoyl)cyclohexyl (2-aminoethyl)carbamate | 628.4 |
| 4.17 | 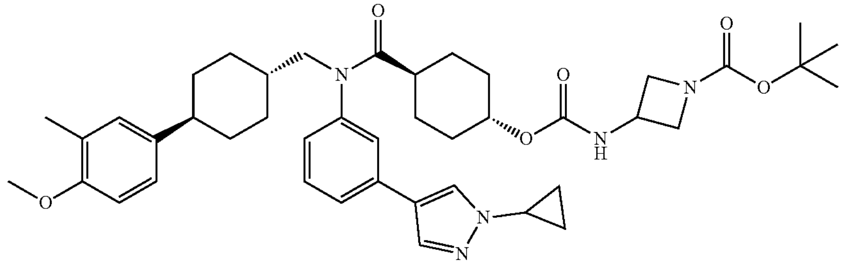 [SMILES: COc1ccc([C@H]2CC[C@H](CN(c3cccc(-c4cnn(C5CC5)c4)c3)C(=O)[C@H]3CC[C@H](OC(=O)NC4CN(C(=O)OC(C)(C)C)C4)CC3)CC2)cc1C] | tert-Butyl-3-(((((trans-443-(1-cyclopropyl-1H-pyrazol-4-yl)phenyl)((trans-4-(4-methoxy-3-methylphenyl)-cyclohexyl)-methyl)carbamoyl)cyclohexyl)oxy)-carbonyl)amino)azetidine-1-carboxylate | 740.6 |
| 4.18[4] | 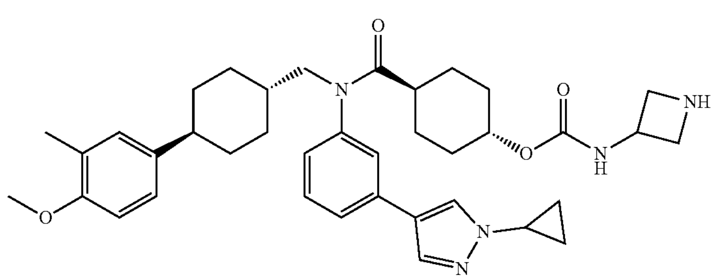 [SMILES: COc1ccc([C@H]2CC[C@H](CN(c3cccc(-c4cnn(C5CC5)c4)c3)C(=O)[C@H]3CC[C@H](OC(=O)NC4CNC4)CC3)CC2)cc1C] | trans-4-((3-(1-Cyclopropyl-1H-pyrazol-4-yl)phenyl)((trans-4-(4-methoxy-3-methylphenyl)-cyclohexyl)-methyl)carbamoyl)cyclohexyl azetidin-3-ylcarbamate | 640.5 |

-continued

| Cmpd | Structure | Name | [M + H]+ |
|---|---|---|---|
| 4.19 | 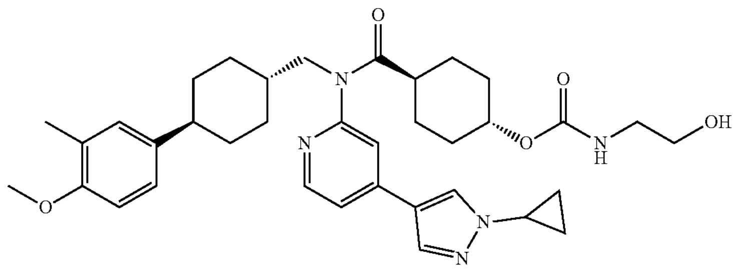 [SMILES: COc1ccc([C@H]2CC[C@H](CN(c3cc(-c4cnn(C5CC5)c4)ccn3)C(=O)[C@H]3CC[C@H](OC(=O)NCCO)CC3)CC2)cc1C] | trans-4-((4-(1-Cyclopropyl-1H-pyrazol-4-yl)pyridin-2-yl)-((trans-4-(4-methoxy-3-methylphenyl)-cyclohexyl)-methyl)carbamoyl)cyclohexyl (2-hydroxyethyl)carbamate | 630.5 |
| 4.20 | 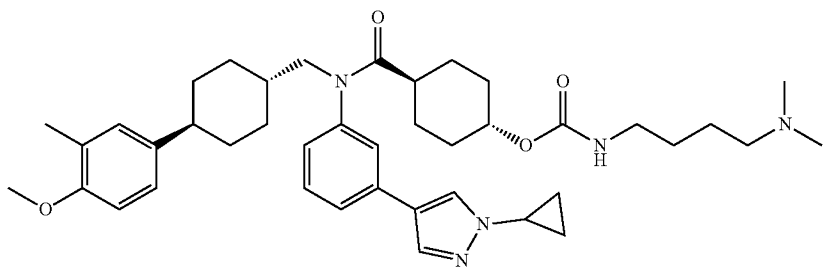 | trans-4-((3-(1-Cyclopropyl-1H-pyrazol-4-yl)phenyl)-((trans-4-(4-methoxy-3-methylphenyl)-cyclohexyl)methyl)carbamoyl)cyclohexyl (4-(dimethylamino)-butyl)carbamate | 684.6 |
| 4.21 | 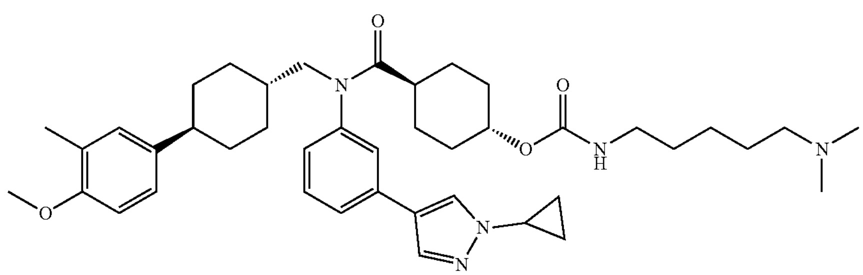 | trans-4-((3-(1-Cyclopropyl-1H-pyrazol-4-yl)phenyl)-((trans-4-(4-methoxy-3-methylphenyl)-cyclohexyl)methyl)carbamoyl)cyclohexyl (5-(dimethylamino)-pentyl)carbamate | 698.7 |
| 4.22 | 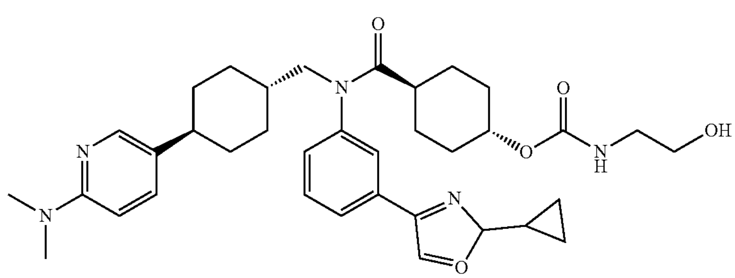 | trans-4-((3-(2-Cyclopropyloxazol-4-yl)phenyl)((trans-4-(6-(dimethylamino)pyridine-3-yl)cyclohexyl)methyl)-carbamoyl)cyclohexyl (2-hydroxyethyl)carbamate | 630.4 |
| 4.23 | 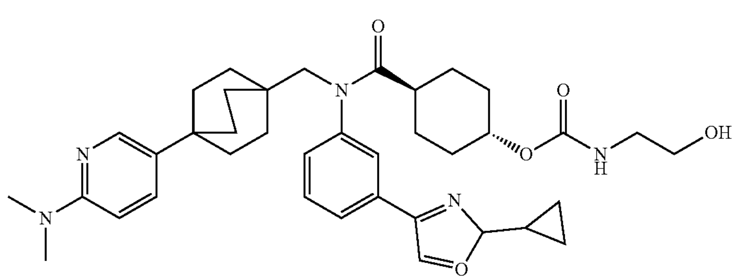 | 4-((3-(2-Cyclopropyloxazol-4-yl)phenyl)((4-(6-(dimethylamino)-pyridin-3-yl)bicyclo[2.2.2]octan-1-yl)methyl)carbamoyl)-cyclohexyl trans-(2-hydroxyethyl)-carbamate | 656.5 |

-continued

| Cmpd | Structure | Name | [M + H]+ |
|---|---|---|---|
| 4.24 | 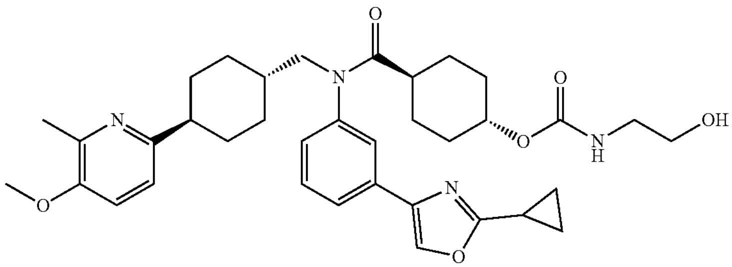 [SMILES: COc1ccc([C@H]2CC[C@H](CN(c3cccc(-c4coc(C5CC5)n4)c3)C(=O)[C@H]3CC[C@H](OC(=O)NCCO)CC3)CC2)nc1C] | trans-4-((4-(2-Cyclopropyloxazol-4-yl)pyridine-2-yl)((trans-4-(5-methoxy-6-methylpyridin-2-yl)cyclohexyl)methyl)carbamoyl)cyclohexyl (2-hydroxyethyl)carbamate | 632.6 |
| 4.25[2] | 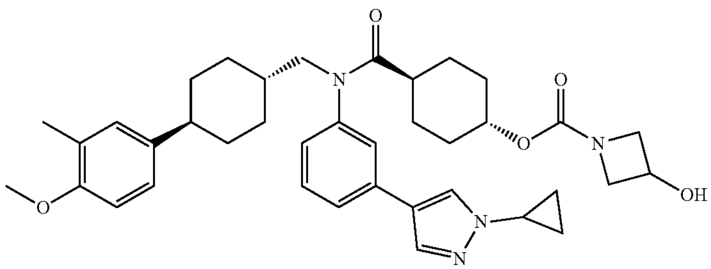 [SMILES: COc1ccc([C@H]2CC[C@H](CN(c3cccc(-c4cnn(C5CC5)c4)c3)C(=O)[C@H]3CC[C@H](OC(=O)N4CC(O)C4)CC3)CC2)cc1C] | trans-4-((3-(1-Cyclopropyl-1H-pyrazol-4-yl)phenyl)((trans-4-(4-methoxy-3-methylphenyl)cyclohexyl)methyl)carbamoyl)cyclohexyl 3-hydroxyazetidine-1-carboxylate | 641.2 |
| 4.26[2] | 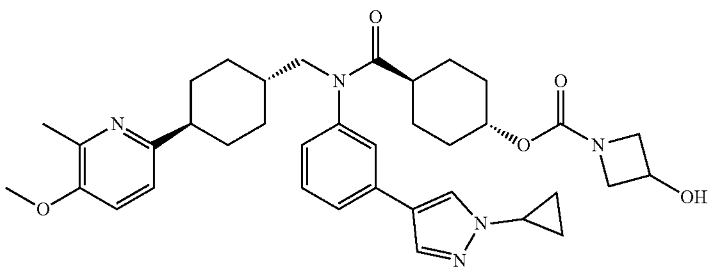 [SMILES: COc1ccc([C@H]2CC[C@H](CN(c3cccc(-c4cnn(C5CC5)c4)c3)C(=O)[C@H]3CC[C@H](OC(=O)N4CC(O)C4)CC3)CC2)nc1C] | trans-4-((3-(1-Cyclopropyl-1H-pyrazol-4-yl)phenyl)((trans-4-(5-methoxy-6-methylpyridin-2-yl)cyclohexyl)methyl)carbamoyl)cyclohexyl 3-hydroxyazetidine-1-carboxylate | 642.4 |
| 4.27[2] | 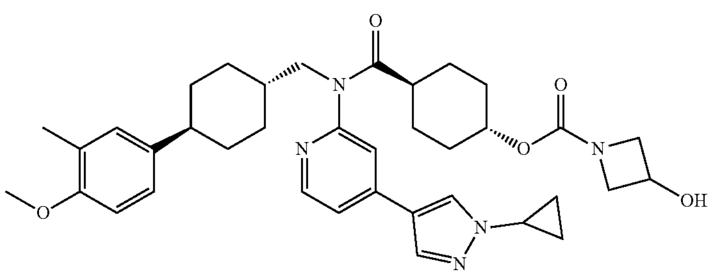 [SMILES: COc1ccc([C@H]2CC[C@H](CN(c3cc(-c4cnn(C5CC5)c4)ccn3)C(=O)[C@H]3CC[C@H](OC(=O)N4CC(O)C4)CC3)CC2)cc1C] | trans-4-((4-(1-Cyclopropyl-1H-pyrazol-4-yl)pyridin-2-yl)((trans-4-(4-methoxy-3-methylphenyl)cyclohexyl)methyl)carbamoyl)cyclohexyl-3-hydroxyazetidine-1-carboxylate | 642.5 |
| 4.28[3] | 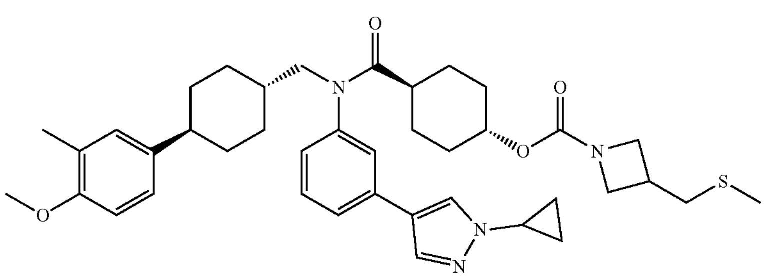 | trans-4-((3-(1-Cyclopropyl-1H-pyrazol-4-yl)phenyl)((trans-4-(4-methoxy-3-methylphenyl)cyclohexyl)methyl)carbamoyl)cyclohexyl 3-((methylthio)methyl)azetidine-1-carboxylate | 685.7 |

Carbamate formation:
[1]CH$_3$OH was added to help solubility;
[2]iPr$_2$NEt was added because mine was an HCl salt;
[3]Et$_3$N was added because amine was an HCl salt.
[4]From deprotection of Compound 4.17 (20% TFA in CH$_2$Cl$_2$).

Compound 5

Trans-4-(((trans-4-(3-Cyano-4-methoxyphenyl)cyclohexyl)methyl)(4-(1-isopropyl-1H-pyrazol-4-yl)pyridin-2-yl)carbamoyl)cyclohexyl ethylcarbamate

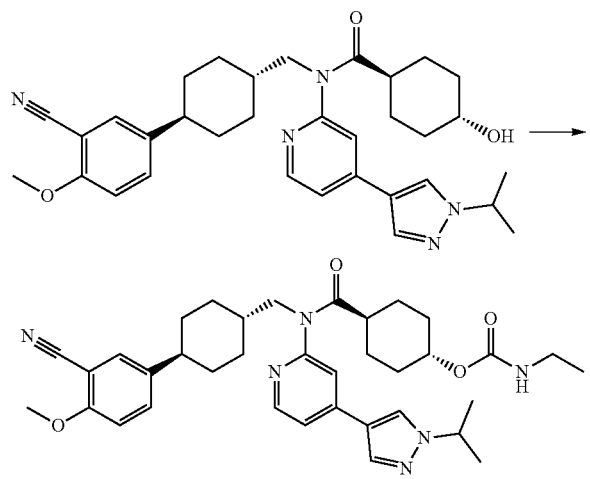

A mixture of Intermediate 30.04 (520 mg, 0.936 mmol), CDI (232 mg, 1.44 mmol), and CH$_3$CN (13 mL) was heated at 80° C. for 165 min. Additional CDI (16 mg, 0.099 mmol) was added to the mixture, and the reaction was heated for 30 min and then allowed to cool to rt. A portion of this solution (1 mL, 0.072 mmol) was added to ethylamine (2 M in THF, 1 mL, 2.0 mmol). The mixture was stirred overnight, diluted with EtOAc (15 mL), washed (15 mL H$_2$O and then 15 mL brine), dried (Na$_2$SO$_4$), filtered and concentrated. The residue was purified by silica gel chromatography (0-5% CH$_3$OH in CH$_2$Cl$_2$) to give trans-4-(((trans-4-(3-cyano-4-methoxyphenyl)cyclohexyl)methyl)(4-(1-isopropyl-1H-pyrazol-4-yl)pyridin-2-yl)carbamoyl)cyclohexyl ethylcarbamate (41 mg, 91%) as a white foam. $^1$H NMR (400 MHz, DMSO-d$_6$): δ 8.55 (s, 1H), 8.43 (d, 1H), 8.14 (s, 1H), 7.66 (s, 1H), 7.56 (dd, 1H), 7.51 (d, 1H), 7.49 (dd, 1H), 7.11 (d, 1H), 6.92 (t, 0.87H), 6.70-6.55 (m, 0.13H), 4.52 (sept, 1H), 4.41-4.27 (m, 1H), 3.85 (s, 3H), 3.68 (d, 2H), 3.00-2.82 (m, 2H), 2.47-2.36 (m, 1H), 2.30-2.14 (m, 1H), 1.91-1.65 (m, 8H), 1.55-1.37 (m, 9H), 1.36-1.22 (m, 2H), 1.08-0.85 (m, 7H); LCMS: 627.5 [M+H]$^+$.

The Compounds below were synthesized using the appropriate Intermediate and the appropriate amine following the procedure described for Compound 5.

| Cmpd | Structure | Name | [M + H]$^+$ |
|---|---|---|---|
| 5.01[3] | 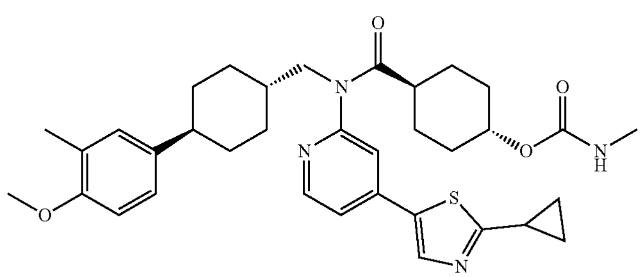 | trans-4-((4-(2-Cyclopropylthiazol-5-yl)pyridin-2-yl)((trans-4-(4-methoxy-3-methylphenyl)cyclohexyl)methyl)carbamoyl)cyclohexyl methylcarbamate | 617.5 |
| 5.02[3] | 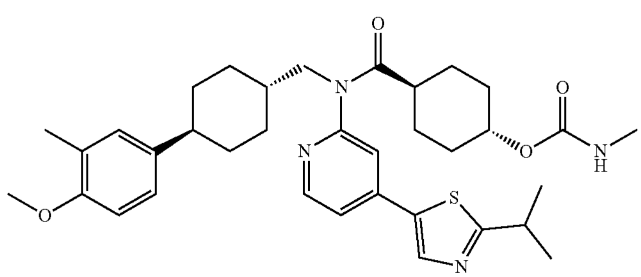 | trans-4-((4-(2-Isopropylthiazol-5-yl)pyridin-2-yl)((trans-4-(4-methoxy-3-methyl phenyl)cyclohexyl)methyl)carbamoyl)cyclohexyl methylcarbamate | 619.5 |
| 5.03[3] | 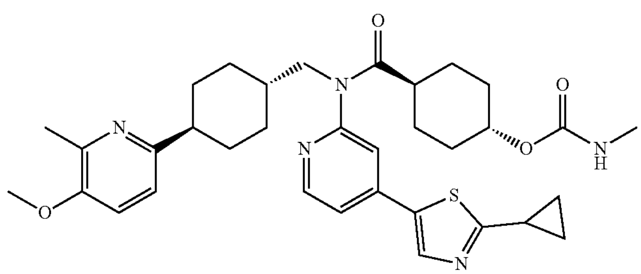 | trans-4-((4-(2-Cyclopropylthiazol-5-yl)pyridin-2-yl)((trans-4-(5-methoxy-6-methylpyridin-2-yl)cyclohexyl)methyl)carbamoyl)cyclohexyl methylcarbamate | 618.5 |

-continued

| Cmpd | Structure | Name | [M + H]+ |
|---|---|---|---|
| 5.04[2] | 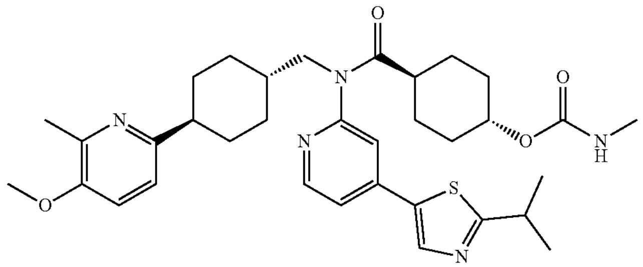 | trans-4-((4-(2-Isopropylthiazol-5-yl)pyridin-2-yl)((trans-4-(5-methoxy-6-methylpyridin-2-yl)cyclohexyl)methyl)carbamoyl)cyclohexyl methylcarbamate | 620.5 |
| 5.05[2] | 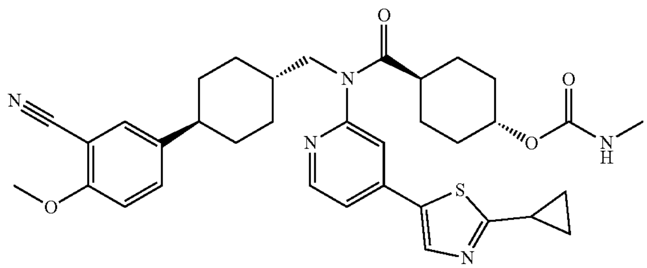 | trans-4-(((trans-4-(3-Cyano-4-methoxyphenyl)cyclohexyl)methyl)(4-(2-cyclopropylthiazol-5-yl)pyridin-2-yl)carbamoyl)cyclohexyl methylcarbamate | 628.4 |
| 5.06[2] | 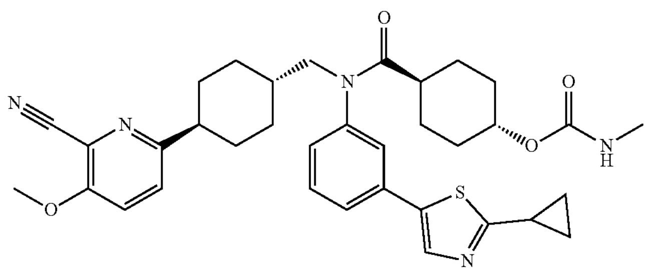 | trans-4-(((trans-4-(6-Cyano-5-methoxypyridin-2-yl)cyclohexyl)methyl)(3-(2-cyclopropylthiazol-5-yl)phenyl)carbamoyl)cyclohexyl methylcarbamate | 628.5 |
| 5.07[2] | 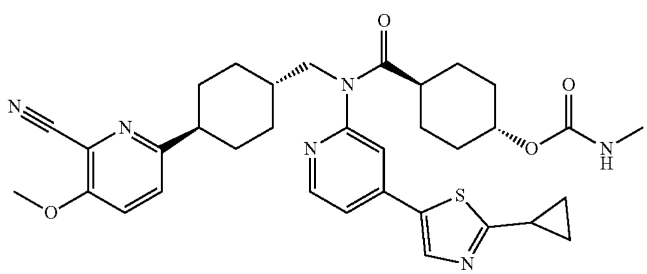 | trans-4-(((trans-4-(6-Cyano-5-methoxypyridin-2-yl)cyclohexyl)methyl)(4-(2-cyclopropylthiazol-5-yl)pyridin-2-yl)carbamoyl)cyclohexyl methyl carbamate | 629.6 |
| 5.08[3] | 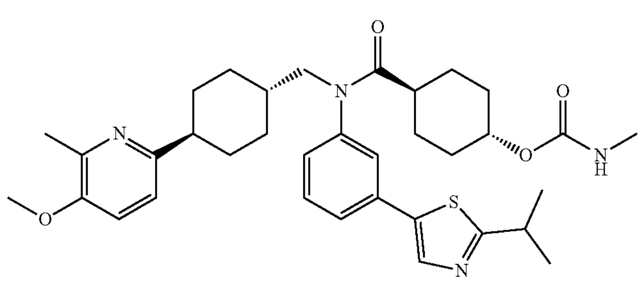 | trans-4-((3-(2-Isopropylthiazol-5-yl)phenyl)((trans-4-(5-methoxy-6-methylpyridin-2-yl)cyclohexyl)methyl)carbamoyl)cyclohexyl methyl carbamate | 619.5 |

-continued

| Cmpd | Structure | Name | [M + H]+ |
|---|---|---|---|
| 5.09[1,3] | 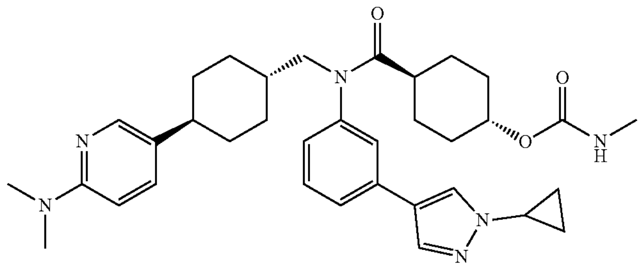 | trans-4-((3-(1-Cyclopropyl-1H-pyrazol-4-yl)phenyl)((trans-4-(6-(dimethylamino)pyridin-3-yl)cyclohexyl)methyl)carbamoyl)cyclohexyl methylcarbamate | 599.5 |
| 5.10[3] | 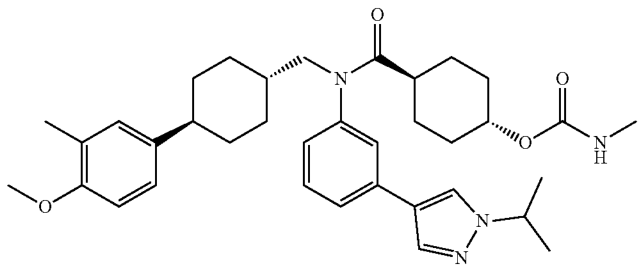 | trans-4-((3-(1-Isopropyl-1H-pyrazol-4-yl)phenyl)((trans-4-(4-methoxy-3-methylphenyl)cyclohexyl)methyl)carbamoyl)cyclohexyl methylcarbamate | 601.6 |
| 5.11[3] | 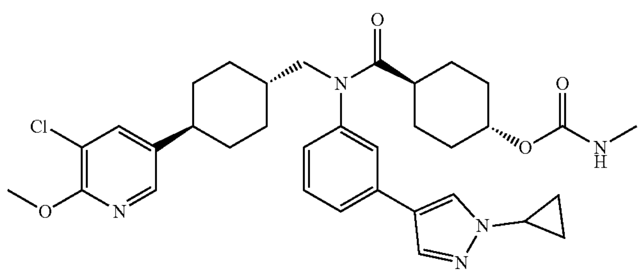 | trans-4-(((trans-4-(5-Chloro-6-methoxypyridin-3-yl)cyclohexyl)methyl)(3-(1-cyclopropyl-1H-pyrazol-4-yl)phenyl)carbamoyl)cyclohexyl methylcarbamate | 620.4 |
| 5.12[3] | 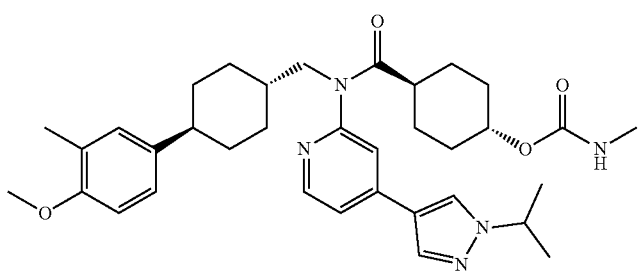 | trans-4-((4-(1-Isopropyl-1H-pyrazol-4-yl)pyridin-2-yl)((trans-4-(4-methoxy-3-methylphenyl)cyclohexyl)methyl)carbamoyl)cyclohexyl methylcarbamate | 602.5 |
| 5.13[3] | 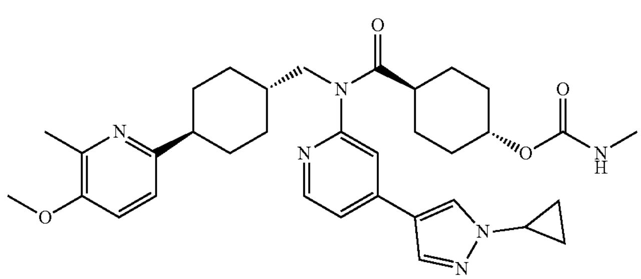 | trans-4-((4-(1-Cyclopropyl-1H-pyrazol-4-yl)pyridin-2-yl)((trans-4-(5-methoxy-6-methylpyridin-2-yl)cyclohexyl)methyl)carbamoyl)cyclohexyl methylcarbamate | 601.5 |

-continued

| Cmpd | Structure | Name | [M + H]+ |
|---|---|---|---|
| 5.14[3] | 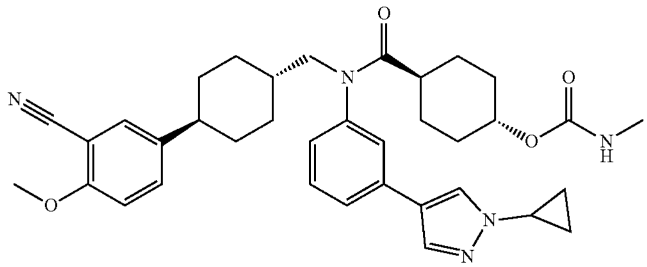 | trans-4-(((trans-4-(3-Cyano-4-methoxyphenyl)cyclohexyl)methyl)(3-(1-cyclopropyl-1H-pyrazol-4-yl)phenyl)carbamoyl)cyclohexyl methylcarbamate | 610.5 |
| 5.15[3] | 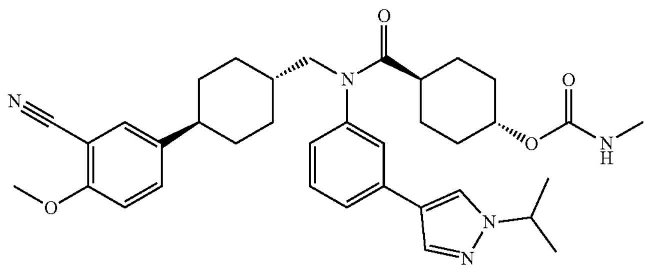 | trans-4-(((trans-4-(3-Cyano-4-methoxyphenyl)cyclohexyl)methyl)(3-(1-Isopropyl-1H-pyrazol-4-yl)phenyl)carbamoyl)cyclohexyl methylcarbamate | 612.3 |
| 5.16[3] | 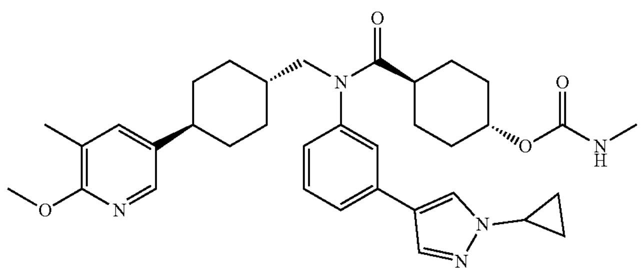 | trans-4-((3-(1-Cyclopropyl-1H-pyrazol-4-yl)phenyl)((trans-4-(6-methoxy-5-methylpyridin-3-yl)cyclohexyl)methyl)carbamoyl)cyclohexyl methylcarbamate | 600.5 |
| 5.17[3] | 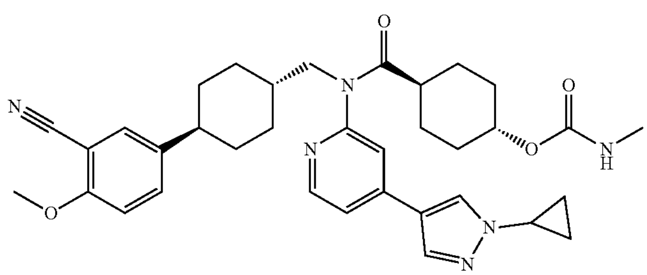 | trans-4-(((trans-4-(3-Cyano-4-methoxyphenyl)cyclohexyl)methyl)(4-(1-cyclopropyl-1H-pyrazol-4-yl)pyridin-2-yl)carbamoyl)cyclohexyl methylcarbamate | 611.5 |
| 5.18[3] | 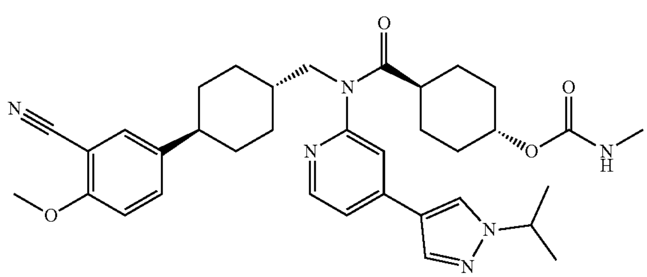 | trans-4-(((trans-4-(3-Cyano-4-methoxyphenyl)cyclohexyl)methyl)(4-(1-isopropyl-1H-pyrazol-4-yl)pyridin-2-yl)carbamoyl)cyclohexyl methylcarbamate | 613.5 |

| Cmpd | Structure | Name | [M + H]+ |
|---|---|---|---|
| 5.19[2] | 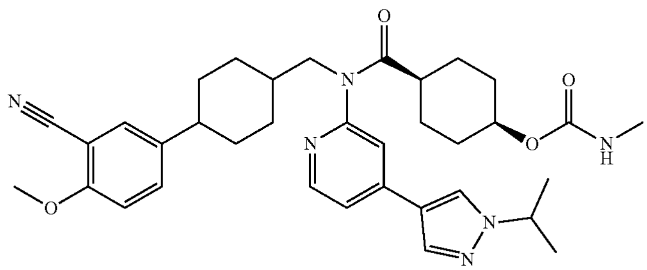 | trans-4-(((4-(3-Cyano-4-methoxyphenyl)cyclohexyl)methyl)(4-(1-isopropyl-1H-pyrazol-4-yl)pyridin-2-yl)carbamoyl)cyclohexyl methylcarbamate | 613.7 |
| 5.20[2] | 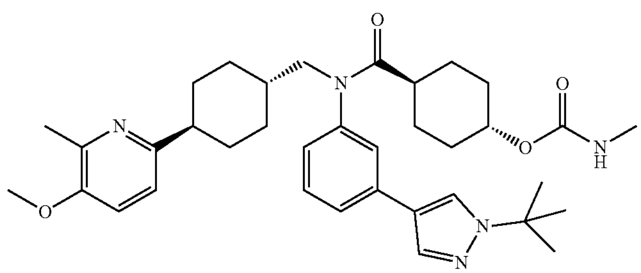 | trans-4-((3-(1-(trans-Butyl)-1H-pyrazol-4-yl)phenyl)((trans-4-(5-methoxy-6-methylpyridin-2-yl)cyclohexyl)methyl)carbamoyl)cyclohexyl methylcarbamate | 616.6 |
| 5.21[2] | 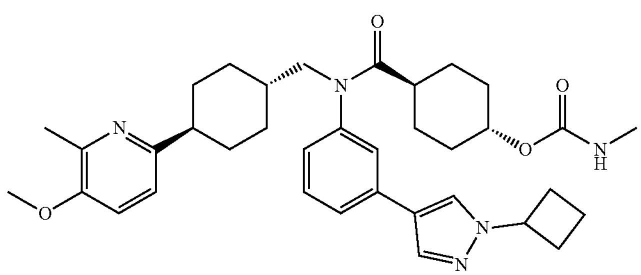 | trans-4-((3-(1-Cyclobutyl-1H-pyrazol-4-yl)phenyl)((trans-4-(5-methoxy-6-methylpyridin-2-yl)cyclohexyl)methyl)carbamoyl)cyclohexyl methylcarbamate | 614.5 |
| 5.22[2] | 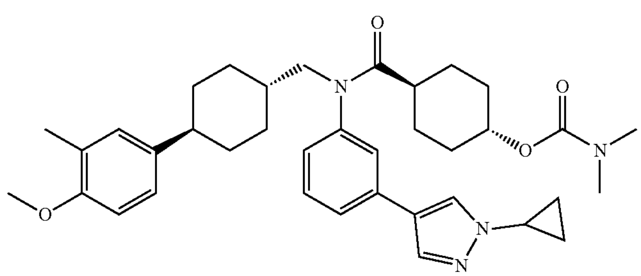 | trans-4-((3-(1-Cyclopropyl-1H-pyrazol-4-yl)phenyl)((trans-4-(4-methoxy-3-methyl phenyl)cyclohexyl)methyl)carbamoyl)cyclohexyl dimethylcarbamate | 613.5 |
| 5.23[2] | 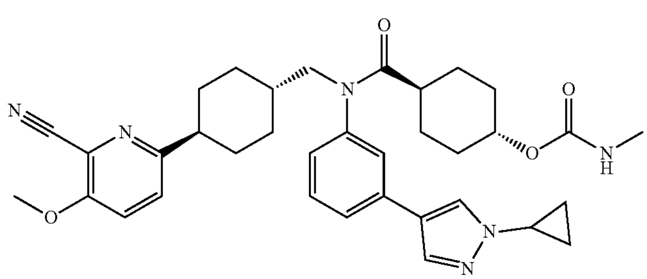 [SMILES: CNC(=O)O[C@H]1CC[C@H](C(=O)N(C[C@H]2CC[C@H](c3ccc(OC)c(C#N)n3)CC2)c2cccc(-c3cnn(C4CC4)c3)c2)CC1] | trans-4-(((trans-4-(6-Cyano-5-methoxypyridin-2-yl)cyclohexyl)methyl)(3-(1-cyclopropyl-1H-pyrazol-4-yl)phenyl)carbamoyl)cyclohexyl methylcarbamate | 611.5 |

-continued

| Cmpd | Structure | Name | [M + H]⁺ |
|---|---|---|---|
| 5.24[2] | 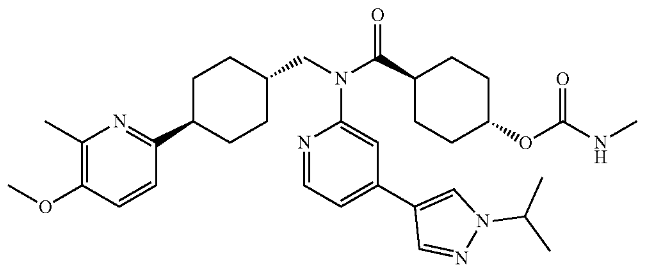 | trans-4-((4-(1-Isopropyl-1H-pyrazol-4-yl)pyridin-2-yl)((trans-4-(5-methoxy-6-methylpyridin-2-yl)cyclohexyl)methyl)carbamoyl)cyclohexyl methylcarbamate | 603.5 |
| 5.25 | 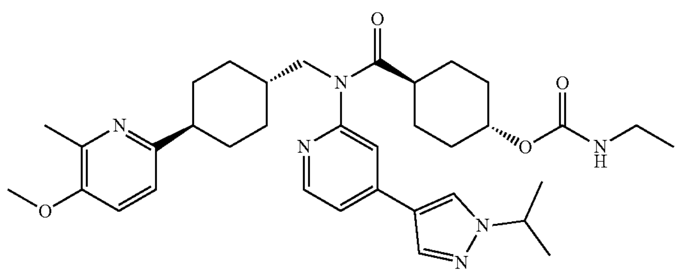 [SMILES: CCNC(=O)O[C@H]1CC[C@H](C(=O)N(C[C@H]2CC[C@H](c3ccc(OC)c(C)n3)CC2)c2cc(-c3cnn(C(C)C)c3)ccn2)CC1] | trans-4-((4-(1-Isopropyl-1H-pyrazol-4-yl)pyridin-2-yl)((trans-4-(5-methoxy-6-methylpyridin-2-yl)cyclohexyl)methyl)carbamoyl)cyclohexyl ethylcarbamate | 617.6 |
| 5.26[2] | 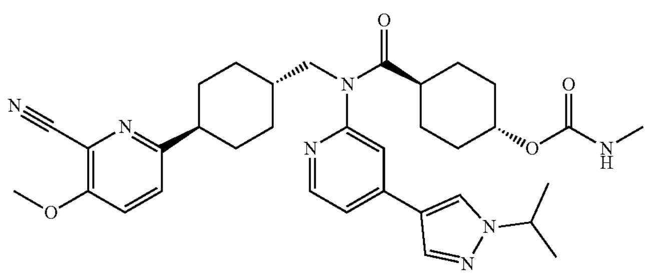 | trans-4-(((trans-4-(6-Cyano-5-methoxypyridin-2-yl)cyclohexyl)methyl)(4-(1-isopropyl-1H-pyrazol-4-yl)pyridin-2-yl)carbamoyl)cyclohexyl methylcarbamate | 614.5 |
| 5.27[2] | 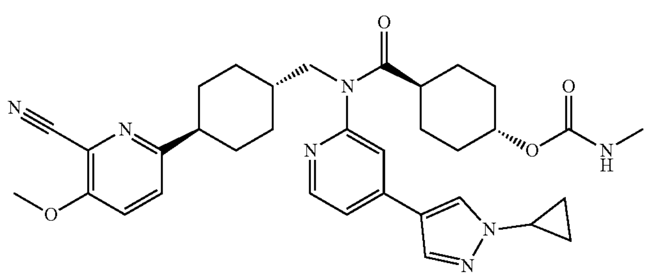 | trans-4-(((trans-4-(6-Cyano-5-methoxypyridin-2-yl)cyclohexyl)methyl)(4-(1-cyclopropyl-1H-pyrazol-4-yl)pyridin-2-yl)carbamoyl)cyclohexyl methylcarbamate | 612.5 |
| 5.28[2] | 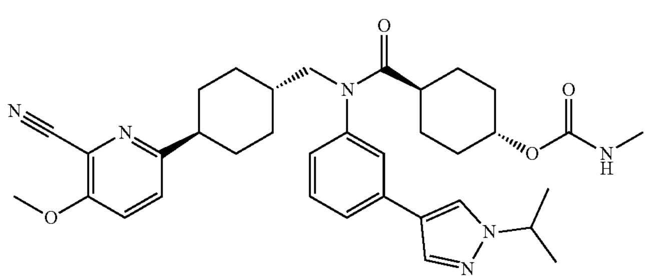 | tmm-4-(((trans-4-(6-Cyano-5-methoxypyridin-2-yl)cyclohexyl)methyl)(3-(1-isopropyl-1H-pyrazol-4-yl)phenyl)carbamoyl)cyclohexyl methylcarbamate | 613.6 |

| Cmpd | Structure | Name | [M + H]+ |
|---|---|---|---|
| 5.29[3] | 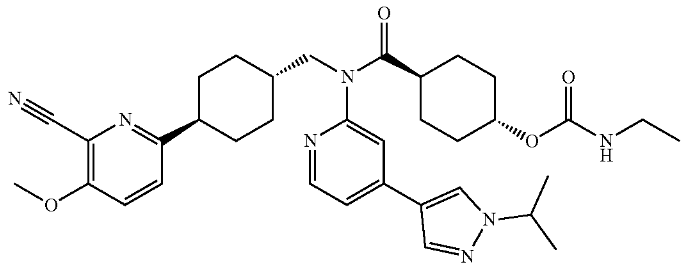 | trans-4-(((trans-4-(6-Cyano-5-methoxypyridin-2-yl)cyclohexyl)methyl)(4-(1-isopropyl-1H-pyrazol-4-yl)pyridin-2-yl)carbamoyl)cyclohexyl ethyl carbamate | 628.5 |
| 5.30[3] | 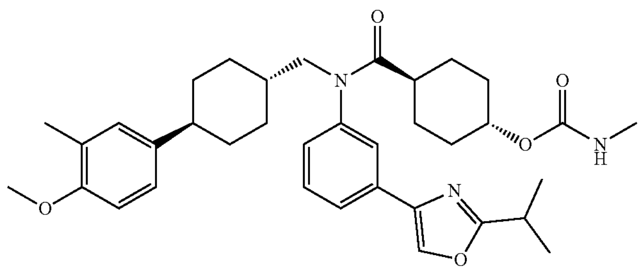 | trans-4-((3-(2-Isopropyloxazol-4-yl)phenyl)((trans-4-(4-methoxy-3-methylphenyl)cyclohexyl)methyl)carbamoyl)cyclohexyl methylcarbamate | 602.5 |
| 5.31[3] | 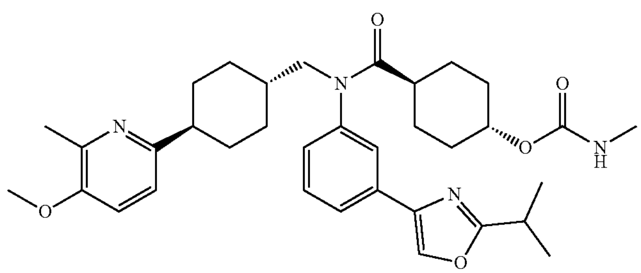 | trans-4-((3-(2-Isopropyloxazol-4-yl)phenyl)((trans-4-(5-methoxy-6-methylpyridin-2-yl)cyclohexyl)methyl)carbamoyl)cyclohexyl methylcarbamate | 603.3 |
| 5.32[3] | 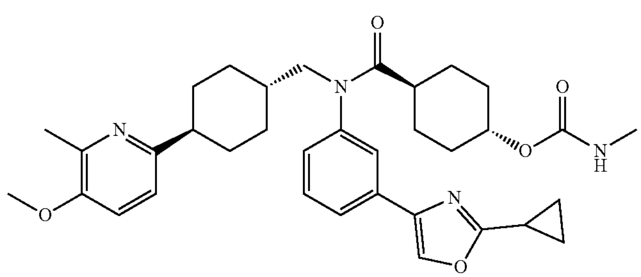 | trans-4-((3-(2-Cyclopropyloxazol-4-yl)phenyl)((trans-4-(5-methoxy-6-methylpyridin-2-yl)cyclohexyl)methyl)carbamoyl)cyclohexyl methyl carbamate | 601.5 |
| 5.33[3] | 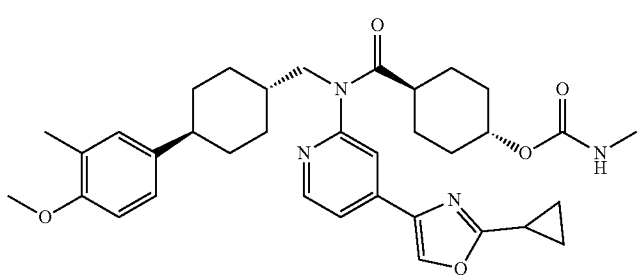 | trans-4-((4-(2-Cyclopropyloxazol-4-yl)pyridine-2-yl)((trans-4-(4-methoxy-3-methylphenyl)cyclohexyl)methyl)carbamoyl)cyclohexyl methylcarbamate | 601.5 |

-continued

| Cmpd | Structure | Name | [M + H]+ |
|---|---|---|---|
| 5.34[3] | 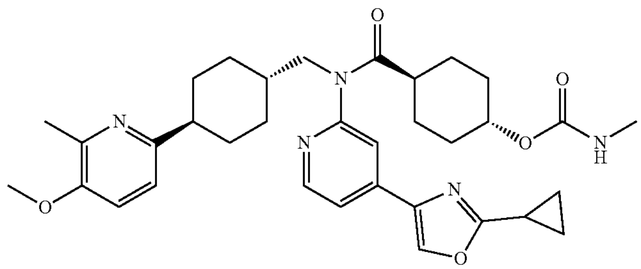 | trans-4-((4-(2-Cyclopropyloxazol-4-yl)pyridine-2-yl)((trans-4-(5-methoxy-6-methylpyridin-2-yl)cyclohexyl)methyl)carbamoyl)cyclohexyl methylcarbamate | 602.5 |
| 5.35[3] | 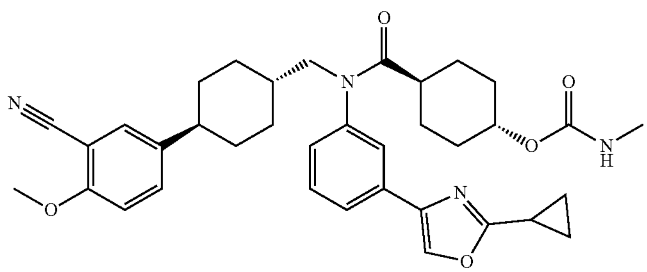 | trans-4-(((trans-4-(3-Cyano-4-methoxyphenyl)cyclohexyl)methyl)(3-(2-cyclopropyloxazol-4-yl)phenyl)carbamoyl)cyclohexyl methylcarbamate | 611.5 |
| 5.36[2] | 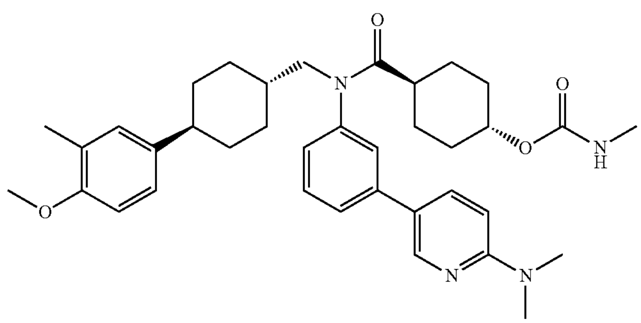 | trans-4-((3-(6-(Dimethylamino)pyridine-3-yl)phenyl)((trans-4-(4-methoxy-3-methylphenyl)cyclohexyl)methyl)carbamoyl)cyclohexyl methylcarbamate | 613.6 |
| 5.37[2] | 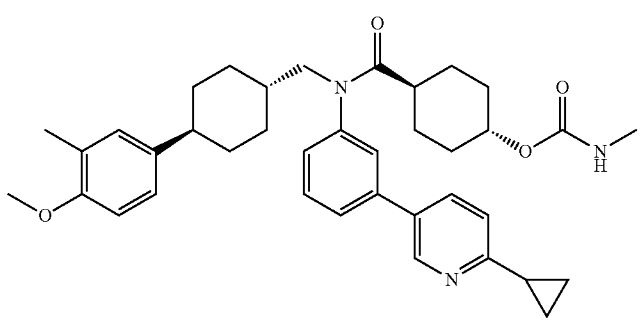 | trans-4-((3-(6-Cyclopropyl pyridin-3-yl)phenyl)((trans-4-(4-methoxy-3-methylphenyl)cyclohexyl)methyl)carbamoyl)cyclohexyl methylcarbamate | 610.5 |
| 5.38[2] | 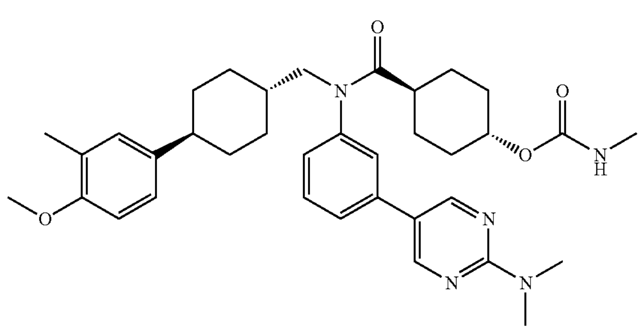 | trans-4-((3-(2-(Dimethylamino)pyrimidin-5-yl)phenyl)((trans-4-(4-methoxy-3-methylphenyl)cyclohexyl)methyl)carbamoyl)cyclohexyl methylcarbamate | 614.6 |

-continued

| Cmpd | Structure | Name | [M + H]⁺ |
|---|---|---|---|
| 5.39² | | trans-4-(((trans-4-(3-Cyano-4-methoxyphenyl)cyclohexyl)methyl)(4-(2-cyclopropyloxazol-4-yl)pyridine-2-yl)carbamoyl)cyclohexyl methylcarbamate | 612.5 |
| 5.40² | | trans-4-((6-(Dimethylamino)-[3,4'-bipyridin]-2'-yl)((trans-4-(4-methoxy-3-methylphenyl)cyclohexyl)methyl)carbamoyl)cyclohexyl methylcarbamate | 614.5 |
| 5.41² | | trans-4-((3-(6-(Dimethylamino)pyridine-3-yl)phenyl)((trans-4-(5-methoxy-6-methylpyridin-2-yl)cyclohexyl)methyl)carbamoyl)cyclohexyl methylcarbamate | 614.5 |
| 5.42² | | trans-4-(((trans-4-(6-Cyano-5-methoxypyridin-2-yl)cyclohexyl)methyl)(3-(2-cyclopropyloxazol-4-yl)phenyl)carbamoyl)cyclohexyl methylcarbamate | 612.7 |
| 5.43² | | trans-4-((4-(2-Isopropyloxazol-4-yl)pyridine-2-yl)((trans-4-(5-methoxy-6-methylpyridin-2-yl)cyclohexyl)methyl)carbamoyl)cyclohexyl methylcarbamate | 604.5 |

-continued

| Cmpd | Structure | Name | [M + H]+ |
|---|---|---|---|
| 5.44[2] | 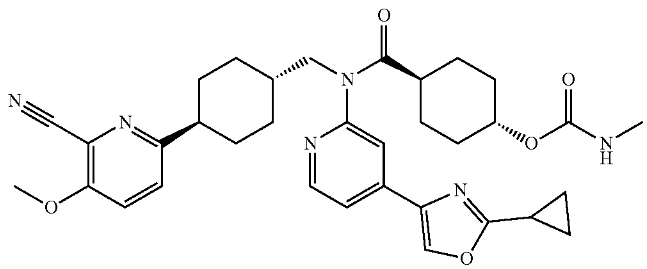 | trans-4-(((trans-4-(6-Cyano-5-methoxypyridin-2-yl)cyclohexyl)methyl)(4-(2-cyclopropyloxazol-4-yl)pyridine-2-yl)carbamoyl)cyclohexyl methylcarbamate | 613.5 |
| 5.45[2] | 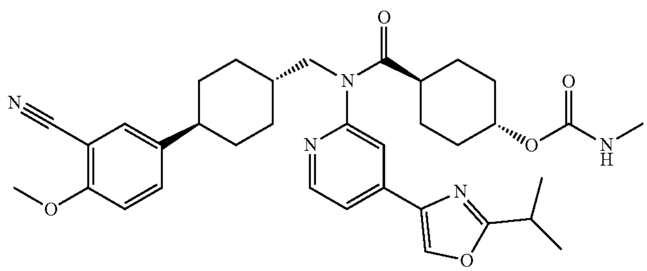 | trans-4-(((trans-4-(3-Cyano-4-methoxyphenyl)cyclo-hexyl)methyl)(4-(2-isopropyloxazol-4-yl)pyridine-2-yl)carbamoyl)cyclohexyl methylcarbamate | 614.5 |
| 5.46[2] | 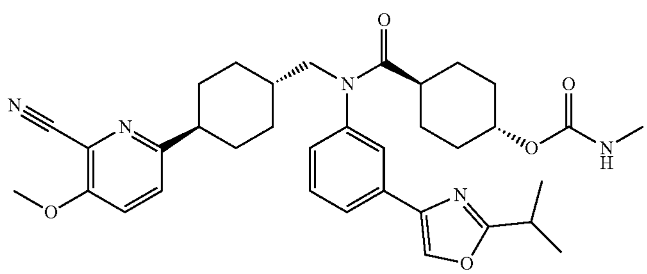 | trans-4-(((trans-4-(6-Cyano-5-methoxypyridin-2-yl)cyclohexyl)methyl)(3-(2-isopropyloxazol-4-yl)phenyl)carbamoyl)cyclohexyl methylcarbamate | 614.4 |
| 5.47 | 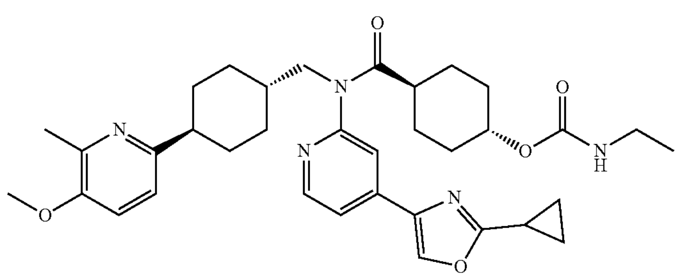 [SMILES: CCNC(=O)O[C@H]1CC[C@H](C(=O)N(C[C@H]2CC[C@H](c3ccc(OC)c(C)n3)CC2)c2cc(-c3coc(C4CC4)n3)ccn2)CC1] | trans-4-((4-(2-Cyclopropyloxazol-4-yl)pyridine-2-yl)((trans-4-(5-methoxy-6-methylpyridin-2-yl)cyclohexyl)methyl)carbamoyl)cyclohe xyl ethylcarbamate | 616.5 |
| 5.48[4] | 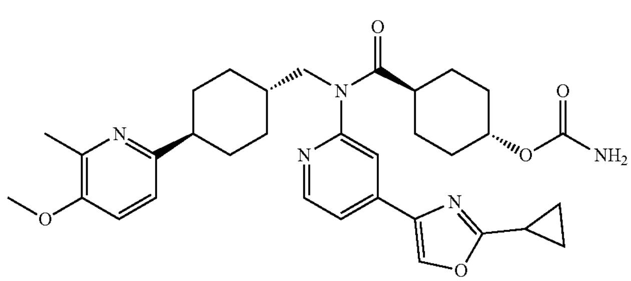 [SMILES: COc1ccc([C@H]2CC[C@H](CN(c3cc(-c4coc(C5CC5)n4)ccn3)C(=O)[C@H]3CC[C@H](OC(N)=O)CC3)CC2)nc1C] | trans-4-((4-(2-Cyclopropyloxazol-4-yl)pyridine-2-yl)((trans-4-(5-methoxy-6-methylpyridin-2-yl)cyclohexyl)methyl)carbamoyl)cyclohe xyl carbamate | 588.4 |

| Cmpd | Structure | Name | [M + H]⁺ |
|---|---|---|---|
| 5.49[6] | 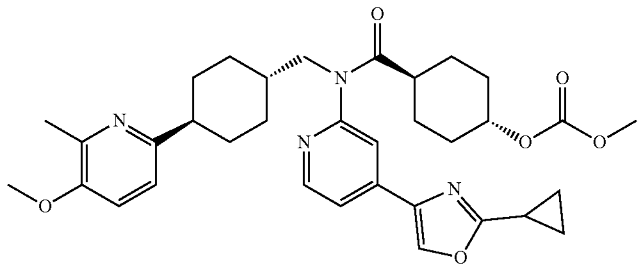 | trans-4-((4-(2-Cyclopropyloxazol-4-yl)pyridine-2-yl)((trans-4-(5-methoxy-6-methylpyridin-2-yl)cyclohexyl)methyl)carbamoyl)cyclohexyl methyl carbonate | 603.4 |
| 5.50[2] | 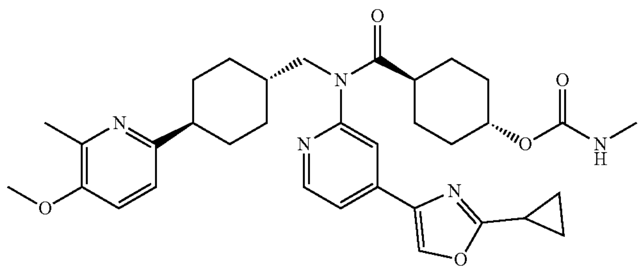 | trans-4-((4-(2-Cyclopropyloxazol-4-yl)pyridine-2-yl)((trans-4-(6-methoxy-5-methylpyridin-3-yl)cyclohexyl)methyl)carbamoyl)cyclohexyl methyl carbamate | 602.4 |
| 5.51[2] | 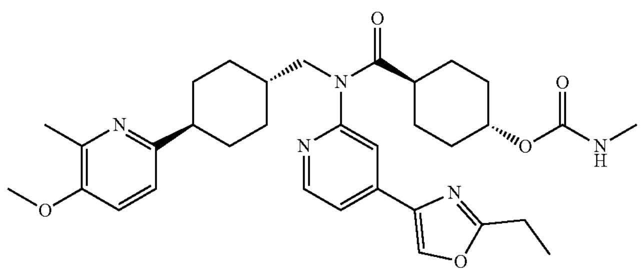 | trar/75-4-((4-(2-Ethyloxazol-4-yl)pyridin-2-yl)((7raR.v-4-(5-methoxy-6-methylpyridin-2-yl)cyclohexyl)methyl)carbamoyl)cyclohexyl methylcarbamate | 590.5 |
| 5.52[2] | 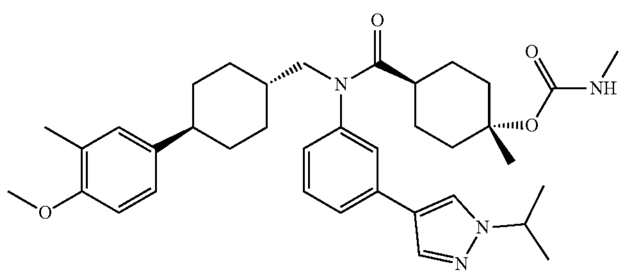 | trans-4-((3-(1-Isopropyl-1H-pyrazol-4-yl)phenyl)((trans-4-(4-methoxy-3-methylphenyl)cyclohexyl)methyl)carbamoyl)-1-methylcyclohexyl methylcarbamate | 615.4 |
| 5.53[2] | 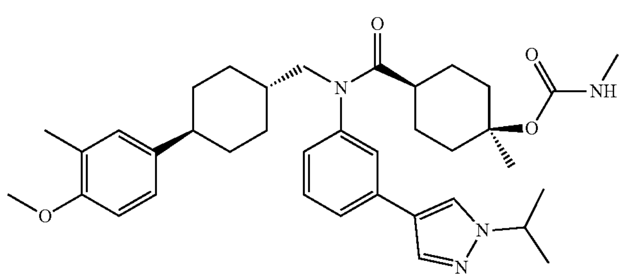 | trans-4-((3-(1-Isopropyl-1H-pyrazol-4-yl)phenyl)((trans-4-(4-methoxy-3-methylphenyl)cyclohexyl)methyl)carbamoyl)-1-methylcyclohexyl methylcarbamate | 615.5 |

Acyl-imidazole formation:
[1]DMF as solvent. Carbamate formation:
[2]M methylamine in THF;
[3]40% methylamine in CH₃OH;
[4]7 M ammonia in CH₃OH;
[5]Stirred at rt for 4 h, heated at 80° C. for 1 h, and then stirred at rt for 1 h.
[6]Isolated during the purification of Compound 5.48.

Compound 6

Trans-4-((4-(2-Isopropyloxazol-4-yl)pyridine-2-yl)((trans-4-(5-methoxy-6-methylpyridin-2-yl)cyclohexyl)methyl)carbamoyl)cyclohexyl morpholine-4-carboxylate

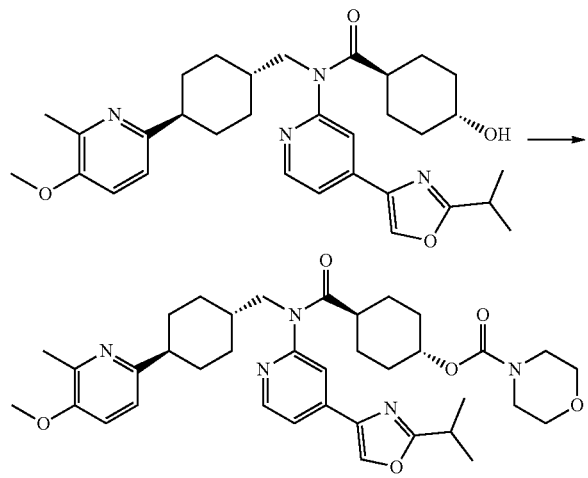

Intermediate 32.13 (98 mg, 0.18 mmol) and CDI (45 mg, 0.28 mmol) were dissolved in CH₃CN (2 mL). The reaction was heated at 80° C. for 15.5 h. Additional CDI (11 mg, 0.068 mmol) was added at rt. The reaction was heated at 80° C. for 1 h and then allowed to cool to rt. A portion of the reaction (1 mL, 0.090 mmol) was added to morpholine (80 µL, 0.915 mmol). The reaction was stirred at rt for 72 h and then diluted with EtOAc (20 mL). The organics were washed with water (20 mL), washed with brine (20 mL), dried (Na₂SO₄), filtered, concentrated, and then purified by silica gel chromatography (0-5% CH₃OH in CH₂Cl₂) to give trans-4-((4-(2-isopropyloxazol-4-yl)pyridine-2-yl)((trans-4-(5-methoxy-6-methylpyridin-2-yl)cyclohexyl)methyl)carbamoyl)cyclohexyl morpholine-4-carboxylate (52 mg, 8800 yield) as an off-white foam. ¹H NM/R (400 MHz, DMSO-d₆): δ 8.85 (s, 1H), 8.55 (d, 1H), 7.71 (s, 1H), 7.70 (d, 1H), 7.18 (d, 1H), 6.97 (d, 1H), 4.48-4.38 (m, 1H), 3.80 (s, 3H), 3.73-3.65 (m, 2H), 3.58-3.42 (m, 4H), 3.30-3.22 (m, 4H), 3.22-3.12 (m, 1H), 2.50-2.42 (m, 1H), 2.28 (s, 3H), 2.28-2.20 (m, 1H), 1.96-1.85 (m, 2H), 1.85-1.72 (m, 6H), 1.58-1.42 (m, 3H), 1.41-1.26 (m, 8H), 1.12-0.96 (in, 4H); LCMS: 660.6 [M+H]⁺.

The Compounds below were synthesized from the appropriate Intermediate and the appropriate amine following the procedure described for Compound 6.

| Cmpd | Structure | Name | [M + H]+ |
|---|---|---|---|
| 6.01[1] | 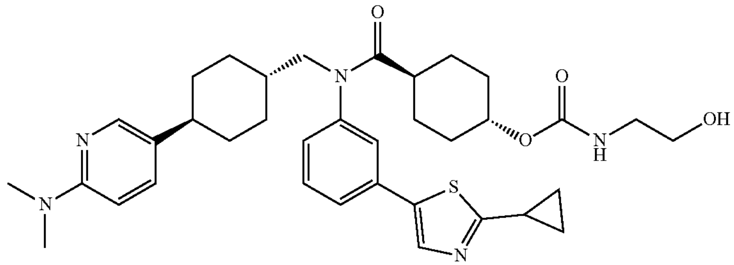 [SMILES: CN(C)c1ccc([C@H]2CC[C@H](CN(c3cccc(-c4cnc(C5CC5)s4)c3)C(=O)[C@H]3CC[C@H](OC(=O)NCCO)CC3)CC2)cn1] | 4-((3-(2-Cyclopropylthiazol-5-yl)phenyl)((trans-4-(6-(dimethylamino)pyridin-3-yl)cyclohexyl)methyl)carbamoyl)cyclohexyl (2-hydroxyethyl)trans-carbamate | 646.5 |
| 6.02 | 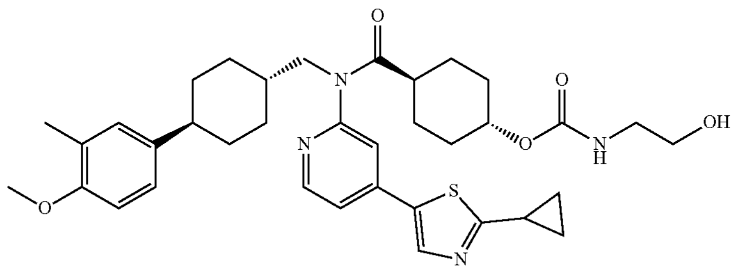 [SMILES: COc1ccc([C@H]2CC[C@H](CN(c3cc(-c4cnc(C5CC5)s4)ccn3)C(=O)[C@H]3CC[C@H](OC(=O)NCCO)CC3)CC2)cc1C] | trans-4-(4-(2-Cyclopropyl thiazol-5-yl)pyridin-2-yl)((trans-4-(4-methoxy-3-methylphenyl)cyclohexyl)methyl)carbamoyl)cyclohexyl (2-hydroxyethyl)carbamate | 647.5 |
| 6.03 | 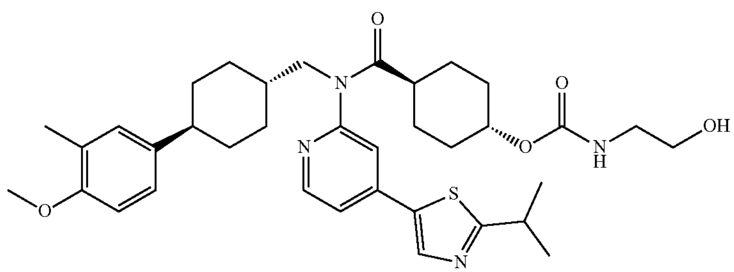 [SMILES: COc1ccc([C@H]2CC[C@H](CN(c3cc(-c4cnc(C(C)C)s4)ccn3)C(=O)[C@H]3CC[C@H](OC(=O)NCCO)CC3)CC2)cc1C] | trans-4-((4-(2-Isopropylthiazol-5-yl)pyridin-2-yl)((trans-4-(4-methoxy-3-methyl phenyl)cyclohexyl)methyl)carbamoyl)cyclohexyl (2-hydroxyethyl)carbamate | 649.6 |

-continued

| Cmpd | Structure | Name | [M + H]+ |
|---|---|---|---|
| 6.04 | 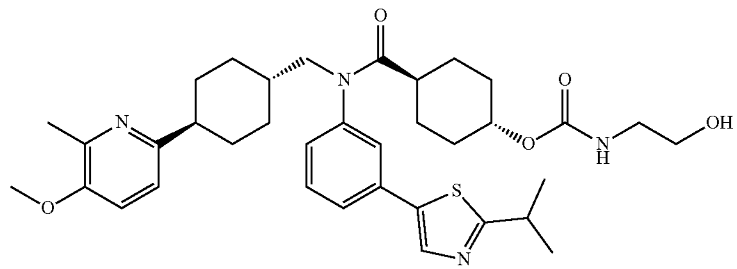 [SMILES: COc1ccc([C@H]2CC[C@H](CN(c3cccc(-c4cnc(C(C)C)s4)c3)C(=O)[C@H]3CC[C@H](OC(=O)NCCO)CC3)CC2)nc1C] | trans-4-((3-(2-Isopropylthiazol-5-yl)phenyl)((trans-4-(5-methoxy-6-methylpyridin-2-yl)cyclohexyl)methyl)carbamoyl)cyclohexyl (2-hydroxyethyl)carbamate | 649.6 |
| 6.05 | 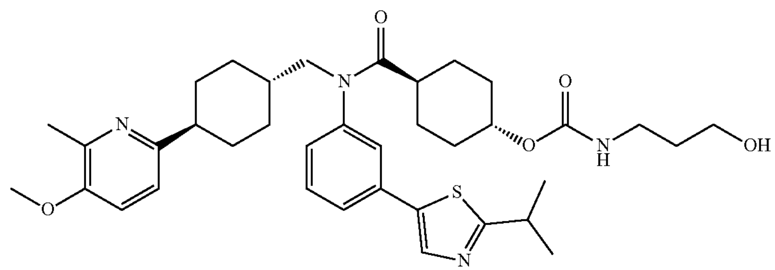 [SMILES: COc1ccc([C@H]2CC[C@H](CN(c3cccc(-c4cnc(C(C)C)s4)c3)C(=O)[C@H]3CC[C@H](OC(=O)NCCCO)CC3)CC2)nc1C] | trans-4-((3-(2-Isopropylthiazol-5-yl)phenyl)((trans-4-(5-methoxy-6-methylpyridin-2-yl)cyclohexyl)methyl)carbamoyl)cyclohexyl (3-hydroxypropyl)carbamate | 663.5 |
| 6.06 | 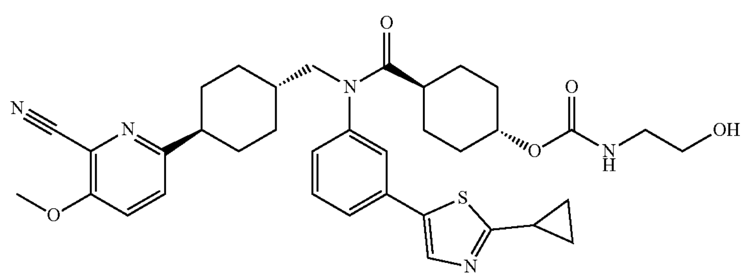 [SMILES: COc1ccc([C@H]2CC[C@H](CN(c3cccc(-c4cnc(C5CC5)s4)c3)C(=O)[C@H]3CC[C@H](OC(=O)NCCO)CC3)CC2)nc1C#N] | trans-4-(((trans-4-(6-Cyano-5-methoxy pyridin-2-yl)cyclohexyl)methyl)(3-(2-cyclopropylthiazol-5-yl)phenyl)carbamoyl)cyclohexyl (2-hydroxyethyl)carbamate | 658.6 |

| Cmpd | Structure | Name | [M + H]⁺ |
|---|---|---|---|
| 6.07 | 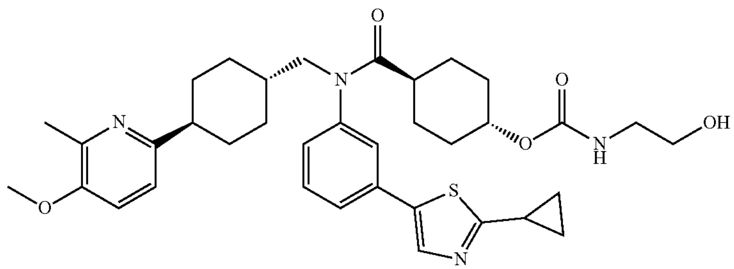 [SMILES: COc1ccc([C@H]2CC[C@H](CN(c3cccc(-c4cnc(C5CC5)s4)c3)C(=O)[C@H]3CC[C@H](OC(=O)NCCO)CC3)CC2)nc1C] | trans-4-((3-(2-Cyclopropylthiazol-5-yl)phenyl)((trans-4-(5-methoxy-6-methylpyridin-2-yl)cyclohexyl)methyl)carbamoyl)cyclohexyl (2-hydroxyethyl)carbamate | 647.5 |
| 6.08[1] | 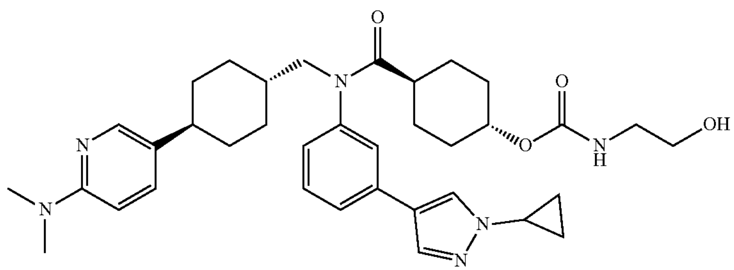 [SMILES: CN(C)c1ccc([C@H]2CC[C@H](CN(c3cccc(-c4cnn(C5CC5)c4)c3)C(=O)[C@H]3CC[C@H](OC(=O)NCCO)CC3)CC2)cn1] | trans-4-((3-(1-Cyclopropyl-1H-pyrazol-4-yl)phenyl)((trans-4-(6-(dimethylamino)pyridin-3-yl)cyclohexyl)methyl)carbamoyl)cyclohexyl (2-hydroxyethyl)carbamate | 629.5 |
| 6.09 | 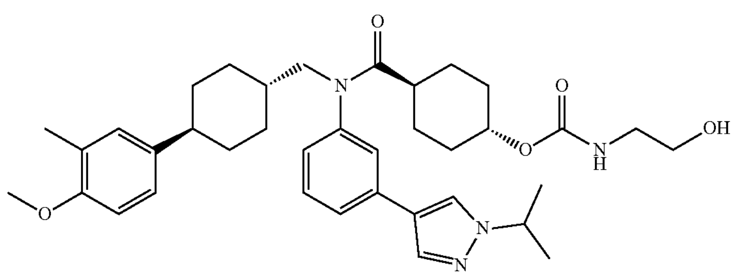 [SMILES: COc1ccc([C@H]2CC[C@H](CN(c3cccc(-c4cnn(C(C)C)c4)c3)C(=O)[C@H]3CC[C@H](OC(=O)NCCO)CC3)CC2)cc1C] | trans-4-((3-(1-Isopropyl-1H-pyrazol-4-yl)phenyl)((trans-4-(4-methoxy-3-methylphenyl)cyclohexyl)methyl)carbamoyl)cyclohexyl (2-hydroxyethyl)carbamate | 631.5 |

| Cmpd | Structure | Name | [M + H]⁺ |
|---|---|---|---|
| 6.10² | | trans-4-((3-(1-Cyclopropyl-1H-pyrazol-4-yl)phenyl)((trans-4-(4-methoxy-3-methylphenyl)cyclohexyl)methyl)carbamoyl)cyclohexyl (2-methoxyethyl)carbamate | 643.5 |
| 6.11 | 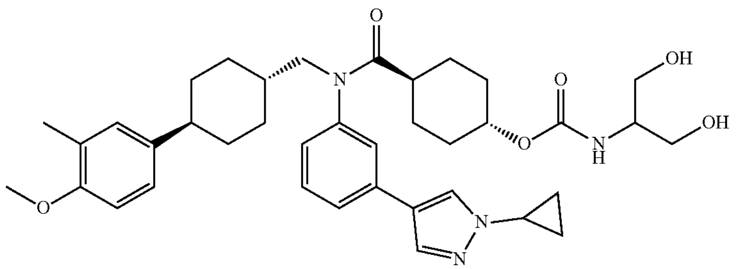 [SMILES: COc1ccc([C@H]2CC[C@H](CN(c3cccc(-c4cnn(C5CC5)c4)c3)C(=O)[C@H]3CC[C@H](OC(=O)NC(CO)CO)CC3)CC2)cc1C] | trans-4-((3-(1-Cyclopropyl-1H-pyrazol-4-yl)phenyl)((trans-4-(4-methoxy-3-methylphenyl)cyclohexyl)methyl)carbamoyl)cyclohexyl (1,3-dihydroxypropan-2-yl)carbamate | 659.5 |
| 6.12 | 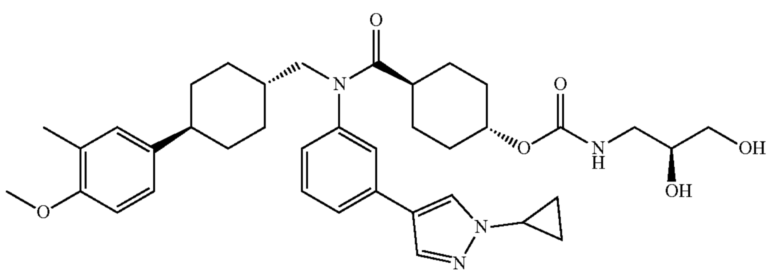 | trans-4-((3-(1-Cyclopropyl-1H-pyrazol-4-yl)phenyl)((trans-4-(4-methoxy-3-methylphenyl)cyclohexyl)methyl)carbamoyl)cyclohexyl ((S)-2,3-dihydroxypropyl)carbamate | 659.5 |

| Cmpd | Structure | Name | [M + H]+ |
|---|---|---|---|
| 6.13 | 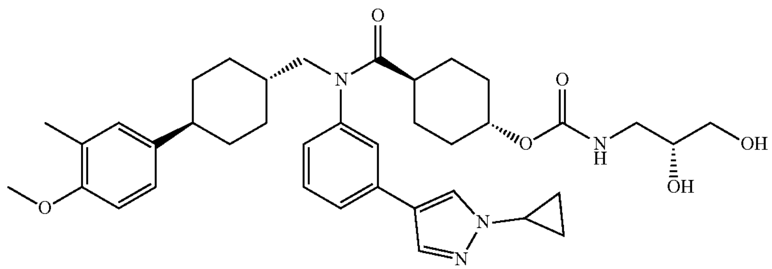 [SMILES: COc1ccc([C@H]2CC[C@H](CN(c3cccc(-c4cnn(C5CC5)c4)c3)C(=O)[C@H]3CC[C@H](OC(=O)NC[C@@H](O)CO)CC3)CC2)cc1C] | trans-4-((3-(1-Cyclopropyl-1H-pyrazol-4-yl)phenyl)((trans-4-(4-methoxy-3-methyl phenyl)cyclohexyl)methyl)carbamoyl)cyclohexyl ((R)-2,3-dihydroxypropyl)carbamate | 659.7 |
| 6.14 | 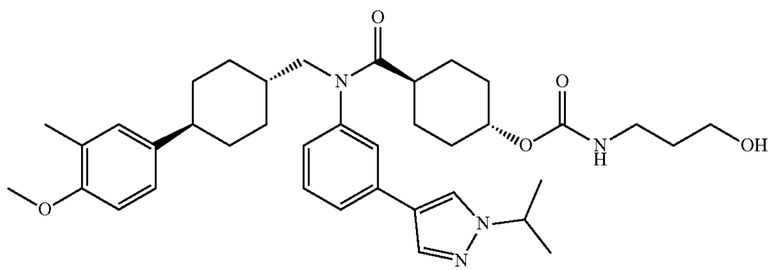 | trans-4-((3-(1-Isopropyl-1H-pyrazol-4-yl)phenyl)((trraH.v-4-(4-methoxy-3-methylphenyl)cyclohexyl)methyl)carbamoyl)cyclohexyl (3-hydroxypropyl)carbamate | 645.4 |
| 6.15 | 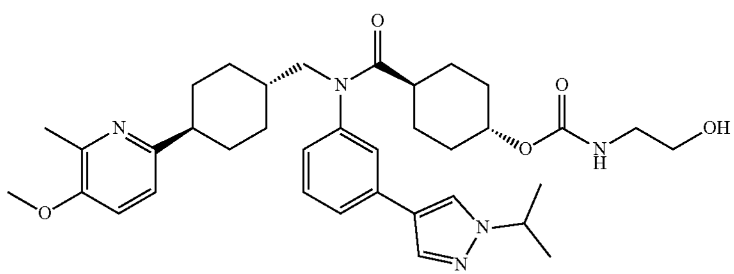 | trans-4-((3-(1-Isopropyl-1H-pyrazol-4-yl)phenyl)((trans-4-(5-methoxy-6-methylpyridin-2-yl)cyclohexyl)methyl)carbamoyl)cyclohexyl (2-hydroxyethyl)carbamate | 632.5 |

| Cmpd | Structure | Name | [M + H]+ |
|---|---|---|---|
| 6.16 | 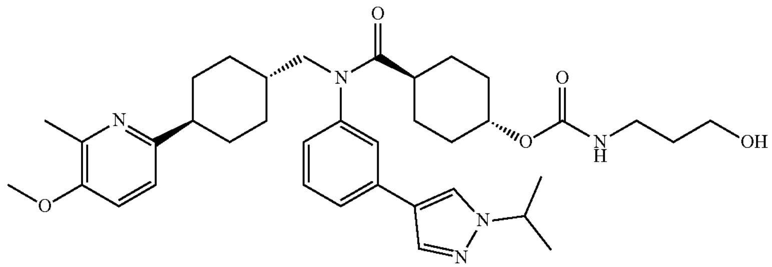 | trans-4-((3-(1-Isopropyl-1H-pyrazol-4-yl)phenyl)(trans-4-(5-methoxy-6-methylpyridin-2-yl)cyclohexyl)methyl)carbamoyl)cyclohexyl (3-hydroxypropyl)carbamate | 646.5 |
| 6.17 | 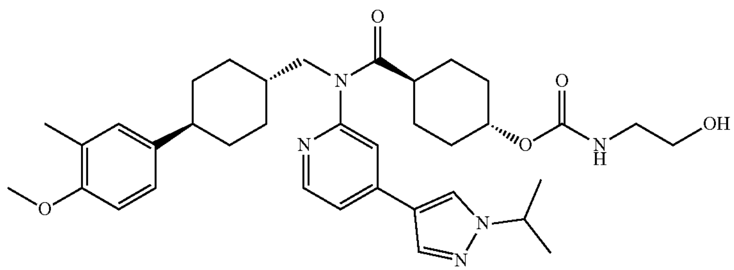 | trans-4-((4-(1-Isopropyl-1H-pyrazol-4-yl)pyridin-2-yl)(trans-4-(4-methoxy-3-methylphenyl)cyclohexyl)methyl)carbamoyl)cyclohexyl (2-hydroxyethyl)carbamate | 632.5 |
| 6.18 | 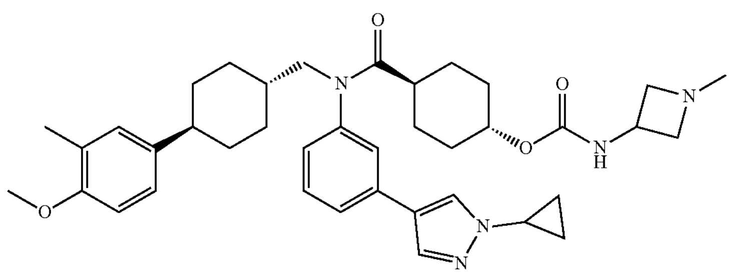 | trans-4-((3-(1-Cyclopropyl-1H-pyrazol-4-yl)phenyl)(trans-4-(4-methoxy-3-methylphenyl)cyclohexyl)methyl)carbamoyl)cyclohexyl (1-methyl azetidin-3-yl)carbamate | 654.5 |

| Cmpd | Structure | Name | [M + H]+ |
|---|---|---|---|
| 6.19 | 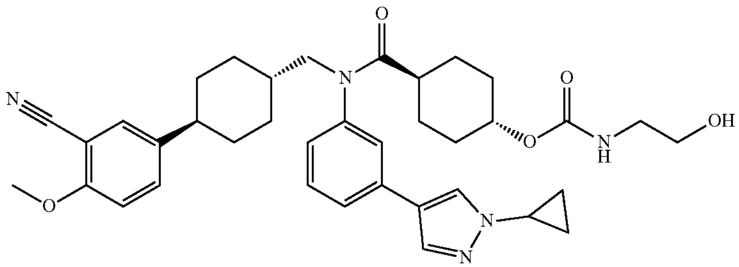 [SMILES: COc1ccc([C@H]2CC[C@H](CN(c3cccc(-c4cnn(C5CC5)c4)c3)C(=O)[C@H]3CC[C@H](OC(=O)NCCO)CC3)CC2)cc1C#N] | trans-4-(((trans-4-(3-Cyano-4-methoxyphenyl)cyclohexyl)methyl)(3-(1-cyclopropyl-1H-pyrazol-4-yl)phenyl)carbamoyl)cyclohexyl (2-hydroxyethyl)carbamate | 662.5 |
| 6.20 | 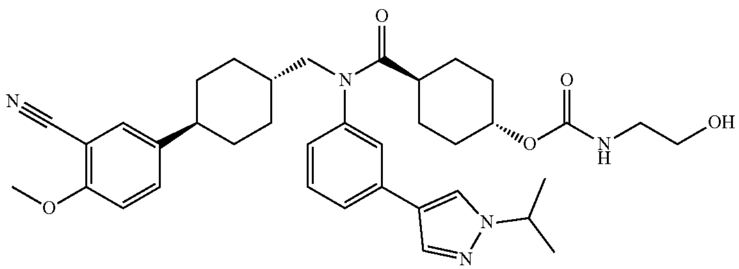 [SMILES: COc1ccc([C@H]2CC[C@H](CN(c3cccc(-c4cnn(C(C)C)c4)c3)C(=O)[C@H]3CC[C@H](OC(=O)NCCO)CC3)CC2)cc1C#N] | trans-4-(((trans-4-(3-Cyano-4-methoxyphenyl)cyclohexyl)methyl)(3-(1-isopropyl-1H-pyrazol-4-yl)phenyl)carbamoyl)cyclohexyl (2-hydroxyethyl)carbamate | |
| 6.21 | 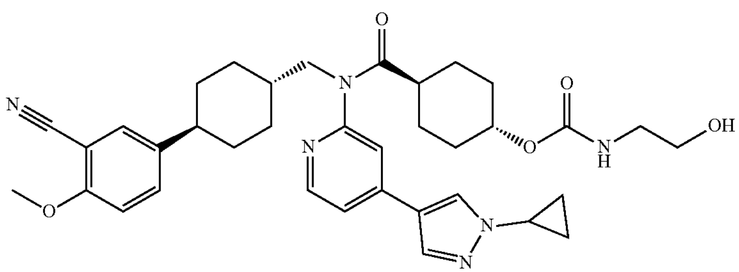 | trans-4-(((trans-4-(3-Cyano-4-methoxyphenyl)cyclohexyl)methyl)(4-(1-cyclopropyl-1H-pyrazol-4-yl)pyridin-2-yl)carbamoyl)cyclohexyl (2-hydroxyethyl)carbamate | 641.5 |

-continued

| Cmpd | Structure | Name | [M + H]+ |
|---|---|---|---|
| 6.22 | 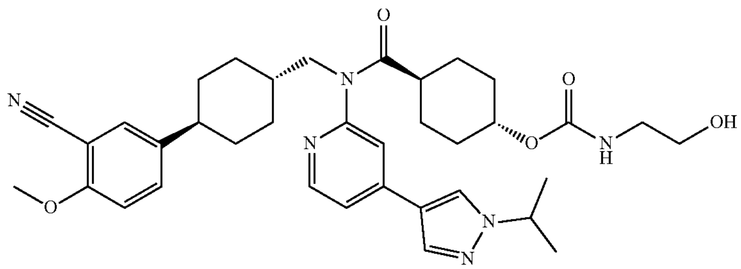 [SMILES: COc1ccc([C@H]2CC[C@H](CN(c3cc(-c4cnn(C(C)C)c4)ccn3)C(=O)[C@H]3CC[C@H](OC(=O)NCCO)CC3)CC2)cc1C#N] | trans-4-(((trans-4-(3-Cyano-4-methoxyphenyl)cyclohexyl)methyl)(4-(1-isopropyl-1H-pyrazol-4-yl)pyridin-2-yl)carbamoyl)cyclohexyl (2-hydroxyethyl)carbamate | 643.5 |
| 6.23 | 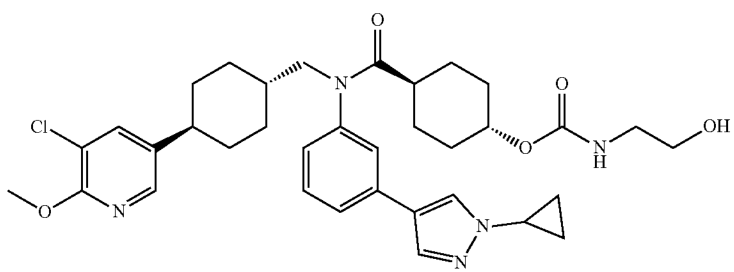 [SMILES: COc1ncc([C@H]2CC[C@H](CN(c3cccc(-c4cnn(C5CC5)c4)c3)C(=O)[C@H]3CC[C@H](OC(=O)NCCO)CC3)CC2)cc1Cl] | trans-4-(((trans-4-(5-Chloro-6-methoxypyridin-3-yl)cyclohexyl)methyl)(3-(1-cyclopropyl-1H-pyrazol-4-yl)phenyl)carbamoyl)cyclohexyl (2-hydroxyethyl)carbamate | 650.3 |
| 6.24 | 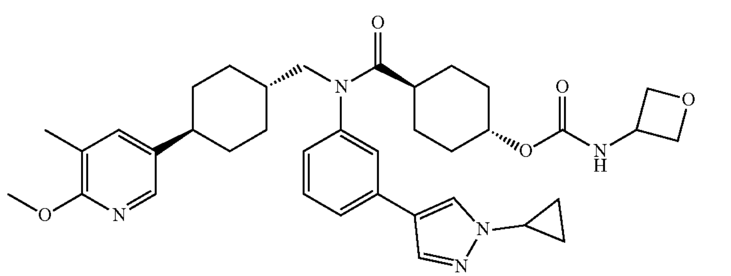 [SMILES: COc1ncc([C@H]2CC[C@H](CN(c3cccc(-c4cnn(C5CC5)c4)c3)C(=O)[C@H]3CC[C@H](OC(=O)NC4COC4)CC3)CC2)cc1C] | trans-4-((3-(1-Cyclopropyl-1H-pyrazol-4-yl)phenyl)((trans-4-(4-methoxy-3-methylphenyl)cyclohexyl)methyl)carbamoyl)cyclohexyl oxetan-3-ylcarbamate | 641.6 |

| Cmpd | Structure | Name | [M + H]+ |
|---|---|---|---|
| 6.25 | 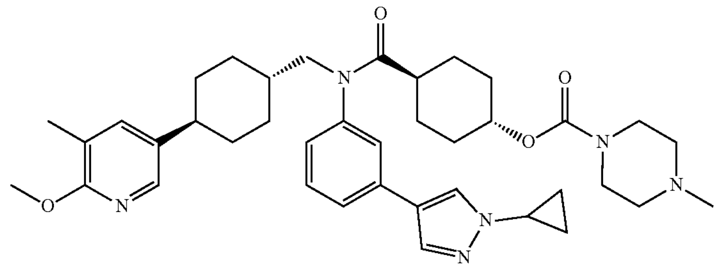 | trans-4-((3-(1-Cyclopropyl-1H-pyrazol-4-yl)phenyl)((trans-4-(4-methoxy-3-methylphenyl)cyclohexyl)methyl)carbamoyl)cyclohexyl 4-methylpiperazine-1-carboxylate | 668.5 |
| 6.26 | 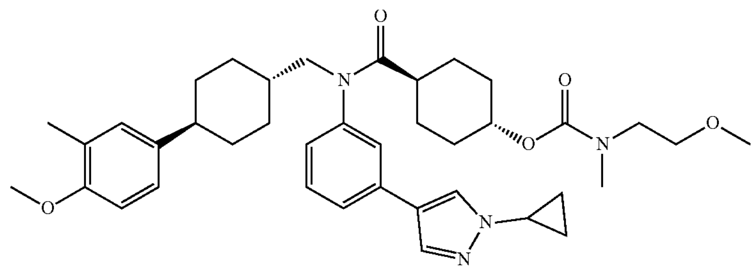 | trans-4-((3-(1-Cyclopropyl-1H-pyrazol-4-yl)phenyl)((trans-4-(4-methoxy-3-methylphenyl)cyclohexyl)methyl)carbamoyl)cyclohexyl (2-methoxyethyl)(methyl)carbamate | 679.6 M + Na |
| 6.27 | 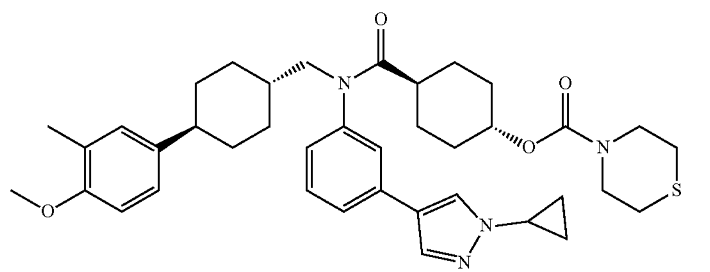 | trans-4-((3-(1-Cyclopropyl-1H-pyrazol-4-yl)phenyl)((trans-4-(4-methoxy-3-methylphenyl)cyclohexyl)methyl)carbamoyl)cyclohexyl thiomorpholine-4-carboxylate | 671.5 |

| Cmpd | Structure | Name | [M + H]⁺ |
|---|---|---|---|
| 6.28 | 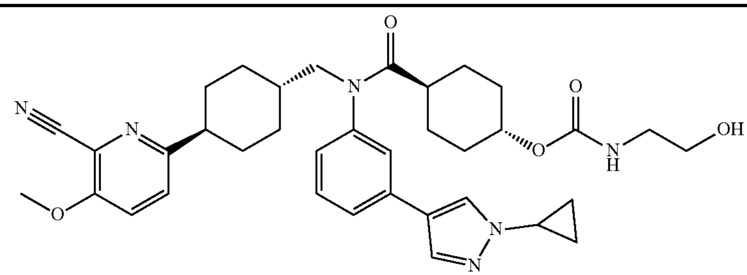 | trans-4-(((trans-4-(6-Cyano-5-methoxypyridin-2-yl)cyclohexyl)methyl)(3-(1-cyclopropyl-1H-pyrazol-4-yl)phenyl)carbamoyl)cyclohexyl (2-hydroxyethyl)carbamate | 641.7 |
| 6.29 | 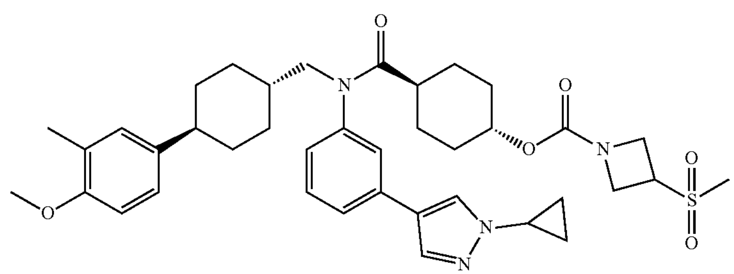 | trans-4-((3-(1-Cyclopropyl-1H-pyrazol-4-yl)phenyl)((trans-4-(4-methoxy-3-methylphenyl)cyclohexyl)methyl)carbamoyl)cyclohexyl 3-(methylsulfonyl)azetidine-1-carboxylate | 703.6 |
| 6.30 | 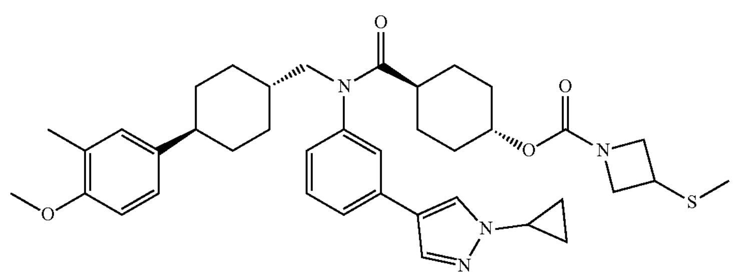 | trans-4-((3-(1-Cyclopropyl-1H-pyrazol-4-yl)phenyl)(trans-4-(4-methoxy-3-methylphenyl)cyclohexyl)methyl)carbamoyl)cyclohexyl 3-(methylthio)azetidine-1-carboxylate | 671.5 |

| Cmpd | Structure | Name | [M + H]+ |
|---|---|---|---|
| 6.31 | 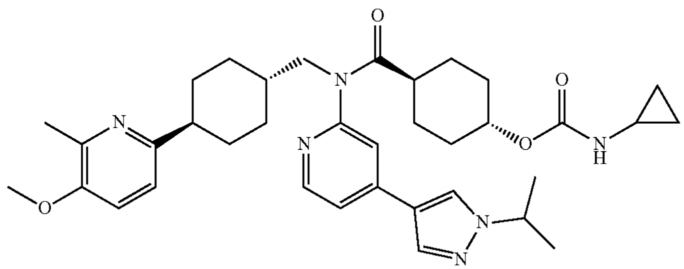 [SMILES: COc1ccc([C@H]2CC[C@H](CN(c3cc(-c4cnn(C(C)C)c4)ccn3)C(=O)[C@H]3CC[C@H](OC(=O)NC4CC4)CC3)CC2)nc1C] | trans-4-((4-(1-Isopropyl-1H-pyrazol-4-yl)pyridin-2-yl)((trans-4-(5-methoxy-6-methylpyridin-2-yl)cyclohexyl)methyl)carbamoyl)cyclohexyl cyclopropyl carbamate | 629.6 |
| 6.32 | 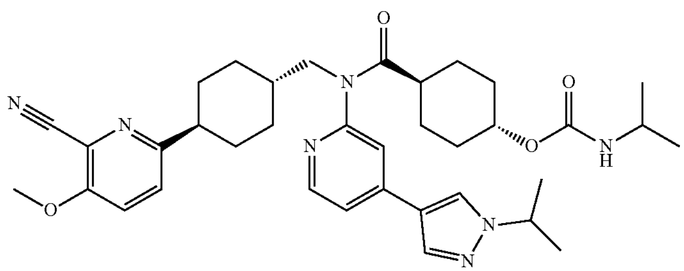 [SMILES: COc1ccc([C@H]2CC[C@H](CN(c3cc(-c4cnn(C(C)C)c4)ccn3)C(=O)[C@H]3CC[C@H](OC(=O)NC(C)C)CC3)CC2)nc1C#N] | trans-4-(((trans-4-(6-Cyano-5-methoxypyridin-2-yl)cyclohexyl)methyl)(4-(1-isopropyl-1H-pyrazol-4-yl)pyridin-2-yl)carbamoyl)cyclohexyl isopropylcarbamate | 642.6 |
| 6.33 | 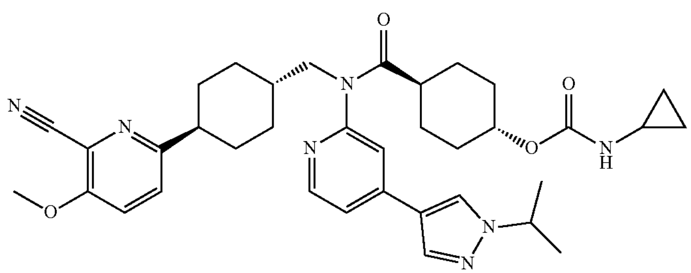 | trans-4-(((trans-4-(6-Cyano-5-methoxypyridin-2-yl)cyclohexyl)methyl)(4-(1-isopropyl-1H-pyrazol-4-yl)pyridin-2-yl)carbamoyl)cyclohexyl cyclopropylcarbamate | 640.6 |

| Cmpd | Structure | Name | [M + H]+ |
|---|---|---|---|
| 6.34 | 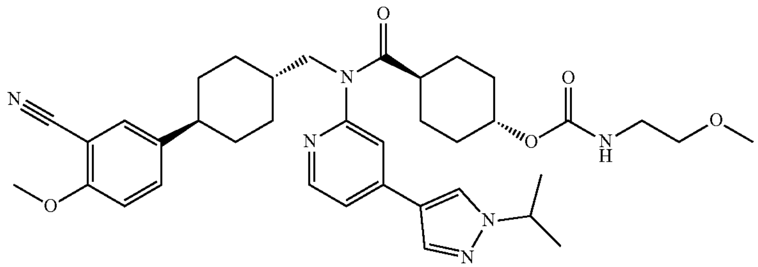 | trans-4-(((trans-4-(3-Cyano-4-methoxyphenyl)cyclohexyl)methyl)(4-(1-isopropyl-1H-pyrazol-4-yl)pyridin-2-yl)carbamoyl)cyclohexyl (2-methoxyethyl)carbamate | 657.5 |
| 6.35 | 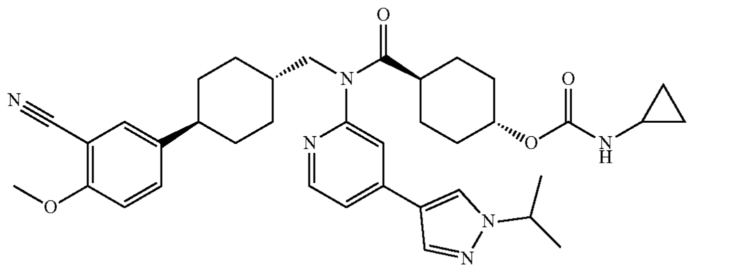 [SMILES: COc1ccc([C@H]2CC[C@H](CN(c3cc(-c4cnn(C(C)C)c4)ccn3)C(=O)[C@H]3CC[C@H](OC(=O)NC4CC4)CC3)CC2)cc1C#N] | trans-4-(((trans-4-(3-Cyano-4-methoxyphenyl)cyclohexyl)methyl)(4-(1-isopropyl-1H-pyrazol-4-yl)pyridin-2-yl)carbamoyl)cyclohexyl cyclopropylcarbamate | 639.6 |
| 6.36 | 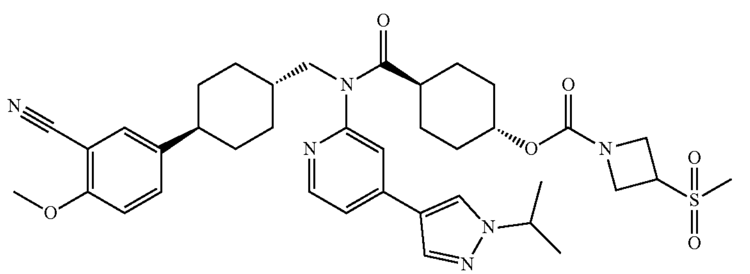 | trans-4-(((trans-4-(3-Cyano-4-methoxyphenyl)cyclohexyl)methyl)(4-(1-isopropyl-1H-pyrazol-4-yl)pyridin-2-yl)carbamoyl)cyclohexyl 3-(methylsulfonyl)azetidine-1-carboxylate | 717.5 |

| Cmpd | Structure | Name | [M + H]+ |
|---|---|---|---|
| 6.37 | 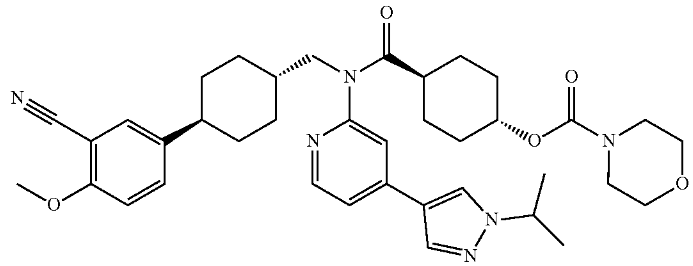 [SMILES: COc1ccc([C@H]2CC[C@H](CN(c3cc(-c4cnn(C(C)C)c4)ccn3)C(=O)[C@H]3CC[C@H](OC(=O)N4CCOCC4)CC3)CC2)cc1C#N] | trans-4-(((trans-4-(3-Cyano-4-methoxyphenyl)cyclohexyl)methyl)(4-(1-isopropyl-1H-pyrazol-4-yl)pyridin-2-yl)carbamoyl)cyclohexyl morpholine-4-carboxylate | 669.6 |
| 6.38 | 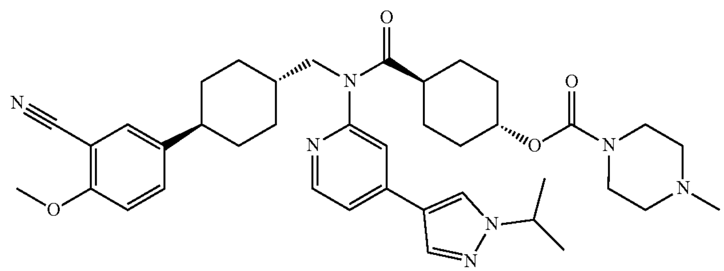 | trans-4-(((trans-4-(3-Cyano-4-methoxyphenyl)cyclohexyl)methyl)(4-(1-isopropyl-1H-pyrazol-4-yl)pyridin-2-yl)carbamoyl)cyclohexyl 4-methylpiperazine-1-carboxylate | 682.5 |
| 6.39 | 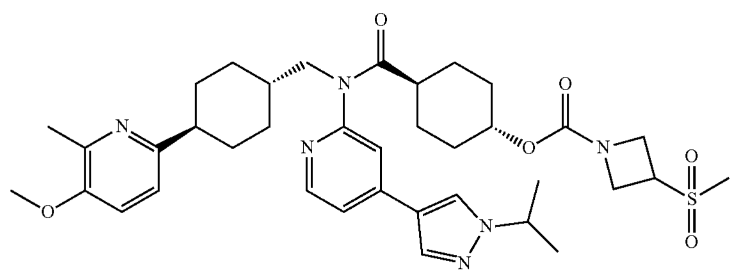 | trans-4-((4-(1-Isopropyl-1H-pyrazol-4-yl)pyridin-2-yl)((trans-4-(5-methoxy-6-methylpyridin-2-yl)cyclohexyl)methyl)carbamoyl)cyclohexyl 3-(methylsulfonyl)azetidine-1-carboxylate | 707.5 |

-continued

| Cmpd | Structure | Name | [M + H]⁺ |
|---|---|---|---|
| 6.40 | 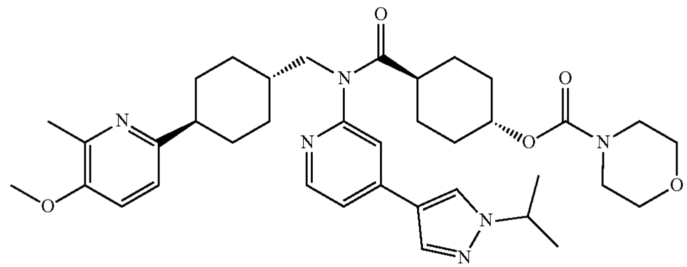 [SMILES: COc1ccc([C@H]2CC[C@H](CN(c3cc(-c4cnn(C(C)C)c4)ccn3)C(=O)[C@H]3CC[C@H](OC(=O)N4CCOCC4)CC3)CC2)nc1C] | trans-4-((4-(1-Isopropyl-1H-pyrazol-4-yl)pyridin-2-yl)((trans-4-(5-methoxy-6-methylpyridin-2-yl)cyclohexyl)methyl)carbamoyl)cyclohexyl morpholine-4-carboxylate | 659.5 |
| 6.41 | 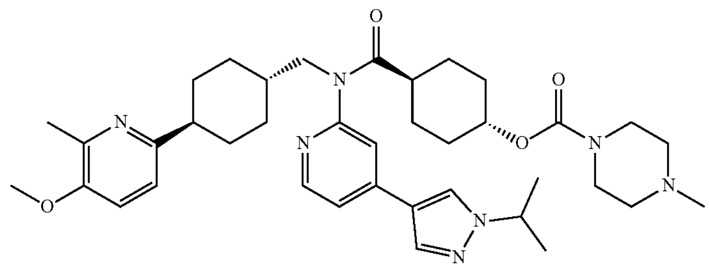 | trans-4-((4-(1-Isopropyl-1H-pyrazol-4-yl)pyridin-2-yl)((trans-4-(5-methoxy-6-methylpyridin-2-yl)cyclohexyl)methyl)carbamoyl)cyclohexyl 4-methylpiperazine-1-carboxylate | 672.5 |
| 6.42 | 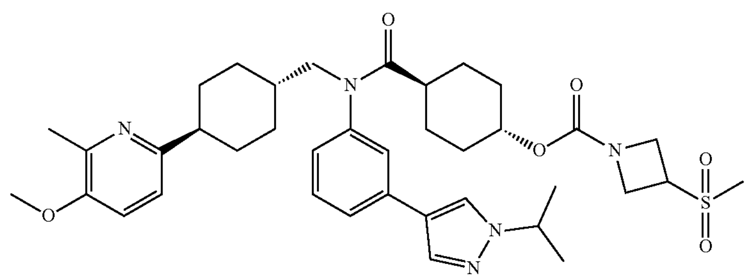 | trans-4-((3-(1-Isopropyl-1H-pyrazol-4-yl)phenyl)((trans-4-(5-methoxy-6-methylpyridin-2-yl)cyclohexyl)methyl)carbamoyl)cyclohexyl 3-(methylsulfonyl)azetidine-1-carboxylate | 706.3 |

-continued

| Cmpd | Structure | Name | [M + H]+ |
|---|---|---|---|
| 6.43 | 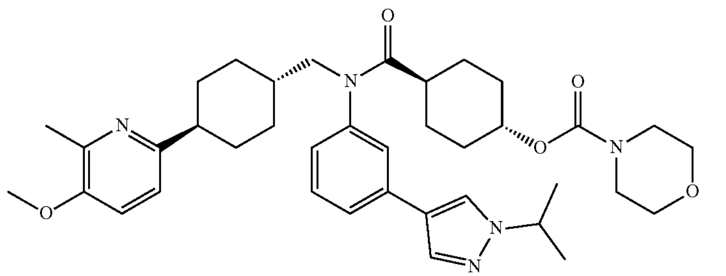 [SMILES: COc1ccc([C@H]2CC[C@H](CN(c3cccc(-c4cnn(C(C)C)c4)c3)C(=O)[C@H]3CC[C@H](OC(=O)N4CCOCC4)CC3)CC2)nc1C] | trans-4-((3-(1-Isopropyl-1H-pyrazol-4-yl)phenyl)((trans-4-(5-methoxy-6-methylpyridin-2-yl)cyclohexyl)methyl)carbamoyl)cyclohexyl morpholine-4-carboxylate | 658.4 |
| 6.44 | 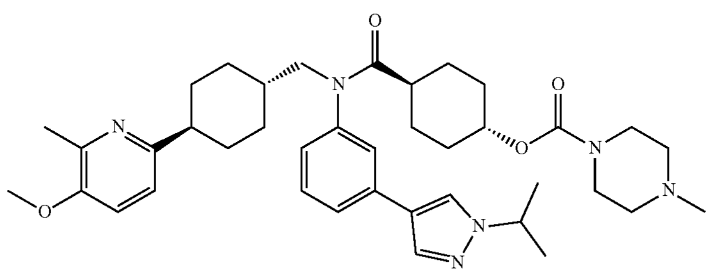 | trans-4-((3-(1-Isopropyl-1H-pyrazol-4-yl)phenyl)((trans-4-(5-methoxy-6-methylpyridin-2-yl)cyclohexyl)methyl)carbamoyl)cyclohexyl 4-methylpiperazine-1-carboxylate | 671.4 |
| 6.45 | 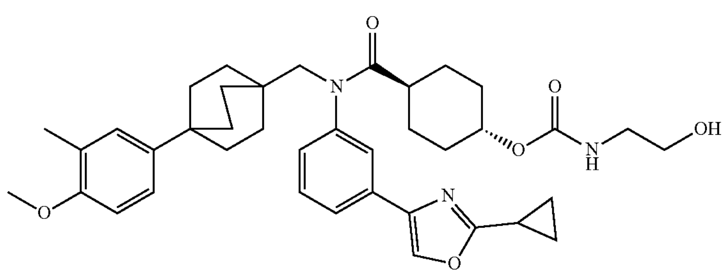 [SMILES: COc1ccc(C23CCC(CN(c4cccc(-c5coc(C6CC6)n5)c4)C(=O)[C@H]4CC[C@H](OC(=O)NCCO)CC4)(CC2)CC3)cc1C] | 4-((3-(2-Cyclopropyloxazol-4-yl)phenyl)(4-(4-methoxy-3-methylphenyl)bicyclo[2.2.2]octan-1-yl)methyl)carbamoyl)cyclohexyl trans-(2-hydroxyethyl)carbamate | 656.7 |

-continued

| Cmpd | Name | [M + H]⁺ |
|---|---|---|
| 6.46¹ | trans-4-((3-(2-Cyclopropyloxazol-4-yl)phenyl)((trans-4-(4-methoxy-3-methylphenyl)cyclohexyl)methyl)carbamoyl)cyclohexyl (2-hydroxyethyl)carbamate | 630.7 |
| 6.47 | trans-4-((3-(2-Isopropyloxazol-4-yl)phenyl)((trans-4-(4-methoxy-3-methylphenyl)cyclohexyl)methyl)carbamoyl)cyclohexyl (2-hydroxyethyl)carbamate | 632.4 |
| 6.48 | trans-4-((3-(2-Isopropyloxazol-4-yl)phenyl)((trans-4-(5-methoxy-6-methylpyridin-2-yl)cyclohexyl)methyl)carbamoyl)cyclohexyl (2-hydroxyethyl)carbamate | 633.6 |

| Cmpd | Structure | Name | [M + H]+ |
|---|---|---|---|
| 6.49 | 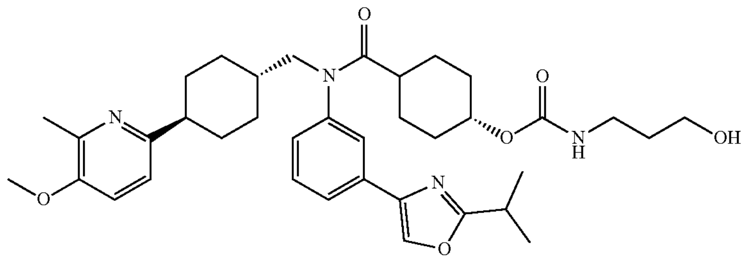 | trans-4-((3-(2-Isopropyloxazol-4-yl)phenyl)((trans-4-(5-methoxy-6-methylpyridin-2-yl)cyclohexyl)methyl)carbamoyl)cyclohexyl (3-hydroxypropyl)carbamate | 647.6 |
| 6.50 | 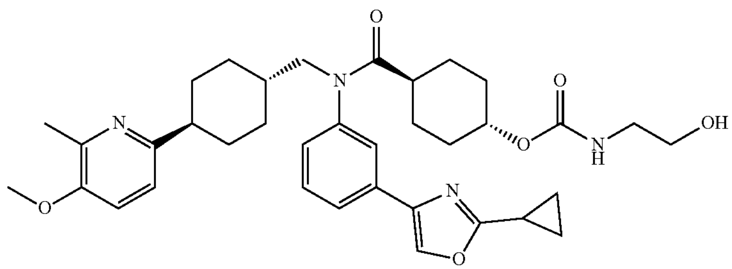 [SMILES: COc1ccc([C@H]2CC[C@H](CN(c3cccc(-c4coc(C5CC5)n4)c3)C(=O)[C@H]3CC[C@H](OC(=O)NCCO)CC3)CC2)nc1C] | trans-4-((3-(2-Cyclopropyloxazol-4-yl)phenyl)((trans-4-(5-methoxy-6-methylpyridin-2-yl)cyclohexyl)methyl)carbamoyl)cyclohexyl (2-hydroxyethyl)carbamate | 631.5 |
| 6.51 | 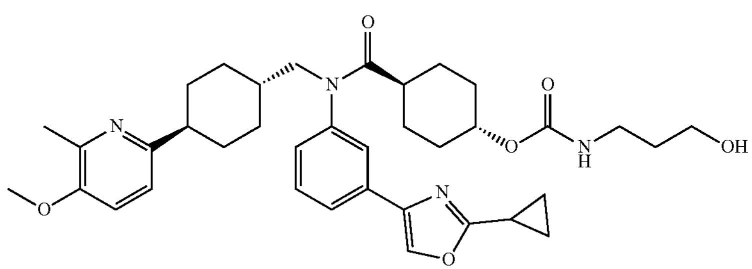 [SMILES: COc1ccc([C@H]2CC[C@H](CN(c3cccc(-c4coc(C5CC5)n4)c3)C(=O)[C@H]3CC[C@H](OC(=O)NCCCO)CC3)CC2)nc1C] | trans-4-((3-(2-Cyclopropyloxazol-4-yl)phenyl)((trans-4-(5-methoxy-6-methylpyridin-2-yl)cyclohexyl)methyl)carbamoyl)cyclohexyl (3-hydroxypropyl)carbamate | 645.5 |

| Cmpd | Structure | Name | [M + H]+ |
|---|---|---|---|
| 6.52 | 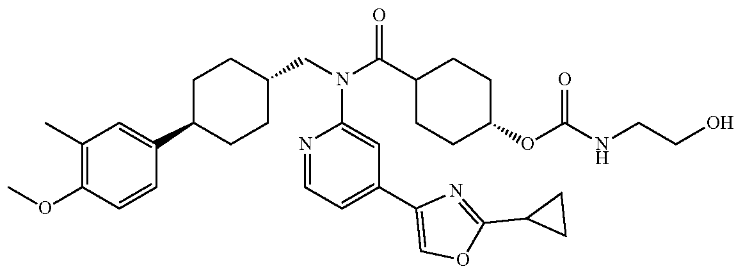 | trans-4-((4-(2-Cyclopropyloxazol-4-yl)pyridine-2-yl)((trans-4-(4-methoxy-3-methylphenyl)cyclohexyl)methyl)carbamoyl)cyclohexyl (2-hydroxyethyl)carbamate | 631.6 |
| 6.53 | 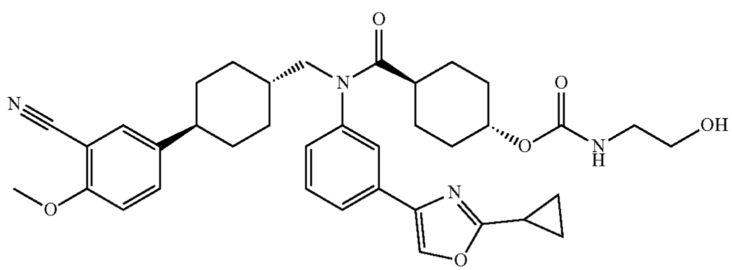 | trans-4-(((trans-4-(3-Cyano-4-methoxyphenyl)cyclohexyl)methyl)(3-(2-cyclopropyloxazol-4-yl)phenyl)carbamoyl)cyclohexyl (2-hydroxyethyl)carbamate | 641.6 |
| 6.54 | 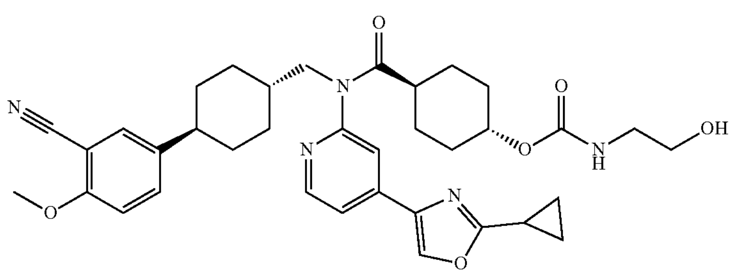 | trans-4-(((trans-4-(3-Cyano-4-methoxyphenyl)cyclohexyl)methyl)(4-(2-cyclopropyloxazol-4-yl)pyridine-2-yl)carbamoyl)cyclohexyl (2-hydroxyethyl)carbamate | 642.6 |

| Cmpd | Structure | Name | [M + H]⁺ |
|---|---|---|---|
| 6.55 | 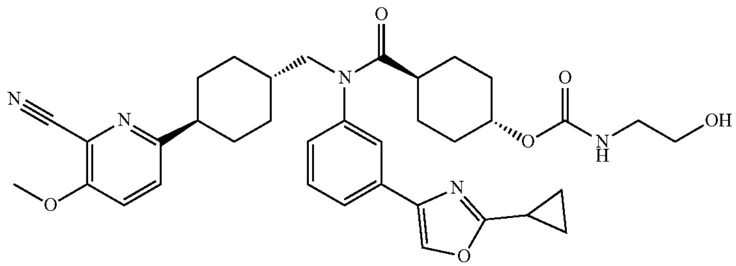 [SMILES: COc1ccc([C@H]2CC[C@H](CN(c3cc(-c4coc(C5CC5)n4)ccn3)C(=O)[C@H]3CC[C@H](OC(=O)NCCO)CC3)CC2)cc1C#N] | trans-4-(((trans-4-(6-Cyano-5-methoxypyridin-2-yl)cyclohexyl)methyl)(3-(2-cyclopropyloxazol-4-yl)phenyl)carbamoyl)cyclohexyl (2-hydroxyethyl)carbamate | 642.4 |
| 6.56 | 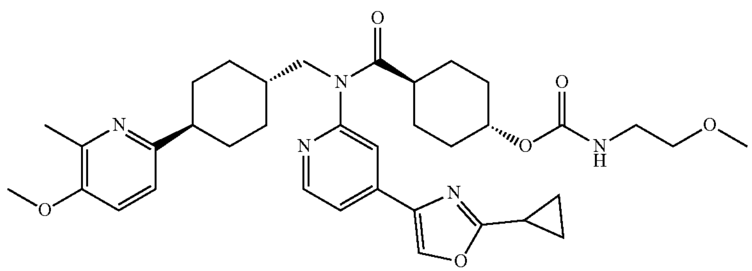 | trans-4-((4-(2-Cyclopropyloxazol-4-yl)pyridine-2-yl)(trans-4-(5-methoxy-6-methylpyridin-2-yl)cyclohexyl)methyl)carbamoyl)cyclohexyl (2-methoxyethyl)carbamate | 646.5 |
| 6.57 | 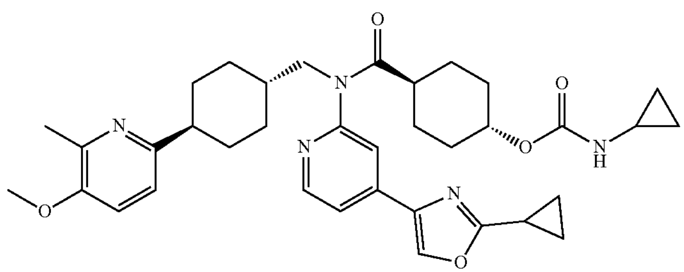 [SMILES: COc1ccc([C@H]2CC[C@H](CN(c3cc(-c4coc(C5CC5)n4)ccn3)C(=O)[C@H]3CC[C@H](OC(=O)NC4CC4)CC3)CC2)nc1C] | trans-4-((4-(2-Cyclopropyloxazol-4-yl)pyridine-2-yl)(trans-4-(5-methoxy-6-methylpyridin-2-yl)cyclohexyl)methyl)carbamoyl)cyclohexyl cyclopropylcarbamate | 628.5 |

| Cmpd | Structure | Name | [M + H]+ |
|---|---|---|---|
| 6.58 | 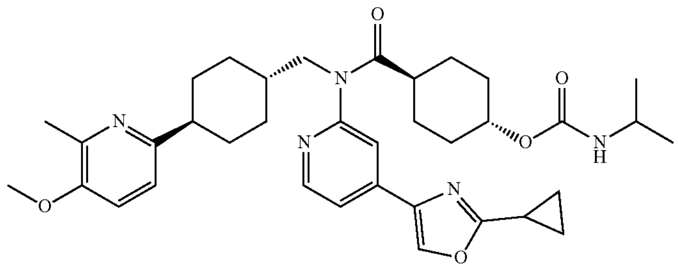 [SMILES: COc1ccc([C@H]2CC[C@H](CN(c3cc(-c4coc(C5CC5)n4)ccn3)C(=O)[C@H]3CC[C@H](OC(=O)NC(C)C)CC3)CC2)nc1C] | trans-4-((4-(2-Cyclopropyloxazol-4-yl)pyridine-2-yl)(trans-4-(5-methoxy-6-methylpyridin-2-yl)cyclohexyl)methyl)carbamoyl)cyclohexyl isopropyl carbamate | 630.6 |
| 6.59 | 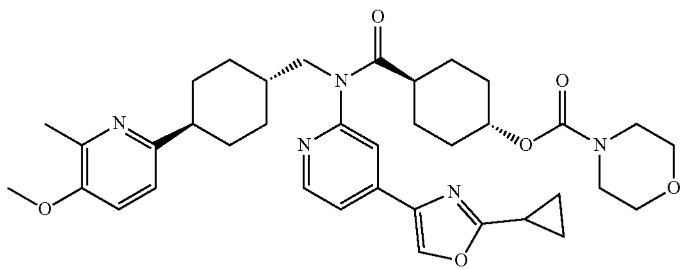 [SMILES: COc1ccc([C@H]2CC[C@H](CN(c3cc(-c4coc(C5CC5)n4)ccn3)C(=O)[C@H]3CC[C@H](OC(=O)N4CCOCC4)CC3)CC2)nc1C] | trans-4-((4-(2-Cyclopropyloxazol-4-yl)pyridine-2-yl)(trans-4-(5-methoxy-6-methylpyridin-2-yl)cyclohexyl)methyl)carbamoyl)cyclohexyl morpholine-4-carboxylate | 658.6 |
| 6.60 | 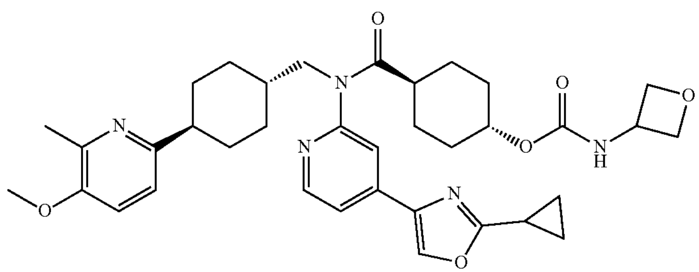 [SMILES: COc1ccc([C@H]2CC[C@H](CN(c3cc(-c4coc(C5CC5)n4)ccn3)C(=O)[C@H]3CC[C@H](OC(=O)NC4COC4)CC3)CC2)nc1C] | trans-4-((4-(2-Cyclopropyloxazol-4-yl)pyridine-2-yl)(trans-4-(5-methoxy-6-methylpyridin-2-yl)cyclohexyl)methyl)carbamoyl)cyclohexyl oxetan-3-ylcarbamate | 644.6 |

| Cmpd | Structure | Name | [M + H]+ |
|---|---|---|---|
| 6.61 | 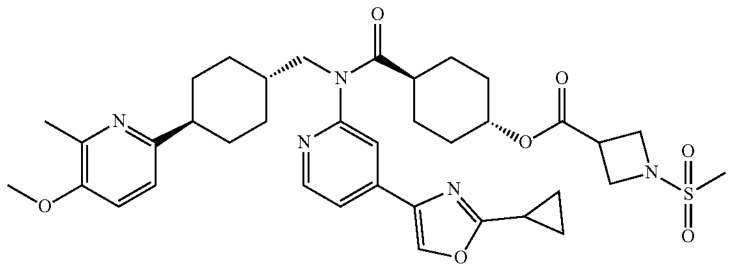 | trans-4-(4-(2-Cyclopropyloxazol-4-yl)pyridine-2-yl)-N-((trans-4-(5-methoxy-6-methyl pyridin-2-yl)cyclohexyl)methyl)-4-(2-(3-(methyl sulfonyl)azetidin-1-yl)-2-oxoethyl)cyclohexanecarboxamide | 706.6 |
| 6.62 | 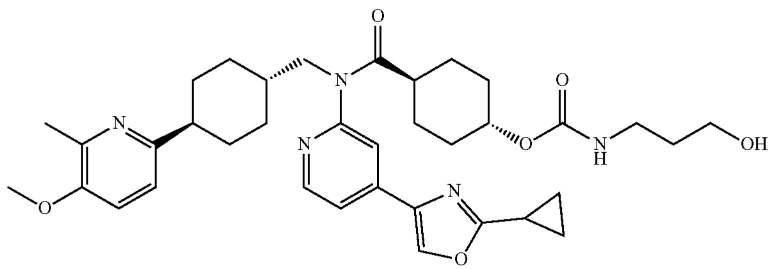 | trans-N-(4-(2-Cyclopropyloxazol-4-yl)pyridine-2-yl)-4-(2-((3-hydroxypropyl)amino)-2-oxoethyl)-N-((trans-4-(5-methoxy-6-methylpyridin-2-yl)cyclohexyl)methyl)cyclohexanecarboxamide | 646.5 |
| 6.63 | 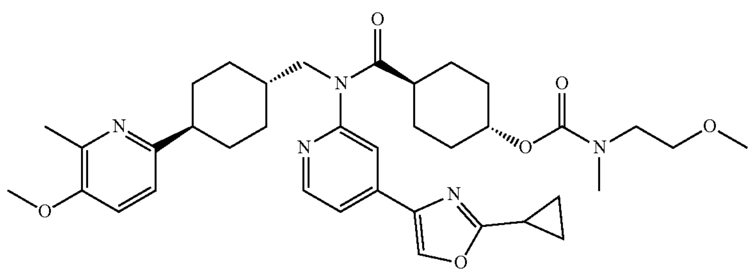 | trans-N-(4-(2-Cyclopropyloxazol-4-yl)pyridine-2-yl)-N-((trans-4-(5-methoxy-6-methylpyridin-2-yl)cyclohexyl)methyl)-4-(2-((2-methoxyethyl)(methyl)amino)-2-oxoethyl)cyclohexanecarboxamide | 660.4 |

| Cmpd | Structure | Name | [M + H]+ |
|---|---|---|---|
| 6.64 | 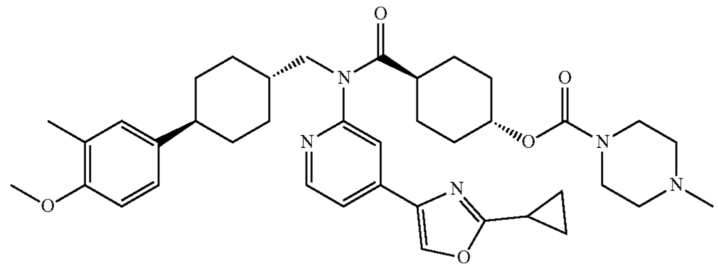 | trans-4-((4-(2-Cyclopropyloxazol-4-yl)pyridine-2-yl)((trans-4-(4-methoxy-3-methylphenyl)cyclohexyl)methyl)carbamoyl)cyclohexyl 4-methyl piperazine-1-carboxylate | 670.6 |
| 6.65 | 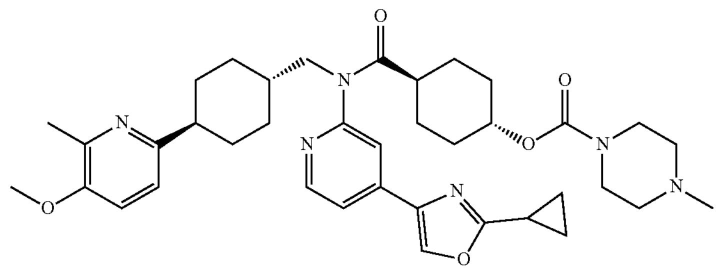 | trans-4-((4-(2-Cyclopropyloxazol-4-yl)pyridine-2-yl)((trans-4-(5-methoxy-6-methylpyridin-2-yl)cyclohexyl)methyl)carbamoyl)cyclohexyl 4-methylpiperazine-1-carboxylate | 671.6 |
| 6.66 | 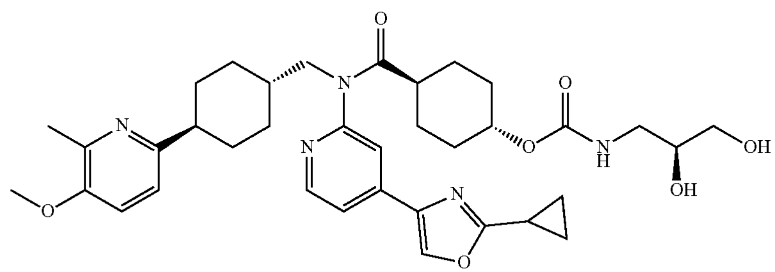 [SMILES: COc1ccc([C@H]2CC[C@H](CN(c3cc(-c4coc(C5CC5)n4)ccn3)C(=O)[C@H]3CC[C@H](OC(=O)NC[C@H](O)CO)CC3)CC2)nc1C] | trans-4-((4-(2-Cyclopropyloxazol-4-yl)pyridine-2-yl)((trans-4-(5-methoxy-6-methylpyridin-2-yl)cyclohexyl)methyl)carbamoyl)cyclohexyl ((S)-2,3-dihydroxypropyl)carbamate | 662.5 |

| Cmpd | Structure | Name | [M + H]+ |
|---|---|---|---|
| 6.67 | 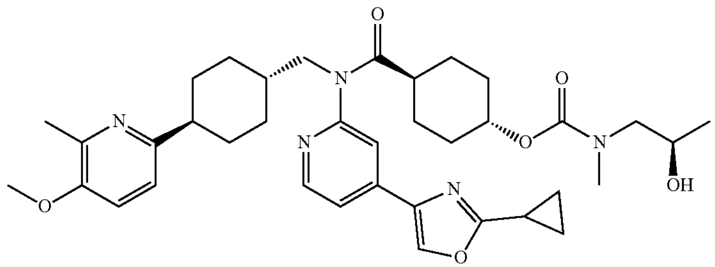 [SMILES: COc1ccc([C@H]2CC[C@H](CN(c3cc(-c4coc(C5CC5)n4)ccn3)C(=O)[C@H]3CC[C@H](OC(=O)N(C)C[C@@H](C)O)CC3)CC2)nc1C] | trans-4-((4-(2-Cyclopropyloxazol-4-yl)pyridin-2-yl)((trans-4-(5-methoxy-6-methylpyridin-2-yl)cyclohexyl)methyl)carbamoyl)cyclohexyl (2-hydroxypropyl)(methyl)carbamate | 660.4 |
| 6.68 | 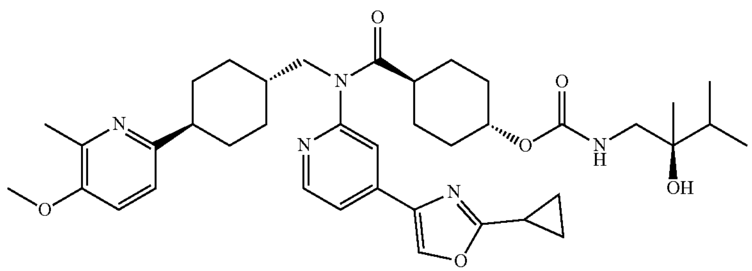 [SMILES: COc1ccc([C@H]2CC[C@H](CN(c3cc(-c4coc(C5CC5)n4)ccn3)C(=O)[C@H]3CC[C@H](OC(=O)NC[C@@](C)(O)C(C)C)CC3)CC2)nc1C] | trans-4-((4-(2-Cyclopropyloxazol-4-yl)pyridin-2-yl)((trans-4-(5-methoxy-6-methylpyridin-2-yl)cyclohexyl)methyl)carbamoyl)cyclohexyl (2-hydroxy-2,3-dimethylbutyl)carbamate | 688.6 |
| 6.69 | 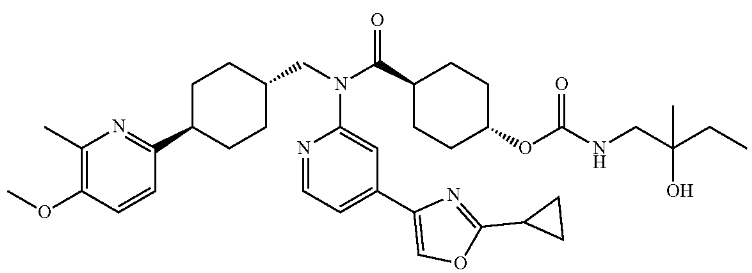 [SMILES: CCC(C)(O)CNC(=O)O[C@H]1CC[C@H](C(=O)N(C[C@H]2CC[C@H](c3ccc(OC)c(C)n3)CC2)c2cc(-c3coc(C4CC4)n3)ccn2)CC1] | trans-4-((4-(2-Cyclopropyloxazol-4-yl)pyridin-2-yl)((trans-4-(5-methoxy-6-methylpyridin-2-yl)cyclohexyl)methyl)carbamoyl)cyclohexyl (2-hydroxy-2-methylbutyl)carbamate | 674.5 |

| Cmpd | Structure | Name | [M + H]+ |
|---|---|---|---|
| 6.70 | 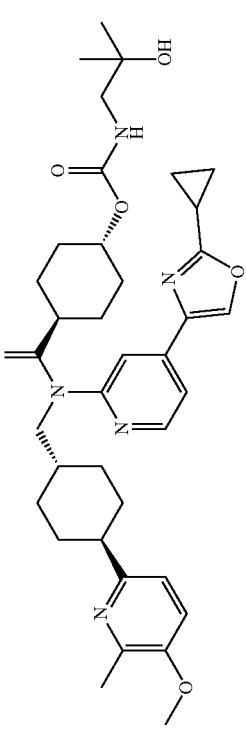 | trans-4-((4-(2-Cyclopropyloxazol-4-yl)pyridin-2-yl)((trans-4-(5-methoxy-6-methylpyridin-2-yl)cyclohexyl)methyl)carbamoyl)cyclohexyl (2-hydroxy-2-methylpropyl)carbamate | 660.5 |
| 6.71 | 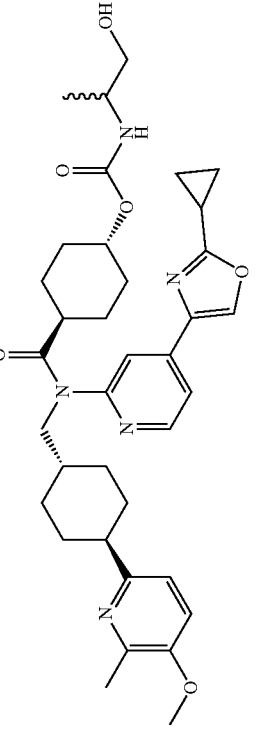 | /raw,y-4-((4-(2-Cyclopropyloxazol-4-yl)pyridin-2-yl)((trans-4-(5-methoxy-6-methylpyridin-2-yl)cyclohexyl)methyl)carbamoyl)cyclohexyl (1-hydroxypropan-2-yl)carbamate | 646.6 |
| 6.72 | 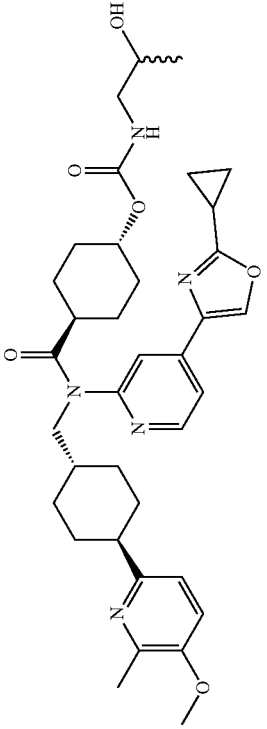 | trans-4-((4-(2-Cyclopropyloxazol-4-yl)pyridin-2-yl)((trans-4-(5-methoxy-6-methylpyridin-2-yl)cyclohexyl)methyl)carbamoyl)cyclohexyl (2-hydroxypropyl)carbamate | 646.7 |

-continued

| Cmpd | Structure | Name | [M + H]⁺ |
|---|---|---|---|
| 6.73 | 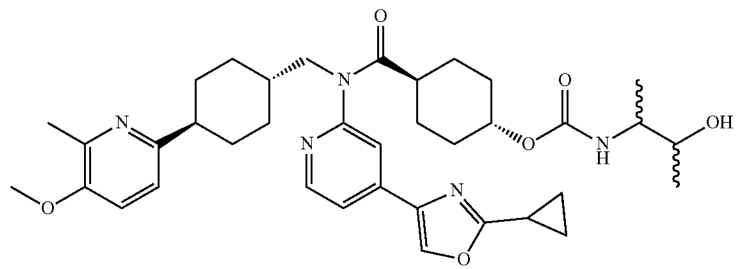 | trans-4-((4-(2-Cyclopropyloxazol-4-yl)pyridin-2-yl)((trans-4-(5-methoxy-6-methylpyridin-2-yl)cyclohexyl)methyl)carbamoyl)cyclohexyl (3-hydroxybutan-2-yl)carbamate | 660.5 |
| 6.74 | 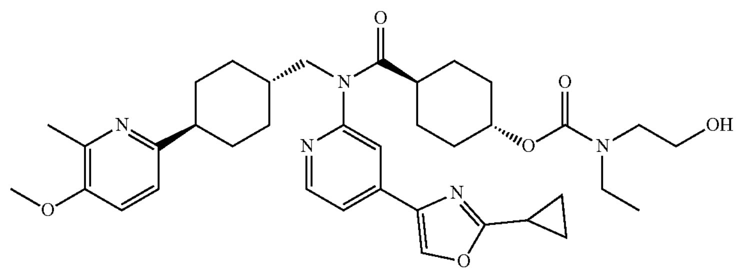 | trans-4-((4-(2-Cyclopropyloxazol-4-yl)pyridin-2-yl)((trans-4-(5-methoxy-6-methylpyridin-2-yl)cyclohexyl)methyl)carbamoyl)cyclohexyl ethyl(2-hydroxyethyl)carbamate | 660.6 |
| 6.75 | 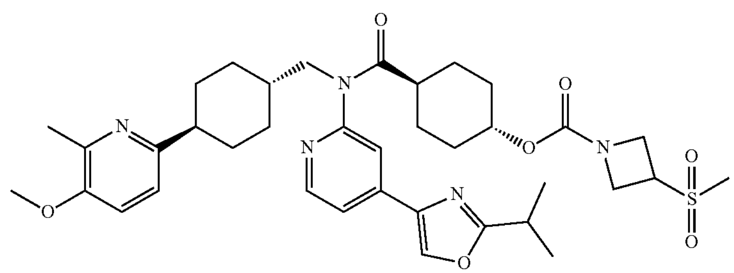 | trans-4-((4-(2-Isopropyloxazol-4-yl)pyridine-2-yl)((trans-4-(5-methoxy-6-methylpyridin-2-yl)cyclohexyl)methyl)carbamoyl)cyclohexyl 3-(methylsulfonyl)azetidine-1-carboxylate | 708.3 |

| Cmpd | Structure | Name | [M + H]+ |
|---|---|---|---|
| 6.76 | 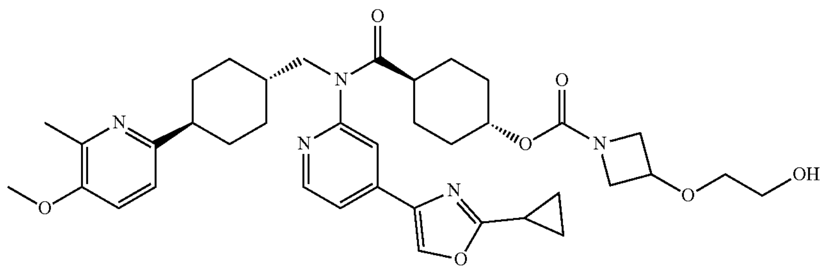 [SMILES: COc1ccc([C@H]2CC[C@H](CN(c3cc(-c4coc(C5CC5)n4)ccn3)C(=O)[C@H]3CC[C@H](OC(=O)N4CC(OCCO)C4)CC3)CC2)nc1C] | trans-4-((4-(2-Cyclopropyloxazol-4-yl)pyridine-2-yl)((trans-4-(5-methoxy-6-methylpyridin-2-yl)cyclohexyl)methyl)carbamoyl)cyclohexyl 3-(2-hydroxyethoxy)azetidine-1-carboxylate | 688.5 |
| 6.77 | 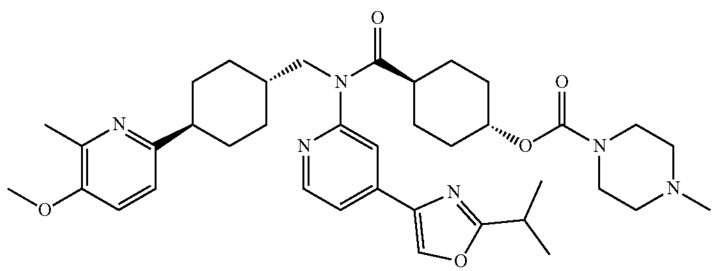 | trans-4-((4-(2-Isopropyloxazol-4-yl)pyridine-2-yl)((trans-4-(5-methoxy-6-methylpyridin-2-yl)cyclohexyl)methyl)carbamoyl)cyclohexyl 4-methylpiperazine-1-carboxylate | 673.5 |
| 6.78[3] | 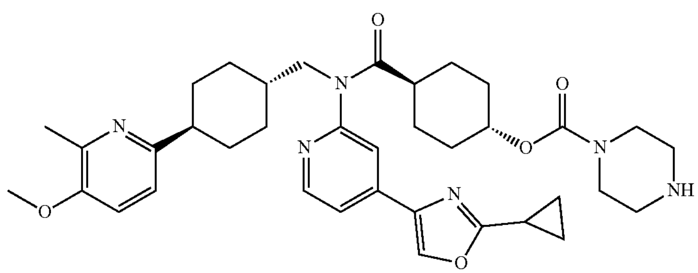 [SMILES: COc1ccc([C@H]2CC[C@H](CN(c3cc(-c4coc(C5CC5)n4)ccn3)C(=O)[C@H]3CC[C@H](OC(=O)N4CCNCC4)CC3)CC2)nc1C] | trans-4-((4-(2-Cyclopropyloxazol-4-yl)pyridine-2-yl)((trans-4-(5-methoxy-6-methylpyridin-2-yl)cyclohexyl)methyl)carbamoyl)cyclohexyl piperazine-1-carboxylate | 657.3 |

-continued

| Cmpd | Structure | Name | [M + H]+ |
|---|---|---|---|
| 6.79 | 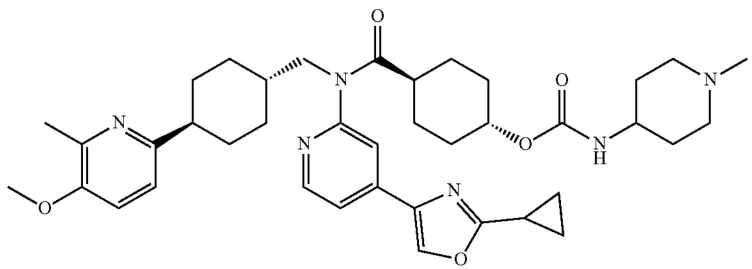 | trans-4-((4-(2-Cyclopropyloxazol-4-yl)pyridine-2-yl)((trans-4-(5-methoxy-6-methylpyridin-2-yl)cyclohexyl)methyl)carbamoyl)cyclohexyl (1-methylpiperidin-4-yl)carbamate | 685.3 |
| 6.80 | 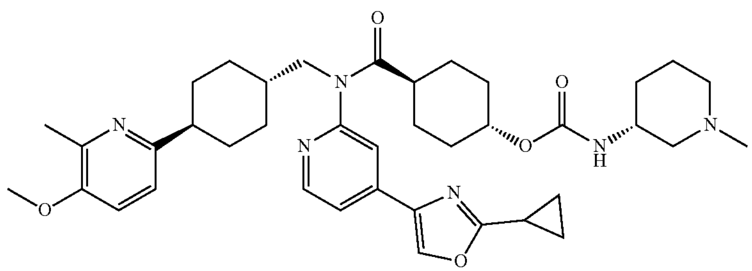 | trans-4-((4-(2-Cyclopropyloxazol-4-yl)pyridin-2-yl)((trans-4-(5-methoxy-6-methylpyridin-2-yl)cyclohexyl)methyl)carbamoyl)cyclohexyl ((R)-1-methylpiperidin-3-yl)carbamate | 685.5 |
| 6.81 | 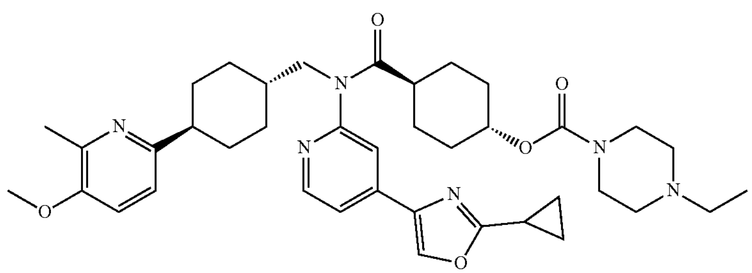 [SMILES: CCN1CCN(C(=O)O[C@H]2CC[C@H](C(=O)N(C[C@H]3CC[C@H](c4ccc(OC)c(C)n4)CC3)c3cc(-c4coc(C5CC5)n4)ccn3)CC2)CC1] | trans-4-((4-(2-Cyclopropyloxazol-4-yl)pyridine-2-yl)((trans-4-(5-methoxy-6-methylpyridin-2-yl)cyclohexyl)methyl)carbamoyl)cyclohexyl 4-ethylpiperazine-1-carboxylate | 685.5 |

-continued

| Cmpd | Structure | Name | [M + H]+ |
|---|---|---|---|
| 6.82 | 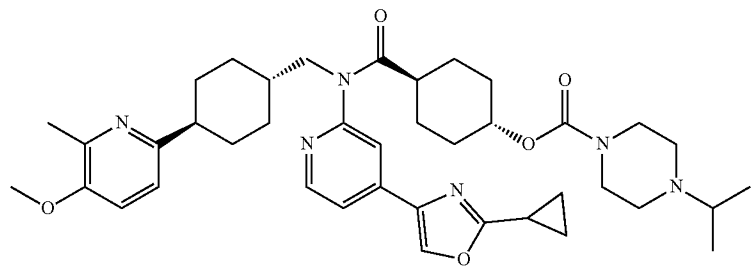 [SMILES: COc1ccc([C@H]2CC[C@H](CN(c3cc(-c4coc(C5CC5)n4)ccn3)C(=O)[C@H]3CC[C@H](OC(=O)N4CCN(C(C)C)CC4)CC3)CC2)nc1C] | trans-4-((4-(2-Cyclopropyloxazol-4-yl)pyridine-2-yl)((trans-4-(5-methoxy-6-methylpyridin-2-yl)cyclohexyl)methyl)carbamoyl)cyclohexyl 4-isopropylpiperazine-1-carboxylate | 699.5 |
| 6.83 | 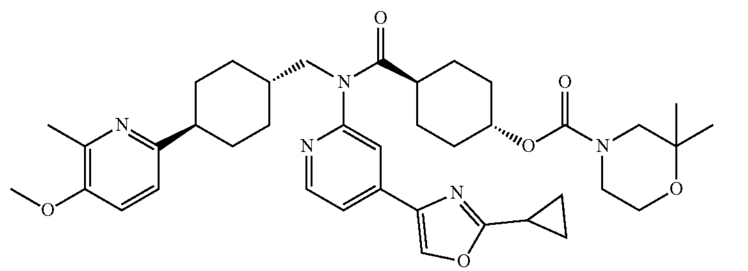 | trans-4-((4-(2-Cyclopropyloxazol-4-yl)pyridin-2-yl)((trans-4-(5-methoxy-6-methylpyridin-2-yl)cyclohexyl)methyl)carbamoyl)cyclohexyl 2,2-dimethylmorpholine-4-carboxylate | 686.8 |
| 6.84 | 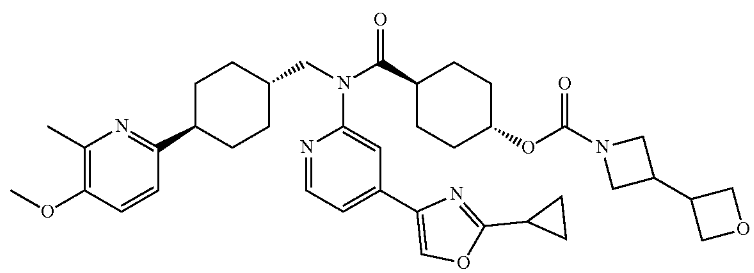 [SMILES: COc1ccc([C@H]2CC[C@H](CN(c3cc(-c4coc(C5CC5)n4)ccn3)C(=O)[C@H]3CC[C@H](OC(=O)N4CC(C5COC5)C4)CC3)CC2)nc1C] | trans-4-((4-(2-Cyclopropyloxazol-4-yl)pyridin-2-yl)((trans-4-(5-methoxy-6-methylpyridin-2-yl)cyclohexyl)methyl)carbamoyl)cyclohexyl 3-(oxetan-3-yl)azetidine-1-carboxylate | 684.6 |

-continued

| Cmpd | Structure | Name | [M + H]+ |
|---|---|---|---|
| 6.85 | 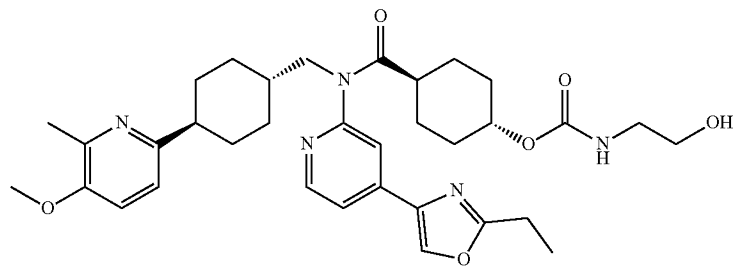 | trans-4-((4-(2-Ethyloxazol-4-yl)pyridin-2-yl)((trans-4-(5-methoxy-6-methylpyridin-2-yl)cyclohexyl)methyl)carbamoyl)cyclohexyl (2-hydroxyethyl)carbamate | 620.4 |
| 6.86 | 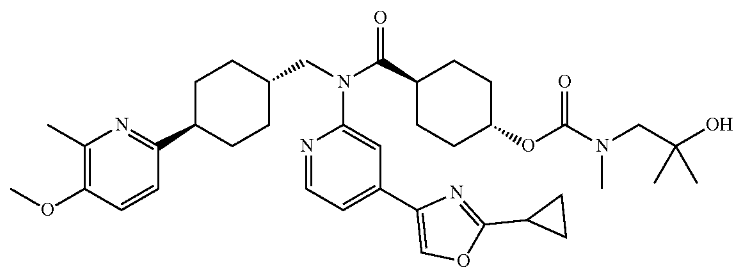 [SMILES: COc1ccc([C@H]2CC[C@H](CN(c3cc(-c4coc(C5CC5)n4)ccn3)C(=O)[C@H]3CC[C@H](OC(=O)N(C)CC(C)(C)O)CC3)CC2)nc1C] | trans-4-((4-(2-Cyclopropyloxazol-4-yl)pyridin-2-yl)((trans-4-(5-methoxy-6-methylpyridin-2-yl)cyclohexyl)methyl)carbamoyl)cyclohexyl (2-hydroxy-2-methyl propyl)(methyl)carbamate | 674.6 |
| 6.87 | 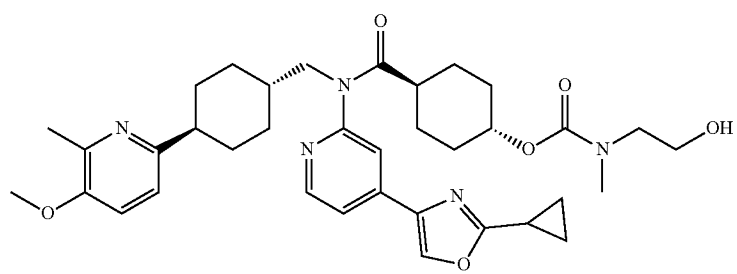 [SMILES: COc1ccc([C@H]2CC[C@H](CN(c3cc(-c4coc(C5CC5)n4)ccn3)C(=O)[C@H]3CC[C@H](OC(=O)N(C)CCO)CC3)CC2)nc1C] | trans-4-((4-(2-Cyclopropyloxazol-4-yl)pyridin-2-yl)((trans-4-(5-methoxy-6-methylpyridin-2-yl)cyclohexyl)methyl)carbamoyl)cyclohexyl (2-hydroxyethyl)(methyl)carbamate | 646.5 |

| Cmpd | Structure | Name | [M + H]+ |
|---|---|---|---|
| 6.88 | 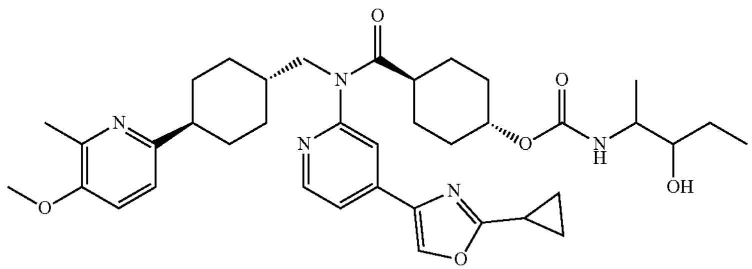 [SMILES: CCC(O)C(C)NC(=O)O[C@H]1CC[C@H](C(=O)N(C[C@H]2CC[C@H](c3ccc(OC)c(C)n3)CC2)c2cc(-c3coc(C4CC4)n3)ccn2)CC1] | trans-4-((4-(2-Cyclopropyloxazol-4-yl)pyridin-2-yl)((trans-4-(5-methoxy-6-methylpyridin-2-yl)cyclohexyl)methyl)carbamoyl)cyclohexyl (3-hydroxypentan-2-yl)carbamate | 674.5 |
| 6.89 | 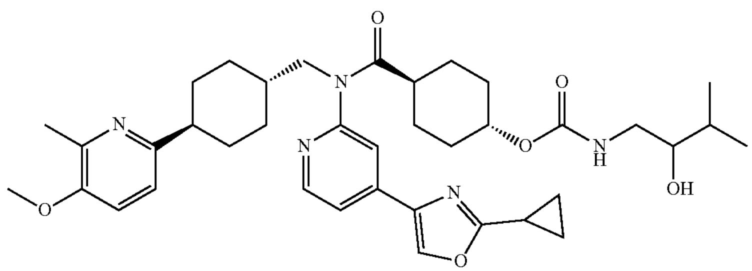 [SMILES: COc1ccc([C@H]2CC[C@H](CN(c3cc(-c4coc(C5CC5)n4)ccn3)C(=O)[C@H]3CC[C@H](OC(=O)NCC(O)C(C)C)CC3)CC2)nc1C] | trans-4-((4-(2-Cyclopropyl oxazol-4-yl)pyridin-2-yl)((trans-4-(5-methoxy-6-methylpyridin-2-yl)cyclohexyl)methyl)carbamoyl)cyclohexyl (2-hydroxy-3-methylbutyl)carbamate | 674.5 |
| 6.90 | 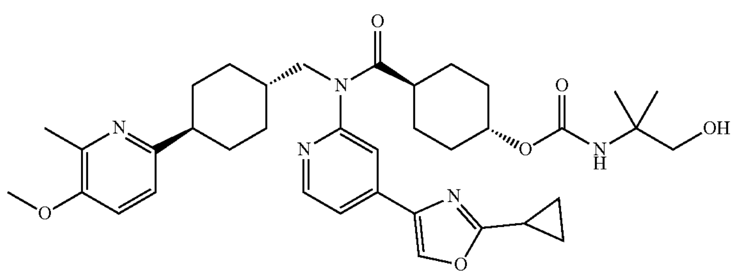 [SMILES: COc1ccc([C@H]2CC[C@H](CN(c3cc(-c4coc(C5CC5)n4)ccn3)C(=O)[C@H]3CC[C@H](OC(=O)NC(C)(C)CO)CC3)CC2)nc1C] | trans-4-((4-(2-Cyclopropyloxazol-4-yl)pyridin-2-yl)((trans-4-(5-methoxy-6-methylpyridin-2-yl)cyclohexyl)methyl)carbamoyl)cyclohexyl (1-hydroxy-2-methylpropan-2-yl)carbamate | 660.7 |

| Cmpd | Structure | Name | [M + H]+ |
|---|---|---|---|
| 6.91 | 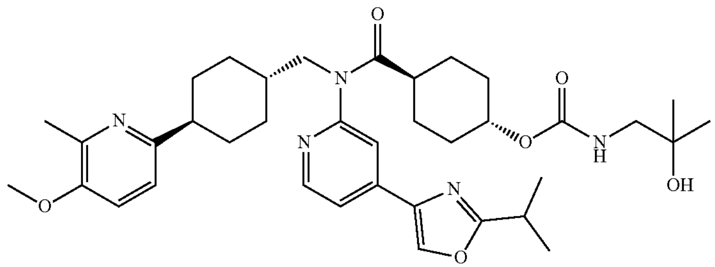 [SMILES: COc1ccc([C@H]2CC[C@H](CN(c3cc(-c4coc(C(C)C)n4)ccn3)C(=O)[C@H]3CC[C@H](OC(=O)NCC(C)(C)O)CC3)CC2)nc1C] | trans-4-((4-(2-Isopropyloxazol-4-yl)pyridin-2-yl)((trans-4-(5-methoxy-6-methylpyridin-2-yl)cyclohexyl)methyl)carbamoyl)cyclohexyl (2-hydroxy-2-methylpropyl)carbamate | 662.4 |
| 6.92 | 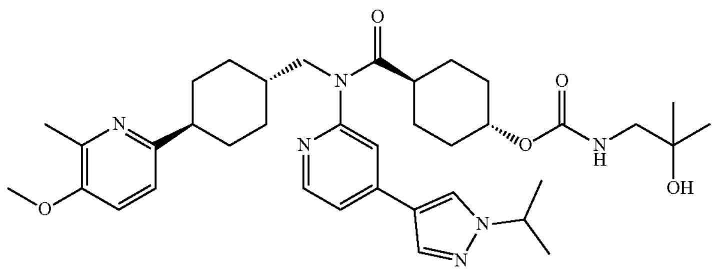 [SMILES: COc1ccc([C@H]2CC[C@H](CN(c3cc(-c4cnn(C(C)C)c4)ccn3)C(=O)[C@H]3CC[C@H](OC(=O)NCC(C)(C)O)CC3)CC2)nc1C] | trans-4-((4-(1-Isopropyl-1H-pyrazol-4-yl)pyridin-2-yl)((trans-4-(5-methoxy-6-methylpyridin-2-yl)cyclohexyl)methyl)carbamoyl)cyclohexyl (2-hydroxy-2-methylpropyl)carbamate | 661.5 |
| 6.93 | 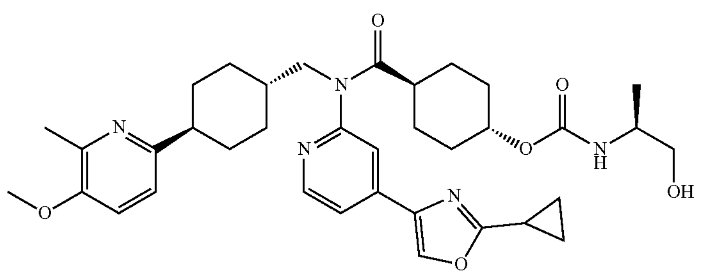 [SMILES: COc1ccc([C@H]2CC[C@H](CN(c3cc(-c4coc(C5CC5)n4)ccn3)C(=O)[C@H]3CC[C@H](OC(=O)N[C@@H](C)CO)CC3)CC2)nc1C] | trans-4-((4-(2-Cyclopropyloxazol-4-yl)pyridin-2-yl)((trans-4-(5-methoxy-6-methylpyridin-2-yl)cyclohexyl)methyl)carbamoyl)cyclohexyl ((S)-1-hydroxypropan-2-yl)carbamate | 646.7 |

| Cmpd | Structure | Name | [M + H]+ |
|---|---|---|---|
| 6.94 | 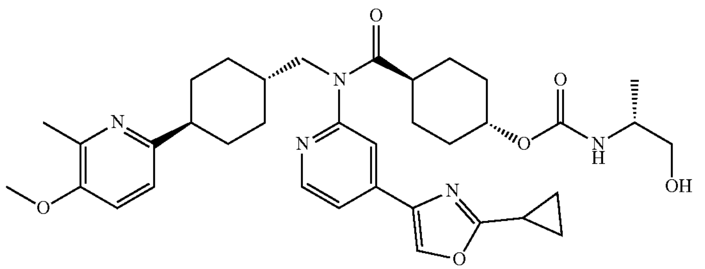 [SMILES: COc1ccc([C@H]2CC[C@H](CN(c3cc(-c4coc(C5CC5)n4)ccn3)C(=O)[C@H]3CC[C@H](OC(=O)N[C@H](C)CO)CC3)CC2)nc1C] | trans-4-((4-(2-Cyclopropyloxazol-4-yl)pyridin-2-yl)((trans-4-(5-methoxy-6-methylpyridin-2-yl)cyclohexyl)methyl)carbamoyl)cyclohexyl ((R)-1-hydroxypropan-2-yl)carbamate | 646.7 |
| 6.95 | 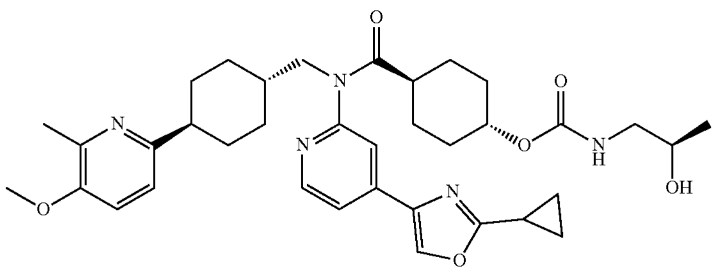 [SMILES: COc1ccc([C@H]2CC[C@H](CN(c3cc(-c4coc(C5CC5)n4)ccn3)C(=O)[C@H]3CC[C@H](OC(=O)NC[C@@H](C)O)CC3)CC2)nc1C] | trans-4-((4-(2-Cyclopropyloxazol-4-yl)pyridin-2-yl)((trans-4-(5-methoxy-6-methylpyridin-2-yl)cyclohexyl)methyl)carbamoyl)cyclohexyl ((R)-2-hydroxypropyl)carbamate | 646.7 |
| 6.96 | 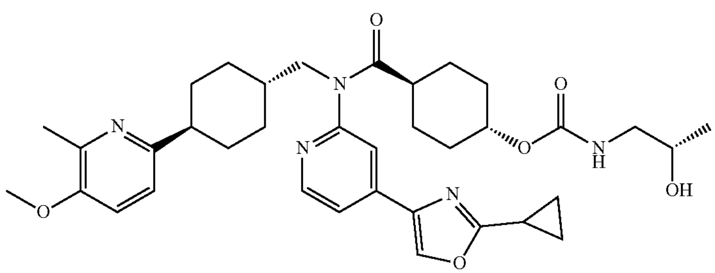 [SMILES: COc1ccc([C@H]2CC[C@H](CN(c3cc(-c4coc(C5CC5)n4)ccn3)C(=O)[C@H]3CC[C@H](OC(=O)NC[C@H](C)O)CC3)CC2)nc1C] | trans-4-((4-(2-Cyclopropyloxazol-4-yl)pyridin-2-yl)((trans-4-(5-methoxy-6-methylpyridin-2-yl)cyclohexyl)methyl)carbamoyl)cyclohexyl ((S)-2-hydroxypropyl)carbamate | 646.6 |

Acyl-imidazole formation:
[1]DMF as solvent. Carbamate formation: Reactions that progressed slowly at rt were either allowed to stir for multiple days or heated (50-80° C.);
[2]Reaction was diluted with CH$_2$Cl$_2$ prior to amine addition.
[3]From N-Boc-piperazine after deprotection (20% TFA in CH$_2$Cl$_2$).

Compound 7

Trans-4-((4-(2-Cyclopropyloxazol-4-yl)pyridine-2-yl)((trans-4-(5-methoxy-6-methylpyridin-2-yl)cyclohexyl)methyl)carbamoyl)cyclohexyl 3-hydroxyazetidine-1-carboxylate

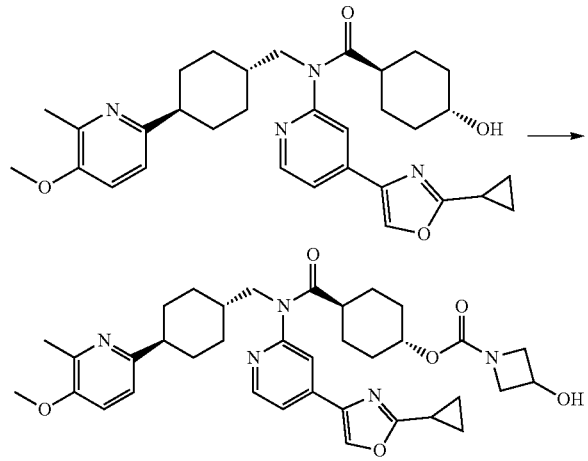

A mixture of Intermediate 32.08 (510 mg, 0.937 mmol), CDI (233 mg, 1.44 mmol), and $CH_3CN$ (8 mL) was heated at 80° C. for 16 h and allowed to cool to rt. Diisopropylethylamine (1.5 mL, 8.6 mmol) and then azetidine-3-ol hydrochloride (465 mg, 4.24 mmol) were added to the reaction mixture at rt. The mixture was stirred for 70 min, diluted with EtOAc (50 mL), washed (50 mL $H_2O$ and then 50 mL brine), dried ($Na_2SO_4$), filtered, and concentrated. The residue was purified by silica gel chromatography (0-7% $CH_3OH$ in $CH_2Cl_2$) to give trans-4-((4-(2-cyclopropyloxazol-4-yl)pyridine-2-yl)((trans-4-(5-methoxy-6-methylpyridin-2-yl)cyclohexyl)methyl)carbamoyl)cyclohexyl 3-hydroxyazetidine-1-carboxylate (567 mg, 92%) as a white foam. $^1$H NMR (400 MHz, DMSO-$d_6$): δ 8.77 (s, 1H), 8.54 (d, 2H), 7.71 (s, 1H), 7.67 (d, 1H), 7.19 (d, 1H), 6.97 (d, 1H), 5.63 (d, 1H), 4.41-4.31 (m, 2H), 4.01-3.94 (m, 2H), 3.74 (s, 3H), 3.73-3.67 (m, 2H), 3.60-3.53 (in 2H), 2.50-2.42 (m, 1H), 2.28 (s, 3H), 2.26-2.17 (m, 1H), 1.90-1.72 (m, 8H), 1.55-1.40 (in 3H), 1.40-1.27 (m, 2H), 1.13-0.94 (in, 8H); LCMS: 644.6 [M+H]$^+$.

The Compounds below were synthesized from the appropriate Intermediate and the appropriate amine following the procedure described for Compound 7.

| Cmpd | Structure | Name | [M + H]⁺ |
|---|---|---|---|
| 7.01 | 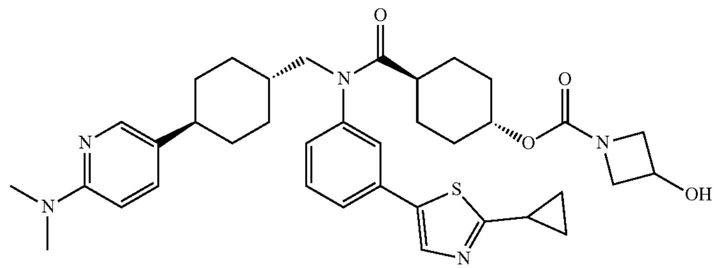 [SMILES: CN(C)c1ccc([C@H]2CC[C@H](CN(c3cccc(-c4cnc(C5CC5)s4)c3)C(=O)[C@H]3CC[C@H](OC(=O)N4CC(O)C4)CC3)CC2)cn1] | trans-4-((3-(2-Cyclopropylthiazol-5-yl)phenyl)((trans-4-(6-(dimethylamino)pyridin-3-yl)cyclohexyl)methyl)carbamoyl)cyclohexyl 3-hydroxyazetidine-1-carboxylate | 658.5 |
| 7.02[1] | 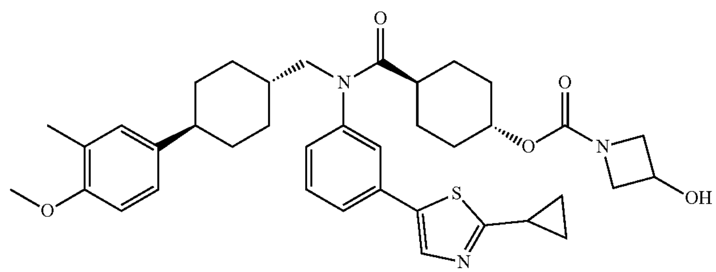 | trans-4-((3-(2-Cyclopropylthiazol-5-yl)phenyl)((trans-4-(4-methoxy-3-methylphenyl)cyclohexyl)methyl)carbamoyl)cyclohexyl 3-hydroxyazetidine-1-carboxylate | 658.4 |
| 7.03 | 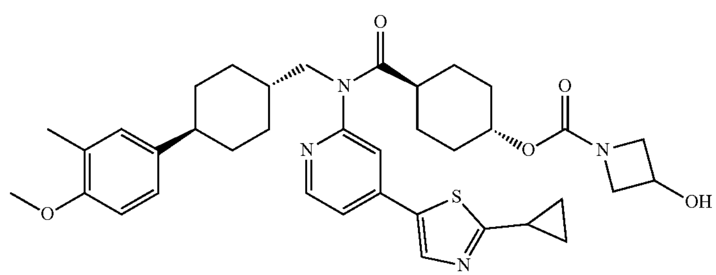 | trans-4-((4-(2-Cyclopropylthiazol-5-yl)pyridin-2-yl)((trans-4-(4-methoxy-3-methylphenyl)cyclohexyl)methyl)carbamoyl)cyclohexyl 3-hydroxyazetidine-1-carboxylate | 659.5 |

| Cmpd | Structure | Name | [M + H]+ |
|---|---|---|---|
| 7.04 | 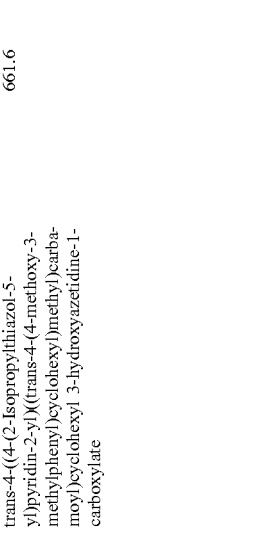 | trans-4-((4-(2-Isopropylthiazol-5-yl)pyridin-2-yl)((trans-4-(4-methoxy-3-methylphenyl)cyclohexyl)methyl)carbamoyl)cyclohexyl 3-hydroxyazetidine-1-carboxylate | 661.6 |
| 7.05 | 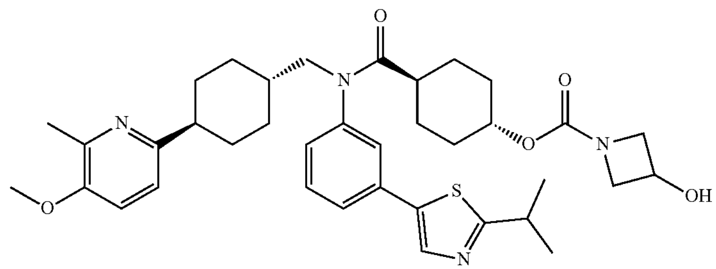 | trans-4-((3-(2-Isopropylthiazol-5-yl)phenyl)((trans-4-(5-methoxy-6-methylpyridin-2-yl)cyclohexyl)methyl)carbamoyl)cyclohexyl 3-hydroxyazetidine-1-carboxylate | 661.4 |
| 7.06 | 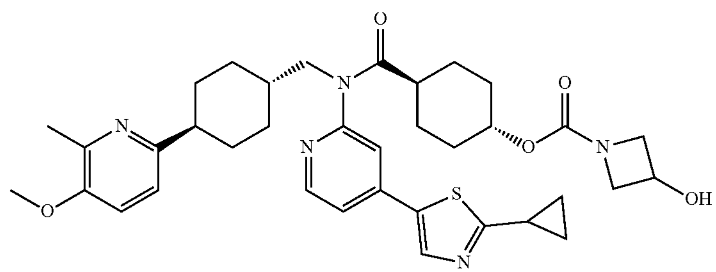 [SMILES: COc1ccc([C@H]2CC[C@H](CN(c3cc(-c4cnc(C5CC5)s4)ccn3)C(=O)[C@H]3CC[C@H](OC(=O)N4CC(O)C4)CC3)CC2)nc1C] | trans-4-((4-(2-Cyclopropylthiazol-5-yl)pyridin-2-yl)((trans-4-(5-methoxy-6-methylpyridin-2-yl)cyclohexyl)methyl)carbamoyl)cyclohexyl 3-hydroxyazetidine-1-carboxylate | 660.6 |

-continued

| Cmpd | Structure | Name | [M + H]+ |
|---|---|---|---|
| 7.07 | 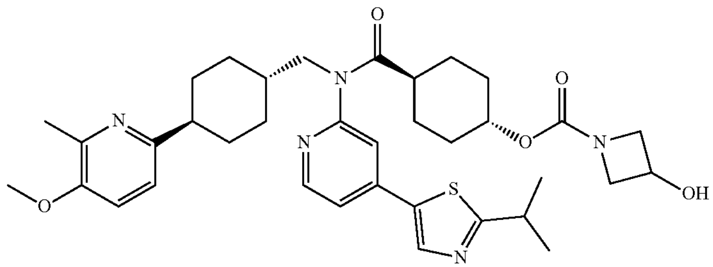 [SMILES: COc1ccc([C@H]2CC[C@H](CN(c3cc(-c4cnc(C(C)C)s4)ccn3)C(=O)[C@H]3CC[C@H](OC(=O)N4CC(O)C4)CC3)CC2)nc1C] | trans-4-((4-(2-Isopropylthiazol-5-yl)pyridin-2-yl)((trans-4-(5-methoxy-6-methylpyridin-2-yl)cyclohexyl)methyl)carbamoyl)cyclohexyl 3-hydroxyazetidine-1-carboxylate | 662.5 |
| 7.08 | 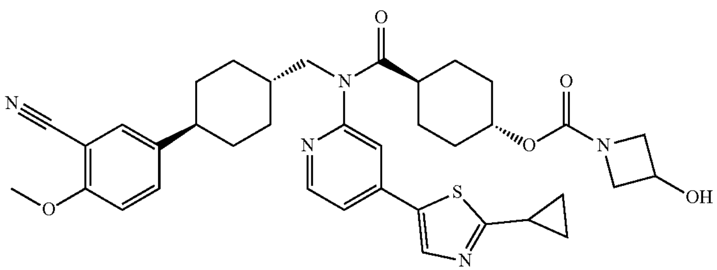 [SMILES: COc1ccc([C@H]2CC[C@H](CN(c3cc(-c4cnc(C5CC5)s4)ccn3)C(=O)[C@H]3CC[C@H](OC(=O)N4CC(O)C4)CC3)CC2)cc1C#N] | trans-4-(((trans-4-(3-Cyano-4-methoxyphenyl)cyclohexyl)methyl)(4-(2-cyclopropylthiazol-5-yl)pyridin-2-yl)carbamoyl)cyclohexyl 3-hydroxyazetidine-1-carboxylate | 670.5 |
| 7.09 | 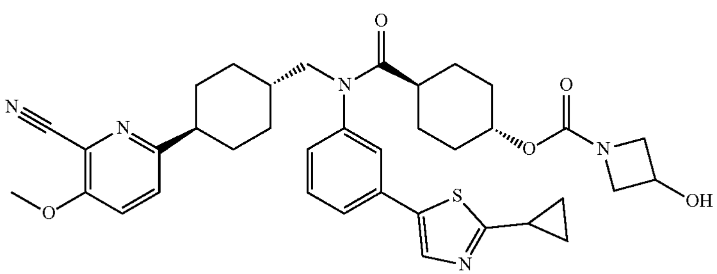 | trans-4-(((trans-4-(6-Cyano-5-methoxypyridin-2-yl)cyclohexyl)methyl)(3-(2-cyclopropylthiazol-5-yl)phenyl)carbamoyl)cyclohexyl 3-hydroxyazetidine-1-carboxylate | 670.5 |

| Cmpd | Structure | Name | [M + H]+ |
|---|---|---|---|
| 7.10 | 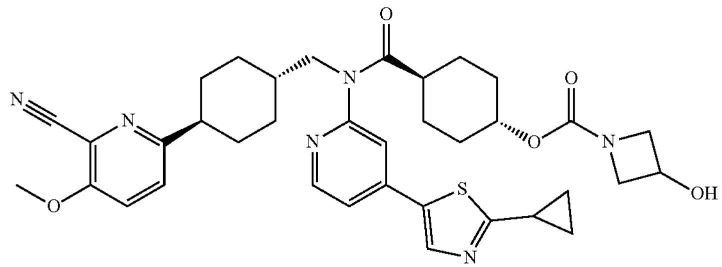 [SMILES: COc1ccc([C@H]2CC[C@H](CN(c3cc(-c4cnc(C5CC5)s4)ccn3)C(=O)[C@H]3CC[C@H](OC(=O)N4CC(O)C4)CC3)CC2)nc1C#N] | trans-4-((trans-4-(6-Cyano-5-methoxypyridin-2-yl)cyclohexyl)methyl)(4-(2-cyclopropylthiazol-5-yl)pyridin-2-yl)carbamoyl)cyclohexyl 3-hydroxyazetidine-1-carboxylate | 671.5 |
| 7.11 | 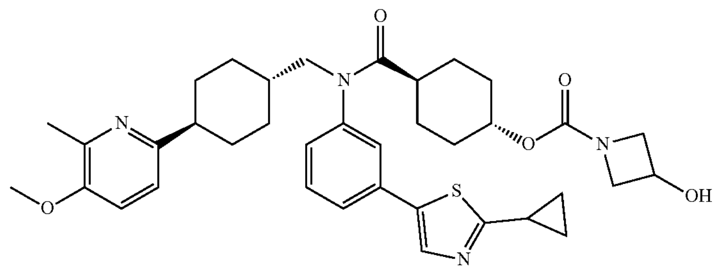 | trans-4-((3-(2-Cyclopropylthiazol-5-yl)phenyl)(trans-4-(5-methoxy-6-methylpyridin-2-yl)cyclohexyl)methyl)carbamoyl)cyclohexyl 3-hydroxyazetidine-1-carboxylate | 659.5 |
| 7.12[1] | 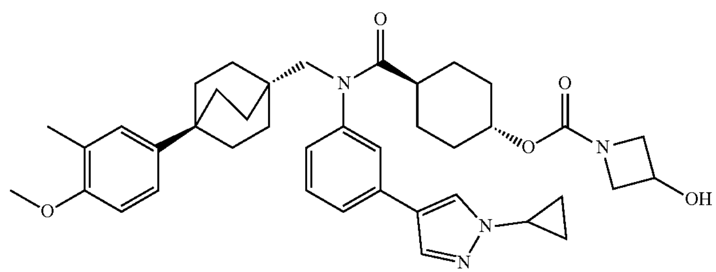 [SMILES: COc1ccc([C@]23CC[C@@](CN(c4cccc(-c5cnn(C6CC6)c5)c4)C(=O)[C@H]4CC[C@H](OC(=O)N5CC(O)C5)CC4)(CC2)CC3)cc1C] | 4-((3-(1-Cyclopropyl-1H-pyrazol-4-yl)phenyl)(4-(4-methoxy-3-methylphenyl)bicyclo[2.2.2]octan-1-yl)methyl)carbamoyl)cyclohexyl trans-3-hydroxyazetidine-1-carboxylate | 667.3 |

| Cmpd | Structure | Name | [M + H]⁺ |
|---|---|---|---|
| 7.13 | 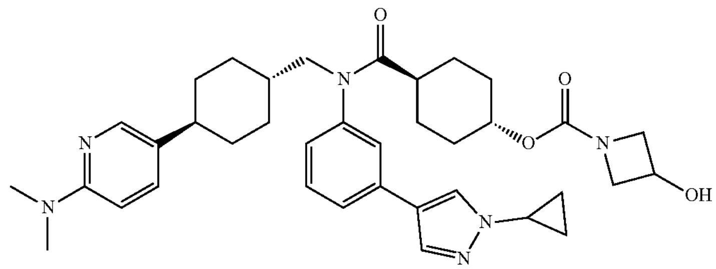 | trans-4-((3-(1-Cyclopropyl-1H-pyrazol-4-yl)phenyl)(trans-4-(6-(dimethyl)aminopyridin-3-yl)cyclohexyl)methyl)carbamoyl)cyclohexyl 3-hydroxyazetidine-1-carboxylate | 641.5 |
| 7.14 | 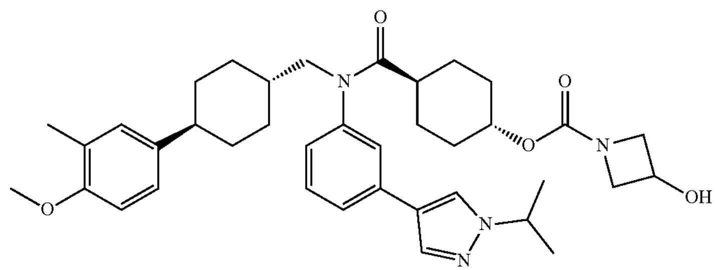 [SMILES: COc1ccc([C@H]2CC[C@H](CN(c3cccc(-c4cnn(C(C)C)c4)c3)C(=O)[C@H]3CC[C@H](OC(=O)N4CC(O)C4)CC3)CC2)cc1C] | trans-4-((3-(1-Isopropyl-1H-pyrazol-4-yl)phenyl)(trans-4-(4-methoxy-3-methyl phenyl)cyclohexyl)methyl)carbamoyl)cyclohexyl 3-hydroxyazetidine-1-carboxylate | 643.4 |
| 7.15 | 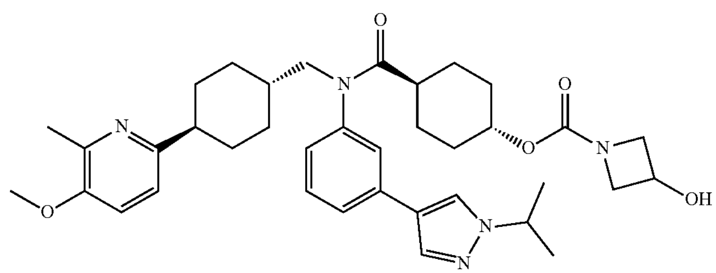 [SMILES: COc1ccc([C@H]2CC[C@H](CN(c3cccc(-c4cnn(C(C)C)c4)c3)C(=O)[C@H]3CC[C@H](OC(=O)N4CC(O)C4)CC3)CC2)nc1C] | trans-4-((3-(1-Isopropyl-1H-pyrazol-4-yl)phenyl)(trans-4-(5-methoxy-6-methylpyridin-2-yl)cyclohexyl)methyl)carbamoyl)cyclohexyl 3-hydroxyazetidine-1-carboxylate | 644.5 |

| Cmpd | Structure | Name | [M + H]+ |
|---|---|---|---|
| 7.16 | 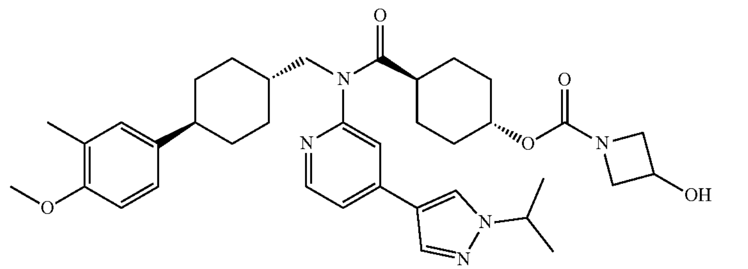 [SMILES: COc1ccc([C@H]2CC[C@H](CN(c3cc(-c4cnn(C(C)C)c4)ccn3)C(=O)[C@H]3CC[C@H](OC(=O)N4CC(O)C4)CC3)CC2)cc1C] | trans-4-((4-(1-Isopropyl-1H-pyrazol-4-yl)pyridin-2-yl)((trans-4-(4-methoxy-3-methylphenyl)cyclohexyl)methyl)carbamoyl)cyclohexyl 3-hydroxyazetidine-1-carboxylate | 644.5 |
| 7.17 | 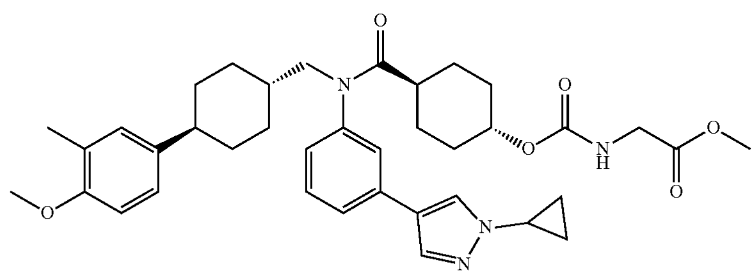 | Methyl 2-((((trans-4-((3-(1-cyclopropyl-1H-pyrazol-4-yl)phenyl)(trans-4-(4-methoxy-3-methylphenyl)cyclohexyl)methyl)carbamoyl)cyclohexyl)oxy)carbonyl)amino)acetate | 657.7 |
| 7.18[5] | 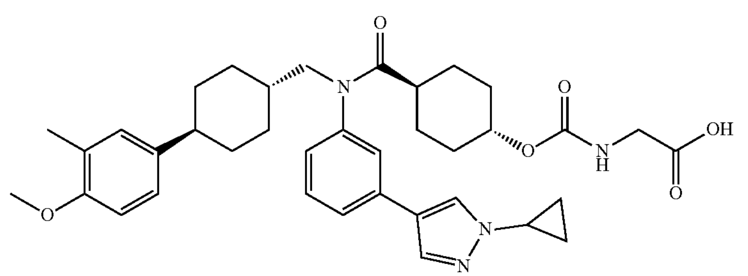 [SMILES: COc1ccc([C@H]2CC[C@H](CN(c3cccc(-c4cnn(C5CC5)c4)c3)C(=O)[C@H]3CC[C@H](OC(=O)NCC(=O)O)CC3)CC2)cc1C] | 2-(((((trans-4-((3-(1-Cyclopropyl-1H-pyrazol-4-yl)phenyl)((trans-4-(4-methoxy-3-methylphenyl)cyclohexyl)methyl)carbamoyl)cyclohexyl)oxy)carbonyl)amino)acetic acid | 643.5 |

| Cmpd | Structure | Name | [M + H]⁺ |
|---|---|---|---|
| 7.19 | 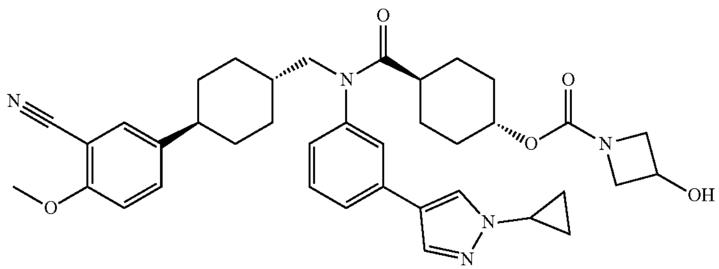 | trans-4-(((trans-4-(3-Cyano-4-methoxyphenyl)cyclohexyl)methyl)(3-(1-cyclopropyl-1H-pyrazol-4-yl)phenyl)carbamoyl)cyclohexyl 3-hydroxyazetidine-1-carboxylate | 674.4 M + Na |
| 7.20 | 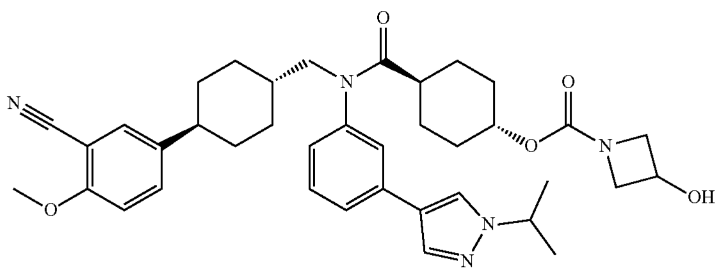 [SMILES: COc1ccc([C@H]2CC[C@H](CN(c3cccc(-c4cnn(C(C)C)c4)c3)C(=O)[C@H]3CC[C@H](OC(=O)N4CC(O)C4)CC3)CC2)cc1C#N] | trans-4-(((trans-4-(3-Cyano-4-methoxyphenyl)cyclohexyl)methyl)(3-(1-isopropyl-1H-pyrazol-4-yl)phenyl)carbamoyl)cyclohexyl 3-hydroxyazetidine-1-carboxylate | 654.5 |
| 7.21 | 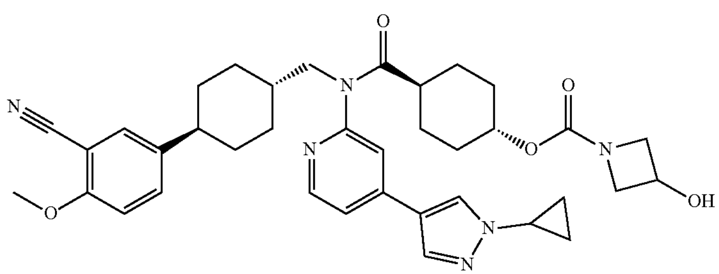 [SMILES: COc1ccc([C@H]2CC[C@H](CN(c3cc(-c4cnn(C5CC5)c4)ccn3)C(=O)[C@H]3CC[C@H](OC(=O)N4CC(O)C4)CC3)CC2)cc1C#N] | trans-4-(((trans-4-(3-Cyano-4-methoxyphenyl)cyclohexyl)methyl)(4-(1-cyclopropyl-1H-pyrazol-4-yl)pyridin-2-yl)carbamoyl)cyclohexyl 3-hydroxyazetidine-1-carboxylate | 653.5 |

| Cmpd | Structure | Name | [M + H]⁺ |
|---|---|---|---|
| 7.22 | 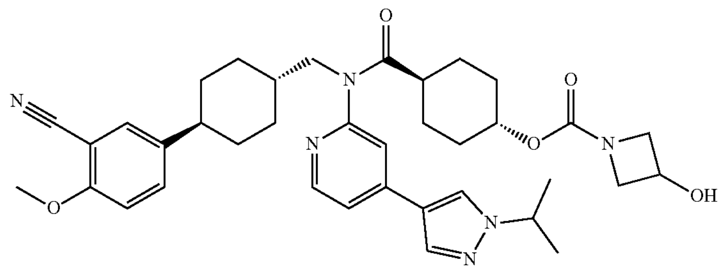 [SMILES: COc1ccc([C@H]2CC[C@H](CN(c3cc(-c4cnn(C(C)C)c4)ccn3)C(=O)[C@H]3CC[C@H](OC(=O)N4CC(O)C4)CC3)CC2)cc1C#N] | trans-4-((trans-4-(3-Cyano-4-methoxyphenyl)cyclohexyl)methyl)(4-(1-isopropyl-1H-pyrazol-4-yl)pyridin-2-yl)carbamoyl)cyclohexyl 3-hydroxyazetidine-1-carboxylate | 655.5 |
| 7.23 | 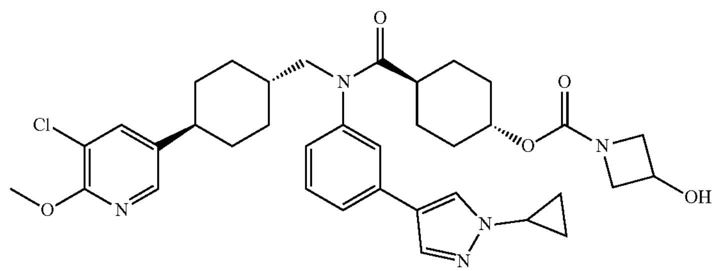 | trans-4-((trans-4-(5-Chloro-6-methoxypyridin-3-yl)cyclohexyl)methyl)(3-(1-cyclopropyl-1H-pyrazol-4-yl)phenyl)carbamoyl)cyclohexyl 3-hydroxyazetidine-1-carboxylate | 662.4 |
| 7.24 | 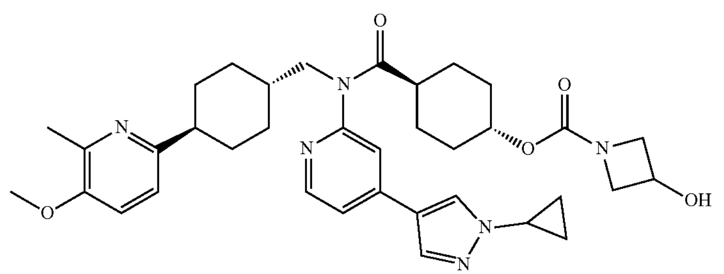 | trans-4-((4-(1-Cyclopropyl-1H-pyrazol-4-yl)pyridin-2-yl)((trans-4-(5-methoxy-6-methylpyridin-2-yl)cyclohexyl)methyl)carbamoyl)cyclohexyl 3-hydroxyazetidine-1-carboxylate | 643.6 |

| Cmpd | Structure | Name | [M + H]+ |
|---|---|---|---|
| 7.25 | 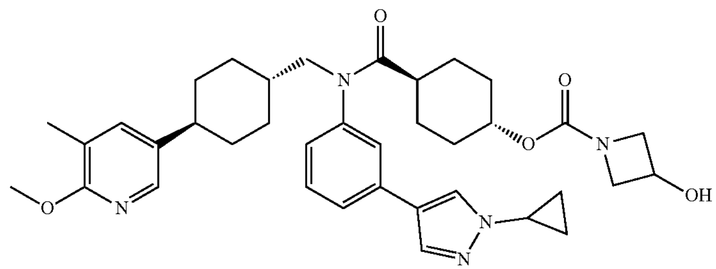 | trans-4-((3-(1-Cyclopropyl-1H-pyrazol-4-yl)phenyl)((trans-4-(6-methoxy-5-methylpyridin-3-yl)cyclohexyl)methyl)carbamoyl)cyclohexyl 3-hydroxyazetidine-1-carboxylate | 642.6 |
| 7.26 | 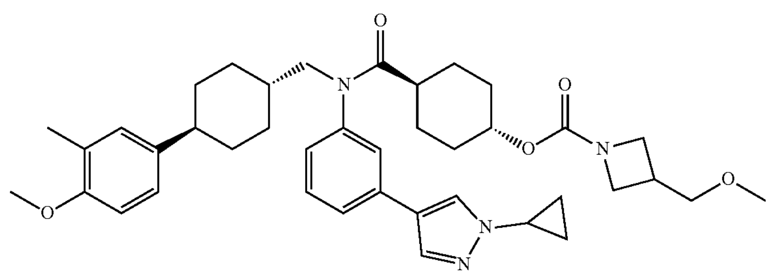 | trans-4-((3-(1-Cyclopropyl-1H-pyrazol-4-yl)phenyl)((trans-4-(4-methoxy-3-methylphenyl)cyclohexyl)methyl)carbamoyl)cyclohexyl 3-(methoxymethyl)azetidine-1-carboxylate | 669.6 |
| 7.27[3] | 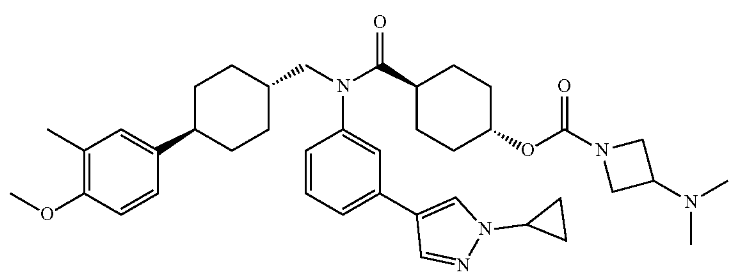 | trans-4-((3-(1-Cyclopropyl-1H-pyrazol-4-yl)phenyl)((trans-4-(4-methoxy-3-methylphenyl)cyclohexyl)methyl)carbamoyl)cyclohexyl 3-(dimethylamino)azetidine-1-carboxylate | 668.6 |

| Cmpd | Structure | Name | [M + H]+ |
|---|---|---|---|
| 7.28 | 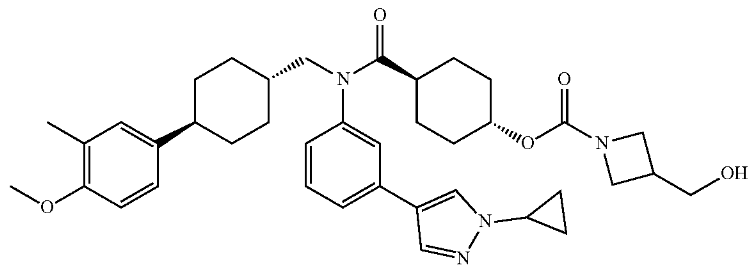 [SMILES: COc1ccc([C@H]2CC[C@H](CN(c3cccc(-c4cnn(C5CC5)c4)c3)C(=O)[C@H]3CC[C@H](OC(=O)N4CC(CO)C4)CC3)CC2)cc1C] | trans-4-((3-(1-Cyclopropyl-1H-pyrazol-4-yl)phenyl)(trans-4-(4-methoxy-3-methylphenyl)cyclohexyl)methyl)carbamoyl)cyclohexyl 3-(hydroxymethyl)azetidine-1-carboxylate | 655.6 |
| 7.29 | 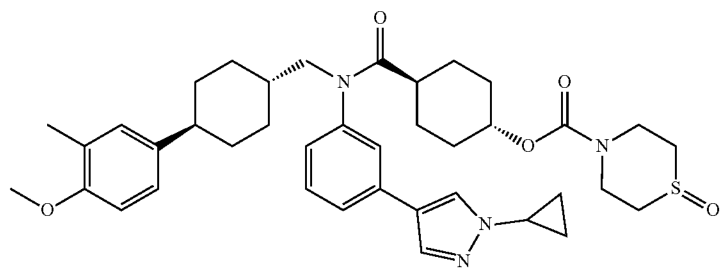 [SMILES: COc1ccc([C@H]2CC[C@H](CN(c3cccc(-c4cnn(C5CC5)c4)c3)C(=O)[C@H]3CC[C@H](OC(=O)N4CCS(=O)CC4)CC3)CC2)cc1C] | trans-4-((3-(1-Cyclopropyl-1H-pyrazol-4-yl)phenyl)(trans-4-(4-methoxy-3-methylphenyl)cyclohexyl)methyl)carbamoyl)cyclohexyl thiomorpholine-4-carboxylate 1-oxide | 687.7 |
| 7.30 | 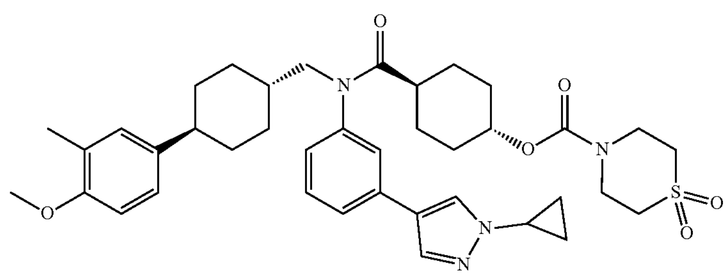 [SMILES: COc1ccc([C@H]2CC[C@H](CN(c3cccc(-c4cnn(C5CC5)c4)c3)C(=O)[C@H]3CC[C@H](OC(=O)N4CCS(=O)(=O)CC4)CC3)CC2)cc1C] | trans-4-((3-(1-Cyclopropyl-1H-pyrazol-4-yl)phenyl)(trans-4-(4-methoxy-3-methylphenyl)cyclohexyl)methyl)carbamoyl)cyclohexyl thiomorpholine-4-carboxylate 1,1-dioxide | 703.6 |

-continued

| Cmpd | Structure | Name | [M + H]+ |
|---|---|---|---|
| 7.31 | 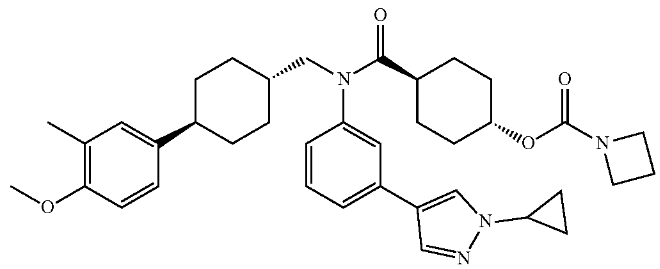 [SMILES: COc1ccc([C@H]2CC[C@H](CN(c3cccc(-c4cnn(C5CC5)c4)c3)C(=O)[C@H]3CC[C@H](OC(=O)N4CCC4)CC3)CC2)cc1C] | trans-4-(3-(1-Cyclopropyl-1H-pyrazol-4-yl)phenyl)((trans-4-(4-methoxy-3-methylphenyl)cyclohexyl)methyl)carbamoyl)cyclohexyl azetidine-1-carboxylate | 625.6 |
| 7.32 | 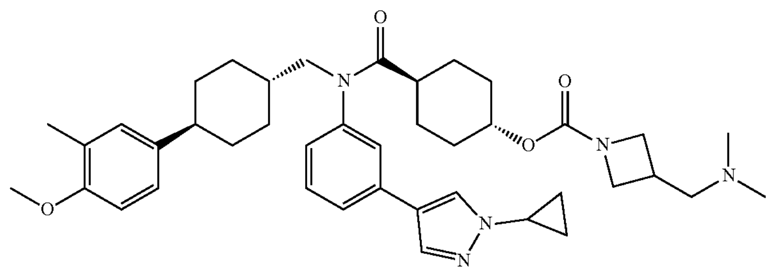 | trans-4-(3-(1-Cyclopropyl-1H-pyrazol-4-yl)phenyl)((trans-4-(4-methoxy-3-methylphenyl)cyclohexyl)methyl)carbamoyl)cyclohexyl 3-((dimethylamino)methyl)azetidine-1-carboxylate | 682.5 |
| 7.33 | 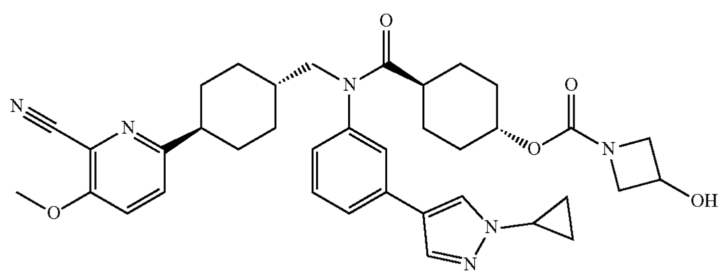 [SMILES: COc1ccc([C@H]2CC[C@H](CN(c3cccc(-c4cnn(C5CC5)c4)c3)C(=O)[C@H]3CC[C@H](OC(=O)N4CC(O)C4)CC3)CC2)nc1C#N] | trans-4-(((trans-4-(6-Cyano-5-methoxypyridin-2-yl)cyclohexyl)methyl)(3-(1-cyclopropyl-1H-pyrazol-4-yl)phenyl)carbamoyl)cyclohexyl 3-hydroxyazetidine-1-carboxylate | 653.4 |

| Cmpd | Structure | Name | [M + H]+ |
|---|---|---|---|
| 7.34 | 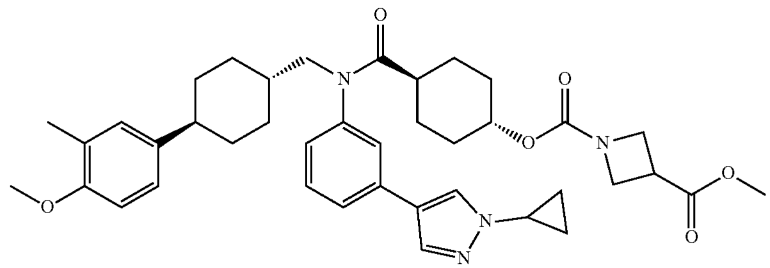 | 1-(trans-4-(3-(1-Cyclopropyl-1H-pyrazol-4-yl)phenyl)((trans-4-(4-methoxy-3-methylphenyl)cyclohexyl)methyl)carbamoyl)cyclohexyl) 3-methyl azetidine-1,3-dicarboxylate | 683.4 |
| 7.35[5] | 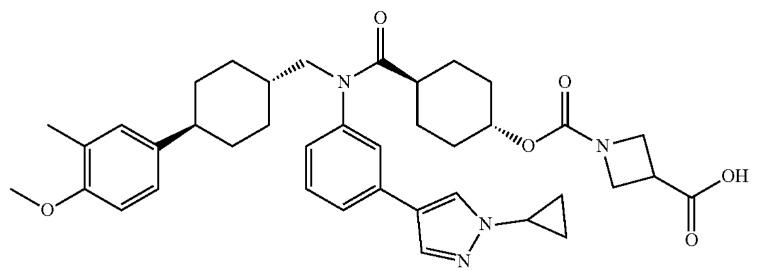 [SMILES: COc1ccc([C@H]2CC[C@H](CN(c3cccc(-c4cnn(C5CC5)c4)c3)C(=O)[C@H]3CC[C@H](OC(=O)N4CC(C(=O)O)C4)CC3)CC2)cc1C] | 1-(((trans-4-((3-(1-Cyclopropyl-1H-pyrazol-4-yl)phenyl)((trans-4-(4-methoxy-3-methylphenyl)cyclohexyl)methyl)carbamoyl)cyclohexyl)oxy)carbonyl)azetidine-3-carboxylic acid | 669.5 |
| 7.36 | 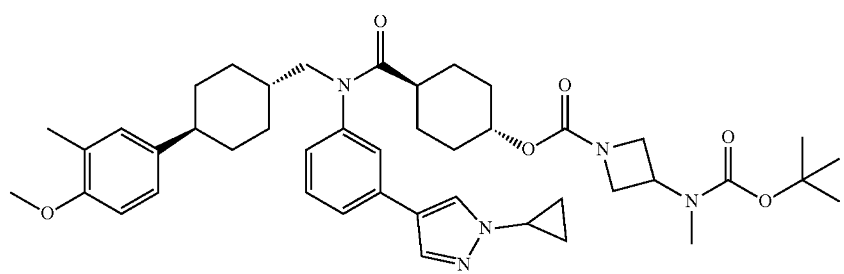 [SMILES: COc1ccc([C@H]2CC[C@H](CN(c3cccc(-c4cnn(C5CC5)c4)c3)C(=O)[C@H]3CC[C@H](OC(=O)N4CC(N(C)C(=O)OC(C)(C)C)C4)CC3)CC2)cc1C] | trans-4-((3-(1-Cyclopropyl-1H-pyrazol-4-yl)phenyl)((trans-4-(4-methoxy-3-methylphenyl)cyclohexyl)methyl)carbamoyl)cyclohexyl 3-((tert-butoxycarbonyl)(methyl)amino)azetidine-1-carboxylate | 754.1 |

| Cmpd | Structure | Name | [M + H]⁺ |
|---|---|---|---|
| 7.37[6] | 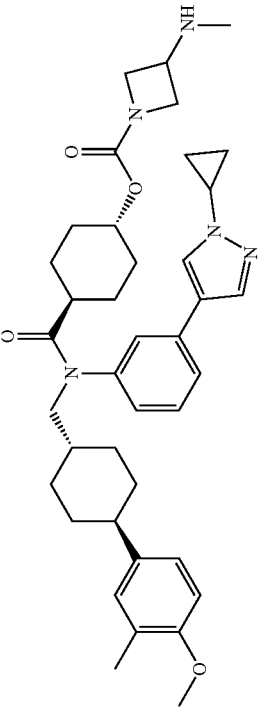 | trans-4-((3-(1-Cyclopropyl-1H-pyrazol-4-yl)phenyl)(trans-4-(4-methoxy-3-methylphenyl)cyclohexyl)methyl)carbamoyl)cyclohexyl 3-(methylamino)azetidine-1-carboxylate | 654.7 |
| 7.38 | 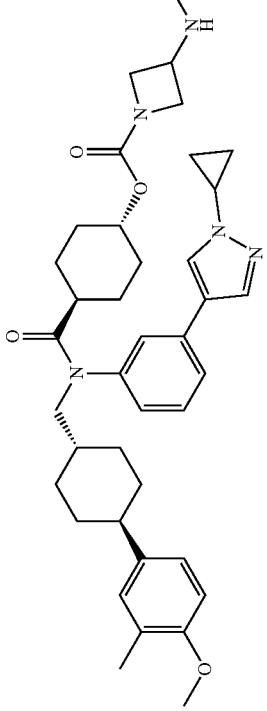 | trans-4-((3-(1-Cyclopropyl-1H-pyrazol-4-yl)phenyl)(trans-4-(4-methoxy-3-methylphenyl)cyclohexyl)methyl)carbamoyl)cyclohexyl 3-((tert-butoxycarbonyl)amino)azetidine-1-carboxylate | 762.6 M + Na |
| 7.39[6] | 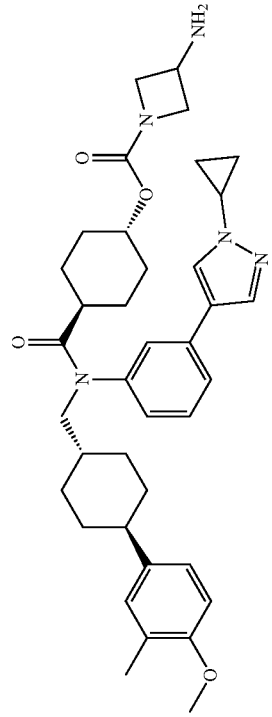 | trans-4-((3-(1-Cyclopropyl-1H-pyrazol-4-yl)phenyl)(trans-4-(4-methoxy-3-methylphenyl)cyclohexyl)methyl)carbamoyl)cyclohexyl 3-aminoazetidine-1-carboxylate | 640.6 |

-continued

| Cmpd | Structure | Name | [M + H]+ |
|---|---|---|---|
| 7.40 | 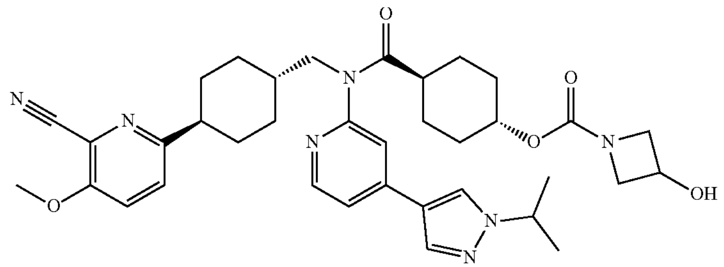 [SMILES: COc1ccc([C@H]2CC[C@H](CN(c3cc(-c4cnn(C(C)C)c4)ccn3)C(=O)[C@H]3CC[C@H](OC(=O)N4CC(O)C4)CC3)CC2)nc1C#N] | trans-4-((trans-4-(6-Cyano-5-methoxypyridin-2-yl)cyclohexyl)methyl)(4-(1-isopropyl-1H-pyrazol-4-yl)pyridin-2-yl)carbamoyl)cyclohexyl 3-hydroxyazetidine-1-carboxylate | 656.5 |
| 7.41[2] | 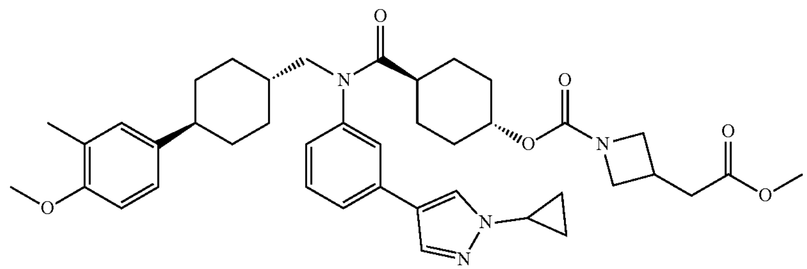 | trans-4-((3-(1-Cyclopropyl-1H-pyrazol-4-yl)phenyl)(trans-4-(4-methoxy-3-methylphenyl)cyclohexyl)methyl)carbamoyl)cyclohexyl 3-(2-methoxy-2-oxoethyl)azetidine-1-carboxylate | 697.8 |
| 7.42[5] | 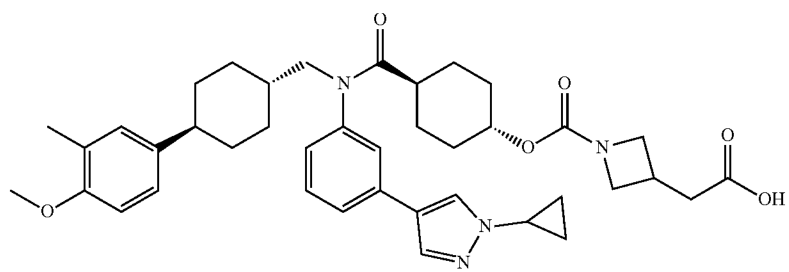 [SMILES: COc1ccc([C@H]2CC[C@H](CN(c3cccc(-c4cnn(C5CC5)c4)c3)C(=O)[C@H]3CC[C@H](OC(=O)N4CC(CC(=O)O)C4)CC3)CC2)cc1C] | 2-(1-(((trans-4-((3-(1-Cyclopropyl-1H-pyrazol-4-yl)phenyl)(trans-4-(4-methoxy-3-methylphenyl)cyclohexyl)methyl)carbamoyl)cyclohexyl)oxy)carbonyl)azetidin-3-yl)acetic acid | 683.8 |

| Cmpd | Structure | Name | [M + H]+ |
|---|---|---|---|
| 7.43 | 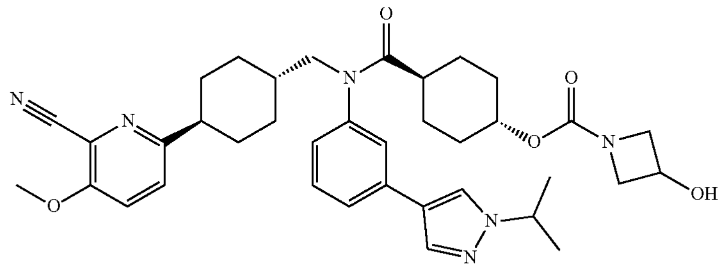 [SMILES: COc1ccc([C@H]2CC[C@H](CN(c3cccc(-c4cnn(C(C)C)c4)c3)C(=O)[C@H]3CC[C@H](OC(=O)N4CC(O)C4)CC3)CC2)nc1C#N] | trans-4-((trans-4-(6-Cyano-5-methoxypyridin-2-yl)cyclohexyl)methyl)(3-(1-isopropyl-1H-pyrazol-4-yl)phenyl)carbamoyl)cyclohexyl 3-hydroxyazetidine-1-carboxylate | 655.7 |
| 7.44 | 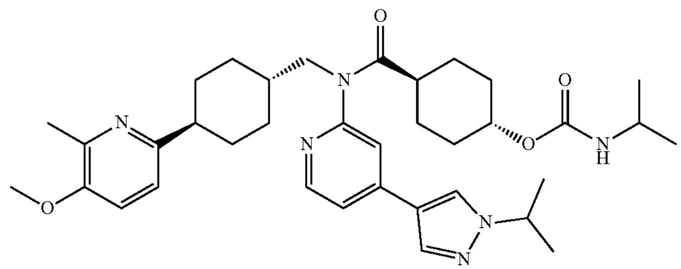 [SMILES: COc1ccc([C@H]2CC[C@H](CN(c3cc(-c4cnn(C(C)C)c4)ccn3)C(=O)[C@H]3CC[C@H](OC(=O)NC(C)C)CC3)CC2)nc1C] | trans-4-((4-(1-Isopropyl-1H-pyrazol-4-yl)pyridin-2-yl)(trans-4-(5-methoxy-6-methylpyridin-2-yl)cyclohexyl)methyl)carbamoyl)cyclohexyl isopropylcarbamate | 631.6 |
| 7.45 | 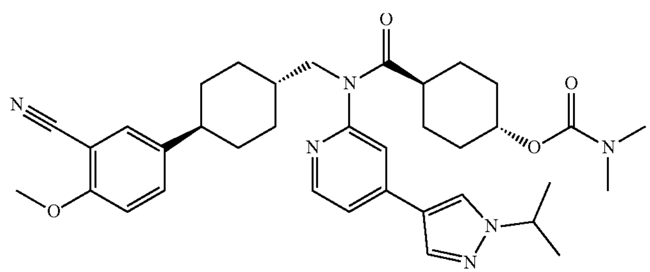 | trans-4-(((trans-4-(3-Cyano-4-methoxyphenyl)cyclohexyl)methyl)(4-(1-isopropyl-1H-pyrazol-4-yl)pyridin-2-yl)carbamoyl)cyclohexyl dimethylcarbamate | 627.6 |

| Cmpd | Structure | Name | [M + H]+ |
|---|---|---|---|
| 7.46 | 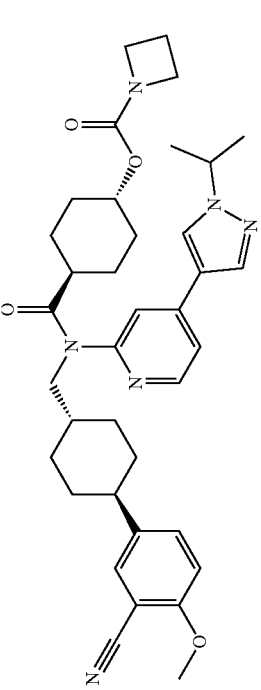 | trans-4-(((trans-4-(3-Cyano-4-methoxyphenyl)cyclohexyl)methyl)(4-(1-isopropyl-1H-pyrazol-4-yl)pyridin-2-yl)carbamoyl)cyclohexyl azetidine-1-carboxylate | 639.5 |
| 7.47 | 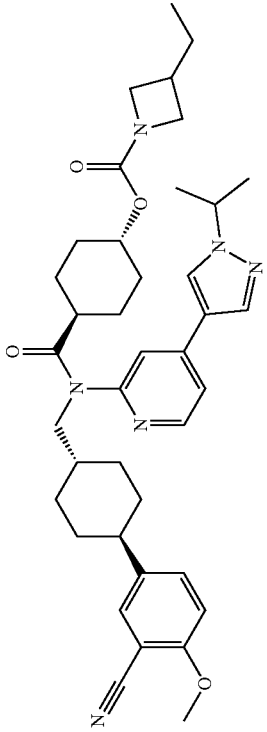 | trans-4-(((trans-4-(3-Cyano-4-methoxyphenyl)cyclohexyl)methyl)(4-(1-isopropyl-1H-pyrazol-4-yl)pyridin-2-yl)carbamoyl)cyclohexyl 3-ethylazetidine-1-carboxylate | 667.6 |
| 7.48 | 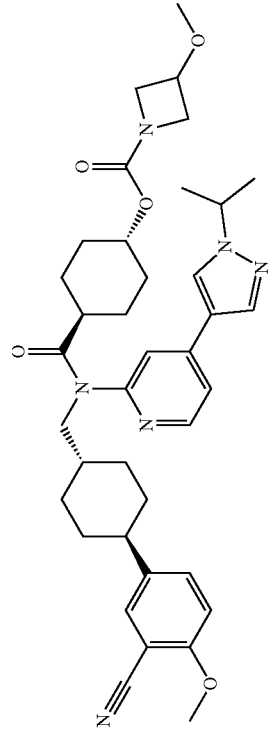 | trans-4-(((trans-4-(3-Cyano-4-methoxyphenyl)cyclohexyl)methyl)(4-(1-isopropyl-1H-pyrazol-4-yl)pyridin-2-yl)carbamoyl)cyclohexyl 3-methoxyazetidine-1-carboxylate | 669.5 |

| Cmpd | Structure | Name | [M + H]+ |
|---|---|---|---|
| 7.49 | 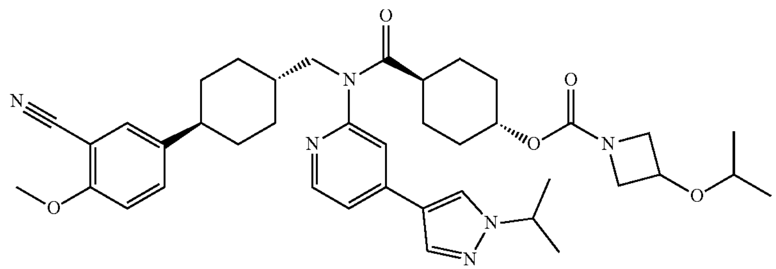 [SMILES: COc1ccc([C@H]2CC[C@H](CN(c3cc(-c4cnn(C(C)C)c4)ccn3)C(=O)[C@H]3CC[C@H](OC(=O)N4CC(OC(C)C)C4)CC3)CC2)cc1C#N] | trans-4-(((trans-4-(3-Cyano-4-methoxyphenyl)cyclohexyl)methyl)(4-(1-isopropyl-1H-pyrazol-4-yl)pyridin-2-yl)carbamoyl)cyclohexyl 3-isopropoxyazetidine-1-carboxylate | 697.6 |
| 7.50 | 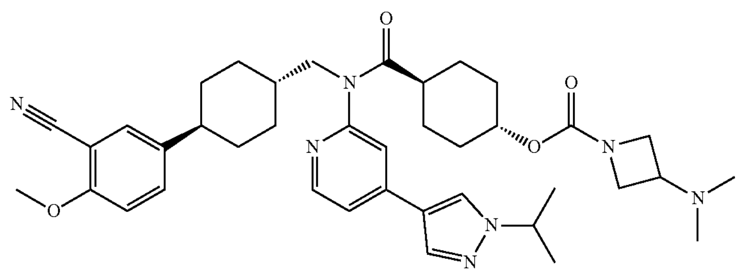 | trans-4-(((trans-4-(3-Cyano-4-methoxyphenyl)cyclohexyl)methyl)(4-(1-isopropyl-1H-pyrazol-4-yl)pyridin-2-yl)carbamoyl)cyclohexyl 3-(dimethylamino)azetidine-1-carboxylate | 682.8 |
| 7.51 | 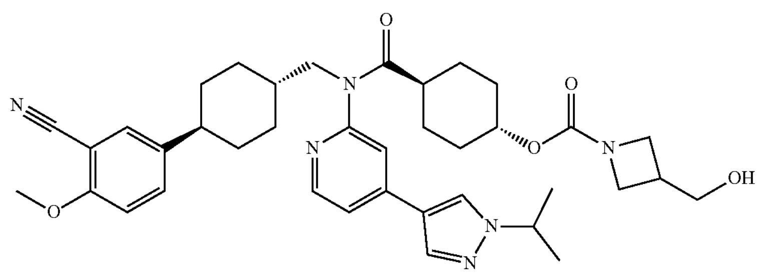 [SMILES: COc1ccc([C@H]2CC[C@H](CN(c3cc(-c4cnn(C(C)C)c4)ccn3)C(=O)[C@H]3CC[C@H](OC(=O)N4CC(CO)C4)CC3)CC2)cc1C#N] | trans-4-(((trans-4-(3-Cyano-4-methoxyphenyl)cyclohexyl)methyl)(4-(1-isopropyl-1H-pyrazol-4-yl)pyridin-2-yl)carbamoyl)cyclohexyl 3-(hydroxymethyl)azetidine-1-carboxylate | 669.8 |

| Cmpd | Structure | Name | [M + H]+ |
|---|---|---|---|
| 7.52 | 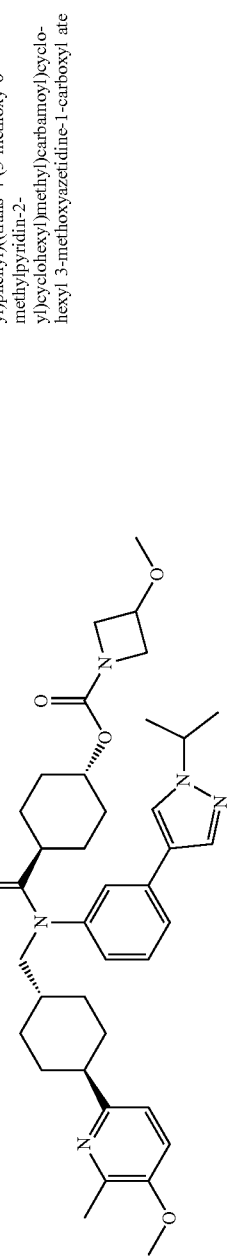 | trans-4-((3-(1-Isopropyl-1H-pyrazol-4-yl)phenyl)((trans-4-(5-methoxy-6-methylpyridin-2-yl)cyclohexyl)methyl)carbamoyl)cyclohexyl 3-methoxyazetidine-1-carboxylate | 658.5 |
| 7.53 | 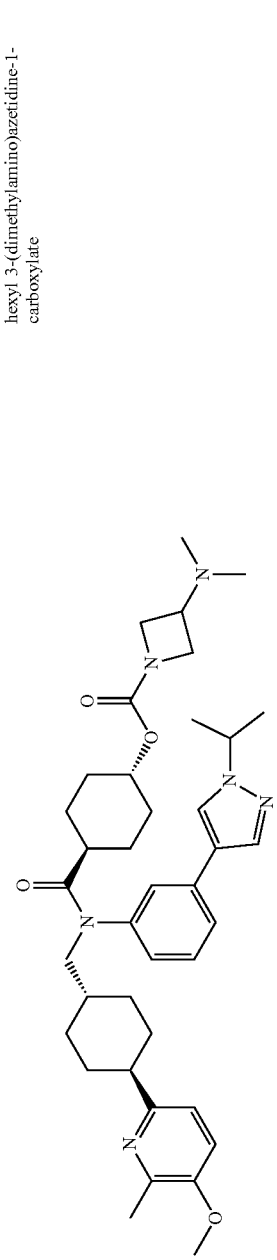 | trans-4-((3-(1-Isopropyl-1H-pyrazol-4-yl)phenyl)((trans-4-(5-methoxy-6-methylpyridin-2-yl)cyclohexyl)methyl)carbamoyl)cyclohexyl 3-(dimethylamino)azetidine-1-carboxylate | 671.6 |
| 7.54 | 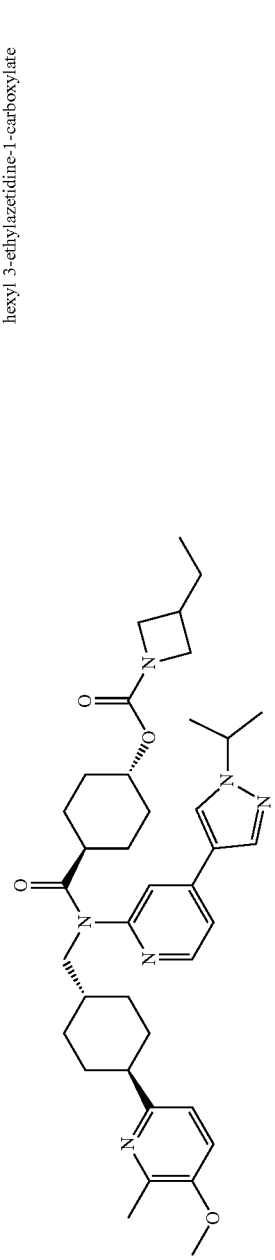 | trans-4-((4-(1-Isopropyl-1H-pyrazol-4-yl)pyridin-2-yl)((trans-4-(5-methoxy-6-methylpyridin-2-yl)cyclohexyl)methyl)carbamoyl)cyclohexyl 3-ethylazetidine-1-carboxylate | 657.5 |

| Cmpd | Structure | Name | [M + H]+ |
|---|---|---|---|
| 7.55 | 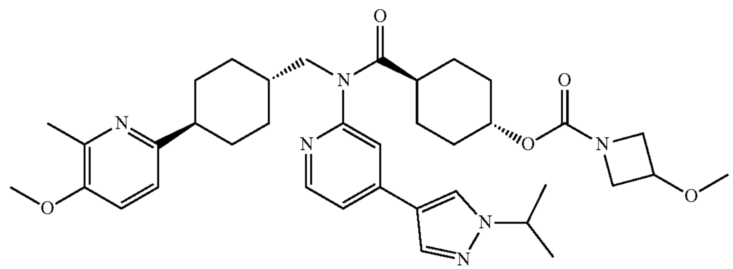 | trans-4-((4-(1-Isopropyl-1H-pyrazol-4-yl)pyridin-2-yl)((trans-4-(5-methoxy-6-methylpyridin-2-yl)cyclohexyl)methyl)carbamoyl)cyclohexyl 3-methoxyazetidine-1-carboxylate | 659.5 |
| 7.56 | 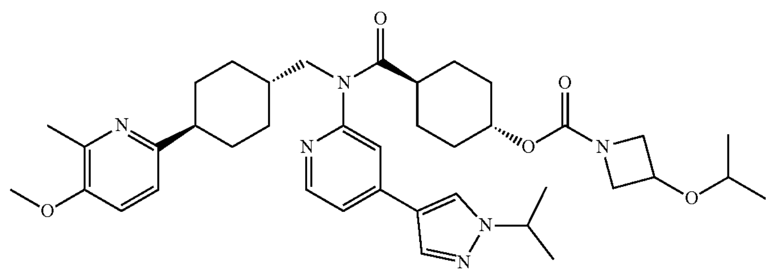 [SMILES: COc1ccc([C@H]2CC[C@H](CN(c3cc(-c4cnn(C(C)C)c4)ccn3)C(=O)[C@H]3CC[C@H](OC(=O)N4CC(OC(C)C)C4)CC3)CC2)nc1C] | trans-4-((4-(1-Isopropyl-1H-pyrazol-4-yl)pyridin-2-yl)((trans-4-(5-methoxy-6-methylpyridin-2-yl)cyclohexyl)methyl)carbamoyl)cyclohexyl 3-isopropoxyazetidine-1-carboxylate | 687.5 |
| 7.57 | 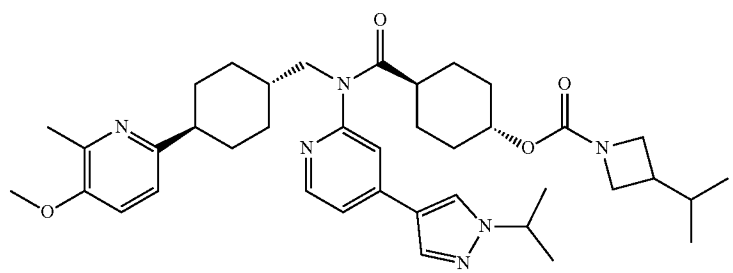 [SMILES: COc1ccc([C@H]2CC[C@H](CN(c3cc(-c4cnn(C(C)C)c4)ccn3)C(=O)[C@H]3CC[C@H](OC(=O)N4CC(C(C)C)C4)CC3)CC2)nc1C] | trans-4-((4-(1-Isopropyl-1H-pyrazol-4-yl)pyridin-2-yl)((trans-4-(5-methoxy-6-methylpyridin-2-yl)cyclohexyl)methyl)carbamoyl)cyclohexyl 3-isopropylazetidine-1-carboxylate | 671.5 |

-continued

| Cmpd | Structure | Name | [M + H]+ |
|---|---|---|---|
| 7.58[3] | 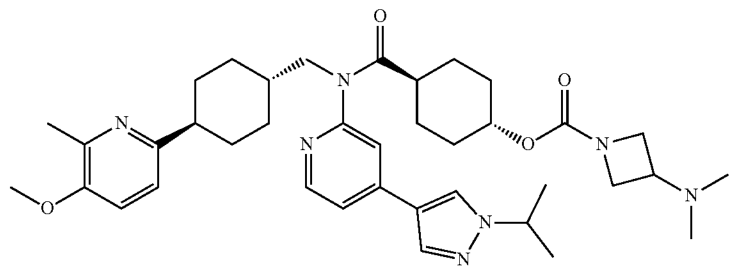 | trans-4-((4-(1-Isopropyl-1H-pyrazol-4-yl)pyridin-2-yl)((trans-4-(5-methoxy-6-methylpyridin-2-yl)cyclohexyl)methyl)carbamoyl)cyclohexyl 3-(dimethylamino)azetidine-1-carboxylate | 672.6 |
| 7.59 | 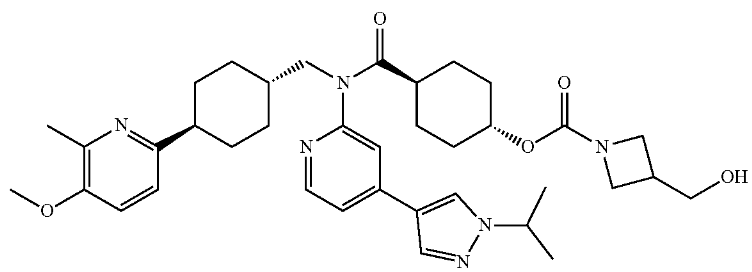 [SMILES: COc1ccc([C@H]2CC[C@H](CN(c3cc(-c4cnn(C(C)C)c4)ccn3)C(=O)[C@H]3CC[C@H](OC(=O)N4CC(CO)C4)CC3)CC2)nc1C] | trans-4-((4-(1-Isopropyl-1H-pyrazol-4-yl)pyridin-2-yl)((trans-4-(5-methoxy-6-methylpyridin-2-yl)cyclohexyl)methyl)carbamoyl)cyclohexyl 3-(hydroxymethyl)azetidine-1-carboxylate | 659.5 |
| 7.60 | 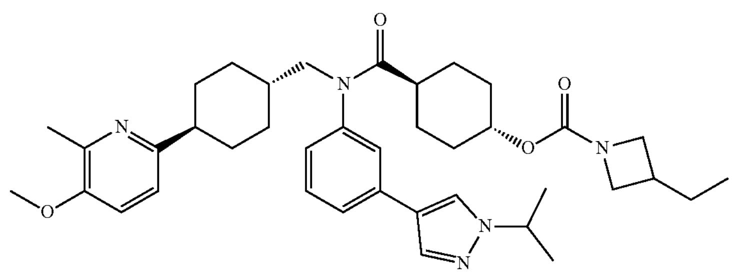 [SMILES: CCC1CN(C(=O)O[C@H]2CC[C@H](C(=O)N(C[C@H]3CC[C@H](c4ccc(OC)c(C)n4)CC3)c3cccc(-c4cnn(C(C)C)c4)c3)CC2)C1] | trans-4-((3-(1-Isopropyl-1H-pyrazol-4-yl)phenyl)((trans-4-(5-methoxy-6-methylpyridin-2-yl)cyclohexyl)methyl)carbamoyl)cyclohexyl 3-ethylazetidine-1-carboxylate | 656.3 |

| Cmpd | Name | [M + H]+ |
|---|---|---|
| 7.61 | trans-4-((3-(1-Isopropyl-1H-pyrazol-4-yl)phenyl)((trans-4-(5-methoxy-6-methylpyridin-2-yl)cyclohexyl)methyl)carbamoyl)cyclohexyl 3-(hydroxymethyl)azetidine-1-carboxylate | 658.4 |
| 7.62[1] | trans-4-((3-(2-Cyclopropyloxazol-4-yl)phenyl)((trans-4-(4-methoxy-3-methyl phenyl)cyclohexyl)methyl)carbamoyl)cyclohexyl 3-hydroxyazetidine-1-carboxylate | 642.4 |
| 7.63 | trans-4-((3-(2-Cyclopropyloxazol-4-yl)phenyl)((trans-4-(6-(dimethylamino)pyridine-3-yl)cyclohexyl)methyl)carbamoyl)cyclohexyl 3-hydroxyazetidine-1-carboxylate | 642.5 |

| Cmpd | Structure | Name | [M + H]+ |
|---|---|---|---|
| 7.64 | 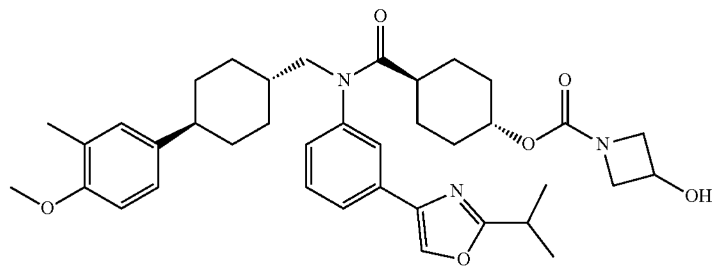 [SMILES: COc1ccc([C@H]2CC[C@H](CN(c3cccc(-c4coc(C(C)C)n4)c3)C(=O)[C@H]3CC[C@H](OC(=O)N4CC(O)C4)CC3)CC2)cc1C] | trans-4-((3-(2-Isopropyloxazol-4-yl)phenyl)(trans-4-(4-methoxy-3-methylphenyl)cyclohexyl)methyl)carbamoyl)cyclohexyl 3-hydroxyazetidine-1-carboxylate | 644.5 |
| 7.65 | 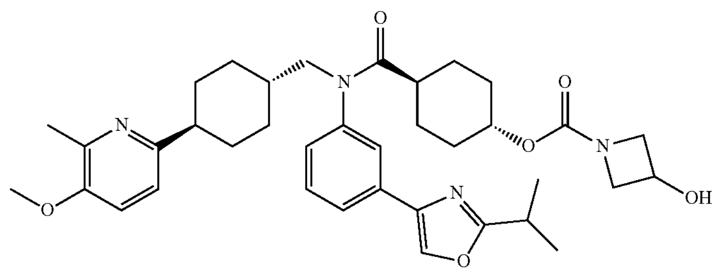 | trans-4-((3-(2-Isopropyloxazol-4-yl)phenyl)(trans-4-(5-methoxy-6-methylpyridin-2-yl)cyclohexyl)methyl)carbamoyl)cyclohexyl 3-hydroxyazetidine-1-carboxylate | 645.5 |
| 7.66 | 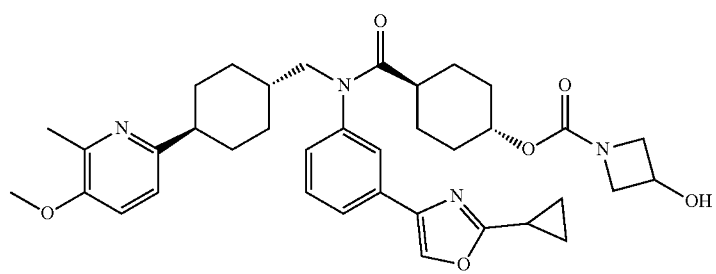 | trans-4-((3-(2-Cyclopropyloxazol-4-yl)phenyl)(trans-4-(5-methoxy-6-methylpyridin-2-yl)cyclohexyl)methyl)carbamoyl)cyclohexyl 3-hydroxyazetidine-1-carboxylate | 643.3 |

| Cmpd | Structure | Name | [M + H]+ |
|---|---|---|---|
| 7.67 | 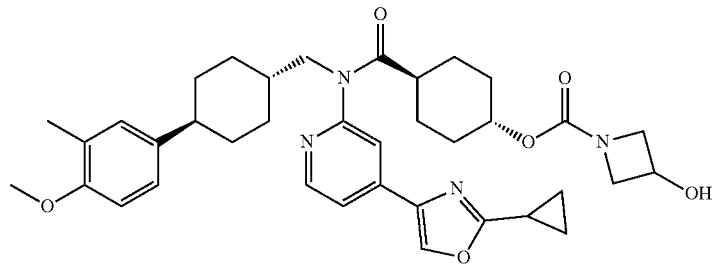 [SMILES: COc1ccc([C@H]2CC[C@H](CN(c3cc(-c4coc(C5CC5)n4)ccn3)C(=O)[C@H]3CC[C@H](OC(=O)N4CC(O)C4)CC3)CC2)cc1C] | trans-4-((4-(2-Cyclopropyloxazol-4-yl)pyridine-2-yl)((trans-4-(4-methoxy-3-methylphenyl)cyclohexyl)methyl)carbamoyl)cyclohexyl 3-hydroxyazetidine-1-carboxylate | 645.5 |
| 7.68 | 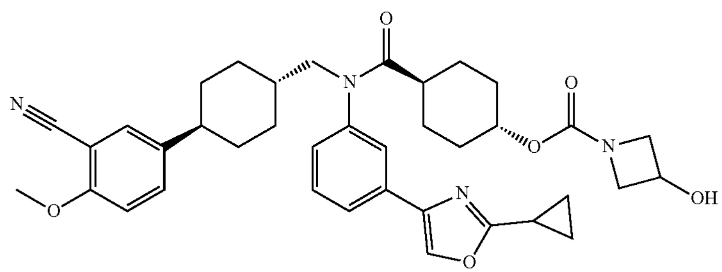 | trans-4-(((trans-4-(3-Cyano-4-methoxyphenyl)cyclohexyl)methyl)(3-(2-cyclopropyloxazol-4-yl)phenyl)carbamoyl)cyclohexyl 3-hydroxyazetidine-1-carboxylate | 653.8 |
| 7.69 | 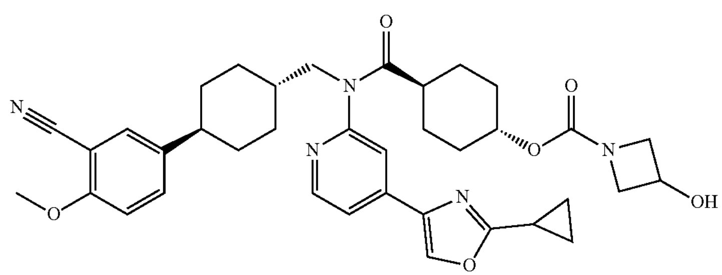 | trans-4-(((trans-4-(3-Cyano-4-methoxyphenyl)cyclohexyl)methyl)(4-(2-cyclopropyloxazol-4-yl)pyridine-2-yl)carbamoyl)cyclohexyl 3-hydroxyazetidine-1-carboxylate | 654.6 |

| Cmpd | Structure | Name | [M + H]+ |
|---|---|---|---|
| 7.70 | 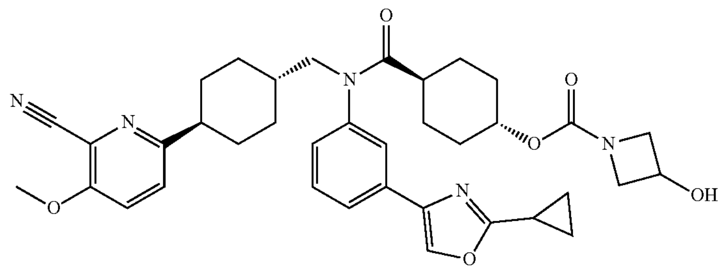 | trans-4-((trans-4-(6-Cyano-5-methoxypyridin-2-yl)cyclohexyl)methyl)(3-(2-cyclopropyloxazol-4-yl)phenyl)carbamoyl)cyclohexyl 3-hydroxyazetidine-1-carboxylate | 654.2 |
| 7.71 | 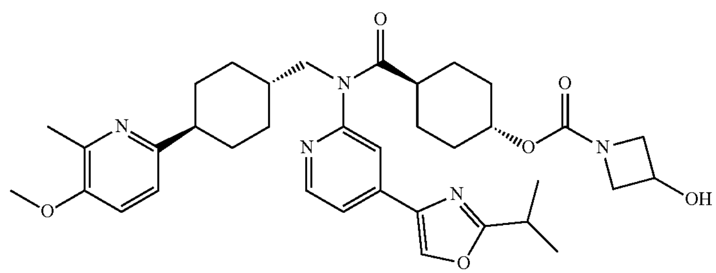 | trans-4-((4-(2-Isopropyloxazol-4-yl)pyridine-2-yl)((trans-4-(5-methoxy-6-methyl pyridin-2-yl)cyclohexyl)methyl)carbamoyl)cyclohexyl 3-hydroxyazetidine-1-carboxylate | 646.6 |
| 7.72 | 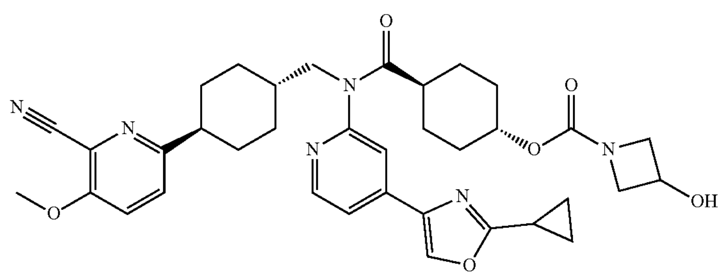 | trans-4-(((trans-4-(6-Cyano-5-methoxypyridin-2-yl)cyclohexyl)methyl)(4-(2-cyclopropyloxazol-4-yl)pyridine-2-yl)carbamoyl)cyclohexyl 3-hydroxyazetidine-1-carboxylate | 655.7 |

| Cmpd | Structure | Name | [M + H]+ |
|---|---|---|---|
| 7.73 | 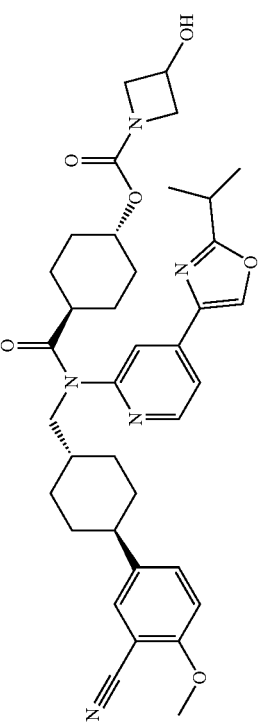 | trans-4-((trans-4-(3-Cyano-4-methoxyphenyl)cyclohexyl)methyl)(4-(2-isopropyloxazol-4-yl)pyridine-2-yl)carbamoyl)cyclohexyl 3-hydroxyazetidine-1-carboxylate | 656.5 |
| 7.74 | 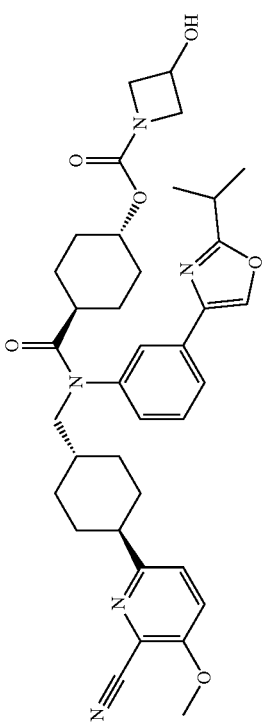 | trans-4-(((trans-4-(6-Cyano-5-methoxypyridin-2-yl)cyclohexyl)methyl)(3-(2-isopropyloxazol-4-yl)phenyl)carbamoyl)cyclohexyl 3-hydroxyazetidine-1-carboxylate | 656.6 |
| 7.75 | 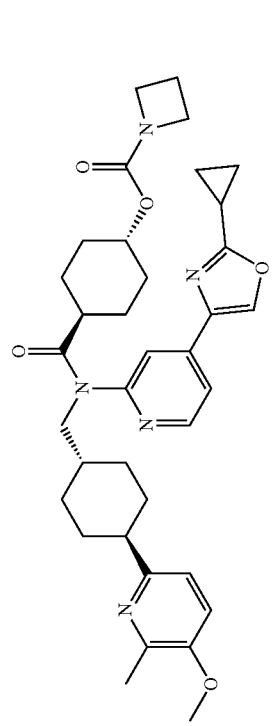 | trans-4-((4-(2-Cyclopropyloxazol-4-yl)pyridine-2-yl)((trans-4-(5-methoxy-6-methyl pyridin-2-yl)cyclohexyl)methyl)carbamoyl)cyclohexyl azetidine-1-carboxylate | 628.6 |

-continued

| Cmpd | Structure | Name | [M + H]+ |
|---|---|---|---|
| 7.76 | 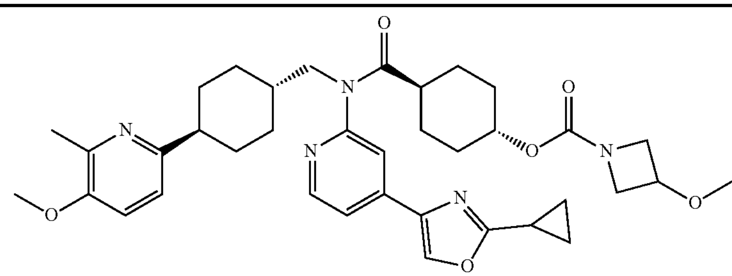 | trans-4-((4-(2-Cyclopropyloxazol-4-yl)pyridine-2-yl)((trans-4-(5-methoxy-6-methylpyridin-2-yl)cyclohexyl)methyl)carbamoyl)cyclohexyl 3-methoxyazetidine-1-carboxylate | 658.5 |
| 7.77 | 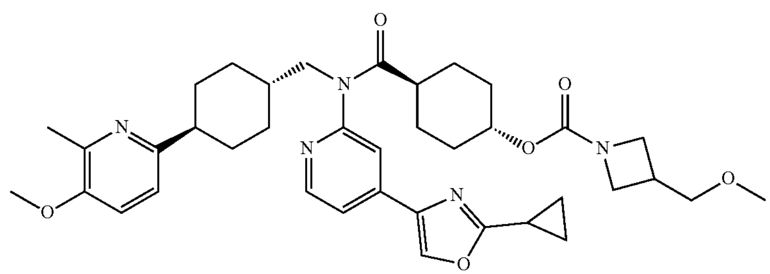 | trans-4-((4-(2-Cyclopropyloxazol-4-yl)pyridine-2-yl)((trans-4-(5-methoxy-6-methylpyridin-2-yl)cyclohexyl)methyl)carbamoyl)cyclohexyl 3-(methoxymethyl)azetidine-1-carboxylate) | 672.6 |
| 7.78 | 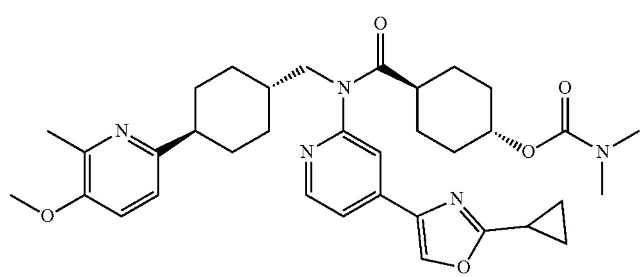 | trans-4-((4-(2-Cyclopropyloxazol-4-yl)pyridine-2-yl)((trans-4-(5-methoxy-6-methylpyridin-2-yl)cyclohexyl)methyl)carbamoyl)cyclohexyl dimethylcarbamate | 616.4 |

-continued

| Cmpd | Structure | Name | [M + H]+ |
|---|---|---|---|
| 7.79 | 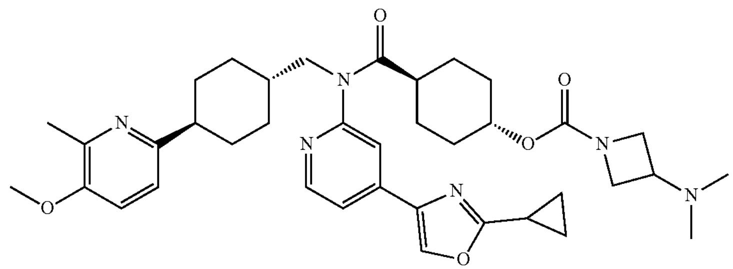 | trans-4-((4-(2-Cyclopropyloxazol-4-yl)pyridine-2-yl)((trans-4-(5-methoxy-6-methylpyridin-2-yl)cyclohexyl)methyl)carbamoyl)cyclohexyl 3-(dimethylamino)azetidine-1-carboxylate | 671.5 |
| 7.80 | 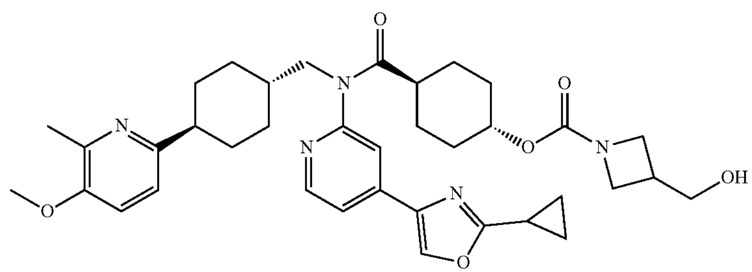 [SMILES: COc1ccc([C@H]2CC[C@H](CN(c3cc(-c4coc(C5CC5)n4)ccn3)C(=O)[C@H]3CC[C@H](OC(=O)N4CC(CO)C4)CC3)CC2)nc1C] | trans-4-((4-(2-Cyclopropyloxazol-4-yl)pyridine-2-yl)((trans-4-(5-methoxy-6-methylpyridin-2-yl)cyclohexyl)methyl)carbamoyl)cyclohexyl 3-(hydroxymethyl)azetidine-1-carboxylate | 658.6 |
| 7.81 | 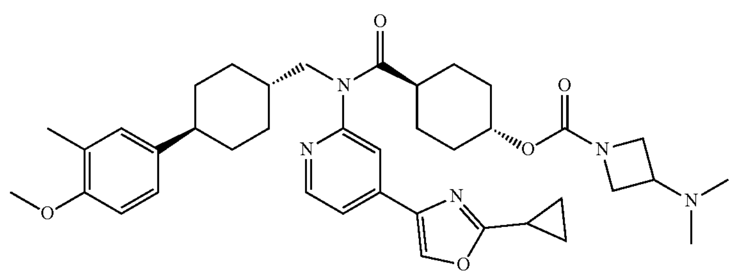 | trans-4-((4-(2-Cyclopropyloxazol-4-yl)pyridine-2-yl)((trans-4-(4-methoxy-3-methylphenyl)cyclohexyl)methyl)carbamoyl)cyclohexyl 3-(dimethylamino)azetidine-1-carboxylate | 650.5 |

| Cmpd | Structure | Name | [M + H]+ |
|---|---|---|---|
| 7.82 | 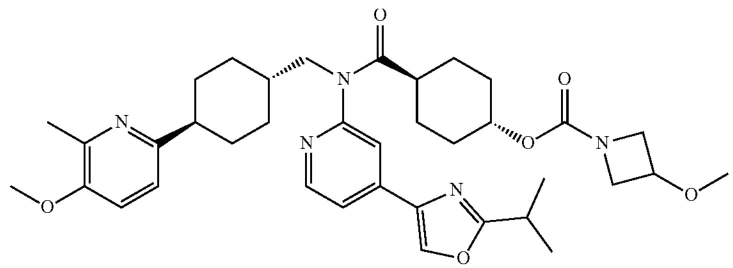 | trans-4-((4-(2-Isopropyloxazol-4-yl)pyridine-2-yl)((trans-4-(5-methoxy-6-methylpyridin-2-yl)cyclohexyl)methyl)carbamoyl)cyclohexyl 3-methoxyazetidine-1-carboxylate | 660.6 |
| 7.83 | 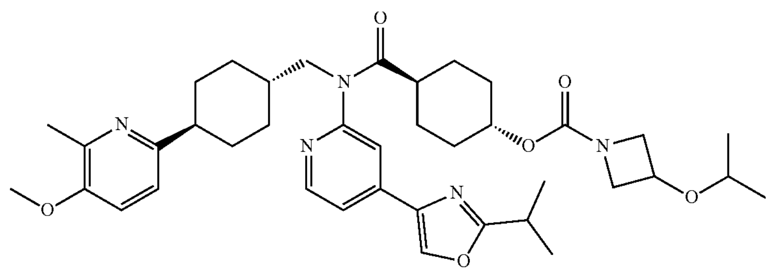 [SMILES: COc1ccc([C@H]2CC[C@H](CN(c3cc(-c4coc(C(C)C)n4)ccn3)C(=O)[C@H]3CC[C@H](OC(=O)N4CC(OC(C)C)C4)CC3)CC2)nc1C] | trans-4-((4-(2-Isopropyloxazol-4-yl)pyridin-2-yl)((trans-4-(5-methoxy-6-methylpyridin-2-yl)cyclohexyl)methyl)carbamoyl)cyclohexyl 3-isopropoxyazetidine-1-carboxylate | 688.8 |
| 7.84 | 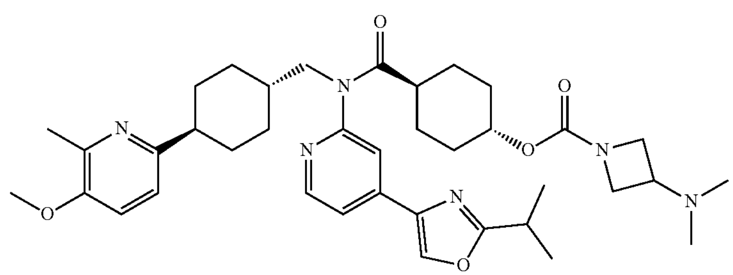 | trans-4-((4-(2-Isopropyloxazol-4-yl)pyridine-2-yl)((trans-4-(5-methoxy-6-methylpyridin-2-yl)cyclohexyl)methyl)carbamoyl)cyclohexyl 3-(dimethylamino)azetidine-1-carboxylate | 673.6 |

-continued

| Cmpd | Structure | Name | [M + H]+ |
|---|---|---|---|
| 7.85[2] | 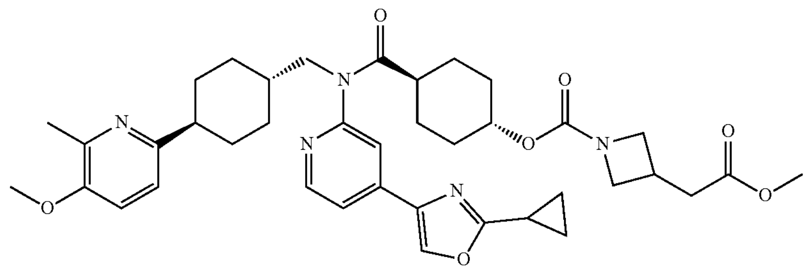 | trans-4-((4-(2-Cyclopropyloxazol-4-yl)pyridine-2-yl)((trans-4-(5-methoxy-6-methylpyridin-2-yl)cyclohexyl)methyl)carbamoyl)cyclohexyl 3-(2-methoxy-2-oxoethyl)azetidine-1-carboxylate | 700.6 |
| 7.86[5] | 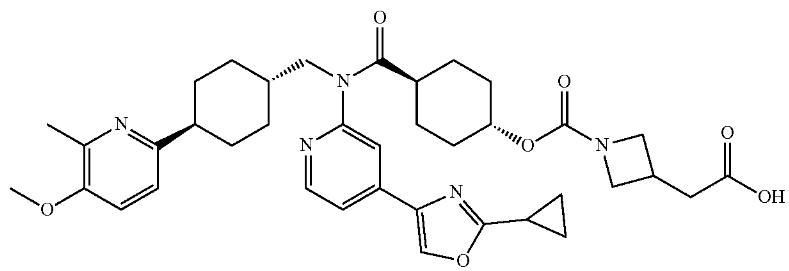 [SMILES: COc1ccc([C@H]2CC[C@H](CN(c3cc(-c4coc(C5CC5)n4)ccn3)C(=O)[C@H]3CC[C@H](OC(=O)N4CC(CC(=O)O)C4)CC3)CC2)nc1C] | 2-(1-(((trans-4-((4-(2-Cyclopropyloxazol-4-yl)pyridine-2-yl)((trans-4-(5-methoxy-6-methylpyridin-2-yl)cyclohexyl)methyl)carbamoyl)cyclohexyl)oxy)carbonyl)azetidin-3-yl)acetic acid | 686.6 |
| 7.87 | 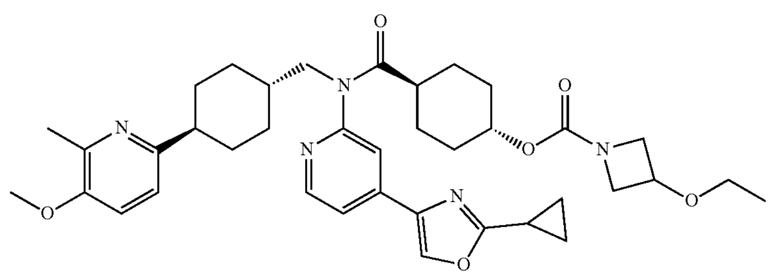 | trans-4-((4-(2-Cyclopropyloxazol-4-yl)pyridine-2-yl)((trans-4-(5-methoxy-6-methylpyridin-2-yl)cyclohexyl)methyl)carbamoyl)cyclohexyl 3-ethoxyazetidine-1-carboxylate | 672.6 |

-continued

| Cmpd | Structure | Name | [M + H]+ |
|---|---|---|---|
| 7.88 | 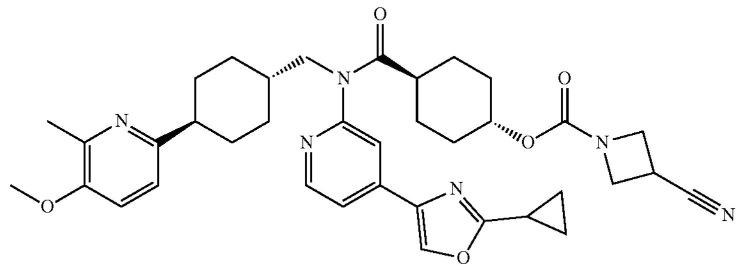 [SMILES: COc1ccc([C@H]2CC[C@H](CN(c3cc(-c4coc(C5CC5)n4)ccn3)C(=O)[C@H]3CC[C@H](OC(=O)N4CC(C#N)C4)CC3)CC2)nc1C] | trans-4-((4-(2-Cyclopropyloxazol-4-yl)pyridine-2-yl)((trans-4-(5-methoxy-6-methylpyridin-2-yl)cyclohexyl)methyl)carbamoyl)cyclohexyl 3-cyanoazetidine-1-carboxylate | 653.6 |
| 7.89 | 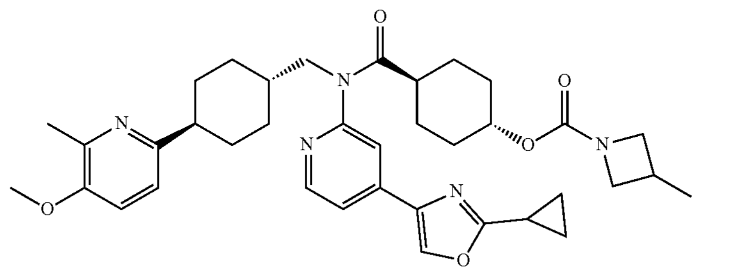 | trans-4-((4-(2-Cyclopropyloxazol-4-yl)pyridine-2-yl)((trans-4-(5-methoxy-6-methylpyridin-2-yl)cyclohexyl)methyl)carbamoyl)cyclohexyl 3-methylazetidine-1-carboxylate | 642.5 |
| 7.90 | 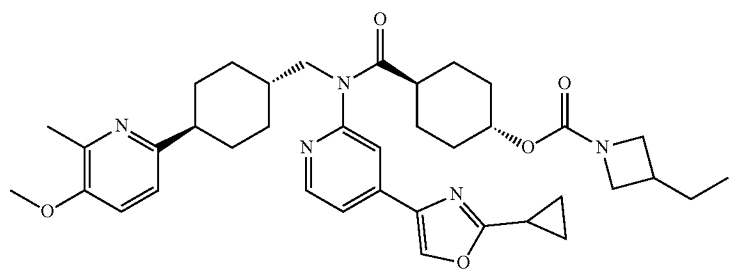 | trans-4-((4-(2-Cyclopropyloxazol-4-yl)pyridine-2-yl)((trans-4-(5-methoxy-6-methyl pyridin-2-yl)cyclohexyl)methyl)carbamoyl)cyclohexyl 3-ethylazetidine-1-carboxylate | 656.5 |

| Cmpd | Structure | Name | [M + H]+ |
|---|---|---|---|
| 7.91 | 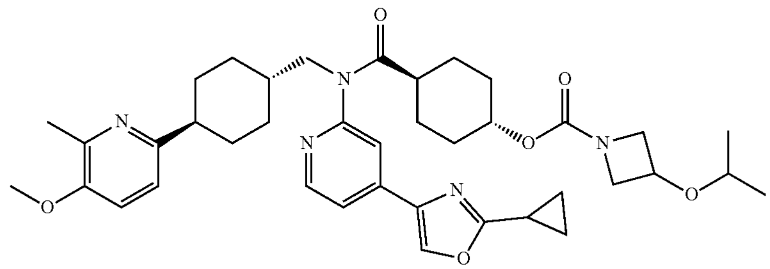 [SMILES: COc1ccc([C@H]2CC[C@H](CN(c3cc(-c4coc(C5CC5)n4)ccn3)C(=O)[C@H]3CC[C@H](OC(=O)N4CC(OC(C)C)C4)CC3)CC2)nc1C] | trans-4-((4-(2-Cyclopropyloxazol-4-yl)pyridine-2-yl)((trans-4-(5-methoxy-6-methylpyridin-2-yl)cyclohexyl)methyl)carbamoyl)cyclohexyl 3-isopropoxyazetidine-1-carboxylate | 686.6 |
| 7.92 | 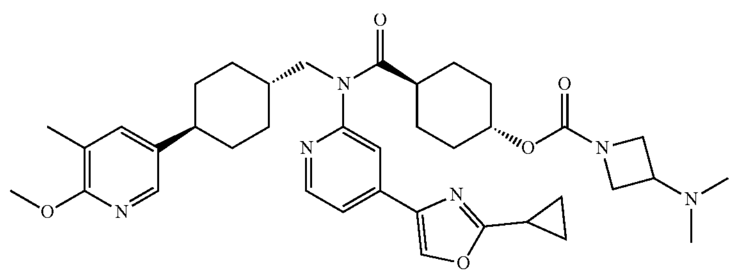 | trans-4-((4-(2-Cyclopropyloxazol-4-yl)pyridine-2-yl)((trans-4-(6-methoxy-5-methyl pyridin-3-yl)cyclohexyl)methyl)carbamoyl)cyclohexyl 3-(dimethylamino)azetidine-1-carboxylate | 671.6 |
| 7.93 | 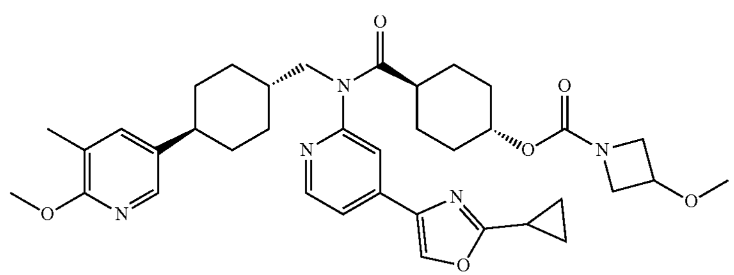 | trans-4-((4-(2-Cyclopropyloxazol-4-yl)pyridine-2-yl)((trans-4-(6-methoxy-5-methylpyridin-3-yl)cyclohexyl)methyl)carbamoyl)cyclohexyl 3-methoxyazetidine-1-carboxylate | 658.6 |

| Cmpd | Structure | Name | $[M+H]^+$ |
|---|---|---|---|
| 7.94 | 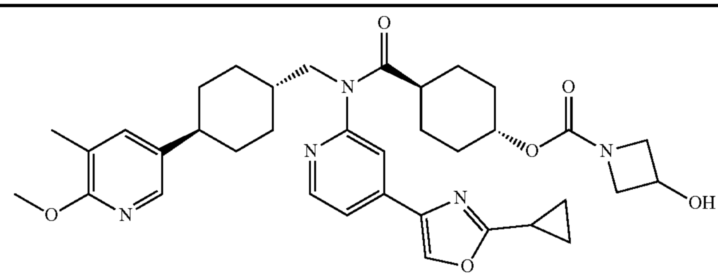 | trans-4-((4-(2-Cyclopropyloxazol-4-yl)pyridine-2-yl)((trans-4-(6-methoxy-5-methylpyridin-3-yl)cyclohexyl)methyl)carbamoyl)cyclohexyl 3-hydroxyazetidine-1-carboxylate | 644.5 |
| 7.95 | 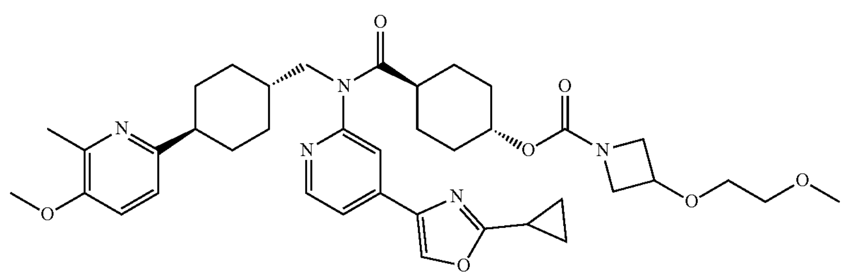 | trans-4-((4-(2-Cyclopropyloxazol-4-yl)pyridine-2-yl)((trans-4-(5-methoxy-6-methylpyridin-2-yl)cyclohexyl)methyl)carbamoyl)cyclohexyl 3-(2-methoxyethoxy)azetidine-1-carboxylate | 702.6 |
| 7.96 | 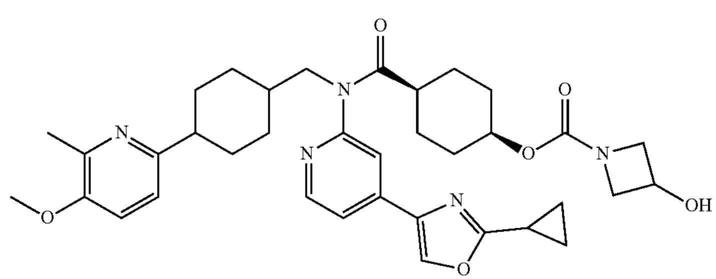 [SMILES: COc1ccc(C2CCC(CN(c3cc(-c4coc(C5CC5)n4)ccn3)C(=O)[C@H]3CC[C@@H](OC(=O)N4CC(O)C4)CC3)CC2)nc1C] | 4-((4-(2-Cyclopropyloxazol-4-yl)pyridine-2-yl)((4-(5-methoxy-6-methylpyridin-2-yl)cyclohexyl)methyl)carbamoyl)cyclohexyl-trans-3-hydroxyazetidine-1-carboxylate | 644.5 |

| Cmpd | Structure | Name | [M + H]+ |
|---|---|---|---|
| 7.97 | 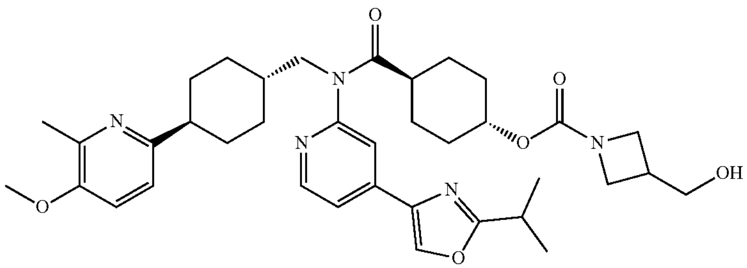 [SMILES: COc1ccc([C@H]2CC[C@H](CN(c3cc(-c4coc(C(C)C)n4)ccn3)C(=O)[C@H]3CC[C@H](OC(=O)N4CC(CO)C4)CC3)CC2)nc1C] | trans-4-((4-(2-Isopropyloxazol-4-yl)pyridine-2-yl)((trans-4-(5-methoxy-6-methylpyridin-2-yl)cyclohexyl)methyl)carbamoyl)cyclohexyl 3-(hydroxymethyl)azetidine-1-carboxylate | 660.4 |
| 7.98 | 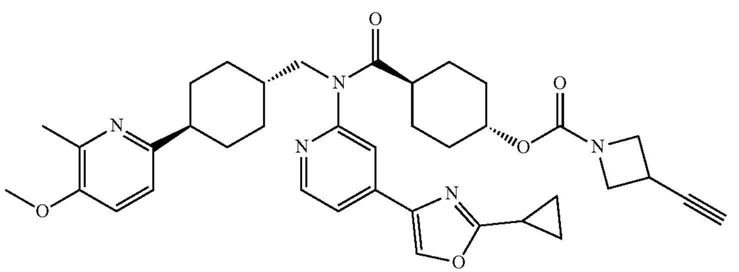 [SMILES: C#CC1CN(C(=O)O[C@H]2CC[C@H](C(=O)N(C[C@H]3CC[C@H](c4ccc(OC)c(C)n4)CC3)c3cc(-c4coc(C5CC5)n4)ccn3)CC2)C1] | trans-4-((4-(2-Cyclopropyloxazol-4-yl)pyridine-2-yl)((trans-4-(5-methoxy-6-methylpyridin-2-yl)cyclohexyl)methyl)carbamoyl)cyclohexyl 3-ethynylazetidine-1-carboxylate | 652.6 |
| 7.99 | 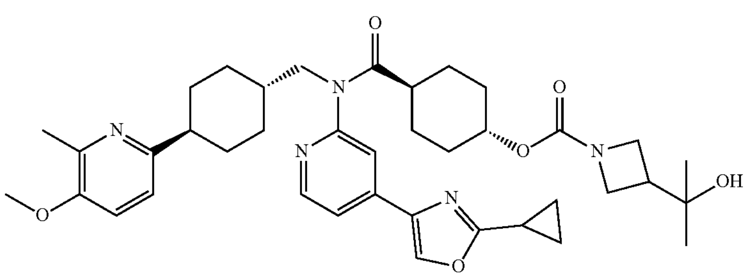 [SMILES: COc1ccc([C@H]2CC[C@H](CN(c3cc(-c4coc(C5CC5)n4)ccn3)C(=O)[C@H]3CC[C@H](OC(=O)N4CC(C(C)(C)O)C4)CC3)CC2)nc1C] | trans-4-((4-(2-Cyclopropyloxazol-4-yl)pyridine-2-yl)((trans-4-(5-methoxy-6-methylpyridin-2-yl)cyclohexyl)methyl)carbamoyl)cyclohexyl 3-(2-hydroxypropan-2-yl)azetidine-1-carboxylate | 686.6 |

| Cmpd | Structure | Name | [M + H]⁺ |
|---|---|---|---|
| 7.100 | 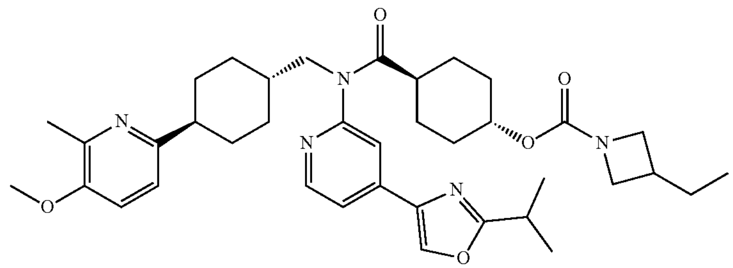 | trans-4-((4-(2-Isopropyloxazol-4-yl)pyridine-2-yl)((trans-4-(5-methoxy-6-methylpyridin-2-yl)cyclohexyl)methyl)carbamoyl)cyclohexyl 3-ethylazetidine-1-carboxylate | 658.5 |
| 7.101 | 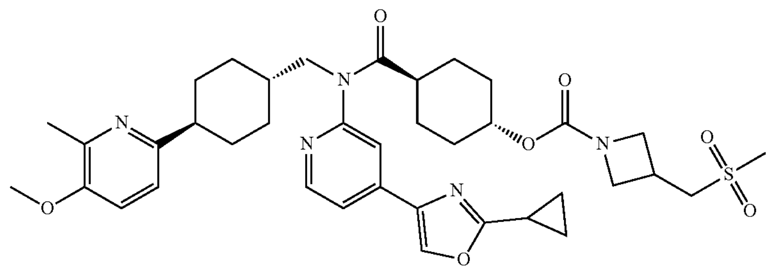 | trans-4-((4-(2-Cyclopropyloxazol-4-yl)pyridine-2-yl)((trans-4-(5-methoxy-6-methylpyridin-2-yl)cyclohexyl)methyl)carbamoyl)cyclohexyl 3-((methylsulfonyl)methyl)azetidine-1-carboxylate | 720.5 |
| 7.102 | 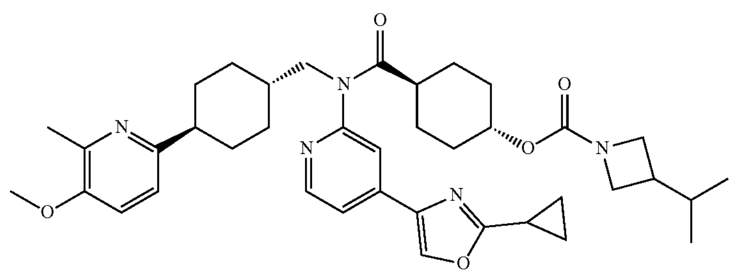 | trans-4-((4-(2-Cyclopropyloxazol-4-yl)pyridine-2-yl)((trans-4-(5-methoxy-6-methylpyridin-2-yl)cyclohexyl)methyl)carbamoyl)cyclohexyl 3-isopropylazetidine-1-carboxylate | 670.5 |

| Cmpd | Structure | Name | [M + H]+ |
|---|---|---|---|
| 7.103 | 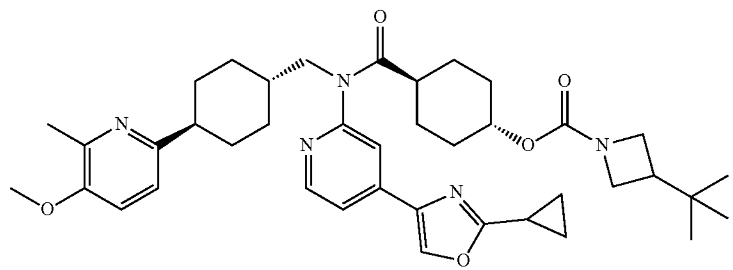 [SMILES: COc1ccc([C@H]2CC[C@H](CN(c3cc(-c4coc(C5CC5)n4)ccn3)C(=O)[C@H]3CC[C@H](OC(=O)N4CC(C(C)(C)C)C4)CC3)CC2)nc1C] | trans-4-((4-(2-Cyclopropyloxazol-4-yl)pyridine-2-yl)((trans-4-(5-methoxy-6-methylpyridin-2-yl)cyclohexyl)methyl)carbamoyl)cyclohexyl 3-(tert-butyl)azetidine-1-carboxylate | 684.5 |
| 7.104 | 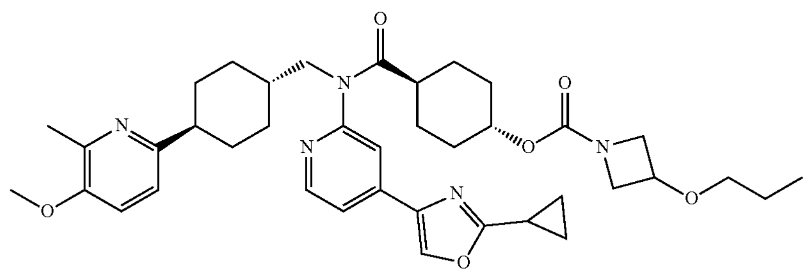 [SMILES: CCCOC1CN(C(=O)O[C@H]2CC[C@H](C(=O)N(C[C@H]3CC[C@H](c4ccc(OC)c(C)n4)CC3)c3cc(-c4coc(C5CC5)n4)ccn3)CC2)C1] | trans-4-((4-(2-Cyclopropyloxazol-4-yl)pyridine-2-yl)((trans-4-(5-methoxy-6-methyl pyridin-2-yl)cyclohexyl)methyl)carbamoyl)cyclohexyl 3-propoxyazetidine-1-carboxylate | 686.5 |
| 7.105 | 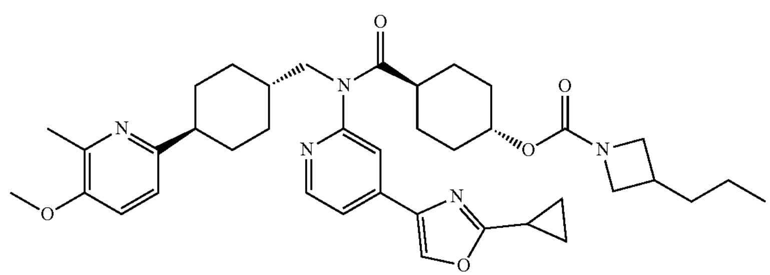 | trans-4-((4-(2-Cyclopropyloxazol-4-yl)pyridin-2-yl)((trans-4-(5-methoxy-6-methylpyridin-2-yl)cyclohexyl)methyl)carbamoyl)cyclohexyl 3-propylazetidine-1-carboxylate | 670.7 |

| Cmpd | Structure | Name | [M + H]+ |
|---|---|---|---|
| 7.106 | 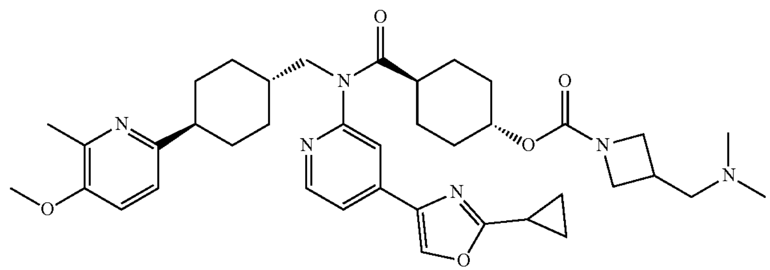 | trans-4-((4-(2-Cyclopropyloxazol-4-yl)pyridin-2-yl)((trans-4-(5-methoxy-6-methylpyridin-2-yl)cyclohexyl)methyl)carbamoyl)cyclohexyl 3-(((dimethylamino)methyl)azetidine-1-carboxylate | 685.5 |
| 7.107 | 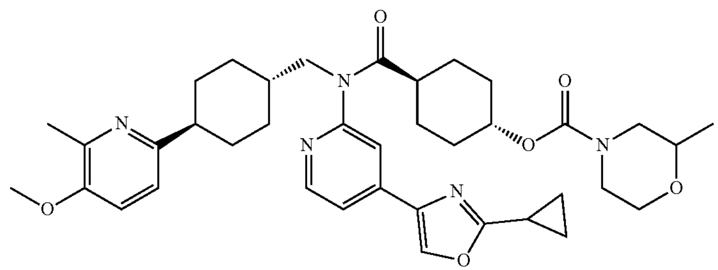 | trans-4-((4-(2-Cyclopropyloxazol-4-yl)pyridin-2-yl)((trans-4-(5-methoxy-6-methylpyridin-2-yl)cyclohexyl)methyl)carbamoyl)cyclohexyl 2-methylmorpholine-4-carboxylate | 672.8 |
| 7.108[4] | 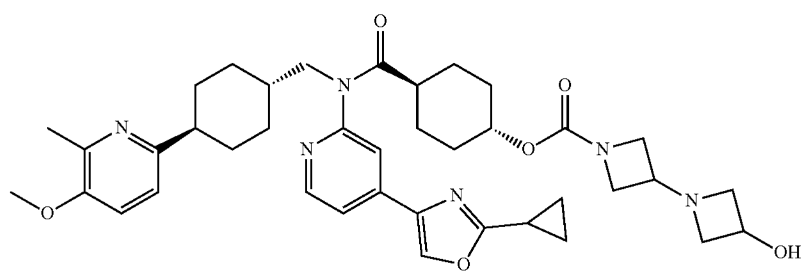 [SMILES: COc1ccc([C@H]2CC[C@H](CN(c3cc(-c4coc(C5CC5)n4)ccn3)C(=O)[C@H]3CC[C@H](OC(=O)N4CC(N5CC(O)C5)C4)CC3)CC2)nc1C] | trans-4-((4-(2-Cyclopropyloxazol-4-yl)pyridin-2-yl)((trans-4-(5-methoxy-6-methylpyridin-2-yl)cyclohexyl)methyl)carbamoyl)cyclohexyl 3-hydroxy-[1,3'-biazetidine]-1'-carboxylate | 699.4 |

-continued

| Cmpd | Structure | Name | [M + H]+ |
|---|---|---|---|
| 7.109 | 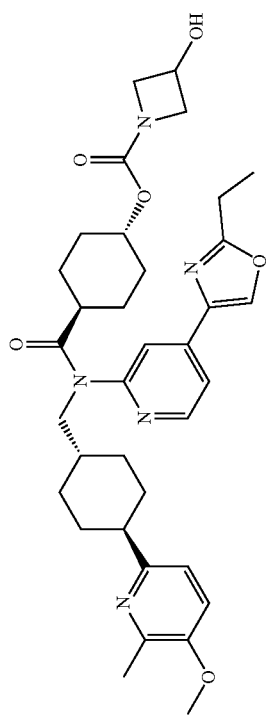 | trans-4-((4-(2-Ethyloxazol-4-yl)pyridin-2-yl)((trans-4-(5-methoxy-6-methylpyridin-2-yl)cyclohexyl)methyl)carbamoyl)cyclohexyl 3-hydroxyazetidine-1-carboxylate | 632.3 |

Acyl-imidazole formation:
[1]DMF as solvent. Carbamate formation: Reactions that progressed slowly at rt were either allowed to stir for multiple days or heated (50-80° C.);
[2]Amine was a TFA salt;
[3]Amine was a dihydrochloride salt;
[4]Amine was an oxalate salt.
[5]From respective methyl ester (1M NaOH, THF, MeOH, rt).
[6]From respective Boc-protected amine (20% TFA in CH₂Cl₂).

Compound 8

Trans-4-((3-(1-Cyclopropyl-1H-pyrazol-4-yl)phenyl)
((trans-4-(4-methoxy-3-methylphenyl)cyclohexyl)
methyl)carbamoyl)cyclohexyl 3-((methylsulfinyl)
methyl)azetidine-1-carboxylate

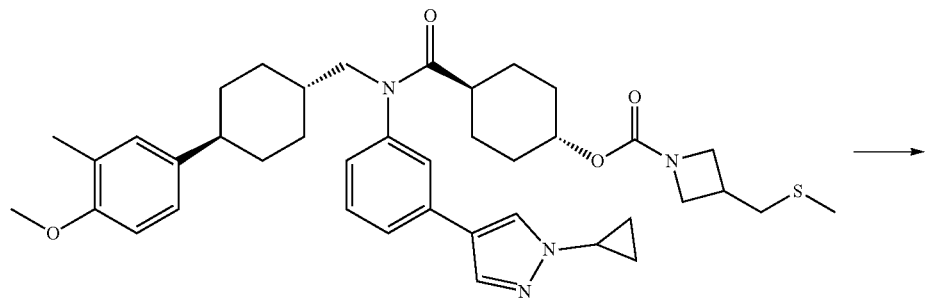

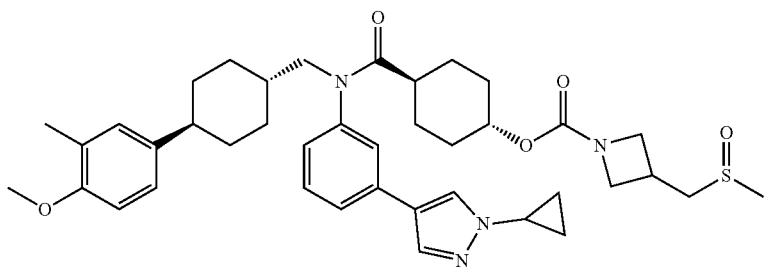

Sodium periodate (0.12 mL, 0.438 mmol, 3.5 M in H₂O) was added to a mixture of Compound 4.28 (200 mg, 0.292 mmol) in THF (1 mL) at 0° C. The mixture was stirred at rt overnight and then diluted with EtOAc (10 mL). The organic layer was washed with sat. aq. NaHCO₃ (2×5 mL) and brine (5 mL), dried over Na₂SO₄, filtered, concentrated, and purified by reverse-phase prep-HPLC (water(0.04% NH₄OH+10 mM NH₄HCO₃)/CH₃CN) to give trans-4-((3-(1-cyclopropyl-1H-pyrazol-4-yl)phenyl)((trans-4-(4-methoxy-3-methylphenyl)cyclohexyl)methyl)carbamoyl)cyclohexyl 3-((methylsulfinyl)methyl)azetidine-1-carboxylate (105 mg, 51%) as a white solid. ¹H NMR (400 MHz, DMSO-d₆) δ 8.34 (s, 1H), 7.94 (s, 1H), 7.61 (d, 1H), 7.55 (s, 1H), 7.44 (t, 1H), 7.10 (d, 1H), 6.99-6.91 (m, 2H), 6.82-6.71 (m, 1H), 4.38-4.26 (m, 1H), 4.01-3.90 (m, 2H), 3.83-3.43 (m, 8H), 3.13-2.82 (m, 3H), 2.51 (s, 3H), 2.38-2.29 (t, 1H), 2.19-2.02 (m, 4H), 1.89-1.63 (m, 8H), 1.55-1.36 (m, 3H), 1.36-1.20 (m, 2H), 1.18-0.83 (m, 8H); LCMS: 701.5 [M+H]⁺.

The Compound below was synthesized from Compound 6.30 following the procedure described for Compound 8.

| Cmpd | Structure | Name | [M + H]⁺ |
|---|---|---|---|
| 8.01[1] | 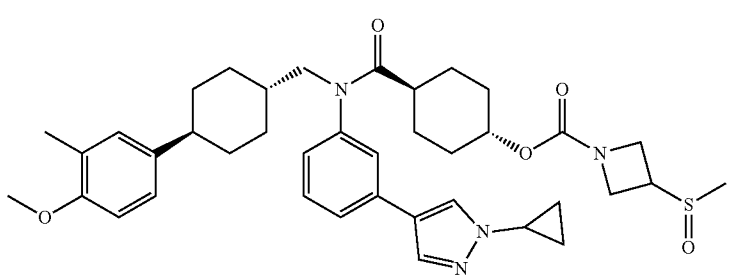 | trans-4-((3-(1-Cyclopropyl-1H-pyrazol-4-yl)phenyl)((trans-4-(4-methoxy-3-methylphenyl)cyclohexyl)methyl)carbamoyl)cyclohexyl 3-(methylsulfinyl)azetidine-1-carboxylate | 687.5 |

[1] NaIO₄ (0.15M in CH₃OH); CH₃OH instead of THF as solvent.

Compound 9

Trans-4-((3-(1-Cyclopropyl-1H-pyrazol-4-yl)phenyl)
((trans-4-(4-methoxy-3-methylphenyl)cyclohexyl)
methyl)carbamoyl)cyclohexyl 3-((methylsulfonyl)
methyl)azetidine-1-carboxylate

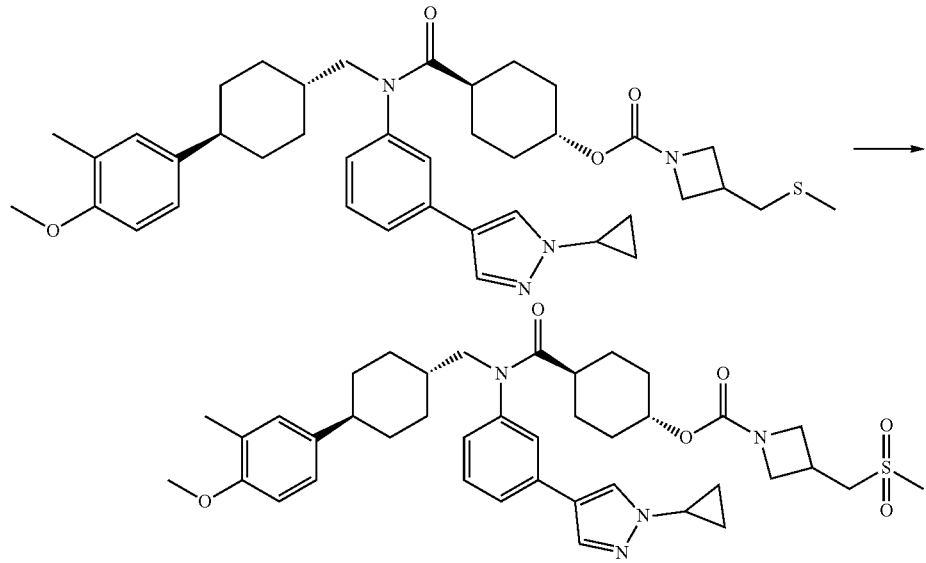

meta-Chloroperoxybenzoic acid (118.5 mg, 0.584 mmol, 85%) was added to a solution of Compound 4.28 (200.0 mg, 0.292 mmol) in CH$_2$Cl$_2$ (10 mL) at 0° C. The reaction was stirred for 1 h at rt and then diluted with EtOAc (10 mL). The organic layer was washed with sat. aq. NaHCO$_3$ (2×5 mL), washed with brine (5 mL), dried over Na$_2$SO$_4$, filtered, concentrated, and then purified by reverse-phase prep-HPLC (water(0.04% NH$_4$OH+10 mM NH$_4$HCO$_3$)/CH$_3$CN) to give trans-4-((3-(1-cyclopropyl-1H-pyrazol-4-yl)phenyl)((trans-4-(4-methoxy-3-methylphenyl)cyclohexyl)methyl)carbamoyl)cyclohexyl 3-((methylsulfonyl)methyl)azetidine-1-carboxylate (80.1 mg, 38%) as a white solid. $^1$H NMR (400 MHz, DMSO-d$_6$) δ 8.35 (s, 1H), 7.95 (s, 1H), 7.61 (d, 1H), 7.56 (s, 1H), 7.45 (t, 1H), 7.11 (d, 1H), 6.99-6.92 (m, 2H), 6.84-6.73 (m, 1H), 4.40-4.26 (m, 1H), 4.01-3.90 (m, 2H), 3.80-3.49 (m, 8H), 3.45 (d, 2H), 3.07-2.96 (m, 1H), 2.92 (s, 3H), 2.39-2.28 (m, 1H), 2.19-2.04 (m, 4H), 1.89-1.65 (m, 8H), 1.57-1.38 (m, 3H), 1.38-1.22 (m, 2H), 1.14-0.82 (m, 8H); LCMS: 717.5 [M+H]$^+$.

Compound 10

Trans-4-((3-(1-Cyclopropyl-1H-pyrazol-4-yl)phenyl)
((trans-4-(4-methoxy-3-methylphenyl)cyclohexyl)
methyl)carbamoyl)cyclohexyl-trans-4-hydroxycyclo-
hexanecarboxylate The title compound was isolated during the purification of Intermediate 29.11. $^1$H NMR (400 MHz, DMSO-d$_6$): δ 8.34 (s, 1H), 7.94 (s, 1H), 7.61 (d, 1H), 7.55 (s, 1H), 7.44 (t, 1H), 7.10 (d, 1H), 6.94 (s, 2H), 6.78 (d, 1H), 4.55-4.44 (m, 2H), 3.78-3.69 (m, 4H), 3.63-3.49 (m, 2H), 3.30-3.25 (m, 1H), 2.39-2.28 (m, 1H), 2.19-2.01 (m, 5H), 1.86-1.66 (m, 12H), 1.56-1.39 (m, 3H), 1.37-1.20 (m, 4H), 1.14-0.87 (m, 10H); LCMS: 668.5 [M+H]$^+$.

Compound 11

Trans-N-(3-(2-Cyclopropylthiazol-5-yl)phenyl)-N-
((trans-4-(4-methoxy-3-methylphenyl)cyclohexyl)
methyl)-4-(2-(methylamino)ethoxy)cyclohexanecar-
boxamide

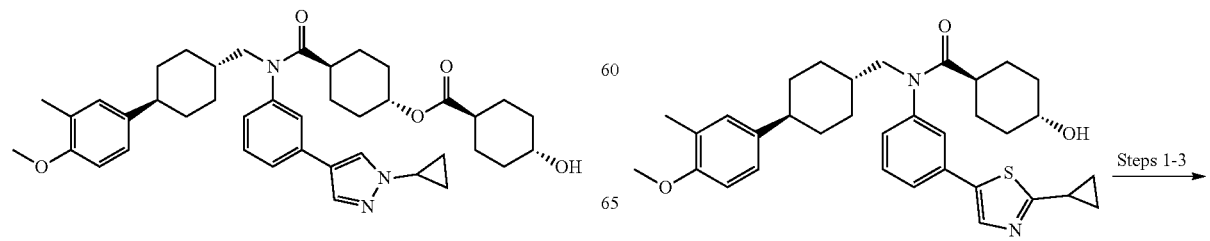

Steps 1-3

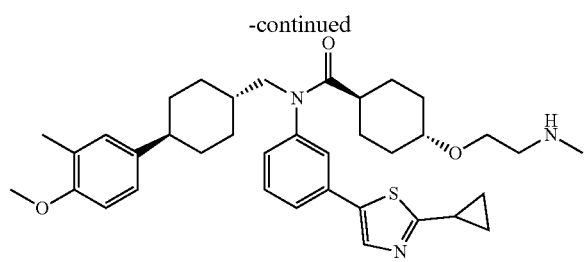

Step 1: Trans-4-(Allyloxy)-N-(3-(2-cyclopropylthiazol-5-yl)phenyl)-N-((trans-4-(4-methoxy-3-methylphenyl)cyclohexyl)methyl)cyclohexanecarboxamide Sodium hydride (178.9 mg, 4.47 mmol, 60% purity) was added to a solution of Intermediate 26 (500 mg, 0.894 mmol) in THF (25 mL) at 0° C. The reaction was stirred at 0° C. for 1 h under $N_2$, and then 3-bromoprop-1-ene (649.5 mg, 5.37 mmol) was added. The reaction was stirred at 70° C. overnight, and then more 3-bromoprop-1-ene (649.5 mg, 5.37 mmol) was added. The reaction was stirred at 70° C. overnight, water (30 mL) was added, and the mixture was extracted with EtOAc (2×50 mL). The organic layers were combined, washed with water (30 mL), dried ($Na_2SO_4$), filtered, concentrated and then purified by chromatography on silica gel (petroleum ether/EtOAc=20/1) to give trans-4-(allyloxy)-N-(3-(2-cyclopropylthiazol-5-yl)phenyl)-N-((trans-4-(4-methoxy-3-methylphenyl)cyclohexyl)methyl)cyclohexanecarboxamide (420 mg, 78%) as a yellow oil. $^1$H NMR (400 MHz, CDCl$_3$): δ 7.69 (s, 1H), 7.47-7.41 (m, 1H), 7.40-7.32 (m, 1H), 7.21 (t, 1H), 7.04 (d, 1H), 6.91-6.86 (m, 2H), 6.66 (d, 1H), 5.86-5.72 (m, 1H), 5.16 (d, 1H), 5.05 (d, 1H), 3.88 (d, 2H), 3.72 (s, 3H), 3.55 (d, 2H), 3.25-3.13 (m, 1H), 2.36-2.22 (m, 2H), 2.14-2.01 (m, 4H), 1.98-1.89 (m, 2H), 1.85-1.63 (m, 6H), 1.61-1.44 (m, 3H), 1.39-1.26 (m, 2H), 1.16-1.01 (m, 6H), 0.96-0.84 (m, 2H); LCMS: 599.4 [M+H]$^+$.

Step 2: Trans-N-(3-(2-Cyclopropylthiazol-5-yl)phenyl)-N-((trans-4-(4-methoxy-3-methylphenyl)cyclohexyl)methyl)-4-(2-oxoethoxy)cyclohexanecarboxamide Potassium osmate(VI) dihydrate (153.8 mg, 0.417 mmol) and 18-crown-6 (441.3 mg, 1.67 mmol) were added to a solution of trans-4-(allyloxy)-N-(3-(2-cyclopropylthiazol-5-yl)phenyl)-N-((trans-4-(4-methoxy-3-methylphenyl)cyclohexyl)methyl)cyclohexanecarboxamide (500 mg, 0.834 mmol), NaIO$_4$ (535.7 mg, 2.50 mmol), THF (16 mL) and H$_2$O (10 mL) at rt. The reaction was stirred at rt overnight, poured into water (20 mL), and extracted with EtOAc (2×50 mL). The combined organic layers were washed with water (10 mL), washed with brine (10 mL), dried (Na$_2$SO$_4$), filtered, concentrated and then purified by prep-TLC (petroleum ether/EtOAc=1/1) to give trans-N-(3-(2-cyclopropylthiazol-5-yl)phenyl)-N-((trans-4-(4-methoxy-3-methylphenyl)cyclohexyl)methyl)-4-(2-oxoethoxy)cyclohexanecarboxamide (130 mg, 26%) as a yellow oil. $^1$H NMR (400 MHz, CDCl$_3$): δ 9.67 (s, 1H), 7.79 (s, 1H), 7.56-7.40 (m, 2H), 7.29-7.26 (m, 1H), 7.12 (d, 1H), 6.99-6.93 (m, 2H), 6.74 (d, 1H), 4.05 (s, 2H), 3.80 (s, 3H), 3.63 (d, 2H), 3.29 (t, 1H), 2.46-2.29 (m, 2H), 2.23-2.10 (m, 4H), 2.09-1.97 (m, 2H), 1.93-1.72 (m, 5H), 1.71-1.58 (m, 2H), 1.44-1.11 (m, 10H), 1.10-0.94 (m, 2H); LCMS: 601.4 [M+H]$^+$.

Step 3: Trans-N-(3-(2-Cyclopropylthiazol-5-yl)phenyl)-N-((trans-4-(4-methoxy-3-methylphenyl)cyclohexyl)methyl)-4-(2-(methylamino)ethoxy)cyclohexanecarboxamide hydrochloride Acetic acid (10.9 mg, 0.183 mmol) was added to a solution of trans-N-(3-(2-cyclopropylthiazol-5-yl)phenyl)-N-((trans-4-(4-methoxy-3-methylphenyl)cyclohexyl)methyl)-4-(2-oxoethoxy)cyclohexanecarboxamide (110 mg, 183.09 umol) and methanamine (2 M in THF, 1.83 mL, 3.66 mmol) in DCE (5 mL) at rt. The reaction was stirred at rt for 3 h. Sodium triacetoxyborohydride (116.4 mg, 0.549 mmol) was added. The reaction was stirred at rt overnight, poured into sat. aq. NaHCO$_3$ (20 mL), and extracted with CH$_2$C$_2$ (5×20 mL). The organic layers were combined, dried (Na$_2$SO$_4$), filtered, concentrated and then purified by reverse-phase HPLC (water(0.05% HCl)/CH$_3$CN) to give trans-N-(3-(2-cyclopropylthiazol-5-yl)phenyl)-N-((trans-4-(4-methoxy-3-methylphenyl)cyclohexyl)methyl)-4-(2-(methylamino)ethoxy)cyclohexanecarboxamide hydrochloride (25.6 mg, 21%) as a yellow solid. $^1$H NMR (400 MHz, DMSO-d$_6$): δ 8.89-8.78 (m, 2H), 8.14 (s, 1H), 7.64-7.58 (m, 2H), 7.58-7.47 (m, 1H), 7.28 (d, 1H), 6.98-6.90 (m, 2H), 6.80-6.76 (m, 1H), 3.72 (s, 3H), 3.64-3.51 (m, 4H), 3.22 (t, 1H), 2.99-2.62 (m, 2H), 2.49-2.42 (m, 4H), 2.33 (t, 1H), 2.12-2.07 (m, 4H), 1.95 (d, 2H), 1.80-1.63 (m, 6H), 1.51-1.36 (m, 3H), 1.35-1.21 (m, 2H), 1.21-1.13 (m, 2H), 1.12-0.97 (m, 4H), 0.87-0.73 (m, 2H); LCMS: 616.4 [M+H]$^+$.

Compound 12

2-((trans-4-((3-(1-Isopropyl-1H-pyrazol-4-yl)phenyl)((trans-4-(4-methoxy-3-methylphenyl)cyclohexyl)methyl)carbamoyl)cyclohexyl)oxy)acetic Acid

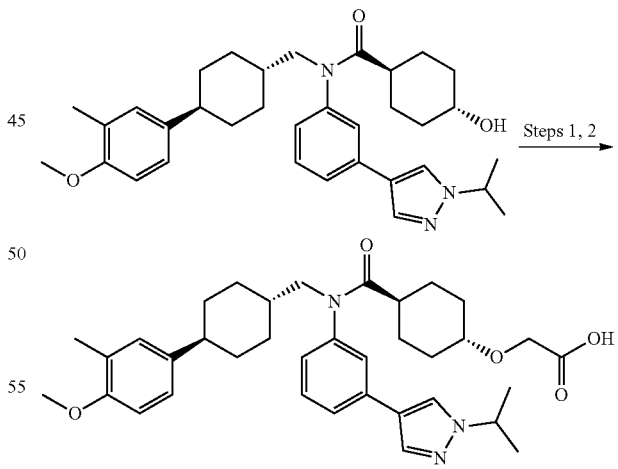

Step 1: Tert-Butyl-2-((trans-4-((3-(1-isopropyl-1H-pyrazol-4-yl)phenyl)((trans-4-(4-methoxy-3-methylphenyl)cyclohexyl)methyl)carbamoyl)cyclohexyl)oxy)acetate tert-Butylammonium bromide (29.6 mg, 0.092 mmol) was added to a mixture of Intermediate 29.12 (500 mg, 0.92 mmol), tert-butyl 2-bromoacetate (896.8 mg, 4.6 mmol), NaOH (4 mL, 50% in H₂O) and toluene (10 mL) at rt. The reaction was heated to 90° C., stirred overnight, poured into H₂O (20 mL) and then extracted with CH₂C₂(3×20 mL). The combined organic layers were washed with brine (20 mL), dried over Na₂SO₄, filtered, concentrated, and then purified by chromatography on silica gel (petroleum ether/EtOAc=50/50) to give tert-butyl-2-((trans-4-((3-(1-isopropyl-1H-pyrazol-4-yl)phenyl)((trans-4-(4-methoxy-3-methylphenyl)cyclohexyl)methyl)carbamoyl)cyclohexyl)oxy)acetate (400 mg, 65%) as a yellow oil. ¹H NMR (400 MHz, DMSO-d₆) δ 8.32 (s, 1H), 7.94 (s, 1H), 7.64-7.58 (m, 1H), 7.55 (s, 1H), 7.44 (t, 1H), 7.09 (d, 1H), 6.97-6.89 (m, 2H), 6.82-6.74 (m, 1H), 4.58-4.42 (m, 1H), 3.94-3.86 (m, 2H), 3.71 (s, 3H), 3.65-3.45 (m, 2H), 3.23-3.10 (m, 1H), 2.40-2.30 (m, 1H), 2.14-2.02 (m, 4H), 1.96-1.85 (m, 2H), 1.80-1.63 (m, 6H), 1.47-1.41 (m, 9H), 1.38 (s, 9H), 1.32-1.23 (m, 2H), 1.08-0.96 (m, 2H), 0.84-0.67 (m, 2H); LCMS: 658.5 [M+H]⁺.

Step 2: 2-((trans-4-((3-(1-Isopropyl-1H-pyrazol-4-yl)phenyl)((trans-4-(4-methoxy-3-methylphenyl)cyclohexyl)methyl)carbamoyl)cyclohexyl)oxy)acetic Acid A mixture of tert-butyl-2-((trans-4-((3-(1-isopropyl-1H-pyrazol-4-yl)phenyl)((trans-4-(4-methoxy-3-methylphenyl)cyclohexyl)methyl)carbamoyl)cyclohexyl)oxy)acetate (400 mg, 0.61 mmol) and HCl in dioxane (4 M, 20 mL) was stirred at rt for 1 h. The reaction mixture was concentrated and then purified by reverse-phase HPLC (water(0.05% HCl)-MeCN) to give a white solid. The solid was dissolved in H₂O (3 mL), adjusted to pH=9 with NaOH (1 M), adjusted to pH=6 with HCl (1 M) at rt, stirred at rt for 10 min, filtered, and then dried under vacuum to give 2-((trans-4-((3-(1-isopropyl-1H-pyrazol-4-yl)phenyl)((trans-4-(4-methoxy-3-methylphenyl)cyclohexyl)methyl)carbamoyl)cyclohexyl)oxy)acetic acid (200 mg, 55%) as a white solid. ¹H NMR (400 MHz, DMSO-d₆) δ 13.44-12.25 (m, 1H), 8.32 (s, 1H), 7.94 (s, 1H), 7.61 (d, 1H), 7.55 (s, 1H), 7.44 (t, 1H), 7.09 (d, 1H), 7.00-6.91 (m, 2H), 6.84-6.74 (m, 1H), 4.58-4.42 (m, 1H), 3.88 (s, 2H), 3.71 (s, 3H), 3.65-3.42 (m, 2H), 3.25-3.13 (m, 1H), 2.40-2.24 (m, 1H), 2.17-2.05 (m, 4H), 1.97-1.85 (m, 2H), 1.81-1.60 (m, 6H), 1.48-1.24 (m, 11H), 1.13-0.96 (m, 2H), 0.85-0.66 (m, 2H); LCMS: 602.4 [M+H]⁺.

Compound 13

Trans-4-(((trans-4-(4-Methoxy-3-methylphenyl)cyclohexyl)methyl)(3-(2-methoxythiazol-5-yl)phenyl)carbamoyl)cyclohexyl dimethylcarbamate

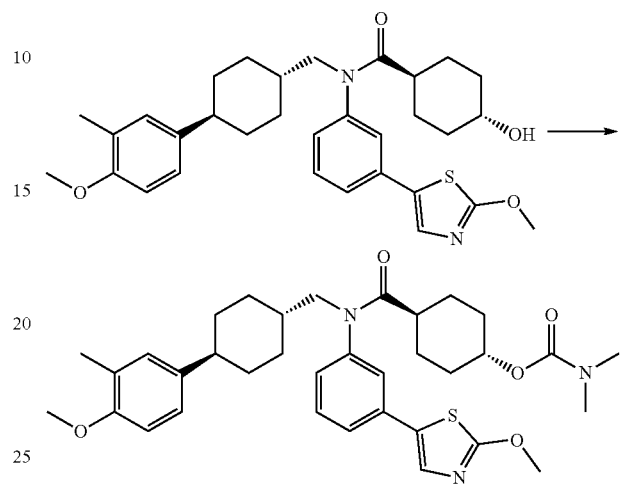

Intermediate 22 (200 mg, 0.364 mmol) was dissolved in THF (5.0 mL) at 0° C. Sodium hydride (60% purity, 43.7 mg, 1.09 mmol) was added at 0° C. The solution was stirred at 0° C. for 0.5 h. Dimethylcarbamic chloride (47.0 mg, 0.437 mmol) in THF (5.0 mL) was added slowly. The solution was stirred at 60° C. overnight, quenched with sat'd NH₄Cl (10 mL), and then extracted with EtOAc (3×15 mL). The organics were washed with brine (2×15 mL), concentrated, and purified first by RP-HPLC [water (10 mM NH₄HCO₃)-MeCN] and then prep-TLC (petroleum ether: EtOAc=1:1) to give trans-4-(((trans-4-(4-methoxy-3-methylphenyl)cyclohexyl)methyl)(3-(2-methoxythiazol-5-yl)phenyl)carbamoyl)cyclohexyl dimethylcarbamate (31.1 mg) as a white solid. ¹H NMR (400 MHz, DMSO-d₆): δ 7.74 (s, 1H), 7.44-7.54 (m, 3H), 7.23 (d, 1H), 6.91-6.93 (m, 2H), 6.76 (d, 1H), 4.32-4.33 (m, 1H), 4.04 (s, 3H), 3.69 (s, 3H), 3.54 (s, 2H), 2.71 (s, 6H), 2.30-2.31 (m, 1H), 2.06-2.08 (m, 4H), 1.82-1.83 (m, 2H), 1.71-1.73 (m, 6H), 1.40-1.53 (m, 3H), 1.20-1.32 (m, 2H), 0.90-1.08 (m, 4H); LCMS: 531.3 [M-OC(O)N(CH₃)₂]⁺.

The Compounds below were synthesized from the appropriate Intermediate and the appropriate alkyl halide following the procedure described for Compound 13.

| Cmpd | Structure | Name | [M + H]⁺ |
|---|---|---|---|
| 13.01 | 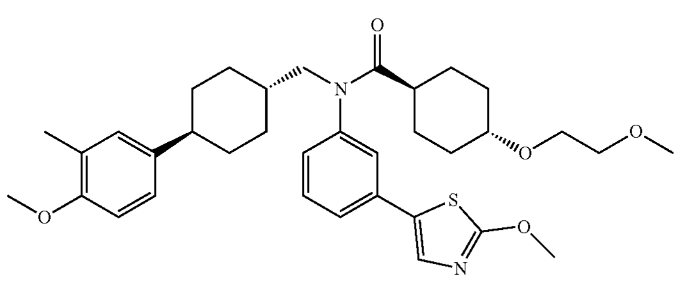 | trans-N-((trans-4-(4-Methoxy-3-methylphenyl)cyclohexyl)methyl)-4-(2-methoxyethoxy)-N-(3-(2-methoxythiazol-5-yl)phenyl)cyclohexanecarboxamide | 607.3 |

| Cmpd | Structure | Name | [M + H]+ |
| --- | --- | --- | --- |
| 13.02 | 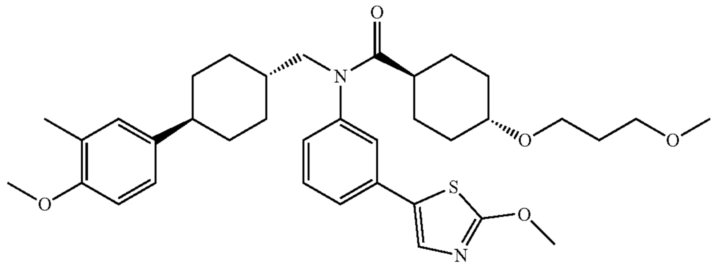 | trans-N-((trans-4-(4-Methoxy-3-methylphenyl)cyclohexyl)methyl)-4-(3-methoxypropoxy)-N-(3-(2-methoxythiazol-5-yl)phenyl)cyclohexanecarboxamide | 621.3 |
| 13.03[2,3] | 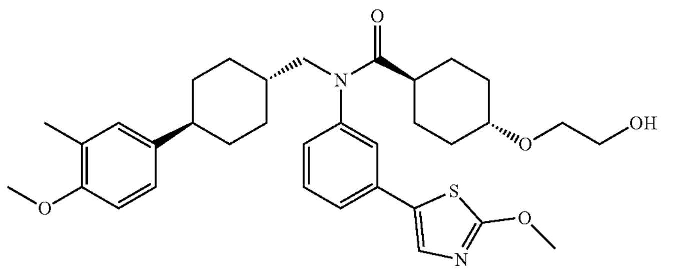 [SMILES: COc1ncc(-c2cccc(N(C[C@H]3CC[C@H](c4ccc(OC)c(C)c4)CC3)C(=O)[C@H]3CC[C@H](OCCO)CC3)c2)s1] | trans-4-(2-Hydroxyethoxy)-N-((trans-4-(4-methoxy-3-methylphenyl)cyclohexyl)methyl)-N-(3-(2-methoxythiazol-5-yl)phenyl)cyclohexanecarboxamide | 593.4 |
| 13.04[4] | 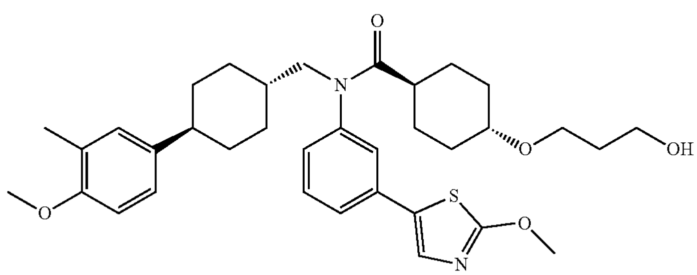 [SMILES: COc1ncc(-c2cccc(N(C[C@H]3CC[C@H](c4ccc(OC)c(C)c4)CC3)C(=O)[C@H]3CC[C@H](OCCCO)CC3)c2)s1] | trans-4-(3-Hydroxypropoxy)-N-((trans-4-(4-methoxy-3-methylphenyl)cyclohexyl)methyl)-N-(3-(2-methoxythiazol-5-yl)phenyl)cyclohexanecarboxamide | 607.3 |
| 13.05[1] | 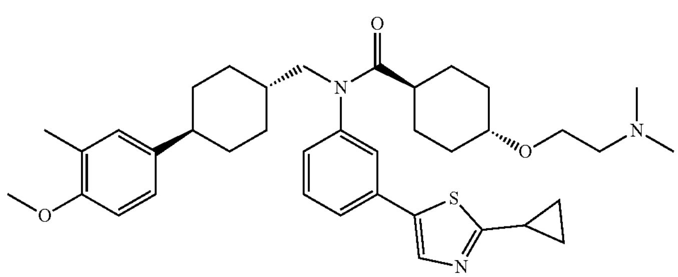 | trans-N-(3-(2-Cyclopropylthiazol-5-yl)phenyl)-4-(2-(dimethylamino)ethoxy)-N-((trans-4-(4-methoxy-3-methylphenyl)cyclohexyl)methyl)cyclohexanecarboxamide | 630.5 |

[1] Heated at 65° C.;

[2] Heated at 70° C.;

[3] From THP-protected bromo-alcohol, the deprotection (p-TsOH•H$_2$O, CH$_2$Cl$_2$, CH$_3$OH, rt, 3 h);

[4] 2-(3-bromopropoxy)tetrahydro-2H-pyran, nBu$_4$NBr, KOH, toluene, rt, overnight; then additional KOH, rt, overnight; then deprotection (p-TsOH•H$_2$O, CH$_2$Cl$_2$, CH$_3$OH, rt, 3 h).

Compound 14

Ethyl 2-(trans-4-((3-(1-cyclopropyl-1H-pyrazol-4-yl)phenyl)((trans-4-(5-methoxy-6-methylpyridin-2-yl)cyclohexyl)methyl)carbamoyl)cyclohexyl)acetate

Compound 15

Trans-N-(3-(1-Cyclopropyl-1H-pyrazol-4-yl)phenyl)-4-(hydroxymethyl)-N-((trans-4-(4-methoxy-3-methylphenyl)cyclohexyl)methyl)cyclohexanecarboxamide

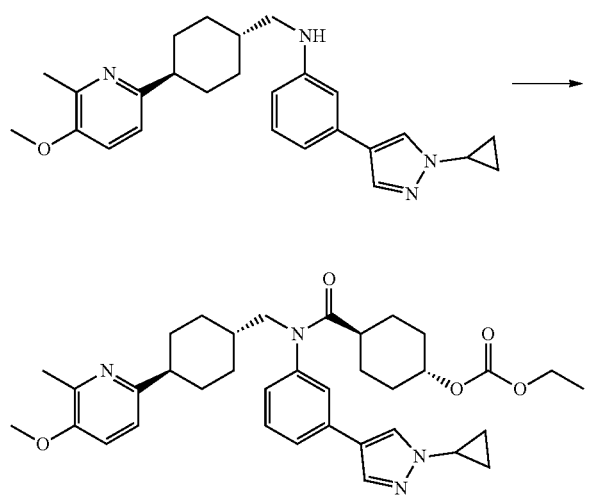

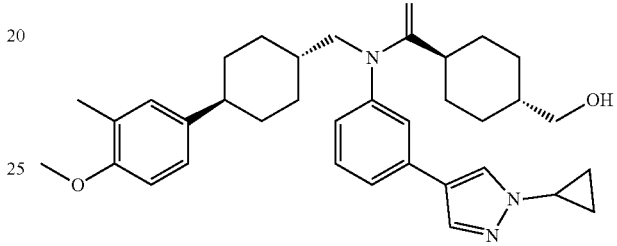

Intermediate 14.28 (50 mg, 0.12 mmol) and trans-4-(2-ethoxy-2-oxoethyl)cyclohexancarboxylic acid (40 mg, 0.19 mmol) were dissolved in $CH_2Cl_2$ (1 mL). Pyridine (40 µL, 0.49 mmol) followed by 1-propylphosphonic acid cyclic anhydride (50 wt. % in $CH_2Cl_2$; 90 µL, 0.19 mmol) were added to the reaction at rt. The reaction was stirred at rt overnight and then heated at 40° C. for 3.5 h. Additional 1-propylphosphonic acid cyclic anhydride (50 wt. % in $CH_2Cl_2$; 3 µL, 0.006 mmol) was added. The reaction was heated at 40° C. for ~7 h and then diluted with EtOAc (20 mL). The organics were washed with water (20 mL), washed with saturated $NaHCO_3$ (20 mL), washed with brine (20 mL), dried ($Na_2SO_4$), filtered, concentrated and then purified by silica gel chromatography (20-70% EtOAc in hexanes) to give ethyl 2-(trans-4-((3-(1-cyclopropyl-1H-pyrazol-4-yl)phenyl)((trans-4-(5-methoxy-6-methylpyridin-2-yl)cyclohexyl)methyl)carbamoyl)cyclohexyl)acetate as an off-white foam (47 mg, 64% yield). $^1H$ NMR (400 MHz, DMSO-$d_6$): δ 8.34 (s, 1H), 7.93 (s, 1H), 7.59 (d, 1H), 7.53 (s, 1H), 7.43 (t, 1H), 7.19 (d, 1H), 7.08 (d, 1H), 6.98 (d, 1H), 3.99 (q, 2H), 3.79-3.70 (m, 4H), 3.67-3.46 (m, 2H), 2.29 (s, 3H), 2.13-2.01 (m, 3H), 1.82-1.72 (m, 4H), 1.70-1.51 (m, 5H), 1.48-1.30 (m, 5H), 1.17-0.95 (m, 10H), 0.70-0.56 (m, 2H); LCMS: 613.6 $[M+H]^+$.

Sodium borohydride (35 mg, 0.92 mmol) was added to a mixture of Compound 18.13 (50 mg, 0.086 mmol), LiCl (9 mg, 0.21 mmol), and THF (2 mL). The mixture was stirred at rt for 25 min, heated at 80° C. for 2 h, allowed to cool to rt, and then diluted with EtOAc (20 mL). The organic layer was washed (2×20 mL saturated $NaHCO_3$ and then 20 mL brine), dried ($Na_2SO_4$), filtered, and concentrated. The residue was purified by silica gel chromatography (0-5% $CH_3OH$ in $CH_2Cl_2$) to give trans-N-(3-(1-cyclopropyl-1H-pyrazol-4-yl)phenyl)-4-(hydroxymethyl)-N-((trans-4-(4-methoxy-3-methylphenyl)cyclohexyl)methyl)cyclohexanecarboxamide (41 mg, 86%) as a white foam. $^1H$ NMR (400 MHz, DMSO-$d_6$): δ 8.34 (s, 1H), 7.93 (s, 1H), 7.58 (d, 1H), 7.55-7.51 (m, 1H), 7.43 (t, 1H), 7.08 (d, 1H), 6.97-6.92 (m, 2H), 6.80-6.75 (m, 1H), 4.26 (t, 1H), 3.77-3.72 (m, 1H), 3.71 (s, 3H), 3.65-3.41 (m, 2H), 3.07 (t, 2H), 2.38-2.27 (m, 1H), 2.08 (s, 3H), 2.07-2.02 (m, 1H), 1.80-1.57 (m, 8H), 1.47-1.18 (m, 6H), 1.11-0.95 (m, 6H), 0.62-0.46 (m, 2H); LCMS: 556.4 $[M+H]^+$.

The Compounds below were synthesized from the appropriate methyl ester following the procedure described for Compound 15.

| Cmpd | Structure | Name | $[M + H]^+$ |
|---|---|---|---|
| 15.01[1] | 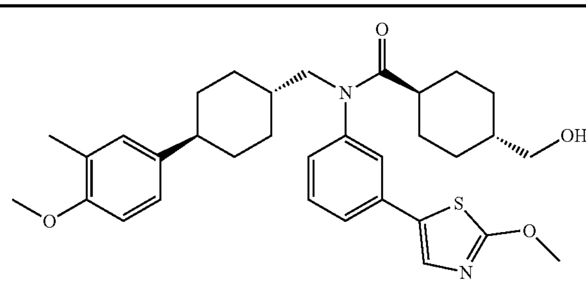 | trans-4-(Hydroxymethyl)-N-((trans-4-(4-methoxy-3-methylphenyl)cyclohexyl)methyl)-N-(3-(2-methoxythiazol-5-yl)phenyl)cyclohexanecarboxamide | 563.5 |

-continued

| Cmpd | Structure | Name | [M + H]+ |
|---|---|---|---|
| 15.02[2] | 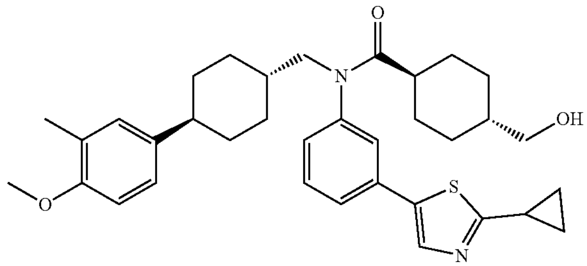 [SMILES: COc1ccc([C@H]2CC[C@H](CN(c3cccc(-c4cnc(C5CC5)s4)c3)C(=O)[C@H]3CC[C@H](CO)CC3)CC2)cc1C] | trans-N-(3-(2-Cyclopropylthiazol-5-yl)phenyl)-4-(hydroxymethyl)-N-((trans-4-(4-methoxy-3-methylphenyl)cyclohexyl)-methyl)cyclohexanecarboxamide | 573.5 |
| 15.03[2] | 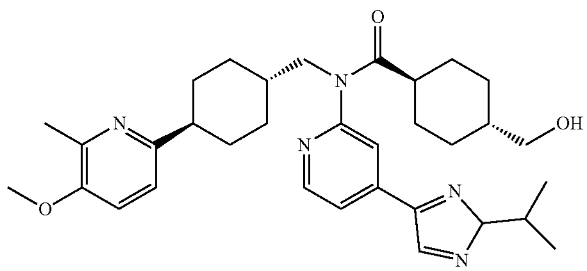 [SMILES: COc1ccc([C@H]2CC[C@H](CN(c3cc(C4=NC(C(C)C)N=C4)ccn3)C(=O)[C@H]3CC[C@H](CO)CC3)CC2)nc1C] | trans-4-(Hydroxymethyl)-N-(4-(1-isopropyl-1H-pyrazol-4-yl)pyridin-2-yl)-N-((trans-4-(5-methoxy-6-methylpyridin-2-yl)cyclohexyl)methyl)cyclohexanecarboxamide | 560.3 |
| 15.04[3] | 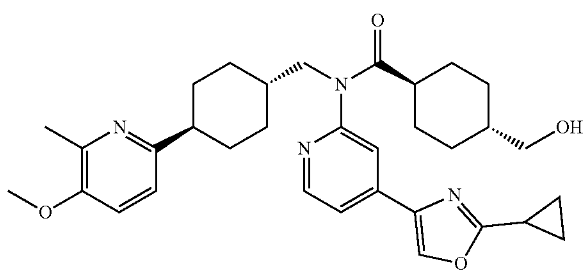 [SMILES: COc1ccc([C@H]2CC[C@H](CN(c3cc(-c4coc(C5CC5)n4)ccn3)C(=O)[C@H]3CC[C@H](CO)CC3)CC2)nc1C] | trans-N-(4-(2-Cyclopropyloxazol-4-yl)pyridin-2-yl)-4-(hydroxymethyl)-N-((trans-4-(5-methoxy-6-methylpyridin-2-yl)cyclohexyl)methyl)cyclohexanecarboxamide | 587.6 |

[1]Heated at 60° C. for 1 h, 70° C. for 4 h, and then 80° C. for 1 h;
[2]Heated at 80° C. overnight;
[3]Heated at 80° C. for 5 h, additional NaBH4 added, and then heated at 80° C. for 1 h.

Compound 16

Trans-4-((3-(2-Cyclopropylthiazol-5-yl)phenyl)((trans-4-(6-(dimethylamino)pyridin-3-yl)cyclohexyl)methyl)carbamoyl)cyclohexanecarboxylic Acid

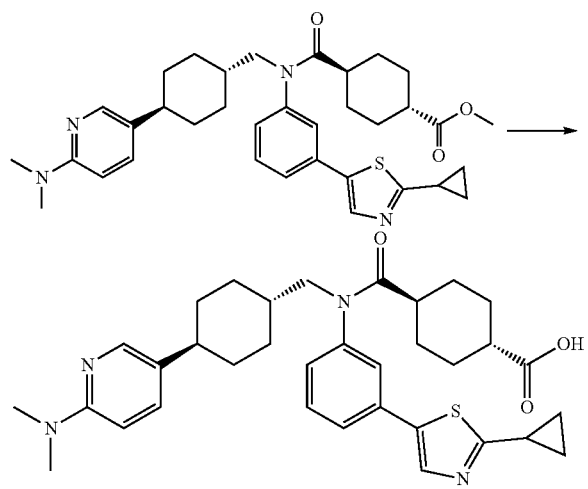

Aqueous sodium hydroxide (1 N, 0.3 mL, 0.3 mmol) was added to a solution of Compound 18.08 (37 mg, 0.061 mmol), THF (0.6 mL) and CH3OH (0.3 mL) at rt. The mixture was stirred for 4.5 h and then poured into a mixture of 20 mL sat'd NH4Cl and 0.3 mL 1 N HCl. This mixture was extracted with EtOAc. Additional 1 N HCl (0.2 mL) was added to the aqueous layer to bring pH from 5 to 3. The aqueous layer was extracted with original EtOAc, and then the EtOAc layer was washed with 20 mL brine, dried (Na2SO4), filtered and concentrated. The compound was observed in both aqueous and organic layers. The aqueous layer was basified with 1 N NaOH until pH-6, added to the concentrated residue, and then extracted with EtOAc (2×20 mL). The combined extracts were dried (Na2SO4), filtered, and concentrated to give trans-4-((3-(2-Cyclopropylthiazol-5-yl)phenyl)((trans-4-(6-(dimethylamino)pyridin-3-yl)cyclohexyl)methyl)carbamoyl)cyclohexanecarboxylic acid (33 mg, 94%) as an off-white foam. $^1$H NMR (400 MHz, DMSO-$d_6$): δ 12.00 (br s, 1H), 8.09 (s, 1H), 7.88-7.82 (m, 1H), 7.62-7.55 (m, 2H), 7.55-7.48 (m, 2H), 7.30-7.24 (m, 1H), 6.75-6.67 (m, 1H), 3.63-3.53 (m, 2H), 3.02 (s, 6H), 2.47-2.41 (m, 1H), 2.41-2.31 (m, 1H), 2.17-2.04 (m, 2H), 1.86-1.65 (m, 8H), 1.51-1.36 (m, 3H), 1.36-1.26 (m, 2H), 1.18-1.11 (m, 2H), 1.11-0.87 (m, 6H); LCMS: 587.4 [M+H]+.

Compound 17

Trans-4-((3-(2-Cyclopropylthiazol-5-yl)phenyl)((trans-4-(4-methoxy-3-methylphenyl)cyclohexyl)methyl)carbamoyl)cyclohexanecarboxylic Acid

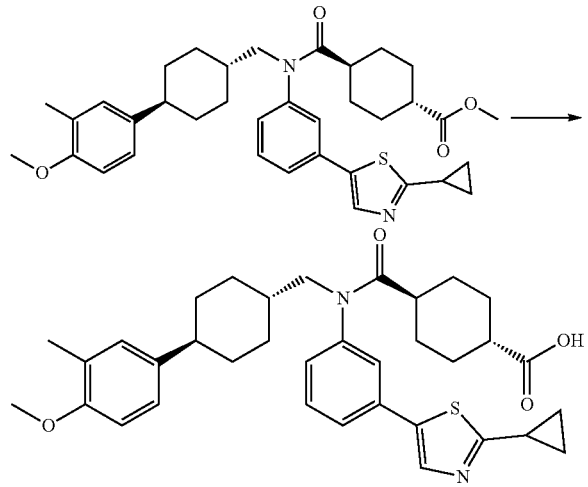

Aqueous sodium hydroxide (1 N, 1.25 mL, 1.25 mmol) was added to a solution of Compound 18.06 (153 mg, 0.25 mmol), CH₃OH (1.25 mL) and THF (2.50 mL) at rt. The reaction was stirred for 2 h, concentrated, diluted with 2 mL water and then acidified at 0° C. with 1.3 mL 1 N HCl. The mixture was diluted with EtOAc. The organics were washed with 30 mL brine, dried (Na$_2$SO$_4$), filtered, concentrated, and dried on high vacuum overnight to give trans-4-((3-(2-cyclopropylthiazol-5-yl)phenyl)((trans-4-(4-methoxy-3-methylphenyl)cyclohexyl)methyl)carbamoyl)cyclohexanecarboxylic acid (142 mg, 95%) as an off-white foam. $^1$H NMR (400 MHz, DMSO-d$_6$): δ 11.99 (s, 1H), 8.10 (s, 1H), 7.63-7.56 (m, 2H), 7.52 (t, 1H), 7.31-7.24 (m, 1H), 6.98-6.91 (m, 2H), 6.82-6.74 (m, 1H), 3.72 (s, 3H), 3.62-3.49 (m, 2H), 2.4-2.39 (m, 1H), 2.39-2.28 (m, 1H), 2.17-2.03 (m, 5H), 1.86-1.64 (m, 8H), 1.50-1.36 (m, 3H), 1.36-1.24 (m, 2H), 1.18-1.11 (m, 2H), 1.11-0.87 (m, 6H); LCMS: 587.4 [M+H]$^+$.

The Compounds below were synthesized from the appropriate ester Intermediates following the procedure described for Compounds 16 and 17.

| Cmpd | Structure | Name | [M + H]$^+$ |
|---|---|---|---|
| 17.01[4] | 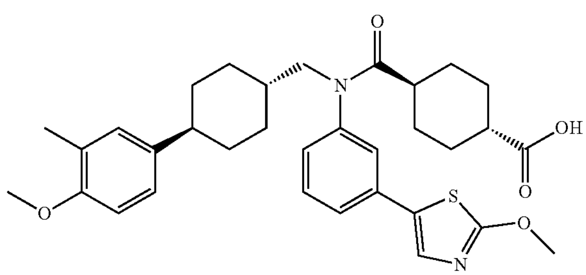 [SMILES: COc1ncc(-c2cccc(N(C[C@H]3CC[C@H](c4ccc(OC)c(C)c4)CC3)C(=O)[C@H]3CC[C@H](C(=O)O)CC3)c2)s1] | trans-4-(((trans-4-(4-Methoxy-3-methylphenyl)cyclohexyl)methyl)(3-(2-methoxythiazol-5-yl)phenyl)-carbamoyl)cyclohexanecarboxylic acid | 577.3 |
| 17.02[4] | 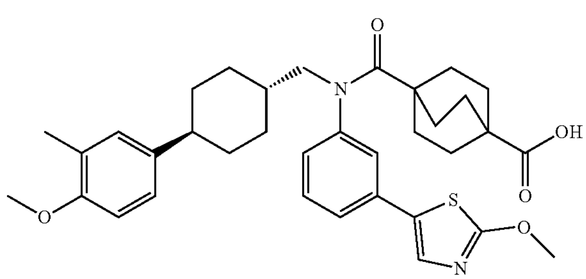 [SMILES: COc1ncc(-c2cccc(N(C[C@H]3CC[C@H](c4ccc(OC)c(C)c4)CC3)C(=O)C34CCC(C(=O)O)(CC3)CC4)c2)s1] | 4-(((trans-4-(4-Methoxy-3-methylphenyl)cyclohexyl)methyl)(3-(2-methoxythiazol-5-yl)phenyl)carbamoyl)bicyclo[2.2.2]octane-1-carboxylic acid | 603.5 |
| 17.03[4] | 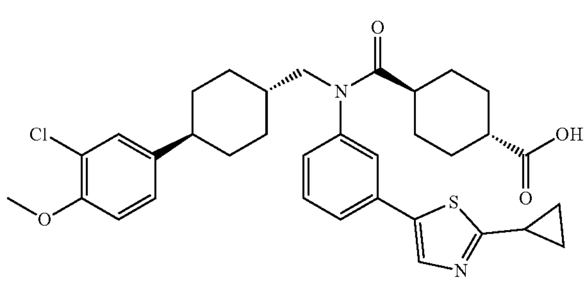 [SMILES: COc1ccc([C@H]2CC[C@H](CN(c3cccc(-c4cnc(C5CC5)s4)c3)C(=O)[C@H]3CC[C@H](C(=O)O)CC3)CC2)cc1Cl] | trans-4-(((trans-4-(3-Chloro-4-methoxyphenyl)cyclohexyl)-methyl)(3-(2-cyclopropylthiazol-5-yl)phenyl)carbamoyl)cyclohexanecarboxylic acid | 607.3 |

-continued

| Cmpd | Structure | Name | [M + H]+ |
|---|---|---|---|
| 17.04 | 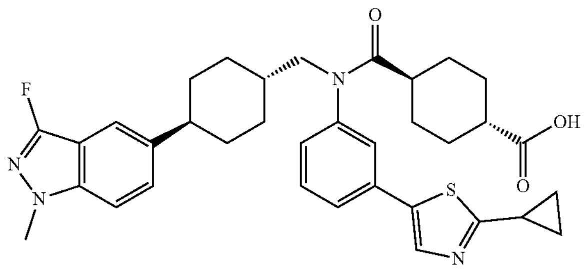 [SMILES: Cn1nc(F)c2cc([C@H]3CC[C@H](CN(c4cccc(-c5cnc(C6CC6)s5)c4)C(=O)[C@H]4CC[C@H](C(=O)O)CC4)CC3)ccc21] | trans-4-((3-(2-Cyclopropylthiazol-5-yl)phenyl)((trans-4-(3-fluoro-1-methyl-1H-indazol-5-yl)cyclohexyl)methyl)carbamoyl)cyclohexanecarboxylic acid | 615.4 |
| 17.05[4] | 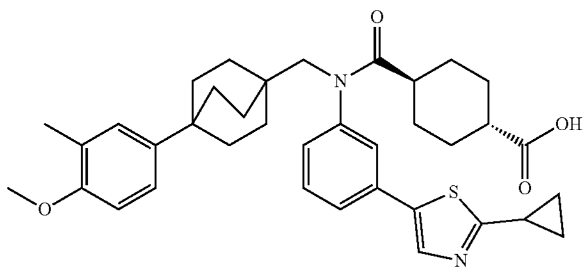 | trans-4-((3-(2-Cyclopropylthiazol-5-yl)phenyl)((4-(4-methoxy-3-methylphenyl)bicyclo[2.2.2]octan-1-yl)methyl)carbamoyl)cyclohexanecarboxylic acid | 613.4 |
| 17.06 | 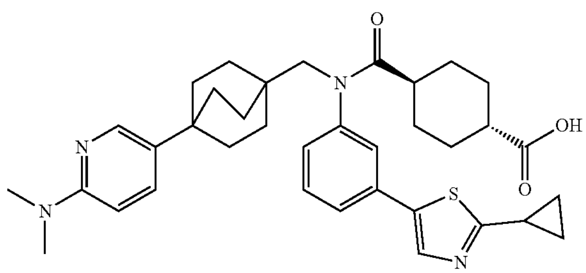 [SMILES: CN(C)c1ccc(C23CCC(CN(c4cccc(-c5cnc(C6CC6)s5)c4)C(=O)[C@H]4CC[C@H](C(=O)O)CC4)(CC2)CC3)cn1] | trans-4-((3-(2-Cyclopropylthiazol-5-yl)phenyl)((4-(6-(dimethylamino)pyridin-3-yl)bicyclo[2.2.2]octan-1-yl)methyl)carbamoyl)cyclohexanecarboxylic acid | 613.4 |
| 17.07[1,5] | 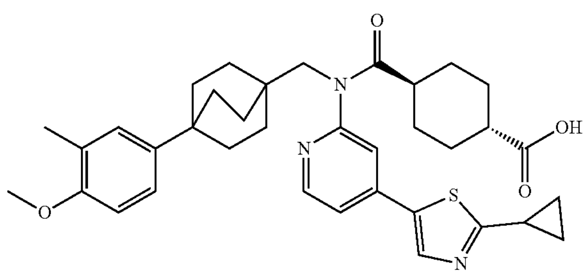 | trans-4-((4-(2-Cyclopropylthiazol-5-yl)pyridin-2-yl)((4-(4-methoxy-3-methylphenyl)bicyclo[2.2.2]octan-1-yl)methyl)carbamoyl)cyclohexanecarboxylic acid | 614.4 |
| 17.08[1] | 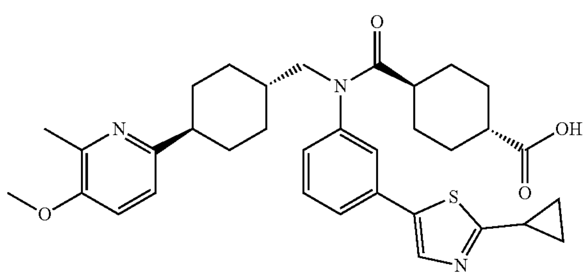 [SMILES: COc1ccc([C@H]2CC[C@H](CN(c3cccc(-c4cnc(C5CC5)s4)c3)C(=O)[C@H]3CC[C@H](C(=O)O)CC3)CC2)nc1C] | trans-4-((3-(2-Cyclopropylthiazol-5-yl)phenyl)((trans-4-(5-methoxy-6-methylpyridin-2-yl)cyclohexyl)methyl)carbamoyl)cyclohexanecarboxylic acid | 588.4 |

-continued

| Cmpd | Structure | Name | [M + H]+ |
|---|---|---|---|
| 17.09[1] | 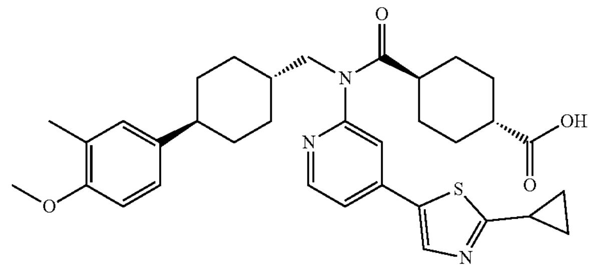 | trans-4-((4-(2-Cyclopropylthiazol-5-yl)pyridin-2-yl)((trans-4-(4-methoxy-3-methylphenyl)cyclohexyl)methyl)carbamoyl)cyclohexanecarboxylic acid | 588.5 |
| 17.10[1] | 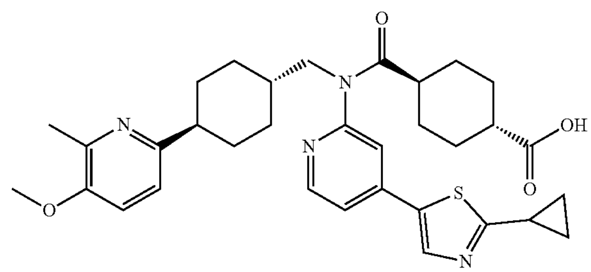 | trans-4-((4-(2-Cyclopropylthiazol-5-yl)pyridin-2-yl)((trans-4-(5-methoxy-6-methylpyridin-2-yl)cyclohexyl)methyl)carbamoyl)cyclohexanecarboxylic acid | 589.4 |
| 17.11[2] | 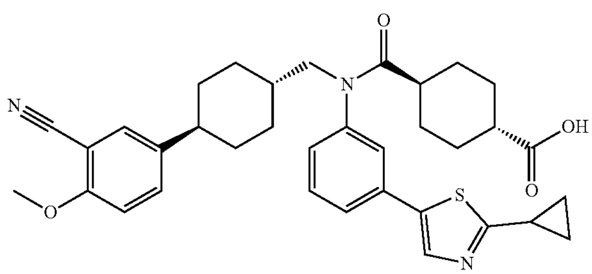 [SMILES: COc1ccc([C@H]2CC[C@H](CN(c3cccc(-c4cnc(C5CC5)s4)c3)C(=O)[C@H]3CC[C@H](C(=O)O)CC3)CC2)cc1C#N] | trans-4-(((trans-4-(3-Cyano-4-methoxyphenyl)cyclohexyl)methyl)(3-(2-cyclopropylthiazol-5-yl)phenyl)carbamoyl)cyclohexanecarboxylic acid | 598.3 |
| 17.12[2] | 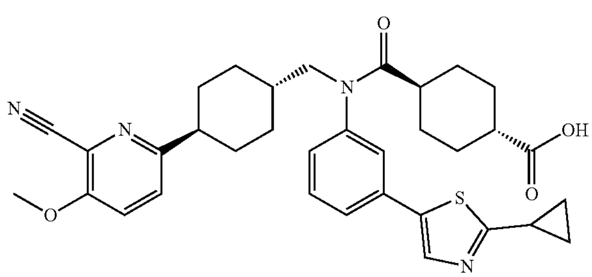 [SMILES: COc1ccc([C@H]2CC[C@H](CN(c3cccc(-c4cnc(C5CC5)s4)c3)C(=O)[C@H]3CC[C@H](C(=O)O)CC3)CC2)nc1C#N] | trans-4-(((trans-4-(6-Cyano-5-methoxypyridin-2-yl)cyclohexyl)methyl)(3-(2-cyclopropylthiazol-5-yl)phenyl)carbamoyl)cyclohexanecarboxylic acid | 599.6 |
| 17.13[6] | 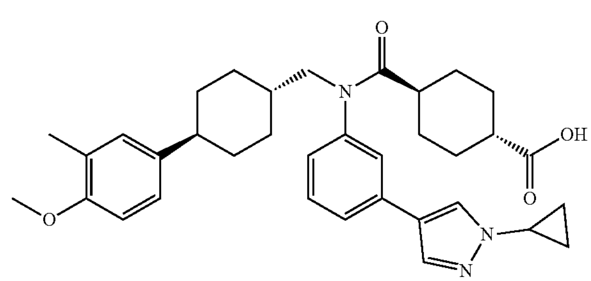 [SMILES: COc1ccc([C@H]2CC[C@H](CN(c3cccc(-c4cnn(C5CC5)c4)c3)C(=O)[C@H]3CC[C@H](C(=O)O)CC3)CC2)cc1C] | trans-4-((3-(1-Cyclopropyl-1H-pyrazol-4-yl)phenyl)((trans-4-(4-methoxy-3-methylphenyl)cyclohexyl)methyl)carbamoyl)cyclohexanecarboxylic acid | 570.4 |

-continued

| Cmpd | Structure | Name | [M + H]⁺ |
|---|---|---|---|
| 17.14[3] | 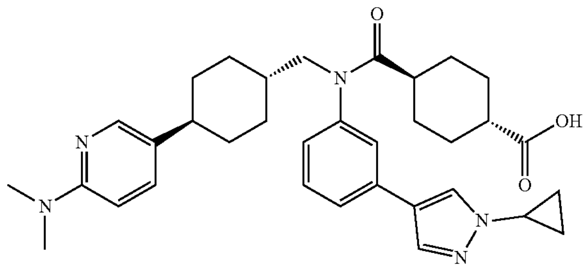 [SMILES: CN(C)c1ccc([C@H]2CC[C@H](CN(c3cccc(-c4cnn(C5CC5)c4)c3)C(=O)[C@H]3CC[C@H](C(=O)O)CC3)CC2)cn1] | trans-4-((3-(1-Cyclopropyl-1H-pyrazol-4-yl)phenyl)((trans-4-(6-(dimethylamino)pyridin-3-yl)-cyclohexyl)methyl)carbamoyl)-cyclohexanecarboxylic acid | 570.5 |
| 17.15[4] | 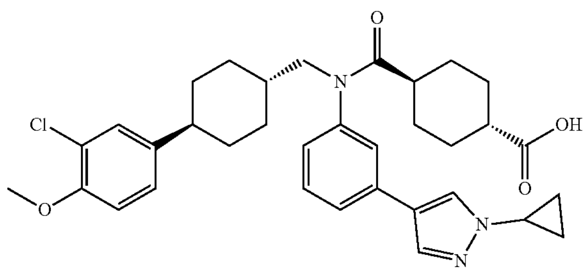 | trans-4-(((trans-4-(3-Chloro-4-methoxyphenyl)cyclohexyl)methyl)-(3-(1-cyclopropyl-1H-pyrazol-4-yl)phenyl)carbamoyl)cyclohexane-carboxylic acid | 590.3 |
| 17.16 | 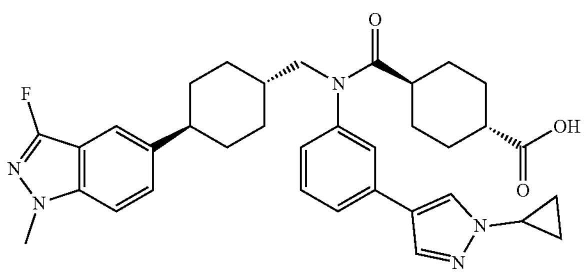 [SMILES: Cn1nc(F)c2cc([C@H]3CC[C@H](CN(c4cccc(-c5cnn(C6CC6)c5)c4)C(=O)[C@H]4CC[C@H](C(=O)O)CC4)CC3)ccc21] | trans-4-((3-(1-Cyclopropyl-1H-pyrazol-4-yl)phenyl)((trans-4-(3-fluoro-1-methyl-1H-indazol-5-yl)-cyclohexyl)methyl)carbamoyl)-cyclohexanecarboxylic acid | 598.3 |
| 17.17[4] | 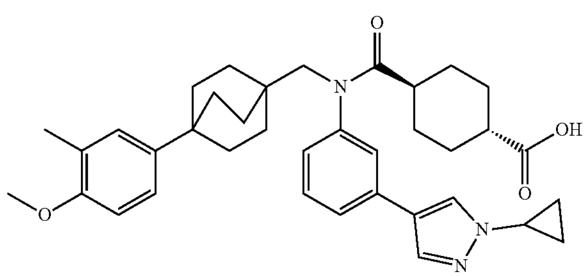 [SMILES: COc1ccc(C23CCC(CN(c4cccc(-c5cnn(C6CC6)c5)c4)C(=O)[C@H]4CC[C@H](C(=O)O)CC4)(CC2)CC3)cc1C] | trans-4-((3-(1-Cyclopropyl-1H-pyrazol-4-yl)phenyl)((4-(4-methoxy-3-methylphenyl)bicyclo[2.2.2]octan-1-yl)methyl)carbamoyl)cyclohexane-carboxylic acid | 596.4 |
| 17.18 | 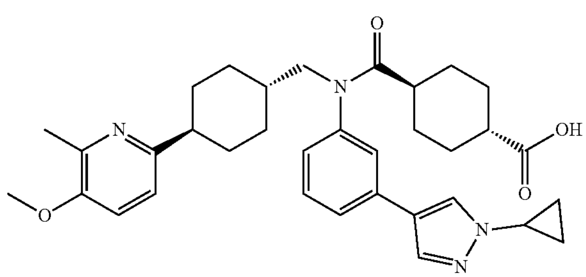 | trans-4-((3-(1-Cyclopropyl-1H-pyrazol-4-yl)phenyl)((trans-4-(5-methoxy-6-methylpyridin-2-yl)cyclohexyl)methyl)carbamoyl)-cyclohexanecarboxylic acid | 571.5 |

-continued

| Cmpd | Structure | Name | [M + H]+ |
|---|---|---|---|
| 17.19[2] | 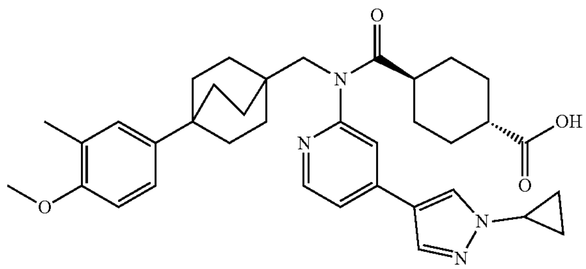 [SMILES: COc1ccc(C23CCC(CN(c4cc(-c5cnn(C6CC6)c5)ccn4)C(=O)[C@H]4CC[C@H](C(=O)O)CC4)(CC2)CC3)cc1C] | trans-4-((4-(1-Cyclopropyl-1H-pyrazol-4-yl)pyridin-2-yl)((4-(4-methoxy-3-methylphenyl)bicyclo-[2.2.2]octan-1-yl)methyl)carbamoyl)cyclohexanecarboxylic acid | 597.5 |
| 17.20 | 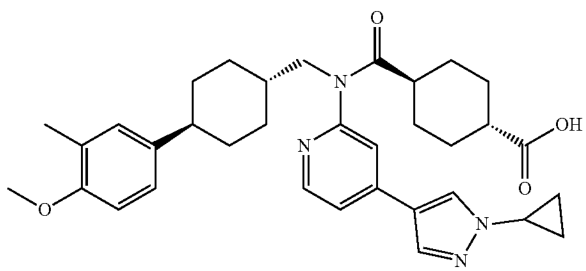 | trans-4-((4-(1-Cyclopropyl-1H-pyrazol-4-yl)pyridin-2-yl)((trans-4-(4-methoxy-3-methyl phenyl)-cyclohexyl)methyl)carb amoyl)-cyclohexanecarboxylic acid | 571.5 |
| 17.21[3,6] | 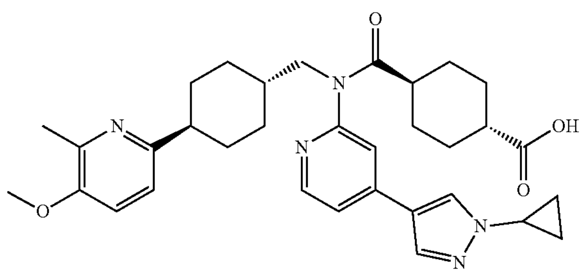 [SMILES: COc1ccc([C@H]2CC[C@H](CN(c3cc(-c4cnn(C5CC5)c4)ccn3)C(=O)[C@H]3CC[C@H](C(=O)O)CC3)CC2)nc1C] | trans-4-((4-(1-Cyclopropyl-1H-pyrazol-4-yl)pyridin-2-yl)((trans-4-(5-methoxy-6-methylpyridin-2-yl)-cyclohexyl)methyl)carbamoyl)cyclo-hexanecarboxylic acid | 572.5 |
| 17.22[2] | 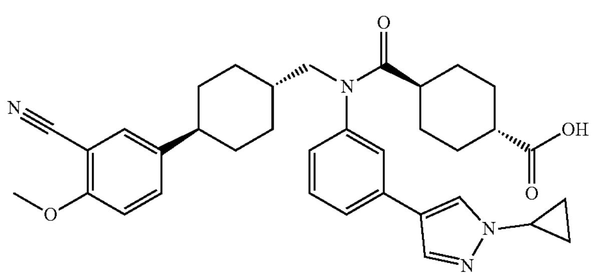 [SMILES: COc1ccc([C@H]2CC[C@H](CN(c3cccc(-c4cnn(C5CC5)c4)c3)C(=O)[C@H]3CC[C@H](C(=O)O)CC3)CC2)cc1C#N] | trans-4-(((trans-4-(3-Cyano-4-methoxyphenyl)cyclohexyl)-methyl)(3-(1-cyclopropyl-1H-pyrazol-4-yl)phenyl)carbamoyl)-cyclohexanecarboxylic acid | 581.5 |
| 17.23[4] | 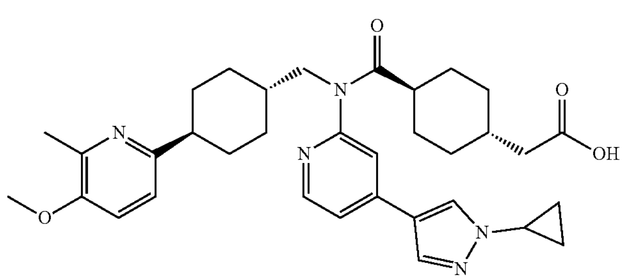 | 2-(trans-4-((4-(1-Cyclopropyl-1H-pyrazol-4-yl)pyridin-2-yl)((trans-4-(5-methoxy-6-methylpyridin-2-yl)cyclohexyl)methyl)carbamoyl)-cyclohexyl)acetic acid | 586.4 |

-continued

| Cmpd | Structure | Name | [M + H]⁺ |
| --- | --- | --- | --- |
| 17.24[4] | 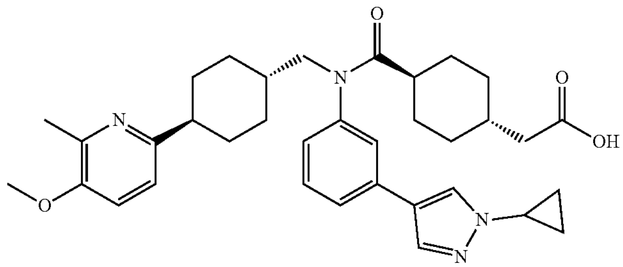 [SMILES: COc1ccc([C@H]2CC[C@H](CN(c3cccc(-c4cnn(C5CC5)c4)c3)C(=O)[C@H]3CC[C@H](CC(=O)O)CC3)CC2)nc1C] | 2-(trans-4-((3-(1-Cyclopropyl-1H-pyrazol-4-yl)phenyl)((trans-4-(5-methoxy-6-methylpyridin-2-yl)-cyclohexyl)methyl)carbamoyl)-cyclohexyl)acetic acid | 585.5 |
| 17.25[6] | 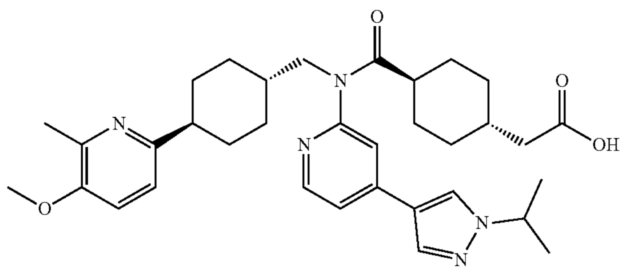 | 2-(trans-4-((4-(1-Isopropyl-1H-pyrazol-4-yl)pyridin-2-yl)((trans-4-(5-methoxy-6-methylpyridin-2-yl)cyclohexyl)methyl)carbamoyl)-cyclohexyl)acetic acid | 588.5 |
| 17.26[3] | 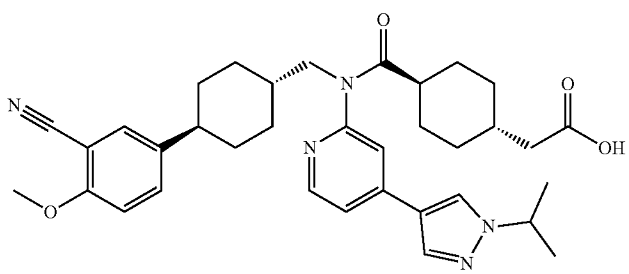 | 2-(trans-4-(((trans-4-(3-Cyano-4-methoxyphenyl)cyclohexyl)methyl)-(4-(1-isopropyl-1H-pyrazol-4-yl)pyridin-2-yl)carbamoyl)cyclo-hexyl)acetic acid | 598.5 |
| 17.27[3] | 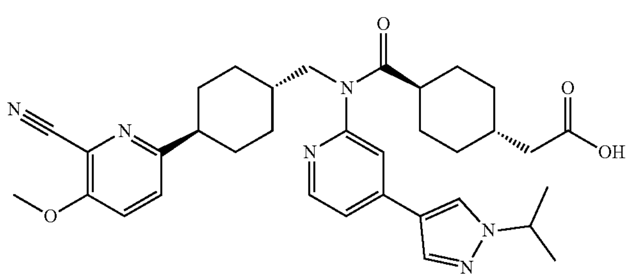 [SMILES: COc1ccc([C@H]2CC[C@H](CN(c3cc(-c4cnn(C(C)C)c4)ccn3)C(=O)[C@H]3CC[C@H](CC(=O)O)CC3)CC2)nc1C#N] | 2-(trans-4-(((trans-4-(6-Cyano-5-methoxypyridin-2-yl)cyclohexyl)-methyl)(4-(1-isopropyl-1H-pyrazol-4-yl)pyridin-2-yl)carbamoyl)cyclo-hexyl)acetic acid | 599.5 |

Alternate conditions:

[1] THF/CH₃OH (1:1);

[2] LiOH•H₂O, THF, 0° C.-rt, 2 h.

Isolation variations:

[3] Acidified to pH = 6 before extraction;

[4] Purifed by silica gel chromatography;

[5] Purified by reverse-phase HPLC;

[6] Isolated as a solid by filtration of aqueous after pH adjustment.

Compound 18

Trans-4-(((trans-4-(3-Cyano-4-methoxyphenyl)cyclohexyl)methyl)(3-(2-cyclopropyloxazol-4-yl)phenyl)carbamoyl)cyclohexanecarboxylic Acid

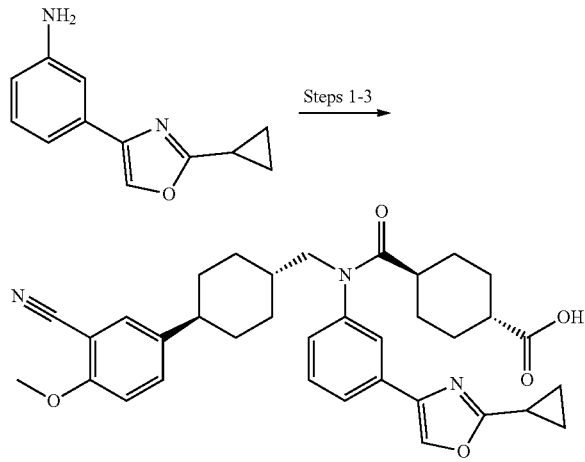

Step 1: 5-(trans-4-(((3-(2-Cyclopropyloxazol-4-yl)phenyl)amino)methyl)cyclohexyl)-2-methoxybenzonitrile Sodium triacetoxyborohydride (436 mg, 2.06 mmol) was added to a solution of Intermediate 3.05 (200 mg, 0.82 mmol), Intermediate 8.01 (165 mg, 0.82 mmol), and DCE (20 mL) at 0° C. under $N_2$. The reaction was stirred at rt overnight, poured into saturated $NaHCO_3$ (30 mL) and extracted with $CH_2Cl_2$ (3×30 mL). The combined organic layers were washed (30 mL brine), dried ($Na_2SO_4$), filtered, and concentrated. The residue was purified by silica gel chromatography (petroleum ether/EtOAc=17/3) to give 5-(trans-4-(((3-(2-cyclopropyloxazol-4-yl)phenyl)amino)methyl)cyclohexyl)-2-methoxybenzonitrile (250 mg, 66%) as a yellow oil. $^1$H NMR (400 MHz, $CDCl_3$): δ 7.71 (s, 1H), 7.42-7.35 (m, 2H), 7.20-7.18 (m, 1H), 7.01-6.97 (m, 2H), 6.90 (d, 1H), 6.56 (d, 1H), 3.90 (s, 3H), 3.07 (d, 2H), 2.50-2.43 (m, 1H), 2.15-2.11 (m, 1H), 2.05-2.00 (m, 2H), 1.99-1.90 (m, 2H), 1.70-1.67 (m, 1H), 1.43-1.39 (m, 2H), 1.13-1.11 (m, 2H), 1.10-1.06 (m, 2H), 1.06-1.04 (m, 2H); LCMS: 428.3 [M+H]$^+$.

Step 2: Trans-Methyl-4-(((trans-4-(3-cyano-4-methoxyphenyl)cyclohexyl)methyl)(3-(2-cyclopropyloxazol-4-yl)phenyl)carbamoyl)cyclohexanecarboxylate Intermediate 19.04 (20 mL in toluene, 1.87 mmol) was added to a solution of 5-(trans-4-(((3-(2-cyclopropyloxazol-4-yl)phenyl)amino)methyl)cyclohexyl)-2-methoxybenzonitrile (200 mg, 0.47 mmol), pyridine (0.76 mL, 9.36 mmol), and dry $CH_2Cl_2$ (10 mL) at 0° C. under $N_2$. The reaction was allowed to warm to rt, stirred overnight, poured into saturated $NaHCO_3$ (30 mL) and then extracted with $CH_2Cl_2$ (3×30 mL). The combined organic layers were washed with brine (30 mL), dried ($Na_2SO_4$), filtered, and concentrated. The residue was purified by silica gel chromatography (petroleum ether/EtOAc=4/1) to give trans-methyl-4-(((trans-4-(3-cyano-4-methoxyphenyl)cyclohexyl)methyl)(3-(2-cyclopropyloxazol-4-yl)phenyl)carbamoyl)cyclohexanecarboxylate (190 mg, 52%) as a yellow oil. $^1$H NMR (400 MHz, $CDCl_3$): δ 7.80 (s, 1H), 7.67 (d, 1H), 7.56 (s, 1H), 7.47-7.42 (m, 1H), 7.35-7.32 (m, 2H), 7.08 (d, 1H), 6.88 (d, 1H), 3.89 (s, 3H), 3.60 (s, 3H), 2.48-2.40 (m, 1H), 2.30-2.23 (m, 1H), 2.20-2.09 (m, 2H), 1.93-1.76 (m, 7H), 1.66-1.56 (m, 5H), 1.48-1.43 (m, 1H), 1.33-1.30 (m, 2H), 1.22-1.11 (m, 6H), 1.11-1.04 (m, 2H); LCMS: 596.4 [M+H]$^+$.

Step 3: Trans-4-(((trans-4-(3-Cyano-4-methoxyphenyl)cyclohexyl)methyl)(3-(2-cyclopropyloxazol-4-yl)phenyl)carbamoyl)cyclohexanecarboxylic Acid Lithium hydroxide monohydrate (169 mg, 4.03 mmol) was added to a solution of trans-methyl-4-(((trans-4-(3-cyano-4-methoxyphenyl)cyclohexyl)methyl)(3-(2-cyclopropyloxazol-4-yl)phenyl)carbamoyl)cyclohexanecarboxylate (300 mg, 0.5 mmol), THF (20 mL), and $H_2O$ (5 mL) at 0° C. The mixture was allowed to warm to rt and stirred overnight. THF was removed under reduced pressure, and the mixture was diluted with $H_2O$ (20 mL). The mixture was concentrated to remove water (5 mL), and then hydrochloric acid (1 M) was added to the solution at 0° C. (pH=6). The resulting solid was collected by filtration, washed with ice $H_2O$ (20 mL), and dried under vacuum. The solid was purified by reverse-phase HPLC (water(0.05% HCl)/$CH_3CN$) to give trans-4-(((trans-4-(3-cyano-4-methoxyphenyl)cyclohexyl)methyl)(3-(2-cyclopropyloxazol-4-yl)phenyl)carbamoyl)cyclohexanecarboxylic acid (130 mg, 44%) as a white solid. $^1$H NMR (400 MHz, DMSO-$d_6$): δ 11.95 (s, 1H), 8.52 (s, 1H), 7.75 (d, 1H), 7.65 (s, 1H), 7.53-7.49 (m, 3H), 7.24 (d, 1H), 7.12 (d, 1H), 3.86 (s, 3H), 3.56 (d, 2H), 2.45-2.42 (m, 1H), 2.19-2.13 (m, 1H), 2.10-2.07 (m, 2H), 1.81-1.72 (m, 6H), 1.69-1.66 (m, 2H), 1.46-1.31 (m, 5H), 1.07-1.04 (m, 4H), 1.00-0.99 (m, 2H), 0.98-0.88 (in, 2H); LCMS: 582.4 [M+H]$^+$.

The following Compounds were synthesized from the appropriate Intermediates following the procedures described for Compound 18.

| Cmpd | Structure | Name | [M + H]$^+$ |
|---|---|---|---|
| 18.01[1,2] | 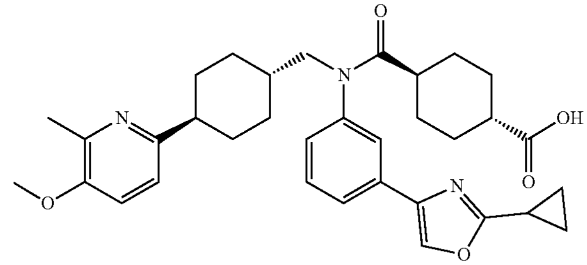 [SMILES: COc1ccc([C@H]2CC[C@H](CN(c3cccc(-c4coc(C5CC5)n4)c3)C(=O)[C@H]3CC[C@H](C(=O)O)CC3)CC2)nc1C] | trans-4-((3-(2-Cyclopropyloxazol-4-yl)phenyl)((trans-4-(5-methoxy-6-methylpyridin-2-yl)cyclohexyl)methyl)carbamoyl)-cyclohexanecarboxylic acid | 572.5 |

-continued

| Cmpd | Structure | Name | [M + H]⁺ |
|---|---|---|---|
| 18.02[1] | 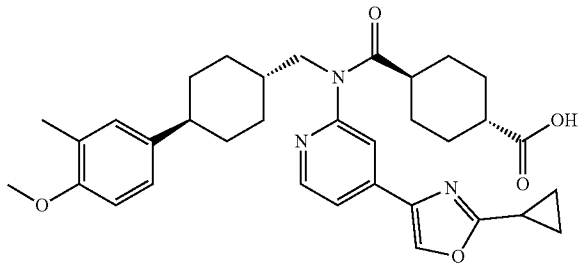 [SMILES: COc1ccc([C@H]2CC[C@H](CN(c3cc(-c4coc(C5CC5)n4)ccn3)C(=O)[C@H]3CC[C@H](C(=O)O)CC3)CC2)cc1C] | trans-4-((4-(2-(2-4-yl)pyridine-2-yl)((trans-4-(4-methoxy-3-methylphenyl)-cyclohexyl)methyl)carba-moyl)cyclohexanecarboxylic acid | 572.5 |
| 18.03[3] | 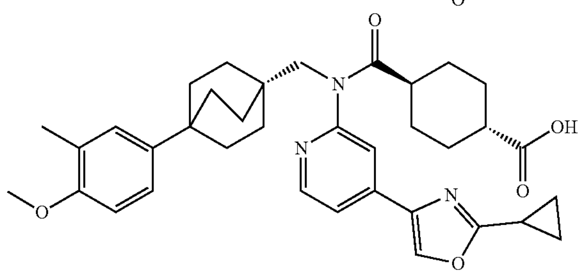 | trans-4-((4-(2-Cyclopropyloxazol-4-yl)pyridin-2-yl)((4-(4-methoxy-3-methylphenyl)bicyclo[2.2.2]octan-1-yl)methyl)carbamoyl)cyclohexane-carboxylic acid | 598.5 |
| 18.04 | 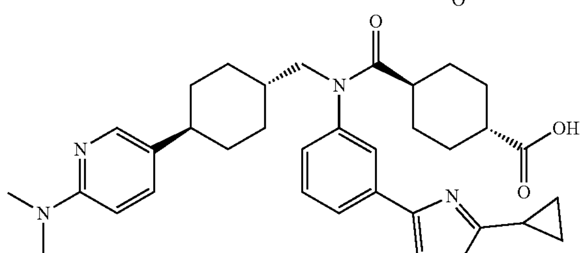 | trans-4-((3-(2-Cyclopropyloxazol-4-yl)phenyl)((trans-4-(6-(dimethylamino)pyridine-3-yl)cyclohexyl)methyl)carba-moyl)cyclohexanecarboxylic acid | 571.4 |
| 18.05 | 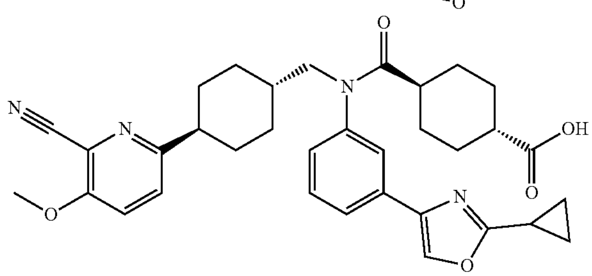 | trans-4-(((trans-4-(6-Cyano-5-methoxypyridin-2-yl)cyclohexyl)methyl)(3-(2-cyclopropyloxazol-4-yl)phenyl)carbamoyl)cyclo-hexanecarboxylic acid | 583.4 |

Alternate condition: Step 2:
[1]Base was Et₃N.
Isolation variations:
[2]Purifed by silica gel chromatography;
[3]Filtered off solids with H₂O rinsing (no further purification).

The following Compounds were synthesized from the appropriate Intermediates following the procedures described for Compound 18, Steps 1 & 2.

| Cmpd | Structure | Name | [M + H]⁺ |
|---|---|---|---|
| 18.06[2] | 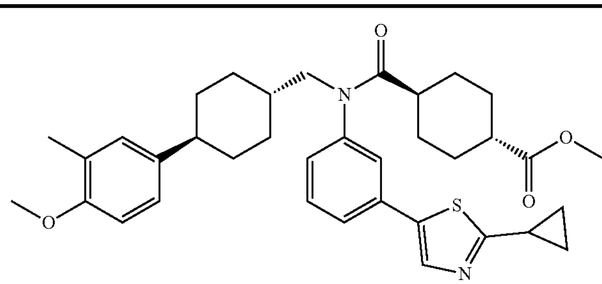 | trans-Methyl 4-(((3-(2-cyclopropylthiazol-5-yl)phenyl)((trans-4-(4-methoxy-3-methylphenyl)cyclohexyl)-methyl)carba-moyl)cyclohexanecarboxylate | 601.4 |

-continued

| Cmpd | Structure | Name | [M + H]+ |
|---|---|---|---|
| 18.07 | 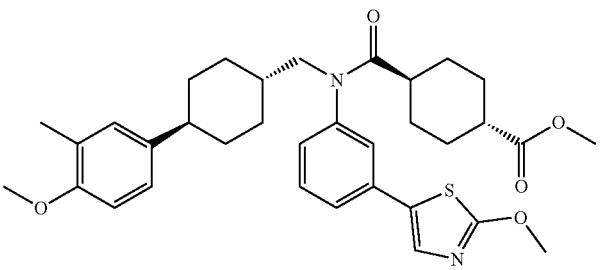 | trans-Methyl 4-(((trans-4-(4-methoxy-3-methylphenyl)cyclohexyl)-methyl)(3-(2-methoxythiazol-5-yl)phenyl)carbamoyl)cyclohexanecarb-xylate | 591.4 |
| 18.08 | 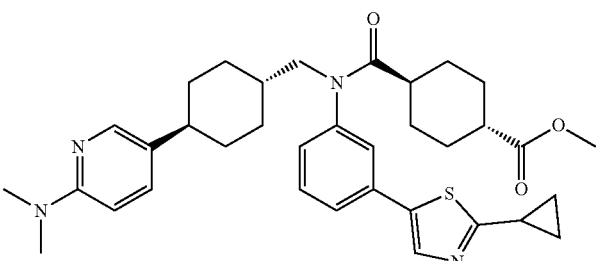 | trans-Methyl 4-((3-(2-cyclopropylthiazol-5-yl)-phenyl)((trans-4-(6-(dimethylamino)pyridin-3-yl)cyclohexyl)methyl)-carbamoyl)-cyclohexanecarboxylate | 601.4 |
| 18.09 | 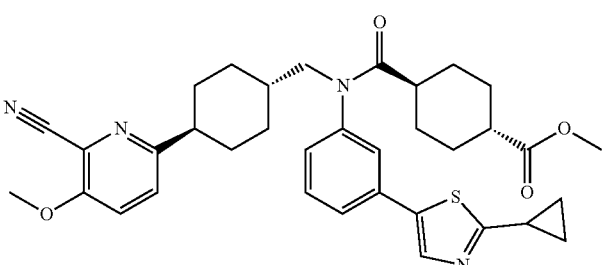 | trans-Methyl 4-(((trans-4-(6-cyano-5-methoxypyridin-2-yl)cyclohexyl)methyl)(3-(2-cyclopropylthiazol-5-yl)phenyl)carbamoyl)-cyclohexane-carbxylate | 613.5 |
| 18.10[2,5] | 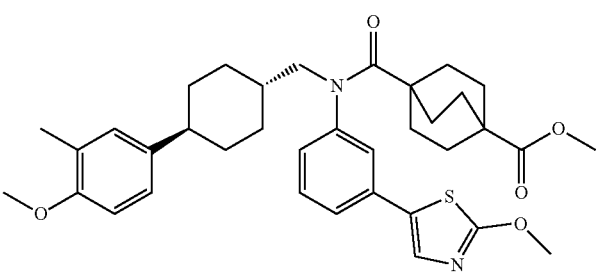 | Methyl 4-(((trans-4-(4-methoxy-3-methyl phenyl)cyclohexyl)-methyl)(3-(2-methoxythiazol-5-yl)phenyl)carbamoyl)-bicyclo[2.2.2]-octane-1-carboxylate | 617.4 |
| 18.11 | 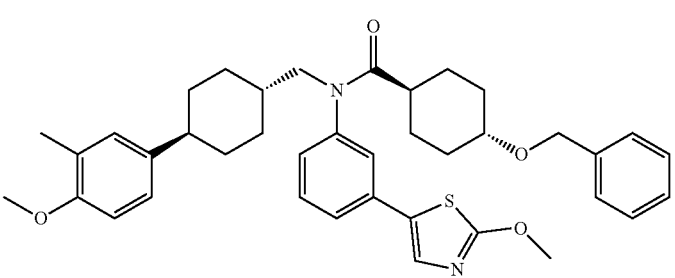 [SMILES: COc1ncc(-c2cccc(N(C[C@H]3CC[C@H](c4ccc(OC)c(C)c4)CC3)C(=O)[C@H]3CC[C@H](OCc4ccccc4)CC3)c2)s1] | trans-4-(Benzyloxy)-N-((trans-4-(4-methoxy-3-methylphenyl)cyclohexyl)-methyl)-N-(3-(2-methoxythiazol-5-yl)phenyl)cyclohexane-carboxamide | 639.5 |

-continued

| Cmpd | Structure | Name | [M + H]+ |
|---|---|---|---|
| 18.12 | 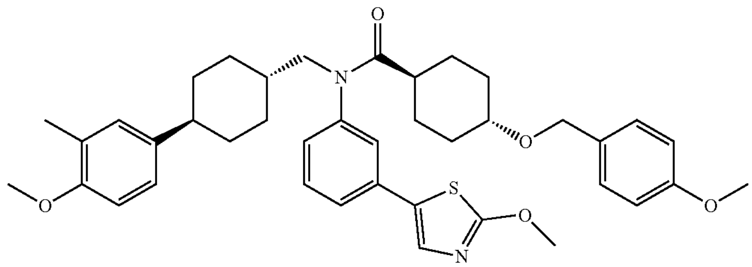 | trans-N-((trans-4-(4-Methoxy-3-methylphenyl)cyclohexyl)-methyl)-4-((4-methoxybenzyl)-oxy)-N-(3-(2-methoxythiazol-5-yl)phenyl)cyclohexanecarboxamide | 669.4 |
| 18.13[2] | 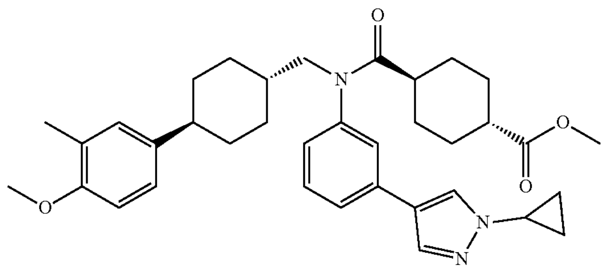 | trans-methyl 4-((3-(1-cyclopropyl-1H-pyrazol-4-yl)phenyl)((trans-4-(4-methoxy-3-methylphenyl)-cyclohexyl)methyl)-carbamoyl)cyclohexane-carboxylate | 584.5 |
| 18.14[2] | 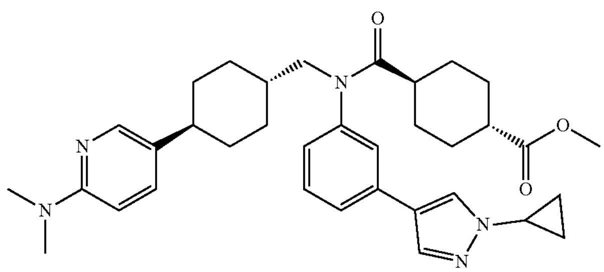 | trans-Methyl 4-((3-(1-cyclopropyl-1H-pyrazol-4-yl)phenyl)((trans-4-(6-(dimethylamino)pyridin-3-yl)cyclohexyl)-methyl)carbamoyl)-cyclohexanecarboxylate | 584.6 |
| 18.15 | 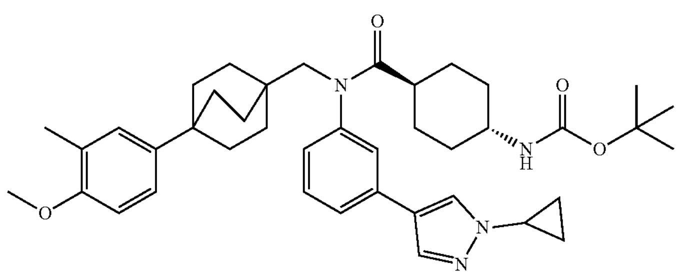 [SMILES: COc1ccc(C23CCC(CN(c4cccc(-c5cnn(C6CC6)c5)c4)C(=O)[C@H]4CC[C@H](NC(=O)OC(C)(C)C)CC4)(CC2)CC3)cc1C] | tert-Butyl (4-((3-(1-cyclopropyl-1H-pyrazol-4-yl)phenyl)((4-(4-methoxy-3-methyl-phenyl)bicyclo[2.2.2]octan-1-yl)methyl)carbamoyl)cyclohexyl)trans-carbamate | 667.4 |
| 18.16 | 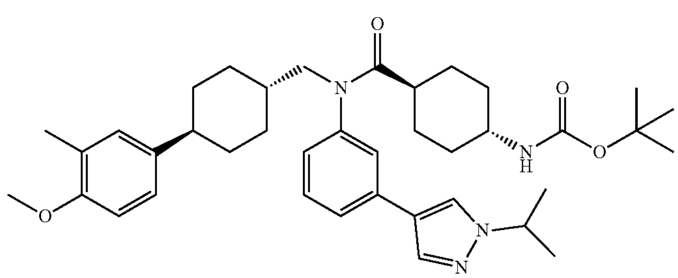 [SMILES: COc1ccc([C@H]2CC[C@H](CN(c3cccc(-c4cnn(C(C)C)c4)c3)C(=O)[C@H]3CC[C@H](NC(=O)OC(C)(C)C)CC3)CC2)cc1C] | tert-Butyl (trans-4-((3-(1-isopropyl-1H-pyrazol-4-yl)phenyl)((trans-4-(4-methoxy-3-methylphenyl)cyclohexyl)-methyl)carbamoyl)cyclohexyl)carbamate | 665.5 |

| Cmpd | Structure | Name | [M + H]⁺ |
|---|---|---|---|
| 18.17[3] | 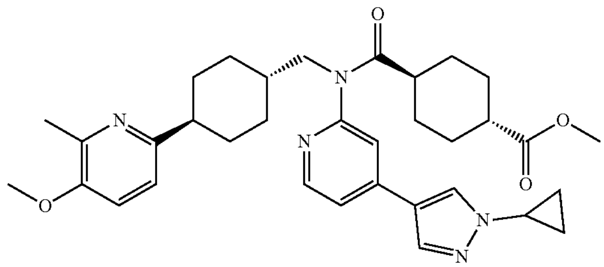 | trans-Methyl 4-((4-(1-cyclopropyl-1H-pyrazol-4-yl)-pyridin-2-yl)((trans-4-(5-methoxy-6-methylpyridin-2-yl)cyclohexyl)methyl)-carbamoyl)-cyclohexanecarboxylate | 586.6 |
| 18.18[3] | 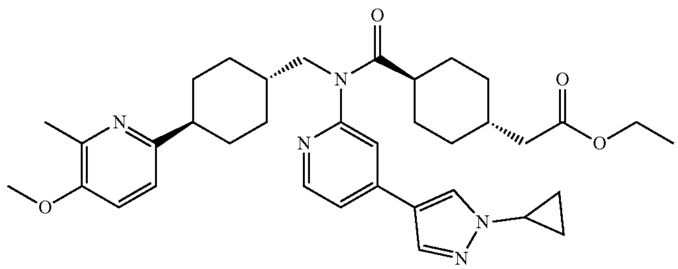 | Ethyl 2-(trans-4-((4-(1-cyclopropyl-1H-pyrazol-4-yl)pyridin-2-yl)((trans-4-(5-methoxy-6-methylpyridin-2-yl)cyclohexyl)methyl)carbamoyl)-cyclohexyl)acetate | 614.6 |
| 18.19[2] | 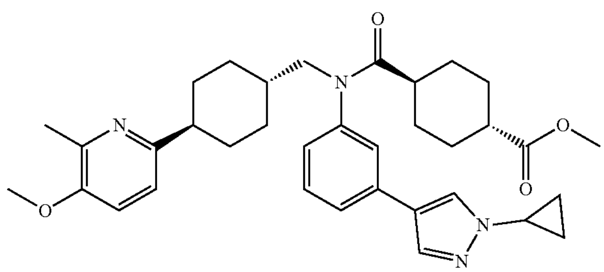 | trans-Methyl 4-((3-(1-cyclopropyl-1H-pyrazol-4-yl)-phenyl)((trans-4-(5-methoxy-6-methylpyridin-2-yl)cyclohexyl)methyl)carbamoyl)-cyclohexanecarboxylate | 585.5 |
| 18.20[4] | 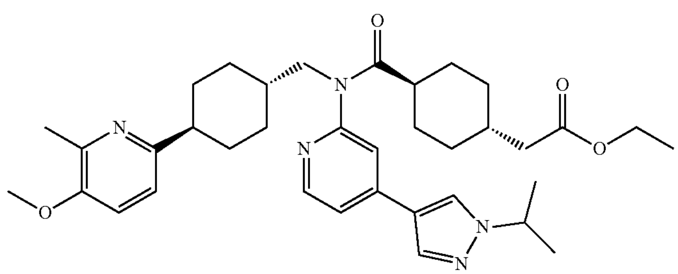 [SMILES: CCOC(=O)C[C@H]1CC[C@H](C(=O)N(C[C@H]2CC[C@H](c3ccc(OC)c(C)n3)CC2)c2cc(-c3cnn(C(C)C)c3)ccn2)CC1] | Ethyl 2-(trans-4-((4-(1-isopropyl-1H-pyrazol-4-yl)pyridin-2-yl)((trans-4-(5-methoxy-6-methylpyridin-2-yl)cyclohexyl)methyl)carbamoyl)-cyclohexyl)acetate | 616.5 |
| 18.21[3] | 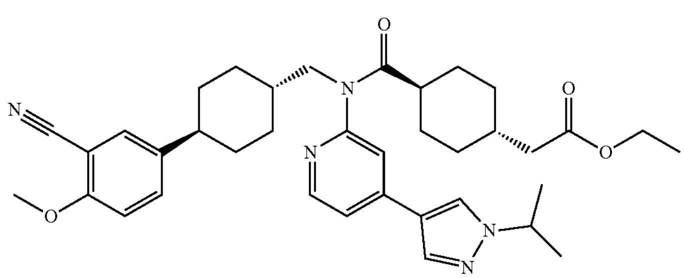 | Ethyl 2-(trans-4-(((trans-4-(3-cyano-4-methoxyphenyl)cyclohexyl)methyl)(4-(1-isopropyl-1H-pyrazol-4-yl)pyridin-2-yl)carbamoyl)cyclohexyl)-acetate | 626.5 |

-continued

| Cmpd | Structure | Name | [M + H]+ |
|---|---|---|---|
| 18.22[3] | 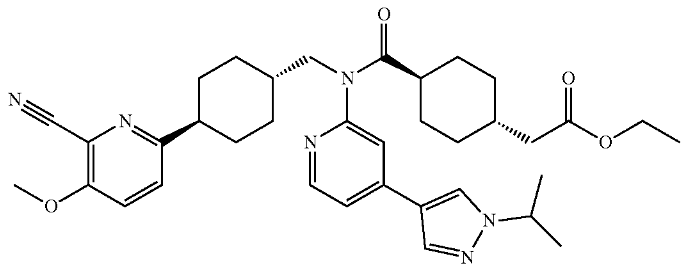 [SMILES: CCOC(=O)C[C@H]1CC[C@H](C(=O)N(C[C@H]2CC[C@H](c3ccc(OC)c(C#N)n3)CC2)c2cc(-c3cnn(C(C)C)c3)ccn2)CC1] | Ethyl 2-(trans-4-(((trans-4-(6-cyano-5-methoxypyridin-2-yl)cyclohexyl)methyl)(4-(1-isopropyl-1H-pyrazol-4-yl)pyridin-2-yl)carbamoyl)cyclohexyl)acetate | 627.5 |
| 18.23[1,4] | 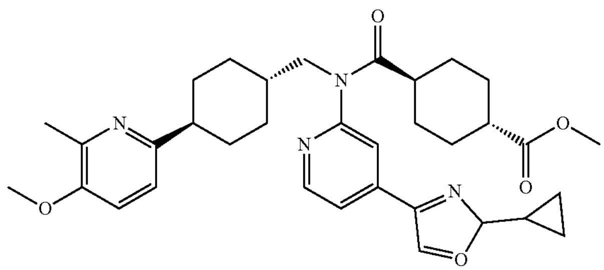 | trans-Methyl 4-((3-(2-cyclopropyloxazol-4-yl)-pyridin-2-yl)((trans-4-(5-methoxy-6-methy-lpyridin-2-yl)cyclohexyl)-methyl)carbamoyl)-cyclohexanecarboxylate | 587.7 |
| 18.24 | 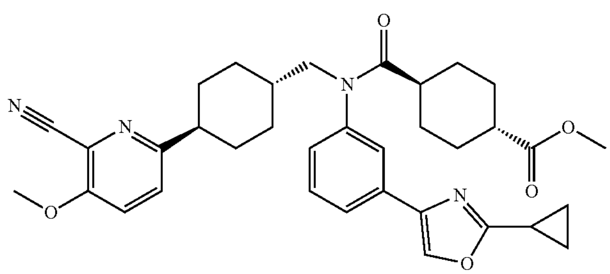 | trans-Methyl 4-(((trans-4-(6-cyano-5-methoxypyridin-2-yl)cyclohexyl)methyl)(3-(2-cyclopropyloxazol-4-yl)phenyl)carbamoyl)cyclo-hexanecarboxylate | 597.4 |

Alternate conditions: Step 1:
[1]Solvent was CH₂Cl₂;
Step 2:
[2]Solvent was toluene;
[3]DMAP, pyridine 80° C.;
[4]DMAP, Et₃N, toluene, 80° C., 2 h;
[5]50° C., overnight.

Alternate conditions: Step 1: [1]Solvent was CH₂Cl₂; Step 2: [2]Solvent was toluene; [3]DMAP, pyridine 80° C.; [4]DMAP, Et₃N, toluene, 80° C., 2 h; [5]50° C., overnight.

Compound 19

2-(trans-4-((3-(2-Cyclopropylthiazol-5-yl)phenyl)((trans-4-(4-methoxy-3-methylphenyl)cyclohexyl)methyl)carbamoyl)cyclohexyl)acetic Acid

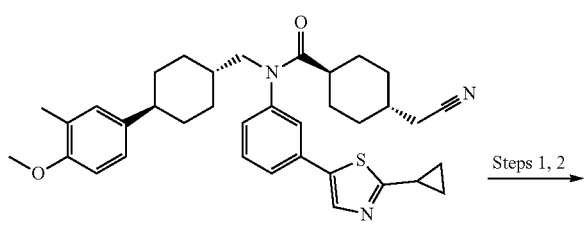

Steps 1, 2

-continued

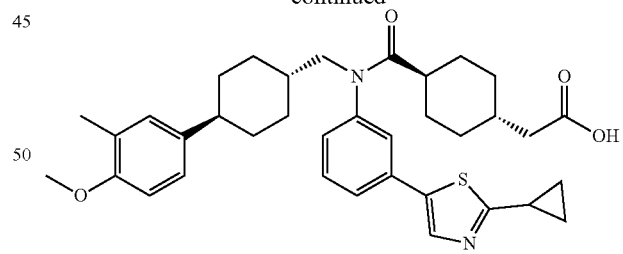

Step 1: Methyl 2-(trans-4-((3-(2-cyclopropylthiazol-5-yl)phenyl)((trans-4-(4-methoxy-3-methylphenyl)cyclohexyl)methyl)carbamoyl)cyclohexyl)acetate A mixture of Intermediate 21.22 (450 mg, 0.773 mmol) and HCl in CH₃OH (4 M, 100 mL, 0.4 mol) was stirred at rt overnight, and then heated to 65° C. for 10 h. The mixture was allowed to cool to rt, concentrated under reduced pressure, and then diluted with EtOAc (50 mL). The organic layer was washed with aq. sat. NaHCO₃ (20 mL), washed with brine (20 mL), dried (Na₂SO₄), filtered, concentrated and then purified by chromatography on silica gel (petroleum ether/EtOAc=5/1) to give methyl 2-(trans-4-((3-(2-cyclopropylthiazol-5-yl)phenyl)((trans-4-(4-methoxy-3-methylphenyl)cyclohexyl)methyl)carbamoyl)cyclohexyl)acetate (270.2 mg, 57%) as a yellow solid. $^1$H NMR (400 MHz, CDCl$_3$): δ 7.77 (s, 1H), 7.55-7.49 (m, 1H), 7.49-7.41 (m, 1H), 7.29 (t, 1H), 7.11 (d, 1H), 7.01-6.91 (m, 2H), 6.74 (d, 1H), 3.80 (s, 3H), 3.68-3.55 (m, 5H), 2.45-2.29 (m, 2H), 2.20 (s, 3H), 2.15-2.06 (m, 3H), 1.94-1.62 (m, 11H), 1.45-1.25 (m, 3H), 1.22-1.08 (m, 6H), 0.82-0.68 (m, 2H); LCMS: 615.4 [M+H]$^+$.

Step 2: 2-(trans-4-((3-(2-Cyclopropylthiazol-5-yl)phenyl)((trans-4-(4-methoxy-3-methylphenyl)cyclohexyl)methyl)carbamoyl)cyclohexyl)acetic Acid Lithium hydroxide monohydrate (273 mg, 6.51 mmol) was added to a solution of methyl 2-(trans-4-((3-(2-cyclopropylthiazol-5-yl)phenyl)((trans-4-(4-methoxy-3-methylphenyl)cyclohexyl)methyl)carbamoyl)cyclohexyl)acetate (200.2 mg, 0.325 mmol), THF (6 mL) and H$_2$O (6 mL) at rt. The mixture was stirred at rt overnight. The organic solvent was removed under reduced pressure, and the aqueous layer was extracted with EtOAc (10 mL). The aqueous layer was adjusted to pH=1 with 3 M HCl and then filtered. The cake was dried by vacuum to give 2-(trans-4-((3-(2-cyclopropylthiazol-5-yl)phenyl)((trans-4-(4-methoxy-3-methylphenyl)cyclohexyl)methyl)carbamoyl)cyclohexyl)acetic acid (166.9 mg, 85%) as a white solid. $^1$H NMR (400 MHz, DMSO-d$_6$): δ 11.96 (s, 1H), 8.07 (s, 1H), 7.63-7.44 (m, 3H), 7.25 (d, 1H), 7.03-6.90 (m, 2H), 6.80-6.65 (m, 1H), 3.71 (s, 3H), 3.59-3.54 (m, 2H), 2.46-2.39 (m, 1H), 2.39-2.27 (m, 1H), 2.14-2.01 (m, 4H), 1.95 (d, 2H), 1.79-1.71 (m, 4H), 1.68-1.58 (m, 4H), 1.56-1.53 (m, 1H), 1.46-1.33 (m, 3H), 1.31-1.21 (m, 2H), 1.18-0.93 (m, 6H), 0.71-0.52 (m, 2H); LCMS: 601.3 [M+H]$^+$.

Compound 20

2-(trans-4-(((trans-4-(3-Cyano-4-methoxyphenyl)cyclohexyl)methyl)(3-(2-cyclopropylthiazol-5-yl)phenyl)carbamoyl)cyclohexyl)acetic Acid

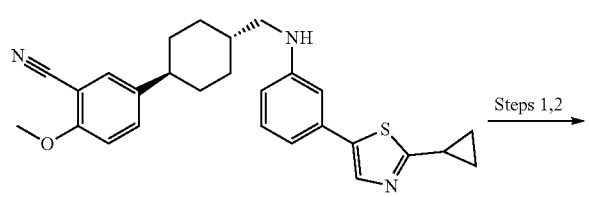

Steps 1,2

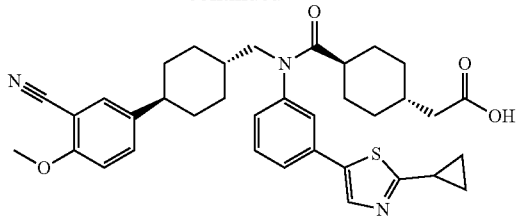

Step 1: Tert-Butyl 2-(trans-4-(((trans-4-(3-cyano-4-methoxyphenyl)cyclohexyl)methyl)(3-(2-cyclopropylthiazol-5-yl)phenyl)carbamoyl)cyclohexyl)acetate Pyridine (1.25 g, 15.78 mmol) was added to a solution of Intermediate 14.10 (200 mg, 0.451 mmol) in CH$_2$Cl$_2$ (5 mL) under N$_2$ at 0° C., and then Intermediate 19.06 (7.7 mL toluene solution, 3.83 mmol) was added. The reaction mixture was warmed to rt, stirred overnight, poured into sat. aq. NaHCO$_3$ (20 mL), and then extracted with EtOAc (3×20 mL). The combined organic layers were washed with brine (20 mL), dried over Na$_2$SO$_4$, filtered, concentrated, and then purified by silica gel chromatography (petroleum ether/EtOAc=20/1→5/1) to give tert-butyl 2-(trans-4-(((trans-4-(3-cyano-4-methoxyphenyl)cyclohexyl)methyl)(3-(2-cyclopropylthiazol-5-yl)phenyl)carbamoyl)cyclohexyl)acetate (150 mg, 47%) as a yellow oil. $^1$H NMR (400 MHz, CDCl$_3$): δ 7.77 (s, 1H), 7.51 (d, 1H), 7.45 (t, 1H), 7.37-7.34 (m, 1H), 7.32-2.30 (m, 1H), 7.28-7.27 (m, 1H), 7.10 (d, 1H), 6.88 (d, 1H), 3.90 (s, 3H), 3.63 (d, 2H), 2.49-2.38 (m, 1H), 2.37-2.30 (m, 1H), 2.17-2.07 (m, 1H), 1.98 (d, 2H), 1.90-1.80 (m, 4H), 1.75-1.69 (m, 5H), 1.66-1.55 (m, 4H), 1.41 (s, 9H), 1.35-1.26 (m, 2H), 1.21-1.12 (m, 5H), 0.80-0.66 (m, 2H); LCMS: 668.4 [M+H]$^+$.

Step 2: 2-(trans-4-(((trans-4-(3-Cyano-4-methoxyphenyl)cyclohexyl)methyl)(3-(2-cyclopropylthiazol-5-yl)phenyl)carbamoyl)cyclohexyl)acetic Acid A mixture of tert-butyl 2-(trans-4-(((trans-4-(3-cyano-4-methoxyphenyl)cyclohexyl)methyl)(3-(2-cyclopropylthiazol-5-yl)phenyl)carbamoyl)cyclohexyl)acetate (150 mg, 0.224 mmol) and HCl in dioxane (4 M, 50 mL) was stirred at rt for 1 h, concentrated to dryness, and then purified by reverse-phase HPLC (water(10 mM HCl)/CH$_3$CN) to give 2-(trans-4-(((trans-4-(3-cyano-4-methoxyphenyl)cyclohexyl)methyl)(3-(2-cyclopropylthiazol-5-yl)phenyl)carbamoyl)cyclohexyl)acetic acid (60 mg, 430) as a white solid. H NMR (400 MHz, DMSO-d$_6$): δ 12.13 (s, 1H), 8.09 (s, 1H), 7.63-7.46 (m, 5H), 7.26 (d, 1H), 7.13 (d, 1H), 3.87 (s, 3H), 3.65-3.50 (m, 3H), 2.47-2.38 (m, 2H), 2.13-2.02 (m, 1H), 1.97 (d, 2H), 1.82-1.71 (m, 4H), 1.70-1.58 (m, 4H), 1.50-1.27 (m, 5H), 1.19-0.96 (m, 6H), 0.73-0.55 (in, 2H); LCMS: 612.3 [M+H]$^+$.

The Compounds below were synthesized from the appropriate Intermediates following the procedures described for Compound 20.

| Cmpd | Structure | Name | [M + H]+ |
|---|---|---|---|
| 20.01 | 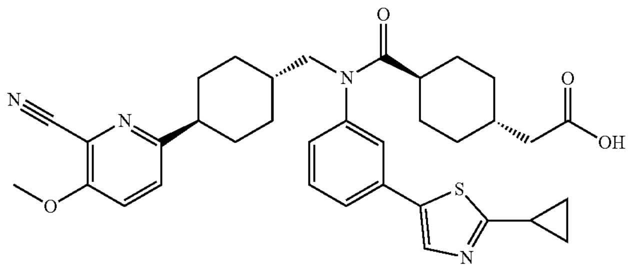 [SMILES: COc1ccc([C@H]2CC[C@H](CN(c3cccc(-c4cnc(C5CC5)s4)c3)C(=O)[C@H]3CC[C@H](CC(=O)O)CC3)CC2)nc1C#N] | 2-(trans-4-(((trans-4-(6-Cyano-5-methoxypyridin-2-yl)cyclohexyl)methyl)(3-(2-cyclopropylthiazol-5-yl)phenyl)carbamoyl)cyclohexyl)acetic acid | 613.5 |
| 20.02[2] | 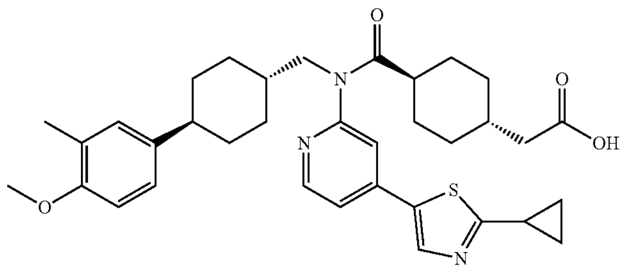 [SMILES: COc1ccc([C@H]2CC[C@H](CN(c3cc(-c4cnc(C5CC5)s4)ccn3)C(=O)[C@H]3CC[C@H](CC(=O)O)CC3)CC2)cc1C] | 2-(trans-4-((4-(2-Cyclopropylthiazol-5-yl)pyridin-2-yl)((trans-4-(4-methoxy-3-methylphenyl)cyclohexyl)methyl)carbamoyl)cyclohexyl)acetic acid | 602.3 |
| 20.03[3] | 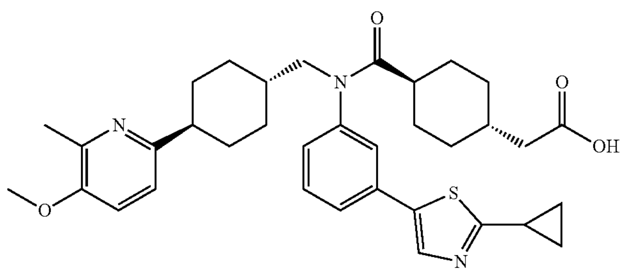 [SMILES: COc1ccc([C@H]2CC[C@H](CN(c3cccc(-c4cnc(C5CC5)s4)c3)C(=O)[C@H]3CC[C@H](CC(=O)O)CC3)CC2)nc1C] | 2-(trans-4-((3-(2-Cyclopropylthiazol-5-yl)phenyl)((trans-4-(5-methoxy-6-methylpyridin-2-yl)cyclohexyl)methyl)carbamoyl)cyclohexyl)acetic acid | 602.4 |
| 20.04[1] | 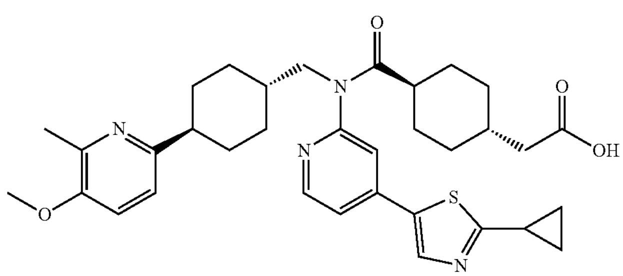 | 2-(trans-4-((4-(2-Cyclopropylthiazol-5-yl)pyridin-2-yl)((trans-4-(5-methoxy-6-methylpyridin-2-yl)cyclohexyl)methyl)carbamoyl)cyclohexyl)acetic acid | 603.5 |
| 20.05 | 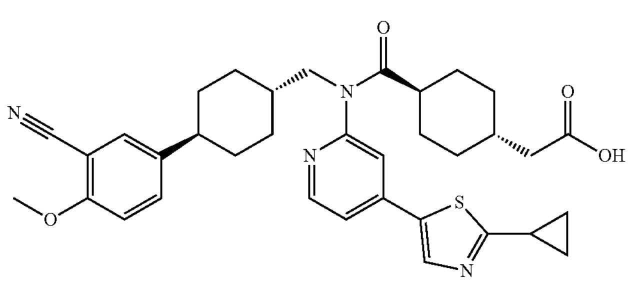 [SMILES: COc1ccc([C@H]2CC[C@H](CN(c3cc(-c4cnc(C5CC5)s4)ccn3)C(=O)[C@H]3CC[C@H](CC(=O)O)CC3)CC2)cc1C#N] | 2-(trans-4-(((trans-4-(3-Cyano-4-methoxyphenyl)cyclohexyl)methyl)(4-(2-cyclopropylthiazol-5-yl)pyridin-2-yl)carbamoyl)cyclohexyl)acetic acid | 613.3 |

-continued

| Cmpd | Structure | Name | [M + H]⁺ |
|---|---|---|---|
| 20.06[5] | 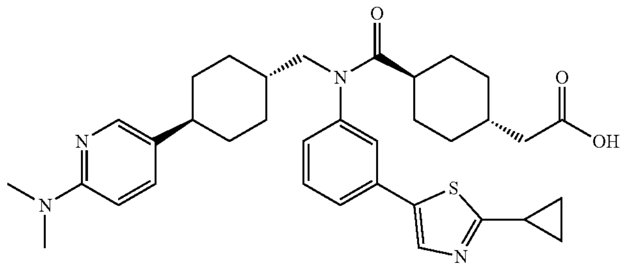 [SMILES: CN(C)c1ccc([C@H]2CC[C@H](CN(c3cccc(-c4cnc(C5CC5)s4)c3)C(=O)[C@H]3CC[C@H](CC(=O)O)CC3)CC2)cn1] | 2-(trans-4-((3-(2-Cyclopropylthiazol-5-yl)phenyl)((trans-4-(6-(dimethylamino)pyridin-3-yl)cyclohexyl)methyl)carbamoyl)cyclohexyl)acetic acid | 601.4 |
| 20.07 | 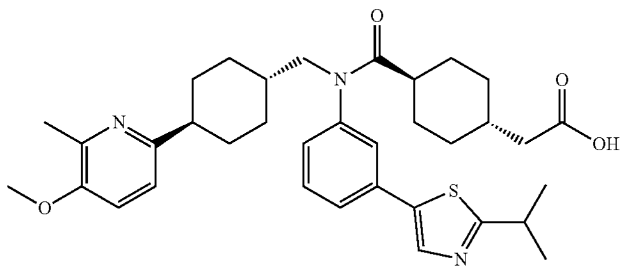 [SMILES: COc1ccc([C@H]2CC[C@H](CN(c3cccc(-c4cnc(C(C)C)s4)c3)C(=O)[C@H]3CC[C@H](CC(=O)O)CC3)CC2)nc1C] | 2-(trans-4-((3-(2-Isopropylthiazol-5-yl)phenyl)((trans-4-(5-methoxy-6-methylpyridin-2-yl)cyclohexyl)methyl)carbamoyl)cyclohexyl)acetic acid | 604.5 |
| 20.08[1] | 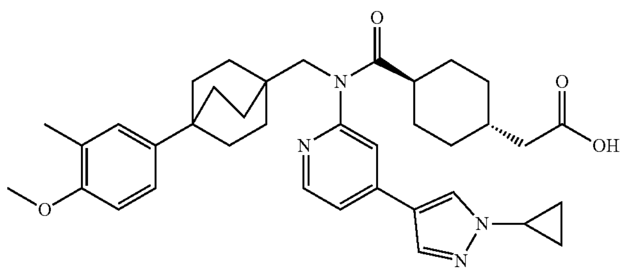 [SMILES: COc1ccc(C23CCC(CN(c4cc(-c5cnn(C6CC6)c5)ccn4)C(=O)[C@H]4CC[C@H](CC(=O)O)CC4)(CC2)CC3)cc1C] | trans-2-(4-(((4-(1-Cyclopropyl-1H-pyrazol-4-yl)pyridin-2-yl)((4-(4-methoxy-3-methylphenyl)bicyclo[2.2.2]octan-1-yl)methyl)carbamoyl)-cyclohexyl)acetic acid | 611.5 |
| 20.09 | 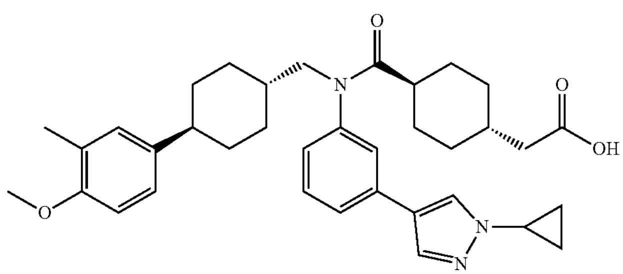 [SMILES: COc1ccc([C@H]2CC[C@H](CN(c3cccc(-c4cnn(C5CC5)c4)c3)C(=O)[C@H]3CC[C@H](CC(=O)O)CC3)CC2)cc1C] | 2-(trans-4-((3-(1-Cyclopropyl-1H-pyrazol-4-yl)phenyl)((trans-4-(4-methoxy-3-methylphenyl)cyclohexyl)methyl)carbamoyl)cyclohexyl)acetic acid | 584.6 |
| 20.10[2] | 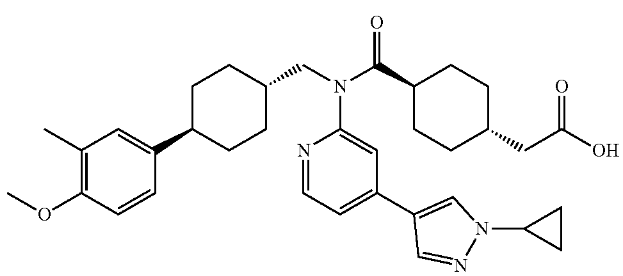 [SMILES: COc1ccc([C@H]2CC[C@H](CN(c3cc(-c4cnn(C5CC5)c4)ccn3)C(=O)[C@H]3CC[C@H](CC(=O)O)CC3)CC2)cc1C] | 2-(trans-4-((4-(1-Cyclopropyl-1H-pyrazol-4-yl)pyridin-2-yl)((trans-4-(4-methoxy-3-methylphenyl)cyclohexyl)methyl)carbamoyl)cyclohexyl)acetic acid | 585.5 |

-continued

| Cmpd | Structure | Name | [M + H]+ |
|---|---|---|---|
| 20.11 | 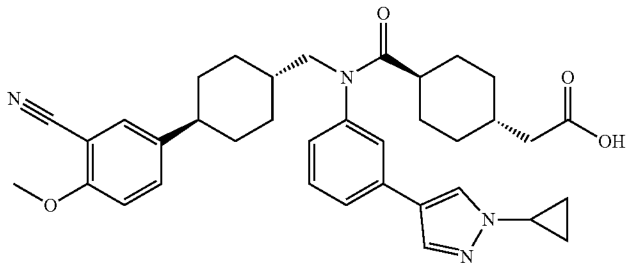 [SMILES: COc1ccc([C@H]2CC[C@H](CN(c3cccc(-c4cnn(C5CC5)c4)c3)C(=O)[C@H]3CC[C@H](CC(=O)O)CC3)CC2)cc1C#N] | 2-(trans-4-(((trans-4-(3-Cyano-4-methoxyphenyl)cyclohexyl)methyl)(3-(1-cyclopropyl-1H-pyrazol-4-yl)phenyl)carbamoyl)-cyclohexyl)acetic acid | 595.6 |
| 20.12[5] | 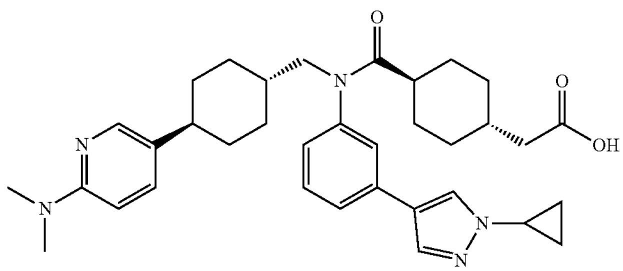 [SMILES: CN(C)c1ccc([C@H]2CC[C@H](CN(c3cccc(-c4cnn(C5CC5)c4)c3)C(=O)[C@H]3CC[C@H](CC(=O)O)CC3)CC2)cn1] | 2-(trans-4-((3-(1-Cyclopropyl-1H-pyrazol-4-yl)phenyl)((trans-4-(6-(dimethylamino)pyridin-3-yl)cyclohexyl)methyl)carbamoyl)cyclohexyl)acetic acid | 584.6 |
| 20.13 | 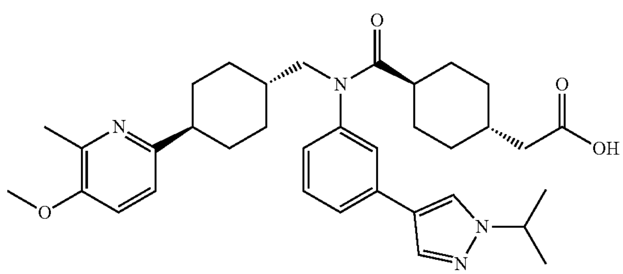 [SMILES: COc1ccc([C@H]2CC[C@H](CN(c3cccc(-c4cnn(C(C)C)c4)c3)C(=O)[C@H]3CC[C@H](CC(=O)O)CC3)CC2)nc1C] | 2-(trans-4-((3-(1-Isopropyl-1H-pyrazol-4-yl)phenyl)((trans-4-(5-methoxy-6-methylpyridin-2-yl)cyclohexyl)methyl)carbamoyl)cyclohexyl)acetic acid | 587.5 |
| 20.14 | 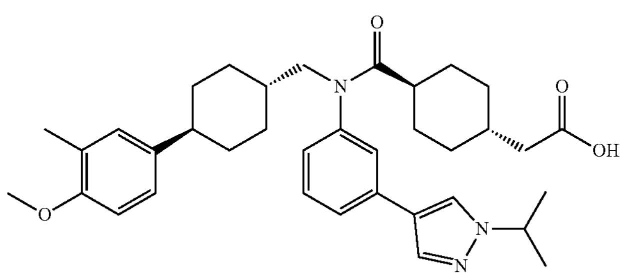 [SMILES: COc1ccc([C@H]2CC[C@H](CN(c3cccc(-c4cnn(C(C)C)c4)c3)C(=O)[C@H]3CC[C@H](CC(=O)O)CC3)CC2)cc1C] | 2-(trans-4-((3-(1-Isopropyl-1H-pyrazol-4-yl)phenyl)((trans-4-(4-methoxy-3-methylphenyl)cyclohexyl)methyl)carbamoyl)cyclohexyl)acetic acid | 586.6 |
| 20.15 | 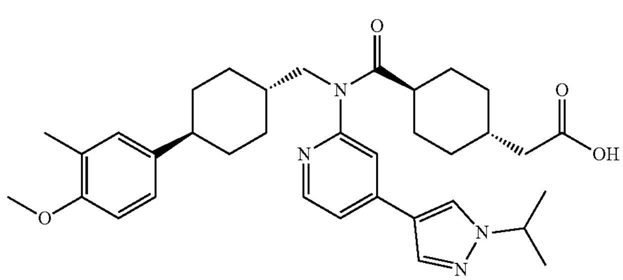 [SMILES: COc1ccc([C@H]2CC[C@H](CN(c3cc(-c4cnn(C(C)C)c4)ccn3)C(=O)[C@H]3CC[C@H](CC(=O)O)CC3)CC2)cc1C] | 2-(trans-4-((4-(1-Isopropyl-1H-pyrazol-4-yl)pyridin-2-yl)((trans-4-(4-methoxy-3-methylphenyl)cyclohexyl)methyl)carbamoyl)cyclohexyl)acetic acid | 587.5 |

| Cmpd | Structure | Name | [M + H]⁺ |
|---|---|---|---|
| 20.16 | 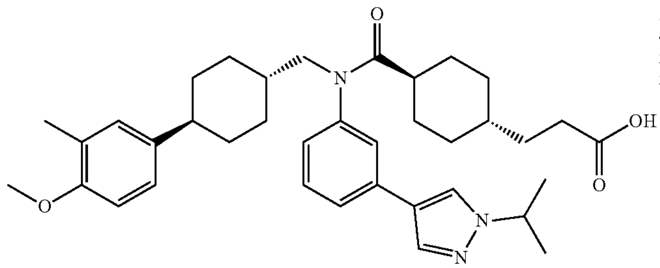 | 3-(trans-4-((3-(1-Isopropyl-1H-pyrazol-4-yl)phenyl)((trans-4-(4-methoxy-3-methylphenyl)cyclohexyl)methyl)carbamoyl)cyclohexyl)propanoic acid | 600.4 |

Alternate conditions: Step 1: [1]Base was Et$_3$N;
[2]Pyridine, DMAP, 50-80° C.;
[3]Amine in Pyridine only (no CH$_2$Cl$_2$);
Step 2:
[4]HCl in EtOAc (4 M);
[5]TFA in CH$_2$Cl$_2$.

Compound 21

Trans-2-(4-((4-(2-Cyclopropyloxazol-4-yl)pyridin-2-yl)((4-(4-methoxy-3-methylphenyl)bicyclo[2.2.2]octan-1-yl)methyl)carbamoyl)cyclohexyl)acetic Acid

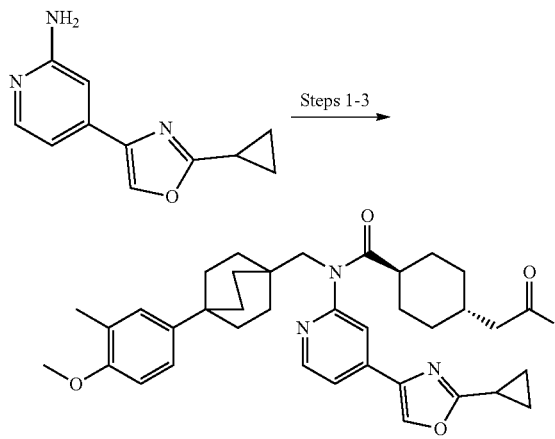

Step 1: 4-(2-Cyclopropyloxazol-4-yl)-N-((4-(4-methoxy-3-methylphenyl)bicyclo[2.2.2]octan-1-yl)methyl)pyridin-2-amine Sodium triacetoxyborohydride (658 mg, 3.11 mmol) was slowly added to a solution of Intermediate 10 (312 mg, 1.55 mmol), Intermediate 5 (401 mg, 1.55 mmol), and DCE (5 mL) at 0° C. The mixture was allowed to warm to rt, stirred for 5 h, poured into water (30 mL), and then extracted with EtOAc (3×20 mL). The combined organic layers were washed with (2×20 mL brine), dried (Na$_2$SO$_4$), filtered, and concentrated. The residue was purified by silica gel chromatography (petroleum ether/EtOAc=10/1→5/1) to give 4-(2-cyclopropyloxazol-4-yl)-N-((4-(4-methoxy-3-methylphenyl)bicyclo[2.2.2]octan-1-yl)methyl)pyridin-2-amine (254 mg, 35%) as a yellow oil. $^1$H NMR (400 MHz, CDCl$_3$): δ 8.05 (d, 1H), 7.82 (s, 1H), 7.13-7.07 (m, 2H), 6.80 (s, 1H), 6.78-6.74 (m, 2H), 4.66-4.55 (m, 1H), 3.81 (s, 3H), 3.15 (d, 2H), 2.22 (s, 3H), 2.18-2.09 (m, 1H), 1.88-1.80 (m, 6H), 1.66-1.58 (m, 6H), 1.17-1.11 (m, 2H), 1.11-1.05 (m, 2H); LCMS: 444.1 [M+H]⁺.

Step 2: Tert-Butyl-2-(trans-4-((4-(2-cyclopropyloxazol-4-yl)pyridin-2-yl)((4-(4-methoxy-3-methylphenyl)bicyclo[2.2.2]octan-1-yl)methyl)carbamoyl)cyclohexyl)acetate Intermediate 19.06 (5 mL in toluene, 0.701 mmol) was added to a solution of 4-(2-cyclopropyloxazol-4-yl)-N-((4-(4-methoxy-3-methylphenyl)bicyclo[2.2.2]octan-1-yl)methyl)pyridin-2-amine (136 mg, 0.306 mmol), Et$_3$N (155 mg, 1.53 mmol), and CH$_2$Cl$_2$ (5 mL) at 0° C. The mixture was allowed to warm to rt, stirred for 1 h, poured into H$_2$O (50 mL), and then extracted with EtOAc (3×30 mL). The combined organic layers were washed (100 mL brine), dried (Na$_2$SO$_4$), filtered, and concentrated. The residue was purified by silica gel chromatography (petroleum ether/EtOAc=20/1→5/1) to give tert-butyl-2-(trans-4-((4-(2-cyclopropyloxazol-4-yl)pyridin-2-yl)((4-(4-methoxy-3-methylphenyl)bicyclo[2.2.2]octan-1-yl)methyl)carbamoyl)cyclohexyl)acetate (155 mg, 76%) as a colorless oil. $^1$H NMR (400 MHz, CDCl$_3$): δ 8.50 (d, 1H), 7.95 (s, 1H), 7.56 (s, 1H), 7.46 (d, 1H), 7.07-6.99 (m, 2H), 6.76-6.69 (m, 1H), 3.88-3.73 (m, 5H), 2.40-2.25 (m, 1H), 2.22-2.10 (m, 4H), 2.01-1.99 (m, 2H), 1.89-1.66 (m, 12H), 1.65-1.55 (m, 3H), 1.48-1.45 (m, 4H), 1.42 (s, 9H), 1.20-1.06 (m, 4H), 0.80-0.71 (m, 2H).

Step 3: 2-(trans-4-((4-(2-Cyclopropyloxazol-4-yl)pyridin-2-yl)((4-(4-methoxy-3-methylphenyl)bicyclo[2.2.2]octan-1-yl)methyl)carbamoyl)cyclohexyl)acetic Acid Hydrogen chloride (8 M in dioxane, 100 mL, 800 mmol) was added to a solution of tert-butyl-2-(trans-4-((4-(2-cyclopropyloxazol-4-yl)pyridin-2-yl)((4-(4-methoxy-3-methylphenyl)bicyclo[2.2.2]octan-1-yl)methyl)carbamoyl)cyclohexyl)acetate (125 mg, 0.187 mmol) and dioxane (10 mL) at 5° C. The mixture was allowed to warm to rt, stirred for 1 h and then concentrated. The residue was purified by RP-HPLC (water(0.05% HCl)/CH$_3$CN) to give trans-2-(4-((4-(2-cyclopropyloxazol-4-yl)pyridin-2-yl)((4-(4-methoxy-3-methylphenyl)bicyclo[2.2.2]octan-1-yl)methyl)carbamoyl)cyclohexyl)acetic acid (43 mg, 38%) as a yellow solid. 1H NMR (400 MHz, DMSO-d$_6$): δ 12.01 (s, 1H), 8.76 (s, 1H), 8.52 (d, 1H), 7.74 (s, 1H), 7.63 (d, 1H), 7.05-6.94 (m, 2H), 6.76 (d, 1H), 3.81-3.62 (m, 5H), 2.30-2.14 (m, 2H), 2.08 (s, 3H), 1.99 (d, 2H), 1.78-1.51 (m, 11H), 1.48-1.24 (m, 8H), 1.13-1.05 (m, 2H), 1.05-0.99 (m, 2H), 0.70-0.67 (m, 2H); LCMS: 612.3[M+H]⁺.

The following Compounds were synthesized from the appropriate Intermediates following the procedures described for Compound 21.

| Cmpd | Structure | Name | [M + H]+ |
|---|---|---|---|
| 21.01 | 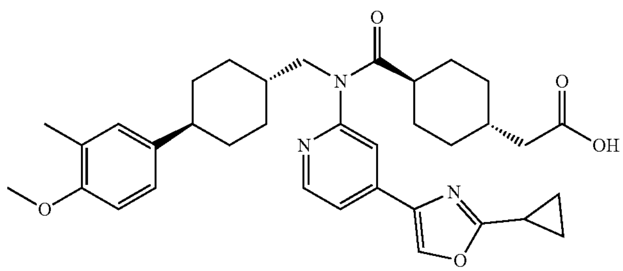 [SMILES: COc1ccc([C@H]2CC[C@H](CN(c3cc(-c4coc(C5CC5)n4)ccn3)C(=O)[C@H]3CC[C@H](CC(=O)O)CC3)CC2)cc1C] | 2-(trans-4-((4-(2-Cyclopropyloxazol-4-yl)pyridin-2-yl)((trans-4-(4-methoxy-3-methylphenyl)-cyclohexyl)methyl)carbamoyl)cyclohexyl)acetic acid | 586.5 |
| 21.02[1,2] | 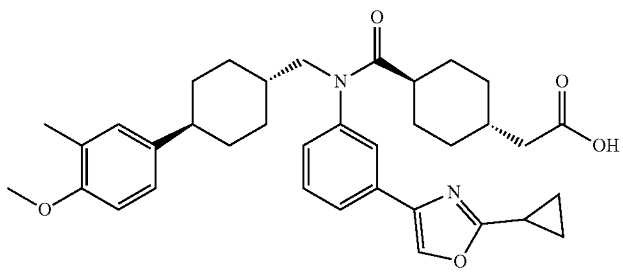 [SMILES: COc1ccc([C@H]2CC[C@H](CN(c3cccc(-c4coc(C5CC5)n4)c3)C(=O)[C@H]3CC[C@H](CC(=O)O)CC3)CC2)cc1C] | 2-(trans-4-((3-(2-Cyclopropyloxazol-4-yl)phenyl)((trans-4-(4-methoxy-3-methylphenyl)cyclohexyl)-methyl)carbamoyl)cyclohexyl)acetic acid | 585.5 |
| 21.03 | 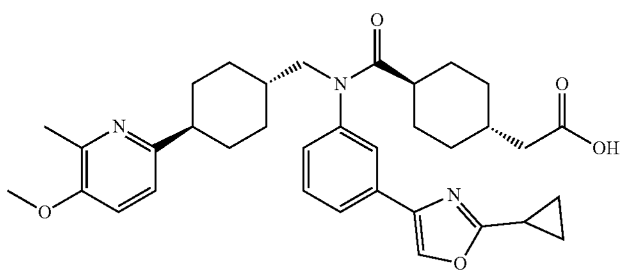 [SMILES: COc1ccc([C@H]2CC[C@H](CN(c3cccc(-c4coc(C5CC5)n4)c3)C(=O)[C@H]3CC[C@H](CC(=O)O)CC3)CC2)nc1C] | 2-(trans-4-((3-(2-Cyclopropyloxazol-4-yl)phenyl)((trans-4-(5-methoxy-6-methylpyridin-2-yl)cyclohexyl)methyl)-carbamoyl)cyclohexyl)acetic acid | 586.5 |
| 21.04[3] | 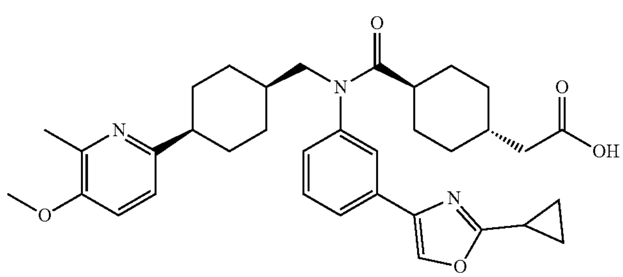 [SMILES: COc1ccc([C@H]2CC[C@@H](CN(c3cccc(-c4coc(C5CC5)n4)c3)C(=O)[C@H]3CC[C@H](CC(=O)O)CC3)CC2)nc1C] | 2-(trans-4-((3-(2-Cyclopropyloxazol-4-yl)phenyl)((cis-4-(5-methoxy-6-methylpyridin-2-yl)cyclohexyl)methyl)-carbamoyl)cyclohexyl)acetic acid | 586.6 |
| 21.05 | 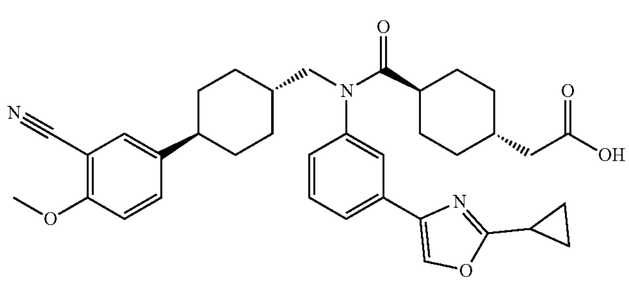 | 2-(trans-4-(((trans-4-(3-Cyano-4-methoxyphenyl)cyclohexyl)methyl)(3-(2-cyclopropyloxazol-4-yl)phenyl)carbamoyl)-cyclohexyl)acetic acid | 596.5 |

| Cmpd | Structure | Name | [M + H]+ |
|---|---|---|---|
| 21.06[1] | 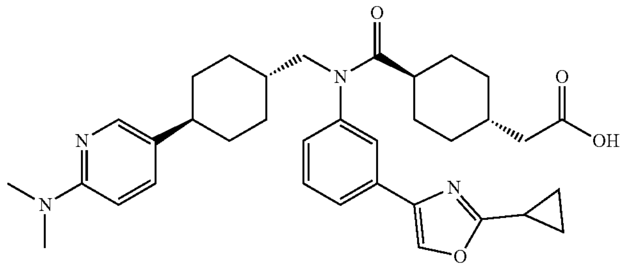 [SMILES: CN(C)c1ccc([C@H]2CC[C@H](CN(c3cccc(-c4coc(C5CC5)n4)c3)C(=O)[C@H]3CC[C@H](CC(=O)O)CC3)CC2)cn1] | 2-(trans-4-((3-(2-Cyclopropyloxazol-4-yl)phenyl)((trans-4-(6-(dimethylamino)pyridin-3-yl)cyclohexyl)methyl)-carbamoyl)cyclohexyl)acetic acid | 585.5 |
| 21.07[1] | 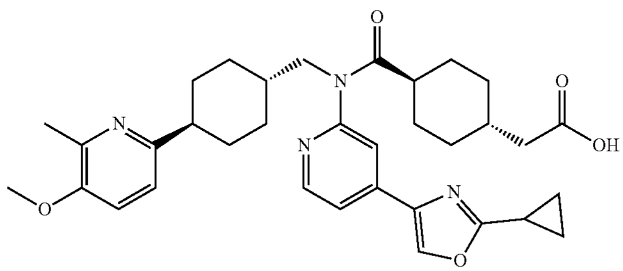 | 2-(trans-4-((4-(2-Cyclopropyloxazol-4-yl)pyridin-2-yl)((trans-4-(5-methoxy-6-methylpyridin-2-yl)cyclohexyl)methyl)-carbamoyl)cyclohexyl)acetic acid | 587.5 |
| 21.08[1] | 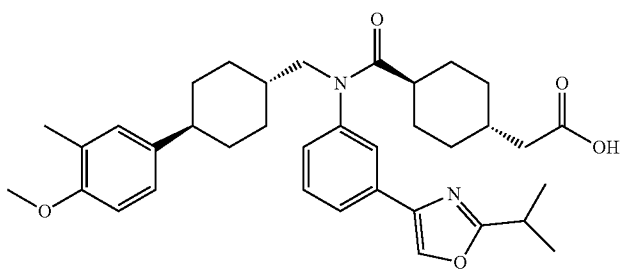 | 2-(trans-4-((3-(2-Isopropyl oxazol-4-yl)phenyl)((trans-4-(4-methoxy-3-methylphenyl)cyclohexyl)-methyl)carbamoyl)-cyclohexyl)acetic acid | 587.4 |
| 21.09[1] | 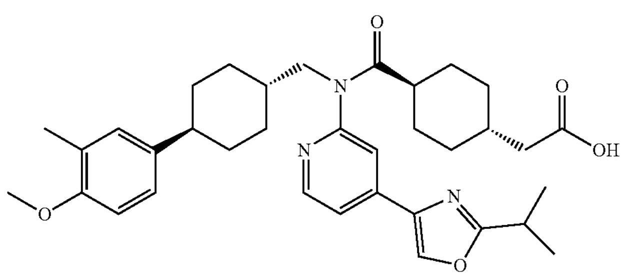 [SMILES: COc1ccc([C@H]2CC[C@H](CN(c3cc(-c4coc(C(C)C)n4)ccn3)C(=O)[C@H]3CC[C@H](CC(=O)O)CC3)CC2)cc1C] | 2-(trans-4-((4-(2-Isopropyloxazol-4-yl)pyridin-2-yl)((trans-4-(4-methoxy-3-methylphenyl)cyclohexyl)-methyl)carbamoyl)-cyclohexyl)acetic acid | 588.4 |
| 21.10 | 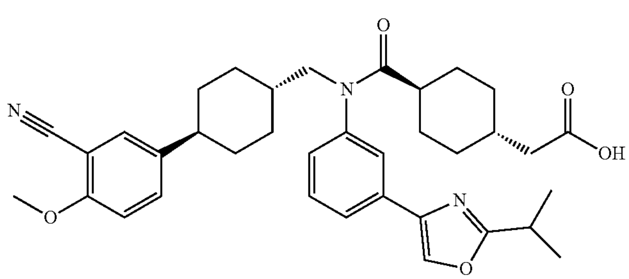 | 2-(trans-4-(((trans-4-(3-Cyano-4-methoxyphenyl)cyclohexyl)-methyl)(3-(2-isopropyloxazol-4-yl)phenyl)carbamoyl)-cyclohexyl)acetic acid | 598.7 |

| Cmpd | Structure | Name | [M + H]⁺ |
|---|---|---|---|
| 21.11 | 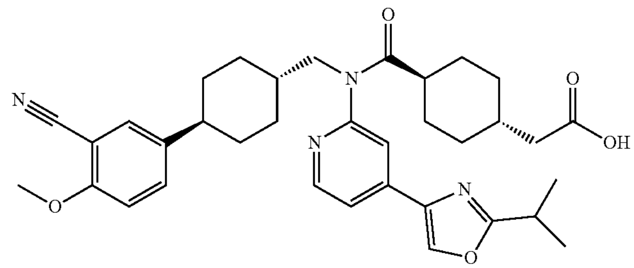 [SMILES: COc1ccc([C@H]2CC[C@H](CN(c3cc(-c4coc(C(C)C)n4)ccn3)C(=O)[C@H]3CC[C@H](CC(=O)O)CC3)CC2)cc1C#N] | 2-(trans-4-(((trans-4-(3-Cyano-4-methoxyphenyl)cyclohexyl)-methyl)(4-(2-isopropyloxazol-4-yl)pyridin-2-yl)carbamoyl)-cyclohexyl)acetic acid | 599.4 |
| 21.12 | 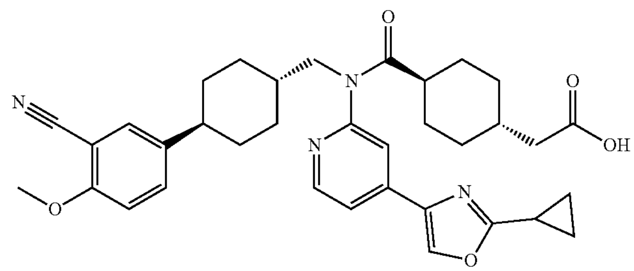 | 2-(trans-4-(((trans-4-(3-Cyano-4-methoxyphenyl)cyclohexyl)-methyl)(4-(2-cyclopropyloxazol-4-yl)pyridin-2-yl)carbamoyl)-cyclohexyl)acetic acid | 597.4 |
| 21.13[1] | 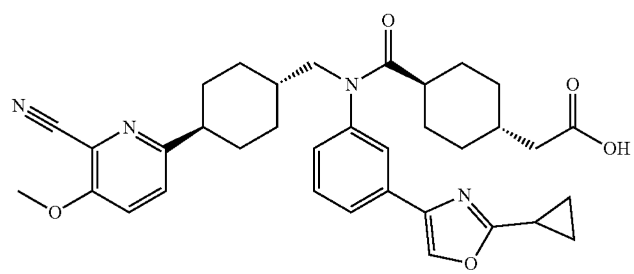 [SMILES: COc1ccc([C@H]2CC[C@H](CN(c3cccc(-c4coc(C5CC5)n4)c3)C(=O)[C@H]3CC[C@H](CC(=O)O)CC3)CC2)nc1C#N] | 2-(trans-4-(((trans-4-(6-Cyano-5-methoxypyridin-2-yl)-cyclohexyl)methyl)(3-(2-cyclopropyloxazol-4-yl)phenyl)carbamoyl)-cyclohexyl)acetic acid | 597.4 |

Alternate conditions:
Step 2:
[1]Base was pyridine;
Step 3:
[2]12 M aq. HCl, CH₃CN.
[3]Cis isomer of Compound 21.03 (Step 2) was separated by via prep-TLC (petroleum ether: EtOAc = 3:2) and then hydrolyzed (4M HCl in dioxane, rt, 1 h).

Compound 22

Trans-Propyl 4-((3-(1-cyclopropyl-1H-pyrazol-4-yl)phenyl)((trans-4-(4-methoxy-3-methylphenyl)cyclohexyl)methyl)carbamoyl)cyclohexanecarboxylate

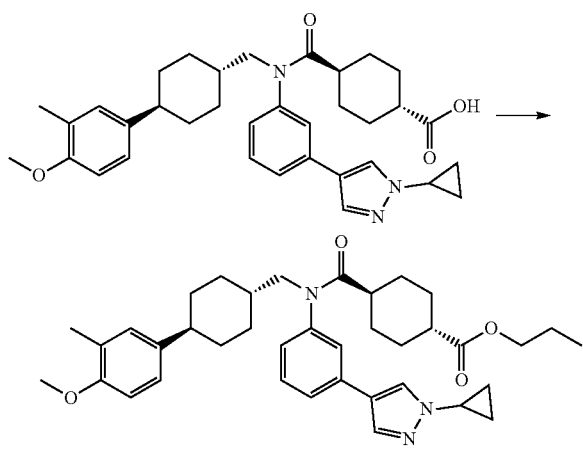

A solution of Compound 17.13 (35 mg, 0.061 mmol), pTsOH.H₂O (10 mg, 0.053 mmol), and 1-propanol (4 mL) was heated at 80° C. for 4 h and then diluted with saturated NaHCO₃ (20 mL) and EtOAc (20 mL). The layers were separated, and the organic phase was washed with brine (20 mL), dried (Na₂SO₄), and concentrated. The residue was purified by silica gel chromatography (0-50% EtOAc in hexanes) to give trans-propyl 4-((3-(1-cyclopropyl-1H-pyrazol-4-yl)phenyl)((trans-4-(4-methoxy-3-methylphenyl)cyclohexyl)methyl)carbamoyl)cyclohexanecarboxylate as a white foam (30 mg, 79%). $^1$H NMR (400 MHz, DMSO-d₆): δ 8.38 (s, 1H), 7.93 (s, 1H), 7.60 (d, 1H), 7.54 (s, 1H), 7.44 (t, 1H), 7.10 (d, 1H), 6.97-6.92 (m, 2H), 6.80-6.75 (m, 1H), 3.88 (t, 2H), 3.77-3.72 (m, 1H), 3.71 (s, 3H), 3.67-3.40 (m, 2H), 2.38-2.28 (m, 1H), 2.26-2.17 (m, 1H), 2.16-2.09 (m, 1H), 2.08 (s, 3H), 1.85-1.65 (m, 8H), 1.56-1.47 (m, 2H), 1.46-1.37 (m, 3H), 1.35-1.21 (m, 2H), 1.11-1.02 (m, 4H), 1.01-0.92 (m, 4H), 0.81 (t, 3H); LCMS: 612.6 [M+H]⁺.

The Compounds below were synthesized from Compound 17.13 or Compound 18.17 and the appropriate alcohol following the procedure described for Compound 22.

| Cmpd | Structure | Name | [M + H]+ |
|---|---|---|---|
| 22.01 | 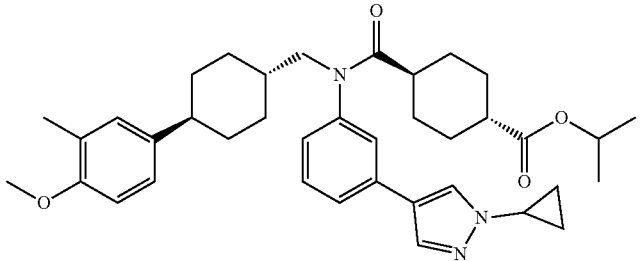 [SMILES: COc1ccc([C@H]2CC[C@H](CN(c3cccc(-c4cnn(C5CC5)c4)c3)C(=O)[C@H]3CC[C@H](C(=O)OC(C)C)CC3)CC2)cc1C] | trans-Isopropyl 4-((3-(1-cyclopropyl-1H-pyrazol-4-yl)phenyl)((trans-4-(4-methoxy-3-methylphenyl)cyclohexyl)methyl)carbamoyl)cyclohexanecarboxylate | 612.6 |
| 22.02 | 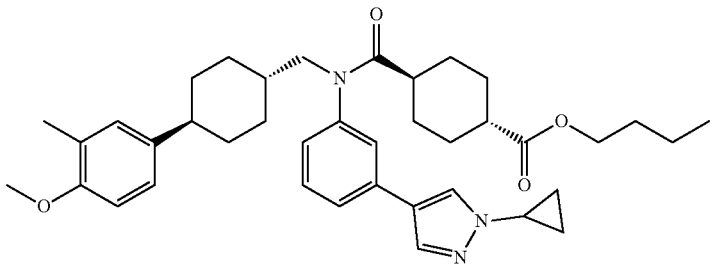 [SMILES: CCCCOC(=O)[C@H]1CC[C@H](C(=O)N(C[C@H]2CC[C@H](c3ccc(OC)c(C)c3)CC2)c2cccc(-c3cnn(C4CC4)c3)c2)CC1] | trans-Butyl 4-((3-(1-cyclopropyl-1H-pyrazol-4-yl)phenyl)((trans-4-(4-methoxy-3-methylphenyl)cyclohexyl)methyl)carbamoyl)cyclohexanecarboxylate | 626.5 |
| 22.03 | 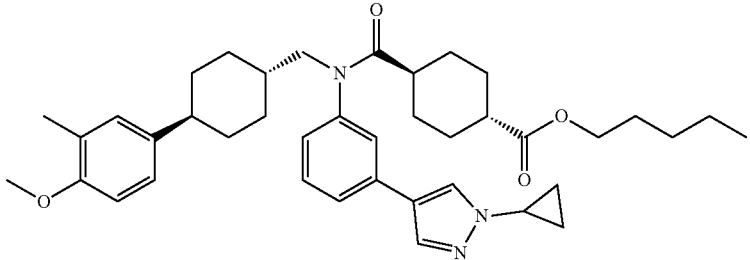 [SMILES: CCCCCOC(=O)[C@H]1CC[C@H](C(=O)N(C[C@H]2CC[C@H](c3ccc(OC)c(C)c3)CC2)c2cccc(-c3cnn(C4CC4)c3)c2)CC1] | trans-Pentyl 4-((3-(1-cyclopropyl-1H-pyrazol-4-yl)phenyl)((trans-4-(4-methoxy-3-methylphenyl)cyclohexyl)methyl)carbamoyl)cyclohexanecarboxylate | 640.3 |
| 22.04 | 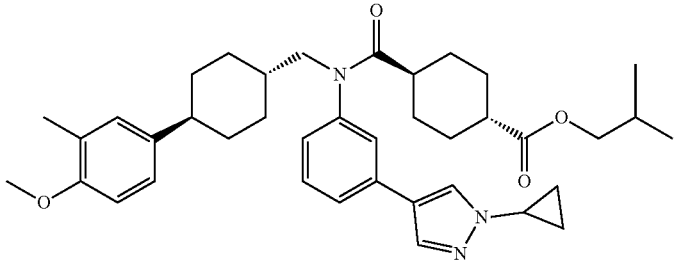 [SMILES: COc1ccc([C@H]2CC[C@H](CN(c3cccc(-c4cnn(C5CC5)c4)c3)C(=O)[C@H]3CC[C@H](C(=O)OCC(C)C)CC3)CC2)cc1C] | trans-Isobutyl 4-((3-(1-cyclopropyl-1H-pyrazol-4-yl)phenyl)((trans-4-(4-methoxy-3-methylphenyl)cyclohexyl)methyl)carbamoyl)cyclohexanecarboxylate | 626.6 |
| 22.05 | 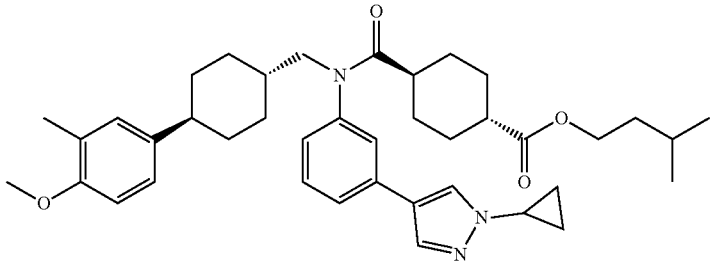 [SMILES: COc1ccc([C@H]2CC[C@H](CN(c3cccc(-c4cnn(C5CC5)c4)c3)C(=O)[C@H]3CC[C@H](C(=O)OCCC(C)C)CC3)CC2)cc1C] | trans-Isopentyl 4-((3-(1-cyclopropyl-1H-pyrazol-4-yl)phenyl)((trans-4-(4-methoxy-3-methylphenyl)cyclohexyl)methyl)carbamoyl)cyclohexanecarboxylate | 640.6 |

| Cmpd | Structure | Name | [M + H]+ |
|---|---|---|---|
| 22.06 | 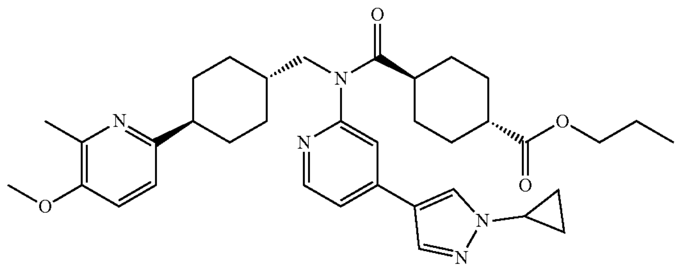 [SMILES: CCCOC(=O)[C@H]1CC[C@H](C(=O)N(C[C@H]2CC[C@H](c3ccc(OC)c(C)n3)CC2)c2cc(-c3cnn(C4CC4)c3)ccn2)CC1] | trans-Propyl 4-((4-(1-cyclopropyl-1H-pyrazol-4-yl)pyridin-2-yl)((trans-4-(5-methoxy-6-methylpyridin-2-yl)cyclohexyl)methyl)carbamoyl)cyclohexanecarboxylate | 614.3 |

Compound 23

Trans-N$^1$-(3-(1-Cyclopropyl-1H-pyrazol-4-yl)phenyl)-N$^4$-(2-hydroxyethyl)-N$^1$-((trans-4-(4-methoxy-3-methylphenyl)cyclohexyl)methyl)cyclohexane-1,4-dicarboxamide Compound 24

Trans-N$^4$-((trans-4-(4-Methoxy-3-methylphenyl)cyclohexyl)methyl)-N$^4$-(3-(2-methoxythiazol-5-yl)phenyl)-N$^4$-methylcyclohexane-1,4-dicarboxamide

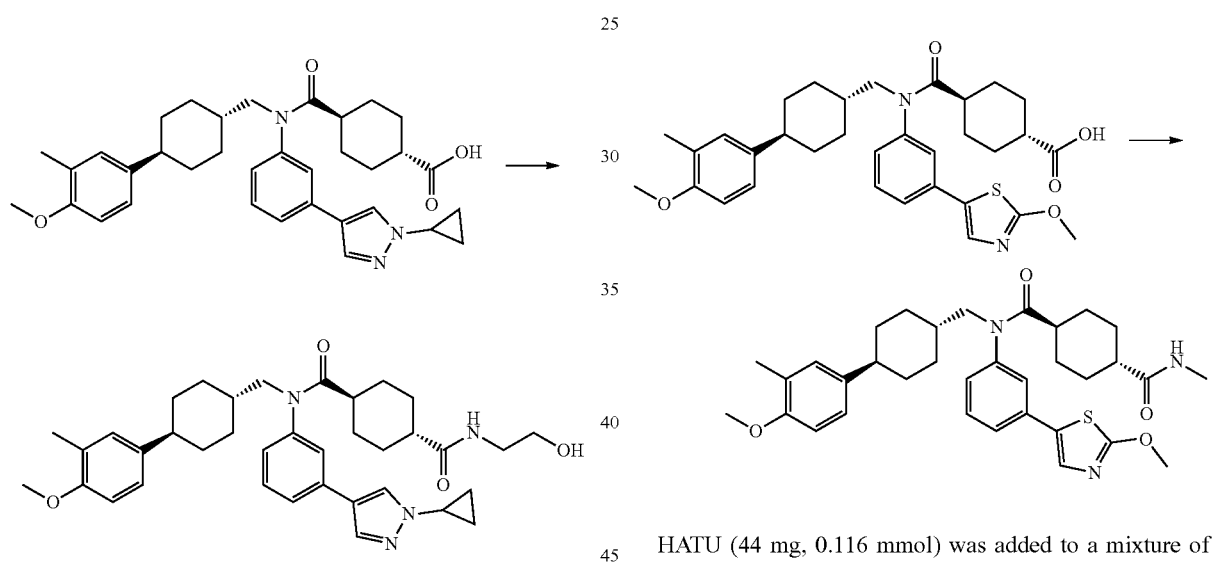

2-Aminoethanol (96.5 mg, 1.58 mmol) was added to a solution of Compound 17.13 (150 mg, 0.263 mmol), EDCI (75.7 mg, 0.394 mmol), DMAP (16.1 mg, 0.131 mmol), Et$_3$N (79.8 mg, 0.790 mmol), HOBt (53.4 mg, 0.395 mmol), and CH$_2$Cl$_2$ (1 mL) at 0$^\circ$ C. The mixture was stirred at rt overnight, poured into water (40 mL), and extracted with EtOAc (3×50 mL). The combined organic layers were dried over Na$_2$SO$_4$, filtered, concentrated, and then purified by reverse-phase prep-HPLC (water(10 mM NH$_4$HCO$_3$)/MeCN) to give trans-Ni-(3-(1-cyclopropyl-1H-pyrazol-4-yl)phenyl)-N$^1$-(2-hydroxyethyl)-N$^1$-((trans-4-(4-methoxy-3-methylphenyl)cyclohexyl)methyl)cyclohexane-1,4-dicarboxamide (89 mg, 550%) as a white solid. $^1$H NMR (400 MHz, DMSO-d$_6$): δ 8.33 (s, 1H), 7.93 (s, 1H), 7.66-7.57 (m, 2H), 7.57-7.53 (m, 1H), 7.44 (t, 1H), 7.10 (d, 1H), 7.00-6.89 (m, 2H), 6.83-6.67 (m, 1H), 4.57 (t, 1H), 3.77-3.68 (m, 4H), 3.68-3.49 (m, 2H), 3.31-3.26 (m, 2H), 3.09-3.01 (m, 2H), 2.39-2.22 (m, 1H), 2.17-1.96 (m, 5H), 1.83-1.53 (m, 8H), 1.52-1.21 (m, 5H), 1.15-0.85 (m, 8H); LCMS: 613.3 [M+H]+.

HATU (44 mg, 0.116 mmol) was added to a mixture of Compound 17.01 (60 mg, 0.104 mmol), iPr$_2$NEt (36 μL, 0.207 mmol), and DMF (1 mL) at 0$^\circ$ C. The mixture was stirred for 10 min, and then methylamine (40% in CH$_3$OH, 0.1 mL, 0.98 mmol) was added. After stirring at 0$^\circ$ C. for 10 min, the reaction was diluted with CH$_2$Cl$_2$ (20 mL), washed (20 mL H$_2$O and then 20 mL brine), dried (Na$_2$SO$_4$), and then concentrated. The residue was purified by silica gel chromatography (0-5% CH$_3$OH in CH$_2$Cl$_2$) to give trans-N-((trans-4-(4-methoxy-3-methylphenyl)cyclohexyl)methyl)-Ni-(3-(2-methoxythiazol-5-yl)phenyl)-N$^4$-methylcyclohexane-1,4-dicarboxamide (38 mg, 62%) as a white foam. $^1$H NMR (400 MHz, DMSO-d$_6$): δ 7.75 (s, 1H), 7.61-7.56 (m, 1H), 7.55-7.47 (m, 3H), 7.28-7.21 (m, 1H), 6.98-6.91 (m, 2H), 6.81-6.76 (m, 1H), 4.06 (s, 3H), 3.71 (s, 3H), 3.65-3.46 (m, 2H), 2.47 (d, 3H), 2.39-2.27 (m, 1H), 2.12-1.92 (m, 5H), 1.80-1.56 (m, 8H), 1.49-1.35 (m, 3H), 1.34-1.21 (m, 2H), 1.12-0.92 (m, 4H); LCMS: 590.4 [M+H]+.

The Compounds below were synthesized from the appropriate amine following the procedure described for Compound 24.

| Cmpd | Structure | Name | [M + H]+ |
|---|---|---|---|
| 24.01 | 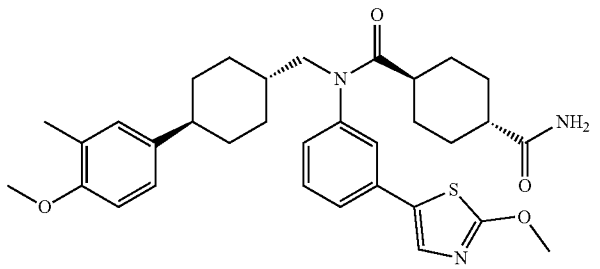 [SMILES: COc1ncc(-c2cccc(N(C[C@H]3CC[C@H](c4ccc(OC)c(C)c4)CC3)C(=O)[C@H]3CC[C@H](C(N)=O)CC3)c2)s1] | trans-N$^1$-((trans-4-(4-Methoxy-3-methylphenyl)cyclohexyl)methyl)-N$^1$-(3-(2-methoxythiazol-5-yl)phenyl)cyclohexane-1,4-dicarboxamide | 576.3 |
| 24.02 | 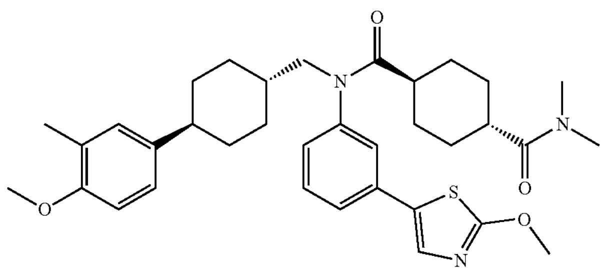 | trans-N$^1$-((trans-4-(4-Methoxy-3-methylphenyl)cyclohexyl)methyl)-N$^1$-(3-(2-methoxythiazol-5-yl)phenyl)-N$^4$,N$^4$-dimethylcyclohexane-1,4-dicarboxamide | 604.4 |
| 24.03 | 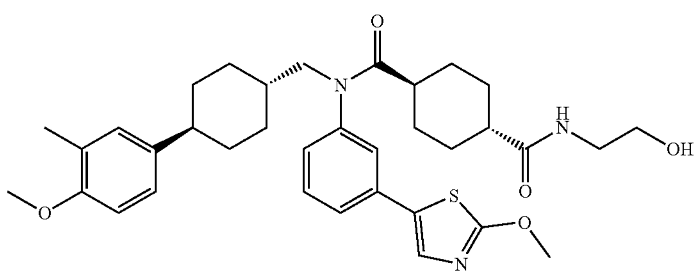 [SMILES: COc1ncc(-c2cccc(N(C[C@H]3CC[C@H](c4ccc(OC)c(C)c4)CC3)C(=O)[C@H]3CC[C@H](C(=O)NCCO)CC3)c2)s1] | trans-N$^1$-(2-Hydroxyethyl)-N$^4$-((trans-4-(4-methoxy-3-methylphenyl)cyclohexyl)methyl)-N$^4$-(3-(2-methoxythiazol-5-yl)phenyl)cyclohexane-1,4-dicarboxamide | 620.4 |
| 24.04 | 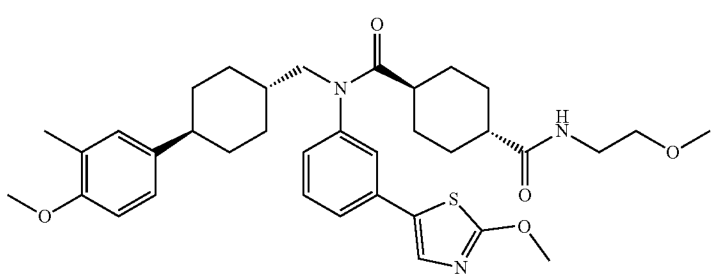 | trans-N$^1$-((trans-4-(4-Methoxy-3-methylphenyl)cyclohexyl)methyl)-N$^4$-(2-methoxyethyl)-N$^1$-(3-(2-methoxythiazol-5-yl)phenyl)cyclohexane-1,4-dicarboxamide | 634.6 |
| 24.05 | 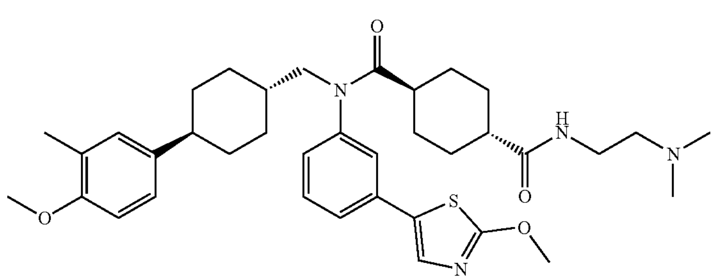 | trans-N$^1$-(2-(Dimethylamino)ethyl)-N$^4$-((trans-4-(4-methoxy-3-methylphenyl)cyclohexyl)methyl)-N$^4$-(3-(2-methoxythiazol-5-yl)phenyl)cyclohexane-1,4-dicarboxamide | 647.5 |

| Cmpd | Structure | Name | [M + H]⁺ |
|---|---|---|---|
| 24.06[1] | 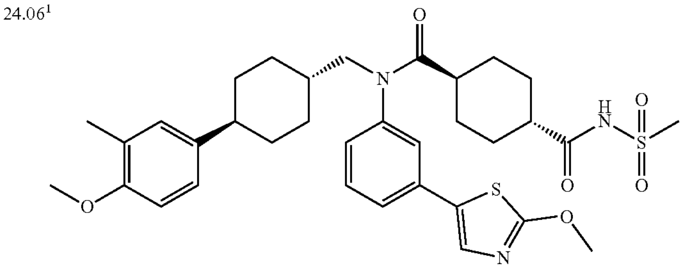 | trans-N[1]-((trans-4-(4-Methoxy-3-methylphenyl)cyclohexyl)methyl)-H[1]-(3-(2-methoxythiazol-5-yl)phenyl)-N[4]-(methylsulfonyl)cyclohexane-1,4-dicarboxamide | 654.4 |

Variation: [1]DBU was also added, rt, 30 min.

Compound 25

Methyl (trans-4-((3-(2-cyclopropylthiazol-5-yl)phenyl)((trans-4-(4-methoxy-3-methylphenyl)cyclohexyl)methyl)carbamoyl)cyclohexyl)carbamate

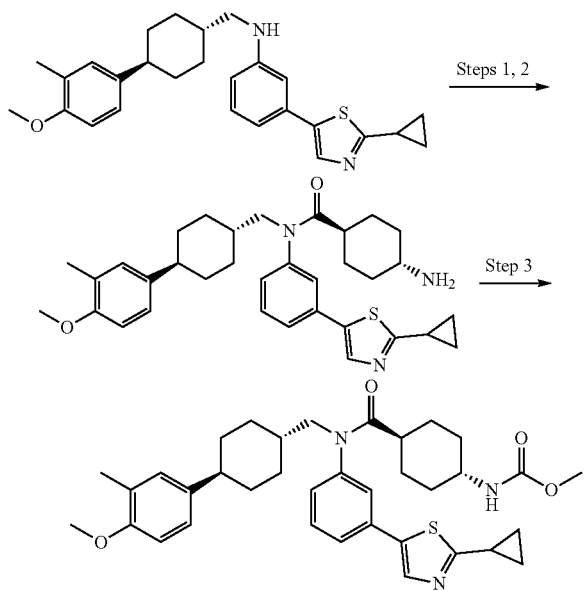

Step 1: Tert-Butyl (trans-4-((3-(2-cyclopropylthiazol-5-yl)phenyl)((trans-4-(4-methoxy-3-methylphenyl)cyclohexyl)methyl)carbamoyl)cyclohexyl)carbamate Pyridine (0.17 mL, 2.10 mmol) and then Intermediate 19.02 (38.6 mg/mL in toluene, 8 mL, 1.18 mmol) were added to a mixture of Intermediate 14.06 (227 mg, 0.53 mmol) and toluene (2 mL) under $N_2$ at rt. The reaction was stirred for 1 h, poured into sat'd NaHCO₃ (30 mL), and then extracted with EtOAc (30 mL). The organics were washed with brine (30 mL). The combined aqueous washes were back extracted with EtOAc (20 mL). The combined extracts were dried ($Na_2SO_4$), filtered, concentrated, and purified by silica gel chromatography (20-50% EtOAc in hexanes) to give tert-butyl (trans-4-((3-(2-cyclopropylthiazol-5-yl)phenyl)((trans-4-(4-methoxy-3-methylphenyl)cyclohexyl) methyl)carbamoyl)cyclohexyl)carbamate (331 mg, 96%) as an off-white foam. ¹H NMR (400 MHz, DMSO-$d_6$): δ 8.10 (s, 1H), 7.62-7.56 (m, 2H), 7.52 (t, 1H), 7.29-7.24 (m, 1H), 6.97-6.92 (m, 2H), 6.81-6.76 (m, 1H), 6.54 (d, 1H), 3.72 (s, 3H), 3.61-3.52 (m, 2H), 3.17-3.06 (m, 1H), 2.47-2.39 (m, 1H), 2.38-2.28 (m, 1H), 2.09 (s, 3H), 2.06-1.96 (m, 1H), 1.79-1.62 (m, 8H), 1.48-1.38 (m, 3H), 1.36-1.22 (m, 11H), 1.18-1.11 (m, 2H), 1.11-1.03 (m, 2H), 1.03-0.98 (m, 2H), 0.86-0.72 (m, 2H); LCMS: 680.8 [M+Na]⁺.

Step 2: Trans-4-Amino-N-(3-(2-cyclopropylthiazol-5-yl)phenyl)-N-((trans-4-(4-methoxy-3-methylphenyl)cyclohexyl)methyl)cyclohexanecarboxamide A solution of tert-butyl (trans-4-((3-(2-cyclopropylthiazol-5-yl)phenyl)((trans-4-(4-methoxy-3-methylphenyl)cyclohexyl)methyl)carbamoyl)cyclohexyl)carbamate (326 mg, 0.50 mmol) and trifluoroacetic acid (20% in $CH_2Cl_2$, 5 mL) was stirred at rt for 2 h, diluted with $CH_2Cl_2$ (25 mL), washed with sat'd NaHCO₃ (2×30 mL), and then washed with brine (30 mL). The combined aqueous washes were back extracted with $CH_2Cl_2$ (20 mL). The combined extracts were dried ($Na_2SO_4$), filtered, concentrated, and dried on high vacuum to give trans-4-amino-N-(3-(2-cyclopropylthiazol-5-yl)phenyl)-N-((trans-4-(4-methoxy-3-methylphenyl)cyclohexyl)methyl)cyclohexanecarboxamide (256 mg, 92%) as an off-white foam. ¹H NMR (400 MHz, DMSO-$d_6$): δ 8.09 (s, 1H), 7.62-7.49 (m, 3H), 7.30-7.23 (m, 1H), 6.98-6.92 (m, 2H), 6.82-6.75 (m, 1H), 3.72 (s, 3H), 3.62-3.50 (m, 2H), 3.38-3.28 (m, 1H), 2.48-2.39 (m, 1H), 2.38-2.29 (m, 1H), 2.09 (s, 3H), 2.06-1.96 (m, 1H), 1.80-1.57 (m, 10H), 1.48-1.37 (m, 3H), 1.35-1.23 (m, 2H), 1.18-1.12 (m, 2H), 1.12-0.97 (m, 4H), 0.73-0.58 (m, 2H); LCMS: 558.5 [M+H]⁺.

Step 3: Methyl (trans-4-((3-(2-cyclopropylthiazol-5-yl)phenyl)((trans-4-(4-methoxy-3-methylphenyl)cyclohexyl)methyl)carbamoyl)cyclohexyl)carbamate A solution of trans-4-amino-N-(3-(2-cyclopropylthiazol-5-yl)phenyl)-N-((trans-4-(4-methoxy-3-methylphenyl)cyclohexyl)methyl)cyclohexanecarboxamide (100 mg, 0.18 mmol) in $CH_2Cl_2$ (2 mL) was cooled in an ice/water bath under $N_2$. Triethylamine (0.10 mL, 0.72 mmol) and then methyl chloroformate (17 μL, 0.22 mmoL) were added at 0° C., and the reaction was stirred for 8 min. The mixture was diluted with 20 mL $CH_2Cl_2$, washed with sat'd NaHCO₃ (2×20 mL), and washed with brine (20 mL). The combined aqueous washes were back extracted with 20 mL $CH_2Cl_2$. The combined extracts were dried ($Na_2SO_4$), filtered, concentrated, and purified by silica gel chromatography (20-80% EtOAc in hexanes) to give methyl (trans-4-((3-(2-cyclopropylthiazol-5-yl)phenyl)((trans-4-(4-methoxy-3-methylphenyl)cyclohexyl)methyl)carbamoyl)cyclohexyl)carbamate (92 mg, 83%) as an off-white foam. $^1$H NMR (400 MHz, DMSO-$d_6$): δ 8.09 (s, 1H), 7.61-7.56 (m, 2H), 7.52 (t, 1H), 7.27 (d, 1H), 6.97-6.92 (m, 2H), 6.87-6.75 (m, 2H), 3.71 (s, 3H), 3.62-3.51 (m, 2H), 3.45 (br s, 3H), 3.23-3.09 (m, 1H), 2.48-2.39 (m, 1H), 2.38-2.28 (m, 1H), 2.09 (s, 3H), 2.06-1.97 (m, 1H), 1.80-1.62 (m, 8H), 1.50-1.36 (m, 3H), 1.36-1.22 (m, 2H), 1.18-1.11 (m, 2H), 1.11-0.97 (m, 4H), 0.88-0.74 (m, 2H); LCMS: 616.4 [M+H]$^+$.

The Compounds below were synthesized from the appropriate starting materials following the procedure described for Compound 25, Step 1.

| Cmpd | Structure | Name | [M + H]$^+$ |
|---|---|---|---|
| 25.01 | 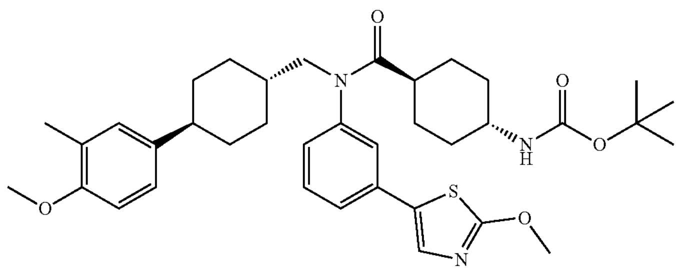 [SMILES: COc1ncc(-c2cccc(N(C[C@H]3CC[C@H](c4ccc(OC)c(C)c4)CC3)C(=O)[C@H]3CC[C@H](NC(=O)OC(C)(C)C)CC3)c2)s1] | tert-Butyl (trans-4-(((trans-4-(4-methoxy-3-methylphenyl)cyclohexyl)methyl)(3-(2-methoxythiazol-5-yl)phenyl)carbamoyl)cyclohexyl)carbamate | 670.5 M + Na |
| 25.02 | 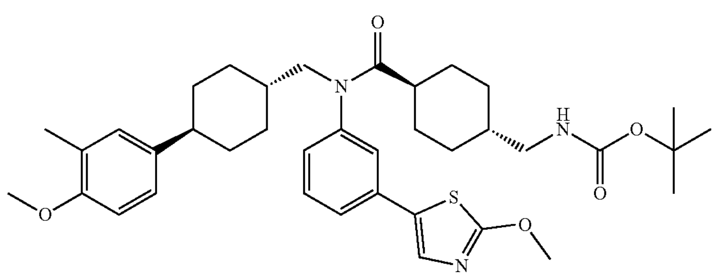 [SMILES: COc1ncc(-c2cccc(N(C[C@H]3CC[C@H](c4ccc(OC)c(C)c4)CC3)C(=O)[C@H]3CC[C@H](CNC(=O)OC(C)(C)C)CC3)c2)s1] | tert-Butyl ((trans-4-(((trans-4-(4-methoxy-3-methylphenyl)cyclohexyl)methyl)(3-(2-methoxythiazol-5-yl)phenyl)carbamoyl)cyclohexyl)methyl)carbamate | 606.4 [(M−tBu + H)+ H]$^+$ |

The Compound below was synthesized from Compound 25.02 following the procedure described for Compound 25, Step 2.

| Cmpd | Structure | Name | [M + H]$^+$ |
|---|---|---|---|
| 25.03[1] | 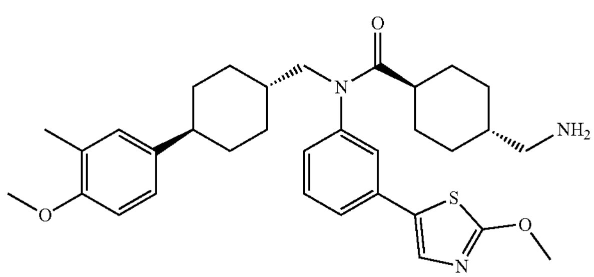 [SMILES: COc1ncc(-c2cccc(N(C[C@H]3CC[C@H](c4ccc(OC)c(C)c4)CC3)C(=O)[C@H]3CC[C@H](CN)CC3)c2)s1] | trans-4-(Aminomethyl)-N-((trans-4-(4-methoxy-3-methylphenyl)cyclohexyl)methyl)-N-(3-(2-methoxythiazol-5-yl)phenyl)cyclohexanecarboxamide | 562.4 |

Variation: [1] 0 °C., 100 min.

The Compounds below were synthesized from the appropriate amine and the appropriate acylating agent following the procedure described for Compound 25.

| Cmpd | Structure | Name | [M + H]+ |
|---|---|---|---|
| 25.04[1,3] | 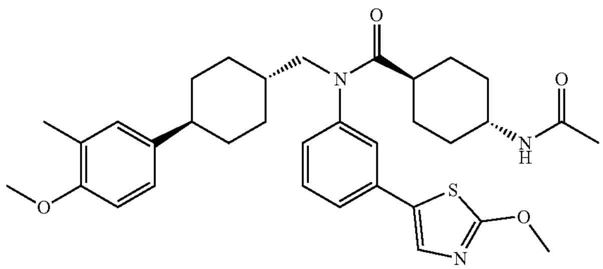 [SMILES: COc1ncc(-c2cccc(N(C[C@H]3CC[C@H](c4ccc(OC)c(C)c4)CC3)C(=O)[C@H]3CC[C@H](NC(C)=O)CC3)c2)s1] | trans-4-Acetamido-N-((trans-4-(4-methoxy-3-methylphenyl)cyclohexyl)methyl)-N-(3-(2-methoxythiazol-5-yl)phenyl)cyclohexanecarboxamide | 590.5 |
| 25.05[1,3] | 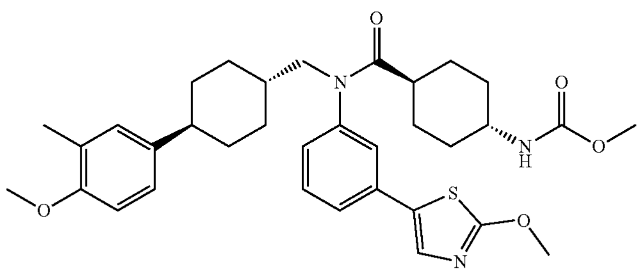 | Methyl (trans-4-(((trans-4-(4-methoxy-3-methylphenyl)cyclohexyl)methyl)(3-(2-methoxythiazol-5-yl)phenyl)carbamoyl)cyclohexyl)carbamate | 606.4 |
| 25.06[2] | 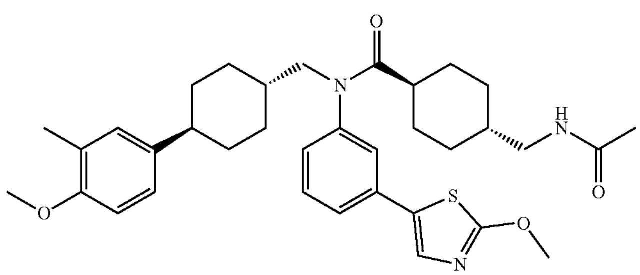 [SMILES: COc1ncc(-c2cccc(N(C[C@H]3CC[C@H](c4ccc(OC)c(C)c4)CC3)C(=O)[C@H]3CC[C@H](CNC(C)=O)CC3)c2)s1] | trans-4-(Acetamidomethyl)-N-((trans-4-(4-methoxy-3-methylphenyl)cyclohexyl)methyl)-N-(3-(2-methoxythiazol-5-yl)phenyl)cyclohexanecarboxamide | 604.4 |
| 25.07 | 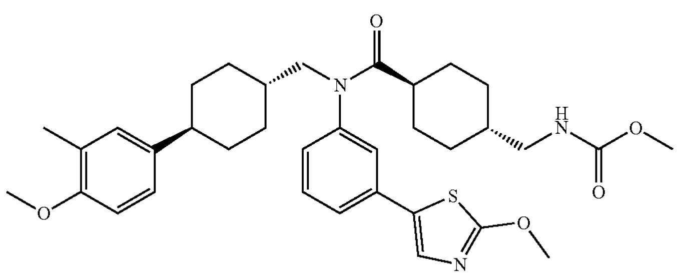 | Methyl ((trans-4-(((trans-4-(4-methoxy-3-methylphenyl)cyclohexyl)methyl)(3-(2-methoxythiazol-5-yl)phenyl)carbamoyl)cyclohexyl)methyl)carbamate | 620.8 |
| 25.08 | 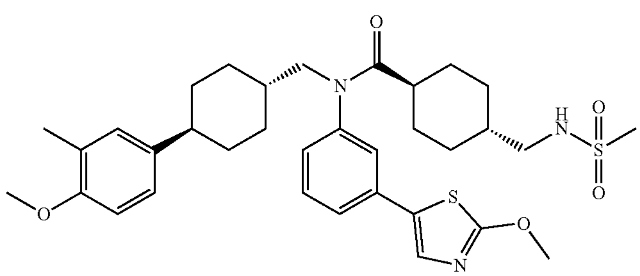 | trans-N-((trans-4-(4-Methoxy-3-methylphenyl)cyclohexyl)methyl)-N-(3-(2-methoxythiazol-5-yl)phenyl)-4-(methylsulfonamidomethyl)cyclohexanecarboxamide | 640.5 |

-continued

| Cmpd | Structure | Name | [M + H]⁺ |
|---|---|---|---|
| 25.09[2,3] | 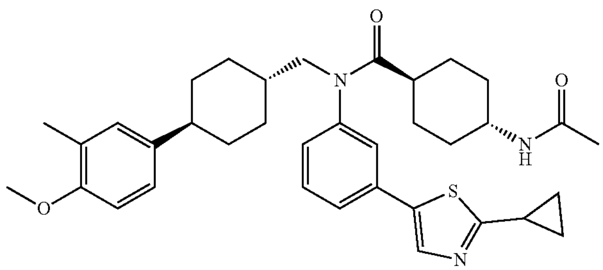 [SMILES: COc1ccc([C@H]2CC[C@H](CN(c3cccc(-c4cnc(C5CC5)s4)c3)C(=O)[C@H]3CC[C@H](NC(C)=O)CC3)CC2)cc1C] | trans-4-Acetamido-N-(3-(2-cyclopropylthiazol-5-yl)phenyl)-N-((trans-4-(4-methoxy-3-methylphenyl)cyclohexyl)methyl)cyclohexanecarboxamide | 600.4 |
| 25.10[5] | 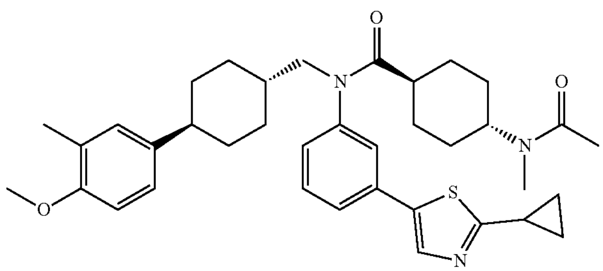 [SMILES: COc1ccc([C@H]2CC[C@H](CN(c3cccc(-c4cnc(C5CC5)s4)c3)C(=O)[C@H]3CC[C@H](N(C)C(C)=O)CC3)CC2)cc1C] | trans-N-(3-(2-Cyclopropylthiazol-5-yl)phenyl)-N-((trans-4-(4-methoxy-3-methylphenyl)cyclohexyl)methyl)-4-(N-methylacetamido)cyclohexanecarboxamide | 614.6 |
| 25.11 | 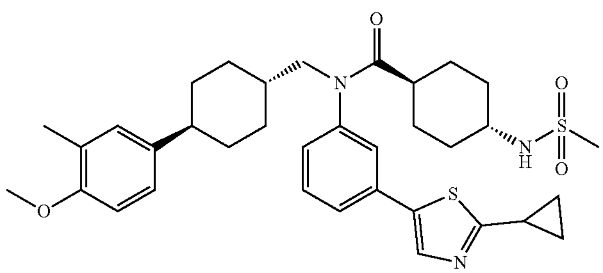 | trans-N-(3-(2-Cyclopropylthiazol-5-yl)phenyl)-N-((trans-4-(4-methoxy-3-methylphenyl)cyclohexyl)methyl)-4-(methylsulfonamido)cyclohexanecarboxamide | 636.4 |
| 25.12[2] | 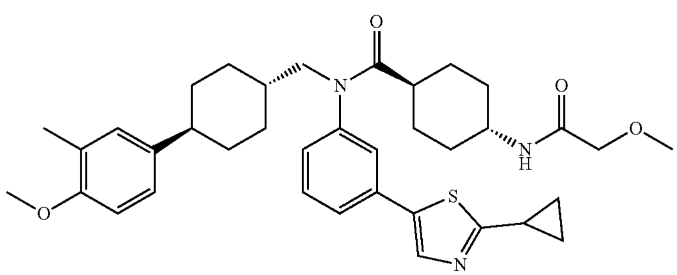 | trans-N-(3-(2-Cyclopropylthiazol-5-yl)phenyl)-N-((trans-4-(4-methoxy-3-methylphenyl)cyclohexyl)methyl)-4-(2-methoxyacetamido)cyclohexanecarboxamide | 630.4 |
| 25.13[2] | 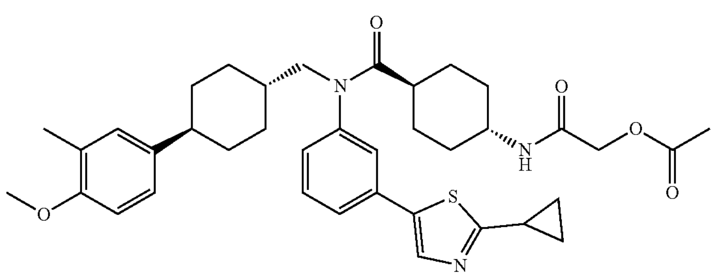 [SMILES: COc1ccc([C@H]2CC[C@H](CN(c3cccc(-c4cnc(C5CC5)s4)c3)C(=O)[C@H]3CC[C@H](NC(=O)COC(C)=O)CC3)CC2)cc1C] | 2-((trans-4-((3-(2-Cyclopropylthiazol-5-yl)phenyl)((trans-4-(4-methoxy-3-methylphenyl)cyclohexyl)methyl)carbamoyl)cyclohexyl)amino)-2-oxoethyl acetate | 658.6 |

| Cmpd | Structure | Name | [M + H]⁺ |
| --- | --- | --- | --- |
| 25.14[3] | 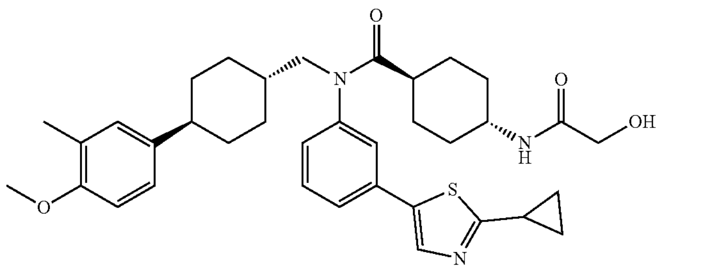 [SMILES: COc1ccc([C@H]2CC[C@H](CN(c3cccc(-c4cnc(C5CC5)s4)c3)C(=O)[C@H]3CC[C@H](NC(=O)CO)CC3)CC2)cc1C] | trans-N-(3-(2-Cyclopropylthiazol-5-yl)phenyl)-4-(2-hydroxyacetamido)-N-((trans-4-(4-methoxy-3-methylphenyl)cyclohexyl)methyl)cyclohexanecarboxamide | 616.3 |
| 25.15[6] | 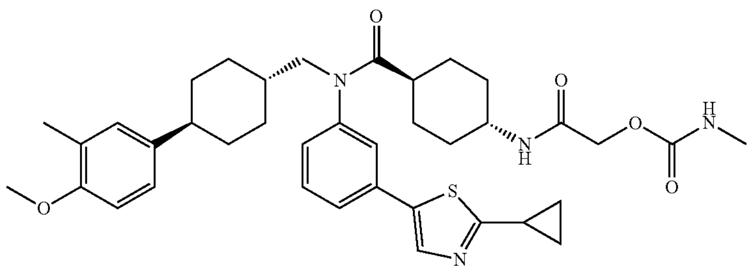 | 2-((trans-4-((3-(2-Cyclopropylthiazol-5-yl)phenyl)((trans-4-(4-methoxy-3-methylphenyl)cyclohexyl)methyl)carbamoyl)cyclohexyl)amino)-2-oxoethyl methylcarbamate | 673.5 |
| 25.16[1] | 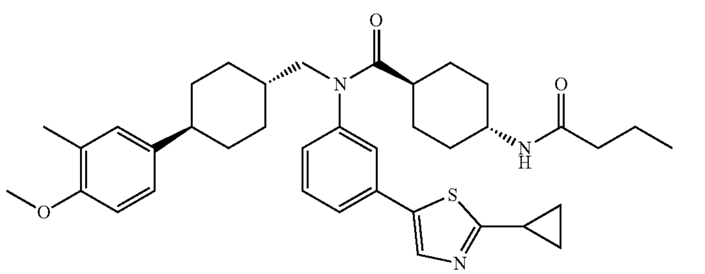 [SMILES: CCCC(=O)N[C@H]1CC[C@H](C(=O)N(C[C@H]2CC[C@H](c3ccc(OC)c(C)c3)CC2)c2cccc(-c3cnc(C4CC4)s3)c2)CC1] | trans-4-Butyramido-N-(3-(2-cyclopropylthiazol-5-yl)phenyl)-N-((trans-4-(4-methoxy-3-methylphenyl)cyclohexyl)methyl)cyclohexanecarboxamide | 628.5 |
| 25.17[1] | 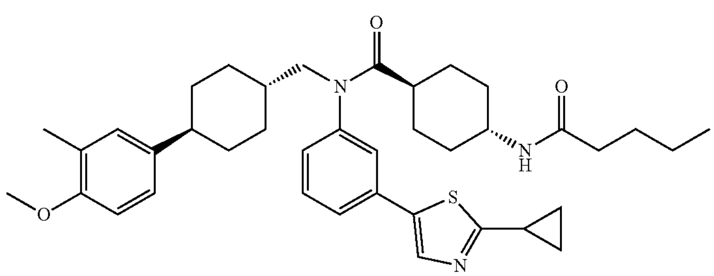 [SMILES: CCCCC(=O)N[C@H]1CC[C@H](C(=O)N(C[C@H]2CC[C@H](c3ccc(OC)c(C)c3)CC2)c2cccc(-c3cnc(C4CC4)s3)c2)CC1] | trans-N-(3-(2-Cyclopropylthiazol-5-yl)phenyl)-N-((trans-4-(4-methoxy-3-methylphenyl)cyclohexyl)methyl)-4-pentanamidocyclohexanecarboxamide | 642.4 |
| 25.18[1] | 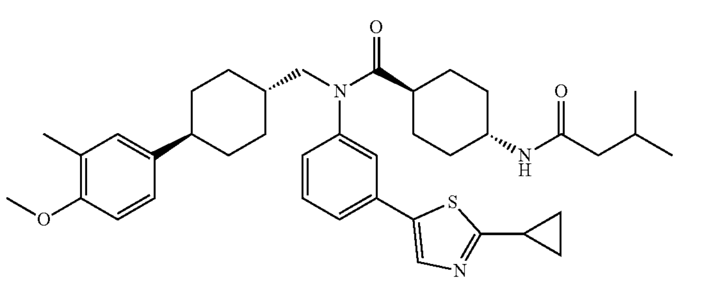 [SMILES: COc1ccc([C@H]2CC[C@H](CN(c3cccc(-c4cnc(C5CC5)s4)c3)C(=O)[C@H]3CC[C@H](NC(=O)CC(C)C)CC3)CC2)cc1C] | trans-N-(3-(2-Cyclopropylthiazol-5-yl)phenyl)-N-((trans-4-(4-methoxy-3-methylphenyl)cyclohexyl)methyl)-4-(3-methylbutanamido)cyclohexanecarboxamide | 642.5 |

Alternate conditions: Step 3: [1]Base was pyridine; [2]Solvent was EtOAc; [3]rt, 0.5-3 h. [4]From Compound 25.13 (1M NaOH, THF CH₃OH, rt). [5]From Compound 25.09 (NaH, THF, CH₃I, 0° C.-rt). [6]From Compound 25.14 (procedure for Compound 2).

Compound 26

Methyl (trans-4-((3-(1-cyclopropyl-1H-pyrazol-4-yl)phenyl)((trans-4-(4-methoxy-3-methylphenyl)cyclohexyl)methyl)carbamoyl)cyclohexyl)carbamate

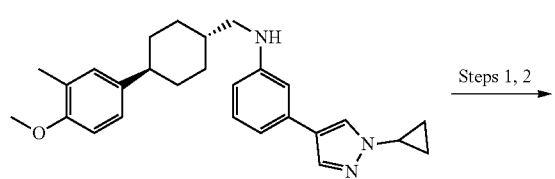

Steps 1, 2

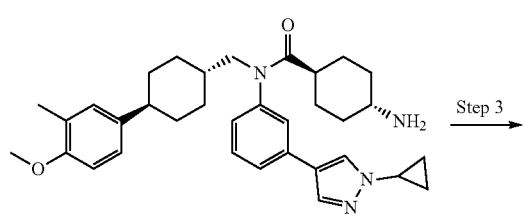

Step 3

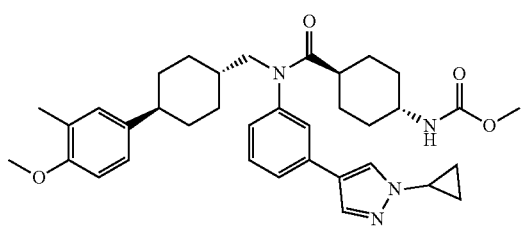

Step 1: Tert-Butyl (trans-4-((3-(1-cyclopropyl-1H-pyrazol-4-yl)phenyl)((trans-4-(4-methoxy-3-methylphenyl)cyclohexyl)methyl)carbamoyl)cyclohexyl)carbamate Pyridine (0.17 mL, 2.10 mmol) and then Intermediate 19.02 (38.6 mg/mL in toluene, 8 mL, 1.18 mmol) were added to a solution of Intermediate 14.22 (223 mg, 0.537 mmol) in toluene (2 mL) at rt. The resulting mixture was stirred at rt for 55 min, poured into 30 mL sat'd NaHCO$_3$ and then extracted with 30 mL EtOAc. The organic layer was washed with 30 mL brine, dried (Na$_2$SO$_4$), filtered, concentrated, and purified by silica gel chromatography (30-60% EtOAc in hexanes) to give tert-butyl (trans-4-((3-(1-cyclopropyl-1H-pyrazol-4-yl)phenyl)((trans-4-(4-methoxy-3-methylphenyl)cyclohexyl)methyl)carbamoyl)cyclohexyl)carbamate (328 mg, 95%) as a white foam. $^1$H NMR (400 MHz, DMSO-d$_6$): δ 8.34 (s, 1H), 7.94 (s, 1H), 7.60 (d, 1H), 7.57-7.52 (m, 1H), 7.44 (t, 1H), 7.10 (d, 1H), 6.98-6.92 (m, 2H), 6.81-6.76 (m, 1H), 6.54 (d, 1H), 3.78-3.69 (m, 4H), 3.64-3.46 (m, 2H), 3.17-3.04 (m, 1H), 2.38-2.28 (m, 1H), 2.12-2.00 (m, 4H), 1.81-1.60 (m, 8H), 1.50-1.22 (m, 15H), 1.12-0.95 (m, 6H), 0.85-0.70 (m, 2H); LCMS: 663.7 [M+Na]$^+$.

Step 2: Trans-4-Amino-N-(3-(1-cyclopropyl-1H-pyrazol-4-yl)phenyl)-N-((trans-4-(4-methoxy-3-methylphenyl)cyclohexyl)methyl)cyclohexanecarboxamide A solution of tert-butyl (trans-4-((3-(1-cyclopropyl-1H-pyrazol-4-yl)phenyl)((trans-4-(4-methoxy-3-methylphenyl)cyclohexyl)methyl)carbamoyl)cyclohexyl)carbamate (321 mg, 0.50 mmol) and trifluoroacetic acid (20% in CH$_2$Cl$_2$, 5 mL) was stirred at rt for 2 h, diluted with 25 mL CH$_2$Cl$_2$, washed with sat'd NaHCO$_3$ (2×30 mL), and then washed with 30 mL brine. The combined aqueous layers were back extracted with 20 mL CH$_2$Cl$_2$. The combined extracts were dried (Na$_2$SO$_4$), filtered, and concentrated to give trans-4-amino-N-(3-(1-cyclopropyl-1H-pyrazol-4-yl)phenyl)-N-((trans-4-(4-methoxy-3-methylphenyl)cyclohexyl)methyl)cyclohexanecarboxamide (267 mg, 98%) as an off-white foam. $^1$H NMR (400 MHz, DMSO-d$_6$): δ 8.34 (s, 1H), 7.94 (s, 1H), 7.60 (d, 1H), 7.56-7.52 (m, 1H), 7.44 (t, 1H), 7.09 (d, 1H), 6.97-6.93 (m, 2H), 6.80-6.76 (m, 1H), 3.77-3.69 (m, 4H), 3.64-3.47 (m, 2H), 3.11-2.87 (m, 1H), 2.47-2.38 (m, 1H), 2.38-2.28 (m, 1H), 2.26-2.13 (m, 1H), 2.11-2.00 (m, 4H), 1.80-1.70 (m, 4H), 1.70-1.58 (m, 4H), 1.48-1.37 (m, 3H), 1.35-1.22 (m, 2H), 1.12-0.95 (m, 6H), 0.72-0.59 (m, 2H); LCMS: 541.6 [M+H]$^+$.

Step 3: Methyl (trans-4-((3-(1-cyclopropyl-1H-pyrazol-4-yl)phenyl)((trans-4-(4-methoxy-3-methylphenyl)cyclohexyl)methyl)carbamoyl)cyclohexyl)carbamate Triethylamine (0.13 mL, 0.74 mmol) and then methyl chloroformate (17 µL, 0.22 mmol) were added to a solution of trans-4-amino-N-(3-(1-cyclopropyl-1H-pyrazol-4-yl)phenyl)-N-((trans-4-(4-methoxy-3-methylphenyl)cyclohexyl)methyl)cyclohexanecarboxamide (100 mg, 0.19 mmol) in CH$_2$Cl$_2$ (2 mL) at 0° C. under N$_2$. The reaction was stirred at 0° C. for 13 min, diluted with 20 mL CH$_2$Cl$_2$, washed with sat'd NaHCO$_3$ (2×20 mL), and then washed with brine (20 mL). The combined aqueous washes were back extracted with 20 mL CH$_2$Cl$_2$. The combined extracts were dried (Na$_2$SO$_4$), filtered, concentrated, and purified by silica gel chromatography (40-90% EtOAc in hexanes) to give methyl (trans-4-((3-(1-cyclopropyl-1H-pyrazol-4-yl)phenyl)((trans-4-(4-methoxy-3-methylphenyl)cyclohexyl)methyl)carbamoyl)cyclohexyl)carbamate (88 mg, 79%) as a white foam. $^1$H NMR (400 MHz, DMSO-d$_6$): δ 8.34 (s, 1H), 7.94 (s, 1H), 7.60 (d, 1H), 7.57-7.53 (m, 1H), 7.44 (t, 1H), 7.10 (d, 1H), 6.97-6.92 (m, 2H), 6.87-6.81 (m, 1H), 6.81-6.76 (m, 1H), 3.77-3.69 (m, 4H), 3.65-3.38 (m, 5H), 3.22-3.09 (m, 1H), 2.38-2.28 (m, 1H), 2.11-2.00 (m, 4H), 1.80-1.62 (m, 8H), 1.49-1.35 (m, 3H), 1.35-1.22 (m, 2H), 1.11-0.95 (m, 6H), 0.87-0.73 (m, 2H); LCMS: 599.4 [M+H]$^+$.

The Compounds below were synthesized from Intermediate 14.22 and the appropriate acylating agent following the procedures described for Compound 26.

| Cmpd | Structure | Name | [M + H]+ |
|---|---|---|---|
| 26.01[1] | 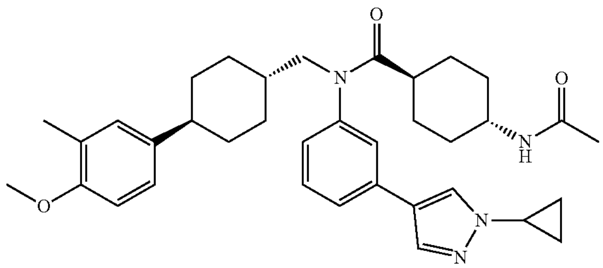 [SMILES: COc1ccc([C@H]2CC[C@H](CN(c3cccc(-c4cnn(C5CC5)c4)c3)C(=O)[C@H]3CC[C@H](NC(C)=O)CC3)CC2)cc1C] | trans-4-Acetamido-N-(3-(1-cyclopropyl-1H-pyrazol-4-yl)phenyl)-N-((trans-4-(4-methoxy-3-methylphenyl)cyclohexyl)methyl)cyclohexanecarboxamide | 583.5 |
| 26.02 | 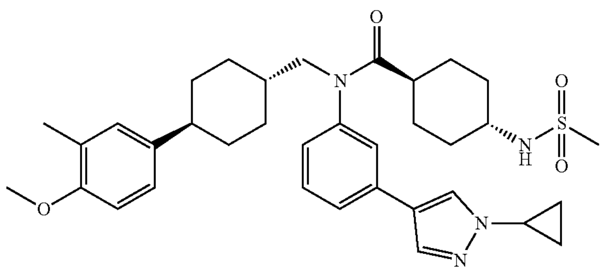 | trans-N-(3-(1-Cyclopropyl-1H-pyrazol-4-yl)phenyl)-N-((trans-4-(4-methoxy-3-methylphenyl)cyclohexyl)methyl)-4-(methylsulfonamido)cyclohexanecarboxamide | 619.5 |
| 26.03[2,6] | 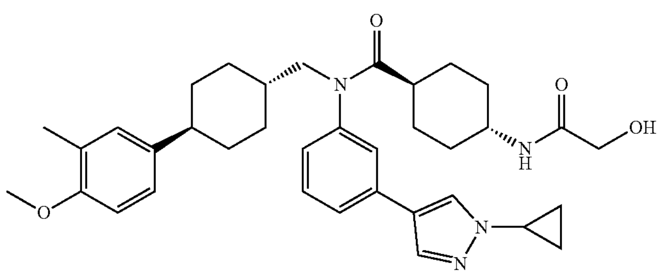 [SMILES: COc1ccc([C@H]2CC[C@H](CN(c3cccc(-c4cnn(C5CC5)c4)c3)C(=O)[C@H]3CC[C@H](NC(=O)CO)CC3)CC2)cc1C] | trans-N-(3-(1-Cyclopropyl-1H-pyrazol-4-yl)phenyl)-4-(2-hydroxyacetamido)-N-((trans-4-(4-methoxy-3-methylphenyl)cyclohexyl)methyl)cyclohexanecarboxamide | 599.5 |
| 26.04[3] | 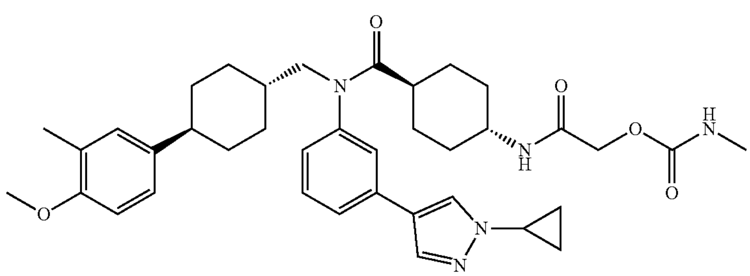 | 2-((trans-4-((3-(1-Cyclopropyl-1H-pyrazol-4-yl)phenyl)((trans-4-(4-methoxy-3-methylphenyl)cyclohexyl)methyl)carbamoyl)cyclohexyl)amino)-2-oxoethyl methylcarbamate | 656.6 |
| 26.05[4] | 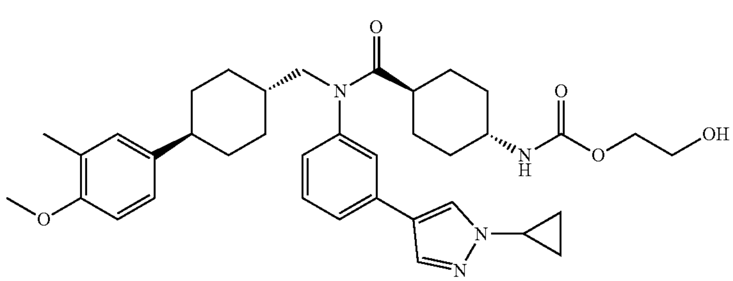 [SMILES: COc1ccc([C@H]2CC[C@H](CN(c3cccc(-c4cnn(C5CC5)c4)c3)C(=O)[C@H]3CC[C@H](NC(=O)OCCO)CC3)CC2)cc1C] | 2-Hydroxyethyl (trans-4-((3-(1-cyclopropyl-1H-pyrazol-4-yl)phenyl)((trans-4-(4-methoxy-3-methylphenyl)cyclohexyl)methyl)carbamoyl)cyclohexyl)carbamate | 629.3 |

-continued

| Cmpd | Structure | Name | [M + H]+ |
|---|---|---|---|
| 26.06[5] | 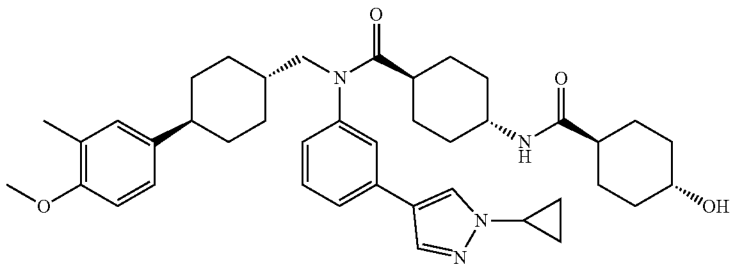 [SMILES: COc1ccc([C@H]2CC[C@H](CN(c3cccc(-c4cnn(C5CC5)c4)c3)C(=O)[C@H]3CC[C@H](NC(=O)[C@H]4CC[C@H](O)CC4)CC3)CC2)cc1C] | trans-N-(3-(1-Cyclopropyl-1H-pyrazol-4-yl)phenyl)-4-(trans-4-hydroxycyclo-hexanecarboxamido)-N-((trans-4-(4-methoxy-3-methylphenyl)cyclohexyl)methyl)cyclohexanecarboxamide | 667.6 |

Alternate conditions: Step 3: [1]Ac$_2$O, Et$_3$N, EtOAc, rt; [2]Solvent was EtOAc. [3]From Compound 26.03 (procedure for Compound 2). [4]From Intermediate 20 (Et$_3$N, CH$_2$Cl$_2$, rt, overnight). [5]From Intermediate 19, then desilylation (1N HCl, THF, CH$_3$OH, 0° C.-rt, 75 min). [6]From acetoxyacetyl chloride, then hydrolysis (1M NaOH, THF, CH$_3$OH, rt).

The Compounds below were synthesized from the appropriate Intermediate and the appropriate acylating agents following the procedures described for Compound 26.

| Cmpd | Structure | Name | [M + H]+ |
|---|---|---|---|
| 26.07[1,4,6] | 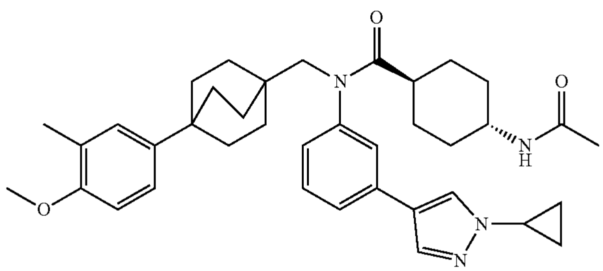 [SMILES: COc1ccc(C23CCC(CN(c4cccc(-c5cnn(C6CC6)c5)c4)C(=O)[C@H]4CC[C@H](NC(C)=O)CC4)(CC2)CC3)cc1C] | trans-4-Acetamido-N-(3-(1-cyclopropyl-1H-pyrazol-4-yl)phenyl)-N-((4-(4-methoxy-3-methylphenyl)bicyclo[2.2.2]octan-1-yl)methyl)cyclohexanecarboxamide | 609.5 |
| 26.08[1,6] | 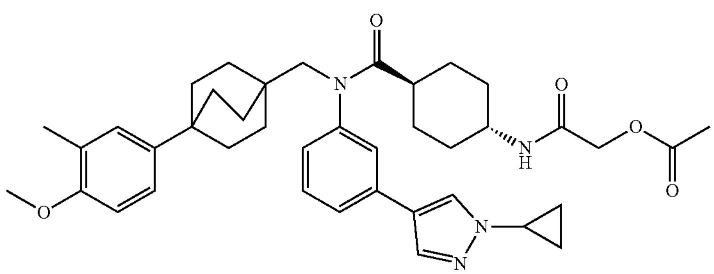 [SMILES: COc1ccc(C23CCC(CN(c4cccc(-c5cnn(C6CC6)c5)c4)C(=O)[C@H]4CC[C@H](NC(=O)COC(C)=O)CC4)(CC2)CC3)cc1C] | 2-((4-((3-(1-Cyclopropyl-1H-pyrazol-4-yl)phenyl)((4-(4-methoxy-3-methylphenyl)bicyclo[2.2.2]octan-1-yl)methyl)carbamoyl)cyclohexyl)amino)-2-oxoethyl trans-acetate | 667.6 |
| 26.09[7] | 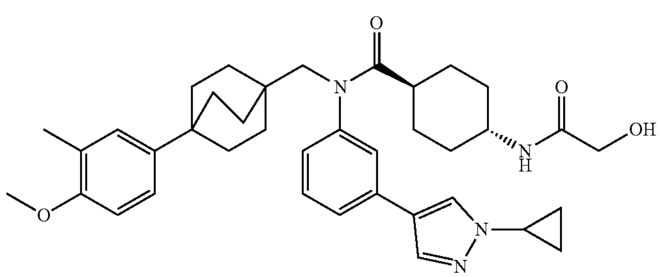 [SMILES: COc1ccc(C23CCC(CN(c4cccc(-c5cnn(C6CC6)c5)c4)C(=O)[C@H]4CC[C@H](NC(=O)CO)CC4)(CC2)CC3)cc1C] | trans-N-(3-(1-Cyclopropyl-1H-pyrazol-4-yl)phenyl)-4-(2-hydroxyacetamido)-N-((4-(4-methoxy-3-methylphenyl)bicyclo[2.2.2]octan-1-yl)methyl)cyclohexanecarboxamide | 625.4 |
| 26.10[1,4,6] | 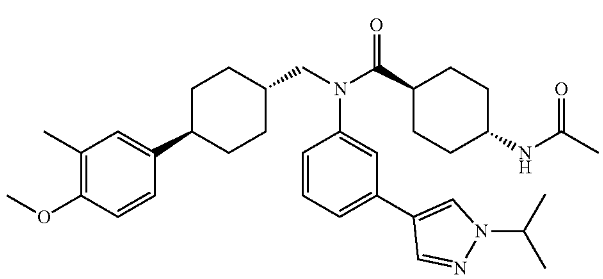 [SMILES: COc1ccc([C@H]2CC[C@H](CN(c3cccc(-c4cnn(C(C)C)c4)c3)C(=O)[C@H]3CC[C@H](NC(C)=O)CC3)CC2)cc1C] | trans-4-Acetamido-N-(3-(1-isopropyl-1H-pyrazol-4-yl)phenyl)-N-((trans-4-(4-methoxy-3-methylphenyl)cyclohexyl)methyl)cyclohexanecarboxamide | 585.5 |

-continued

| Cmpd | Structure | Name | [M + H]+ |
|---|---|---|---|
| 26.11[1,6] | 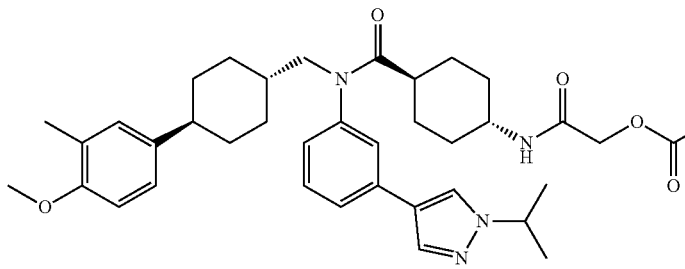 | 2-((trans-4-((3-(1-Isopropyl-1H-pyrazol-4-yl)phenyl)((trans-4-(4-methoxy-3-methylphenyl)cyclohexyl)methyl)carbamoyl)cyclohexyl)amino)-2-oxoethyl acetate | 643.5 |
| 26.12[7] | 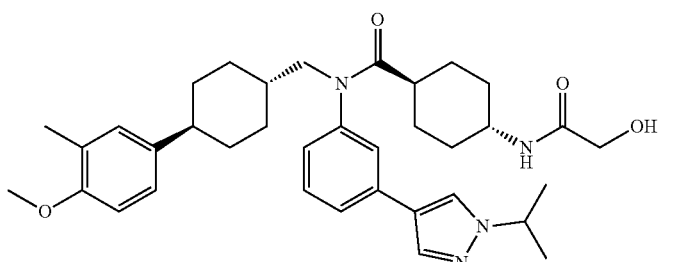 | trans-4-(2-Hydroxyacetamido)-N-(3-(1-isopropyl-1H-pyrazol-4-yl)phenyl)-N-((trans-4-(4-methoxy-3-methylphenyl)cyclohexyl)methyl)cyclohexanecarboxamide | 601.5 |
| 26.13[1,5] | 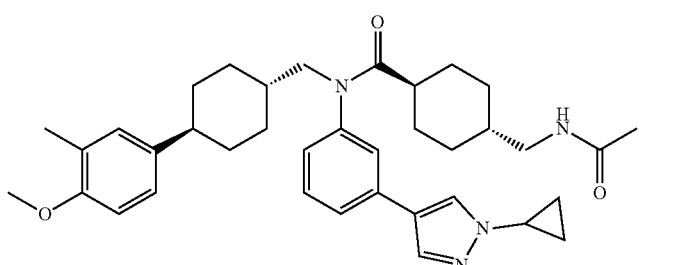 | trans-4-(Acetamidomethyl)-N-(3-(1-cyclopropyl-1H-pyrazol-4-yl)phenyl)-N-((trans-4-(4-methoxy-3-methylphenyl)cyclohexyl)methyl)cyclohexanecarboxamide | 597.3 |
| 26.14[1,5] | 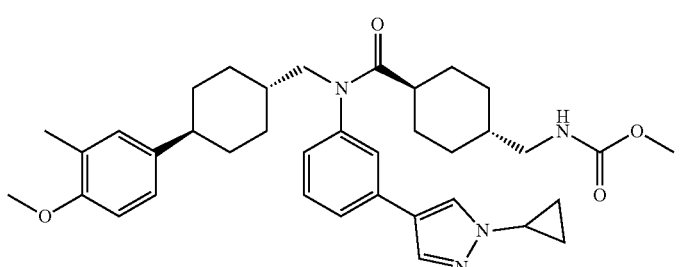 | Methyl ((trans-4-((3-(1-cyclopropyl-1H-pyrazol-4-yl)phenyl)((trans-4-(4-methoxy-3-methylphenyl)cyclohexyl)methyl)carbamoyl)cyclohexyl)methyl)carbamate | 613.6 |
| 26.15[1,5] | 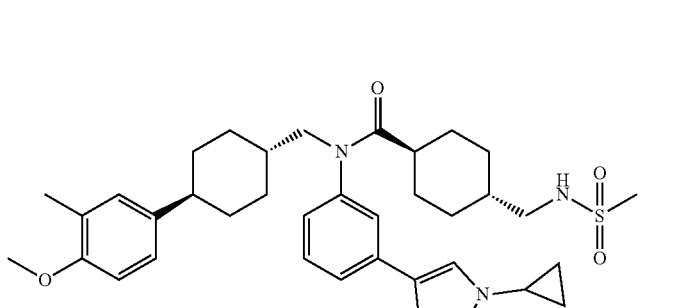 | trans-N-(3-(1-Cyclopropyl-1H-pyrazol-4-yl)phenyl)-N-((trans-4-(4-methoxy-3-methylphenyl)cyclohexyl)methyl)-4-(methylsulfonamidomethyl)cyclohexanecarboxamide | 633.5 |

-continued

| Cmpd | Structure | Name | [M + H]+ |
| --- | --- | --- | --- |
| 26.16[1,7] | 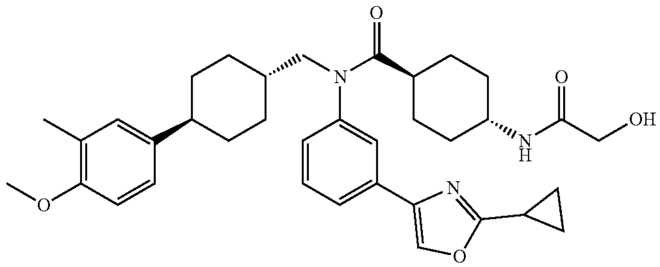 [SMILES: COc1ccc([C@H]2CC[C@H](CN(c3cccc(-c4coc(C5CC5)n4)c3)C(=O)[C@H]3CC[C@H](NC(=O)CO)CC3)CC2)cc1C] | trans-N-(3-(2-Cyclopropyloxazol-4-yl)phenyl)-4-(2-hydroxyacetamido)-N-((trans-4-(4-methoxy-3-methylphenyl)cyclohexyl)methyl)cyclohexanecarboxamide | 600.4 |
| 26.17[2,6] | 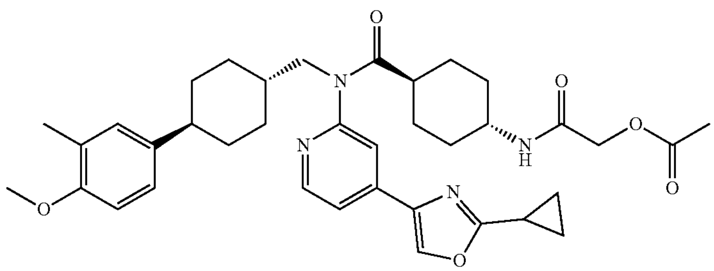 [SMILES: COc1ccc([C@H]2CC[C@H](CN(c3cc(-c4coc(C5CC5)n4)ccn3)C(=O)[C@H]3CC[C@H](NC(=O)COC(C)=O)CC3)CC2)cc1C] | 2-((trans-4((4-(2-cyclopropyloxazol-4-yl)pyridine-2-yl)((trans-4-(4-methoxy-3-methylphenyl)cyclohexyl)methyl)carbamoyl)cyclohexyl)amino)-2-oxoethyl acetate | 643.6 |
| 26.18[7] | 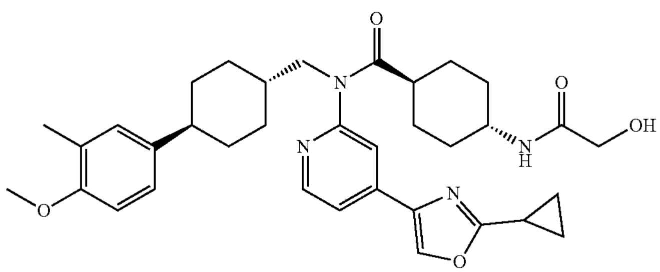 [SMILES: COc1ccc([C@H]2CC[C@H](CN(c3cc(-c4coc(C5CC5)n4)ccn3)C(=O)[C@H]3CC[C@H](NC(=O)CO)CC3)CC2)cc1C] | trans-N-(4-(2-Cyclopropyloxazol-4-yl)pyridin-2-yl)-4-(2-hydroxyacetamido)-N-((trans-4-(4-methoxy-3-methylphenyl)cyclohexyl)methyl)cyclohexanecarboxamide | 601.4 |
| 26.19[1,4] | 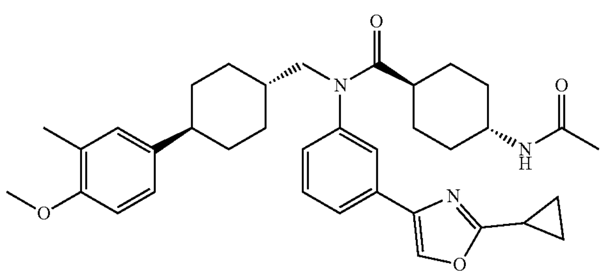 | trans-4-Acetamido-N-(3-(2-cyclopropyloxazol-4-yl)phenyl)-N-((trans-4-(4-methoxy-3-methylphenyl)cyclohexyl)methyl)cyclohexanecarboxamide | 584.5 |
| 26.20[2,4,6] | 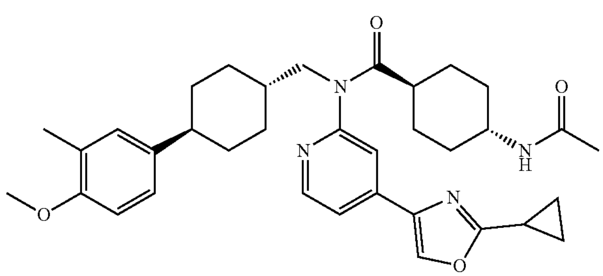 | trans-4-Acetamido-N-(4-(2-cyclopropyloxazol-4-yl)pyridine-2-yl)-N-((trans-4-(4-methoxy-3-methylphenyl)cyclohexyl)methyl)cyclohexanecarboxamide | 585.5 |

| Cmpd | Structure | Name | [M + H]+ |
|---|---|---|---|
| 26.21[3] | 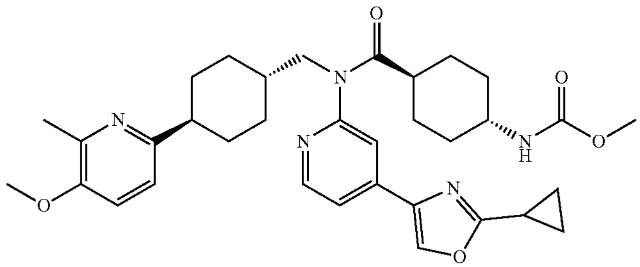 | Methyl (trans-4-((4-(2-cyclopropyloxazol-4-yl)pyridine-2-yl)((trans-4-(5-methoxy-6-methylpyridin-2-yl)cyclohexyl)methyl)carbamoyl)cyclohexyl)carbamate | 602.4 |
| 26.22[3,8] | 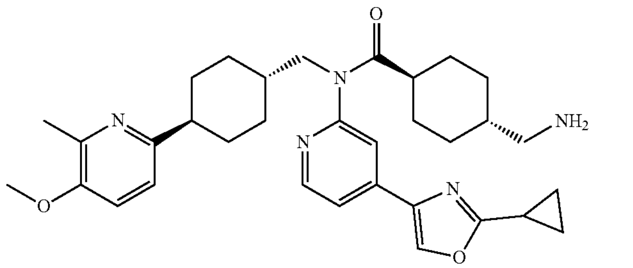 [SMILES: COc1ccc([C@H]2CC[C@H](CN(c3cc(-c4coc(C5CC5)n4)ccn3)C(=O)[C@H]3CC[C@H](CN)CC3)CC2)nc1C] | trans-4-(Aminomethyl)-N-(4-(2-cyclopropyloxazol-4-yl)pyridin-2-yl)-N-((trans-4-(5-methoxy-6-methylpyridin-2-yl)cyclohexyl)methyl)cyclohexanecarboxamide | 558.5 |

Alternate conditions: Step 1: [1]Solvent was CH$_2$Cl$_2$; [2]DMAP, pyridine, 80° C.; [3]DMAP, Et$_3$N, toluene, 80° C.; Step 3: [4]Ac$_2$O; [5]Base was pyridine; [6]Solvent was EtOAc. [7]From hydrolysis of acetylated Compound (1M NaOH, THF CH$_3$OH, rt). [8]Steps 1 & 2 only.

The Compounds below were synthesized from Compound 4.16 or Compound 26.22 following the procedure described for Compound 26, Step 3.

| Cmpd | Structure | Name | [M + H]+ |
|---|---|---|---|
| 26.23[1] | 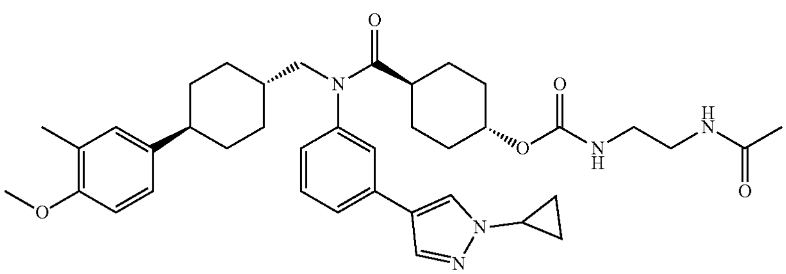 [SMILES: COc1ccc([C@H]2CC[C@H](CN(c3cccc(-c4cnn(C5CC5)c4)c3)C(=O)[C@H]3CC[C@H](OC(=O)NCCNC(C)=O)CC3)CC2)cc1C] | trans-4-((3-(1-Cyclopropyl-1H-pyrazol-4-yl)phenyl)((trans-4-(4-methoxy-3-methylphenyl)cyclohexyl)methyl)carbamoyl)cyclohexyl (2-acetamidoethyl)carbamate | 670.5 |
| 26.24[2] | 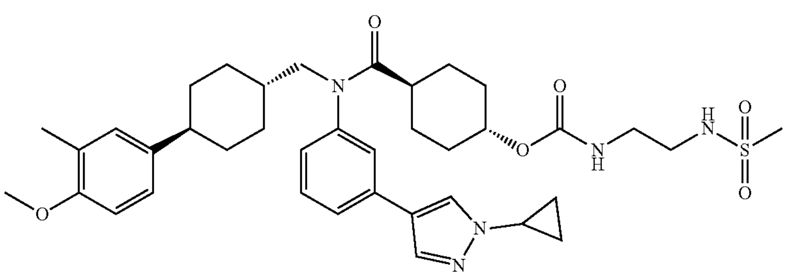 | trans-4-((3-(1-Cyclopropyl-1H-pyrazol-4-yl)phenyl)((trans-4-(4-methoxy-3-methylphenyl)cyclohexyl)methyl)carbamoyl)cyclohexyl (2-(methylsulfonamido)ethyl)carbamate | 706.6 |
| 26.25 | 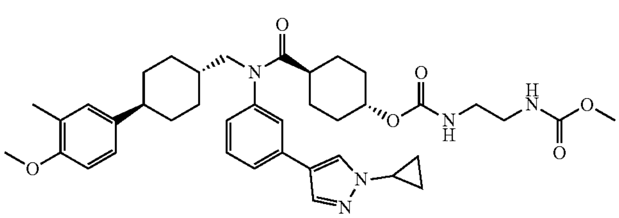 | trans-4-((3-(1-Cyclopropyl-1H-pyrazol-4-yl)phenyl)((trans-4-(4-methoxy-3-methylphenyl)cyclohexyl)methyl)carbamoyl)cyclohexyl methyl ethane-1,2-diyldicarbamate | 686.8 |

-continued

| Cmpd | Structure | Name | [M + H]⁺ |
|---|---|---|---|
| 26.26 | 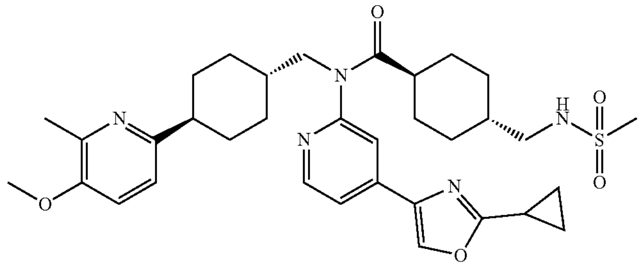 | trans-N-(4-(2-Cyclopropyloxazol-4-yl)pyridin-2-yl)-N-((trans-4-(5-methoxy-6-methylpyridin-2-yl)cyclohexyl)methyl)-4-(methylsulfonamidomethyl)cyclohexanecarboxamide | 636.6 |
| 26.27 | 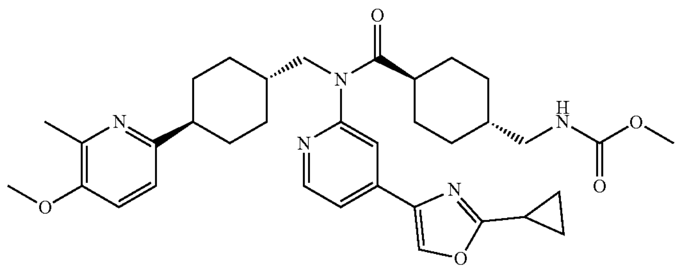 | Methyl ((trans-4-((4-(2-cyclopropyloxazol-4-yl)pyridin-2-yl)((trans-4-(5-methoxy-6-methylpyridin-2-yl)cyclohexyl)methyl)carbamoyl)cyclohexyl)methyl)carbamate | 616.6 |
| 26.28 | 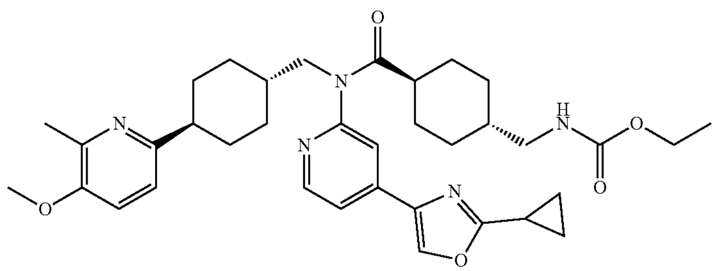 [SMILES: CCOC(=O)NC[C@H]1CC[C@H](C(=O)N(C[C@H]2CC[C@H](c3ccc(OC)c(C)n3)CC2)c2cc(-c3coc(C4CC4)n3)ccn2)CC1] | Ethyl ((trans-4-((4-(2-cyclopropyloxazol-4-yl)pyridin-2-yl)((trans-4-(5-methoxy-6-methylpyridin-2-yl)cyclohexyl)methyl)carbamoyl)cyclohexyl)methyl)carbamate | 630.6 |
| 26.29[3] | 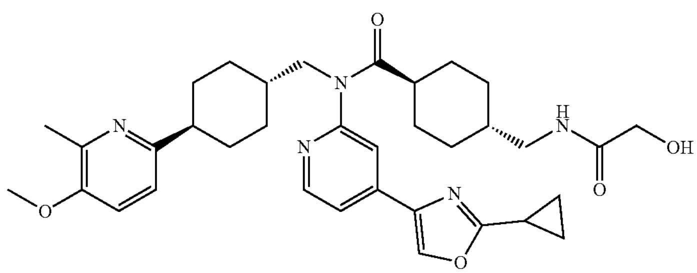 [SMILES: COc1ccc([C@H]2CC[C@H](CN(c3cc(-c4coc(C5CC5)n4)ccn3)C(=O)[C@H]3CC[C@H](CNC(=O)CO)CC3)CC2)nc1C] | trans-N-(4-(2-Cyclopropyloxazol-4-yl)pyridin-2-yl)-4-((2-hydroxyacetamido)methyl)-N-((trans-4-(5-methoxy-6-methylpyridin-2-yl)cyclohexyl)methyl)cyclohexanecarboxamide | 616.5 |

Step 3: [1]Ac2O, Et3N, EtOAc, rt; [2]Solvent was EtOAc. [3]From acetoxyacetyl chloride then hydrolysis (1M NaOH, THF CH3OH, rt).

The Compounds below were synthesized from Intermediate 23.07 or Intermediate 23.08 following the procedures described for Compound 26, Steps 2 & 3.

| Cmpd | Structure | Name | [M + H]⁺ |
|---|---|---|---|
| 26.30[1] | 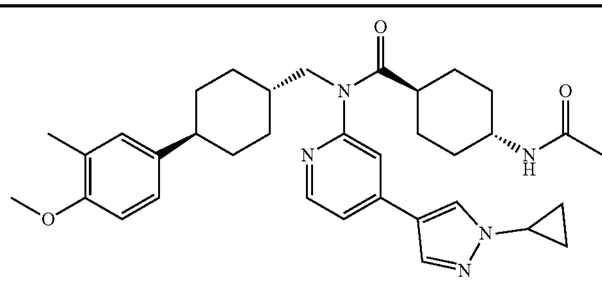 | trans-4-Acetamido-N-(4-(1-cyclopropyl-1H-pyrazol-4-yl)pyridin-2-yl)-N-((trans-4-(4-methoxy-3-methylphenyl)cyclohexyl)methyl)cyclohexanecarboxamide | 584.5 |

| Cmpd | Structure | Name | [M + H]+ |
|---|---|---|---|
| 26.31 | 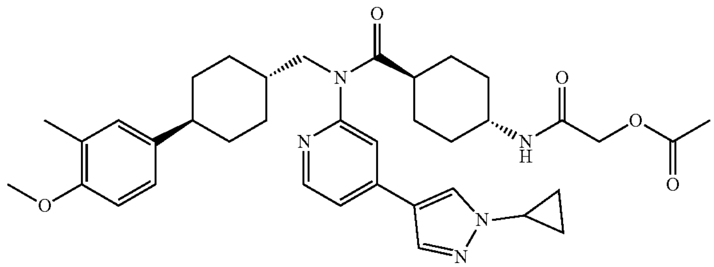 [SMILES: COc1ccc([C@H]2CC[C@H](CN(c3cc(-c4cnn(C5CC5)c4)ccn3)C(=O)[C@H]3CC[C@H](NC(=O)COC(C)=O)CC3)CC2)cc1C] | 2-((trans-4-((4-(1-Cyclopropyl-1H-pyrazol-4-yl)pyridin-2-yl)((trans-4-(4-methoxy-3-methylphenyl)cyclohexyl)methyl)carbamoyl)cyclohexyl)amino)-2-oxoethyl acetate | 642.6 |
| 26.32[2] | 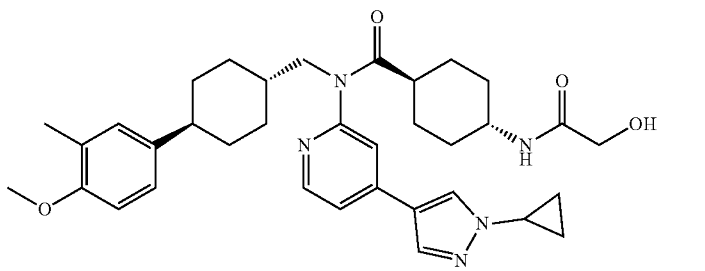 [SMILES: COc1ccc([C@H]2CC[C@H](CN(c3cc(-c4cnn(C5CC5)c4)ccn3)C(=O)[C@H]3CC[C@H](NC(=O)CO)CC3)CC2)cc1C] | trans-N-(4-(1-Cyclopropyl-1H-pyrazol-4-yl)pyridin-2-yl)-4-(2-hydroxyacetamido)-N-((trans-4-(4-methoxy-3-methylphenyl)cyclohexyl)methyl)cyclohexanecarboxamide | 600.4 |
| 26.33[1] | 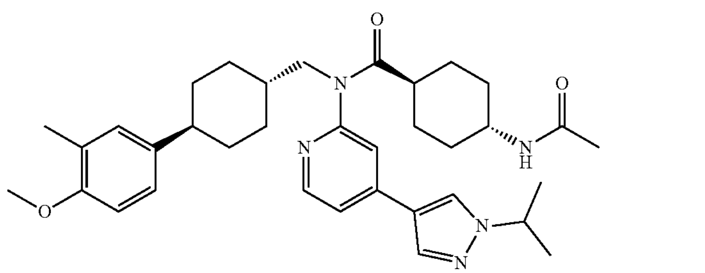 [SMILES: COc1ccc([C@H]2CC[C@H](CN(c3cc(-c4cnn(C(C)C)c4)ccn3)C(=O)[C@H]3CC[C@H](NC(C)=O)CC3)CC2)cc1C] | trans-4-Acetamido-N-(4-(1-isopropyl-1H-pyrazol-4-yl)pyridin-2-yl)-N-((trans-4-(4-methoxy-3-methylphenyl)cyclohexyl)methyl)cyclohexanecarboxamide | 586.5 |
| 26.34 | 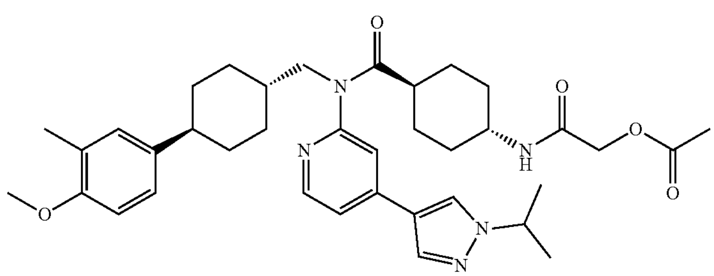 [SMILES: COc1ccc([C@H]2CC[C@H](CN(c3cc(-c4cnn(C(C)C)c4)ccn3)C(=O)[C@H]3CC[C@H](NC(=O)COC(C)=O)CC3)CC2)cc1C] | 2-((trans-4-((4-(1-Isopropyl-1H-pyrazol-4-yl)pyridin-4-yl)((trans-4-(4-methoxy-3-methylphenyl)cyclohexyl)methyl)carbamoyl)cyclohexyl)amino)-2-oxoethyl acetate | 644.6 |
| 26.35[2] | 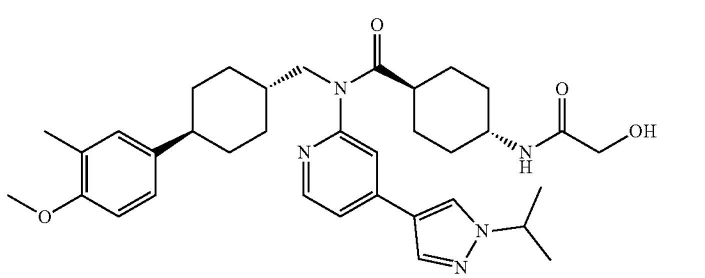 [SMILES: COc1ccc([C@H]2CC[C@H](CN(c3cc(-c4cnn(C(C)C)c4)ccn3)C(=O)[C@H]3CC[C@H](NC(=O)CO)CC3)CC2)cc1C] | trans-4-(2-Hydroxyacetamido)-N-(4-(1-isopropyl-1H-pyrazol-4-yl)pyridin-2-yl)-N-((trans-4-(4-methoxy-3-methylphenyl)cyclohexyl)methyl)cyclohexanecarboxamide | 602.5 |

Step 3: [1]Ac$_2$O, Et$_3$N, CH$_2$Cl$_2$, rt. [2]From hydroysis of acetylated Compound (1M NaOH, THF CH$_3$OH, rt).

The Compounds below were synthesized from Compound 25, Step 2 or Compound 26, Step 2 following the procedure described for Compound 5 using methylamine (40% in CH$_3$OH).

| Cmpd | Structure | Name | [M + H]$^+$ |
|---|---|---|---|
| 26.36 | 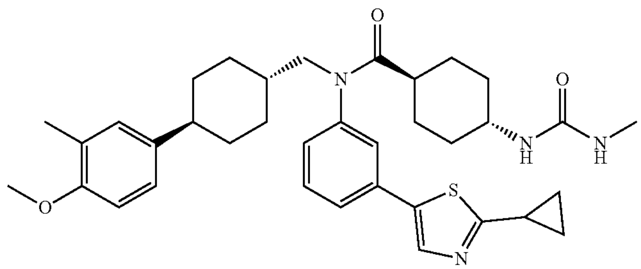 | trans-N-(3-(2-Cyclopropylthiazol-5-yl)phenyl)-N-((trans-4-(4-methoxy-3-methylphenyl)cyclohexyl)methyl)-4-(3-methylureido)cyclohexanecarboxamide | 615.5 |
| 26.37 | 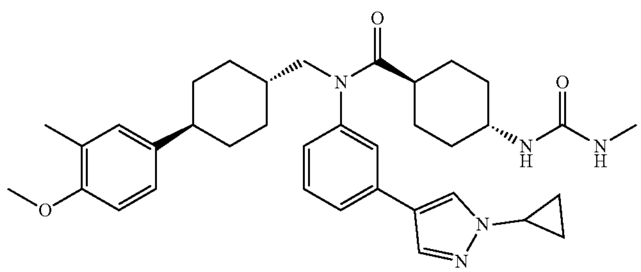 | trans-N-(3-(1-Cyclopropyl-1H-pyrazol-4-yl)phenyl)-N-((trans-4-(4-methoxy-3-methylphenyl)cyclohexyl)methyl)-4-(3-methylureido)cyclohexanecarboxamide | 598.5 |

Compound 27

Trans-N-(3-(2-Cyclopropylthiazol-5-yl)phenyl)-4-(2-hydroxy-2-methylpropanamido)-N-((trans-4-(4-methoxy-3-methylphenyl)cyclohexyl)methyl)cyclohexanecarboxamide

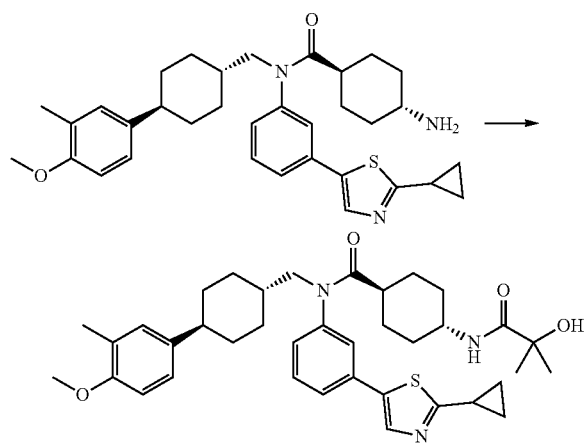

((1H-Benzo[d][1,2,3]triazol-1-yl)oxy)tri(pyrrolidin-1-yl)phosphonium hexafluorophosphate(V) (229.9 mg, 0.442 mmol) and iPr$_2$NEt (0.804 mmol, 0.14 mL) were added to a solution of Compound 25, Step 2 (205.4 mg, 0.368 mmol), 2-hydroxy-2-methylpropanoic acid (46.1 mg, 0.442 mmol) and DMF (2 mL) at 0° C. under N$_2$. The reaction was stirred at rt overnight, poured into water (30 mL), and then extracted with EtOAc (3×20 mL). The organic layers were combined, washed with brine (2×20 mL), dried (Na$_2$SO$_4$), filtered, concentrated, and then purified by reverse-phase HPLC (water(10 mM NH$_4$HCO$_3$)/CH$_3$CN) to give trans-N-(3-(2-cyclopropylthiazol-5-yl)phenyl)-4-(2-hydroxy-2-methylpropanamido)-N-((trans-4-(4-methoxy-3-methylphenyl)cyclohexyl)methyl)cyclohexanecarboxamide (76.8 mg, 32%) as a white solid. $^1$H NMR (400 MHz, DMSO-d$_6$): δ 8.09 (s, 1H), 7.63-7.56 (m, 2H), 7.55-7.47 (i, 1H), 7.27 (d, 1H), 7.21 (d, 1H), 6.98-6.91 (m, 2H), 6.78-6.76 (m, 1H), 5.17 (s, 1H), 3.71 (s, 3H), 3.55-3.49 (m, 2H), 3.42-3.40 (m, 1H), 2.47-2.39 (m, 1H), 2.33 (t, 1H), 2.08-2.03 (m, 4H), 1.80-1.57 (m, 8H), 1.51-1.37 (m, 3H), 1.35-1.22 (m, 2H), 1.19-1.11 (m, 8H), 1.11-0.90 (in, 6H); LCMS: 644.3 [M+H]$^+$.

The Compounds below were synthesized from Compound 25, Step 2 and the appropriate acid following the procedure described for Compound 27.

| Cmpd | Structure | Name | [M + H]+ |
|---|---|---|---|
| 27.01 | 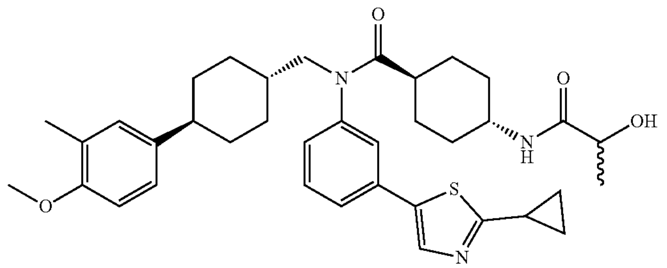 [SMILES: COc1ccc([C@H]2CC[C@H](CN(c3cccc(-c4cnc(C5CC5)s4)c3)C(=O)[C@H]3CC[C@H](NC(=O)C(C)O)CC3)CC2)cc1C] | trans-N-(3-(2-Cyclopropylthiazol-5-yl)phenyl)-4-(2-hydroxypropanamido)-N-((trans-4-(4-methoxy-3-methylphenyl)cyclohexyl)methyl)cyclohexanecarboxamide | 630.4 |
| 27.02 | 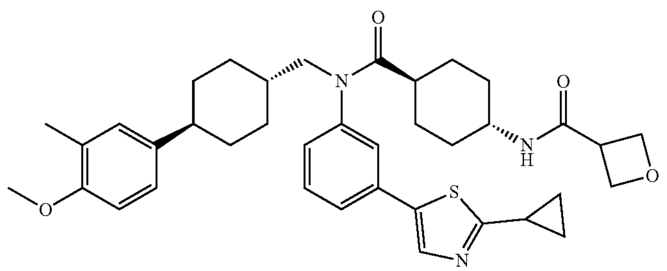 [SMILES: COc1ccc([C@H]2CC[C@H](CN(c3cccc(-c4cnc(C5CC5)s4)c3)C(=O)[C@H]3CC[C@H](NC(=O)C4COC4)CC3)CC2)cc1C] | N-(trans-4-((3-(2-Cyclopropylthiazol-5-yl)phenyl)((trans-4-(4-methoxy-3-methylphenyl)cyclohexyl)methyl)carbamoyl)cyclohexyl)oxetane-3-carboxamide | 642.5 |
| 27.03 | 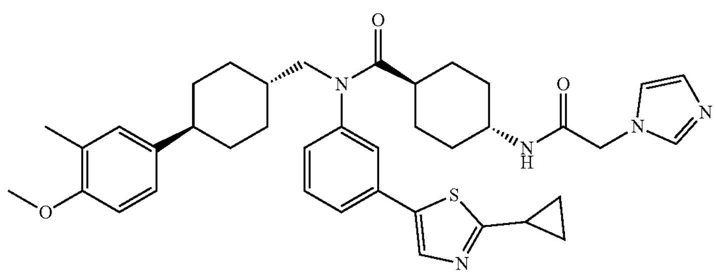 [SMILES: COc1ccc([C@H]2CC[C@H](CN(c3cccc(-c4cnc(C5CC5)s4)c3)C(=O)[C@H]3CC[C@H](NC(=O)Cn4ccnc4)CC3)CC2)cc1C] | trans-4-(2-(1H-Imidazol-1-yl)acetamido)-N-(3-(2-cyclopropylthiazol-5-yl)phenyl)-N-((trans-4-(4-methoxy-3-methylphenyl)cyclohexyl)methyl)cyclohexanecarboxamide | 666.5 |
| 27.04 | 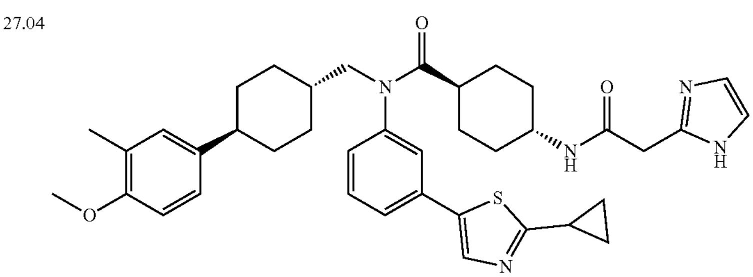 | trans-4-(2-(1H-Imidazol-2-yl)acetamido)-N-(3-(2-cyclopropylthiazol-5-yl)phenyl)-N-((trans-4-(4-methoxy-3-methylphenyl)cyclohexyl)methyl)cyclohexanecarboxamide | 666.6 |
| 27.05 | 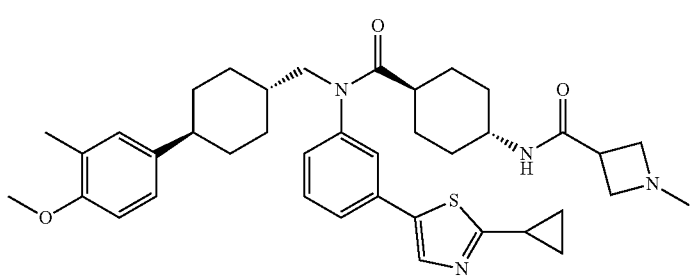 | N-(trans-4-((3-(2-Cyclopropylthiazol-5-yl)phenyl)((trans-4-(4-methoxy-3-methylphenyl)cyclohexyl)methyl)carbamoyl)cyclohexyl)-1-methylazetidine-3-carboxamide | 655.5 |

| Cmpd | Structure | Name | [M + H]⁺ |
|---|---|---|---|
| 27.06 | 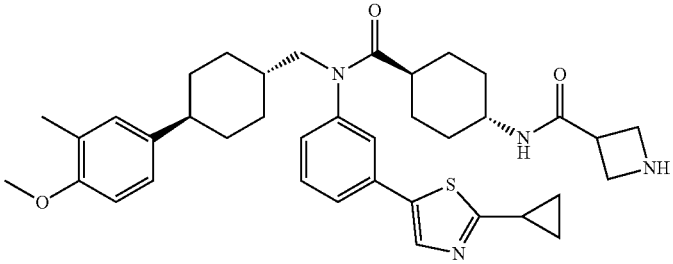 [SMILES: COc1ccc([C@H]2CC[C@H](CN(c3cccc(-c4cnc(C5CC5)s4)c3)C(=O)[C@H]3CC[C@H](NC(=O)C4CNC4)CC3)CC2)cc1C] | N-(trans-4-((3-(2-Cyclopropylthiazol-5-yl)phenyl)((trans-4-(4-methoxy-3-methylphenyl)cyclohexyl)methyl)carbamoyl)cyclohexyl)azetidine-3-carboxamide | 641.5 |

[1]From 1-(tert-butoxycarbonyl)azetidine-3-carboxylic acid after deprotection (TFA/CH₂Cl₂).

Compound 28

2-Hydroxyethyl (trans-4-((3-(2-cyclopropylthiazol-5-yl)phenyl)((trans-4-(4-methoxy-3-methylphenyl)cyclohexyl)methyl)carbamoyl)cyclohexyl)carbamate

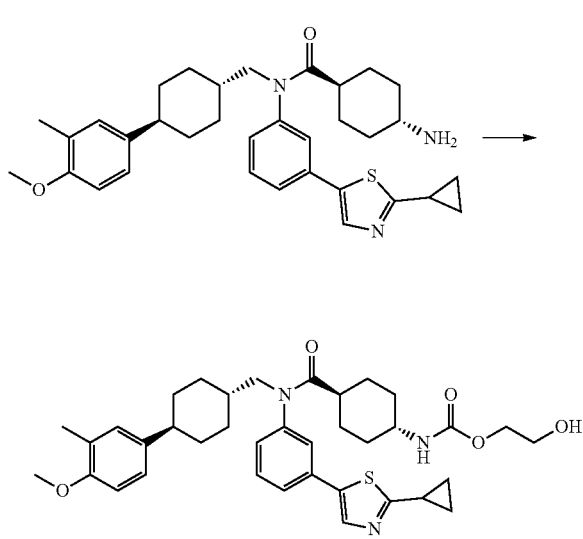

Potassium carbonate (148.6 mg, 1.07 mmol) was added to a solution of Compound 25, Step 2 (200 mg, 0.358 mmol) and 1,3-dioxolan-2-one (94.7 mg, 1.08 mmol) in DMF (5 mL) at rt. The mixture was heated at 120° C. overnight under N₂, poured into water (50 mL), and extracted with EtOAc (3×50 mL). The organic layers were combined, dried over Na₂SO₄, filtered, concentrated, and then purified by reverse-phase HPLC (water(10 mM NH₄HCO₃)-MeCN) to give 2-hydroxyethyl (trans-4-((3-(2-cyclopropylthiazol-5-yl)phenyl)((trans-4-(4-methoxy-3-methylphenyl)cyclohexyl)methyl)carbamoyl)cyclohexyl)carbamate (19 mg, 8%) as a white solid. ¹H NMR (400 MHz, DMSO-d₆): δ 8.09 (s, 1H), 7.48-7.63 (m, 3H), 7.27 (d, 1H), 6.94-6.86 (m, 3H), 6.79-6.738 (m, 1H), 4.69-4.63 (m, 1H), 3.89-3.83 (m, 2H), 3.72 (s, 3H), 3.70-3.49 (m, 4H), 3.19-3.12 (m, 1H), 2.34-2.33 (m, 1H), 2.15-1.96 (m, 4H), 1.85-1.55 (m, 9H), 1.48-1.38 (m, 3H), 1.37-1.27 (d, 2H), 1.18-0.97 (m, 6H), 0.93-0.81 (m, 2H); LCMS: 646.3 [M+H]⁺.

Compound 29

2-((trans-4-((3-(1-Isopropyl-1H-pyrazol-4-yl)phenyl)((trans-4-(4-methoxy-3-methylphenyl)cyclohexyl)methyl)carbamoyl)cyclohexyl)amino)acetic Acid

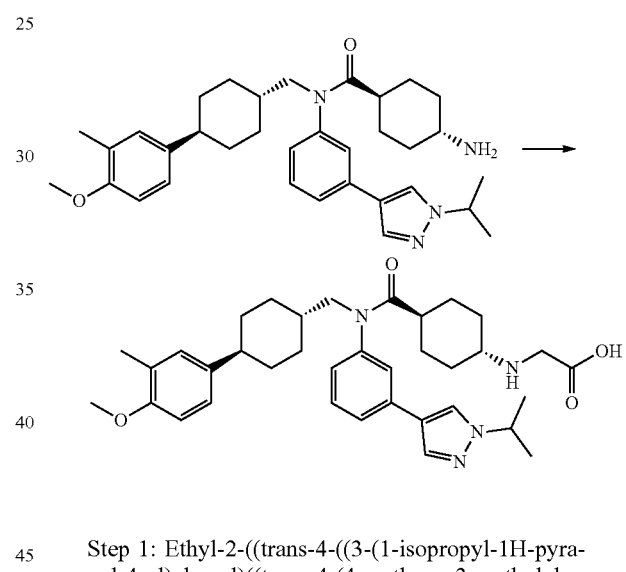

Step 1: Ethyl-2-((trans-4-((3-(1-isopropyl-1H-pyrazol-4-yl)phenyl)((trans-4-(4-methoxy-3-methylphenyl)cyclohexyl)methyl)carbamoyl)cyclohexyl)amino)acetate Ethyl-2-bromoacetate (257.2 mg, 1.54 mmol) was added to a solution of Compound 26.10, Step 2 (380 mg, 0.7 mmol), Et₃N (0.22 mL, 1.54 mmol), and CH₂C₂(5 mL). The reaction was stirred at rt overnight, concentrated, and then purified by silica gel chromatography (petroleum ether/EtOAc/EtOH=4/3/1). The compound was further purified by reverse-phase HPLC (water(0.05% HCl)/MeCN) to give ethyl-2-((trans-4-((3-(1-isopropyl-1H-pyrazol-4-yl)phenyl)((trans-4-(4-methoxy-3-methylphenyl)cyclohexyl)methyl)carbamoyl)cyclohexyl)amino)acetate (65.5 mg, 15%) as a white solid. ¹H NMR (400 MHz, DMSO-d₆) δ 8.32 (s, 1H), 7.94 (s, 1H), 7.60 (d, 1H), 7.55-7.51 (m, 1H), 7.43 (t, 1H), 7.12-7.02 (m, 1H), 6.98-6.90 (m, 2H), 6.82-6.73 (m, 1H), 4.58-4.42 (m, 1H), 4.04 (q, 2H), 3.71 (s, 3H), 3.64-3.44 (m, 2H), 3.38-3.32 (m, 4H), 2.40-2.21 (m, 1H), 2.15-2.00 (m, 4H), 1.83-1.58 (m, 8H), 1.48-1.41 (m, 7H), 1.40-1.22 (m, 4H), 1.11 (t, 3H), 1.07-0.96 (m, 2H), 0.70-0.51 (m, 2H); LCMS: 629.5 [M+H]⁺.

Step 2: 2-((trans-4-((3-(1-Isopropyl-1H-pyrazol-4-yl)phenyl)((trans-4-(4-methoxy-3-methylphenyl)cyclohexyl)methyl)carbamoyl)cyclohexyl)amino)acetic Acid Lithium hydroxide monohydrate (53.4 mg, 1.27 mmol) was added to a solution of ethyl-2-((trans-4-((3-(1-isopropyl-1H-pyrazol-4-yl)phenyl)((trans-4-(4-methoxy-3-methylphenyl)cyclohexyl)methyl)carbamoyl)cyclohexyl)amino)acetate (100 mg, 0.16 mmol), THF (4 mL), and H$_2$O (1 mL) at 0° C. The reaction was allowed to warm to rt and stirred overnight. The resulting solution was concentrated at rt to remove most of the THF, diluted with H$_2$O (10 mL), and then further concentrated until 5 mL of H$_2$O was removed. The mixture was cooled to 0° C. and 1 M HCl was added dropwise under vigorous stirring (to avoid clumping) to pH=6. The solid was filtered, washed with ice H$_2$O (20 mL), and then dried on high vacuum to give 2-((trans-4-((3-(1-isopropyl-1H-pyrazol-4-yl)phenyl)((trans-4-(4-methoxy-3-methylphenyl)cyclohexyl)methyl)carbamoyl)cyclohexyl)amino)acetic acid (70 mg, 73%) as a white solid. $^1$H NMR (400 MHz, DMSO-d$_6$) δ 8.34 (s, 1H), 7.95 (s, 1H), 7.61 (d, 1H), 7.56 (s, 1H), 7.45 (t, 1H), 7.14-7.05 (m, 1H), 7.02-6.87 (m, 2H), 6.83-6.70 (m, 1H), 4.59-4.42 (m, 1H), 3.85-3.55 (m, 5H), 3.15-3.01 (m, 2H), 2.88-2.72 (m, 1H), 2.40-2.27 (m, 1H), 2.21-2.03 (m, 4H), 2.01-1.85 (m, 2H), 1.85-1.65 (m, 6H), 1.53-1.24 (m, 11H), 1.15-0.86 (m, 4H); LCMS: 601.4 [M+H]$^+$.

Compound 30

Trans-N-(3-(1-Cyclopropyl-1H-pyrazol-4-yl)phenyl)-N-((trans-4-(4-methoxy-3-methylphenyl)cyclohexyl)methyl)-4-(3-methoxycyclobutanecarboxamido)cyclohexanecarboxamide

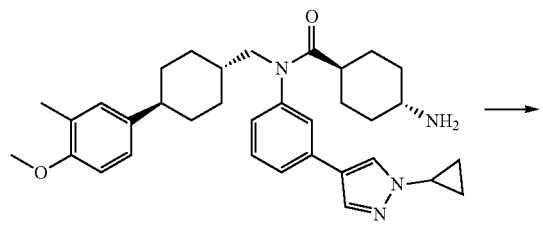

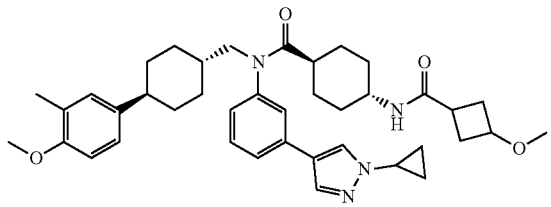

A mixture of Compound 26, Step 2 (80 mg, 0.15 mmol), 3-methoxycyclobutane carboxylic acid (30 mg, 0.23 mmol), EDCI (47 mg, 0.24 mmol), iPr$_2$NEt (89 μL, 0.51 mmol) and dichloromethane (0.8 mL) was stirred at rt for 4 h and then diluted with EtOAc (10 mL). The organics were washed with water (10 mL), washed with brine (10 mL), dried (Na$_2$SO$_4$), filtered, concentrated and then purified by silica gel chromatography (0-10% methanol in dichloromethane) to give trans-N-(3-(1-cyclopropyl-1H-pyrazol-4-yl)phenyl)-N-((trans-4-(4-methoxy-3-methylphenyl)cyclohexyl)methyl)-4-(3-methoxycyclobutanecarboxamido)cyclohexanecarboxamide as a pale yellow foam (77 mg, 79% yield). $^1$H NMR (400 MHz, DMSO-d$_6$) δ 8.34 (s, 1H), 7.93 (s, 1H), 7.59 (d, 1H), 7.54 (s, 1H), 7.44 (t, 1H), 7.40 (d, 1H), 7.10 (d, 1H), 6.97-6.92 (m, 2H), 6.78 (d, 1H), 3.77-3.69 (m, 4H), 3.69-3.60 (m, 1H), 3.60-3.49 (m, 2H), 3.46-3.35 (m, 1H), 3.07 (s, 3H), 2.38-2.25 (m, 2H), 2.23-2.14 (m, 2H), 2.11-2.01 (m, 4H), 1.89-1.80 (m, 2H), 1.80-1.61 (m, 8H), 1.48-1.36 (m, 3H), 1.36-1.22 (m, 2H), 1.11-0.95 (m, 6H), 0.84-0.70 (m, 2H); LCMS: 653.6 [M+H]$^+$.

The Compound below was synthesized from the appropriate amine and the appropriate acid following the procedure described for Compound 30.

| Cmpd | Structure | Name | [M + H]$^+$ |
|---|---|---|---|
| 30.01 | 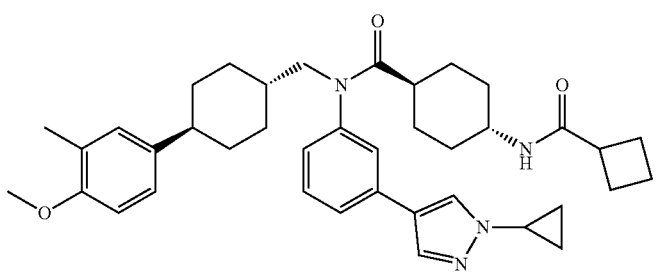 [SMILES: COc1ccc([C@H]2CC[C@H](CN(c3cccc(-c4cnn(C5CC5)c4)c3)C(=O)[C@H]3CC[C@H](NC(=O)C4CCC4)CC3)CC2)cc1C] | trans-4-(Cyclobutanecarboxamido)-N-(3-(1-cyclopropyl-1H-pyrazol-4-yl)phenyl)-N-((trans-4-(4-methoxy-3-methylphenyl)cyclohexyl)methyl)cyclohexanecarboxamide | 623.5 |

-continued

| Cmpd | Structure | Name | [M + H]+ |
|---|---|---|---|
| 30.02 | 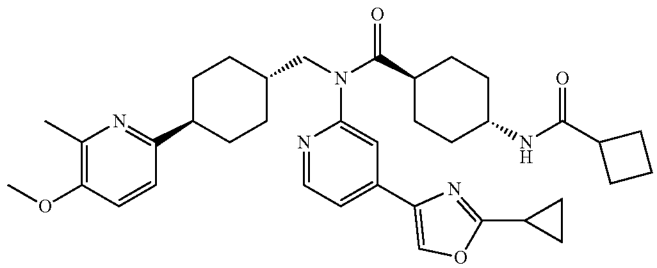 [SMILES: COc1ccc([C@H]2CC[C@H](CN(c3cc(-c4coc(C5CC5)n4)ccn3)C(=O)[C@H]3CC[C@H](NC(=O)C4CCC4)CC3)CC2)nc1C] | trans-4-(cyclobutanecarboxamido)-trans-(4-(2-cyclopropyloxazol-4-yl)pyridine-2-yl)-N-((trans-4-(5-methoxy-6-methylpyridin-2-yl)cyclohexyl)methyl)cyclohexanecarboxamide | 626.5 |
| 30.03 | 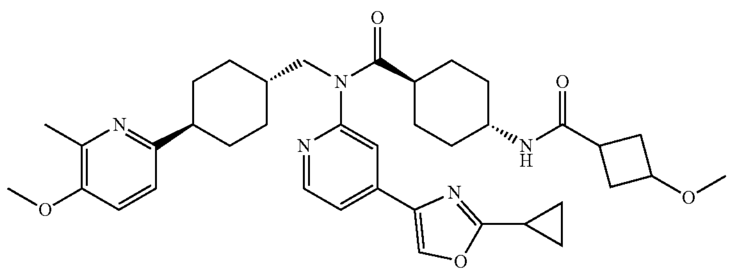 | trans-N-(4-(2-Cyclopropyloxazol-4-yl)pyridin-2-yl)-N-((trans-4-(5-methoxy-6-methylpyridin-2-yl)cyclohexyl)methyl)-4-(3-methoxycyclobutanecarboxamido)cyclohexanecarboxamide | 656.7 |
| 30.04 | 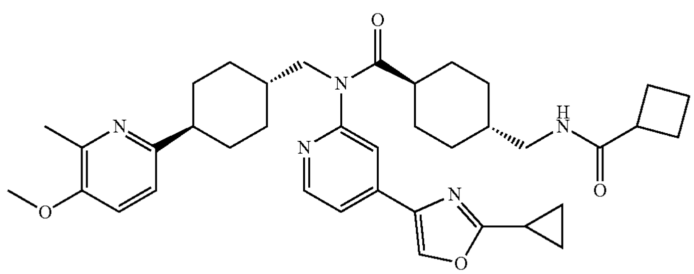 [SMILES: COc1ccc([C@H]2CC[C@H](CN(c3cc(-c4coc(C5CC5)n4)ccn3)C(=O)[C@H]3CC[C@H](CNC(=O)C4CCC4)CC3)CC2)nc1C] | trans-4-(Cyclobutanecarboxamidomethyl)-N-(4-(2-cyclopropyloxazol-4-yl)pyridin-2-yl)-N-((trans-4-(5-methoxy-6-methylpyridin-2-yl)cyclohexyl)methyl)cyclohexanecarboxamide | 640.6 |
| 30.05 | 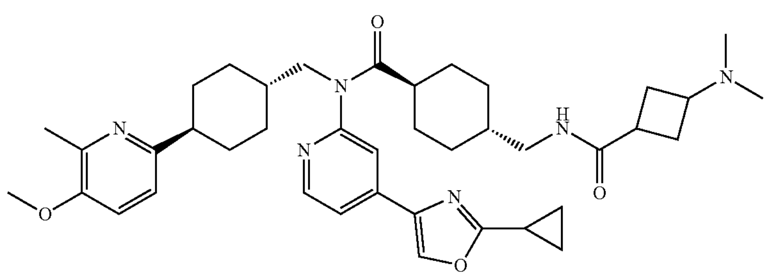 | trans-N-(4-(2-Cyclopropyloxazol-4-yl)pyridin-2-yl)-4((3-(dimethylamino)cyclobutanecarboxamido)methyl)-N-((trans-4-(5-methoxy-6-methylpyridin-2-yl)cyclohexyl)methyl)cyclohexanecarboxamide | 683.4 |
| 30.06[1] | 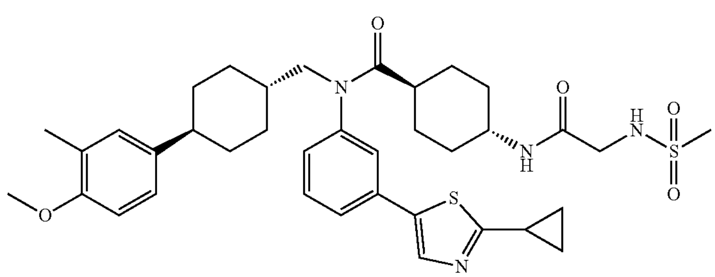 | trans-N-(3-(2-Cyclopropylthiazol-5-yl)phenyl)-N-((trans-4-(4-methoxy-3-methylphenyl)cyclohexyl)methyl)-4-(2-(methylsulfonamido)acetamido)cyclohexanecarboxamide | 693.3 |

[1] EDCI, HOBt, iPr2NEt, DMF, 0° C.-rt, overnight.

Compound 31

Methyl (2-((trans-4-((3-(1-cyclopropyl-1H-pyrazol-4-yl)phenyl)((trans-4-(4-methoxy-3-methylphenyl)cyclohexyl)methyl)carbamoyl)cyclohexyl)amino)-2-oxoethyl)carbamate

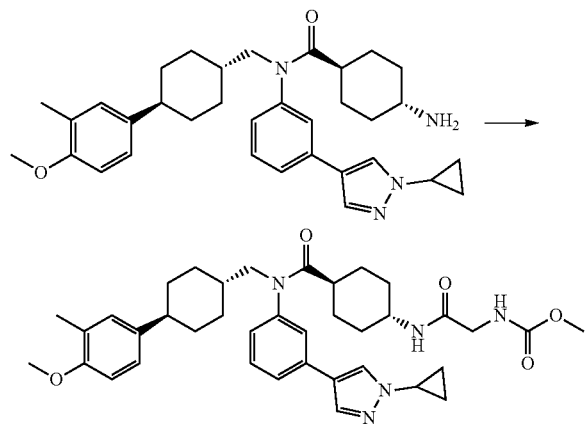

Triethylamine (449.1 mg, 4.44 mmol) was added to a solution of Compound 26, Step 2 (200 mg, 0.37 mmol) and 2-((methoxycarbonyl)amino)acetic acid (147.7 mg, 1.11 mmol) in DMF (3 mL) under $N_2$ at 0° C. Then 2,4,6-tripropyl-1,3,5,2,4,6-trioxatriphosphinane 2,4,6-trioxide (942 mg, 1.48 mmol, 50% purity) was added dropwise at 0° C. The mixture was allowed to warm to rt and stirred overnight. The mixture was poured into $H_2O$ (40 mL) and then extracted with EtOAc (3×50 mL). The combined organic layers were washed with brine (30 mL), dried over $Na_2SO_4$, filtered, concentrated, and then purified by reverse-phase prep-HPLC (water(10 mM $NH_4HCO_3$)/MeCN) to give methyl (2-((trans-4-((3-(1-cyclopropyl-1H-pyrazol-4-yl)phenyl)((trans-4-(4-methoxy-3-methylphenyl)cyclohexyl)methyl)carbamoyl)cyclohexyl)amino)-2-oxoethyl)carbamate (35.1 mg, 14%) as a white solid. $^1$H NMR (400 MHz, DMSO-$d_6$): δ 8.34 (s, 1H), 7.93 (s, 1H), 7.60 (d, 1H), 7.55 (s, 1H), 7.51-7.41 (m, 2H), 7.18-7.08 (m, 2H), 6.97-6.92 (m, 2H), 6.81-6.74 (m, 1H), 3.78-3.69 (m, 4H), 3.65-3.52 (m, 2H), 3.49 (s, 3H), 3.46-3.38 (m, 3H), 2.38-2.28 (m, 1H), 2.12-2.03 (m, 4H), 1.81-1.62 (m, 8H), 1.50-1.37 (m, 3H), 1.35-1.22 (m, 2H), 1.12-0.95 (m, 6H), 0.91-0.77 (in, 2H); LCMS: 656.3 [M+H]$^+$.

The Compounds below were synthesized from Compound 26, Step 2 or Compound 25, Step 2 and the appropriate acids following the procedure described for Compound 31.

| Cmpd | Structure | Name | [M + H]$^+$ |
|---|---|---|---|
| 31.01 | 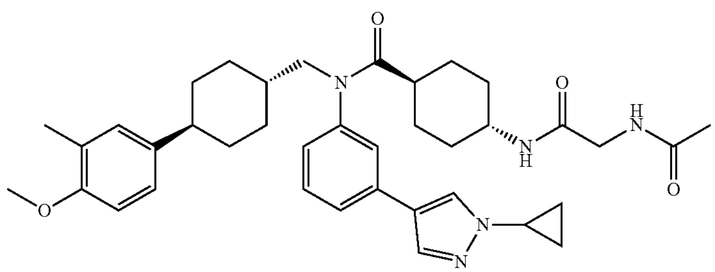 [SMILES: COc1ccc([C@H]2CC[C@H](CN(c3cccc(-c4cnn(C5CC5)c4)c3)C(=O)[C@H]3CC[C@H](NC(=O)CNC(C)=O)CC3)CC2)cc1C] | trans-4-(2-Acetamidoacetamido)-N-(3-(1-cyclopropyl-1H-pyrazol-4-yl)phenyl)-N-((trans-4-(4-methoxy-3-methylphenyl)cyclohexyl)methyl)cyclohexanecarboxamide | 640.6 |
| 31.02 | 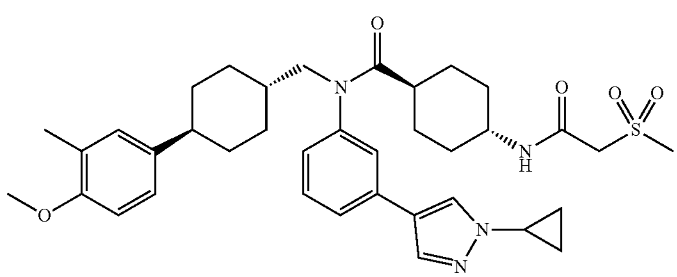 | trans-N-(3-(1-Cyclopropyl-1H-pyrazol-4-yl)phenyl)-N-((trans-4-(4-methoxy-3-methylphenyl)cyclohexyl)methyl)-4-(2-(methylsulfonyl)acetamido)cyclohexanecarboxamide | 661.3 |
| 31.03 | 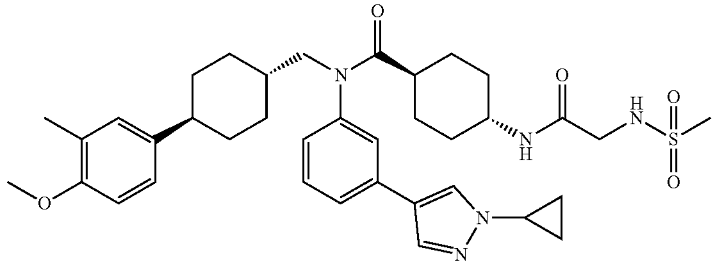 | trans-N-(3-(1-Cyclopropyl-1H-pyrazol-4-yl)phenyl)-N-((trans-4-(4-methoxy-3-methylphenyl)cyclohexyl)methyl)-4-(2-(methylsulfonamido)acetamido)cyclohexanecarboxamide | 676.6 |

-continued

| Cmpd | Structure | Name | [M + H]+ |
|---|---|---|---|
| 31.04[1] | 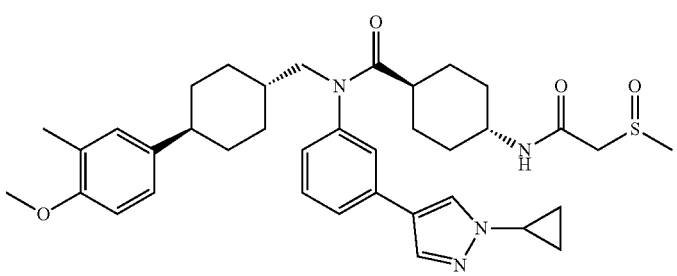 | trans-N-(3-(1-Cyclopropyl-1H-pyrazol-4-yl)phenyl)-N-((trans-4-(4-methoxy-3-methylphenyl)cyclohexyl)methyl)-4-(2-(methylsulfinyl)acetamido)cyclohexanecarboxamide | 645.3 |
| 31.05 | 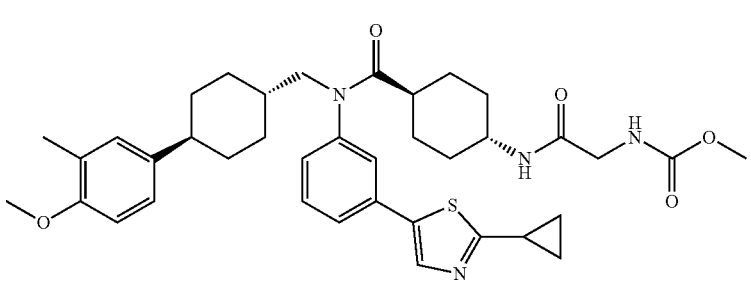 | Methyl (2-((trans-4-((3-(2-cyclopropylthiazol-5-yl)phenyl)((trans-4-(4-methoxy-3-methylphenyl)cyclohexyl)methyl)carbamoyl)cyclohexyl)amino)-2-oxoethyl)carbamate | 673.3 |
| 31.06 | 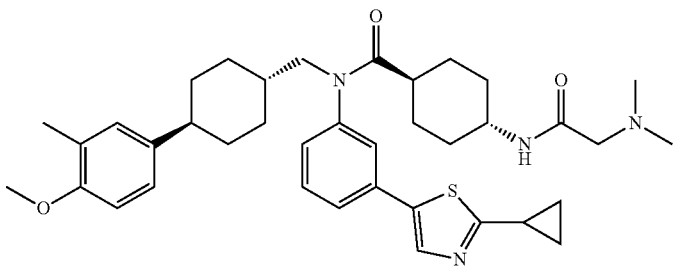 | trans-N-(3-(2-Cyclopropylthiazol-5-yl)phenyl)-4-(2-(dimethylamino)acetamido)-N-((trans-4-(4-methoxy-3-methylphenyl)cyclohexyl)methyl)cyclohexanecarboxamide | 643.4 |
| 31.07[3] | 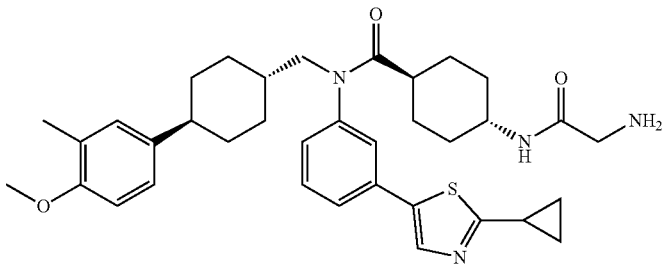 [SMILES: COc1ccc([C@H]2CC[C@H](CN(c3cccc(-c4cnc(C5CC5)s4)c3)C(=O)[C@H]3CC[C@H](NC(=O)CN)CC3)CC2)cc1C] | trans-4-(2-Aminoacetamido)-N-(3-(2-cyclopropylthiazol-5-yl)phenyl)-N-((trans-4-(4-methoxy-3-methylphenyl)cyclohexyl)methyl)cyclohexanecarboxamide | 615.4 |
| 31.08[3] | 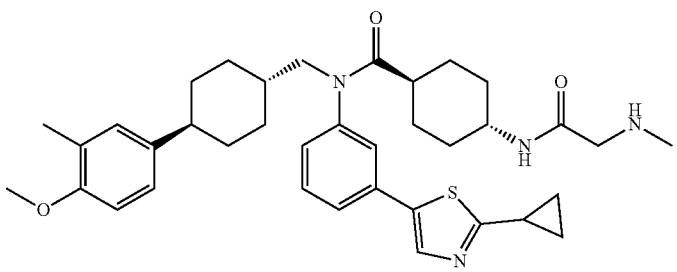 | trans-N-(3-(2-Cyclopropylthiazol-5-yl)phenyl)-N-((trans-4-(4-methoxy-3-methylphenyl)cyclohexyl)methyl)-4-(2-(methylamino)acetamido)cyclohexanecarboxamide | 629.5 |

-continued

| Cmpd | Structure | Name | [M + H]+ |
|---|---|---|---|
| 31.09 | 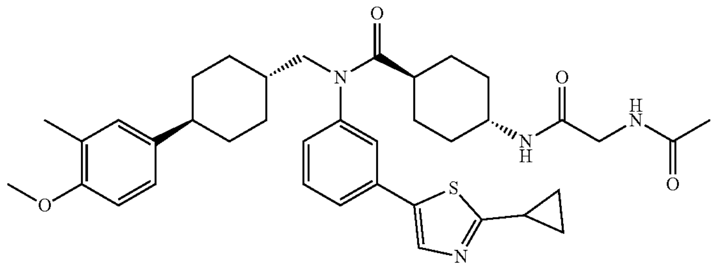 [SMILES: COc1ccc([C@H]2CC[C@H](CN(c3cccc(-c4cnc(C5CC5)s4)c3)C(=O)[C@H]3CC[C@H](NC(=O)CNC(C)=O)CC3)CC2)cc1C] | trans-4-(2-Acetamidoacetamido)-N-(3-(2-cyclopropylthiazol-5-yl)phenyl)-N-((trans-4-(4-methoxy-3-methylphenyl)cyclohexyl)methyl)cyclohexanecarboxamide | 657.4 |
| 31.10 | 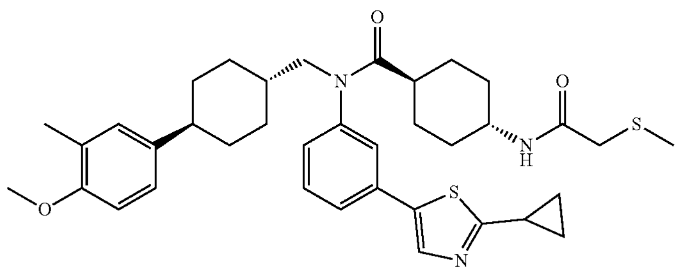 | trans-N-(3-(2-Cyclopropylthiazol-5-yl)phenyl)-N-((trans-4-(4-methoxy-3-methylphenyl)cyclohexyl)methyl)-4-(2-(methylthio)acetamido)cyclohexanecarboxamide | 646.6 |
| 31.11[2] | 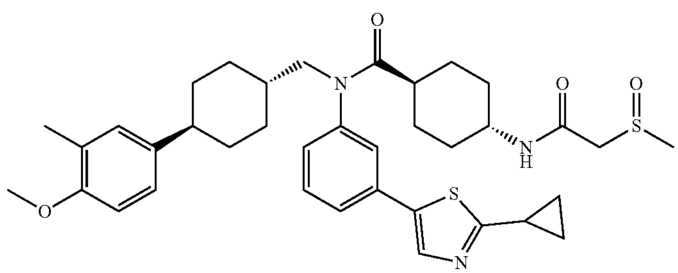 | trans-N-(3-(2-Cyclopropylthiazol-5-yl)phenyl)-N-((trans-4-(4-methoxy-3-methylphenyl)cyclohexyl)methyl)-4-(2-(methylsulfinyl)acetamido)cyclohexanecarboxamide | 662.5 |
| 31.12 | 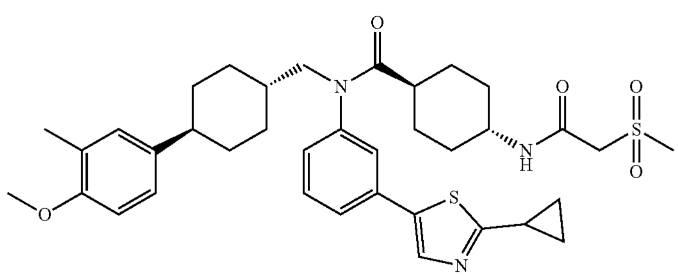 | trans-N-(3-(2-Cyclopropylthiazol-5-yl)phenyl)-N-((trans-4-(4-methoxy-3-methylphenyl)cyclohexyl)methyl)-4-(2-(methylsulfonyl)acetamido)cyclohexanecarboxamide | 678.5 |
| 31.13[1] | 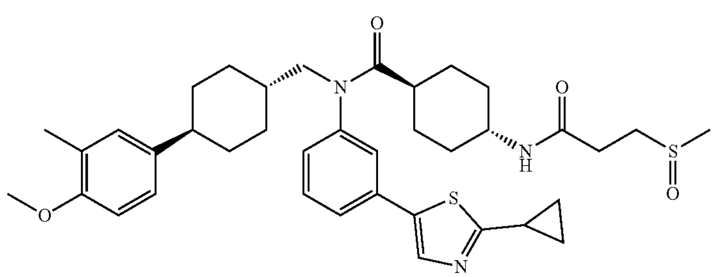 | trans-N-(3-(2-Cyclopropylthiazol-5-yl)phenyl)-N-((trans-4-(4-methoxy-3-methylphenyl)cyclohexyl)methyl)-4-(3-(methylsulfinyl)propanamido)cyclohexanecarboxamide | 676.2 |

| Cmpd | Structure | Name | [M + H]+ |
|---|---|---|---|
| 31.14 | 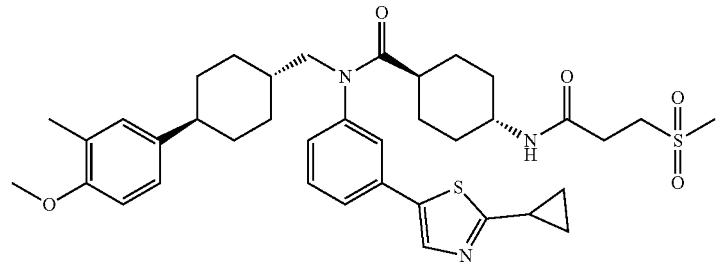 | trans-N-(3-(2-Cyclopropylthiazol-5-yl)phenyl)-N-((trans-4-(4-methoxy-3-methylphenyl)cyclohexyl)methyl)-4-(3-(methylsulfonyl)propanamido)cyclohexanecarboxamide | 692.5 |
| 31.15 | 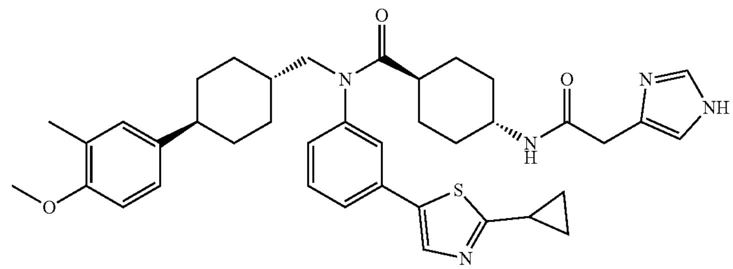 [SMILES: COc1ccc([C@H]2CC[C@H](CN(c3cccc(-c4cnc(C5CC5)s4)c3)C(=O)[C@H]3CC[C@H](NC(=O)Cc4c[nH]cn4)CC3)CC2)cc1C] | trans-4-(2-(1H-Imidazol-4-yl)acetamido)-N-(3-(2-cyclopropylthiazol-5-yl)phenyl)-N-((trans-4-(4-methoxy-3-methylphenyl)cyclohexyl)methyl)cyclohexanecarboxamide | 666.5 |

[1]From oxidation of sulfide (NaOI4, THF/H2O, 0° C.-rt, overnight). [2]From Compound 31.10 (m-CPBA, CH2Cl2, 0° C.-rt, 2h). [3]After removal of Boc (HCl/EtOAc).

Compound 32

Trans-N-(3-(1-Cyclopropyl-1H-pyrazol-4-yl)phenyl)-4-(2-(3-hydroxypropoxy)acetamido)-N-((trans-4-(4-methoxy-3-methylphenyl)cyclohexyl)methyl)cyclohexanecarboxamide

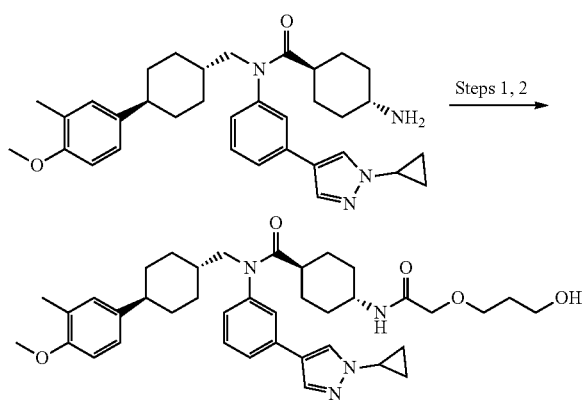

Step 1: Trans-4-(2-Chloroacetamido)-N-(3-(1-cyclopropyl-1H-pyrazol-4-yl)phenyl)-N-((trans-4-(4-methoxy-3-methylphenyl)cyclohexyl)methyl)cyclohexanecarboxamide A solution of Compound 26, Step 2 (500 mg, 0.924 mmol) and pyridine (789.9 mg, 9.99 mmol) in $CH_2Cl_2$ (5 mL) was degassed and purged with $N_2$ 3 times at 0° C. 2-Chloroacetyl chloride (313.3 mg, 2.77 mmol) was added. The mixture was allowed to warm to rt and stirred for 2 h under $N_2$. The mixture was poured into water (60 mL) and extracted with EtOAc (3×40 mL). The organic layer was combined, dried over $Na_2SO_4$, filtered, concentrated, and then purified by prep-TLC ($SiO_2$, $CH_2Cl_2/CH_3OH$=10/1) to give trans-4-(2-chloroacetamido)-N-(3-(1-cyclopropyl-1H-pyrazol-4-yl)phenyl)-N-((trans-4-(4-methoxy-3-methylphenyl)cyclohexyl)methyl)cyclohexanecarboxamide (400 mg, 70%) as a black brown solid. $^1$H NMR (400 MHz, $CDCl_3$): δ 7.75 (d, 2H), 7.51-7.40 (m, 2H), 7.29-7.24 (m, 1H), 7.04 (d, 1H), 6.99-6.93 (m, 2H), 6.74 (d, 1H), 6.23 (d, 1H), 3.98 (s, 2H), 3.80 (s, 3H), 3.78-3.71 (m, 1H), 3.70-3.57 (m, 3H), 2.46-2.34 (m, 1H), 2.25-2.11 (m, 4H), 2.07-1.92 (m, 2H), 1.92-1.68 (m, 8H), 1.43-1.28 (m, 2H), 1.27-1.05 (m, 7H), 1.03-0.87 (m, 2H); LCMS: 617.2 [M+H]+.

Step 2: Trans-N-(3-(1-Cyclopropyl-1H-pyrazol-4-yl)phenyl)-4-(2-(3-hydroxypropoxy)acetamido)-N-((trans-4-(4-methoxy-3-methylphenyl)cyclohexyl)methyl)cyclohexanecarboxamide Sodium hydride (12.2 mg, 0.303 mmol, 60% purity) was added to a solution of propane-1,3-diol (31.4 mg, 0.413 mmol) in DMF (5 mL) at 0° C. under $N_2$. After 30 min at 0° C., trans-4-(2-chloroacetamido)-N-(3-(1-cyclopropyl-1H-pyrazol-4-yl)phenyl)-N-((trans-4-(4-methoxy-3-methylphenyl)cyclohexyl)methyl)cyclohexanecarboxamide (170 mg, 0.275 mmol) was added, and the reaction was allowed to stir at rt overnight. The mixture was poured into water (30 mL) and extracted with EtOAc (3×50 mL). The combined organic layers were dried over $Na_2SO_4$, filtered, concentrated, and then purified by reverse-phase HPLC (water(10 mM $NH_4HCO_3$)/MeCN) to give trans-N-(3-(1-cyclopropyl-1H-pyrazol-4-yl)phenyl)-4-(2-(3-hydroxypropoxy)acetamido)-N-((trans-4-(4-methoxy-3-methylphenyl)cyclohexyl)methyl)cyclohexanecarboxamide (18.1 mg, 10%) as a white solid. $^1$H NMR (400 MHz, DMSO-$d_6$): δ 8.33 (s, 1H), 7.93 (s, 1H), 7.59 (d, 1H), 7.54 (s, 1H), 7.44 (t, 1H), 7.37 (d, 1H), 7.10 (d, 1H), 7.01-6.88 (m, 2H), 6.84-6.68 (m, 1H), 4.45-4.41 (m, 1H), 3.81-3.71 (m, 5H), 3.64-3.45 (m, 3H), 3.45-3.39 (m, 5H), 2.39-2.26 (m, 1H), 2.12-2.01 (m, 4H), 1.84-1.54 (m, 10H), 1.52-1.35 (m, 3H), 1.33-1.21 (m, 2H), 1.14-0.85 (m, 8H); LCMS: 657.4 [M+H]+.

The Compounds below were synthesized from the appropriate starting materials following the procedures described for Compound 32.

| Cmpd | Structure | Name | [M + H]⁺ |
|---|---|---|---|
| 32.01 | 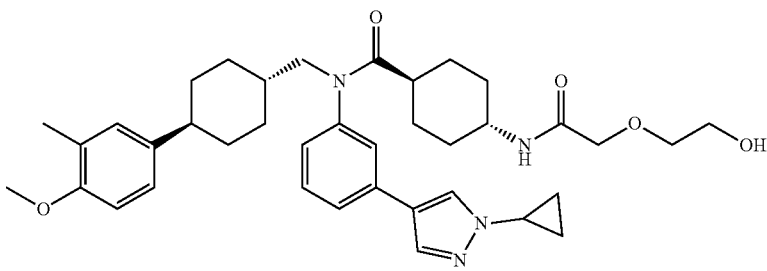 [SMILES: COc1ccc([C@H]2CC[C@H](CN(c3cccc(-c4cnn(C5CC5)c4)c3)C(=O)[C@H]3CC[C@H](NC(=O)COCCO)CC3)CC2)cc1C] | trans-N-(3-(1-Cyclopropyl-1H-pyrazol-4-yl)phenyl)-4-(2-(2-hydroxyethoxy)acetamido)-N-((trans-4-(4-methoxy-3-methylphenyl)cyclohexyl)methyl)cyclohexanecarboxamide | 643.8 |
| 32.02 | 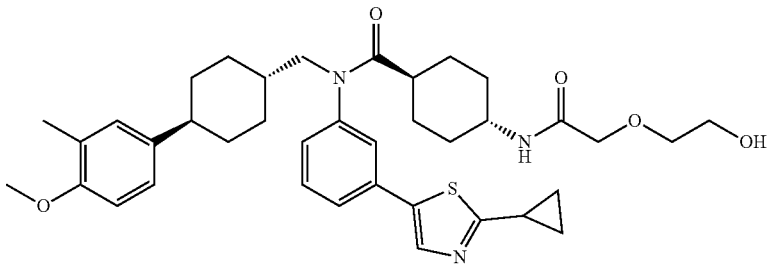 [SMILES: COc1ccc([C@H]2CC[C@H](CN(c3cccc(-c4cnc(C5CC5)s4)c3)C(=O)[C@H]3CC[C@H](NC(=O)COCCO)CC3)CC2)cc1C] | trans-N-(3-(2-Cyclopropylthiazol-5-yl)phenyl)-4-(2-(2-hydroxyethoxy)acetamido)-N-((trans-4-(4-methoxy-3-methylphenyl)cyclohexyl)methyl)cyclohexanecarboxamide | 660.6 |
| 32.03 | 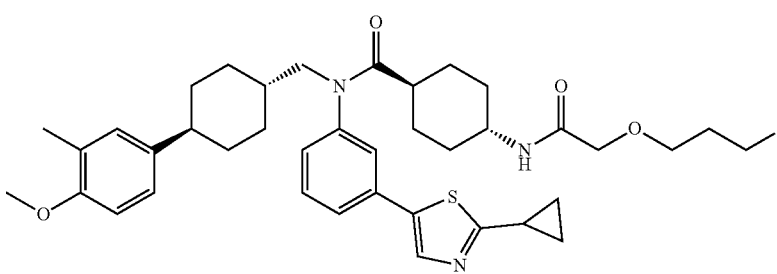 | trans-N-(3-(2-Cyclopropylthiazol-5-yl)phenyl)-4-(2-(3-hydroxypropoxy)acetamido)-N-((trans-4-(4-methoxy-3-methylphenyl)cyclohexyl)methyl)cyclohexanecarboxamide | 674.5 |
| 32.04 | 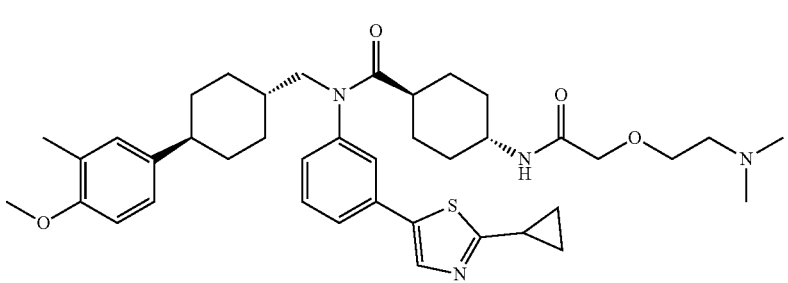 | trans-N-(3-(2-Cyclopropylthiazol-5-yl)phenyl)-4-(2-(2-(dimethylamino)ethoxy)acetamido)-N-((trans-4-(4-methoxy-3-methylphenyl)cyclohexyl)methyl)cyclohexanecarboxamide | 687.6 |

| Cmpd | Structure | Name | [M + H]+ |
|---|---|---|---|
| 32.05[1] | 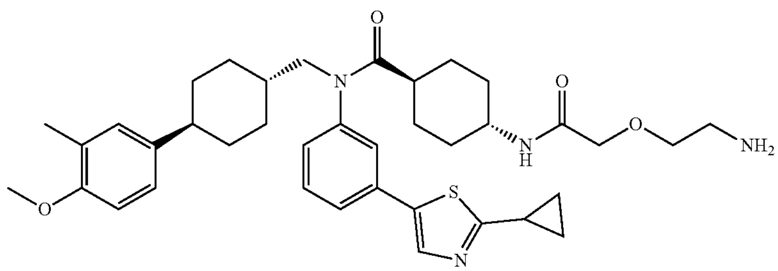 [SMILES: COc1ccc([C@H]2CC[C@H](CN(c3cccc(-c4cnc(C5CC5)s4)c3)C(=O)[C@H]3CC[C@H](NC(=O)COCCN)CC3)CC2)cc1C] | trans-4-(2-(2-Aminoethoxy)acetamido)-N-(3-(2-cyclopropylthiazol-5-yl)phenyl)-N-((trans-4-(4-methoxy-3-methylphenyl)cyclohexyl)methyl)cyclohexanecarboxamide | 659.5 |
| 32.06 | 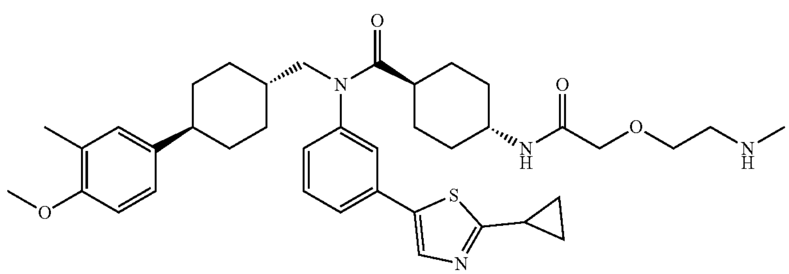 | trans-N-(3-(2-Cyclopropylthiazol-5-yl)phenyl)-N-((trans-4-(4-methoxy-3-methylphenyl)cyclohexyl)methyl)-4-(2-(2-(methylamino)ethoxy)acetamido)cyclohexanecarboxamide | 673.5 |

[1]From Boc-protected amino alcohol (NaOH TBAI, toluene, 80° C.; then TFA/CH$_2$Cl$_2$, rt, 3 h).

Compound 33

Trans-N-(3-(2-Cyclopropylthiazol-5-yl)phenyl)-N-((trans-4-(4-methoxy-3-methylphenyl)cyclohexyl)methyl)-4-(2H-tetrazol-5-yl)cyclohexanecarboxamide

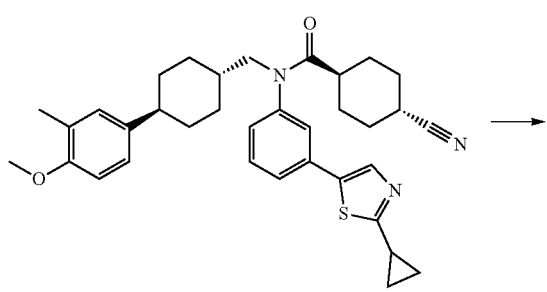

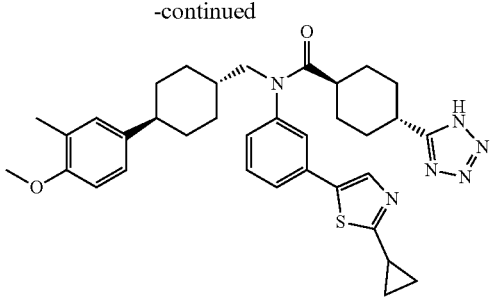

A solution of Intermediate 21.21 (345 mg, 0.607 mmol), TMSN$_3$ (700 mg, 6.08 mmol), dibutylstannanone (75.63 mg, 0.303 mmol) and toluene (25 mL) was heated at 120° C. overnight under N$_2$, allowed to cool to rt, and then concentrated to dryness. The crude product was purified by reverse-phase prep-HPLC (water(0.05% HCl))/CH$_3$CN) to give trans-N-(3-(2-cyclopropylthiazol-5-yl)phenyl)-N-((trans-4-(4-methoxy-3-methylphenyl)cyclohexyl)methyl)-4-(2H-tetrazol-5-yl)cyclohexanecarboxamide (108.2 mg, 29%) as a white solid. H NMR (400 MHz, CD$_3$OD): δ 7.99 (s, 1H), 7.69 (d, 1H), 7.63-7.56 (m, 2H), 7.34 (d, 1H), 7.01-6.91 (m, 2H), 6.77 (d, 1H), 3.78 (s, 3H), 3.76-3.60 (m, 2H), 3.09-2.96 (m, 1H), 2.47-2.32 (m, 3H), 2.15 (s, 3H), 2.07 (d, 2H), 1.98-1.82 (m, 6H), 1.81-1.68 (m, 2H), 1.64-1.51 (m, 1H), 1.49-1.30 (m, 4H), 1.30-1.17 (m, 4H), 1.14-1.08 (m, 2H); LCMS: 611.3 [M+H]+.

The Compound below was synthesized from Intermediate 21.23 following the procedure described for Compound 33.

| Cmpd | Structure | Name | [M + H]+ |
|---|---|---|---|
| 33.01 | 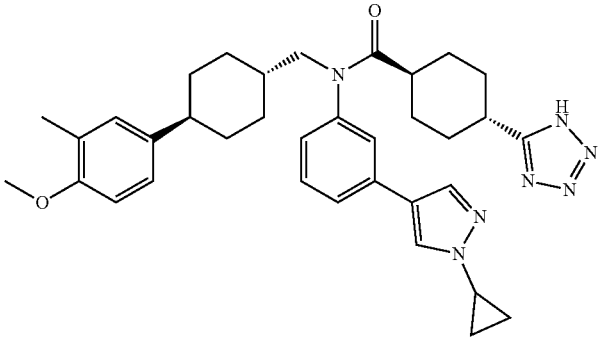 [SMILES: COc1ccc([C@H]2CC[C@H](CN(c3cccc(-c4cnn(C5CC5)c4)c3)C(=O)[C@H]3CC[C@H](c4nnn[nH]4)CC3)CC2)cc1C] | trans-N-(3-(1-Cyclopropyl-1H-pyrazol-4-yl)phenyl)-N-((trans-4-(4-methoxy-3-methylphenyl)cyclohexyl)methyl)-4-(2H-tetrazol-5-yl)cyclohexanecarboxamide | 594.3 |

Compound 34

Trans-N-(3-(1-Cyclopropyl-1H-pyrazol-4-yl)phenyl)-N-((trans-4-(4-methoxy-3-methylphenyl)cyclohexyl)methyl)-4-(5-oxo-4,5-dihydro-1,2,4-oxadiazol-3-yl)cyclohexanecarboxamide

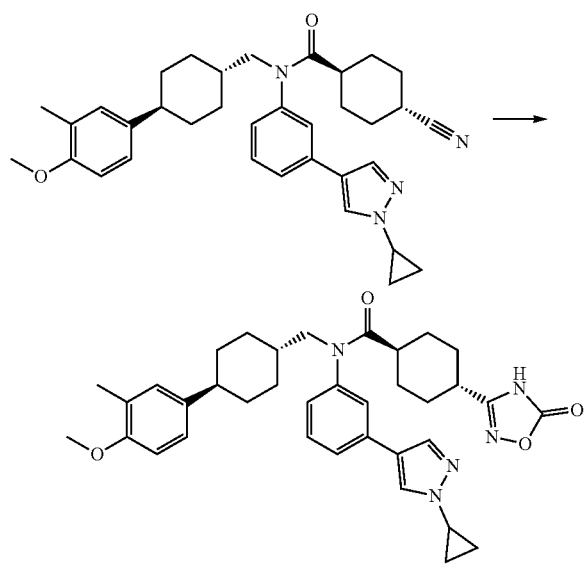

Step 1: Trans-N-(3-(1-Cyclopropyl-1H-pyrazol-4-yl)phenyl)-4-((Z)-N'-hydroxycarbamimidoyl)-N-((trans-4-(4-methoxy-3-methylphenyl)cyclohexyl)methyl)cyclohexanecarboxamide Hydroxylamine hydrochloride (1.21 g, 17.43 mmol) in water (5 mL) was added dropwise to a solution of sodium carbonate (1.54 g, 18.30 mmol) in water (25 mL). This mixture was added to a solution of Intermediate 21.23 (240 mg, 0.435 mmol) in EtOH (10 mL). The mixture was heated at 80° C., stirred overnight, and then allowed to cool to rt. The organic solvent was removed from the mixture. The aqueous layer was extracted with i-PrOH/CHCl$_2$ (1:3; 3×20 mL). The combined layers were washed with water (5 mL), washed with brine (5 mL), dried over Na$_2$SO$_4$, filtered, concentrated, and then purified by prep-TLC (SiO$_2$, 100% EtOAc) to give trans-N-(3-(1-cyclopropyl-1H-pyrazol-4-yl)phenyl)-4-((Z)-N-hydroxycarbamimidoyl)-N-((trans-4-(4-methoxy-3-methylphenyl)cyclohexyl)methyl)cyclohexanecarboxamide (200 mg, 79%) as a white solid. $^1$H NMR (400 MHz, DMSO-d$_6$): δ 8.60 (s, 1H), 8.34 (s, 1H), 7.93 (s, 1H), 7.60 (d, 1H), 7.54 (s, 1H), 7.44 (t, 1H), 7.10 (d, 1H), 7.00-6.90 (m, 2H), 6.81-6.74 (m, 1H), 5.19 (s, 2H), 3.82-3.69 (m, 4H), 3.66-3.45 (m, 2H), 3.31-3.28 (m, 1H), 2.38-2.29 (m, 1H), 2.18-2.12 (m, 1H), 2.09 (s, 3H), 1.92-1.85 (m, 1H), 1.78-1.60 (m, 7H), 1.50-1.37 (m, 3H), 1.35-1.20 (m, 3H), 1.10-1.05 (m, 4H), 1.04-0.95 (m, 3H); LCMS: 584.3 [M+H]$^+$.

Step 2: Trans-N-(3-(1-Cyclopropyl-1H-pyrazol-4-yl)phenyl)-N-((trans-4-(4-methoxy-3-methylphenyl)cyclohexyl)methyl)-4-(5-oxo-4,5-dihydro-1,2,4-oxadiazol-3-yl)cyclohexanecarboxamide A mixture of trans-N-(3-(1-cyclopropyl-1H-pyrazol-4-yl)phenyl)-4-((Z)-N-hydroxycarbamimidoyl)-N-((trans-4-(4-methoxy-3-methylphenyl)cyclohexyl)methyl)cyclohexanecarboxamide (200 mg, 0.342 mmol), CDI (83.3 mg, 0.513 mmol) and dioxane (2 mL) was stirred at 100° C. for 0.5 h, and then allowed to cool to rt. The mixture was poured into water (40 mL) and extracted with EtOAc (3×5 mL). The combined organic layers were dried over Na$_2$SO$_4$, filtered, concentrated, and then purified by prep-TLC (SiO$_2$, 100% EtOAc) to give trans-N-(3-(1-cyclopropyl-1H-pyrazol-4-yl)phenyl)-N-((trans-4-(4-methoxy-3-methylphenyl)cyclohexyl)methyl)-4-(5-oxo-4,5-dihydro-1,2,4-oxadiazol-3-yl)cyclohexanecarboxamide (42.5 mg, 20%) as a white solid. $^1$H NMR (400 MHz, DMSO-d$_6$): δ 11.98 (s, 1H), 8.34 (s, 1H), 7.94 (s, 1H), 7.61 (d, 1H), 7.56 (s, 1H), 7.47-7.43 (m, 1H), 7.12 (d, 1H), 6.99-6.90 (m, 2H), 6.81-6.74 (m, 1H), 3.78-3.68 (m, 4H), 3.67-3.46 (m, 2H), 2.57-2.51 (m, 1H), 2.36-2.31 (m, 1H), 2.2-2.15 (m, 1H), 2.09 (s, 3H), 1.86-1.69 (m, 8H), 1.58-1.37 (m, 3H), 1.36-1.21 (m, 3H), 1.12-1.04 (m, 5H), 1.02-0.96 (m, 2H); LCMS: 610.4 [M+H]$^+$.

Example A-1: Parenteral Pharmaceutical Composition

To prepare a parenteral pharmaceutical composition suitable for administration by injection (subcutaneous, intravenous), 1-1000 mg of a compound described herein, or a pharmaceutically acceptable salt or solvate thereof, is dissolved in sterile water and then mixed with 10 mL of 0.9% sterile saline. A suitable buffer is optionally added as well as optional acid or base to adjust the pH. The mixture is incorporated into a dosage unit form suitable for administration by injection

Example A-2: Oral Solution

To prepare a pharmaceutical composition for oral delivery, a sufficient amount of a compound described herein, or a pharmaceutically acceptable salt thereof, is added to water (with optional solubilizer(s), optional buffer(s) and taste masking excipients) to provide a 20 mg/mL solution.

Example A-3: Oral Tablet

A tablet is prepared by mixing 20-50% by weight of a compound described herein, or a pharmaceutically acceptable salt thereof, 20-50% by weight of microcrystalline cellulose, 1-10% by weight of low-substituted hydroxypropyl cellulose, and 1-10% by weight of magnesium stearate or other appropriate excipients. Tablets are prepared by direct compression. The total weight of the compressed tablets is maintained at 100-500 mg.

Example A-4: Oral Capsule

To prepare a pharmaceutical composition for oral delivery, 10-500 mg of a compound described herein, or a pharmaceutically acceptable salt thereof, is mixed with starch or other suitable powder blend. The mixture is incorporated into an oral dosage unit such as a hard gelatin capsule, which is suitable for oral administration.

In another embodiment, 10-500 mg of a compound described herein, or a pharmaceutically acceptable salt thereof, is placed into Size 4 capsule, or size 1 capsule (hypromellose or hard gelatin) and the capsule is closed.

Example A-5: Topical Gel Composition

To prepare a pharmaceutical topical gel composition, a compound described herein, or a pharmaceutically acceptable salt thereof, is mixed with hydroxypropyl celluose, propylene glycol, isopropyl myristate and purified alcohol USP. The resulting gel mixture is then incorporated into containers, such as tubes, which are suitable for topical administration.

Example B-1: In Vitro FXR Assay (TK)

Seeding

CV-1 cells were seeded at a density of 2,000,000 cells in a T175 flask with DMEM+10% charcoal double-stripped FBS and incubated at 37° C. in 5% $CO_2$ for 18 h (O/N).

Transfection

After 18 h of incubation, the medium in the T175 flask was changed with fresh DMEM+10% charcoal super-stripped serum. In a polypropylene tube, 2500 µL OptiMEM (Life Technologies, Cat #31985-062) was combined with expression plasmids for hFXR, hRXR, TK-ECRE-luc and pCMX-YFP. The tube was then briefly vortexed and incubated at room temperature for 5 minutes. Transfection reagent (X-tremeGENE HP from Roche, Cat #06 366 236 001) was added to the OptiMEM/plasmid mixture vortexed and incubated at room temperature for 20 minutes. Following incubation, the transfection reagent/DNA mixture complex was added to cells in the T175 flask and the cells were incubated at 37° C. in 5% $CO_2$ for 18 h (O/N).

Test Compounds

Compounds were serially diluted in DMSO and added to transfected CV-1 cells. The cells were then incubated for 18 hrs. The next day cells were lysed and examined for luminescence.

Representative data for exemplary compounds disclosed herein is presented in the following table.

TABLE 3

| Compound No | TK hFXR: $EC_{50}$ (uM) |
|---|---|
| 1 | +++ |
| 1.01 | +++ |
| 1.02 | +++ |
| 1.03 | +++ |
| 1.04 | +++ |
| 1.05 | +++ |
| 1.06 | +++ |
| 1.07 | +++ |
| 1.08 | +++ |
| 1.09 | +++ |
| 1.10 | +++ |
| 2 | +++ |
| 2.01 | +++ |
| 2.02 | +++ |
| 2.03 | +++ |
| 2.04 | +++ |
| 2.05 | +++ |
| 2.06 | +++ |
| 2.07 | +++ |
| 2.08 | +++ |
| 3 | +++ |
| 3.01 | +++ |
| 3.02 | +++ |
| 3.03 | +++ |
| 3.04 | +++ |
| 3.05 | +++ |
| 4 | +++ |
| 4.01 | +++ |
| 4.02 | +++ |
| 4.03 | +++ |
| 4.04 | +++ |
| 4.05 | +++ |
| 4.06 | +++ |
| 4.07 | +++ |
| 4.08 | +++ |
| 4.09 | +++ |
| 4.10 | +++ |
| 4.11 | +++ |
| 4.12 | +++ |
| 4.13 | +++ |
| 4.14 | +++ |
| 4.15 | +++ |
| 4.16 | +++ |
| 4.17 | +++ |
| 4.18 | +++ |
| 4.19 | +++ |
| 4.20 | +++ |
| 4.21 | +++ |
| 4.22 | +++ |
| 4.23 | +++ |
| 4.24 | +++ |
| 4.25 | +++ |
| 4.26 | +++ |
| 4.27 | +++ |
| 4.28 | +++ |
| 5 | +++ |
| 5.01 | +++ |
| 5.02 | +++ |
| 5.03 | +++ |
| 5.04 | +++ |
| 5.05 | +++ |
| 5.06 | +++ |
| 5.07 | +++ |
| 5.08 | +++ |
| 5.09 | +++ |
| 5.10 | +++ |
| 5.11 | +++ |
| 5.12 | +++ |
| 5.13 | +++ |
| 5.14 | +++ |
| 5.15 | +++ |
| 5.16 | +++ |
| 5.17 | +++ |

TABLE 3-continued

| Compound No | TK hFXR: EC$_{50}$ (uM) |
|---|---|
| 5.18 | +++ |
| 5.19 | +++ |
| 5.20 | +++ |
| 5.21 | +++ |
| 5.22 | +++ |
| 5.23 | +++ |
| 5.24 | +++ |
| 5.25 | +++ |
| 5.26 | +++ |
| 5.27 | +++ |
| 5.28 | +++ |
| 5.29 | +++ |
| 5.30 | +++ |
| 5.31 | +++ |
| 5.32 | +++ |
| 5.33 | +++ |
| 5.34 | +++ |
| 5.35 | +++ |
| 5.36 | +++ |
| 5.37 | +++ |
| 5.38 | +++ |
| 5.39 | +++ |
| 5.40 | +++ |
| 5.41 | +++ |
| 5.42 | +++ |
| 5.43 | +++ |
| 5.44 | +++ |
| 5.45 | +++ |
| 5.46 | +++ |
| 5.47 | +++ |
| 5.48 | +++ |
| 5.49 | +++ |
| 5.50 | +++ |
| 5.51 | +++ |
| 5.52 | +++ |
| 5.53 | +++ |
| 6 | +++ |
| 6.01 | +++ |
| 6.02 | +++ |
| 6.03 | +++ |
| 6.04 | +++ |
| 6.05 | +++ |
| 6.06 | +++ |
| 6.07 | +++ |
| 6.08 | +++ |
| 6.09 | +++ |
| 6.10 | +++ |
| 6.11 | +++ |
| 6.12 | +++ |
| 6.13 | +++ |
| 6.14 | +++ |
| 6.15 | +++ |
| 6.16 | +++ |
| 6.17 | +++ |
| 6.18 | +++ |
| 6.19 | +++ |
| 6.20 | +++ |
| 6.21 | +++ |
| 6.22 | +++ |
| 6.23 | +++ |
| 6.24 | +++ |
| 6.25 | +++ |
| 6.26 | +++ |
| 6.27 | +++ |
| 6.28 | +++ |
| 6.29 | +++ |
| 6.30 | +++ |
| 6.31 | +++ |
| 6.32 | +++ |
| 6.33 | +++ |
| 6.34 | +++ |
| 6.35 | +++ |
| 6.36 | +++ |
| 6.37 | +++ |
| 6.38 | +++ |
| 6.39 | +++ |
| 6.40 | +++ |
| 6.41 | +++ |
| 6.42 | +++ |
| 6.43 | +++ |
| 6.44 | +++ |
| 6.45 | +++ |
| 6.46 | +++ |
| 6.47 | +++ |
| 6.48 | +++ |
| 6.49 | +++ |
| 6.50 | +++ |
| 6.51 | +++ |
| 6.52 | +++ |
| 6.53 | +++ |
| 6.54 | +++ |
| 6.55 | +++ |
| 6.56 | +++ |
| 6.57 | +++ |
| 6.58 | +++ |
| 6.59 | +++ |
| 6.60 | +++ |
| 6.61 | +++ |
| 6.62 | +++ |
| 6.63 | +++ |
| 6.64 | +++ |
| 6.65 | +++ |
| 6.66 | ++ |
| 6.67 | +++ |
| 6.68 | +++ |
| 6.69 | +++ |
| 6.70 | +++ |
| 6.71 | +++ |
| 6.72 | +++ |
| 6.73 | +++ |
| 6.74 | +++ |
| 6.75 | +++ |
| 6.76 | +++ |
| 6.77 | +++ |
| 6.78 | ++ |
| 6.79 | +++ |
| 6.80 | +++ |
| 6.81 | +++ |
| 6.82 | +++ |
| 6.83 | +++ |
| 6.84 | +++ |
| 6.85 | +++ |
| 6.86 | +++ |
| 6.87 | +++ |
| 6.88 | +++ |
| 6.89 | +++ |
| 6.90 | +++ |
| 6.91 | +++ |
| 6.92 | +++ |
| 6.93 | +++ |
| 6.94 | +++ |
| 6.95 | +++ |
| 6.96 | +++ |
| 7 | +++ |
| 7.01 | +++ |
| 7.02 | +++ |
| 7.03 | +++ |
| 7.04 | +++ |
| 7.05 | +++ |
| 7.06 | +++ |
| 7.07 | +++ |
| 7.08 | +++ |
| 7.09 | +++ |
| 7.10 | +++ |
| 7.11 | +++ |
| 7.12 | +++ |
| 7.13 | +++ |
| 7.14 | +++ |
| 7.15 | +++ |
| 7.16 | +++ |
| 7.17 | +++ |
| 7.18 | +++ |
| 7.19 | +++ |
| 7.20 | +++ |

TABLE 3-continued

| Compound No | TK hFXR: EC$_{50}$ (uM) |
|---|---|
| 7.21 | +++ |
| 7.22 | +++ |
| 7.23 | +++ |
| 7.24 | +++ |
| 7.25 | +++ |
| 7.26 | +++ |
| 7.27 | +++ |
| 7.28 | +++ |
| 7.29 | +++ |
| 7.30 | +++ |
| 7.31 | +++ |
| 7.32 | +++ |
| 7.33 | +++ |
| 7.34 | +++ |
| 7.35 | +++ |
| 7.36 | +++ |
| 7.37 | +++ |
| 7.38 | +++ |
| 7.39 | +++ |
| 7.40 | +++ |
| 7.41 | +++ |
| 7.42 | +++ |
| 7.43 | +++ |
| 7.44 | +++ |
| 7.45 | +++ |
| 7.46 | +++ |
| 7.47 | +++ |
| 7.48 | +++ |
| 7.49 | +++ |
| 7.50 | +++ |
| 7.51 | +++ |
| 7.52 | +++ |
| 7.53 | +++ |
| 7.54 | +++ |
| 7.55 | +++ |
| 7.56 | +++ |
| 7.57 | +++ |
| 7.58 | +++ |
| 7.59 | +++ |
| 7.60 | +++ |
| 7.61 | +++ |
| 7.62 | +++ |
| 7.63 | +++ |
| 7.64 | +++ |
| 7.65 | +++ |
| 7.66 | +++ |
| 7.67 | +++ |
| 7.68 | +++ |
| 7.69 | +++ |
| 7.70 | +++ |
| 7.71 | +++ |
| 7.72 | +++ |
| 7.73 | +++ |
| 7.74 | +++ |
| 7.75 | +++ |
| 7.76 | +++ |
| 7.77 | +++ |
| 7.78 | +++ |
| 7.79 | +++ |
| 7.80 | +++ |
| 7.81 | +++ |
| 7.82 | +++ |
| 7.83 | +++ |
| 7.84 | +++ |
| 7.85 | +++ |
| 7.86 | ++ |
| 7.87 | +++ |
| 7.88 | +++ |
| 7.89 | +++ |
| 7.90 | +++ |
| 7.91 | +++ |
| 7.92 | +++ |
| 7.93 | +++ |
| 7.94 | +++ |
| 7.95 | +++ |
| 7.96 | ++ |
| 7.97 | +++ |
| 7.98 | +++ |
| 7.99 | +++ |
| 7.100 | +++ |
| 7.101 | +++ |
| 7.102 | +++ |
| 7.103 | +++ |
| 7.104 | +++ |
| 7.105 | +++ |
| 7.106 | +++ |
| 7.107 | +++ |
| 7.108 | +++ |
| 7.109 | +++ |
| 8 | +++ |
| 8.01 | +++ |
| 9 | +++ |
| 10 | +++ |
| 11 | ++ |
| 12 | +++ |
| 13 | +++ |
| 13.01 | +++ |
| 13.02 | +++ |
| 13.03 | +++ |
| 13.04 | +++ |
| 13.05 | ++ |
| 14 | +++ |
| 15 | +++ |
| 15.01 | +++ |
| 15.02 | +++ |
| 15.03 | +++ |
| 15.04 | +++ |
| 16 | +++ |
| 17 | +++ |
| 17.01 | +++ |
| 17.02 | +++ |
| 17.03 | +++ |
| 17.04 | +++ |
| 17.05 | +++ |
| 17.06 | +++ |
| 17.07 | +++ |
| 17.08 | +++ |
| 17.09 | +++ |
| 17.10 | ++ |
| 17.11 | +++ |
| 17.12 | +++ |
| 17.13 | +++ |
| 17.14 | +++ |
| 17.15 | +++ |
| 17.16 | +++ |
| 17.17 | +++ |
| 17.18 | ++ |
| 17.19 | +++ |
| 17.20 | +++ |
| 17.21 | + |
| 17.22 | +++ |
| 17.23 | ++ |
| 17.24 | +++ |
| 17.25 | +++ |
| 17.26 | +++ |
| 17.27 | + |
| 18 | +++ |
| 18.01 | +++ |
| 18.02 | +++ |
| 18.03 | +++ |
| 18.04 | +++ |
| 18.05 | +++ |
| 18.06 | +++ |
| 18.07 | +++ |
| 18.08 | +++ |
| 18.09 | +++ |
| 18.10 | +++ |
| 18.11 | + |
| 18.12 | + |
| 18.13 | +++ |
| 18.14 | +++ |
| 18.15 | +++ |
| 18.16 | +++ |
| 18.18 | +++ |

TABLE 3-continued

| Compound No | TK hFXR: EC$_{50}$ (uM) |
|---|---|
| 18.19 | +++ |
| 18.20 | +++ |
| 18.21 | +++ |
| 18.22 | +++ |
| 18.23 | +++ |
| 18.24 | +++ |
| 19 | +++ |
| 20 | +++ |
| 20.01 | +++ |
| 20.02 | +++ |
| 20.03 | +++ |
| 20.04 | +++ |
| 20.05 | +++ |
| 20.06 | +++ |
| 20.07 | +++ |
| 20.08 | +++ |
| 20.09 | +++ |
| 20.10 | +++ |
| 20.11 | +++ |
| 20.12 | +++ |
| 20.13 | +++ |
| 20.14 | +++ |
| 20.15 | +++ |
| 20.16 | +++ |
| 21 | +++ |
| 21.01 | +++ |
| 21.02 | +++ |
| 21.03 | +++ |
| 21.04 | + |
| 21.05 | +++ |
| 21.06 | +++ |
| 21.07 | +++ |
| 21.08 | +++ |
| 21.09 | +++ |
| 21.10 | +++ |
| 21.11 | +++ |
| 21.12 | +++ |
| 21.13 | +++ |
| 22 | +++ |
| 22.01 | +++ |
| 22.02 | +++ |
| 22.03 | + |
| 22.04 | +++ |
| 22.05 | ++ |
| 22.06 | ++ |
| 23 | ++ |
| 24 | +++ |
| 24.01 | +++ |
| 24.02 | +++ |
| 24.03 | +++ |
| 24.04 | +++ |
| 24.05 | ++ |
| 24.06 | +++ |
| 25 | +++ |
| 25.01 | ++ |
| 25.02 | ++ |
| 25.03 | + |
| 25.04 | +++ |
| 25.05 | +++ |
| 25.06 | +++ |
| 25.07 | +++ |
| 25.08 | +++ |
| 25.09 | +++ |
| 25.10 | +++ |
| 25.11 | +++ |
| 25.12 | +++ |
| 25.13 | +++ |
| 25.14 | +++ |
| 25.15 | +++ |
| 25.16 | +++ |
| 25.17 | +++ |
| 25.18 | +++ |
| 26 | +++ |
| 26.01 | +++ |
| 26.02 | +++ |
| 26.03 | +++ |
| 26.04 | +++ |
| 26.05 | +++ |
| 26.06 | +++ |
| 26.07 | +++ |
| 26.08 | +++ |
| 26.09 | +++ |
| 26.10 | +++ |
| 26.11 | +++ |
| 26.12 | +++ |
| 26.13 | +++ |
| 26.14 | +++ |
| 26.15 | +++ |
| 26.16 | +++ |
| 26.17 | +++ |
| 26.18 | +++ |
| 26.19 | +++ |
| 26.20 | +++ |
| 26.21 | +++ |
| 26.22 | + |
| 26.23 | +++ |
| 26.24 | +++ |
| 26.25 | +++ |
| 26.26 | +++ |
| 26.27 | +++ |
| 26.28 | +++ |
| 26.29 | ++ |
| 26.30 | +++ |
| 26.31 | +++ |
| 26.32 | +++ |
| 26.33 | +++ |
| 26.34 | +++ |
| 26.35 | +++ |
| 26.36 | +++ |
| 26.37 | +++ |
| 27 | +++ |
| 27.01 | +++ |
| 27.02 | +++ |
| 27.03 | ++ |
| 27.04 | +++ |
| 27.05 | + |
| 27.06 | + |
| 28 | +++ |
| 29 | + |
| 30 | +++ |
| 30.01 | +++ |
| 30.02 | +++ |
| 30.03 | +++ |
| 30.04 | +++ |
| 30.05 | + |
| 30.06 | +++ |
| 31 | +++ |
| 31.01 | + |
| 31.02 | ++ |
| 31.03 | + |
| 31.04 | ++ |
| 31.05 | +++ |
| 31.06 | +++ |
| 31.07 | ++ |
| 31.08 | +++ |
| 31.09 | +++ |
| 31.10 | +++ |
| 31.11 | +++ |
| 31.12 | +++ |
| 31.13 | ++ |
| 31.14 | +++ |
| 31.15 | +++ |
| 32 | +++ |
| 32.01 | +++ |
| 32.02 | +++ |
| 32.03 | +++ |
| 32.04 | +++ |
| 32.05 | ++ |
| 32.06 | + |
| 33 | +++ |

TABLE 3-continued

| Compound No | TK hFXR: EC$_{50}$ (uM) |
|---|---|
| 33.01 | +++ |
| 34 | +++ |

Where '+++' means EC$_{50}$ ≤0.25 uM; '++' means EC$_{50}$ >0.25 uM & <1 uM; '+' means EC$_{50}$ ≥1 uM.
Compounds with a maximum efficacy of <25% of the Fexarmine control were classified as '+'.

Example B-2: In Vitro FXR Assay (hSHP)

Seeding

CV-1 cells were seeded at a density of 2,000,000 cells in a T175 flask with DMEM+10% charcoal double-stripped FBS and incubated at 37° C. in 500 $CO_2$ for 18 h (O/N).

Transfection

After 18 h of incubation, the medium in the T175 flask was changed with fresh DMEM+10% charcoal super-stripped serum. In a polypropylene tube, 2500 µL OptiMEM (Life Technologies, Cat #31985-062) was combined with expression plasmids for hFXR, hRXR, hSTIP-luc and pCMX-YFP. The tube was then briefly vortexed and incubated at room temperature for 5 minutes. Transfection reagent (X-tremeGENE HP from Roche, Cat #06 366 236 001) was added to the OptiMEM/plasmid mixture vortexed and incubated at room temperature for 20 minutes. Following incubation, the transfection reagent/DNA mixture complex was added to cells in the T175 flask and the cells were incubated at 37° C. in 5% $CO_2$ for 18 h (O/N).

Test Compounds

Compounds were serially diluted in DMSO and added to transfected CV-1 cells. The cells were then incubated for 18 hrs. The next day cells were lysed and examined for luminescence.

Example B-3: NASH Activity Study (STZ Model)

NASH can be induced in male C57BL/6 by a single subcutaneous injection of 200 ug STZ 2 days after birth followed by feeding high fat diet (HFD) ad libitum after 4 weeks of age. While continuing HFD, compounds can be dosed for 4-8 weeks to determine the effects on NASH. Fasting glucose can be measured throughout the study with a hand-held glucose meter. Serum alanine aminotransferase (ALT), aspartate aminotransferase (AST) and triglyceride (TG) can be measured by a clinical chemistry analyzer. The contents of TG in the liver tissue can be measured using the Triglyceride E-test kit (Wako, Tokyo, Japan). Histological analysis of liver sections can be performed on tissue embedded in Tissue-TEK O.C.T. compound, snap frozen in liquid nitrogen, and stored at −80 C. The sections can be cut (5 um), air dried and fixed in acetone. For hematoxylin and eosin staining, liver sections can be prefixed by Bouin's solution and then stained with hematoxylin and eosin solution. The degree of (zone-3) liver fibrosis can be assessed with Sirius red staining.

Example B-4: NASH Activity Study (AMLN Model)

NASH is induced in male C57BL/6 mice by diet-induction with AMLN diet (DIO-NASH) (D09100301, Research Diet, USA) (40% fat (18% trans-fat), 40% carbohydrates (20% fructose) and 2% cholesterol). The animals are kept on the diet for 29 weeks. After 26 weeks of diet induction, liver biopsies are performed for base line histological assessment of disease progression (hepatosteatosis and fibrosis), stratified and randomized into treatment groups according to liver fibrosis stage, steatosis score, and body weight. Three weeks after biopsy the mice are stratified into treatment groups and dosed daily by oral gavage with FXR agonists for 8 weeks. At the end of the study liver biopsies are performed to assess hepatic steatosis and fibrosis by examining tissue sections stained with H&E and Sirius Red, respectively. Total collagen content in the liver is measured by colorimetric determination of hydroxyproline residues by acid hydrolysis of collagen. Triglycerides and total cholesterol content in liver homogenates are measured in single determinations using autoanalyzer Cobas C-111 with commercial kit (Roche Diagnostics, Germany) according to manufacturer's instructions.

Example B-5: $CCl_4$ Fibrosis Model

Fibrosis can be induced in BALB/c male mice by bi-weekly administration of $CCl_4$ administered by intraperitoneal injection. $CCl_4$ is formulated 1:1 in oil and is injected IP at 1 mL/kg. After 2-4 weeks of fibrosis induction the compounds can be administered daily by oral gavage for 2-6 weeks of treatment while continuing $CCl_4$ administration. At study termination livers can be formalin fixed and stained with Sirius Red stain for histopathological evaluation of fibrosis. Total collagen content can be measured by colorimetric determination of hydroxyproline residues by acid hydrolysis of collagen. Serum alanine aminotransferase (ALT) and aspartate aminotransferase (AST) can be measured by a clinical chemistry analyzer.

Example B-6: Intrahepatic Cholestasis Model

Experimental intrahepatic cholestasis induced by 17a-ethynylestradiol (EE2) treatment in rodents is a widely used in vivo model to examine the mechanisms involved in estrogen-induced cholestasis. Intrahepatic cholestasis can be induced in adult male mice by subcutaneous injection of 10 mg/kg 17a-ethynylestradiol (E2) daily for 5 days. Testing of FXR ligands can be performed by administration of compounds during E2 induction of cholestasis. Cholestatic effects can be quantitated by assessing liver/body weight ratio and measuring serum total bile acids and alkaline phosphatase levels can be measured using reagents and controls from Diagnostic Chemicals Ltd. and the Cobas Mira plus CC analyzer (Roche Diagnostics). For histology and mitosis measurements, liver samples from each mouse can be fixed in 10% neutral buffered formalin. Slides are stained with hematoxylin and eosin using standard protocols and examined microscopically for structural changes. Hepatocyte proliferation is evaluated by immunohistochemical staining for Ki67.

Example B-7: Direct Target Gene Regulation

Direct target gene regulation by FXR ligands can be assessed by dosing mice either acutely or chronically with compounds and collecting tissues at various time points after dosing. RNA can be isolated from tissues such as the ileum and liver, and reverse transcribed to cDNA for quantitative PCR analysis of genes known in the literature to be directly and indirectly regulated by FXR such as SHP, BSEP, IBABP, FGF15, CYP7A1, CYP8B1 and C3.

Example B-8: Mouse PK Study

The plasma pharmacokinetics of any one of the compounds disclosed herein as a test article test article is measured following a single bolus intravenous and oral administration to mice (CD-1, C57BL, and diet induced obesity mice). Test article is formulated for intravenous administration in a vehicle solution of DMSO, PEG400, hydroxypropyl-β-cyclodextrin (HPPCD) and is administered (for example at a dose volume of 3 mL/kg) at selected dose levels. An oral dosing formulation is prepared in appropriate oral dosing vehicles (vegetable oils, PEG400, Solutol, citrate buffer, or carboxymethyl cellulose) and is administered at a dose volume of 5-10 mL/kg at selected dose levels. Blood samples (approximately 0.15 mL) are collected by cheek pouch method at pre-determined time intervals post intravenous or oral doses into tubes containing EDTA. Plasma is isolated by centrifugation of blood at 10,000 g for 5 minutes, and aliquots are transferred into a 96-well plate and stored at −60° C. or below until analysis.

Calibration standards of test article are prepared by diluting DMSO stock solution with DMSO in a concentration range. Aliquots of calibration standards in DMSO are combined with plasma from naïve mouse so that the final concentrations of calibration standards in plasma are 10-fold lower than the calibration standards in DMSO. PK plasma samples are combined with blank DMSO to match the matrix. The calibration standards and PK samples are combined with ice-cold acetonitrile containing an analytical internal standard and centrifuged at 1850 g for 30 minutes at 4° C. The supernatant fractions are analyzed by LC/MS/MS and quantitated against the calibration curve. Pharmacokinetic parameters (area under the curve (AUC), $C_{max}$, $T_{max}$, elimination half-life ($T_{1/2}$), clearance (CL), steady state volume of distribution ($V_{dss}$), and mean residence time (MRT)) are calculated via non-compartmental analysis using Microsoft Excel (version 2013).

Example B-9: Rat ANIT Model

A compound described herein is evaluated in a chronic treatment model of cholestasis over a range of doses (for example, doses in the range of 0.01 to 100 mg/kg). This model is used to evaluate the suitability of the use of FXR agonists, e.g. a compound described herein, for the treatment of cholestatic liver disorders such as bile acid malabsorption (e.g., primary or secondary bile acid diarrhea), bile reflux gastritis, collagenous colitis, lymphocytic colitis, diversion colitis, indeterminate colitis, Alagille syndrome, biliary atresia, ductopenic liver transplant rejection, bone marrow or stem cell transplant associated graft versus host disease, cystic fibrosis liver disease, and parenteral nutrition-associated liver disease.

Rats are treated with alpha-naphthylisothiocyanate (ANIT) (0.1% w/w) in food for 3 days prior to treatment with a compound described herein, at a range of doses (for example, doses in the range of 0.01 to 100 mg/kg). A noncholestatic control group is fed standard chow diet without ANIT and serves as the noncholestatic control animals ("Control"). After 14 days of oral dosing, rat serum is analyzed for levels of analytes. LLQ, lower limit of quantitation. Mean±SEM; n=5.

Levels of hepatobiliary injury indicators are measured in rat serum, such as elevated levels of circulating aspartate aminotransferase (AST), alanine aminotransferase (ALT), bilirubin and bile acids. ANIT exposure induces profound cholestasis and hepatocellular damage. A compound that improves many of these indicators is useful in the treatment of the aforementioned diseases or conditions.

Reductions in the accumulation of bile acids in the liver, enhancements in bile acid excretion in the biliary tract and inhibition of bile acid synthesis is consistent with the pharmacological action of a FXR agonist. An improvement in the serum conjugated bilirubin (a direct indicator for hepatic function) implies recovery from cholestasis with improved bile excretion.

Furthermore, an analysis is made to ascertain the effects of the compound described herein on serum FGF15 fibroblast growth factor 15 (FGF15 in rodent; FGF19 in human) expression, a hormone that is secreted in the portal blood and signals to the liver to repress CYP7A1 expression synergistically with SHP. The direct FXR-dependent induction of FGF15/19 along with FGF15/19's anti-cholestatic properties makes it a convenient serum biomarker for detecting target engagement of FXR agonists.

Serum FGF15 levels are quantified using an FGF15 Meso Scale Discovery (MSD) assay. For example, Mouse FGF15 antibody from R&D Systems (AF6755) is used both as capture and detection antibody in the assay. MSD SULFO-TAG NHS-Ester is used to label the FGF15 antibody. MSD standard 96-well plates are coated with the FGF15 capture antibody and the plates are blocked with MSD Blocker A (R93AA-2). After washing the plate with PBS+0.05% Tween 20, MSD diluent 4 is dispensed into each well and incubated for 30 min. 25 pi of calibrator dilutions or samples (serum or EDTA plasma) are dispensed into each well and incubated with shaking at RT.

After washing, detection antibody is added and incubated with shaking for 1 h at RT. After washing and the addition of MSD Read buffer (R92TC-2), the plate is read on an MSD SECTOR Imager 6000. Plots of the standard curve and unknown samples are calculated using MSD data analysis software.

The examples and embodiments described herein are for illustrative purposes only and various modifications or changes suggested to persons skilled in the art are to be included within the spirit and purview of this application and scope of the appended claims.

Example B-10: Mouse Chronic DSS Colitis Model

The chronic Dextran Sodium Sulfate (DSS)-induced mouse can be used to test the therapeutic potential of compounds against inflammatory bowel disease (IBD). Chronic colitis can be induced by feeding mice DSS in drinking water. For example, 2% DSS in drinking water for 5 days and regular drinking water for 5 days, then this feeding cycle can be repeated two more times with higher concentrations of DSS, 2.5% and 3%, respectively for a total of three cycles. Colitis develops approximately after the first cycle of DSS feeding, which can be monitored by loss of body weight, stool consistency and rectal bleeding. An FXR agonist can be tested by administering to mice at the same time of starting 2% DSS water feeding. Alternatively, testing of an FXR agonist can be performed post the first feeding cycle of 2% DSS water and regular water. During the period of administering the FXR agonist to mice, the therapeutic effects can be monitored by observations on body weights, stool consistency and rectal bleeding. After euthanasia, the disease development and effects of the FXR agonist can be further quantified by measuring colon weight and length, colon histology by H&E staining for inflammation and structural changes in mucosa, and protein and RNA expression of genes related to the disease.

Example B-11: Adoptive T-Cell Transfer Colitis Mouse Model

The adoptive T-cell transfer colitis model is accepted as a relevant mouse model for human inflammatory bowel disease (IBD). To induce colitis in this model, the CD4 T-lymphocyte population is isolated from the spleens of donor mice, subsequently a subpopulation of CD4+CD45RB high T-cells is purified by cell sorting using flow cytometry. The purified CD4+CD45RB high T-cells are injected into the peritoneal cavity of the recipient SCID mice. Colitis develops approximately three to six weeks after T-cell transfer, which can be monitored by loss of body weight (although loss of body weight can be variable), inconsistent stool or bloody diarrhea. Testing of an FXR agonist can be initiated at the same time of injecting purified CD4+CD45RB high T-cells to the recipient SCID mice. Alternatively, the FXR agonist can be administered two or three weeks post T-cell transfer, when colitis has already developed in the model. During the period of administering the FXR agonist to mice, the therapeutic effects can be monitored by observations on body weights, stool consistency and rectal bleeding. After euthanasia, the disease development and effects of the FXR agonist can be further quantified by measuring colon weight and length, colon and ileum histology by H&E staining for inflammation and structural changes in mucosa, and protein and RNA expression of genes related to the disease.

Example B-12: Mdr1a−/− Mouse Model

The Mdr1a−/− mouse model is a spontaneous colitis model that has been used in testing new therapies for human IBD. Loss of the Mdr1a gene in this model leads to impaired intestinal barrier function, which results in increased infiltration of gut bacteria and subsequent colitis. Under proper housing conditions, Mdr1a−/− mice can develop colitis at about 8 to 13 weeks of age. During disease progression, a disease activity index (DAI) summing the clinical observation scores on rectal prolapse, stool consistency and rectal bleeding can be used to monitor the disease. Testing of an FXR agonist can be started at the initial stage of disease, generally with DAI score less than 1.0. Alternatively, administration of an FXR agonist can be initiated when colitis has developed, typically with a DAI score above 2.0. Therapeutic effects of the FXR agonist can be monitored by measuring the DAI, and testing can be terminated when desired disease severity has been achieved, generally with a DAI score around 5.0. After euthanasia, the disease development and effects of the FXR agonist can be further quantified by measuring colon weight and length, colon histology by H&E staining for inflammation and structural changes in mucosa, and protein and RNA expression of genes related to the disease.

The examples and embodiments described herein are for illustrative purposes only and various modifications or changes suggested to persons skilled in the art are to be included within the spirit and purview of this application and scope of the appended claims.

What is claimed is:

1. A compound that has the structure of Formula (I), or a pharmaceutically acceptable salt or solvate thereof:

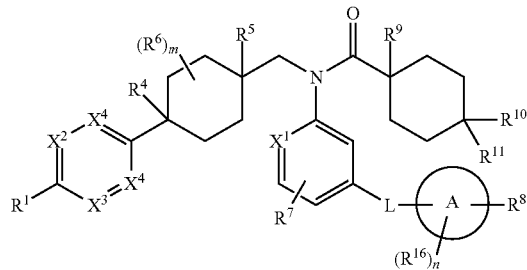

Formula (I)

wherein, ring A is a 5-membered heteroaryl that is oxazolyl, thiazolyl, pyrazolyl, furanyl, thienyl, pyrrolyl, imidazolyl, triazolyl, tetrazolyl, isoxazolyl, isothiazolyl, oxadiazolyl, or thiadiazolyl;

or ring A is a 6-membered heteroaryl that is pyridinyl, pyrimidinyl, pyrazinyl, pyridazinyl, or triazinyl;

or ring A is phenyl;

$X^1$ is CH or N;

$R^1$ is H, D, halogen, —CN, —OH, —N($R^{15}$)$_2$, —N$R^{15}$S(=O)$_2$(C$_1$-C$_4$alkyl), —S(=O)$_2$N($R^{15}$)$_2$, —OC(=O)(C$_1$-C$_4$alkyl), —CO$_2$H, —CO$_2$(C$_1$-C$_4$alkyl), —C(=O)N($R^{15}$)$_2$, —N$R^{15}$C(=O)(C$_1$-C$_4$alkyl), —N$R^{15}$C(=O)O(C$_1$-C$_4$alkyl), —OC(=O)N($R^{15}$)$_2$, —N$R^{15}$C(=O)N($R^{15}$)$_2$, —SH, —S(C$_1$-C$_4$alkyl), —S(=O)(C$_1$-C$_4$alkyl), —S(=O)$_2$(C$_1$-C$_4$alkyl), C$_1$-C$_4$alkyl, C$_2$-C$_4$alkenyl, C$_2$-C$_4$alkynyl, C$_1$-C$_4$alkoxy, C$_1$-C$_4$deuteroalkyl, C$_1$-C$_4$deuteroalkoxy, C$_1$-C$_4$fluoroalkyl, C$_1$-C$_4$fluoroalkoxy, C$_1$-C$_4$heteroalkyl, or substituted or unsubstituted monocyclic C$_2$-C$_5$heterocycloalkyl;

$X^2$ is CR$^2$ or N;

$R^2$ is H, D, halogen, —CN, —OH, —N($R^{15}$)$_2$, —N$R^{15}$S(=O)$_2$(C$_1$-C$_4$alkyl), —S(=O)$_2$N($R^{15}$)$_2$, —OC(=O)(C$_1$-C$_4$alkyl), —CO$_2$H, —CO$_2$(C$_1$-C$_4$alkyl), —C(=O)N($R^{15}$)$_2$, —N$R^{15}$C(=O)(C$_1$-C$_4$alkyl), —N$R^{15}$C(=O)O(C$_1$-C$_4$alkyl), —OC(=O)N($R^{15}$)$_2$, —N$R^{15}$C(=O)N($R^{15}$)$_2$, —SH, —S(C$_1$-C$_4$alkyl), —S(=O)(C$_1$-C$_4$alkyl), —S(=O)$_2$(C$_1$-C$_4$alkyl), C$_1$-C$_4$alkyl, C$_2$-C$_4$alkenyl, C$_2$-C$_4$alkynyl, C$_1$-C$_4$alkoxy, C$_1$-C$_4$deuteroalkyl, C$_1$-C$_4$deuteroalkoxy, C$_1$-C$_4$fluoroalkyl, C$_1$-C$_4$fluoroalkoxy, C$_1$-C$_4$heteroalkyl, or substituted or unsubstituted monocyclic C$_2$-C$_5$heterocycloalkyl;

or $R^1$ and $R^2$ are taken together with the intervening atoms to form a substituted or unsubstituted fused 5- or 6-membered ring with 0-3 N atoms and 0-2 O or S atoms in the ring;

$X^3$ is CR$^3$ or N;

$R^3$ is H, D, halogen, —CN, —OH, —N($R^{15}$)$_2$, —N$R^{15}$S(=O)$_2$(C$_1$-C$_4$alkyl), —OC(=O)(C$_1$-C$_4$alkyl), —CO$_2$H, —CO$_2$(C$_1$-C$_4$alkyl), —C(=O)N($R^{15}$)$_2$, —N$R^{15}$C(=O)(C$_1$-C$_4$alkyl), C$_1$-C$_4$alkyl, C$_2$-C$_4$alkenyl, C$_2$-C$_4$alkynyl, C$_1$-C$_4$alkoxy, C$_1$-C$_4$deuteroalkyl, C$_1$-C$_4$deuteroalkoxy, C$_1$-C$_4$fluoroalkyl, C$_1$-C$_4$fluoroalkoxy, or C$_1$-C$_4$heteroalkyl;

each $X^4$ is independently CH or N;

$R^4$ and $R^5$ are taken together to form a bridge that is —CH$_2$— or —CH$_2$CH$_2$—;

each $R^6$ is independently H, D, F, —OH, or —CH$_3$;

m is 0, 1, or 2;

$R^7$ is H, D, halogen, —CN, —OH, $C_1$-$C_4$alkyl, $C_2$-$C_4$alkenyl, $C_2$-$C_4$alkynyl, $C_1$-$C_4$alkoxy, $C_1$-$C_4$deuteroalkyl, $C_1$-$C_4$deuteroalkoxy, $C_1$-$C_4$fluoroalkyl, $C_1$-$C_4$fluoroalkoxy, or $C_1$-$C_4$heteroalkyl;

L is absent, —$Y^2$-$L^1$-, -$L^1$-$Y^2$—, cyclopropylene, cyclobutylene or bicyclo[1.1.1]pentylene;

$Y^2$ is absent, —O—, —S—, —S(=O)—, —S(=O)$_2$—, —S(=O)$_2$NR$^{15}$—, —CH$_2$—, —CH=CH—, —C≡C—, —C(=O)—, —C(=O)O—, —OC(=O)—, —OC(=O)O—, —C(=O)NR$^{15}$—, —NR$^{15}$C(=O)—, —OC(=O)NR$^{15}$—, —NR$^{15}$C(=O)O—, —NR$^{15}$C(=O)NR$^{15}$—, —NR$^{15}$S(=O)$_2$—, or —NR$^{15}$;

$L^1$ is absent or substituted or unsubstituted $C_1$-$C_4$alkylene;

$R^8$ is H, D, $C_1$-$C_6$alkyl, $C_1$-$C_6$deuteroalkyl, $C_1$-$C_6$fluoroalkyl, $C_1$-$C_6$heteroalkyl, —C(=O)($C_1$-$C_4$alkyl), —CO$_2$($C_1$-$C_4$alkyl), —C(=O)N(R$^{15}$)$_2$, —S(=O)$_2$($C_1$-$C_4$alkyl), —S(=O)$_2$N(R$^{15}$)$_2$, substituted or unsubstituted C3-C6cycloalkyl, or substituted or unsubstituted monocyclic $C_2$-$C_6$heterocycloalkyl, substituted or unsubstituted phenyl, or substituted or unsubstituted monocyclic heteroaryl;

$R^9$ is H, D, F or —CH$_3$;

$R^{10}$ is $C_1$-$C_6$heteroalkyl, —C(=O)R$^{14}$, —OC(=O)OR$^{14}$, tetrazolyl, imidazole, 5-oxo-4,5-dihydro-1,2,4-oxadiazol-3-yl, —S(=O)$_2$N(R$^{12}$)$_2$, —NR$^{15}$S(=O)$_2$R$^{14}$, —C(=O)NR$^{15}$S(=O)$_2$R$^{14}$, —S(=O)$_2$NR$^1$C(=O)R$^{14}$, —CH$_2$N(R$^{12}$)$_2$, —C(=O)N(R$^{12}$)$_2$, —NR$^{15}$C(=O)N(R$^{12}$)$_2$, —C(=NH)NH$_2$, —NHC(=NH)NH$_2$, —C(=O)NHC(=NH)NH$_2$, —S(=O)$_2$OH or —OP(=O)(OR$^{15}$)$_2$;

or $R^{10}$ is -$L^2$-$L^3$-$L^4$-$R^{13}$;

$L^2$ is absent, substituted or unsubstituted $C_1$-$C_6$alkylene, or substituted or unsubstituted $C_1$-$C_6$heteroalkylene;

$L^3$ is absent, —O—, —S—, —S(=O)—, —S(=O)$_2$—, —NR$^{15}$—, —C(=O)—, —C(=O)NR$^{15}$—, —NR$^{15}$C(=O)—, —C(=O)O—, —OC(=O)—, —OC(=O)NR$^{15}$—, —NR$^{15}$C(=O)NR$^{15}$—, —NR$^{15}$C(=O)O—, —OP(=O)(OR$^{15}$)O—, or —(OCH$_2$CH$_2$)$_r$—, r is 1 or 2;

$L^4$ is substituted or unsubstituted $C_1$-$C_6$alkylene, or substituted or unsubstituted $C_1$-$C_6$heteroalkylene;

$R^{13}$ is H, —CN, —N(R$^{12}$)$_2$, —NR$^{15}$S(=O)$_2$R$^{14}$, —S(=O)$_2$N(R$^{12}$)$_2$, —SR$^{12}$, —S(=O)R$^{14}$, —S(=O)$_2$R$^{14}$, —SO$_3$H, —OP(=O)(OR$^{15}$)$_2$, —C(=O)R$^{14}$, —OC(=O)OR$^{14}$, —C(=O)N(R$^{12}$)$_2$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_3$-$C_6$cycloalkyl, substituted or unsubstituted $C_2$-$C_6$heterocycloalkyl, substituted or unsubstituted phenyl, or substituted or unsubstituted monocyclic heteroaryl;

$R^{11}$ is H, D, F, or —CH$_3$;

or $R^9$ and $R^{11}$ are taken together to form a bridge that is —CH$_2$— or —CH$_2$CH$_2$—;

each $R^{12}$ is independently H, $C_1$-$C_4$alkyl, $C_1$-$C_4$deuteroalkyl, $C_1$-$C_4$fluoroalkyl, $C_1$-$C_4$heteroalkyl, substituted or unsubstituted $C_3$-$C_6$cycloalkyl, substituted or unsubstituted $C_2$-$C_6$heterocycloalkyl, substituted or unsubstituted phenyl, substituted or unsubstituted benzyl, or substituted or unsubstituted monocyclic heteroaryl;

$R^{14}$ is $C_1$-$C_4$alkyl, $C_1$-$C_4$deuteroalkyl, $C_1$-$C_4$fluoroalkyl, $C_1$-$C_4$heteroalkyl, substituted or unsubstituted $C_3$-$C_6$cycloalkyl, substituted or unsubstituted $C_2$-$C_6$heterocycloalkyl, substituted or unsubstituted phenyl, substituted or unsubstituted benzyl, or substituted or unsubstituted monocyclic heteroaryl;

$R^{15}$ is H or substituted or unsubstituted $C_1$-$C_6$alkyl;

each $R^{16}$ is independently H, D, halogen, —CN, —OH, —N(R$^{15}$)$_2$, —NR$^{15}$S(=O)$_2$($C_1$-$C_4$alkyl), —S($C_1$-$C_4$alkyl), —S(=O)($C_1$-$C_4$alkyl), —S(=O)$_2$($C_1$-$C_4$alkyl), —S(=O)$_2$N(R$^{15}$)$_2$, —C(=O)($C_1$-$C_4$alkyl), —OC(=O)($C_1$-$C_4$alkyl), —CO$_2$H, —CO$_2$($C_1$-$C_4$alkyl), —NR$^{15}$C(=O)($C_1$-$C_4$alkyl), —C(=O)N(R$^{15}$)$_2$, —NR$^{15}$C(=O)O($C_1$-$C_4$alkyl), —OC(=O)N(R$^{15}$)$_2$, $C_1$-$C_4$alkyl, $C_2$-$C_4$alkenyl, $C_2$-$C_4$alkynyl, $C_1$-$C_4$alkoxy, $C_1$-$C_4$deuteroalkyl, $C_1$-$C_4$deuteroalkoxy, $C_1$-$C_4$fluoroalkyl, $C_1$-$C_4$fluoroalkoxy, $C_1$-$C_4$heteroalkyl, substituted or unsubstituted $C_3$-$C_6$cycloalkyl, substituted or unsubstituted monocyclic $C_2$-$C_6$heterocycloalkyl, substituted or unsubstituted phenyl, or substituted or unsubstituted monocyclic heteroaryl;

n is 0, 1, or 2.

2. The compound of claim 1, or a pharmaceutically acceptable salt or solvate thereof, wherein:

ring A is a 5-membered heteroaryl that is thiazolyl, oxazolyl, isothiazolyl, isoxazolyl, pyrazolyl, pyrrolyl, oxadiazolyl, imidazolyl, triazolyl, tetrazolyl, or thiadiazolyl.

3. The compound of claim 1, or a pharmaceutically acceptable salt or solvate thereof, wherein:

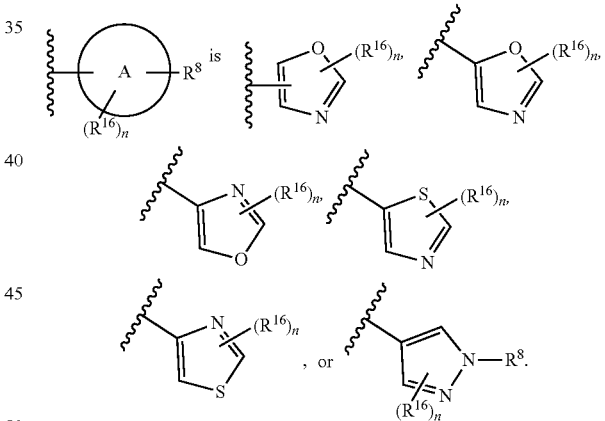

4. The compound of claim 3, or a pharmaceutically acceptable salt or solvate thereof, wherein:

L is absent, —O—, —S—, —CH$_2$—, —CH$_2$CH$_2$—, —CH$_2$O—, —OCH$_2$—, —CH$_2$NR$^{15}$—, —NR$^{15}$CH$_2$—, —CH=CH—, —C≡C—, —C(=O)NR$^{15}$—, —NR$^{15}$C(=O)—, —OC(=O)NR$^{15}$—, —NR$^{15}$C(=O)O—, —NR$^{15}$C(=O)NR$^{15}$—, —NR$^{15}$S(=O)$_2$—, —NR$^{15}$—, cyclopropylene, cyclobutylene or bicyclo[1.1.1]pentylene.

5. The compound of claim 3, or a pharmaceutically acceptable salt or solvate thereof, wherein:

L is absent or —C≡C—.

6. The compound of claim 5, or a pharmaceutically acceptable salt or solvate thereof, wherein:

$R^9$ is H;

$R^{11}$ is H;

or R⁹ and R¹¹ are taken together to form a bridge that is —CH₂CH₂—.

7. The compound of claim 6, or a pharmaceutically acceptable salt or solvate thereof, wherein:
R⁴ and R⁵ are taken together to form a bridge that is —CH₂CH₂—.

8. The compound of claim 7, or a pharmaceutically acceptable salt or solvate thereof, wherein the compound has the structure of Formula (V), or a pharmaceutically acceptable salt or solvate thereof:

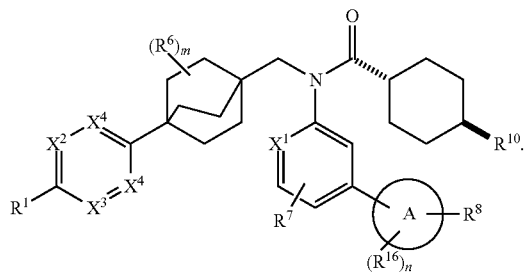

Formula (V)

9. The compound of claim 7, or a pharmaceutically acceptable salt or solvate thereof, wherein:
R¹⁰ is C₁-C₆heteroalkyl, —C(=O)R¹⁴, —OC(=O)OR¹⁴, —C(=O)N(R¹²)₂, or —NR¹⁵C(=O)N(R¹²)₂;
or R¹⁰ is -L²-L³-L⁴-R¹³;
L² is absent or —CH₂—;
L³ is absent, —O—, —NH—, —C(=O)NH—, —NHC(=O)—, —OC(=O)NH—, or —NHC(=O)O—;
L⁴ is —CH₂—, —CH₂CH₂—, —CH(CH₂OH)CH₂—, —CH₂CH₂CH₂— or —CH₂CH(OH)CH₂—; and
R¹³ is H, —CN, —OH, —N(R¹²)₂, —CH₃, —CH₂CH₃, —CH₂CH₂CH₃, —CH(CH₃)₂, —CH₂CH₂CH₂CH₃, —CH₂CH(CH₃)₂, —C(CH₃)₃, —CH₂OH, —CH₂OCH₃, —CH₂OCH₂CH₃, —CH₂CH₂OH, —CH₂CH₂OCH₃, —CH₂CH₂OCH₂CH₃, —CH₂NH₂, —CH₂NHCH₃, —CH₂N(CH₃)₂, —CO₂H, —C(=O)NHCH₃, —OC(=O)NHCH₃, NHC(=O)CH₃, NHC(=O)OCH₃, NHS(=O)₂CH₃, SO₂CH₃, substituted or unsubstituted cyclopropyl, substituted or unsubstituted cyclobutyl, substituted or unsubstituted cyclopentyl, substituted or unsubstituted cyclohexyl, substituted or unsubstituted phenyl, or substituted or unsubstituted monocyclic heteroaryl.

10. The compound of claim 9, or a pharmaceutically acceptable salt or solvate thereof, wherein:
R¹⁰ is C₁-C₆heteroalkyl, or —C(=O)N(R¹²)₂.

11. The compound of claim 10, or a pharmaceutically acceptable salt or solvate thereof, wherein:
X² is CR²;
X³ is CR³ or N;
each X⁴ is CH; or each X⁴ is N; or one X⁴ is N and the other X⁴ is CH.

26312. The compound of claim 11, or a pharmaceutically acceptable salt or solvate thereof, wherein:
R¹ is —OH, —NH₂, —NH(CH₃), —N(CH₃)₂, —CH₃, —OCH₃, —SCH₃, —CD₃, —OCD₃, —CH₂F, —CHF₂, —CF₃, —OCH₂F, —OCHF₂, —OCF₃, or —OCH₂CF₃;
R² is H, D, F, Cl, —CH₃, —CD₃, —CH₂F, —CHF₂, or —CF₃;
R³ is H.

13. The compound of claim 12, or a pharmaceutically acceptable salt or solvate thereof, wherein:

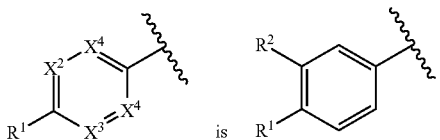

14. The compound of claim 13, or a pharmaceutically acceptable salt or solvate thereof, wherein:
R⁸ is H, —CH₃, —CH₂CH₃, —CH₂CH₂CH₃, —CH(CH₃)₂, —CH₂CH₂CH₂CH₃, —CH(CH₃)CH₂CH₃, —CH₂CH(CH₃)₂, —C(CH₃)₃, —CD₃, —CH₂F, —CHF₂, —CF₃, —CH₂CF₃, —CHFCH₃, —CH₂CH₂F, —CH₂CH₂OH, —CH₂CH₂OCH₃, —CH₂CH₂NH₂, —CH₂CH₂NHCH₃, —CH₂CH₂N(CH₃)₂, substituted or unsubstituted cyclopropyl, substituted or unsubstituted cyclobutyl, substituted or unsubstituted cyclopentyl, substituted or unsubstituted cyclohexyl, substituted or unsubstituted oxetanyl, substituted or unsubstituted tetrahydrofuranyl, or substituted or unsubstituted tetrahydropyranyl.

15. The compound of claim 14, or a pharmaceutically acceptable salt or solvate thereof, wherein:
each R¹⁶ is independently is H, D, F, Cl, —CH₃, —CH₂CH₃, —CH(CH₃)₂, —C(CH₃)₃, —OCH₃, —OCH₂CH₃, —OCH(CH₃)₂, —SCH₃, —SCH₂CH₃, —SCH(CH₃)₂, —CD₃, —CH₂F, —CHF₂, —CF₃, —CH₂CF₃, substituted or unsubstituted cyclopropyl, or substituted or unsubstituted cyclobutyl.

16. A pharmaceutical composition comprising a compound of claim 1, or a pharmaceutically acceptable salt, or solvate thereof, and at least one pharmaceutically acceptable excipient.

17. A method of treating liver fibrosis, liver inflammation, or a gastrointestinal disease or condition in a mammal, comprising administering to the mammal a compound of claim 1, or a pharmaceutically acceptable salt or solvate thereof.

18. The method of claim 17, wherein
the liver fibrosis is in a mammal diagnosed with hepatitis C virus (HCV), nonalcoholic steatohepatitis (NASH), primary sclerosing cholangitis (PSC), cirrhosis, Wilson's disease, hepatitis B virus (HBV), HIV associated steatohepatitis and cirrhosis, chronic viral hepatitis, non-alcoholic fatty liver disease (NAFLD), alcoholic steatohepatitis (ASH), primary biliary cirrhosis (PBC), or biliary cirrhosis;
the liver inflammation is in a mammal diagnosed with hepatitis C virus (HCV), nonalcoholic steatohepatitis (NASH), primary sclerosing cholangitis (PSC), cirrhosis, Wilson's disease, hepatitis B virus (HBV), HIV associated steatohepatitis and cirrhosis, chronic viral hepatitis, non-alcoholic fatty liver disease (NAFLD), alcoholic steatohepatitis (ASH), primary biliary cirrhosis (PBC), or biliary cirrhosis; or
the liver inflammation is in a mammal diagnosed with inflammatory bowel disease; or
the liver inflammation is associated with inflammation in the gastrointestinal tract;

the gastrointestinal disease or condition is necrotizing enterocolitis, gastritis, ulcerative colitis, Crohn's disease, inflammatory bowel disease, irritable bowel syndrome, gastroenteritis, radiation induced enteritis, pseudomembranous colitis, chemotherapy induced enteritis, gastro-esophageal reflux disease (GERD), peptic ulcer, non-ulcer dyspepsia (NUD), celiac disease, intestinal celiac disease, post-surgical inflammation, gastric carcinogenesis, graft versus host disease or any combination thereof; or the gastrointestinal disease or condition is irritable bowel syndrome with diarrhea (IBS-D), irritable bowel syndrome with constipation (IBS-C), mixed IBS (IBS-M), unsubtyped IBS (IBS-U), or bile acid diarrhea (BAD).

\* \* \* \* \*